United States Patent
Edwards et al.

(10) Patent No.: US 6,639,063 B1
(45) Date of Patent: Oct. 28, 2003

(54) EST'S AND ENCODED HUMAN PROTEINS

(75) Inventors: Jean-Baptiste Dumas Milne Edwards, Paris (FR); Severin Jobert, Paris (FR); Jean-Yves Giordano, Paris (FR)

(73) Assignee: Genset S.A. (FR)

( * ) Notice: Subject to any disclaimer, the term of this patent is extended or adjusted under 35 U.S.C. 154(b) by 0 days.

(21) Appl. No.: 09/621,976

(22) Filed: Jul. 21, 2000

Related U.S. Application Data

(60) Provisional application No. 60/147,499, filed on Aug. 5, 1999.

(51) Int. Cl.[7] .................. C07H 21/04; C07K 14/435
(52) U.S. Cl. .................. 536/23.5; 536/24.1; 530/300
(58) Field of Search ............... 536/23.5, 24.1, 536/24.2, 24.3, 24.31; 530/300

(56) References Cited

FOREIGN PATENT DOCUMENTS

| WO | WO 96/34981 A2 | 11/1996 |
| WO | WO 99/47540 A1 | 9/1999 |
| WO | WO 99/53051 A2 | 10/1999 |

OTHER PUBLICATIONS

Mark D. Adams, et al..; "3,400 New Expressed Sequence Tags Identify Diversity of Transcripts in Human Brain"; Nature, Genetics, US, New York, NY, vol. 4, Jul. 1993; pp. 256–267.

Mark D. Adams, et al.; "Rapid CDNA Sequencing (Expressed Sequence Tags) from a Directionally Cloned Human Infant Brain CDNA Library"; Nature Genetics, US, New York, NY, vol. 4, Aug. 1, 1993, pp. 373–380.

Kei Tashiro, et al.; "Signal Sequence Trap: A Cloning Strategy for Secreted Proteins and Type 1 Membrane Proteins"; Science, vol. 261, Jul. 30, 1993, pp. 600–603.

Piero Carninci, et al.; "High–Efficiency Full–Length CDNA Cloning by Biotinylated Cap Trapper"; Genomics. US, Academic Press, San Diego, vol. 37, No. 3, Nov. 1, 1996, pp. 327–336.

Seisho Kato, et al.; "Construction of a Human Full–Length CDNA Bank"; Gene, Elsevier Biomedical Press., Amsterdam, NL, vol. 150, 1994, pp. 243–250.

*Primary Examiner*—Michael P. Woodward
*Assistant Examiner*—Marjorie A. Moran
(74) *Attorney, Agent, or Firm*—Saliwanchik, Lloyd & Saliwanchik

(57) ABSTRACT

The sequences of 5' ESTs and consensus contigated 5' ESTs derived from mRNAs encoding secreted proteins are disclosed. The 5' ESTs and consensus contigated 5' ESTs may be used to obtain cDNAs and genomic DNAs corresponding to the 5' ESTs and consensus contigated 5' ESTs. The 5' ESTs and consensus contigated 5' ESTs may also be used in diagnostic, forensic, gene therapy, and chromosome mapping procedures. Upstream regulatory sequences may also be obtained using the 5' ESTs and consensus contigated ESTs. The 5' ESTs and consensus contigated 5' ESTs may also be used to design expression vectors and secretion vectors.

20 Claims, 10 Drawing Sheets

| Minimum signal peptide score | false positive rate | false negative rate | proba(0.1) | proba(0.2) |
|---|---|---|---|---|
| 3.5 | 0.121 | 0.036 | 0.467 | 0.664 |
| 4 | 0.096 | 0.06 | 0.519 | 0.708 |
| 4.5 | 0.078 | 0.079 | 0.565 | 0.745 |
| 5 | 0.062 | 0.098 | 0.615 | 0.782 |
| 5.5 | 0.05 | 0.127 | 0.659 | 0.813 |
| 6 | 0.04 | 0.163 | 0.694 | 0.836 |
| 6.5 | 0.033 | 0.202 | 0.725 | 0.855 |
| 7 | 0.025 | 0.248 | 0.763 | 0.878 |
| 7.5 | 0.021 | 0.304 | 0.78 | 0.889 |
| 8 | 0.015 | 0.368 | 0.816 | 0.909 |
| 8.5 | 0.012 | 0.418 | 0.836 | 0.92 |
| 9 | 0.009 | 0.512 | 0.856 | 0.93 |
| 9.5 | 0.007 | 0.581 | 0.863 | 0.934 |
| 10 | 0.006 | 0.679 | 0.835 | 0.919 |

Figure 2

Description of Transcription Factor Binding Sites Present on Promoters Isolated From SignalTag Sequences

Promoter sequence P13H2 (546 bp):

| Matrix | Position | Orientation | Score | Length | Sequence |
|---|---|---|---|---|---|
| CMYB_01 | -502 | + | 0.983 | 9 | TGTCAGTTG |
| MYOD_Q6 | -501 | - | 0.961 | 10 | CCCAACTGAC |
| S8_01 | -444 | - | 0.960 | 11 | AATAGAATTAG |
| S8_01 | -425 | + | 0.966 | 11 | AACTAAATTAG |
| DELTAEF1_01 | -390 | - | 0.960 | 11 | GCACACCTCAG |
| GATA_C | -364 | - | 0.964 | 11 | AGATAAATCCA |
| CMYB_01 | -349 | + | 0.958 | 9 | CTTCAGTTG |
| GATA1_02 | -343 | + | 0.959 | 14 | TTGTAGATAGGACA |
| GATA_C | -339 | + | 0.953 | 11 | AGATAGGACAT |
| TAL1ALPHAE47_01 | -235 | + | 0.973 | 16 | CATAACAGATGGTAAG |
| TAL1BETAE47_01 | -235 | + | 0.983 | 16 | CATAACAGATGGTAAG |
| TAL1BETAITF2_01 | -235 | + | 0.978 | 16 | CATAACAGATGGTAAG |
| MYOD_Q6 | -232 | - | 0.954 | 10 | ACCATCTGTT |
| GATA1_04 | -217 | - | 0.953 | 13 | TCAAGATAAAGTA |
| IK1_01 | -126 | + | 0.963 | 13 | AGTTGGGAATTCC |
| IK2_01 | -126 | + | 0.985 | 12 | AGTTGGGAATTC |
| CREL_01 | -123 | + | 0.962 | 10 | TGGGAATTCC |
| GATA1_02 | -96 | + | 0.950 | 14 | TCAGTGATATGGCA |
| SRY_02 | -41 | - | 0.951 | 12 | TAAAACAAAACA |
| E2F_02 | -33 | + | 0.957 | 8 | TTTAGCGC |
| MZF1_01 | -5 | - | 0.975 | 8 | TGAGGGGA |

Promoter sequence P15B4 (861bp):

| Matrix | Position | Orientation | Score | Length | Sequence |
|---|---|---|---|---|---|
| NFY_Q6 | -748 | - | 0.956 | 11 | GGACCAATCAT |
| MZF1_01 | -738 | + | 0.962 | 8 | CCTGGGGA |
| CMYB_01 | -684 | + | 0.994 | 9 | TGACCGTTG |
| VMYB_02 | -682 | - | 0.985 | 9 | TCCAACGGT |
| STAT_01 | -673 | + | 0.968 | 9 | TTCCTGGAA |
| STAT_01 | -673 | - | 0.951 | 9 | TTCCAGGAA |
| MZF1_01 | -556 | - | 0.956 | 8 | TTGGGGGA |
| IK2_01 | -451 | + | 0.965 | 12 | GAATGGGATTTC |
| MZF1_01 | -424 | + | 0.986 | 8 | AGAGGGGA |
| SRY_02 | -398 | - | 0.955 | 12 | GAAAACAAAACA |
| MZF1_01 | -216 | + | 0.960 | 8 | GAAGGGGA |
| MYOD_Q6 | -190 | + | 0.981 | 10 | AGCATCTGCC |
| DELTAEF1_01 | -176 | + | 0.958 | 11 | TCCCACCTTCC |
| S8_01 | 5 | - | 0.992 | 11 | GAGGCAATTAT |
| MZF1_01 | 16 | - | 0.986 | 8 | AGAGGGGA |

Promoter sequence P29B6 (555 bp):

| Matrix | Position | Orientation | Score | Length | Sequence |
|---|---|---|---|---|---|
| ARNT_01 | -311 | + | 0.964 | 16 | GGACTCACGTGCTGCT |
| NMYC_01 | -309 | + | 0.965 | 12 | ACTCACGTGCTG |
| USF_01 | -309 | + | 0.985 | 12 | ACTCACGTGCTG |
| USF_01 | -309 | - | 0.985 | 12 | CAGCACGTGAGT |
| NMYC_01 | -309 | - | 0.956 | 12 | CAGCACGTGAGT |
| MYCMAX_02 | -309 | - | 0.972 | 12 | CAGCACGTGAGT |
| USF_C | -307 | + | 0.997 | 8 | TCACGTGC |
| USF_C | -307 | - | 0.991 | 8 | GCACGTGA |
| MZF1_01 | -292 | - | 0.968 | 8 | CATGGGGA |
| ELK1_02 | -105 | + | 0.963 | 14 | CTCTCCGGAAGCCT |
| CETS1P54_01 | -102 | + | 0.974 | 10 | TCCGGAAGCC |
| AP1_Q4 | -42 | - | 0.963 | 11 | AGTGACTGAAC |
| AP1FJ_Q2 | -42 | - | 0.961 | 11 | AGTGACTGAAC |
| PADS_C | 45 | + | 1.000 | 9 | TGTGGTCTC |

Figure 5

| Step | Search characteristic | | | Selection Characteristics | | |
|---|---|---|---|---|---|---|
| | Program | Strand | Parameters | Identity (%) | Length (bp) | Comments |
| miscellanaeous | FASTA | both | - | 90 | 15 | |
| tRNA | FASTA | both | - | 80 | 60 | |
| rRNA | BLASTN | both | S=108 | 80 | 40 | |
| mtRNA | BLASTN | both | S=108 | 80 | 40 | |
| Procaryotic | BLASTN | both | S=144 | 90 | 40 | |
| Fungal | BLASTN | both | S=144 | 90 | 40 | |
| Alu | BLASTN | both | S=72, B=5 | 70 | 40 | max 5 matches, masking |
| L1 | BLASTN | both | S=72, B=5 | 70 | 40 | max 5 matches, masking |
| Repeats | BLASTN | both | S=72 | 70 | 40 | masking |
| PolyA | BLAST2N | top | W=6, S=10, E=1000, N=-12 | 90 | 10 | in the last 100 nucleotides |
| Polyadenylation signal | - | top | AATAAA allowing 1 mismatch | | | in the 50 nucleotides preceding the 5' end of the polA |
| Vertebrate | BLASTN then FASTA | both | | 90 then 70 | 30 | first BLASTN and then FASTA on matching sequences |
| ESTs | BLAST2N | both | - | 90 | 30 | |
| Geneseq | BLASTN | both | W=8, B=10 | 90 | 30 | |
| ORF | BLASTP | top | W=8, B=10 | - | - | on ORF proteins, max 10 matches |
| Proteins | BLASTX | top | E = 0.001 | 70 | 30 | |

Figure 10

EST'S AND ENCODED HUMAN PROTEINS

RELATED APPLICATIONS

This application claims benefit of U.S. Provisional Patent Application Ser. No. 60/147,499, filed Aug. 5, 1999, the disclosure of which is incorporated herein by reference in its entirety.

BACKGROUND OF THE INVENTION

The estimated 50,000–100,000 genes scattered along the human chromosomes offer tremendous promise for the understanding, diagnosis, and treatment of human diseases. In addition, probes capable of specifically hybridizing to loci distributed throughout the human genome find applications in the construction of high resolution chromosome maps and in the identification of individuals.

In the past, the characterization of even a single human gene was a painstaking process, requiring years of effort. Recent developments in the areas of cloning vectors, DNA sequencing, and computer technology have merged to greatly accelerate the rate at which human genes can be isolated, sequenced, mapped, and characterized.

Currently, two different approaches are being pursued for identifying and characterizing the genes distributed along the human genome. In one approach, large fragments of genomic DNA are isolated, cloned, and sequenced. Potential open reading frames in these genomic sequences are identified using bioinformatics software. However, this approach entails sequencing large stretches of human DNA which do not encode proteins in order to find the protein encoding sequences scattered throughout the genome. In addition to requiring extensive sequencing, the bioinformatics software may mischaracterize the genomic sequences obtained, i.e., labeling non-coding DNA as coding DNA and vice versa.

An alternative approach takes a more direct route to identifying and characterizing human genes. In this approach, complementary DNAs (cDNAs) are synthesized from isolated messenger RNAs (mRNAs) which encode human proteins. Using this approach, sequencing is only performed on DNA which is derived from protein coding portions of the genome. Often, only short stretches of the cDNAs are sequenced to obtain sequences called expressed sequence tags (ESTs). The ESTs may then be used to isolate or purify extended cDNAs which include sequences adjacent to the EST sequences. The extended cDNAs may contain all of the sequence of the EST which was used to obtain them or only a portion of the sequence of the EST which was used to obtain them. In addition, the extended cDNAs may contain the full coding sequence of the gene from which the EST was derived or, alternatively, the extended cDNAs may include portions of the coding sequence of the gene from which the EST was derived. It will be appreciated that there may be several extended cDNAs which include the EST sequence as a result of alternate splicing or the activity of alternative promoters. Alternatively, ESTs having partially overlapping sequences may be identified and contigs comprising the consensus sequences of the overlapping ESTs may be identified.

In the past, these short EST sequences were often obtained from oligo-dT primed cDNA libraries. Accordingly, they mainly corresponded to the 3' untranslated region of the mRNA. In part, the prevalence of EST sequences derived from the 3' end of the mRNA is a result of the fact that typical techniques for obtaining cDNAs, are not well suited for isolating cDNA sequences derived from the 5' ends of mRNAs (Adams et al., *Nature* 377:3–174, 1996, Hillier et al., *Genome Res.* 6:807–828, 1996).

In addition, in those reported instances where longer cDNA sequences have been obtained, the reported sequences typically correspond to coding sequences and do not include the full 5' untranslated region (5' UTR) of the mRNA from which the CDNA is derived. Indeed, 5' UTRs have been shown to affect either the stability or translation of mRNAs. Thus, regulation of gene expression may be achieved through the use of alternative 5' UTRs as shown, for instance, for the translation of the tissue inhibitor of metalloprotease mRNA in mitogenically activated cells (Waterhouse et al, *J Biol Chem*. 265:5585–9. 1990). Furthermore, modification of 5' UTR through mutation, insertion or translocation events may even be implied in pathogenesis. For instance, the fragile X syndrome, the most common cause of inherited mental retardation, is partly due to an insertion of multiple CGG trinucleotides in the 5' UTR of the fragile X mRNA resulting in the inhibition of protein synthesis via ribosome stalling (Feng et al, *Science* 268:731–4, 1995). An aberrant mutation in regions of the 5' UTR known to inhibit translation of the proto-oncogene c-myc was shown to result in upregulation of C-myc protein levels in cells derived from patients with multiple myelomas (Willis et al, *Curr Top Microbiol Immunol* 224:269–76, 1997). In addition, the use of oligo-dT primed cDNA libraries does not allow the isolation of complete 5' UTRs since such incomplete sequences obtained by this process may not include the first exon of the mRNA, particularly in situations where the first exon is short. Furthermore, they may not include some exons, often short ones, which are located upstream of splicing sites. Thus, there is a need to obtain sequences derived from the 5' ends of mRNAs.

While many sequences derived from human chromosomes have practical applications, approaches based on the identification and characterization of those chromosomal sequences which encode a protein product are particularly relevant to diagnostic and therapeutic uses. In some instances, the sequences used in such therapeutic or diagnostic techniques may be sequences which encode proteins which are secreted from the cell in which they are synthesized. Those sequences encoding secreted proteins as well as the secreted proteins themselves, are particularly valuable as potential therapeutic agents. Such proteins are often involved in cell to cell communication and may be responsible for producing a clinically relevant response in their target cells. In fact, several secretory proteins, including tissue plasminogen activator, G-CSF, GM-CSF, erythropoietin, human growth hormone, insulin, interferon-α, interferon-β, interferon-γ, and interleukin-2, are currently in clinical use. These proteins are used to treat a wide range of conditions, including acute myocardial infarction, acute ischemic stroke, anemia, diabetes, growth hormone deficiency, hepatitis, kidney carcinoma, chemotherapy-induced neutropenia and multiple sclerosis. For these reasons, extended cDNAs encoding secreted proteins or portions thereof represent a valuable source of therapeutic agents. Thus, there is a need for the identification and characterization of secreted proteins and the nucleic acids encoding them.

In addition to being therapeutically useful themselves, secretory proteins include short peptides, called signal peptides, at their amino termini which direct their secretion. These signal peptides are encoded by the signal sequences located at the 5' ends of the coding sequences of genes encoding secreted proteins. These signal peptides can be used to direct the extracellular secretion of any protein to which they are operably linked. In addition, portions of the signal peptides called membrane-translocating sequences, may also be used to direct the intracellular import of a peptide or protein of interest. This may prove beneficial in gene therapy strategies in which it is desired to deliver a particular gene product to cells other than the cells in which it is produced. Signal sequences encoding signal peptides also find application in simplifying protein purification techniques. In such applications, the extracellular secretion of the desired protein greatly facilitates purification by reducing the number of undesired proteins from which the desired protein must be selected. Thus, there exists a need to identify and characterize the 5' portions of the genes for secretory proteins which encode signal peptides.

Sequences coding for non-secreted proteins may also find application as therapeutics or diagnostics. In particular, such sequences may be used to determine whether an individual is likely to express a detectable phenotype, such as a disease, as a consequence of a mutation in the coding sequence of a protein. In instances where the individual is at risk of suffering from a disease or other undesirable phenotype as a result of a mutation in such a coding sequence, the undesirable phenotype may be corrected by introducing a normal coding sequence using gene therapy. Alternatively, if the undesirable phenotype results from overexpression of the protein encoded by the coding sequence, expression of the protein may be reduced using antisense or triple helix based strategies.

The secreted or non-secreted human polypeptides encoded by the coding sequences may also be used as therapeutics by administering them directly to an individual having a condition, such as a disease, resulting from a mutation in the sequence encoding the polypeptide. In such an instance, the condition can be cured or ameliorated by administering the polypeptide to the individual.

In addition, the secreted or non-secreted human polypeptides or portions thereof may be used to generate antibodies useful in determining the tissue type or species of origin of a biological sample. For example, the antibodies may be used to distinguish between human and non-human cells and tissues or to distinguish between human tissues that do and do not express the polypeptides. The antibodies may also be used to determine the cellular localization of the secreted or non-secreted human polypeptides or the cellular localization of polypeptides which have been fused to the human polypeptides. In addition, the antibodies may also be used in immunoaffinity chromatography techniques to isolate, purify, or enrich the human polypeptide or a target polypeptide which has been fused to the human polypeptide. Public information on the number of human genes for which the promoters and upstream regulatory regions have been identified and characterized is quite limited. In part, this may be due to the difficulty of isolating such regulatory sequences. Upstream regulatory sequences such as transcription factor binding sites are typically too short to be utilized as probes for isolating promoters from human genomic libraries. Recently, some approaches have been developed to isolate human promoters. One of them consists of making a CpG island library (Cross et al., *Nature Genetics* 6: 236–244, 1994). The second consists of isolating human genomic DNA sequences containing SpeI binding sites by the use of SpeI binding protein (Mortlock et al., *Genome Res.* 6:327–335, 1996). Both of these approaches have their limits due to a lack of specificity and of comprehensiveness. Thus, there exists a need to identify and systematically characterize the 5' portions of the genes.

The present 5' ESTs may be used to efficiently identify and isolate 5' UTRs and upstream regulatory regions which control the location, developmental stage, rate, and quantity of protein synthesis, as well as the stability of the mRNA. Once identified and characterized, these regulatory regions may be utilized in gene therapy or protein purification schemes to obtain the desired amount and locations of protein synthesis or to inhibit, reduce, or prevent the synthesis of undesirable gene products. The regulatory regions may also be used for expressing polypeptides in cell types from which the 5' ESTs of the present invention were isolated.

In addition, ESTs containing the 5' ends of protein genes may include sequences useful as probes for chromosome mapping and the identification of individuals. Thus, there is a need to identify and characterize the sequences upstream of the 5' coding sequences of genes.

SUMMARY OF THE INVENTION

The present invention relates to purified, isolated, or enriched 5' ESTs which include sequences derived from the authentic 5' ends of their corresponding mRNAs. The term "corresponding mRNA" refers to the mRNA which was the template for the cDNA synthesis which produced the 5' EST. These sequences will be referred to hereinafter as "5' ESTs". The present invention also includes purified, isolated or enriched nucleic acids comprising contigs assembled by determining a consensus sequences from a plurality of ESTs containing overlapping sequences. These contigs will be referred to herein as "consensus contigated ESTs."

As used herein, the term "purified" does not require absolute purity; rather, it is intended as a relative definition. Individual 5' EST clones isolated from a cDNA library have been conventionally purified to electrophoretic homogeneity. The sequences obtained from these clones could not be obtained directly either from the library or from total human DNA. The cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^4$–$10^6$ fold purification of the native message. Purification of starting material or natural material to at least one order of magnitude, preferably two or three orders, and more preferably four or five orders of magnitude is expressly contemplated. Alternatively, purification may be expressed as "at least" a percent purity relative to heterologous polynucleotides (DNA, RNA or both). As a preferred embodiment, the polynucleotides of the present invention are at least; 10%, 20%, 30%, 40%, 50%, 60%, 70%, 80%, 90%, 95%, 96%, 96%, 98%, 99%, or 100% pure relative to heterologous polynucleotides. As a further preferred embodiment the polynucleotides have an "at least" purity ranging from any number, to the thousandth position, between 90% and 100% (e.g., 5' EST at least 99.995% pure) relative to heterologous polynucleotides. Additionally, purity of the polynucleotides may be expressed as a percentage (as described above) relative to all materials and compounds other than the carrier solution. Each number, to the thousandth position, may be claimed as individual species of purity.

As used herein, the term "isolated" requires that the material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated. Specifically excluded from the definition of "isolated" are: naturally occurring chromosomes (e.g., chromosome spreads) artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein the 5' EST makes up less than 5% of the number of nucleic acid inserts in the vector molecules. Further specifically excluded are whole cell genomic DNA or whole cell RNA preparations (including said whole cell preparations which are mechanically sheared or enzymaticly digested). Further specifically excluded are the above whole cell preparations as either an in vitro preparation or as a heterogeneous mixture separated by electrophoresis (including blot transfers of the same) wherein the polynucleotide of the invention have not been further separated from the heterologous polynucleotides in the electrophoresis medium (e.g., further separating by excising a single band from a heterogeneous band population in an agarose gel or nylon blot).

As used herein, the term "recombinant" means that the 5' EST is adjacent to "backbone" nucleic acid to which it is not adjacent in its natural environment. Additionally, to be "enriched" the 5' ESTs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched 5' ESTs represent 15% or more of the number of nucleic acid inserts in the population of recombinant backbone molecules. More preferably, the enriched 5' ESTs represent 50% or more of the number of nucleic acid inserts in the population of recombinant backbone molecules. In a highly preferred embodiment, the enriched 5' ESTs represent 90% or more (including any integer between 90 and 100%, to the thousandth position, e.g., 99.5%) of the number of nucleic acid inserts in the population of recombinant backbone molecules.

"Stringent", "moderate," and "low" hybridization conditions are as defined below.

The term "polypeptide" refers to a polymer of amino acids without regard to the length of the polymer; thus, peptides, oligopeptides, and proteins are included within the definition of polypeptide. This term also does not specify or exclude chemical or post-expression modifications of the polypeptides of the invention, although chemical or post-expression modifications of these polypeptides may be included excluded as specific embodiments. Therefore, for example, modifications to polypeptides which include the covalent attachment of glycosyl groups, acetyl groups, phosphate groups, lipid groups and the like are expressly encompassed by the term polypeptide. Further, polyeptides with these modifications may be specified as individual species to be included or excluded from the present invention. The natural or other chemical modifications, such as those listed in example above, can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).). Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

As used interchangeably herein, the terms "nucleic acids", "oligonucleotides", and "polynucleotides" include RNA or DNA (either double or single stranded (coding or antisense), or RNA/NA hybrid sequences of more than one nucleotide in either single chain or duplex form (although each of the above species may be particularly specified). The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethyl-aminomethyl-2-thiouridine, 5-carboxymethylamino-methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine. Methylenemethylimino linked oligonucleosides as well as mixed backbone compounds having, may be prepared as described in U.S. Pat. Nos. 5,378,825; 5,386,023; 5,489,677; 5,602,240; and 5,610,289. Formacetal and thioformacetal linked oligonucleosides may be prepared as described in U.S. Pat. Nos. 5,264,562 and 5,264,564. Ethylene oxide linked oligonucleosides may be prepared as described in U.S. Pat. No. 5,223,618. Phosphinate oligonucleotides may be prepared as described in U.S. Pat. No. 5,508,270. Alkyl phosphonate oligonucleotides may be prepared as described in U.S. Pat. No. 4,469,863. 3'-Deoxy-3'-methylene phosphonate oligonucleotides may be prepared as described in U.S. Pat. Nos. 5,610,289 or 5,625,050. Phosphoramidite oligonucleotides may be prepared as described in U.S. Pat. No. 5,256,775 or U.S. Pat. No. 5,366,878. Alkylphosphonothioate oligonucleotides may be prepared as described in published PCT applications WO 94/17093 and WO 94/02499. 3'-Deoxy-3'-amino phosphoramidate oligonucleotides may be prepared as described in U.S. Pat. No. 5,476,925. Phosphotriester oligonucleotides may be prepared as described in U.S. Pat. No. 5,023,243. Borano phosphate oligonucleotides may be prepared as described in U.S. Pat. Nos. 5,130,302 and 5,177,198.

The polynucleotide sequences of the invention may be prepared by any known method, including synthetic, recombinant, ex vivo generation, or a combination thereof, as well as utilizing any purification methods known in the art.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 10 kb, 7.5 kb, 5 kb, 2.5 kb, 2 kb, 1.5 kb, or 1 kb in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 75, 50, 25, 20, 15, 10, 5, 4, 3, 2, or 1 genomic flanking gene(s).The terms "base paired" and "Watson & Crick base paired" are used interchangeably herein to refer to nucleotides which can be hydrogen bonded to one another be virtue of their sequence identities in a manner like that found in double-helical DNA with thymine or uracil residues linked to adenine residues by two hydrogen bonds and cytosine and guanine residues linked by three hydrogen bonds (See Stryer, L., *Biochemistry*, 4$^{th}$ edition, 1995).

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind. Preferably, a "complementary" sequence is a sequence which an A at each position where there is a T on the opposite strand, a T at each position where there is an A on the opposite strand, a G at each position where there is a C on the opposite strand and a C at each position where there is a G on the opposite strand.

The terms "vertebrate nucleic acid" and "vertebrate polypeptide" are used herein to refer to any nucleic acid or polypeptide respectively which are derived from a vertebrate species including birds and more usually mammals, preferably primates such as humans, farm animals such as swine, goats, sheep, donkeys, and horses, rabbits or rodents, more preferably rats or mice. As used herein, the term "vertebrate" is used to refer to any vertebrate, preferably a mammal. The term "vertebrate" expressly embraces human subjects unless preceded with the term "non-human".

Thus, 5' ESTs in CDNA libraries in which one or more 5' ESTs make up 5% or more of the number of nucleic acid inserts in the backbone molecules are "enriched recombinant 5' ESTs" as defined herein. Likewise, 5' ESTs in a population of plasmids in which one or more 5' ESTs of the present invention have been inserted such that they represent 5% or more of the number of inserts in the plasmid backbone are "enriched recombinant 5' ESTs" as defined herein. However, 5' ESTs in cDNA libraries in which 5' ESTs constitute less than 5% of the number of nucleic acid inserts in the population of backbone molecules, such as libraries in which backbone molecules having a 5' EST insert are extremely rare, are not "enriched recombinant 5' ESTs."

The term"capable of hybridizing to the polyA tail of said mRNA" refers to and embraces all primers containing stretches of thymidine residues, so-called oligo(dT) primers, that hybridize to the 3' end of eukaryotic poly(A)+ mRNAs to prime the synthesis of a first cDNA strand. Techniques for generating said oligo(dT) primers and hybridizing them to mRNA to subsequently prime the reverse transcription of said hybridized mRNA to generate a first cDNA strand are well known to those skilled in the art and are described in *Current Protocols in Molecular Biology*, John Wiley and Sons, Inc. 1997 and Sambrook et al., *Molecular Cloning: A Laboratory Manual*, Second Edition, Cold Spring Harbor Laboratory Press, 1989, the entire disclosures of which are incorporated herein by reference. Preferably, said oligo(dT) primers are present in a large excess in order to allow the hybridization of all mRNA 3' ends to at least one oligo(dT) molecule. The priming and reverse transcription step are preferably performed between 37° C. and 55° C. depending on the type of reverse transcriptase used.

Preferred oligo(dT) primers for priming reverse transcription of mRNAs are oligonucleotides containing a stretch of thymidine residues of sufficient length to hybridize specifically to the polyA tail of mRNAs, preferably of 12 to 18 thymidine residues in length. More preferably, such oligo(T) primers comprise an additional sequence upstream of the poly(dT) stretch in order to allow the addition of a given sequence to the 5' end of all first cDNA strands which may then be used to facilitate subsequent manipulation of the cDNA. Preferably, this added sequence is 8 to 60 residues in length. For instance, the addition of a restriction site in 5' of cDNAs facilitates subcloning of the obtained cDNA. Alternatively, such an added 5' end may also be used to design primers of PCR to specifically amplify cDNA clones of interest.

In some embodiments, the present invention relates to 5' ESTs which are derived from genes encoding secreted proteins. As used herein, a "secreted" protein is one which, when expressed in a suitable host cell, is transported across or through a membrane, including transport as a result of signal peptides in its amino acid sequence. "Secreted" proteins include without limitation proteins secreted wholly (e.g. soluble proteins), or partially (e.g. receptors) from the cell in which they are expressed. "Secreted" proteins also include without limitation proteins which are transported across the membrane of the endoplasmic reticulum.

Such 5' ESTs include nucleic acid sequences, called signal sequences, which encode signal peptides which direct the extracellular secretion of the proteins encoded by the genes from which the 5' ESTs are derived. Generally, the signal peptides are located at the amino termini of secreted proteins. Polypeptides comprising these signal peptides (as delineated in the sequence listing), and polynucleotides encoding the same, are preferred embodiments of the present invention.

Secreted proteins are translated by ribosomes associated with the "rough" endoplasmic reticulum. Generally, secreted proteins are co-translationally transferred to the membrane of the endoplasmic reticulum. Association of the ribosome with the endoplasmic reticulum during translation of secreted proteins is mediated by the signal peptide. The signal peptide is typically cleaved following its co-translational entry into the endoplasmic reticulum. After delivery to the endoplasmic reticulum, secreted proteins may proceed through the Golgi apparatus. In the Golgi apparatus, the proteins may undergo post-translational modification before entering secretory vesicles which transport them across the cell membrane.

The 5' ESTs of the present invention have several important applications. For example, the 5' EST sequences of the sequence listing, and fragments thereof, may be used to distinguish human tissues or cells from non-human tissues or cells and to distinguish between human tissues or cells that do and do not express polynucleotides comprising the 5' EST sequences of the present invention. By knowing the tissue expression pattern of the 5' EST sequences, either through routine experimentation or by using the Tables herein, the polynucleotides of the present invention may be used in methods of determining the identity of an unknown tissue or cell sample. For example, if a 5' EST is expressed in a particular tissue or cell type, as shown in the Tables below, and the unknown tissue or cell sample does not express the 5' EST, it may be inferred that the unknown tissue or cells are either not human or not the same human tissue or cell type as that which expresses the 5' EST. Conversely, if a 5' EST is not expressed in a particular tissue or cell type, as shown in the Tables below, and the unknown tissue or cell sample does express the 5' EST, it may be inferred that the unknown tissue or cells are either not human or not the same human tissue or cell type as that which does not express the 5' EST. The above procedure may be used for either homogeneous tissue or cell samples or heterogeneous tissue or cell samples since one may only want to narrow the identity to human or non-human or to a tissue type. Further assays may be used in conjunction with the above methods to narrow or confirm the identification process. These methods of determining tissue or cell identity are based on methods which detect the presence or absence of the 5' EST sequences in a tissue or cell sample using methods well know in the art (e.g., hybridization or PCR methods).

In other useful applications, fragments of the 5' EST sequences encoding signal peptides as well as degenerate polynucleotides encoding the same, may be ligated to sequences encoding either the polypeptide from the same gene or to sequences encoding a heterologous polypeptide to facilitate secretion The 5' EST sequences, and fragments thereof, may also be used to obtain and express cDNA clones which include the full protein coding sequences of the corresponding gene products, including the authentic translation start sites derived from the 5' ends of the coding sequences of the mRNAs from which the 5' ESTs are derived. These cDNAs will be referred to hereinafter as "full-length cDNAs." These cDNAs may also include DNA derived from mRNA sequences upstream of the translation start site. The full-length cDNA sequences may be used to express the proteins corresponding to the 5' ESTs. As discussed above, secreted proteins and non-secreted proteins may be therapeutically important. Thus, the proteins expressed from the cDNAs may be useful in treating or controlling a variety of human conditions.

The 5' ESTs may also be used to obtain the corresponding genomic DNA. The term "corresponding genomic DNA" refers to the genomic DNA which encodes the mRNA from which the 5' EST was derived.

Another use of the polynucleotides of the present invention is to map and clone promoter regions and open reading frames from a genomic sequence. For example, the 5' ESTs can be used in combination with the sequence information from genome sequencing projects, such as the U.S. Human Genome Project or other public and private genome sequencing projects, to map and clone regions of the genome that comprise promoters and expressed open reading frames. The polynucleotides of the present invention are particularly useful for mapping and identifying coding regions (regions containing expressed open reading frames) from a genomic sequence since the vast majority of the human genome does not encode expressed genes and because of the difficulty in identifying authentic open reading frames (open reading frames that encode expressed genes). The 5' EST sequences of the present invention can be used in conjunction with various algorithms to identify promoter or entire ORF sequences.

Alternatively, the 5' ESTs may be used to obtain and express extended cDNAs encoding portions of the protein. In the case of secreted proteins, the portions may comprise the signal peptides of the secreted proteins or the mature proteins generated when the signal peptide is cleaved off.

The present invention includes isolated, purified, or enriched "EST-related nucleic acids." The terms "isolated", "purified" or "enriched" have the meanings provided above.

As used herein, the term "EST-related nucleic acids" means the nucleic acids of SEQ ID NOs. 24–3883 and 7744–19335, extended cDNAs obtainable using the nucleic acids of SEQ ID NOs. 24–3883 and 7744–19335, full-length cDNAs obtainable using the nucleic acids of SEQ ID NOs. 24–3883 and 7744–19335 or genomic DNAs obtainable using the nucleic acids of SEQ ID NOs. 24–3883 and 7744–19335. The present invention also includes the sequences complementary to, or allelic variants of, the EST-related nucleic acids.

The present invention also includes isolated, purified, or enriched "fragments of EST-related nucleic acids." The terms "isolated", "purified" and "enriched" have the meanings described above. As used herein the term "fragments of EST-related nucleic acids" means fragments comprising at least 8, 10, 12, 15, 18, 20, 23, 25, 28, 30, 35, 40, 50, 75, 100, 200, 300, 500, or 1000 consecutive nucleotides of the EST-related nucleic acids to the extent that fragments of these lengths are consistent with the lengths of the particular EST-related nucleic acids being referred to. The present invention also includes the sequences complementary to the fragments of the EST-related nucleic acids. In particular, fragments of EST-related nucleic acids refer to the polynucleotides described in Tables IVa and IVb, and polynucleotides described in Tables IVa and IVb updated as defined below.

The present invention also includes isolated, purified, or enriched "positional segments of EST-related nucleic acids." The terms "isolated", "purified", or "enriched" have the meanings provided above. As used herein, the term "positional segments of EST-related nucleic acids" includes segments comprising nucleotides 1–25, 26–50, 51–75, 76–100, 101–125, 126–150, 151–175, 176–200, 201–225, 226–250, 251–300, 301–325, 326–350, 351–375, 376–400, 401–425, 426–450, 451–475, 476–500, 501–525, 526–550, 551–575, 576–600 and 601-the terminal nucleotide of the EST-related nucleic acids to the extent that such nucleotide positions are consistent with the lengths of the particular EST-related nucleic acids being referred to, and wherein position "1" is defined as the 5' most position defined in the sequence listing or Tables below. The term "positional segments of EST-related nucleic acids also includes segments comprising nucleotides 1–50, 51–100, 101–150, 151–200, 201–250, 251–300, 301–350, 351–400, 401–450, 450–500, 501–550, 551–600 or 601-the terminal nucleotide of the EST-related nucleic acids to the extent that such nucleotide positions are consistent with the lengths of the particular EST-related nucleic acids being referred to. The term "positional segments of EST-related nucleic acids" also includes segments comprising nucleotides 1–100, 101–200, 201–300, 301–400, 501–500, 500–600, or 601—the terminal nucleotide of the EST-related nucleic acids to the extent that such nucleotide positions are consistent with the lengths of the particular EST-related nucleic acids being referred to. In addition, the term "positional segments of EST-related nucleic acids" includes segments comprising nucleotides 1–200, 201–400, 400–600, or 601-the terminal nucleotide of the EST-related nucleic acids to the extent that such nucleotide positions are consistent with the lengths of the particular EST related nucleic acids being referred to. The present invention also includes the sequences complementary to the positional segments of EST-related nucleic acids.

The present invention also includes isolated, purified, or enriched "fragments of positional segments of EST-related nucleic acids." The terms "isolated", "purified", or "enriched" have the meanings provided above. As used herein, the term "fragments of positional segments of EST-related nucleic acids" refers to fragments comprising at least 8, 10, 15, 18, 20, 23, 25, 28, 30, 35, 40, 50, 75, 100, 150, or 200 consecutive nucleotides of the positional segments of EST-related nucleic acids. The present invention also includes the sequences complementary to the fragments of positional segments of EST-related nucleic acids.

In addition to the above "positional segments of EST-related nucleic acids" and "fragments of positional segments of EST-related nucleic acids", for the nucleic acids of SEQ ID NOs. 24–3883 and 7744–19335, further preferred nucleic acids comprise at least 8 nucleotides, wherein "at least 8" is defined as any integer between 8 and the integer representing the 3' most nucleotide position in the sequence listing or Tables below. Further included are nucleic acid fragments at least 8 nucleotides in length, as described above, that are further specified in terms of their 5' and 3' position. The 5' and 3' positions are represented by the position number set forth in the sequence listing below. Therefore, every combination of a 5' and 3' nucleotide position that a fragment at least 8 contiguous nucleotides in length could occupy is included in the invention as an individual species. The polynucleotide fragment specified by 5' and 3' positions can be immediately envisaged and are therefore not individually listed solely for the purpose of not unnecessarily lengthening the specifications. It is noted that the above species of polynucleotides fragments of the present invention may alternatively be described by the formula "a to b"; where "a" equals the 5" nucleotide position and "b" equals 3" nucleotide position of the polynucleotide fragment; and further where "a" equals an integer between 1 and the number of nucleotides of the polynucleotide sequence of the present invention minus 8, and where "b" equals an integer between 9 and the number of nucleotides of the polynucleotide sequence of the present invention; and where "a" is an integer smaller then "b" by at least 8.

The present invention also provides for the exclusion of any polynucleotide fragments specified by 5' and 3' positions or by size in nucleotides as described above. Any number of fragments specified by 5' and 3' positions or by size in nucleotides, as described above, may be excluded.

The present invention also includes isolated or purified "EST-related polypeptides." The terms "isolated" or "purified" have the meanings provided above. As used herein, the term "EST-related polypeptides" means the polypeptides encoded by the EST-related nucleic acids, including the polypeptides of SEQ ID NOs. 3884–7743.

The present invention also includes isolated or purified "fragments of EST-related polypeptides." The terms "isolated" or "purified" have the meanings provided above. As used herein, the term "fragments of EST-related polypeptides" means fragments comprising at least 5, 10, 15, 20, 25, 30, 35, 40, 50, 75, 100, or 150 consecutive amino acids of an EST-related polypeptide to the extent that fragments of these lengths are consistent with the lengths of the particular EST-related polypeptides being referred to. In particular, fragments of EST-related polypeptides refer to polypeptides encoded by polynucleotides described in Tables IVa and IVb, and polynucleotides described in Tables IVa and IVb updated.

The present invention also includes isolated or purified "positional segments of EST-related polypeptides." As used herein, the term "positional segments of EST-related polypeptides" includes polypeptides comprising amino acid residues 1–25, 26–50, 51–75, 76–100, 101–125, 126–150, 151–175, 176–200, or 201-the C-terminal amino acid of the EST-related polypeptides to the extent that such amino acid residues are consistent with the lengths of the particular EST-related polypeptides being referred to. The term "positional segments of EST-related polypeptides also includes segments comprising amino acid residues 1–50, 51–100, 101–150, 151–200 or 201-the C-terminal amino acid of the EST-related polypeptides to the extent that such amino acid residues are consistent with the lengths of the particular EST-related polypeptides being referred to. The term "positional segments of EST-related polypeptides" also includes segments comprising amino acids 1–100 or 101–200 of the EST-related polypeptides to the extent that such amino acid residues are consistent with the lengths of particular EST-related polypeptides being referred to. In addition, the term "positional segments of EST-related polypeptides" includes segments comprising amino acid residues 1–200 or 201-the C-terminal amino acid of the EST-related polypeptides to the extent that amino acid residues are consistent with the lengths of the particular EST related polypeptides being referred to.

The present invention also includes isolated or purified "fragments of positional segments of EST-related polypeptides." The terms "isolated" or "purified" have the meanings provided above. As used herein, the term "fragments of positional segments of EST-related polypeptides" means fragments comprising at least 5, 10, 15, 20, 25, 30, 35, 40, 50, 75, 100, or 150 consecutive amino acids of positional segments of EST-related polypeptides to the extent that fragments of these lengths are consistent with the lengths of the particular EST-related polypeptides being referred to.

In addition to the above "positional segments of EST-related polypeptides" and "fragments of positional segments of EST-related polypeptides", for the polypeptides of the present invention, further preferred polypeptides comprise at least 8 amino acids, wherein "at least 8" is defined as any integer between 8 and the integer representing the C-terminal amino acid of the polypeptide of the present invention including the polypeptide sequences of the sequence listing below. Further included are polypeptide fragments at least 8 amino acids in length, as described above, that are further specified in terms of their N-terminal and C-terminal positions. Preferred polypeptide fragment species specified by their N-terminal and C-terminal positions include the signal peptides delineated in the sequence listing below. However, included in the present invention as individual species are all polypeptide fragments, at least 5 amino acids in length, as described above, and may be particularly specified by a N-terminal and C-terminal position.

The present invention also provides for the exclusion of any fragments specified by N-terminal and C-terminal positions or by size in amino acid residues as described above. Any number of fragment species specified by N-terminal and C-terminal positions or sub-genus of fragments specified by size in amino acid residues as described above may be excluded from the present invention.

The polypeptide fragments of the present invention can be immediately envisaged using the above description and are therefore not individually listed solely for the purpose of not unnecessarily lengthening the specification. The above fragments need not be active since they would be useful, for example, inimmunoassays, in epitope mapping, epitope tagging, as vaccines, to raise antibodies, stimulate an immune response in a heterologous species, and as molecular weight markers. The above fragments may also be used to generate antibodies to a particular portion of the polypeptide. These antibodies can then be used in immunoassays well known in the art to distinguish between human and non-human cells and tissues or to determine whether cells or tissues in a biological sample are or are not of the same type which express the polypeptide of the present invention. Further preferred polypeptide fragments of the present invention comprise the signal peptides as delineated in the sequence listing. These signal peptides may be used to facilitate secretion of either the polypeptide of the same gene or a heterologous polypeptide.

The present invention also includes antibodies which specifically recognize the EST-related polypeptides, fragments of EST-related polypeptides, positional segments of EST-related polypeptides, or fragments of positional segments of EST-related polypeptides. In the case of secreted proteins, such as those of SEQ ID NOs. 5199–5919 antibodies which specifically recognize the mature protein generated when the signal peptide is cleaved may also be obtained as described below. Similarly, antibodies which specifically recognize the signal peptides of SEQ ID NOs. 3884–4243 or 5199–5919 may also be obtained.

In some embodiments and in the case of secreted proteins, the EST-related nucleic acids, fragments of EST-related nucleic acids, positional segments of EST-related nucleic acids, or fragments of positional segments of nucleic acids include a signal sequence. In other embodiments, the EST-related nucleic acids, fragments of EST-related nucleic acids, positional segments of EST-related nucleic acids, or fragments of positional segments of nucleic acids may include the full coding sequence for the protein or, in the case of secreted proteins, the full coding sequence of the mature protein (i.e. the protein generated when the signal polypeptide is cleaved off). In addition, the EST-related nucleic acids, fragments of EST-related nucleic acids, positional segments of EST-related nucleic acids, or fragments of positional segments of nucleic acids may include regulatory regions upstream of the translation start site or downstream of the stop codon which control the amount, location, or developmental stage of gene expression.

As discussed above, both secreted and non-secreted human proteins may be therapeutically important. Thus, the proteins expressed from the EST-related nucleic acids, fragments of EST-related nucleic acids, positional segments of EST-related nucleic acids, or fragments of positional segments of nucleic acids may be useful in treating or controlling a variety of human conditions.

The EST-related nucleic acids, fragments of EST-related nucleic acids, positional segments of EST-related nucleic acids, or fragments of positional segments of nucleic acids may be used in forensic procedures to identify individuals or in diagnostic procedures to identify individuals having genetic diseases resulting from abnormal gene expression. In addition, the EST-related nucleic acids, fragments of EST-related nucleic acids, positional segments of EST-related nucleic acids, or fragments of positional segments of nucleic acids are useful for constructing a high resolution map of the human chromosomes.

The present invention also relates to secretion vectors capable of directing the secretion of a protein of interest. Such vectors may be used in gene therapy strategies in which it is desired to produce a gene product in one cell which is to be delivered to another location in the body. Secretion vectors may also facilitate the purification of desired proteins. The secretion vectors may also be used to express a desired protein, such as a heterologous protein, such that the protein is secreted into the culture medium, thereby facilitating purification.

The present invention also relates to expression vectors capable of directing the expression of an inserted gene in a desired spatial or temporal manner or at a desired level. Such vectors may include sequences upstream of the EST-related nucleic acids, fragments of EST-related nucleic acids, positional segments of EST-related nucleic acids, or fragments of positional segments of nucleic acids, such as promoters or upstream regulatory sequences. Preferred chimeric polypeptides, and vectors encoding the same, comprise a signal peptide set forth in the sequence listing below.

The present invention also comprises fusion vectors for making chimeric polypeptides comprising a first polypeptide and a second polypeptide. Such vectors are useful for determining the cellular localization of the chimeric polypeptides or for isolating, purifying or enriching the chimeric polypeptides.

The EST-related nucleic acids, fragments of EST-related nucleic acids, positional segments of EST-related nucleic acids, or fragments of positional segments of nucleic acids may also be used for gene therapy to control or treat genetic diseases. In the case of secreted proteins, signal peptides may be fused to heterologous proteins to direct their extracellular secretion.

Bacterial clones containing Bluescript plasmids having inserts containing the sequence of the non-aligned 5' ESTs, also referred to as singletons, and sequences of the 5' ESTs which were aligned to yield consensus contigated 5' ESTs are presently stored at −80° C. in 4% (v/v) glycerol in the inventor's laboratories under internal designations. The non-aligned 5' ESTs of the invention are those sequences which are present in the sequence listing but which identification number either corresponds to a single EST from a single tissue in the second column of Table V or is absent from the first column of Table V. The inserts may be recovered from the stored materials by growing the appropriate clones on a suitable medium. The Bluescript DNA can then be isolated using plasmid isolation procedures familiar to those skilled in the art such as alkaline lysis minipreps or large scale alkaline lysis plasmid isolation procedures. If desired the plasmid DNA may be further enriched by centrifugation on a cesium chloride gradient, size exclusion chromatography, or anion exchange chromatography. The plasmid DNA obtained using these procedures may then be manipulated using standard cloning techniques familiar to those skilled in the art. Alternatively, a PCR can be performed with primers designed at both ends of the inserted EST-related nucleic acids, fragments of EST-related nucleic acids, positional segments of EST-related nucleic acids, or fragments of positional segments of nucleic acids. The PCR product which corresponds to the EST-related nucleic acids, fragments of EST-related nucleic acids, positional segments of EST-related nucleic acids, or fragments of positional segments of nucleic acids can then be manipulated using standard cloning techniques familiar to those skilled in the art.

One embodiment of the present invention is a purified nucleic acid comprising a sequence selected from the group consisting of SEQ ID NOs. 24–3883 and SEQ ID NOs. 7744–19335 and sequences complementary to the sequences of SEQ ID NOs. 24–3883 and SEQ ID NOs. 7744–19335.

Another embodiment of the present invention is a purified nucleic acid comprising at least 8, 10, 12, 15, 18, 20, 23, 25, 28, 30, 35, 40, 50, 75, 100, 200, 300, 500, or 1000 consecutive nucleotides, to the extent that fragments of these lengths are consistent with the specific sequence, of a sequence selected from the group consisting of SEQ ID NOs. 24–3883 and SEQ ID NOs. 7744–19335 and sequences complementary to the sequences of SEQ ID NOs. 24–3883 and SEQ ID NOs. 7744–19335.

A further aspect of this embodiment is a purified vertebrate nucleic acid comprising at least 8, 10, 12, 15, 18, 20, 23, 25, 28, 30, 35, 40, 50, 75, 100, 200, 300, 500, or 1000 consecutive nucleotides, to the extent that fragments of these lengths are consistent with the specific sequence, of a sequence selected from the group consisting of SEQ ID NOs. 24–3883 and SEQ ID NOs. 7744–19335 and sequences complementary to the sequences of SEQ ID NOs. 24–3883 and SEQ ID NOs. 7744–19335.

A further aspect of this embodiment is a purified human nucleic acid comprising at least 8, 10, 12, 15, 18, 20, 23, 25, 28, 30, 35, 40, 50, 75, 100, 200, 300, 500, or 1000 consecutive nucleotides, to the extent that fragments of these lengths are consistent with the specific sequence, of a sequence selected from the group consisting of SEQ ID NOs. 24–3883 and SEQ ID NOs. 7744–19335 and sequences complementary to the sequences of SEQ ID NOs. 24–3883 and SEQ ID NOs. 7744–19335.

Another embodiment of the present invention is a purified nucleic acid comprising at least 8, 10, 12, 15, 18, 20, 23, 25, 28, 30, 35, 40, 50, 75, 100, 200, 300, 500, or 1000 consecutive nucleotides, to the extent that fragments of these lengths are consistent with the specific sequence, of a sequence selected from the group consisting of the preferred polynucleotides described in Tables IVa and IVb and sequences complementary to the sequences the preferred polynucleotides described in Tables IVa and IVb.

Another embodiment of the present invention is a purified nucleic acid comprising at least 8, 10, 12, 15, 18, 20, 23, 25, 28, 30, 35, 40, 50, 75, 100, 200, 300, 500, or 1000 consecutive nucleotides, to the extent that fragments of these lengths are consistent with the specific sequence, of a sequence selected from the group consisting of the preferred polynucleotides described in Tables IVa and IVb updated and sequences complementary to the sequences the preferred polynucleotides described in Tables IVa and IVb updated.

Another embodiment of the present invention is a purified nucleic acid comprising at least 15 consecutive nucleotides of a sequence selected from the group consisting of SEQ ID NOs. 24–3883 and SEQ ID NOs. 7744–19335 and sequences complementary to the sequences of SEQ ID NOs. 24–3883 and SEQ ID NOs. 7744–19335.

A further aspect of this embodiment is a purified vertebrate nucleic acid comprising at least 15 consecutive nucleotides of a sequence selected from the group consisting of SEQ ID NOs. 24–3883 and SEQ ID NOs. 7744–19335 and sequences complementary to the sequences of SEQ ID NOs. 24–3883 and SEQ ID NOs. 7744–19335.

A further aspect of this embodiment is a purified human nucleic acid comprising at least 15 consecutive nucleotides of a sequence selected from the group consisting of SEQ ID NOs. 24–3883 and SEQ ID NOs. 7744–19335 and sequences complementary to the sequences of SEQ ID NOs. 24–3883 and SEQ ID NOs. 7744–19335.

Another embodiment of the present invention is a purified nucleic acid comprising at least 15 consecutive nucleotides of a sequence selected from the group consisting of the preferred polynucleotides described in Tables IVa and IVb and sequences complementary to the sequences of the preferred polynucleotides described in Tables IVa and IVb.

A further embodiment of the present invention is a purified nucleic acid comprising the coding sequence of a sequence selected from the group consisting of 24–3883.

Yet another embodiment of the present invention is a purified nucleic acid comprising the full coding sequences of a sequence selected from the group consisting of SEQ ID NOs. 1339–2059 wherein the full coding sequence comprises the sequence encoding the signal peptide and the sequence encoding the mature protein.

Still another embodiment of the present invention is a purified nucleic acid comprising a contiguous span of a sequence selected from the group consisting of SEQ ID NOs. 1339–2059 which encodes the mature protein.

Another embodiment of the present invention is a purified nucleic acid comprising a contiguous span of a sequence selected from the group consisting of SEQ ID NOs. 24–383 and 1339–2059 which encodes the signal peptide.

Another embodiment of the present invention is a purified nucleic acid encoding a polypeptide comprising a sequence selected from the group consisting of the sequences of SEQ ID NOs. 3884–7743.

Another embodiment of the present invention is a purified nucleic acid encoding a polypeptide comprising a sequence selected from the group consisting of the sequences of SEQ ID NOs. 5199–5919.

Another embodiment of the present invention is a purified nucleic acid encoding a polypeptide comprising a mature protein included in a sequence selected from the group consisting of the sequences of SEQ ID NOs. 5199–5919.

Another embodiment of the present invention is a purified nucleic acid encoding a polypeptide comprising a signal peptide included in a sequence selected from the group consisting of the sequences of SEQ ID NOs. 3884–4243 and 5199–5919.

Another embodiment of the present invention is a purified nucleic acid of at least 15, 18, 20, 23, 25, 28, 30, 35, 40, 50, 75, 100, 200, 300, 500 or 1000 nucleotides in length which hybridizes under stringent conditions to a sequence selected from the group consisting of SEQ ID NOs. 24–3883 and SEQ ID NOs. 7744–19335 and sequences complementary to the sequences of SEQ ID NOs. 24–3883 and SEQ ID NOs. 7744–19335.

Another embodiment of the present invention is a vertebrate purified nucleic acid of at least 15, 18, 20, 23, 25, 28, 30, 35, 40, 50, 75, 100, 200, 300, 500 or 1000 nucleotides in length which hybridizes under stringent conditions to a sequence selected from the group consisting of SEQ ID NOs. 24–3883 and SEQ ID NOs. 7744–19335 and sequences complementary to the sequences of SEQ ID NOs. 24–3883 and SEQ ID NOs. 7744–19335.

Another embodiment of the present invention is a human purified nucleic acid of at least 15, 18, 20, 23, 25, 28, 30, 35, 40, 50, 75, 100, 200, 300, 500 or 1000 nucleotides in length which hybridizes under stringent conditions to a sequence selected from the group consisting of SEQ ID NOs. 24–3883 and SEQ ID NOs. 7744–19335 and sequences complementary to the sequences of SEQ ID NOs. 24–3883 and SEQ ID NOs. 7744–19335.

Another embodiment of the present invention is a purified or isolated polypeptide comprising a sequence selected from the group consisting of the sequences of SEQ ID NOs. 3884–7743.

Another embodiment of the present invention is a purified or isolated polypeptide comprising a sequence selected from the group consisting of SEQ ID NOs. 5199–5919.

Another embodiment of the present invention is a purified or isolated polypeptide comprising a mature protein of a polypeptide selected from the group consisting of SEQ ID NOs. 5199–5919.

Another embodiment of the present invention is a purified or isolated polypeptide comprising a signal peptide of a sequence selected from the group consisting of the polypeptides of SEQ ID NOs. 3884–4243 and 5199–5919.

Another embodiment of the present invention is a purified or isolated polypeptide comprising at least 5, 8, 10, 12, 15, 18, 20, 23, 25, 28, 30, 35, 40, 50, 75, 100, 200, 300, 500, or 1000 consecutive amino acids, to the extent that fragments of these lengths are consistent with the specific sequence, of a sequence selected from the group consisting of the sequences of SEQ ID NOs. 3884–7743.

Another embodiment of the present invention is a method of making a cDNA comprising the steps of contacting a collection of mRNA molecules from human cells with a primer comprising at least 12, 15, 18, 20, 23, 25, 28, 30, 35, 40, or 50 consecutive nucleotides of a sequence selected from the group consisting of the sequences complementary to SEQ ID NOs. 24–3883 and SEQ ID NOs. 7744–19335, hybridizing said primer to an mRNA in said collection that encodes said protein, reverse transcribing said hybridized primer to make a first cDNA strand from said mRNA, making a second cDNA strand complementary to said first cDNA strand and isolating the resulting cDNA encoding said protein comprising said first cDNA strand and said second cDNA strand.

Another embodiment of the present invention is a purified cDNA obtainable by the method of the preceding paragraph. In one aspect of this embodiment, the cDNA encodes at least a portion of a human polypeptide.

Another embodiment of the present invention is a purified cDNA obtained by a method of making a cDNA of the invention. In one aspect of this embodiment, the cDNA encodes at least a portion of a human polypeptide.

Another embodiment of the present invention is a method of making a cDNA comprising the steps of contacting a cDNA collection with a detectable probe comprising at least 12, 15, 18, 20, 23, 25, 28, 30, 35, 40, or 50 consecutive nucleotides of a sequence selected from the group consisting of SEQ ID NOs. 24–3883 and SEQ ID NOs. 7744–19335 and the sequences complementary to SEQ ID NOs. 24–3883 and SEQ ID NOs. 7744–19335 under conditions which permit said probe to hybridize to cDNA, identifying a cDNA which hybridizes to said detectable probe, and isolating said cDNA which hybridizes to said probe.

Another embodiment of the present invention is a purified cDNA obtainable by the method of the preceding paragraph. In one aspect of this embodiment, the cDNA encodes at least a portion of a human polypeptide.

Another embodiment of the present invention is a method of making a cDNA comprising the steps of contacting a collection of mRNA molecules from human cells with a first primer capable of hybridizing to the polyA tail of said mRNA, hybridizing said first primer to said polyA tail, reverse transcribing said mRNA to make a first cDNA strand, making a second cDNA strand complementary to said first cDNA strand using at least one primer comprising at least 12, 15, 18, 20, 23, 25, 28, 30, 35, 40, or 50 consecutive nucleotides of a sequence selected from the group consisting of SEQ ID NOs. 24–3883 and SEQ ID NOs. 7744–19335, and isolating the resulting cDNA comprising said first cDNA strand and said second cDNA strand. In another aspect of this method the second cDNA strand is made by contacting said first cDNA strand with a second primer comprising at least 12, 15, 18, 90, 23, 25, 28, 30, 35, 40, or 50 consecutive nucleotides of a sequence selected from the group consisting of SEQ ID NOs. 24–3883 and SEQ ID NOs. 7744–19335 and a third primer which sequence is fully included within the sequence of said first primer, performing a first polymerase chain reaction with said second and third primers to generate a first PCR product, contacting said first PCR product with a fourth primer, comprising at least 12, 15, 18, 20, 23, 25, 28, 30, 35, 40, or 50 consecutive nucleotides of said sequence selected from the group consisting of SEQ ID NOs. 24–3883 and SEQ ID NOs. 7744–19335, and a fifth primer, which sequence is fully included within the sequence of said third primer, wherein said fourth and fifth hybridize to sequences within said first PCR product, and performing a second polymerase chain reaction, thereby generating a second PCR product. Alternatively, the second cDNA strand may be made by contacting said first cDNA strand with a second primer comprising at least 12, 15, 18, 20, 23, 25, 28, 30, 35, 40, or 50 consecutive nucleotides of a sequence selected from the group consisting of SEQ ID NOs. 24–3883 and SEQ ID NOs. 7744–19335 and a third primer which sequence is fully included within the sequence of said first primer, performing a polymerase chain reaction with said second and third primers to generate said second cDNA strand. Alternatively, the second cDNA strand may be made by contacting said first cDNA strand with a second primer comprising at least 12, 15, 18, 20, 23, 25, 28, 30, 35, 40, or 50 consecutive nucleotides of a sequence selected from the group consisting of SEQ ID NOs. 24–3883 and SEQ ID NOs. 7744–19335, hybridizing said second primer to said first strand cDNA, and extending said hybridized second primer to generate said second cDNA strand.

Another embodiment of the present invention is a purified cDNA obtainable by a method of making a cDNA of the invention. In one aspect of this embodiment, said cDNA encodes at least a portion of a human polypeptide.

Another embodiment of the present invention is a method of making a polypeptide comprising the steps of obtaining a cDNA which encodes a polypeptide encoded by a nucleic acid comprising a sequence selected from the group consisting of SEQ ID NOs. 24–3883 or a cDNA which encodes a polypeptide comprising at least 6, 8, 10, 12, 15, 18, 20, 23, 25, 28, 30, 35, 40, or 50 consecutive amino acids of a polypeptide encoded by a sequence selected from the group consisting of SEQ ID NOs. 24–3883, inserting said cDNA in an expression vector such that said cDNA is operably linked to a promoter, introducing said expression vector into a host cell whereby said host cell produces the protein encoded by said cDNA, and isolating said protein.

Another embodiment of the present invention is a method of obtaining a promoter DNA comprising the steps of obtaining genomic DNA located upstream of a nucleic acid comprising a sequence selected from the group consisting of SEQ ID NOs. 24–3883 and SEQ ID NOs. 7744–19335 and the sequences complementary to the sequences of SEQ ID NOs. 24–3883 and SEQ ID NOs. 7744–19335, screening said genomic DNA to identify a promoter capable of directing transcription initiation, and isolating said DNA comprising said identified promoter.

In one aspect of this embodiment, said obtaining step comprises walking from genomic DNA comprising a sequence selected from the group consisting of SEQ ID NOs. 24–3883 and SEQ ID NOs. 7744–19335 and the sequences complementary to SEQ ID NOs. 24–3883 and SEQ ID NOs. 7744–19335. In another aspect of this embodiment, said screening step comprises inserting genomic DNA located upstream of a sequence selected from the group consisting of SEQ ID NOs. 24–3883 and SEQ ID NOs. 7744–19335 and the sequences complementary to SEQ ID NOs. 24–3883 and SEQ ID NOs. 7744–19335 into a promoter reporter vector. For example, said screening step may comprise identifying motifs in genomic DNA located upstream of a sequence selected from the group consisting of SEQ ID NOs. 24–3883 and SEQ ID NOs. 7744–19335 and the sequences complementary to SEQ ID NOs. 24–3883 and SEQ ID NOs. 7744–19335 which are transcription factor binding sites or transcription start sites.

Another embodiment of the present invention is a isolated promoter obtainable by the methods of the above paragraphs.

Another embodiment of the present invention is a isolated promoter obtained by the methods described in the above paragraphs.

Another embodiment of the present invention is the inclusion of at least one sequence selected from the group consisting of SEQ ID NOs. 24–3883 and SEQ ID NOs. 7744–19335, the sequences complementary to the sequences of SEQ ID NOs. 24–3883 and SEQ ID NOs. 7744–19335 and fragments comprising at least 12, 15, 18, 20, 23, 25, 28, 30, 35, 40, 50, or 100 consecutive nucleotides of said sequence in an array of discrete ESTs or fragments thereof of at least 12, 15, 18, 20, 23, 25, 28, 30, 35, 40, 50, or 100 nucleotides in length. In some aspects of this embodiment, the array includes at least two sequences selected from the group consisting of SEQ ID NOs. 24–3883 and SEQ ID NOs. 7744–19335, the sequences complementary to the sequences of SEQ ID NOs. 24–3883 and SEQ ID NOs. 7744–19335, and fragments comprising at least 12, 15, 18, 20, 23, 25, 28, 30, 35, 40, 50, or 100 consecutive nucleotides of said sequences. In another aspect of this embodiment, the array includes at least one, three, five, ten, fifteen, or twenty sequences selected from the group consisting of SEQ ID NOs. 24–3883 and SEQ ID NOs. 7744–19335, the sequences complementary to the sequences of SEQ ID NOs. 24–3883 and SEQ ID NOs. 7744–19335 and fragments comprising at least 12, 15, 18, 20, 23, 25, 28, 30, 35, 40, 50, or 100 consecutive nucleotides of said sequences.

Another embodiment of the present invention is an enriched population of recombinant nucleic acids, said recombinant nucleic acids comprising an insert nucleic acid and a backbone nucleic acid, wherein at least 0.01%, 0.05%, 0.1%, 0.5%, 1%, 2%, 5%, 10%, or 20% of said insert nucleic acids in said population comprise a sequence selected from the group consisting of SEQ ID NOs. 24–3883 and SEQ ID NOs. 7744–19335 and the sequences complementary to SEQ ID NOs. 24–3883 and SEQ ID NOs. 7744–19335.

Another embodiment of the present invention is a purified or isolated antibody capable of specifically binding to a polypeptide comprising a sequence selected from the group consisting of SEQ ID NOs. 3884–7743.

Another embodiment of the present invention is a purified or isolated antibody capable of specifically binding to a polypeptide comprising at least 6, 8, 10, 12, 15, 18, 20, 23, 25, 28, 30, 35, 40, or 50 consecutive amino acids of a sequence selected from the group consisting of SEQ ID NOs. 3884–7743.

Yet, another embodiment of the present invention is an antibody composition capable of selectively binding to an epitope-containing fragment of a polypeptide comprising a contiguous span of at least 8, 10, 12, 15, 18, 20, 23, 25, 28, 30, 35, 40, or 50 amino acids of any of SEQ ID NOs. 3884–7743, wherein said antibody is polyclonal or monoclonal.

Another embodiment of the present invention is a computer readable medium having stored thereon a sequence selected from the group consisting of a nucleic acid code of SEQ ID NOs. 24–3883 and 7744–19335 and a polypeptide code of SEQ ID NOs. 3884–7743.

Another embodiment of the present invention is a computer system comprising a processor and a data storage device wherein said data storage device has stored thereon a sequence selected from the group consisting of a nucleic acid code of SEQ ID NOs. 24–3883 and 7744–19335 and a polypeptide code of SEQ ID NOs. 3884–7743. In one aspect of this embodiment the computer system further comprises a sequence comparer and a data storage device having reference sequences stored thereon. For example, the sequence comparer may comprise a computer program which indicates polymorphisms. In another aspect of this embodiment, the computer system further comprises an identifier which identifies features in said sequence.

Another embodiment of the present invention is a method for comparing a first sequence to a reference sequence wherein said first sequence is selected from the group consisting of a nucleic acid code of SEQ ID NOs. 24–3883 and 7744–19335 and a polypeptide code of SEQ ID NOs. 3884–7743 comprising the steps of reading said first sequence and said reference sequence through use of a computer program which compares sequences and determining differences between said first sequence and said reference sequence with said computer program. In some aspects of this embodiment, said step of determining differences between the first sequence and the reference sequence comprises identifying polymorphisms.

Another embodiment of the present invention is a method for identifying a feature in a sequence selected from the group consisting of a nucleic acid code of SEQ ID NOs. 24–3883 and 7744–19335 and a polypeptide code of SEQ ID NOs. 3884–7743 comprising the steps of reading said sequence through the use of a computer program which identifies features in sequences and identifying features in said sequence with said computer program.

Another embodiment of the present invention is a vector comprising a nucleic acid according to any one of the nucleic acids described above.

Another embodiment of the present invention is a host cell containing the above vector.

Another embodiment of the present invention is a method of making any of the nucleic acids described above comprising the steps of introducing said nucleic acid into a host cell such that said nucleic acid is present in multiple copies in each host cell and isolating said nucleic acid from said host cell.

Another embodiment of the present invention is a method of making a nucleic acid of any of the nucleic acids described above comprising the step of sequentially linking together the nucleotides in said nucleic acids.

Another embodiment of the present invention is a method of making any of the polypeptides described above wherein said polypeptides is 150 amino acids in length or less comprising the step of sequentially linking together the amino acids in said polypeptide.

Another embodiment of the present invention is a method of making any of the polypeptides described above wherein said polypeptides is 120 amino acids in length or less comprising the step of sequentially linking together the amino acids in said polypeptides.

BRIEF DESCRIPTION OF THE SEQUENCE LISTING

SEQ ID NOs. 1, 3, 5, 7, 9, 11, and 13 are full-length cDNAs prepared using the methods described herein.

SEQ ID NOs. 2, 4 and 6 are the signal peptides encoded by the nucleic acids of SEQ ID NOs. 1, 3 and 5 respectively.

SEQ ID NOs. 8, 10, 12, and 14 are the polypeptides encoded by the nucleic acids of SEQ ID NOs. 7, 9, 11, and 13 respectively.

SEQ ID NOs. 15, 16, 18, 19, 21 and 22 are primers whose use is described in the specification.

SEQ ID NOs. 17, 20, and 23 are the sequences of nucleic acids containing transcription factor binding sites which were obtained as described below.

SEQ ID NOs. 24–383 are nucleic acids having an incomplete ORF which encodes a signal peptide. As used herein, an "incomplete ORF" is an open reading frame in which a start codon has been identified but no stop codon has been identified. The locations of the incomplete ORFs and sequences encoding signal peptides are listed in the accompanying Sequence Listing. In addition, the von Heijne score of the signal peptide computed as described below is listed as the "score" in the accompanying Sequence Listing. The sequence of the signal-peptide is listed as "seq" in the accompanying Sequence Listing. The "/" in the signal peptide sequence indicates the location where proteolytic cleavage of the signal peptide occurs to generate a mature protein.

SEQ ID NOs. 384–1338 are nucleic acids having an incomplete ORF in which no sequence encoding a signal peptide has been identified to date. However, it remains possible that subsequent analysis will identify a sequence encoding a signal peptide in these nucleic acids. The locations of the incomplete ORFs are listed in the accompanying Sequence Listing.

SEQ ID NOs. 1339–2059 are nucleic acids having a complete ORF which encodes a signal peptide. As used herein, a "complete ORF" is an open reading frame in which a start codon and a stop codon have been identified. The locations of the complete ORFs and sequences encoding signal peptides are listed in the accompanying Sequence Listing. In addition, the von Heijne score of the signal peptide computed as described below is listed as the "score" in the accompanying Sequence Listing. The sequence of the signal-peptide is listed as "seq" in the accompanying Sequence Listing. The "/" in the signal peptide sequence indicates the location where proteolytic cleavage of the signal peptide occurs to generate a mature protein.

SEQ ID NOs. 2060–3883 are nucleic acids having a complete ORF in which no sequence encoding a signal peptide has been identified to date. However, it remains possible that subsequent analysis will identify a sequence encoding a signal peptide in these nucleic acids. The locations of the complete ORFs are listed in the accompanying Sequence Listing.

SEQ ID NOs. 3884–4243 are "incomplete polypeptide sequences" which include a signal peptide. Incomplete polypeptide sequences" are polypeptide sequences encoded by nucleic acids in which a start codon has been identified but no stop codon has been identified. These polypeptides are encoded by the nucleic acids of SEQ ID NOs. 24–383. The location of the signal peptide is listed in the accompanying Sequence Listing.

SEQ ID NOs. 4244–5198 are incomplete polypeptide sequences in which no signal peptide has been identified to date. However, it remains possible that subsequent analysis will identify a signal peptide in these polypeptides. These polypeptides are encoded by the nucleic acids of SEQ ID NOs. 384–1338.

SEQ ID NOs. 5199–5919 are "complete polypeptide sequences" which include a signal peptide. "Complete polypeptide sequences" are polypeptide sequences encoded by nucleic acids in which a start codon and a stop codon have been identified. These polypeptides are encoded by the nucleic acids of SEQ ID NOs. 1339–2059. The location of the signal peptide is listed in the accompanying Sequence Listing.

SEQ ID NOs. 5920–7743 are complete polypeptide sequences in which no signal peptide has been identified to date. However, it remains possible that subsequent analysis will identify a signal peptide in these polypeptides. These polypeptides are encoded by the nucleic acids of SEQ ID NOs.2060–3883.

SEQ ID NOs. 7744–19335 are nucleic acid sequences in which no open reading frame of at least 150 nucleotides has been conclusively identified to date. However, it remains possible subsequent analysis will identify an open reading frame in these nucleic acids.

In the accompanying Sequence Listing, all instances of the symbol "n" in the nucleic acid sequences mean that the nucleotide can be adenine, guanine, cytosine or thymine. In some instances the polypeptide sequences in the Sequence Listing contain the symbol "Xaa." These "Xaa" symbols indicate either (1) a residue which cannot be identified because of nucleotide sequence ambiguity or (2) a stop codon in the determined sequence where applicants believe one should not exist (if the sequence were determined more accurately). In some instances, several possible identities of the unknown amino acids may be suggested by the genetic code.

In the case of secreted proteins, it should be noted that, in accordance with the regulations governing Sequence Listings, in the appended Sequence Listing, the encoded protein (i.e. the protein containing the signal peptide and the mature protein or part thereof) extends from an amino acid residue having a negative number through a positively numbered amino acid residue. Thus, the first amino acid of the mature protein resulting from cleavage of the signal peptide is designated as amino acid number 1, and the first amino acid of the signal peptide is designated with the appropriate negative number.

BRIEF DESCRIPTION OF THE DRAWINGS

FIG. 2 is an analysis of the 43 amino terminal amino acids of all human SwissProt proteins to determine the frequency of false positives and false negatives using the techniques for signal peptide identification described herein.

FIG. 5 describes the transcription factor binding sites present in each of the promoters of FIG. 4.

FIG. 10 is a table describing algorithms, parameters and criteria that can be used for each step of extended cDNA analysis.

DETAILED DESCRIPTION OF THE PREFERRED EMBODIMENT

Figure 1:
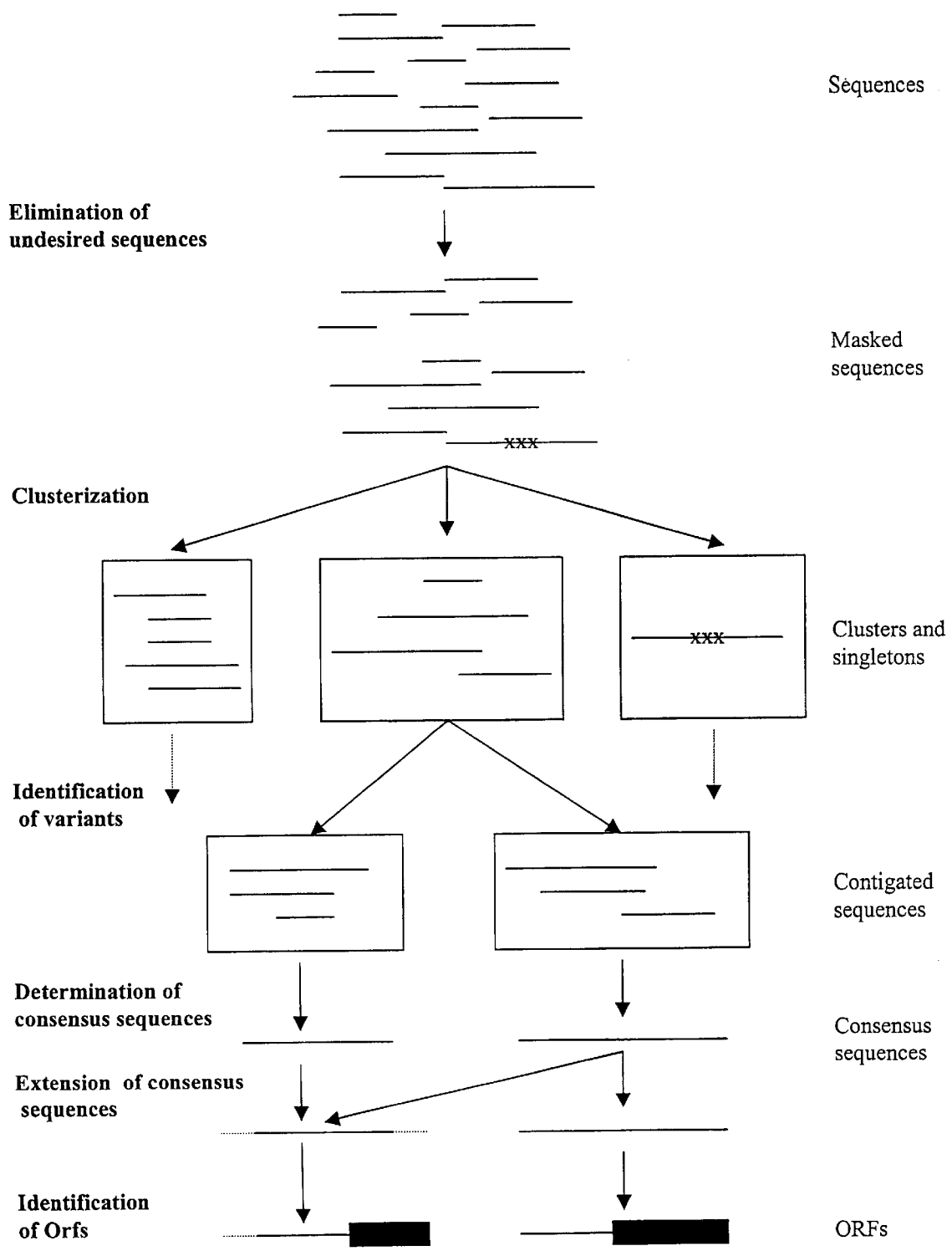
FIG. 1 summarizes the computer analysis procedure for obtaining consensus contigated ESTs.

1. General Methods for Obtaining 5' ESTs Derived From mRNAs With Intact 5' ends

The 5' ESTs of the present invention were obtained from cDNA libraries derived from mRNAs having intact 5' ends as described in Examples 1 to 5 using either a chemical or enzymatic approach.

EXAMPLE 1

Preparation of mRNA

Total human RNAs or polyA+ RNAs derived from different tissues were respectively purchased from LABIMO and CLONTECH and used to generate cDNA libraries as described below. The purchased RNA had been isolated from cells or tissues using acid guanidium thiocyanate-phenol-chloroform extraction (Chomczyniski and Sacchi, *Analytical Biochemistry* 162:156–159, 1987). PolyA+ RNA was isolated from total RNA (LABIMO) by two passes of oligo dT chromatography, as described by Aviv and Leder, *Proc. Natl. Acad. Sci. USA* 69:1408–1412, 1972) in order to eliminate ribosomal RNA.

The quality and the integrity of the polyA+ RNAs were checked. Northern blots hybridized with a probe corresponding to an ubiquitous mRNA, such as elongation factor 1 or elongation factor 2, were used to confirm that the mRNAs were not degraded. Contamination of the polyA+ mRNAs by ribosomal sequences was checked using Northern blots and a probe derived from the sequence of the 28S rRNA. Preparations of mRNAs with less than 5% of rRNAs were used in library construction. To avoid constructing libraries with RNAs contaminated by exogenous sequences (prokaryotic or fungal), the presence of bacterial 16S ribosomal sequences and of two highly expressed fungal mRNAs was examined using PCR.

EXAMPLE 2

Methods for Obtaining mRNAs Having Intact 5' Ends

Following preparation of the mRNAs from various tissues as described above, selection of mRNA with intact 5' ends and specific attachment of an oligonucleotide tag to the 5' end of said mRNA is performed using either a chemical or enzymatic approach. Both techniques take advantage of the presence of the "cap" structure, which characterizes the 5' end of intact mRNAs and which comprises a guanosine generally methylated once, at the 7 position.

The chemical modification approach involves the optional elimination of the 2',3'-cis diol of the 3' terminal ribose, the oxidation of the 2',3', -cis diol of the ribose linked to the cap of the 5' ends of the mRNAs into a dialdehyde, and the coupling of the said obtained dialdehyde to a derivatized oligonucleotide tag. Further detail regarding the chemical approaches for obtaining mRNAs having intact 5' ends are disclosed in International Application No. WO96/34981, published Nov. 7, 1996, the disclosure of which is incorporated herein by reference in its entirety.

The enzymatic approach for ligating the oligonucleotide tag to the 5' ends of mRNAs with intact 5' ends involves the removal of the phosphate groups present on the 5' ends of uncapped incomplete mRNAs, the subsequent decapping of mRNAs with intact 5' ends and the ligation of the phosphate present at the 5' end of the decapped mRNA to an oligonucleotide tag. Further detail regarding the enzymatic approaches for obtaining mRNAs having intact 5' ends are disclosed in Dumas Milne Edwards J. B. (Doctoral Thesis of Paris VI University, Le clonage des ADNc complets: difficultes et perspectives nouvelles. Apports pour l'etude de la regulation de l'expression de la tryptophane hydroxylase de rat, Dec. 20, 1993), EPO 625572 and Kato et al., *Gene*

150:243–250 (1994), the disclosures of which are incorporated herein by reference in their entireties.

In either the chemical or the enzymatic approach, the oligonucleotide tag has a restriction enzyme site (e.g. EcoRI sites) therein to facilitate later cloning procedures. Following attachment of the oligonucleotide tag to the mRNA, the integrity of the mRNA was then examined by performing a Northern blot using a probe complementary to the oligonucleotide tag.

EXAMPLE 3 cDNA Synthesis Using mRNA Templates Having Intact 5' Ends

For the mRNAs joined to oligonucleotide tags using either the chemical or the enzymatic method, first strand cDNA synthesis was performed using a thermostable reverse transcriptase with an oligo-dT primer. In some instances, this oligo-dT primer contained an internal tag of at least 4 nucleotides which is different from one tissue to the other. In order to protect internal EcoRI sites in the cDNA from digestion at later steps in the procedure, methylated dCTP was used for first strand synthesis. After removal of RNA by an alkaline hydrolysis, the first strand of cDNA was precipitated using isopropanol in order to eliminate residual primers.

The second strand of the cDNA was then synthesized with a Klenow fragment using a primer corresponding to the 5' end of the ligated oligonucleotide. Preferably, the primer is 20–25 bases in length. Methylated dCTP was also used for second strand synthesis in order to protect internal EcoRI sites in the cDNA from digestion during the cloning process.

EXAMPLE 4

Cloning of cDNAs Derived From mRNA With Intact 5' Ends

Following second strand synthesis, the cDNAs were cloned into the phagemid pBlueScript II SK⁻ vector (Stratagene) or one of its derivative. The ends of the cDNAs were blunted with T4 DNA polymerase (Biolabs) and the cDNA was digested with EcoRI. Since methylated dCTP was used during cDNA synthesis, the EcoRI site present in the tag was the only hemi-methylated site, hence the only site susceptible to EcoRI digestion. In some instances, to facilitate subcloning, an HindIII adaptor was added to the 3' end of cDNAs.

The cDNAs were then size fractionated using either exclusion chromatography (AcA, Biosepra) or electrophoretic separation which yields 3 or 6 different fractions. The cDNAs were then directionally cloned either into pBlueScript using either the EcoRI and SmaI restriction sites or the EcoRI and HindIII restriction sites when the HindIII adaptor was present in the cDNAs. The ligation mixture was electroporated into bacteria and propagated under appropriate antibiotic selection.

EXAMPLE 5

Selection of Clones Having the Oligonucleotide Tag Attached Thereto

Clones containing the oligonucleotide tag attached to cDNAs were then selected as follows.

The plasmid DNAs containing cDNA libraries made as described above were purified (Qiagen). A positive selection of the tagged clones was performed as follows. Briefly, in this selection procedure, the plasmid DNA was converted to single stranded DNA using gene II endonuclease of the phage F1 in combination with an exonuclease (Chang et al., *Gene* 127:95–8, 1993) such as exonuclease III or T7 gene 6 exonuclease. The resulting single stranded DNA was then purified using paramagnetic beads as described by Fry et al., *Biotechniques*, 13: 124–131, 1992. In this procedure, the single stranded DNA was hybridized with a biotinylated oligonucleotide having a sequence corresponding to the 3' end of the oligonucleotide tag described in Example 2. Preferably, the primer has a length of 20–25 bases. Clones including a sequence complementary to the biotinylated oligonucleotide were captured by incubation with streptavidin coated magnetic beads followed by magnetic selection. After capture of the positive clones, the plasmid DNA was released from the magnetic beads and converted into double stranded DNA using a DNA polymerase such as the ThermoSequenase obtained from Amersham Pharmacia Biotech. Alternatively, protocols such as the Gene Trapper kit (Gibco BRL) may be used. The double stranded DNA was then electroporated into bacteria. The percentage of positive clones having the 5' tag oligonucleotide was estimated to typically rank between 90 and 98% using dot blot analysis.

Following electroporation, the libraries were ordered in 384-microtiter plates (MTP). A copy of the MTP was stored for future needs. Then the libraries were transferred into 96 MTP and sequenced.

EXAMPLE 6

Sequencing of Inserts in Selected Clones

Plasmid inserts were first amplified by PCR on PE-9600/PE-9700 thermocyclers (PE Biosystems, Applied Biosystems Division, Foster City, Calif.) or tetrades thermocyclers (MJ Research), using L7AF3 and SETA primers (Genset SA), ExTaq polymerase (Takara), dNTPs (Boehringer), buffer and cycling conditions as recommended by the PE Biosystems Corporation. PCR products were then sequenced using MegaBace Capillary sequencers (Molecular Dynamics). Sequencing reactions were performed using PE 9600/PE-9700 thermocyclers with ET primer (Energy Transfer) chemistry and ThermoSequenase (Amersham Pharmacia Biotech). The primer used was Reverse Primer (RP) (Amersham Pharmacia Biotech) as appropriate. The dNTPs and ddNTPs used in the sequencing reactions were purchased from Boehringer. Sequencing buffer, reagent concentrations and cycling conditions were as recommended by Amersham. Following the sequencing reaction, the samples were purified with Sephadex (G50) and injected in the capillaries of the MegaBace. Injection was performed for 12 seconds at 10000 V and electrophoresis for 100 minutes at 1000V. The sequence data were collected and analyzed using the Instrument Control Manager analysis software of the MegaBace prior to the Genset's proprietary sequence verification software.

Alternatively, plasmid inserts were first amplified by PCR on PE-9600 thermocyclers (PE Biosystems, Applied Biosystems Division, Foster City, Calif.), using standard SETA-A and SETA-B primers (Genset SA), AmpliTaqGold (PE Biosystems), dNTPs (Boehringer), buffer and cycling conditions as recommended by the PE Biosystems Corporation. PCR products were then sequenced using automatic ABI Prism 377 sequencers (PE Biosystems). Sequencing reactions were performed using PE 9600 thermocyclers with standard dye-primer chemistry and ThermoSequenase (Amersham Pharmacia Biotech). The primers used were either T7 or 21M13 (available from Genset SA) as appropriate. The primers were labeled with the JOE, FAM, ROX and TAMRA dyes. The dNTPs and ddNTPs used in the sequencing reactions were purchased from Boehringer. Sequencing buffer, reagent concentrations and cycling conditions were as recommended by Amersham. Following the sequencing reaction, the samples were precipitated with ethanol, resuspended in formamide loading buffer, and loaded on a standard 4% acrylamide gel. Electrophoresis was performed for 2.5 hours at 3000V on an ABI 377 sequencer, and the sequence data were collected and analyzed using the ABI Prism DNA Sequencing Analysis Software, version 2.1.2.

II. Computer Analysis of the Isolated 5' ESTs

The sequence data from the different cDNA libraries made as described above were transferred to a database, where quality control and validation steps were performed. A base-caller, working using a Unix system, automatically flagged suspect peaks, taking into account the shape of the peaks, the inter-peak resolution, and the noise level. The proprietary base-caller also performed an automatic trimming. Any stretch of 25 or fewer bases having more than 4 suspect peaks was considered unreliable and was discarded. Sequences corresponding to cloning vector or ligation oligonucleotides were automatically removed from the 5' EST sequences. However, the resulting 5' EST sequences may contain 1 to 5 bases belonging to the above mentioned sequences at their 5' end. If needed, these can easily be removed on a case to case basis.

Following sequencing as described above, the sequences of the 5ESTs were entered in a database for storage and manipulation as described below and as depicted in FIG. 1. Before searching the 5' ESTs in the database for sequences of interest, 5' ESTs derived from mRNAs which were not of interest were identified. Briefly, such undesired sequences may be of three types. First, contaminants of either endogenous (ribosomal RNAs, transfert RNAs, mitochondrial RNAs) or exogenous (prokaryotic RNAs and fungal RNAs) origins were identified. Second, uninformative sequences, namely redundant sequences, small sequences and highly degenerate sequences were identified. Third, repeated sequences (Alu, L1, THE and MER repeats, SSTR sequences or satellite, micro-satellite, or telomeric repeats) were identified and masked in further processing.

Then, in order to determine the accuracy of the sequencing procedure as well as the efficiency of the 5' selection described above, the analyses described in Examples 7 and 8 respectively were performed on 5' ESTs.

EXAMPLE 7

Measurement of Sequencing Accuracy by Comparison to Known Sequences

To further determine the accuracy of the sequencing procedure described in Example 6, the sequences of 5' ESTs derived from known sequences were identified and compared to the original known sequences. First, a FASTA analysis with overhangs shorter than 5 bp on both ends was conducted on the 5' ESTs to identify those matching an entry in the public human mRNA database available at the time of filing the present documents. The 5' ESTs which matched a known human mRNA were then realigned with their cognate mRNA and dynamic programming was used to include substitutions, insertions, and deletions in the list of "errors" which would be recognized. Errors occurring in the last 10 bases of the 5' EST sequences were ignored to avoid the inclusion of spurious cloning sites in the analysis of sequencing accuracy. This analysis revealed that the sequences incorporated in the database had an accuracy of more than 99.3% using Megabaces Capillary sequencers and more than 99.5% using ABI 377 sequencers.

EXAMPLE 8

Determination of Efficiency of 5' EST Selection

To determine the efficiency at which the above selection procedures isolated cDNAs which include the 5' ends of their corresponding mRNAs, the sequences of 5' ESTs were aligned with a reference pool of complete mRNA/cDNA extracted from the EMBL release 57 using the FASTA algorithm. The reference mRNA/cDNA starting at the most 5' transcription start site was obtained, and then compared to the 5' transcription start site position of the 5' EST. More than 75% of 5' ESTs had their 5' ends close to the 5' ends of the known sequence. As some of the mRNA sequences available in the EMBL database are deduced from genomic sequences, a 5' end matching with these sequences will be counted as an internal match. Thus, the method used here underestimates the yield of 5' ESTs including the authentic 5' ends of their corresponding mRNAs.

EXAMPLE 9

Generation of Consensus Contigated 5' ESTs

Since the cDNA libraries made above include multiple 5' ESTs derived from the same mRNA, overlapping 5' ESTs may be assembled into continuous sequences. The following method describes how to efficiently align multiple 5' ESTs in order to yield not only consensus contigated 5' EST sequences for mRNAs derived from different genes but also consensus contigated 5' EST sequences for different mRNAs, so called variants, transcribed from the same gene such as alternatively spliced mRNAs.

A subset of 5' ESTs free from endogenous contaminants and uninformative sequences, and following the masking of repeats, was first selected.

This whole set of sequences was first partitioned into small clusters containing sequences which exhibited perfect matches with each other on a given length and which derived from a small number of different genes. Some 5' EST sequences, so called singletons, were not aligned using this approach because they were not homologous to any other sequence.

Thereafter, all variants of a given gene were identified in each cluster using a proprietary software. 5' EST sequences belonging to the same variant were then contigated and consensus contigated 5' EST sequences generated for each variant. All consensus contigated 5' EST sequences were subsequently compared to the whole set of individual 5' EST sequences used to obtained them.

If desired, the consensus contigated 5' EST sequences may be verified by identifying clones in nucleic acid samples derived from biological tissues, such as cDNA libraries, which hybridize to the probes based on the sequences of the consensus contigated 5' ESTs using any methods described herein and sequencing those clones.

To assess the yield of new sequences, the 5' ESTs obtained and consensus contigated 5' ESTs were compared to all known complete human mRNAs extracted from the EMBL release 58 using BLASTN with the following parameters S=1000, S2=1000, V=5 and B=5. All sequences with high scoring pairs whose significance was above e-100 were kept. Then, the obtained 5' ESTs and consensus contigated 5' ESTs were compared to all the human proteins extracted from SwissProt release 37, TrEMBL release 58 and Genseqp (Derwent's database of patented amino acid sequences) release 35.3 on both strands using blastx with the following parameters: S=450, S2=450, V=5 and B=5. All sequences with high scoring pairs whose significance was above e-50 were kept. Using this process, about 86% of 5' ESTs or consensus assembled 5' ESTs were considered unidentified.

EXAMPLE 10

Identification of the Most Probable Open Reading Frame of 5' ESTs

Subsequently, consensus contigated 5' ESTs and 5' ESTs were screened to identify those having an open reading frame (ORF).

The nucleic acid sequence was first divided into several subsequences which coding propensity was evaluated separately using one or several different methods known to those skilled in the art such as the evaluation of N-mer frequency and its variants (Fickett and Tung, *Nucleic Acids Res*; 20:6441–50 (1992)) or the Average Mutual Information method (Grosse et al, International Conference on Intelligent Systems for Molecular Biology, Montreal, Canada. Jun. 28–Jul. 1, 1998). Each of the scores obtained by the techniques described above were then normalized by their distribution extremities and then fused using a neural network into a unique score that represents the coding probability of a given subsequence. The coding probability scores obtained for each subsequence, thus the probability score profiles obtained for each reading frame, was then linked to the initiation codons present on the sequence. For each open reading frame, defined as a nucleic acid sequence beginning with an ATG codon, an ORF score was determined. Preferably, this score is the sum of the probability scores computed for each subsequence corresponding to the considered ORF in the correct reading frame corrected by a function that negatively accounts for locally high score values and positively accounts for sustained high score values. The most probable ORF with the highest score was selected.

Alternatively, open reading frames were simply defined as uninterrupted nucleic acid sequences longer than 150 nucleotides and beginning with an ATG codon.

In some embodiments, nucleic acid sequences encoding an "incomplete ORF", as described herein, namely an open reading frame in which a start codon has been identified but no stop codon has been identified, were obtained.

In other embodiments, nucleic acid sequences encoding a "complete ORF", as used herein, namely an open reading frame in which a start codon and a stop codon have been identified, are obtained.

In a preferred embodiment, open reading frames encoding polypeptides of at least 50 amino acids were obtained.

To confirm that the chosen ORF actually encodes a polypeptide, the consensus contigated 5' EST or 5' EST may be used to obtain an extended cDNA using any of the techniques described herein, and especially those described in Examples 17 and 18. Then, such obtained extended cDNAs may be screened for the most probable open reading frame using any of the techniques described herein. The amino acid sequence of the ORF encoded by the consensus contigated 5' EST or 5' EST may then be compared to the amino acid sequence of the ORF encoded by the extended cDNA using any of the algorithms and parameters described herein in order to determine whether the ORF encoded by the extended cDNA is basically the same as the one encoded by the consensus contigated 5' EST or 5' EST.

Alternatively, to confirm that the chosen ORF actually encodes a polypeptide, the consensus contigated 5' EST or 5' EST may be used to obtain an extended cDNA using any of the techniques described herein, and especially those described in Examples 17 and 18. Such an extended cDNA may then be inserted into an appropriate expression vector and used to express the polypeptide encoded by the extended cDNA as described herein. The expressed polypeptide may be isolated, purified, or enriched as described herein. Several methods known to those skilled in the art may then be used, including in combination, to determine whether the expressed polypeptide is the one actually encoded by the chosen ORF, herein referred to as the expected polypeptide. Such methods are based on the determination of predictable features of the expressed polypeptide, including but not limited to its amino acid sequence, its size or its charge, and the comparison of these features to those predicted for the expected polypeptide. The following paragraphs present examples of such methods.

One of these methods involves the determination of at least a portion of the amino acid sequence of the expressed polypeptide using any technique known to those skilled in the art. For example, the amino-terminal residues may be determined using automated techniques based on Edman's degradation of polypeptides in which N-terminal residues are sequentially labeled and cleaved from the polypeptide of interest (see Stryer, Exploring proteins in Biochemistry, Freeman and Company, New York, (1995)). The amino acid sequence of the expressed polypeptide may then be compared to the one predicted for the expected polypeptide using any algorithm and parameters described therein.

Alternatively, the size of the expressed polypeptides may be determined using techniques familiar to those skilled in the art such as Coomassie blue or silver staining and subsequently compared to the size predicted for the expected polypeptide. Generally, the band corresponding to the expressed polypeptide will have a mobility near that expected based on the number of amino acids in the open reading frame of the extended cDNA. However, the band may have a mobility different than that expected as a result of modifications such as glycosylation, ubiquitination,or enzymatic cleavage.

Alternatively, specific antibodies or antipeptides may be generated against the expected polypeptideas described in Example 33 and used to perform immunoblotting or immunoprecipitationstudies against the expressed polypeptide. The presence of a band in samples from cells containing the expression vector with the extended cDNA which is absent in samples from cells containing the expression vector encoding an irrelevant polypeptide indicates that the expected polypeptide or portion thereof is being expressed. Generally, the band corresponding to the expressed polypeptide will have a mobility near that expected based on the number of amino acids in the open reading frame of the extended cDNA. However, the band may have a mobility different than that expected as a result of modifications such as glycosylation, ubiquitination, or enzymatic cleavage.

EXAMPLE 11

Identification of Potential Signal Sequences in 5' ESTs

The 5' ESTs or consensus contigated 5' ESTs found to include an ORF were then searched to identify potential signal motifs using slight modifications of the procedures disclosed in Von Heijne, *Nucleic Acids Res.* 14:4683–4690, 1986. Those sequences encoding a peptide with a score of at least 3.5 in the Von Heijne signal peptide identification matrix were considered to possess a signal sequence.

EXAMPLE 12

Confirmation of Accuracy of Identification of Potential Signal Sequences in 5' ESTs The accuracy of the above procedure for identifying signal sequences encoding signal peptides was evaluated by applying the method to the 43 amino acids located at the N terminus of all human SwissProt proteins. The computed Von Heijne score for each protein was compared with the known characterization of the protein as being a secreted protein or a non-secreted protein. In this manner, the number of non-secreted proteins having a score higher than 3.5 (false positives) and the number of secreted proteins having a score lower than 3.5 (false negatives) could be calculated.

Using the results of the above analysis, the probability that a peptide encoded by the 5' region of the mRNA is in fact a genuine signal peptide based on its Von Heijne's score was calculated based on either the assumption that 10% of human proteins are secreted or the assumption that 20% of human proteins are secreted. The results of this analysis are shown in FIG. 2.

Using the above method of identification of secretory proteins, 5' ESTs of the following polypeptides known to be secreted were obtained: human glucagon, gamma interferon induced monokine precursor, secreted cyclophilin-like protein, human pleiotropin, and human biotinidase precursor. Thus, the above method successfully identified those 5' ESTs which encode a signal peptide.

To confirm that the signal peptide encoded by the 5' ESTs or consensus contigated 5' ESTs actually functions as a signal peptide, the signal sequences from the 5' ESTs or consensus contigated 5' ESTs may be cloned into a vector designed for the identification of signal peptides. Such vectors are designed to confer the ability to grow in selective medium only to host cells containing a vector with an operably linked signal sequence. For example, to confirm that a 5' EST or consensus contigated 5' EST encodes a genuine signal peptide, the signal sequence of the 5' EST or consensus contigated 5' EST may be inserted upstream and in frame with a non-secreted form of the yeast invertase gene in signal peptide selection vectors such as those described in U.S. Pat. No. 5,536,637. Growth of host cells containing signal sequence selection vectors with the correctly inserted 5' EST or consensus contigated 5' EST signal sequence confirms that the 5' EST or consensus contigated 5' ESTs encodes a genuine signal peptide.

Alternatively, the presence of a signal peptide may be confirmed by cloning the extended cDNAs obtained using the ESTs or consensus contigated 5' ESTs into expression vectors such as pXT1 as described below, or by constructing promoter-signal sequence-reporter gene vectors which encode fusion proteins between the signal peptide and an assayable reporter protein. After introduction of these vectors into a suitable host cell, such as COS cells or NIH 3T3 cells, the growth medium may be harvested and analyzed for the presence of the secreted protein. The medium from these cells is compared to the medium from control cells containing vectors lacking the signal sequence or extended cDNA insert to identify vectors which encode a functional signal peptide or an authentic secreted protein.

EXAMPLE 13

Analysis of the Sequences of the Invention

The set of the nucleic acid sequences of the invention (SEQ ID NOs. 24–3883 and 7744–19335) was obtained as described in Example 9. Subsequently, the most probable open reading frame was determined and signal sequences were searched, as described in Examples 10 and 11, for all sequences of the invention.

The nucleotide sequences of the SEQ ID NOs. 24–3883 and 7744–19335 and the preferred polypeptides sequences encoded by SEQ ID NOs. 24–3883 (i.e. polypeptide sequences of SEQ ID NOs. 3884–7743) are provided in the appended sequence listing. In addition, for each of the nucleic acid sequences of the invention as referred to by its sequence identification number in the first column, Table I provides the positions of the first and last codons for each of the corresponding open reading frames in the second column.

For each of the consensus contigated 5' ESTs of the invention as referred to by its sequence identification number in the first column of Table II, the second column gives a list of the positions of the biological 5' ESTs which were used to obtain this consensus contigated 5' EST. For example, if the first column indicates 250 and the second column indicates 1–120; 6–230; 200–350, this means that the consensus contigated 5' ESTs of SEQ ID NO:250 was computed from 3 different 5' ESTs, the first one matching from positions 1 to 120 of the consensus contigated 5' EST, the second one from positions 6 to 230 of the consensus contigated 5' EST, and the third one from positions 200 to 350 of the consensus contigated 5' EST.

If one of the nucleic acid sequences of SEQ ID NOs. 24–3883 and 7744–19335 is suspected of containing one or more incorrect or ambiguous nucleotides, the ambiguities can readily be resolved by resequencing a fragment containing the nucleotides to be evaluated. If one or more incorrect or ambiguous nucleotides are detected, the corrected sequences should be included in the clusters from which the sequences were isolated, and used to compute other consensus contigated sequences on which other ORFs would be identified. Nucleic acid fragments for resolving sequencing errors or ambiguities may be obtained from deposited clones or can be isolated using the techniques described herein. Resolution of any such ambiguities or errors may be facilitated by using primers which hybridize to sequences located close to the ambiguous or erroneous sequences. For example, the primers may hybridize to sequences within 50–75 bases of the ambiguity or error. Upon resolution of an error or ambiguity, the corresponding corrections can be made in the protein sequences encoded by the DNA containing the error or ambiguity. The amino acid sequence of the protein encoded by a particular clone can also be determined by expression of the clone in a suitable host cell, collecting the protein, and determining its sequence.

In addition, if one of the sequences of SEQ ID NOs. 3884–7743 is suspected of containing a truncated ORF as the result of a frameshift in the sequence, such frameshifting errors may be corrected by combining the following two approaches. The first one involves thorough examination of all double predictions, i.e. all cases where the probability scores as defined in Example 10 for two ORFs located on different reading frames are high and close; preferably different by less than 0.4. The fine examination of the region where the two possible ORFs overlap may help to detect the frameshift. In the second approach, homologies with known proteins are used to correct suspected frameshifts.

Of the identified clusters, some were shown to be multivariant, i.e. to contain several variants of the same gene. Table III gives for each of the multivariant clusters named by its internal reference (first column), the list of all variant consensus contigated 5' ESTs (second column), each being represented by a different sequence identification number.

EXAMPLE 14

Categorization of 5' ESTs and Consensus Contigated 5' ESTs

The nucleic acid sequences of the present invention (SEQ ID NOs. 24–3883 and 7744–19335) were grouped based on their homology to known sequences as follows. All sequences were compared to the nucleic acid sequences of all vertebrates present in the EMBL release 58 and Genseqn (Derwent's database of patented nucleic acids) releases 35.3 or release 36. It should be noted that, because of the large number of sequences of the invention, the comparison of the polynucleotides of the invention to public sequences was done in a time frame of 15 days, meaning that the first sequences were compared to Geneseqn release 35.3 and the last ones with Geneseqn release 36. The comparison to EMBL vertebrate sequences was performed after masking of repeated sequences and using blastn with the parameters S=108 and X=16 followed by fasta. The comparison to Geneseqn was performed after masking of repeated sequences and using blastn with the parameters S=108 and X=16.

All matches with a minimum of 30 nucleotides with 95% identity or 100% identity were retrieved and used to compute Tables IVa and IVb respectively. Tables IVa and IVb give for each sequence of the invention referred to by its sequence identification number in the first column, the positions of their preferred fragments in the second column entitled "Positions of preferred fragments." These preferred fragments are novel fragments which do not match any publicly available vertebrate sequence according to the algorithm, parameters and criteria defined above. As used herein the term "polynucleotides described in Tables IVa and IVb" refers to all of the preferred polynucleotide fragments defined in Tables IVa and IVb in this manner.

The term "polynucleotides described in Tables IVa and IVb updated" refers to all of the preferred polynucleotide fragments defined in manner described above except that the most recent updates of the EMBL and Derwent databases are used to define the preferred fragments as of the filing date of the instant application.

The present invention encompasses isolated, purified, or recombinant nucleic acids which consist of, consist essentially of, or comprise a contiguous span of at least 8, 10, 12, 15, 18, 20, 25, 35, 40, 50, 70, 80, 100, 250, or 500 nucleotides in length, to the extent that a contiguous span of these lengths is consistent with the lengths of the particular polynucleotide, of a polynucleotide described in Tables IVa and IVb, or a sequence complementary thereto, wherein said polynucleotide described in Tables IVa and IVb is selected individually or in any combination from the polynucleotides described in Tables IVa and IVb. In particular, the present invention encompasses isolated, purified, or recombinant vertebrate nucleic acids which consist of, consist essentially of, or comprise a contiguous span of at least 8, 10, 12, 15, 18, 20, 25, 35, 40, 50, 70, 80, 100, 250, or 500 nucleotides in length, to the extent that a contiguous span of these lengths is consistent with the lengths of the particular polynucleotide, of a polynucleotide described in Tables IVa and IVb, or a sequence complementary thereto, wherein said polynucleotide described in Tables IVa and IVb is selected individually or in any combination from the polynucleotides described in Tables IVa and IVb. In particular, the present invention encompasses isolated, purified, or recombinant human nucleic acids which consist of, consist essentially of, or comprise a contiguous span of at least 8, 10, 12, 15, 18, 20, 25, 35, 40, 50, 70, 80, 100, 250, or 500 nucleotides in length, to the extent that a contiguous span of these lengths is consistent with the lengths of the particular polynucleotide, of a polynucleotide described in Tables IVa and IVb, or a sequence complementary thereto, wherein said polynucleotide described in Tables IVa and IVb is selected individually or in any combination from the polynucleotides described in Tables IVa and IVb.

The present invention also encompasses isolated, purified, or recombinant nucleic acids which comprise, consist of, or consist essentially of a polynucleotide described in Tables IVa and IVb, or a sequence complementary thereto, wherein said polynucleotide is selected individually or in any combination from the polynucleotides described in Tables IVa and IVb. In particular, the present invention encompasses isolated, purified, or recombinant vertebrate nucleic acids which comprise, consist of, or consist essentially of a polynucleotide described in Tables IVa and IVb, or a sequence complementary thereto, wherein said polynucleotide is selected individually or in any combination from the polynucleotides described in Tables IVa and IVb. In particular, the present invention encompasses isolated, purified, or recombinant human nucleic acids which comprise, consist of, or consist essentially of a polynucleotide described in Tables IVa and IVb, or a sequence complementary thereto, wherein said polynucleotide is selected individually or in any combination from the polynucleotides described in Tables IVa and IVb.

The present invention encompasses isolated, purified, or recombinant nucleic acids which consist of, consist essentially of, or comprise a contiguous span of at least 8, 10, 12, 15, 18, 20, 25, 35, 40, 50, 70, 80, 100, 250, or 500 nucleotides in length, to the extent that a contiguous span of these lengths is consistent with the lengths of the particular polynucleotide, of a polynucleotide described in Tables IVa and IVb, or a sequence complementary thereto, wherein said polynucleotide described in Tables IVa and IVb is selected individually or in any combination from the polynucleotides described in Tables IVa and IVb updated. In particular, the present invention encompasses isolated, purified, or recombinant vertebrate nucleic acids which consist of, consist essentially of, or comprise a contiguous span of at least 8, 10, 12, 15, 18, 20, 25, 35, 40, 50, 70, 80, 100, 250, or 500 nucleotides in length, to the extent that a contiguous span of these lengths is consistent with the lengths of the particular polynucleotide, of a polynucleotide described in Tables IVa and IVb, or a sequence complementary thereto, wherein said polynucleotide described in Tables IVa and IVb is selected individually or in any combination from the polynucleotides described in Tables IVa and IVb updated. In particular, the present invention encompasses isolated, purified, or recombinant human nucleic acids which consist of, consist essentially of, or comprise a contiguous span of at least 8, 10, 12, 15, 18, 20, 25, 35, 40, 50, 70, 80, 100, 250, or 500 nucleotides in length, to the extent that a contiguous span of these lengths is consistent with the lengths of the particular polynucleotide, of a polynucleotide described in Tables IVa and IVb, or a sequence complementary thereto, wherein said polynucleotide described in Tables IVa and IVb is selected individually or in any combination from the polynucleotides described in Tables IVa and IVb updated.

The present invention also encompasses isolated, purified, or recombinant nucleic acids which comprise, consist of, or consist essentially of a polynucleotide described in Tables IVa and IVb, or a sequence complementary thereto, wherein said polynucleotide is selected individually or in any combination from the polynucleotides described in Tables IVa and IVb updated. In particular, the present invention encompasses isolated, purified, or recombinant vertebrate nucleic acids which consist of or consist essentially of a polynucleotide described in Tables IVa and IVb, or a sequence complementary thereto, wherein said polynucleotide is selected individually or in any combination from the polynucleotides described in Tables IVa and IVb updated. In particular, the present invention encompasses isolated, purified, or recombinant human nucleic acids which consist of or consist essentially of a polynucleotide described in Tables IVa and IVb, or a sequence complementary thereto, wherein said polynucleotide is selected individually or in any combination from the polynucleotides described in Tables IVa and IVb updated.

III. Evaluation of Spatial and Temporal Expression of mRNAs Corresponding to the 5' ESTs or Extended cDNAs Each of the SEQ ID NOs. 24–3883 and 7744–19335 was also categorized based on the tissue from which its corresponding mRNA was obtained, as described below in Example 15.

EXAMPLE 15

Expression Patterns of mRNAs From Which the 5' ESTs Were Obtained

Table V shows the spatial distribution of each nucleic acid sequence of the invention (SEQ ID NOs. 24–3883 and 7744–19335) referred to by its internal designation in the first column and the number of individual 5' ESTs used to assemble the consensus contigated 5' ESTs per tissue in the second column. A singleton is thus represented by a single 5' EST from a single tissue. Each type of tissue listed in Table V is encoded by a letter. The correspondence between the letter code and the tissue type is given in Table VI. For example, if the first column contains 47 and the second column contains the following list: A:1 C:4 F:3, this means that the consensus contigated 5' EST of SEQ ID NO. 47 was obtained from one 5' EST from brain, four 5' ESTs from fetal kidney, and three 5' ESTs from liver.

The bias in spatial distribution of the sequences of the invention was examined by comparing the relative proportions of the biological 5' ESTs of a given tissue in each cluster using the following statistical analysis. The under- or over-representation of 5' ESTs of a given cluster in a given tissue was performed using the normal approximation of the binomial distribution. When the observed proportion of 5' ESTs of a given tissue in a given consensus had less than 1% chance to occur randomly according to the chi2 test, the frequency bias was reported as "low" or "high". The results are given in Table VII as follows. For each consensus contigated 5' ESTs showing a bias in tissue distribution as referred to by its sequence identification number in the first column, the list of tissues where some 5' ESTs were under-represented is given in the second column entitled "low frequency" and the list of tissues where some 5' ESTs are over-represented is given in the third column entitled "high frequency".

In addition to categorizing the 5' ESTs and consensus contigated 5' ESTs with respect to their tissue of origin, the spatial and temporal expression patterns of the mRNAs corresponding to the 5' ESTs and consensus contigated 5' ESTs, as well as their expression levels, may be determined as described in Example 16 below.

Characterization of the spatial and temporal expression patterns and expression levels of these mRNAs is useful for constructing expression vectors capable of producing a desired level of gene product in a desired spatial or temporal manner, as will be discussed in more detail below.

Furthermore, 5' ESTs and consensus contigated 5' ESTs whose corresponding mRNAs are associated with disease states may also be identified. For example, a particular disease may result from the lack of expression, over expression, or under expression of a mRNA corresponding to a 5' EST or consensus contigated 5' EST. By comparing mRNA expression patterns and quantities in samples taken from healthy individuals with those from individuals suffering from a particular disease, 5' ESTs or consensus contigated 5' ESTs responsible for the disease may be identified.

It will be appreciated that the results of the above characterization procedures for 5' ESTs and consensus contigated 5' ESTs also apply to extended cDNAs (obtainable as described below) which contain sequences adjacent to the 5' ESTs and consensus contigated 5' ESTs. It will also be appreciated that if desired, characterization may be delayed until extended cDNAs have been obtained rather than characterizing the 5' ESTs or consensus contigated 5' ESTs themselves.

EXAMPLE 16

Evaluation of Expression Levels and Patterns of mRNAs Corresponding to EST-Related Nucleic Acids Expression levels and patterns of mRNAs corresponding to EST-related nucleic acids may be analyzed by solution hybridization with long probes as described in International Patent Application No. WO 97/05277, the entire contents of which are hereby incorporated by reference. Briefly, an EST-related nucleic acid, fragment of an EST related nucleic acid, positional segment of an EST-related nucleic acid, or fragment of a positional segment of an EST-related nucleic acid corresponding to the gene encoding the mRNA to be characterized is inserted at a cloning site immediately downstream of a bacteriophage (T3, T7 or SP6) RNA polymerase promoter to produce antisense RNA. Preferably, the EST-related nucleic acid, fragment of an EST related nucleic acid, positional segment of an EST-related nucleic acid, or fragment of a positional segment of an EST-related nucleic acid is 100 or more nucleotides in length. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40–50° C. for 16 hours in an 80% formamide, 0.4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

The EST-related nucleic acid, fragment of an EST related nucleic acid, positional segment of an EST-related nucleic acid, or fragment of a positional segment of an EST-related nucleic acid may also be tagged with nucleotide sequences for the serial analysis of gene expression (SAGE) as disclosed in UK Patent Application No. 2 305 241 A, the entire contents of which are incorporated by reference. In this method, cDNAs are prepared from a cell, tissue, organism or other source of nucleic acid for which gene expression patterns must be determined. The resulting cDNAs are separated into two pools. The cDNAs in each pool are cleaved with a first restriction endonuclease, called an anchoring enzyme, having a recognition site which is likely to be present at least once in most cDNAs. The fragments which contain the 5' or 3' most region of the cleaved cDNA are isolated by binding to a capture medium such as streptavidin coated beads. A first oligonucleotide linker having a first sequence for hybridization of an amplification primer and an internal restriction site for a so called tagging endonuclease is ligated to the digested cDNAs in the first pool. Digestion with the second endonuclease produces short tag fragments from the cDNAs.

A second oligonucleotide having a second sequence for hybridization of an amplification primer and an internal restriction site is ligated to the digested cDNAs in the second pool. The cDNA fragments in the second pool are also digested with the tagging endonuclease to generate short tag fragments derived from the cDNAs in the second pool. The tags resulting from digestion of the first and second pools with the anchoring enzyme and the tagging endonuclease are ligated to one another to produce so called ditags. In some embodiments, the ditags are concatamerized to produce ligation products containing from 2 to 200 ditags. The tag sequences are then determined and compared to the sequences of the EST-related nucleic acid, fragment of an EST related nucleic acid, positional segment of an EST-related nucleic acid, or fragment of a positional segment of an EST-related nucleic acid to determine which 5' ESTs, consensus contigated 5' ESTs, or extended cDNAs are expressed in the cell, tissue, organism, or other source of nucleic acids from which the tags were derived. In this way, the expression pattern of the 5' ESTs, consensus contigated 5' ESTs, or extended cDNAs in the cell, tissue, organism, or other source of nucleic acids is obtained.

Quantitative analysis of gene expression may also be performed using arrays. As used herein, the term array means a one dimensional, two dimensional, or multidimensional arrangement of EST-related nucleic acids, fragments of EST related nucleic acids, positional segments EST-related nucleic acids, or fragments of positional segments of EST-related nucleic acids. Preferably, the EST-related nucleic acids, fragments of EST related nucleic acids, positional segments EST-related nucleic acids, or fragments of positional segments of EST-related nucleic acids are at least 15 nucleotides in length. More preferably, the EST-related nucleic acids, fragments of EST related nucleic acids, positional segments EST-related nucleic acids, or fragments of positional segments of EST-related nucleic acids are at least 100 nucleotide long. More preferably, the fragments are more than 100 nucleotides in length. In some embodiments, the EST-related nucleic acids, fragments of EST related nucleic acids, positional segments EST-related nucleic acids, or fragments of positional segments of EST-related nucleic acids may be more than 500 nucleotides long.

For example, quantitative analysis of gene expression may be performed with EST-related nucleic acids, fragments of EST related nucleic acids, positional segments EST-related nucleic acids, or fragments of positional segments of EST-related nucleic acids in a complementary DNA microarray as described by Schena et al. (*Science* 270:467–470, 1995; *Proc. Natl. Acad Sci. U.S.A.* 93:10614–10619, 1996). EST-related nucleic acids, fragments of EST related nucleic acids, positional segments EST-related nucleic acids, or fragments of positional segments of EST-related nucleic acids are amplified by PCR and arrayed from 96-well microtiter plates onto sylilated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 $cm^2$ microarrays under a 14×14 mm glass coverslip for 6–12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the expression of genes may also be performed with EST-related nucleic acids, fragments of EST related nucleic acids, positional segments EST-related nucleic acids, or fragments of positional segments of EST-related nucleic acids in complementary DNA arrays as described by Pietu et al. (*Genome Research* 6:492–503, 1996). The EST-related nucleic acids, fragments of EST related nucleic acids, positional segments EST-related nucleic acids, or fragments of positional segments of EST-related nucleic acids thereof are PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis of the EST-related nucleic acids, fragments of EST related nucleic acids, positional segments EST-related nucleic acids, or fragments of positional segments of EST-related nucleic acids can be done through high density nucleotide arrays as described by Lockhart et al. (*Nature Biotechnology* 14: 1675–1680, 1996) and Sosnowsky et al. (*Proc. Natl. Acad. Sci.* 94:1119–1123, 1997). Oligonucleotides of 15–50 nucleotides corresponding to sequences of EST-related nucleic acids, fragments of EST related nucleic acids, positional segments EST-related nucleic acids, or fragments of positional segments of EST-related nucleic acids are synthesized directly on the chip (Lockhart et al., supra) or synthesized and then addressed to the chip (Sosnowsky et al., supra). Preferably, the oligonucleotides are about 20 nucleotides in length.

cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip.

After washing as described in Lockhart et al, supra and application of different electric fields (Sonowsky et al, supra.), the dyes or labeling compounds are detected and quantified. Duplicate hybridizations are performed. Comparative analysis of the intensity of the signal originating from cDNA probes on the same target oligonucleotide in different cDNA samples indicates a differential expression of the mRNA corresponding to the 5' EST, consensus contigated 5' EST or extended cDNA from which the oligonucleotide sequence has been designed.

IV. Use of 5' ESTs or Consensus Contigated 5' ESTs to Clone Extended cDNAs and to Clone the Corresponding Genomic DNAs Once 5' ESTs or consensus contigated 5' ESTs which include the 5' end of the corresponding mRNAs have been selected using the procedures described above, they can be utilized to isolate extended cDNAs which contain sequences adjacent to the 5' ESTs or consensus contigated 5' ESTs. The extended cDNAs may include the entire coding sequence of the protein encoded by the corresponding mRNA, including the authentic translation start site. If the extended cDNA encodes a secreted protein, it may contain the signal sequence, and the sequence encoding the mature protein remaining after cleavage of the signal peptide. Extended cDNAs which include the entire coding sequence of the protein encoded by the corresponding mRNA are referred to herein as "full-length cDNAs." Alternatively, the extended cDNAs may not include the entire coding sequence of the protein encoded by the corresponding mRNA, although they do include sequences adjacent to the 5' ESTs or consensus contigated 5' ESTs. In some embodiments in which the extended cDNAs are derived from an mRNA encoding a secreted protein, the extended cDNAs may include only the sequence encoding the mature protein remaining after cleavage of the signal peptide, or only the sequence encoding the signal peptide.

Example 17 below describes a general PCR based method for obtaining extended cDNAs using 5' ESTs or consensus contigated 5' ESTs. Example 18 describes hybridization based methods to obtain genomic DNAs which encode the mRNAs from which the 5' ESTs or consensus contigated 5' ESTS were derived, mRNAs from which the 5' ESTs or consensus contigated 5' ESTS were derived, or nucleic acids which are homologous to 5' ESTs-related nucleic acids. Example 19 below describes the cloning and sequencing of several extended cDNAs, including extended cDNAs which include the entire coding sequence and authentic 5' end of the corresponding mRNA for several secreted proteins.

The methods of Examples 17 and 18 can also be used to obtain extended cDNAs which encode less than the entire coding sequence of proteins encoded by the genes corresponding to the 5' ESTs or consensus contigated ESTs. In some embodiments, the extended cDNAs isolated using these methods encode at least 5, 10, 15, 20, 25, 30, 35, 40, 50, 75, 100, or 150 consecutive amino acids of one of the proteins encoded by the sequences of SEQ ID NOs. 24–3883 and 7744–19335. In some embodiments, the extended cDNAs isolated using these methods encode at least 5, 10, 15, 20, 25, 30, 35, 40, 50, 75, 100, or 150 consecutive amino acids of one of the proteins encoded by the sequences of SEQ ID NOs. 24–3883.

EXAMPLE 17

Figure 3:
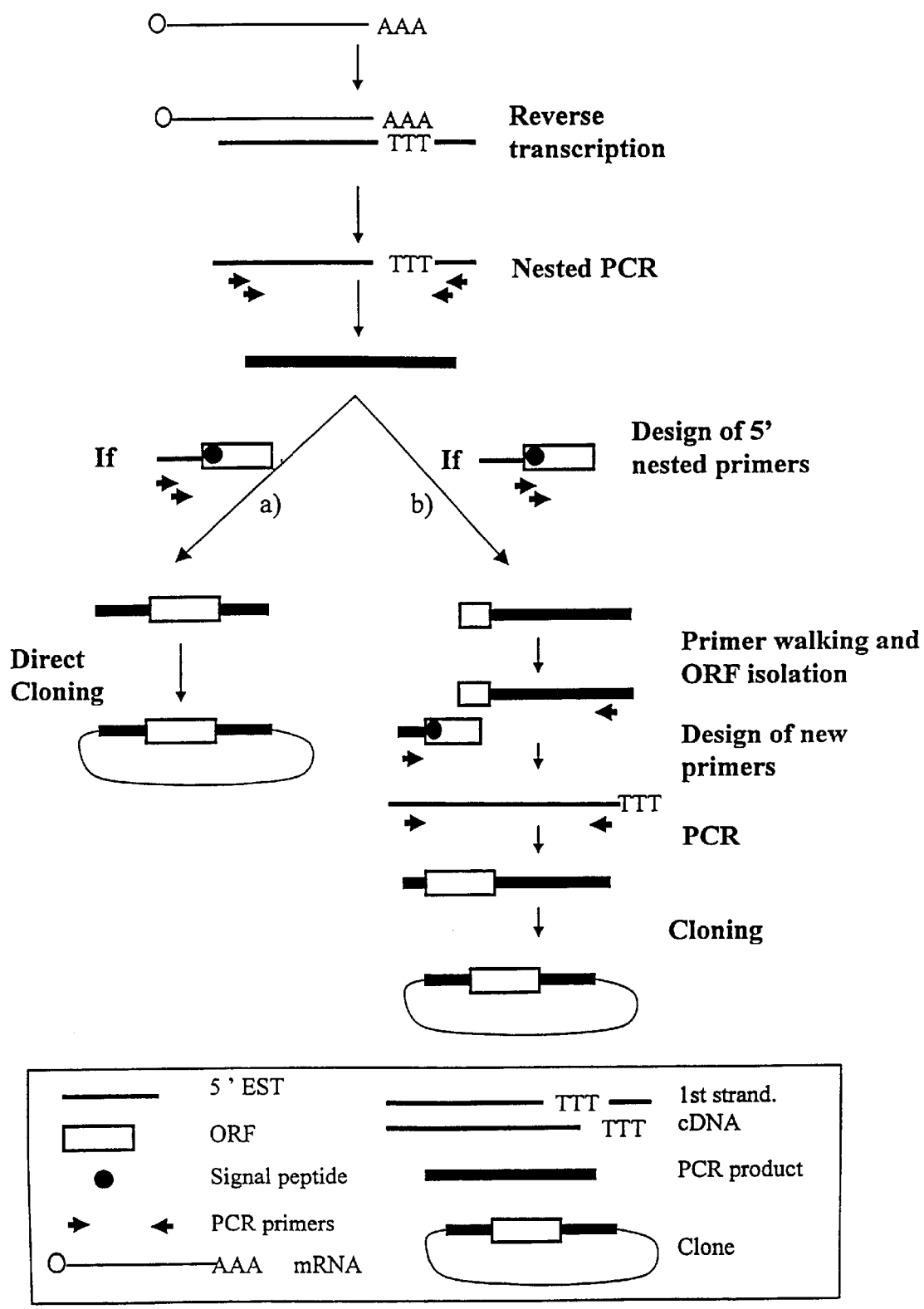
FIG. 3 summarizes a general RT-PCR-based-method used to clone and sequence extended cDNAs containing sequences adjacent to 5' ESTs.

General Method for Using 5' ESTs or Consensus Contigated 5' ESTs to Clone and Sequence Extended cDNAs Which Include the Entire Coding Region and the Authentic 5' End of the Corresponding mRNA The following general method may be used to quickly and efficiently isolate extended cDNAs including sequence adjacent to the sequences of the 5' ESTs or consensus contigated 5' ESTs used to obtain them. This method may be applied to obtain extended cDNAs for any 5' EST or consensus contigated 5' EST of the invention, including those 5' ESTs and consensus contigated 5' ESTs encoding secreted proteins. This method is illustrated in FIG. 3.

1. Obtaining Extended cDNAs

The method takes advantage of the known 5' sequence of the mRNA. A reverse transcription reaction is conducted on purified mRNA with a poly dT primer containing a nucleotide sequence at its 5' end allowing the addition of a known sequence at the end of the cDNA which corresponds to the 3' end of the mRNA. Such a primer and a commercially-available reverse transcriptase enzyme are added to a buffered mRNA sample yielding a reverse transcript anchored at the 3' polyA site of the RNAs. Preferably, a thermostable enzyme is used. Nucleotide monomers are then added to complete the first strand synthesis.

After removal of the mRNA hybridized to the first cDNA strand by alkaline hydrolysis, the products of the alkaline hydrolysis and the residual poly dT primer can be eliminated with an exclusion column.

Subsequently, a pair of nested primers on each end of the cDNA to be amplified is designed based on the known 5' sequence from the 5' EST or consensus contigated 5' EST and the known 3' end added by the poly dT primer used in the first strand synthesis. Software used to design primers are either based on GC content and melting temperatures of oligonucleotides, such as OSP (Illier and Green, *PCR Meth. Appl.* 1:124–128, 1991), or based on the octamer frequency disparity method (Griffais et al., *Nucleic Acids Res.* 19:3887–3891, 1991) such as PC-Rare (see Worldwide Website: bioinformatics.weizmann.ac.il/software/PC-Rare/doc/manuel.litml). Preferably, the nested primers at the 5' end and the nested primers at the 3' end are separated from one another by four to nine bases. These primer sequences may be selected to have melting temperatures and specificities suitable for use in PCR.

A first PCR run is performed using the outer primer from each of the nested pairs. A second PCR run using the inner primer from each of the nested pairs is then performed on a small sample of the first PCR product. Thereafter, the primers and remaining nucleotide monomers are removed.

It will be appreciated that a simple PCR reaction using a primer on each end of the cDNA to be amplified may also be performed rather than using a couple of primers for in a nested PCR procedure. However because of the possibility of PCR artifacts in this method, a nested PCR protocol is preferred.

2. Sequencing Extended cDNAs or Fragments Thereof

Due to the lack of position constraints on the design of 5' nested primers compatible for PCR use using the OSP software, amplicons of two types are obtained. Preferably, the second 5' primer is located upstream of the translation initiation codon thus yielding a nested PCR product containing the entire coding sequence. Such an extended cDNA may be used in a direct cloning procedure as described in section a below. However, in some cases, the second 5' primer is located downstream of the translation initiation codon, thereby yielding a PCR product containing only part of the ORF. Such incomplete PCR products are submitted to a modified procedure described in section b below.

a) Nested PCR Products Containing Complete ORFs

When the resulting nested PCR product contains the complete coding sequence, as predicted from the 5' EST or consensus contigated 5' EST sequence, it is directly cloned in an appropriate vector as described in section 3.

b) Nested PCR Products Containing Incomplete ORFs

When the amplicon does not contain the complete coding sequence, intermediate steps are necessary to obtain both the complete coding sequence and a PCR product containing the full coding sequence. The complete coding sequence can be assembled from several partial sequences determined directly from different PCR products.

Once the full coding sequence has been completely determined, new primers compatible for PCR use are then designed to obtain amplicons containing the whole coding region. However, in such cases, 3' primers compatible for PCR use are located inside the 3' UTR of the corresponding mRNA, thus yielding amplicons which lack part of this region, i.e. the polyA tract and sometimes the polyadenylation signal, as illustrated in FIG. 3. Such extended cDNAs are then cloned into an appropriate vector as described in section 3.

c) Sequencing Extended cDNAs

Sequencing of extended cDNAs can be performed using a Dye Terminator approach with the AmpliTaq DNA polymerase FS kit available from Perkin Elmer.

In order to sequence long PCR fragments, primer walking is performed using software such as OSP to choose primers and automated computer software such as ASMG (Sutton et al., *Genome Science Technol.* 1: 9–19, 1995) to construct contigs of walking sequences including the initial 5' tag. Preferably, primer walking is performed until the sequences of full length cDNAs are obtained.

Completion of the sequencing of a given extended cDNA fragment may be assessed by comparing the sequence length to the size of the corresponding nested PCR product. When Northern blot data are available, the size of the mRNA detected for a given PCR product may also be used to finally assess that the sequence is complete. Sequences which do not fulfill these criteria are discarded and will undergo a new isolation procedure.

3. Cloning Extended cDNAs

The PCR product containing the full coding sequence is then cloned in an appropriate vector. For example, the extended cDNAs can be cloned into any expression vector known in the art, such as pED6dpc2 for extended cDNA encoding potentially secreted proteins (DiscoverEase, Genetics Institute, Cambridge, Mass.).

Cloned PCR products are then entirely sequenced in order to obtain at least two sequences per clone. Preferably, the sequences are obtained from both sense and antisense strands according to the aforementioned procedure with the following modifications. First, both 5' and 3' ends of cloned PCR products are sequenced in order to confirm the identity of the clone. Second, primer walking is performed if the full coding region has not been obtained yet. Contigation is then performed using primer walking sequences for cloned products as well as walking sequences that have already contigated for uncloned PCR products. The sequence is considered complete when the resulting contigs include the whole coding region as well as overlapping sequences with vector DNA on both ends. All the contigated sequences for each cloned amplicon are then used to obtain a consensus sequence.

4. Selection of Cloned Full Length Sequences a) Computer Analysis of Extended cDNAs Following identification of contaminants and masking of repeats, structural features, e.g. polyA tail and polyadenylation signal, of the sequences of extended cDNAs are subsequently determined using methods known to those skilled in the art. For example, the algorithm, parameters and criteria defined in FIG. 10 may be used. Briefly, a polyA tail is defined as a homopolymeric stretch of at least 11 A with at most one alternative base within it. The polyA tail search is restricted to the last 20 nucleotides of the sequence and limited to stretches of 11 consecutive A's because sequencing reactions are often not readable after such a polyA stretch. To search for a polyadenylation signal, the polyA tail is clipped from the full-length sequence. The 50 nucleotides preceding the polyA tail are searched for the canonic polyadenylation AAUAAA signal allowing one mismatch to account for possible sequencing errors as well as known variation in the canonical sequence of the polyadenylation signal.

Functional features, e.g. ORFs and signal sequences, of the sequences of extended cDNAs are subsequently determined as follows. The 3 upper strand frames of extended cDNAs are searched for ORFs defined as the maximum length fragments beginning with a translation initiation codon and ending with a stop codon. ORFs encoding at least 80 amino acids are preferred. If extended cDNAs encoding secreted proteins are desired, each identified ORF is then scanned for the presence of a signal peptide using the matrix method described in Example 11.

Sequences of extended cDNAs are then compared, on a nucleotidic or proteic basis, to public sequences available at the time of filing.

b) Selection of Full-length cDNAs of Interest

A negative selection may then be performed in order to eliminate unwanted cloned sequences resulting from either contaminants or PCR artifacts as follows. Sequences matching contaminant sequences such as vector DNA, tRNA, mtRNA, rRNA sequences are discarded as well as those encoding ORF sequences exhibiting extensive homology to repeats. Sequences obtained by direct cloning (section 1a) but lacking polyA tail may be discarded. Only ORFs ending either before the polyA tail (section 1a) or before the end of the cloned 3' UTR (section 1b) may be selected. If extended cDNAs encoding secreted proteins are desired, ORFs containing a signal peptide are considered. In addition, ORFs containing unlikely mature proteins such as mature proteins which size is less than 20 amino acids or less than 25% of the immature protein size may be eliminated if necessary.

Then, for each remaining full length cDNA containing several ORFs, a preselection of ORFs may be performed using the following criteria. The longest ORF is preferred. If extended cDNAs encoding secreted proteins are desired and if the ORF sizes are similar, the chosen ORF is the one which signal peptide has the highest score according to Von Heijne method.

Sequences of full length cDNA clones may then be compared pairwise after masking of the repeat sequences. Full-length cDNA sequences exhibiting extensive homology may be clustered in the same class. Each cluster may then be subjected to a cluster analysis that detects sequences resulting from internal priming or from alternative splicing, identical sequences or sequences with several frameshifts. A selection may be operated between clones belonging to the same class in order to detect clones encoding homologous but distinct ORFs which may be both selected if they both contain sequences of interest.

Selection of full-length cDNA clones encoding sequences of interest may subsequently be performed using the following criteria. Structural parameters (initial tag, polyadenylation site and signal) are first checked. Then, homologies with known nucleic acids and proteins are examined in order to determine whether the clone sequence match a known nucleotide/protein sequence and, in the latter case, its covering rate and the date at which the sequence became public.

If there is no extensive match with sequences other than ESTs or genomic DNA, or if the clone sequence provides substantial new information, such as encoding a protein resulting from alternative splicing of an mRNA coding for an already known protein, the sequence is kept. Examples of such cloned full-length cDNAs containing sequences of interest are described in Example 19. Sequences resulting from chimera or double inserts or located on chromosome breaking points as assessed by homology to other sequences may be discarded during this procedure.

Extended cDNAs prepared as described above may be subsequently engineered to obtain nucleic acids which include desired portions of the extended cDNA using conventional techniques such as subcloning, PCR, or in vitro oligonucleotide synthesis. For example, nucleic acids which include only the full coding sequences may be obtained using techniques known to those skilled in the art. Alternatively, conventional techniques may be applied to obtain nucleic acids which contain only part of the coding sequences. In the case of nucleic acids encoding secreted proteins, nucleic acids containing only the coding sequence for the mature protein remaining after the signal peptide is cleaved off or nucleic acids which contain only the coding sequences for the signal peptides may be obtained.

Similarly, nucleic acids containing any other desired portion of the coding sequences for the encoded protein may be obtained. For example, the nucleic acid may contain at least 10, 15, 18, 20, 25, 28, 30, 35, 40, 50, 75, 100, 150, 200, 300, 400, 500, 1000 or 2000 consecutive bases of an extended cDNA.

Once an extended cDNA has been obtained, it can be sequenced to determine the amino acid sequence it encodes. Once the encoded amino acid sequence has been determined, one can create and identify any of the many conceivable cDNAs that will encode that protein by simply using the degeneracy of the genetic code. For example, allelic variants or other homologous nucleic acids can be identified as described below. Alternatively, nucleic acids encoding the desired amino acid sequence can be synthesized in vitro.

In a preferred embodiment, the coding sequence may be selected using the known codon or codon pair preferences for the host organism in which the cDNA is to be expressed.

In addition to PCR based methods for obtaining cDNAs which include the authentic 5' end of the corresponding mRNA as well as the complete protein coding sequence of the corresponding mRNA, traditional hybridization based methods may also be employed. These methods may also be used to obtain the genomic DNAs which encode the mRNAs from which the 5' ESTs or consensus contigated 5' ESTS were derived, mRNAs from which the 5' ESTs or consensus contigated 5' ESTS were derived, or nucleic acids which are homologous to EST-related nucleic acids. In particular, such methods may be used to obtain extended cDNAs which include the entire coding region of the mRNAs from which the 5' EST or consensus contigated 5' ESTs was derived. Example 18 below provides examples of such methods.

EXAMPLE 18

Methods for Obtaining Extended cDNAs Which Include the Entire Coding Region and the Authentic 5' End of the Corresponding mRNA or Nucleic Acids Homologous to Extended cDNAs 5' ESTs or Consensus Contigated 5' ESTs A full-length cDNA library can be made using the strategies described in Examples 1–5. Alternatively, a cDNA library or genomic DNA library may be obtained from a commercial source or made using techniques familiar to those skilled in the art.

Such cDNA or genomic DNA libraries may be used to isolate extended cDNAs obtained from 5' ESTs or consensus contigated 5' ESTs or nucleic acids homologous to extended cDNAs, 5' ESTs, or consensus contigated 5' ESTs as follows. The cDNA library or genomic DNA library is hybridized to a detectable probe. The detectable probe may comprise at least 10, 15, 18, 20, 25, 28, 30, 35, 40, 50, 75, 100, 150, 200, 300, 400 or 500 consecutive nucleotides of the 5' EST, consensus contigated 5' EST, or extended cDNA. Techniques for identifying cDNA clones in a cDNA library which hybridize to a given probe sequence are disclosed in Sambrook et al., *Molecular Cloning: A Laboratory Manual* 2d Ed., Cold Spring Harbor Laboratory Press, 1989, the disclosure of which is incorporated herein by reference. The same techniques may be used to isolate genomic DNAs.

Briefly, cDNA or genomic DNA clones which hybridize to the detectable probe are identified and isolated for further manipulation as follows. The detectable probe described in the preceding paragraph is labeled with a detectable label such as a radioisotope or a fluorescent molecule. Techniques for labeling the probe are well known and include phosphorylation with polynucleotide kinase, nick translation, in vitro transcription, and non radioactive techniques. The cDNAs or genomic DNAs in the library are transferred to a nitrocellulose or nylon filter and denatured. After blocking of non specific sites, the filter is incubated with the labeled probe for an amount of time sufficient to allow binding of the probe to cDNAs or genomic DNAs containing a sequence capable of hybridizing thereto.

By varying the stringency of the hybridization conditions used to identify cDNAs or genomic DNAs which hybridize to the detectable probe, cDNAs or genomic DNAs having different levels of homology to the probe can be identified and isolated as described below.

1. Identification of cDNA or Genomic DNA Sequences Having a High Degree of Homology to the Labeled Probe To identify cDNAs or genomic DNAs having a high degree of homology to the probe sequence, the melting temperature of the probe may be calculated using the following formulas:

For probes between 14 and 70 nucleotides in length the melting temperature (Tm) is calculated using the formula: $Tm=81.5+16.6(\log(Na+))+0.41(\text{fraction } G+C)-(600/N)$ where N is the length of the probe.

If the hybridization is carried out in a solution containing formamide, the melting temperature may be calculated using the equation $Tm=81.5+16.6(\log(Na+))+0.41(\text{fraction } G+C)-(0.63\% \text{ formamide})-(600/N)$ where N is the length of the probe.

Prehybridization may be carried out in 6×SSC, 5×Denhardt's reagent, 0.5% SDS, 100 g denatured fragmented salmon sperm DNA or 6×SSC, 5×Denhardt's reagent, 0.5% SDS, 100 g denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to extended cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 15–25° C. below the Tm. Preferably, for hybridizations in 6×SSC, the hybridization is conducted at approximately 68° C. Preferably, for hybridizations in 50% formamide containing solutions, the hybridization is conducted at approximately 42° C.

All of the foregoing hybridizations would be considered to be under "stringent" conditions.

Following hybridization, the filter is washed in 2×SSC, 0.1% SDS at room temperature for 15 minutes. The filter is then washed with 0.1×SSC, 0.5% SDS at room temperature for 30 minutes to 1 hour. Thereafter, the solution is washed at the hybridization temperature in 0.1×SSC, 0.5% SDS. A final wash is conducted in 0.1×SSC at room temperature.

cDNAs or genomic DNAs which have hybridized to the probe are identified by autoradiography or other conventional techniques.

2. Obtaining cDNA or Genomic DNA Sequences Having Lower Degrees of Homology to the Labeled Probe The above procedure may be modified to identify cDNAs or genomic DNAs having decreasing levels of homology to the probe sequence. For example, to obtain cDNAs or genomic DNAs of decreasing homology to the detectable probe, less stringent conditions may be used. For example, the hybridization temperature may be decreased in increments of 5° C. from 68° C. to 42° C. in a hybridization buffer having a sodium concentration of approximately 1M. Following hybridization, the filter may be washed with 2×SSC, 0.5% SDS at the temperature of hybridization. These conditions are considered to be "moderate" conditions above 50° C. and "low" conditions below 50° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide.

cDNAs or genomic DNAs which have hybridized to the probe are identified by autoradiography.

3. Determination of the Degree of Homology Between the Obtained cDNAs or Genomic DNAs and 5' ESTs, Consensus Contigated 5' ESTs or Extended cDNAs or Between the Polypeptides Encoded by the Obtained cDNAs or Genomic DNAs and the Polypeptides Encoded by the 5' ESTs Consensus Contigated 5' ESTs or Extended cDNAs To determine the level of homology between the hybridized cDNA or genomic DNA and the 5' EST, consensus contigated 5' EST or extended cDNA from which the probe was derived, the nucleotide sequences of the hybridized nucleic acid and the 5' EST, consensus contigated 5' EST or extended cDNA from which the probe was derived are compared. The sequences of the 5' EST, consensus contigated 5' EST or extended cDNA from which the probe was derived and the sequences of the cDNA or genomic DNA which hybridized to the detectable probe may be stored on a computer readable medium as described below and compared to one another using any of a variety of algorithms familiar to those skilled in the art, those described below.

To determine the level of homology between the polypeptide encoded by the hybridizing cDNA or genomic DNA and the polypeptide encoded by the 5' EST, consensus contigated 5' EST or extended cDNA from which the probe was derived, the polypeptide sequence encoded by the hybridized nucleic acid and the polypeptide sequence encoded by the 5' EST, consensus contigated 5' EST or extended cDNA from which the probe was derived are compared. The sequences of the polypeptide encoded by the 5' EST, consensus contigated 5' EST or extended cDNA from which the probe was derived and the polypeptide sequence encoded by the cDNA or genomic DNA which hybridized to the detectable probe may be stored on a computer readable medium as described below and compared to one another using any of a variety of algorithms familiar to those skilled in the art, those described below.

Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, *Proc. Natl. Acad. Sci. USA* 85(8):2444–2448; Altschul et al., 1990, *J. Mol. Biol.* 215(3):403–410; Thompson et al., 1994, *Nucleic Acids Res.* 22(2):4673–4680; Higgins et al., 1996, *Methods Enzymol.* 266:383–402; Altschul et al., 1990, *J. Mol. Biol.* 215(3):403–410; Altschul et al., 1993, *Nature Genetics* 3:266–272).

In a particularly preferred embodiment, protein and nucleic acid sequence homologies are evaluated using the Basic Local Alignment Search Tool ("BLAST") which is well known in the art (see, e.g., Karlin and Altschul, 1990, *Proc. Natl. Acad Sci. USA* 87:2267–2268; Altschul et al., 1990, *J. Mol. Biol.* 215:403–410; Altschul et al., 1993, *Nature Genetics* 3:266–272; Altschul et al., 1997, *Nuc. Acids Res.* 25:3389–3402). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992, *Science* 256:1443–1445; Henikoff and Henikoff, 1993, *Proteins* 17:49–61). Less preferably, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation)

The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990, *Proc. Natl. Acad. Sci. USA* 87:2267–2268).

The parameters used with the above algorithms may be adapted depending on the sequence length and degree of homology studied. In some embodiments, the parameters may be the default parameters used by the algorithms in the absence of instructions from the user.

In some embodiments, the level of homology between the hybridized nucleic acid and the extended cDNA, 5' EST, or 5' consensus contigated EST from which the probe was derived may be determined using the FASTDB algorithm described in Brutlag et al. *Comp. App. Biosci.* 6:237–245, 1990. In such analyses the parameters may be selected as follows: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the sequence which hybridizes to the probe, whichever is shorter. Because the FASTDB program does not consider 5' or 3' truncations when calculating homology levels, if the sequence which hybridizes to the probe is truncated relative to the sequence of the extended cDNA, 5' EST, or consensus contigated 5' EST from which the probe was derived the homology level is manually adjusted by calculating the number of nucleotides of the extended cDNA, 5' EST, or consensus contigated 5' EST which are not matched or aligned with the hybridizing sequence, determining the percentage of total nucleotides of the hybridizing sequence which the non-matched or non-aligned nucleotides represent, and subtracting this percentage from the homology level. For example, if the hybridizing sequence is 700 nucleotides in length and the extended cDNA, 5' EST, or consensus contigated 5' EST sequence is 1000 nucleotides in length wherein the first 300 bases at the 5' end of the extended cDNA, 5' EST, or consensus contigated 5' EST are absent from the hybridizing sequence, and wherein the overlapping 700 nucleotides are identical, the homology level would be adjusted as follows. The non-matched, non-aligned 300 bases represent 30% of the length of the extended cDNA, 5' EST, or consensus contigated 5' EST. If the overlapping 700 nucleotides are 100% identical, the adjusted homology level would be 100−30=70% homology. It should be noted that the preceding adjustments are only made when the non-matched or non-aligned nucleotides are at the 5' or 3' ends. No adjustments are made if the non-matched or non-aligned sequences are internal or under any other conditions.

For example, using the above methods, nucleic acids having at least 95% nucleic acid homology, at least 96% nucleic acid homology, at least 97% nucleic acid homology, at least 98% nucleic acid homology, at least 99% nucleic acid homology, or more than 99% nucleic acid homology to the extended cDNA, 5' EST, or consensus contigated 5' EST from which the probe was derived may be obtained and identified. Such nucleic acids may be allelic variants or related nucleic acids from other species. Similarly, by using progressively less stringent hybridization conditions one can obtain and identify nucleic acids having at least 90%, at least 85%, at least 80% or at least 75% homology to the extended cDNA, 5' EST, or consensus contigated 5' EST from which the probe was derived.

Using the above methods and algorithms such as FASTA with parameters depending on the sequence length and degree of homology studied, for example the default parameters used by the algorithms in the absence of instructions from the user, one can obtain nucleic acids encoding proteins having at least 99%, at least 98%, at least 97%, at least 96%, at least 95%, at least 90%, at least 85%, at least 80% or at least 75% homology to the protein encoded by the extended cDNA, 5' EST, or consensus contigated 5' EST from which the probe was derived. In some embodiments, the homology levels can be determined using the "default" opening penalty and the "default" gap penalty, and a scoring matrix such as PAM 250 (a standard scoring matrix; see Dayhoff et al., in: Atlas of Protein Sequence and Structure, Vol. 5, Supp. 3 (1978)).

Alternatively, the level of polypeptide homology may be determined using the FASTDB algorithm described by Brutlag et al. Comp. App. Biosci. 6:237–245, 1990. In such analyses the parameters may be selected as follows: Matrix=PAM 0, k-tuple=2, Mismatch Penalty=1, Joining Penalty=20, Randomization Group Length=0, Cutoff Score=1, Window Size=Sequence Length, Gap Penalty=5, Gap Size Penalty=0.05, Window Size=500 or the length of the homologous sequence, whichever is shorter. If the homologous amino acid sequence is shorter than the amino acid sequence encoded by the extended cDNA, 5' EST, or consensus contigated 5' EST as a result of an N terminal and/or C terminal deletion the results may be manually corrected as follows. First, the number of amino acid residues of the amino acid sequence encoded by the extended cDNA, 5' EST, or consensus contigated 5' EST which are not matched or aligned with the homologous sequence is determined. Then, the percentage of the length of the sequence encoded by the extended cDNA, 5' EST, or consensus contigated 5' EST which the non-matched or non-aligned amino acids represent is calculated. This percentage is subtracted from the homology level. For example wherein the amino acid sequence encoded by the extended cDNA, 5' EST, or consensus contigated 5' EST is 100 amino acids in length and the length of the homologous sequence is 80 amino acids and wherein the amino acid sequence encoded by the extended cDNA or 5' EST is truncated at the N terminal end with respect to the homologous sequence, the homology level is calculated as follows. In the preceding scenario there are 20 non-matched, non-aligned amino acids in the sequence encoded by the extended cDNA, 5' EST, or consensus contigated 5' EST. This represents 20% of the length of the amino acid sequence encoded by the extended cDNA, 5' EST, or consensus contigated 5' EST. If the remaining amino acids are 1005 identical between the two sequences, the homology level would be 100%−20%=80% homology. No adjustments are made if the non-matched or non-aligned sequences are internal or under any other conditions.

In addition to the above described methods, other protocols are available to obtain extended cDNAs using 5' ESTs or consensus contigated 5' ESTs as outlined in the following paragraphs.

Extended cDNAs may be prepared by obtaining mRNA from the tissue, cell, or organism of interest using mRNA preparation procedures utilizing polyA selection procedures or other techniques known to those skilled in the art. A first primer capable of hybridizing to the polyA tail of the mRNA is hybridized to the mRNA and a reverse transcription reaction is performed to generate a first cDNA strand.

The first cDNA strand is hybridized to a second primer containing at least 10 consecutive nucleotides of the sequences of SEQ ID NOs 24–3883 and 7744–19335. Preferably, the primer comprises at least 10, 12, 15, 17, 18, 20, 23, 25, or 28 consecutive nucleotides from the sequences of SEQ ID NOs 24–3883 and 7744–19335. In some embodiments, the primer comprises more than 30 nucleotides from the sequences of SEQ ID NOs 24–3883 and 7744–19335. If it is desired to obtain extended cDNAs containing the full protein coding sequence, including the authentic translation initiation site, the second primer used contains sequences located upstream of the translation initiation site. The second primer is extended to generate a second cDNA strand complementary to the first cDNA strand. Alternatively, RT-PCR may be performed as described above using primers from both ends of the cDNA to be obtained.

Extended cDNAs containing 5' fragments of the mRNA may be prepared by hybridizing an mRNA comprising the sequences of SEQ ID NOs. 24–3883 and 7744–19335 with a primer comprising a complementary to a fragment of an EST-related nucleic acid hybridizing the primer to the mRNAs, and reverse transcribing the hybridized primer to make a first cDNA strand from the mRNAs. Preferably, the primer comprises at least 10, 12, 15, 17, 18, 20, 23, 25, or 28 consecutive nucleotides of the sequences complementary to SEQ ID NOs. 24–3883 and 7744–19335.

Thereafter, a second cDNA strand complementary to the first cDNA strand is synthesized. The second cDNA strand may be made by hybridizing a primer complementary to sequences in the first cDNA strand to the first cDNA strand and extending the primer to generate the second cDNA strand.

The double stranded extended cDNAs made using the methods described above are isolated and cloned. The extended cDNAs may be cloned into vectors such as plasmids or viral vectors capable of replicating in an appropriate host cell. For example, the host cell may be a bacterial, mammalian, avian, or insect cell.

Techniques for isolating mRNA, reverse transcribing a primer hybridized to mRNA to generate a first cDNA strand, extending a primer to make a second cDNA strand complementary to the first cDNA strand, isolating the double stranded cDNA and cloning the double stranded cDNA are well known to those skilled in the art and are described in *Current Protocols in Molecular Biology*, John Wiley & Sons, Inc. 1997 and Sambrook et al., Molecular Cloning: A Laboratory Manual, Second Edition, Cold Spring Harbor Laboratory Press, 1989, the entire disclosures of which are incorporated herein by reference.

Alternatively, other procedures may be used for obtaining fill-length cDNAs or extended cDNAs. In one approach, full-length or extended cDNAs are prepared from mRNA and cloned into double stranded phagemids as follows. The cDNA library in the double stranded phagemids is then rendered single stranded by treatment with an endonuclease, such as the Gene II product of the phage F1 and an exonuclease (Chang et al., *Gene* 127:95–8, 1993). A biotinylated oligonucleotide comprising the sequence of a fragment of an EST-related nucleic acid is hybridized to the single stranded phagemids. Preferably, the fragment comprises at least 10, 12, 15, 17, 18, 20, 23, 25, or 28 consecutive nucleotides of the sequences of SEQ ID NOs. 24–3883 and 7744–19335.

Hybrids between the biotinylated oligonucleotide and phagemids are isolated by incubating the hybrids with streptavidin coated paramagnetic beads and retrieving the beads with a magnet (Fry et al., *Biotechniques*, 13: 124–131, 1992). Thereafter, the resulting phagemids are released from the beads and converted into double stranded DNA using a primer specific for the 5' EST or consensus contigated 5' EST sequence used to design the biotinylated oligonucleotide. Alternatively, protocols such as the Gene Trapper kit (Gibco BRL) may be used. The resulting double stranded DNA is transformed into bacteria. Extended cDNAs or full length cDNAs containing the 5' EST or consensus contigated 5' EST sequence are identified by colony PCR or colony hybridization.

EXAMPLE 19

Extended cDNAs and Full Length cDNAs

The procedure described in Example 17 was used to obtain extended cDNAs or full length cDNAs derived from 5' ESTs in a variety of tissues. The following list provides a few examples of thus obtained cDNAs.

Using this procedure, the full length cDNA of SEQ ID NO.1 (internal identification number 58-34-2-E7-FL2) was obtained. This cDNA encodes the signal peptide MWWFQQGLSFLPSALVIWTSA(SEQ ID NO.2) having a von Heijne score of 5.5.

Using this approach, the full length cDNA of SEQ ID NO.3 (internal identification number 48-19-3-G1-FL1) was obtained. This cDNA encodes the signal peptide MKKV-LLLITAILAVAVG (SEQ ID NO. 4) having a von Heijne score of 8.2.

The full length cDNA of SEQ ID NO.5 (internal identification number 58-35-2-F10-FL2) was also obtained using this procedure. This cDNA encodes a signal peptide LWLL-FFLVTAIHA (SEQ ID NO.6) having a von Heijne score of 10.7.

Furthermore, the polypeptides encoded by the extended or full-length cDNAs may be screened for the presence of known structural or functional motifs or for the presence of signatures, small amino acid sequences which are well conserved amongst the members of a protein family. The results obtained for the polypeptides encoded by a few full-length cDNAs derived from 5' ESTs that were screened for the presence of known protein signatures and motifs using the Proscan software from the GCG package and the Prosite 15.0 database are provided below.

The protein of SEQ ID NO. 8 encoded by the full-length cDNA SEQ ID NO. 7 (internal designation 78-8-3-E6-CL0_1C) and expressed in adult prostate belong to the phosphatidylethanolamine-binding protein from which it exhibits the characteristic PROSITE signature. Proteins from this widespread family, from nematodes to fly, yeast, rodent and primate species, bind hydrophobic ligands such as phospholipids and nucleotides. They are mostly expressed in brain and in testis and are thought to play a role in cell growth and/or maturation, in regulation of the sperm maturation, motility and in membrane remodeling. They may act either through signal transduction or through oxidoreduction reactions (for a review see Schoentgen and Jollès, *FEBS Letters*, 369:22–26 (1995)). Taken together, these data suggest that the protein of SEQ ID NO. 8 may play a role in cell growth, maturation and in membrane remodeling and/or may be related to male fertility. Thus, these protein may be useful in diagnosing and/or treating cancer, neurodegenerative diseases, and/or disorders related to male fertility and sterility.

The protein of SEQ ID NOs. 10 encoded by the extended cDNA SEQ ID NO. 9 (internal designation 59-9-2-E6-FL0_1C) belong to the stomatin or band 7 family. The human stomatin is an integral membrane phosphoprotein thought to regulate the cation. conductance by interacting with other proteins of the junctional complex of the membrane skeleton (Gallagher and Forget, *J. Biol. Chem.*, 270:26358–26363 (1995)). The protein of SEQ ID NO. 10 exhibits the PROSITE signature typical for the band 7 family signature. Taken together, these data suggest that the protein of SEQ ID NO. 10 plays a role in the regulation of ion transport, hence in the control of cellular volume. This protein may find applications in diagnosing and/or treating stomatocytosis and/or cryohydrocytosis.

The protein of SEQ ID NO. 12 encoded by the extended cDNA SEQ ID NO. 11 (internal designation 19-10-1-C2-CL1 3) shows homology with the bovine subunit B14.5B of the NADH-ubiquinone oxidureductase complex (Arizmendi et al., *FEBS Left.*, 313:80–84 (1992) and Swissprot accession number Q02827). This complex is the first of four complexes located in the inner mitochondrial membrane which make up the mitochondrial electron transport chain. Complex I is involved in the dehydrogenation of NADH and the transportation of electrons to coenzyme Q. It is composed of 7 subunits encoded by the mitochondrial genome and 34 subunits encoded by the nuclear genome. It is also thought to play a role in the regulation of apoptosis and necrosis. Mitochondriocytopathies due to complex I deficiency are frequently encountered and affect tissues with a high energy demand such as brain (mental retardation, convulsions, movement disorders), heart (cardiomyopathy, conduction disorders), kidney (Fanconi syndrome), skeletal muscle (exercise intolerance, muscle weakness, hypotonia) and/or eye (opthmaloplegia, ptosis, cataract and retinopathy). For a review on complex I see Smeitink et al., *Hum. Mol. Gent.*, 7:1573–1579 (1998). Taken together, these data suggest that the protein of SEQ ID NO. 12 may be part of the mitochondrial energy-generating system, probably as a subunit of the NADH-ubiquinone oxidoreductase complex. Thus, this protein or part therein, may find applications in diagnosing and/or treating several disorders including, but not limited to, brain disorders (mental retardation, convulsions, movement disorders), heart disorders (cardiomyopathy, conduction disorders), kidney disorders (Fanconi syndrome), skeletal muscle disorders (exercise intolerance, muscle weakness, hypotonia) and/or eye disorders opthmalmoplegia, ptosis, cataract and retinopathy).

The protein of SEQ ID NO. 14 encoded by the extended cDNA SEQ ID NO. 13 (internal designation 77-13-1-C11-FL2__2C) exhibits an extensive homology with a murine protein named MP1 for MEK binding partner 1 (Genbank accession number AF082526). MP1 was shown to enhance enzymatic activation of mitogen-activated protein (MAP) kinase cascade. The MAP kinase pathway is one of the important enzymatic cascade that is conserved among all eukaryotes from yeast to human. This kind of pathway is involved in vital functions such as the regulation of growth, differentiation and apoptosis. MP1 probably acts by facilitating the interaction of the two sequentially acting kinases MEK1 and ERK1 (Schaffer et al., *Science*, 281:1668–1671 (1998)). Taken together, these data suggest that the protein of SEQ ID NO. 14 may be involved in regulating protein-protein interaction in the signal transduction pathways. Thus, this protein may be useful in diagnosing and/or treating several types of disorders including, but not limited to, cancer, neurodegenerative diseases, cardiovascular disorders, hypertension, renal injury and repair and septic shock.

Bacterial clones containing plasmids containing the full length cDNAs described above are presently stored in the inventor's laboratories under the internal identification numbers provided above. The inserts may be recovered from the deposited materials by growing an aliquot of the appropriate bacterial clone in the appropriate medium. The plasmid DNA can then be isolated using plasmid isolation procedures familiar to those skilled in the art such as alkaline lysis minipreps or large scale alkaline lysis plasmid isolation procedures. If desired the plasmid DNA may be further enriched by centrifugation on a cesium chloride gradient, size exclusion chromatography, or anion exchange chromatography. The plasmid DNA obtained using these procedures may then be manipulated using standard cloning techniques familiar to those skilled in the art. Alternatively, a PCR can be done with primers designed at both ends of the EST insertion. The PCR product which corresponds to the 5' EST can then be manipulated using standard cloning techniques familiar to those skilled in the art.

Using any of the above described methods in section IV, a plurality of extended cDNAs containing full-length protein coding sequences or portions of the protein coding sequences may be provided as cDNA libraries for subsequent evaluation of the encoded proteins or use in diagnostic assays as described below.

V. Expression of Proteins Encoded by EST-related Nucleic Acids

EST-related nucleic acids, fragments of EST-related nucleic acids, positional segments of EST-related nucleic acids, and fragments of positional segments of EST-related nucleic acids may be used to express the polypeptides which they encode. In particular, they may be used to express EST-related polypeptides, fragments of EST-related polypeptides, positional segments of EST-related polypeptides, or fragments of positional segments of EST-related polypeptides. In some embodiments, the EST-related nucleic acids, positional segments of EST-related nucleic acids, and fragments of positional segments of EST-related nucleic acids may be used to express the full polypeptide (i.e. the signal peptide and the mature polypeptide) of a secreted protein, the mature protein (i.e. the polypeptide generated after cleavage of the signal peptide), or the signal peptide of a secreted protein. If desired, nucleic acids encoding the signal peptide may be used to facilitate secretion of the expressed protein. It will be appreciated that a plurality of EST-related nucleic acids, fragments of EST-related nucleic acids, positional segments of EST-related nucleic acids, or fragments of positional segments of EST-related nucleic acids may be simultaneously cloned into expression vectors to create an expression library for analysis of the encoded proteins as described below.

EXAMPLE 20

Expression of the Proteins Encoded by the Genes Corresponding to the 5' ESTs or Consensus Contigated 5' ESTs To express their encoded proteins the EST-related nucleic acids, fragments of EST-related nucleic acids, positional segments of EST-related nucleic acids, or fragments of positional segments of EST-related nucleic acids are cloned into a suitable expression vector. In some instances, nucleic acids encoding EST-related polypeptides, fragments of EST-related polypeptides, positional segments of EST-related polypeptides or fragments of positional segments of EST-related polypeptides may be cloned into a suitable expression vector.

In some embodiments, the nucleic acids inserted into the expression vector may comprise the coding sequence of a sequence selected from the group consisting of 24–3883. In other embodiments, the nucleic acids inserted into the expression vector may comprise may comprise the full coding sequence (i.e. the nucleotides encoding the signal peptide and the mature polypeptide) of one of SEQ ID NOs.

1339–2059. In some embodiments, the nucleic acid inserted into the expression vector may comprise the nucleotides of one of the sequences of SEQ ID NOs. 1339–2059 which encode the mature polypeptide (i.e. the nucleotides encoding the polypeptide generated after cleavage of the signal peptide). In further embodiments, the nucleic acids inserted into the expression vector may comprise the nucleotides of SEQ ID NOs. 24–383 and 1339–2059 which encode the signal peptide to facilitate secretion of the expressed protein. The nucleic acids inserted into the expression vectors may also contain sequences upstream of the sequences encoding the signal peptide, such as sequences which regulate expression levels or sequences which confer tissue specific expression.

The nucleic acid inserted into the expression vector may encode a polypeptide comprising the one of the sequences of SEQ ID NOs. 3884–7743. In some embodiments, the nucleic acid inserted into the expression vector may encode the full polypeptide sequence (i.e. the signal peptide and the mature polypeptide) included in one of SEQ ID NOs. 5199–5919. In other embodiments, the nucleic acid inserted into the expression vector may encode the mature polypeptide (i.e. the polypeptide generated after cleavage of the signal peptide) included in one of the sequences of SEQ ID NOs. 5199–5919. In further embodiments, the nucleic acids inserted into the expression vector may encode the signal peptide included in one of the sequences of 3884–4243 and 5199–5919.

The nucleic acid encoding the protein or polypeptide to be expressed is operably linked to a promoter in an expression vector using conventional cloning technology. The expression vector may be any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism in which the expression vector is introduced, as explained by Hatfield, et al., U.S. Pat. No. 5,082,767, incorporated herein by this reference.

The following is provided as one exemplary method to express the proteins encoded by the nucleic acids described above. In some instances the nucleic acid encoding the protein or polypeptide to be expressed includes a methionine initiation codon and a poly A signal. If the nucleic acid encoding the polypeptide to be expressed lacks a methionine to serve as the initiation site, an initiating methionine can be introduced next to the first codon of the nucleic acid using conventional techniques. Similarly, if the nucleic acid encoding the protein or polypeptide to be expressed lacks a polyA signal, this sequence can be added to the construct by, for example, splicing out the polyA signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex thymidine kinase promoter and the selectable neomycin gene. The nucleic acid encoding the polypeptide to be expressed is obtained by PCR from the bacterial vector using oligonucleotide primers complementary to the nucleic acid encoding the protein or polypeptide to be expressed and containing restriction endonuclease sequences for PstI incorporated into the 5' primer and BglII at the 5' end of 3' primer, taking care to ensure that the nucleic acid encoding the protein or polypeptide to be expressed is correctly positioned with respect to the poly A signal. The purified fragment obtained from the resulting PCR reaction is digested with PstI, blunt ended with an exonuclease, digested with BglII, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 g/ml G418 (Sigma, St. Louis, Mo.).

Alternatively, the nucleic acid encoding the protein or polypeptide to be expressed may be cloned into pED6dpc2 as described above. The resulting pED6dpc2 constructs may be transfected into a suitable host cell, such as COS 1 cells. Methotrexate resistant cells are selected and expanded. The expressed protein or polypeptide may be isolated, purified, or enriched as described above.

To confirm expression of the desired protein or polypeptide, the proteins or polypeptides produced by cells containing a vector with a nucleic acid insert encoding the protein or polypeptide are compared to those lacking such an insert. The expressed proteins are detected using techniques familiar to those skilled in the art such as Coomassie blue or silver staining or using antibodies against the protein or polypeptide encoded by the nucleic acid insert. Antibodies capable of specifically recognizing the protein of interest may be generated using synthetic 15-mer peptides having a sequence encoded by the appropriate nucleic acid. The synthetic peptides are injected into mice to generate antibody to the polypeptide encoded by the nucleic acid.

If the proteins or polypeptides encoded by the nucleic acid inserts are secreted, medium prepared from the host cells or organisms containing an expression vector which contains a nucleic acid insert encoding the desired protein or polypeptide is compared to medium prepared from the control cells or organism. The presence of a band in medium from the cells containing the nucleic acid insert which is absent from preparations from the control cells indicates that the protein or polypeptide encoded by the nucleic acid insert is being expressed and secreted. Generally, the band corresponding to the protein encoded by the nucleic acid insert will have a mobility near that expected based on the number of amino acids in the open reading frame of the nucleic acid insert. However, the band may have a mobility different than that expected as a result of modifications such as glycosylation, ubiquitination, or enzymatic cleavage.

Alternatively, if the protein expressed from the above expression vectors does not contain sequences directing its secretion, the proteins expressed from host cells containing an expression vector with an insert encoding a secreted protein or portion thereof can be compared to the proteins expressed in control host cells containing the expression vector without an insert. The presence of a band in samples from cells containing the expression vector with an insert which is absent in samples from cells containing the expression vector without an insert indicates that the desired protein or portion thereof is being expressed. Generally, the band will have the mobility expected for the secreted protein or portion thereof. However, the band may have a mobility different than that expected as a result of modifications such as glycosylation, ubiquitination,or enzymatic cleavage.

The expressed protein or polypeptide may be purified, isolated or enriched using a variety of methods. In some methods, the protein or polypeptide may be secreted into the culture medium via a native signal peptide or a heterologous signal peptide operably linked thereto. In some methods, the protein or polypeptide may be linked to a heterologous polypeptide which facilitates its isolation, purification, or enrichment such as a nickel binding polypeptide. The protein or polypeptide may also be obtained by gel electrophoresis, ion exchange chromatography, size chromatography, hplc, salt precipitation, immunoprecipitation, a combination of any of the preceding methods, or any of the isolation, purification, or enrichment techniques familiar to those skilled in the art.

The protein encoded by the nucleic acid insert may also be purified using standard immunochromatography techniques using immunoaffinity chromatography with antibodies directed against the encoded protein or polypeptide as described in more detail below. If antibody production is not possible, the nucleic acid insert encoding the desired protein or polypeptide may be incorporated into expression vectors designed for use in purification schemes employing chimeric polypeptides. In such strategies, the coding sequence of the nucleic acid insert is ligated in frame with the gene encoding the other half of the chimera. The other half of the chimera may be -globin or a nickel binding polypeptide. A chromatography matrix having antibody to -globin or nickel attached thereto is then used to purify the chimeric protein. Protease cleavage sites may be engineered between the β-globin gene or the nickel binding polypeptide and the extended cDNA or portion thereof. Thus, the two polypeptides of the chimera may be separated from one another by protease digestion.

One useful expression vector for generating -globin chimerics is pSG5 (Stratagene), which encodes rabbit -globin. Intron II of the rabbit -globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (*Basic Methods in Molecular Biolog*, L. G. Davis, M. D. Dibner, and J. F. Battey, ed., Elsevier Press, N.Y., 1986) and many of the methods are available from Stratagene, Life Technologies, Inc., or Promega. Polypeptide may additionally be produced from the construct using in vitro translation systems such as the In vitro Express™ Translation Kit (Stratagene).

Following expression and purification of the proteins or polypeptides encoded by the nucleic acid inserts, the purified proteins may be tested for the ability to bind to the surface of various cell types as described in Example 21 below. It will be appreciated that a plurality of proteins expressed from these nucleic acid inserts may be included in a panel of proteins to be simultaneously evaluated for the activities specifically described below, as well as other biological roles for which assays for determining activity are available.

EXAMPLE 21

Analysis of Secreted Proteins or Polypeptides to Determine Whether They Bind to the Cell Surface The EST-related nucleic acids, fragments of EST-related nucleic acids, positional segments of EST-related nucleic acids, fragments of positional segments of EST-related nucleic acids, nucleic acids encoding the EST-related polypeptides, nucleic acids encoding fragments of the EST-related polypeptides, nucleic acids encoding positional segments of EST-related polypeptides, or nucleic acids encoding fragments of positional segments of EST-related polypeptides are cloned into expression vectors such as those described in Example 20. The encoded proteins or polypeptides are purified, isolated, or enriched as described above. Following purification, isolation, or enrichment, the proteins or polypeptides are labeled using techniques known to those skilled in the art. The labeled proteins or polypeptides are incubated with cells or cell lines derived from a variety of organs or tissues to allow the proteins to bind to any receptor present on the cell surface. Following the incubation, the cells are washed to remove non-specifically bound proteins or polypeptides. The specifically bound labeled proteins or polypeptides are detected by autoradiography. Alternatively, unlabeled proteins or polypeptides may be incubated with the cells and detected with antibodies having a detectable label, such as a fluorescent molecule, attached thereto.

Specificity of cell surface binding may be analyzed by conducting a competition analysis in which various amounts of unlabeled protein or polypeptide are incubated along with the labeled protein or polypeptide. The amount of labeled protein or polypeptide bound to the cell surface decreases as the amount of competitive unlabeled protein or polypeptide increases. As a control, various amounts of an unlabeled protein or polypeptide unrelated to the labeled protein or polypeptide is included in some binding reactions. The amount of labeled protein or polypeptide bound to the cell surface does not decrease in binding reactions containing increasing amounts of unrelated unlabeled protein, indicating that the protein or polypeptide encoded by the nucleic acid binds specifically to the cell surface.

As discussed above, human proteins have been shown to have a number of important physiological effects and, consequently, represent a valuable therapeutic resource. The human proteins or polypeptides made as described above may be evaluated to determine their physiological activities as described below.

EXAMPLE 22

Assaying the Expressed Proteins or Polypeptides for Cytokine Cell Proliferation or Cell Differentiation Activity As discussed above, some human proteins act as cytokines or may affect cellular proliferation or differentiation. Many protein factors discovered to date, including all known cytokines, have exhibited activity in one or more factor dependent cell proliferation assays, and hence the assays serve as a convenient confirmation of cytokine activity. The activity of a protein or polypeptide of the present invention is evidenced by any one of a number of routine factor dependent cell proliferation assays for cell lines including, without limitation, 32D, DA2, DA1G, T10, B9, B9/11, BaF3, MC9/G, M$^+$ (preB M$^+$), 2E8, RB5, DA1, 123, T1165, HT2, CTLL2, TF-1, Mo7c and CMK. The proteins or polypeptides prepared as described above may be evaluated for their ability to regulate T cell or thymocyte proliferation in assays such as those described above or in the following references, which are incorporated herein by reference: *Current Protocols in Immunology*, Ed. by J. E. Coligan et al., Greene Publishing Associates and Wiley-Interscience; Takai et al. *J. Immunol.* 137:3494–3500, 1986, Bertagnolli et al. *J. Immunol.*145:1706–1712, 1990, Bertagnolli et al., *Cellular Immunology* 133:327–341, 1991. Bertagnolli, et al. *J. Immunol.* 149:3778–3783, 1992; Bowman et al. *J. Immunol.* 152:1756–1761, 1994.

In addition, numerous assays for cytokine production and/or the proliferation of spleen cells, lymph node cells and thymocytes are known. These include the techniques disclosed in *Current Protocols in Immunology.* J. E. Coligan et al. Eds., 1:3.12.1–3.12.14, John Wiley and Sons, Toronto. 1994; and Schreiber, R. D. In *Current Protocols in Immunology., supra* 1: 6.8.1–6.8.8.

The proteins or polypeptides prepared as described above may also be assayed for the ability to regulate the proliferation and differentiation of hematopoietic or lymphopoietic cells. Many assays for such activity are familiar to those skilled in the art, including the assays in the following references, which are incorporated herein by reference: Bottomly et al., In *Current Protocols in Immunology., supra.* 1:6.3.1–6.3.12,; deVries et al., *J. Exp. Med.* 173:1205–1211, 1991; Moreau et al., *Nature* 36:690–692, 1988; Greenberger et al. *Proc. Natl. Acad. Sci. USA.* 80:2931–2938, 1983; Nordan, R., In *Current Protocols in Immunology., supra.* 1:6.6.1–6.6.5; Smith et al., *Proc. Nat. Acad. Sci. USA.* 83:1857–1861, 1986; Bennett et al. in *Current Protocols in Immunology supra.* 1: 6.15.1; Ciarletta et al. In *Current Protocols in Immunology. supra* 1:6.13.1.

The proteins or polypeptides prepared as described above may also be assayed for their ability to regulate T-cell responses to antigens. Many assays for such activity are familiar to those skilled in the art, including the assays described in the following references, which are incorporated herein by reference: Chapter 3 (In vitro Assays for Mouse Lymphocyte Function), Chapter 6 (Cytokines and Their Cellular Receptors) and Chapter 7, (Immunologic Studies in Humans) in *Current Protocols in Immunology supra*; Weinberger et al., *Proc. Natl Acad. Sci. USA* 77:6091–6095, 1980; Weinberger et al., *Eur. J. Immun.* 11:405–411, 1981; Takai et al., *J. Immunol.* 137:3494–3500, 1986; Takai et al., *J. Immunol.* 140:508–512, 1988.

Those proteins or polypeptides which exhibit cytokine, cell proliferation, or cell differentiation activity may then be formulated as pharmaceuticals and used to treat clinical conditions in which induction of cell proliferation or differentiation is beneficial.

Alternatively, as described in more detail below, nucleic acids encoding these proteins or polypeptides or nucleic acids regulating the expression of these proteins or polypeptides may be introduced into appropriate host cells to increase or decrease the expression of the proteins or polypeptides as desired.

EXAMPLE 23

Assaying the Expressed Proteins or Polypeptides for Activity as Immune System Regulators The proteins or polypeptides prepared as described above may also be evaluated for their effects as immune regulators. For example, the proteins or polypeptides may be evaluated for their activity to influence thymocyte or splenocyte cytotoxicity. Numerous assays for such activity are familiar to those skilled in the art including the assays described in the following references, which are incorporated herein by reference: Chapter 3 (In vitro Assays for Mouse Lymphocyte Function 3.1–3.19) and Chapter 7 (Immunologic studies in Humans) in *Current Protocols in Immunology*, J. E. Coligan et al. Eds, Greene Publishing Associates and Wiley-Interscience; Herrmann et al., *Proc. Natl. Acad Sci. USA* 78:2488–2492, 1981; Herrmann et al., *J. Immunol.* 128:1968–1974, 1982; Handa et al., *J. Immunol.* 135:1564–1572, 1985; Takai et al., *J. Immunol.* 137:3494–3500, 1986; Takai et al., *J. Immunol.* 140:508–512, 1988; Bowman et al., *J. Virology* 61:1992–1998; Bertagnolli et al. *Cell. Immunol.* 133:327–341, 1991; Brown et al., *J. Immunol.* 153:3079–3092, 1994.

The proteins or polypeptides prepared as described above may also be evaluated for their effects on T-cell dependent immunoglobulin responses and isotype switching. Numerous assays for such activity are familiar to those skilled in the art, including the assays disclosed in the following references, which are incorporated herein by reference: Maliszewski, *J. Immunol.* 144:3028–3033, 1990; Mond et al. in *Current Protocols in Immunology*, 1:3.8.1–3.8.16, supra.

The proteins or polypeptides prepared as described above may also be evaluated for their effect on immune effector cells, including their effect on Th1 cells and cytotoxic lymphocytes. Numerous assays for such activity are familiar to those skilled in the art, including the assays disclosed in the following references, which are incorporated herein by reference: Chapter 3 (In vitro Assays for Mouse Lymphocyte Function 3.1–3.19) and Chapter 7 (Immunologic Studies in Humans) in *Current Protocols in Immunology, supra*; Takai et al., *J. Immunol.* 137:3494–3500, 1986; Takai et al.; *J. Immunol.* 140:508–512, 1988; Bertagnolli et al., *J. Immunol.* 149:3778–3783, 1992.

The proteins or polypeptides prepared as described above may also be evaluated for their effect on dendritic cell mediated activation of naive T-cells. Numerous assays for such activity are familiar to those skilled in the art, including the assays disclosed in the following references, which are incorporated herein by reference: Guery et al., *J. Immunol.* 134:536–544, 1995; Inaba et al., *J. Exp. Med.* 173:549–559, 1991; Macatonia et al., *J. Immunol.* 154:5071–5079, 1995; Porgador et al., *J. Exp. Med.* 182:255–260, 1995; Nair et al., *J. Virol.* 67:4062–4069, 1993; Huang et al., *Science* 264:961–965, 1994; Macatonia et al., *J. Exp. Med* 169:1255–1264, 1989; Bhardwaj et al., *Journal of Clinical Investigation* 94:797–807, 1994; and Inaba et al., *J. Exp. Med* 172:631–640, 1990.

The proteins or polypeptides prepared as described above may also be evaluated for their influence on the lifetime of lymphocytes. Numerous assays for such activity are familiar to those skilled in the art, including the assays disclosed in the following references, which are incorporated herein by reference: Darzynkiewicz et al., *Cytometry* 13:795–808, 1992; Gorczyca et al., *Leukemia* 7:659–670, 1993; Gorczyca et al., *Cancer Res.* 53:1945–1951, 1993; Itoh et al., *Cell* 66:233–243, 1991; Zacharchuk, *J. Immunol.* 145:4037–4045, 1990; Zamai et al., *Cytometry* 14:891–897, 1993; Gorczyca et al., *Int. J. Oncol.* 1:639–648, 1992.

The proteins or polypeptides prepared as described above may also be evaluated for their influence on early steps of T-cell commitment and development. Numerous assays for such activity are familiar to those skilled in the art, including without limitation the assays disclosed in the following references, which are incorporated herein by references: Antica et al., *Blood* 84:111–117, 1994; Fine et al., *Cell. Immunol.* 155:111–122, 1994; Galy et al., *Blood* 85:2770–2778, 1995; Toki et al., *Proc. Nat. Acad Sci. USA* 88:7548–7551, 1991.

Those proteins or polypeptides which exhibit activity as immune system regulators activity may then be formulated as pharmaceuticals and used to treat clinical conditions in which regulation of immune activity is beneficial. For example, the protein or polypeptide may be useful in the treatment of various immune deficiencies and disorders (including severe combined immunodeficiency), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases caused by viral, bacterial, fungal or other infection may be treatable using the protein or polypeptide including infections by HIV, hepatitis viruses, herpesviruses, mycobacteria, Leishmania spp., plamodium and various fungal infections such as candidiasis. Of course, in this regard, a protein or polypeptide may also be useful where a boost to the immune system generally may be desirable, i.e., in the treatment of cancer.

Alternatively, the proteins or polypeptides prepared as described above may be used in treatment of autoimmune disorders including, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease. Such a protein or polypeptide may also to be useful in the treatment of allergic reactions and conditions, such as asthma (particularly allergic asthma) or other respiratory problems. Other conditions, in which immune suppression is desired (including, for example, organ transplantation), may also be treatable using the protein or polypeptide.

Using the proteins or polypeptides of the invention it may also be possible to regulate immune responses either up or down. Down regulation may involve inhibiting or blocking an immune response already in progress or may involve preventing the induction of an immune response. The functions of activated T-cells may be inhibited by suppressing T cell responses or by inducing specific tolerance in T cells, or both. Immunosuppression of T cell responses is generally an active non-antigen-specificprocess which requires continuous exposure of the T cells to the suppressive agent. Tolerance, which involves inducing non-responsiveness or anergy in T cells, is distinguishable from immunosuppression in that it is generally antigen-specific and persists after the end of exposure to the tolerizing agent. Operationally, tolerance can be demonstrated by the lack of a T cell response upon reexposure to specific antigen in the absence of the tolerizing agent.

Down regulating or preventing one or more antigen functions (including without limitation B lymphocyte antigen functions, such as, for example, B7 costimulation), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation, can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al. *Science* 257:789–792 (1992)and Turka et al., *Proc. Natl. Acad. Sci USA*, 89:11102–11105 (1992). In addition, murine models of GVHD (see Paul ed., *Fundamental Immunology*, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor/ligand interactions of B lymphocyte antigens can be used to inhibit T cell activation and prevent production of autoantibodies or T cell-derived cytokines which potentially involved in the disease process. Additionally, blocking reagents may induce antigen-specifictolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/pr/pr mice or NZB hybrid mice, murine autoimmuno collagen arthritis, diabetes mellitus in OD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may involve either enhancing an existing immune response or eliciting an initial immune response as shown by the following examples. For instance, enhancing an immune response through stimulating B lymphocyte antigen function may be useful in cases of viral infection. In addition, systemic viral diseases such as influenza, the common cold, and encephalitis might be alleviated by the administration of stimulatory form of B lymphocyte antigens systemically.

Alternatively, antiviral immune responses may be enhanced in an infected patient by removing T cells from the patient, costimulating the T cells in vitro with viral antigen-pulsed APCs either expressing the proteins or polypeptides described above or together with a stimulatory form of the protein or polypeptide and reintroducing the in vitro primed T cells into the patient. The infected cells would now be capable of delivering a costimulatory signal to T cells in vivo, thereby activating the T cells.

In another application, upregulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with one of the above-described nucleic acids encoding a protein or polypeptide can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the protein or polypeptide encoded by the nucleic acids described above having the activity of a B lymphocyte antigen(s) on the surface of the tumor cell provides the necessary costimulation signal to T cells to induce a T cell mediated immune response against the transfected tumor cells. In addition, tumor cells which lack or which fail to reexpress sufficient amounts of MHC class I or MHC class II molecules can be transfected with nucleic acids encoding all or a portion of (e.g., a cytoplasmic-domain truncated portion) of an MHC class I chain and microglobulin or an MHC class II α chain and an MHC class II chain to thereby express MHC class I or MHC class II proteins on the cell surface, respectively. Expression of the appropriate MHC class I or class II molecules in conjunction with a peptide having the activity of a B lymphocyte antigen (e.g., B7-1, B7-2, B7-3) induces a T cell mediated immune response against the transfected tumor cell. Optionally, a nucleic acid encoding an antisense construct which blocks expression of an MHC class II associated protein, such as the invariant chain, can also be cotransfected with a DNA encoding a protein or polypeptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject. Alternatively, as described in more detail below, nucleic acids encoding these immune system regulator proteins or polypeptides or nucleic acids regulating the expression of such proteins or polypeptides may be introduced into appropriate host cells to increase or decrease the expression of the proteins as desired.

EXAMPLE 24

Assaying the Expressed Proteins or Polypeptides for Hematopoiesis Regulating Activity The proteins or polypeptides encoded by the nucleic acids described above may also be evaluated for their hematopoiesis regulating activity. For example, the effect of the proteins or polypeptides on embryonic stem cell differentiation may be evaluated. Numerous assays for such activity are familiar to those skilled in the art, including the assays disclosed in the following references, which are incorporated herein by reference: Johansson et al. Cell. Biol. 15:141–151, 1995; Keller et al., Mol. Cell. Biol. 13:473–486, 1993; McClanahan et al., Blood 81:2903–2915, 1993.

The proteins or polypeptides encoded by the nucleic acids described above may also be evaluated for their influence on the lifetime of stem cells and stem cell differentiation. Numerous assays for such activity are familiar to those skilled in the art, including the assays disclosed in the following references, which are incorporated herein by reference: Freshney, M. G. Methylcellulose Colony Forming Assays, in Culture of Hematopoietic Cells. R. I. Freshney, et al. Eds. pp. 265–268, Wiley-Liss, Inc., New York, N.Y. 1994; Hirayama et al., Proc. Natl. Acad. Sci. USA 89:5907–5911, 1992; McNiece, I. K. and Briddell, R. A. Primitive Hematopoietic Colony Forming Cells with High Proliferative Potential, in Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Ploemacher, R. E. Cobblestone Area Forming Cell Assay, In Culture of Hematopoietic Cells. R. I. Freshney, et al. Eds. pp. 1–21, Wiley-Liss, Inc., New York, N.Y. 1994; Spooncer, E., Dexter, M. and Allen, T. Long Term Bone Marrow Cultures in the Presence of Stromal Cells, in Culture of Hematopoietic Cells. R. I. Freshney, et al. Eds. pp. 163–179, Wiley-Liss, Inc., New York, N.Y. 1994; and Sutherland, H. J. Long Term Culture Initiating Cell Assay, in Culture of Hematopoietic Cells. R. I. Freshney, et al. Eds. pp. 139–162, Wiley-Liss, Inc., New York, N.Y. 1994.

Those proteins or polypeptides which exhibit hematopoiesis regulatory activity may then be formulated as pharmaceuticals and used to treat clinical conditions in which regulation of hematopoeisis is beneficial. For example, a protein or polypeptide of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantion, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy. Alternatively, as described in more detail below, nucleic acids encoding these proteins or polypeptides or nucleic acids regulating the expression of these proteins or polypeptides may be introduced into appropriate host cells to increase or decrease the expression of the proteins as desired.

EXAMPLE 25

Assaying the Expressed Proteins or Polypeptides for Regulation of Tissue Growth The proteins or polypeptides encoded by the nucleic acids described above may also be evaluated for their effect on tissue growth. Numerous assays for such activity are familiar to those skilled in the art, including the assays disclosed in International Patent Publication No. WO95/16035, International Patent Publication No. WO95/05846 and International Patent Publication No. WO91/07491, which are incorporated herein by reference.

Assays for wound healing activity include, without limitation, those described in: Winter, *Epidermal Wound Healing*, pps. 71–112 (Maibach, H1 and Rovee, D T, eds.), Year Book Medical Publishers, Inc., Chicago, as modified by Eaglstein and Mertz, J. Invest. Dermatol 71:382–84 (1978) which are incorporated herein by reference.

Those proteins or polypeptides which are involved in the regulation of tissue growth may then be formulated as pharmaceuticals and used to treat clinical conditions in which regulation of tissue growth is beneficial. For example, a protein or polypeptide may have utility in compositions used for bone, cartilage, tendon, ligament and/or nerve tissue growth or regeneration, as well as for wound healing and tissue repair and replacement, and in the treatment of burns, incisions and ulcers.

A protein or polypeptide encoded by the nucleic acids described above which induces cartilage and/or bone growth in circumstances where bone is not normally formed, has application in the healing of bone fractures and cartilage damage or defects in humans and other animals. Such a preparation employing a protein or polypeptide of the invention may have prophylactic use in closed as well as open fracture reduction and also in the improved fixation of artificial joints. De novo bone synthesis induced by an osteogenic agent contributes to the repair of congenital, trauma induced, or oncologic resection induced craniofacial defects, and also is useful in cosmetic plastic surgery.

A protein or polypeptide of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the proteins or polypeptides encoded by the nucleic acids described above is tendon/ligament formation. A protein or polypeptide encoded by the nucleic acids described above, which induces tendon/ligament-liketissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-liketissue formation induced by a protein or polypeptide of the present invention contributes to the repair of tendon or ligaments defects of congenital, traumatic or other origin and is also useful in cosmetic plastic surgery for attachment or repair of tendons or ligaments. The proteins or polypeptides of the present invention may provide an environment to attract tendon- or ligament-forming cells, stimulate growth of tendon- or ligament-forming cells, induce differentiation of progenitors of tendon- or ligament-forming cells, or induce growth of tendon/ligamentcells or progenitors ex vivo for return in vivo to effect tissue repair. The proteins or polypeptides of the invention may also be useful in the treatment of tendinitis, carpal tunnel syndrome and other tendon or ligament defects. The therapeutic compositions may also include an appropriate matrix and/or sequestering agent as a carrier as is well known in the art.

The proteins or polypeptides of the present invention may also be useful for proliferation of neural cells and for regeneration of nerve and brain tissue, i.e., for the treatment of central and peripheral nervous system diseases and neuropathies, as well as mechanical and traumatic disorders, which involve degeneration, death or trauma to neural cells or nerve tissue. More specifically, a protein or polypeptide may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovasculardiseases such as stroke. Peripheral neuropathies resulting from chemotherapy or other medical therapies may also be treatable using a protein or polypeptide of the invention.

Proteins or polypeptides of the invention may also be useful to promote better or faster closure of non-healing wounds, including without limitation pressure ulcers, ulcers associated with vascular insufficiency, surgical and traumatic wounds, and the like.

It is expected that a protein or polypeptide of the present invention may also exhibit activity for generation or regeneration of other tissues, such as organs (including, for example, pancreas, liver, intestine, kidney, skin, endothelium) muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to generate. A protein or polypeptide of the invention may also exhibit angiogenic activity.

A protein or polypeptide of the present invention may also be useful for gut protection or regeneration and treatment of lung or liver fibrosis, reperfusion injury in various tissues, and conditions resulting from systemic cytokine damage.

A protein or polypeptide of the present invention may also be useful for promoting or inhibiting differentiation of tissues described above from precursor tissues or cells; or for inhibiting the growth of tissues described above.

Alternatively, as described in more detail below, nucleic acids encoding tissue growth regulating activity proteins or polypeptides or nucleic acids regulating the expression of such proteins or polypeptides may be introduced into appropriate host cells to increase or decrease the expression of the proteins as desired.

EXAMPLE 26

Assaying the Expressed Proteins or Polypeptides for Regulation of Reproductive Hormones The proteins or polypeptides of the present invention may also be evaluated for their ability to regulate reproductive hormones, such as follicle stimulating hormone. Numerous assays for such activity are familiar to those skilled in the art, including the assays disclosed in the following references, which are incorporated herein by reference: Vale et al., *Endocrinol.* 91:562–572, 1972; Ling et al., *Nature* 321:779–782, 1986; Vale et al., *Nature* 321:776–779, 1986; Mason et al., *Nature* 318:659–663, 1985; Forage et al., *Proc. Natl. Acad. Sci. USA* 83:3091–3095, 1986. Chapter 6.12 in *Current Protocols in Immunology*, J. E. Coligan et al. Eds. Greene Publishing Associates and Wiley-Intersciece; Taub et al. *J. Clin. Invest.* 95:1370–1376, 1995; Lind et al. *APMIS* 103:140–146, 1995; Muller et al., *Eur. J. Immunol.* 25:1744–1748; Gruber et al. *J. Immunol.* 152:5860–5867, 1994; Johnston et al. *J Immunol.* 153:1762–1768, 1994.

Those proteins or polypeptides which exhibit activity as reproductive hormones or regulators of cell movement may then be formulated as pharmaceuticals and used to treat clinical conditions in which regulation of reproductive hormones are beneficial. For example, a protein or polypeptide may exhibit activin- or inhibin-related activities. Inhibins are characterized by their ability to inhibit the release of follicle stimulating hormone (FSH), while activins are characterized by their ability to stimulate the release of FSH. Thus, a protein or polypeptide of the present invention, alone or in heterodimers with a member of the inhibin a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein or polypeptide of the invention, as a homodimer or as a heterodimer with other protein subunits of the inhibin-B group, may be useful as a fertility inducing therapeutic, based upon the ability of activin molecules in stimulating FSH release from cells of the anterior pituitary. See, for example, U.S. Pat. No. 4,798, 885, the disclosure of which is incorporated herein by reference. A protein or polypeptide of the invention may also be useful for advancement of the onset of fertility in sexually immature mammals, so as to increase the lifetime reproductive performance of domestic animals such as cows, sheep and pigs.

Alternatively, as described in more detail below, nucleic acids encoding reproductive hormone regulating activity proteins or polypeptides or nucleic acids regulating the expression of such proteins or polypeptides may be introduced into appropriate host cells to increase or decrease the expression of the proteins or polypeptides as desired.

EXAMPLE 27

Assaying the Expressed Proteins or Polypeptides For Chemotactic/Chemokinetic Activity The proteins or polypeptides of the present invention may also be evaluated for chemoatactic/chemokinetic acitivity. For example, a protein or polypeptide of the present invention may have chemotactic or chemokinetic activity (e.g., act as a chemokine) for mammalian cells, including, for example, monocytes, fibroblasts, neutrophils, T-cells, mast cells eosinophils, epithelial and/or endothelial cells. Chemotactic and chemokinetic proteins or polypeptides can be used to mobilize or attract a desired cell population to a desired site of action. Chemotactic or chemokinetic proteins or polypeptides provide particular advantages in treatment of wounds and other trauma to tissues, as well as in treatment of localized infections. For example, attraction of lymphocytes, monocytes or neutrophils to tumors or sites of infection may result in improved immune response against the tumor or infecting agent.

A protein or polypeptide has chemotactic activity for a particular cell population if it can stimulate, directly or indirectly, the directed orientation or movement of such cell population. Preferably, the protein or polypeptide has the ability to directly stimulate directed movement of cells. Whether a particular protein or polypeptide has chemotactic activity for a population of cells can be readily determined by employing such protein or polypeptide in any known assay for cells chemotaxis.

The activity of a protein or polypeptide of the invention may, among other means, be measured by the following methods:

Assays for chemotactic activity (which will identify proteins or polypeptides that induce or prevent chemotaxis) consist of assays that measure the ability of a protein or polypeptide to induce the migration of cells across a membrane as well as the ability of a protein or polypeptide to induce the adhesion of one cell population to another cell population. Suitable assays for movement and adhesion include, without limitation, those described in: *Current Protocols in Immunology*, Ed by J. E. Coligan, A. M. Kruisbeek, D. H. Margulies, E. M. Shevach, W. Strober, Pub. Greene Publishing Associates and Wiley-Interscience, Chapter 6.12: 6.12.1–6.12.28; Taub et al. *J. Clin. Invest.* 95:1370–1376, 1995; Lind et al. *APMIS* 103:140–146, 1995; Mueller et al., *Eur. J. Immunol.* 25:1744–1748; Gruber et al. *J. Immunol.* 152:5860–5867, 1994; Johnston et al. *J. Immunol.*, 153:1762–1768, 1994.

EXAMPLE 28

Assaying the Expressed Proteins or Polypeptides for Regulation of Blood Clotting The proteins or polypeptides of the present invention may also be evaluated for their effects on blood clotting. Numerous assays for such activity are familiar to those skilled in the art, including the assays disclosed in the following references, which are incorporated herein by reference: Linet et al., *J. Clin. Pharmacol.* 26:131–140, 1986; Burdick et al., *Thrombosis Res.* 45:413–419, 1987; Humphrey et al, *Fibrinolysis* 5:71–79 (1991); Schaub, *Prostaglandins* 35:467–474, 1988.

Those proteins or polypeptides which are involved in the regulation of blood clotting may then be formulated as pharmaceuticals and used to treat clinical conditions in which regulation of blood clotting is beneficial. For example, a protein or polypeptide of the invention may also exhibit hemostatic or thrombolytic activity. As a result, such a protein or polypeptide is expected to be useful in treatment of various coagulations disorders (including hereditary disorders, such as hemophilias) or to enhance coagulation and other hemostatic events in treating wounds resulting from trauma, surgery or other causes. A protein or polypeptide of the invention may also be useful for dissolving or inhibiting formation of thromboses and for treatment and prevention of conditions resulting therefrom (such as infarction of cardiac and central nervous system vessels (e.g., stroke)). Alternatively, as described in more detail below, nucleic acids encoding blood clotting activity proteins or polypeptides or nucleic acids regulating the expression of such proteins or polypeptides may be introduced into appropriate host cells to increase or decrease the expression of the proteins or polypeptides as desired.

EXAMPLE 29

Assaying the Expressed Proteins or Polypeptides for Involvement in Receptor/Ligand Interactions The proteins or polypeptides of the present invention may also be evaluated for their involvement in receptor/ligand interactions. Numerous assays for such involvement are familiar to those skilled in the art, including the assays disclosed in the following references, which are incorporated herein by reference: Chapter 7. 7.28.1–7.28.22) in *Current Protocols in Immunology*, J. E. Coligan et al. Eds. Greene Publishing Associates and Wiley-Interscience; Takai et al., *Proc. Natl. Acad. Sci. USA* 84:6864–6868, 1987; Bierer et al., *J. Exp. Med.* 168:1145–1156, 1988; Rosensteinet al., *J. Exp. Med.* 169:149–160, 1989; Stoltenborg et al., *J. Immunol. Methods* 175:59–68, 1994; Stitt el al., *Cell* 80:661–670, 1995; Gyuris et al., *Cell* 75:791–803, 1993.

For example, the proteins or polypeptides of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein or polypeptide of the present invention (including, without limitation, fragments of receptors and ligands) may be useful as inhibitors of receptor/ligand interactions. Alternatively, as described in more detail below, nucleic acids encoding proteins or polypeptides involved in receptor/ligand interactions or nucleic acids regulating the expression of such proteins or polypeptides may be introduced into appropriate host cells to increase or decrease the expression of the proteins or polypeptides as desired.

EXAMPLE 30

Assaying the Proteins or Polypeptides for Anti-Inflammatory Activity

The proteins or polypeptides of the present invention may also be evaluated for anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins or polypeptides exhibiting such activities can be used to treat inflammatory conditions including chronic or acute conditions, including without limitation inflammation associated with infection (such as septic shock, sepsis or systemic inflammatory response syndrome), ischemia-reperfusioninury, endotoxin lethality, arthritis, complement-mediated hyperacute rejection, nephritis, cytokine- or chemokine-induced lung injury, inflammatory bowel disease, Crohn's disease or resulting from over production of cytokines such as TNF or IL-1. Proteins or polypeptides of the invention may also be useful to treat anaphylaxis and hypersensitivity to an antigenic substance or material. Alternatively, as described in more detail below, nucleic acids encoding anti-inflammatory activity proteins or polypeptides or nucleic acids regulating the expression of such proteins or polypeptides may be introduced into appropriate host cells to increase or decrease the expression of the proteins or polypeptides as desired.

EXAMPLE 31

Assaying the Expressed Proteins or Polypeptides for Tumor Inhibition Activity

The proteins or polypeptides of the present invention may also be evaluated for tumor inhibition activity. In addition to the activities described above for immunological treatment or prevention of tumors, a protein or polypeptide of the invention may exhibit other anti-tumor activities. A protein or polypeptide may inhibit tumor growth directly or indirectly (such as, for example, via ADCC). A protein or polypeptide may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth. Alternatively, as described in more detail below, nucleic acids encoding proteins or polypeptides with tumor inhibition activity or nucleic acids regulating the expression of such proteins or polypeptides may be introduced into appropriate host cells to increase or decrease the expression of the proteins or polypeptides as desired.

A protein or polypeptide of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein. Alternatively, as described in more detail below, nucleic acids encoding proteins or polypeptides involved in any of the above mentioned activities or nucleic acids regulating the expression of such proteins may be introduced into appropriate host cells to increase or decrease the expression of the proteins or polypeptides as desired.

EXAMPLE 32

Identification of Proteins or Polypeptides Which Interact With Proteins or Polypeptides of the Present Invention Proteins or polypeptides which interact with the proteins or polypeptides of the present invention, such as receptor proteins, may be identified using two hybrid systems such as the Matchmaker Two Hybrid System 2 (Catalog No. K1604-1, Clontech). As described in the manual accompanying the kit which is incorporated herein by reference, nucleic acids encoding the proteins or polypeptides of the present invention, are inserted into an expression vector such that they are in frame with DNA encoding the DNA binding domain of the yeast transcriptional activator GAL4. cDNAs in a CDNA library which encode proteins or polypeptides which might interact with the proteins or polypeptides of the present invention are inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain plasmids encoding proteins or polypeptides which interact with the proteins or polypeptides of the present invention.

Alternatively, the system described in Lustig et al., *Methods in Enzymology* 283: 83–99 (1997), the disclosure of which is incorporated herein by reference, may be used for identifying molecules which interact with the proteins or polypeptides of the present invention. In such systems, in vitro transcription reactions are performed on a pool of vectors containing nucleic acid inserts which encode the proteins or polypeptides of the present invention. The nucleic acid inserts are cloned downstream of a promoter which drives in vitro transcription. The resulting pools of mRNAs are introduced into *Xenopus laevis* oocytes. The oocytes are then assayed for a desired activity.

Alternatively, the pooled in vitro transcription products produced as described above may be translated in vitro. The pooled in vitro translation products can be assayed for a desired activity or for interaction with a known protein or polypeptide.

Proteins, polypeptides or other molecules interacting with proteins or polypeptides of the present invention can be found by a variety of additional techniques. In one method, affinity columns containing the protein or polypeptide of the present invention can be constructed. In some versions, of this method the affinity column contains chimeric proteins in which the protein or polypeptide of the present invention is fused to glutathione S-transferase. A mixture of cellular proteins or pool of expressed proteins as described above and is applied to the affinity column. Molecules interacting with the protein or polypeptide attached to the column can then be isolated and analyzed on 2-D electrophoresis gel as described in Ramunsen et al. *Electrophoresis*, 18, 588–598 (1997), the disclosure of which is incorporated herein by reference. Alternatively, the molecules retained on the affinity column can be purified by electrophoresis based methods and sequenced. The same method can be used to isolate antibodies, to screen phage display products, or to screen phage display human antibodies.

Molecules interacting with the proteins or polypeptides of the present invention can also be screened by using an Optical Biosensor as described in Edwards & Leatherbarrow, *Analytical Biochemistry*, 246, 1–6 (1997), the disclosure of which is incorporated herein by reference. The main advantage of the method is that it allows the determination of the association rate between the protein or polypeptide and other interacting molecules. Thus, it is possible to specifically select interacting molecules with a high or low association rate. Typically a target molecule is linked to the sensor surface (through a carboxymethl dextran matrix) and a sample of test molecules is placed in contact with the target molecules. The binding of a test molecule to the target molecule causes a change in the refractive index and/or thickness. This change is detected by the Biosensor provided it occurs in the evanescent field (which extend a few hundred nanometers from the sensor surface). In these screening assays, the target molecule can be one of the proteins or polypeptides of the present invention and the test sample can be a collection of proteins, polypeptides or other molecules extracted from tissues or cells, a pool of expressed proteins, combinatorial peptide and/or chemical libraries, or phage displayed peptides. The tissues or cells from which the test molecules are extracted can originate from any species.

In other methods, a target protein or polypeptide is immobilized and the test population is a collection of unique proteins or polypeptides of the present invention.

To study the interaction of the proteins or polypeptides of the present invention with drugs, the microdialysis coupled to HPLC method described by Wang et al., *Chromatographia*, 44, 205–208(1997) or the affinity capillary electrophoresis method described by Busch et al., *J. Chromatogr*. 777:311–328 (1997), the disclosures of which are incorporated herein by reference can be used.

The system described in U.S. Pat. No. 5,654,150, the disclosure of which is incorporated herein by reference, may also be used to identify molecules which interact with the proteins or polypeptides of the present invention. In this system, pools of nucleic acids encoding the proteins or polypeptides of the present invention are transcribed and translated in vitro and the reaction products are assayed for interaction with a known polypeptide or antibody.

It will be appreciated by those skilled in the art that the proteins or polypeptides of the present invention may be assayed for numerous activities in addition to those specifically enumerated above. For example, the expressed proteins or polypeptides may be evaluated for applications involving control and regulation of inflammation, tumor proliferation or metastasis, infection, or other clinical conditions. In addition, the proteins or polypeptides may be useful as nutritional agents or cosmetic agents.

Epitopes and Antibody Fusions

A preferred embodiment of the present invention is directed to eiptope-bearing polypeptides and epitope-bearing polypeptide fragments. These epitopes may be "antigenic epitopes" or both an "antigenic epitope" and an "immunogenic epitope". An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes. See, e.g., Geysen, et al. (1983) Proc. Natl. Acad. Sci. USA 81:39984002. It is particularly noted that although a particular epitope may not be immunogenic, it is nonetheless useful since antibodies can be made in vitro to any epitope.

An epitope can comprise as few as 3 amino acids in a spatial conformation which is unique to the epitope. Generally an epitope consists of at least 6 such amino acids, and more often at least 8–10 such amino acids. In preferred embodiment, antigenic epitopes comprise a number of amino acids that is any integer between 3 and 50. Fragments which function as epitopes may be produced by any conventional means. See, e.g., Houghten, R. A., Proc. Natl. Acad. Sci. USA 82:5131–5135 (1985), further described in U.S. Pat. No. 4,631,211, the disclosures of which are incorporated herein by reference in their entireties. Methods for determining the amino acids which make up an immunogenic epitope include x-ray crystallography, 2-dimensional nuclear magnetic resonance, and epitope mapping, e.g., the Pepscan method described by H. Mario Geysen et al. (1984); Proc. Natl. Acad. Sci. U.S.A. 81:3998–4002; PCT Publication No. WO 84/03564; and PCT Publication No. WO 84/03506, the disclosures of which are incorporated herein by reference in their entireties. Another example is the algorithm of Jameson and Wolf, Comp. Appl. Biosci. 4:181–186 (1988) (said references incorporated by reference in their entireties). The Jameson-Wolf antigenic analysis, for example, may be performed using the computer program PROTEAN, using default parameters (Version 4.0 Windows, DNASTAR, Inc., 1228 South Park Street Madison, Wis.

The epitope-bearing fragments of the present invention preferably comprises 6 to 50 amino acids (i.e. any integer between 6 and 50, inclusive) of a polypeptide of the present invention. Also, included in the present invention are antigenic fragments between the integers of 6 and the full length sequence of the sequence listing. All combinations of sequences between the integers of 6 and the full-length sequence of a polypeptide of the present invention are included. The epitope-bearing fragments may be specified by either the number of contiguous amino acid residues (as a sub-genus) or by specific N-terminal and C-terminal positions (as species) as described above for the polypeptide fragments of the present invention. Any number of epitope-bearing fragments of the present invention may also be excluded in the same manner.

Antigenic epitopes are useful, for example, to raise antibodies, including monoclonal antibodies that specifically bind the epitope (See, Wilson et al., 1984; and Sutcliffe, J. G. et al., 1983). The antibodies are then used in various techniques such as diagnostic and tissue/cell identification techniques, as described herein, and in purification methods.

Similarly, immunogenic epitopes can be used to induce antibodies according to methods well known in the art (See, Sutcliffe et al., supra; Wilson et al., supra; Chow, M. et al.; (1985) and Bittle, F. J. et al., (1985). A preferred immunogenic epitope includes the polypeptides of the sequence listing. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.).

Epitope-bearing polypeptides of the present invention are used to induce antibodies according to methods well known in the art including, but not limited to, in vivo immunization, in vitro immunization, and phage display methods (See, e.g., Sutcliffe, et al., supra; Wilson, et al., supra, and Bittle, et al., 1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as—maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 $\mu$gs of peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins (See, e.g., EPA 0,394,827; and Traunecker et al., 1988). Fusion proteins that have a disulfide-linked dimeric structure due to the IgG portion can also be more efficient in binding and neutralizing other molecules than monomeric polypeptides or fragments thereof alone (See, e.g., Fountoulakis et al., 1995). Nucleic acids encoding the above epitopes can also be recombined with a gene of interest as an epitope tag to aid in detection and purification of the expressed polypeptide.

Additonal fusion proteins of the invention may be generated through the techniques of gene-shuffling, motif-shuffling, exon-shuffling, or codon-shuffling (collectively referred to as "DNA shuffling"). DNA shuffling may be employed to modulate the activities of polypeptides of the present invention thereby effectively generating agonists and antagonists of the polypeptides. See, for example, U.S. Pat. Nos.: 5,605,793; 5,811,238; 5,834,252; 5,837,458; and Patten, P. A., et al., (1997); Harayama, S., (1998); Hansson, L. O., et al (1999); and Lorenzo, M. M. and Blasco, R., (1998). (Each of these documents are hereby incorporated by reference). In one embodiment, one or more components, motifs, sections, parts, domains, fragments, etc., of coding polynucleotides of the invention, or the polypeptides encoded thereby may be recombined with one or more components, motifs, sections, parts, domains, fragments, etc. of one or more heterologous molecules.

Antibodies

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial regions of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991) J. Immunol. 147:60–69; U.S. Pat. Nos. 5,573,920, 4,474,893, 5,601,819, 4,714,681, 4,925,648; Kostelny, S. A. et al. (1992) J. Immunol. 148:1547–1553, the disclosures of which are incorporated herein by reference in their entireties.

In some embodiments, the antibodies may be capable of specifically binding to a protein or polypeptide encoded by EST-related nucleic acids, fragments of EST-related nucleic acids, positional segments of EST-related nucleic acids or fragments of positional segments of EST-related nucleic acids. In some embodiments, the antibody may be capable of binding an antigenic determinant or an epitope in a protein or polypeptide encoded by EST-related nucleic acids, fragments of EST-related nucleic acids, positional segments of EST-related nucleic acids or fragments of positional segments of EST-related nucleic acids.

In other embodiments, the antibodies may be capable of specifically binding to an EST-related polypeptide, fragment of an EST-related polypeptide, positional segment of an EST-related polypeptide or fragment of a positional segment of an EST-related polypeptide. In some embodiments, the antibody may be capable of binding an antigenic determinant or an epitope in an EST-related polypeptide, fragment of an EST-related polypeptide, positional segment of an EST-related polypeptide or fragment of a positional segment of an EST-related polypeptide.

Antibodies of the present invention may be described or specified in terms of the epitope(s) or portion(s) of a polypeptide of the present invention which are recognized or specifically bound by the antibody.

In the case of secreted proteins, the antibodies may specifically bind a full-length protein encoded by a nucleic acid of the present invention, a mature protein (i.e. the protein generated by cleavage of the signal peptide) encoded by a nucleic acid of the present invention, or a signal peptide encoded by a nucleic acid of the present invention. Moreover, the epitope(s) or polypeptide portion(s) may be specified as described herein, e.g., by N-terminal and C-terminal positions, by size in contiguous amino acid residues, or listed in the Tables and sequence listing. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *ANTIBODIES: A LABORATORY MANUAL*, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387, the disclosures of which are incorporated herein by reference in their entireties.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "antibody" refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen., which allows an immunological reaction with the antigen. The term "monoclonal antibody" refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (See, e.g., Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties). Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) J. Immunol. Methods 182:41–50; Ames, R. S. et al. (1995) J. Immunol. Methods 184:177–186; Kettleborough, C. A. et al. (1994) Eur. J. Immunol. 24:952–958; Persic, L. et al. (1997) Gene 187 9–18; Burton, D. R. et al. (1994) Advances in Immunology 57:191–280; PCT/GB91/01134; WO 90/02809; WO91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' F(ab)2 and F(ab')2 fragments can also be employed using methods known in the art such as those disclosed in WO 92/22324; Mullinax, R. L. et al. (1992) BioTechniques 12(6):864–869; and Sawai, H. et al. (1995) AJRI 34:26–34; and Better, M. et al. (1988) Science 240:1041–1043 (said references incorporated by reference in their entireties).

Examples of techniques which can be used to produce single-chain Fvs and antibodies include those described in U.S. Pat. Nos. 4,946,778 and 5,258,498; Huston et al. (1991) Methods in Enzymology 203:46–88; Shu, L. et al. (1993) PNAS 90:7995–7999; and Skerra, A. et al. (1988) Science 240:1038–1040, the disclosures of which are incorporated herein by reference in their entireties. For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies, S. D. et al. (1989) J. Immunol. Methods 125:191–202; and U.S. Pat. No. 5,807,715. Antibodies can be humanized using a variety of techniques including CDR-grafting (EP 0 239 400; WO 91/09967; U.S. Pat. No. 5,530,101; and 5,585,089), veneering or resurfacing (EP 0 592 106; EP 0 519 596; Padlan E. A., (1991) Molecular Immunology 28(4/5):489–498; Studnicka G. M. et al. (1994) Protein Engineering 7(6):805–814; Roguska M. A. et al. (1994) PNAS 91:969–973), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; WO 98/46645; WO 98/50433; WO 98/24893; WO 96/34096; WO 96/33735; and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al. (1994) Immunol. Lett. 39:91–99; U.S. Pat. No. 5,474,981; Gillies, S. O. et al. (1992) PNAS 89:1428–1432; Fell, H. P. et al. (1991) J. Immunol. 146:2446–2452 (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991) PNAS 88:10535–10539; Zheng, X. X. et al. (1995) J. Immunol. 154:5590–5600; and Vil, H. et al. (1992) PNAS 89:11337–11341 (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully.

Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998) Blood 92(6):1981–1988; Chen, Z. et al. (1998) Cancer Res. 58(16):3668–3678; Harrop, J. A. et al. (1998) J. Immunol. 161(4):1786–1794; Zhu, Z. et al. (1998) Cancer Res. 58(15):3209–3214; Yoon, D. Y. et al. (1998) J. Immunol. 60(7):3170–3179; Prat, M. et al. (1998) J. Cell. Sci. 111 (Pt2):237–247; Pitard, V. et al. (1997) J. Immunol. Methods 205(2):177–190; Liautard, J. et al. (1997) Cytokinde 9(4):233–241; Carlson, N. G. et al. (1997) J. Biol. Chem. 272(17):11295–11301; Taryman, R. E. et al. (1995) Neuron 14(4):755–762; Muller, Y. A. et al. (1998) Structure 6(9):1153–1167; Bartunek, P. et al. (1996) Cytokine 8(1):14–20 (said references incorporated by reference in their entireties).

As discussed above, antibodies of the polypeptides of the invention can, in turn, be utilized to generate anti-idiotypic antibodies that "mimic" polypeptides of the invention using techniques well known to those skilled in the art. See, e.g. Greenspan and Bona, FASEB J. 7(5):437–444 (1989); Nissinoff, J. Immunol. 147(8):2429–2438 (1991), the disclosures of which are incorporated herein by reference in their entireties. For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and therby block its biological activity.

EXAMPLE 33

Production of an Antibody to a Human Polyleptide or Protein

The above described EST-related nucleic acids, fragments of EST-related nucleic acids, positional segments of EST-related nucleic acids or fragments of positional segments of EST-related nucleic acids or nucleic acids encoding EST-related polypeptides, fragments of EST-related polypeptides, positional segments of EST-related polypeptides or fragments of positional segments of EST-related polypeptides are operably linked to promoters and introduced into cells as described above.

In the case of secreted proteins, nucleic acids encoding the full protein (i.e. the mature protein and the signal peptide), nucleic acids encoding the mature protein (i.e. the protein generated by cleavage of the signal peptide), or nucleic acids encoding the signal peptide are operably linked to promoters and introduced into cells as described above.

The encoded proteins or polypeptides are then substantially purified or isolated as described above. The concentration of protein in the final preparation is adjusted, for example, by concentration on an Amicon filter device, to the level of a few g/ml. Monoclonal or polyclonal antibody to the protein or polypeptide can then be prepared as follows:

1. Monoclonal Antibody Production by Hybridoma Fusion

Monoclonal antibody to epitopes of any of the proteins or polypeptides identified and isolated as described can be prepared from murine hybridomas according to the classical method of Kohler, and Milstein, Nature 256:495 (1975) or derivative methods thereof. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, Meth. Enzymol 70:419 (1980), the disclosure of which is incorporated herein by reference and derivative methods thereof. Selected positive clones can be expanded and their monoclonal antibody product harvested for use. Detailed procedures for monoclonal antibody production are described in Davis, L. et al. in Basic Methods in Molecular Biology Elsevier, New York. Section 21-2, the disclosure of which is incorporated herein by reference.

2. Polyclonal Antibody Production by Immunization

Polyclonal antiserum containing antibodies to heterogenous epitopes of a single protein or polypeptide can be prepared by immunizing suitable animals with the expressed protein or peptides derived therefrom, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals response vary depending on site of inoculations and doses, with both inadequate or excessive doses of antigen resulting in low titer antisera. Small doses (ng level) of antigen administered at multiple intradermal sites appears to be most reliable. An effective immunization protocol for rabbits can be found in Vaitukaitis. et al. J. Clin. Endocrinol. Metab. 33:988–991 (1971), the disclosure of which is incorporated herein by reference.

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, et al., Chap. 19 in: Handbook of Experimental Immunology D. Wier (ed) Blackwell (1973), the disclosure of which is incorporated herein by reference. Plateau concentration of antibody is usually in the range of 0.1 to 0.2 mg/ml of serum (about 12 M). Affinity of the antisera for the antigen is determined by preparing competitive binding curves, as described, for example, by Fisher, D., Chap. 42 in: Manual of Clinical Immunology, 2d Ed. (Rose and Friedman, Eds. ) Amer. Soc. For Microbiol., Washington, D.C. (1980), the disclosure of which is incorporated herein by reference.

Antibody preparations prepared according to either of the above protocols are useful in a variety of contexts. In particular, the antibodies may be used in immunoaffinity chromatography techniques such as those described below to facilitate large scale isolation, purification, or enrichment of the proteins or polypeptides encoded by EST-related nucleic acids, positional segments of EST-related nucleic acids or fragments of positional segments of EST-related nucleic acids or for the isolation, purification or enrichment of EST-related polypeptides, fragments of EST-related polypeptides, positional segments of EST-related polypeptides or fragments of positional segments of EST-related polypeptides.

In the case of secreted proteins, the antibodies may be used for the isolation, purification, or enrichment of the full protein (i.e. the mature protein and the signal peptide), the mature protein (i.e. the protein generated by cleavage of the signal peptide), or the signal peptide are operably linked to promoters and introduced into cells as described above.

Additionally, the antibodies may be used in immunoaffinity chromatography techniques such as those described below to isolate, purify, or enrich polypeptides which have been linked to the proteins or polypeptides encoded by EST-related nucleic acids, positional segments of EST-related nucleic acids or fragments of positional segments of EST-related nucleic acids or to isolate, purify, or enrich EST-related polypeptides, fragments of EST-related polypeptides, positional segments of EST-related polypeptides or fragments of positional segments of EST-related polypeptides.

The antibodies may also be used to determine the cellular localization of polypeptides encoded by the proteins or polypeptides encoded by EST-related nucleic acids, positional segments of EST-related nucleic acids or fragments of positional segments of EST-related nucleic acids or the cellular localization of EST-related polypeptides, fragments of EST-related polypeptides, position EST-related polypeptides or fragments of positional segments of EST-related polypeptides.

In addition, the antibodies may also be used to determine the cellular localization of polypeptides which have been linked to the proteins or polypeptides encoded by EST-related nucleic acids, positional segments of EST-related nucleic acids or fragments of positional segments of EST-related nucleic acids or polypeptides which have been linked EST-related polypeptides, fragments of EST-related polypeptides, positional segments of EST-related polypeptides or fragments of positional segments of EST-related polypeptides.

The antibodies may also be used in quantitative immunoassays which determine concentrations of antigen-bearing substances in biological samples; they may also used semi-quantitatively or qualitatively to identify the presence of antigen in a biological sample or to identify the type of tissue present in a biological sample. The antibodies may also be used in therapeutic compositions for killing cells expressing the protein or reducing the levels of the protein in the body.

VI. Use of 5' ESTs and Consensus Contigated 5' ESTs or Sequences Obtainable Therefrom or Portions Thereof as Reagents The EST-related nucleic acids, positional segments of EST-related nucleic acids or fragments of positional segments of EST-related nucleic acids may be used as reagents in isolation procedures, diagnostic assays, and forensic procedures. For example, sequences from the EST-related nucleic acids, positional segments of EST-related nucleic acids or fragments of positional segments of EST-related nucleic acids, may be detectably labeled and used as probes to isolate other sequences capable of hybridizing to them. In addition, the he EST-related nucleic acids, positional segments of EST-related nucleic acids or fragments of positional segments of EST-related nucleic acids may be used to design PCR primers to be used in isolation, diagnostic, or forensic procedures.

1. Use of EST-related Nucleic Acids Positional Segments of EST-related Nucleic Acids or Fragments of Positional Segments of EST-related Nucleic Acids in Isolation, Diagnostic and Forensic Procedures

EXAMPLE 34

Preparation of PCR Primers and Amplification of DNA

The EST-related nucleic acids, positional segments of EST-related nucleic acids or fragments of positional segments of EST-related nucleic acids may be used to prepare PCR primers for a variety of applications, including isolation procedures for cloning nucleic acids capable of hybridizing to such sequences, diagnostic techniques and forensic techniques. In some embodiments, the PCR primers at least 10, 15, 18, 20, 23, 25, 28, 30, 40, or 50 nucleotides in length. In some embodiments, the PCR primers may be more than 30 bases in length. It is preferred that the primer pairs have approximately the same G/C ratio, so that melting temperatures are approximately the same. A variety of PCR techniques are familiar to those skilled in the art. For a review of PCR technology, see Molecular Cloning to Genetic Engineering White, B. A. Ed. in *Methods in Molecular Biology* 67: Humana Press, Totowa 1997, the disclosure of which is incorporated herein by reference. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites.

EXAMPLE 35

Use of the EST-related Nucleic Acids Positional Segments of EST-related Nucleic Acids or Fragments of Positional Segments of EST-related Nucleic Acids as Probes Probes derived from EST-related nucleic acids, positional segments of EST-related nucleic acids or fragments of positional segments of EST-related nucleic acids may be labeled with detectable labels familiar to those skilled in the art, including radioisotopes and non-radioactive labels, to provide a detectable probe. The detectable probe may be single stranded or double stranded and may be made using techniques known in the art, including in vitro transcription, nick translation, or kinase reactions. A nucleic acid sample containing a sequence capable of hybridizing to the labeled probe is contacted with the labeled probe. If the nucleic acid in the sample is double stranded, it may be denatured prior to contacting the probe. In some applications, the nucleic acid sample may be immobilized on a surface such as a nitrocellulose or nylon membrane. The nucleic acid sample may comprise nucleic acids obtained from a variety of sources, including genomic DNA, cDNA libraries, RNA, or tissue samples.

Procedures used to detect the presence of nucleic acids capable of hybridizing to the detectable probe include well known techniques such as Southern blotting, Northern blotting, dot blotting, colony hybridization, and plaque hybridization. In some applications, the nucleic acid capable of hybridizing to the labeled probe may be cloned into vectors such as expression vectors, sequencing vectors, or in vitro transcription vectors to facilitate the characterization and expression of the hybridizing nucleic acids in the sample. For example, such techniques may be used to isolate and clone sequences in a genomic library or cDNA library which are capable of hybridizing to the detectable probe as described in Example 18 above.

PCR primers made as described in Example 34 above may be used in forensic analyses, such as the DNA fingerprinting techniques described in Examples 36–40 below. Such analyses may utilize detectable probes or primers based on the sequences of the EST-related nucleic acids, positional segments of EST-related nucleic acids or fragments of positional segments of EST-related nucleic acids.

EXAMPLE 36

Forensic Matching by DNA Sequencing

In one exemplary method, DNA samples are isolated from forensic specimens of, for example, hair, semen, blood or skin cells by conventional methods. A panel of PCR primers based on a number of the EST-related nucleic acids, positional segments of EST-related nucleic acids or fragments of positional segments of EST-related nucleic acids is then utilized in accordance with Example 34 to amplify DNA of approximately 100–200 bases in length from the forensic specimen. Corresponding sequences are obtained from a test subject. Each of these identification DNAs is then sequenced using standard techniques, and a simple database comparison determines the differences, if any, between the sequences from the subject and those from the sample. Statistically significant differences between the suspect's DNA sequences and those from the sample conclusively prove a lack of identity. This lack of identity can be proven, for example, with only one sequence. Identity, on the other hand, should be demonstrated with a large number of sequences, all matching. Preferably, a minimum of 50 statistically identical sequences of 100 bases in length are used to prove identity between the suspect and the sample.

EXAMPLE 37

Positive Identification by DNA Sequencing

The technique outlined in the previous example may also be used on a larger scale to provide a unique fingerprint-type identification of any individual. In this technique, primers are prepared from a large number of EST-related nucleic acids, positional segments of EST-related nucleic acids or fragments of positional segments of EST-related nucleic acids. Preferably, 20 to 50 different primers are used. These primers are used to obtain a corresponding number of PCR-generated DNA segments from the individual in question in accordance with Example 34. Each of these DNA segments is sequenced, using the methods set forth in Example 36. The database of sequences generated through this procedure uniquely identifies the individual from whom the sequences were obtained. The same panel of primers may then be used at any later time to absolutely correlate tissue or other biological specimen with that individual.

EXAMPLE 38

Southern Blot Forensic Identification

The procedure of Example 37 is repeated to obtain a panel of at least 10 amplified sequences from an individual and a specimen. Preferably, the panel contains at least 50 amplified sequences. More preferably, the panel contains 100 amplified sequences. In some embodiments, the panel contains 200 amplified sequences. This PCR-generated DNA is then digested with one or a combination of, preferably, four base specific restriction enzymes. Such enzymes are commercially available and known to those of skill in the art. After digestion, the resultant gene fragments are size separated in multiple duplicate wells on an agarose gel and transferred to nitrocellulose using Southern blotting techniques well known to those with skill in the art. For a review of Southern blotting see Davis et al. (Basic Methods in Molecular Biology, 1986, Elsevier Press. pp 62–65), the disclosure of which is incorporated herein by reference.

A panel of probes based on the sequences of the EST-related nucleic acids, positional segments of EST-related nucleic acids or fragments of positional segments of EST-related nucleic acids are radioactively or calorimetrically labeled using methods known in the art, such as nick translation or end labeling, and hybridized to the Southern blot using techniques known in the art (Davis et al., supra). Preferably, the probe is at least 10, 12, 15, 18, 20, 25, 28, 30, 35, 40, 50, 75, 100, 150, 200, 300, 400 or 500 nucleotides in length. Preferably, the probes are at least 10, 12, 15, 18, 20, 25, 28, 30, 35, 40, 50, 75, 100, 150, 200, 300, 400 or 500 nucleotides in length. In some embodiments, the probes are oligonucleotides which are 40 nucleotides in length or less.

Preferably, at least 5 to 10 of these labeled probes are used, and more preferably at least about 20 or 30 are used to provide a unique pattern. The resultant bands appearing from the hybridization of a large sample of EST-related nucleic acids, positional segments of EST-related nucleic acids or fragments of positional segments of EST-related nucleic acids will be a unique identifier. Since the restriction enzyme cleavage will be different for every individual, the band pattern on the Southern blot will also be unique. Increasing the number of probes will provide a statistically higher level of confidence in the identification since there will be an increased number of sets of bands used for identification.

EXAMPLE 39

Dot Blot Identification Procedure

Another technique for identifying individuals using the EST-related nucleic acids, positional segments of EST-related nucleic acids or fragments of positional segments of EST-related nucleic acids disclosed herein utilizes a dot blot hybridization technique.

Genomic DNA is isolated from nuclei of subject to be identified. Probes are prepared that correspond to at least 10, preferably 50 sequences from the EST-related nucleic acids, positional segments of EST-related nucleic acids or fragments of positional segments of EST-related nucleic acids. The probes are used to hybridize to the genomic DNA through conditions known to those in the art. The oligonucleotides are end labeled with $P^{32}$ using polynucleotide kinase (Pharmacia). Dot Blots are created by spotting the genomic DNA onto nitrocellulose or the like using a vacuum dot blot manifold (BioRad, Richmond Calif.). The nitrocellulose filter containing the genomic sequences is baked or UV linked to the filter, prehybridized and hybridized with labeled probe using techniques known in the art (Davis et al., supra). The $^{32}$P labeled DNA fragments are sequentially hybridized with successively stringent conditions to detect minimal differences between the 30 bp sequence and the DNA. Tetramethylammoniumchloride is useful for identifying clones containing small numbers of nucleotide mismatches (Wood et al., Proc. Natl. Acad. Sci. USA 82(6):1585–1588 (1985)) which is hereby incorporated by reference. A unique pattern of dots distinguishes one individual from another individual.

EST-related nucleic acids, positional segments of EST-related nucleic acids or fragments of positional segments of EST-related nucleic acids can be used as probes in the following alternative fingerprinting technique. In some embodiments, the probes are oligonucleotides which are 40 nucleotides in length or less.

Preferably, a plurality of probes having sequences from different EST-related nucleic acids, positional segments of EST-related nucleic acids or fragments of positional segments of EST-related nucleic acids are used in the alternative fingerprinting technique. Example 40 below provides a representative alternative fingerprinting procedure in which the probes are derived from EST-related nucleic acids, positional segments of EST-related nucleic acids or fragments of positional segments of EST-related nucleic acids.

EXAMPLE 40

Alternative "Fingerprint" Identification Technique

Oligonucleotides are prepared from a large number, e.g. 50, 100, or 200, EST-related nucleic acids, positional segments of EST-related nucleic acids or fragments of positional segments of EST-related nucleic acids using commercially available oligonucleotide services such as Genset, Paris, France. Preferably, the oligonucleotides are at least 10, 15, 18, 20, 23, 25 28, or 30 nucleotides in length. However, in some embodiments, the oligonucleotides may be more than 30 nucleotides in length.

Cell samples from the test subject are processed for DNA using techniques well known to those with skill in the art. The nucleic acid is digested with restriction enzymes such as EcoRI and XbaI. Following digestion, samples are applied to wells for electrophoresis. The procedure, as known in the art, may be modified to accommodate polyacrylamide electrophoresis, however in this example, samples containing 5 ug of DNA are loaded into wells and separated on 0.8% agarose gels. The gels are transferred onto nitrocellulose using standard Southern blotting techniques.

10 ng of each of the oligonucleotides are pooled and end-labeled with $P^{32}$. The nitrocellulose is prehybridized with blocking solution and hybridized with the labeled probes. Following hybridization and washing, the nitrocellulose filter is exposed to X-Omat AR X-ray film. The resulting hybridization pattern will be unique for each individual.

It is additionally contemplated within this example that the number of probe sequences used can be varied for additional accuracy or clarity.

In addition to their applications in forensics and identification, EST-related nucleic acids, positional segments of EST-related nucleic acids or fragments of positional segments of EST-related nucleic acids may be mapped to their chromosomal locations. Example 41 below describes radiation hybrid (RH) mapping of human chromosomal regions using EST-related nucleic acids, positional segments of EST-related nucleic acids or fragments of positional segments of EST-related nucleic acids. Example 42 below describes a representative procedure for mapping EST-related nucleic acids, positional segments of EST-related nucleic acids or fragments of positional segments of EST-related nucleic acids to their locations on human chromosomes. Example 43 below describes mapping of EST-related nucleic acids, positional segments of EST-related nucleic acids or fragments of positional segments of EST-related nucleic acids on metaphase chromosomes by Fluorescence In Situ Hybridization (FISH).

2. Use of EST-related Nucleic Acids Positional Segments of EST-related Nucleic Acids or Fragments of Positional Segments of EST-related Nucleic Acids in Chromosome Mapping

EXAMPLE 41

Radiation Hybrid Mapping of EST-related Nucleic Acids, Positional Segments of EST-related Nucleic Acids or Fragments of Positional Segments of EST-related Nucleic Acids to the Human Genome Radiation hybrid (RH) mapping is a somatic cell genetic approach that can be used for high resolution mapping of the human genome. In this approach, cell lines containing one or more human chromosomes are lethally irradiated, breaking each chromosome into fragments whose size depends on the radiation dose. These fragments are rescued by fusion with cultured rodent cells, yielding subclones containing different portions of the human genome. This technique is described by Benham et al. (Genomics 4:509–517, 1989) and Cox et al, (Science 250:245–250, 1990), the entire contents of which are hereby incorporated by reference. The random and independent nature of the subclones permits efficient mapping of any human genome marker. Human DNA isolated from a panel of 80–100 cell lines provides a mapping reagent for ordering EST-related nucleic acids, positional segments of EST-related nucleic acids or fragments of positional segments of EST-related nucleic acids. In this approach, the frequency of breakage between markers is used to measure distance, allowing construction of fine resolution maps as has been done using conventional ESTs (Schuler et al, Science 274:540–546, 1996, hereby incorporated by reference).

RH mapping has been used to generate a high-resolution whole genome radiation hybrid map of human chromosome 17q22-q25.3 across the genes for growth hormone (GH) and thymidine kinase (TK) (Foster et al, Genomics 33:185–192, 1996), the region surrounding the Gorlin syndrome gene (Obermayr et al, Eur. J. Hum. Genet. 4:242–245, 1996), 60 loci covering the entire short arm of chromosome 12 (Raeymaekers et al, Genomics 29:170–178, 1995), the region of human chromosome 22 containing the neurofibromatosis type 2 locus (Frazer et al, Genomics 14:574–584, 1992) and 13 loci on the long arm of chromosome 5 (Warrington et al., Genomics 11:701–708, 1991).

EXAMPLE 42

Mapping of EST-related Nucleic Acids, Positional Segments of EST-related Nucleic Acids or Fragments of Positional Segments of EST-related Nucleic Acids to Human Chromosomes Using PCR Techniques EST-related nucleic acids, positional segments of EST-related nucleic acids or fragments of positional segments of EST-related nucleic acids may be assigned to human chromosomes using PCR based methodologies. In such approaches, oligonucleotide primer pairs are designed from EST-related nucleic acids, positional segments of EST-related nucleic acids or fragments of positional segments of EST-related nucleic acids to minimize the chance of amplifying through an intron. Preferably, the oligonucleotide primers are 18–23 bp in length and are designed for PCR amplification. The creation of PCR primers from known sequences is well known to those with skill in the art. For a review of PCR technology see Erlich. in PCR Technology; Principles and Applications for DNA Amplification. 1992. W.H. Freeman and Co., New York, the disclosure of which is incorporated herein by reference.

The primers are used in polymerase chain reactions (PCR) to amplify templates from total human genomic DNA. PCR conditions are as follows: 60 ng of genomic DNA is used as a template for PCR with 80 ng of each oligonucleotide primer, 0.6 unit of Taq polymerase, and 1 Cu of a $^{33}$P-labeled deoxycytidine triphosphate. The PCR is performed in a microplate thermocycler (Techne) under the following conditions: 30 cycles of 94° C., 1.4 min; 55° C., 2 min; and 72° C., 2 min; with a final extension at 72° C. for 10 min. The amplified products are analyzed on a 6% polyacrylamide sequencing gel and visualized by autoradiography. If the length of the resulting PCR product is identical to the distance between the ends of the primer sequences in the 5' EST from which the primers are derived, then the PCR reaction is repeated with DNA templates from two panels of human-rodent somatic cell hybrids, BIOS PCRable DNA (BIOS Corporation) and NIGMS Human-Rodent Somatic Cell Hybrid Mapping Panel Number 1 (NIGMS, Camden, N.J.).

PCR is used to screen a series of somatic cell hybrid cell lines containing defined sets of human chromosomes for the presence of a given 5' EST. DNA is isolated from the somatic hybrids and used as starting templates for PCR-reactions using the primer pairs from the EST-related nucleic acids, positional segments of EST-related nucleic acids or fragments of positional segments of EST-related nucleic acids. Only those somatic cell hybrids with chromosomes containing the human gene corresponding to the EST-related nucleic acids, positional segments of EST-related nucleic acids or fragments of positional segments of EST-related nucleic acids will yield an amplified fragment. The 5' ESTs are assigned to a chromosome by analysis of the segregation pattern of PCR products from the somatic hybrid DNA templates. The single human chromosome present in all cell hybrids that give rise to an amplified fragment is the chromosome containing that EST-related nucleic acids, positional segments of EST-related nucleic acids or fragments of positional segments of EST-related nucleic acids. For a review of techniques and analysis of results from somatic cell gene mapping experiments. (See Ledbetter et al., Genomics 6:475–481 (1990)., the disclosure of which is incorporated herein by reference.)

Alternatively, the EST-related nucleic acids, positional segments of EST-related nucleic acids or fragments of positional segments of EST-related nucleic acids may be mapped to individual chromosomes using FISH as described in Example 43 below.

EXAMPLE 43

Mapping of EST-related Nucleic Acids, Positional Segments of EST-related Nucleic Acids or Fragments of Positional Segments of EST-related Nucleic Acids to Chromosomes Using Fluorescence In Situ Hybridization Fluorescence in situ hybridization allows the EST-related nucleic acids, positional segments of EST-related nucleic acids or fragments of positional segments of EST-related nucleic acids to be mapped to a particular location on a given chromosome. The chromosomes to be used for fluorescence in situ hybridization techniques may be obtained from a variety of sources including cell cultures, tissues, or whole blood.

In a preferred embodiment, chromosomal localization of EST-related nucleic acids, positional segments of EST-related nucleic acids or fragments of positional segments of EST-related nucleic acids are obtained by FISH as described by Cherif et al. (*Proc. Natl. Acad. Sci. U.S.A.*, 87:6639–6643, 1990), the disclosure of which is incorporated herein by reference. Metaphase chromosomes are prepared from phytohemagglutinin (PHA)-stimulated blood cell donors. PHA-stimulated lymphocytes from healthy males are cultured for 72 h in RPMI-1640 medium. For synchronization, methotrexate (10 M) is added for 17 h, followed by addition of 5-bromodeoxyuridine (5-BrdU, 0.1 mM) for 6 h. Colcemid (1 g/ml) is added for the last 15 min before harvesting the cells. Cells are collected, washed in RPMI, incubated with a hypotonic solution of KCl (75 mM) at 37° C. for 15 min and fixed in three changes of methanol:aceticacid (3:1). The cell suspension is dropped onto a glass slide and air dried. The EST-related nucleic acids, positional segments of EST-related nucleic acids or fragments of positional segments of EST-related nucleic acids is labeled with biotin-16 dUTP by nick translation according to the manufacturer's instructions (Bethesda Research Laboratories, Bethesda, Md.), purified using a Sephadex G-50 column (Pharmacia, Upsala, Sweden) and precipitated. Just prior to hybridization, the DNA pellet is dissolved in hybridization buffer (50% formamide, 2×SSC, 10% dextran sulfate, 1 mg/ml sonicated salmon sperm DNA, pH 7) and the probe is denatured at 70° C. for 5–10 min.

Slides kept at −20° C. are treated for 1 h at 37° C. with RNase A (100 g/ml), rinsed three times in 2×SSC and dehydrated in an ethanol series. Chromosome preparations are denatured in 70% formamide, 2×SSC for 2 min at 70° C., then dehydrated at 4° C. The slides are treated with proteinase K (10 g/100 ml in 20 mM Tris-HCl, 2 mM CaCl) at 37° C. for 8 min and dehydrated. The hybridization mixture containing the probe is placed on the slide, covered with a coverslip, sealed with rubber cement and incubated overnight in a humid chamber at 37° C. After hybridization and post-hybridization washes, the biotinylated probe is detected by avidin-FITC and amplified with additional layers of biotinylated goat anti-avidin and avidin-FITC. For chromosomal localization, fluorescent R-bands are obtained as previously described (Cherif et al., supra.). The slides are observed under a LEICA fluorescence microscope (DMRXA). Chromosomes are counterstained with propidium iodide and the fluorescent signal of the probe appears as two symmetrical yellow-green spots on both chromatids of the fluorescent R-band chromosome (red). Thus, a particular EST-related nucleic acids, positional segments of EST-related nucleic acids or fragments of positional segments of EST-related nucleic acids may be localized to a particular cytogenetic R-band on a given chromosome.

Once the EST-related nucleic acids, positional segments of EST-related nucleic acids or fragments of positional segments of EST-related nucleic acids have been assigned to particular chromosomes using the techniques described in Examples 41–43 above, they may be utilized to construct a high resolution map of the chromosomes on which they are located or to identify the chromosomes in a sample.

EXAMPLE 44

Use of EST-related Nucleic Acids Positional Segments of EST-related Nucleic Acids or Fragments of Positional Segments of EST-related Nucleic Acids to Construct or Expand Chromosome Maps Chromosome mapping involves assigning a given unique sequence to a particular chromosome as described above. Once the unique sequence has been mapped to a given chromosome, it is ordered relative to other unique sequences located on the same chromosome. One approach to chromosome mapping utilizes a series of yeast artificial chromosomes (YACs) bearing several thousand long inserts derived from the chromosomes of the organism from which the EST-related nucleic acids, positional segments of EST-related nucleic acids or fragments of positional segments of EST-related nucleic acids are obtained. This approach is described in Ramaiah Nagaraja et al, *Genome Research* 7:210–222, March 1997, the disclosure of which is incorporated herein by reference. Briefly, in this approach each chromosome is broken into overlapping pieces which are inserted into the YAC vector. The YAC inserts are screened using PCR or other methods to determine whether they include the EST-related nucleic acids, positional segments of EST-related nucleic acids or fragments of positional segments of EST-related nucleic acids whose position is to be determined. Once an insert has been found which includes the 5' EST, the insert can be analyzed by PCR or other methods to determine whether the insert also contains other sequences known to be on the chromosome or in the region from which the EST-related nucleic acids, positional segments of EST-related nucleic acids or fragments of positional segments of EST-related nucleic acids was derived. This process can be repeated for each insert in the YAC library to determine the location of each of the EST-related nucleic acids, positional segments of EST-related nucleic acids or fragments of positional segments of EST-related nucleic acids relative to one another and to other known chromosomal markers. In this way, a high resolution map of the distribution of numerous unique markers along each of the organisms chromosomes may be obtained.

As described in Example 45 below EST-related nucleic acids, positional segments of EST-related nucleic acids or fragments of positional segments of EST-related nucleic acids may also be used to identify genes associated with a particular phenotype, such as hereditary disease or drug response.

3. Use of EST-related Nucleic Acids Positional Segments of EST-related Nucleic acids or Fragments of Positional Segments of EST-related Nucleic Acids Gene Identification

EXAMPLE 45

Identification of Genes Associated With Hereditary Diseases or Drug Response This example illustrates an approach useful for the association of EST-related nucleic acids, positional segments of EST-related nucleic acids or fragments of positional segments of EST-related nucleic acids with particular phenotypic characteristics. In this example, a particular EST-related nucleic acids, positional segments of EST-related nucleic acids or fragments of positional segments of EST-related nucleic acids is used as a test probe to associate that EST-related nucleic acids, positional segments of EST-related nucleic acids or fragments of positional segments of EST-related nucleic acids with a particular phenotypic characteristic.

EST-related nucleic acids, positional segments of EST-related nucleic acids or fragments of positional segments of EST-related nucleic acids are mapped to a particular location on a human chromosome using techniques such as those described in Examples 41 and 42 or other techniques known in the art. A search of Mendelian Inheritance in Man (V. McKusick, *Mendelian Inheritance in Man* (available on line through Johns Hopkins University Welch Medical Library) reveals the region of the human chromosome which contains the EST-related nucleic acids, positional segments of EST-related nucleic acids or fragments of positional segments of EST-related nucleic acids to be a very gene rich region containing several known genes and several diseases or phenotypes for which genes have not been identified. The gene corresponding to this EST-related nucleic acids, positional segments of EST-related nucleic acids or fragments of positional segments of EST-related nucleic acids thus becomes an immediate candidate for each of these genetic diseases.

Cells from patients with these diseases or phenotypes are isolated and expanded in culture. PCR primers from the EST-related nucleic acids, positional segments of EST-related nucleic acids or fragments of positional segments of EST-related nucleic acids are used to screen genomic DNA, mRNA or cDNA obtained from the patients. EST-related nucleic acids, positional segments of EST-related nucleic acids or fragments of positional segments of EST-related nucleic acids that are not amplified in the patients can be positively associated with a particular disease by further analysis. Alternatively, the PCR analysis may yield fragments of different lengths when the samples are derived from an individual having the phenotype associated with the disease than when the sample is derived from a healthy individual, indicating that the gene containing the EST-related nucleic acids, positional segments of EST-related nucleic acids or fragments of positional segments of EST-related nucleic acids may be responsible for the genetic disease.

VII. Use of EST-related Nucleic Acids, Positional Segments of EST-related Nucleic Acids or Fragments of Positional Segments of EST-related Nucleic Acids to Construct Vectors and Uses Thereof The present EST-related nucleic acids, positional segments of EST-related nucleic acids or fragments of positional segments of EST-related nucleic acids may also be used to construct secretion vectors capable of directing the secretion of the proteins encoded by genes therein. Such secretion vectors may facilitate the purification or enrichment of the proteins encoded by genes inserted therein by reducing the number of background proteins from which the desired protein must be purified or enriched. Exemplary secretion vectors are described in Example 46 below.

1. Construction of Vectors and Uses Thereof

EXAMPLE 46

Construction of Secretion Vectors

The secretion vectors of the present invention include a promoter capable of directing gene expression in the host cell, tissue, or organism of interest. Such promoters include the Rous Sarcoma Virus promoter, the SV40 promoter, the human cytomegaloviruspromoter, and other promoters familiar to those skilled in the art.

A signal sequence from one of the EST-related nucleic acids, positional segments of EST-related nucleic acids or fragments of positional segments of EST-related nucleic acids is operably linked to the promoter such that the mRNA transcribed from the promoter will direct the translation of the signal peptide. Preferably, the signal sequence is from one of the nucleic acids of SEQ ID NOs.24–3883. The host cell, tissue, or organism may be any cell, tissue, or organism which recognizes the signal peptide encoded by the signal sequence in the EST-related nucleic acids, positional segments of EST-related nucleic acids or fragments of positional segments of EST-related nucleic acids. Suitable hosts include mammalian cells, tissues or organisms, avian cells, tissues, or organisms, insect cells, tissues or organisms, or yeast.

In addition, the secretion vector contains cloning sites for inserting genes encoding the proteins which are to be secreted. The cloning sites facilitate the cloning of the insert gene in frame with the signal sequence such that a fusion protein in which the signal peptide is fused to the protein encoded by the inserted gene is expressed from the mRNA transcribed from the promoter. The signal peptide directs the extracellular secretion of the fusion protein.

The secretion vector may be DNA or RNA and may integrate into the chromosome of the host, be stably maintained as an extrachromosomal replicon in the host, be an artificial chromosome, or be transiently present in the host. Preferably, the secretion vector is maintained in multiple copies in each host cell. As used herein, multiple copies means at least 2, 5, 10, 20, 25, 50 or more than 50 copies per cell. In some embodiments, the multiple copies are maintained extrachromosomally. In other embodiments, the multiple copies result from amplification of a chromosomal sequence.

Many nucleic acid backbones suitable for use as secretion vectors are known to those skilled in the art, including retroviral vectors, SV40 vectors, Bovine Papilloma Virus vectors, yeast integrating plasmids, yeast episomal plasmids, yeast artificial chromosomes, human artificial chromosomes, P element vectors, baculovirus vectors, or bacterial plasmids capable of being transiently introduced into the host.

The secretion vector may also contain a polyA signal such that the polyA signal is located downstream of the gene inserted into the secretion vector.

After the gene encoding the protein for which secretion is desired is inserted into the secretion vector, the secretion vector is introduced into the host cell, tissue, or organism using calcium phosphate precipitation, DEAE-Dextran, electroporation, liposome-mediatedtransfection, viral particles or as naked DNA. The protein encoded by the inserted gene is then purified or enriched from the supernatant using conventional techniques such as ammonium sulfate precipitation, immunoprecipitation, immunoaffinitychromatography, size exclusion chromatography, ion exchange chromatography, and HPLC. Alternatively, the secreted protein may be in a sufficiently enriched or pure state in the supernatant or growth media of the host to permit it to be used for its intended purpose without further enrichment.

The signal sequences may also be inserted into vectors designed for gene therapy. In such vectors, the signal sequence is operably linked to a promoter such that mRNA transcribed from the promoter encodes the signal peptide. A cloning site is located downstream of the signal sequence such that a gene encoding a protein whose secretion is desired may readily be inserted into the vector and fused to the signal sequence. The vector is introduced into an appropriate host cell. The protein expressed from the promoter is secreted extracellularly, thereby producing a therapeutic effect.

EXAMPLE 47

Fusion Vectors

The EST-related nucleic acids, positional segments of EST-related nucleic acids or fragments of positional segments of EST-related nucleic acids may be used to construct fusion vectors for the expression of chimeric polypeptides. The chimeric polypeptides comprise a first polypeptide portion and a second polypeptide portion. In the fusion vectors of the present invention, nucleic acids encoding the first polypeptide portion and the second polypeptide portion are joined in frame with one another so as to generate a nucleic acid encoding the chimeric polypeptide. The nucleic acid encoding the chimeric polypeptide is operably linked to a promoter which directs the expression of an mRNA encoding the chimeric polypeptide. The promoter may be in any of the expression vectors described herein including those described in Examples 20 and 46.

Preferably, the fusion vector is maintained in multiple copies in each host cell. In some embodiments, the multiple copies are maintained extrachromosomally. In other embodiments, the multiple copies result from amplification of a chromosomal sequence.

The first polypeptide portion may comprise any of the polypeptides encoded by the EST-related nucleic acids, positional segments of EST-related nucleic acids or fragments of positional segments of EST-related nucleic acids. In some embodiments, the first polypeptide portion may be one of the EST-related polypeptides, fragments of EST-related polypeptides, positional segments of EST-related polypeptides, or fragments of positional segments of EST-related polypeptides.

The second polypeptide portion may comprise any polypeptide of interest. In some embodiments, the second polypeptide portion may comprise a polypeptide having a detectable enzymatic activity such as green fluorescent protein or β galactosidase. Chimeric polypeptides in which the second polypeptide portion comprises a detectable polypeptide may be used to determine the intracellular localization of the first polypeptide portion. In such procedures, the fusion vector encoding the chimeric polypeptide is introduced into a host cell under conditions which facilitate the expression of the chimeric polypeptide. Where appropriate, the cells are treated with a detection reagent which is visible under the microscope following a catalytic reaction with the detectable polypeptide and the cellular location of the detection reagent is determined. For example, if the polypeptide having a detectable enzymatic activity is β galactosidase, the cells may be treated with Xgal. Alternatively, where the detectable polypeptide is directly detectable without the addition of a detection reagent, the intracellular location of the chimeric polypeptide is determined by performing microscopy under conditions in which the dectable polypeptide is visible. For example, if the detectable polypeptide is green fluorescent protein or a modified version thereof, microscopy is performed by exposing the host cells to light having an appropriate wavelength to cause the green fluorescent protein or modified version thereof to fluoresce.

Alternatively, the second polypeptide portion may comprise a polypeptide whose isolation, purification, or enrichment is desired. In such embodiments, the isolation, purification, or enrichment of the second polypeptide portion may be achieved by performing the immunoaffinity chromatography procedures described below using an immunoaffinity column having an antibody directed against the first polypeptide portion coupled thereto.

The proteins encoded by the EST-related nucleic acids, positional segments of EST-related nucleic acids or fragments of positional segments of EST-related nucleic acids or the EST-related polypeptides, fragments of EST-related polypeptides, positional segments of EST-related polypeptides, or fragments of positional segments of EST-related polypeptides may also be used to generate antibodies as explained in Examples 20 and 33 in order to identify the tissue type or cell species from which a sample is derived as described in Example 48.

EXAMPLE 48

Identification of Tissue Types or Cell Species by Means of Labeled Tissue Specific Antibodies Identification of specific tissues is accomplished by the visualization of tissue specific antigens by means of antibody preparations according to Examples 20 and 33 which are conjugated, directly or indirectly to a detectable marker. Selected labeled antibody species bind to their specific antigen binding partner in tissue sections, cell suspensions, or in extracts of soluble proteins from a tissue sample to provide a pattern for qualitative or semi-qualitative interpretation.

Antisera for these procedures must have a potency exceeding that of the native preparation, and for that reason, antibodies are concentrated to a mg/ml level by isolation of the gamma globulin fraction, for example, by ion-exchange chromatography or by ammonium sulfate fractionation. Also, to provide the most specific antisera, unwanted antibodies, for example to common proteins, must be removed from the gamma globulin fraction, for example by means of insoluble immunoabsorbents, before the antibodies are labeled with the marker. Either monoclonal or heterologous antisera is suitable for either procedure.

1. Immunohistochemical Techniques

Purified, high-titer antibodies, prepared as described above, are conjugated to a detectable marker, as described, for example, by Fudenberg, H., Chap. 26 in: *Basic 503 Clinical Immunology*, $3^{rd}$ Ed. Lange, Los Altos, Calif. (1980) or Rose, et al., Chap. 12 in: *Methods in ImmunodiagNOsis*, 2d Ed. John Wiley and Sons, New York (1980), the disclosures of which are incorporated herein by reference.

A fluorescent marker, either fluorescein or rhodamine, is preferred, but antibodies can also be labeled with an enzyme that supports a color producing reaction with a substrate, such as horseradish peroxidase. Markers can be added to tissue-bound antibody in a second step, as described below. Alternatively, the specific antitissue antibodies can be labeled with ferritin or other electron dense particles, and localization of the ferritin coupled antigen-antibody complexes achieved by means of an electron microscope. In yet another approach, the antibodies are radiolabeled, with, for example $^{125}I$, and detected by overlaying the antibody treated preparation with photographic emulsion.

Preparations to carry out the procedures can comprise monoclonal or polyclonal antibodies to a single protein or peptide identified as specific to a tissue type, for example, brain tissue, or antibody preparations to several antigenically distinct tissue specific antigens can be used in panels, independently or in mixtures, as required.

Tissue sections and cell suspensions are prepared for immunohistochemical examination according to common histological techniques. Multiple cryostat sections (about 4 m, unfixed) of the unknown tissue and known control, are mounted and each slide covered with different dilutions of the antibody preparation. Sections of known and unknown tissues should also be treated with preparations to provide a positive control, a negative control, for example, preimmune sera, and a control for non-specific staining, for example, buffer.

Treated sections are incubated in a humid chamber for 30 min at room temperature, rinsed, then washed in buffer for 30–45 min. Excess fluid is blotted away, and the marker developed.

If the tissue specific antibody was not labeled in the first incubation, it can be labeled at this time in a second antibody-antibody reaction, for example, by adding fluorescein- or enzyme-conjugated antibody against the immunoglobulin class of the antiserum-producing species, for example, fluorescein labeled antibody to mouse IgG. Such labeled sera are commercially available.

The antigen found in the tissues by the above procedure can be quantified by measuring the intensity of color or fluorescence on the tissue section, and calibrating that signal using appropriate standards.

2. Identification of Tissue Specific Soluble Proteins

The visualization of tissue specific proteins and identification of unknown tissues from that procedure is carried out using the labeled antibody reagents and detection strategy as described for immunohistochemistry; however the sample is prepared according to an electrophoretic technique to distribute the proteins extracted from the tissue in an orderly array on the basis of molecular weight for detection.

A tissue sample is homogenized using a Virtis apparatus; cell suspensions are disrupted by Dounce homogenization or osmotic lysis, using detergents in either case as required to disrupt cell membranes, as is the practice in the art. Insoluble cell components such as nuclei, microsomes, and membrane fragments are removed by ultracentrifugation, and the soluble protein-containing fraction concentrated if necessary and reserved for analysis.

A sample of the soluble protein solution is resolved into individual protein species by conventional SDS polyacrylamide electrophoresis as described, for example, by Davis, L. el al., Section 19-2 in: *Basic Methods in Molecular Biology* (P. Leder, ed), Elsevier, New York (1986), the disclosure of which is incorporated herein by reference, using a range of amounts of polyacrylamide in a set of gels to resolve the entire molecular weight range of proteins to be detected in the sample. A size marker is run in parallel for purposes of estimating molecular weights of the constituent proteins. Sample size for analysis is a convenient volume of from 5 to 55 l, and containing from about 1 to 100 g protein. An aliquot of each of the resolved proteins is transferred by blotting to a nitrocellulose filter paper, a process that maintains the pattern of resolution. Multiple copies are prepared. The procedure, known as Western Blot Analysis, is well described in Davis, L. et al., supra Section 19-3. One set of nitrocellulose blots is stained with Coomassie Blue dye to visualize the entire set of proteins for comparison with the antibody bound proteins. The remaining nitrocellulose filters are then incubated with a solution of one or more specific antisera to tissue specific proteins prepared as described in Examples 20 and 33. In this procedure, as in procedure A above, appropriate positive and negative sample and reagent controls are run.

In either procedure described above a detectable label can be attached to the primary tissue antigen-primary antibody complex according to various strategies and permutations thereof. In a straightforward approach, the primary specific antibody can be labeled; alternatively, the unlabeled complex can be bound by a labeled secondary anti-IgG antibody. In other approaches, either the primary or secondary antibody is conjugated to a biotin molecule, which can, in a subsequent step, bind an avidin conjugated marker. According to yet another strategy, enzyme labeled or radioactive protein A, which has the property of binding to any IgG, is bound in a final step to either the primary or secondary antibody.

EXAMPLE 49

Immunohistochemical Localization of Polypeptides

The antibodies prepared as described in Examples 20 and 33 above may be utilized to determine the cellular location of a polypeptide. The polypeptide may be any of the polypeptides encoded by EST-related nucleic acids, positional segments of EST-related nucleic acids or fragments of positional segments of EST-related nucleic acids or the polypeptide may be one of the EST-related polypeptides, fragments of EST-related polypeptides, positional segments of EST-related polypeptides, or fragments of positional segments of EST-related polypeptides. In some embodiments, the polypeptide may be a chimeric polypeptide such as those encoded by the fusion vectors of Example 47.

Cells expressing the polypeptide to be localized are applied to a microscope slide and fixed using any of the procedures typically employed in immunohistochemical localization techniques, including the methods described in *Current Protocols in Molecular Biology*, John Wiley and Sons, Inc. 1997. Following a washing step, the cells are contacted with the antibody. In some embodiments, the antibody is conjugated to a detectable marker as described above to facilitate detection. Alternatively, in some embodiments, after the cells have been contacted with an antibody to the polypeptide to be localized, a secondary antibody which has been conjugated to a detectable marker is placed in contact with the antibody against the polypeptide to be localized.

Thereafter, microscopy is performed under conditions suitable for visualizing the cellular location of the polypeptide.

The visualization of tissue specific antigen binding at levels above those seen in control tissues to one or more tissue specific antibodies, directed against the polypeptides encoded by EST-related nucleic acids, positional segments of EST-related nucleic acids or fragments of positional segments of EST-related nucleic acids or antibodies against the EST-related polypeptides, fragments of EST-related polypeptides, positional segments of EST-related polypeptides, or fragments of positional segments of EST-related polypeptides, can identify tissues of unknown origin, for example, forensic samples, or differentiated tumor tissue that has metastasized to foreign bodily sites.

The antibodies of Example 20 and 33 may also be used in the immunoaffinity chromatography techniques described below to isolate, purify or enrich the polypeptides encoded by the EST-related nucleic acids, positional segments of EST-related nucleic acids or fragments of positional segments of EST-related nucleic acids or to isolate, purify or enrich EST-related polypeptides, fragments of EST-related polypeptides, positional segments of EST-related polypeptides, or fragments of positional segments of EST-related polypeptides. The immunoaffinity chromatography techniques described below may also be used to isolate, purify or enrich polypeptides which have been linked to the polypeptides encoded by the EST-related nucleic acids, positional segments of EST-related nucleic acids or fragments of positional segments of EST-related nucleic acids or to isolate, purify or enrich polypeptides which have been linked to EST-related polypeptides, fragments of EST-related polypeptides, positional segments of EST-related polypeptides, or fragments of positional segments of EST-related polypeptides.

EXAMPLE 50

Immunoaffinity Chromatography

Antibodies prepared as described above are coupled to a support. Preferably, the antibodies are monoclonal antibodies, but polyclonal antibodies may also be used. The support may be any of those typically employed in immunoaffinity chromatography, including Sepharose CL-4B (Pharmacia, Piscataway, N.J.), Sepharose CL-2B (Pharmacia, Piscataway, N.J.), Affi-gel 10 (Biorad, Richmond, Calif.), or glass beads.

The antibodies may be coupled to the support using any of the coupling reagents typically used in immunoaffinity chromatography, including cyanogen bromide. After coupling the antibody to the support, the support is contacted with a sample which contains a target polypeptide whose isolation, purification or enrichment is desired. The target polypeptide may be a polypeptide encoded by the EST-related nucleic acids, positional segments of EST-related nucleic acids or fragments of positional segments of EST-related nucleic acids or the target polypeptide may be one of the EST-related polypeptides, fragments of EST-related polypeptides, positional segments of EST-related polypeptides, or fragments of positional segments of EST-related polypeptides. The target polypeptides may also be polypeptides which have been linked to the polypeptides encoded by the EST-related nucleic acids, positional segments of EST-related nucleic acids or fragments of positional segments of EST-related nucleic acids or the target polypeptides may be polypeptides which have been linked to EST-related polypeptides, fragments of EST-related polypeptides, positional segments of EST-related polypeptides, or fragments of positional segments of EST-related polypeptides using the fusion vectors described above.

Preferably, the sample is placed in contact with the support for a sufficient amount of time and under appropriate conditions to allow at least 50% of the target polypeptide to specifically bind to the antibody coupled to the support.

Thereafter, the support is washed with an appropriate wash solution to remove polypeptides which have non-specifically adhered to the support. The wash solution may be any of those typically employed in immunoaffinity chromatography, including PBS, Tris-lithium chloride buffer (01 M lysine base and 0.5 M lithium chloride, pH 8.0), Tris-hydrochloride buffer (0.05 M Tris-hydrochloride, pH 8.0), or Tris/Triton/NaCl buffer (50 Mm Tris.cl, pH 8.0 or 9.0, 0.1% Triton X1100, and 0.5 MNaCl).

After washing, the specifically bound target polypeptide is eluted from the support using the high pH or low pH elution solutions typically employed in immunoaffinity chromatography. In particular, the elution solutions may contain an eluant such as triethanolamine, diethylamine, calcium chloride, sodium thiocyanate, potasssium bromide, acetic acid, or glycine. In some embodiments, the elution solution may also contain a detergent such as Triton X-100 or octyl-β-D-glucoside.

The EST-related nucleic acids, positional segments of EST-related nucleic acids or fragments of positional segments of EST-related nucleic acids may also be used to clone sequences located upstream of the 5' ESTs which are capable of regulating gene expression, including promoter sequences, enhancer sequences, and other upstream sequences which influence transcription or translation levels. Once identified and cloned, these upstream regulatory sequences may be used in expression vectors designed to direct the expression of an inserted gene in a desired spatial, temporal, developmental, or quantitative fashion. Example 51 describes a method for cloning sequences upstream of the EST-related nucleic acids, positional segments of EST-related nucleic acids or fragments of positional segments of EST-related nucleic acids.

2. Identification of Upstream Sequences With Promoting or Regulatory Activities

EXAMPLE 51

Use of EST-related Nucleic Acids Positional Segments of EST-related Nucleic Acids or Fragments of Positional Segments of EST-related Nucleic Acids to Clone Upstream Sequences From Genomic DNA Sequences derived from EST-related nucleic acids, positional segments of EST-related nucleic acids or fragments of positional segments of EST-related nucleic acids may be used to isolate the promoters of the corresponding genes using chromosome walking techniques. In one chromosome walking technique, which utilizes the Genome Walker kit available from Clontech, five complete genomic DNA samples are each digested with a different restriction enzyme which has a 6 base recognition site and leaves a blunt end. Following digestion, oligonucleotide adapters are ligated to each end of the resulting genomic DNA fragments.

For each of the five genomic DNA libraries, a first PCR reaction is performed according to the manufacturer's instructions (which are incorporated herein by reference) using an outer adapter primer provided in the kit and an outer gene specific primer. The gene specific primer should be selected to be specific for 5' EST of interest and should have a melting temperature, length, and location in the EST-related nucleic acids, positional segments of EST-related nucleic acids or fragments of positional segments of EST-related nucleic acids which is consistent with its use in PCR reactions. Each first PCR reaction contains 5ng of genomic DNA, 5 μl of 10×Tth reaction buffer, 0.2 Mm of each dNTP, 0.2 μM each of outer adapter primer and outer gene specific primer, 1.1 Mm of Mg(OAc)$_2$, and 1 μl of the Tth polymerase 50×mix in a total volume of 50 μl. The reaction cycle for the first PCR reaction is as follows: 1 min at 94° C./2 sec at 94° C., 3 min at 72° C. (7 cycles)/2 sec at 94° C., 3 min at 67° C. (32 cycles)/5 min at 67° C.

The product of the first PCR reaction is diluted and used as a template for a second PCR reaction according to the manufacturer's instructions using a pair of nested primers which are located internally on the amplicon resulting from the first PCR reaction. For example, 5 μl of the reaction product of the first PCR reaction mixture may be diluted 180 times. Reactions are made in a 50 μl volume having a composition identical to that of the first PCR reaction except the nested primers are used. The first nested primer is specific for the adapter, and is provided with the Genome Walker kit. The second nested primer is specific for the particular EST-related nucleic acids, positional segments of EST-related nucleic acids or fragments of positional segments of EST-related nucleic acids for which the promoter is to be cloned and should have a melting temperature, length, and location in the EST-related nucleic acids, positional segments of EST-related nucleic acids or fragments of positional segments of EST-related nucleic acids which is consistent with its use in PCR reactions. The reaction parameters of the second PCR reaction are as follows: 1 min at 94° C./2 sec at 94° C., 3 min at 72° C. (6 cycles)/2 sec at 94° C., 3 min at 67° C. (25 cycles)/5 min at –67° C. The product of the second PCR reaction is purified, cloned, and sequenced using standard techniques.

Alternatively, two or more human genomic DNA libraries can be constructed by using two or more restriction enzymes. The digested genomic DNA is cloned into vectors which can be converted into single stranded, circular, or linear DNA. A biotinylated oligonucleotide comprising at least 15 nucleotides from the EST-related nucleic acids, positional segments of EST-related nucleic acids or fragments of positional segments of EST-related nucleic acids sequence is hybridized to the single stranded DNA. Hybrids between the biotinylated oligonucleotide and the single stranded DNA containing the EST-related nucleic acids, positional segments of EST-related nucleic acids or fragments of positional segments of EST-related nucleic acids are isolated as described above. Thereafter, the single stranded DNA containing the EST-related nucleic acids, positional segments of EST-related nucleic acids or fragments of positional segments of EST-related nucleic acids is released from the beads and converted into double stranded DNA using a primer specific for the EST-related nucleic acids, positional segments of EST-related nucleic acids or fragments of positional segments of EST-related nucleic acids or a primer corresponding to a sequence included in the cloning vector. The resulting double stranded DNA is transformed into bacteria. cDNAs containing the EST-related nucleic acids, positional segments of EST-related nucleic acids or fragments of positional segments of EST-related nucleic acids are identified by colony PCR or colony hybridization.

Once the upstream genomic sequences have been cloned and sequenced as described above, prospective promoters and transcription start sites within the upstream sequences may be identified by comparing the sequences upstream of the EST-related nucleic acids, positional segments of EST-related nucleic acids or fragments of positional segments of EST-related nucleic acids with databases containing known transcription start sites, transcription factor binding sites, or promoter sequences.

In addition, promoters in the upstream sequences may be identified using promoter reporter vectors as described in Example 52.

EXAMPLE 52

Identification of Promoters in Cloned Upstream Sequences

The genomic sequences upstream of the EST-related nucleic acids, positional segments of EST-related nucleic acids or fragments of positional segments of EST-related nucleic acids are cloned into a suitable promoter reporter vector, such as the pSEAP-Basic, pSEAP-Enhancer, pβgal-Basic, pβgal-Enhancer, or pEGFP-1 Promoter Reporter vectors available from Clontech. Briefly, each of these promoter reporter vectors include multiple cloning sites positioned upstream of a reporter gene encoding a readily assayable protein such as secreted alkaline phosphatase, β galactosidase, or green fluorescent protein. The sequences upstream of the EST-related nucleic acids, positional segments of EST-related nucleic acids or fragments of positional segments of EST-related nucleic acids are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for augmenting transcription levels from weak promoter sequences. A significant level of expression above that observed with the vector lacking an insert indicates that a promoter sequence is present in the inserted upstream sequence.

Appropriate host cells for the promoter reporter vectors may be chosen based on the results of the above described determination of expression patterns of the EST-related nucleic acids, positional segments of EST-related nucleic acids or fragments of positional segments of EST-related nucleic acids. For example, if the expression pattern analysis indicates that the mRNA corresponding to a particular EST-related nucleic acids, positional segments of EST-related nucleic acids or fragments of positional segments of EST-related nucleic acids is expressed in fibroblasts, the promoter reporter vector may be introduced into a human fibroblast cell line.

Promoter sequences within the upstream genomic DNA may be further defined by constructing nested deletions in the upstream DNA using conventional techniques such as Exonuclease III digestion. The resulting deletion fragments can be inserted into the promoter reporter vector to determine whether the deletion has reduced or obliterated promoter activity. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into the cloning sites in the promoter reporter vectors.

EXAMPLE 53

Cloning and Identification of Promoters

Using the method described in Example 51 above with 5' ESTs, sequences upstream of several genes were obtained. Using the primer pairs GGG AAG ATG GAG ATA GTA TTG CCT G (SEQ ID NO.15) and CTG CCA TGT ACA TGA TAG AGA GAT TC (SEQ ID NO.16), the promoter having the internal designation p13H2 (SEQ ID NO.17) was obtained.

Using the primer pairs GTA CCA GGGG ACT GTG ACC ATT GC (SEQ ID NO.18) and CTG TGA CCA TTG CTC CCA AGA GAG (SEQ ID NO.19), the promoter having the internal designation P15B4 (SEQ ID NO.20) was obtained.

Using the primer pairs CTG GGA TGG AAG GCA CGG TA (SEQ ID NO.21) and GAG ACC ACA CAG CTA GAC AA (SEQ ID NO.22), the promoter having the internal designation P29B6 (SEQ ID NO.23) was obtained.

Figure 4:
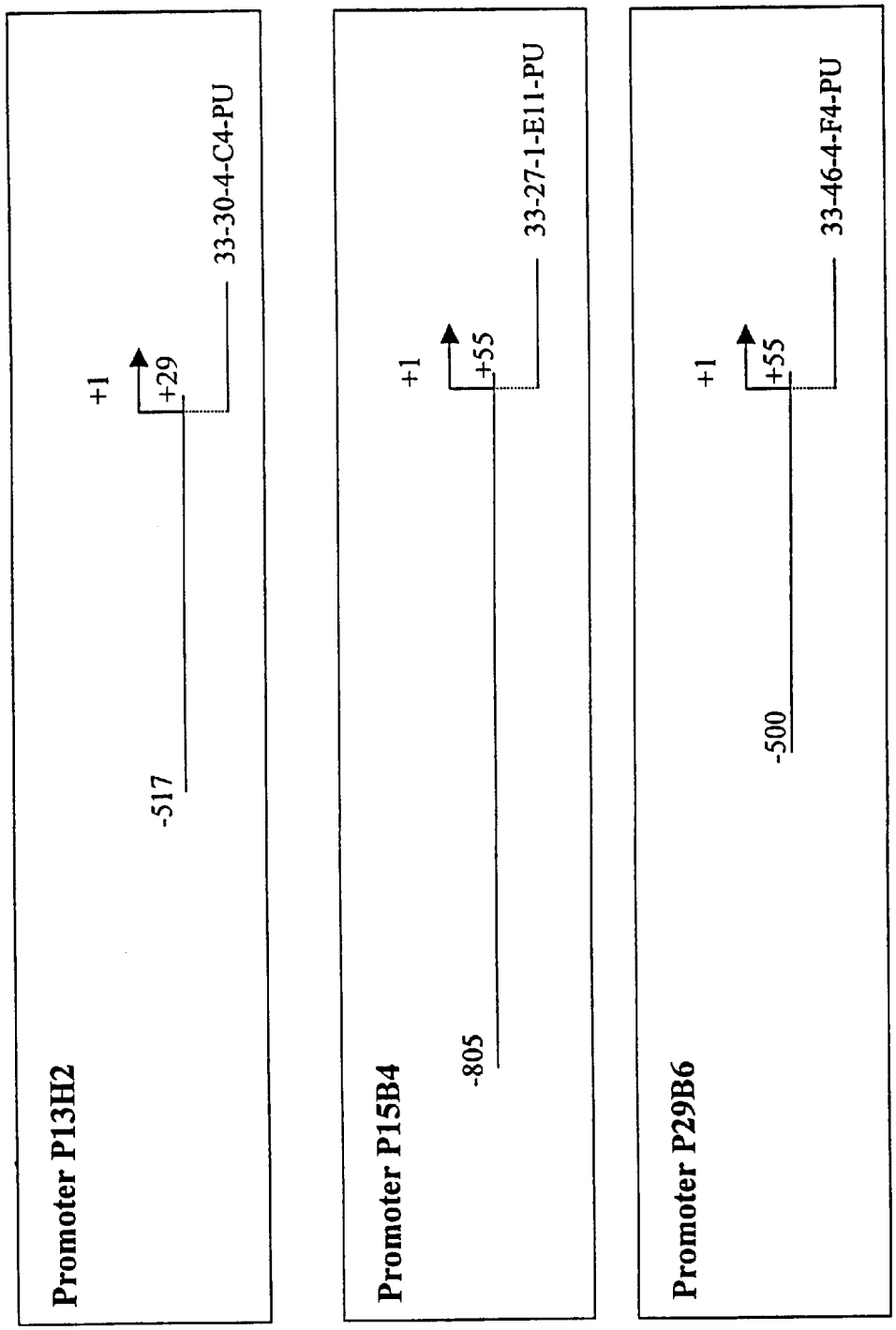
FIG. 4 provides a schematic description of the promoters isolated and the way they are assembled with the corresponding 5' ESTs.

FIG. 4 provides a schematic description of the promoters isolated and the way they are assembled with the corresponding 5'tags. The upstream sequences were screened for the presence of motifs resembling transcription factor binding sites or known transcription start sites using the computer program MatInspector release 2.0, August 1996.

FIG. 5 describes the transcription factor binding sites present in each of these promoters. The columns labeled matrice provides the name of the MatInspector matrix used. The column labeled position provides the 5' position of the promoter site. Numeration of the sequence starts from the transcription site as determined by matching the genomic sequence with the 5' EST sequence. The column labeled "orientation" indicates the DNA strand on which the site is found, with the + strand being the coding strand as determined by matching the genomic sequence with the sequence of the 5' EST. The column labeled "score" provides the MatInspector score found for this site. The column labeled "length" provides the length of the site in nucleotides. The column labeled "sequence" provides the sequence of the site found.

Bacterial clones containing plasmids containing the promoter sequences described above described above are presently stored in the inventor's laboratories under the internal identification numbers provided above. The inserts may be recovered from the deposited materials by growing an aliquot of the appropriate bacterial clone in the appropriate medium. The plasmid DNA can then be isolated using plasmid isolation procedures familiar to those skilled in the art such as alkaline lysis minipreps or large scale alkaline lysis plasmid isolation procedures. If desired the plasmid DNA may be further enriched by centrifugation on a cesium chloride gradient, size exclusion chromatography, or anion exchange chromatography. The plasmid DNA obtained using these procedures may then be manipulated using standard cloning techniques familiar to those skilled in the art. Alternatively, a PCR can be done with primers designed at both ends of the inserted EST-related nucleic acids, positional segments of EST-related nucleic acids or fragments of positional segments of EST-related nucleic acids. The PCR product which corresponds to the EST-related nucleic acids, positional segments of EST-related nucleic acids or fragments of positional segments of EST-related nucleic acids can then be manipulated using standard cloning techniques familiar to those skilled in the art.

The promoters and other regulatory sequences located upstream of the EST-related nucleic acids, positional segments of EST-related nucleic acids or fragments of positional segments of EST-related nucleic acids may be used to design expression vectors capable of directing the expression of an inserted gene in a desired spatial, temporal, developmental, or quantitative manner. A promoter capable of directing the desired spatial, temporal, developmental, and quantitative patterns may be selected using the results of the expression analysis described above. For example, if a promoter which confers a high level of expression in muscle is desired, the promoter sequence upstream of EST-related nucleic acids, positional segments of EST-related nucleic acids or fragments of positional segments of EST-related nucleic acids derived from an mRNA which are expressed at a high level in muscle, as determined by the methods above, may be used in the expression vector.

Preferably, the desired promoter is placed near multiple restriction sites to facilitate the cloning of the desired insert downstream of the promoter, such that the promoter is able to drive expression of the inserted gene. The promoter may be inserted in conventional nucleic acid backbones designed for extrachromosomal replication, integration into the host chromosomes or transient expression. Suitable backbones for the present expression vectors include retroviral backbones, backbones from eukaryotic episomes such as SV40 or Bovine Papilloma Virus, backbones from bacterial episomes, or artificial chromosomes.

Preferably, the expression vectors also include a polyA signal downstream of the multiple restriction sites for directing the polyadenylation of mRNA transcribed from the gene inserted into the expression vector.

Following the identification of promoter sequences using the procedures of Examples 51–53, proteins which interact with the promoter may be identified as described in Example 54 below.

EXAMPLE 54

Identification of Proteins Which Interact With Promoter Sequences, Upstream Regulatory Sequences, or mRNA Sequences within the promoter region which are likely to bind transcription factors may be identified by homology to known transcription factor binding sites or through conventional mutagenesis or deletion analyses of reporter plasmids containing the promoter sequence. For example, deletions may be made in a reporter plasmid containing the promoter sequence of interest operably linked to an assayable reporter gene. The reporter plasmids carrying various deletions within the promoter region are transfected into an appropriate host cell and the effects of the deletions on expression levels is assessed. Transcription factor binding sites within the regions in which deletions reduce expression levels may be further localized using site directed mutagenesis, linker scanning analysis, or other techniques familiar to those skilled in the art.

Nucleic acids encoding proteins which interact with sequences in the promoter may be identified using one-hybrid systems such as those described in the manual accompanying the Matchmaker One-Hybrid System kit available from Clontech (Catalog No. K1603–1), the disclosure of which is incorporated herein by reference. Briefly, the Matchmaker One-hybrid system is used as follows. The target sequence for which it is desired to identify binding proteins is cloned upstream of a selectable reporter gene and integrated into the yeast genome. Preferably, multiple copies of the target sequences are inserted into the reporter plasmid in tandem. A library comprised of fusions between cDNAs to be evaluated for the ability to bind to the promoter and the activation domain of a yeast transcription factor, such as GAL4, is transformed into the yeast strain containing the integrated reporter sequence. The yeast are plated on selective media to select cells expressing the selectable marker linked to the promoter sequence. The colonies which grow on the selective media contain genes encoding proteins which bind the target sequence. The inserts in the genes encoding the fusion proteins are further characterized by sequencing. In addition, the inserts may be inserted into expression vectors or in vitro transcription vectors. Binding of the polypeptides encoded by the inserts to the promoter DNA may be confirmed by techniques familiar to those skilled in the art, such as gel shift analysis or DNAse protection analysis.

VIII. Use of EST-related Nucleic Acids, Positional Segments of EST-related Nucleic Acids or Fragments of Positional Segments of EST-related Nucleic Acids in Gene Therapy The present invention also comprises the use of EST-related nucleic acids, positional segments of EST-related nucleic acids or fragments of positional segments of EST-related nucleic acids in gene therapy strategies, including antisense and triple helix strategies as described in Examples 55 and 56 below. In antisense approaches, nucleic acid sequences complementary to an mRNA are hybridized to the mRNA intracellularly, thereby blocking the expression of the protein encoded by the mRNA. The antisense sequences may prevent gene expression through a variety of mechanisms. For example, the antisense sequences may inhibit the ability of ribosomes to translate the mRNA. Alternatively, the antisense sequences may block transport of the mRNA from the nucleus to the cytoplasm, thereby limiting the amount of mRNA available for translation. Another mechanism through which antisense sequences may inhibit gene expression is by interfering with mRNA splicing. In yet another strategy, the antisense nucleic acid may be incorporated in a ribozyme capable of specifically cleaving the target mRNA.

EXAMPLE 55

Preparation and Use of Antisense Oligonucleotides

The antisense nucleic acid molecules to be used in gene therapy may be either DNA or RNA sequences. They may comprise a sequence complementary to the sequence of the EST-related nucleic acids, positional segments of EST-related nucleic acids or fragments of positional segments of EST-related nucleic acids. The antisense nucleic acids should have a length and melting temperature sufficient to permit formation of an intracellular duplex with sufficient stability to inhibit the expression of the mRNA in the duplex. Strategies for designing antisense nucleic acids suitable for use in gene therapy are disclosed in Green et al., *Ann. Rev. Biochem.* 55:569–597 (1986) and Izant and Weintraub, *Cell* 36:1007–1015 (1984), which are hereby incorporated by reference.

In some strategies, antisense molecules are obtained from a nucleotide sequence encoding a protein by reversing the orientation of the coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of the antisense nucleic acids in vivo by operably linking DNA containing the antisense sequence to a promoter in an expression vector.

Alternatively, oligonucleotides which are complementary to the strand normally transcribed in the cell may be synthesized in vitro. Thus, the antisense nucleic acids are complementary to the corresponding mRNA and are capable of hybridizing to the mRNA to create a duplex. In some embodiments, the antisense sequences may contain modified sugar phosphate backbones to increase stability and make them less sensitive to RNase activity. Examples of modifications suitable for use in antisense strategies are described by Rossi et al., *Pharmacol. Ther.* 50(2):245–254, (1991) which is hereby incorporated by reference.

Various types of antisense oligonucleotides complementary to the sequence of the EST-related nucleic acids, positional segments of EST-related nucleic acids or fragments of positional segments of EST-related nucleic acids may be used. In one preferred embodiment, stable and semi-stable antisense oligonucleotides described in International Application No. PCT WO94/23026, hereby incorporated by reference, are used. In these molecules, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides against herpes simplex virus types 1 and 2 described in International Application No. WO 95/04141, hereby incorporated by reference, are used.

In yet another preferred embodiment, the covalently cross-linked antisense oligonucleotides described in International Application No. WO 96/31523, hereby incorporated by reference, are used. These double- or single-stranded oligonucleotides comprise one or more, respectively, inter- or intra-oligonucleotidecovalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, incorporated by reference, may also be used. These molecules are stable to degradation and contain at least one transcription control recognition sequence which binds to control proteins and are effective as decoys therefor. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0 572 287 A2, hereby incorporated by reference are used. These ligated oligonucleotide "dumbbells" contain the binding site for a transcription factor and inhibit expression of the gene under control of the transcription factor by sequestering the factor.

Use of the closed antisense oligonucleotides disclosed in International Application No. WO 92/19732, hereby incorporated by reference, is also contemplated. Because these molecules have no free ends, they are more resistant to degradation by exonucleases than are conventional oligonucleotides. These oligonucleotides may be multifunctional, interacting with several regions which are not adjacent to the target mRNA.

The appropriate level of antisense nucleic acids required to inhibit gene expression may be determined using in vitro expression analysis. The antisense molecule may be introduced into the cells by diffusion, injection, infection or transfection using procedures known in the art. For example, the antisense nucleic acids can be introduced into the body as a bare or naked oligonucleotide,oligonucleotide encapsulated in lipid, oligonucleotide sequence encapsidated by viral protein, or as an oligonucleotide operably linked to a promoter contained in an expression vector. The expression vector may be any of a variety of expression vectors known in the art, including retroviral or viral vectors, vectors capable of extrachromosomal replication, or integrating vectors. The vectors may be DNA or RNA.

The anti sense molecules are introduced onto cell samples at a number of different concentrations preferably between $1 \times 10^{-1}$M to $1 \times 10^{4}$M. Once the minimum concentration that can adequately control gene expression is identified, the optimized dose is translated to a dosage suitable for use in vivo. For example, an inhibiting concentration in culture of $1 \times 10^{-7}$ translates into a dose of approximately 0.6 mg/kg bodyweight. Levels of oligonucleotide approaching 100 mg/kg bodyweight or higher may be possible after testing the toxicity of the oligonucleotide in laboratory animals. It is additionally contemplated that cells from the vertebrate are removed, treated with the antisense oligonucleotide, and reintroduced into the vertebrate.

It is further contemplated that the antisense oligonucleotide sequence is incorporated into a ribozyme sequence to enable the antisense to specifically bind and cleave its target mRNA. For technical applications of ribozyme and antisense oligonucleotides see Rossi et al., supra.

In a preferred application of this invention, the polypeptide encoded by the gene is first identified, so that the effectiveness of antisense inhibition on translation can be monitored using techniques that include but are not limited to antibody-mediated tests such as RIAs and ELISA, functional assays, or radiolabeling.

The EST-related nucleic acids, positional segments of EST-related nucleic acids or fragments of positional segments of EST-related nucleic acids may also be used in gene therapy approaches based on intracellular triple helix formation. Triple helix oligonucleotides are used to inhibit transcription from a genome. They are particularly useful for studying alterations in cell activity as it is associated with a particular gene. The EST-related nucleic acids, positional segments of EST-related nucleic acids or fragments of positional segments of EST-related nucleic acids of the present invention or, more preferably, a portion of those sequences, can be used to inhibit gene expression in individuals having diseases associated with expression of a particular gene. Similarly, the EST-related nucleic acids, positional segments of EST-related nucleic acids or fragments of positional segments of EST-related nucleic acids can be used to study the effect of inhibiting transcription of a particular gene within a cell. Traditionally, homopurine sequences were considered the most useful for triple helix strategies. However, homopyrimidine sequences can also inhibit gene expression. Such homopyrimidine ligonucleotides bind to the major groove at homopurine:homopyrimidine sequences. Thus, both types of sequences from the EST-related nucleic acids, positional segments of EST-related nucleic acids or fragments of positional segments of EST-related nucleic acids are contemplated within the scope of this invention.

EXAMPLE 56

Preparation and Use of Triple Helix Probes

The sequences of the EST-related nucleic acids, positional segments of EST-related nucleic acids or fragments of positional segments of EST-related nucleic acids are scanned to identify 10-mer to 20-mer homopyrimidine or homopurine stretches which could be used in triple-helix based strategies for inhibiting gene expression. Following identification of candidate homopyrimidine or homopurine stretches, their efficiency in inhibiting gene expression is assessed by introducing varying amounts of oligonucleotides containing the candidate sequences into tissue culture cells which normally express the target gene. The oligonucleotides may be prepared on an oligonucleotide synthesizer or they may be purchased commercially from a company specializing in custom oligonucleotide synthesis, such as GENSET, Paris, France.

The oligonucleotides may be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced gene expression using techniques such as Northern blotting, RNase protection assays, or PCR based strategies to monitor the transcription levels of the target gene in cells which have been treated with the oligonucleotide. The cell functions to be monitored are predicted based upon the homologies of the target genes corresponding to the EST-related nucleic acids, positional segments of EST-related nucleic acids or fragments of positional segments of EST-related nucleic acids from which the oligonucleotide were derived with known gene sequences that have been associated with a particular function. The cell functions can also be predicted based on the presence of abnormal physiologies within cells derived from individuals with a particular inherited disease, particularly when the EST-related nucleic acids, positional segments of EST-related nucleic acids or fragments of positional segments of EST-related nucleic acids are associated with the disease using techniques described herein.

The oligonucleotides which are effective in inhibiting gene expression in tissue culture cells may then be introduced in vivo using the techniques described above and in Example 55 at a dosage calculated based on the in vitro results, as described in Example 55.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (*Science* 245:967–971 (1989), which is hereby incorporated by this reference).

EXAMPLE 57

Use of EST-related Nucleic Acids, Positional Segments of EST-related Nucleic Acids or Fragments of Positional Segments of EST-related Nucleic Acids to Express an Encoded Protein in a Host Organism The EST-related nucleic acids, positional segments of EST-related nucleic acids or fragments of positional segments of EST-related nucleic acids may also be used to express an encoded protein or polypeptide in a host organism to produce a beneficial effect. In addition, nucleic acids encoding the EST-related polypeptides, positional segments of EST-related polypeptides or fragments of positional segments of EST-related polypeptides may be used to express the encoded protein or polypeptide in a host organism to produce a beneficial effect.

In such procedures, the encoded protein or polypeptide may be transiently expressed in the host organism or stably expressed in the host organism. The encoded protein or polypeptide may have any of the activities described above. The encoded protein or polypeptide may be a protein or polypeptide which the host organism lacks or, alternatively, the encoded protein may augment the existing levels of the protein in the host organism.

In some embodiments in which the protein or polypeptide is secreted, nucleic acids encoding the full length protein (i.e. the signal peptide and the mature protein), or nucleic acids encoding only the mature protein (i.e. the protein generated when the signal peptide is cleaved off) is introduced into the host organism.

The nucleic acids encoding the proteins or polypeptides may be introduced into the host organism using a variety of techniques known to those of skill in the art. For example, the extended cDNA may be injected into the host organism as naked DNA such that the encoded protein is expressed in the host organism, thereby producing a beneficial effect.

Alternatively, the nucleic acids encoding the protein or polypeptide may be cloned into an expression vector downstream of a promoter which is active in the host organism. The expression vector may be any of the expression vectors designed for use in gene therapy, including viral or retroviral vectors. The expression vector may be directly introduced into the host organism such that the encoded protein is expressed in the host organism to produce a beneficial effect. In another approach, the expression vector may be introduced into cells in vitro. Cells containing the expression vector are thereafter selected and introduced into the host organism, where they express the encoded protein or polypeptide to produce a beneficial effect.

EXAMPLE 58

Use of Signal Peptides to Import Proteins Into Cells

The short core hydrophobic region (h) of signal peptides encoded by the sequences of SEQ ID NOs. 24–383 and 1339–2059 may also be used as a carrier to import a peptide or a protein of interest, so-called cargo, into tissue culture cells (Lin et al., *J. Biol. Chem.*, 270: 14225–14258 (1995); Du et al., *J. Peptide Res.*, 51: 235–243 (1998); Rojas et al., *Nature Biotech.*, 16: 370–375 (1998)).

When cell permeable peptides of limited size (approximately up to 25 amino acids) are to be translocated across cell membrane, chemical synthesis may be used in order to add the h region to either the C-terminus or the N-terminus to the cargo peptide of interest. Alternatively, when longer peptides or proteins are to be imported into cells, nucleic acids can be genetically engineered, using techniques familiar to those skilled in the art, in order to link the extended cDNA sequence encoding the h region to the 5' or the 3' end of a DNA sequence coding for a cargo polypeptide. Such genetically engineered nucleic acids are then translated either in vitro or in vivo after transfection into appropriate cells, using conventional techniques to produce the resulting cell permeable polypeptide. Suitable hosts cells are then simply incubated with the cell permeable polypeptide which is then translocated across the membrane.

This method may be applied to study diverse intracellular functions and cellular processes. For instance, it has been used to probe functionally relevant domains of intracellular proteins and to examine protein-protein interactions involved in signal transduction pathways (Lin et al., supra; Lin et al., *J. Biol. Chem.*, 271: 5305–5308 (1996); Rojas et al., *J. Biol. Chem.*, 271: 27456–27461 (1996); Liu et al., *Proc. Natl. Acad. Sci. USA*, 93: 11819–11824 (1996); Rojas et al., *Bioch. Biophys. Res. Commun.*, 234: 675–680 (1997)).

Such techniques may be used in cellular therapy to import proteins producing therapeutic effects. For instance, cells isolated from a patient may be treated with imported therapeutic proteins and then re-introduced into the host organism.

Alternatively, the h region of signal peptides of the present invention could be used in combination with a nuclear localization signal to deliver nucleic acids into cell nucleus. Such oligonucleotides may be antisense oligonucleotides or oligonucleotides designed to form triple helixes, as describedabove, in order to inhibit processing and maturation of a target cellular RNA.

EXAMPLE 59

Computer Embodiments

As used herein the term "cDNA codes of SEQ ID NOs. 24–3883 and 7744–19335" encompasses the nucleotide sequences of SEQ ID NOs. 24–3883 and 7744–19335, fragments of SEQ ID NOs. 24–3883 and 7744–19335, nucleotide sequences homologous to SEQ ID NOs. 24–3883 and 7744–19335 or homologous to fragments of SEQ ID NOs. 24–3883 and 7744–19335, and sequences complementary to all of the preceding sequences. The fragments include fragments of SEQ ID NOs. 24–3883 and 7744–19335 comprising at least 8, 10, 12, 15, 18, 20, 25, 28, 30, 35, 40, 50, 75, 100, 150, 200, 300, 400, 500, 1000 or 2000 consecutive nucleotides of SEQ ID NOs. 24–3883 and 7744–19335. Preferably, the fragments are novel fragments. Preferably the fragments include polynucleotides described in Tables IVa and IVb, polynucleotides described in Tables IVa and IVb updated, or fragments thereof comprising at least 8, 10, 12, 15, 18, 20, 25, 28, 30, 35, 40, 50, 75, 100, 150, 200, 300, 400, 500, 1000 or 2000 consecutive nucleotides of the polynucleotides described in Tables IVa and IVb, or polynucleotides described in Tables IVa and IVb updated. Homologous sequences and fragments of SEQ ID NOs. 24–3883 and 7744–19335 refer to a sequence having at least 99%, 98%, 97%, 96%, 95%, 90%, 85%, 80%, or 75% homology to these sequences. Homology may be determined using any of the computer programs and parameters described in Example 17, including BLAST2N with the default parameters or with any modified parameters. Homologous sequences also include RNA sequences in which uridines replace the thymines in the cDNA codes of SEQ ID NOs. 24–3883 and 7744–19335. The homologous sequences may be obtained using any of the procedures described herein or may result from the correction of a sequencing error as described above. Preferably the homologous sequences and fragments of SEQ ID NOs. 24–3883 and 7744–19335 include polynucleotides described in Tables IVa and IVb, polynucleotides described in Tables IVa and IVb updated, or fragments comprising at least 8, 10, 12, 15, 18, 20, 25, 28, 30, 35, 40, 50, 75, 100, 150, 200, 300, 400, 500, 1000 or 2000 consecutive nucleotides of the polynucleotides described in Tables IVa and IVb, or polynucleotides described in Tables IVa and IVb updated. It will be appreciated that the cDNA codes of SEQ ID NOs. 24–3883 and 7744–19335 can be represented in the traditional single character format (See the inside back cover of Styer, Lubert. *Biochemistry*, $3^{rd}$ edition. W. H Freeman & Co., New York.) or in any other format which records the identity of the nucleotides in a sequence.

As used herein the term "polypeptide codes of SEQ ID NOS. 3884–7743" encompasses the polypeptide sequence of SEQ ID NOs. 3884–7743 which are encoded by the cDNAs of SEQ ID NOs. 24–3883, polypeptide sequences homologous to the polypeptides of SEQ ID NOS. 3884–7743, or fragments of any of the preceding sequences. Homologous polypeptide sequences refer to a polypeptide sequence having at least 99%, 98%, 97%, 96%, 95%, 90%, 85%, 80%, 75% homology to one of the polypeptide sequences of SEQ ID NOS. 3884–7743. Homology may be determined using any of the computer programs and parameters described herein, including FASTA with the default parameters or with any modified parameters. The homologous sequences may be obtained using any of the procedures described herein or may result from the correction of a sequencing error as described above. The polypeptide fragments comprise at least 5, 8, 10, 12, 15, 20, 25, 30, 35, 40, 50, 60, 75, 100, 150 or 200 consecutive amino acids of the polypeptides of SEQ ID NOS. 3884–7743. Preferably, the fragments are novel fragments. Preferably, the fragments include polypeptides encoded by the polynucleotides described in Tables IVa and IVb, polynucleotides described in Tables IVa and IVb updated, or fragments thereof comprising at least 5, 10, 15, 20, 25, 30, 35, 40, 50, 75, 100, or 150 consecutive amino acids of the polypeptides encoded by the polynucleotides described in Tables IVa and IVb, or polynucleotides described in Tables IVa and IVb updated. It will be appreciated that the polypeptide codes of the SEQ ID NOS. 3884–7743 can be represented in the traditional single character format or three letter format (See the inside back cover of Starrier, Lubert. *Biochemistry*, $3^{rd}$ edition. W. H Freeman & Co., New York.) or in any other format which relates the identity of the polypeptides in a sequence.

It will be appreciated by those skilled in the art that the cDNA codes of SEQ ID NOs. 24–3883 and 7744–19335 and polypeptide codes of SEQ ID NOS. 3884–7743 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the cDNA codes of SEQ ID NOs. 24–3883 and 7744–19335, one or more of the polypeptide codes of SEQ ID NOS. 3884–7743. Another aspect of the present invention is a computer readable medium having recorded thereon at least 2, 5, 10, 15, 20, 25, 30, or 50 cDNA codes of SEQ ID NOs. 24–3883 and 7744–19335. Another aspect of the present invention is a computer readable medium having recorded thereon at least 2, 5, 10, 15, 20, 25, 30, or 50 polypeptide codes of SEQ ID NOS. 3884–7743.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 6:
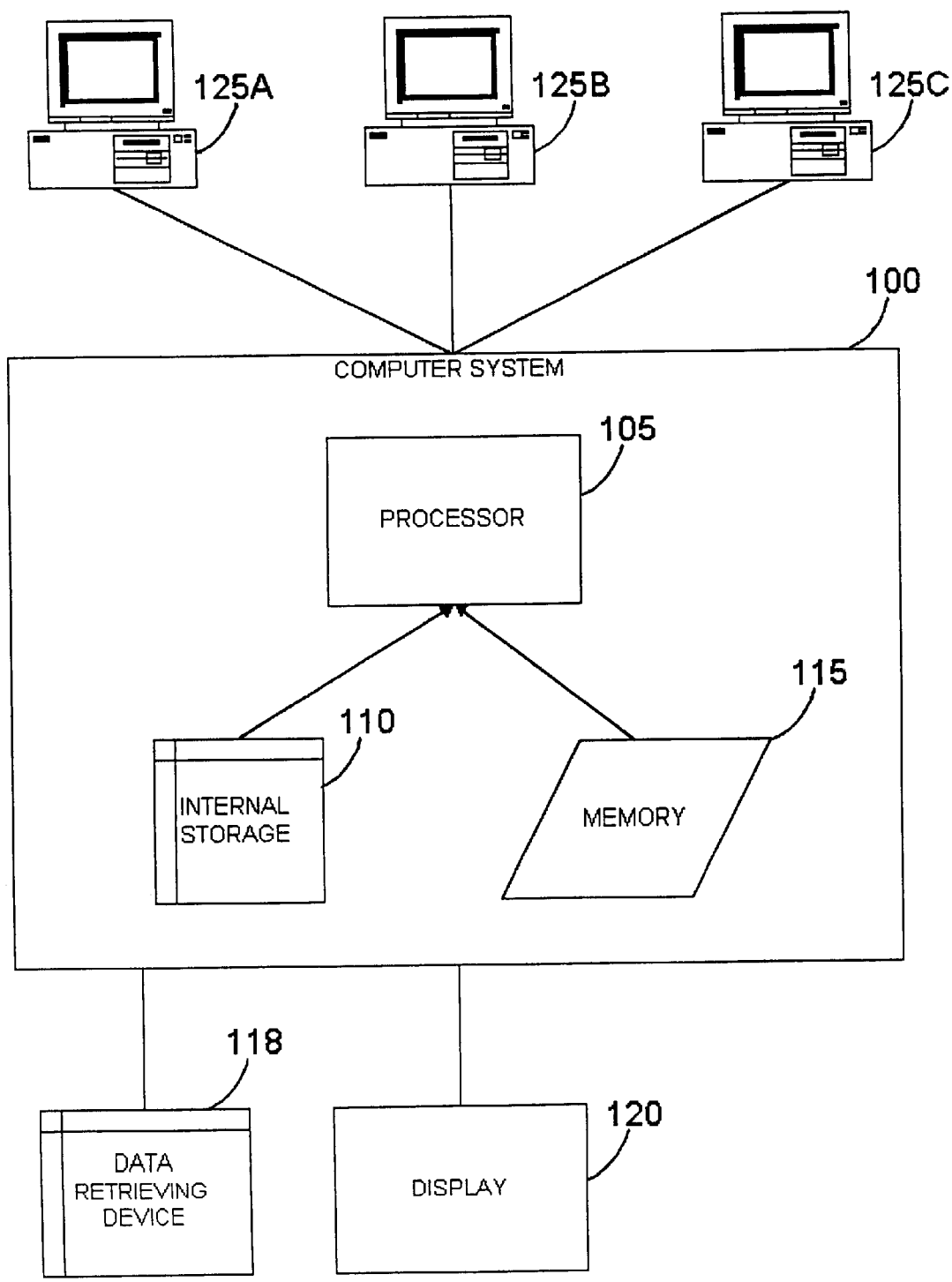
FIG. 6 is a block diagram of an exemplary computer system.

Embodiments of the present invention include systems, particularly computer systems which store and manipulate the sequence information described herein. One example of a computer system 100 is illustrated in block diagram form in FIG. 6. As used herein, "a computer system" refers to the hardware components, software components, and data storage components used to analyze the nucleotide sequences of the cDNA codes of SEQ ID NOs. 24–3883 and 7744–19335, or the amino acid sequences of the polypeptide codes of SEQ ID NOS. 3884–7743. In one embodiment, the computer system 100 is a Sun Enterprise 1000 server (Sun Microsystems, Palo Alto, Calif.). The computer system 100 preferably includes a processor for processing, accessing and manipulating the sequence data. The processor 105 can be any well-known type of central processing unit, such as the Pentium III from Intel Corporation, or similar processor from Sun, Motorola, Compaq or International Business Machines.

Preferably, the computer system 100 is a general purpose system that comprises the processor 105 and one or more internal data storage components 105 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 18 for reading the data stored on the internal data storage devices 101.

The data retrieving device 118 may represent, for example, a floppy disk drive, a compact disk drive, a magnetic tape drive, etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a–c in a network or wide area network to provide centralized access to the computer system 100.

Software for accessing and processing the nucleotide sequences of the cDNA codes of SEQ ID NOs. 24–3883 and 7744–19335, or the amino acid sequences of the polypeptide codes of SEQ ID NOS. 3884–7743 (such as search tools, compare tools, and modeling tools etc.) may reside in main memory 115 during execution.

In some embodiments, the computer system 100 may further comprise a sequence comparer for comparing the above-described cDNA codes of SEQ ID NOs. 24–3883 and 7744–19335 or polypeptide codes of SEQ ID NOS. 3884–7743 stored on a computer readable medium to reference nucleotide or polypeptide sequences stored on a computer readable medium. A "sequence comparer" refers to one or more programs which are implemented on the computer system 100 to compare a nucleotide or polypeptide sequence with other nucleotide or polypeptide sequences and/or compounds including but not limited to peptides, peptidomimetics, and chemicals stored within the data storage means. For example, the sequence comparer may compare the nucleotide sequences of the cDNA codes of SEQ ID NOs. 24–3883 and 7744–19335, or the amino acid sequences of the polypeptide codes of SEQ ID NOS. 3884–7743 stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention.

Figure 7:
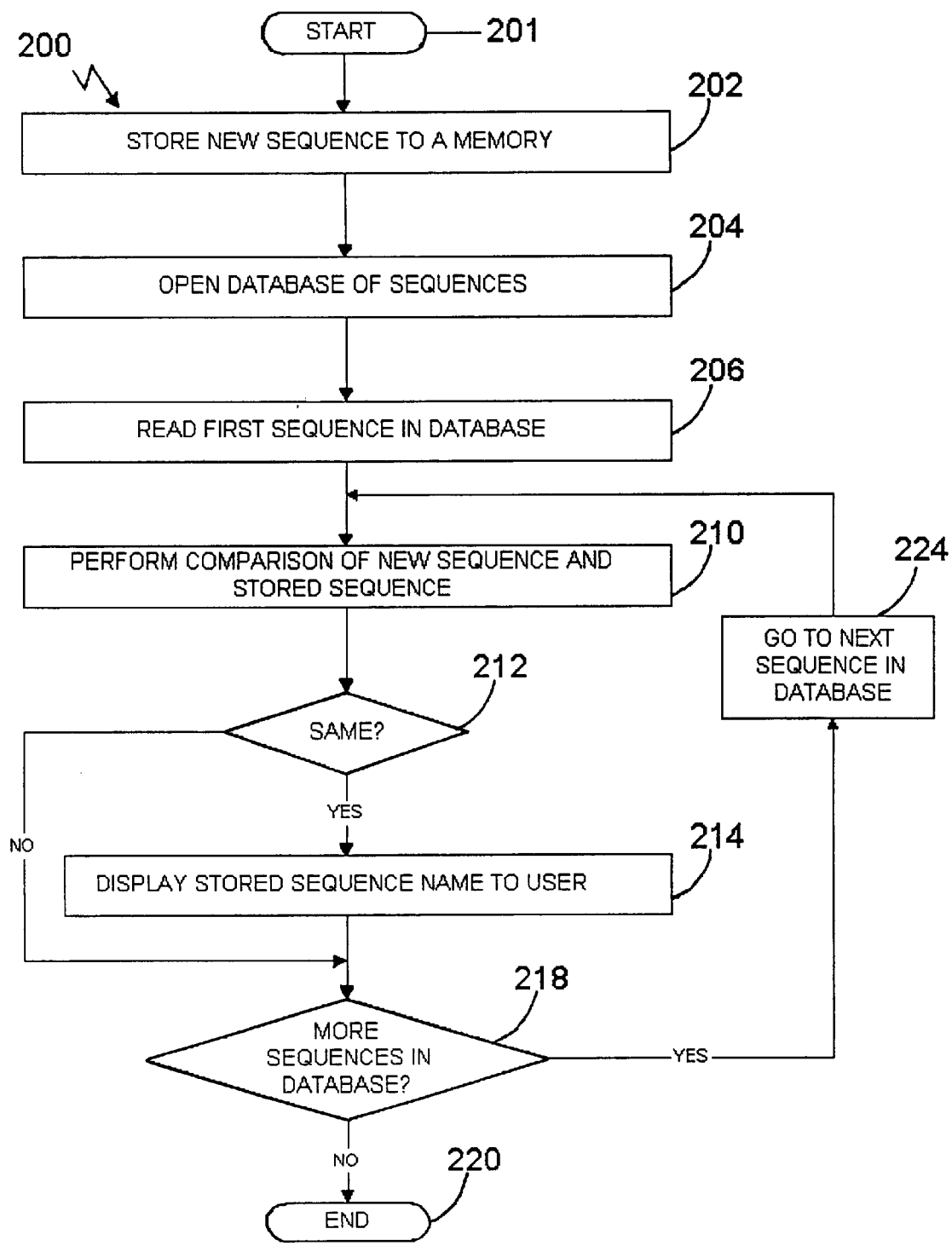
FIG. 7 is a flow diagram illustrating one embodiment of a process 200 for comparing a new nucleotide or protein sequence with a database of sequences in order to determine the homology levels between the new sequence and the sequences in the database.

FIG. 7 is a flow diagram illustrating one embodiment of a process 200 for comparing a new nucleotide or protein sequence with a database of sequences in order to determine the homology levels between the new sequence and the sequences in the database. The database of sequences can be a private database stored within the computer system 100, or a public database such as GENBANK, PIR or SWISSPROT that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the present invention is a computer system comprising a processor, a data storage device having stored thereon a nucleic acid code of SEQ ID NOs. 24–3883 and 7744–19335 or a polypeptide code of SEQ ID NOS. 3884–7743, a data storage device having retrievably stored thereon reference nucleotide sequences or polypeptide sequences to be compared to the nucleic acid code of SEQ ID NOs. 24–3883 and 7744–19335 or polypeptide code of SEQ ID NOS. 3884–7743 and a sequence comparer for conducting the comparison. The sequence comparer may indicate a homology level between the sequences compared or identify structural motifs in the above described nucleic acid code of SEQ ID NOs. 24–3883 and 7744–19335 and polypeptide codes of SEQ ID NOS. 3884–7743 or it may identify structural motifs in sequences which are compared to these cDNA codes and polypeptide codes. In some embodiments, the data storage device may have stored thereon the sequences of at least 2, 5, 10, 15, 20, 25, 30, or 50 of the cDNA codes of SEQ ID NOs. 24–3883 and 7744–19335 or polypeptide codes of SEQ ID NOS. 3884–7743.

Another aspect of the present invention is a method for determining the level of homology between a nucleic acid code of SEQ ID NOs. 24–3883 and 7744–19335 and a reference nucleotide sequence, comprising the steps of reading the nucleic acid code and the reference nucleotide sequence through the use of a computer program which determines homology levels and determining homology between the nucleic acid code and the reference nucleotide sequence with the computer program. The computer program may be any of a number of computer programs for determining homology levels, including those specifically enumerated herein, including BLAST2N with the default parameters or with any modified parameters. The method may be implemented using the computer systems described above. The method may also be performed by reading 2, 5, 10, 15, 20, 25, 30, or 50 of the above described cDNA codes of SEQ ID NOs. 24–3883 and 7744–19335 through use of the computer program and determining homology between the cDNA codes and reference nucleotide sequences.

Figure 8:
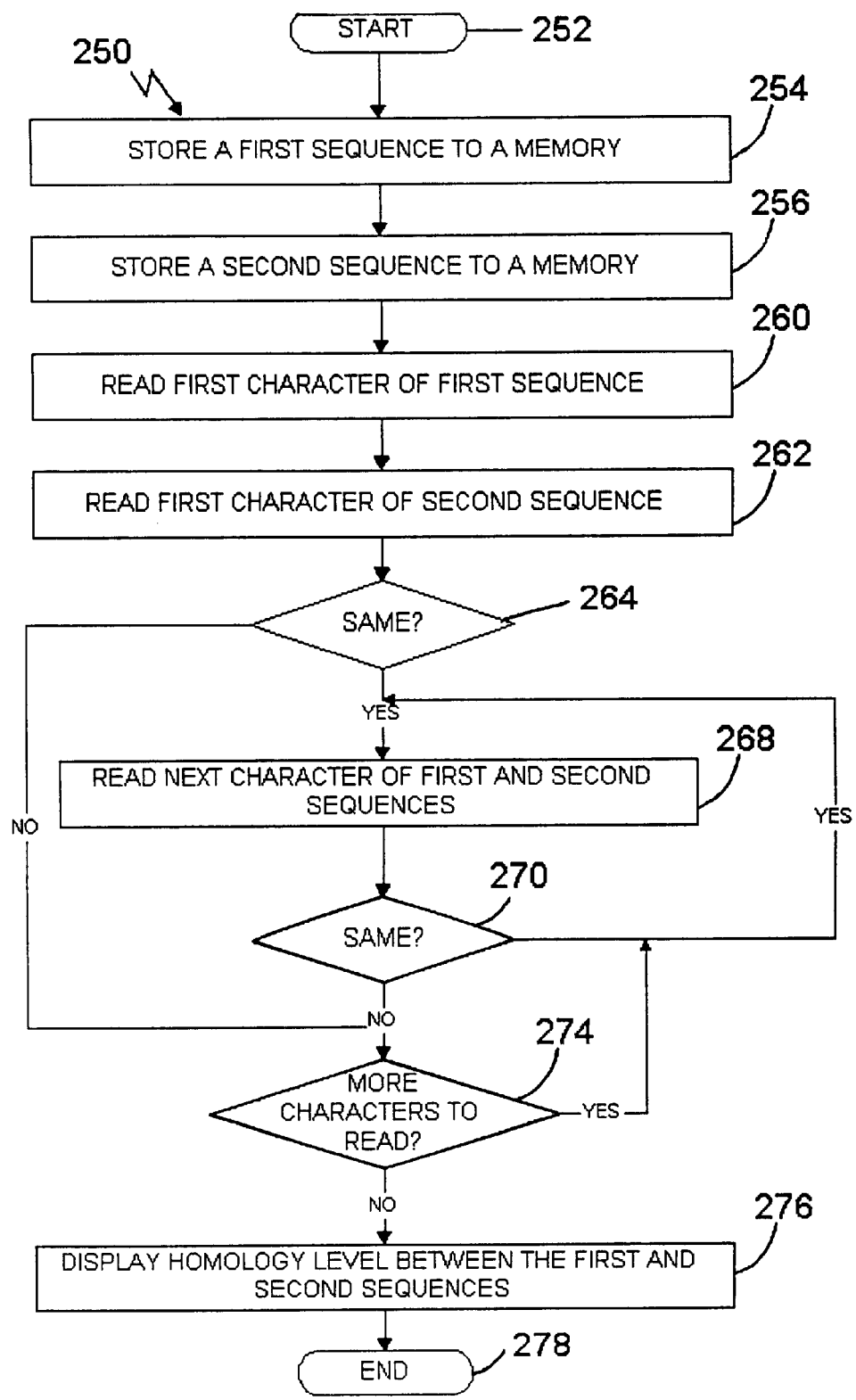
FIG. 8 is a flow diagram illustrating one embodiment of a process 250 in a computer for determining whether two sequences are homologous.

FIG. 8 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it should be in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there aren't any more characters to read, then the process 250 moves to a state 276 wherein the level of homology between the first and second sequences is displayed to the user. The level of homology is determined by calculating the profragment of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of the cDNA codes of the present invention, to reference nucleotide sequences in order to determine whether the nucleic acid code of SEQ ID NOs. 24–3883 and 7744–19335 differs from a reference nucleic acid sequence at one or more positions. Optionally such a program records the length and identity of inserted, deleted or substituted nucleotides with respect to the sequence of either the reference polynucleotide or the nucleic acid code of SEQ ID NOs. 24–3883 and 7744–19335. In one embodiment, the computer program may be a program which determines whether the nucleotide sequences of the cDNA codes of SEQ ID NOs. 24–3883 and 7744–19335 contain a biallelic marker or single nucleotide polymorphism (SNP) with respect to a reference nucleotide sequence. This single nucleotide polymorphism may comprise a single base substitution, insertion, or deletion, while this biallelic marker may comprise about one to ten consecutive bases substituted, inserted or deleted.

Another aspect of the present invention is a method for determining the level of homology between a polypeptide code of SEQ ID NOS. 3884–7743 and a reference polypeptide sequence, comprising the steps of reading the polypeptide code of SEQ ID NOS. 3884–7743 and the reference polypeptide sequence through use of a computer program which determines homology levels and determining homology between the polypeptide code and the reference polypeptide sequence using the computer program.

Accordingly, another aspect of the present invention is a method for determining whether a nucleic acid code of SEQ ID NOs. 24–3883 and 7744–19335 differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 8. The method may also be performed by reading at least 2, 5, 10, 15, 20, 25, 30, or 50 of the cDNA codes of SEQ ID NOs. 24–3883 and 7744–19335 and the reference nucleotide sequences through the use of the computer program and identifying differences between the cDNA codes and the reference nucleotide sequences with the computer program.

In other embodiments the computer based system may further comprise an identifier for identifying features within the nucleotide sequences of the cDNA codes of SEQ ID NOs. 24–3883 and 7744–19335 or the amino acid sequences of the polypeptide codes of SEQ ID NOS. 3884–7743.

An "identifier" refers to one or more programs which identifies certain features within the above-described nucleotide sequences of the cDNA codes of SEQ ID NOs. 24–3883 and 7744–19335 or the amino acid sequences of the polypeptide codes of SEQ ID NOS. 3884–7743. In one embodiment, the identifier may comprise a program which identifies an open reading frame in the cDNAs codes of SEQ ID NOs. 24–3883 and 7744–19335.

Figure 9:
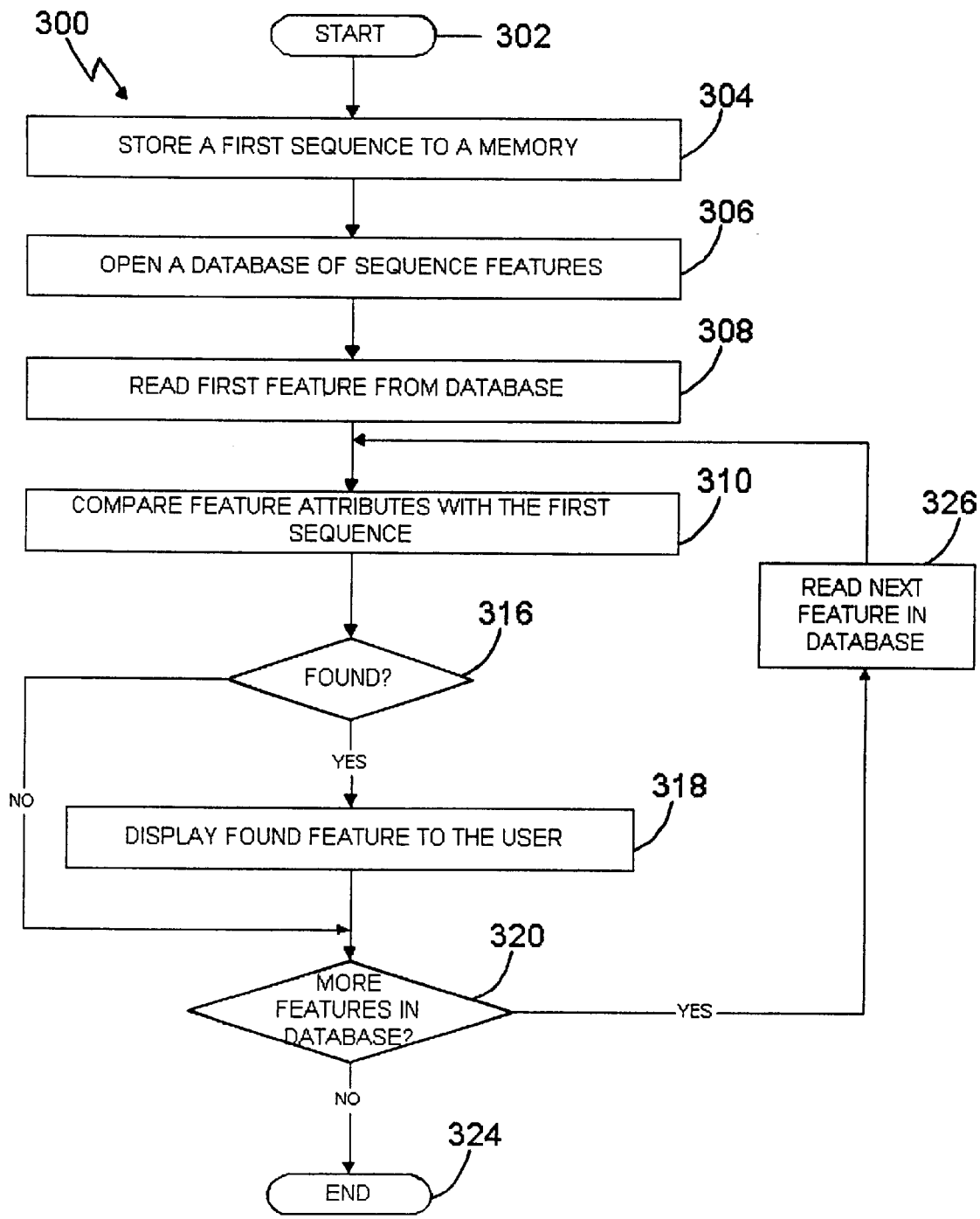
FIG. 9 is a flow diagram illustrating one embodiment of an identifier process 300 for detecting the presence of a feature in a sequence.

FIG. 9 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature+s attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (see Worldwide Website: gcg.com).

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

In another embodiment, the identifier may comprise a molecular modeling program which determines the 3-dimensional structure of the polypeptides codes of SEQ ID NOS. 3884–7743. In some embodiments, the molecular modeling program identifies target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to define the structurally conserved regions in that family. This protein modeling technique also uses the known three-dimensional structure of a homologous protein to approximate the structure of the polypeptide codes of SEQ ID NOS. 3884–7743. (See e.g., Srinivasan, et al., U.S. Pat. No. 5,557,535 issued Sept. 17, 1996). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods now enables the identification of likely folding patterns in a number of situations where the structural relatedness between target and template(s) is not detectable at the sequence level. Hybrid methods, in which fold recognition is performed using Multiple Sequence Threading (MST), structural equivalencies are deduced from the threading output using a distance geometry program DRAGON to construct a low resolution model, and a full-atom representation is constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalencies obtained from the MST output are converted into inter-residue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszódi et al., Proteins:Structure, Function, and Genetics, Supplement 1:38–42 (1997)).

The results of the molecular modeling analysis may then be used in rational drug design techniques to identify agents which modulate the activity of the polypeptide codes of SEQ ID NOS. 3884–7743.

Accordingly, another aspect of the present invention is a method of identifying a feature within the cDNA codes of SEQ ID NOs. 24–3883 and 7744–19335 or the polypeptide codes of SEQ ID NOS. 3884–7743 comprising reading the nucleic acid code(s) or the polypeptide code(s) through the use of a computer program which identifies features therein and identifying features within the nucleic acid code(s) or polypeptide code(s) with the computer program. In one embodiment, computer program comprises a computer program which identifies open reading frames. In a further embodiment, the computer program identifies structural motifs in a polypeptide sequence. In another embodiment, the computer program comprises a molecular modeling program. The method may be performed by reading a single sequence or at least 2, 5, 10, 15, 20, 25, 30, or 50 of the cDNA codes of SEQ ID NOs. 24–3883 and 7744–19335 or the polypeptide codes of SEQ ID NOS. 3884–7743 through the use of the computer program and identifying features within the cDNA codes or polypeptide codes with the computer program.

The cDNA codes of SEQ ID NOs. 24–3883 and 7744–19335 or the polypeptide codes of SEQ ID NOS. 3884–7743 may be stored and manipulated in a variety of data processor programs in a variety of formats. For example, the cDNA codes of SEQ ID NOs. 24–3883 and 7744–19335 or the polypeptide codes of SEQ ID NOS. 3884–7743 may be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the cDNA codes of SEQ ID NOs. 24–3883 and 7744–19335 or the polypeptide codes of SEQ ID NOS. 3884–7743. The following list is intended not to limit the invention but to provide guidance to programs and databases which are useful with the cDNA codes of SEQ ID NOs. 24–3883 and 7744–19335 or the polypeptide codes of SEQ ID NOS. 3884–7743. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCB1), BLASTN and BLASTX (Altschul et al, *J. Mol. Biol.* 215: 403 (1990)), FASTA (Pearson and Lipman, *Proc. Natl. Acad. Sci. USA*, 85: 2444 (1988)), FASTDB (Brutlag et al. Comp. App. Biosci. 6:237–245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

EXAMPLE 60

Methods of Making Nucleic Acids

The present invention also comprises methods of making the EST-related nucleic acids, fragments of EST-related nucleic acids, positional segments of the EST-related nucleic acids, or fragments of positional segments of the EST-related nucleic acids. The methods comprise sequentially linking together nucleotides to produce the nucleic acids having the preceding sequences. A variety of methods of synthesizing nucleic acids are known to those skilled in the art.

In many of these methods, synthesis is conducted on a solid support. These included the 3' phosphoramidite methods in which the 3' terminal base of the desired oligonucleotide is immobilized on an insoluble carrier. The nucleotide base to be added is blocked at the 5' hydroxyl and activated at the 3' hydroxyl so as to cause coupling with the immobilized nucleotide base. Deblocking of the new immobilized nucleotide compound and repetition of the cycle will produce the desired polynucleotide. Alternatively, polynucleotides may be prepared as described in U.S. Pat. No. 5,049,656, the disclosure of which is incorporated herein by reference. In some embodiments, several polynucleotides prepared as described above are ligated together to generate longer polynucleotides having a desired sequence.

EXAMPLE 61

Methods of Making Polypeptides

The present invention also comprises methods of making the polynucleotides encoded by EST-related nucleic acids, fragments of EST-related nucleic acids, positional segments of the EST-related nucleic acids, or fragments of positional segments of the EST-related nucleic acids and methods of making the EST-related polypeptides, fragments of EST-related polypeptides, positional segments of EST-related polypeptides, or fragments of EST-related polypeptides. The methods comprise sequentially linking together amino acids to produce the nucleic polypeptides having the preceding sequences. In some embodiments, the polypeptides made by these methods are 150 amino acid or less in length. In other embodiments, the polypeptides made by these methods are 120 amino acids or less in length.

A variety of methods of making polypeptides are known to those skilled in the art, including methods in which the carboxyl terminal amino acid is bound to polyvinyl benzene or another suitable resin. The amino acid to be added possesses blocking groups on its amino moiety and any side chain reactive groups so that only its carboxyl moiety can react. The carboxyl group is activated with carbodiimide or another activating agent and allowed to couple to the immobilized amino acid. After removal of the blocking group, the cycle is repeated to generate a polypeptide having the desired sequence. Alternatively, the methods described in U.S. Pat. No. 5,049,656, the disclosure of which is incorporated herein by reference, may be used.

As discussed above, the EST-related nucleic acids, fragments of the EST-related nucleic acids, positional segments of the EST-related nucleic acids, or fragments of positional segments of the EST-related nucleic acids can be used for various purposes. The polynucleotides can be used to express recombinant protein for analysis, characterization or therapeutic use; production of secreted polypeptides or chimeric polypeptides, antibody production, as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; for selecting and making oligomers for attachment to a "gene chip" or other support, including for examination for expression patterns; to raise anti-protein antibodies using DNA immunization techniques; and as an antigen to raise anti-DNA antibodies or elicit another immune response. Where the polynucleotide encodes a protein or polypeptide which binds or potentially binds to another protein or polypeptide (such as, for example, in a receptor-ligand interaction), the polynucleotide can also be used in interaction trap assays (such as, for example, that described in Gyuris et al., Cell 75:791–803 (1993), the disclosure of which is hereby incorporated by reference) to identify polynucleotides encoding the other protein or polypeptide with which binding occurs or to identify inhibitors of the binding interaction.

The proteins or polypeptides provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein or polypeptide binds or potentially binds to another protein or polypeptide (such as, for example, in a receptor-ligand interaction), the protein can be used to identify the other protein with which binding occurs or to identify inhibitors of the binding interaction. Proteins or polypeptides involved in these binding interactions can also be used to screen for peptide or small molecule inhibitors or agonists of the binding interaction.

Any or all of these research utilities are capable of being developed into reagent grade or kit format for commercializationas research products.

Methods for performing the uses listed above are well known to those skilled in the art. References disclosing such methods include without limitation "Molecular Cloning; A Laboratory Manual", 2d ed., Cold Spring Harbor Laboratory Press, Sambrook, J., E. F. Fritsch and T. Maniatis eds., 1989, and "Methods in Enzymology; Guide to Molecular Cloning Techniques", Academic Press, Berger, S. L. and A. R. Kimmel eds., 1987.

Polynucleotides and proteins or polypeptides of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

TABLE I (Positions of all ORFs)

| Seq Id No. | Positions of Open Reading Frame(s) | Seq Id No. | Positions of Open Reading Frame(s) |
|---|---|---|---|
| 24 | [109–342],[188–340] | 70 | [159–395],[317–472] |
| 25 | [63–365] | 71 | [143–328] |
| 26 | [73–555] | 72 | [65–487],[142–486] |
| 27 | [363–512] | 73 | [38–268] |
| 28 | [21–485] | 74 | [85–417] |
| 29 | [105–332] | 75 | [85–420] |
| 30 | [166–366] | 76 | [196–483],[248–484] |
| 31 | [52–504] | 77 | [171–434] |
| 32 | [107–517] | 78 | [26–190],[263–793] |
| 33 | [157–477] | 79 | [168–443] |
| 34 | [233–397] | 80 | [112–306],[153–308] |
| 35 | [60–482] | 81 | [147–323] |
| 36 | [284–454] | 82 | [21–569] |
| 37 | [35–481],[238–432] | 83 | [289–468] |
| 38 | [77–490] | 84 | [101–298],[295–459] |
| 39 | [107–676] | 85 | [255–419],[289–468] |
| 40 | [31–249] | 86 | [30–179],[300–515] |
| 41 | [81–440] | 87 | [221–673] |
| 42 | [23–424],[196–351] | 88 | [153–401] |
| 43 | [53–511] | 89 | [209–472] |
| 44 | [118–339] | 90 | [278–472] |
| 45 | [185–544] | 91 | [116–286],[355–570] |
| 46 | [9–482],[238–483] | 92 | [164–586] |
| 47 | [69–494] | 93 | [54–311] |
| 48 | [316–534] | 94 | [127–450] |
| 49 | [27–431] | 95 | [40–324] |
| 50 | [54–410] | 96 | [1–381],[24–263] |
| 51 | [164–463] | 97 | [227–670] |

TABLE I-continued (Positions of all ORFs)

| Seq Id No. | Positions of Open Reading Frame(s) | Seq Id No. | Positions of Open Reading Frame(s) |
|---|---|---|---|
| 52 | [94–546] | 98 | [76–450],[99–281] |
| 53 | [74–481] | 99 | [117–482] |
| 54 | [27–503] | 100 | [34–498] |
| 55 | [260–544] | 101 | [76–504],[95–250] |
| 56 | [297–506] | 102 | [72–248] |
| 57 | [27–479] | 103 | [113–349] |
| 58 | [163–390] | 104 | [72–356] |
| 59 | [85–273] | 105 | [73–276] |
| 60 | [85–273] | 106 | [167–487] |
| 61 | [31–273] | 107 | [257–490] |
| 62 | [46–255] | 108 | [274–453] |
| 63 | [154–342] | 109 | [144–500],[331–498] |
| 64 | [34–276] | 110 | [195–569] |
| 65 | [5–172] | 111 | [33–269],[116–583] |
| 66 | [144–479] | 112 | [153–416] |
| 67 | [233–478] | 113 | [14–400] |
| 68 | [115–321] | 114 | [9–524] |
| 69 | [72–443] | 115 | [258–479] |
| 116 | [223–495] | 162 | [32–721] |
| 117 | [206–622] | 163 | [298–495] |
| 118 | [344–496] | 164 | [306–491] |
| 119 | [290–541] | 165 | [45–593] |
| 120 | [86–451] | 166 | [156–308],[161–499] |
| 121 | [100–465] | 167 | [297–479] |
| 122 | [13–213] | 168 | [233–562],[270–515],[280–498] |
| 123 | [93–371],[202–465] | | |
| 124 | [195–488] | 169 | [164–490],[318–488] |
| 125 | [201–491] | 170 | [250–540] |
| 126 | [144–488] | 171 | [127–528] |
| 127 | [44–463] | 172 | [242–448] |
| 128 | [131–553] | 173 | [96–599] |
| 129 | [88–465],[153–410] | 174 | [239–514],[306–461] |
| 130 | [61–456] | 175 | [80–313],[96–458] |
| 131 | [194–391] | 176 | [140–499],[261–431] |
| 132 | [124–477] | 177 | [74–508] |
| 133 | [7–306],[89–289],[129–308] | 178 | [90–542] |
| 134 | [222–422] | 179 | [110–301] |
| 135 | [142–570] | 180 | [44–502] |
| 136 | [59–415],[265–414] | 181 | [293–454],[309–542] |
| 137 | [39–500] | 182 | [35–205],[150–509] |
| 138 | [143–493] | 183 | [198–500] |
| 139 | [259–645] | 184 | [202–465] |
| 140 | [236–496] | 185 | [274–561] |
| 141 | [292–456] | 186 | [229–483] |
| 142 | [54–488] | 187 | [202–519] |
| 143 | [62–217] | 188 | [148–330] |
| 144 | [6–290],[265–522] | 189 | [86–262] |
| 145 | [112–513] | 190 | [110–550] |
| 146 | [152–523] | 191 | [223–405] |
| 147 | [276–437] | 192 | [35–247] |
| 148 | [72–263] | 193 | [148–324] |
| 149 | [221–499] | 194 | [154–333] |
| 150 | [88–318] | 195 | [148–336] |
| 151 | [293–511] | 196 | [182–490] |
| 152 | [71–496] | 197 | [177–482] |
| 153 | [112–501] | 198 | [86–415],[304–471] |
| 154 | [19–225] | 199 | [72–521] |
| 155 | [354–542] | 200 | [362–829] |
| 156 | [21–209] | 201 | [290–475] |
| 157 | [303–473] | 202 | [346–522] |
| 158 | [198–587] | 203 | [272–451] |
| 159 | [55–531] | 204 | [6–503] |
| 160 | [4–507] | 205 | [73–276] |
| 161 | [8–307] | 206 | [298–699] |
| 208 | [211–483],[306–485] | 207 | [213–497] |
| 209 | [69–458] | 254 | [272–478] |
| 210 | [8–559] | 255 | [41–325] |
| 211 | [167–481] | 256 | [97–474] |
| 212 | [21–452] | 257 | [127–504] |
| 213 | [286–471] | 258 | [36–446],[289–447] |
| 214 | [214–444] | 259 | [172–432],[218–400] |
| 215 | [236–451] | 260 | [89–466] |

TABLE I-continued (Positions of all ORFs)

| Seq Id No. | Positions of Open Reading Frame(s) | Seq Id No. | Positions of Open Reading Frame(s) | Seq Id No. | Positions of Open Reading Frame(s) | Seq Id No. | Positions of Open Reading Frame(s) |
|---|---|---|---|---|---|---|---|
| 216 | [183–470] | 261 | [89–508] | 332 | [303–494] | 378 | [96–284] |
| 217 | [78–461] | 262 | [78–476] | 333 | [3–161],[272–496] | 379 | [21–320],[323–496] |
| 218 | [187–468] | 263 | [103–501] | 334 | [174–461] | 380 | [110–493] |
| 219 | [187–468] | 264 | [217–570] | 335 | [303–473] | 381 | [242–529],[297–530], [328–528] |
| 220 | [330–479] | 265 | [233–496] | 336 | [319–471] | | |
| 221 | [142–363],[198–362] | 266 | [357–551] | 337 | [196–501],[279–638] | 382 | [15–299],[139–300] |
| 222 | [178–483] | 267 | [221–481] | 338 | [292–561],[338–535] | 383 | [15–569],[92–328] |
| 223 | [55–213],[318–488] | 268 | [112–597] | 339 | [180–428] | 384 | [153–479] |
| 224 | [97–492] | 269 | [254–466] | 340 | [30–509] | 385 | [233–421] |
| 225 | [142–315],[315–563] | 270 | [4–171] | 341 | [116–487] | 386 | [125–496] |
| 226 | [19–210],[306–497] | 271 | [222–737] | 342 | [68–460],[82–279] | 387 | [290–496] |
| 227 | [130–372],[252–524], [302–523] | 272 | [330–479] | 343 | [1–450] | 388 | [57–473] |
| | | 273 | [15–449],[263–427] | 344 | [86–478] | 389 | [136–318] |
| 228 | [89–283] | 274 | [71–472] | 345 | [34–285],[152–472] | 390 | [71–490] |
| 229 | [97–450],[216–422], [242–415] | 275 | [43–540] | 392 | [38–307] | 391 | [35–457] |
| | | 276 | [175–468] | 393 | [186–347] | 438 | [153–341] |
| 230 | [83–304] | 277 | [204–482] | 394 | [50–502] | 439 | [255–428] |
| 231 | [111–350] | 278 | [35–472] | 395 | [8–409],[73–306] | 440 | [138–536] |
| 232 | [97–522],[215–385] | 279 | [261–509] | 396 | [32–205],[208–450] | 441 | [149–358] |
| 233 | [85–252] | 280 | [158–313],[186–398], [286–498] | 397 | [107–442] | 442 | [329–502] |
| 234 | [146–403] | | | 398 | [65–370],[370–573] | 443 | [91–465] |
| 235 | [182–592] | 281 | [104–442],[178–471] | 399 | [139–369] | 444 | [215–454],[285–464] |
| 236 | [214–399] | 282 | [34–489] | 400 | [225–455] | 445 | [141–503] |
| 237 | [145–480],[258–476] | 283 | [23–478] | 401 | [185–481] | 446 | [56–475],[258–407] |
| 238 | [118–663] | 284 | [171–488] | 402 | [11–286],[31–180] | 447 | [49–504] |
| 239 | [114–539],[229–432] | 285 | [166–465] | 403 | [67–216] | 448 | [95–493] |
| 240 | [98–559] | 286 | [176–451] | 404 | [193–417] | 449 | [51–368],[299–502] |
| 241 | [131–478] | 287 | [63–254],[104–607], [261–410] | 405 | [18–434] | 450 | [20–460] |
| 242 | [30–515] | | | 406 | [104–448] | 451 | [6–506] |
| 243 | [167–556] | 288 | [24–296] | 407 | [226–510] | 452 | [154–480] |
| 244 | [258–476] | 289 | [140–502] | 408 | [227–433] | 453 | [265–510] |
| 245 | [27–470],[155–466] | 290 | [17–385] | 409 | [185–484] | 454 | [337–492] |
| 246 | [65–451] | 291 | [94–498],[116–319] | 410 | [37–237] | 455 | [176–592] |
| 247 | [94–456] | 292 | [518–670] | 411 | [223–480],[276–482] | 456 | [99–482] |
| 248 | [266–472] | 293 | [139–510] | 412 | [331–480] | 457 | [242–463] |
| 249 | [13–321],[50–322] | 294 | [330–488] | 413 | [96–419] | 458 | [119–376] |
| 250 | [60–548] | 295 | [107–322] | 414 | [188–463] | 459 | [144–515] |
| 251 | [118–453] | 296 | [40–201] | 415 | [37–219] | 460 | [197–475] |
| 252 | [22–576] | 297 | [247–495] | 416 | [66–458] | 461 | [303–527] |
| 253 | [36–671] | 298 | [220–492] | 417 | [297–473] | 462 | [89–283] |
| 300 | [9–248] | 299 | [4–222],[267–476] | 418 | [223–507] | 463 | [161–457] |
| 301 | [221–487] | 346 | [197–535] | 419 | [1–171] | 464 | [37–186] |
| 302 | [170–481] | 347 | [22–486] | 420 | [8–505] | 465 | [239–460] |
| 303 | [264–494] | 348 | [51–470] | 421 | [323–502] | 466 | [223–495] |
| 304 | [136–378],[233–622] | 349 | [15–563],[331–498] | 422 | [28–270] | 467 | [192–479] |
| 305 | [74–520],[291–476] | 350 | [199–492] | 423 | [51–314],[56–226] | 468 | [125–490] |
| 306 | [109–498] | 351 | [251–520] | 424 | [54–212] | 469 | [40–387],[161–376] |
| 307 | [38–487] | 352 | [28–489] | 425 | [176–406] | 470 | [197–478] |
| 308 | [28–495] | 353 | [70–360],[164–490] | 426 | [105–323] | 471 | [81–467] |
| 309 | [28–483] | 354 | [76–363] | 427 | [329–478] | 472 | [170–526] |
| 310 | [142–465] | 355 | [23–232],[69–233] | 428 | [318–497] | 473 | [87–548] |
| 311 | [201–434] | 356 | [206–520] | 429 | [67–309] | 474 | [26–301] |
| 312 | [339–491] | 357 | [6–485],[121–288] | 430 | [286–468] | 475 | [10–168] |
| 313 | [180–569],[281–535] | 358 | [80–274],[250–468] | 431 | [278–463] | 476 | [177–470] |
| 314 | [99–386] | 359 | [42–332] | 432 | [167–493] | 477 | [71–250] |
| 315 | [323–481] | 360 | [117–413] | 433 | [174–413] | 478 | [248–472] |
| 316 | [171–476],[268–432], [296–463] | 361 | [81–737],[421–588] | 434 | [104–322],[138–290] | 479 | [110–508] |
| | | 362 | [110–469] | 435 | [386–547] | 480 | [356–505] |
| 317 | [66–458] | 363 | [271–450] | 436 | [184–492] | 481 | [188–352] |
| 318 | [67–555],[129–464] | 364 | [79–486] | 437 | [78–455] | 482 | [20–286] |
| 319 | [92–586] | 365 | [432–596] | 484 | [91–243] | 483 | [18–449],[193–387] |
| 320 | [32–319],[304–489] | 366 | [80–274],[250–453] | 485 | [228–482] | 530 | [209–472] |
| 321 | [303–473] | 367 | [21–494] | 486 | [149–382] | 531 | [17–178],[306–467] |
| 322 | [304–462] | 368 | [229–411] | 487 | [164–370] | 532 | [104–487] |
| 323 | [302–472] | 369 | [53–226],[243–482] | 488 | [24–266] | 533 | [331–489] |
| 324 | [242–496] | 370 | [277–513] | 489 | [1–282] | 534 | [7–192] |
| 325 | [355–519] | 371 | [62–436] | 490 | [273–458],[277–456] | 535 | [105–395] |
| 326 | [303–479] | 372 | [204–392] | 491 | [299–457] | 536 | [248–502] |
| 327 | [136–291] | 373 | [276–473] | 492 | [125–484],[237–461] | 537 | [232–501] |
| 328 | [320–514] | 374 | [156–317] | 493 | [244–450] | 538 | [43–225] |
| 329 | [303–512] | 375 | [265–429] | 494 | [121–294] | 539 | [177–401] |
| 330 | [166–342],[224–541] | 376 | [100–522] | 495 | [217–486] | 540 | [272–472] |
| 331 | [303–473] | 377 | [95–457] | 496 | [65–268],[291–467] | 541 | [20–451] |

TABLE I-continued (Positions of all ORFs)

| Seq Id No. | Positions of Open Reading Frame(s) | Seq Id No. | Positions of Open Reading Frame(s) | Seq Id No. | Positions of Open Reading Frame(s) | Seq Id No. | Positions of Open Reading Frame(s) |
|---|---|---|---|---|---|---|---|
| 497 | [189–479] | 542 | [185–505],[324–506] | 615 | [188–487],[324–488] | | [300–458] |
| 498 | [127–294] | 543 | [260–469] | 616 | [303–479] | 661 | [55–210],[197–451] |
| 499 | [143–421] | 544 | [211–372],[291–488] | 617 | [148–492] | 662 | [27–485] |
| 500 | [184–459] | 545 | [282–467] | 618 | [121–357] | 663 | [308–457] |
| 501 | [312–506] | 546 | [10–198],[228–452] | 619 | [121–360] | 664 | [1–153],[199–354], [264–533] |
| 502 | [109–426] | 547 | [155–484] | 620 | [121–309] | | |
| 503 | [263–481] | 548 | [344–526] | 621 | [123–278] | 665 | [43–363],[249–488] |
| 504 | [12–314],[190–489] | 549 | [251–484] | 668 | [177–497] | 666 | [324–539] |
| 505 | [7–315],[147–500] | 550 | [71–283],[283–456] | 669 | [9–539] | 667 | [20–490],[42–257] |
| 506 | [52–456] | 551 | [154–525] | 670 | [280–495] | 714 | [116–532],[361–534] |
| 507 | [334–501] | 552 | [177–458] | 671 | [33–269],[116–505] | 715 | [336–524] |
| 508 | [271–471] | 553 | [287–511],[363–512] | 672 | [32–286],[303–491] | 716 | [178–453] |
| 509 | [272–469] | 554 | [130–462] | 673 | [236–463] | 717 | [290–451] |
| 510 | [106–486] | 555 | [36–230] | 674 | [27–467] | 718 | [305–493] |
| 511 | [25–204] | 556 | [287–490] | 675 | [279–491] | 719 | [116–490] |
| 512 | [130–318] | 557 | [164–472],[315–473] | 676 | [247–429] | 720 | [97–468] |
| 513 | [135–317],[169–468], [320–469] | 558 | [252–470] | 677 | [95–496] | 721 | [205–483] |
| | | 559 | [216–383] | 678 | [204–473] | 722 | [265–558] |
| 514 | [259–453] | 560 | [293–469] | 679 | [9–209],[209–451] | 723 | [94–276],[315–497] |
| 515 | [296–478] | 561 | [91–504] | 680 | [229–459] | 724 | [56–238],[277–468] |
| 516 | [88–495] | 562 | [222–488] | 681 | [13–399] | 725 | [257–529] |
| 517 | [226–477] | 563 | [151–468] | 682 | [267–506] | 726 | [256–501] |
| 518 | [267–458] | 564 | [166–345],[297–479] | 683 | [109–534] | 727 | [157–396] |
| 519 | [24–560],[184–390] | 565 | [166–345],[297–491] | 684 | [106–306] | 728 | [96–476],[149–376] |
| 520 | [93–464] | 566 | [74–508] | 685 | [298–450] | 729 | [243–470] |
| 521 | [290–478] | 567 | [94–477] | 686 | [262–495] | 730 | [132–512] |
| 522 | [94–276] | 568 | [308–466] | 687 | [44–496] | 731 | [198–518] |
| 523 | [105–416],[238–417] | 569 | [135–374] | 688 | [264–497] | 732 | [136–378] |
| 524 | [288–464] | 570 | [307–486] | 689 | [15–467],[205–366] | 733 | [189–380] |
| 525 | [1–468] | 571 | [176–601] | 690 | [33–521] | 734 | [129–278] |
| 526 | [157–459] | 572 | [99–251] | 691 | [263–472] | 735 | [313–489],[341–490] |
| 527 | [71–481] | 573 | [343–495] | 692 | [255–503] | 736 | [110–304],[304–495] |
| 528 | [207–455] | 574 | [133–495],[321–494] | 693 | [269–457] | 737 | [310–474] |
| 529 | [4–204],[242–493] | 575 | [51–449] | 694 | [100–540] | 738 | [311–496] |
| 576 | [149–451] | 622 | [214–474] | 695 | [177–338] | 739 | [228–515] |
| 577 | [130–507],[236–505] | 623 | [241–411] | 696 | [21–170] | 740 | [229–453] |
| 578 | [195–641] | 624 | [50–448] | 697 | [100–279],[289–558] | 741 | [237–461] |
| 579 | [191–508],[273–485] | 625 | [140–292],[401–550] | 698 | [104–433] | 742 | [79–501] |
| 580 | [188–412] | 626 | [203–463] | 699 | [4–210],[242–517] | 743 | [31–327] |
| 581 | [43–480] | 627 | [168–380],[380–580] | 700 | [139–387] | 744 | [89–448],[156–365] |
| 582 | [216–509] | 628 | [282–479] | 701 | [161–310],[310–486] | 745 | [290–472] |
| 583 | [121–456] | 629 | [174–476] | 702 | [64–480] | 746 | [217–519],[326–505] |
| 584 | [226–537] | 630 | [422–607] | 703 | [9–494],[113–268] | 747 | [91–474],[200–379] |
| 585 | [202–513] | 631 | [255–458] | 704 | [289–492] | 748 | [91–471],[200–379] |
| 586 | [196–531] | 632 | [212–502] | 705 | [128–304],[163–477] | 749 | [91–453],[200–379] |
| 587 | [67–327] | 633 | [326–484] | 706 | [228–671] | 750 | [91–459],[200–379] |
| 588 | [183–491],[221–454] | 634 | [13–462] | 707 | [147–401] | 751 | [91–477],[200–379] |
| 589 | [258–734] | 635 | [292–492] | 708 | [44–499] | 752 | [6–377],[19–183], [226–375] |
| 590 | [192–344],[280–450] | 636 | [84–479] | | | | |
| 591 | [138–521],[229–390] | 637 | [147–305],[152–448] | 709 | [213–398] | 753 | [28–180] |
| 592 | [211–468] | 638 | [147–344] | 710 | [28–471] | 754 | [43–486] |
| 593 | [72–233] | 639 | [202–468] | 711 | [211–369] | 755 | [236–499] |
| 594 | [68–238] | 640 | [109–426] | 712 | [305–484] | 756 | [6–305],[125–307] |
| 595 | [199–372] | 641 | [91–306],[273–458] | 713 | [193–489] | 757 | [36–494] |
| 596 | [300–458] | 642 | [246–497],[265–495] | 760 | [68–466] | 758 | [136–390] |
| 597 | [157–459] | 643 | [119–271] | 761 | [100–351] | 759 | [211–366] |
| 598 | [64–498] | 644 | [170–352] | 762 | [75–326],[151–324] | 806 | [59–508] |
| 599 | [335–520] | 645 | [11–166],[297–545] | 763 | [36–386],[196–378] | 807 | [280–474] |
| 600 | [79–504] | 646 | [175–336] | 764 | [303–470] | 808 | [225–491] |
| 601 | [14–169] | 647 | [124–366] | 765 | [141–455],[248–406] | 809 | [131–376] |
| 602 | [40–246] | 648 | [161–481],[333–482] | 766 | [149–490] | 810 | [104–388] |
| 603 | [257–529] | 649 | [166–510] | 767 | [159–518] | 811 | [252–518] |
| 604 | [205–477] | 650 | [308–487] | 768 | [263–544] | 812 | [92–256] |
| 605 | [14–271],[154–453] | 651 | [120–509] | 769 | [68–538] | 813 | [12–191],[34–189] |
| 606 | [93–326] | 652 | [273–488] | 770 | [138–476] | 814 | [223–483] |
| 607 | [279–521] | 653 | [153–314],[325–519] | 771 | [330–506] | 815 | [209–541] |
| 608 | [105–383] | 654 | [107–343] | 772 | [151–375],[176–337] | 816 | [269–478],[319–480] |
| 609 | [256–417] | 655 | [99–506] | 773 | [153–497] | 817 | [32–220],[99–356], [298–507] |
| 610 | [142–414],[251–415] | 656 | [244–486] | 774 | [342–497] | | |
| 611 | [133–459] | 657 | [51–509] | 775 | [192–497],[247–498] | 818 | [60–212],[263–526] |
| 612 | [96–338] | 658 | [78–551] | 776 | [255–485],[310–459] | 819 | [60–212],[263–526] |
| 613 | [145–333],[218–511] | 659 | [57–263] | 777 | [99–746],[493–726] | 820 | [89–331] |
| 614 | [187–504],[347–505] | 660 | [43–234],[286–459], | 778 | [91–588] | 821 | [36–407] |

TABLE I-continued

(Positions of all ORFs)

| Seq Id No. | Positions of Open Reading Frame(s) | Seq Id No. | Positions of Open Reading Frame(s) | Seq Id No. | Positions of Open Reading Frame(s) | Seq Id No. | Positions of Open Reading Frame(s) |
|---|---|---|---|---|---|---|---|
| 779 | [78–470] | 822 | [212–376] | 944 | [38–529] | 940 | [228–539] |
| 780 | [131–703] | 823 | [376–534] | 945 | [213–605] | 941 | [224–556] |
| 781 | [196–501],[251–412] | 824 | [78–350] | 946 | [219–488] | 942 | [37–477],[179–427] |
| 782 | [312–485] | 825 | [44–325],[147–326] | 947 | [94–285] | 943 | [158–313],[217–474] |
| 783 | [352–516] | 826 | [313–465] | 948 | [43–345] | 990 | [150–458] |
| 784 | [291–467] | 827 | [218–418] | 949 | [238–555] | 991 | [214–549] |
| 785 | [351–515] | 828 | [58–315] | 950 | [64–351],[195–353] | 992 | [94–549] |
| 786 | [248–514] | 829 | [331–480] | 951 | [213–515] | 993 | [208–564] |
| 787 | [76–474] | 830 | [340–501] | 952 | [141–506] | 994 | [85–531] |
| 788 | [306–617],[337–537] | 831 | [75–227] | 953 | [195–464] | 995 | [72–227] |
| 789 | [212–376] | 832 | [39–317],[104–289],[265–492] | 954 | [99–476],[185–409] | 996 | [229–417] |
| 790 | [53–493] | | | 955 | [149–505] | 997 | [54–218] |
| 791 | [242–391],[273–464] | 833 | [125–301],[304–495] | 956 | [202–438] | 998 | [180–353],[307–474] |
| 792 | [206–484] | 834 | [489–650] | 957 | [1–207],[395–628] | 999 | [139–357] |
| 793 | [244–492] | 835 | [21–257] | 958 | [183–524] | 1000 | [38–319] |
| 794 | [24–452] | 836 | [195–485] | 959 | [209–496],[249–446] | 1001 | [29–490],[153–449] |
| 795 | [68–310],[352–546] | 837 | [149–301] | 960 | [195–500] | 1002 | [128–583] |
| 796 | [113–487] | 838 | [2–223] | 961 | [188–523] | 1003 | [188–520] |
| 797 | [182–496] | 839 | [7–228],[164–535] | 962 | [70–444],[108–443],[245–421] | 1004 | [218–490] |
| 798 | [279–476] | 840 | [54–509] | | | 1005 | [196–450],[242–433] |
| 799 | [24–452] | 841 | [61–342] | 963 | [122–334] | 1006 | [217–474] |
| 800 | [124–576] | 842 | [105–512] | 964 | [184–456] | 1007 | [201–458],[247–396] |
| 801 | [20–193],[42–194] | 843 | [80–535] | 965 | [12–203],[288–497] | 1008 | [201–443],[247–396] |
| 802 | [191–442] | 844 | [286–525] | 966 | [128–310] | 1009 | [185–424],[231–380] |
| 803 | [21–284],[233–466] | 845 | [52–459] | 967 | [13–180] | 1010 | [168–506],[214–363] |
| 804 | [21–446] | 846 | [315–503] | 968 | [215–547] | 1011 | [201–467],[247–396] |
| 805 | [271–483] | 847 | [35–469] | 969 | [230–493] | 1012 | [201–428],[247–396] |
| 852 | [148–363],[324–473] | 848 | [41–484] | 970 | [247–459] | 1013 | [172–492],[218–367] |
| 853 | [244–546] | 849 | [217–387],[258–518] | 971 | [29–229],[240–452],[248–490] | 1014 | [201–533],[247–396] |
| 854 | [35–229],[126–497] | 850 | [275–475] | | | 1015 | [201–428],[247–396] |
| 855 | [131–280],[175–483] | 851 | [116–490] | 972 | [131–469] | 1016 | [159–413],[205–354] |
| 856 | [139–471] | 898 | [11–307],[208–453] | 973 | [214–471] | 1017 | [159–428],[205–354] |
| 857 | [261–500] | 899 | [116–496] | 974 | [83–280] | 1018 | [176–508],[222–371] |
| 858 | [176–514] | 900 | [69–422] | 975 | [171–320] | 1019 | [159–515],[205–354] |
| 859 | [228–479] | 901 | [69–359] | 976 | [101–478] | 1020 | [201–506],[247–396] |
| 860 | [273–506] | 902 | [68–496],[114–284] | 977 | [1–174],[180–329],[281–514] | 1021 | [207–410],[253–402] |
| 861 | [226–534],[348–533] | 903 | [31–363] | | | 1022 | [172–486],[218–367] |
| 862 | [31–504] | 904 | [42–539] | 978 | [278–493] | 1023 | [171–479],[217–366] |
| 863 | [17–403] | 905 | [213–368] | 979 | [67–459] | 1024 | [169–441],[215–364] |
| 864 | [171–482] | 906 | [24–485] | 980 | [254–481] | 1025 | [201–440],[247–396] |
| 865 | [156–557],[266–544] | 907 | [271–462] | 981 | [350–502] | 1026 | [173–463],[219–368] |
| 866 | [388–537] | 908 | [242–469] | 982 | [119–388] | 1027 | [159–524],[205–354] |
| 867 | [288–494] | 909 | [147–707] | 983 | [131–412] | 1028 | [211–381],[218–367] |
| 868 | [288–491] | 910 | [147–602] | 984 | [71–538] | 1029 | [172–477],[218–367] |
| 869 | [85–351] | 911 | [22–216],[270–452] | 985 | [227–481],[255–425],[283–480] | 1030 | [130–474] |
| 870 | [279–515] | 912 | [7–171] | | | 1031 | [129–554] |
| 871 | [305–466] | 913 | [157–411],[200–412] | 986 | [290–487] | 1032 | [152–385],[376–537] |
| 872 | [154–348] | 914 | [77–400] | 987 | [32–427] | 1033 | [140–424] |
| 873 | [160–387],[387–542] | 915 | [55–243],[86–244] | 988 | [135–314],[185–490] | 1034 | [134–460] |
| 874 | [133–489] | 916 | [285–491] | 989 | [206–508] | 1035 | [97–453] |
| 875 | [211–369] | 917 | [75–272] | 1036 | [260–445] | 1082 | [131–478] |
| 876 | [314–550] | 918 | [46–462] | 1037 | [289–450] | 1083 | [216–488] |
| 877 | [56–244] | 919 | [46–516] | 1038 | [11–298],[178–453] | 1084 | [193–417] |
| 878 | [312–473] | 920 | [178–354] | 1039 | [133–291] | 1085 | [189–491] |
| 879 | [234–485] | 921 | [79–525] | 1040 | [53–520],[129–398] | 1086 | [192–413] |
| 880 | [83–463] | 922 | [83–478] | 1041 | [250–453] | 1087 | [211–480] |
| 881 | [152–334],[394–711] | 923 | [31–474],[290–472] | 1042 | [44–478] | 1088 | [69–254] |
| 882 | [220–489] | 924 | [252–434] | 1043 | [39–221],[363–530] | 1089 | [153–581] |
| 883 | [90–542] | 925 | [725–898] | 1044 | [327–515] | 1090 | [98–346] |
| 884 | [170–346] | 926 | [130–522] | 1045 | [82–471] | 1091 | [344–625] |
| 885 | [232–483] | 927 | [113–358] | 1046 | [82–354] | 1092 | [252–482] |
| 886 | [261–497] | 928 | [303–512] | 1047 | [24–176] | 1093 | [221–493] |
| 887 | [231–455] | 929 | [166–546] | 1048 | [78–494] | 1094 | [141–512] |
| 888 | [117–452] | 930 | [222–485] | 1049 | [94–468] | 1095 | [337–519] |
| 889 | [158–487] | 931 | [112–456] | 1050 | [229–531] | 1096 | [56–439] |
| 890 | [163–525] | 932 | [54–527] | 1051 | [363–515] | 1097 | [190–549] |
| 891 | [88–408] | 933 | [205–501] | 1052 | [13–273],[116–274],[120–272] | 1098 | [272–517],[336–515] |
| 892 | [21–266],[304–516] | 934 | [31–339] | | | 1099 | [104–484],[270–455] |
| 893 | [125–478],[169–384] | 935 | [76–402] | 1053 | [171–515] | 1100 | [191–463] |
| 894 | [140–547] | 936 | [108–503] | 1054 | [119–316],[268–456] | 1101 | [303–482] |
| 895 | [224–499] | 937 | [274–600] | 1055 | [21–242] | 1102 | [10–234] |
| 896 | [24–323] | 938 | [140–493] | 1056 | [98–484] | 1103 | [84–251] |
| 897 | [165–467] | 939 | [228–521] | 1057 | [219–422] | 1104 | [69–485],[127–471] |

TABLE I-continued (Positions of all ORFs)

| Seq Id No. | Positions of Open Reading Frame(s) | Seq Id No. | Positions of Open Reading Frame(s) |
|---|---|---|---|
| 1058 | [59–448] | 1105 | [191–514] |
| 1059 | [366–566] | 1106 | [303–491] |
| 1060 | [13–450],[209–361] | 1107 | [117–491] |
| 1061 | [95–418] | 1108 | [341–526] |
| 1062 | [98–400] | 1109 | [207–482] |
| 1063 | [98–466] | 1110 | [341–523] |
| 1064 | [100–555] | 1111 | [137–349] |
| 1065 | [145–486] | 1112 | [96–257] |
| 1066 | [97–315] | 1113 | [96–482] |
| 1067 | [98–481] | 1114 | [116–331] |
| 1068 | [98–379] | 1115 | [10–261] |
| 1069 | [98–505] | 1116 | [204–365] |
| 1070 | [98–493] | 1117 | [341–523] |
| 1071 | [362–529] | 1118 | [218–406] |
| 1072 | [180–395] | 1119 | [37–246] |
| 1073 | [118–327] | 1120 | [35–238],[163–615] |
| 1074 | [140–562],[378–551] | 1121 | [116–283] |
| 1075 | [239–490] | 1122 | [386–559] |
| 1076 | [96–479],[196–357] | 1123 | [69–398] |
| 1077 | [59–262],[346–519] | 1124 | [324–551] |
| 1078 | [224–397],[250–480] | 1125 | [9–161],[179–484] |
| 1079 | [308–538] | 1126 | [381–533] |
| 1080 | [30–254],[286–507] | 1127 | [65–223] |
| 1081 | [262–444] | 1174 | [71–313],[274–498] |
| 1128 | [316–501] | 1175 | [191–505] |
| 1129 | [214–426] | 1176 | [361–510] |
| 1130 | [52–258] | 1177 | [351–530] |
| 1131 | [99–470] | 1178 | [108–524] |
| 1132 | [270–527] | 1179 | [351–914],[397–567] |
| 1133 | [178–348] | 1180 | [156–326],[194–556] |
| 1134 | [191–505] | 1181 | [104–691] |
| 1135 | [157–564] | 1182 | [108–566] |
| 1136 | [138–287],[296–520] | 1183 | [31–435] |
| 1137 | [93–524] | 1184 | [334–486] |
| 1138 | [42–356] | 1185 | [75–599] |
| 1139 | [322–609] | 1186 | [161–391],[279–548],[358–534] |
| 1140 | [203–478] | 1187 | [36–509],[205–462] |
| 1141 | [283–492] | 1188 | [277–471] |
| 1142 | [36–392],[196–393] | 1189 | [290–472],[315–470] |
| 1143 | [66–509] | 1190 | [32–535] |
| 1144 | [94–468] | 1191 | [294–476] |
| 1145 | [71–238] | 1192 | [53–205],[331–552] |
| 1146 | [27–341] | 1193 | [290–574] |
| 1147 | [265–528] | 1194 | [65–469] |
| 1148 | [86–481] | 1195 | [22–174],[128–478],[289–450] |
| 1149 | [39–503] | 1196 | [86–553] |
| 1150 | [218–517] | 1197 | [51–482],[163–366] |
| 1151 | [137–529] | 1198 | [92–460] |
| 1152 | [191–370] | 1199 | [138–467] |
| 1153 | [136–450] | 1200 | [106–270],[171–485] |
| 1154 | [70–453] | 1201 | [24–206] |
| 1155 | [253–459] | 1202 | [343–510] |
| 1156 | [147–494] | 1203 | [91–333],[287–496],[360–749] |
| 1157 | [272–556] | 1204 | [106–348],[302–511],[375–533] |
| 1158 | [182–457] | 1205 | [288–452] |
| 1159 | [280–480] | 1206 | [188–463] |
| 1160 | [323–535] | 1207 | [15–506],[70–279] |
| 1161 | [339–506] | 1208 | [157–456] |
| 1162 | [338–499] | 1209 | [157–486] |
| 1163 | [338–487] | 1210 | [273–599] |
| 1164 | [342–491] | 1211 | [372–560] |
| 1165 | [299–475] | 1212 | [267–452] |
| 1166 | [339–488] | 1213 | [145–402] |
| 1167 | [337–492] | 1214 | [373–549] |
| 1168 | [118–321] | 1215 | [17–223],[22–522],[249–485] |
| 1169 | [14–457],[282–458] | 1216 | [104–505] |
| 1170 | [255–404],[353–517] | 1217 | [199–348] |
| 1171 | [204–455] | 1218 | [267–455] |
| 1172 | [151–564] | 1222 | [274–459],[278–448] |
| 1173 | [23–469] | 1223 | [262–462] |
| 1220 | [268–453],[272–442] | 1224 | [261–458] |
| 1221 | [27–485] | 1225 | [182–346] |
| 1219 | [267–452] | 1226 | [51–200] |
| 1266 | [157–306] | 1227 | [262–456] |
| 1267 | [291–515] | 1228 | [178–594] |
| 1268 | [189–611] | 1229 | [109–579] |
| 1269 | [84–542] | 1230 | [103–504] |
| 1270 | [154–495] | 1231 | [62–517],[192–350] |
| 1271 | [132–287],[378–530] | 1232 | [155–316] |
| 1272 | [193–474] | 1233 | [13–270],[270–473] |
| 1273 | [41–433] | 1234 | [57–488] |
| 1274 | [33–227] | 1235 | [141–317] |
| 1275 | [205–519] | 1236 | [114–485] |
| 1276 | [130–540] | 1237 | [75–455] |
| 1277 | [102–494] | 1238 | [74–223],[105–536] |
| 1278 | [134–487] | 1239 | [29–466] |
| 1279 | [28–222],[238–480],[330–482] | 1240 | [307–567] |
| 1280 | [358–603] | 1241 | [73–246] |
| 1281 | [306–491] | 1242 | [250–408] |
| 1282 | [114–512] | 1243 | [261–539] |
| 1283 | [276–518] | 1244 | [309–563] |
| 1284 | [4–474] | 1245 | [293–544] |
| 1285 | [94–246],[135–476] | 1246 | [75–476] |
| 1286 | [235–516] | 1247 | [268–504] |
| 1287 | [135–488] | 1248 | [55–525] |
| 1288 | [91–243],[132–488] | 1249 | [221–466] |
| 1289 | [89–418] | 1250 | [33–536] |
| 1290 | [279–512] | 1251 | [41–568] |
| 1291 | [377–526] | 1252 | [41–490] |
| 1292 | [94–435],[161–457] | 1253 | [40–528],[254–526] |
| 1293 | [167–406],[253–483] | 1254 | [32–514] |
| 1294 | [68–364] | 1255 | [32–511] |
| 1295 | [125–466] | 1256 | [34–480] |
| 1296 | [70–300],[242–493] | 1257 | [33–482] |
| 1297 | [98–271] | 1258 | [89–454] |
| 1298 | [20–472] | 1259 | [324–524] |
| 1299 | [30–224],[49–225] | 1260 | [121–552] |
| 1300 | [37–561] | 1261 | [245–649] |
| 1301 | [33–188],[340–501] | 1262 | [141–491] |
| 1302 | [233–574],[279–638] | 1263 | [199–507] |
| 1303 | [73–597] | 1264 | [66–488],[316–489] |
| 1304 | [305–511],[342–497] | 1265 | [159–539] |
| 1305 | [299–469] | 1312 | [267–515] |
| 1306 | [105–482] | 1313 | [96–293],[269–469] |
| 1307 | [228–485] | 1314 | [105–503] |
| 1308 | [30–338],[173–337] | 1315 | [99–491] |
| 1309 | [162–449] | 1316 | [13–333] |
| 1310 | [37–459],[233–436] | 1317 | [68–469] |
| 1311 | [14–487],[228–461] | 1318 | [49–201],[207–503] |
| 1357 | [39–212] | 1319 | [104–562],[358–561] |
| 1358 | [176–421],[354–521] | 1320 | [143–367] |
| 1359 | [70–354],[204–401] | 1321 | [235–468] |
| 1360 | [21–404] | 1322 | [28–249] |
| 1361 | [264–701],[355–564] | 1323 | [28–204] |
| 1362 | [53–526] | 1324 | [28–240] |
| 1363 | [137–454] | 1325 | [28–210] |
| 1364 | [103–255] | 1326 | [154–510] |
| 1365 | [230–400] | 1327 | [208–480],[251–430] |
| 1366 | [185–613] | 1328 | [294–470] |
| 1367 | [61–267] | 1329 | [5–169],[208–453] |
| 1368 | [118–399] | 1330 | [127–498] |
| 1369 | [87–329],[332–616] | 1331 | [35–526] |
| 1370 | [99–281] | 1332 | [11–475] |
| 1371 | [208–429] | 1333 | [3–347] |
| 1372 | [316–495] | 1334 | [221–394] |
| 1373 | [32–277],[193–402] | 1335 | [93–341] |
| 1374 | [99–356],[113–364] | 1336 | [39–317] |
| 1375 | [132–317],[215–457] | 1337 | [137–478] |
| 1376 | [56–355] | 1338 | [60–212] |
| 1377 | [53–247] | 1339 | [1–477],[152–415] |
| 1378 | [201–491] | 1340 | [200–430] |
| 1379 | [7–216],[189–452] | | |
| 1380 | [113–346],[301–474] | | |
| 1381 | [183–434] | | |

TABLE I-continued (Positions of all ORFs)

| Seq Id No. | Positions of Open Reading Frame(s) | Seq Id No. | Positions of Open Reading Frame(s) | Seq Id No. | Positions of Open Reading Frame(s) | Seq Id No. | Positions of Open Reading Frame(s) |
|---|---|---|---|---|---|---|---|
| 1341 | [105–395] | 1382 | [40–246] | 1503 | [72–296] | 1543 | [174–527] |
| 1342 | [92–412] | 1383 | [10–216] | 1504 | [72–296] | 1544 | [121–390] |
| 1343 | [90–479] | 1384 | [218–457],[294–485] | 1505 | [30–242] | 1545 | [93–344] |
| 1344 | [33–263],[224–388] | 1385 | [42–440] | 1506 | [76–234] | 1546 | [88–339] |
| 1345 | [9–446],[199–363],[314–622],[493–774] | 1386 | [70–252],[114–299] | 1507 | [36–404],[112–417] | 1547 | [133–339] |
| | | 1387 | [37–429] | 1508 | [238–480] | 1548 | [139–426] |
| 1346 | [9–491],[199–438] | 1388 | [37–474] | 1509 | [96–359] | 1549 | [84–326] |
| 1347 | [189–464] | 1389 | [56–601] | 1510 | [125–415] | 1550 | [205–354] |
| 1348 | [112–387] | 1390 | [97–381] | 1511 | [138–338] | 1551 | [43–360] |
| 1349 | [56–214] | 1391 | [142–354] | 1512 | [190–393] | 1552 | [221–535],[252–461] |
| 1350 | [132–443],[190–396] | 1392 | [322–483] | 1513 | [77–457] | 1553 | [13–180],[240–443] |
| 1351 | [14–163] | 1393 | [125–352],[198–482] | 1514 | [279–473] | 1554 | [107–298] |
| 1352 | [57–215] | 1394 | [7–162],[36–221] | 1515 | [27–278] | 1555 | [93–383],[202–510] |
| 1353 | [169–423] | 1395 | [55–297] | 1516 | [257–505] | 1556 | [224–382],[271–429] |
| 1354 | [183–398] | 1396 | [90–326] | 1517 | [342–581] | 1557 | [151–363],[294–491] |
| 1355 | [133–417] | 1397 | [76–273] | 1518 | [77–367] | 1558 | [50–520],[360–539] |
| 1356 | [310–906] | 1398 | [225–428] | 1519 | [165–443] | 1559 | [92–310] |
| 1403 | [10–504] | 1399 | [111–371] | 1520 | [16–297] | 1560 | [233–454] |
| 1404 | [101–442] | 1400 | [40–189] | 1521 | [52–264],[155–346] | 1561 | [179–397] |
| 1405 | [94–441] | 1401 | [38–262],[88–366] | 1522 | [1–495] | 1562 | [179–397] |
| 1406 | [155–340] | 1402 | [113–319] | 1523 | [192–476] | 1563 | [28–363] |
| 1407 | [30–527] | 1449 | [6–164],[25–240] | 1524 | [156–422] | 1564 | [28–363] |
| 1408 | [106–453] | 1450 | [6–164],[25–237] | 1525 | [77–472] | 1565 | [90–257] |
| 1409 | [169–381] | 1451 | [6–164],[25–240] | 1526 | [56–505] | 1566 | [4–339] |
| 1410 | [137–367],[180–362] | 1452 | [6–164],[25–237] | 1527 | [179–433] | 1567 | [22–327],[297–470],[346–519] |
| 1411 | [50–205],[241–402] | 1453 | [21–380] | 1528 | [107–298] | | |
| 1412 | [69–356] | 1454 | [121–288] | 1529 | [237–398] | 1568 | [281–451] |
| 1413 | [18–257] | 1455 | [41–286],[324–506] | 1530 | [237–398] | 1569 | [201–578],[371–523] |
| 1414 | [140–472] | 1456 | [153–335] | 1531 | [117–467] | 1570 | [109–381] |
| 1415 | [95–346],[213–533] | 1457 | [153–335] | 1532 | [8–343] | 1571 | [23–370] |
| 1416 | [67–390],[206–403] | 1458 | [121–375] | 1533 | [14–247],[205–447] | 1572 | [72–296] |
| 1417 | [56–217],[163–336] | 1459 | [153–335] | 1534 | [229–456] | 1573 | [267–479] |
| 1418 | [204–353] | 1460 | [17–187],[132–287],[160–378] | 1535 | [129–554],[202–564] | 1574 | [176–439] |
| 1419 | [55–261],[261–425] | | | 1536 | [176–424] | 1575 | [33–224],[193–348] |
| 1420 | [57–320] | 1461 | [21–266] | 1537 | [111–272] | 1576 | [114–332] |
| 1421 | [243–467],[302–538] | 1462 | [133–336] | 1538 | [281–430] | 1577 | [21–179],[195–347] |
| 1422 | [68–334] | 1463 | [138–671] | 1539 | [289–462] | 1578 | [51–254] |
| 1423 | [33–218],[302–475] | 1464 | [11–166],[279–458] | 1540 | [216–380] | 1579 | [75–332] |
| 1424 | [31–207],[51–260],[269–430] | 1465 | [21–584] | 1587 | [261–452] | 1580 | [275–448] |
| | | 1466 | [64–213] | 1588 | [148–411] | 1581 | [21–377] |
| 1425 | [172–447] | 1467 | [250–408] | 1589 | [16–315],[212–427] | 1582 | [272–481] |
| 1426 | [454–615] | 1468 | [9–170],[204–431],[271–444] | 1590 | [72–296] | 1583 | [143–433] |
| 1427 | [43–225],[237–428] | | | 1591 | [81–368] | 1584 | [225–458] |
| 1428 | [18–314] | 1469 | [100–441] | 1592 | [176–367] | 1585 | [229–465] |
| 1429 | [210–386] | 1470 | [158–442] | 1593 | [115–411] | 1586 | [40–234],[69–443] |
| 1430 | [206–355] | 1471 | [68–235] | 1594 | [99–443] | 1633 | [130–303] |
| 1431 | [10–273] | 1472 | [1–309],[144–464],[320–484] | 1595 | [95–409],[213–386] | 1634 | [104–319] |
| 1432 | [72–287] | | | 1596 | [44–427] | 1635 | [70–483] |
| 1433 | [69–305] | 1473 | [11–331] | 1597 | [75–317] | 1636 | [266–439],[315–473] |
| 1434 | [17–259] | 1474 | [204–443] | 1598 | [202–477] | 1637 | [13–165],[21–182] |
| 1435 | [218–418] | 1475 | [273–437] | 1599 | [260–544],[571–723] | 1638 | [22–333] |
| 1436 | [332–574] | 1476 | [47–280] | 1600 | [136–435] | 1639 | [47–274] |
| 1437 | [229–429] | 1477 | [312–497] | 1601 | [21–233] | 1640 | [52–210] |
| 1438 | [77–247] | 1478 | [1–309],[144–461],[320–514] | 1602 | [165–536] | 1641 | [64–240] |
| 1439 | [83–259] | | | 1603 | [44–217],[123–494] | 1642 | [67–225] |
| 1440 | [68–238],[169–339],[254–529] | 1479 | [206–358],[362–532] | 1604 | [49–213],[117–539],[422–676] | 1643 | [16–183],[211–459] |
| | | 1480 | [13–216],[263–466] | | | 1644 | [18–230],[140–352] |
| 1441 | [39–284],[49–222] | 1481 | [102–326],[292–444] | 1605 | [35–187] | 1645 | [196–396] |
| 1442 | [188–472],[256–429] | 1482 | [125–316],[238–402] | 1606 | [139–513],[389–556] | 1646 | [67–225] |
| 1443 | [157–318] | 1483 | [191–355] | 1607 | [65–247] | 1647 | [19–315] |
| 1444 | [58–363] | 1484 | [77–235] | 1608 | [83–241] | 1648 | [201–410] |
| 1445 | [6–164],[25–237] | 1485 | [59–319] | 1609 | [80–304] | 1649 | [194–379] |
| 1446 | [155–334] | 1486 | [209–475] | 1610 | [96–290],[208–381] | 1650 | [75–275],[134–379] |
| 1447 | [78–248] | 1487 | [14–478],[237–485] | 1611 | [114–308],[172–423] | 1651 | [145–318] |
| 1448 | [50–304] | 1488 | [39–347],[142–354] | 1612 | [67–237],[113–352],[252–425] | 1652 | [47–397] |
| 1495 | [42–491] | 1489 | [32–217] | | | 1653 | [322–513] |
| 1496 | [293–502] | 1490 | [69–383],[154–366] | 1613 | [127–285] | 1654 | [167–331] |
| 1497 | [273–452] | 1491 | [83–316] | 1614 | [130–300] | 1655 | [191–448] |
| 1498 | [148–474] | 1492 | [167–379] | 1615 | [135–320] | 1656 | [94–375] |
| 1499 | [73–267] | 1493 | [186–368] | 1616 | [42–536],[119–331] | 1657 | [26–370],[307–480] |
| 1500 | [71–385] | 1494 | [38–283] | 1617 | [32–307] | 1658 | [163–468],[380–628] |
| 1501 | [53–334],[277–435] | 1541 | [239–394] | 1618 | [75–251] | 1659 | [35–319] |
| 1502 | [137–286] | 1542 | [90–290] | 1619 | [65–253] | 1660 | [183–413] |

TABLE I-continued (Positions of all ORFs)

| Seq Id No. | Positions of Open Reading Frame(s) | Seq Id No. | Positions of Open Reading Frame(s) | Seq Id No. | Positions of Open Reading Frame(s) | Seq Id No. | Positions of Open Reading Frame(s) |
|---|---|---|---|---|---|---|---|
| 1620 | [154–471],[216–383] | 1661 | [43–264] | 1784 | [60–242] | 1821 | [129–323] |
| 1621 | [30–284] | 1662 | [32–385] | 1785 | [120–347] | 1822 | [243–479] |
| 1622 | [126–371],[340–525] | 1663 | [187–405],[282–443],[290–499] | 1786 | [20–247] | 1823 | [50–202] |
| 1623 | [140–304] | | | 1787 | [17–178] | 1824 | [154–351],[236–403],[291–470] |
| 1624 | [226–447] | 1664 | [76–675] | 1788 | [123–332] | | |
| 1625 | [223–435] | 1665 | [228–401] | 1789 | [148–333] | 1825 | [56–274] |
| 1626 | [34–327] | 1666 | [191–439] | 1790 | [77–388] | 1826 | [161–334] |
| 1627 | [17–298],[46–270] | 1667 | [76–276] | 1791 | [34–315],[336–548] | 1827 | [153–431] |
| 1628 | [54–224] | 1668 | [228–401] | 1792 | [95–349] | 1828 | [23–382] |
| 1629 | [124–333] | 1669 | [5–334] | 1793 | [29–259] | 1829 | [5–175] |
| 1630 | [60–209] | 1670 | [26–214] | 1794 | [238–462] | 1830 | [29–271],[147–374] |
| 1631 | [8–184],[189–434] | 1671 | [76–276],[330–530] | 1795 | [5–409] | 1831 | [73–378],[282–431] |
| 1632 | [55–459] | 1672 | [94–324] | 1796 | [186–398] | 1832 | [70–366] |
| 1679 | [111–377] | 1673 | [66–251],[258–416] | 1797 | [269–439] | 1833 | [109–450],[293–517] |
| 1680 | [96–497],[452–685] | 1674 | [159–368] | 1798 | [280–474] | 1834 | [56–229] |
| 1681 | [180–377],[197–370] | 1675 | [44–193] | 1799 | [174–329],[214–378] | 1835 | [173–511] |
| 1682 | [11–487] | 1676 | [203–352] | 1800 | [42–320] | 1836 | [123–359] |
| 1683 | [41–304] | 1677 | [97–477] | 1801 | [182–451] | 1837 | [79–435] |
| 1684 | [194–427] | 1678 | [41–337] | 1802 | [142–384] | 1838 | [92–298] |
| 1685 | [315–536],[439–648] | 1725 | [21–209] | 1803 | [1–453],[120–353],[381–569] | 1839 | [359–547] |
| 1686 | [24–329] | 1726 | [108–275] | | | 1840 | [243–401] |
| 1687 | [76–408] | 1727 | [234–407] | 1804 | [30–218] | 1841 | [18–239],[139–438] |
| 1688 | [75–242] | 1728 | [128–319] | 1805 | [90–371],[139–297] | 1842 | [129–323] |
| 1689 | [28–324] | 1729 | [17–187] | 1806 | [207–419] | 1843 | [32–274] |
| 1690 | [138–350] | 1730 | [147–326] | 1807 | [186–449] | 1844 | [71–256],[195–461] |
| 1691 | [239–397] | 1731 | [50–241] | 1808 | [123–284],[356–514] | 1845 | [216–635],[434–652] |
| 1692 | [2–157] | 1732 | [28–387] | 1809 | [6–212] | 1846 | [40–231] |
| 1693 | [196–351],[240–407] | 1733 | [73–390] | 1810 | [167–508] | 1847 | [244–453] |
| 1694 | [114–287] | 1734 | [235–525] | 1811 | [132–419],[287–520] | 1848 | [264–443] |
| 1695 | [23–202],[33–293] | 1735 | [52–372],[90–242] | 1812 | [122–382] | 1849 | [16–201] |
| 1696 | [139–378] | 1736 | [51–368],[259–432],[356–505] | 1813 | [87–245] | 1850 | [17–373] |
| 1697 | [240–395],[284–451] | | | 1814 | [183–443] | 1851 | [144–308] |
| 1698 | [8–325],[76–432] | 1737 | [86–244],[271–438],[317–520] | 1815 | [14–460] | 1852 | [150–434] |
| 1699 | [56–310] | | | 1816 | [28–282] | 1853 | [143–361] |
| 1700 | [188–679],[243–521] | 1738 | [50–340] | 1863 | [31–321],[305–535] | 1854 | [266–547],[303–497] |
| 1701 | [51–209] | 1739 | [2–250] | 1864 | [102–362] | 1855 | [16–201] |
| 1702 | [83–358] | 1740 | [23–247],[73–294] | 1865 | [232–450] | 1856 | [99–395],[172–486] |
| 1703 | [79–288],[291–455] | 1741 | [194–346] | 1866 | [20–343] | 1857 | [37–3219],[206–433] |
| 1704 | [49–432] | 1742 | [128–412] | 1867 | [166–435],[414–611] | 1858 | [102–263],[205–387] |
| 1705 | [35–526] | 1743 | [132–449] | 1868 | [10–204] | 1859 | [222–374] |
| 1706 | [148–402] | 1744 | [86–244],[271–438],[317–466] | 1869 | [101–436] | 1860 | [255–422] |
| 1707 | [110–526],[226–381] | | | 1870 | [21–497] | 1861 | [17–178] |
| 1708 | [187–360] | 1745 | [83–658] | 1871 | [219–443] | 1862 | [7–162],[436–585] |
| 1709 | [94–267] | 1746 | [79–276] | 1872 | [125–301],[136–357] | 1909 | [186–446] |
| 1710 | [176–325] | 1747 | [63–299] | 1873 | [111–386] | 1910 | [70–354],[149–304] |
| 1711 | [50–403] | 1748 | [73–249] | 1874 | [53–229],[214–378] | 1911 | [122–352] |
| 1712 | [178–507] | 1749 | [17–316] | 1875 | [6–287] | 1912 | [205–408] |
| 1713 | [110–277] | 1750 | [85–333],[186–539],[424–585] | 1876 | [29–304],[258–428] | 1913 | [78–233] |
| 1714 | [5–274],[278–481] | | | 1877 | [174–443] | 1914 | [170–346] |
| 1715 | [235–414] | 1751 | [155–376],[429–581] | 1878 | [152–673] | 1915 | [30–356],[67–504] |
| 1716 | [170–319] | 1752 | [286–465] | 1879 | [152–448] | 1916 | [13–441] |
| 1717 | [229–471],[261–494] | 1753 | [262–501] | 1880 | [50–253] | 1917 | [291–455] |
| 1718 | [53–271] | 1754 | [46–249] | 1881 | [22–432],[32–472],[141–362] | 1918 | [69–299] |
| 1719 | [278–463] | 1755 | [33–218] | | | 1919 | [15–179] |
| 1720 | [202–351] | 1756 | [19–168] | 1882 | [27–203] | 1920 | [199–618],[453–641] |
| 1721 | [56–271] | 1757 | [55–399] | 1883 | [184–438] | 1921 | [138–368] |
| 1722 | [62–235] | 1758 | [9–380] | 1884 | [179–475] | 1922 | [226–411] |
| 1723 | [8–214] | 1759 | [62–385] | 1885 | [237–389] | 1923 | [91–366] |
| 1724 | [55–240] | 1760 | [78–311] | 1886 | [75–596] | 1924 | [119–421] |
| 1771 | [244–465] | 1761 | [216–395] | 1887 | [53–229],[214–378] | 1925 | [17–193] |
| 1772 | [31–213] | 1762 | [43–312] | 1888 | [144–428] | 1926 | [18–266],[302–463] |
| 1773 | [159–470],[178–408] | 1763 | [131–346] | 1889 | [274–432] | 1927 | [7–354],[195–410],[215–475] |
| 1774 | [21–227],[190–435],[239–451] | 1764 | [107–313] | 1890 | [4–180] | | |
| | | 1765 | [17–244] | 1891 | [98–361],[129–329] | 1928 | [25–267],[257–475] |
| 1775 | [5–328],[79–399] | 1766 | [43–312] | 1892 | [143–418] | 1929 | [41–220],[289–471] |
| 1776 | [5–328],[79–426] | 1767 | [107–313] | 1893 | [167–493] | 1930 | [13–360],[201–416],[221–481] |
| 1777 | [84–284] | 1768 | [184–444] | 1894 | [61–429] | | |
| 1778 | [30–410] | 1769 | [65–370] | 1895 | [62–430] | 1931 | [269–418] |
| 1779 | [5–328],[79–426] | 1770 | [216–401] | 1896 | [95–475] | 1932 | [237–473],[241–495] |
| 1780 | [22–210],[122–280] | 1817 | [106–441],[164–391] | 1897 | [24–209] | 1933 | [105–287] |
| 1781 | [2–151],[220–456] | 1818 | [62–220] | 1898 | [61–429] | 1934 | [1–291] |
| 1782 | [232–381] | 1819 | [21–335] | 1899 | [148–414] | 1935 | [189–464] |
| 1783 | [87–311],[395–544] | 1820 | [111–293],[259–546] | 1900 | [139–327] | 1936 | [344–577] |

TABLE I-continued (Positions of all ORFs)

| Seq Id No. | Positions of Open Reading Frame(s) | Seq Id No. | Positions of Open Reading Frame(s) |
|---|---|---|---|
| 1901 | [218–370],[285–512] | 1937 | [34–195] |
| 1902 | [38–310] | 1938 | [84–296] |
| 1903 | [125–313] | 1939 | [34–195] |
| 1904 | [126–398] | 1940 | [34–195] |
| 1905 | [9–167],[175–354] | 1941 | [8–169] |
| 1906 | [124–351] | 1942 | [34–195] |
| 1907 | [222–380] | 1943 | [34–195] |
| 1908 | [65–316] | 1944 | [34–195] |
| 1955 | [181–333],[189–347] | 1945 | [195–530],[253–480] |
| 1956 | [16–243] | 1946 | [139–330] |
| 1957 | [195–407] | 1947 | [333–482],[585–740] |
| 1958 | [181–333],[189–347] | 1948 | [285–506] |
| 1959 | [80–301] | 1949 | [122–271],[153–329] |
| 1960 | [171–419] | 1950 | [206–403] |
| 1961 | [37–279],[98–634] | 1951 | [82–297],[221–427] |
| 1962 | [209–397] | 1952 | [181–333],[189–347] |
| 1963 | [248–469] | 1953 | [133–327] |
| 1964 | [93–341] | 1954 | [133–327] |
| 1965 | [206–403] | 2001 | [106–348] |
| 1966 | [17–391] | 2002 | [7–234] |
| 1967 | [252–440] | 2003 | [98–340],[202–567] |
| 1968 | [142–411],[453–608] | 2004 | [108–350],[212–490] |
| 1969 | [29–367],[330–662],[370–708] | 2005 | [211–570],[230–430] |
| 1970 | [126–350],[221–394] | 2006 | [181–384],[353–523],[403–792] |
| 1971 | [7–186] | 2007 | [79–297] |
| 1972 | [92–340] | 2008 | [58–228] |
| 1973 | [47–199],[229–405] | 2009 | [125–373],[286–474] |
| 1974 | [233–424] | 2010 | [148–315] |
| 1975 | [99–410] | 2011 | [295–474] |
| 1976 | [80–238] | 2012 | [62–244] |
| 1977 | [203–433] | 2013 | [219–374] |
| 1978 | [19–474] | 2014 | [271–426] |
| 1979 | [15–221] | 2015 | [218–373] |
| 1980 | [97–327] | 2016 | [218–379] |
| 1981 | [64–234],[105–332] | 2017 | [284–439] |
| 1982 | [41–352] | 2018 | [39–266],[184–492] |
| 1983 | [180–455] | 2019 | [54–350] |
| 1984 | [385–768] | 2020 | [14–469],[255–428] |
| 1985 | [83–325],[126–314] | 2021 | [7–330] |
| 1986 | [7–258] | 2022 | [104–367],[157–435] |
| 1987 | [102–398] | 2023 | [24–185] |
| 1988 | [98–331] | 2024 | [161–589] |
| 1989 | [52–255] | 2025 | [32–187] |
| 1990 | [76–339] | 2026 | [88–312] |
| 1991 | [162–356] | 2027 | [21–290],[239–406] |
| 1992 | [236–391] | 2028 | [57–248] |
| 1993 | [301–477] | 2029 | [53–454] |
| 1994 | [99–290] | 2030 | [174–530] |
| 1995 | [150–569] | 2031 | [130–288] |
| 1996 | [94–276] | 2032 | [187–342] |
| 1997 | [94–276] | 2033 | [221–466] |
| 1998 | [206–436],[211–534] | 2034 | [22–357] |
| 1999 | [6–164],[71–268] | 2035 | [102–377] |
| 2000 | [119–304] | 2036 | [266–502] |
| 2047 | [212–400] | 2037 | [36–224],[241–507] |
| 2048 | [155–433] | 2038 | [128–367] |
| 2049 | [102–377] | 2039 | [157–318] |
| 2050 | [147–389] | 2040 | [115–288] |
| 2051 | [114–449],[194–364] | 2041 | [102–377] |
| 2052 | [21–290],[239–397] | 2042 | [126–290] |
| 2053 | [52–315] | 2043 | [52–315] |
| 2054 | [102–377] | 2044 | [40–318],[318–479] |
| 2055 | [21–566] | 2045 | [272–430] |
| 2056 | [44–214] | 2046 | [23–352] |
| 2057 | [1–189] | 2093 | [39–245] |
| 2058 | [88–312] | 2094 | [167–355] |
| 2059 | [36–353] | 2095 | [12–203],[288–446] |
| 2060 | [225–455] | 2096 | [279–449] |
| 2061 | [65–265],[192–383] | 2097 | [179–379],[288–476] |
| 2062 | [9–161],[262–417] | 2098 | [119–313] |
| 2063 | [231–404] | 2099 | [18–239],[223–372] |
| 2064 | [115–288] | 2100 | [168–356] |
| 2065 | [158–325],[219–377] | 2101 | [85–267] |
| 2066 | [24–173] | 2102 | [54–224] |
| 2067 | [39–191] | 2103 | [3–176] |
| 2068 | [57–320] | 2104 | [280–504] |
| 2069 | [189–461],[313–501] | 2105 | [18–206] |
| 2070 | [146–433] | 2106 | [196–363] |
| 2071 | [3–176] | 2107 | [10–177] |
| 2072 | [42–215] | 2108 | [193–453],[221–373] |
| 2073 | [46–249] | 2109 | [71–253],[265–495] |
| 2074 | [140–313] | 2110 | [3–215] |
| 2075 | [74–379] | 2111 | [101–256],[160–381] |
| 2076 | [104–430] | 2112 | [11–349] |
| 2077 | [229–411] | 2113 | [19–222] |
| 2078 | [3–185] | 2114 | [125–322] |
| 2079 | [273–422] | 2115 | [47–256] |
| 2080 | [212–427] | 2116 | [127–378],[215–391] |
| 2081 | [76–303],[350–505] | 2117 | [25–219] |
| 2082 | [231–584] | 2118 | [152–346] |
| 2083 | [140–313] | 2119 | [178–339],[242–439] |
| 2084 | [118–363],[266–463] | 2120 | [25–204] |
| 2085 | [223–444] | 2121 | [102–320] |
| 2086 | [231–455],[310–504] | 2122 | [122–379] |
| 2087 | [13–195],[223–444] | 2123 | [115–378] |
| 2088 | [79–378],[128–358] | 2124 | [84–248],[182–352] |
| 2089 | [265–432] | 2125 | [12–203],[288–437] |
| 2090 | [178–330] | 2126 | [169–354] |
| 2091 | [22–180],[131–427] | 2127 | [163–330] |
| 2092 | [12–209] | 2128 | [139–324] |
| 2139 | [85–297] | 2129 | [292–474] |
| 2140 | [89–289] | 2130 | [103–372] |
| 2141 | [14–205],[144–449] | 2131 | [47–295] |
| 2142 | [330–494] | 2132 | [106–366] |
| 2143 | [287–466] | 2133 | [199–420] |
| 2144 | [92–256] | 2134 | [50–208] |
| 2145 | [218–406] | 2135 | [9–200] |
| 2146 | [83–259] | 2136 | [191–349] |
| 2147 | [56–244] | 2137 | [280–429] |
| 2148 | [310–462] | 2138 | [47–226] |
| 2149 | [70–237] | 2185 | [55–390] |
| 2150 | [160–315] | 2186 | [224–454] |
| 2151 | [174–440] | 2187 | [64–213] |
| 2152 | [136–330] | 2188 | [92–280],[136–306] |
| 2153 | [18–239],[223–396] | 2189 | [44–478] |
| 2154 | [20–181] | 2190 | [59–448] |
| 2155 | [103–450],[288–485] | 2191 | [150–314] |
| 2156 | [280–450] | 2192 | [213–467] |
| 2157 | [17–400] | 2193 | [64–321] |
| 2158 | [175–483] | 2194 | [88–315] |
| 2159 | [8–193],[227–472] | 2195 | [88–315],[363–566] |
| 2160 | [138–311],[247–408] | 2196 | [21–209] |
| 2161 | [24–257] | 2197 | [158–424] |
| 2162 | [17–223] | 2198 | [132–422] |
| 2163 | [106–276] | 2199 | [4–192],[116–304] |
| 2164 | [75–224] | 2200 | [88–480],[356–520] |
| 2165 | [79–246] | 2201 | [110–268] |
| 2166 | [66–275] | 2202 | [53–214],[308–463] |
| 2167 | [197–376],[238–426] | 2203 | [93–272] |
| 2168 | [173–322] | 2204 | [129–356] |
| 2169 | [83–319],[205–384] | 2205 | [181–345] |
| 2170 | [18–497] | 2206 | [208–366] |
| 2171 | [29–214] | 2207 | [257–463] |
| 2172 | [213–431] | 2208 | [113–364] |
| 2173 | [327–476] | 2209 | [36–569] |
| 2174 | [262–525] | 2210 | [39–188] |
| 2175 | [12–209] | 2211 | [32–337],[216–455] |
| 2176 | [158–379] | 2212 | [122–286],[258–458] |
| 2177 | [59–346] | 2213 | [6–386] |
| 2178 | [27–338] | 2214 | [137–439] |
| 2179 | [287–457] | 2215 | [85–252] |
| 2180 | [49–243] | 2216 | [112–363] |
| 2181 | [86–265],[172–450] | 2217 | [58–306] |
| 2182 | [135–428] | 2218 | [67–381],[360–509] |
| 2183 | [206–385],[231–413] | 2219 | [98–442] |

TABLE I-continued (Positions of all ORFs)

| Seq Id No. | Positions of Open Reading Frame(s) | Seq Id No. | Positions of Open Reading Frame(s) | Seq Id No. | Positions of Open Reading Frame(s) | Seq Id No. | Positions of Open Reading Frame(s) |
|---|---|---|---|---|---|---|---|
| 2184 | [85–243] | 2220 | [217–393] | 2348 | [54–260],[254–409] | 2383 | [76–261] |
| 2231 | [3–239],[106–255] | 2221 | [55–237] | 2349 | [27–194] | 2384 | [175–375],[339–569], [425–622] |
| 2232 | [24–242] | 2222 | [57–212] | 2350 | [11–202] | | |
| 2233 | [90–431],[295–465] | 2223 | [29–181] | 2351 | [34–381],[407–616] | 2385 | [190–369] |
| 2234 | [27–212] | 2224 | [5–214] | 2352 | [48–197] | 2386 | [49–210] |
| 2235 | [20–181] | 2225 | [44–283] | 2353 | [301–459] | 2387 | [64–336],[101–343], [267–515] |
| 2236 | [107–409],[117–308] | 2226 | [189–386] | 2354 | [46–318],[209–478] | | |
| 2237 | [60–209] | 2227 | [56–298] | 2355 | [168–350] | 2388 | [29–232],[78–308] |
| 2238 | [125–274],[187–357] | 2228 | [201–353] | 2356 | [154–315] | 2389 | [211–369] |
| 2239 | [130–306] | 2229 | [48–230],[140–295] | 2357 | [144–353] | 2390 | [33–368] |
| 2240 | [69–323] | 2230 | [32–253] | 2358 | [148–432] | 2391 | [78–329] |
| 2241 | [104–421],[222–467] | 2277 | [188–409] | 2359 | [1–195],[141–293] | 2392 | [159–533] |
| 2242 | [63–440],[157–324] | 2278 | [99–254] | 2360 | [209–400] | 2393 | [23–202] |
| 2243 | [66–227] | 2279 | [129–293] | 2361 | [70–351],[285–470] | 2394 | [170–328],[285–467] |
| 2244 | [120–290],[293–460] | 2280 | [202–432] | 2362 | [257–412] | 2395 | [160–453] |
| 2245 | [28–234],[137–433], [259–471] | 2281 | [33–212],[216–386] | 2363 | [36–368] | 2396 | [101–274] |
| | | 2282 | [82–234],[290–520] | 2364 | [24–182] | 2397 | [267–482] |
| 2246 | [123–383] | 2283 | [199–405] | 2365 | [3–329],[247–480] | 2398 | [80–274] |
| 2247 | [125–337] | 2284 | [133–381],[222–533] | 2366 | [166–402] | 2399 | [96–443] |
| 2248 | [129–446] | 2285 | [206–367] | 2367 | [118–285],[269–457] | 2400 | [224–418] |
| 2249 | [90–242] | 2286 | [131–349] | 2368 | [266–454] | 2401 | [145–486],[296–466] |
| 2250 | [290–469] | 2287 | [83–394],[238–480] | 2415 | [34–201] | 2402 | [38–202] |
| 2251 | [182–496] | 2288 | [218–370] | 2416 | [182–487] | 2403 | [263–415] |
| 2252 | [101–406] | 2289 | [110–295] | 2417 | [388–687],[751–930] | 2404 | [102–305] |
| 2253 | [296–478] | 2290 | [62–223] | 2418 | [105–296],[223–423] | 2405 | [1–411],[65–337] |
| 2254 | [126–383] | 2291 | [188–457] | 2419 | [49–321] | 2406 | [112–339] |
| 2255 | [113–385],[268–492] | 2292 | [130–309] | 2420 | [98–253] | 2407 | [77–241] |
| 2256 | [58–270] | 2293 | [46–324] | 2421 | [162–317] | 2408 | [59–268],[190–372] |
| 2257 | [6–155] | 2294 | [202–357] | 2422 | [93–293] | 2409 | [81–269],[347–514] |
| 2258 | [58–270] | 2295 | [47–271] | 2423 | [251–487] | 2410 | [199–399] |
| 2259 | [58–450] | 2296 | [182–355] | 2424 | [19–321] | 2411 | [44–238],[102–254] |
| 2260 | [131–298] | 2297 | [54–401],[193–474], [248–475] | 2425 | [96–251],[319–486] | 2412 | [192–437],[211–378] |
| 2261 | [207–380] | | | 2426 | [44–259],[300–485] | 2413 | [123–302] |
| 2262 | [216–368] | 2298 | [99–269] | 2427 | [38–463] | 2414 | [95–376],[297–467] |
| 2263 | [195–356] | 2299 | [36–242],[133–333] | 2428 | [17–442] | 2461 | [64–552] |
| 2264 | [11–169],[237–389] | 2300 | [53–274] | 2429 | [16–441] | 2462 | [53–217] |
| 2265 | [133–423] | 2301 | [33–188] | 2430 | [66–263] | 2463 | [288–446] |
| 2266 | [226–375] | 2302 | [25–204] | 2431 | [143–373] | 2464 | [187–336] |
| 2267 | [187–453] | 2303 | [226–450] | 2432 | [66–446] | 2465 | [52–390] |
| 2268 | [153–317],[245–457] | 2304 | [165–344] | 2433 | [190–465] | 2466 | [37–372] |
| 2269 | [257–421] | 2305 | [87–263] | 2434 | [52–360] | 2467 | [237–509],[329–484] |
| 2270 | [192–422] | 2306 | [13–186] | 2435 | [341–490] | 2468 | [72–317] |
| 2271 | [106–369] | 2307 | [301–462] | 2436 | [35–454] | 2469 | [214–375] |
| 2272 | [266–469] | 2308 | [189–455],[212–442], [277–498] | 2437 | [42–308],[59–361] | 2470 | [125–418],[214–363] |
| 2273 | [43–213] | | | 2438 | [174–377],[275–433] | 2471 | [202–357] |
| 2274 | [36–197] | 2309 | [5–154] | 2439 | [146–310] | 2472 | [51–215] |
| 2275 | [215–424],[234–389] | 2310 | [163–345] | 2440 | [168–428],[313–507] | 2473 | [206–364] |
| 2276 | [219–407] | 2311 | [165–473] | 2441 | [99–272] | 2474 | [133–375] |
| 2323 | [46–207] | 2312 | [283–450] | 2442 | [6–215] | 2475 | [146–334] |
| 2324 | [2–166] | 2313 | [132–281] | 2443 | [155–382] | 2476 | [149–298] |
| 2325 | [95–265] | 2314 | [96–281] | 2444 | [180–401] | 2477 | [28–204] |
| 2326 | [115–294] | 2315 | [14–232] | 2445 | [161–328] | 2478 | [105–332] |
| 2327 | [140–349] | 2316 | [3–254] | 2446 | [63–254],[104–430], [261–410] | 2479 | [38–211] |
| 2328 | [238–399] | 2317 | [65–304] | | | 2480 | [124–489],[284–502] |
| 2329 | [210–413] | 2318 | [34–201] | 2447 | [115–321] | 2481 | [235–516] |
| 2330 | [33–230],[149–412] | 2319 | [62–370],[225–422] | 2448 | [116–298] | 2482 | [18–254],[103–390] |
| 2331 | [123–350] | 2320 | [135–335],[280–471] | 2449 | [151–423] | 2483 | [149–298] |
| 2332 | [80–313],[210–452] | 2321 | [7–174],[270–422] | 2450 | [95–289] | 2484 | [172–489] |
| 2333 | [50–310] | 2322 | [87–326] | 2451 | [58–222] | 2485 | [271–528] |
| 2334 | [251–400] | 2369 | [13–330],[96–344] | 2452 | [238–387] | 2486 | [231–410] |
| 2335 | [95–331] | 2370 | [34–216],[207–452] | 2453 | [276–467] | 2487 | [137–301],[204–386] |
| 2336 | [133–462] | 2371 | [18–191] | 2454 | [260–448] | 2488 | [177–401] |
| 2337 | [62–217] | 2372 | [141–515],[247–468] | 2455 | [228–398] | 2489 | [108–266],[134–292] |
| 2338 | [23–268] | 2373 | [219–464] | 2456 | [130–282] | 2490 | [226–387] |
| 2339 | [132–281] | 2374 | [74–265] | 2457 | [259–450] | 2491 | [257–406] |
| 2340 | [239–388] | 2375 | [219–464] | 2458 | [259–450] | 2492 | [175–405] |
| 2341 | [27–194] | 2376 | [261–503] | 2459 | [259–450] | 2493 | [124–498] |
| 2342 | [8–193] | 2377 | [203–385],[231–440] | 2460 | [276–467] | 2494 | [256–426] |
| 2343 | [301–462] | 2378 | [169–378] | 2507 | [81–326],[266–469] | 2495 | [56–250] |
| 2344 | [296–478] | 2379 | [12–398] | 2508 | [22–255] | 2496 | [8–367],[160–465] |
| 2345 | [106–288] | 2380 | [12–368] | 2509 | [22–270] | 2497 | [109–396] |
| 2346 | [141–308] | 2381 | [129–395] | 2510 | [264–452],[313–483] | 2498 | [153–437],[298–483] |
| 2347 | [42–218],[134–319] | 2382 | [169–414] | 2511 | [16–165] | 2499 | [288–443] |

TABLE I-continued (Positions of all ORFs)

| Seq Id No. | Positions of Open Reading Frame(s) | Seq Id No. | Positions of Open Reading Frame(s) | Seq Id No. | Positions of Open Reading Frame(s) | Seq Id No. | Positions of Open Reading Frame(s) |
|---|---|---|---|---|---|---|---|
| 2512 | [57–236],[202–462] | 2500 | [10–195] | 2627 | [147–335] | 2662 | [38–286] |
| 2513 | [107–376] | 2501 | [131–334] | 2628 | [147–335] | 2663 | [164–454] |
| 2514 | [171–449],[247–498] | 2502 | [22–213] | 2629 | [147–335] | 2664 | [44–208] |
| 2515 | [37–192] | 2503 | [22–444] | 2630 | [147–335] | 2665 | [164–355] |
| 2516 | [279–545] | 2504 | [191–376] | 2631 | [147–335] | 2666 | [113–358] |
| 2517 | [74–274],[298–468] | 2505 | [39–527] | 2632 | [147–335] | 2667 | [2–205],[186–338] |
| 2518 | [86–325] | 2506 | [31–261] | 2633 | [147–335] | 2668 | [129–329],[226–552] |
| 2519 | [300–455] | 2553 | [83–274] | 2634 | [147–335] | 2669 | [219–431] |
| 2520 | [65–454] | 2554 | [14–286] | 2635 | [199–357] | 2670 | [17–169] |
| 2521 | [68–238] | 2555 | [30–344],[310–477] | 2636 | [147–335] | 2671 | [93–251],[157–402] |
| 2522 | [49–228],[276–446] | 2556 | [241–390] | 2637 | [12–374] | 2672 | [60–284],[169–348] |
| 2523 | [20–349],[165–473] | 2557 | [60–221] | 2638 | [124–324] | 2673 | [63–308] |
| 2524 | [20–349],[165–473], [412–567] | 2558 | [73–261] | 2639 | [147–335] | 2674 | [135–299] |
| 2525 | [2–238] | 2559 | [115–288] | 2640 | [113–409] | 2675 | [473–652] |
| 2526 | [68–223] | 2560 | [107–289],[180–437], [356–505] | 2641 | [110–310] | 2676 | [253–447] |
| 2527 | [119–313] | | | 2642 | [34–213],[84–443] | 2677 | [49–222] |
| 2528 | [21–326] | 2561 | [90–368] | 2643 | [147–335] | 2678 | [152–337] |
| 2529 | [13–165] | 2562 | [182–379] | 2644 | [165–374] | 2679 | [23–220] |
| 2530 | [105–314] | 2563 | [168–380] | 2691 | [282–470] | 2680 | [116–283],[258–419] |
| | | 2564 | [9–221],[37–306], [215–433] | 2692 | [203–355] | 2681 | [116–283],[258–419] |
| | | | | 2693 | [144–302],[154–330] | 2682 | [247–453] |
| 2531 | [111–410] | 2565 | [18–272] | 2694 | [250–501] | 2683 | [93–299],[445–594] |
| 2532 | [171–389] | 2566 | [256–429] | 2695 | [85–336] | 2684 | [19–315] |
| 2533 | [22–318] | 2567 | [108–266],[169–360] | 2696 | [15–197],[197–445] | 2685 | [75–281] |
| 2534 | [80–247] | 2568 | [72–335] | 2697 | [12–275] | 2686 | [261–422] |
| 2535 | [232–402] | 2569 | [326–556] | 2698 | [248–397] | 2687 | [195–350] |
| 2536 | [115–339],[243–464] | 2570 | [132–281] | 2699 | [65–229],[229–408] | 2688 | [206–364] |
| 2537 | [160–405] | 2571 | [68–238] | 2700 | [325–489] | 2689 | [26–226] |
| 2538 | [261–476] | 2572 | [25–231] | 2701 | [4–420] | 2690 | [26–424],[90–245] |
| 2539 | [85–297] | 2573 | [57–224] | 2702 | [233–397] | 2737 | [110–271] |
| 2540 | [284–442],[351–521], [524–904] | 2574 | [497–826] | 2703 | [191–442] | 2738 | [13–162] |
| | | 2575 | [264–422] | 2704 | [202–387],[230–415] | 2739 | [41–226] |
| 2541 | [170–346] | 2576 | [60–215],[202–447] | 2705 | [105–446] | 2740 | [46–471],[95–259] |
| 2542 | [189–455] | 2577 | [57–212],[124–411] | 2706 | [83–418],[219–431] | 2741 | [163–312] |
| 2543 | [49–243],[275–457] | 2578 | [57–212],[124–411] | 2707 | [137–337] | 2742 | [125–316],[235–444] |
| 2544 | [143–418],[154–306] | 2579 | [91–246] | 2708 | [179–412] | 2743 | [30–329] |
| 2545 | [257–454] | 2580 | [210–392] | 2709 | [234–410] | 2744 | [97–288] |
| 2546 | [4–270] | 2581 | [110–328],[270–449] | 2710 | [52–252],[263–448] | 2745 | [95–454] |
| 2547 | [56–277] | 2582 | [69–308],[250–429] | 2711 | [11–232] | 2746 | [93–416] |
| 2548 | [197–364] | 2583 | [110–328],[270–449] | 2712 | [269–472],[300–485] | 2747 | [12–191] |
| 2549 | [168–365] | 2584 | [1–207],[355–609] | 2713 | [142–435] | 2748 | [41–232] |
| 2550 | [220–399] | 2585 | [166–420] | 2714 | [21–230] | 2749 | [77–241] |
| 2551 | [193–348] | 2586 | [119–334] | 2715 | [21–230] | 2750 | [115–354] |
| 2552 | [113–391] | 2587 | [53–208],[372–539] | 2716 | [103–327] | 2751 | [93–257] |
| 2599 | [67–228] | 2588 | [92–283],[247–501] | 2717 | [343–504] | 2752 | [231–440] |
| 2600 | [57–245] | 2589 | [48–326] | 2718 | [42–263] | 2753 | [8–202],[78–323] |
| 2601 | [65–310],[211–366] | 2590 | [214–456] | 2719 | [3–176] | 2754 | [59–307] |
| 2602 | [117–290] | 2591 | [233–439] | 2720 | [46–249],[293–481] | 2755 | [362–514] |
| 2603 | [128–331],[255–452] | 2592 | [9–368] | 2721 | [1–156] | 2756 | [46–264] |
| 2604 | [2–151],[301–495] | 2593 | [32–220] | 2722 | [131–388] | 2757 | [139–525] |
| 2605 | [287–490] | 2594 | [142–432],[221–388] | 2723 | [71–379] | 2758 | [39–356] |
| 2606 | [12–191] | 2595 | [4–186],[302–475] | 2724 | [71–379] | 2759 | [48–341] |
| 2607 | [2–166] | 2596 | [4–168] | 2725 | [333–683] | 2760 | [125–445] |
| 2608 | [158–331] | 2597 | [91–270] | 2726 | [103–261] | 2761 | [147–497] |
| 2609 | [9–314] | 2598 | [132–305] | 2727 | [151–360],[341–505] | 2762 | [81–254] |
| 2610 | [179–358],[259–411] | 2645 | [147–335] | 2728 | [105–377] | 2763 | [81–374] |
| 2611 | [217–450] | 2646 | [147–335] | 2729 | [74–250],[129–401] | 2764 | [276–440] |
| 2612 | [279–443],[446–697] | 2647 | [285–443] | 2730 | [57–329] | 2765 | [115–405],[360–509] |
| 2613 | [64–249],[253–417] | 2648 | [275–469] | 2731 | [16–234] | 2766 | [64–306] |
| 2614 | [2–217],[362–526], [529–780] | 2649 | [212–391] | 2732 | [26–193],[81–287] | 2767 | [135–314] |
| | | 2650 | [41–271] | 2733 | [217–387] | 2768 | [64–306] |
| 2615 | [101–253] | 2651 | [20–184],[103–258] | 2734 | [198–380] | 2769 | [64–306] |
| 2616 | [164–400] | 2652 | [229–462],[398–568] | 2735 | [63–221],[170–481] | 2770 | [24–266] |
| 2617 | [285–458] | 2653 | [204–437],[373–540] | 2736 | [142–294],[189–389] | 2771 | [58–237] |
| 2618 | [286–447] | 2654 | [185–355] | 2783 | [119–328] | 2772 | [170–448],[351–506] |
| 2619 | [146–322] | 2655 | [298–465] | 2784 | [299–499] | 2773 | [118–267] |
| 2620 | [66–464],[76–249] | 2656 | [121–273] | 2785 | [90–491] | 2774 | [285–497] |
| 2621 | [281–460] | 2657 | [26–406] | 2786 | [16–210] | 2775 | [134–472] |
| 2622 | [56–226],[138–332] | 2658 | [28–222],[173–334] | 2787 | [91–315] | 2776 | [338–487] |
| 2623 | [147–335] | 2659 | [11–172],[165–335] | 2788 | [123–449] | 2777 | [109–351] |
| 2624 | [147–335] | 2660 | [113–295],[126–398], [301–456] | 2789 | [174–344] | 2778 | [256–411] |
| 2625 | [147–335] | | | 2790 | [10–297],[281–487] | 2779 | [130–438] |
| 2626 | [147–335] | 2661 | [73–285],[107–337] | 2791 | [20–313] | 2780 | [73–429],[350–502] |

TABLE I-continued (Positions of all ORFs)

| Seq Id No. | Positions of Open Reading Frame(s) | Seq Id No. | Positions of Open Reading Frame(s) | Seq Id No. | Positions of Open Reading Frame(s) | Seq Id No. | Positions of Open Reading Frame(s) |
|---|---|---|---|---|---|---|---|
| 2792 | [3–161],[473–700] | 2781 | [189–581] | 2908 | [267–533] | 2943 | [163–345],[305–508] |
| 2793 | [216–431] | 2782 | [88–249],[194–355] | 2909 | [32–235],[132–293] | 2944 | [23–364] |
| 2794 | [74–226],[154–342] | 2829 | [155–391],[168–353] | 2910 | [287–460] | 2945 | [120–410],[367–543] |
| 2795 | [94–276],[224–454] | 2830 | [82–372],[375–533] | 2911 | [177–521] | 2946 | [43–321] |
| 2796 | [96–278],[226–459] | 2831 | [79–228],[179–334] | 2912 | [64–354] | 2947 | [132–317] |
| 2797 | [96–278],[226–459] | 2832 | [181–588] | 2913 | [22–225] | 2948 | [22–408] |
| 2798 | [96–278],[226–456] | 2833 | [74–271] | 2914 | [174–335] | 2949 | [18–209] |
| 2799 | [95–277],[225–461] | 2834 | [103–330],[338–508] | 2915 | [236–469] | 2950 | [37–222],[95–397] |
| 2800 | [96–278],[226–432] | 2835 | [99–308] | 2916 | [174–356] | 2951 | [179–472] |
| 2801 | [96–278],[226–456] | 2836 | [33–230],[286–462] | 2917 | [33–296] | 2952 | [102–476],[259–525] |
| 2802 | [96–278],[226–456] | 2837 | [100–276] | 2918 | [34–201] | 2953 | [34–201] |
| 2803 | [95–277],[225–431] | 2838 | [109–261],[161–490],[336–515] | 2919 | [94–498] | 2954 | [190–486] |
| 2804 | [95–277],[225–458] | | | 2966 | [76–384] | 2955 | [3–215] |
| 2805 | [94–276],[224–472] | 2839 | [11–205],[307–468] | 2967 | [34–216],[227–385] | 2956 | [34–201] |
| 2806 | [89–268] | 2840 | [130–333] | 2968 | [116–286] | 2957 | [34–201] |
| 2807 | [276–434] | 2841 | [21–182] | 2969 | [66–305],[353–520] | 2958 | [121–447],[203–433] |
| 2808 | [227–433] | 2842 | [85–267] | 2970 | [160–390],[260–481] | 2959 | [380–532] |
| 2809 | [187–495] | 2843 | [216–395] | 2971 | [310–462] | 2960 | [34–201] |
| 2810 | [293–487] | 2844 | [111–335],[272–499] | 2972 | [181–369] | 2961 | [124–288] |
| 2811 | [313–486] | 2845 | [126–467],[193–504] | 2973 | [116–280] | 2962 | [143–355] |
| 2812 | [171–458],[176–325] | 2846 | [92–433],[159–470] | 2974 | [48–347] | 2963 | [94–465] |
| 2813 | [235–399] | 2847 | [95–436],[162–473] | 2975 | [304–549] | 2964 | [80–286] |
| 2814 | [30–392] | 2848 | [92–433],[159–470] | 2976 | [187–399] | 2965 | [273–443] |
| 2815 | [69–233] | 2849 | [16–180] | 2977 | [192–353],[196–369] | 3012 | [120–401] |
| 2816 | [364–546] | 2850 | [12–161],[127–282] | 2978 | [297–494] | 3013 | [135–293],[212–361] |
| 2817 | [6–158] | 2851 | [258–416] | 2979 | [20–463],[247–489] | 3014 | [46–432] |
| 2818 | [34–201] | 2852 | [78–233],[344–511] | 2980 | [35–331],[172–483],[213–419] | 3015 | [3–215] |
| 2819 | [142–396] | 2853 | [84–275] | | | 3016 | [277–495] |
| 2820 | [57–224],[227–454],[743–922] | 2854 | [76–324],[221–403] | 2981 | [44–196],[247–513] | 3017 | [182–445] |
| | | 2855 | [259–465] | 2982 | [60–434] | 3018 | [354–509] |
| 2821 | [167–361] | 2856 | [88–513] | 2983 | [75–227] | 3019 | [129–281] |
| 2822 | [114–275] | 2857 | [271–426] | 2984 | [12–260],[202–369] | 3020 | [73–249],[146–433] |
| 2823 | [126–377],[230–502] | 2858 | [7–198],[179–343] | 2985 | [575–769] | 3021 | [161–439] |
| 2824 | [144–374] | 2859 | [119–334] | 2986 | [63–467],[205–393] | 3022 | [82–393] |
| 2825 | [14–190],[195–464] | 2860 | [219–398] | 2987 | [115–288] | 3023 | [200–391] |
| 2826 | [94–270] | 2861 | [225–455] | 2988 | [34–201] | 3024 | [134–469] |
| 2827 | [199–456] | 2862 | [161–412] | 2989 | [195–350] | 3025 | [114–491],[388–582] |
| 2828 | [111–323] | 2863 | [121–273],[243–575] | 2990 | [244–411] | 3026 | [20–217],[190–354] |
| 2875 | [93–257],[242–493] | 2864 | [173–322] | 2991 | [180–515] | 3027 | [13–162],[513–713] |
| 2876 | [110–463],[147–326] | 2865 | [4–162],[303.455] | 2992 | [195–428] | 3028 | [57–218] |
| 2877 | [380–595] | 2866 | [238–405] | 2993 | [202–432] | 3029 | [114–464] |
| 2878 | [153–359] | 2867 | [160–333] | 2994 | [8–181],[295–477] | 3030 | [123–356],[169–360] |
| 2879 | [177–488] | 2868 | [468–617] | 2995 | [202–459] | 3031 | [85–234] |
| 2880 | [268–474] | 2869 | [49–201] | 2996 | [39–371] | 3032 | [248–418] |
| 2881 | [23–253],[133–552],[267–491] | 2870 | [189–455] | 2997 | [48–332],[178–414] | 3033 | [144–368] |
| | | 2871 | [189–455] | 2998 | [120–431],[253–504] | 3034 | [295–477] |
| 2882 | [243–434] | 2872 | [177–368] | 2999 | [104–271] | 3035 | [219–446] |
| 2883 | [85–258] | 2873 | [180–338] | 3000 | [265–441],[291–467] | 3036 | [56–340],[111–374] |
| 2884 | [347–556] | 2874 | [93–257],[242–430],[310–486] | 3001 | [110–271] | 3037 | [67–366],[261–461] |
| 2885 | [169–381],[311–460] | | | 3002 | [248–439] | 3038 | [395–553] |
| 2886 | [63–242] | 2920 | [38–208] | 3003 | [336–515] | 3039 | [226–432] |
| 2887 | [97–297] | 2921 | [62–268] | 3004 | [85–300],[191–373] | 3040 | [204–365] |
| 2888 | [173–484] | 2922 | [79–402],[173–358] | 3005 | [141–536] | 3041 | [8–160],[180–389],[223–420] |
| 2889 | [202–432] | 2923 | [224–472] | 3006 | [203–361] | | |
| 2890 | [37–348] | 2924 | [326–490] | 3007 | [127–453] | 3042 | [209–475] |
| 2891 | [48–455],[274–486] | 2925 | [114–359],[136–285] | 3008 | [127–297],[200–457] | 3043 | [90–278] |
| 2892 | [68–406] | 2926 | [88–276] | 3009 | [114–284],[187–441] | 3044 | [141–326] |
| 2893 | [14–328],[58–393] | 2927 | [270–431] | 3010 | [112–267],[53–413],[179–337] | 3045 | [88–273],[312–518] |
| 2894 | [22–204] | 2928 | [213–422] | | | 3046 | [75–236] |
| 2895 | [69–326] | 2929 | [278–454] | 3011 | [25–462],[191–358],[222–392],[492–698] | 3047 | [136–354],[245–508] |
| 2896 | [73–255],[155–325],[310–513],[437–586] | 2930 | [207–461] | | | 3048 | [177–359] |
| | | 2931 | [25–210] | 3057 | [261–446] | 3049 | [38–262],[87–308] |
| 2897 | [10–216] | 2932 | [341–490] | 3058 | [140–403] | 3050 | [183–455] |
| 2898 | [7–357],[41–205] | 2933 | [117–305] | 3059 | [229–444],[320–481] | 3051 | [183–461] |
| 2899 | [81–353] | 2934 | [180–437] | 3060 | [188–391] | 3052 | [104–562] |
| 2900 | [40–456],[203–484] | 2935 | [123–407] | 3061 | [135–341] | 3053 | [147–782] |
| 2901 | [34–201] | 2936 | [101–394] | 3062 | [149–355] | 3054 | [257–418] |
| 2902 | [99–704],[493–651] | 2937 | [25–252],[312–500] | 3063 | [116–286] | 3055 | [53–367] |
| 2903 | [34–201] | 2938 | [53–676] | 3064 | [93–431] | 3056 | [118–273] |
| 2904 | [199–354] | 2939 | [44–262] | 3065 | [20–382] | 3103 | [337–486] |
| 2905 | [139–303] | 2940 | [25–210] | 3066 | [171–380] | 3104 | [147–356] |
| 2906 | [108–374],[169–387] | 2941 | [81–359] | 3067 | [222–392] | 3105 | [231–410] |
| 2907 | [175–507] | 2942 | [11–268] | 3068 | [23–259] | 3106 | [193–402] |

TABLE I-continued (Positions of all ORFs)

| Seq Id No. | Positions of Open Reading Frame(s) | Seq Id No. | Positions of Open Reading Frame(s) | Seq Id No. | Positions of Open Reading Frame(s) | Seq Id No. | Positions of Open Reading Frame(s) |
|---|---|---|---|---|---|---|---|
| 3069 | [112–282] | 3107 | [207–368] | 3187 | [50–199] | 3224 | [3–164] |
| 3070 | [121–417],[230–484] | 3108 | [137–286] | 3188 | [60–233],[154–444] | 3225 | [120–281] |
| 3071 | [69–422] | 3109 | [201–512] | 3189 | [22–171] | 3226 | [41–217],[217–462] |
| 3072 | [16–240],[295–450] | 3110 | [91–294],[194–379] | 3190 | [102–263] | 3227 | [100–480] |
| 3073 | [81–392],[97–306] | 3111 | [261–455] | 3191 | [127–288] | 3228 | [198–437] |
| 3074 | [94–345] | 3112 | [36–287] | 3192 | [183–404] | 3229 | [44–244] |
| 3075 | [240–410] | 3113 | [60–293] | 3193 | [370–558],[521–718] | 3230 | [27–536],[184–384] |
| 3076 | [34–204],[231–425] | 3114 | [68–265] | 3194 | [132–284],[289–456] | 3231 | [27–389],[184–468] |
| 3077 | [109–285] | 3115 | [182–346] | 3241 | [62–292],[181–570], | 3232 | [85–252] |
| 3078 | [57–299] | 3116 | [160–441] |  | [408–653] | 3233 | [214–366] |
| 3079 | [22–231] | 3117 | [83–496],[228–452] | 3242 | [266–475],[375–524] | 3234 | [109–360],[296–463] |
| 3080 | [122–286],[279–428] | 3118 | [313–480] | 3243 | [120–326],[160–444] | 3235 | [32–295],[314–478] |
| 3081 | [105–299] | 3119 | [34–201] | 3244 | [63–248] | 3236 | [115–411] |
| 3082 | [56–277] | 3120 | [39–188],[98–466] | 3245 | [389–553] | 3237 | [115–342] |
| 3083 | [249–434] | 3121 | [79–501] | 3246 | [150–353] | 3238 | [115–474] |
| 3084 | [214–453] | 3122 | [79–501] | 3247 | [157–360] | 3239 | [62–292],[181–609], |
| 3085 | [61–255] | 3123 | [293–460] | 3248 | [217–381] |  | [405–590] |
| 3086 | [25–231] | 3124 | [69–296],[128–478], | 3249 | [212–370] | 3240 | [187–402] |
| 3087 | [144–320] |  | [315–479] | 3250 | [90–269] | 3287 | [16–282] |
| 3088 | [144–320] | 3125 | [69–296],[128–490], | 3251 | [90–314] | 3288 | [153–410] |
| 3089 | [144–320] |  | [315–491] | 3252 | [90–302],[184–483] | 3289 | [34–462],[120–344] |
| 3090 | [144–320] | 3126 | [12–203],[360–707] | 3253 | [90–269],[184–484] | 3290 | [34–186],[176–403] |
| 3091 | [144–320] | 3127 | [269–478],[333–503] | 3254 | [91–408] | 3291 | [34–186] |
| 3092 | [144–320] | 3128 | [165–407],[310–477] | 3255 | [22–339] | 3292 | [34–186],[176–403] |
| 3093 | [43–240] | 3129 | [72–443],[112–342] | 3256 | [31–252] | 3293 | [171–416] |
| 3094 | [253–411] | 3130 | [2–205] | 3257 | [31–189],[125–349] | 3294 | [138–296] |
| 3095 | [213–410] | 3131 | [135–299] | 3258 | [284–523],[303–533] | 3295 | [155–421] |
| 3096 | [17–484] | 3132 | [57–230] | 3259 | [85–396],[113–316] | 3296 | [67–306],[149–301] |
| 3097 | [208–423] | 3133 | [90–281],[300–509] | 3260 | [90–248] | 3297 | [33–329] |
| 3098 | [184–360] | 3134 | [84–275],[294–449] | 3261 | [10–213],[278–460] | 3298 | [26–331],[72–341] |
| 3099 | [159–431] | 3135 | [53–244],[263–418] | 3262 | [36–305] | 3299 | [50–199] |
| 3100 | [135–362] | 3136 | [84–281],[300–455] | 3263 | [131–466] | 3300 | [211–426] |
| 3101 | [209–373] | 3137 | [7–303],[95–250] | 3264 | [125–427],[312–461] | 3301 | [334–519] |
| 3102 | [96–425] | 3138 | [253–408] | 3265 | [146–334] | 3302 | [83–412] |
| 3149 | [292–558] | 3139 | [6–578] | 3266 | [164–346],[273–509] | 3303 | [204–362] |
| 3150 | [102–521] | 3140 | [141–377] | 3267 | [76–333] | 3304 | [142–300],[194–385] |
| 3151 | [99–476] | 3141 | [171–515] | 3268 | [183–383] | 3305 | [137–358] |
| 3152 | [26–277],[225–482] | 3142 | [92–253] | 3269 | [158–310] | 3306 | [152–430] |
| 3153 | [150–329] | 3143 | [185–346] | 3270 | [54–248],[187–414] | 3307 | [103–354] |
| 3154 | [142–417] | 3144 | [66–299] | 3271 | [33–239] | 3308 | [24–464] |
| 3155 | [202–474] | 3145 | [410–604] | 3272 | [67–285] | 3309 | [13–243] |
| 3156 | [160–381],[419–589] | 3146 | [85–291] | 3273 | [27–218] | 3310 | [62–268] |
| 3157 | [53–337] | 3147 | [205–486] | 3274 | [147–335] | 3311 | [101–286],[232–444] |
| 3158 | [36–251] | 3148 | [150–302] | 3275 | [146–433],[288–458] | 3312 | [362–562] |
| 3159 | [53–337] | 3195 | [63–389] | 3276 | [123–404],[265–474] | 3313 | [302–499] |
| 3160 | [122–382],[258–494] | 3196 | [204–377] | 3277 | [32–223],[105–473] | 3314 | [26–190],[298–471] |
| 3161 | [53–337] | 3197 | [5–226],[339–494] | 3278 | [268–420] | 3315 | [72–302] |
| 3162 | [165–341] | 3198 | [119–307] | 3279 | [284–448] | 3316 | [183–461] |
| 3163 | [9–263],[64–282] | 3199 | [50–226] | 3280 | [53–208] | 3317 | [172–351] |
| 3164 | [196–423],[233–445] | 3200 | [110–313] | 3281 | [128–376] | 3318 | [30–248] |
| 3165 | [167–490] | 3201 | [28–198] | 3282 | [13–255],[108–431] | 3319 | [312–530] |
| 3166 | [58–264],[254–418] | 3202 | [161–337] | 3283 | [245–421] | 3320 | [4–180] |
| 3167 | [17–202] | 3203 | [75–380] | 3284 | [45–197] | 3321 | [307–525] |
| 3168 | [117–299],[299–469] | 3204 | [101–415] | 3285 | [18–260],[272–466] | 3322 | [199–360] |
| 3169 | [101–265] | 3205 | [16–403] | 3286 | [83–250] | 3323 | [13–252],[216–449], |
| 3170 | [224–388] | 3206 | [154–396] | 3333 | [147–296] |  | [316–477] |
| 3171 | [124–321],[255–410] | 3207 | [129–320] | 3334 | [33–209],[104–316] | 3324 | [19–168] |
| 3172 | [557–736] | 3208 | [178–351] | 3335 | [268–429] | 3325 | [106–393] |
| 3173 | [128–322] | 3209 | [173–421] | 3336 | [95–385],[153–392] | 3326 | [27–242] |
| 3174 | [63–356] | 3210 | [70–297] | 3337 | [100–438] | 3327 | [259–480] |
| 3175 | [93–266],[235–414] | 3211 | [102–500],[266–493] | 3338 | [16–255] | 3328 | [249–401] |
| 3176 | [70–300] | 3212 | [4–153],[149–322] | 3339 | [75–239] | 3329 | [50–208],[217–417] |
| 3177 | [279–434] | 3213 | [147–335] | 3340 | [5–157] | 3330 | [50–208],[217–471] |
| 3178 | [30–422] | 3214 | [100–294] | 3341 | [51–476] | 3331 | [199–420] |
| 3179 | [161–364] | 3215 | [69–359] | 3342 | [3–185] | 3332 | [124–354],[236–391] |
| 3180 | [51–233],[170–373] | 3216 | [100–294] | 3343 | [120–464] | 3379 | [13–282],[138–344] |
| 3181 | [112–282] | 3217 | [285–521] | 3344 | [115–402] | 3380 | [147–347] |
| 3182 | [52–282] | 3218 | [36–491] | 3345 | [154–402] | 3381 | [172–462] |
| 3183 | [12–266] | 3219 | [89–358] | 3346 | [184–336],[346–507], | 3382 | [302–577] |
| 3184 | [75–260] | 3220 | [100–294] |  | [351–503] | 3383 | [132–338] |
| 3185 | [151–414] | 3221 | [119–460] | 3347 | [184–348] | 3384 | [48–461] |
| 3186 | [35–193],[135–407], | 3222 | [29–211] | 3348 | [74–247] | 3385 | [58–246],[156–419] |
|  | [274–537] | 3223 | [160–492] | 3349 | [357–509] | 3386 | [110–277] |

TABLE I-continued

(Positions of all ORFs)

| Seq Id No. | Positions of Open Reading Frame(s) | Seq Id No. | Positions of Open Reading Frame(s) | Seq Id No. | Positions of Open Reading Frame(s) | Seq Id No. | Positions of Open Reading Frame(s) |
|---|---|---|---|---|---|---|---|
| 3350 | [165–317] | 3387 | [151–318] | 3469 | [191–436] | 3504 | [54–257] |
| 3351 | [127–444] | 3388 | [339–542] | 3470 | [152–451] | 3505 | [15–218],[241–408] |
| 3352 | [97–444] | 3389 | [22–345],[374–565] | 3517 | [21–215] | 3506 | [1–153] |
| 3353 | [217–450] | 3390 | [110–277] | 3518 | [452–727],[462–665] | 3507 | [6–206] |
| 3354 | [291–491] | 3391 | [338–487] | 3519 | [364–630] | 3508 | [62–250] |
| 3355 | [291–491] | 3392 | [64–393] | 3520 | [240–434] | 3509 | [89–313] |
| 3356 | [141–344] | 3393 | [37–360] | 3521 | [291–494] | 3510 | [87–242] |
| 3357 | [211–384] | 3394 | [176–355] | 3522 | [93–332] | 3511 | [48–272] |
| 3358 | [152–430] | 3395 | [42–452],[244–426] | 3523 | [134–382] | 3512 | [204–476] |
| 3359 | [3–176],[166–411] | 3396 | [66–311] | 3524 | [43–348] | 3513 | [6–209],[307–459] |
| 3360 | [87–344] | 3397 | [161–373] | 3525 | [150–356] | 3514 | [46–348] |
| 3361 | [72–254] | 3398 | [222–392] | 3526 | [200–370] | 3515 | [17–214] |
| 3362 | [91–315] | 3399 | [75–236] | 3527 | [195–389],[295–579] | 3516 | [34–207] |
| 3363 | [91–315] | 3400 | [82–246],[86–256] | 3528 | [147–482] | 3563 | [69–302] |
| 3364 | [91–315] | 3401 | [63–215],[118–402] | 3529 | [214–435] | 3564 | [136–294] |
| 3365 | [19–243] | 3402 | [138–326] | 3530 | [105–254] | 3565 | [101–370] |
| 3366 | [60–284],[337–516] | 3403 | [6–161],[211–366] | 3531 | [200–376] | 3566 | [101–370] |
| 3367 | [26–250] | 3404 | [1–234] | 3532 | [4–171],[149–496],[313–510] | 3567 | [172–360] |
| 3368 | [202–405],[408–566] | 3405 | [196–354],[281–508],[354–506] | 3533 | [56–280],[99–344] | 3568 | [316–492] |
| 3369 | [237–440] | | | | | 3569 | [378–554] |
| 3370 | [172–399],[218–367] | 3406 | [222–572],[505–726] | 3534 | [138–347] | 3570 | [7–171] |
| 3371 | [176–475],[222–371] | 3407 | [22–210],[290–457] | 3535 | [56–244] | 3571 | [341–517] |
| 3372 | [173–337],[219–383] | 3408 | [10–348] | 3536 | [55–234] | 3572 | [338–514] |
| 3373 | [201–365],[247–414] | 3409 | [151–423] | 3537 | [153–326] | 3573 | [131–310],[267–425] |
| 3374 | [237–440] | 3410 | [14–184] | 3538 | [76–321],[282–461] | 3574 | [5–244] |
| 3375 | [203–511],[249–398] | 3411 | [55–261] | 3539 | [57–236],[211–390] | 3575 | [185–361] |
| 3376 | [201–545],[247–396] | 3412 | [113–460] | 3540 | [237–485] | 3576 | [34–207] |
| 3377 | [200–364],[246–422] | 3413 | [39–191],[94–285] | 3541 | [128–304] | 3577 | [81–269] |
| 3378 | [122–496],[168–317] | 3414 | [71–223] | 3542 | [240–437] | 3578 | [255–404] |
| 3425 | [96–425] | 3415 | [157–342],[215–430] | 3543 | [202–405] | 3579 | [16–195],[62–307] |
| 3426 | [98–340] | 3416 | [19–171] | 3544 | [184–366] | 3580 | [109–285] |
| 3427 | [98–442] | 3417 | [1–507],[98–295] | 3545 | [34–207] | 3581 | [91–426],[161–331] |
| 3428 | [111–341] | 3418 | [50–277] | 3546 | [105–398] | 3582 | [318–476] |
| 3429 | [201–350] | 3419 | [117–371] | 3547 | [37–402] | 3583 | [91–315] |
| 3430 | [618–782] | 3420 | [125–358] | 3548 | [74–433] | 3584 | [217–510],[293–451] |
| 3431 | [13–285] | 3421 | [174–458] | 3549 | [1–156] | 3585 | [14–304] |
| 3432 | [22–294] | 3422 | [98–571] | 3550 | [59–247],[207–401] | 3586 | [148–396],[165–389] |
| 3433 | [152–424] | 3423 | [98–421] | 3551 | [89–250],[186–428] | 3587 | [28–300] |
| 3434 | [263–442] | 3424 | [43–198],[183–386] | 3552 | [135–344] | 3588 | [170–337],[334–558] |
| 3435 | [218–460],[376–540] | 3471 | [37–405],[344–511] | 3553 | [21–494] | 3589 | [348–614],[410–622] |
| 3436 | [284–469] | 3472 | [156–347] | 3554 | [34–207] | 3590 | [4–177] |
| 3437 | [63–284] | 3473 | [78–242],[287–436] | 3555 | [185–448] | 3591 | [97–255],[255–458] |
| 3438 | [284–526] | 3474 | [44–256] | 3556 | [185–448] | 3592 | [72–314],[116–280],[296–532],[348–506] |
| 3439 | [1–222] | 3475 | [13–198],[179–328] | 3557 | [34–201] | | |
| 3440 | [155–640] | 3476 | [27–266] | 3558 | [16–303] | 3593 | [90–464] |
| 3441 | [34–207] | 3477 | [37–276] | 3559 | [287–460] | 3594 | [84–404] |
| 3442 | [16–285] | 3478 | [239–475] | 3560 | [159–344] | 3595 | [255–461] |
| 3443 | [89–319],[280–504] | 3479 | [173–334] | 3561 | [30–347],[352–540] | 3596 | [175–342] |
| 3444 | [158–322] | 3480 | [253–414] | 3562 | [40–204] | 3597 | [108–539] |
| 3445 | [70–261] | 3481 | [7–207] | 3608 | [11–220],[174–353] | 3598 | [130–327],[135–419],[512–775] |
| 3446 | [76–288] | 3482 | [183–545] | 3609 | [326–478],[418–627] | | |
| 3447 | [79–360],[171–326] | 3483 | [137–337] | 3610 | [242–475] | 3599 | [265–924],[500–658] |
| 3448 | [73–402],[88–376] | 3484 | [152–370] | 3611 | [14–181] | 3600 | [80–292],[316–468] |
| 3449 | [247–474] | 3485 | [117–290] | 3612 | [159–566] | 3601 | [73–237] |
| 3450 | [102–395] | 3486 | [89–307] | 3613 | [129–344] | 3602 | [95–265] |
| 3451 | [31–231] | 3487 | [89–553] | 3614 | [93–350] | 3603 | [196–402] |
| 3452 | [13–180] | 3488 | [89–307] | 3615 | [137–406] | 3604 | [58–255] |
| 3453 | [13–180] | 3489 | [256–411] | 3616 | [120–335],[320–469] | 3605 | [50–466] |
| 3454 | [89–244] | 3490 | [107–454] | 3617 | [189–353] | 3606 | [75–443] |
| 3455 | [175–498],[350–538] | 3491 | [120–359],[338–493],[399–560] | 3618 | [123–575] | 3607 | [9–434],[178–486] |
| 3456 | [248–406] | | | 3619 | [33–296] | 3654 | [324–554] |
| 3457 | [248–553] | 3492 | [119–358],[337–492] | 3620 | [48–416] | 3655 | [30–347],[209–445] |
| 3458 | [313–471] | 3493 | [205–411] | 3621 | [82–300] | 3656 | [46–348] |
| 3459 | [114–353] | 3494 | [204–419] | 3622 | [133–282] | 3657 | [46–348] |
| 3460 | [118–330] | 3495 | [213–521],[283–456] | 3623 | [28–366] | 3658 | [145–441] |
| 3461 | [195–398],[232–462] | 3496 | [109–264] | 3624 | [117–476] | 3659 | [180–464] |
| 3462 | [82–252] | 3497 | [147–359],[160–327] | 3625 | [37–393] | 3660 | [179–385] |
| 3463 | [300–461] | 3498 | [186–515] | 3626 | [51–239] | 3661 | [180–410] |
| 3464 | [112–303] | 3499 | [56–328],[162–320] | 3627 | [36–452] | 3662 | [76–252] |
| 3465 | [43–342] | 3500 | [366–593] | 3628 | [1–486] | 3663 | [295–510],[317–532],[674–865],[711–1043] |
| 3466 | [530–742] | 3501 | [69–239],[205–510] | 3629 | [94–309],[524–835] | | |
| 3467 | [10–189] | 3502 | [112–276] | 3630 | [121–270],[161–355] | 3664 | [153–416] |
| 3468 | [303–503] | 3503 | [119–277] | 3631 | [123–482] | 3665 | [177–380] |

TABLE I-continued (Positions of all ORFs)

| Seq Id No. | Positions of Open Reading Frame(s) | Seq Id No. | Positions of Open Reading Frame(s) |
|---|---|---|---|
| 3632 | [29–271],[192–476] | 3666 | [152–415] |
| 3633 | [208–402] | 3667 | [177–383] |
| 3634 | [4–156],[48–209] | 3668 | [70–333] |
| 3635 | [82–231],[234–404] | 3669 | [177–380] |
| 3636 | [110–292],[192–389] | 3670 | [77–364] |
| 3637 | [21–257],[227–466] | 3671 | [252–401] |
| 3638 | [112–390] | 3672 | [145–432] |
| 3639 | [215–427] | 3673 | [252–401] |
| 3640 | [16–291] | 3674 | [30–242],[166–318] |
| 3641 | [19–294] | 3675 | [252–401] |
| 3642 | [16–291] | 3676 | [96–299] |
| 3643 | [174–365] | 3677 | [65–340] |
| 3644 | [250–429] | 3678 | [188–343],[219–455] |
| 3645 | [37–207] | 3679 | [72–287] |
| 3646 | [4–153] | 3680 | [387–644] |
| 3647 | [246–482],[250–420] | 3681 | [61–354] |
| 3648 | [53–253] | 3682 | [2–181] |
| 3649 | [197–367] | 3683 | [73–306] |
| 3650 | [301–480] | 3684 | [261–479] |
| 3651 | [267–488] | 3685 | [34–183],[228–425] |
| 3652 | [150–398],[319–522] | 3686 | [44–232] |
| 3653 | [7–216] | 3687 | [95–250] |
| 3699 | [242–640] | 3688 | [130–318] |
| 3700 | [60–212] | 3689 | [369–521] |
| 3701 | [95–391] | 3690 | [62–493],[192–350] |
| 3702 | [131–307] | 3691 | [42–203],[301–483] |
| 3703 | [92–331] | 3692 | [70–276] |
| 3704 | [92–433] | 3693 | [49–213],[117–458] |
| 3705 | [31–204],[110–277] | 3694 | [49–234],[117–314] |
| 3706 | [142–492] | 3695 | [132–284] |
| 3707 | [34–207] | 3696 | [63–260] |
| 3708 | [76–396] | 3697 | [110–328] |
| 3709 | [76–396] | 3698 | [106–366] |
| 3710 | [99–326] | 3745 | [51–233],[260–427] |
| 3711 | [161–313] | 3746 | [84–371] |
| 3712 | [141–317] | 3747 | [54–350],[160–477] |
| 3713 | [176–352] | 3748 | [110–397] |
| 3714 | [139–366] | 3749 | [96–341],[223–381] |
| 3715 | [148–435] | 3750 | [25–348] |
| 3716 | [40–213],[386–703] | 3751 | [25–348] |
| 3717 | [113–430] | 3752 | [141–353] |
| 3718 | [86–403] | 3753 | [173–382] |
| 3719 | [48–503] | 3754 | [211–414],[236–394] |
| 3720 | [48–341],[331–627] | 3755 | [126–392] |
| 3721 | [194–400] | 3756 | [136–366] |
| 3722 | [122–451] | 3757 | [31–279] |
| 3723 | [90–305],[151–426] | 3758 | [81–278],[152–457] |
| 3724 | [174–383],[187–429] | 3759 | [165–485] |
| 3725 | [95–310] | 3760 | [105–281] |
| 3726 | [31–483],[369–521] | 3761 | [225–401] |
| 3727 | [360–557],[376–579] | 3762 | [144–329] |
| 3728 | [141–353] | 3763 | [116–445] |
| 3729 | [88–318] | 3764 | [124–453] |
| 3730 | [6–185],[161–394] | 3765 | [7–411],[338–502] |
| 3731 | [56–388],[300–449] | 3766 | [249–434] |
| 3732 | [111–440],[352–501] | 3767 | [165–395] |
| 3733 | [128–394] | 3768 | [141–353] |
| 3734 | [105–332],[289–444] | 3769 | [169–348],[290–460] |
| 3735 | [94–366] | 3770 | [215–397] |
| 3736 | [141–353] | 3771 | [364–519] |
| 3737 | [139–294],[333–497] | 3772 | [88–237] |
| 3738 | [9–173] | 3773 | [2–166] |
| 3739 | [67–354] | 3774 | [390–542],[828–1022] |
| 3740 | [225–389] | 3775 | [134–313] |
| 3741 | [191–376] | 3776 | [28–642],[344–628],[703–852] |
| 3742 | [345–530] | | |
| 3743 | [13–579],[21–203] | 3777 | [159–362] |
| 3744 | [54–236],[263–484] | 3778 | [249–428] |
| 3791 | [155–316] | 3779 | [96–248],[137–361] |
| 3792 | [163–369] | 3780 | [96–248],[137–361] |
| 3793 | [122–328] | 3781 | [110–466] |
| 3794 | [258–452] | 3782 | [12–329],[59–466] |
| 3795 | [108–314] | 3783 | [133–300] |
| 3796 | [102–254],[143–424],[283–432] | 3784 | [123–323] |
| 3797 | [77–283],[317–472] | 3785 | [200–382] |
| 3798 | [77–283] | 3786 | [175–396] |
| 3799 | [107–313] | 3787 | [71–502] |
| 3800 | [96–248],[137–301] | 3788 | [8–175],[294–491] |
| 3801 | [92–448] | 3789 | [18–266] |
| 3802 | [92–448] | 3790 | [99–281] |
| 3803 | [116–577],[553–906],[788–985] | 3837 | [92–484],[351–548] |
| | | 3838 | [169–429] |
| 3804 | [142–354] | 3839 | [3–224],[220–372] |
| 3805 | [34–207] | 3840 | [3–224],[220–372] |
| 3806 | [249–410] | 3841 | [165–389] |
| 3807 | [146–364] | 3842 | [143–370] |
| 3808 | [208–366] | 3843 | [100–303] |
| 3809 | [97–516] | 3844 | [34–201] |
| 3810 | [35–490] | 3845 | [5–181] |
| 3811 | [162–512] | 3846 | [139–300],[318–491],[376–591],[533–760] |
| 3812 | [87–242] | 3847 | [81–323] |
| 3813 | [11–361] | 3848 | [132–317],[317–469] |
| 3814 | [17–445] | 3849 | [130–402] |
| 3815 | [11–190] | 3850 | [129–401] |
| 3816 | [138–344] | 3851 | [129–401] |
| 3817 | [93–350] | 3852 | [130–402] |
| 3818 | [165–395] | 3853 | [130–417] |
| 3819 | [181–438],[365–514] | 3854 | [129–401] |
| 3820 | [181–438] | 3855 | [130–417] |
| 3821 | [96–260] | 3856 | [131–403] |
| 3822 | [350–508] | 3857 | [131–403] |
| 3823 | [140–352] | 3858 | [131–403] |
| 3824 | [240–389] | 3859 | [129–416] |
| 3825 | [33–338],[317–487] | 3860 | [134–379] |
| 3826 | [68–355],[396–602] | 3861 | [99–356] |
| 3827 | [141–353] | 3862 | [140–421] |
| 3828 | [189–353] | 3863 | [17–166] |
| 3829 | [98–262] | 3864 | [11–220],[58–210] |
| 3830 | [220–378] | 3865 | [100–264],[269–430] |
| 3831 | [8–268] | 3866 | [273–428] |
| 3832 | [219–410] | 3867 | [115–348],[197–466] |
| 3833 | [195–413],[310–462] | 3868 | [281–445] |
| 3834 | [327–509] | 3869 | [240–440] |
| 3835 | [42–335] | 3870 | [274–492] |
| 3836 | [8–295] | 3871 | [12–170] |
| 3882 | [25–480],[293–484] | 3872 | [240–440] |
| 3883 | [24–197] | 3873 | [62–364],[273–458] |
| | | 3874 | [276–440],[443–613] |
| | | 3875 | [4–255] |
| | | 3876 | [18–176],[23–232] |
| | | 3877 | [147–359] |
| | | 3878 | [111–335] |
| | | 3879 | [114–335],[281–463] |
| | | 3880 | [2–217],[364–624] |
| | | 3881 | [82–249],[285–458] |

TABLE II (Tiling path)

| Seq Id No. | Positions of biological 5'ESTs |
|---|---|
| 26 | 1–494;1–380;1–434;1–494;1–557;1–455 |
| 28 | 1–467;3–323;3–487;3–470 |
| 30 | 1–368;1–135 |
| 32 | 1–177;45–519 |
| 33 | 1–186;1–471;1–479;40–259 |
| 36 | 1–454;247–358 |
| 38 | 1–294;4–486;4–486;4–491;12–107;12–107;12–107;12–107;12–107;12–105;12–105;12–107;12–107;12–107;12–107;12–107;12– |

TABLE II-continued (Tiling path)

| Seq Id No. | Positions of biological 5'ESTs |
|---|---|
|  | 105;12–104;12–105;12–107;12–107;12–105;12–107;12–107;12–107;12–107;12–105;12–105;12–105;12–105;12–107;12–105;12–107;12–94;12–94;12–105;12–105;12–105;12–105;12–105;12–107;12–94;12–107;12–105;12–423;12–105;12–105;12–107;12–107;12–105;12–105;12–105;12–105;12–105;12–107;12–107;12–107;12–105;12–105;32–490 |
| 39 | 1–541;1–424;177–678 |
| 40 | 1–249;1–177;1–176;1–176;19–144 |
| 42 | 1–224;1–320;1–241;1–425;1–241;1–392 |
| 43 | 1–483;1–489;1–450;1–477;2–376;2–445;2–478;2–434;2–424;2–495;2–442;2–498;2–234;2–460;2–404;2–484;2–64;2–473;2–419;2–414;2–277;3–449;3–438;12–442;12–412;39–512;39–348;39–502;39–481 |
| 44 | 1–234;1–296;1–339;1–245;1–294;1–326 |
| 45 | 1–324;38–528;38–504;46–496;46–499;47–502;47–511;47–511;47–485;47–464;48–433;48–490;48–544 |
| 48 | 1–535;3–479;30–435 |
| 49 | 1–413;7–432 |
| 51 | 1–293;1–373;1–464;1–465 |
| 54 | 1–491;4–505 |
| 55 | 1–546;1–453;1–441;1–446;1–421 |
| 56 | 1–503;1–485;1–276;1–367;1–507 |
| 63 | 1–343;1–145;1–343 |
| 64 | 1–225;1–277;1–277 |
| 65 | 1–172;1–174;1–172;1–174;1–174;1–170;1–171;1–174;1–174;1–172;1–174;1–164;1–174;1–174;1–174;1–174 |
| 67 | 1–478;1–476 |
| 68 | 1–323;1–323 |
| 70 | 1–473;1–406 |
| 71 | 1–329;1–329;1–329 |
| 72 | 1–488;3–476;3–453;3–479;3–426;3–356;3–373;4–445;4–461 |
| 74 | 1–415;1–417;1–392 |
| 76 | 1–360;1–486 |
| 78 | 1–429;6–461;12–341;12–395;13–432;13–793;15–458;18–436;18–73;18–313;18–459;18–428 |
| 82 | 1–92;15–570;15–385;15–418;15–424 |
| 83 | 1–203;1–468;1–442;1–105 |
| 87 | 1–440;130–616;194–674 |
| 88 | 1–78;1–402 |
| 90 | 1–135;1–474;1–210;1–428;1–443 |
| 91 | 1–388;46–118;49–284;51–464;56–402;56–397;56–411;71–217;71–470;71–390;71–463;74–463;77–415;84–470;85–470;85–425;85–399;85–565;85–235;85–463;85–401;85–291;85–409;85–303;85–392;85–416;85–569;86–399;86–405;90–460;95–236 |
| 92 | 1–479;1–399;3–499;3–484;3–502;3–277;3–381;32–482;75–575;75–568;75–551;75–571;75–523;75–570;76–569;94–368;128–586;137–553 |
| 94 | 1–452;1–350 |
| 95 | 1–323;1–326 |
| 97 | 1–462;1–480;59–480;59–475;59–431;59–465;59–576;59–517;59–576;59–557;59–483;59–536;59–498;60–672 |
| 99 | 1–459;1–482;1–466;3–418 |
| 100 | 1–479;1–498 |
| 101 | 1–480;1–214;1–504 |
| 103 | 1–351;1–192 |
| 108 | 1–274;1–453 |
| 109 | 1–500;1–488 |
| 110 | 1–570;19–481 |
| 111 | 1–476;79–570;106–584;06–520;106–233;106–565;106–570;106–570;106–550;106–513;106–207;106–526 |
| 112 | 1–225;1–417;1–370 |

TABLE II-continued (Tiling path)

| Seq Id No. | Positions of biological 5'ESTs |
|---|---|
| 114 | 1–494;1–480;1–423;1–451;1–365;1–355;1–451;1–525;1–511 |
| 115 | 1–471;1–480;1–478 |
| 117 | 1–382;75–623 |
| 118 | 1–462;1–481;1–451;1–497;1–436;1–456 |
| 119 | 1–542;1–436;1–537;1–521;1–465 |
| 120 | 1–453;1–441;1–411;1–229 |
| 123 | 1–465;1–407 |
| 125 | 1–371;1–493;1–427 |
| 127 | 1–463;1–70 |
| 128 | 1–495;1–491;1–494;7–498;7–493;7–515;7–495;9–495;9–494;9–440;10–498;10–554;10–414;10–109;11–466 |
| 132 | 1–477;29–367 |
| 134 | 1–422;1–421;1–327;1–421;1–412 |
| 135 | 1–452;1–498;1–528;1–528;6–490;6–452;6–481;6–490;6–420;6–173;6–516;6–498;6–461;6–516;6–464;6–516;6–476;6–515;6–463;6–490;6–452;6–410;6–497;6–284;6–476;6–464;6–464;6–496;6–464;6–452;6–462;6–486;6–531;6–461;6–515;6–492;6–507;6–515;6–516;6–531;6–549;6–548;6–486;6–533;6–450;6–452;6–464;6–507;6–530;6–531;6–462;6–516;6–516;6–498;6–507;6–451;6–481;6–484;6–488;6–478;6–452;6–481;6–488;6–569;6–532;7–485;7–488;7–534;7–461;7–403;7–487;7–530;7–484;7–419;7–450;8–437;10–528;10–477;10–485;11–420;15–452;15–360;22–539;22–537;22–490;23–498;23–481;23–539;26–451;31–524;31–528;31–464;31–527;31–552;31–452;31–538;31–481;31–507;31–535;31–464;31–516;31–360;31–569;34–553;34–530;34–539;34–570;34–516;34–532;34–537;34–516;34–553;34–528;34–464;35–516;35–534;35–464;35–255;35–420;35–552;35–475;35–528;35–516;35–498;35–557;35–498;35–516;35–452;35–516;35–498;35–534;35–516;35–548;35–568;35–516;36–451;38–528;38–498;39–516;44–314;56–528;56–547;56–481;56–561;56–515;56–548;56–384;56–563;56–452;56–452;56–564;56–549;56–539;56–552;56–536;56–552 |
| 136 | 1–416;1–101 |
| 137 | 1–495;1–466;1–461;1–473;1–390;1–407;1–346;1–502 |
| 138 | 1–332;1–495 |
| 139 | 1–444;1–434;1–441;1–410;1–443;1–387;1–438;1–467;1–468;1–437;283–646 |
| 140 | 1–497;1–459;1–481;1–490;1–462;1–492;1–252;1–432;19–136 |
| 144 | 1–446;1–416;1–385;1–524 |
| 146 | 1–448;40–525 |
| 149 | 1–123;9–501 |
| 150 | 1–85;1–320 |
| 151 | 1–439;1–370;25–512;25–465 |
| 152 | 1–487;1–497;1–495;1–272 |
| 153 | 1–501;27–458;27–456;27–458;27–458;27–458 |
| 155 | 1–497;1–376;1–455;1–542;1–443;1–434;1–486 |
| 158 | 1–421;1–515;1–587;1–544;1–283 |
| 159 | 1–481;1–130;1–466;1–490;1–481;1–498;1–423;1–453;1–489;1–480;1–499;1–486;1–495;1–466;1–488;1–473;1–199;1–485;1–492;1–497;1–485;1–488;1–498;1–290;1–533;1–500;1–502;1–495;1–464;1–498;1–514;1–499;1–473;1–507 |
| 160 | 1–509;73–470 |
| 162 | 1–314;236–721 |
| 165 | 1–594;1–466;29430;29–430;29–434;29–434;59–512 |
| 167 | 1–82;48–260;50–425;50–481 |

TABLE II-continued (Tiling path)

| Seq Id No. | Positions of biological 5'ESTs |
|---|---|
| 170 | 1–75;13–510;13–542 |
| 172 | 1–369;1–450;1–419 |
| 173 | 1–376;1–352;1–466;1–94;1–460;3–466;3–469;3–434;3–243;3–468;3–448;4–4 11;15–447;19–597;38–599;38–316;38–404;40–436;65–535;67–377 |
| 174 | 1–355;29–504;29–444;29–514;29–444;29–513 |
| 175 | 1–458;1–446;1–125;38–111 |
| 176 | 1–86;1–501;1–448;1–477;1–477;1–95;–185;1–462 |
| 178 | 1–362;–541;1–300 |
| 179 | 1–303;1–283;1–303;1–172;1–79;1–294;1–293 |
| 180 | 1–417;1–466;1–504;1–475;1–460 |
| 181 | 1–508;1–496;1–542;4–429;5–400;5–102;11–319;11–337;11–526;11–436;31–508;31–240;31–353;31–427;31–353;31–499;31–526;31–444;31–434;31–441;31–461;31–538;31–526;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–132;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–135;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;35–136;3 |
| 182 | 1–488;1–403;1–314;1–456;1–472;1–509;1–464;1–488;1–461 |
| 185 | 1–470;138–562 |
| 186 | 1–435;1–485 |
| 187 | 1–419;1–521;8–486 |
| 190 | 1–516;1–374;1–408;1–552;1–516;1–501 |
| 199 | 1–451;43–492;45–523 |
| 200 | 1–275;1–433;1–456;1–448;1–450;1–180;1–459;1–292;1–460;1–409;1–452;1–393;1–119;1–292;1–400;1–245;1–334;233–567;250–732;256–696;280–729;280–745;280–703;280–733;280–774;280–611;281–432;281–625;281–453;284–694;284–651;285–651;289–643;290–561;290–554;290–736;291–457;297–643;303–719;303–703;303–691;308–749;308–651;308–576;308–633;308–651;308–475;308–802;314–637;317–636;349–829 |
| 203 | 1–451;1–412 |
| 204 | 1–481;1–505 |
| 206 | 1–372;1–483;1–525;210–701 |
| 207 | 1–105;60–130;87–499 |
| 209 | 1–365;1–452;4–422;4–458;4–169 |
| 212 | 1–452;1–452 |
| 217 | 1–442;8–443;8–443;8–395;8–443;8–96;8–461;8–311;8–431;8–387;8–395;8–443 |
| 220 | 1–480;17–420 |
| 224 | 1–410;19–491;19–492 |
| 225 | 1–564;1–486 |
| 227 | 1–480;1–499;1–422;1–435;1–299;1–416;1–367;1–523;1–356;1–355;1–358;1–508;1–309;1–524;1–484 |
| 228 | 1–283;1–269;1–283 |
| 229 | 1–450;1–430;1–440;1–439 |
| 231 | 1–308;70–351 |
| 232 | 1–454;24–482;28–454;28494;28–522;28–433;29–439;29–485;33–194;35–433;61–406 |
| 235 | 1–269;12–445;12–481;58–594;58–562 |
| 236 | 1–400;1–400 |
| 237 | 1–481;1–356 |
| 238 | 1–365;25–522;25–486;25–516;51–517;51–663;51–555 |
| 239 | 1–508;6–540;6–453;12–299 |
| 241 | 1–479;10–429 |
| 242 | 1–461;1–516 |
| 243 | 1–504;1–485;1–491;1–446;1–427;1–495;1–498;1–225;1–400;1–513;–523;1–457;1–556;1–262;1–498;1–403;1–453;1–558 |
| 248 | 1–436;1–473;1–464 |
| 249 | 1–313;1–322;1–322 |
| 252 | 1–425;1–578 |
| 253 | 1–466;1–477;19–512;19–502;19–397;414–672 |
| 254 | 1–442;1–479 |
| 259 | 1–168,1–433 |
| 260 | 1–64;10–467;10–332;17–256;17–459;17–:451 |
| 261 | 1–64;10–485;10–508;10–332;10–500;17–456;17–459;17–451 |
| 263 | 1–416;24–492;24–404;24–286;24–397;24–503;24–478 |
| 264 | 1–225;1–141;2–388;2–142;2–446;2–297;2–475;2–451;2–493;2–571;17–230;7–319 |
| 265 | 1–424;–478;1–171;1–176;1–497;1–383;1–382;1–438 |
| 266 | 1–472;1–552;1–468 |
| 268 | 1–104;1–467;1–467;1–141;1–529;88–588;88–573;88–287;88–545;88–599;88–471;88–579;88–598;88–578;88–554;88–531;88–558;112–477 |
| 271 | 1–477;219–739;219–705;219–628 |
| 272 | 1–135;1–135;2–475;17–418 |
| 273 | 1–264;1–449 |
| 275 | 1–65;29–416;29–374;29–542;29–367;29–420;29–434 |
| 277 | 1–417;1–333;1–349;1–407;1–41 7;1–484 |
| 279 | 1–426;1–511;1–321 |
| 280 | 1–91;1–494;2–82;22–84;23–499;47–100;51–456 |
| 283 | 9–219;9–337;12–276 |
| 284 | 1–473;1–431;1–476;1–298;1–199;1–466;1–474;1–489;1–449;1–420 |
| 285 | 1–426;1–466 |
| 287 | 1–367;32–609;32–525;32–477;32–466 |
| 292 | 1–333;1–281;1–671 |
| 293 | 1–453;32–512;32–484 |
| 297 | 1–496;1–430 |
| 298 | 1–492;1–57;1–369;1–375;1–483;1–363;1–424;1–458 |
| 300 | 1–246;1–248 |
| 301 | 1–455;1–489;1–370 |
| 302 | 1–483;1–195;19–413 |
| 303 | 1–345;6–446;28–496 |
| 304 | 1–491;1–495;1–473;1–361;1–312;1–391;1–469;1–473;1–497;1–541;3–455;3–454;3–365;3–477;3–397;6–572;6–428;6–477;44–497;44–539;44–537;44–501;44–469;44–547;44–456;44–521;44–518;44–473;44–553;45–566;45–558;45–302;45–454;83–571;83–577;83–578;83–560;83–590;83–549;83–566;112–622;112–571 |

TABLE II-continued

(Tiling path)

| Seq Id No. | Positions of biological 5'ESTs |
|---|---|
| 305 | 1–466;1–462;1–469;1–489;1–522;1–447;9–133 |
| 306 | 1–472;1–479;15–500;15–481;15–239 |
| 313 | 1–494;1–434;1–444;1–509;1–471;4–469;72–570 |
| 318 | 1–175,1–410,1–180;1–434;2–482;2–454;36–518;36–557;36–482;36–188;36–483 |
| 319 | 1–587;1–451 |
| 320 | 1–239;6–444;6–413 |
| 324 | 1–463;1–302;1–495;1–496 |
| 328 | 1–427;15–503;15–450;15–432;15–430;15–515;15–461;15–280 |
| 330 | 1–422;1–543;70–520 |
| 337 | 1–638;1–344 |
| 338 | 1–562;52–474;52–474;52–472 |
| 341 | 1–418;–244,4–475;4–302;34–487 |
| 342 | 1–460;3–451 |
| 344 | 1–478;4–264;4–378 |
| 346 | 1–481;1–476;1–537;1–444;1–378;1–423;1–475;1–502 |
| 347 | 1–461;1–461;7–488 |
| 348 | 1–470;15–352 |
| 349 | 1–384;1–395;63–550;63–509;67–564 |
| 356 | 1–465;29–429;29–429;29–433;29–433;29–522;59–511 |
| 361 | 1–448;2–491;21–223;21–737;21–392 |
| 364 | 1–137;1–441;1–474;1–470;1–322;1–473;1–425;1–413;2–488 |
| 365 | 1–82;48–551;48–525;48–525;48–571;48–530;48–260;48–515;48–475;48–535;48–549;48–531;48–406;48–542;48–597;48–536;48–503;48–527;48–559;48–496;48–519;48–531;48–397;48–541;48–593;48–589;48–556;48–556;48–53;48–535;49–532 |
| 368 | 1–412;1–391;1–381 |
| 370 | 1–342;1–466;1–352;1–257;1–220;1–365;8–426;50–367;50–488;89–513 |
| 376 | 1–506;1–237;28–524;28–473 |
| 380 | 1–449;1–495 |
| 381 | 1–530;1–431 |
| 383 | 1–463;1–410;1–379;1–569 |
| 387 | 1–413;1–217;1–497;1–217;1–418;1–122;1–490;1–486 |
| 396 | 1–332;1–450;3–326;3–449;3–401;3–252;3–297 |
| 407 | 1–473;1–510 |
| 418 | 1–400;1–507;1–422;1–328 |
| 426 | 1–324;1–324;1–320;1–324;1–320;1–320;1–324;1–320;1–324;1–324;1–274;1–324;1–324;1–324;1–321;1–324;1–320;1–324;1–324 |
| 427 | 1–469;1–480;1–480 |
| 439 | 1–333;32–428;32–352;32–341 |
| 440 | 1–384;1–481;1–388;1–537 |
| 449 | 1–420;1–481;1–503;1–483 |
| 451 | 1–506;1–507 |
| 459 | 1–453,11–492;11–447;11–450;11–431;11–517 |
| 460 | 1–411;1–475 |
| 467 | 1–116;5–480 |
| 470 | 1–398;1–478 |
| 472 | 1–510;1–437;40–527;40–405 |
| 473 | 1–469;1–378;1–460;66–550 |
| 480 | 1–505;1–465;3–464 |
| 504 | 1–358;7–489 |
| 513 | 1–470;1–137 |
| 521 | 1–461;1–479;1–468 |
| 561 | 1–498;1–504;4–461;18–437 |
| 562 | 1–470;1–76;1–488;1–483 |
| 564 | 1–465;–480;–481 |
| 566 | 1–321;1–488;1–381;1–429;1–391;1–369;1–244;1–376;1–458;1–355;1–444;1–458;1–433;1–490;1–177;1–437;1–442;1–345;1–499;1–436;1–458;1–367;1–369;1–490;1–509;1–371;–493;1–183;1–207;1–466;1–497;1–431;1–363;1–443;1–480;1–261;1–424;1423;1–391;1–269;1–386;1–390;1–479;1–489 |
| 570 | 1–473;1–486 |
| 571 | 1–426;94–583;94–601;94–523;94–566 |
| 573 | 1–474;1–352;1–496 |
| 574 | 1–467;1–496;1–288 |
| 575 | 1–449;1–406 |
| 578 | 1–387;1–504;1–456;1–455;1–480;1–484;1–456;1–125;1–407;225–643 |
| 579 | 1–472;1–455;1–212;1–473;1–161;1–413;1–467;1–495;1–435;1–383;1–432;1–340;1–420;1–420;1–440;1–388;1–430;1–453;1–510;1–510;1–433;1–279;1–378;1–386;1–437;1–391;34–436 |
| 581 | 1–268;1–454;1–364;1–472;1–480 |
| 582 | 1–402;15–457;15–474;15–424;15–445;20–500;32–458;53–488;53–498;53–475;53–496;53–478;53–509;53–484;53–500;53–499;53–474;53–476;53–478;53–509;53–488;53–486;53–501;53–486;53–501;53–484;53–495 |
| 584 | 1–73;1–538 |
| 585 | 1–513;1–431 |
| 586 | 1–356;2–451;3–460;3–500;27–412;30–460;57–530;129–510 |
| 588 | 1–491;1–302 |
| 589 | 1–489;257–736 |
| 591 | 1–137;1–523;1–492;1–424;1–480 |
| 593 | 1–233;1–228;1–232 |
| 597 | 1–461_ 1–287 1–256;1–430;15–366 |
| 599 | 1–434;8–521 |
| 606 | 1–301;5–328 |
| 611 | 1–432;1–459;1–451;1–439 |
| 613 | 1–437;1–295;1–181;1–433;1–283;1–507;1–370;1–433;1–433;1–425;1–513;1–239;1–468;2–419;3–305;3–303 |
| 617 | 1–494;33–478 |
| 622 | 1–476;1–463 |
| 624 | 1–282;1–448 |
| 625 | 1–475;80–552 |
| 626 | 1–463;1–459 |
| 627 | 1–461;1–492;1–507;1–419;57–522;57–521;138–580 |
| 630 | 1–487;142–607 |
| 632 | 1–476;1–487;1–502;4–478 |
| 633 | 1–459;1–425;1–428;1–446;1–485;1–149;1–451;1–392;1–447;1–441;2–304 |
| 634 | 1–463;1–455;1–464 |
| 636 | 1–464;1–480 |
| 637 | 1–450;1–421;1–421 |
| 642 | 1–471;1–29;1–475;1–432;1–497;1–463;5–197;5–442;5–371;5–411;5–473;5–153;5–495;5–404;5–26;5–96 |
| 644 | 1–353;11–251 |
| 645 | 1–388;1–494;1–501;1–348;1–504;1–546;1–451;1–473;1–475 |
| 646 | 1–333;1–333;1–336;1–208;1–336;1–333;1–332;1–336;1–336;1–336;1–333 |
| 649 | 1–511;1–375;1–488;1–463;1–481;1–440;1–364 |
| 650 | 1–402;1–489;1–473;1–442;1–434;1–479 |
| 651 | 1–511;1–469;1–485;1–448;1–403;1–501;1–443;1–477;1–496;1–470 |
| 652 | 1–354;1–365;1–427;1–489 |
| 655 | 1–456;15–392;15–479;15–502;15–479;15–494;15–491;15–269;15–482;15–412;15–503;15–430;15–477;15–508 |
| 657 | 1–467;1–456;1–429;1–510 |
| 661 | 1–72;1–451 |
| 662 | 1–387;1–487;1–469;1–487;19–90;24–362;24–267 |
| 663 | 1–458;1–383 |

TABLE II-continued

(Tiling path)

| Seq Id No. | Positions of biological 5'ESTs |
|---|---|
| 666 | 1–469;19–539 |
| 667 | 1–479;1–490;1–467 |
| 669 | 1–504;1–532;1–354;1–532;1–464;1–540 |
| 671 | 1–476;106–506;106–233;106–207 |
| 672 | 1–238;6–443;6–412 |
| 674 | 1–281;1–467;1–469;1–416;1–404;23–451;23–269;23–467 |
| 677 | 1–419;1–497;1–492 |
| 682 | 1–464;1–466;1–508;1–499 |
| 683 | 1–458;1–486;1–485;1–354;1–481;1–446;1–465;1–346;1–495;1–490;1–270;1–482;1–535;1–450;1–499;1–461;1–406;1–435;1–477;1–499;1–373 |
| 686 | 1–321;1–350;1–259;1–321;1–333;1–320;1–338;1–288;1–168;1–321;1–336;1–347;1–347;1–338;1–321;1–330;1–331;1–347;1–251;1–336;1–330;1–321;1–347;1–335;1–321;1–347;1–347;1–341;1–332;1–320;1–321;1–329;1–347;1–323;2–244;5–468;5–495 |
| 687 | 1–453;1–497;1–486 |
| 688 | 1–499;1–487 |
| 689 | 1–454;6–467;6–465;7–67 |
| 690 | 1–523;9–479 |
| 692 | 1–503;1–467;1–463 |
| 694 | 1–488;1–482;1–423;1–523;1–541;1–425;1–462 |
| 697 | 1–296;1–248;45–136;45–315;45–252;45–304;45–491;45–94;45–224;45–282;45–558;45–210;45–303;45–251;45–272;45–316;45–234;45–3 19;45–94;45–211;45–215;45–536;45–258;45–488;45–537;45–96;45–473;45–311;45–238;45–403;45–318;45–272 |
| 702 | 1–425;1–480 |
| 703 | 1–423;1–495 |
| 704 | 1–492;1–455;1–381;35–206 |
| 705 | 1–204;1–399;1–479;1–457;1–457;1–179;1–368;1–127;1–409;1–449;1–450;1–467;1–58;1–450;1–452;1–450;1–327;1–402 |
| 706 | 1–378;94–595;94–582;94–584;94–583;94–402;94–552;94–554;94–672;95–610;101–604;101–577;101–620;101–366;105–505;118–596;118–472 |
| 710 | 1–451;1–472 |
| 712 | 1–333;1–391;1–432;15–484 |
| 714 | 1–484;1–503;1–534;2–480;2–469;2–476;2–358;125–483;125–210 |
| 715 | 1–468;1–512;1–492;1–484;1–178;1–491;1–327;1–443;1–509;1–319;1–434;1–491;1–393;1–493;1–180;1–393;1–514;1–443;1–490;1–484;1–477;1–477;1–441;1–525;1–493;1–469;1–490;1–509;1–442;1–461;1–477 |
| 718 | 1–474;1–495;1–462;1–476 |
| 719 | 1–55;1–416;1–482;1–439;1–457;14–492 |
| 720 | 1–423;1–469;2–326;12–469;12–425 |
| 721 | 1–485;1–471 |
| 722 | 1–251;1–419;1–434;1–560;1–490 |
| 725 | 1–470;1–508;1–531 |
| 726 | 1–503;1–431 |
| 727 | 1–371;1–350;32–396 |
| 728 | 1–477;28–389 |
| 730 | 1–480;25–511;25–512 |
| 731 | 1–509;13–465;18–463;18–493;18–498;18–499;18–519;18–511;18–257;18–460;18–496;18–307;18–463;19–482;21–492;22–509;22–496;22–499;23–421;26–455 |
| 732 | 1–380;1–345;1–380 |
| 739 | 1–464;18–478;18–511;18–516;18–506;18–483;19–371;19–509;19–301 |
| 740 | 1–123;78–150 |
| 742 | 1–453;1–421;1–494;1–469;5–439;6–467;7–456;17–489;17–465;17–93;17–502 |
| 753 | 1–182;1–76 |
| 754 | 1–344;1–487;8–472;13–475 |
| 757 | 1–453;12–494 |
| 758 | 1–392;1–370;1–381 |
| 760 | 1–355;1–467 |
| 764 | 1–314;1–456;1–472 |
| 768 | 1–466;8–350;13–474;13–544;13–523;19–488;19–490;22–234;22–512;22–226;22–222;39–537;39–430;42–307 |
| 769 | 1–504;1–508;1–480;1–484;–429;1–485;1–484;–474;1–482;1–465;1–303;1–523;1–502;4–500;4–476;4–495;4–538;4–504;4–437;4–500;4–519;4–528;4–501;4–495;4–500;4–496;4–498;4–476;4–501 |
| 771 | 1–265;1–450;153–506 |
| 773 | 1–432;1–499;4–386 |
| 774 | 1–476;1–492;1–295;1–479;1–477;1–498;1–472;1–462 |
| 775 | 1–450;1–428;5–420;5–372;5–498 |
| 777 | 1–317;1–439;1–470;1–433;1–432;235–732;235–690;249–603;249–748 |
| 778 | 1–136;28–456;28–526;28–420;28–494;61–360;61–522;61–495;61–331;61–431;61–450;63–558;63–386;64–534;66–457;66–358;66–560;66–342;66–533;70–589;70–320;72–512;73–534;73–542;73–451;73–533;73–512;73–528;73–508;73–541 |
| 780 | 1–520;69–415;101–595;101–585;101–583;101–470;108–595;108–572;108–513;108–588;108–595;108–610;108–595;108–646;108–605;108–577;110–653;247–704 |
| 781 | 1–394;1–491;1–502;1–497;1–502;1–476;1–403;1–470 |
| 783 | 1–484;9–516 |
| 786 | 1–384;1–486;10–515;10–482 |
| 787 | 1–476;1–463 |
| 788 | 1–312;1–310,1–384,7–514;49–401;55–499;55–532,56–552,56–435;56–584;56–521;56–618;56–560;56–567;56–576;56–415;56–521;56–512 |
| 790 | 1–445;16–474;16–396;27–410;27–465;27–443;28–281;28–249;30–484;30–145;30–330;30–429;30–427;30–462;30–462;30–466;30–444;30–386;30–467;30–459;30–462;30–462;30–410;30–423;30–463;30–494;30–480;30–253;30–405;30–430;30–483;30–379;30–398;30–426;30–410;30–443;30–459;30–442;30–449;30–459;30–427;30–485;30–463;30–445;30–478;30–398;30–458;30–451;30–324;30–453;30–462;30–483;30–432;30–440;30–458;30–494;30–426;30–477;30–334;30–396;30–397;30–447;30–459;30–331;30–444;30–410;30–494;30–482;30–468;30–189;30–444;30–444;30–456;30–494;30–478;30–485;30–466;30–291;30–470;30–485;30–402;30–322;30–410;30–416;30–416;30–468;30–197;30–462;30–448;30–415;30–410;30–469;30–469;30–395;30–474;30–372;30–494;30–449;30–410;30–418;30–410;30–399;30–462;30–468;30–223;30–468;30–416;30–410;30–398;30–430;30–481;30–462;30–448;30–245;30–410;30–420;30–494;30–485;30–365;30–410;30–448;30–485;30–483;30–454;30–457;30–444;30–441;30–150;30–378;30–494;30–442;30–409;30–407;30–478;30–454;30–483;30–474;30–484;30–448;30–409;30–374;30–453;31–396;32–410;32–147;32–443;32– |
| 792 | 1–484;1–470 |
| 793 | 1–445;1–492;1–419 |

TABLE II-continued (Tiling path)

| Seq Id No. | Positions of biological 5'ESTs |
|---|---|
| 795 | 1–492;–374;1–547:1–355;1–356;1–366;1–547;1–324;1–453;1–476;1–422;18–294 |
| 796 | 1–489;1–160 |
| 797 | 1–443;1–227;3–415;5–215;5–479;5–290;5–453;5–279;5–419;5–477;5–380;6–373;6–413;6–496;6–462;6–343;6–472;6–279;6–297;6–448;6–492;6–313;6–474;6–340;6–485 |
| 798 | 1–461;1–465;5–452;5–425;5–478 |
| 800 | 1–395;1–500;1–450;1–491;1–302;1–367;1–432;1–454;68–577 |
| 802 | 1–444;1–179 |
| 803 | 1–424;1–394;1–466;1–456;1–418 |
| 804 | 1–448;1–422;1–392;1–416 |
| 805 | 1–453;1–484;1–456 |
| 806 | 1–309;17–510 |
| 809 | 1–376;21–129;21–129 |
| 811 | 1–270;1–520;1–117 |
| 813 | 1–191,1–191 |
| 815 | 1–474;1–399;1–465;110–489;110–464;110–263;110–279;110–543 |
| 817 | 1–437;1–413;1–485;5–507;6–265;6–436;6–438;6–434;6–381 |
| 818 | 27–510;28–519;28–512;28–517;28–497;28–510;28–512;28–511;28–333;28–515;28–526;28–510;28–488;29–520;30–517;31–316;31–385;31–504;31–509;31–520;31–406;31–494;31–504;31–496;31–511;31–488;31–493;31–524;31–513;31–488;31–488;31–497;31–395;31–337;31–506;31–512 |
| 819 | 17–482;24–512;27–526;28–510;28–517;28–463;28–510;28–488;28–515;28–511;28–333;28–510;28–519;28–512;28–482;28–497;29–520;29–463;30–517;30–483;31–496;31–513;31–478;31–511;31–504;31–478;31–458;31–494;31–316;31–477;31–496;31–509;31–520;31–504;31–488;31–493;31–524;31–497;31–488;31–478;31–442;31–488;31–476;31–337;31–506;31–512 |
| 820 | 1–331;51–332;51–332;51–332 |
| 824 | 1–144;1–351 |
| 826 | 1–466;1–264 |
| 827 | 1–309;1–374;1–255;1–420 |
| 832 | 1–372;1–461;1–281;1–461;1–486;1–486;1–492;1–494;1–479 |
| 834 | 1–224;180–269;180–650 |
| 836 | 1–431;1–486 |
| 839 | 1–272;51–278;51–433;51–482;51–397;51–537;51–537 |
| 842 | 1–403;14–513 |
| 843 | 1–432;74–536 |
| 844 | 1–434;29–526 |
| 846 | 1–431;6–367;6–164;6–503;6–432;6–413;6–424;6–495;6–422;6–369;8–430;8–410;8–409;8–403;8–462 |
| 848 | 1–408;32–308;32–476;32–484 |
| 849 | 1–367;1–491;1–518;1–466;1–505;1–478;1–494;1–492;1–513;1–432 |
| 850 | 1–474;22–377 |
| 851 | 1–431;1–492;1–164 |
| 852 | 1–474;1–370 |
| 854 | 1–402;1–489;7–499;15–344;16–473 |
| 855 | 1–296;1–428;1–484;1–484;1–411 |
| 856 | 1–471;1–473;36–376;36–409;76–440 |
| 857 | 1–426;1–502;1–321 |
| 859 | 1–481;1–382 |
| 860 | 1–344;52–508 |
| 861 | 1–489;1–390;–465;1–349;15–390;35–148;40–367;40–146;40–504;41–440;41–160;41–506;41–382;41–157;41–386;41–490;41–535 |
| 862 | 1–484;1–502;1–390;1–504;1–409;2–435;2–287 |
| 864 | 1–280;1–483;1–355;1–429;1–448;8–302 |

TABLE II-continued (Tiling path)

| Seq Id No. | Positions of biological 5'ESTs |
|---|---|
| 865 | 1–324;1–415;1–451;1–478;1–557;1–481;1–518 |
| 867 | 1–471;1–484;1–463;1–496;1–303;1–373;1–101;4–387;4–398;4–472;4–428;4–366;4–466 |
| 868 | 1–471;1–484;1–463;1–303;1–373;1–491;1–101;4–387;4–366;4–472;4–428;4–466 |
| 871 | 1–444;1–467;1–443 |
| 873 | 1–210;1–413;1–430;27–79;27–506;27–521;27–432;27–478;27–498;27–509;27–504;27–453;27–101;27–287;27–510;27–493;27–483;27–507;27–101;27–505;27–444;27–506;28–506;28–509;28–465;28–505;28–423;28–478;28–476;28–507;28–490;28–502;28–502;28–431;28–542;28–365;28–506;28–454;28–477;28–280;28–495;28–415;28–478;28–458;28–464;28–284;28–516;28–225;28–491;28–439;29–515;29–411;30–435;33–466;33–499;33–515;35–328;50–285;50–506;50–517;50–517;54–507;54–505 |
| 878 | 1–337;1–473;1–408;1–472 |
| 880 | 1–410;1–422;1–447;1–464;1–450 |
| 881 | 1–351;1–301;11–252;11–442;11–372;15–361;28–276;28–337;28–305;29–500;29–165;29–177;29–429;29–100;29–178;29–165;29–165;29–152;29–110;29–173;29–512;30–439;30–165;30–151;30–506;30–322;30–482;30–178;30–165;30–452;30–141;30–258;30–165;30–294;31–165;31–425;31–158;31–178;31–165;40–272;40–272;40–272;87–323;88–536;226–623;226–695;226–304;226–681;226–688;226–624;226–708 |
| 882 | 1–489;1–449 |
| 883 | 1–295;7–93;17–245;41–508;41–542;41–445 |
| 885 | 1–484;1–309;1–455;1–474;1–321 |
| 886 | 1–456;1–499;1–420;5–200 |
| 887 | 1–455;1–347 |
| 888 | 1–452;1–428;1–272;2–436 |
| 890 | 1–460;1–471;1–525 |
| 892 | 1–517;1–335;1–368;1–514;1–92;1–246;1–385 |
| 893 | 1–431;1–479 |
| 894 | 1–478;20–433;20–437;21–318;37–456;48–119;48–113;51–548;52–240;59–504 |
| 897 | 1–441;8–467 |
| 898 | 1–445;1–159;1–366;1–453 |
| 902 | 1–498;1–477;1–438 |
| 904 | 1–481;1–537;1–443;1–539 |
| 905 | 1–326;1–314;1–368;1–321;1–332;1–365;1–369;1–365;1–365 |
| 906 | 1–485;1–304 |
| 907 | 1–417;1–464;1–449;–462;1–422 |
| 908 | 1–469;1–454 |
| 909 | 1–467;49–419;50–506;50–546;55–381;66–480;67–486;67–573;67–563;68–543;68–467;68–567;68–523;68–511;68–542;68–559;68–544;68–559;68–549;68–530;68–566;68–514;68–559;68–505;68–438;68–707;71–561;71–561;71–568;76–591;76–412;76–612;76–613;83–419;83–620;83–505;83–634;86–607 |
| 910 | 1–467;49–419;55–381;66–480;67–486;68–467;68–438;68–500;72–604;76–412;83–419;83–500 |
| 911 | 1–314;1–452;1–392;9–295;9–317 |
| 913 | 1–304;1–387;1–413;1–405 |
| 915 | 1–245;1–240;1–159 |
| 917 | 1–274;1–181 |
| 918 | 1–439;1–443;1–427;1–333;1–452;1–410;1–462;1–460 |

TABLE II-continued

(Tiling path)

| Seq Id No. | Positions of biological 5'ESTs |
|---|---|
| 919 | 1–517;1–439;1–443;1–427;1–333;1–505;1–452;1–481;1–410;1–513;1–504;1–456 |
| 921 | 1–374;2–346;2–526 |
| 923 | 1–474;1–370 |
| 924 | 1–404;1–434 |
| 925 | 1–367;1–198;36–373;36–474;36–459;36–521;36–519;36–438;461–898;461–900 |
| 926 | 1–466;1–512;1–522 |
| 929 | 1–338;40–324;42–540;42–538;42–547;42–445;46–500;46–539 |
| 930 | 1–478;1–486 |
| 931 | 1–402;1–413;67–458 |
| 932 | 1–509;1–529;1–484 |
| 933 | 1–438;1–469;1–443;1–501;1–472 |
| 936 | 1–458;1–504 |
| 937 | 1–474;1–429;1–372;2–525;2–443;2–482;2–415;2–472;2–398;2–472;2–480;2–488;2–510;3–443;3–414;3–479;3–456;3–427;3–451;3–477;3–461;27–512;27–486;27–335;27–499;27–601;27–506;27–467;27–331;27–267;27–484 |
| 938 | 1–397;1–462;1–495;1–462 |
| 939 | 1–494;1–489;1–468;1–491;1–513;1–388;1–514;1–486;1–488;1–484;1–521;1–486;1–383;1–401;1–487;1–511;1–490;1–497;1–478;1–483;1–209 |
| 940 | 1–494;1–489;1–468;1–491;1–513;1–388;1–514;1–539;1–486;1–484;1–488;1–486;1–383;1–401;1–487;1–511;1–490;1–497;1–478;1–483;1–209 |
| 941 | 1–463;1–557 |
| 942 | 1–223;1–479 |
| 943 | 1–351;1–476;1–475 |
| 944 | 1–529;20–488 |
| 945 | 1–253;1–263;1–502;1–511;1–463;1–502;1–284;1–369;6–605 |
| 946 | 1–488;1–420;1–479 |
| 949 | 1–482;32–460;32–186;32–510;32–510;32–422;32–507;32–484;32–519;32–333;32–529;32–424;34–533;38–392;38–557;38–482;38–418 |
| 950 | 1–50;1–55;1–353 |
| 951 | 1–446;1–424;1–515 |
| 952 | 1–355;1–508;1–463 |
| 953 | 1–466;5–421;5–433;5–449;5–466 |
| 954 | 1–454;1–476 |
| 955 | 1–274;6–506 |
| 956 | 1–440;12–440;12–428 |
| 957 | 1–227;1–144;1–295;1–435;15–366;144–572;144–628 |
| 958 | 1–525;1–419 |
| 959 | 1–375;1–497;1–370;1–424;1–402;1–363;1–400;1–337;1–437;1–448 |
| 960 | 1–502;1–273;1–317 |
| 961 | 1–525;1–398;1–405;1–461;1–453;1–481;1–467;1–504;1–450;1–510;11–455 |
| 962 | 1–284;1–444;1–323 |
| 963 | 1–334;27–165 |
| 966 | 1–311;1–258;1–309;1–311;1–311;1–307;1–289;1–301;1–296;1–308;1–292;1–298;1–298;1–289;1–301 |
| 968 | 1–437;1–499;34–511;34–548;34–526;34–473;34–496;34–479;34–529;34–496 |
| 969 | 1–495;1–405;1–375;1–491 |
| 971 | 1–492;3–466 |
| 972 | 1–458;1–402;1–420;1–346;1–416;1–471 |
| 973 | 1–412;1–425;1–464;1–472;1–201;1–366;10–137 |
| 974 | 1–219;1–282 |
| 975 | 1–322;24–290 |
| 976 | 1–475;1–479;318–452;318–452;318–452 |
| 977 | 1–385;1–410;1–381;22–366;22–219;46–514 |
| 978 | 1–462;1–463;1–489;1–493;1–414;1–379;1–445;1–473 |
| 979 | 1–427;1–459;1–166;1–334;1–459;1–367 |
| 980 | 1–104;1–481 |
| 981 | 1–405;1–503;1–394;1–415;1–253 |
| 984 | 1–473;1–528;1–477;1–540 |
| 985 | 1–482;1–439 |
| 987 | 1–429;1–410 |
| 988 | 1–488;22–492;31–201;32–473 |
| 989 | 1–380;1–490;1–504;1–501;1–507;1–508;4–369 |
| 992 | 1–497;23–549 |
| 993 | 1–465;1–466;1–388;1–433;1–565;1–290;1–471;1–487;1–487;1–190;1–469;2–320 |
| 994 | 1–453;2–464;2–438;2–528;2–459;2–445;2–486;2–519;2–454;2–338;2–359;2–477;2–58;5–495;8–424;8–445;8–518;8–494;8–392;8–367;8–459;8–434;8–488;9–56;47–533;47–367;47–529 |
| 998 | 1–476;3–342 |
| 1002 | 1–470;1–527;1–391;1–462;1–584;1–412;1–193;1–469;1–53;1–495;1–487;–482;3–152;3–156 |
| 1003 | 1–377;1–211;1–520;1–466;1–395;1–507;1–452;1–486;1–425;1–360;1–410;1–96;1–478;1–387 |
| 1004 | 1–403;1–490 |
| 1005 | 1–418;20–452 |
| 1006 | 1–453;1–469;1–474;1–463 |
| 1030 | 1–461;1–474;4–107;25–222;65–360;65–400;66–310;66–36 1;66–358;66–214 |
| 1031 | 1–478;2–467;2–483;2–106;3–471;3–460;3–556;24–221;54–503;54–539;54–515;64–359;64–399;65–499;65–360;65–357;65–309;65–213 |
| 1032 | 1–537;1–537;67–165 |
| 1033 | 1–425;1–422;1–390 |
| 1035 | 1–455;1–358 |
| 1036 | 1–110;1–447;1–391 |
| 1037 | 1–317;1–450;1–424 |
| 1038 | 1–319;1–453 |
| 1040 | 1–510;1–481;1–488;1–520;1–503;1–477;1–295;1–405;1–491 |
| 1042 | 1–436;1–479 |
| 1043 | 1–532;4–463;4–269;4–188;6–103 |
| 1044 | 1–516;1–382 |
| 1045 | 1–471;1–470 |
| 1048 | 1–380;2–496;22–490 |
| 1051 | 1–488;1–443;1–461;1–467;1–516;1–469;1–503;1–295;1–422;1–467;1–446;1–209;1–468;1–445;1–440;1–484;1–92 |
| 1054 | 1–325;1–449;1–405;1–457;1–71;1–230;1–406;1–449 |
| 1055 | 1–242;1–228;1–242;1–220;1–242;1–210;1–242 |
| 1056 | 1–369;1–462;1–431;1–486;1–340 |
| 1058 | 1–443;1–450;81–141 |
| 1059 | 1–567;1449;1–509 |
| 1061 | 1–418;6–382 |
| 1062 | 1–265;1–164;1–181;1–245;1–76;1–268;1–70;1–97;1–264;1–142;1–54;1–126;1–242;1–268;81–402 |
| 1065 | 1–486;1–473;1–466 |
| 1071 | 1–316;1–283;1–269;1–298;1–299;1–305;1–338;1–306;1–282;1–331;1–239;31–455;31–387;39–125;39–529;39–237;39–522 |
| 1074 | 1–463;–433;1–302;48–557;48–564;48–342;77–550;77–433;77–485;77–498 |
| 1075 | 1–483;1–492;1–424 |
| 1076 | 1–315;1–480 |
| 1078 | 1–480;1–353 |
| 1079 | 1–480;4–491;4–336;4–490;4–493;4–491;4–475;4–470;4–470;4–538;4–491;4–491;4–435;4–394;22–476 |
| 1081 | 1–279;1–201;20–444 |
| 1082 | 1–480;31–410;31–400;31–415;31–251 |

TABLE II-continued

(Tiling path)

| Seq Id No. | Positions of biological 5'ESTs |
|---|---|
| 1083 | 1–490;–55;28–396;31–446;42–403;42–413 |
| 1084 | 1–415;7–417 |
| 1085 | 1–369;4491;6–419;7–485;15–376;15–386 |
| 1088 | 1–148;1–191;2–129;2–150;2–145;2–138;3–149;3–150;27–149;27–123;27–123;28–29;28–144;28–129;28–131;28–129;28–149;28–140;29–129;30–149;31–143;32–148;33–148;33–144;33–183;33–134;33–150;33–150;33–141;33–149;33–137;33–191;33–151;33–147;33–150;33–179;33–134;33–254;33–150;33–149;33–150;33–148;33–150;33–91;33–131;33–122;33–87;33–151;33–149;33–151;33–149;33–150;33–135;33–105;33–150;33–138;33–135;33–151;33–144;34–93;34–150;34–138;34–150;34–129;34–135;34–145;34–149;34–140;34–149;34–148;34–179;34–148;34–131;34–142;34–139;34–140;35–148;35–150;35–135;35–140;35–108;36–136;36–150;36–141 |
| 1089 | 1–484;1–397;1–413;40–519;40–468;40–523;40–204;40–514;40–502;40–526;40–507;40–509;40–528;40–515;40–540;40–394;40–472;40–524;40–491;40–499;40–453;40–416;40–491;40–518;40–532;40–493;40–534;40–512;40–539;40–488;40–515;40–491;40–536;40–518;42–551;106–252;106–582;107–501;107–544;107–577;107–546 |
| 1090 | 1–321;1–318;1–201;1–333;1–333;1–333;1–332;1–329;1–329;1–344;1–333;1–121;1–309;1–346;1–330;1–330;1–345 |
| 1091 | 1–328;1–330;1–489;1–492;1–476;1–518;1–475;1–477;1–590;1–468;1–511;1–468;1–532;1–590;1–142;1–476;1–501;1–486;1–356;1–492;1–624;1–518;1–265;1–94;1–590 |
| 1092 | 1–478;1–484 |
| 1093 | 1–493;1–495;1–139;1–394 |
| 1094 | 1–480;1–494;1–479;1–378;1–505;1–486;1–513;1–453;6–347;9–485;9–454;9–504;9–506;17–117;30–168;30–507;30–506;30–407 |
| 1097 | 1–534;1–534;1–550;1–439;1–398;1–550 |
| 1107 | 1–465;28–481;28–437;28–492;28–492;28–329;29–373 |
| 1109 | 1–87;1–484 |
| 1113 | 1–484;1–468;1–482;1–433;1–481;1–457 |
| 1119 | 1–248;4–64 |
| 1120 | 1–615;4–538;4–325;4–561;4–615 |
| 1122 | 1–559;12–75 |
| 1123 | 1–141;1–360;1–399 |
| 1124 | 1–497;1–463;–480;13–506;31–239;31–518;31–524;31–482;31–190;31–479;37–328;37–328;37–212;37–292;37–328;37–522;37–335;38–496;38–543;38–312;61–506;61–526;66–547;66–509;66–486;66–503;66–543;80–551;111–547 |
| 1125 | 1–64;1–440;1–484;1–447;1–470;1–477 |
| 1128 | 1–502;1–456 |
| 1132 | 1–528;2–307 |
| 1134 | 1–454;1–506;1–293 |
| 1135 | 1–473;1–491;1–495;1–449;1–438;1–468;45–495;105–564 |
| 1137 | 1–460;1–268;25–524;33–408 |
| 1140 | 1–63;21–479 |
| 1141 | 1–485;1–482;1–341;1–466;1–494 |
| 1144 | 1–75;1–462;1–208;1–236;1–436;1–351;1–487;28–515;28–516 330;1–151;1–435;1–153;1–227;1–365;1–395;1–264;1–382;1–372;1–269;1–244;1–410;1–353;1–344;1–468;1–273 |
| 1145 | 1–239;1–238 |
| 1146 | 1–343;1–337 |
| 1147 | 1–484;83–528 |
| 1148 | 1–448;1–483 |
| 1149 | 1–440;1–429;4–85;6–504 |
| 1151 | 1–503;1–366;1–473;74–529;74–526 |
| 1156 | 1–494;1–130;1–208;1–266 |
| 1157 | 1–537;1–269;1–557;1–292;1–503;21–361 |
| 1158 | 1–335;1–458;1–127;1–268;1–269 |
| 1160 | 1–132;15–205;25–147;56–536 |
| 1170 | 1–447;1–301;1–457;1–228;1–502;1–466;1–499;1–443;1–434;1–519;1–456;1–321;1–477;1–488;1–459;1–404;1–395 |
| 1172 | 1–497;1–494;T–445;1–505;1–488;1–512;1–498;1–495;1–504;1–502;1–461;1–60;1–500;1–498;1–437;1–445;1–522;1–459;1–477;1–371;1–460;1–522;1–511;1494;1–502;1–440;1–499;1–427;10483;1–194;1–436;1–422;1–453;1–402;1–377;1–552;1–210;1–564;1–239;1–209;1–456;1–465;1–498;1–393;1–559;1–460;1–494;1–469;1–460;1–469;1–494;1–501;1–478 |
| 1173 | 1–469;1–413;1–357;1–469 |
| 1174 | 1–386;1–425;1–208;1–471;1–482;1–476;1–359;1–498;–467 |
| 1175 | 1–505;1–390 |
| 1177 | 1–388;1–531;1–442 |
| 1178 | 1–437;1–488;1–490;1–526 |
| 1179 | 1–468;1–391;1–490;1–468;1–340;1–150;1–433;1–371;385–915 |
| 1180 | 1–542;3–480;4–495;4–517;6–490;6–498;6–536;6–488;6–482;6–407;6–498;6–476;6–290;6–480;6–476;6–491;6–465;6–271;6–557;6–474;6–514;6–494;6–74;6–423;6–536;6–416;6–480;6–488;6–474;6–69;6–450;6–406;6–74;6–550;6–550;6–69;13–497;13–534;13–69;13–69;13–292;13–488;13–461;13–515 |
| 1181 | 1–388;1–477;2–448;136–581;136–648;151–604;151–474;151–598;151–679;151–584;151–691;159–530;159–646;159–620;159–658;159–591;166–502;166–639 |
| 1182 | 1–396;1–520;1–503;1–436;1–364;1–567 |
| 1185 | 1–458;1–448;1–446;1–248;1–599;1–371;1–525;1–361;1–533;1–470;1–424;1–465;1–391;1–413;1–447;1–346;1–362;1–441;16–566;16–453;23–495;23–495;23–490;23–491;23–520;25–496;26–431;26–469;28–558;28–505;28–516;28–524;28–554;28–487;28–515;28–516 |
| 1186 | 2–536;2–415;2–502;2–466;2–415;2–525;2–421;3–502;3–548;3–425;3–524;3–472;3–300;3–494;3–494;3–438;3–502;3–505;3–502;3–502;3–494;3–472;3–505;3–269;3–492;3–418;3–355;3–471;3–505;3–525;3–494;3–494;3–236;3–494;3–337;3–505;3–439;3–492;3–502;3–502;3–406;3–523;3–473;3–536;3–57;3–493;3–403;3–456;3–479;3–419;3–502;3–302;3–494;3–525;3–439;3–356;3–337;4–302;5–536;5–505;5–492;5–415;5–361;5–476;5–481;5–502;5–494;5–543;5–476;5–525;5–522;5–337;5–412;6–502;6–536;6–505;6–422;6–502;6–493;6–494;6–492;6–536;6–525;6–422;6–467;6–408;6–478;6–502;6–543;6–525;6–456;6–465;6–415;6–472;6–358;6–502;6–525;6–264;6–473;6–525;6–327;6–502;6–426;6–400;6–426;6–481;6–502;6–213;6–509;6–525;6–425;6–213;6–412;6–361;6–416;6–477;6–522;6–71;6–333;6–426;6–543;6–492;6–543;6–401;6–213;6–536;6–213;6–415;6–418;6–529;6–400;6–415;6–415;6–503;6–213;6–467;6–493;6–424;6–544;6–351;6–459;6–472;6–416;6–505;6–483;6–75 |
| 1187 | 1–470;1–510;2–69;2–382;9–354;31–457 |
| 1188 | 1–77;1–122;1–90;1–108;2–472 |
| 1189 | 1–60;4–408;4–472;4–458;4–445 |

TABLE II-continued (Tiling path)

| Seq Id No. | Positions of biological 5'ESTs |
|---|---|
| 1190 | 1–63;5–380;5–528;5–449;5–477;5–492;5–536;5–386;5–386;5–445 |
| 1191 | 1–438;1–476;1–398;1–437;1–255;1–472;1–467 |
| 1192 | 1–553;1–475 |
| 1193 | 1–574;1–480 |
| 1195 | 1–479;1–375;1–458;1–477 |
| 1196 | 1–454;1–454;31–405;31–447;31–489;31–505;31–543;36–554;36–521 |
| 1197 | 1–262;12–476;16–377;17–448;17–482 |
| 1198 | 1–270;1–461 |
| 1200 | 1–486;1–429;1–472 |
| 1202 | 1–512;1–472 |
| 1203 | 1–486;1–750;1–234;1–198;1–491;1–459;1–531;1–392;1–388;1–357;1–440;1–471; 208;1–460;1–439;2–150;3–423;3–328;3–161;3–392;3–347;3–368;3–192 |
| 1204 | 1–534;17–207;17–383;17–176;17–407;17–438;18–506;18–474;18–249;18–223;18–501;18–213;18–454;18–475;18–455;18–372;18–407;18–403;18–486;18–165 |
| 1207 | 1–464;1–469;1–491;1–498;1–452;1–398;11–464;11–440;11–476;11–444;11–361;11–473;11–507 |
| 1208 | 1–457;1–424;2–424;2–373;2–396;2–424;33–325 |
| 1209 | 1–396;2–468;2–424;2–373;2424;2–424;5–487;33–456;33–325 |
| 1210 | 1–512;15–440;35–555;35–601;35–550;35–144;38–500;42–321;42–443;42–550;42–301;42–446;42–480;42–550;42–437;42–158;42–541;42–536;42–490;42–550;42–550;42–550;42–523;42–437;42–547;42–435;42–545;42–550;42–552;42–447;42–456;42–387;42–550;42–550;42–547;42–541;42–543;42–547;42–391;42–395;42–500;42–553;42–547;42–547;42–533;42–498;42–480;42–553;42–543;55–550;59–601;63–534;63–601;63–319;63–308;63–588 |
| 1214 | 1–409;3–549 |
| 1215 | 1–479;1–492;1–412;1–294;1–439;1–473;1–464;1–524;1–498;1–478;–482;1–449;5–456;6–436;6–317 |
| 1216 | 1–446;1–505 |
| 1217 | 1–328;102–350;102–309 |
| 1221 | 1–476;1–440;1–486 |
| 1228 | 1–534;19–477;19–530;19–426;19–594;19–482 |
| 1229 | 1–284;71–533;71–579 |
| 1230 | 1–504;1–504 |
| 1231 | 1–488;1–438;1–517;1–465;41–473;41–517;41–473 |
| 1233 | 1–238;1–474 |
| 1234 | 1–459;72–489 |
| 1236 | 1–453;1–369;1–431;1–474;1–471;2–451;21–473;30–485;59–234;231–482 |
| 1237 | 1–454;1–442;1–438;1–443;1–438;1–442;1–433;1–441;1–433;1–437;1–280;1–261;1–336;1–455;1–437;1–437;1–429;2–454;20–195;192–443 |
| 1238 | 1–349;1–470;1–407;–491;20–177;20–536 |
| 1239 | 1–468;1–468;1–461;1–451;47–162 |
| 1240 | 1–567;1–287;1–459;1–456 |
| 1243 | 1–423;1–437;36–541;36–541;40–453 |
| 1245 | 1–375;1–508;1–516;1–473;1–525;1–437;1–475;1–475;1–522;1–436;1–451;1–462;1–310;1–498;1–481;1–489;1–314;1–427;1–485;1–241;35–478;35–388;35–518;35–526;35–527;36–503;36–545;36–533;39–479;41–526;43–461 |
| 1246 | 1–386;1–461;1–478;1–477 |
| 1247 | 1–486;1–504;1–253 |
| 1248 | 1–305;1–471;1–412;5–411;7–474;7–517;9– |

| Seq Id No. | Positions of biological 5'ESTs |
|---|---|
| 1250 | 1–488;1–411;16–526;16–500;16–380;16–439;16–524;16–486;16–497;16–468;16–296;16–531;16–485;16–277;16–453;16–486;16–280;16–277;16–275;20–451;20–135;20–509;20–507;20–505;20–435;20–452;20–484;20–406;20–496;20–381;20–505;20–460;20–459;20–504;20–505;21–537;21–525;21–519;21–402;21–530;21–501;21–489 |
| 1251 | 1–467;1–475;1–453;1–437;1–477;1–478;1–371;1–363;1–548;1–375;1–441;3–461;3–475;3–497;3–221;3–361;3–477;3–505;3–272;3–484;3–502;8–465;8–463;8–362;8–501;8–469;8–504;8–376;8–484;8–483;8–464;8–464;8–481;8–466;8–463;8–504;8–339;8–481;8–516;8–474;8–480;8–500;8–490;8–379;8–496;8–437;8–496;8–473;8–531;8–435;8–389;8–468;8–500;8–464;9–545;9–482;9–480;9–409;9–481;9–496;9–313;9–397;9–351;9–494;10–481;10–447;10–481;10–180;10–536;10–371;10–339;10–481;10–501;10–375;10–568;10–434;10–464;10–464;10–428;10–461;10–484;10–382;10–371;10–476;10–161;10–491;10–161;10–498;10–548;10–464;10–453;10–424;10–502;10–477;10–466;10–496;10–354;10–505;10–451;10–484;10–345;10–363;10–513;10–540;10–522;10–233;10–356;10–149;10–464;10–312;10–485;10–465;10–500;10–459;10–336;10–468;10–520;10–522;10–518;10–465;10–406;10–502;10–436;10–468;10–453;10–438;10–518;10–480;10–496;10–499;10–315;10–191;10–479;10–371;10–482;10–486;10–506;10–496;10–382;10–475;10–481;10–436;10–460;10–472;10–524;10–400;10–296;10–136;10–463;10–482;10–533;10–192;10–443;10–480;10– |
| 1252 | 1–375;1–363;1–432;1–371;3–221;3–361;3–272;8–432;8–376;8–379;8–362;8–432;8–389;8–339;9–351;9–313;9–409;9–397;10–363;10–382;10–424;10–432;10–428;10–371;10–371;10–132;10–339;10–233;10–345;10–161;10–161;10–406;10–400;10–324;10–426;10–356;10–312;10–336;10–149;10–375;10–191;10–315;10–180;10–371;10–492;10–354;10–382;10–432;10–296;10–136;10–192;10–267;10–82;10–363;10–432;10–432;10–426;10–243;10–161;10–313;10–410;10–364;10–351;10–432;10–420;10–350;10–161;10–74;10–163;10–85;10–390;10–430;10–390;11–363;11–424;12–271 |
| 1253 | 1–271;1–220;7–335;9–160;9–131;9–323;9–179;9–160;9–232;9–335;9–295;9–73;9–135;9–242;9–162;9–477;9–335;9–148;9–84;9–191;9–160;9–528;9–190;9–314;9–266;9–8;9–160;11–270 |
| 1258 | 1–439;1–454;1–453;1–451;1–306 |
| 1259 | 1–444;–401;1–458;1–525;1–468;1–401;1–454 |
| 1260 | 1–501;35–516;35–554;35–532;35–510;35–514;37–381;45–514;54–534;54–51;54–531;54–346;54–278 |
| 1261 | 1–216;1–459;5–181;5–184;5–171;5–171;5–171;5–184;5–181;5–181;5–68;5–184;5–184;5–651;5–181;5–181;5–180;5–184;5–184;5–171;5–184;5–184;5–181;5–151;5–179;5–180;5–184;5–184;5–180;5–184;5–184;5–164;5–160;5–184;5–181;5–126;5–114;5–378;5–181;5–184;5–184;5–86;36–229;36–226;36–226;36–226;36–229;36–229;36–222;36–226;36–229;36–229 |
| 1262 | 1–90;1–73;1–491 |

TABLE II-continued

(Tiling path)

| Seq Id No. | Positions of biological 5'ESTs |
|---|---|
| 1264 | 1–353;1–409;1–465;1–490;1–357;1–409 |
| 1265 | 1–475;9–540 |
| 1267 | 1–409;1–428;38–516;59–255;59–261;59–260;59–483;59–260 |
| 1268 | 1–498;19–501;21–496;21–465;21–565;21–612;21–469;27–545;28–516;44–482;44–536;44–517;47–549;47–529;47–458;51–434 |
| 1269 | 1–379;1–544 |
| 1270 | 1–492;1–497;1–480 |
| 1273 | 1–435;1–312 |
| 1275 | 1–447;1–479;1–480;1–390;1–476;1–480;78–519 |
| 1276 | 1–430;1–473;1–540 |
| 1277 | 1–461;1–496 |
| 1279 | 1–178;35–482;35–439;35–482;35–413;35–463;36–176 |
| 1280 | 1–472;1–474;51–519;51–527;51–536;51–470;143–274;145–603 |
| 1281 | 1–472;1–492;1–478 |
| 1282 | 1–450;1–451;1–433;1–465;1–474;1–484;1–512;1–458;1–469 |
| 1283 | 1–440;1–435;1–459;1–353;1–479;1–459;1–416;1–420;1–463;1–445;1–468;1–479;122–282;122–519 |
| 1284 | 1–476;1–423;1–369 |
| 1286 | 1–463;1–301;1–457;1–266;1–483;1–518 |
| 1287 | 1–444;1–490;1–437;1–431;1–439 |
| 1289 | 1–420;1–340;1–420;8–338 |
| 1290 | 1–484;1–475;1–499;1–512;1–498 |
| 1293 | 1–484;1–441 |
| 1295 | 1–463;3–459;3–445;3–458;3–462;25–349;25–392;25–467 |
| 1296 | 1–245;21–486;21–428;25–427;27–249;40–333;40–458;40493;40–475;42–475;42–468;52–452 |
| 1298 | 1–218;1–264;1–472;1–332 |
| 1299 | 1–225;6–105 |
| 1300 | 1–562;2–518;2–505;2–506;3–452 |
| 1301 | 1–446;–291;6–489;6–457;6–350;6–354;6–354;15–501;16–417;16–373;16–224;16–364;16–443;16–491;16–456;16–213;16–274;19–443 |
| 1302 | 1–443;1–399;1–453;142–576;171–567;171–441;171–585;173–534;173–607;173–619;173–596;173–638;173–320;173–639 |
| 1303 | 1–349;1–530;13–445;13–502;32–522;32–597;33–464 |
| 1304 | 1–96;1–381;1–459;1–511 |
| 1305 | 1–471;1–464 |
| 1306 | 1–457;10–482;10–484;10–413 |
| 1307 | 1–387;1–485;1–480 |
| 1308 | 1–339;1–221;3–280;24–96;26–249 |
| 1311 | 1–487;1–447 |
| 1312 | 1–407;1–236;1–269;1–90;–344;1–475;1–460;1–454;1–459;1–416;1–362;1–440;4–454;4–80;17–511;17–295;17–388;17–423;17–82;17–465;17–439;17–467;17–501;17–474;17–516;17–479 |
| 1313 | 1–471;1–347 |
| 1314 | 1–455;6–468;6–504 |
| 1318 | 1–505;1–450 |
| 1319 | 1–562;1–462;1–444;1–428 |
| 1321 | 1–470;27–414;33–227 |
| 1326 | 1–453;1–438;1–54;1–457;1–511;1–176;1–443;1–457;1–509;1–106 |
| 1327 | 1–474;1–469;1–480;2–72;3–293 |
| 1328 | 1–472;1–463 |
| 1329 | 1–411;1–431;1–357;1–444;1–453;1–378 |
| 1330 | 1–480;1–498 |
| 1337 | 1–479;1–480 |
| 1339 | 1–432;5–512;5–247;5–297;18–502;18–512;21–339 |
| 1343 | 1–523;1–453;1–495;1–463;1–415;1–365;1–500;2–415;2–283;2–922;2–442;28–413;28–531;28–922;28–495;28–431;28–504;28–341;28–505;28–417;28–247;28–350;31–340;31–488;31–504;31–339;31–514;31–496;31–501;31–335;31–529;31–487;31–494;31–450;31–546;31–247;31–210;31–495;31–531;31–495;31–532;31–507;31–522;31–504;31–481;31–343;31–480;31–533;31–435 |
| 1344 | 1–82;4–417 |
| 1345 | 1–361;273–692;273–666;273–698;273–358;276–628;278–646;278–694;279–699;279–697;279–654;279–675;279–338;279–643;279–696;279–656;279–697;279–699;279–699;279–698;279–699;279–699;279–646;279–390;279–644;279–693;279–666;279–688;279–699;279–699;279–372;279–699;279–694;279–474;279–684;279–628;279–684;279–696;279–699;279–657;279–695;279–697;279–687;279–696;279–661;279–690;279–692;279–699;279–697;279–699;280–654;280–556;280–614;280–692;280–802;280–683;280–591;280–666;280–483;280–692;280–699;280–599;280–699;280–555;280–562;280–699;280–600;280–390;280–655;280–445;280–681;280–580;280–699;280–613;280–644;280–681;280–690;280–699;280–696;280–680;280–717;280–370;280–696;280–694;280–556;280–675;280–626;280–699;280–685;280–380;280–665;280–674;280–684;280–370;280–666;280–598;280–685;280–699;280–699;280–642;280–579;280–696;280–730;280–677;280–640;280–794;280–696;280–614;280–613;280–696;280–726;280–680;280–692;280–675;280–640;280–376;280–672;280–614;280–699;280–692;280–698;280–697;280–691;280–699;280–685;280–332;280–696;280–677;28 |
| 1346 | 1–361;273–357;276–609;278–626;279–338;279–631;279–553;279–393;279–605;279–620;279–391;279–633;279–466;279–626;279–619;279–471;279–613;279–632;279–629;279–647;279–370;280–473;280–633;280–574;280–392;280–629;280–594;280–546;280–540;280–378;280–618;280–374;280–562;280–594;280–495;280–439;280–611;280–368;280–592;280–539;280–368;280–540;280–585;280–603;280–561;280–368;280–630;280–578;280–616;280–471;280–594;280–592;280–620;280–550;280–616;280–579;280–332;280–494;280–518;280–384 |
| 1347 | 1–397;26–519;26–463;28–382;28–382;30–582;30–142;30–457 |
| 1348 | 1–456;1–400;1–563;2–400;3–434 |
| 1355 | 1–414;1–402;1–492;1–529;1–619;1–533;1–532 |
| 1356 | 1–1108;1–509;380–876 |
| 1357 | 1–327;1–343;1–380;1–323 |
| 1358 | 1–337;1–455;1–509;1–337;1–403;1–481;1–257;1–494;1–523;1–465;1–466;1–412;1–249 |
| 1359 | 1–488;5–518 |
| 1360 | 1–275;1–263;1–264;1–486 |
| 1361 | 1–445;1–822 |
| 1362 | 1–489;1–483;1–450;1–477;2–434;2–445;2–478;2–536;2–376;2–495;2–442;2–498;2–473;2–460;2–234;2–277;2–414;2–484;2– |

TABLE II-continued (Tiling path)

| Seq Id No. | Positions of biological 5'ESTs |
|---|---|
|  | 64;2–404;2–419;3–449;3–438;12–442;12–412;12–642;39–502;39–481;39–536;39–533;39–348;39–514 |
| 1363 | 1–469;86–318;86–361;86–148 |
| 1364 | 1–465;1–489 |
| 1365 | 1–379;1–259;1–432;1–567 |
| 1366 | 1–324;38–504;38–529;43–551;46–499;46–496;47–502;47–464;47–511;47–586;47–555;47–511;47–485;48–433;48–490;96–556;125–639;178–634 |
| 1367 | 1–71;2–131;2–127;19–487 |
| 1368 | 1–462;1–498 |
| 1369 | 1–617;1–216;60–492 |
| 1371 | 1–483;31–511 |
| 1375 | 1–473;1–490;18–394 |
| 1376 | 1–476;1–409 |
| 1377 | 1–256;12–336;12–367;12–487;12–106;12–411;12–359;12–109;12–403;12–409;12–315;12–308;12–388;12–351;12–384;12–390;12–361;12–346;12–385;12–349;12–221;13–349;13–359;13–363;14–209;14–359;14–147 |
| 1378 | 1–278;1–511 |
| 1379 | 1–570;1–368;56–388 |
| 1382 | 1–482;31–579 |
| 1384 | 1–436;32–496;32–500;32–518;32–557;32–509;78–539;78–902 |
| 1386 | 1–289;1–289;1–254;1–333;3–372;23–216 |
| 1387 | 1–61;1–456;1–508;34–473;34–476 |
| 1388 | 1–488;1–61;1–479;1–492 |
| 1389 | 1–613;1–388;1–499;1–475 |
| 1391 | 1–649;1–803;2–342;22–389 |
| 1392 | 1–385;1–471;171–540 |
| 1393 | 1–365;1–498 |
| 1395 | 1–101;1–340 |
| 1397 | 1–165;1–201;1–466;1–430;1–204;1–463;2–181;2–493 |
| 1398 | 1–263;1–477;1–487;1–421;1–490;1–393 |
| 1402 | 1–469;1–496 |
| 1403 | 1–382;2–507;2–524;2–416;2–460 |
| 1404 | 1–79;1–484 |
| 1405 | 1–294;1455;1–320;1–279;178–481 |
| 1406 | 1–500;1–445;1–389;1–769 |
| 1407 | 1–495;1–496;1–322;1–487;1–568;1–436 |
| 1408 | 1–448;1–328;1474;1–415;1–485;1–424;1–461;1–134;1–393;1–426;1–506;1–269;1–472;1–483;1–503;1–463;1–473;3–459;3–434;7–515;7–500;7–500;7–441;7–260;7–532;7–386 |
| 1409 | 1–457;1–465;1–421;1–354;1–466;1–411;1–431;1–368;1–81;1–397;1–465;1–417;1–462;1–433;1–434;1–471;1–465;1–442;1–422;1–458;1–462;1–472;1–433;1–451;20–470;26–459;26–475;26–453;26–441;26–471;26–444;26–449;26–422 |
| 1410 | 1–291;1–552 |
| 1412 | 1–475;4–381;15–451;15–440 |
| 1415 | 1–112;7–507;8–526;8–499;8–507;8–581;8–464;8–428;8–508;8–522;8–509;8–432;8–464;8–507;8–482;8–508;8–433;8–476;8–507;8–435;8–297;8–482;8–181;8–313;8–272;8–528;8–528;8–463;8–475;8–528;8–477;10–528;10–537;10–568;10–528;10–363;10–583;10–522;10–461;10–380;10–528;10–509;10–509;10–522;10–472;10–477;10–522;10–497;10–398;10–568;10–522;10–522;10–477;10–508;10–508;10–528;10–453;10–531;10–469;10–508;10–526;10–507;11–360;11–508;11–303;11–507;11–507;11–482;11–562;11–576;11–562;11–482;11–556;12–509;12–363;12–482;13–331;13–511;13–499;13–407;13–482;13–482;14–497;14–362;14–535;14–507;14–480;14–522;14–531;14–482;14– |

| Seq Id No. | Positions of biological 5'ESTs |
|---|---|
|  | 316;14–522;15–577;30–453;30–522;30–467;30–576;30–507;30–482;30–526;30–509;30–140;30–577;30–527;30–556;30–509;30–477;30–556;30–513;30–517;30–427;30–482;30–296;30–499;30–556;30–556;30–397;30–109;30–241;30–528;30–435;30–522;30–556;30–499;30–469;30–315;30–577;31–528;31–526;31–507;31–562;31–482;31–574;31–359;31–510;31–517;31–522;31–528;31–389;31–529;31–507;31–497;31–508;31–407;31–287;31–508;31–464;31–507;31–577;31–507;31–57 |
| 1393 | 1–365;1–498 |
| 1395 | 1–101;1–340 |
| 1397 | 1–165;1–201;1–466;1–430;1–204;1–463;2–181;2–493 |
| 1398 | 1–263;1–477;1–487;1–421;1–490;1–393 |
| 1402 | 1–469;1–496 |
| 1403 | 1–382;2–507;2–524;2–416;2–460 |
| 1404 | 1–79;1–484 |
| 1416 | 1–309;1–396;1–199;1–309;1–404;1–389;1–382;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–102;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–105;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106;5–106 |
| 1417 | 1–353;1–420 |
| 1418 | 1–472;1–65;31–83;31–83;32–82;351–531 |
| 1419 | 1–354;1–509;1–437;1–370;157–510;157–510;157–510;157–513;157–447;157–504;157–421;157–505;157–510;157–488;157–510;157–486;157–510;157–522;157–486;157–523;157–510;157–487;157–525;157–510;157–492;157–492;157–503;157–522;157–510;157–506;157–506;157–473;157–510;157–510 |
| 1420 | 1–484;1–474;1–122;1–490 |
| 1421 | 1–484;5–86;37–493;52–264;52–480;52–493;54–430;54–524;54–539 |
| 1422 | 1–520;1–520 |
| 1425 | 1–544;1–237 |
| 1426 | 1–481;67–670 |
| 1430 | 1–495;1–456;1–473;1–471 |
| 1431 | 1–293;1–592 |
| 1432 | 1–466;39–540;39–553;43–531;43–545 |
| 1434 | 1–424;1–476;1–500 |
| 1435 | 1–466;1–510;1–481;1–449;1–418;1–472;1–450;1–460;1–386 |
| 1437 | 1–466;1–291;1–497 |
| 1440 | 1–443;307–587 |
| 1446 | 1–351;1–484;1–432;1–421 |
| 1447 | 1–470;1–256 |
| 1448 | 1–424;1–461 |
| 1453 | 1–92;15–457;15–686 |
| 1454 | 1–285;2–457;3–403 |
| 1455 | 1–454;1–501;21–388;21–112;21–266;21–355;35–506 |

TABLE II-continued

(Tiling path)

| Seq Id No. | Positions of biological 5'ESTs |
|---|---|
| 1458 | 1–437;2–281 |
| 1461 | 1–368;1–335;1–92;1–246;1–474 |
| 1462 | 1–469;1–373 |
| 1463 | 1–446;1–830;79–412 |
| 1465 | 1–410;1–600;15–478;16–494;16–473;16–510;16–475;16–445;16–489;17–433;17–382;17–623 |
| 1466 | 1–457;1–425 |
| 1468 | 1–487;1–487 |
| 1470 | 1–460;1–474;1–505 |
| 1471 | 1–493;1–76;1–484;41–515;41–603 |
| 1472 | 1–353;68–486;69–135;69–357;69–278;69–372;69–459;95–480;95–177 |
| 1473 | 1–348;1–387 |
| 1477 | 1–1111;1–449 |
| 1478 | 1–353;69–516;69–357;69–278;69–372;69–135;95–177 |
| 1480 | 1–51;1–375;1–116;1–305;1–105;7–161;7–113;7–226;7–468;7–118;7–335 |
| 1483 | 1–504;1–474;1–612;1–76;1–482;1–486;1–227;1–468;1–495;1–513;1–483;36–466 |
| 1484 | 1–365;1–450;1–110 |
| 1485 | 1–144;19–429;19–440;32–329;32–495;32–512;32–510;32–512;33–464;33–510;33–506 |
| 1487 | 1–160;2–420;2–424;2–349;2–373;2–217;7–485;12–409 |
| 1488 | 1–520;1–296;1–242;1–295;1–296 |
| 1489 | 1–407;1–436 |
| 1490 | 1–678;1–433;1–499;1–394 |
| 1491 | 1–453;1–329 |
| 1493 | 1–391;1–496 |
| 1495 | 1–407;5–490;5–350;5–445;5–495;5–499;5–448;5–462;5–393;5–468;5–480 |
| 1496 | 1–453;1–510;1–466 |
| 1497 | 1–450;1–475;1–474;1–465;1–463;1–291;1–540;1–463;1–426;1–479 |
| 1498 | 1–488;1–776 |
| 1502 | 1–478;1–485 |
| 1513 | 1–362;1–364;1–297;40–484 |
| 1515 | 1–358;1–335;3–320 |
| 1516 | 1–474;1–521;1–435;1–499;1–421;1–425;1–514;1–456;1–482;1–358;1–498;1–437;1–482;1–481;1–509;1–543;1–467;1–486;1–423;1–510;1–474;1–367;1–514;1–469;1–485;1–515;1–486;1–543;1–449;1–513;1–482;1–447;1–191;1–460;1–439;1–415 |
| 1517 | 1–456;30–487;31–439;37–564;280–752 |
| 1519 | 1–480;1–485;1–493;1–509;1–338;1–425;1–484;1–472;1–419;1–502;1–482;1–457;1–506;1–487;1–476;1–479;1–479;1–468;1–479;77–415 |
| 1521 | 1–532;1–377;1–419;1–430;1–485 |
| 1522 | 1–279;11–147;11–339;11–169;11–151;11–163;11–106;11–501;11–418;11–276;11–281;11–107;11–135;11–195;11–131;54–477 |
| 1524 | 1–444;1–354;1–438 |
| 1525 | 1–452;14–512;33–495 |
| 1526 | 1–277;11–337;11–149;11–145;11–167;11–161;11–193;11–104;11–133;11–129;11–105;11–279;11–274;52–515;52–541;52–492;52–534;52–545;52–518;52–531;52–516;52–434;52–589;52–490 |
| 1527 | 1–566;1–295;1–356 |
| 1532 | 1–459;1–232 |
| 1533 | 1–416;1–509 |
| 1534 | 1–475;1–502 |
| 1535 | 1–532;97–597 |
| 1536 | 1–491;4–99 |
| 1538 | 1–496;1–394 |
| 1539 | 1–345;1–501;1–437 |
| 1540 | 1–464;1–524;1–406;1–442 |
| 1543 | 1–478;1–465;1–922;1–475;1–492;1–529;1–488 |
| 1546 | 1–496;1–499;1–477;6–392;6–534;6–535;16–499;16–506;16–290;20–286;52–518;53–492;58–519 |
| 1548 | 1–260;1–496 |
| 1551 | 1–506;1–508;1–459 |
| 1552 | 1–502;2–471;2–463;2–378;2–478;2–400;2–494;2–512;3–139;3–466;3–139;3–139;3–402;3–504;3–503;3–456;3–139;3–465;3–453;3–399;3–471;3–448;3–139;3–456;3–139;3–272;3–139;3–478;3–496;3–537;3–467;3–482;3–139;3–466;3–466;3–265;3–506;3–139;3–139;3–386;3–478;3–521;3–139;4–380;4–469;8–467;40–468;40–520 |
| 1553 | 1–415;1–459;1–679;1–254;1–485;1–385;1–573;1–441;1–385;1–377;1–422;1–423;1–485;1–385 |
| 1555 | 1–546;1–477;1–419 |
| 1557 | 1–466;1–235;1–492 |
| 1558 | 1–339;36–540 |
| 1562 | 1–486;1–490;1–498;1–493;1–331;1–483;1–384;1–409;1–411;1–411;1–485;1–444;1–506;1–440;1–433;1–499;1–398;1–500;1–500;1–524;1–479 |
| 1563 | 1–438;1–487;1–473;1–395;2–474;3–400;3–326;4–456;4–330;4–474;6–442;6–513;6–461;6–243;7–430;7–246;8–432;8–357;8–487;8–482;8–443;8–502;8–442;8–484;8–413;8–480;8–486;8–457;8–481;8–345;8–495;8–495;8–492;8–509;8–507;8–418;8–458;8–491;8–479;8–491;8–458;8–479;8–486;8–401;8–446;8–382;8–481;8–446;8–495;8–437;8–491;8–479;25–455;25–512;25–478;25–475;25–499;25–488;25–486;25–486;25–507;25–488;25–495;25–490;25–486;25–494;25–492;25–451;25–505;25–491;25–495;25–492;25–496;25–515;25–506;25–499;25–488;25–485;25–492;25–449;25–479;25478;25–485;25–380;25–486;25–457;25–480;26–500;91488 |
| 1564 | 1–438;1–487;1–473;1–395;2–474;3–326;3–400;4–474;4–456;4–330;6–442;6–461;6–243;7–246;7–430;8–357;8–500;8–413;8–487;8–443;8–432;8–499;8–442;8–486;8–492;8–480;8–437;8–457;8–481;8–498;8–345;8–503;8–491;8–479;8–482;8–484;8–458;8–491;8–479;8–486;8–491;8–446;8–446;8–382;8–481;8–418;8–458;8–495;8–401;25–491;25–486;25–485;25–475;25–488;25–485;25–457;25–380;25–488;25–495;25–478;25–451;25–494;25–492;25–495;25–492;25–495;25–495;25–478;25–495;25–488;25–486;25–486;25–449;25–479;25–492;25–490;25–455;25–486;25–480;26–497;91–522;91–488 |
| 1567 | 1–460;1–451;3–448;3–521 |
| 1569 | 1–546;1–371;1–505;1–673;1–427;1–450;1–496 |
| 1570 | 1–222;1–421;1–509 |
| 1571 | 1–307;1–482 |
| 1574 | 1–552;1–566 |
| 1575 | 1–248;1–503 |
| 1578 | 1–352;1–334;1–404 |
| 1580 | 1–462;1–507;1–215;1–468;1–510;1–410;1–459;1–470 |
| 1582 | 1–131;6–487 |
| 1585 | 1–481;1–492 |
| 1586 | 1457;1–499 |
| 1587 | 1–74;1–52;1–154;39–492 |
| 1588 | 1–484;1–484;7–106 |
| 1591 | 1–470;22–375;22–219;22–427;22–277;22–447;22–417;22–73;22–412;22–461;22–176;22–374;22–95;44–486;44–332 |
| 1592 | 1–471;22–492;22–510;22–218;22–426;22–509;22–276;22–494;22–512;22–506;22– |

TABLE II-continued (Tiling path)

| Seq Id No. | Positions of biological 5'ESTs |
|---|---|
| | 507;22–518;22–446.22–411;22–460;22–373;22–95;22–374;22–416;22–509;22–513;22–175;22–512;22–507;44–331 |
| 1593 | 1–472;1–611 |
| 1594 | 1–511;1–427;1–393;1–444 |
| 1596 | 1–71;1–79;1–79;1–71;1–71;1–79;1–71;1–71;1–71;1–71;1–71;1–71;1–79;1–79;1–71;1–68;1–79;1–71;1–79;1–71;1–79;1–71;28–534;28–538;28–526;28–454;28–444;28–514;28–473;28–540;28–87;28–278;28–492;28–535;28–409;28–485;28–488;28–477;28–411;28–348;28–472;28–496;28–436;28–523;28–531;28–349;28–537;28–514;28–534;28–505;28–496;28–506;28–514;28–540;28–535;28–457;28–496;28–127;28–506;28–539;28–523;28–534;28–444;28–514;28–421;28–492;28–493;29–493;29–411;29–523;30–514;30–257;30–473;30–354;30–464;30–411;30–412;30–535;30–514;30–415;30–514;30–462;30–514;30–392;30–536;30–493;30–431;30–514;30–455;30–514;30–514;30–444;30–534;30–536;30–464;30–514;30–514;30–496;30–536;30–532;30–523;30–333;30–514;30–506;30–514;30–436;30–473;30–529;30–405;30–378;30–496;30–465;30–459;30–539;30–514;30–506;30–493;30–464;30–537;30–314;30–493;30–473;30–540;30–436;30–460;30–361;30–514;30–412;30–541;30–492;30–492;30–538;30–349;30–374;31–420;31–539;31–536;31–496;31–490;31–534;31–541;31–492 |
| 1599 | 1–425;262–780 |
| 1600 | 1–462;1–322;1–432;30–527;30–527;30–355 |
| 1601 | 1–427;1–465 |
| 1602 | 1–373;–400;–440;1–458;62–464;62–341;113–561 |
| 1603 | 1–456;1–452;14–377;14–466;23–536;23–452;54–555;54–462;54–105;54–488 |
| 1604 | 1–324;242–678;252–672 |
| 1606 | 1–409;64–583;64–489;64–545;64–279;64–526;64–479;64–527;64–558;64–529;64–314;64–544;64–563;64–503;64–551;64–441;64–557;64–562;64–563;64–266;64–409;64–471;64–474;64–478;64–496;64–524;64–503;64–537;64–466;64–522;64–567;64–550;75–353;75–490;75–435;77–570;77–524;77–458;77–316;77–460;77–563;77–581;77–497;77–335;77–272;77–566;77–460;77–503;77–460;77–476;77–563;77–562;77–562;77–541;77–522;77–496;77–561;77–524 |
| 1607 | 1–494;1–480;1–506 |
| 1610 | 1–324;1–491;1–432 |
| 1611 | 1–430;1–394 |
| 1613 | 1–478;1–433 |
| 1615 | 1–481;1–494;1–504;1–509;1–480;1–511;1–500;1–467;1–438;1–504;1–481;1–513;1–385;1–418;1–378 |
| 1616 | 1–954;1–367;1–468;1–465 |
| 1617 | 1–482;1–483;1–363 |
| 1620 | 1–412;1–472 |
| 1621 | 1–423;54–499 |
| 1622 | 1–377;1–495;14–526;14–449;14–475;14–284;14–491;14–483 |
| 1624 | 1–477;1–403;1–302;1–410 |
| 1625 | 1–179;1–393;1–486;1–291;1–483;1–177;1–338;1–521 |
| 1626 | 1–437;1–463 |
| 1627 | 1–429;1–504;1–195;1–508 |
| 1629 | 1–348;1–332 |
| 1630 | 1–143;1–486 |
| 1631 | 1–472;1–472 |
| 1632 | 1–478;1–429;1–485;6–408;7–468;11–484;11–407;13–233;25–504;26–313;26–508;26–436;26–494;26–456;26–521;26–503;26–474;26–545;26–471;26–471;28–502;28–457;28–483;28–499;28–446;28–477;34–430 |
| 1634 | 1–485;1–464 |
| 1635 | 1–245;21–431;21–492;25–430;25–509;27–249;39–529;40–533;40–334;40–460;40–519;40–480;40–493;40–528;40–493;40–570;40–493;40–546;42–508;42–524;42–481;42–527;42–502;42–470;52–454 |
| 1638 | 1–428;5–437 |
| 1640 | 1–450;1–484 |
| 1642 | 1–163;1–456 |
| 1643 | 1–308;1–461;1–461;1–499;1–387;1–465;1–369;1–289;1–279;1–498;1–357;1–404;1–285;1–298;1–438;1–444;1–282;1–277;1–80;1–247;1–355;1–451;–311;1–600 |
| 1646 | 1–488;1–462;1–466;1–282;1–458;1–461;1–462;1–325;1–333;1–464 |
| 1647 | 1–201;–201;2–74;2–74;2–201;2–370;2–74;2–74;3–175 |
| 1649 | 1–403;16–483;30–575;44–568;44–535;44–542;44–527;44–568;44–564;44–182;44–405;44–407;44–535;44–420;44–568;44–205;44–581;44–568;44–539;44–406;44–563;44–526;44–250;44–494;44–449;44–525;48–527;51–474;51–559;51–143;51–438;60–574;104–419;117–218;117–568;119–571;119–568;119–542;119–453;119–575;119–575;120–454;120–185;120–576;120–412;123–558;150–413;150–505;150–581;150–579 |
| 1650 | 1–384;1–412;1–413 |
| 1652 | 1–222;1–449;1–458;1–473;1–400;1–385;1–473 |
| 1653 | 1–278;1–493;1–506;1–517 |
| 1654 | 1–429;1–477;1–478;1–505;1–480 |
| 1655 | 1–452;1–474;1–204;1–467 |
| 1658 | 1–276;1–380;2–398;85–542;85–584;85–554;93–367;93–637;93–470 |
| 1659 | 1–262;1–443;1–58;1–491;1–197;4–459;15–485;17–414;25–552;25–513 |
| 1660 | 1–227;10–422;10–451 |
| 1663 | 1–374;1–581 |
| 1664 | 1–105;1–145;4–489;4–477;4–489;4–737;4–438;4–375;4–498;6–356;6–491;6–407;6–505;6–487 |
| 1665 | 1–485;1–480 |
| 1666 | 1–430;1–641;88–515;88–568;88–566;90–571;135–374 |
| 1667 | 1–105;1–474;1–145;1–456 |
| 1669 | 1–520;1–329;2–473;2–481;2–484;2–423;2–483;2–520;2–422;2–444;2–222;2–470;2–445;2–438;2–525;2–483;2–286;2–480;2–445;2–447;2–483;2–352;2–505;2–447;2–520;2–482;2–585;2–520;2–421;2–223;2–267;2–449;2–478;2–447;2–485;2–464;2–483;2–444;2–452;2–451;2–505;2–523;2–447;2–483;2–505;2–514 |
| 1670 | 1–267;39–267 |
| 1671 | 1–105;1–459;1–145;4–489;4–455;4–531 |
| 1672 | 1–219;1–395;1–458;1–471 |
| 1677 | 1–583;2–601;2–505;2–523;2–490;2–501;2–549;2–95;2–353;2–377;2–581;2–510;2–461;2–554;2–467;2–525;4–469;4–467;4–435;4–449;4–470;4–244;5–412;16–448;39–405;39–501;39–493;39–518;39–500;39–501;39–513;39–595;39–317;41–437;41–562;41–520;41–549;41–560;55–495;68–378 |
| 1678 | 1–398;1–418;1–399;1–407;1–415;1–408;1–401;1–398 |

TABLE II-continued (Tiling path)

| Seq Id No. | Positions of biological 5'ESTs |
|---|---|
| 1680 | 1–376;1–352;1–94;3–243;38–55;38–686;38–316;67–377 |
| 1682 | 1–517;19–213 |
| 1683 | 1–433;68–484;68–485;68–463;68–465;68–485;68–484;68–484;68–484;68–484;68–461;68–467;68–452;68–445;68–467;68–483;68–411;68–461;68–460;68–473;68–477;68–484 |
| 1685 | 1–461;1–691 |
| 1687 | 1–390;1–517 |
| 1696 | 1–577;1–469 |
| 1704 | 1–503;1–621 |
| 1705 | 1–486;1–438;1–288;1–440;1–544;1–353;1–478;1–289;1–318;1–456;1–273;1–352;1–509;1–453;1–443;1–436;2–444 |
| 1706 | 1–489;1–312 |
| 1707 | 1–443;43–421;43–509;64–270;72–542 |
| 1709 | 1–347;1–509 |
| 1711 | 1–509;1–495;1–468;20–479;24–239;27–509;27–336;27–501;30–501;37–485;38–508 |
| 1714 | 1–305;1–481;1–434 |
| 1717 | 1–396;1–437;1–496;1–487 |
| 1718 | 1–476;1–429 |
| 1719 | 1–403;28–476;28–419;28–46;28–442;28–447;28–425;28–406;28–506;39–430 |
| 1720 | 1–511;1–401 |
| 1721 | 1–421;1–350;1–1062;1–355 |
| 1723 | 1–492;1–365;1–323;1–498;1–246;1–351;1–443;1–389;1–271 |
| 1726 | 1–474;1–494 |
| 1727 | 1–457;1–567 |
| 1733 | 1–483;1–466;1–485;1–499;1–479;1–466;1–465;1–483;1–467;1–471;1–492;1–568;1–416;1–498;1–500 |
| 1734 | 1–383;1–510;1–540 |
| 1736 | 1–476;1–505;1–465;1–477;1–477;1–481 |
| 1737 | 1–557;1–617;1–416;1–545;1–712 |
| 1738 | 1–575;1–501;1–649 |
| 1740 | 1–296;1–296;1–296;1–296;1–296;1–296;1–296;1–292;1–296;1–292;1–296;1–292;1–296 |
| 1741 | 1–289;1–478;1–478 |
| 1743 | 1–440;1–440;1–441;1–487 |
| 1744 | 1–512;1–416 |
| 1745 | 1–482;1–767 |
| 1750 | 1–498;1–453;1–486;6–483;6–492;6–365;6–540;6–485;6–465;6–484;6–423;6–486;6–521;6–465;6–514;6–453;6–506;6–489;6–433;6–492;6–478;6–506;6–486;6–465;6–434;6–492;6–484;6–498;6–257;8–464;8–453;18–492;18–492;18–435;18–453;18–431;37–541;40–353;40–525;40–492;40–531;40–511;40–344;40–113;40–529;40–540;40–542;40–541;40–550;40–550;40–492;40–531;41–453;56–571;56–498;56–543;56–559;56–543;56–438;56–531;56–548;56–544;56–542;56–554;56–549;56–587;56–547;56–560 |
| 1754 | 1–462;1–438;1–475 |
| 1755 | 1–466;1–487 |
| 1757 | 1–528;1–700 |
| 1758 | 1–517;8–224 |
| 1759 | 1–409;1–418;3–117 |
| 1760 | 1–127;8–105;9–492;9–186;9–229 |
| 1761 | 1–475;1–455 |
| 1765 | 1–301;1–544;1–374 |
| 1770 | 1–460;1–358;1–421 |
| 1771 | 1–421;1–664 |
| 1772 | 1–414;1–474;1–196;1–581;1–496 |
| 1773 | 1–472;1–50;1–51 |
| 1775 | 1–425;1–483;1–497;1–502;1–476;1–470;1–470;1–467;1–507;1–480;1–464;1–407;1–502;1–379;1–480;1–477;1–499;1–359;1–335;1–488;1–489;1–469;1–496;1–417;1–517;1–496;1–498;1–392;1–480;1–488;1–546;1–505;1–393;1–497;1–272;1–464;1–503;1–520;1–434;1–497;1–467;1–458;1–488;1–462;1–262;1–378;1–463;1–507;1–86;1–452;1–502;1–445;1–444;1–393;1–497;1–368;1–359;1–505;1–464;1–480;1–505;1–386;1–435;1–423;1–50;1–475;1–392;1–493;1–452;1–509;1–500;1–500;–393;1–431;1–556;1–498;1–505;1–489;1–392;1–468;1–489;1–369;1–502;1–435;1–377;1–398;1–409;1–421;1–496;1–467;1–51;1–470;1–499;1–509;1–480;1–439;1–480;1–543;1–502;1–516;1–429;1–491;1–487;1–435;1–500;1–502;1–274;1–393;1–413;1–494;1–464;1–489;1–452;1–328;1–488;1–535;1–554;1–482;1–488;1–464;1–414;1–385;1–469;1–358;1–386;1–392;1–493;1–495;1–386;1–237;1–515;1–339;1–480;1–386;1–240;1–504;2–375;2–456;5–379 |
| 1777 | 1–441;1–462 |
| 1782 | 1–512;1–385 |
| 1783 | 1–297;1–297;8–714;8–493;8–380;8–296;16–297;66–474 |
| 1786 | 1–622;1–509 |
| 1787 | 1–296;1–231;1–304;1–294;1–304;1–308;1–308;1–304;1–308;1–269;1–304;1–304;1–308;1–308;1–308;1–308;1–308;1–304;1–304;1–304;1–304;1–308;1–308;1–304;1–304;1–308 |
| 1788 | 1–435;1–190;1–497 |
| 1791 | 1–518;1–499;1–504;1–508;1–548;1–121;1–450;1–493;1–445;1–500;1–452;1–529;1–417;1–487;1–488;1–499 |
| 1792 | 1–514;1–542;1–517;1–525;1–468;1–558;1–517;1–483;1–502;1–441;1–558;1–160;1–512;1–558;1–428;1–523;1–558;1–517;1–536 |
| 1794 | 1–420;1–477;1–470 |
| 1795 | 1–513;1–477;13–389;16–489;20–462 |
| 1796 | 1–413;1–302;24–433;24–446;24–416;52–462;52–413;52–412;66–554 |
| 1797 | 1–497;1–497;1–331 |
| 1799 | 1–503;1–462;1–486 |
| 1801 | 1–269;12–444;58–465 |
| 1802 | 1–465;1–448;1–509 |
| 1803 | 1–521;55–499;64–385;72–522;72–402;72–580;72–560;72–479;72–534;72–573;72–524;94–548;95–565;95–407;95–510;95–514;95–540;95–594;95–578;95–521;95–601;95–581;95–540;95–606;99–375;99–559;99–642;99–629;99–494;99–242;99–598;99–565;99–575;99–272;99–559;99–590;99–617;99–590;99–586;99–629;99–585;99–474 |
| 1806 | 1–502;1–483;1–500;3–499;6–459;6–484;6–491;6–504;6–460;6–510;6–503;28–438;28–472;28–344;28–500;28–387;28–479;28–500;28–476;28–491;28–439;29–460;29–438;29–387;29–379;29–504;29–451;29–460;29–458;29–460;29–289;31–503;32–506;33–500;33–460;33–404;33–489;39–327;42–504;48–486;48–490 |
| 1808 | 1–469;1–280;1–456;10–77;10–75;10–75;10–77;10–75;10–75;10–75;10–77;10–75;10–75;10–75;10–77;10–77;10–75;10–75;10–77;10–77;10–75;10–75;10–77;10–77;10–75;10–75;10–75;10–77;10–77;10–75;48–411;55–471;55–421;55–459;57–398;66–526;76–418;97–518;99–478;103–475 |
| 1812 | 1–382;1–490;1–473 |
| 1814 | 1–534;1–712 |
| 1815 | 1–516;3–434 |

TABLE II-continued (Tiling path)

| Seq Id No. | Positions of biological 5'ESTs |
|---|---|
| 1818 | 1–450;1–519 |
| 1819 | 1–453;–234;3–425;5–485;5–298;5–222;5–491;5–359;5–463;5–286;5–485;5–429;5–388;6–423;6–472;6–351;6–484;6–286;6–305;6–458;6–321;6–382;6–348;6–495;6–482 |
| 1820 | 1–439;1–580 |
| 1822 | 1–486;1–579;1–476;13–187;15–85;15–85;15–85;15–85;15–354;15–85;16–118 |
| 1824 | 1–482;1–460 |
| 1827 | 1–331;17–381;17–428;17–428;51–338;56–402;57–547;57–306 |
| 1828 | 1–446;19–642;19–500 |
| 1830 | 1–449;1–462 |
| 1833 | 1–429;1–517 |
| 1835 | 1–459;1–527;3–558;38–615;38–443;38–478;38–462;68–545;68–513;68–559 |
| 1836 | 1–454;1–458 |
| 1837 | 1–473;1–437;1–486;1–373;1–262;1–438 |
| 1839 | 1–454;1–451;1–466;1–484;1–440;1–452;1–564;1–454;1–445;24–467 |
| 1842 | 1–476;1–455 |
| 1845 | 1–384;9–478;36–491;36–425;15–577;115–444;115–642;115–642;115–463;115–537;115–626;115–546;142–652;142–641 |
| 1847 | 1–461;1–461 |
| 1848 | 1–462;1–456 |
| 1850 | 1–504;1–526 |
| 1852 | 1–517;1–487;1–452 |
| 1854 | 1–428;1–671;18–508;19–437;21–504;21–595;21–517;21–593;21–494;21–436;21–522;21–514;21–463;21–384;21–443;21–533;21–488;39–415;39–425;66–558 |
| 1856 | 1–440;64–436;64–488;64–404;64–474;64–155;64–385;64–504;64–480;64–507;64–510;74–510 |
| 1859 | 1–408;1–465;1–452 |
| 1860 | 1–78;1–302;1–477;1–477;1–471;1–456;1–326;1–463;1–443;1–454;1–450;1–444;1–477;1–462;1–237;1–354;1–477;1–477;1–444;1–482;1–439;1–480;1–459;1–457;1–431;1–443;1–338;1–314;1–477;1–57;1–460;1–367;1–462;1–263;1–477;1–476;1–435;1–487;1–227;1–433 |
| 1862 | 1–490;1–612 |
| 1863 | 1–463;1–492;1–204;1–344;1–469;1–457;1–464;1–492;1–468;1–498;1–230;1–352;1–391;1–465;1–457;4–596;4–406;24–487;28–458;28–529;28–31 5;28–526;28–529;29–509;33–520;33–529 |
| 1864 | 1–362;1–468;1–411 |
| 1866 | 1–216;1–436;1–500;1–334;2–418;2–503;9–273 |
| 1867 | 1–430;371–836;373–765;373–870;373–771;374–773;374–870;375–871;376–882;376–865;376–824;378–771;378–763;378–773;378–876;391–764;394–773;394–748;396–702;396–871;401–880;401–826;401–773;401–773;401–768;401–722;401–881;401–934;401–909;401–761;401–900;401–754;401–810;401–884;401–899;401–886;401–899;401–752;401–773;401–765;401–800;401–872;401–772;401–799;401–891;401–871;401–876;401–811;401–836;401–871;404–881;404–764;404–894;404–844;404–888;404–862;404–774;404–889;404–872;404–773;406–764;407–882;407–861;407–674;409–880;409–865;409–884 |
| 1869 | 1–447;1–476 |
| 1870 | 1–498;1–509;1–480 |
| 1873 | 1–487;1–487;1–470;108–604;108–540;536–935 |
| 1874 | 1–501;1–450;1–417;1–448;1–508;1–514 |
| 1875 | 1–514;1–480;1–533;1–726 |
| 1877 | 1–496;–294;1–667 |
| 1879 | 1–395;78–493 |
| 1881 | 1–212;2–195;2–471;14–457;14–171;14–113;16–192 |
| 1884 | 1–485;1–406;1–331;1–483;3–488;51–487;51–521 |
| 1887 | 1–501;1–515;1–450;1–417;1–448;1–510 |
| 1891 | 1–522;1–479;44–201;44–600;44–640 |
| 1892 | 1–146;1–443 |
| 1893 | 1–284;1–497;1–431;14–436;61–477 |
| 1900 | 1–491;1–498 |
| 1901 | 1–264;1–559 |
| 1904 | 1–447;1–501 |
| 1905 | 1–540;1–406;1–419;1–464;1–453 |
| 1906 | 1–486;56–158 |
| 1907 | 1–424;1–470;1–413;1–474 |
| 1909 | 1–499;22–396 |
| 1913 | 1–463;1–386;1–397;1–509;1–394;1–393;1–405;1–411;1–487;1–467;1–458;1–465;1–472 |
| 1914 | 1–456;1–322 |
| 1918 | 1–453;1–83;1–419 |
| 1919 | 1–470;1–471 |
| 1920 | 1–524;1–535;1–663 |
| 1923 | 1–234;1–208;1–198;2–150;3–192;3–388;3–161 |
| 1925 | 1–418;1–487 |
| 1930 | 1–404;1–486;1–488;4–468;4–477;4–168;8–352;8–439;8–428;8–367;8–474;8–324 |
| 1934 | 1–530;1–475 |
| 1936 | 1–293;4–386;41–265;41–438;41–402;41–468;41–650;41–400 |
| 1945 | 1–654;1–413;18–491;19–422;21–487;2–578;21–500;21–576;21–421;21–477;21–505;21–497;21–370;21–448;21–430;21–516;21–471;39–410;39–400 |
| 1947 | 1–492;1–1013;1–468;1–193;1–355;1–544;1–481;1–485;1–452;1–442;1–491 |
| 1950 | 1–442;1–477;1–450;1–481;3–533 |
| 1951 | 1–260;1–304;1–427 |
| 1955 | 1–447;1–495;1–432;1–475;1–506 |
| 1957 | 1–439;1–486 |
| 1960 | 1–552;30–501;30–410 |
| 1961 | 1–485;1–531;1–385;1–435;160–668 |
| 1962 | 1–435;1–493;1–508;1–440 |
| 1963 | 1–74;1–83;5–482;7–427;8–482;8–468 |
| 1964 | 1–325;1–427;1–534 |
| 1965 | 1–442;1–490;1–477;1–450;1–486 |
| 1967 | 1–350;1–473;1–393;1–548 |
| 1968 | 1–511;162–531;162–609 |
| 1969 | 1–708;1–486;428–708 |
| 1970 | 1–496;47–209 |
| 1971 | 1–483;171–488;171–482;171–430;171–483 |
| 1972 | 1–440;1–474;1–407;1–484;1–570;1–495;1–519;1–415;1–366;1–444;1–542;1–429;1–251;1–198;1–373;1–418;1–466;1–402;1–452;1–377;1–483;1–563;1–306;1–484 |
| 1973 | 24–427;24–446;24–429;24–175;24–445;24–446;26–326;26–442;26–404;26–442;27–440;27–326;31–446;31–446;31–456;31–462;33–249;33–450;33–206;33–447;33–442;33–440;33–424;33–442;33–467;33–444;33–430;33–447;33–444;33–440;33–437;33–444;33–444;33–442;33–426;33–448;33–303;33–451;33–444;33–290;33–442;33–448;33–447;33–448;33–440;33–110;33–441;33–441;33–459;33–442;33–442;33–442;33–442;33–461;33–424;33–444;33–441;33–440;33–430;33–449;33–282;33–448;33–442;33–458;33–442;33–417;33–461;33–416;33–463;33–444;33–447;33–417;33–457;33–442;33–444;33– |

TABLE II-continued (Tiling path)

| Seq Id No. | Positions of biological 5'ESTs |
|---|---|
| | 431;33–441;33–423;33–421;33–406;33–436;33–413;33–459;33–429;33–462;34–446;36–447;36–447;36–423;36–447;36–447;36–464;36–423;36–447;36–428;36–292 |
| 1974 | 1–374;1–391;2–137;2–261;2–137;2–137;2–137;2–137;2–137;2–137;2–380;2–137;2–391;2–268;2–137;2–137;2–137;2–125;3–376;37–502 |
| 1975 | 1–470;1–426 |
| 1976 | 1–394;1–398;1–398 |
| 1977 | 1–276;1–478 |
| 1978 | 1–439;1–439;1–358;1–491 |
| 1979 | 1–450;1–381;1–91;1–396 |
| 1980 | 1–278;7–370;80–345;97–340 |
| 1982 | 1–470;1–471 |
| 1983 | 1–441;1–512;1–230;1–396;1–489;1–437;1–456;1–490;1–489 |
| 1984 | 1–408;14–405;320–731;320–686;320–809;320–733;320–704;320–782;320–451;320–747;320–786;320–834;320–792;320–734;320–777;320–726;514–717 |
| 1985 | 1–507;1–455 |
| 1993 | 1–281;1–486;1–444 |
| 1994 | 1–482;1–451;1–372 |
| 1995 | 1–503;1–479;1–540;3–621 |
| 1997 | 1–474;1–468;1–477;2–452;2–237;34–439 |
| 1998 | 1–463;5–543;5–463 |
| 2000 | 1–497;1–487 |
| 2003 | 1–464;1–456;1–464;1–345;1–480;1–463;18–475;49–567 |
| 2004 | 1–454;11–466;11–474;11–474;11–355;11–490;11–473;28–485 |
| 2005 | 1–256;1–511;1–427;2–376;2–419;2–256;3–471;3–473;3–491;3–493;3–464;3–417;3–446;3–261;3–213;3–494;3–280;3–424;3–425;3–350;3–491;3–428;3–471;3–401;3–459;3–500;3–464;3–446;3–355;3–417;3–416;3–493;3–403;3–464;3–626;3–468;3–446;3–467;3–418;3–471 |
| 2006 | 1–422;1–423;1–464;1–357;2–468;2–412;2–447;2–250;2–455;2–455;2–464;2–468;2–453;2–463;4–502;4–452;4–487;14–447;14–420;14–424;36–336;36–109;36–345;37–445;52–427;273–800 |
| 2007 | 1–46;1–432 |
| 2008 | 1–260;1–495 |
| 2009 | 1–494;2–518;2–518;3–434;6–478;7–497;7–434;10–471;10–498;11–215;13–449;32–495;32–502;32–449;32–499;32–478;32–503;32–517;32–506;33–497;33–400;33–522;33–449;33–505;33–517;33–497;33–520;33–495;33–519;33–492;34–501;34–493;34–495;34–501;34–476;34–513;34–478;34–515;34–489;34–497;36–449;36–511;38–494;38–492;38–498;38–475;38–496;38–502;38–494;38–496;38–501;38–508;38–519;38–188;38–520;38–426;38–495;38–501;38–492;38–440;38–449;38–510;38–499;38–478;38–478;38–497;38–478;38–495;38–395;45–504;45–498;45–495;45–478;45–510;45–473;45–519;46–493;47–426;49–497;49–476;49–505;49–491;50–473;50–502;50–508;50–520;50–510;50–408;50–492;50–449;50–504;50–502;50–510;50–470;51–497;55–370;55–520;55–519;55–277;70–512;78–508;78–497;78–510;78–496;78–510;78–478;78–505;78–478;78–489;78–504;78–501;78–520;78–510;78–507;78–522;78–513;78–513;78–513;78–496;78–487;78–510;78–394;78–20 1;78–507;78–505;78–510;78–520;78–497;78–284;78–355;78–509 |
| 2010 | 1–419;1–421;1–370;1–419;1–404;1–421;1–418;1–420;1–419 |

TABLE II-continued (Tiling path)

| Seq Id No. | Positions of biological 5'ESTs |
|---|---|
| 2011 | 1–514;1–508;1–472;1–509;1–428;1–484;1–498;1–478;1–455 |
| 2017 | 1–497;1–506;1–517;1–489;12–401;12–346;12–517;12–453;12–227;12–381;12–223;12–260;18–585;21–507;23–510;23–532;33–524;33–603;33–454;34–469;34–456;34–229;34–527;34–520;34–521;34–525;34–517;34–475;34–349;34–455;34–537;34–546;34–409;34–438;34–557;34–351;34–506;34–457;34–493;34–523;34–418;34–482;34–635;34–473;34–355;34–532;34–531;37–358;37–502;37–518;37–508;37–545;40–377;40–497;43–516;44–528;45–507;46–596;52–363;64–252;64–544;67–546;166–617;226–635;226–583 |
| 2018 | 1–502;8–468;11–481;11–455;11–456 |
| 2019 | 1–432;1–603;1–67 |
| 2020 | 1–389;1–473 |
| 2021 | 1–491;1–515;1–420;1–486;1–445;1–84;1–435;1–474;1–503;1–491;1–479;1–444;1–439;1–497;1–341;1–472;1–405;1–494;1–497 |
| 2024 | 1–594;2–365;2–489;2–477 |
| 2028 | 1–255;1–345 |
| 2029 | 1–462;1470;1–422;1–380 |
| 2030 | 1–534;1–427 |
| 2034 | 1–482;1–463;1–500;1–506 |
| 2035 | 1–468;1–492 |
| 2036 | 1–473;1–573;1–587 |
| 2037 | 1–143;1–55;1–507 |
| 2038 | 1–466;1–365 |
| 2040 | 1–475;1–497;1–501 |
| 2042 | 1–430;29–494 |
| 2043 | 1–483;1–464 |
| 2044 | 1–220;9–131;9–179;9–160;9–232;9–73;9–162;9–160;9–242;9–135;9–481;9–58;9–148;9–191;9–84;9–160;9–190;9–160;9–81 |
| 2046 | 1–386;1–462;1–462 |
| 2048 | 1–516;1–526;1–223 |
| 2050 | 1–440;1–457;1–482 |
| 2051 | 1–539;1–464;1–521;11–487;11–397;11–507;11–538;11–510;11–429;11–476;11–462;22–453;25–450;25–387;25–530 |
| 2053 | 1–462;182–666;182–477;227–733;412–820 |
| 2055 | 1–279;1–662;1–481 |
| 2067 | 1–461;1–236 |
| 2068 | 1–466;312–617 |
| 2069 | 1–446;1–503;1–435 |
| 2075 | 1–460;1–558 |
| 2082 | 1–602;219–665;219–670;219–616;219–665;219–513;219–672;219–665;219–658;219–524;219–671;219–640;219–634;219–642;219–601;219–669;219–673;219–664;219–665;219–663;219–665;219–664;219–664;219–661;219–665;219–658;219–677;219–662;219–616;219–665;219–671;221–669;221–673;221–665;221–660;221–625;221–673;221–670;221–673;221–591;221–578;221–667;221–666;221–672;221–667;221–673;221–440;221–669;221–655;221–668;221–665;221–640;221–685;221–657;221–580;221–640;221–675;221–493;221–434;221–670;221–654;233–657 |
| 2090 | 1–448;1–390;1–363;1–356;1–415;1–480;1–415 |
| 2100 | 1–466;1–481;1–486;1–435;1–501;1–492;1–309;1–480;1–453;1–484;1–313;1–451;1–501;1–457;1–448;1–505;1–438;1–375;1–439;1–424;1–477;1–476;1–490;1–478;1–420;1–505;1–503;1–482;1–96;1–300;1–503;1–488;1–501;1–434;1–470;1–491;1–305;1–479;1–488;1–483;1–461;1–501;1– |

TABLE II-continued

(Tiling path)

| Seq Id No. | Positions of biological 5'ESTs |
|---|---|
| | 501;1–436;1–501;1–397;1–375;1–505;1–394;1–475;1–459 |
| 2121 | 1–406;24–407;95–241;95–240;95–240;95–241;95–179;95–236;95–402 |
| 2123 | 1–396;1–533 |
| 2132 | 1–388;1–371;1–376;3–335 |
| 2144 | 1–451;1–533 |
| 2156 | 1–600;1–478;1–471;1–510 |
| 2167 | 1–512;1–476;1–479;1–481;1–473;1–464 |
| 2170 | 1–192;1–489;1–532;1–297;1–505 |
| 2174 | 1–315;2–543;2–444;2–469;2–462;2–564;2–479 |
| 2187 | 1–428;9–451 |
| 2189 | 1–488;1–503 |
| 2194 | 1–455;1–266;1–320;1–394;18–404;18–487 |
| 2195 | 1–455;1–266;1–320;1–394;18–404;18–568 |
| 2198 | 1–439;1–439 |
| 2200 | 1–205;1–413;1–506;1–475;1–544;1–393;1–476;1–543 |
| 2209 | 1–397;3–475;405–892 |
| 2210 | 1–499;1–486 |
| 2218 | 1–426;1–510 |
| 2220 | 1–341;1–473 |
| 2239 | 1–482;1–482;1–370;1–401;1–508 |
| 2256 | 1–428;25–507;25–514;25–517;25–516;25–537;25–508;25–553;25–453;25–475;25–510;25–518;25–525;25–472 |
| 2258 | 1–428;25–508;25–453;25–475;25–472 |
| 2260 | 1–470;1–395;1–315;1–404;1–472;1–472;1–460;1–460 |
| 2261 | 1–345;1–460;1–428 |
| 2262 | 1–283;1–599;1–497 |
| 2282 | 1–466;1–495;1–471;1–456;1–451;1–501;1–537;1–414;1–468;1–430;1–426 |
| 2312 | 1–425;1–468 |
| 2334 | 1–428;1–360;1–443 |
| 2351 | 1–387;86–616 |
| 2355 | 1–479;1–339;1–413 |
| 2356 | 1–181;1–407;1–476;1–488;1–404;1–470;1–477;1–488 |
| 2360 | 1–376;26–190;26–540 |
| 2366 | 1–478;1–531;1–478;1–513 |
| 2367 | 1–494;1–357;1–534;5–212;5–551;5–311;5–558;5–500;5–398;5–372;5–505;5–496;5–358;5–507;5–554;5–499;5–510;5–374;5–221;5–389;5–373;5–340;6–543;6–389;6–366;6–108;6–339;6–136;6–537;6–560;6–393;6–389;6–533;6–492;6–199;6–551;6–388;6–73;6–500;6–510;6–388;6–388;6–507;6–559;6–540;6–505;6–565;6–68;6–309;6–374;6–290;6–136;6–558;6–366;6–537;6–537;6–213;6–507;6–403;6–487;6–136;6–374;6–494;6–136;6–499;6–236;6–496;6–374;6–542;6–321;6–561;6–507;6–321;6–374;6–275;6–299;6–193;6–512;6–489;6–356;6–368;6–494;6–384;6–226;6–366;6–308;6–497;6–385;6–137;6–501;6–374;6–340;6–559;6–138;6–496;6–136;6–506;6–382;6–490;6–120;6–494;6–374;6–134;6–134;6–511;6–338;6–374;6–333;6–540;6–493;6–503;6–136;6–507;6–511;6–374;6–374;6–374;6–558;6–533;6–499;6–235;6–128;6–500;6–386;6–134;7–290;7–294;7–503;7–200;7–373;7–374;8–213;9–385;11–340;11–145;11–558;11–537;11–339;11–509;11–272;11–554;11–496;11–558;11–134;11–558;11–199;11–507;11–489;11–496;11–403;11–292;11–312;11–235;11–558;11–355;11–507;11–546;11–147;11–389;11–339;11–374;11–554;11–300;11–138;11–300;11–5 |
| 2368 | 1–350;1–148;1–437;1–472 |
| 2369 | 1–441;1–489;1–489 |
| 2370 | 1–348;1–427;1–454;1–294;2–220 |
| 2371 | 1–388;1–371;1–388;1–374;1–387;1–50 |
| 2372 | 1–474;12–474;22–481;22–510;22–455;22–462;46–502;46–552;121–556;138–531 |
| 2373 | 1–523;1–427;1–497;1–413;1–471;1–457;1–470;1–517;1–458;1–497 |
| 2376 | 1–430;1–520;1–472 |
| 2379 | 1–528;1–488;1–442;1–531;1–458;1–528;1–528;1–515;1–515;1–534;1–534;1–507;1–515;1–515;1–530;1–528;1–515;1–528;1–507;1–514;1–528;1–489;1–473;1–415;1–515;1–507;1–512;1–534;1–515;1–515;1–529;1–515;1–515;1–429;1–515;1–435;1–507;1–528;1–531;1–534;1–503;1–531;1–528;1–458;1–527;1–481;1–507;1–515;1–514;1–531;1–530;1–529;1–528;1–515;1–485;1–515;1–515;1–531;1–507;1–515;1–502;1–515;1–425;1–473;1–534;1–379;1–515;1–524;1–531;1–443;1–423;1–479;1–458;1–507;1–376;1–499;1–386;1–458;1–528;1–517;1–515;1–515;1–421;1–454;1–515;1–531;1–423;1–507;1–530;1–529;1–531;1–516;1–515;1–507;1–392;1–531;1–515;1–514;1–515;1–515;1–502;1–514;1–478;1–482;1–499;1–531;1–433;1–454;1–380;1–463;1–54;1–534;1–531;4–507 |
| 2384 | 1–459;1–432;1–456;1–249;1–455;1–170;1–239;1–429;1–247;1–246;1–84;1–247;1–244;1–232;1–239;1–246;1–415;1–243;1–389;1–319;1–226;1–430;1–372;1–84;1–456;1–397;1–85;1–379;1–456;1–389;1–84;1–154;1–200;1–198;1–456;1–93;1–265;1–153;1–239;1–212;1–93;1–242;1–355;1–420;1–389;1–385;1–395;1–383;1–456;1–52;1–170;1–75;1–247;1–322;1–343;1–443;1–250;1–456;1–103;1–105;1–105;1–104;1–429;1–264;1–389;1–56;1–295;1–154;1–245;1–245;1–267;1–225;1–219;1–264;1–104;1–395;1–120;1–456;1–246;1–264;1–459;1–73;1–250;1–247;38–434;211–649;211–626;222–467;302–660 |
| 2387 | 1–355;1–439;1–447;1–517;1–488;1–488 |
| 2390 | 1–445;1–523;1–471;1–477;1–489;1–354;1–445 |
| 2392 | 1–489;369–856 |
| 2396 | 1–349;1–487;57–497 |
| 2397 | 1–370;1–513;1–584;1–529;1–485;1–580;1–579;1–489;1–505;1–488;1–464;1–467;1–423;1–529;1–318;1–314 |
| 2400 | 1–396;1–459 |
| 2401 | 1–487;10–348;10–407;10–442;10–256;10–217;10–442;16–457 |
| 2407 | 1–496;1–339 |
| 2408 | 1–171;1–374 |
| 2410 | 1–360;1–451;1–468;1–460 |
| 2411 | 1–437;1–465;2–248;2–392;2–515;2–476;2–287;2–472;2–244;2–385;2–183;2–480;2–427;2–96;2–75;2–535;2–445;2–168;2–287;2–472;2–244;2–385;2–183;2–480;2–427;2–96;2–75;2–535;2–445;2–168;2–558;2–485;2–117;2–296;2–519;2–123;2–483;2–516;2–444;2–340;2–519;2–298;2–529;2–239;2–445;2–91;2–503;2–366;2–477;2437;2–325;2–350;2–334;3–210;3–119;4–284;4–502;4–483;4–491;4–337;4–471;4–234;232–762;333–392;410–781;490–845;490–857 |
| 2414 | 1–458;2–447;19–548;26–416 |
| 2416 | 1–426;1–199;1–199;1–199;3–64;3–306;3–226;5–208;75–488;75–490 |
| 2417 | 1–41;14–408;322–739;322–693;322–814;322–741;322–711;322–790;322–454;322–755;322–794;322–800;322–742;322–785;322–734;518–723;534–930 814;322–741;322–711;322–790;322– |

TABLE II-continued

(Tiling path)

| Seq Id No. | Positions of biological 5'ESTs |
|---|---|
| | 454;322–755;322–794;322–800;322–742;322–785;322–734;518–723;534–930 |
| 2418 | 1–489;1–369 |
| 2419 | 1–220;101–505 |
| 2421 | 1–345;1–476 |
| 2423 | 1–501;1–491;6–463 |
| 2424 | 1–347;1–251 |
| 2425 | 1–480;1–488 |
| 2426 | 1–506;1–398;1–475;1–444 |
| 2427 | 1–492;13–447;17–516;18–442;18–445;18–475;18–480;18–481;18–491;18–256;18–445;18–478;18–306;19–464;21–474;21–425;22–495;22–478;22–481;23–404;26–437;32–506 |
| 2431 | 1–433;1–520;1–469;1–380;1–542;1–476;1–433;1–511;1–309;1–465 |
| 2432 | 1–482;1–489;20–490 |
| 2433 | 1–158;1–376;1–377;1–537 |
| 2435 | 1–461;1–388;1–557;1–337;1–490 |
| 2436 | 1–380;21–493;32–471;32–336 |
| 2438 | 1–422;1–433 |
| 2439 | 1–496;1–581;1–489 |
| 2440 | 1–265;1–522;1–480;1–456;1–432 |
| 2442 | 1–401;1–444 |
| 2445 | 1–472;1–504 |
| 2446 | 1–367;1–430 |
| 2447 | 1–229;19–485 |
| 2452 | 1–196;1–461;1–230;1–309;1–467;1–425;1–437;1–449;1–417;1–460;1–465 |
| 2453 | 1–480;18–450;18–514;18–465;18–562;18–330;18–520;18–476;18–432;18–375;18–494;18–406;18–426;18–468;18–494;18–522;18–435;18–554;18–220;18–368;18–466;18–469;18–428;18–543;18–129;18–477;18–466;18–234;18–417;18–502;18–469;18–513;18–560;18–553;18–388;18–435;18–433;18–525;18–446;18–514;33–506;34–489;34–502;34–369;34–571;34–410;34–397;34–516;34–448;34–506;34–569;34–480;34–259;34–336;34–571;34–421;34–563;34–450;34–514;34–531;34–261;34–536;34–525;34–551;34–506;34–565;34–96;38–371;49–505;49–510;49–131;49–242;49–525;49–453;49–571;49–530;49–469;49–543;49–544;49–518 |
| 2454 | 1–434;1–551;83–285;83–194;83–299;99–323;99–323;99–161;114–196;114–307 |
| 2462 | 1–484;1–498;1–490 |
| 2464 | 1–250;1–499 |
| 2465 | 1–434;1–478;1–498;1–389 |
| 2466 | 1–453;18–378;18–489;18–483;18–386 |
| 2467 | 1–399;1–205;1–358;1–383;1–511;1–385 |
| 2468 | 1–314;1–465;1–408;1–493;1–441;1–292;1–492 |
| 2469 | 1–452;41–358 |
| 2470 | 1–263;1–381;1–293;1–422;1–553;1–556;2–462;2–382;2–200;2–473;2–429 |
| 2471 | 1–362;1–396;1–457 |
| 2475 | 1–527;1–501 |
| 2478 | 1–270;1–266;1–266;1–86;1–255;1–268;1–270;1–267;1–467 |
| 2479 | 1–323;1–360;1–357 |
| 2481 | 1–537;1–483 |
| 2482 | 1–343;1–479 |
| 2484 | 1–514;1–449;1–342 |
| 2485 | 1–430;1–458;1–459;1–469;1–102;6–259;7–532;7–464;7–331;7–348;8–443;8–488;8–282;8–422;8–472;8–582;8–419;8–55;8–330;8–437;8–55;13–433;50–547;50–525;50–507;50–547;50–561;50–533;50–524;50–531;50–530;50–319;53–549;53–552;53–545;53–524;53–417 |
| 2486 | 1–406;1–420 |
| 2487 | 1–549;3–410;3–526;3–507;3–541;3–276;3–506;3–518;3–378;3–435;3–489;3–542;3–509;3–518;3–276;3–317;3–462;3–548;4–308;4–436;4–542;4–518;4–180;4–498;4–526;4–492;4–461;4–462;4–462;4–462;4–462;4–518;4–512;4–510;4–167;4–509;4–498;4–489;4–324;4–332;4–462;4–430;4–494;4–462;4–526;4–518;4–480;4–498;4–543;4–493;4–489;4–410;4–526;4–518;4–518;4–509;4–526;4–526;4–495;4–526;4–461;4–481;6–498;6–393;6–548;6–509;6–122;6–518;6–526;6–542;6–549;6–551;6–317;6–410;6–435;6–506;6–435;6–325;6–492;6–498;6–462;6–442;6–332;6–507;6–549;6–509;6–518;6–546;6–526;6–548;6–410;6–462;6–460;6–462;6–462;6–526;6–492;6–495;6–317;6–533;6–518;6–462;6–506;6–518;6–402;6–548;6–545;6–509;6–518;6–461;6–484;6–496;6–541;6–509;6–498;6–462;6–489;6–440;6–493;6–283;6–435;6–286;6–427;6–489;6–518;6–481;6–526;6–410;6–462;6–497;6–507;6–492;6–461;6–518;6–518;6–518;6–544;6–498;6–143;6–526;6–332;6–462;6–506;6–480;6–443;6–435;6–526;6–461;6–462;6–492;6–380;6–376;6–518;6–526;6–462;6–518;6–551;6–462;6–498;6–526;6–494;6–460;6–462;6–308;6–518;6–462;6–518;6–462;6–542;6–489;6–54 |
| 2489 | 1–344;1–410;1–241 |
| 2490 | 1–406;1–493;1–358 |
| 2492 | 1–533;1–377 |
| 2493 | 1–50;1–50;1–453;397–895 |
| 2494 | 1–561;1–498;1–339;1–404;1–377;1–494;1–477;1–462;1–453;1–508;1–486;1–498 |
| 2496 | 1–486;1–458 |
| 2497 | 1–491;295–793 |
| 2499 | 1–503;322–780 |
| 2500 | 1–278;1–300;1–291;1–290;1–277;1–240;1–278;1–300 |
| 2502 | 1–391;1–405;1–392 |
| 2503 | 1–377;1–453;1–457;1–476;1–334;1–316 |
| 2505 | 1–428;15–509;15–431;15–519;15–463;15–448;15–432;15–493;15–281;21–492;21–543;21–443 |
| 2506 | 1–479;1–507 |
| 2508 | 1–468;1–479;1–465;1–477;1–442;1–465;1–471;1–469;1–449;1–368;1–479;1–479;1–467;1–465;1–468;1–411;1–479;1–423;1–479;1–466;1–464;1–479;1–472;1–376;1–464;1–488;1–269;1–465;1–464;1–479;1–467;1–407;1–479;1–479;1–479;1–464;1–410;1–479;1–466;1–465;1–479;1–488;1–391;1–431;1–277;1–464;1–463;1–479;1–468 |
| 2510 | 1–489;32–423 |
| 2511 | 1–508;1–407;1–447;1–491;1–258;1–504 |
| 2516 | 1–317;1–553 |
| 2520 | 1–486;27–498;37–495;37–511;37–518;37–507;37–517;37–518;37–525;37–516;38–507 |
| 2522 | 1–436;1–452;1–394 |
| 2523 | 1–510;1–538;1–430;1–469;1–367;1–482;1–492;1–509;1–520;1–470;17–380;17–370;17–519 |
| 2524 | 1–510;1–492;1–600;1–430;1–469;1–367;1–482;1–509;1–520;1–470;17–555;17–380;17–370;17–519 |
| 2528 | 1–495;1–473;1–442;1–513;1–475;1–492 |
| 2529 | 1–358;1–494;1–77;1–128;1–490;1–228;1–493;1–429;1–481;1–483;1–326;1–257;1–504;1–507;1–501;1–525;1–508;1–257 |
| 2530 | 1–444;1–500;1–448;1–393;1–496;1–232 |
| 2535 | 1–463;1–381 |
| 2539 | 1–448;27–484 |

TABLE II-continued (Tiling path)

| Seq Id No. | Positions of biological 5'ESTs |
|---|---|
| 2540 | 1–575;1–402;1–388;2–467;2–508;2–327;13–398;41–552;70–546;70–497;74–566;74–560;131–224;131.224;131–224;131–224;131–224;131–224;520–985 |
| 2541 | 1–508;1–418 |
| 2542 | 1–484;1–484 |
| 2543 | 1–544;1–496;1–496 |
| 2544 | 1–224;1–408;1–450 |
| 2545 | 1–499;27–498;38–519;48–545;51–525;51–538;51–504;51–514;51–520;65–564;65–356;69–558;69–558;69–486;69–537;69–563;72–566;81–549;81–559;81–558;82–549;83–564;83–547;83–557;83–529;83–561;83–561;83–563;83–581;83–584;83–572;83–568;83–235;83–563;84–567;85–567;85–571;85–542;85–557;85–280;85–535;86–566;86–579;87–557;91–575;91–435;91–545;95–557;127–569 |
| 2546 | 1–428;1–429;1–438;1–428;1–433;1–433;1–412;1–428;1–418;1–386;1–399 |
| 2548 | 1–497;1–397 |
| 2550 | 1–337;1–478;1–467;1–370;1–395 |
| 2553 | 1–374;1–390 |
| 2560 | 1–361;28–503;28–407;28–438;28–450;28–420;28–503;28–505 |
| 2562 | 1–472;22–491;57–539;57–504;57–522;57–589;57–578;57–541;57–573;57–522 |
| 2564 | 1–243;3–513;3–424 |
| 2566 | 1–349;1–482;1–459;1–69;5–510 |
| 2568 | 1–256;1–483;1–466;40–460 |
| 2571 | 1–483;1–475 |
| 2572 | 1–452;1–162 |
| 2574 | 1–359;1–530;362–786;362–554;362–798;362–834 |
| 2575 | 1–530;1–455 |
| 2576 | 1–456;6–77 |
| 2577 | 1–98;1–94;8–493;8–497;8–479;31–253;48–534;48–517 |
| 2578 | 1–98;1–94;8–493;8–497;8–479;31–253;43–534;48–517 |
| 2579 | 1–496;1–497;3–501;3–501;3–556;3–453 |
| 2580 | 1–430;6–352;6–427;6–473;6–622;6–473;6–391;6–399;6–318;6–391;6–331;6–458;6–520;6–472;6–419;6–513 |
| 2582 | 1–436;1–450 |
| 2584 | 1–489;1–439;1–144;1–295;1–468;1–227;15–366;16–506;18–513;141–596;141–510;141–647;144–615;144–603;147–631 |
| 2587 | 1–490;1–496;1–502;1–463;2–388;2–458;2–491;2–549;2–508;2–447;2–511;2–455;2–497;2–473;2–486;2–242;2–64;2–417;2–432;2–427;2–287;3–451;3–462;12–425;12–455;39–546;39–549;39–527;39–494;39–515;39–560;39–355 |
| 2589 | 1–321;1–422;1–482;1–492 |
| 2591 | 1–368;1–462;1–499;3–533;3–216;3–279;3–465;37–541;37–454 |
| 2592 | 1–272;92–574;92–563;92–554;92–575;94–558;94–573 |
| 2593 | 1–490;1–439 |
| 2594 | 1–485;1–233;1–479;1–486;1–99;1–383;1–433;1–522;1–500;1–453;1–475 |
| 2596 | 1–489;1–330;1–473;1–506;1–493;1–459;1–467 |
| 2598 | 1–479;1–504 |
| 2599 | 1–506;1–386;1–290;16–480 |
| 2605 | 1–508;1–538;1–444 |
| 2608 | 1–355;39–409;55–447;55–444;55–447;55–447;55–447;55–436;55–447;55–447;55–418;55–447;55–441;55–447;55–447;55–447;55–422;55–432;55–305;55–447;55–424;55–432;55–373;55–447;55–379;55–447;55–447;55–447;55–432;55–443;55–447;55–385;55–443;55–416;55–423;55–447;55–447;55–443;55–420;55–447;55–465;55–437;55–445;55–432;55–447;70–466;70–454;70–446;70–453;70–447;72–450;72–466;72–419;72–467;72–471;72–466;76–454;77–440;77–439;77–466;77–465;77–451;77–466;80–467;80–447;80–467;80–454;80–454;92–459;104–447;104–440;104–453;104–465;104–448;104–441;104–458;104–454;104–466;104–461;104–454;106–456;138–466;138–454;138–466;138–386;138–466;138–443;138–471;138–466;138–420;138–446;138–466 |
| 2612 | 1–420;180–664;189–629;189–664;189–659;189–656;189–607;189–720;189–654;192–631;192–422;193–492;193–679;193–631;193–455;193–625;193–607;193–642;193–631;193–648;193–551;193–683 |
| 2613 | 1–421;1–468;1–487;1–466;58–552;58–551;71–556 |
| 2614 | 1–450;266–747;275–747;275–739;275–690;275–742;275–712;275–803;275–737;278–714;278–505;279–714;279–575;279–762;279–538;279–708;279–690;279–725;279–714;279–731;279–634;279–766 |
| 2617 | 1–460;09–578;109–165 |
| 2618 | 1–510;1–511;1–461;2–378;3–267;8–472 |
| 2619 | 1–483;23–400;23–209;25–77;51–386;51–489;51–476;51–428;54–346;56–570;63–554;63–545;63–533;97–619 |
| 2620 | 1–488;1–472 |
| 2622 | 1–429;14–241 |
| 2623 | 1–351;1–428;1–434;1–326;1–432;1–436;1–433;1–424;1–437;1–432;1–421;1–431;1–435;1–317;1–436;1–437;1–433;1–433;1–421;1–262;1–433;1–339;1–432;1–427;1–394;1–414;1–435;1–391;1–244;1–384;1–437;1–331;1–425;1–424;1–437;1–430;1–427;1–431;1–319;1–416;1–128;1–432;1–425;1–425;1–421 |
| 2635 | 1–488;1–312;1–439 |
| 2638 | 1–158;1–243;1–388;1–367;1–388;1–384;1–371;1–375;1–371;1–386;1–371;1–360;1–388;1–363;1–371;4–153;14–113;14–113;16–234;16–174 |
| 2642 | 1–444;1–367 |
| 2644 | 1–487;1–471;1–493 |
| 2647 | 1–493;1–436;1–433;1–459;1–522;1–493;1–107;1–483;1–327 |
| 2651 | 1–347;1–354;1–346;1–355;1–357 |
| 2652 | 1466;1–238;1–464;1–467;1–440;1–483;1–440;1–453;1–472;15–457;18–483;18–529;18–504;18–495;18–545;18–421;18–372;18–424;18–492;18–447;18–534;18–100;18–534;18–529;18–511;18–305;18–586;18–304;18–555;18–534;18–472;18–239;18–584;18–499;19–487;21–551;26–528;26–513;26–485;26–486;26–513;26–440;26–547;26–557;26–372;26–533;26–532;26–504 |
| 2654 | 1–472;1–435 |
| 2655 | 1–425;7–512 |
| 2656 | 1–400;1–406;1–389;1–395;1–407;1–407;250–372 |
| 2657 | 1–461;1–450 |
| 2658 | 1–97;20–414 |
| 2660 | 1–300;1–455;2–407;3–484;3–331;3–175;3–289;3–459;3–454;3–355;3–253;3–274;3–204;3–335;3–305;3–388;3–333;3–311;3–455;4–111;6–367;6–379;6–459;6–224;6–237 |
| 2663 | 1–489;2–489;2–481;2–361 |

TABLE II-continued (Tiling path)

| Seq Id No. | Positions of biological 5'ESTs |
|---|---|
| 2664 | 1–490;1–381;1–483 |
| 2665 | 1–430;1–470;1–461 |
| 2667 | 1–483;1–445;1–447;1–491 |
| 2668 | 1–425;36–462;60–553;60–503;60–535;60–429 |
| 2669 | 1–485;1–453 |
| 2671 | 1–481;25–495;25–505;25–510;91–510;91–503;95–481;98–496;98–301;99–491;99–189;99–502;102–458;102–510;102–261;102–231;102–508;102–478;102–508;102–508;102–509;102–355;102–509;102–499;102–508;102–495;102–508;102–508;102–423;102–413;102–508;102–187;102–510;102–468;102–502;102–508;102–508;102–370;102–510;102–490;102–510;102–508;102–366;102–494;102–510;102–510;102–458;102–509;102–487;102–509;102–504;102–509;102–439;102–508;102–510;102–508;102–456;102–509;102–502;102–502;102–285;102–481;102–489;102–260;102–508;102–508;102–510;102–504;102–508;102–507;102–508;102–508;102–188;102–499;102–510;102–509;102–510;102–510;102–510;102–497;102–508;102–507;102–502;102–493;107–502;107–510;107–602;107–509;107–357;107–496;107–567;107–571;107–493;107–509;107–491;107–510;107–607;107–540;108–509;108–424;108–254;119–479;119–509;119–493;119–443;119–510;119–483;119–483 |
| 2672 | 1–346;1–320;1–293;1–335;1–288;1–222;1–333;1–348;1–227;1–327;1–330;1–348;1–282;1–204;1–479;2–92;5–134;5–90;5–91;5–163;5–188;5–164;10–425;11–157 |
| 2673 | 1–452;1–422;4–207;5–95;8–137;8–167;8–364;8–261;8–329;8–276;8–345;8–272;8–319;8–362;8–93;8–278;8–94;8–364;8–166;8–191;13–263;14–160;14–330;25–349 |
| 2675 | 1–530;1–481;1–384;1–498;1–391;1–448;1–446;1–613;1–497;1–400;1–482;1–392;1–439;1–627;1–481;1–440;1–446;1–489;1–496;1–499;1–748;1–374;1–550;1–125;1–495;1–499;1–530;1–486;1–446;1–553;1–329;1–613;1–446;1–477;1–400;1–499;1–631;1–496;1–446;1–406;1–446;1–481;1–487;1–549;1–624;1–498;1–477;1–624;1–344;1–542;1–543;1–613;1–556;1–542;1–551;1–543;1–315;1–499;1–431;1–425;1–427;1–205;1–497;1–499;1–446;1–613;1–324;1–543;1–496;1–543;1–499;1–553;1–551;1–613;1–494;1–609;1–486;1–599;1–497;1–481;1–484;1–488;1–439;1–552;1–617;1–431;1–613;1–287;1–211;1–495;1–374;1–539;1–415;1–497;1–484;1–506;1–599;1–312;1–415;1–487;1–477;1–495;1–481;1–599;1–491;1–486;1–387;1–371;1–359;1–428;1–534;3–398;8–641 |
| 2677 | 1–417;1–497;1–393;1–456 |
| 2679 | 1–410;1–481;1–448 |
| 2680 | 1–461;1–520;1–465;1–469;1–455;1–455;1–425;1–500;1–475;1–461;1–461;1–460;1–451;1–487;1–495;1–396 |
| 2681 | 1–461;1–460;1–461;1–461;1–451;1484;1–466;1–465;1–455;1–455;1–425;1–396 |
| 2682 | 1–53;1–152;1–481 |
| 2683 | 1–403;1–381;1–403;19–596;19–584;19–417;19–584;19–472;19–471;19–540 |
| 2690 | 1–422;1–491;1–436 |
| 2691 | 1–507;1–373;11–466 |
| 2693 | 1–510;1–522 |
| 2694 | 1–429;15–266;16–572;33–150 |

TABLE II-continued (Tiling path)

| Seq Id No. | Positions of biological 5'ESTs |
|---|---|
| 2697 | 1–364;1–392 |
| 2698 | 1–229;1–461 |
| 2699 | 1–499;1–479;1–499 |
| 2702 | 1–403;1–481 |
| 2703 | 1–411;1–474;1–511;2–497 |
| 2704 | 1–464;1–384 |
| 2707 | 1–404;1–481;1–451;1–426;1–483 |
| 2709 | 1–474;1–424 |
| 2710 | 1–473;1–446 |
| 2711 | 1–419;1–457;1–483;1–419;1–501;1–489;1–196;1–440;1–513;1–185;1–512;1–511 |
| 2713 | 1–385;1–417;1–482;1–440;1–469;1–171;1–484;1–197;1–469;1–471;1–501;1–352;158–250 |
| 2717 | 1–490;1–337;1–514 |
| 2718 | 1–463;1–521 |
| 2720 | 1–327;1–481 |
| 2721 | 1–497;1–490;1–449 |
| 2722 | 1–459;1–340;1–426;1–61 |
| 2723 | 1–433;49–495;61–260;71–457 |
| 2727 | 1–458;1–583 |
| 2728 | 1–302;1–253;45–545;45–508;45–438;45–229;45–462;45–460;45–450;45–485;45–453;45–141;45–485;45–509;45–509;45–430;45–321;45–385;45–257;45–438;45–487;45–487;45–501;45–450;45–485;45–503;45–471;45–569;45–518;45–510;45–510;45–310;45–506;45–439;45–504;45–408;45–465;45–471;45–288;45–493;45–485;45–278;45–239;45–496;45–459;45–485;45–510;45–501;45–340;45–453;45–430;45–215;45–508;45–459;45–440;45–309;45–482;45–510;45–458;45–485;45–509;45–510;45–475;45–256;45–496;45–342;45–498;45–510;45–503;45–499;45–508;45–472;45–394;45–509;45–505;45–510;45–509;45–472;45–485;45–509;45–500;45–415;45–369;45–461;45–322;45–482;45–430;45–458;45–493;45–243;45–325;45–485;45–438;45–216;45–461;45–441;45–485;45–456;45–510;45–375;45–510;45–489;45–485;45–483;45–510;45–332;45–464;45–503;45–263;45–477;45–509;45–327;45–485;45–278;45–428;45–317;45–467;45–531;45–485;45–507;45–488;45–568;45–415;45–442;45–495;45–510;45–509;46–489;46–474;46–459;47–469 |
| 2729 | 1–484;1–480;1–481;1–549;1–297 |
| 2731 | 1–166;1–279 |
| 2732 | 1–425;82–477;82–415 |
| 2734 | 1–414;212–554;212–543 |
| 2735 | 1–481;1–461 |
| 2739 | 1–492;1–449;1–467 |
| 2740 | 1–372;1–471;1–462;1–454;33–470;33–462;37–475;37–413;37–407;38–549;38–504;38–374;38–473;38–522;38–484;40–459;42–469 |
| 2743 | 1–503;1–465;1–502;1–497;1–501;1–488;1–332;1–500;1–443;1–478;1–511;1–546;1–461;1–501;1–458;1–484;1–488;1–498;1–433;1–505;1–500;1–318;1–505;1–499;1–222 |
| 2744 | 1–346;1–484;1–368 |
| 2745 | 1–516;1–389;2–534;4–500 |
| 2748 | 1–472;1–390 |
| 2750 | 1–489;31–595;31–607;38–529;41–509;41–313;41–350;45–192 |
| 2754 | 1–256;1–445;1–447;1–447;1–145;1–441;1–443 |
| 2756 | 1–481;1–482 |
| 2759 | 1–235;1–466;1–509;1–464;24–459;43–563 |
| 2760 | 1–417;1–497;1–516;65–670 |
| 2761 | 1–379;1–414;1–493;1–335;1–493;1–457;1–471;1–64;1480;1–152;1–480;1–398;1– |

TABLE II-continued (Tiling path)

| Seq Id No. | Positions of biological 5'ESTs |
|---|---|
| | 389;1–439;1–284;1–471;1–480;1–420;1–321;1–494;1–471;1–471;1–457;1–492;1–480;1–328;29–501 |
| 2762 | 1–472;4–86 |
| 2763 | 1–485;4–86;17–539 |
| 2765 | 1–509;1–357;124–209 |
| 2766 | 1–356;23–399;23–408;23–407;23–404;23–406;23–407;23–415;23–415;23–410;24–407;24–271;24–375;24–204;24–403;24–399;25–403;25–390;27–389;36–436;36–429;41–389;43–416;43–402;43–402;43–414;43–407;43–416;43–402;43–402;43–394;43–143;43–416;43–355;64–403;64–387;73–416 |
| 2767 | 1–424;1–421;1–408;1–197 |
| 2768 | 1–356;23–399;23–408;23–404;23–415;23–410;23–415;23–407;23–406;23–407;24–271;24–399;24–407;24–403;24–204;24–375;24–423;25–390;25–403;27–389;41–389;43–421;43–402;43–419;43–143;43–402;43–420;43–414;43–402;43–407;43–394;43–402;43–355;64–403;64–387;73–421 |
| 2769 | 1–356;5–518;22–482;23–408;23–399;23–407;23–404;23–407;23–415;23–410;23–406;23–415;24–407;24–271;24–375;24–204;24–403;24–399;25–390;25–403;25–536;27–524;27–470;27–523;27–425;27–389;28–507;41–389;41–496;41–496;41–450;41–496;41–456;41–496;43–414;43–402;43–416;43–416;43–407;43–402;43–355;43–402;43–402;43–416;43–43;43–394;46–488;46–541;46–449;46–532;46–526;46–526;46–524;46–556;64–403;64–545;64–536;64–387;73–416 |
| 2772 | 1–85;12–84;12–98;12–99;12–139;12–180;12–85;12–159;18–149;18–149;18–98;44–157;44–157;45–157;45–157;45–157;45–506;45–154;45–134;45–157;45–154;45–135 |
| 2773 | 1–426;19–119;19–516;19–454;19–138;19–294;20–435;20–426;20–494;54–495 |
| 2777 | 1–222;1–506;1–422 |
| 2779 | 1–468;1–471 |
| 2780 | 1–496;1–502;1–412;1–295;1–472;1–100;1–109 |
| 2782 | 1–136;1–246;1–200;6–234;15–459;15–519 |
| 2783 | 1–435;3–488 |
| 2785 | 1–414;1–498;1–420;1–397;1–384;1–396;1–485;1–397;1–403;1–342;13–527;47–451;47–423;47–523;47–424 |
| 2786 | 1–430;1–320 |
| 2787 | 1–443;1459;1–184;1–451;1–527;1–459;1–376 |
| 2790 | 1–314;2–477;2–434;2–459;2–477;2–487;2–433;2–268;2–402 |
| 2791 | 1–53;6–483;11–442;11–172;11–256;18–93;18–93;18–93;18–93;18–93;18–93;18–93;18–93;18–93;18–93;18–93;18–93;18–93;18–93 |
| 2792 | 1–163;–903 |
| 2794 | 1–501;1–481;1–376;1–477;1–429;1–434;1–492 |
| 2807 | 1–98;1–82;1–98;1–474;1–451;1–425;1–96;1–98 |
| 2813 | 1–484;370–795;370–795;471–811;471–832;471–818;471–832;471–816;471–604;471–822;471–818 |
| 2815 | 1–194;1–148;2–200;2–129;2–145;2–150;2–138;3–149;3–150;27–123;27–149;27–123;28–129;28–144;28–129;28–131;28–129;28–140;28–149;29–129;30–149;31–143;31–200;32–148;33–148;33–134;33–148;33–149;33–151;33–150;33–141;33–149;33–150;33–134;33–193;33–137;33– |

| Seq Id No. | Positions of biological 5'ESTs |
|---|---|
| | 147;33–151;33–179;33–150;33–152;33–183;33–200;33–144;33–200;33–150;33–91;33–150;33–407;33–122;33–87;33–144;33–149;33–149;33–138;33–151;33–135;33–105;33–150;33–150;33–150;33–135;33–131;34–93;34–145;34–151;34–138;34–151;34–129;34–135;34–148;34–149;34–140;34–149;34–179;34–131;34–148;34–142;34–139;35–140;35–148;35–150;35–200;35–135;35–140;35–108;36–136;36–150;36–141 |
| 2816 | 1–468;1–383;1–336;1–462;1–440;1–501;1–473;1–398;1–443;1–298;1–355;1–312;1–171;1–395;1–443;1–483;1–430;1–148;1–171;1–566;1–485 |
| 2820 | 1–427;91–621;566–1035 |
| 2822 | 1–494;11–509 |
| 2823 | 1–273;1–515;1–396 |
| 2825 | 1–524;3–502 |
| 2827 | 1–386;1–460;1–476 |
| 2828 | 1–337;4–491;4–263;4–415;4–516;4–485;4–483;4–503;4–493;4–483;4–425;4–478;4–336;4–464;4–327;4–494;4–466;4–427;4–467;4–484;4–494;4–53;4–412;4–487;4–464;4–507;4–406;4–464;4–474;4–415;4–493;4–439;4–447;4–184;4–410;4–490 |
| 2832 | 1–68;13–483;13–480;13–450;13–427;13–410;13–450;13–466;28–625 |
| 2834 | 1–418;1–418;1–391;1–319;1–416;1–417;1–369;1–403;1–405;1–393;1–410;8–483;8–444;8–508;25–406 |
| 2836 | 1–542;14–430;14–145 |
| 2838 | 1–462;1–462;1–517 |
| 2839 | 1–330;73–333;73–469;73–469;73–301 |
| 2844 | 1–201;23–500;23–358;23–129 |
| 2845 | 1–299;1–388;1–459;1–502;1–406;1–443;1–422;10–475;10–250;16–216;16–513;16–520;16–521;16–425;16–496;16–495;32–501;32–526;32–511;32–428;33–242;33–508;33–349;33–515;33–456;33–494;33–511;33–248;33–456;33–357;33–434;33–498;33–309;33–507;33–534;34–401;34–539;34–519;34–459;35–471;35–458;35–423;36–500;37–456;37–524;37–384;37–227;37–311;37–481;37–456;37–397;37–443;37–511;37–539;37–144;37–551;37–500;37–512;37–475;37–512;37–521;37–481;37–540;37–519;37–415;42–409;42–543;60–310;60–521;60–567;60–416;60–512;60–416;60–556;61–505;61–475;61–521;61–526;61–531;61–557;69–477 |
| 2849 | 1–428;1–521 |
| 2852 | 1–268;1–240;1–449;1–413;1–512;1–75;1–322;1–387;1–502;1–430;1–165 |
| 2853 | 1–404;1–436;1–292;1–436;1–420;1–436;1–436;1–307;5–449;6–483 |
| 2854 | 1–473;3–410;42–263;42–522;42–444;42–450 |
| 2855 | 1–112;1–217;1–203;1–313;16–527;17–319;17–242;17–244;17–79;32–225;32–114 |
| 2856 | 1–458;15–434;26–528 |
| 2860 | 1–324;1–504;1–408;1–500;1–416;1–509 |
| 2863 | 1–60;2–435;2–491;3–424;3–477;3–471;3–73;3–599;3–474;3–388;3–253;3–490;3–396;3–577;42–289;43–501;43–594;43–512;46–465;46–465;46–465;46–500;46–595;46–456;46–304;46–548;46–450;46–465;46–465;46–465;46–465;46–501;46–461;46–450;46–465;46–465;46–465;46–465;46–424;46–592;46–465;46–461;46–543 |
| 2864 | 1–495;3–394 |
| 2865 | 1–420;1–497 |
| 2866 | 1–494;1–366 |
| 2867 | 1–179;1–539;1–458;1–395 |

TABLE II-continued

(Tiling path)

| Seq Id No. | Positions of biological 5'ESTs |
|---|---|
| 2868 | 1-513;334-713;334-414 |
| 2869 | 1-374;1-476;1-457;1-457 |
| 2870 | 1-280;1-485;1-418;1-394;1-396;1-382;1-396;4-493;4-357;4-405;4-490;4-399;4-445;4-221;4-462;4-406;9-492;25-519;25-487;25-492;27-531;27-520;27-50;27-372;27-486;27-479;27-400;27-249;27-444 |
| 2873 | 1-524;5-362;5-362 |
| 2874 | 1-462;1-460;1-486;1-408;1-464;1-45 227;1-477;1-426;1-466;1-486;1-486;1-397;1-447;1-306;1-474;1-471;1-447;1-486;1-476;1-311;1-465;1-486;1-445;1-459;1-461;1-486;1-421;1-446;1-257;1-473;1-420;1-251;1-449;1-486;1-323;3-486;3-373 |
| 2876 | 1-485;-484;-486 |
| 2877 | 1-706;1-363;1-481 |
| 2878 | 1-489;8-531 |
| 2879 | 1-240;1497;1-502;1-476 |
| 2880 | 1-482;1-295 |
| 2881 | 1-346;1-380;1-433;1-293;1-337;1-514;1-433;1-394;1-575;1-400;1-513;1-505;1-506;1-494;1-424;1-363;1-333;1-270;1-477;1-482;1-326;1-204;1-438;1-399;1-330 |
| 2884 | 1-511;1-493;1-408;1-560;1-441;1-259 |
| 2887 | 1-451;1-503;1-353;1-473 |
| 2888 | 1-447;3-551;3-504;3-460;3-399;23-548;28-507;28-423 |
| 2891 | 1-480;2-317;2-399;2-489;2-62 |
| 2892 | 1-303;13-446;13-499;13-486;13-414;13-490;13-480 |
| 2893 | 1-452;1-452;1-336;1-380;1-452;1-459;1-442;1-194 |
| 2894 | 1-492;1-470;1-489;1-547;1-471;1-501;1-441;1-280;1-311;1-317;1-471;1-497;1-499;1-292 |
| 2896 | 1-230;3-461;363-644 |
| 2899 | 1-505;1-503;1-511;1-279;1-203 |
| 2900 | 1-486;1-90 |
| 2902 | 1-317;1-440;1-470;-433;1-432;249-721;249-603 |
| 2904 | 1-474;1-486;1-506;1-495;1-476;1-438;1-484 |
| 2905 | 1-474;1-467;1-473 |
| 2907 | 1-308;103-523;103-276 |
| 2908 | 1-503;1-453;1-468;1-502;1-539;1-371;1-455;1-482;1-500;1-503;1-505;1-503;1-389;1-506;1-472 |
| 2911 | 1-490;1-490;4-424;4-508;4-89;4-484;4-473;4-531;4-401;4-506;4-463;5-312;15-444 |
| 2912 | 1-438;64-475 |
| 2913 | 1-459;1-483 |
| 2914 | 1-307;103-482;103-571;103-275;103-434 |
| 2916 | 1-426;1-426;1-425;1-431;1-429;1-271;1-432;1-133;1-372;1-384;1-436;1-420;1-357;1-410;1-452 |
| 2919 | 1-486;49-537;50-575;50-502 |
| 2920 | 1-454;1-317 |
| 2921 | 1-462;1-480;2-457;2-481;2-432;2-492;19-490;19-342;19-492;19-480;22-465 |
| 2922 | 1-479;1-518;1-484 |
| 2924 | 1-467;217-610;217-582;217-607;217-615 |
| 2925 | 1-363;2-413;4-240;4-414;4-317;4-265;4-423;4-423;4-443;4-411;4-393;4-369;4-167;4-507;4-447;4-438;4-348;4-417;4-380;4-449;4-301;4-514;4-499;4-423;5-418;7-328 |
| 2926 | 1-483;1-463;1-408 |
| 2927 | 1-464;1-577 |
| 2928 | 1-489;1-474 |
| 2931 | 1-122;1-117;2-61;2-405;2-347;2-169;2-479;4-119;4-92;4-122;226-500;226-496;226-496;226-496;226-496;226-446;226-496;226-496;226-500;226-496;226-358;226-500;226-496;226-496;226-501;226-496;226-496;226-496;226-496;226-496;226-496;226-496;226-501;226-496;226-496;226-496;226-496;226-496;226-496;226-496;226-496;226-370;226-501;226-496;226-496;226-496;226-501;226-496;226-496;226-496;226-501;226-496;226-496;226-496;226-496;226-496;226-496;226-496;393-669;393-664;397-709;397-706;397-693;397-708;397-690;397-709;397-706;397-693;397-686;397-690;397-694;397-709;397-706;397-693;397-693;397-681 |
| 2932 | 1-528;1-308;1-581 |
| 2933 | 1-372;2-369;3-474;16-324;16-339;16-324;16-324;16-477;16-135;16-328;16-300;16-422;16-328;16-324;16-339;16-433;16-339;16-530;16-215;16-324;16-324;16-339;16-474;16-230;16-339;16-335;16-339;16-339;16-327;16-328;16-448;16-342;16-324;16-121;16-328;16-230;16-133;16-324;16-339;16-327;16-328;16-321;16-467 |
| 2934 | 1-486;1-269 |
| 2936 | 1-464;1-300;1-456 |
| 2937 | 1-396;1-117;1-381;1-406;1-515;1-467 |
| 2938 | 16-491;16-611;16-396;16-491;16-497;16-474;27-410;27-443;27-494;27-465;27-492;28-507;28-281;28-249;29-574;29-566;30-484;30-547;30-558;30-505;30-426;30-330;30-493;30-536;30-491;30-585;30-493;30-145;30-427;30-429;30-386;30-491;30-505;30-467;30-462;30-410;30-459;30-423;30-466;30-197;30-504;30-499;30-444;30-462;30-625;30-448;30-556;30-507;30-462;30-462;30-462;30-538;30-410;30-447;30-504;30-537;30-463;30-322;30-642;30-636;30-480;30-503;30-253;30-503;30-405;30-504;30-430;30-512;30-603;30-483;30-379;30-398;30-515;30-410;30-542;30-443;30-497;30-459;30-507;30-523;30-442;30-416;30-449;30-510;30-415;30-469;30-459;30-506;30-427;30-513;30-486;30-463;30-449;30-418;30-504;30-502;30-578;30-503;30-398;30-507;30-458;30-451;30-324;30-504;30-399;30-458;30-491;30-453;30-504;30-398;30-501;30-462;30-495;30-483;30-432;30-483;30-530;30-462;30-625;30-512;30-470;30-518;30-504;30-510;30-426;30-504;30-498;30-491;30-477;30-491;30-494;30-500;30-334;30-396;30-397;30-507;30-574;30-492;30-459;30-457;30-492;30-502;30-504;30-522;30-444;30-374;30 |
| 2940 | 1-117;1-122;2-169;2-161;2-405;2-479;2-347;4-119;4-122;4-92;226-496;226-496;226-446;226-496;226-496;226-500;226-496;226-496;226-501;226-500;226-496;226-496;226-496;226-501;226-496;226-496;226-496;226-496;226-358;226-496;226-496;226-501;226-496;226-496;226-496;226-501;226-496;226-496;226-496;226-500;226-496;226-496;226-496;226-496;226-501;226-496;226-496;226-496;226-370;226-496;226-496;226-496;393-664;393-669;393-687;393-687 |
| 2941 | 1-493;1-438;1-252 |
| 2943 | 1-506;1-509;1-491 |
| 2944 | 1-422;1-369;1-465;1-402;1-414 |

TABLE II-continued (Tiling path)

| Seq Id No. | Positions of biological 5'ESTs |
|---|---|
| 2945 | 1–489;12–347;17–398;17–372;17–67;17–493;17–229;17–362;17–424;17–430;17–481;17–164;17–378;17–489;17–161;17–481;42–350;62–489;62–489;64–278;69–516;69–518;69–486;69–492;69–510;69–487;69–325;69–521;69–161;71–145;71–494;71–531;71–543;71–489;71–502;80–537 |
| 2947 | 1–490;1–538 |
| 2949 | 1–488;1–434;1–404;1–440;3–355;3–330;3–411;3–403;3–492;3–505 |
| 2951 | 1–502;1–506;1–483 |
| 2952 | 1–415;80–470;80–525;80–410 |
| 2959 | 1–590;1–294 |
| 2962 | 1–499;1–453 |
| 2963 | 1–455;31–539 |
| 2964 | 1–499;1–364;1–334;1–483;1–403;1–469 |
| 2966 | 1–452;1–421 |
| 2968 | 1–388;46–118;49–284;51–462;56–397;56–402;56–411;71–462;71–390;71–217;74–462;77–415;85–462;85–399;85–235;85–401;85–425;85–291;85–303;85–392;85–409;85–416;86–405;86–399;90–460;95–236;95–575 |
| 2969 | 1–520;1–387 |
| 2970 | 28–507;28–527;28–480;28–541;28–550;28–408;28–581;28–463;28–562;28–533;28–440;28–489;28–543;43–531;48–555;50–158;50–550;50–342;50–547;50–572;50–158;50–480;88–578;135–631 |
| 2971 | 1–488;1–491 |
| 2974 | 1–409;1–517;1–260;1–482;1–443 |
| 2976 | 1–470;1–377 |
| 2978 | 1–473;1–508;1–234;1–517;1–515;1–427 |
| 2979 | 1–303;1–490 |
| 2980 | 1–122;1–467;9–484;9–456 |
| 2981 | 1–466;1–405;3–539;5–403;8–496;11–510;12–501;12–517;12–494;12–503;12–472;12–447;12–494;12–499;12–516;12–495;12–481;12–524;12–517;12–530;12–317;12–527;12–494;12–466;12–496;13–447;13–504;13–531;13–530;14–501;14–467;15–407;15–495;15–548;15–478;15–522;15–480;15–493;15–472;15–480;15–462;15–462;15–460;15–488;15–462;15–442;15–369;15–300;15–426;15–461;15–577;15–574;15–519;15–504;15–558;15–488;15–472;15–477;15–508;15–390;15–472;15–463;15–539;15–472;15–481;15–567;15–404;15–321;15–379;15–490;15–496;18–518 |
| 2984 | 1–501;1–490;1–493;1–451;1–461 |
| 2985 | 1–423;1–491;1–338;1–404;1–462;2–450;358–783 |
| 2986 | 1–502;1–459;1–484 |
| 2989 | 1–374;1–478 |
| 2990 | 1–419;1–482 |
| 2991 | 1–451;1–422;18–549;18–449;19–442 |
| 2995 | 1–465;1–446;1–438;10–483;10–482;10–509;10–437;10–494;10–466;10–437;10–472;10–472;10–475;10–473 |
| 2996 | 1–354;5–466 |
| 2997 | 1–359;1–460;1–461;1–467;1–444;1–486;1–469;1–486;1–467;1–483;1–482;1–370;1–334;1–443;1–442 |
| 2998 | 1–449;1–546 |
| 3001 | 1–578;28–467;28–447;28–512;28–474;28–439;28–450;28–525;28–473;28–519;28–458;104–559;104–507;104–584;104–579;104–452;104–579;104–513;104–548 |
| 3002 | 1–483;2–482 |
| 3003 | 1–518;2–480;4–123;4–297;4–317 |
| 3005 | 1–437;1–468;1–414;1–485;1–421;1–436;1–493;7–504;7–452;7–420;35–334;35–486;35–454;35–458;35–348;35–538;35–475;35–549;35–535;35–538;35–457;35–533;35–486;35–509;35–486;35–469;35–439;35–529;35–422;35–418;35–457;35–277;35–466;35–523;35–491;35–502;35–557;35–434;35403;35–335;35–519;35–454;35–454 |
| 3006 | 1–327;1–306;1–263;1–148;1–169;23–388;29–161 |
| 3007 | 1–357;1–493;1–359;1–450;1–453;1–522;1–411;1–470;1–509;1–451;1–386;14–525;14–523;22–500;22–127;39–548;41–538;53–501;53–485 |
| 3008 | 1–358;1–360;22–127;24–513 |
| 3010 | 1–507;1–451;1–173;1–455;1–422 |
| 3011 | 1–462;213–604;217–704 |
| 3012 | 1–205;13–505 |
| 3013 | 1–97;1–479;1–556;1–441;1–486;2–556;2–351;11–337;15–481;15–479;15–476;15–485;15–165;15–351 |
| 3014 | 1–320;12–467 |
| 3016 | 1–497;8–513;12–324 |
| 3017 | 1–469;1–448 |
| 3018 | 1–372;1–531;1–406 |
| 3019 | 1–459;1–610 |
| 3021 | 1–530;1–43 |
| 3022 | 1–54;1–436 |
| 3023 | 1–494;1–483;1–470;1–473 |
| 3024 | 1–472;1–474;1–488;1–275 |
| 3025 | 1–425;40–524;40–505;40–523;40–311;40–383;40–582;40–520;40–534;40–513;40–460;40–548 |
| 3027 | 1–807;1–604 |
| 3029 | 1–503;1–483;1–487;1–503;1–510;1–497;1–510;1–454;1–472;1–482;1–494;1–488;1–450;1–533;1–428 |
| 3030 | 1–472;1–505;1–440;1–370;1–485;1–382;1–464;1–316;1–468;1–493;1–470;1–467;1–493 |
| 3031 | 1–520;1–489 |
| 3032 | 1–585;1–495 |
| 3034 | 1–337;1–493;1–463;1–321;1–230;1–148;1–402;1–490;1–431;1–554;1–431;1–478;1–448;1–487;1–464;1–459;1–387;1–486;1–387;1–377;1–444;1–167;2–188;2–471;37–573;37–328;37–566;37–573;37–371 |
| 3036 | 1–87;1–135;17–375 |
| 3037 | 1–462;1–96 |
| 3038 | 1–584;1–410;1–226 |
| 3039 | 1–436;1–456;1–472;6–483 |
| 3041 | 1–374;1–373;1–382;4–241;20–265;20–524;20–152;20–382;20–523;20–378;20–135 |
| 3044 | 1–474;1–491;1–290 |
| 3046 | 1–450;1–477;1–313;1–387 |
| 3047 | 1–539;272–690;272–691;272–669;272–671;272–691;272–690;272–690;272–690;272–690;272–667;272–673;272–658;272–651;272–673;272–689;272–617;272–667;272–666;272–679;272–683;272–690 |
| 3049 | 1–536;–326;1–397;30–470;30–544;30–465;30–467;38–518;38–485;38–527;38–535;56–540;56–563;56–547;56–436;58–439;62–466;152–547;152–321 |
| 3053 | 1–438;1–475;311–787 |
| 3056 | 1–335;3–185;4–503 |
| 3057 | 1–121;1–425;1–468;1–335 |
| 3058 | 1–479;1–558;1–495 |
| 3059 | 1–481;1–469 |
| 3060 | 1–453;1–108;2–494;2–410;2–415;2–110;3–119;3–122 |
| 3061 | 1–493;1–493;15–406;15–479;15–484;15–236;15–523;15–505;25–188 |
| 3064 | 1–519;1–488 |
| 3066 | 1–456;22–375;22–432 |

TABLE II-continued (Tiling path)

| Seq Id No. | Positions of biological 5'ESTs |
|---|---|
| 3067 | 1–266;1–417;4–517;4–79;29–468;29–393;29–443;29–561;29–471;50–551 |
| 3068 | 1–395;1–438;1–463;1–433;1–436;1–415;1–435;1–463 |
| 3069 | 1–460;1–394;1–338;1–464;1–468;1–416;1–411;1–513;1–415;1–404 |
| 3070 | 1–420;28–484 |
| 3071 | 1–196;1–473 |
| 3072 | 1–389;5–434;5–360;5–222;5–449;9–423;37–452;37–120;37–233;37–438 |
| 3076 | 1–400;1–500;1–494 |
| 3084 | 1–326;1–498;1–314;1–472;1–485;1–439;1–528;1–441;1–471;1–483;1–498;1–357;1–502;1–462;1–500;1–299;1–502;1–500;1–329;1–429;1–210;1–497;1–470 |
| 3085 | 1–199;1–279 |
| 3086 | 1–458;1–513 |
| 3087 | 1–259;1–391;1–390;1–392;1–387;1–328;1–387;1–208;1–391;1–379;1–390;1–390;1–388;1–388;1–371 |
| 3093 | 1–490;1–478;1–330;1–421 |
| 3094 | 1–478;1–505;1–435 |
| 3096 | 1–469;1–168;1–239;1–498;1–423;1–294;1–425;1–365;1–399;1–505;1–497;1–498;1–482;1–476;1–499;1–508;1–503;1–345;1–505;1–254 |
| 3099 | 1–364;1–482;1–209;27–79;27–286;27–101;27–101;28–493;28–501;28–515;28–502;28–224;28–484;28–533;28–283;28–471;28–484;28–362;28–279;28–504;28–493;28–331;29–407;29–470;35–323;50–284;50–423 |
| 3103 | 1–490;1–489 |
| 3104 | 1–87;1–458;1–501 |
| 3107 | 1–542;1–498;1–294;1–540;1–484;1–454;1–509 |
| 3109 | 1–451;1–460;1–478;1–477;1–500;1–442;–430;1–537;1–438 |
| 3111 | 1–246;2–454;2–64;2–442;2–454;2–491 |
| 3112 | 1–255;1–255;2–480 |
| 3114 | 1–525;1–187;1–487;1–357 |
| 3115 | 1–475;1–189 |
| 3116 | 1–492;1–509;1–495;1–197 |
| 3117 | 1–482;1–428;1–477;1–369;1–367;1–498 |
| 3118 | 1–357;1–509 |
| 3121 | 1–428;1–418;1–313;8–267;9–451;9–451;10–459;37–513;43–452;43–582;43–568;43–515;43–423;43–565;43–481;43–546;43–582;43–557;43–554;43–551;43–521;43–311;51–532;51–528;51–527;51–466;51–466;51–479;51–522;51–519;51–541;51–350;51–459;51–363;51–556;51–519;51–502;51–552;51–535;51–515;51–487;51–487;51–423;51–552;51–563;51–525;51–519;51–536;51–519;51–515;51–557;51–384;51–540;51–549;51–632;51–486;51–231;51–260;51–354;51–356;53–578;54–538;60–515;60–445;60–480 |
| 3122 | 1–428;1–418;1–313;8–267;9–451;9–451;10–459;37–513;43–452;43–568;43–582;43–557;43–612;43–565;43–551;43–554;43–546;43–423;43–515;43–521;43–481;43–582;51–527;51–466;51–519;51–522;51–479;51–528;51–350;51–563;51–502;51–466;51–459;51–363;51–532;51–384;51–519;51–556;51–515;51–535;51–515;51–487;51–616;51–487;51–423;51–541;51–552;51–519;51–525;51–519;51–536;51–552;51–557;51–540;51–549;51–486;51–231;51–260;51–356;51–354;53–578;54–538;60–515;60–445;60–480 |
| 3124 | 1–454;1–479 |
| 3125 | 1–454;1–492 |
| 3126 | 1–483;254–707 |
| 3127 | 1–488;1–382;1–411;1–503;1–56;1–488 |
| 3128 | 1–479;1–462;1–123;1–205;1–130;1–443 |
| 3130 | 1–497;1–106;1–467;1–477 |
| 3133 | 1–473;1–410;1–469;1–487;1–491;1–506;–494;1–504;1–436;1–516;1–341;1–513;1–255;1–414;1–452;4–494;5–482;5–510;5–448;5–472;5–426;5–426;6–504;6–458;6–517;6–450;13–506;13–474;38–493;38–544;38–528;38–531;39–525;39–511;39–532;39–516;39–472;39–535;39–461;39–532;39–479;39–527;39–511;39–522;39–222;39–480;39–179;39–532;39–504;39–454;39–492;39–532;39–515;39–521;39–510;39–451;39–529;39–162;39–525;39–525;39–339;39–487;39–501;39–483;39–529;39–518;39–516;39–534;39–525;39–522;39–516;39–526;39–226;39–517;39–546;39–510;39–205;39–441;39–509;39–507;41–485;44–451;78–544;80–461;80–509;80–541 |
| 3138 | 1–489;1–464 |
| 3139 | 1–435;97–596 |
| 3142 | 1–438;1–428 |
| 3143 | 1–513;1–492 |
| 3144 | 2–491;2–491;2–465;2–459;2–292;2–302;2–491;2–412;2–55;2–509;2–448;2–474;2–473;2–484;2–505;2–404;2–498;2–505;2–490;2–416;2–488;2–508;2–164;2–484;2–364;2–506;2–548;2–510;2–481;2–519;2–485;2–485;2–487;2–421;2–484;2–464;2–445;2–357;2–249;2–422;2–490;2–501;2–448;2–447;2–490;2–482;2–482;2–328;2–487;3–455;4–503;10–462;10–320;10–493;10–509;10–504;10–481;10–447;12–473;14–509;17–506;18–482;22–231;35–342;35–514;35–487;35–511;35–484;35–411;35–459;35–493;37–510;38–380;40–106;40–523;41–463;41–509;41–504;41–484;41–482;41–511;41–493;41–538;41–447;41–113;41–520;41–517;42–420;44–518;44–509;44–515;44–161;44–526;44–509;44–483;44–504;49–525;59–497;59–537;73–517 |
| 3145 | 1–465;47–480;47–597;47–473;47–575;56–601;56–493;56–487;56–570;56–574;56–501;56–725;56–286;56–500;59–491;89–587;89–473;89–473;89–191;89–575;89–587;89–479;89–460;89–473;89–473;89–501;89–479;89–479;89–490;89–464;89–463;89–493;89–493;89–196;89–597;89–224;89–460;89–459;89–602;89–500;89–481;89–473;89–492;89–232;89–489;89–441;89–493;90–528;90–606;90–490;91–473;98–501;101–501 |
| 3146 | 1–86;1–414;1–476;1–465;30–401 |
| 3147 | 1–467;1–476;1–488;1–408;1–479;43–500 |
| 3148 | 1–455;1–452;–462 |
| 3149 | 1–382;1–376;1–627;1–165;1–436;10–334;10–410;0–60;10–289;13–410;13–463;13–293;3–469;13–390;13–420;13–449;3–375;13–449;13–399;13–498;354;13–139 |
| 3150 | 1–484;14–559;402–864 |
| 3151 | 1–461;51–568;61–518;61–479;61–493;61–446;61–431;61–655 |
| 3152 | 1–89;1–351;1–430;2–484;2–475 |
| 3153 | 1–361;1–383;1–435;1–459 |
| 3155 | 1–340;1–448;1–464;1–505;1–491 |
| 3156 | 1–502;1–469;1–468;4–473;5–467;5–414;45–490;45–114;45–554;45–591;45–600;45–571;45–528;45–554;45–540;45–559;45–464;45–526;45–554;45–550;45–461;45–516;45–485;45–555;45–476;45–540;45–517;45–551;45–559;45–551;45–516;45– |

TABLE II-continued

(Tiling path)

| Seq Id No. | Positions of biological 5'ESTs |
|---|---|
| | 515;45–605;45–518;45–605;45–545;45–542;45–540;45–308;45–549;45–494;45–441;45–555;45–545;45–520;45–526;45–529;45–602;45–559;45–498;45–471;45–549;45–546;45–557;45–546;45–559;45–536;45–502;45–502;45–494;45–555;45–519;45–465;45–559;45–516;45–534;45–589;45–231;45–516;45–557;45–510;45–545;45–556;45–581;45–529;45–543;45–502;45–572;45–529;45–544;45–526;45–555;45–539;45–554;45–519;45–531 |
| 3157 | 1–124;1–317;1–366;5–321;5–392;185–409;185–409 |
| 3158 | 1–470;1–464;1–482;1–464 |
| 3159 | 1–406;1–124;1–486;1–317;1–461;1–524;1–436;1–366;1–489;1–418;5–451;5–321;5–392;34–528;34–471;39–479;40–511 |
| 3160 | 1–127;1–321;1–467;1–488;1–424;1–371;1–442;5–325;5–457;5–397;11–494;34–477;39–485 |
| 3162 | 1–398;1–433;1–482;1–161;1–490;1–394;1–463;1–394;1–494;1–455;1–332;1–361;1–490;1–484;1–490 |
| 3163 | 1–466;71–478;71–475 |
| 3164 | 1–443;1–467;1–480;1–508;1–491 |
| 3165 | 1–426;1–463;1–498;1–353;1–439;1–486 |
| 3166 | 1–479;20–538 |
| 3168 | 1–471;21–468;21–420 |
| 3169 | 1–490;1–475 |
| 3170 | 1–563;1–447;3–484;3–218;3–445;9–485;9–550;9–397 |
| 3171 | 1–459;1–489 |
| 3172 | 1–503;1–277;93–598;113–583;113–545;161–694;175–640;221–661;221–712;222–324;222–771;222–709;222–712;222–659;222–466;222–691;222–713;222–558;222–692;222–716;222–717;250–751;250–746;250–744;250–735;250–639;250–732;256–784;347–826 |
| 3173 | 1–376;1–455 |
| 3175 | 1–484;1–202;1–426 |
| 3176 | 1–482;1–457 |
| 3177 | 1–431;1–482 |
| 3178 | 1–441;1–434;1–412;1–441;1–368;1–443;1–435;1–447;1–441;2–406;9–435;9–406;12–432;12–250;12–438;12–435;12–441;12–431;12–435;12–403;12–291;12–440;12–441;12–258;13–317;13–497 |
| 3179 | 1–485;33–400;33–353;33–309 |
| 3181 | 1–461;4–380;4–451;4–517;5–243 |
| 3182 | 1–470;1–501;1–510;1–248;1–393;1–516;1–362;1–496;1–475;1–491;1–489;1–473;1–577;1–468;1–499;1–473;2–479;2–496;2–509;2–517;31–254;48–485 |
| 3183 | 1–349;3–434;3–447;3–356;3–439;3–434;3–433;3–437;3–414;3–494;3–434;3–451;3–439;3–437;3–404;3–446;3–428;3–355;3–420;3–447;3–406 |
| 3186 | 1–454;1–501;1–539;1–474;1–474;1–460;1–539 |
| 3187 | 1–478;1–520;1–497;1–415 |
| 3188 | 1–196;1–254;1–74;1–52;1–153;7–411;7–444;23–309 |
| 3192 | 1–438;1–446;1–66;22–517;30–302;30–527;34–324 |
| 3193 | 1–495;1–757;1–455 |
| 3194 | 1–406;1–479;1–474;1–413;1–462;1–503;1–439;–387 |
| 3195 | 1–484;1–388;1–486 |
| 3196 | 1–482;1–489;1–410 |
| 3197 | 1–494;1–473 |
| 3199 | 1–496;1–401 |
| 3204 | 1–375;1–526;1–331;1–405;25–442;25–510;25–526;25–508;25–509;30–495;35– |
| | 531;36–517;36–442;36–517;36–532;36–404;36–435;36–532;37–484;37–478;37–517;42–517;42–406;42–478;42–403;43–403;43–380;43–499;43–526;44–477;44–517;44–484;52–480;57–483;57–347;57–538;58–516;58–498;58–517 |
| 3205 | 1–455;1–533;1–453;1–461;1–474;1–490;1–517 |
| 3208 | 1–381;5–518;6–478 |
| 3209 | 1–505;17–413 |
| 3211 | 1–75;26–403;57–385;57–345;57–419;98–344;98–577 |
| 3215 | 1–474;1–344 |
| 3217 | 1–413;1–453;1–469;1–526;1–500;1–448;1–501;1–454;1–413;31–328 |
| 3219 | 1–480;1–509;1–480;1–475;1–444;1–477 |
| 3221 | 1–354;1–492 |
| 3223 | 1–411;1–141;1–136;1–220;1–419;1–517 |
| 3225 | 1–473;1–471;1–321;1–497;1–459 |
| 3226 | 1–432;50–333;98–536;98–564;98–573;99–511;126–601;134–576 |
| 3227 | 1–185;1–420;1–476;1–403;1–516 |
| 3228 | 1–513;1–184;1–377 |
| 3230 | 1–455;1–471;1–321;1–473;2–483;2–454;6–459;6–458;9–509;9–548;11–360 |
| 3231 | 1–321;5–522;5–539;8–514;8–443;11–360 |
| 3232 | 1–487;1–523 |
| 3236 | 1–342;6–465;6–516;6–580;6–469;6–411;6–354;56–524;56–513 |
| 3237 | 1–342;20–499 |
| 3238 | 1–489;1–347;1–587 |
| 3239 | 1–484;1–473;1–454;1–493;1–321;1–483;1–485;173–614;178–576;179–600;179–346;179–597;198–600;208–725;216–748;216–303;216–707;216–665;217–736 |
| 3240 | 1–468;1–397;1–371 |
| 3241 | 1–488;1–487;1–457;1–486;1–321;1–496;1–476;173–620;78–581;179–345;179–690;179–599;216–303;216–671 |
| 3242 | 1–490;1–461;1–71;1–290;1–440;1–454;1–382;1–460;3–334;6–525 |
| 3243 | 1–466;1–465 |
| 3245 | 1–367;1–597 |
| 3248 | 1–445;19–508;19–500 |
| 3249 | 1–499;1–489 |
| 3250 | 1–494;1–134;1–503;1–199;1–484;1–461;1–444;22–108;27–158;27–268;27–167;27–98;27–94;27–229;27–82;27–125;27–230;27–257;27–123;27–248;27–215;27–268;27–182;27–150;27–112;27–231;27–201;27–212;27–257;35–120;37–130;37–218;37–237;40–149;40–245;40–186;60–115;60–159;60–254;60–172 |
| 3251 | 1–199;1–134;1–430;22–108;27–257;27–230;27–212;27–273;27–158;27–229;27–269;27–94;27–248;27–268;27–98;27–125;27–257;27–167;27–150;27–201;27–456;27–12;27–215;27–231;27–82;27–123;27–182;35–120;37–28;37–237;37–130;40–186;40–149;40–245;60–172;60–159;60–254;60–115 |
| 3252 | 1–199;1–134;22–108;27–98;27–167;27–248;27–182;27–123;27–158;27–94;27–215;27–257;27–229;27–269;27–125;27–268;27–230;27–387;27–257;27–231;27–201;27–212;27–82;27–50;27–112;35–120;37–130;37–237;37–218;40–149;40–245;40–524;40–474;40–507;40–186;60–172;60–115;60–254;60–159;72–507 |
| 3253 | 1–199;–134;22–108;27–67;27–98;27–381;27–158;27–248;27–257;27–380;27–229;27–396;27–474;27–125;27–231;27–230;27–381;27–352;27–201;27–123;27–257;27–268;27–182;27–94;27–150;27– |

TABLE II-continued (Tiling path)

| Seq Id No. | Positions of biological 5'ESTs |
|---|---|
| 3254 | 112;27–268;27–82;27–212;27–215;35–120;37–130;37–218;37–237;40–149;40–245;40–186;60–172;60–159;60–115;60–254 1–473;1–512;2–135;2–515;2–200;2–441;2–478;2–410;2–407;2–439;2–362;2–473;23–386;23–109;28–517;28–510;28–533;28–468;28–478;28–505;28–530;28–168;28–515;28–506;28–99;28–366;28–409;28–546;28–445;28–524;28–546;28–283;28–437;28–451;28–505;28–435;28–521;28–533;28–434;28–432;28–533;28–473;28–467;28–385;28–533;28–552;28–503;28–533;28–446;28–419;28–507;28–432;28–505;28–431;28–448;28–518;28–321;28–546;28–502;28–514;28–546;28–493;28–288;28–495;28–358;28–552;28–511;28–510;28–479;28–159;28–449;28–546;28–455;28–431;28–455;28–468;28–474;28–432;28–469;28–462;28–471;28–505;28–384;28–467;28–513;28–466;28–434;28–409;28–505;28–419;28–471;28–441;28–412;28–435;28–357;28–495;28–517;28–435;28–505;28–514;28–419;28–480;28–434;28–531;28–513;28–276;28–521;28–443;28–432;28–499;28–258;28–459;28–411;28–546;28–415;28–510;28–528;28–230;28–431;28–552;28–552;28–321;28–468;28–410;28–446;28–449;28–419;28–505;28–513;28–435;28–450;28–511;28–420;28–126;28–450;28–514;28–496;28–455;28–546;28–503;28–364;28–546;28–446;28–398;28–546;28–95;28–513;28–515;28 |
| 3258 | 1–468;67–533 |
| 3259 | 1–464;1–463 |
| 3264 | 1–344;1–445;1–469 |
| 3265 | 1–460;1–435 |
| 3266 | 1–103;1–86;1–507;1–511;1–505;1–486;1–362;1–278;1–426;1–458;1–471;1–402;1–479;1–158;1–483;1–481;2–482 |
| 3269 | 1–447;1–496;1–503;1–490 |
| 3271 | 1–494;7–92;7–427;7–220;7–93;7–509;7–491;7–56;7–92;8–529;8–473;9–154 |
| 3273 | 1–401;1–381 |
| 3275 | 1–461;25–325;32–399;32–407;47–185;47–400;47–364;47–378;47–240 |
| 3276 | 1–302;4–465;8–499;8–470;8–384;8–376;8–465;25–501;25–217;25–162;25–377;25–500;25–593;25–355;25–341;25–513;146–627 |
| 3277 | 1–420;20–475 |
| 3280 | 1–308;1–478;1–215;1–311;1–505 |
| 3281 | 1–468;1–513 |
| 3282 | 1–444;1–479;1–444;1–461;1–246;1–486 |
| 3283 | 1–470;1–338;1–555;1–450 |
| 3285 | 1–353;7–468 |
| 3287 | 1–423;253–479 |
| 3288 | 1–452;9–482 |
| 3290 | 1–488;1–484;1A01;1–480;1–478;1–393;1–417;1–428;1–463;1–453;1–489;1–401;1–481;1–482;1–458;1–439;1–480;1–480;1–411;1–476;1–480;1–465;1–411 |
| 3293 | 1–460;1–460 |
| 3295 | 1–53;1–477;1–551;1–469;1–499;1–500;1–159;1–280;1–482;1–507;1–499;1–502;1–493;1–463;1–481;1–453;1–573;1–442;1–457;83–561 |
| 3297 | 1–376;1–468;1–509;1–449;1–442;1–122;3–465;11–468;11–449;11–418;1–354;11–462;11–490 |
| 3301 | 1–438;1–542;1–391;1–440;1–288;1–430 |
| 3305 | 1–399;1–427;4–441;4–407;5–454;11–407;21–441;22–449;22–423;22–432;31–453;31–405;38–243;40–127;43–379;43–460;43–255;43–420;43–407;43–400;43–300 |
| 3306 | 1–478;1–472 |
| 3308 | 1–98;1–435;1–524;1–488 |
| 3309 | 1–308;1–309;1–306 |
| 3311 | 1–444;2–75;2–75;3–435 |
| 3312 | 1–135;1–932 |
| 3319 | 1–361;1–338;5–556;8–501 |
| 3321 | 1–496;1–599 |
| 3322 | 1–213;1–222;1–402;1–397;1–75;1–75;1–456;1–473;1–359;1–397;1–437;106–292;106–282 |
| 3323 | 1–326;1–367;1–468;1–176;1–406;1–342;1–479;1–142 |
| 3325 | 1–329;2–440;2–425;2–467;2–460;2–480;2–479;2–465;2–172;2–480;2–464;2–477;2–466;2–480;2–464;2–479;30–485 |
| 3327 | 1–485;51–572 |
| 3328 | 1–473;1–527;1–466;1–464 |
| 3329 | 1–397;1–481 |
| 3330 | 1–397;1–471 |
| 3331 | 1–446;2–445;2–266;2–407;10–477;14–503;40–427;40–266;40–442;40–528;44–501;44–503;44–342;44–483;44–484;44–486 |
| 3335 | 1–479;1–401 |
| 3337 | 1–473;1–468;29–463;432–846 |
| 3338 | 1–481;10–177;10–527;10–505;13–495;13–514;13–525;15–503;15–488 |
| 3340 | 1–123;12–431 |
| 3341 | 1–431;26–505 |
| 3342 | 1–464;1–232;1–219 |
| 3343 | 1–522;1–531;1–554;1–519;1–474;1–468;1–286;4–530;27–581;29–468;41–537;41–510;41–592;41–536;41–565;41–537;41–554;41–448;41–467;41–510;41–539;41–493;41–568;41–590;41–537;41–540;41–567;41–220;41–563;41–584;41–581;42–521;42–583;42–583;42–511;42–509;42–589;42–511;42–519;42–595;42–533;42–572;42–511;42–554;42–490;42–466;42–565;42–530;42–494;42–548;44–509;44–297;44–588;44–537;44–575;45–540;45–559;45–403;45–510;45–511;45–511;45–509;45–510;45–540;45–572;45–540;45–532;45–510;45–559;45–519;45–563;45–540;45–207;45–531;45–403;45–574;45–475;45–510;45–500;45–467;45–538;45–567;45–492;45–564;45–579;45–540;45–445;45–500;45–551;45–479;45–509;45–296;45–595;45–530;45–192;45–540;45–510;45–540;45–530;45–493;45–416;45–500;45–567;45–596;45–581;45–530;45–530;45–511;45–553;45–240;45–591;45–540;45–297;45–530;45–183;45–540;45–471;45–510;45–592;45–537;45–493;45–579;45–492;45–530;45–519;45–491;45–530;45–509;45–559;45–540;45–530;45–570;45–567;45–568;45–567;45–540;45–220;45–520;45–581;45–595;45–430;45–563;45–211;45–540;45–568;45–509;45–584;45–535;45– |
| 3344 | 1–275;40–404;41473;41–496;41–213;41–464;41–481;41–465;41–454;41–496;41–164;41–407;41–473;41–476;41–495;41–489;4–496;41–480;4485;41–481;41–474;41–481;45–212;45–184;45–281;45–245;45–198;45–202;45–175;45–228;45–281;46–124;46–492;46–478;46–281;47–218;47–281;49–478 |
| 3345 | 1–393;1–550;1–394;1–413;1–311;1–340 |
| 3346 | 1–507;1–504;1–392;1–269;1–485;1–506;1–416;1–475;1–109;1–482;5–287;5–82 |
| 3347 | 1–269;1–109;5–496;5–287;5–82 |
| 3349 | 1–471;1–527 |

TABLE II-continued

(Tiling path)

| Seq Id No. | Positions of biological 5'ESTs |
|---|---|
| 3353 | 1–461;88–458 |
| 3354 | 1–455;1–454;1–504;1–472;1–447;1–365;1–502;1–405;1–494;1–454;1–387;1–477;1–480;1–477;1–488 |
| 3357 | 1–453;1–479;1–532;1–468;1–513;1–436 |
| 3358 | 1–475;1–426 |
| 3360 | 1–454;245–593 |
| 3361 | 1–460;1–509 |
| 3362 | 1–456;1–457;1–220;1–470;1–496;1–502;1–362;1–472;32–429;34–589;34–362;34–243;34–511;34–518;34–500;34–421;34–489;34–483;34–580;34–448;34–475;34–428;34–447;34–514;34–458;34–492;34–516;34–50;34–437;34–488;34–364;34–483;34–214;34–499;34–590;34–397;34–475;34–430;34–418;34–488;34–551;34–362;34–590;34–473;34–590;34–471;34–457;34–517;34–498;34–449;34–483;34–342;34–492;34–510;34–387;34–532;34–475;34–541;34–486;34–523;34–433;34–482;34–515;34–462;34–594;34–489;34–434;34–541;34–234;34–580;34–483;34–431;34–378;34–590;34–492;34–488;34–590;34–515;34–569;34–287;34–575;34–513;34–518;34–487;34–511;34–580;34–499;34–301;34–522;34–528;34–576;34–498;34–488;34–480;34–555;34–338;34–342;34–507;34–489;34–429;34–488;34–507;34–520;34–487;34–483;34–574;34–487;34–487;34–498;34–541;34–361;34–523;34–551;34–590;34–487;34–447;34–471;34–510;34–519;34–561;34–422;34–442;34–517;34–313;34–544;34–456;34–551;34–195;34–494;34–458;34–472;34–482;34–590;34–492;34–459;34–363;34–478;34–315;34–546;34–486;34–497;34–501;34–539;34–478;34–417;66–501;66–550;66–3 |
| 3363 | 1–457;1–220;1–470;1–496;1–456;1–502;1–362;1–472;32–429;34–362;34–487;34–500;34–518;34–421;34–489;34–483;34–475;34–448;34–428;34–520;34–487;34–492;34–456;34–342;34–539;34–362;34–364;34–483;34–499;34–214;34–458;34–475;34–397;34–418;34–551;34–546;34–488;34–471;34–517;34–473;34–498;34–483;34–342;34–510;34–492;34–387;34–532;34–449;34–541;34–486;34–475;34–555;34–515;34–462;34–489;34–88;34–523;34–234;34–483;34–378;34–492;34–433;34–515;34–567;34–541;34–513;34–518;34–487;34–499;34–458;34–301;34–522;34–482;34–514;34–498;34–437;34–488;34–431;34–287;34–480;34–501;34–429;34–488;34–487;34–195;34–430;34–551;34–498;34–487;34–519;34–361;34–523;34–482;34–544;34–338;34–471;34–447;34–510;34–243;34–51 ;34–447;34–516;34–483;34–457;34–434;34–315;34–494;34–541;34–507;34–492;34–459;34–422;34–486;34–501;34–507;34–528;34–472;34–363;34–478;34–442;34–497;34–478;34–417;34–488;34–551;34–517;34–313;34–511;34–489;66–550;66–376;66–501;67–503;70–480;70–548;70–488;72–544;72–512;72–567;72–475;72–539;72–513;72–561;72–497;72–507;72–566;72–566;72–5 |
| 3364 | 1–220;1–457;1–470;1–496;1–456;1–502;1–362;1–472;32–429;34–589;34–362;34–510;34–243;34–511;34–518;34–421;34–489;34–500;34–580;34–448;34–475;34–608;34–428;34–483;34–608;34–458;34–492;34–607;34–429;34–576;34–608;34– |
| | 612;34–364;34–483;34–499;34–214;34–590;34–397;34–475;34–456;34–418;34–551;34–362;34–590;34–488;34–471;34–590;34–88;34–517;34–473;34–498;34–483;34–342;34–510;34–492;34–532;34–387;34–449;34–541;34–486;34–475;34–523;34–287;34–515;34–462;34–595;34–489;34–546;34–433;34–234;34–580;34–483;34–342;34–378;34–590;34–492;34–541;34–590;34–515;34–569;34–488;34–513;34–575;34–518;34–487;34–580;34–523;34–499;34–301;34–522;34–482;34–608;34–498;34–514;34–442;34–555;34–480;34–338;34–516;34–501;34–488;34–437;34–539;34–608;34–482;34–520;34–487;34–430;34–447;34–498;34–487;34–517;34–361;34–422;34–483;34–434;34–611;34–447;34–487;34–590;34–528;34–561;34–507;34–544;34–431;34–457;34–590;34–478;34–487;34–494;34–541;34–519;34–486;34–492;34–459;34–497;34–501;34–315;34–488;34–507;34–472;34–551;34–363;34–417;34–458;34–551;34–478;34–1 |
| 3368 | 1–105;6–540;46–568;49–535;49–524;49–540 |
| 3369 | 1–105;1–473;1–311;1–465;1–437;1–478;1–463;1–455;1–471;1–457;1–461;1–460;1–452;1–465;6–458;20–361;21–307;26–489;26–498;26–511;26–484;26–479;26–461;26–488;26–397;26–480;26–193;28–469;28–488;28–161;38–532;38–498;46–439;46–520;49–451;49–409;51–308;51–545;51–308;51–469;58–493 |
| 3379 | 1–446;1–461 |
| 3380 | 1–147;1–490 |
| 3382 | 1–510;142–673;142–657;179–556;181–724;182–602;182–660;193–738;199–680;205–680;205–680;214–671;214–526;214–679;217–315 |
| 3383 | 1–486;1–443 |
| 3384 | 1–467;1–494;1–462;1–354;1–261;1–485;1–487;1–473;1–500;1–289;1–451;1–474;1–456;15–436;29–413;29–519;40–505;40–534;63–559;63–532;64–560;64–457;64–457 |
| 3385 | 1–421;1–301;1–163;1–340 |
| 3387 | 1–480;1–254;1–453 |
| 3388 | 1–579;1–252;11–527 |
| 3389 | 1–566;1–490 |
| 3391 | 1–401;1–459;1–526;1–492;1–445;1–360;1–457;1–485;1–410;1–480 |
| 3392 | 1–434;–478 |
| 3394 | 1–465;1–160 |
| 3395 | 1–380;1–469 |
| 3396 | 1–211;3–316 |
| 3397 | 1–463;–477;1–450 |
| 3402 | 1–349;1–498 |
| 3406 | 1–577;1–406;1–413;7–356;7–490;14–480;14–461;14–456;14–484;219–618;219–726 |
| 3410 | 1–451;–227 |
| 3411 | 1–488;475;1–495;1–488;1–487;1–406;1–424 |
| 3412 | 1–484;3–167 |
| 3415 | 1–463;116–585 |
| 3417 | 1–413;11–423;12–547 |
| 3418 | 1–509;2–203;10–86 |
| 3419 | 1–339;1–250;1–339;1–330;1–429;1–419;1–427;1–359;1–357;1–345;1–405;1–519 |
| 3420 | 1–436;1–151 |
| 3421 | 1–472;8–77;8–83;8–104;8–149;8–61;8–133 |
| 3422 | 1–485;1–522;1–265;1–422;1–392;1–446;1–485;1–506;1–528;1–505;1–490;1–578;1–431;1–558;1–434;1–522;1–358;1–489;1– |

TABLE II-continued

(Tiling path)

| Seq Id No. | Positions of biological 5'ESTs |
|---|---|
|  | 460;1–499;1–491;1–164;1–503;1–298;1–181;1–442;1–487;1–481;1–493;1–435;1–496;1–483;1–503;1–485;1–344;1–588;1–446;1–381;1–313;1–489;1–555;1–477;1–519;1–399;1–503;1–510;1–588;1–473;1–497;1–419;1–535;1–519;1–519;1–387;1–380;1–568;1–594;1–485;1–518;1–436;1–485;1–364;1–341;1–448;1–364;1–499;1–587;1–555;1–530;1–245;1–486;1–420;1–369;1–501;1–426;1–448;1–491;1–460;1–360;1–401;1–268;1–492;1–501;1–447;1–316;1–407;1–499;1–481;1–560;1–419;1–483;1–555;1–519;1–444;1–429;1–498;1–485;1–555;1–486;1–555;1–451;1–499;1–495;1–574;1–322;1–394;1–472;1–486;1–519;1–478;1–512;1–499;1–426;1–477;1–485;1–471;1–329;1–588;1–588;1–76;1–97;1–475;1–473;1–503;1–484;1–485;1–421;1–561;1–476;1–474;1–342;1–560;1–472;1–503;1–478;1–426;1–481;1–485;1–492;1–562;1–519;1–349;1–479;1–378;1–264;1–368;1–503;1–429;1–142;1–303;1–464;1–477;1–54;1–386;1–546;1–440;1–436;1–503;1–489;1–555;1–499;1–578;1–126;1–457;1–472;1–397;1–491;1–440;1–568;1–501;1–242;1 |
| 3423 | 1–265;1–76;1–97;1–164;1–298;1–181;1–378;1–429;1–378;1–264;1–142;1–54;1–378;1–126;1–245;1–242;1–268;1–268;1–70 |
| 3430 | 1–502;1–498;1–474;1–499;–418;1–283;1–804;1–499;1–298;1–269;1–487;1–527;1–452;1–512;1–475;1–305;1–488;1–338;1–316;1–534;1–282;1–469;1–507;1–239;1–299;1–500;1–484;1–306;1–331;1–507;1–509;1–499;1–457;39–125;39–237;48–366;48–499;48–421;48–353 |
| 3431 | 1–299;1–290;1–332;1–496;1–524;1–363;1–493;1–385;1–470;4–509;4–489;4–357;4–442;5–476;10–457 |
| 3433 | 1–182;1–277;1–420;1–473;1–440;1–420;1–466 |
| 3434 | 1–448;7489 |
| 3435 | 1–475;1–588;30–410;46–508;48–547;48–425;48–300;65–414;65–553 |
| 3436 | 1–475;1–465;1–135;1–446 |
| 3438 | 1–476;1–465;1–135;1–488;1–446;3–556 |
| 3440 | 1–471;142–550;150–614;150–599;150–651 |
| 3441 | 1–410;1–324;1–362;1–364;1–453;1–356;1–399;1–356;1–362 |
| 3442 | 1–406;1–436;1–450;1–335;1–222 |
| 3443 | 1–505;58–515;58–138 |
| 3444 | 1–311;1–439 |
| 3446 | 1–387;40–536;323–600;527–741 |
| 3447 | 1–469;1–495 |
| 3448 | 1–518;1–398;13–463;13–410;13–346;13–389;13–393;13–374;13–487;13–497;13–488 |
| 3450 | 1–387;1–382;1–503;1–372;1–222;1–455 |
| 3451 | 1–452;1–441;1–426 |
| 3454 | 1–283;4–167;4–95;4–101;4–179;4–177;4–125 |
| 3455 | 1–498;1–540;1–540;7–103 |
| 3456 | 1–325;1–327;1–450;1–140;1–353;1–264;1–94 |
| 3457 | 1–325;1–327;1–486;1–489;1–473;1–472;1–515;1–474;1–465;1–508;1–465;1–529;1–140;1–473;1–498;1–489;1–483;1–353;1–515;1–264;1–571;1–94 |
| 3458 | 1–478;1–357;1–462;1–323;1–427 |
| 3459 | 1–549;9–520;9–254;9–435;9–508;9–565;9–492;9–448 |
| 3460 | 1–481;1–432;4–482;40–475;40–442;40–423;51–543;51–423;57–385 |
| 3462 | 1–546;1–525 |
| 3465 | 1–526;3–440 |
| 3466 | 1–490;2–486;3–260;3–519;3–643;3–562;3–260;4–538;4–560;4–519;4–501;4–546;6–499;6–517;6–521;6–498;6–518;6–473;6–260;6–574;6–442;6–518;6–412;6–468;6–490;6–487;6–248;6–378;6–386;6–442;6–485;6–442;6–501;6–457;6–501;6–537;6–275;6–490;6–458;6–518;6–474;6–486;6–368;6–501;6–360;6–561;6–509;6–499;6–501;6–477;6–385;6–490;6–543;6–291;6–485;6–583;6–384;6–431;6–490;6–518;6–562;6–457;6–153;6–458;6–490;6–477;6–486;6–487;6–597;6–458;6–509;6–517;6–159;6–57;6–518;6–538;6–501;6–384;6–493;6–470;6–500;6–521;6–498;6–458;6–486;6–487;6–471;6–597;6–400;6–249;6–518;6–431;6–563;6–548;6–546;6–474;6–521;6–583;6–578;6–487;6–509;6–477;6–500;6–487;6–500;6–202;6–214;6–482;6–501;6–517;6–483;6–442;6–478;6–431;6–501;6–260;6–548;6–487;6–499;6–427;6–548;6–521;6–601;6–509;6–518;6–316;6–547;6–501;6–521;6–486;6–483;6–537;6–487;6–521;6–518;6–546;6–538;6–537;6–518;6–509;6–417;6–455;6–477;6–548;6–521;6–474;6–517;6–574;6–501;6–583;6–249;6–548;6–485;6–490;6–486;6–519;6–509;6–484;6–489;6–259;6–597;6–501;6–427;6–517;6–533;6–471;6–501;6–519;6–536;6–537;6–426 |
| 3467 | 1–468;1–510;1–491 |
| 3472 | 1–402;1–492 |
| 3473 | 1–427;1438 |
| 3474 | 1–512;1–451 |
| 3476 | 1–404;3–511;3–394 |
| 3478 | 1–498;1–443 |
| 3482 | 1–482;19–504;19–555;35–370;35–304;36–354;46–470;54–484;54–350;54–506;54–531;54–535;54–647;54–647;54–521;54–570;54–659;54–540;54–506;54–555;54–554;54–523;54–566 |
| 3483 | 1–258;3–556;3–306;3–469;17–481;17–468;17–493;21–302;49–129 |
| 3484 | 1–518;1–468;17–337;17–273;18–321;28–435;36–498;36–484;36–503;36–473;36–518;36–517;36–449;36–317;36–486;36–494;36–470 |
| 3489 | 1–527;1–523 |
| 3490 | 1–482;1–432;1–421;1–457;1–450;1–342;1–337;1–419;1–480;1–425;21–435;21–385 |
| 3491 | 1–467;14–350;14–352;34–512;34–483;34–399;37–503;40–401;59–551;75–553;83–561;102–559;103–510 |
| 3492 | 1–466;14–349;14–351;34–398;34–482;37–502;40–400;45–522;102–509 |
| 3493 | 1–231;1–477 |
| 3494 | 1–230;19–494 |
| 3497 | 1–433;138–520 |
| 3498 | 1–366;20–500;147–684;164–673;164–681 |
| 3499 | 1–465;1–461 |
| 3500 | 1–358;24–608;27–438 |
| 3501 | 1–467;1–141;1–325;1–498;1–502;1–511;1–499 |
| 3505 | 1–502;1–440 |
| 3507 | 1–350;1–497 |
| 3508 | 1–470;1–452 |
| 3509 | 1–487;1–406;1–467;1–490;1–530;1–481;3–469;3–290;3–469;3–141;3–479;4–361;4–455;4–465;4–409;5–475;8–87;8–92;8–406;8–485;8–123;8–223;8–268;8–508;8–478;8–151;8–105;8–110;8–486;8–347;8–480;8–511;8–468;8–239;0–508;10–471;11–553;11–242;11–166;11–457;11–153;11–470;11–494;11–497;11–457;11–557;11–523;11–412;11–469;11–278;11– |

TABLE II-continued (Tiling path)

| Seq Id No. | Positions of biological 5'ESTs |
|---|---|
|  | 481;21–154;27–163;27–418;27–156;27–394;27–50;27–465;27–473;27–346;27–92;28–92;39–270;41–93;41–462;41–415;41–409;41–521;41–269;41–515;41–489;41–402;41–532;41–481;41–159;41–415;41–515;41–461;41–395;41–396;41–535;41–552;41–552;41–539;41–467;41–518;41–468;41–272;43–409;43–523;43–117;43–112;43–275;49–133;49–489;49–460;49–529;49–547 |
| 3510 | 1–139;6–85;6–90;6–121;6–108;6–103;6–149;9–151;9–164;19–152;25–154;25–90;25–161;26–90;39–157;39–91;41–110;41–115;47–131;49–495 |
| 3512 | 1–492;1–155;1–405 |
| 3514 | 1–450;1–217;1–469;1–459;1–421;1–441;1–245;1–450;1–460;1–461;1–454;1–450;1–432;1–454;1–414;1–369;15–467;30–391 |
| 3518 | 1–492;19–470;21–475;50–491;361–752;361–754 |
| 3519 | 1–459;263–657;263–655 |
| 3520 | 1–489;1–490 |
| 3521 | 1–88;1–517 |
| 3522 | 1–267;66–530;66–406;66–521;66–423;66–477;66–461;66–500 |
| 3523 | 1–497;1–503;1–490 |
| 3524 | 1–477;2–456;2–484;4–513;22–350;22–486;38–545 |
| 3525 | 1–419;1–502;1–461;1–464;80–472;80–545;80–572;80–551;81–215 |
| 3528 | 1–462;1–476;1–463;1–407;1–475;1–477;1–420;1–473;1–502;1–470;2–407;5–410;5–485;5–471;5–466;5–450 |
| 3534 | 1–343;1–218;279–765;331–787 |
| 3535 | 1–260;1–482 |
| 3538 | 1–462;1–469;1–468;1–494;1–393;1–395;1–485;1–464 |
| 3540 | 1–52;1–500;1–499 |
| 3546 | 1–440;1–83;1–447;1–466 |
| 3547 | 1–83;7–470 |
| 3548 | 1–382;1496 |
| 3551 | 1–354;93–370;101–494 |
| 3552 | 1–490;1–433 |
| 3553 | 1–484;1–500;1–479;1–481;1–381;1–370;1–523;1–455;1–454;1–456;1–394;1–452;1–420 |
| 3555 | 1–493;6–354;31–531;72–424;72–413;85–561;85–561;85–565;85–561;85–565;85–412;85–548;85–560;85–532;85–557;85–548;85–561;85–549;85–487;85–565;85–178;85–481;85–565;85–565;85–531;85–539;85–408;85–565;85–357;85–547;85–554;85–563;85–556;86–664 |
| 3556 | 1–493;6–354;31–531;72–413;72–424;85–561;85–581;85–565;85–561;85–567;85–412;85–561;85–549;85–560;85–581;85–532;85–557;85–565;85–548;85–556;85–487;85–563;85–178;85–481;85–565;85–566;85–531;85–539;85–408;85–566;85–357;85–547;85–554;85–548;85–561;85–579 |
| 3557 | 1–242;1–244;1–244;1–239 |
| 3559 | 1–548;1–347;1–454 |
| 3561 | 1–448;2–394;5–332;5–330;5–481;5–435;5 405;12–415;12–478;12–489;12–466;16–155;23–447;23–540;27–478;27–479;27–489;27–507;27–522 |
| 3564 | 1–410;1–481;1–510;1–427;1–535;1–524;1–456;1–201;1–428;1–526;1–472;1–435;1–363;1–471;1–319;1–377;1–517;1–271;1–471;1–313;1–470;1–334;1–508;1–516;1–216;1–401;1–334;1–442;1–503;1–473;1–553;1–344;1–376;1–535;1–498;1–421;1–475 |
| 3565 | 1–478;1–491;1–467;1–477;1–444 |
| 3567 | 1–416;1–459 |
| 3568 | 1–499;31–489;39–471;39–509;39–194;39–117;39–108;39–448;39–410;39–432;40–538;41–451;41–458;41–437;41–196;41–289;41–518;41–514;41–297;41–368;41–512;41–482;41–512;41–449;41–519;41–502;41–391;41–513;41–480;41–521;41–494;41–470;41–279;41–392;41–466;41–487;41–220;41–522;41–519;41–478;41–502;41–532;41–531;41–491;41–130;41–498;41–494;41–521;41–434;41–482;41–482;41–145;41–301;41–306;41–496;41–498;41–419;41–533;41–439;41–280;41–522;41–482;41–453;41–469;41–477;41–532;41–516;41–191;42–161;42–451;42–499;42–269;42–472;42–439;42–420 |
| 3569 | 1–381;10–433;11–482;39–487;39–533;39–522;39–543;39–541;39–487;39–578;39–375;39–433;39–462;39–503;39–108;39–533;39–485;39–567;39–117;41–494;41–411;41–505;41–532;41–289;41–581;41–529;41–549;41–499;41–496;41–482;41–384;41–220;41–508;41–531;41–324;41–530;41–534;41–418;41–196;41–482;41–519;41–526;41–539;41–539;41–556;41–518;41–453;41–531;41–486;41–595;41–506;41–534;41–524;41–484;41–280;41–548;41–451;41–515;41–532;41–493;41–536;41–522;41–492;41–508;41–544;41–434;41–573;41–489;41–391;41–453;41–532;41–297;41–482;41–441;41–529;41–543;41–339;41–517;41–548;41–508;41–411;41–440;41–306;41–488;41–496;41–489;41–480;41–518;41–560;41–532;42–532;42–557;42–526;42–540;42–532;42–439;42–507;42–531;42–269;42–542;42–557;42–562;42–531;42–533;42–492;42–506;42–481;43–464;43–481;43–511;165–325 |
| 3573 | 1–436;1–464;1–459;1–390;1–436;1–429;1–478;1–437;1–500;1–405;1–409;1–504 |
| 3574 | 1–325;1–483;55–557 |
| 3578 | 1–301;1–228;1–413;1–321;1–395;1–404 |
| 3581 | 1–271;13–479;16–448;16–458;16–426;16–492 |
| 3582 | 1–489;1–461;2–382;2–493;2–455;2–391;2–465;2–482;2–483;2–302;2–295;2–503;2–468;2–339;2–413;2–446;2–466;2–484;2–489;2–482;2–468;3–505;3–494;3–510;3–483;5–466;5–471;5–487;5–303;5–460;5–167;5–527;5–481;37–496 |
| 3583 | 1–443;1–516;1–459;1–184;1–451;1–459;1–376 |
| 3584 | 1–491;2–461;2–483;2–439;2–393;2–453;2–501;2–468;2–371;3–492;3–137;3–456;3–137;3–137;3–395;3–446;3–137;3–455;3–443;3–392;3–461;3–438;3–137;3–446;3–493;3–266;3–137;3–468;3–137;3–477;3–485;3–468;3–137;3–456;3–456;3–259;3–125;3–457;3–495;3–137;3–510;3–137;3–379;3–137;4–459;4–373;8–457;40–458;40–509 |
| 3588 | 1–406;1–446;1–379;1–439;1–484;1–539;1–468;1–461;1–533;1–363;1–192;1–454;1–446;1–465;1–558 |
| 3589 | 1–637;1–475 |
| 3590 | 1–477;1–448;1–441;1–397;1–259;1–436;1–474;1–373;1–308;1–436;1–447;1–474;1–441;1–473;1–477 |
| 3591 | 1–459;1–449 |
| 3593 | 1–327;1–446;1–475;1–459;1–418;1–418;4–492;4–308;4–446;4–446;4–489;4–414;4–203;4–384;4–467;4–385;4–436;4–451;4–319;4–469;4–385;4–472;4–418;4–411;4–492;4–349;4–426;4–376;4–400;4–67;4– |

TABLE II-continued

(Tiling path)

| Seq Id No. | Positions of biological 5'ESTs |
|---|---|
| | 470;4–70;4–72;4–461;4–426;4–67;5–446;5–474;11–69;11–446;11–68;11–487 |
| 3594 | 1–350;1–465;1–388;1–512;1–382;1–321 |
| 3595 | 1–486;1–90;1–505;1–571;1–313;1–446 |
| 3597 | 1–396;1–520;1–503;1–436;1–560;1–364 |
| 3598 | 1–417;257–826 |
| 3599 | 1–537;17–489;20–484;23–276;422–853;422–946;422–940 |
| 3600 | 1–477;1–477;9–205;9–64;9–102 |
| 3601 | 1–57;1–380;1–95;1–375;1–392;1–366;1–380;1–307;1–312;1–393;1–394;1–372;1–385;1–198;1–283;1–394;1–376;1–377;1–380;1–379;1–392;1–393;1–372;1–354;1–391;1–376;1–379 |
| 3604 | 1–441;3–416 |
| 3607 | 1–429;4–488 |
| 3608 | 1–475;1–433;1–501;1–469;1–414;1–483;1–304;1–479;1–449;1–430;1–377;1–469;1–402;1–473;1–458;1–428;1–402 |
| 3609 | 1–422;1–492;1–425;207–638 |
| 3610 | 1–440;1–490;1–478 |
| 3612 | 1–438;27–421;27–448;27–421;27–450;27–421;27–510;27–450;27–510;27–421;27–389;27–450;27–442;27–421;28–517;28–429;28–489;28–364;28–450;28–488;28–421;28–421;28–95;28–429;28–416;28–394;29–88;31–436;31–406;31–168;31–450;33–347;337–583;337–699 |
| 3614 | 1–146;1–125;1–179;23–493;42–263 |
| 3615 | 1–491;1–439 |
| 3616 | 1–395;9–549;9–497;9–522;9–527;9–455;9–466;9–117;9–523;9–523;9–455;9–493;9–495;9–466;10–471;16–456;18–227 |
| 3617 | 1–292;1–489 |
| 3618 | 1–467;1–454;1–278;10–77;10–75;10–75;10–75;10–75;10–75;10–77;10–77;10–77;10–77;10–75;10–75;10–75;10–75;10–75;10–77;10–75;10–75;10–75;10–75;10–77;10–75;10–75;10–75;10–75;10–77;10–75;10–75;10–75;10–75;10–77;48–409;55–469;55–419;55–457;57–396;66–547;76–416;97–515;99–473;103–539;103–473;103–557;103–538;262–753 |
| 3622 | 1–479;1–450 |
| 3623 | 1–454;1–501;1–487;1–505 |
| 3624 | 1–439;1–461;1–479 |
| 3627 | 1–508;11–202;14–553;14–463;18–458;18–381;24–524;24–548;24–460 |
| 3628 | 1–503;–522;1–428;1–455;1–436;1–366;1–437;1–489 |
| 3629 | 1–507;1–477;18–490;390–850 |
| 3631 | 1–427;25–458;25–471;25–500 |
| 3637 | 1–310;1–442;1–386;1–406;1–460;1–488 |
| 3638 | 1–352;1–474 |
| 3639 | 1–454;1–486;1–393 |
| 3644 | 1–440;1–485;1–471;1–436 |
| 3650 | 1–473;1–484 |
| 3652 | 1–346;1–414;2–442;3–453;3–458;3–517;3–409;3–443;3–453;3–440;7–456;8–153;18–522 |
| 3653 | 1–400;1–472;1–501;1–160;1–492 |
| 3662 | 1–362;1–347 |
| 3663 | 1–1043;1–456 |
| 3664 | 1–425;22–515;22–520;22–515;48–510;49–517;54–247;55–523;55–527;58–527;63–509;63–498;63–399;63–485;63–498;63–517;63–472;81–391;82–531;82–517;83–260;83–504;83–515;83–506;83–451;83–476;83–477;83–524;83–516;83–498;83–504;83–324;83–260;83–492;83–468;83–506;83–468;83–505;83–401;83–512;83–517;83–484;83–485;84–530;84–493;84–428;84–381;84–527;84–498;84–530;84–524;84–519;84–511;84–516;84–530;84–468;84–510;84–469;84–536;84–422;84–485;84–531;84–492;84–480;84–469;84–491;84–521;84–531;84–529;84–535;84–512;84–517;84–467;84–504;84–532;84–516;84–439;84–512;84–517;84–525;84–517;84–509;84–405;84–510;84–480;84–531;84–516;84–472;84–532;84–535;84–533;84–321;84–506;84–531;84–489;84–507;84–374;84–500;84–456;84–530;84–509;84–467;84–375;84–507;84–492;84–531;84–527;84–518;84–338;84–511;84–531;84–449;84–533;84–485;84–382;84–498;84–472;84–506;84–532;84–525;84–485;84–532;84–522;84–509;84–477;84–527;84–520;84–164;84–531;84–477;84–456;84–510;84–509;84–53;84–523;84–531;84–428;84–304;84–531;84–527;84–523;84–516;84–320;84–525;84–480;84–531;84– |
| 3666 | 1–424;53–246;62–497;62–484;62–398;62–503;62–497;62–471;80–390;82–475;82–400;82–484;82–323;82–467;82–483;82–503;82–497;82–503;82–503;82491;82–503;82–259;82–450;82–503;82–476;82–467;82–259;83–438;83–503;83–479;83–468;83–421;83–488;83–479;83–503;83–478;83–404;83–499;83–467;83–320;83–497;83–484;83–380;83–427;83–497;83–374;83–492;83–491;83–443;83–494;83–337;83–136;83–484;83–471;83–381;83–471;83–496;83–468;83–503;83–567;83–448;83–317;83–503;83–476;83–455;83–503;83–427;83–373;83–319;83–479;83–503;83–398;83–478;83–466;83–503;83–503;83–503;83–503;83–491;83–455;83–448;83–402;83–503;83–284;83477;83–466;83–404;83–467;83–475;83–502;83–324;83–503;83–163;83–490;83–484;83–443;83–471;83–500;83–276;83–448;83–484;83–490;83–466;83–163;83–242;83–284;83–503;83–443;83–443;83–503;83–243;83–490;83–455;83–303;83–503;83–439;83–486;83–483;83–503;83–484;83–443;83–442;83–503;83–476;83–503;83–414;83–494;83–450;83–503;83–428;83–428;83–476;83–492;83–503;83–411;83–494;83–503;83–493;83–436;83–503;83–444;83–503;83–484;83–499;83–472;83–455;83– |
| 3670 | 1–463;8–550;8–490;8–483;8–330;8–453;8–335 |
| 3671 | 1–444;1–514;1–342 |
| 3672 | 1–460;1–480;1–518;1–488;1–535;1–398;2–335;41–476;43–473;76–597;76–585;76–398;76–369;76–550;76–573;76–546;76–587 |
| 3676 | 1–489;1–586 |
| 3678 | 1–471;1–464 |
| 3679 | 1–343;1–132;1–425;1–495;1–446;1–372;1–422;1–492;1–524 |
| 3680 | 1–336;1–421;1–941;34–497 |
| 3681 | 1–410;12–447;12–496;23–587;32–490;35–537;52–543;52–543;52–484;52–483 |
| 3684 | 1–508;1–414;1–449;1–472;1–504;1–490;1–474;1–466;1–441;2–421 |
| 3685 | 1–284;1–427 |
| 3688 | 1–471;1–465 |
| 3689 | 1–339;1–356;1–525 |
| 3690 | 1–488;1–438;1–513;1–465;41–473;41–473 |
| 3691 | 1–377;1–477;1–529;1–529;1–506;1–564;1–477;1–524;1–560;1–471;1–477;1–508;1–488 |
| 3693 | 1–324;39–473 |
| 3694 | 1–410;45–461 |
| 3697 | 1–469;1–467 |
| 3698 | 1–195;1–454;1–382;–485;5–327 |

TABLE II-continued (Tiling path)

| Seq Id No. | Positions of biological 5'ESTs |
|---|---|
| 3699 | 1–858;1–444 |
| 3701 | 1–273;1–499;1–479;1–334;1–467;1–460;1–493;1–496;1–493;1–462;1–525;1–477;1–496;–223;–296;1–514;1–478;1–479;1–487;1–229;1–194;1–482;1–388;1–475;1–572;1–459;1–387;1–497 |
| 3702 | 1–500;1–374;1–479;1–470;1–480;1–504;1–543 |
| 3703 | 1–483;1–487;1–485;1–394;1–487;1–492;1–503;1–491;1–488;1–445;1–452;1–339;1–493;1–471 |
| 3706 | 1–442;8–499;19–451;19–409;42–458 |
| 3708 | 1–496;1–331;13–499;13–517;13–128;13–512;13–514;13–453;13–525;13–506;38–444;57–633;57–500;58–505 |
| 3709 | 1–331;13–128;13–451;38–444;57–500;234–504;234–504 |
| 3710 | 1–560;5–382 |
| 3711 | 1–426;1–461;1–430 |
| 3712 | 1–460;1–471;1–415;1–462;14–457;14–456;14–457;14–466;14–452 |
| 3713 | 1–482;4–350;5–497;5–485;5–499;5–490;28–495;29–494;29–471;36–450;36–499;36–495;49–492;49–492;49–487;49–491;49–497 |
| 3715 | 1–507;1–142 |
| 3716 | 1–483;13–182;239–771;246–675;270–652;270–665 |
| 3717 | 1–501;1–472;1–459;1–508;1–494;1–423;1–478;33–350;72–599;72–558;72–550;72–597;72–513;72–421;72–578 |
| 3719 | 1–435;2–449;2–205;2–511;2–423;3–64;3–462;3–423;3–406;4–388;22–443;25–443;25–140 |
| 3720 | 1–816;1–436;2–450;2–205;2–424;3–64;3–463;3–424;3–407;4–530;4–507;4–389;8–510;22–444;22–816;25–140;25–444 |
| 3721 | 1–469;1–442 |
| 3722 | 1–379;1–466;1–473;1–496;1–331;1–466;1–242;1–486;1–403 |
| 3723 | 1–304;1–408;1–409;1–477;1–465;1–366 |
| 3724 | 1–412;1–469 |
| 3726 | 1–507;1–339;1–491;1–523 |
| 3727 | 1–472;1–483;1–496;1–579 |
| 3731 | 1–250;1–494 |
| 3732 | 1–425;1–524;41–486;57–302 |
| 3733 | 1–381;1–415;1–364;1–479 |
| 3738 | 1–468;1–245;1–463;1470;1–457;1–244;1–452;1–375;17–432;48–439;48–522;48–544;48–493;48–362;48–466;48–375;48–515;48–397;48–523;48–454;48–467;48–145;48–485;48–520;48–465;48–361;49–328;52–523;52–514;52–516;52–132;52–432;52–430;52–535;52–431;52–477;52–467;52–371;59–542;59–447;59–525;59–481;59–340;59–423;59–375;59–248;59–484;59–357;59–357;59–410;59–447;59–544;59–546;59–564;59–444;59–485;59–428;59–417;59–521;59–351;59–528;59–466;59–467;59–564;59–510;66–534;67–484;67–549;86–556;86–562;86–456;86–360;86–514;86–546;86–531;86–530;86–534;86–485;86–251;86–552 |
| 3739 | 1–433;1–98;5–85;5–68 |
| 3740 | 1–476;1–457;1–473 |
| 3742 | 1–425;4–429;4–382;4–464;4–503;8–67;8–500;8–484;8–500;11–478;18–431;29–509;41–481;41–475;44–496;45–489;45–490;45–484;45–492;45–547;45–515;45–509;45–494;45–508;45–427;45–474;45–509;45–333;45–490;45–415;45–171;45–474;45–463;45–358;45–382;46–395;46–327;46–335;46–413;81–585;82–497;82–499;82–513;82–464;82–523;100–488;100–573;100–506;100–491;100–603;100–500;100–491;100–581;100–591;100–500;112–510;112–504;112–510 |
| 3743 | 1–490;158–613 |
| 3744 | 1–312;1–308;1–247;1–271;2–295;2–193;2–243;2–274;2–159;2–321;2–200;2–212;2–324;2–468;2–288;2–133;2–71;2–491;2–269;2–133;2–331;2–268;2–213;2–159;2–477;4–319;4–303;4–328;4–148;4–331;4–282;5–275;5–145;5–266;5–313;5–323;5–221;5–322;5–325;5–266;5–290;5–327;5–266;5–329;5–266 |
| 3746 | 1–409;1–418;1–301 |
| 3748 | 1–437;50–519;50–495;51–425;51–534 |
| 3749 | 1–380;1–403;1–377;1–446;1–387;1–392;1–373;1–125;1–370;1–393;2–324;16–484;16–506;16–471;16–447;31–379;36–366;38–111 |
| 3750 | 1–389;2–421;2–424;2–405;2–421;2–421 |
| 3751 | 1–389;1–444;2–405 |
| 3753 | 1–499;1–457;1–131;1–462;1–508;2–231;2–465;2–313;2–456;2–332;2–478;3–557;3–281;3–455;3–452;4–513;4–405;4–456;4–357;5–429;11–455;11–63;11–461;11–531;11–465;11–451;11–483;11–453;14–342;23–504 |
| 3754 | 1–380;1–166;1–231;1–371;30–171;99–495 |
| 3756 | 1–448;2–512;2–99;2–132;2–352;2–98;2–439;2–134;2–245;2–100;2–100;2–100;2–225;2–100;2–134;2–100;2–96;2–117;2–100;4–444;4–494;5–487;5–431;5–525;16–455 |
| 3757 | 1–362;1–350;24–473 |
| 3759 | 1–402;3–518;5–380;5–376;5–438;5–419;5–103;5–365;5–480;5–439;5–478;5–497;24–444;24–440 |
| 3760 | 1–485;1–490;1–58 |
| 3761 | 1–111;1–454;1–447 |
| 3763 | 1–472;1–469;1–372;1–477 |
| 3764 | 1–473;1–480 |
| 3766 | 1–566;1–221;128–470;265–728 |
| 3767 | 1–371;22–478 |
| 3769 | 1–461;1–457 |
| 3771 | 1–69;24–548;24–438;24–477;24–228;24–504;24–471;99–401;113–604;113–612;113–563;113–466;113–441;113–615;113–618;113–465;113–578 |
| 3772 | 1–464;1–177;1–492 |
| 3773 | 1–505;1–370 |
| 3774 | 1–488;1–379;81–518;243–762;598–1060;653–759;714–1157;814–157;814–1149;822–1101 |
| 3775 | 1–461;1–455;1–466;1–473;1–452;1–443;1–459;1–443;1–443;1–439;1–451;1–453;1–440;1–464;1–473;1–470;1–444;1–342;1–330;1–463;1–443;1–470;1–451;1–460;1–355;1–442;1–464;1–397;1–460 |
| 3776 | 1–178;1–461;1–406;5494;5–476;5–457;5–542;5–491;5–449;5–452;5–521;5–506;5–520;6–392;17–518;19–517;19–405;19–521;19–1100;19–498;36–176 |
| 3777 | 1–324;1–516 |
| 3778 | 1–64;1–65;1–75;28–504;28–488;28–427;28–505;28–510;28–505;28–496;28–167;28–444;28–494;28–314;28–505;32–183;67–687;67–550;67–405;67–496;72–496;72–597 |
| 3779 | 1–407;2–445;2–425;2–503;2–488;2–459;2–396;2–488;2–413;2–426;2–431;2–494;2–494;2–420;2–391;2–494;2–464;2–454;2–463;2–435;2–444;2–471;2–461;2–497;2–187;2–489;2–443;2–474;2–473;2–424;2–489;2–470;2–484;2–477;2–481;2–499;3–493;3–457;3–474;3–392;3–499;3–301;3–478;3–485;3–485;3–304;3–510;3–495;3–495;3–507;3–483;3–471;3–474;3–303;3–479;5–489;5–490;5–507;5–484;5–484;5– |

TABLE II-continued (Tiling path)

| Seq Id No. | Positions of biological 5'ESTs |
|---|---|
| | 497;5–443;5–275;5–485;5–496;5–495;5–527;5–473;5–496;5–510;5–484;5–306;5–445;5–472;5–476;5–489;5–388;5–484;5–469;5–479;5–387;5–412;5–488;5–492;5–484;5–443;5–477;5–192;5–496;5–471;5–503;5–492;5–476;5–479;5–484;6–453;6–362;7–415;7–485;7–494;7–487;7–484;7–497;7–476;7–408;7–501;7–192;11–334;13–362;13–299;13–489;33–465;33–496;33–413;33–486;33–485;33–520;33–332;33–466;33–502;33–408;33–51;33–478;33–429;33–492;33–306;33–508;54–386 |
| 3780 | 1–407;2–445;2–484;2–425;2–488;2–536;2–396;2–464;2–499;2–494;2–420;2–494;2–426;2–391;2–463;2–494;2–459;2–431;2–444;2–454;2–471;2–481;2–497;2–488;2–484;2–461;2–503;2–474;2–489;2–413;2–473;2–489;2–435;2–187;2–552;2–470;2–477;2–443;3–457;3–552;3–499;3–392;3–485;3–474;3–485;3–478;3–301;3–493;3–542;3–479;3–510;3–507;3–304;3–495;3–483;3–495;3–471;3–474;3–303;5–490;5–531;5–489;5–306;5–497;5–484;5–443;5–507;5–496;5–485;5–495;5–476;5–473;5–510;5–484;5–445;5–496;5–472;5–484;5–275;5–479;5–387;5–471;5–532;5–484;5–484;5–469;5–489;5–388;5–479;5–492;5–492;5–503;5–412;5–488;5–192;5–477;5–484;5–476;5–496;5–443;6–362;6–453;7–497;7–494;7–484;7–501;7–485;7–415;7–408;7–476;7–487;7–192;11–555;11–334;13–299;13–362;13–489;13–546;33–540;33–465;33–552;33–523;33–496;33–486;33–413;33–332;33–502;33–511;33–485;33–531;33–466;33–492;33–408;33–429;33–306;33–527;33–508;33–478;54–386 |
| 3781 | 1–451;83–534 |
| 3782 | 1–467;2–357 |
| 3784 | 1–484;1–484;1–261 |
| 3785 | 1–291;1–421;1–348;1–442 |
| 3786 | 1–420;1–416;1–414;1–420;1–416;1–420;1–416;1–163;1–416;1–404;1–416;1–416;1–420;1–420;1–416;1–420;1–350;1–416 |
| 3787 | 1–419;1–505 |
| 3788 | 1–491;1–466 |
| 3789 | 1–478;1–488 |
| 3790 | 1–495;1–443;1–255;1–450 |
| 3791 | 1–389;1–373;–391;1–398;1–39;1–373 |
| 3792 | 1–488;1–448;1–450;1–287;1–71;1–474;–430;1–495;2–465 |
| 3793 | 4–363;4–410;13–469;3–481;13–482;13–455;13–480;15–406;15–487;15–461;15–147;15–391;15–425;16–498;16–144;16–492;16–434;16–487;16–449;16–145;16–129;16–479;16–397;16–462;16–391;16–483;16–472;16–484;16–463;16–497;16–443;16–472;16–477;16–491;16–481;16–485;16–483;16–333;16–482;16–443;16–471;16–434;16–481;16–486;16–145;16–480;16–420;16–421;16–434;16–479;16–406;16–462;16–480;16–86;16–484;16–487;16–458;16–446;16–471;16–204;16–139;16–435;16–141;16–480;16–145;16–452;16–403;16–435;16–387;16–458;16–459;16–458;16–482;16–472;16–493;16–243;16–434;16–478;16–470;16–117;16–487;16–450;16–485;16–458;16–441;16–486;16–442;16–422;16–490;16–482;16–460;16–483;16–469;16–418;16–472;17–433;17–441;17–462;17–480;17–423;17–453;17–484;17–484;17–484;17–469;17–451;17–474;17–477;17–303;17–462;17–469;17–463;17–461;17–404;17–462;17–458;17–124;17–440;17–471;17–495;17–419;17–327;17–479;17–445;17–487;17–420;20–344;20–485;20–480;20–386;20–475;46–325;46–349;46–484;46–20 |
| 3794 | 1–522;1494;1–492;12–440;12–389;22–563;22–521;22–563;22–522;22–492;22–544;24–437;24–522;24–458;24–420;24–498;24–160;25–534;25–158;25–533;25–551;25–534;25–498;25–544;25–513;25–544;25–483;25–143;25–420;25–522;25–589;25–544;25–498;25–522;25–525;25–522;25–513;25–532;25–521;25–522;25–159;25–572;25–522;25–475;25–475;25–356;25–534;25–561;25–544;25–521;25–522;25–159;25–421;25–450;25–450;25–572;25–513;25–544;25–437;25–571;25–498;25–522;25–534;25–93;25–547;25–522;25–519;25–522;25–542;25–450;25–531;25–522;25–131;25–222;25–542;25–153;25–155;25–544;25–483;25–483;25–495;25–495;25–513;25–534;25–534;25–589;25–495;25–495;25–522;25–429;25–573;25–534;25–553;25–159;25–534;25–450;25–553;25–522;25–496;25–522;25–497;25–544;25–475;25–475;25–563;25–262;25–522;25–534;26–544;26–513;26–522;26–498;26–450;26–522;26–544;26–475;26–483;26–498;26–544;26–475;26–498;26–513;26–138;26–498;26–553;26–544;26–429;26–522;26–319;26–498;26–542;26–544;26–450;26–534;26–475;26–495;26–522;26–450;26–552;26–513;26–563;26–350;29–513;29–577;29–368;57–553;57–544 |
| 3801 | 1–273;1–403;1–403;1–366;1–157;1–462;3–290 |
| 3802 | 1–273;1–468;1–403;1–403;1–366;1–157;3–290 |
| 3803 | 1–475;5–449;50–407;50–507;50–508;50–552;50–547;52–521;52–534;52–533;52–526;52–517;52–238;52–574;88–536;88–579;468–985 |
| 3807 | 1–471;1–445;4–452;4–464;40–498;40–209 |
| 3808 | 1–499;1–446 |
| 3809 | 1–462;1–484;1–473;1–450;1–455;6–477;12–590;36–418;39–538 |
| 3810 | 1–503;1–450 |
| 3811 | 1–476;41–528;46–527;46–509;46–519;46–518;49–526 |
| 3812 | 1–467;29–519 |
| 3813 | 1–483;1–451;1–345;1–518;1–486 |
| 3814 | 1–449;6–515;7–478 |
| 3815 | 1–478;1–480 |
| 3816 | 1–443;1–458 |
| 3817 | 1–85;45–455 |
| 3818 | 1–371;4–484 |
| 3819 | 1–527;1–368 |
| 3820 | 1–368;1–480 |
| 3821 | 1–449;–436 |
| 3822 | 1–481;1–459;1–487;1–437;1–435;1–465;1–569;–491;1–535;1–513;1–447;1–468;1–469;1–481;1–552;1–414;1–490;1–447;1–459;1–509;1–278 |
| 3825 | 1–463;1–487 |
| 3826 | 1–220;19–511;19–472;19–512;19–448;19–315;28–465;28–480;28–531;28–515;28–199;28–453;28–517;28–456;28–495;28–536;28–495;28–515;28–469;28–411;28–545;3–506;31–532;31–389;31–95;31–480;31–484;31–511;3–518;31–459;31–511;3–459;31–505;31–489;31–507;31–459;3–518;31–441;31–506;31–95;31–508;31–488;31–506;31–95;31–407;31–543;31–463;31–95;31–220;31–107;31–518;31–505;31–476;31–536;31–226;31– |

TABLE II-continued (Tiling path)

| Seq Id No. | Positions of biological 5'ESTs |
|---|---|
|  | 503;31–481;31–95;31–496;31–494;31–500;31–496;31–95;31–491;31–480;31–481;31–491;31–483;32–237;32–368;32–468;34–505;42–506;42–493;42–503;57–603 |
| 3827 | 1–105;1–432;1–453;1–400;1–432;1–439;1–351;1–362;1–440;1–261;1–332;1–444;1–352;1–362;1–430;1–441;1–339;1–398;1–419;1–421;1–191;1–287;1–144;1–345;1–432;1–413;1–356;1–190;1–161;1–414;1–379;1–445;1–99;1–441;1–432;1–434;1–464;1–63;1–442;1–441;1–290;1–359;1–451;1–172;1–224;1–285;1–442;1–427;1–270;1–275;1–400;1–453;1–432;1–446;1–419;1–227;1–421;1–459;1–280;1–88;1–454;1–281;1–444;1–442;1–458;1–369;1–464;1–78;1–441;1–431;1–336;1–350;1–442;1–207;1–453;1–453;1–298;1–457;1–431;1–440;1–355;1–465;1–457;1–283;1–340;1–432;1–464;1–231;1–216 |
| 3829 | 1–346;8–577;14–503;16–483;16–455;16–496;16–482;16–478;16–211;16–479;16–517;16–500;16–378;16–457;16–398;35–519;57–530;57–589 |
| 3830 | 1–484;2–335;2–561;2–456;2–480;2–512;2–395;2–550;2–485;2–60;2–470 |
| 3831 | 1–477;1–542 |
| 3834 | 1–592;1–493 |
| 3835 | 1–452;1–209 |
| 3837 | 1–550;1–542 |
| 3839 | 1–517;1–70;1–489;1–456;1–488;1–446;1–533;1–408;1–267;1–456;1–442;1–483;1–529;1–497;1–533;1–536;1–432;1–533;1–506;1–396;1–389;1–469;1–243;11–374 |
| 3840 | 1–70;1–489;1–434;1–456;1–483;1–488;1–408;1–494;1–267;1–456;1–442;1–446;1–426;1–495;1–441;1–432;1–396;1–389;1–469;1–243;1–508;11–374 |
| 3845 | 1–351;1–213 |
| 3846 | 1–432;248–768 |
| 3848 | 1–547;1–539;1–539;1–447;1–314;1–547;1–349;1–539;1–438;1–554;1–547;1–539;1–449;1–554;1–539;1–674;1–497;1–547;1–547;1–375;1–547;1–438;1–547;1–547;1–539;1–438;1–539;1–606;1–438;1–554;1–438;1–564;1–438;1–554;1–547;1–542;1–547;1–547;1–547;1–485;1–438;1–61;1–426;1–480;1–567;1–539;1–438;1–483;1–547;1–485;1–554;1–547;1–423;1–547;1–539 |
| 3860 | 1–468;1–243 |
| 3861 | 1–335;1–424;1–54 |
| 3864 | 1–500;1–513 |
| 3865 | 1–495;8–151;8–166;8–176;8–176;8–158;8–176;8–165;8–179;8–176 |
| 3866 | 1–461;1–470;1–470;1–446 |
| 3868 | 1–368;1–61;1–446;1–467;1–398;1–409;1–450;1–424;1–450;1–425;1–418;1–467;1–278;1–458;1–470;1–500;1–478 |
| 3870 | 1–457;1–503 |
| 3874 | 1–417;189–604;192–419;193–613;193–489;193–548;193–452;193–604 |
| 3880 | 1–452;275–698;278–508;279–707;279–578;279–541;279–698;279–635 |
| 3882 | 1–202;2–205;4–485;6–221;6–221;6–221;6–218;17–114;21–193 |
| 7819 | 1–205;1–186;1–200;1–200;1–200;1–182;1–200;1–200;1–194;1–200;1–196 |
| 7828 | 1–498;58–547;58–418;58–584 |
| 7837 | 1–355;21–477;21–395;57–547 |
| 7845 | 1–355;21–477;21–395;65–562 |
| 7851 | 1–432;1–449 |
| 7872 | 1–106;1–556;1–449;1–523;1–551;1–415;1–468;1–556;1–501;1–449;1–556;1–556;1–452;1–496;1–361;1–556;1–556;1–566;1–372;1–452;1–263;1–341;1–487;1–462;1–362;1–372;1–498;1–447;1–507;1–545;1–491;1–507;1–347;1–556;1–413;1–433;1–556;11433;1–556;1–556;1–194;1–292;1–556;1–551;1–146;1–355;1–449;1–429;1–366;1–552;1–556;1–556;1–193;1–163;1–430;1–488;1–386;1–508;1–463;1–556;1–566;1–466;1–556;1–100;1–449;1–556;1–556;1–556;1–451;1–64;1–479;1–460;1–556;1–497;1–491;1–295;1–489;1–556;1–369;1–510;1–498;1–491;1–179;1–468;1–479;1–228;1–290;1–460;1–79;1–444;1–275;1–487;1–280;1–566;1–500;1–415;1–468;1–509;1–449;1–464;1–433;1–231;1–433;1–478;1–511;1–285;1–556;1–89;1–537;1–468;1–286;1–501;1–462;1–460;1–465;1–466;1–477;1–466;1–508;1–572;1–554;1–489;1–471;1–468;1–507;1–205;1–556;1–488;1–448;1–556;1–344;1–360;1–556;1–487;1–544;1–556;1–564;1–569;1–566;1–556;1–460;1–468;1–365;1–479;1–300;1–499;1–476;1–448;1–452;1–535;1–556;1–220;1–476;1–541;1–288;1–347;1–449;1–479;1–235;2–553;2–538 |
| 7920 | 1–112;1–112;1–171;1–128;2–149 |
| 7945 | 1–238;1–238 |
| 7963 | 1–334;1–334;1–328;1–297;1–334;1–322;1–327 |
| 7991 | 1–450;1–279;1–369;1–519 |
| 8242 | 1–450;1–429 |
| 8292 | 1–401;1–416;1–369;1–457;1–406;1–436 |
| 8324 | 1–459;1–459 |
| 8351 | 1–411;1–476;1–477;1–443 |
| 8377 | 1–150;1–150;1–150 |
| 8385 | 1–438;1–393 |
| 8393 | 1–463;1–322 |
| 8401 | 1–557;1–382;1–425;1–448;1–386;1–419;1–415 |
| 8413 | 1–434;1–492 |
| 8421 | 1–420;1–467;1–484;1–455;1–442 |
| 8436 | 1–518;1–586;4–496 |
| 8452 | 1–429;1–547 |
| 8477 | 1–369;33–114 |
| 8508 | 1–421;1–421;1–421;1–421;1–421;1–363;1–421 |
| 8529 | 1–411;2–223;4–460 |
| 8538 | 1–433;1–459;1–222;3–409 |
| 8560 | 1–379;1–267;1–442;15–233 |
| 8586 | 1–439;1–272 |
| 8627 | 1–411;123–506 |
| 8689 | 1–96;1–366 |
| 8821 | 1–410;1–369 |
| 8830 | 1–446;1–469;1–500;1–505;1–498;1–321;1–213;1–493;1–356;1–480;1–482;1–467;1–454;1–362;1–544;1–136;1–477;1–218;2–537;2–500 |
| 8841 | 1–467;1–475 |
| 8862 | 1–320;1–212;1–355;1–361;1–135;1–217;1–379 |
| 8884 | 1–193;1–206;1–206;1–203;1–206;1–206;1–194;1–194;1–194;1–206;1–194;1–205;1–206;1–206;1–206;1–195;1–199;1–157;1–208;1–206;1–206;1–184;1–194;1–206;1–206;1–206;1–194;1–194;1–205;1–158;1–189;1–194;1–194;1–194;1–206;1–194;1–206;1–194;1–194;1–206;1–206;1–206;1–206;1–206;1–205;1–206;1–187;1–206;1–194;1–146;1–194;1–206;1–206;1–163;1–193;1–193;1–206;3–201 |
| 8885 | 1–437;1–442 |
| 8905 | 1–212;1–212;1–212;1–212 |
| 8955 | 1–326;1–371;1–445 |
| 8976 | 1–399;32–388 |
| 8992 | 1–341;1–469;1–478 |

TABLE II-continued (Tiling path)

| Seq Id No. | Positions of biological 5'ESTs |
|---|---|
| 9016 | 1–468;1–515 |
| 9024 | 1–380;1–387 |
| 9064 | 1–431;4–439;5–194 |
| 9093 | 1–175;1–175;1–175;1–170;1–171;1–171;1–55;1–175;1–175;1–171;1–171;1–175;1–175;1–171;1–175;1–171;1–175;1–175;1–171;1–175;1–175 |
| 9097 | 1–445;1–556;1–294;1–428;1–153;1–435;1–537 |
| 9121 | 1–433;1–205;1–434 |
| 9177 | 1–377;1–377;1–86;1–377;1–376;1–377;1–377;1–377;1–109;1–377;1–377;1–139;1–377;1–377;1–362;1–377;1–377;1–377;1–377;1–377;1–377;1–377;1–377;1–377;1–377;1–349;1–377;1–377;1–377;1–377;1–364;1–377;1–377;1–377;1–377;1–377;1–377;1–377;1–377;1–377;1–377;1–377;1–151;1–377;1–377;1–377;1–377;1–377;1–365;1–377;1–377;1–164;1–377;1–377;1–377;1–377;1–377;1–377;1–377;1–377;1–377;1–361;1–377;1–372;1–377;1–377;1–377;1–376;1–375;1–377;1–377;1–376;1–377;1–344;1–377;1–349;1–377;1–377;1–346;1–377;1–377;1–372;1–375;1–377;1–346;1–377;1–377;1–377;1–377;1–376;1–376;1–341;1–377;1–377;1–149;1–377;1–342;1–377;1–377;1–377;1–377;1–349;1–377;1–377;1–377;1–377;1–377;1–377;1–377;1–377;1–377;1–377;1–377;1–377;1–377;1–377;1–377;1–377;1–377;1–377;1–377;1–377;1–376;1–377;1–365;1–377;1–376;1–377;1–146;1–348;1–377;1–377;1–377;1–377;1–377;1–377;1–346;1–377;1–375;1–377;1–377;1–377;1–377;1–377;1–377;1–377;1–377;1–377;1–377;1–384;1–377;1–377;1–169;1–270;1–345;1–377;1–343;1–377;1–377;1–377;1–377;1–377;1–377;1–367;1–377;1–377;1–377;1–377;1–377;1–377;1–377;1–377;1–377;1–341 |
| 9185 | 1–386;1–386;1–88;1–392;1–385;1–386;1–386;1–386;1–111;1–386;1–386;1–392;1–142;1–386;1–371;1–386;1–386;1–386;1–386;1–386;1–386;1–386;1–386;1–386;1–373;1–386;1–386;1–386;1–386;1–386;1–386;1–386;1–349;1–386;1–386;1–386;1–386;1–386;1–386;1–154;1–386;1–386;1–386;1–386;1–386;1–374;1–386;1–386;1–167;1–386;1–386;1–385;1–386;1–386;1–386;1–386;1–386;1–386;1–370;1–386;1–381;1–386;1–386;1–386;1–385;1–384;1–386;1–386;1–388;1–386;1–350;1–386;1–386;1–392;1–386;1–386;1–350;1–389;1–386;1–381;1–386;1–384;1–350;1–386;1–387;1–386;1–386;1–385;1–386;1–374;1–386;1–386;1–152;1–349;1–386;1–392;1–386;1–386;1–386;1–386;1–386;1–386;1–386;1–386;1–386;1–386;1–386;1–386;1–386;1–386;1–386;1–386;1–387;1–386;1–386;1–386;1–386;1–385;1–386;1–387;1–386;1–386;1–392;1–392;1–385;1–149;1–386;1–386;1–386;1–386;1–386;1–386;1–386;1–350;1–384;1–386;1–386;1–386;1–386;1–350;1–392;1–386;1–386;1–386;1–386;1–386;1–392;1–386;1–386;1–172;1–386;1–272;1–386;1–392;1–386;1–386;1–386;1–387;1–386;1–386;1–376;1–386;1–349;1–386;1–386;1–386;1–350;1–386 |
| 9192 | 1–298;1–31.2;1–274;1–293;1–313 |
| 9208 | 1–473;1–438 |
| 9217 | 1–397;1–445;1–452;1–451;1–452;1–389;1–442;1–452;1–465;1–449;1–398;1–443;1–429;1–442;1–407;1–432;1–380;1–445;1–452;1–445;1–438;1–133;1–453;1–437;1–434;1–463;1–465;1–448;1–448;1–452;1–448;20–167 |
| 9218 | 1–459;1–447;364–861 |
| 9256 | 1–489;1–490;1–312;1–510;1–490;1–480;1–461;1–434;1–490;1–494;1–417;1–514;1–517;1–531;1–473;1–364;1–476;1–480;1–341;1–134;1–497 |
| 9279 | 1–454;1–288;1–429;1–354;1–497;1–366;1–512;1–444 |
| 9299 | 1–299;1–298 |
| 9307 | 1–394;1–408;1–409;1–420;1–387;1–419 |
| 9339 | 1–483;1–467 |
| 9357 | 1–379;1–389 |
| 9362 | 1–63;1–64;1–62;1–63 |
| 9396 | 1–118;31–328;31–463;31–437;31–476;31–476;31–360;31–463;31–470;31–466;31–460;31–469;31–479;31–401;31–358;31–479;31–344;31–209;31–198;31–364;31–442;31–472;31–255;31–156;31–358;31–402;31–472;31–455;31–460;31–453;31–448;31–400;31–482;31–230;31–339;31–485;31–471;31–469;31–476;31–214;31–359;31–404;31–230;31–470;31–470;31–479;31–323;31–391;31–463;31–485;31–476;31–472;31–100;31–241;31–447;31–460;31–448;31–478;31–470;31–356;31–437;31–214;31–479;31–476;31–379;31–314;31–351;31–482;31–381;31–295;31–485;31–466;31–482;31–466;31–442;31–437;31–472;31–400;31–314;31–470;31–485;31–437;31–345;31–452;31–214;31–482;31–469;31–449;31–349;31–379;31–323;31–482;31–392;31–448;31–252;31–328;31–468;31–476;31–339;31–479;31–358;31–483;31–101 |
| 9403 | 1–119;1–176;31–99;31–100 |
| 9411 | 1–119;31–488;31–531;31–366;31–522;31–530;31–529;31–545;31–483;31–544;31–544;31–451;31–544;31–531;31–347;31–523;31–201;31–505;31–530;31–537;31–485;3–532;31–533;31–466;31–365;31–409;31–506;31–496;31–530;31–234;31–344;3–499;31–532;31–506;31–544;31–430;31–521;31–543;31–485;31–520;31–243;31–101;31–453;31–442;31–529;31–530;31–544;31–544;31–220;31437;31–547;31–540;31–387;31–543;31–505;31–532;31–543;31–439;31–389;31–496;31–508;31–530;31–522;31–538;31–449;31–521;31–524;31–416;31–438;31–530;31–551;31–525;31–354;31–544;31–400;31–533;31–544;31–530;31–508;31–544;31–504;31–508;31–531;31–439;31–531;31–531;31–437;31–544;31–430;31–102;31–333;31–508;31–440;31–520;31–532;31–522;31–508;31–508;31–436;31–540;31–529;31–532;31–506;31–517;31–533;31–522;31–531;31–442;31–158;31–428;31–464;31–523;31–544;31–544;31–507;31–530;31–430;31–482;31–519;31–543;31–544;31–416;31–542;31–488;31–499;31–453;31–437;31–553;31–488;31–544;31–504;31–506;31–530;31–531;31–354;31–521;31–300;31–496;31–544;31–440;31–537;31–455;31–507;31–319;31–437;31–521;31– |
| 9420 | 1–352;1–357;1–354;1–368;1–358;1–166;1–345;1–358;1–362;1–362;1–359;1–119;1–367;31–100;31–99 |
| 9462 | 1–441;4–105 |
| 9546 | 1–511;1–471;1–256;1–482;47–511;49–501 |
| 9553 | 1–409;1–245 |
| 9597 | 1–456;1–454 |
| 9614 | 1–478;3–244 |

TABLE II-continued (Tiling path)

| Seq Id No. | Positions of biological 5'ESTs |
|---|---|
| 9622 | 1–496;1–458;1–479;1–242;1–290;1–357;1–511 |
| 9633 | 1–386;2–432;2–444;2–455 |
| 9643 | 1–420;1–447;1–468;1–453 |
| 9652 | 1–458;95–569 |
| 9669 | 1–285;1–145 |
| 9677 | 1–434;1–405 |
| 9721 | 1–377;1–359;25–376;25–358;30–377;30–378;30–36 |
| 9731 | 1–543;1–543;1–543;1–511;1–494;1–543;1–447;1–621;1–586;1–482;1–543;1–556;1–429;1–543;1–378;1–541;1–543;1–543;1–556;1–511;1–425;1–543;1–538;1–369;1–537;1–543;1–458;2–428 |
| 9748 | 1–368;1–501 |
| 9759 | 1–487;1–453 |
| 9769 | 1–447;1–466 |
| 9780 | 1–415;1–425;1–460;1–542;1–459;1–461;1–432;1–468;1–450;1–402;1–450 |
| 9800 | 1–396;1–393;1–370;1–375;1–399;1–369;1–381;1–391;1–394;1–404;1–387;1–379;1–405;1–383;1–403;1–215;1–388;1–390;1–397;1–387;1–403;1–387;1–304;1–404;1–391;1–404;1–404;1–403;1–387;1–403;1–387;1–377;1–404;1–403;1–341;1–403;1–389;1–384;1–388;1–387;1–389 |
| 9836 | 1–483;1–407;1–497;1–489;3–151 |
| 9861 | 1–455;1–485;1–335;1–523;3–185;3–553;3–472;4–447;4–466;4–496 |
| 9879 | 1–491;1–498;1–504;1–472;1–485 |
| 9880 | 1–191;1–179;1–179;1–191;1–194;1–191;1–121;1–191;1–194;1–194;1–191;1–191;1–194;1–194;1–194;1–191;1–194;1–194;1–194;1–194;1–194;1–179;1–179;1–179;1–191;1–191;1–194;1–194;1–191;1–191;1–191;1–194;1–194;1–194;1–191;1–194;1–194;1–194 |
| 9885 | 1–382;1–453;97–572;97–585;97–458;97–572;97–578;97–578 |
| 9893 | 1–482;1–468 |
| 9918 | 1–451;345–836;345–822;345–853;345–869;345–867;345–838;345–556;345–840;345–617;345–673;345–777;345–830;345–891;345–816;345–702;345–836;345–827;345–819;345–834;345–503;444–732 |
| 9964 | 1–356;4–469 |
| 9988 | 1–447;1–472;1–467;1–488;1–334;1–474;1–355 |
| 10032 | 1–310;14–527;14–439;14–441;16–395;23–564 |
| 10042 | 1–483;1–406 |
| 10073 | 1–509;1–439 |
| 10079 | 1–497;1–476;1–443;1–498 |
| 10088 | 1–519;1–485 |
| 10106 | 1–351;1–441 |
| 10153 | 1–477;1–413;1–496;1–458;1–349;1–203;1–466;1–399;1–450;1–484 |
| 10178 | 1–243;1–242;1–239;1–210;1–239;1–187;1–246;1–209;1–235;1–221;1–244;1–177;1–91;3–221 |
| 10295 | 1–476;1–491;1–511;1–493;1–501;1–512;1–269;2–463;16–463;29–508;29–475;29–515;29–509;29–361;29–463;29–515;29–127;29–476;29–432;29–476;29–476;30–492;30–509;30–481;30–412;30–463;30–480;30–322;30–420;30–460;30–476;30–246;30–510;30–322;30–412;30–498;30–501;30–453;30–511;30–501;30–185;30–511;30–405;30–500;30–506;30–474;30–509;31–503;31–308;31–597;31–507;31–374;31–503;31–510;31–514;31–498;31–358;31–415;31–517;31–494;31–410;31–496;31–504;31–510;31–487;31–503;31–490;31–509;31–494;31–412;31–501;31–502;31–508;31–493;31–474;31–405;31–213;31–248;31–206;31–382;31–509;31–412;31–454;31–512;31–507;31–512;31–127;31–457;31–510;31463;31–435;31–501;31–496;31–404;31–267;31–496;31–499;31–512;31–460;31–474;31–185;31–270;31–480;31–449;31–90;31–528;31–552;31–500;31–389;31–477;31–499;31–499;31–515;31–510;31–300;31–433;31–553;32–510;32–319;32–474;32–488;32–206;32–382;32–308;32–335;32–322;32–463;32–495;32–499;32–501;32–476;32–427;32–457;32–548;32–390;32–484;32–158;32–508;32–335;32–512;32–126;32–322;32–420;32–496;32–430;32–489;32–506;32–5 |
| 10296 | 1–476;1–481;1–480;1–477;1–393;1–474 |
| 10331 | 1–259;1–259 |
| 10339 | 1–115;1–370;1–361;1–364;1–394;1–427;1–315;1–369;1–364;1–525;1–306;1–457 |
| 10348 | 1–115;1–370;1–361;1–364;1–394;1–427;1–315;1–369;1–525;1–364;1–306;1–457;1–557 |
| 10363 | 1–341;1–401 |
| 10377 | 1–323;1–327;1–103;1–315 |
| 10378 | 1–392;1–444 |
| 10408 | 1–424;1–536;1–525 |
| 10413 | 1–457;1–505;1–474 |
| 10421 | 1–255;1–425 |
| 10427 | 1–198;1–171 |
| 10438 | 1–438;1–476;1–462;1–500;1–419;1–468 |
| 10444 | 1–238;1463 |
| 10445 | 1–470;1–417;1–470;1–474;1–471 |
| 10453 | 1–75;1–75;1–75;1–75;1–77 |
| 10523 | 1–251;51–530;51–534 |
| 10531 | 1–251;41–300 |
| 10538 | 1–491;74–581;74–514;74–561;75–530 |
| 10597 | 1–445;1–362 |
| 10652 | 1–249;1–404;1–445;1–384 |
| 10661 | 1–419;1–423;1–283;1–407;1–413;1–395;1–412;1–414;1–428;1–420;1–207;1–420;1–415 |
| 10679 | 1–351;1–351 |
| 10700 | 1–468;1–470;1–454 |
| 10709 | 1–120;1–418;1–417 |
| 10734 | 1–472;1–230;1–436 |
| 10798 | 1–375;1–415;1–417;1–362;1–406;1–398;1–416;1–401;1–414;1–414;1–416;1–415;1–167;1–414;1–416 |
| 10834 | 1–55;4–440;4–69;4–165;4–75 |
| 10835 | 1–384;1–418 |
| 10845 | 1–471;1–407;1–407 |
| 10903 | 1–476;1–469;1–262 |
| 10963 | 1–448;157–597 |
| 10976 | 1–338;1–520;1–444;1–284;1–472;1–375;1–512;1–510;1–388 |
| 11004 | 1–486;1–502;1–446;1–359;1–493;1–484;1–436;1–410;1–329;1–441;1–413;1–418;1–544 |
| 11011 | 1–350;1–458;1–312;1–453;1–457;1–371;1–341 |
| 11036 | 1–501;1–482;1–462;1–479 |
| 11056 | 1–347;1–340;1–343;1–343 |
| 11067 | 1–493;1–491;1–511;1–476;1–269;1–501;1–512;2–463;16–463;29–127;29–475;29–463;29–508;29–361;29–515;29–515;29–509;29–476;29–476;29–432;29–476;30–412;30–492;30–509;30–463;30–480;30–481;30–185;30–460;30–511;30–474;30–476;30–322;30–498;30–420;30–529;30–453;30–501;30–322;30–246;30–506;30–501;30–412;30–511;30–509;30–405;30–527;30–510;30–500;30–529;31–507;31– |

TABLE II-continued (Tiling path)

| Seq Id No. | Positions of biological 5'ESTs |
|---|---|
| | 248;31–487;31–510;31–494;31–374;31–308;31–415;31–503;31–358;31–410;31–522;31–496;31–510;31–503;31–412;31–494;31–490;31–509;31–498;31–514;31–501;31–504;31–508;31–493;31–474;31–405;31–213;31–502;31–503;31–412;31–382;31–509;31–206;31–507;31–510;31–300;31–512;31–496;31–510;31–127;31–501;31–457;31–463;31–500;31–435;31–528;31–454;31–404;31–267;31–496;31–474;31–512;31–270;31–480;31–449;31–499;31–460;31–389;31–477;31–433;31–499;31–512;31–499;31–90;31–185;31–515;31–530;32–510;32–488;32–319;32–484;32–489;32–427;32–463;32–322;32–506;32–499;32–501;32–474;32–308;32–457;32–531;32–390;32–496;32–158;32–508;32–335;32–512;32–126;32–322;32–420;32–476;32–335;32–495;32–430;32–382;32–4 |
| 11076 | 1–436;42–448 |
| 11090 | 1–275;12–103 |
| 11135 | 1–469;13–459 |
| 11144 | 1–383;1–540 |
| 11158 | 1–279;1–405;1–561;1–379;1–566;1–486;1–384;1–482;1–470;1–413 |
| 11172 | 1–529;1–252;1–529 |
| 11179 | 1–522;1–434;1–498;1–434;1–495 |
| 11189 | 1–488;1–408 |
| 11207 | 1–108;1–106;1–108;1–106;1–108 |
| 11214 | 1–367;1–381 |
| 11279 | 1–469;2–386;2–387 |
| 11310 | 1–444;1–485;1–487;1–438;1–489 |
| 11321 | 1–380;1–450 |
| 11341 | 1–162;1–162;1–162;1–162;1–162;1–162;1–162 |
| 11350 | 1–410;1–272 |
| 11360 | 1–293;1–464 |
| 11366 | 1–459;1–505 |
| 11378 | 1–295;2–76;2–184;2–188 |
| 11387 | 1–415;1–184;2–268;2–276;2–480;2–270;2–377;2–309;2–284;2–76;2–309;2–188;2–276;2–493;2–406;3–428 |
| 11449 | 1–485;1–217 |
| 11457 | 1–233;1–292;1–374 |
| 11465 | 1–231;1–289;3–349 |
| 11473 | 1–293;1–311 |
| 11484 | 1–127;1–267;1–453;1–476 |
| 11499 | 1–477;1–478;1–482;1–504 |
| 11509 | 1–212;1–201;1–212 |
| 11527 | 1–490;76–572;166–589;166–597 |
| 11537 | 1–314;1–371 |
| 11565 | 1–387;1–277;2–236 |
| 11584 | 1–367;1–451;117–460 |
| 11595 | 1–245;1–236;1–245 |
| 11606 | 1–250;1–96 |
| 11696 | 1–337;1–430;1–415;1–403;1–418;5–393 |
| 11707 | 1–93;1–338;1–397 |
| 11717 | 1–128;1–439 |
| 11737 | 1–503;1–525;1–132;1–508;2–308 |
| 11747 | 1–474;1–451;1–501;1–483;1–497;1–477;1–454;1–493;1–562;1–315;1–368;1–460;1–565;1–183;1–482;1–522;1–562;1–565;1–344;1–565;1–446;1–319;1–562;1–467 |
| 11757 | 1–462;1–429 |
| 11768 | 1–448;1–314;1–396 |
| 11779 | 1–189;1–205;1–207;1–100;1–205 |
| 11790 | 1–393;1–279;1–335;1–430;1–479 |
| 11801 | 1–206;1–294;1–196;1–223 |
| 11811 | 1–233;1–235 |
| 11822 | 1–460;2–400;2–460;2–460;2–456;2–460;2–460;2–110;2–348;2–110;2–460;2–456;2–445;2–400;2–460 |
| 11833 | 1–492;1–415;1–492;1–334;1–363 |
| 11854 | 1–96;1–373;7–373 |
| 11884 | 1–423;1–547 |
| 11895 | 1–406;1–402;1–270;1–346;1–386;1–483;1–340;1–401;1–350;1–392;1–464;1–395;1–406 |
| 11927 | 1–489;1–509 |
| 11977 | 1–243;1–437 |
| 12071 | 1–441;1–452 |
| 12072 | 1–412;1–206 |
| 12082 | 1–490;1–365 |
| 12091 | 1–488;1–433 |
| 12112 | 1–478;1–358 |
| 12123 | 1–376;1–72 |
| 12134 | 1–138;4–205 |
| 12145 | 1–264;15–458 |
| 12177 | 1–479;1–450;1–520;1–479;1–465 |
| 12197 | 1–111;1–443;1–438;1–270 |
| 12208 | 1–441;1–465;1–500;1–374;1–472 |
| 12218 | 1–440;1–267 |
| 12239 | 1–446;1–485;1–468;1–410 |
| 12278 | 1–353;1–401 |
| 12317 | 1–400;1–133 |
| 12327 | 1–125;1–126;1–103;1–113;1–128;1–103;1–125;1–125;1–125;1–117;1–125;1–123;1–125;1–114;1–119;1–109;1–74;1–127;1–90;1–113;1–126;1–113;1–113;1–125;1–125;1–81;1–125;1–125;1–121;1–64;1–125;1–125;1–128;1–118;1–125;1–125;1–126;1–127;1–125;1–81;1–128;1–113;1–125;1–64;1–128;1–128;1–125;1–118;1–127;1–113;1–120;1–128;1–125;1–108;1–120;1–125;1–113;1–125;1–128;1–125;1–125;1–126;1–125;1–123;1–125;1–112;1–113;1–90;1–113;1–113;1–125;1–125;1–128;1–97;1–128;1–113;1–128;1–128;1–125;1–125;1–113;1–117;1–125;1–125;1–104;1–125;1–128;1–117;1–104;1–125;1–125;1–97;1–109;1–113;1–90;1–124;1–128;3–126 |
| 12437 | 1–505;1–505;1–431;1–462;1–435;1–434;1–492;1–479 |
| 12476 | 1–478;1–470;1–422;3–434 |
| 12485 | 1–474;1–377;1–483;1–467;1–437;1–418;1–423;1–474 |
| 12509 | 1–418;1–364;1–384;1–445;1–422 |
| 12580 | 1–444;1–406 |
| 12590 | 1–429;1–440 |
| 12605 | 1–377;1–102 |
| 12618 | 1–486;1–259;1–446;1–378;1–477;1–544;1–268 |
| 12625 | 1–438;2–404 |
| 12635 | 1–509;1–553 |
| 12636 | 1–426;30–250 |
| 12670 | 1–257;1–220;71–526 |
| 12678 | 1–397;1–184 |
| 12687 | 1–332;15–378;15–393;15–395;15–393;15–375;15–238;15–394 |
| 12719 | 1–290;1–333 |
| 12835 | 1–552;6–490 |
| 12844 | 1–500;1–497;1–429 |
| 12854 | 1–488;1–446;1–508;1–513 |
| 12879 | 1–263;1–502;117–591;117–573;117–597;129–600;129–598;129–541;129–611;129–597;200–604;200–561;241–530 |
| 12900 | 1–393;1–459;1–455 |
| 12945 | 1–199;1–199;1–199;3–482;3–64;5–208 |
| 13008 | 1–176;1–346 |
| 13056 | 1–542;1–483 |
| 13085 | 1–458;1–447 |
| 13090 | 1–266;1–266 |
| 13110 | 1–164;1–375 |
| 13117 | 1–461;1–186 |
| 13133 | 1–363;1–389;1–389;1–385;1–294;1–385 |
| 13142 | 1–395;1–395 |

TABLE II-continued

(Tiling path)

| Seq Id No. | Positions of biological 5'ESTs |
|---|---|
| 13150 | 1–471;1–459;1–630 |
| 13172 | 1–382;1–381 |
| 13180 | 1–457;258–667 |
| 13188 | 1–87;1–317 |
| 13193 | 1–66;1–66 |
| 13198 | 1–479;1–475;1–474 |
| 13207 | 1–237;1–450 |
| 13233 | 1–439;1–455 |
| 13240 | 1–406;1–414 |
| 13267 | 1–395;1–482;1–398;1–479;1–464;1–396;1–398;1–470;1–333;1–406 |
| 13277 | 1–466;2–290 |
| 13286 | 1–303;1–290 |
| 13294 | 1–433;1–402 |
| 13330 | 1–157;1–160 |
| 13336 | 1–485;1–500 |
| 13366 | 1–263;1–328;1–309;1–311;1–316;1–328;1–316;1–326 |
| 13449 | 1–182;40–167;40–175;40–177;40–177;40–178;40–176;40–174;40–167;40–166;40–179;40–179;40–177;40–174;40–168;40–179;40–132;40–175;40–168;40–168;40–177;40–132;40–183;40–174;40–167;40–174;40–167;40–181;40–174;40–182;40–183;40–176;40–177;40–103;40–183;40–168;40–168;40–175;40–162;40–175;40–174;40–179;40–108;40–154;40–175;40–168;40–178;40–166;40–154;40–164;41–179;85–182;104–177;104–182;104–171;104–163;104–170;104–173;104–177;104–166;104–172;104–176;104–171;104–156;104–182;104–182;104–163;104–182;104–182;104–183;104–182;104–183;104–169;104–223;104–180;104–174;104–269;104–174;104–182;104–182;104–175;104–183;104–183;104–182;104–182;104–166;104–173;104–154;104–174;104–167;104–182;104–161;104–174;104–180;104–182;104–177;104–182;104–226;104–183;104–182;104–171;104–177;104–192;104–255;104–180;104–174;104–182;104–181;104–183;104–182;104–167;104–173;104–173;104–162;104–174;104–171;104–182;104–166;104–182;104–173;104–182;104–182 |
| 13491 | 1–480;1–410;1–470;1–482 |
| 13520 | 1–258;1–256;1–247;1–246;1–271;1–260;1–260;1–260;1–255;1–260 |
| 13592 | 1–113;79–132 |
| 13614 | 1–165;1–151;1–154;1–164 |
| 13621 | 1–468;1–397;1–522;1–419;1–360;1–491 |
| 13627 | 1–266;1–266;1–261;1–261;1–250;1–117;1–266;1–261;1–248;1–266;1–247;1–260;1–266;1–250;1–225;1–261;1–194;1–234;1–214;1–261;1–226;1–261;1–251;1–126;1–261;1–261;1–249;1–231;1–250;1–261;1–223;1–194;1–266;1–231;1–261;1–266;1–251;1–266;1–266;1–266;1–261;1–261;1–218;1–252;1–194;1–235;1–261;1–250 |
| 13653 | 1–475;1–450;1–472;1–471 |
| 13675 | 1–402;2–451;2–479;2–451;2–301;34–87 |
| 13690 | 1–492;1–492;1–368;1–510;1–386;1–496;1–418;1–346;1–248 |
| 13712 | 1–358;11–254;13–158;13–158;13–158;13–158;13–97;13–154 |
| 13722 | 1–452;7–383;7–468;7–468 |
| 13731 | 1–357;1–336;1–370 |
| 13735 | 1–263;1–224 |
| 13767 | 1–415;1–386;1–380;1–355;1–470;1–471;1–358;1–369;1–369;1–543;1–473;1–510;1–390;1–473;1–419;1–474;1–369;1–415;1–470;1–397;1–295;1–491;1–471 |
| 13774 | 1–441;1–408;1–521;1–232;1–430;1–415;1–491;1–470;1–545;1–413;1–472;1–397;1–439;1–495;1–232;1–274;1–430;1–555;1–582;1–471 |
| 13779 | 1–487;1–534 |
| 13788 | 1–465;72–546;73–530;76–391;76–391;94–554;94–532;94–503;94–575;100–570;100–588;100–525;100–510;102–605 |
| 13809 | 1–283;1–446;1–471 |
| 13835 | 1–443;1–485;1–449;1–462;1–487;1–445;1–292;1–51 |
| 13850 | 1–485;1–355;1–496;1–544 |
| 13859 | 1–398;1–458;1–466;1–256;1–468;1–458;1–306;1–281;163–667;163–667;163–554;163–597;163–531;163–574;163–554;163–587;163–652;163–590;163–654 |
| 13870 | 1–249;1–268 |
| 13879 | 1–480;1–467 |
| 13891 | 1–574;1–458 |
| 13911 | 1–600;1–544 |
| 13922 | 1–504;234–691 |
| 13931 | 1–463;36–391 |
| 13947 | 1–45&;1–194;1–441;1–53;1–341;1–398 |
| 13969 | 1–293;1–485 |
| 14022 | 1–285;1–387;1–387;1–387;1–329;1–387;1–14546 1–495;1–495;1–51;1–492;2–493;2–495;2–386;1–386;1–280;1–383;1–386;1–310 |
| 14065 | 1–460;1–477 |
| 14075 | 1–408;1–468 |
| 14088 | 1–425;1–466;1–503 |
| 14093 | 1–326;1–326;1–326 |
| 14094 | 1–501;1–514 |
| 14104 | 1–404;2–607;67–310 |
| 14134 | 1–480;2–52;2–51 553;81–605;81–519;81–504;81–607;81– |
| 14143 | 1–439;1–50;1–51 |
| 14180 | 1–296;1–294;1–301 |
| 14224 | 1–459;1–475;47–186 |
| 14232 | 1–437;48–187 |
| 14250 | 1–485;1–474;1–471;1–443;1–480;1–487;1–502;5–391 |
| 14278 | 1–459;1–480;1–474;1–486;1–522;1–480;2–462;4–504;4–490;4–486 |
| 14286 | 1–157;1–156;1–157;1–156;1–141;1–141;1–154;1–154;1–154;1–154;1–157;1–154;1–157;1–154;1–157;1–157;1–154;1–154;1–157 |
| 14295 | 1–175;43–433;43–256;43–433;43–420;43–159 |
| 14304 | 1–401;1–383;1–453;1–293;1–439;1–396 |
| 14312 | 1–409;1–364 |
| 14341 | 1–262;1–314 |
| 14367 | 1–436;1–164;1–79 |
| 14386 | 1–359;1–372 |
| 14427 | 1–360;7–415 |
| 14455 | 1–373;1–461 |
| 14465 | 1–96;1–93 |
| 14475 | 1–458;1–328;1–450 |
| 14508 | 1–339;1–278;1–342;1–338 |
| 14519 | 1–461;1–461 |
| 14529 | 1–448;1–504 |
| 14538 | 1–425;1–372;1–295 |
| 14546 | 1–495;1–495;1–51;1–492;2–493;2–495;2–478;3–491;3–474;3–432;3–529;3–219;6–269;8–623;20–376;31–544;34–495;39–544;54–572;54–576;54–550;54–562;54–600;54–495;66–562;69–118;71–560;71–491;71–478;71–269;80–601;81–495;81–495;81–594;81–512;81–594;81–562;81–617;81–408;81–619;81–507;81–562;81–432;81–583;81–616;81–573;81–509;81–553;81–605;81–519;81–504;81–607;81–603;81–616;81–363;81–506;81–215;81–515;81–576;81–479;82–561;82–603;83– |

TABLE II-continued

(Tiling path)

| Seq Id No. | Positions of biological 5'ESTs |
|---|---|
| | 637;83–562;83–530;83–576;85–619;85–576;85–597;85–622;85–600;85–495;85–576;85–621;85–544;85–466;85–489;85–492;86–334;86–619;86–606;86–569;86–193;86–590;86–584;86–626;87–504;87–544;87–618;87–562;87–576;87–479;87–612;87–604;87–631;97–619;97–544;102–619;118–479;118–643;129–636;130–495 |
| 14559 | 1–471;1–418;1445 |
| 14595 | 1–180;1–238 |
| 14604 | 1–551;1–562;1–420;1–598 |
| 14610 | 1–335;1–335 |
| 14624 | 1–381;1–472 |
| 14630 | 1–116;1–129;1–126;1–129;1–129;1–129;1–126;1–116;1–129;1–119;1–116;1–126;1–126;1–129;1–129 |
| 14654 | 1–137;1–183;1–184;1–183;1–183;1–126;1–183;1–183;1–184;1–183;1–183;1–183;1–128;1–183;1–184;1–171;1–183;1–183;1–137;1–183;1–183;1–161;1–183;1–66;1–183;1–183;1–183;1–183;1–183;1–167;1–151;1–172;1–163;1–183;1–183;1–161;1–183;1–181;1–183;1–183;1–150;1–183;1–183;1–184;1–183;1–182;1–128;1–182;1–388;1–183;1–183;1–183;1–180;1–178;1–183;1–183;1–173;1–183;1–183;1–183;1–183;1–183;1–183;1–172;1–179;1–163;1–182;1–105;1–137;1–132;1–132;1–183;1–183;1–126;1–169;1–183;1–183;1–183;1–183;1–158;1–61;1–164;1–124;1–172;1–156;1–122;1–183;1–127;1–183;1–183;2–173;2–175;2–183;2–166;2–183;2–183;2–183;2–133;2–166;2–183;2–183;2–182;2–183;2–183;22–207;22–214;22–103 |
| 14709 | 1–440;1–469;1–452;1–237;1–509 |
| 14719 | 1–274;1–271 |
| 14730 | 1–407;1–319;1–197 |
| 14746 | 1–288;1–463;1–376 |
| 14817 | 1–496;153–552;375–551;375–564;375–566;375–563 |
| 14852 | 1–413;1–423;1–404;1–410;1–411;1–415;1–420;1–414;1–422 |
| 14933 | 1–432;3–434 |
| 14956 | 1–501;1–501 |
| 14964 | 1–187;1–187;1–187;1–187;1–187 |
| 15005 | 1–241;1–245;1–245;1–218 |
| 15013 | 1–404;1–463;25–459;29–507;29–423;29–451;29–518;29–120;29–517;29–300;29–138;30–418;30–580;30–458;30–392;30–409;30–521;30–475;30–464;30–520;30–133;30–423;30–521;30–520;30–390;30–500;30–491;30–472;30–481;30–537;30–436;30–539;30–514;30–471;30–504;30–527;31–465;31–504;32–463;32–434;38–518;38–503;38–508;61–533 |
| 15032 | 1–265;49–432 |
| 15042 | 1–283;1–490;1–459;1–481;1–503 |
| 15053 | 1–271;1–456;1–539;1–439;1–548 |
| 15077 | 1–348;1–329;1–349 |
| 15088 | 1–371;1–329;1–371;1–369;1–373 |
| 15095 | 1–351;32–172 |
| 15097 | 1–506;123–452 |
| 15098 | 1–465;1–463;1–520 |
| 15101 | 1–478;32–503;32–311;32–573;32–546;32–531 |
| 15102 | 1–206;53–290 |
| 15103 | 1–362;1–405;1–379;1–405;1–337;6–489;6–428 |
| 15104 | 1–368;1–359;1–348;1–361;1–361;1–360;1–172;1–364;1–172;1–346;1–365;3–363 |
| 15105 | 1–454;12–359;12–366;12–366;12–183;12–183;12–357 |
| 15108 | 1–337;1–334;1–335;1–135 |
| 15110 | 1–360;1–481 |
| 15111 | 1–372;1–356;1–357;1–356;1–358 |
| 15113 | 1–406;1–265 |
| 15114 | 1–486;1–508;1–539;16–368;16–414;16–391;32–172;33–384 |
| 15115 | 1–408;1–408;3–63 |
| 15116 | 1–464;1–539;1–430;1–454;1–558;1–418;1–457;1–492;1–508;1–473;1–448 |
| 15118 | 1–407;15–394 |
| 15119 | 1–409;1–495 |
| 15120 | 1–473;1–478;2–58 |
| 15121 | 1–483;1–57 |
| 15122 | 1–424;1–524;1–57 |
| 15123 | 1–477;1–388;1–478 |
| 15124 | 1–358;1–375 |
| 15125 | 1–61;1–64;1–64;1–61;1–61;1–61;1–64;1–64;1–64;1–61;1–61;1–61;1–63;1–64 |
| 15126 | 1–95;1–100 |
| 15129 | 1–201;1–220;1–159;1–220;1–220;1–219;1–220;1–217;1–235;1–220;1–219;1–226;1–220;1–232;1–220;1–202;1–233;1–235;1–220;1–220;1–212;1–135;1–222;1–220;1–220;1–232;1–220;4–220;4–232;4–220;4–233;4–234;4–220;4–200;4–233;4–231;4–233;4–220;4–220;4–232;4–220;4–234;4–209;4–220;4–201;4–232;4–220;4–232;4–222;4–220;4–222;4–220;4–219;4–215;4–220;5–225;5–233;5–232 |
| 15130 | 1–421;1–417 |
| 15131 | 1–617;56–617;56–528 |
| 15132 | 1–540;1–451 |
| 15135 | 1–438;1–440 |
| 15136 | 1–472;1–397;1–396;1–468;1–402;1–405;1–493 |
| 15137 | 1–320;1–187;1–348;1–159;15–313 |
| 15138 | 1–398;1–399;14–269;14–380 |
| 15139 | 1–225;1–225;1–225;1–225;1–225;1–225;1–224;1–223;1–225;1–223;1–225 |
| 15140 | 1–63;31–535;31–528 |
| 15141 | 1–358;1–362;1–339;1–353;1–358;6–391;6–350;6–439;6–367;6–161;6–372;6–391;6–344;17–411;22–431;22–427;22–392;22–366;22–421;22–427;22–438;22–339;22–432;22–434;22–409;22–364;22–431;22–390;22–407;22–424;22–436;22–434;22–430;27–401 |
| 15143 | 1–479;1–466 |
| 15145 | 1–456;1–301 |
| 15146 | 1–266;1–462;1–462 |
| 15147 | 1–56;1–353 |
| 15148 | 1–372;1–413;1–486 |
| 15149 | 1–417;1–408;1–437;1–310 |
| 15150 | 1–324;1–468;1–570;1–298 |
| 15151 | 1–464;1–445 |
| 15153 | 1–342;1–344 |
| 15154 | 1–481;1–484;1–480 |
| 15155 | 1–530;388–795;390–896;501–733 |
| 15157 | 1–62;1–67;1–79 |
| 15158 | 1–301;1–315 |
| 15159 | 1–495;1–412 |
| 15160 | 1–455;2–495 |
| 15162 | 1–293;1–355;1–420 |
| 15164 | 1–533;1–449;1–322;1–342;1–342;1–514;1–477;2–86 |
| 15165 | 1–246;1–233;1–253;1–247;1–254 |
| 15166 | 1–406;1–414;1–474;1–484;1–407;1–475 |
| 15168 | 1–285;1–294 |
| 15170 | 1–477;1–437;1–468;1–150;1–462;1–370;1–467;1–277;1–472;1–478 |
| 15171 | 1–416;1–87 |
| 15173 | 1–468;6–475 |
| 15174 | 1–508;1–397;1–497;1–466;1–458;1–466 |
| 15175 | 1–146;1–480;1–373;1–483;1–487 |
| 15177 | 1–455;1–478 |
| 15178 | 1–312;1–278 |

TABLE II-continued (Tiling path)

| Seq Id No. | Positions of biological 5'ESTs |
|---|---|
| 15179 | 1–473;1–425 |
| 15180 | 1–463;6–73 |
| 15181 | 1–501;11–376;101–591 |
| 15182 | 1–248;2–232;2–240;2–246;2–250;2–235;2–241;2–241;2–248;2–248;2–248;2–248;2–232;2–248 |
| 15183 | 1–377;1–232 |
| 15184 | 1–439;1–454;1–448;1–452 |
| 15185 | 1–298;1–376;1–311;1–292 |
| 15186 | 1–257;1–436;1–436 |
| 15187 | 1–251;1–382 |
| 15188 | 1–494;1–361;1–361 |
| 15189 | 1–521;1–426 |
| 15190 | 1–503;1–431 |
| 15191 | 1–358;1–433 |
| 15192 | 1–494;1–482;1–567 |
| 15193 | 1–215;1–112 |
| 15194 | 1–264;1–264;1–264 |
| 15195 | 1–408;1–451 |
| 15196 | 1–351;1–362;1–297;1–355;1–343;1–366;2–355;2–355;2–245;2–354;2–356;2–355;2–95;2–362;2–357;2–368;2–367;2–355;2–362;2–342;2–352;2–123;2–295;2–62;2–363;2–354;2–355;2–355;2–355;2–362;2–355;2–360;2–366;2–355;2–356;2–57 |
| 15197 | 1–280;1–248;1–93;1–302;1–61;1–287;1–281;1–56 |
| 15198 | 1–459;1–341;1–347;1–297;2–95;2–245;2–341;2–347;2–123;2–295;2–62;2–57 |
| 15199 | 1–94;1–431;1–122;1–61;1–56 |
| 15200 | 1–442;5–444;5–392;5–366;7–454;8–365;8–444;8–437;8–452;8–418;8–413;8–449;8–452;8–451;9–458;9–430;9–421;9–373;9–404;9–250;9–440;9–450;9–440;9–433;9–374;9–433;9–436;9–364;9–445;9–439;9–421;9–435;9–455;9–439;9–437;9–458;9–448;9–447;9–458;9–453;9–442;9–430;9–436;9–442;9–415;9–440;9–459;9–444;9–432;9–430;9–410;9–440;9–309;9–338;9–417;9–430;9–441;9–419;9–101;9–444;9–439;9–456;9–453;9–435;9–407;9–412;9–439;9–360;9–452;9–399;9–424;9–254;9–422;9–460;9–441;9–440;9–442;9–453;9–453;9–456;9–457;9–454;9–435;9–421;9–351;9–433;9–457;9–434;9–409;9–440;9–364;9–385;9–437;9–417;9–441;9–385;9–434;9–406;9–452;9–433;9–452;9–452;9–351;9–435;9–364;9–421;9–321;9–451;9–438;9–436;9–452;9–437;9–383;9–437;9–437;9–437;9–430;9–129;9–449;9–442;9–418;9–453;9–455;9–433;9–446;9–417;9–430;9–287;9–453;9–68;9–441;9–316;9–292;9–449;9–421;9–437;9–440;9–403;9–443;9–437;9–450;9–430;9–439;9–442;9–420;9–358;9–443;9–430;9–446;9–442;9–319;9–440;9–421;9–453;9–399;9–456;9–440;9–429;9–291;9–431;9–451;9–439;9–424;9–391;9–435;9–442;9–416;9–442;9–453;9–385;9–293 |
| 15201 | 1–375;4–355;5–423;5–216;5–350;5–453;5–356;5–443;5–464;5–438;5–299;6–449;6– |
| 15202 | 464;6–462 5–392;5–366;5–437;8–365;8–437;8–418;8–413;9–442;9–430;9–250;9–430;9–421;9–404;9–433;9–437;9–439;9–436;9–373;9–374;9–437;9–364;9–442;9–421;9–432;9–437;9–360;9–436;9–471;9–439;9–421;9–435;9–440;9–415;9–479;9–435;9–433;9–437;9–437;9–430;9–410;9–309;9–338;9–439;9–430;9–417;9–101;9–419;9–439;9–254;9–407;9–412;9–439;9–439;9–399;9–424;9–437;9–422;9–437;9–437;9–437;9–433;9–435;9–434;9–471;9–351;9–442;9–409;9–414;9–365;9–385;9–364;9–441;9–417;9–385;9–436;9–406;9–434;9–433;9–351;9–435;9–364;9–321;9–421;9–436;9–438;9–437;9–383;9–437;9–437;9–437;9–430;9–129;9–444;9–439;9–418;9–433;9–442;9–417;9–430;9–287;9–68;9–316;9–437;9–292;9–439;9–421;9–439;9–403;9–442;9–437;9–430;9–429;9–442;9–358;9–420;9–439;9–430;9–496;9–319;9–439;9–440;9–421;9–399;9–442;9–439;9–291;9–431;9–385;9–424;9–391;9–435;9–437;9–416;9–437;9–293;9–372;9–437;9–423;9–429;9–442;9–63;10–242;13–477 |
| 15211 | 1–474;1–332;26–98 |
| 15212 | 1–509;1–454 |
| 15213 | 1–461;1–487;1–490 |
| 15214 | 1–472;1–471 |
| 15215 | 1–454;1–461 |
| 15216 | 1–406;1–318 |
| 15217 | 1–423;1–469 |
| 15218 | 1–447;1–460 |
| 15219 | 1–469;1–368;1–510;1–491;1–423;1–405;1–466;1–519 |
| 15220 | 1–378;9–456;9–507;9–506;9–326;9–487;9–544;9–507;9–442;9–469;9–539;9–71 |
| 15222 | 1–378;1–478;1–539;1–434;1–556 |
| 15223 | 1–395;1–456;1–423;1–495;1–544 |
| 15224 | 1–494;1–332 |
| 15225 | 1–484;1–413 |
| 15226 | 1–86;1–86;1–86;1–86;1–86;1–86 |
| 15227 | 1–335;1–92;1–410;23–417 |
| 15228 | 1–523;1–458 |
| 15229 | 1–487;1–505;1–453;1–413;1–507;1–472;1–498;1–511;1–311;1–416 |
| 15231 | 1–334;1–507;1–92;1–409;1–504;13–444;13–468;13–415;13–421;23–517;23–517 |
| 15232 | 1–297;1–300 |
| 15235 | 1–297;1–338 |
| 15236 | 1–292;1–306;1–306;1–311;1–298;1–311 |
| 15237 | 1–430;21–416;23–419;23–514;24–408;33–460 |
| 15238 | 1–430;21–415;23–418;23–435;23–442;24–407 |
| 15239 | 1–394;1–347 |
| 15240 | 1–464;1–475;1–137 |
| 15241 | 1–415;1–434;1–417;1–419;1–435 |
| 15242 | 1–394;1–272 |
| 15243 | 1–117;1–276;1–193;1–205;1–163;1–238 |
| 15244 | 1–256;1–256;1–256;1–256;1–256;1–256;1–256;1–256;53–560;56–390;56–544;56–396;56–581;56–538;56–494;56–527;56–406;81–347;81–356;82–256;82–561;82–534;82–534;82–256;82–542;82–167;82–506;82–578;82–261;82–462;82–254;82–256;82–534;82–256;83–449;84–415;84–601;84–534;84–534;84–593;87–530;112–579 |
| 15245 | 1–374;1–501;1–506 |
| 15247 | 1–468;1–309 |
| 15248 | 1–256;1–263;1–345 |
| 15250 | 1–108;1–109 |
| 15251 | 1–406;111–576 |
| 15253 | 1–185;1–185;1–185 |
| 15254 | 1–434;1–410 |
| 15256 | 1–501;1–458;1–396 |
| 15257 | 1–489;1–151;1–412;1–493 |
| 15258 | 1–454;1–207 |
| 15259 | 1–466;1–341 |
| 15260 | 1–199;1–173 |
| 15261 | 1–392;3–390;3–380;3–402;3–399;3–402;3–380 |
| 15262 | 1–440;1–448 |
| 15264 | 1–377;1–381 |
| 15265 | 1–453;1–530 |
| 15266 | 1–437;1–420 |

TABLE II-continued

(Tiling path)

| Seq Id No. | Positions of biological 5'ESTs |
|---|---|
| 15267 | 1–438;1–162;1–488;1–110 |
| 15273 | 1–512;1–434 |
| 15279 | 1–389;1–533 |
| 15280 | 1–459;1–455 |
| 15281 | 1–274;1–405;1–416;1–460;1–438;1–89;1–389;1–287;1–364 |
| 15282 | 1–274;1–405;1–416;1–480;1–483;1–438;1–89;1–389;1–506;1–287;1–485;1–364 |
| 15283 | 1–385;145–641 |
| 15284 | 1–295;1–279 |
| 15285 | 1–441;1–428;1–445 |
| 15288 | 1–243;42–503;83–487 |
| 15289 | 1–377;1–256 |
| 15290 | 1–505;1–506;1–464;1–533 |
| 15291 | 1–100;1–404 |
| 15292 | 1–230;1–223 |
| 15293 | 1–389;1–534 |
| 15294 | 1–140;1–140;2–142;2–140;2–142;2–132;2–142;2–140;2–142;2–140;2–142;2–142;2–142;2–142;2–140;2–140;2–142;2–142;2–142;2–140;2–140;2–142;2–142;2–142;2–140;2–140;2–142;2–140;2–142;2–140;2–142;2–140;2–142;2–140;2–142;2–142;2–142;2–142;2–142;2–132;2–140;2–142;2–142;2–142;2–142;2–142;2–140;2–142;2–140;2–140;2–142;2–140;2–142;2–140;2–140;2–140;2–140;2–142;2–140;2–140;2–140;2–140;2–140;2–140;2–140;2–142;2–140;2–142;2–142;2–140;2–142;2–142;2–142;2–140;2–142;2–142;2–140;2–142;2–142;2–142;2–140;2–142;2–132;2–140;2–142;2–142;2–142;2–142;2–142;2–140;2–140;2–142;2–140;2–140;2–142;2–142;2–140;2–140;2–142;2–142;2–140;2–142;2–142;2–140;2–142;2–142;2–140;2–142;2–142;2–140;2–142;2–142;2–140;2–89;2–142;2–132;2–142;2–142;2–140;2–142;2–140;2–142;2–142;2–142;2–140;2–140;2–142;2–140;2–140;2–140;2–142;2–142;2–142;2–140;2–140;2–142;2–142;2–140;2–140;2–142;2–142;2–140;2–140;2–142;2–142;2–140;2–140;2–142;2–142;2–140;2–140;2–140;2–142;2–140;2–142;2–140;2–140;2–140;2–142;2–142;2–140;2–142;2–142;2–140;2–142;2–142;2–142;2–140;2–142;2–142;2–142 |
| 15296 | 1–412;1–100 |
| 15297 | 1–350;1–425;1–459;1–531;13–521;13–411;13–523;28–504;28–510;28–548;28–518;31–496;31–519;31–510;31–540;31–485;31–544;31–433;31–510;31–505;31–527;31–529;31–467;31–510;31–544;31–528;31–275;31–531;31–564;31–531;31–247;31–527;31–510;31–543 |
| 15299 | 1–372;1–491;1–446 |
| 15300 | 1–416;1–387 |
| 15301 | 1–377;1–382;1–379;1–384;1–398;1–390;1–410;1–351;1–316;1–402;1–409;1–401;1–412;1–409;1–379;1–398;1–379;1–379;1–379;1–383;1–380;1–142;1–369;1–398;1–379;1–391 |
| 15303 | 1–494;1–367;1–480;1–304;1–541;93–784;93–459 |
| 15304 | 1–488;1–473 |
| 15305 | 1–276;1–445 |
| 15308 | 1–462;1–490;1–481 |
| 15309 | 1–494;1–367;1–480;1–304;1–542;93–606;93–459 |
| 15310 | 1–478;1–483;25–511 |
| 15311 | 1–464;1–497;1–436;1–474;1–496;1–220 |
| 15312 | 1–116;1–121;1–136;1–159;1–129;1–150;1–152;1–117;1–135;1–157;1–142;1–131;1–155;1–153;1–150;1–159;1–147;1–141 |
| 15315 | 1–489;1–483 |
| 15324 | 1–449;1–450;1–410 |
| 15325 | 1–432;46–416;46–98;50–573 |
| 15326 | 1–381;1–378 |
| 15327 | 1–432;1–468;1–490;1–379;1–475;1–432;1–308;1–464 |
| 15328 | 1–286;8–504 |
| 15330 | 1–398;7–434;7–385;7–408;7–545;7–489;7–502;7–517;7–276;7–490 |
| 15331 | 1–167;1–167 |
| 15334 | 1–353;1–457 |
| 15336 | 1–349;1–361;1–325 |
| 15338 | 1–488;1–429 |
| 15339 | 1–200;1–198;1–200;1–200;1–198;1–198;1–198;1–198;1–198;1–198;1–200;1–198;1–200;1–200;1–200;1–200 |
| 15340 | 1–522;1–511 |
| 15341 | 1–191;1–180;1–180;1–114;1–196;1–196;1–193;1–196;1–196;1–197;1–183;1–114;1–196;1–196;1–183;1–190;1–196;1–196;1–197;1–196;1–183;1–176;1–114;1–161;1–114;1–180;1–195;1–183;1–196;1–197;1–196;1–177;1–191;1–182;1–184;1–196;1–114;1–114;1–180;1–194;1–174;1–197;1–172;1–196;1–196 |
| 15344 | 1–357;1–319;1–428;1–295;1–263;1–378;1–254;1–256 |
| 15345 | 1–333;1–462;1–463;1–464;1–482;1–465;1–469;1–460;1–466;1–467;1–424;1–471 |
| 15346 | 1–499;3–439 |
| 15347 | 1–427;1–447;1–436;1–387 |
| 15348 | 1–101;1–395;1–98;1–395;1–301;1–389;1–392;1–395;1–392;1–389;3–395 |
| 15349 | 1–263;1–92 |
| 15354 | 1–485;1–444 |
| 15356 | 1–402;1–105;1–388;1–402;1–400;1–402;1–208;1–400;1–312;1–399;1–303;1–402;1–402;2–158;3–500;3–484;3–481 |
| 15363 | 1–418;1–130;1–417;1–433;1–423;1–402 |
| 15368 | 1–275;1–416;1–442 |
| 15369 | 1–549;1–282;1–429;1–468;1–484;1–399;1–476;1–431 |
| 15371 | 1–501;1–476 |
| 15372 | 1–446;1–460;1–320;1–489;1–495 |
| 15373 | 1–506;1–485 |
| 15374 | 1–408;1–396;1–415;1–420 |
| 15375 | 1–497;1–526 |
| 15376 | 1–496;1–448 |
| 15377 | 1–451;89–176;89–569 |
| 15378 | 1–189;21–126;22–108;22–108;50–187;50–106;51–109;52–106 |
| 15379 | 1–125;1–125;1–125;1–125;1–125;1–125;1–125 |
| 15380 | 1–506;1–437 |
| 15381 | 1–487;1–425;1–465 |
| 15383 | 1–491;1–428 |
| 15384 | 1–79;1–201 |
| 15385 | 1–79;1–465 |
| 15386 | 1–106;1–172;1–51;1–87;34–99 |
| 15390 | 1–398;1–391;1–404;1–417;1–137 |
| 15391 | 1–213;11–442;11–419 |
| 15392 | 1–122;1–122;1–122;1–93;1–128 |
| 15394 | 1–410;1–409;1–441;1–397;1–426;1–444 |
| 15397 | 1–490;1–283 |
| 15398 | 1–368;1–431 |
| 15399 | 1–486;1–411;1–447 |
| 15400 | 1–458;111–575 |
| 15401 | 1–472;1–490 |
| 15402 | 1–336;1–483 |
| 15403 | 1–466;1–486;1–411;1–412;1–435 |
| 15404 | 1–107;10–115;15–275;29–129;29–115;29–128;29–80;29–136;29–118;29–93;30–104;30–109;30–129 |
| 15405 | 1–108;8–175;8–238;8–256;8–294;8–279;10–208;10–361;10–116;11–286;13–311;14– |

TABLE II-continued

(Tiling path)

| Seq Id No. | Positions of biological 5'ESTs |
|---|---|
|  | 297;29–221;30–135;30–195;30–116;30–253;30–279;30–255;30–242;30–235;30–167;30–188;30–81;30–223;30–94;30–139;30–249;30–202;30–292;30–260;30–237;30–214;30–119;30–234;30–281;31–110;31–291;31–272;31–105;31–268;31–278;31–227;31–296;31–134;31–226;60–141;60–308;64–179;64–273 |
| 15406 | 1–106;10–114;28–133;28–114;28–127;28–79;28–134;28–117;28–92;29–148;29–103;29–108;29–132;58–134 |
| 15407 | 1–295;1–279 |
| 15408 | 1–430;83–440 |
| 15413 | 1–86;1–144;1–112;1–109 |
| 15415 | 1–362;1–360;1–140;1–345 |
| 15416 | 1–220;1–207;1–220;1–220;1–221;1–220 |
| 15417 | 1–426;1–471 |
| 15418 | 1–444;1–121;1–472;1–449;1–451;1–416 |
| 15419 | 1–528;3–436;6–540;6–372;6–321;6–387;6–504;6–475;6–389;6–445;6–540;6–539;6–540;6–445;6–445;6–431;6–540;6–372;6–540;6–540;6–445;6–540;6–539;6–506;6–179;6–321;6–179;6–380;6–536;6–444;6–279;6–392;6–539;6–372;6–459;6–437;6–308;6–394;6–426;6–445;6–540;6–593;6–457;6–127;6–349;6–540;6–524;6–388;6–462;6–371;6–165;6–91;6–540;6–154;6–415;6–189;6–459;6–493;6–540;6–389;6–382;6–372;6–474;6–493;6–540;6–179;6–525;6–540;6–258;6–504;6–544;6–189;6–462;8–129;10–372;14–436 |
| 15420 | 1–391;1–390;1–391 |
| 15421 | 1–515;1–293 |
| 15422 | 1–395;1–416 |
| 15423 | 1–479;1–412;1–426 |
| 15424 | 1–462;1–258;1–417;1–120;1–461 |
| 15425 | 1–414;1–451;1–466;1–476;1–490;1–480;1–465 |
| 15426 | 1–467;394–801;394–800 |
| 15428 | 1–495;1–439;1–491 |
| 15429 | 1–285;1–291;1–279 |
| 15430 | 1–508;1–456;1–437 |
| 15431 | 1–361;1–166 |
| 15432 | 1–145;1–125;1–314 |
| 15433 | 1–488;1–457;12–117;12–79 |
| 15435 | 1–402;1–410 |
| 15442 | 1–202;1–273;1–275;1–384 |
| 15443 | 1–98;1–85;1–200;1–84;1–200;1–109;1–66;1–172;1–200;1–97 |
| 15444 | 1–463;1–498;1–312;1–316 |
| 15445 | 1–477;1–524;1–394;3–568;3–482;3–394 |
| 15447 | 1–148;1–144;1–148;1–135;1–148;1–144;1–148;1–144;1–148;1–148;1–144;1–144;1–144;1–144;1–144;1–144 |
| 15448 | 1–504;6–186 |
| 15449 | 1–402;1–401 |
| 15450 | 1–446;1–326;1–449;1–519;1–450;1–454;1–459;1–426;1–491;1–476 |
| 15451 | 1–511;1–338 |
| 15452 | 1–377;1–129;1–181 |
| 15453 | 1–103;1–109;1–109;1–109;1–113;1–113;1–113;1–113;1–113;1–109;1–113;1–109;1–113;1–113;1–113;1–113;1–113;1–109;1–113;1–113;1–109;1–113;1–109;1–113;1–109;1–76;1–109;1–113;1–113;1–109;1–113;1–113;1–113;1–103;1–109;1–113;1–113;1–113;1–113;1–109;1–109;1–109;1–113;1–109;1–113;1–109;1–109;1–109;1–109;1–109;1–109;1–113;1–113;1–113;1–113;1–113;1–113;1–103;1–113;1–113;1–113;1–109;1–109;1–113;1–113;1–109;1–113;1–113;1–109;1–113;1–109;1–114;1–109;1–113;1–113;1–113;1–113;1–113;1–113;1–113;1–109;1–113;1–103;1–113;1–113;1–113;1–113;1–103;1–113;1–109;1–109;1–113;1–113;1–113;4–109;4–109 |
| 15454 | 1–311;48–411 |
| 15455 | 1–517;125–540 |
| 15457 | 1–417;1–457 |
| 15459 | 1–355;63–492;63–484;63–429 |
| 15460 | 1–407;1–410;43–404 |
| 15462 | 1–468;1–466 |
| 15463 | 1–375;1–415;1–569;1–552;1–391 |
| 15464 | 1–410;1–405 |
| 15466 | 2–371;2–370;2–371;38–88;38–95 |
| 15471 | 1–376;1–376 |
| 15473 | 1–447;1–461;1–452 |
| 15474 | 1–459;1–432;1–466 |
| 15475 | 1–447;1–289 |
| 15476 | 1–306;1–461;1–457;1–411;1–478;1–373;2–294;2–477;2–379;2–422;2–398 |
| 15477 | 1–403;1–394;1–366 |
| 15478 | 1–453;1–345 |
| 15479 | 1–408;1–478 |
| 15480 | 1–188;1–297 |
| 15481 | 1–340;3–267 |
| 15482 | 1–111;1–460;1–305;1–476 |
| 15483 | 1–455;1–506;1–479 |
| 15484 | 1–459;1–500 |
| 15485 | 1–468;1–470;1–464;1–465 |
| 15486 | 1–488;1–298;1–512 |
| 15487 | 1–307;1–444 |
| 15488 | 1–353;1–343;1–354;1–354;1–355 |
| 15489 | 1–350;1–352 |
| 15490 | 1–454;1–497;4–466;4–494;4–476;4–442;4–425;4–458;4–486;4–536;25–492;28–536;32–524;32–443;32–533;32–542;32–505;43–505;46–508;46–489;46–496;46–522;46–300;46–536;52–515;52–535;52–533;52–607;52–443;52–512;53–129;53–129;53–129;53–129;53–129;53–129;53–130;53–129;53–130;53–129;53–129;53–129;53–129;53–130;53–129;53–129;53–129;53–129;53–129;53–130;53–129;53–129;53–129;53–129;53–129;53–129;53–129;53–129;53–129;53–129;53–129;53–129;53–129;53–129;53–129;53–129;53–129;53–130;53–129;53–130;53–130;53–129;53–129;53–130;53–129;53–129;53–129;53–129;53–129;53–129;53–129;53–129;53–129;53–129;53–129;53–129;53–129;53–129;53–129;53–129;53–130;53–129;53–129;53–129;53–130;53–129;53–129;53–129;53–129;53–129;53–129;53–129;53–129;53–129;53–129;53–129;53–129;53–129;53–129;53–129;53–129;53–129;53–130;53–130;53–129;53–129;53–129;53–129;53–129;53–129;53–129;53–129;53–129;53–129;53–129;53–129;53–129;53–129;53–129;53–130;53–129;53–129;53–129;53–130;53–129;53–129;53–12 |
| 15491 | 50–547;50–533;50–531;50–530;50–524;50–525;50–549;57–547;57–553;57–547;57–524;57–553;57–545 |
| 15492 | 1–464;1–248;1–464;1–465;1–454 |
| 15493 | 1–497;1–478 |
| 15494 | 1–471;1–445;1–488;1–476;1–464;1–382;1–483;1–484 |
| 15498 | 1–457;1–489 |
| 15499 | 1–477;1–461 |
| 15500 | 1–422;1–436 |
| 15501 | 1–331;1–432 |
| 15502 | 1–367;1–354 |
| 15503 | 1–372;4–516;7–453 |

TABLE II-continued (Tiling path)

| Seq Id No. | Positions of biological 5'ESTs |
|---|---|
| 15512 | 1–416;1–416;1–416;1–414;1–416;1–416;1–416;1–416;1–414;1–416;1–416;1–416;1–414;1–370;1–416;1–76;1–414;1–414;1–416;1–414;1–416;1–416;1–414;1–414;1–376;1–416;1–416;1–400 |
| 15513 | 1–444;4–114;6–74;8–136;24–159 |
| 15515 | 1–454;1–450;1–465;1–371;1–479 |
| 15516 | 1–343;1–240 |
| 15517 | 1–176;1–180;1–176;1–155 |
| 15518 | 1–198;1–165;1–198;1–185;1–185 |
| 15519 | 1–93;1–300;1–457;1–423 |
| 15520 | 17–442;17–408;17–451;17–447;17–374;17–444;17–445;17–446;17–459;17–462;17–432;17–449;17–368;17–460;17–460;17–447;17–446;17–444;17–442;17–439;17–459;17–448;17–435;17–143;17–422;17–461;17–443;17–434;17–451;17–451;17–395;17–447;17–422;17–277;17–396;17–450;17–442;17–418;17–422;17–405;17–448;17–354;17–439;17–456;17–447;17–440;17–443;17–407;17–427;17–447;17–460;17–416;17–352;17–439;17–442;17–422;17–344;17–427;17–451;17–441;17–374;17–361;17–442;17–199;17–375;17–449;17–366;17–447;17–454;17–420;17–450;17–422;17–447;17–362;17–325;17–447;17–462;17–378;17–426;17–442;17–429;17–420;17–459;17–430;17–213;17–427;17–427;17–438;17–445;17–442;17–454;17–444;17–439;17–447;17–451;17–136;17–446;17–427;17–402;17–452;17–448;20–460;22–460;22–238;22–114;22–441;22–460;23–407;26–431;40–441;40–454;40–438;40–457;40–442;43–443;43–461;43–455;43–447;43–455;43–460;43–443;43–269;43–441;43–439;43–251;43–459;43–427;43–438;43–459;43–447;43–447;43–451;43–427;43–460;43–453;43–381;43–459;46–460;46–460;46–452;46–457;46–449;46–441;46–441;46–421;49–432;51 |
| 15523 | 1–432;1–432;1–495;1–483;1–412;1–437;1–497;1–458;1–453;1–493;1–481 |
| 15524 | 1–428;7–510;7–269 |
| 15525 | 1–542;32–459;38–300 |
| 15529 | 1–445;1–447 |
| 15531 | 1–290;1–288;1–104 |
| 15532 | 1–399;1–467;1–478;1–507;1–358;1–471;1–477 |
| 15534 | 1–463;1–446 |
| 15536 | 1–585;1–279 |
| 15537 | 1–432;1–92;1–515 |
| 15539 | 1–399;1–424 |
| 15540 | 1–499;1–489 |
| 15541 | 1–72;11–71 |
| 15542 | 1–182;1–182;1–184;1–182;1–185;1–185;1–182;1–182;1–182;1–172;1–182;1–185;1–182;1–172;1–184;1–182;1–182;1–184;1–162;1–182;1–169;1–182;1–188;1–182;1–182;1–170;1–188;1–182;1–182;1–182;1–182;1–172;1–168;1–182;1–182;1–185;1–188;1–188;1–182;1–182;1–177;1–182;1–182;1–162;1–185;1–182;1–182;1–183;1–182;1–182;1–182;1–182;1–182;1–188;1–185;1–183;1–171;1–188;1–150;1–182;1–182;1–182;1–169;1–172;1–182;1–182;1–182;1–188;1–188;1–183;1–182;1–185;1–182;1–182;1–185;1–159;1–183;1–182;1–185;1–188;1–182;1–182;1–182;1–182;1–183;1–185;1–188;1–185;1–72;1–183;1–183;1–182;1–182;1–182;1–147;1–182;1–145;1–182;1–182;1–182;1–182;1–172;1–182;1–182;1–182;1–182;1–182;1–183;1–182;1–188;1–182;1–182;1–150;1–183;1–188;1–182;1–80;1–188;1–185;1–182;1–182;1–183;1–183;1–172;1–174;1–182;1–163;1–171;1–182;1–182;1–182;1–183;1–128;1–188;1–182;1–183;1–182;1–171;1–182;1–182;1–183;1–182;1–183;1–183;1–182;1–181;1–162;1–182;1–182;1–183;1–172;1–177;1–188;1–151;1–171;1–183;1–183;1–185;1–182;1–182;1–182;1–182;1–184;1–182;1–182;1–182;1–182;1–182;1–182;1–182; |
| 15544 | 1–476;1–485;1–496;1–460;1–499;1–496 |
| 15545 | 1–442;1–476 |
| 15546 | 1–338;1–358 |
| 15547 | 1–501;1–183 |
| 15548 | 1–232;1–370;1–456;1–487;1–487;1–454;1–490 |
| 15550 | 1–477;1–508;1–472;1–477;1–372 |
| 15552 | 1–350;1–414;1–456;1–128 |
| 15553 | 1–158;1–157;1–157;1–162;1–157;1–157;1–157;1–157;1–161;1–161;1–161;1–157;1–157;1–157;1–157;1–157;1–157;1–157;1–157;1–157;1–157;1–157;1–157;1–157;1–157;1–157;1–158;1–162;1–157;1–157;1–157;1–161;1–161;1–161;1–157;1–157;1–157;1–157;1–157;1–157;1–157;1–157;1–157;1–157;1–157;1–157;1–157;1–94 |
| 15554 | 1–226;1–241;1–242 |
| 15555 | 1–404;1–359;1–399;1–406;2–396 |
| 15556 | 1–226;1–387;1–418;1–372 |
| 15557 | 1–499;1–508;1–119;1–509;1–477;1–447;1–508;1–345;1–525;1–491;1–525;1–441;1–494;1–583;1–84;1–476;1–485;1–494;1–507;1–503;1–503;1–115;1–524;1–483;1–299;1–432 |
| 15558 | 1–83;1–254;1–103;1–254;1–254;1–101;1–104;1–254;1–252;1–254;1–103;1–254;1–254;1–254;1–254;1–252;1–166;1–255;1–103;1–254;1–254;1–254;1–254;2–276 |
| 15560 | 1–501;1–205;1–427;1–467 |
| 15561 | 1–188;1–420 |
| 15562 | 1–310;1–291;1–281;1–387;1–287;1–300;1–279;1–284;1–249;1–80;1–357;1–313 |
| 15563 | 1–467;1–476 |
| 15564 | 1–294;1–399;1–408;1–403;1–404;1–408;1–398;1–399;1–391;1–395;1–385;1–402;1–298 |
| 15565 | 1406;1–121 |
| 15566 | 1–92;1–96;1–92;1–79;1–79;1–88;1–94 |
| 15567 | 1–460;1–428;1–460;1–451;1–476;1–424;1–444 |
| 15568 | 1–205;1–205;7–216;7–216;7–216;7–200;7–210;7–205;7–206;7–205;7–205;7–206;7–205;7–192;7–205;7–210;7–216;7–95;7–205;7–106;7–216;7–205;11–207;11–205;11–205;11–216;15–153;15–117;15–205;15–204;15–162;15–206;15–204;15–206;15–167;15–204;15–176;22–217;44–191;54–171;54–195 |
| 15569 | 1–407;3–395 |
| 15570 | 1–455;1–524;1–350 |
| 15571 | 1–420;1–396 |
| 15572 | 1–541;1–577 |
| 15573 | 1–440;4–438;7–424;8–441;8–437;8–415;8–437;8–327;8–349;8–437;8–411;8–434;8–423;8–437;8–443;8–434;8–390;8437;11–439;11–434;11–441;11–441;11–441;11–441;11–438;11–369;11–390;11–430;11–534;11–400;11–441;11–441;11–441;11–459;11–438;11–435;11–320;11–339;11–440;11–490;11–441;11–422;11–363;11–415;11–417;11–437;11–417;11–436;11–441;11–208;11–356;11–438;11–272;11–370;11–437;11–441;11–391;11–441;11– |

TABLE II-continued

(Tiling path)

| Seq Id No. | Positions of biological 5'ESTs |
|---|---|
|  | 131;11–413;11–441;11–441;11–441;11–373;11–441;11–441;11–421;11–441;11–422;11–422;11–441;11–397;11–422;11–437;11–433;11–441;11–425;11–417;11–347;11–434;11–422;11–417;11–361;11–194;12–434;12–417;12–369;12–437;12–357;12–437;12–403;12–402;12–427;12–437;12–437;12–437;12–439;12–138;12–429;17–109;17–233;17–436;18–402;21–426;35–433;35–436;35–437;38–422;38–264;38–438;38–441;38–441;38–492;38–438;38–436;38–422;38–434;38–441;38–376;38–433;38–441;38–246;41–509;41–416;41–436;41–436;44–427;46–423;46–442;46–439;46–437;46–437;46–438;46–358;46–439;46–437;46–442;46–422;47–97;47–401;47–173;47–134;47–147;47–104;47–441;48–133;52–365;52–435;52–436; |
| 15574 | 1–484;1–415;1–474 |
| 15575 | 1–433;1–427 |
| 15576 | 1–465;1–333 |
| 15577 | 1–504;1–453;1–444;1–470 |
| 15578 | 1–821;1–358;1–358;1–440 |
| 15580 | 1–488;1–433 |
| 15581 | 1–172;35–389 |
| 15582 | 1–389;1–388 |
| 15583 | 1–519;1–486 |
| 15584 | 1–331;1–153 |
| 15586 | 1–371;1–498;1–486;1–448;1–471;1–489;1–488;1–521;1–561;1–443;1–275;1–475;1–488 |
| 15588 | 1–311;1–289;1–297;1–270;1–294;1–309;1–297;1–298;1–308;1–290;1–302;1–296;1–293;1–309;1–128;1–309;1–309;1–296;1–309;1–311;5–311 |
| 15590 | 1–513;1–462 |
| 15591 | 1–417;1–569;1–360 |
| 15592 | 1–358;1–368;1–359 |
| 15593 | 1–346;1–393;5–99 |
| 15594 | 1–469;1–329;1–484;1–453;1–493;1–484;1–485;1–430;1–400;1–429;1–442;1–469;1–397;1–388;1–446;1–454;1–360;1–370;1–313;1–397;1–429;1–361;1–370;1–453;1–246;1–429;1–465;1–446;1–442 |
| 15595 | 1–436;1–291 |
| 15596 | 1–385;1–286;1–443;1–419;2–408 |
| 15597 | 1–502;1–504 |
| 15598 | 1–388;11–410 |
| 15600 | 1–446;1–402;1–442;1–374;1–438 |
| 15603 | 1–493;1–491;1–449;1–368;1–490;1–473;1–544;1–500;1–476;1–325;1–498;1–453;1–510;1–506 |
| 15604 | 1–473;1–470;1–489 |
| 15605 | 1–419;1–409;1–414;1–422;1–413;1–421;1–390;1–419;1–405;1–404;1–409;1–412;1–412;1–422 |
| 15606 | 1–470;1–487;1–462 |
| 15607 | 1–375;1–406 |
| 15608 | 1–365;1–500 |
| 15609 | 1–383;1–359 |
| 15610 | 1–473;1–463;65–600;65–530;65–454 |
| 15612 | 1–481;1–425 |
| 15613 | 1–220;1–220;1–220;1–216;1–220;1–216;1–216;1–216;1–216;1–216;1–220;1–220;1–220;1–220;1–216;1–220;1–220;1–220;1–220;1–220;1–216;1–220;1–220;1–216;1–216;1–216;1–216;1–216;1–216;1–216;1–220;1–220;1–220;1–216;1–220;1–220;1–220;1–216 |
| 15614 | 1–342;5–61;5–202;18–138;18–202;19–145;24–116;54–154;54–382;54–141;54–485;54–111;54–350;54–228;54–227;54–104;54–382;54–463;54–181;55–140 |
| 15615 | 1–77;1–409;2–450 |
| 15617 | 1–371;1–372 |
| 15618 | 1–456;1–456 |
| 15619 | 1–516;1–448;1–597 |
| 15621 | 1–376;1–462 |
| 15622 | 1–566;1–565 |
| 15623 | 1–453;6–447;15–494;15–459;15–423;17–504 |
| 15627 | 1–576;1–361;1–501 |
| 15628 | 1–443;1–476 |
| 15629 | 1–381;1–380;1–304 |
| 15630 | 1–520;2–497 |
| 15631 | 1–455;1–476;1–503;1–87;1–488;1–457 |
| 15632 | 1–50;1–63 |
| 15633 | 1–368;1–396;1–396 |
| 15634 | 1–403;1–393 |
| 15635 | 1–349;1–507 |
| 15636 | 1–507;1–446;1–508 |
| 15637 | 1–304;1–372 |
| 15638 | 1–444;1–462 |
| 15639 | 1–490;1–497;1–489;1–492;2–486;8–497 |
| 15640 | 1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–150;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–220;1–224;1–220;1–220;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224;1–224 |
| 15641 | 1–510;1456 |
| 15642 | 1–280;1–324 |
| 15643 | 1–366;1–404;1–406;1–381;1–57;1–400;1–405;1–418;1–373;1–374;1–69;1–400;1–406;1–417;1–378;1–133 |
| 15646 | 1–298;1–316 |
| 15647 | 1–525;1–475 |
| 15649 | 1–466;1–404 |
| 15650 | 1–463;76–526 |
| 15651 | 1–402;1–368;1–387;1–232;1–415;1–229;1–409;1–402;1–408;1–414;1–422;1–318;1–399;1–204;1–405;1–229;1–295;1–387;1–413;1–312;1–400;1421;1400;1409;1–94;1–409;1–287;1–280;1–392;1–398;1–326;1–378;1–391;39425 |
| 15657 | 1–419;12–435;12–459;12–396;12–382;12–458;12–447;12–381;12–460;12–431;12–433;12–467;12–460;12–445;12–368 |
| 15658 | 1–58;1–248;2–199;3–254;9–332;9–396;12–354;15–397;15–352;15–396;15–213;15–135;15–277;15–344;15–199;15–325;16–142;21–113;21–238;42–269;42–379;42–251;51–108;51–101;51–138;51–178;51–151;52–137;58–315;79–292 |
| 15659 | 1–498;196–694;196–665;196–662;196–681;196–651;196–601;196–633;196–697;196–695;196–634;196–695;196–694;196–662;196–658;196–694;196–661;196–672;196–682;196–690;196–681;196–549;196–667;196–694;196–661;196–648;196–646;196–568;196–692;196–380;196–627;198–491 |
| 15661 | 1–308;1–302 |
| 15662 | 1–207;1–100;1–206;1–207 |
| 15663 | 1–100;1–206;1–207;1–207 |
| 15665 | 1–482;9–160 |
| 15666 | 1–491;7–296 |
| 15670 | 1–220;1–99;1–463 |
| 15673 | 1–560;1–181 |
| 15674 | 1–493;1–458;1–437 |

TABLE II-continued (Tiling path)

| Seq Id No. | Positions of biological 5'ESTs |
|---|---|
| 15675 | 1–494;1–505;1–408 |
| 15676 | 1–227;1–144;1–295;1–435;13–537;15–366 |
| 15677 | 1–157;1–163;1–87;1–144;1–152;2–65 |
| 15678 | 1–183;1–184;1–178;1–165;1–175;1–152;1–164;1–402;1–183;1–144;1–181;1–160;1–184;1–182;1–182;1–87;1–184;1–184;1–179;1–196;2–65;2–167;2–183;3–185 |
| 15679 | 1–399;1–461;1–365;1–470 |
| 15680 | 1–532;1–451 |
| 15681 | 1–446;1–471 |
| 15682 | 1–117;1–106;1–122;1–121 |
| 15683 | 1–466;1–489 |
| 15684 | 1–475;1–446 |
| 15685 | 1–532;1–436;1–532;1–517;1–513;1–351;1–532;1–453;1–493;1–405;1–450;1–516;1–492;1–513;1–428;1–466;1–450;1–410;1–516;1–334;1–382;1–469;1–241 |
| 15687 | 1–422;3–428;10–400 |
| 15688 | 1–148;1–418;1–438 |
| 15690 | 1–438;34–368;34–389 |
| 15691 | 1–497;1–479;1–464;1–480 |
| 15693 | 1–499;1–451;1–587 |
| 15694 | 1–201;1–120;1–201 |
| 15697 | 1–457;1–466 |
| 15698 | 1–276;1–276;1–276;1–284 |
| 15702 | 1–502;1–482 |
| 15703 | 1–482;1–477 |
| 15704 | 1–432;1–391;1–101;1–423;1–162;1–470;1–503 |
| 15705 | 1–379;1–439;13–503;13–498;13–451;13–445;13–481;13–490;13–481;13–173 |
| 15709 | 1–283;1–272 |
| 15710 | 1–328;1–278;1–72;1–80 |
| 15711 | 1–440;4–438;7–424;8–454;8–445;8–327;8–349;8–437;8–454;8–434;8–447;8–441;8–434;8–411;8–437;8–415;8–442;8–457;8–437;8–390;8–423;8–437;11–442;11–441;11–455;11–430;11–439;11–369;11–434;11–443;11–446;11–390;11–439;11–444;11–457;11–454;11–441;11–440;11–363;11–445;11–347;11–400;11–443;11–361;11–422;11–417;11–438;11–435;11–456;11–131;11–438;11–442;11–422;11–442;11–446;11–391;11–373;11–413;11–442;11–437;11–397;11–417;11–437;11–415;11–446;11–436;11–442;11–356;11–449;11–272;11–370–11–444;11–441;11–421;11–208;11–454;11–422;11–417;11–445;11–447;11–194;11–425;11–446;11–339;11–422;11–443;11–434;11–442;11–449;11–422;11–320;11–440;11–433;11–417;12–369;12–439;12–455;12–427;12–429;12–437;12–434;12–446;12–138;12–442;12–455;12–403;12–442;12–442;12–402;12–357;12–451;12–454;12–437;12–417;15–455;17–233;17–455;17–109;17–436;17–455;18–402;21–426;35–437;35–449;35–452;35–436;35–433;38–246;38–456;38–438;38–264;38–422;38–450;38–454;38–422;38–442;38–448;38–454;38–442;38–376;38–436;38–442;38–454;38–455;38–438;38–455;38–450;38–433;38–434;38– |
| 15712 | 1–420;1–338;1–412;1–497 |
| 15714 | 1–425;1–489;1–472 |
| 15715 | 1–423;3–456;4–316;4–357;4–309 |
| 15717 | 1–409;22–149;22–123 |
| 15718 | 1–496;1–441;1–551 |
| 15719 | 1–493;1–471 |
| 15721 | 1–364;1–126;1–420;1–383;1–324;1–389;1–405;1–375;1–404 |
| 15722 | 1–78;27–410;27–193;29–98 |
| 15726 | 1–336;1–304;1–340 |
| 15727 | 1–448;1–288 |
| 15728 | 1–133;1–184 |
| 15730 | 1–361;8–276;8–338;8–339;11–408 |
| 15731 | 1–352;1–409;1–423;1–357 |
| 15733 | 1–102;1–396 |
| 15734 | 1–476;1–457 |
| 15735 | 21–222;25–397 |
| 15736 | 1–361;1–404;1–505 |
| 15738 | 1–245;6–494;6–457 |
| 15739 | 1–423;1–414 |
| 15740 | 1–242;28–253 |
| 15742 | 1–323;1–323 |
| 15743 | 1–338;1–370;1–345;1–349 |
| 15745 | 1–100;1–274;8–503 |
| 15746 | 1–459;1–338;1–427;1–429;1–450;1–113;1–427;1–395;1–399;1–380;1–453 |
| 15747 | 1–96;1–78;1–80;1–96;1–96;1–96;1–96;1–97;1–96;1–97;1–95;1–96;1–97;1–96;1–96;1–97;1–84;1–97;1–96;1–97;1–72;1–97;1–96;1–96;1–80;1–96;1–84;1–96;1–96;1–97;1–96;1–96;1–97;1–97;1–80;1–96;1–97;1–96;1–95;2–113;2–129;2–128;2–129;2–129;2–129;2–125;2–126;2–129;2–134;2–129;2–129;2–129;2–115;2–129;2–129;2–113;2–129;2–71;2–129;2–129;2–116;2–129;2–129;2–129;2–129;2–129;2–134;2–126;2–104;2–129;2–123;2–129;2–104;2–126;2–129;2–115;2–129;2–129;2–120;2–129;2–128;2–115;2–95;2–129;2–73;2–129;2–129;2–126;2–129;2–134;2–129;2–129;2–126;2–128;2–129;2–129;2–129;2–134;2–134;2–129;2–129;2–104;2–129;2–129;2–129;2–134;2–134;2–105;2–129;2–129;2–129;2–134;2–115;2–125;2–129;2–134;2–103;2–129;2–134;2–105;2–129;2–129;2–134;2–125;2–129;2–129;2–129;2–115;2–129;2–128;2–129;2–129;2–129;2–129;2–124;2–117;2–129;2–129;2–125;2–134;2–134;2–134;2–113;2–105;2–122;2–126;2–129;2–129;2–125;2–129;2–129;2–107;2–129;2–121;2–126;2–129;2–126;2–134;2–134;2–134;2–134;2–129;2–129;2–125;2–129;2–129;2–129;2–129;2–129;2–125;2–129;2–129;2–129;2–129;2–126;2–126;2–129;2–12 |
| 15748 | 1–516;1–503;2–479;4–480;4–459;4–483;4–459;4–459;4–459;4–454;4–268;4–61;5–407;5–478;5–459;5–459;5–274;5–457;5–408;5–483;5–459;5–481;5–457;5–457;5–479;5–480;5–457;5–480;5–392;5–457;5–459;5–480;6–501;11–358;11–459;11–425;11–479;11–479;12–483;13–485;14–445;14–382;14–479;14–479;14–459;14–480;14–455;17–478;17–457;17–459;17–390;17–483;17–532;17–298;17–405;17–479;17–501;17–483;17–483;17–425;17–480;7–408;17–477;17–483;17–479;17–483;17–459;17–483;17–481;17–483;17–459;17–469;17–479;17–483;17–483;17–483;17–469;17–483;17–577;17–480;17–404;17–479;17–457;17–483;17–392;17–374;17–483;17–482;17–392;17–217;17–457;17–480;17–483;17–483;17–425;17–459;17–459;17–371;17–346;17–453;17–483;17–455;17–459;17–483;17–457;17–231;17–146;17–483;18–442;18–148;18–479;18–469;18–391;18–404;18–479;18–479;18–479;18–457;18–479;18–481;18–468;23–478;23–257;23–117;24–441;27–467;41–479;41–478;44–290;55–481;55–459;55–459;55–468;55–481;55–392;55–479;55–163;55–479;55–484;55–480;55–483;55–484;55–148;55–479;55–190;56–148;60–483;60–477;60–478;60–483;60–400;6 |

TABLE II-continued

(Tiling path)

| Seq Id No. | Positions of biological 5'ESTs |
|---|---|
| 15791 | 1–453;1481;1–465;1–483 |
| 15802 | 1–492;1–72;1–541 |
| 15823 | 1–199;1–127 |
| 15992 | 1–165;1–183;1–85;1–180 |
| 16002 | 1–337;2–377 |
| 16003 | 1–363;1–424;1–376 |
| 16004 | 1–471;1–495;1–403;1–468;1–498 |
| 16007 | 1–269;1–236;1–272;1–272;1–272;1–272;1–270;1–272;1–250;1–250;1–64;1–272 |
| 16036 | 1–449;1–526 |
| 16047 | 1–175;1–115 |
| 16062 | 1–110;2–107 |
| 16063 | 1–447;3–247 |
| 16064 | 1–376;1–450;1–128;1–311;1–428;1–311;1–327 |
| 16065 | 1–206;1–225;1–225;1–225;1–225;1–213;1–212;1–225;1–127;1–225;1–214;1–215;1–224;1–225;1–213;1–227;1–224;1–224;1–225;1–225;1–226;1–225;1–225;1–216;1–226;1–225;1–209 |
| 16066 | 1–405;1–405;1–394 |
| 16067 | 1–516;6–442 |
| 16068 | 1–217;1–234 |
| 16069 | 1–404;4–172 |
| 16070 | 1–399;1–169 |
| 16071 | 1–479;1–482;1–480;1–308;1–471 |
| 16072 | 1–323;1–451;1–321;2–439;3–357;3–453;3–455;3–296;3–415;3–311;3–416;3–289;3–403;3–355;4–464;4–498;5–93;5–53;5–274;5–364;5–319;5–78;6–382;6–481;7–398 |
| 16073 | 1–455;13–500;18–168;18–212;18–144 |
| 16074 | 1–276;1–276;1–270 |
| 16075 | 1–458;1–470 |
| 16076 | 1–328;1–308;1–328;1–79;1–319;1–318;1–293 |
| 16078 | 1–357;1–351 |
| 16079 | 1–362;1–430 |
| 16083 | 1–215;1–215;1–215;1–215;1–213;1–215;1–213;1–137;1–213;1–215 |
| 16084 | 1–52;1–52 |
| 16085 | 1–388;6–373;18–301 |
| 16086 | 1–376;1–334 |
| 16087 | 1–499;1–489;1–436 |
| 16088 | 1–411;1–413;1–422 |
| 16089 | 1–479;1–529 |
| 16091 | 1–96;1–285;29–276;29–283;29–300;29–139;29–300;29–272;29–281;29–299;29–287;29–278;29–278;29–300;29–302;29–301;29–299;29–286;29–296;29–301;29–301;29–301;29–301;29–287;29–302;29–302;29–287;29–287;29–298;29–283;29–287;29–299;29–299;29–291;29–284;29–287;29–287;29–290;29–300;29–94;29–299;29–275;34–299 |
| 16094 | 1–333;37–492;43–538;49–572;49–372 |
| 16095 | 1–234;130–280;130–273;172–234 |
| 16098 | 1–486;1–556 |
| 16102 | 1–316;1–321;1–145 |
| 16103 | 1–70;1–384;1–470 |
| 16104 | 1–460;13–569 |
| 16105 | 1–219;1–216;1–351;1–238 |
| 16106 | 1–258;1–472;1–485;1–517 |
| 16107 | 1–462;1–466;1–230 |
| 16112 | 1–422;1–440;1–440;1–395 |
| 16113 | 1–76;1–72 |
| 16116 | 1–485;1–105;1–105;1–362 |
| 16117 | 1–459;1–470;1–438;1–105;1–105;1–455;1–528 |
| 16119 | 1–466;1–740 |
| 16121 | 1–116;1–395 |
| 16123 | 1–272;1–258 |
| 16124 | 1–512;1–441 |
| 16127 | 1–157;1–282;1–272;1–267;1–280;1–283;1–288;1–277;1–206;1–270;1–206;1–258;1–220;1–175;1–281;1–259;1–269;1–270;1–286;1–140;1–286;1–284;1–276;1–270;1–279;1–219;1–287;1–284;1–262;1–190;1–275;1–262;1–239;1–288;1–76;1–272;1–271;1–260;1–264;1–280;1–282;1–248;1–287;1–284;1–293;1–272;1–266;1–280;1–288;1–270;1–284;1–275;1–274;1–283;1–282;1–284;1–293;1–263 |
| 16146 | 1–479;1–408 |
| 16150 | 1–434;2–77 |
| 16151 | 1–350;1–309;1–350;1–350;1–249;1–350;36–337;36–347;36–342;36–353;36–353;36–127;36–353;36–351;36–353;36–350;36–352;36–315;36–350;36–353;36–115;36–314;36–353;36–353;36–346;36–353;36–315;36–315;36–351;36–352;36–353;36–352;36–353;36–350;36–140;36–352;36–333;36–297;36–340;36–343;36–315;36–316;36–305;36–350;36–351;36–336;36–327;36–346;36–204;36–350;36–328;36–353;36–350;36–351;36–353;36–341;36–338;36–350;36–353;36–352;36–350;36–353;36–350;36–353;36–315;36–317;36–351;36–353;36–140;36–351;36–352;36–353;36–349;36–351;36–349;36–330;36–140;36–315;36–344;36–321;36–350;36–317;36–345;36–353;36–353;36–349;36–211;36–353;36–353;36–349;36–276;36–353;36–349;36–353;36–353;36–350;36–351;36–138;36–353;36–350;36–350;36–315;36–350;36–308;36–334;36–347 |
| 16153 | 1–504;1–517;1–499;1–371;1–477;1–450;1–378;1–437;1–433;1–476;1–491;1–439;1–387;1–472;1–461;1–379;1–423;1–460;1–424;1–431;1–468;1–559;1–475;1–489;1–478;1–366;1–524;1–474;1–479;1–121;1–504;1–485;1–527;1–465;1–432;1–319;1–449;1–441;1–431;1–456;1–387;1–482;1–441;1–475;1–433;1–489;1–398;1–432;1–460;1–466;1–523;1–477;1–456;1–333;1–517;1–516;1–146;1–452;1–530;1–516;1–525;1–460;1–204;1–306;1–419;1–441;1–410;1–412;1–476;1–198;1–483;1–433;1–314;1–517;1–475;1–517;1–478;1–525;1–473;1–486;1–465;1–354;1–460;1–441;1–476;1–463;1–467;1–423;1–526;1–481;1–527;1–278;1–362;1–456;1–474;1–513;1–487;1–452;1–418;1–476;1–463;1–444;1–487;1–303;1–405;1–452;1–402;1–488;1–470;1–544;1–466;1–474;1–489;1–460;1–489;1–465;1–374;1–359;1–350;1–413;1–508;3–385 |
| 16154 | 1–193;1–121;1–146 |
| 16157 | 1–512;1–453 |
| 16158 | 1–435;1–476 |
| 16159 | 1–446;1–493;1–439;4–523 |
| 16160 | 1–122;1–157 |
| 16168 | 1–456;1–478;1–527;1–469;1–451;1–507;1–493;1–497 |
| 16169 | 1–420;1–489 |
| 16170 | 1–409;2–349;2–361;2–113 |
| 16171 | 1–252;19–136;19–492 |
| 16172 | 1–347;1–435;1–446;1–460;1–444;1–489 |
| 16173 | 1–369;1–479 |
| 16176 | 1–504;1–441 |
| 16178 | 1–531;1–173 |
| 16179 | 1–403;1–366;1–402 |
| 16181 | 1–396;10–387 |
| 16182 | 1–388;1–473;1–494;1–449;1–493;1–462;1–494;1–416;1–231;1–111;1–255;1–508;1–472;1–341;1–508;1–427;1–104;1–494;1–508;1–547;1–403;1–351;1–465;1–355;1–494;1–492 |
| 16183 | 1–448;1–481 |

TABLE II-continued

(Tiling path)

| Seq Id No. | Positions of biological 5'ESTs |
|---|---|
| 16184 | 1–243;1–409 |
| 16185 | 1–372;1–362;1–367;1–403;1–388;1–411;1–413;1–398;1–399;1–413;1–395;1–401;1–413;1–396;1–411;1–320;1–351;1–401;1–225;1–256;1–361;1–399;1–398;1–411;1–399;1–403;1–155;1–401;1–378;1–396;1–400;1–389;1–368;1–411;1–397;1–389;1–412;1–412;1–398;1–412;1–401;1–394;1–125;1–249 |
| 16186 | 1–431;1–418 |
| 16187 | 1–198;1–198;1–198;1–199 |
| 16191 | 1–418;1–418;1–418;1–418;1–418;1–477;1–418;1–418;1–416;1–418;1–418;1–416;1–416;1–397;1–412;1–418;1–408;1–418;1–418;1–364;1–418;4–146 |
| 16192 | 1–488;32–446;32–446;32–446;32–446;32–446;32–446;32–446;32–444;32–444;32–446;32–446;32–174;32–444;32–425;32–446;32–440;32–436;32–446;32–446;32–392;32–446 |
| 16193 | 1–211;4–146 |
| 16196 | 1–362;1–493;1–456 |
| 16207 | 1–414;2–430;2–341 |
| 16210 | 1–203;1–204;1–203 |
| 16211 | 1–388;1–393 |
| 16212 | 1–304;1–343 |
| 16213 | 1–384;1–440;1–412 |
| 16214 | 1–471;1–507 |
| 16220 | 1–250;1–536 |
| 16221 | 1–291;1–290;1–291;1–291 |
| 16222 | 1–201;1–493;1–255 |
| 16223 | 1–278;1–460;6–403 |
| 16224 | 1–421;1–585;1–518;1–537 |
| 16228 | 1–70;10–401;10–409 |
| 16229 | 1–416;1–409;1–188;48–117 |
| 16230 | 1–428;1–469;1–469;1–304;1–451;1–335;1–499;1–471;1–408;1–385;1–516 |
| 16231 | 1–448;1–459;1–459;1–458;1–483;1–327;1–272;1–472;1–419;1–92;1–327;1–402;1–377;1–218;1–92;1–377;1–402;1–478;1–386 |
| 16232 | 1–333;1–68;1–385 |
| 16235 | 1–464;1–372;1–464 |
| 16236 | 1–393;1–451;78–598;78–583;78–591;78–527 |
| 16237 | 1–246;1–248;1–246;1–249;4–112;4–108;4–111;4–100;4–108;4–102;4–108;4–108;4–107;4–61;4–108;4–108;4–90;4–111;4–111;4–100;4–108;4–108;4–74;4–90;4–114;4–107;4–108;4–108;4–108;4–106;4–108;4–108;4–99;4–84;4–91;4–108;4–91;4–108;4–92;4–108;4–108;4–91;4–107;4–101;4–108;4–108;4–108;4–100;4–73;4–88;4–108;4–84;4–90;4–85;4–108;4–11;4–91;4–107;4–110;4–107;4–83;4–78;4–107;4–108;4–108;4–108;4–111;4–93;4–111;4–108;4–108;4–111;4–99;4–107;4–83;4–108;4–108;4–90;4–108;4–102;4–108;4–111;4–108;4–111;4–107;4–91;4–107;4–108;4–111;4–108;4–108;4–107;4–108;4–85;4–69;4–107;4–108;4–108;4–111;4–107;4–108;4–100 |
| 16238 | 1–118;1–104;1–118;1–118;1–118;1–124;1–118;1–118;1–118;1–119;1–118;1–118;1–118;1–118;1–105;1–118;1–118;1–119;1–118;1–104;1–118;1–105;1–118;1–97;1–81;1–71;1–117;1–81;1–118;1–118;1–118;1–105;1–105;1–118;1–118;1–124;1–118;1–118;1–118;1–118;1–105;1–118;1–105;1–118;1–118;1–118;1–118;1–105;1–118;1–118;1–124;1–118;1–118;1–118;1–97;1–118;1–119;1–118;1–118;1–118;1–124;1–118;1–118;1–118;1–118;1–118;1–118;1–118;1–80;1–118;1–118;1–118;1–119;1–118;1–118;1–118;1–118;1–118;1–118;1–118;1–118;1–118;1–118;1–118;1–118;1–118;1–118;1–118;1–118;1–118;1–118;1–105;1–118;1–105;1–119;1–118;1–88;1–118;1–118;1–119;1–124;1–118;1–118;1–111;1–118;1–118;1–118;1–104;1–118;1–82;1–118;1–118;1–118;1–118;1–120;1–104;1–118;1–118;1–118;1–118;1–118;1–124;1–105;1–118;1–124;1–118;1–118;1–118;1–118;1–118;1–118;1–124;1–124;1–118;1–104;1–124;1–105;1–111;1–118;1–118;1–119;1–118;1–105;1–87;1–120;1–118;1–118;1–118;1–109;1–118;1–118;1–111;1–98;1–118;1–118;1–105;1–118;1–124;1–118;1–118;1–96;1–118;1–105;1–88;1–118;1–118;1–118;1–118;1–118;1–89;1–118;1–118;1–118;1–118;1–118;1–118;1–124 |
| 16241 | 1–295;1–282;1–129;1–317;1–288;1–308;1–274;1–273;1–307;1–317;1–275;1–306;1–289;1–317;1–307;1–305;1–308;1–308 |
| 16242 | 1–92;1–52;1–81;1–93;1–92;1–81;1–92;1–92;1–84;1–83;1–68;1–97;1–97;1–92 |
| 16243 | 1–497;1–382;1–483;1–498;1–487;1–474;1–400;1–497;1–497;1–401;1–497;1–349;1–464;1–489;1–478;1–484;1–397;1–501;1–501;1–502;1–497;1–489;1–496;1–473;1–363 |
| 16244 | 1–401;1–401 |
| 16245 | 1–496;1–446 |
| 16246 | 1–331;1–337;1–317;1–331 |
| 16247 | 1–237;1–239 |
| 16248 | 1–138;1–138;1–163;1–136;1–135;1–163;1–138;1–160;1–138;1–138;1–88;1–163;1–525;1–136;1–136;1–136;1–163;1–160;1–160;1–163;1–138;1–138;1–163;1–129;1–136;1–163;1–138;1–136;1–138;1–160;1–136;1–163;1–138;1–136;1–136;1–160;1–136;1–136;1–376;1–138;1–138;1–163;1–136;1–138;1–136;1–136;1–144;1–136;1–163;1–138;1–138;1–136;1–138;1–138;1–160;1–138;1–144;1–138;1–163;1–136;1–136;1–163;1–136;1–163;1–144;1–136;1–138;1–136;1–136;1–160;1–163;1–136;1–138;1–138;1–163;1–138;1–163;1–160;1–138;1–160;1–136;1–160;1–136;1–160;1–136;1–88;1–136;1–163;1–138;1–138;1–136;1–136;1–136;1–136;1–136;1–138;1–136;1–136;1–138;1–160;1–163;1–138;1–136;1–324;1–160;1–136;1–138;1–160;1–163;1–138;1–136;1–163;1–136;1–136;1–136;1–129;1–163;1–163;1–138;1–138;1–138;1–163;1–138;1–163;1–136;1–138;1–138;1–163;1–137;1–138;1–136;1–138;1–163;1–136;1–160;1–163;1–160;1–138;1–138;1–163;1–163;1–138;1–163;1–138;1–160;1–138;1–138;1–129;1–136;1–138;1–138;1–160;1–163;3–523;3–476;3–510;3–378;3–497;3–453;3–483;3–482;3–500;3–447;3–475;3–512;3–509;3–526;3509;3 631;3–498;3–483;3–500;3–496;3–525;3–499;3–498;3–525; |
| 16263 | 1–252;1–322 |
| 16264 | 1–216;1–225;1–226;1–226;1–226;1–225 |
| 16265 | 1–490;1–456 |
| 16266 | 1–207;1–353 |
| 16269 | 1–166;1–430 |
| 16270 | 1–408;1–141 |
| 16271 | 1–141;1–508;1–502 |
| 16272 | 1–471;44–519 |
| 16274 | 1–336;1–333 |
| 16275 | 1–371;81–552 |
| 16276 | 1–77;1–352;1–458;1–453;1–458 |
| 16277 | 1–411;141–412;141–406;141–371;141–333;141–412;141–412;141–401;141–412;141–412;141–412;141–412;141–412;141–412;141–412;141–391;141– |

TABLE II-continued

(Tiling path)

| Seq Id No. | Positions of biological 5'ESTs |
|---|---|
| | 412;141–412;141–412;141–412;141–401;141–412;141–389 |
| 16278 | 1–283;1–454 |
| 16282 | 1–506;1–384 |
| 16285 | 1–176;1–492 |
| 16287 | 1–394;1–512 |
| 16296 | 1–348;1–363 |
| 16297 | 1–400;1–575 |
| 16299 | 1–306;1–477;1–491;1–477 |
| 16300 | 1–474;1–474 |
| 16301 | 1–449;13–285;17–164 |
| 16302 | 1–272;1–531;1–461;1–462;1–460;1–321;1–556;1–441;1–493;1–503;1–487;1–414;1–510;1–560;1–447;1–487;1–77;1–357;1–461;1–413;1–342;1–575;1–567;1–464;1–526;1–481;1–417;1–585;1–400;1–489;1–577;1–445;1–458;1–174;1–493;1–496;1–522;1–518;1–475;1–331;1–577;1–134;1–363;1–336 |
| 16303 | 1–348;1–180 |
| 16307 | 1–491;291–495 |
| 16308 | 1–457;10–429;27–442 |
| 16309 | 1–103;1–176;2–107 |
| 16310 | 1–248;1–248 |
| 16311 | 1–454;1–535;156–655;156–652;156–640 |
| 16312 | 1–494;1–515;1–425;1–481;1–501;1–472;1–508;1–435;1–396;1–511;1–502;1–424;1–423;1–420;1–337;1–497;1–473;1–488;1–523;1–473;1–542;1–501;1–473;1–424;1–498;1–444;1–411;1–490 |
| 16315 | 1–162;1–144;1–160;1–166;1–165 |
| 16325 | 1–342;1–413 |
| 16327 | 1–535;1–269;81–568;81–393;81–538;81–587;81–577;81–562;81–574 |
| 16328 | 1–270;1–536;1–559;81–539;81–394 |
| 16329 | 1–423;1–489 |
| 16332 | 1–359;22–488;23–404;23–413;23–409;23–420;23–420;23–415;23–412;23–411;23–412;24–274;24–412;24–404;24–379;24–205;24–408;25–395;25–408;27–476;27–394;27–431;41–497;41–497;41–504;41–497;41–498;41–394;41–462;41–497;41–456;43–407;43–144;43–358;43–422;43–422;43–407;43–422;43–412;43–419;43–407;43–399;43–407;46–455;46–492;66–408;66–392;74–422 |
| 16333 | 1–140;1–146 |
| 16334 | 1–451;1–487 |
| 16335 | 1–493;1–317 |
| 16336 | 1–223;1–442;1–379;1–357;1–417 |
| 16337 | 1–484;1–513;1–423;5–227;5–362 |
| 16338 | 1–56;1–164;1–205;1–203;1–148 |
| 16346 | 1–239;1–239;1–239 |
| 16348 | 1–499;1–443 |
| 16351 | 1–257;1–85;1–269;12–84;12–183;12–141;12–99;12–269;12–98;12–85;12–160;12–271;18–151;18–151;18–98;44–159;44–159;45–272;45–299;45–299;45–159;45–292;45–295;45–159;45–304;45–300;45–282;45–159;45–299;45–304;45–156;45–292;45–156;45–293;45–137;45–293;45–159;45–136 |
| 16352 | 1–251;1–375;1–85;1–403;1–331;1–263;1–358;12–84;12–347;12–363;12–85;12–99;12–263;12–158;12–403;12–416;12–138;12–98;12–407;12–265;12–179;18–98;18–148;18–148;44–404;44–156;44–410;44–156;44–405;45–291;45–305;45–133;45–311;45–291;45–284;45–305;45–300;45–311;45–291;45–156;45–307;45–301;45–156;45–311;45–296;45–292;45–267;45–287;45–291;45–311;45–284;45–276;45–311;45–156;45–296;45–153;45–307;45–301;45–156;45–153;45–307;45– |
| | 311;45–134;45–314;45–285;45–305;45–300;45–285;45–304;45–304;45–311;45–311 |
| 16354 | 1–445;1–399;1–98;23–420;29–417;29–417;29–416;29–416;29–123;29–253;29–447 |
| 16355 | 1–433;1–436;1–399;1–436;1–98;21–435;23–424;23–423;29–421;29–253;29–418;29–433;29–423;29–416;29–427;29–416;29–123;29–435 |
| 16358 | 1–473;1–173 |
| 16359 | 1–323;1–416;1–452;1–494;1–451 |
| 16360 | 1–432;1–408;1–404 |
| 16361 | 1–281;1–281 |
| 16363 | 1–505;1–482 |
| 16364 | 1–443;1–457 |
| 16365 | 1–299;1–438 |
| 16367 | 1–483;1–519 |
| 16368 | 1–382;1–382;1–390;2–333;2–389;2–378;2–389;2–388;2–389;2–384;3–388;4–391;4–372;4–377;4–389;4–389;4–383 |
| 16369 | 1–452;2–54 |
| 16370 | 1–478;1–470;1–430 |
| 16371 | 1–406;3–399 |
| 16372 | 1–451;2–500;2–335;2–501;2–352;2–396;2–507;2–476;2–542;2–495;2–518;2–479;2–500;3–376;35–529 |
| 16374 | 1–495;1–444;1–462;1–488;1–445 |
| 16376 | 1–402;1–469;1–463;1–491;1–341;1–465;1–469 |
| 16378 | 1–247;20–302;31–309;31–109 |
| 16379 | 1–301;1–424 |
| 16380 | 1–400;1–372 |
| 16382 | 1–80;1–82;1–68;1–68;1–82;1–82;1–82;1–80;1–80;1–68;1–80;1–80;1–82;1–80 |
| 16383 | 1–497;1–431;1–487 |
| 16384 | 1–472;1–372 |
| 16385 | 1–344;1–334;1–346;1–345 |
| 16386 | 1–443;1–490;1–404;1–435 |
| 16387 | 1–391;1–359 |
| 16388 | 1–440;1–490 |
| 16389 | 1–132;1–119;1–161;1–118;1–118;1–100;1–148;1–118 |
| 16390 | 1–365;44–440 |
| 16393 | 1–360;4–56;4–403;14–404;14–379;14–402;14–386;14–386;14–393;14–404;14–385;14–393;14–383;14–386;14–390;14–397;14–381;14–393;14–390;14–389;14–406;14–389;14–390;14–390;14–383;14–405;14–390;14–395;14–393;14–386;14–380;14–175;14–398;14–393;14–405;14–404;14–390;14–393;14–402;14–405;14–377;14–406;14–390;14–395;14–403;14–404;14–390;14–390;14–389;14–400;14–383;14–402;14–390;14–401;14–259;14–405;14–403;14–394;14–349;15–394;21–96;21–96;21–96;21–96;21–96;21–96;21–96;21–96;21–96;21–96;21–96;21–96;21–96;21–96;21–96 |
| 16395 | 1–440;1–446;1–336;1–439;1–449 |
| 16396 | 1–359;3–506;3–403;13–465;48–482;48–497;48–525;48–451;48–506;49–280;49–523;49–448;49–505;49–434;49–538;49–521;52–505;52–536;66–555;80–538;80–463;80–549;80–538;80–279;80–520;80–313;80–560;80–504;80–552;80–538;86–534;86–538;86–538;86–518;86–362;86–538;87–418;87–246;87–442;88–566;88–557;88–532;88–588;88–498;88–545;88–555;88–569;88–566;89–533;89–547;89–323;89–220;90–521;92–527;92–594;104–549;104–597;104–559;111–545;111–594;111–611;111–556;111–165;111–585;111–561;113–551;113–591;118–579 |
| 16397 | 1–472;14–465 |
| 16399 | 1–508;1–478;51–433 |

TABLE II-continued (Tiling path)

| Seq Id No. | Positions of biological 5'ESTs |
|---|---|
| 16401 | 1–536;350–848 |
| 16402 | 1–257;1–257;1–257;1–231;1–257;1–257;1–257;1–257 |
| 16403 | 1–421;8–321 |
| 16404 | 1–443;1–496 |
| 16410 | 1–137;1–53;1–153;1–112;1–147;1–443;1–167;1–528;52–568 |
| 16411 | 1–510;1–480;4–500;4–512;4–464;4–503;4–496;4–485;4–480;4–498;4–496;4–496;4–470;4–495;4–460;4–494;4–496;4–480;4–495;4–407;4–484;4–526;4–483;4–495;4–494;4–485;4–485;4–460;4–452;4–496;4–456;4–449;4–494;4–526;4–495;4–495;4–494;4–480;4–460;4–481;4–482;4–485;4–485;4–504;4–470;4495;4–485;4–526;4–512;4–460;4–498;4–485;4–460;4–495;4–498;4–480;4–526;4–497;4–495;4–485;4–497;4–494;4–503;4–460;4–498;4–145;4–498;4–495;4–484;4–526;4–510;4–478;4–501;4–496;4–526;4–508;4–501;4–499;4–502;4–485;4–485;4–482;4–470;4–498;4–504;4–460;4–460;4–512;4–485;4–502;4–495;4–507;4–480;4–496;4–483;4–495;4–498;4–407;4–505;4–494;4–400;4–482;4–481;4–468;4–460;4–457;4–485;4–480;4–526;4–515;4–493;4–497;4–507;4–501;4–485;4–482;4–497;4–498;4–485;4–507;4–502;4–503;4–526;4–502;4–513;4–485;4–482;4–485;4–497;4–526;4–501;4–402;4–450;4–482;4–499;4–482;4–502;4–510;4–498;4–239;4–507;4–442;4–495;4–485;4–514;4–485;4–482;4–506;4–501;4–455;4–495;4–480;4–470;4–505;4–452;4–495;4–526;4–498;4–375;4–502;4–496;4–506;4–498;4–501;4–510;4–502;4–485;4–495;4–498;4–504;4–49 |
| 16412 | 1–138;1–54;1–371;1–372;1–326;1–372;1–223;1–349;1–154;1–317;1–305;1–113;1–300;1–148;1–273;1–170;1–349 |
| 16422 | 1–388;1–392 |
| 16423 | 1–464;1–413;1–178 |
| 16425 | 1–193;1–155 |
| 16427 | 1–397;1–504 |
| 16436 | 1–139;1–135;1–135;1–139;1–135;1–139 |
| 16439 | 1–505;1–75;1–361 |
| 16443 | 1–96;1–392;1–470;2–489 |
| 16444 | 1–367;1–492 |
| 16445 | 1–312;1–373;1–388;1–372 |
| 16446 | 1–173;1–468;1–485 |
| 16447 | 1–363;4–269 |
| 16448 | 1–482;4–489;5–478;5–380;5–458 |
| 16449 | 1–206;21–214;21–216;21–466;21–216;21–216;21–216;28–135 |
| 16451 | 1–93;1–91 |
| 16452 | 1–109;1–350;1–132;1–118;1–115;1–122;1–150;1–355;5–149 |
| 16453 | 1–109;1–118;1–115;1–175;1–122;1–151;1–172;1–133;5–150 |
| 16459 | 1–368;1–374 |
| 16460 | 1–416;1–486;1–477;33–293;33–476 |
| 16461 | 1–191;34–479;34–481;34–521;34–490;34–505;34–230 |
| 16462 | 1–495;1–349;4–59;4–296 |
| 16463 | 1–445;1–454 |
| 16466 | 1–489;1–457 |
| 16467 | 1–101;1–86 |
| 16470 | 1–392;1–364 |
| 16471 | 1–123;1–115;1–237;1–234;1–390;1–248;1–470;1–372;1–486;1–370;1–240;1–424;1–196;1–369;1–404;1–234;1–387;1–67;1–248;1–388;1–337;1–463;7–486;45–529 |
| 16473 | 1–462;1–443;1–442 |
| 16474 | 1–442;9–452 |
| 16477 | 1–138;1–160;1–113;1–103;1–111;1–128;4–70;4–159;4–157;4–161;4–146;4–118;4–115;4–159;4–110;4–113;4–159;4–158;4–127;4–114;4–114;4–114;4–157;4–158;4–108;4–114;4–135;4–160;4–150;4–160;4–136;4–118;4–135;4–160;4–150;4–160;4–158;4–162;4–109;4–158;4–158;4–146;4–101;4–104;4–113;4–158;4–135;4–128;4–114;4–158;4–106;4–87;4–159;4–158;4–116;4–114;4–158;4–113;4–103;4–158;4–158;4–157;4–136;4–138;4–131;4–158;4–140;4–135;4–161;4–108;4–158;4–109;4–161;4–115;4–140;4–160;4–142;4–140;4–159;4–118;4–161;4–137;4–151;4–145;4–124;4–160;4–135;4–118;4–157;4–118;4–158;4–117;4–161;4–70;4–158;4–128;4–109;4–157;4–158;4–104;4–125 |
| 16484 | 1–439;1–441 |
| 16488 | 1–514;1–496;1–479;13–523;31–105;31–251;31–541;31–498;31–495;31–535;31–193;37–306;37–539;37–342;37–342;37–342;37–349;38–560;38–326;61–543;61–523;66–564;66–526;66–502;66–520;66–560;113–564 |
| 16497 | 1–435;1–455;1–412;1–421;1–486;1–485;1–466;1–277;1–497;1–412;1–513;1–486;1–337;1–361;1–364;1–472;1–491;1–487;1–487;1–485;1–479;1–406;1–230;1–513;1–473;1–470;1–492;1–497;1–478;1–513;1–343;1–408 |
| 16498 | 1–418;13–513;39–492;39–501 |
| 16502 | 1–327;2–429 |
| 16503 | 1–272;1–272;1–269;1–269;108–247;108–270;108–200 |
| 16506 | 1–484;20–433 |
| 16507 | 1–555;7–466;7–555 |
| 16508 | 1–477;1–418;1–477;1–420 |
| 16511 | 1–379;1–473;1–461;1–433;1–490;1–491;1–509;1–406 |
| 16513 | 1–131;1–131 |
| 16517 | 1–403;1–105;1–403 |
| 16518 | 1–353;1–446;1–96 |
| 16519 | 1–305;1–382;1–153 |
| 16521 | 1–200;23–426;23–129 |
| 16523 | 1–187;1–193 |
| 16525 | 1–401;1–411;6–410;6–413 |
| 16526 | 1–101;1–537;4–482;40–482;137–192 |
| 16529 | 1–400;1–430;1–413;1–404;1–423;6–422;6–426 |
| 16534 | 1–121;1–125;1–159 |
| 16554 | 1–539;1–479;1–472 |
| 16560 | 1–472;1–358 |
| 16561 | 1–434;378–875;378–903 |
| 16563 | 1–438;3–121 |
| 16564 | 1–417;5–125 |
| 16565 | 1–222;1–222;46–222;46–222 |
| 16566 | 1–240;9–431 |
| 16567 | 1–112;1–112;1–112 |
| 16568 | 1–496;96–606 |
| 16571 | 1–484;1–289;1–382;1–452 |
| 16572 | 1–461;1–453 |
| 16573 | 1–222;1–166 |
| 16574 | 1–400;1–434;1–430;54–446;54–272;54–382;107–478;107–495 |
| 16576 | 1–244;1–355;1–389;1–396 |
| 16577 | 1–244;1–354;1–387;1–403 |
| 16579 | 1–501;1–508 |
| 16580 | 1–342;1–240 |
| 16582 | 1–178;1–380;1–378;1–380;3–381 |
| 16583 | 1–454;1–477;1–488;1–481 |
| 16585 | 1–447;1–432;1–443 |
| 16586 | 1–157;33–87;33–94 |
| 16589 | 1–493;1–486;1–499;1–475;1–224 |
| 16590 | 1–401;1–421 |

TABLE II-continued (Tiling path)

| Seq Id No. | Positions of biological 5'ESTs |
|---|---|
| 16591 | 1–515;1–424;1–484;1–497 |
| 16592 | 1–149;28–506 |
| 16593 | 1–119;1–187 |
| 16595 | 1–510;1–502;1–320 |
| 16596 | 1–422;1–197 |
| 16597 | 1–488;1–369;1–479;1–499;1–447;1–480;1–480;1–484;1–499;1–355;1–498;1–469;1–480;1–428;1–469;1–477;1–368;1–499;1–422;1–480;1–468;1–453;1–433;1–574;1–527;1–480;2–499 |
| 16598 | 1–336;1–328;1–331;1–355;1–355;1–355 |
| 16599 | 1–271;1–327;41–391;155–377;155–388;205–385;205–404 |
| 16600 | 1–396;1–442 |
| 16601 | 1–416;1–487 |
| 16602 | 1–275;1–257;1–202 |
| 16603 | 1–306;1–308;1–334;1–69;1–343;1–314;1–333;1–71;1–334;1–307;1–327;1–313;1–314 |
| 16604 | 1–450;1–468 |
| 16605 | 1–230;1–235;1–244;1–241;30–132 |
| 16612 | 1–440;1–402 |
| 16613 | 1–467;1–424 |
| 16614 | 1–523;4–258 |
| 16615 | 1–493;1–471;1–156;1–399;31–285 |
| 16616 | 1–434;1–423 |
| 16617 | 1–298;1–106 |
| 16618 | 1–458;1–424;1–432;1–431;1–458;1–444;1–458;1–469;1–445;1–193;1–435;1–461 |
| 16621 | 1–491;1–338 |
| 16622 | 1–222;1–422;1–425;1–431;1–418 |
| 16623 | 1–60;1–57 |
| 16624 | 1–211;1–458 |
| 16625 | 1–144;1–144;12–488;12–144 |
| 16626 | 1–473;1–454 |
| 16627 | 1–419;2–397;2–454;2–461;2–490;2–479;2–479;2–389;2–384;2–479 |
| 16628 | 1–323;1–325;1–334;1–62;1–334 |
| 16633 | 1–68;1–433;1–388 |
| 16634 | 1–132;1–182;1–182;1–107;1–166;1–182;1–169 |
| 16635 | 1–399;1–372 |
| 16637 | 1–413;1–443;1–280 |
| 16638 | 1–480;1–406 |
| 16639 | 1–367;1–367 |
| 16640 | 1–392;7–390 |
| 16641 | 1–452;1–482 |
| 16642 | 1–464;1–455 |
| 16643 | 1–75;1–123;1–130;1–135;1–134;1–135;1–91;1–125;3–90;55–126 |
| 16644 | 1–143;1–348;1–345;1–336;1–345 |
| 16645 | 1–414;1–281 |
| 16648 | 1–466;6–458 |
| 16651 | 1–415;1–434;1–516 |
| 16652 | 1–411;1–377;2–436 |
| 16653 | 1–369;1–408;1–124;1–517;1–464;1–473;1–517;1–517;1–498;1–448 |
| 16654 | 1–375;1–375;1–353;1–374;1–375 |
| 16655 | 1–367;1–354 |
| 16656 | 1–371;1–430 |
| 16657 | 1–430;373–900;373–757;373–761;373–879;374–823;375–901;376–912;377–849;377–865;378–761;378–906;388–803;388–868;388–784;388–803;391–761;394–748;396–901;396–793;396–702;396–885;401–906;401–901;401–911;401–902;401–722;401–750;401–891;401–761;401–750;401–914;401–828;401–794;401–762;401–901;404–902;404–911;404–892;404–856;404–761;406–761;407–912;407–891;407–674;409–910;409–895 |
| 16659 | 1–457;1–198;1–444 |
| 16660 | 1–445;1–387;1–463;1–445 |
| 16661 | 1–475;1–464;1–446;1–450 |
| 16662 | 1–452;1–438 |
| 16663 | 1–455;10–326;10–475 |
| 16665 | 1–439;1–504;4–119 |
| 16667 | 1–528;1–401;1–203;1–325;1–473;1–475 |
| 16668 | 1–469;1–472 |
| 16670 | 1–550;4–417;4–255;4–473;4–441;27–235 |
| 16671 | 7–427;7–489;49–497;49–259;49–308;49–478;49–517 |
| 16674 | 1–498;1–506;1–230;1–498;1–527;1–318;1–506;1–521;1–506;1–498;1–249 |
| 16675 | 1–183;6–395 |
| 16676 | 1–609;1–470 |
| 16679 | 1–115;1–216;1–210;1–216;1–216;1–204;1–216 |
| 16681 | 1–463;1–379;1–499;1–454;1–445;1–531;1–497 |
| 16682 | 1–430;1–571;1–439;1–469 |
| 16683 | 1–85;1–56;1–57;1–87;1–100;1–88;1–81;1–84;1–80;1–96;1–93;1–95;23–80 |
| 16684 | 1–85;1–56;1–85;1–81;1–85;1–57;1–80;1–84;23–244;23–239;23–235;23–264;23–244;23–243;23–244;23–243;23–253;23–243;23–357;23–361;23–256;23–247;23–80;23–243;23–243;23–260;23–256;23–254;23–360 |
| 16697 | 1–394;1–377 |
| 16698 | 1–447;1–472;1–370;1–450 |
| 16699 | 1–498;1–297 |
| 16700 | 1–482;1–476;1–513;1–432;1–449;1–478;1–457 |
| 16701 | 1–155;1–155 |
| 16702 | 1–486;1–446;1–464;1–409;1–477;1–491;1–498;1–452;1–467;1–487;1–260 |
| 16703 | 1–241;1–211 |
| 16704 | 1–418;1–472;1–481;1–466 |
| 16709 | 1–269;1–396;1–417;1–212;1–484;1–408;1–362;1–448;1–470;1–448;1–459;1–484;3–453;3–472;39–468 |
| 16715 | 1–378;1–443;1–385;2–146 |
| 16716 | 1–451;1–395;1–496 |
| 16717 | 1–159;1–176 |
| 16718 | 1–372;1–486;1–451;1–527;1–478;1–497;1–475;1–467 |
| 16722 | 1–214;1–214;1–214;1–214;1–211;1–214;1–214;1–211;1–214;1–214;1–214;1–214;1–214;1–214 |
| 16723 | 1–476;12–485 |
| 16726 | 1–482;107–569;107–569;107–575;107–581;107–562 |
| 16728 | 1–492;1–480;1–480;1–479 |
| 16737 | 1–457;1–527 |
| 16738 | 1–128;1–128;1–128;1–117;1–117;1–117;1–117;1–118;1–117;1–118;1–118;1–128;1–117;1–118;1–118;1–118;1–117;1–118;1–128;1–118;1–128;1–128;1–118;1–128;1–118;1–117;1–118;1–118;1–117;1–117;1–117;1–128;1–121;1–118;1–118 |
| 16739 | 1–116;1–116 |
| 16742 | 1–527;1–558;1–565;1–488 |
| 16743 | 1–339;1–342 |
| 16744 | 1–432;1–282 |
| 16745 | 1–536;1–536 |
| 16746 | 1–87;1–87;1–89;1–89;1–84;1–89;1–84;1–87;1–89;1–87;1–89;54–498 |
| 16747 | 1–428;1–461 |
| 16748 | 1–473;1–467;1–474 |
| 16749 | 1–484;1–503;1–498;1–480;1–477 |
| 16750 | 1–293;41–386;41–265;41–438;41–530;41–402;41–468;41–400 |
| 16751 | 1–65;19–462;31–194;308–794 |
| 16752 | 1–65;9–337;19–394;31–197 |
| 16753 | 1–490;36–475 |
| 16754 | 1–488;1–440;33–367;33–139 |
| 16756 | 1–245;1–245;1–244 |

TABLE II-continued

(Tiling path)

| Seq Id No. | Positions of biological 5'ESTs |
|---|---|
| 16757 | 1–248;1–203 |
| 16758 | 1–217;1–206;1–206;1–120;1–216;1–216;1–217;1–222;1–222;1–216;1–216;1–217;1–217;1–203;1–217 |
| 16761 | 1–324;1–525;1–511 |
| 16764 | 1–374;1–498;1–418;1–374;1–442;1–442;1–448;1–314 |
| 16765 | 1–330;1–322;1–325;1–300;1–322;1–330 |
| 16766 | 1–121;22–117;26–233;26–112 |
| 16769 | 1–460;1–464 |
| 16770 | 1–346;1–342;1–338;1–358 |
| 16771 | 1–412;1–412 |
| 16772 | 1–461;1–463;1–468;1–505;1–492;1–478;1–439;1–217;1–542;1–494;1–480;1–371;1–232;1–489;1–464;1–397;1–218;1–463;1–483 |
| 16773 | 1–215;1–398;35–418 |
| 16774 | 1–251;1–256;1–256 |
| 16775 | 1–358;1–355;1–347;1–356;2–354;2–354;3–342;3–234;3–190 |
| 16776 | 1–112;1–113;1–113;1–132;1–128;3–127;3–100;3–114;3–113;3–128;3–128;3–113;3–117;3–130;3–128;4–111;4–130;5–108;5–103;5–130;5–95;5–106;5–130;5–103;5–128;5–127;5–130;5–71;5–130;5–121;5–131;5–102;5–126;5–126;5–107;5–126;5–130;5–126;5–130;5–94;5–129 |
| 16777 | 1–233;1–189;2–253 |
| 16787 | 1–118;1–196;1–104;1–116;1–213 |
| 16790 | 1–540;1–475;16–421;16–651;16–501;16–531;27–436;27–527;27–529;27–497;28–296;28–543;28–266;29–613;29–605;30–541;30–624;30–518;30–347;30–453;30–456;30–586;30–597;30–528;30–541;30–496;30–493;30–453;30–490;30–450;30–496;30–528;30–531;30–665;30–405;30–501;30–576;30–493;30–493;30–540;30–493;30–436;30–617;30–493;30–552;30–682;30–676;30–514;30–539;30–272;30–639;30–551;30–456;30–548;30–403;30–517;30–436;30–423;30–546;30–582;30–490;30–531;30–543;30–439;30–439;30–476;30–496;30–476;30–542;30–490;30–476;30–453;30–519;30–549;30–493;30–439;30–540;30–501;30–423;30–517;30–543;30–489;30–345;30–476;30–540;30–424;30–540;30–489;30–484;30–540;30–531;30–493;30–530;30–456;30–517;30–531;30–665;30–517;30–567;30–548;30–541;30–552;30–546;30–595;30–453;30–540;30–493;30–529;30–356;30–421;30–422;30–543;30–527;30–490;30–423;30–527;30–485;30–613;30–488;30–516;30–528;30–394;30–496;30–435;30–543;30–575;30–436;30–202;30–560;30–665;30–487;30–598;30–433;30–493;30–563;30–519;30–496;30–312;30–539;30–496;30–624;30–548;30–519;30–424;30–439;30–439;30–4 |
| 16794 | 1–470;1–482 |
| 16795 | 1–117;31–429 |
| 16796 | 23–334;23–406;23–332;71–423 |
| 16798 | 1–108;1–80 |
| 16808 | 1–447;1–425;1–428 |
| 16809 | 1–430;1–437;1–457;1–424 |
| 16810 | 1–243;1–262;1–400;1–390 |
| 16811 | 1–463;1–528 |
| 16815 | 1–453;110–574;110–562;110–547;110–574 |
| 16817 | 1–233;1–395;1–361;1–455;1–432 |
| 16818 | 1–118;1–290;1–265 |
| 16820 | 1–311;1–524;1–495;1–340 |
| 16821 | 1–559;1–440 |
| 16822 | 1–483;1–492;1–500;1–499;1–504 |
| 16823 | 1–531;1–166 |
| 16824 | 1–194;1–183;19–93;19–107;70–371;70–154;71–195;71–160 |
| 16826 | 1–348;1–448 |
| 16828 | 1–558;1–486 |
| 16830 | 1–450;1–293 |
| 16838 | 1–268;1–263;1–256 |
| 16839 | 1–415;1–463;1–526;1–339;1–485;1–344;1–282;1–412;1–344 |
| 16840 | 1–515;1–386;1–474 |
| 16841 | 1–334;1–89;1–343 |
| 16844 | 1–459;1–453 |
| 16845 | 1–372;1–93;1–501;2–410;11–432 |
| 16846 | 1–471;1–436;1–349 |
| 16847 | 1–197;1–194;1–174;1–174 |
| 16848 | 1–432;1–130 |
| 16849 | 1–447;1–255;1–475;1–493;1–495 |
| 16850 | 1–429;1–270 |
| 16851 | 1–427;297–843 |
| 16853 | 1–175;10–92;10–107;10–70;10–72;10–72;10–126;10–155;10–87 |
| 16855 | 1–517;1–310 |
| 16856 | 1–275;1–250 |
| 16857 | 1–478;1–476 |
| 16859 | 1–418;1–418;1–392;1–436;1–237;1–425 |
| 16860 | 1–419;1–408;1–373 |
| 16861 | 1–445;1–416 |
| 16863 | 1–411;1–430 |
| 16864 | 1–436;35–391 |
| 16865 | 1–375;1–111;1–386;1–390;1–399;1–81;1–246;1–392;1–400;1–400;1–381;1–382;1–381;1–382;1–399;1–381;1–399;1–395;1–391;1–383;1–382;1–394;1–379;1–399;1–381;1–391;1–400;1–147;1–392;1–386;1–83;1–386;1–400;1–389;1–386;1–400;1–313;1–389 |
| 16866 | 1–291;1–286;1–302 |
| 16867 | 1–156;1–156;1–156;1–156;1–155;1–156;1–155;1–156;1–156;1–155;1–156;1–156;1–156;1–155;1–156;1–155;1–156;1–156;1–155;1–156;1–155;1–156;1–144;1–156;1–65;1–155;1–155;1–156;1–155;1–156;1–155;1–156;1–156;1–156;1–155;1–156;1–156;1–155;1–155 |
| 16868 | 1–122;1–112 |
| 16874 | 1–461;1–281 |
| 16875 | 1–237;1–237 |
| 16876 | 1–50;1–474 |
| 16877 | 1–454;1–304 |
| 16878 | 1–471;1–449;1–476;1–562;1–499;1–563;1–325;1–500;1–551;1–583;1–465;1–468;1–486;1–485;1–552;1–551;1–56;1–457;1–471;1–486;1–445;1–480;1–358;1–230;1–479;1–442;1–365;1–495;1–497;1–333;1–486;1–421;1–442;1–491;1–496;1–562;1–353;1–175;1–496;1–453;1–440;1–563;1–450;1–488;1–450;1–465;1–434;1–443;1–77;1–378;1–571;1–563;1–419;1–188;1–469;1–484;1–457;1–478;1–487;1–190;1–496;2–403 |
| 16880 | 1–426;17–370;56–541;56–488;56–461;56–347;56–172;56–548;56–434 |
| 16881 | 1–337;36–602 |
| 16882 | 1–424;1–371;1–383;1–277 |
| 16883 | 1–313;1–299 |
| 16884 | 1–439;1–216;1–474;1–474;1–482;1–346 |
| 16885 | 1–514;1–432;1–474 |
| 16886 | 1–470;1–434;1–295 |
| 16887 | 1–543;1–524;1–508;1–356;1–429;1–582;1–584;1–583;1–561;1–602;1–557;1–528;1–582;1–582;1–585;1–525;1–582;1–485;1–582;1–583;1–582 |
| 16888 | 1–169;4–127 |
| 16889 | 1–342;28–333 |
| 16890 | 1–370;2–366;5–380;18–425;24–431 |

TABLE II-continued

(Tiling path)

| Seq Id No. | Positions of biological 5'ESTs |
|---|---|
| 16891 | 1–138;1–136;1–157;1–150 |
| 16892 | 1–405;1–405 |
| 16894 | 1–453;10–513 |
| 16895 | 1–438;1–496 |
| 16896 | 1–466;1–472;1–357;1–561 |
| 16898 | 1–337;1–373;1–540;1–311;1–337 |
| 16899 | 1–473;1–426;1–339;1–407;1–465;2–453 |
| 16900 | 1–426;256–681 |
| 16901 | 1–368;1–337;51–338;51–338;51–338 |
| 16902 | 1–524;1–306;1–576 |
| 16904 | 1–177;1–198;1–199;1–456 |
| 16905 | 1–480;1–448;1–496;1–234;1–122;1–462;1–333;1–491;1–513;1–281;1–527;1–480;1–490;1–496;1–442;1–480;1–481;1–514;1–493;1–512;1–526;1–491;1–501;1–501;1–478;1–480;1–489;1–492;1–464;1–511;1–487;1–445;1–509;1–402;1–482;1–490;1–509;1–513;1–522;1–253;1–492;1–486;1–496;1–493;1–480;1–514;1–452;1–413;1–520 |
| 16906 | 1–431;1–135 |
| 16908 | 1–432;1–422;1–449 |
| 16909 | 1–334;1–349;1–348 |
| 16910 | 1–216;1–216;1–216;9–98 |
| 16911 | 1–350;1–435 |
| 16912 | 1–472;1–427 |
| 16913 | 1–422;1–439 |
| 16914 | 1–385;1–449 |
| 16915 | 1–382;1–305;1–510;1–476 |
| 16916 | 1–192;1–193;1–193;1–193;1–180;1–193 |
| 16917 | 1–487;1–494;1–503;1–471;1–420;1–435;1–373;1–399;1–119;1–445;1–391 |
| 16919 | 1–505;1–457 |
| 16920 | 1–478;1–458 |
| 16924 | 1–152;1–154;1–154 |
| 16925 | 1–175;1;215;1–208;1–166;1–144;1–215;1–178;1–212;1–219;2–217;3–104 |
| 16947 | 1–477;1–528;1–528 |
| 16948 | 1–425;9–308 |
| 16959 | 1–403;1–370;1–521;1–372;1–458;1–262;1–461;1–371;1–448;1–410;1–492;1–372;1–405;1–448;1–429;1–326;1–200;1–403;7–399;16–428;16–477;16–279;16–469;16–526 |
| 17000 | 1–372;1–349;1–361;1–360 |
| 17011 | 1–431;1–335;1–474;1–431 |
| 17032 | 1–491;1–57 |
| 17043 | 1–487;1–470 |
| 17065 | 1–207;1–207;1–219;1–119;1–215 |
| 17076 | 1–429;1–470;1–487 |
| 17084 | 1–395;1–418 |
| 17085 | 1–248;1–248;1–249;1–248 |
| 17086 | 1–463;1–234;1–513;1–502 |
| 17087 | 1–137;1–223 |
| 17089 | 1–487;1–460 |
| 17091 | 1–214;1–163;1–132;6–130;25–133;25–189 |
| 17092 | 1–263;1–291 |
| 17093 | 1–508;1–472 |
| 17094 | 1–243;1–150;1–414 |
| 17098 | 1–72;1–72;1–72;1–68;1–72;1–72 |
| 17099 | 1–380;1–449 |
| 17100 | 1–466;308–710;312–381 |
| 17101 | 1–414;1–482;1–482;1–408;1–454;1–402;1–434;1–442;1–213;1–482;1–419 |
| 17102 | 1–466;1–477;1–498;1–498;1–534;1–471;1–428 |
| 17105 | 1–455;1–542 |
| 17106 | 1–77;1–92 |
| 17107 | 1–477;1–287 |
| 17108 | 1–411;1–275 |
| 17110 | 1–139;1–138;1–139;1–138 |
| 17112 | 1–449;1–399 |
| 17113 | 1–510;1–455 |
| 17117 | 1–91;1–91;1–91;1–91;1–91;1–91;1–91;1–91;1–91 |
| 17118 | 1–310;1–500;1–89;1–327;1–442;1–496;1–488;1–432;1–507 |
| 17119 | 1–405;3–426 |
| 17121 | 1–471;1–469 |
| 17122 | 1–448;1–452 |
| 17123 | 1–295;1–302;1–301;1–271;1–304;1–295;1–306;1–306;1–310;1–305;1–295;1–271;1–312 |
| 17125 | 1–430;1–545;1–480;1–562;1–462 |
| 17127 | 1–505;1–492;1–465 |
| 17128 | 1–379;1–338 |
| 17129 | 1–399;1–407;1–414;1–406;1–412;1–415;1–414 |
| 17130 | 1–547;1–397;1–298;1–439 |
| 17131 | 1–455;1–470;234–414 |
| 17132 | 1–487;46–520 |
| 17133 | 1–369;1–351;1–351;1–369;1–371;1–351;1–344;1–368;1–369;1–368;1–345 |
| 17134 | 1–439;1–472;1–510 |
| 17135 | 1–476;21–192 |
| 17137 | 1–447;1–434;1–441 |
| 17138 | 1–336;1–346 |
| 17139 | 1–294;1–457;1–459;1–487;1–410;1–469;1–503 |
| 17141 | 1–90;1–195;1–250 |
| 17143 | 1–168;1–168;1–167;1–168;1–169;1–168;1–126;1–168;1–127;1–168;1–168;1–143;1–168;1–127;1–168;1–119;1–137;1–167;1–128;1–128;1–167;1–168;1–168;1–168;1–168;1–128;1–116;1–168;1–113;1–168;1–168;1–126;1–127;1–152;1–168;1–128;1–168;1–116;1–127;1–168;1–168;1–150;1–168;1–168;1–168;1–138;1–136;1–78;1–168;1–121;1–86;1–126;1–122;1–168;1–131;1–150;1–120;1–168;1–122;1–168;1–164;1–132;1–117;1–126;1–163;1–70;2–153 |
| 17150 | 1–376;1–505;1–364;1–462 |
| 17152 | 1–107;1–107;1–107;1–107;1–107;1–107;1–107;1–107;1–107;1–114;1–107;1–107;1–107;1–107;1–107 |
| 17153 | 1–141;1–269 |
| 17154 | 1–430;1–498;1–400;1–433;39–201 |
| 17155 | 1–449;1–199 |
| 17156 | 1–342;1–356;1–101 |
| 17157 | 1–515;1–479;1–486 |
| 17158 | 1–500;1–575 |
| 17161 | 1–417;2–192 |
| 17162 | 1–383;1–195;1–410;1–416;1–384 |
| 17163 | 1–520;1–378;1–476 |
| 17164 | 1–376;1–372;1–463;1–501 |
| 17166 | 1–297;1–460;1–397;1–422;1–457;1–341;1–440;1–179;1–354;1–477;1–456;1–449;1–103;1–364;1–458;1–462;1–326;1–456;1–457;1–314;1–352;1–362 |
| 17167 | 1–297;1–625;1–397;1–422;1–487;1–457;1–495;1–551;1–440;1–341;1–449;1–478;1–484;1–364;1–564;1–507;1–314;1–352;1–460;1–362;1–477;1–550;1–103;1–571;1–354;1–179;1–456;1–449;1–477;1–458;1–565;1–551;1–462;1–457;1–326;1–456;4–551 |
| 17170 | 1–453;1–438;1–472;7–418;7–474;7–479;11–476;14–426;14–410;17–351;25–222;25–337;25–349;25–498;25–480;25–258;30–480;30–506;30–465 |
| 17171 | 1–350;4–483;22–219;22–482;22–490;22–564;22–255;24–460;53–515 |
| 17174 | 1–347;1–105 |
| 17175 | 1–477;3–437 |
| 17176 | 1–431;356–844;356–853;356–845;356–836;356–745;356–808;356–814;356–752 |
| 17177 | 1–498;1–480 |
| 17178 | 1–91;1–103;1–132;1–142;1–142;1–142;1–140;1–132;1–132;1–123;1–132;1–132;1– |

TABLE II-continued

(Tiling path)

| Seq Id No. | Positions of biological 5'ESTs |
|---|---|
| | 132;1–132;1–142;1–50;1–122;1–132;1–137;1–132;1–142;1–131;1–140;1–131;1–133;1–142;1–122;1–130;1–142;1–132;1–132;1–132;1–122;1–142;1–132;1–123;1–123;1–141;1–142;1–142;1–135;1–138;1–131;1–132;1–106;1–132;1–132;1–132;1–95;1–138;1–142;1–132;1–132;1–131;1–108 |
| 17179 | 1–571;1–566 |
| 17180 | 1–165;1–165 |
| 17181 | 1–372;1–433 |
| 17189 | 1–491;50–453 |
| 17190 | 1–375;66–290 |
| 17191 | 1–387;1–450 |
| 17192 | 1–527;1–348;1–527 |
| 17193 | 1–121;58–416;58–443;58–426;58–424;58–302;58–415;58–431;58–362 |
| 17194 | 1–70;1–134;1–457;1–491;1–232;1–424;1–519;1–431;1–424 |
| 17195 | 1–319;1–319;1–319;1–308;1–305;1–302;1–308;1–304 |
| 17196 | 1–348;1–315 |
| 17197 | 1–451;20–504;40–223;40–454;40–153;42–521;42–300;42–521;42–475;42–397;45–538;45–151;45–374;45–475;45–550;45–194;45–531;45–414;45–526;46–162;46–164;47–565;47–287;54–565 |
| 17198 | 1–54;1–51;1–51;1–54;1–51;1–51;1–54;1–51;1–51;1–51;1–51;1–51;1–54;1–54;1–54;1–54;1–51;1–54;1–51;1–51;1–54;1–54;1–54;1–51;1–54;1–51;1–54;1–54;1–54;1–51;1–54;1–51;1–54;1–54;1–51;1–51;1–51;1–51 |
| 17201 | 1–261;1–203;1–401;1–377;1–399;1–401;1–401;1–368;1–387;1–134;1–398;1–373;1–260;1–262;1–252;1–399;1–387;1–255;1–225 |
| 17203 | 1–331;1–414 |
| 17204 | 1–384;1–398;1–386 |
| 17205 | 1–369;1–133;1–127;1–70;2–119 |
| 17206 | 1–391;1–438;1–424;1–465;1–268;1–278;1–70;1–133;1–422;1–127;1–393;1–444;1–296;1–395;2–119 |
| 17207 | 1–580;1–554 |
| 17208 | 1–450;2–79 |
| 17211 | 1–441;1–398;1–462 |
| 17212 | 1–290;1–447 |
| 17215 | 1–393;1–404 |
| 17216 | 1–80;1–439 |
| 17217 | 1–432;1–182 |
| 17218 | 1–221;1–138;1–59 |
| 17219 | 1–263;1–85;1–390;1–381;1–380;1–390;1–400;1–388 |
| 17220 | 1–288;1–493;1–535;1–482;1–138;1–368;1–505;1–480;1–509 |
| 17221 | 1–369;34–546;35–565;35–507;35–486;35–501 |
| 17222 | 1–369;34–546;35–507;35–486;35–501;35–571 |
| 17224 | 1–436;1–447;1–406;1–425;1–479;1–473;1–436;1–392;1–456;1–470;1–477;1–473;1–406;1–472;1–404;1–442;1–450;1–477;1–410;1–473;1–477;1–364;1–406;1–477;1–477;1–475;1–461;1–442 |
| 17225 | 1–249;1–285 |
| 17226 | 1–412;1–462;1–413 |
| 17227 | 1–126;1–126;1–126;1–126;1–126;1–126;1–126;1–126;1–126;1–71;1–126;1–126;1–126;1–126;1–107;1–116;1–126;1–100;3–126 |
| 17228 | 1–222;1–377 |
| 17230 | 1–453;1–429 |
| 17231 | 1–233;1–247;1–248;1–248;1–248;1–241;1–246;1–247;1–246;1–210;1–246;1–202;1–247;1–247;1–222;1–229;1–242;1–244 |
| 17236 | 1–280;1–286 |
| 17237 | 1–352;1–348;1–463;1–460;96–158 |
| 17238 | 1–414;7–388;7–415;7–62;7–409 |
| 17239 | 1–276;1–272 |
| 17240 | 1–172;1–324 |
| 17241 | 1–523;1–357 |
| 17242 | 1–257;1–329 |
| 17243 | 1–468;1–510 |
| 17244 | 1–468;1–466 |
| 17245 | 1–249;1–424;1–343;1–407;3–173 |
| 17247 | 1–311;1–311 |
| 17248 | 1–229;1–384 |
| 17249 | 1–287;1–193;1–457 |
| 17250 | 1–291;1–125 |
| 17251 | 1–258;1–274;1–274 |
| 17253 | 1–409;1–559;1–519;1–457 |
| 17254 | 1–331;16–433 |
| 17255 | 1–333;1–321;1–335 |
| 17256 | 1–490;283–722 |
| 17257 | 1–261;4–276;29–447;29–200 |
| 17258 | 1–479;5–263;6–278;31–202 |
| 17259 | 1–350;1–351 |
| 17260 | 1–382;1–480 |
| 17262 | 1–536;1–235 |
| 17263 | 1–464;1–466;1–310;29–260 |
| 17264 | 1–383;1–349;1–454;23–204;27–326 |
| 17265 | 1–479;1–489 |
| 17266 | 1–329;1–461;1–463;1–395;1–462;1–454;1–457;1–457;1–447;1–434;1–468;1–457;1–451;1–408;1–450;1–444;1–442;1–452;1–424;1–457;1–169;1–453;1–450;1–447;1–451;1–451;1–443;1–462;1–472;1–365;1–452 |
| 17267 | 1–354;1–402;1–458;1–439;1–544;1–444;1–459;1–102;1–444 |
| 17268 | 1–520;1–508;11–453;40–509;40–507;40–509;40–527;40–486;40–512;40–283;40–442;40–512;40–528;40–528;40–455;40–456;40–528;40–470;40–498;40–442;40–363;40–528;40–487;40–497;40–402;40–530;40–528;40–498;40–425;40–478;40–472;40–478;40–512;40–555;40–498;40–452;40–523;40–261;40–527;40–528;40–475;40–443;40–439;40–403;40–134;40–506;40–506;40–528;40–438;40–528;40–509;40–512;40–496;40–385;40–300;40–509;40–99;44–477 |
| 17269 | 1–530;1–518;11–462;40–546;40–546;40–508;40–434;40–519;40–517;40–581;40–519;40–535;40–549;40–546;40–549;40–545;40–496;40–451;40–571;40–568;40–522;40–280;40–568;40–549;40–580;40–549;40–522;40–567;40–544;40–567;40–570;40–464;40–465;40–544;40–535;40–568;40–569;40–580;40–546;40–568;40–508;40–567;40–451;40–545;40–549;40–559;40–569;40–497;40–488;40–568;40–412;40–507;40–549;40–535;40–535;40–568;40–581;40–571;40–567;40–582;40–508;40–535;40–581;40–562;40–544;40–584;40–563;40–575;40–413;40–568;40–586;40–567;40–482;40–488;40–575;40–581;40–581;40–522;40–508;40–581;40–584;40–461;40–568;40–533;40–568;40–568;40–262;40–569;40–584;40–535;40–535;40–583;40–549;40–572;40–485;40–565;40–568;40–452;40–448;40–557;40–516;40–570;40–522;40–516;40–568;40–543;40–447;40–563;40–549;40–535;40–547;40–581;40–519;40–134;40–545;40–568;40–568;40–579;40–302;40–396;40–506;40–549;40–519;40–99;40–549;43–581;44–487 |
| 17270 | 1–219;1–59;1–94;14–456;14–451;33–464 |
| 17274 | 1–321;1–283 |

TABLE II-continued

(Tiling path)

| Seq Id No. | Positions of biological 5'ESTs |
|---|---|
| 17275 | 1–473;1–413 |
| 17278 | 1–486;1–376;1–135 |
| 17279 | 1–421;1–340 |
| 17280 | 1–500;1–475;16–524;16–447;16–180;16–474;16–505 |
| 17281 | 1–260;1–267;1–448 |
| 17282 | 1–486;1–475 |
| 17283 | 1–468;39–439 |
| 17284 | 1–492;1–394;1–474;1–499 |
| 17287 | 1–369;1–154 |
| 17288 | 1–510;1–483 |
| 17289 | 1–501;1–436;1–493 |
| 17290 | 1–559;1–455 |
| 17293 | 1–446;1–399;1–471 |
| 17298 | 1–422;1–488;1–471 |
| 17300 | 1–147;3–139;3–126;3–372;3–152;3–151;3–139;3–75;3–139;3–277;3–85;5–125;5–139;5–139;5–115;5–152;5–139;6–139;6–139;6–132;6–152 |
| 17301 | 1–83;1–73;1–123;3–122;3–130;3–112;4–92 |
| 17302 | 1–204;1–197 |
| 17304 | 1–307;1–348 |
| 17305 | 1–456;1–278 |
| 17306 | 1–411;21–442 |
| 17307 | 1–62;1–499 |
| 17308 | 1–56;1–85;1–82;1–79;1–80;1–73;1–61;1–87;1–55;1–137;1–78;1–81;1–82 |
| 17309 | 1–332;11–478 |
| 17314 | 1–471;1–443;1–460 |
| 17315 | 1–274;38–412 |
| 17316 | 1–520;1–457;1–486;1–466;1–457;1–479;1–503;1–169;1–491;1–425;1–435;3–474 |
| 17317 | 1–453;1–429;1–317;1–492;1–469;1–461 |
| 17318 | 1–83;1–75;1–83;1–83;1–83;1–83;1–83;1–83;1–83;1–83;1–84;1–74;1–84;1–83;1–83;1–83;1–83;1–82;1–50;1–74 |
| 17319 | 1–514;1–503;1–525;1–513 |
| 17320 | 1–250;1–250 |
| 17321 | 1–490;1–83 |
| 17322 | 1–402;4–86 |
| 17324 | 1–498;1–454 |
| 17325 | 1–424;1–293;1–492;1–517 |
| 17326 | 1–396;1–312 |
| 17327 | 1–453;1–542 |
| 17328 | 1–595;1–353;1–483 |
| 17329 | 1–541;1–149;1–467 |
| 17330 | 1–368;1–104;1–191;1–160;1–518;1–445;1–489;1–345;1–427;1–333;1–406;1–489;1–400;1–468;2–190;2–205;316–751;330–757;330–427;330–464;330–736;330–749;330–544;330–763;330–728;330–553;330–733;330–677;330–736;330–794;451–902;462–677;462–812;554–671;592–1053;673–1041;673–1040;673–999;880–1349;1241–1549 |
| 17331 | 1–156;3–346 |
| 17332 | 1–492;1–440;1–433 |
| 17333 | 1–447;1–420;1–425;4–431 |
| 17334 | 1–469;1–499 |
| 17337 | 1–447;1–390;1–447 |
| 17338 | 1–169;1–169 |
| 17339 | 1–481;13–197 |
| 17340 | 1–406;1–476;1–536;1–477;1–390;1–493;2–250;6–445;42–500;42–218;42–494;42–278;42–459;42–365 |
| 17341 | 1–365;1–443 |
| 17342 | 1–392;33–316 |
| 17343 | 1–299;1–299;1–299;1–299;1–175;1–299;1–299;1–299;1–299;1–299;1–301;1–299;1–301;1–299;1–301;1–301;1–121 |
| 17345 | 1–380;1–435 |
| 17347 | 1–469;15–441;15–470 |
| 17348 | 1–478;1–488;1–480;235–672 |
| 17349 | 1–501;1–483;1–480;48–503;48–512;56–450;72–543 |
| 17350 | 1–97;1–230;1–109;1–167;1–111;1–214;1–198;1–230;1–257;1–231;1–231;1–221;1–231;1–230;1–215;1–231;1–257;1–231;1–222;1–230;1–92;1–231;1–138;1–228;1–231;1–231;1–123;1–222;1–257;1–257;1–230;1–231;1–219;1–121;1–257;1–122 |
| 17351 | 1–97;1–246;1–246;1–246;1–246;1–245;1–246;1–246;1–230;1–167;1–109;1–246;1–246;1–246;1–111;1–198;1–214;1–230;1–246;1–246;1–246;1–246;1–246;1–231;1–246;1–246;1–246;1–246;1–246;1–232;1–246;1–246;1–245;1–246;1–246;1–245;1–246;1–221;1–245;1–232;1–246;1–246;1–230;1–243;1–1–238;1–245;1–215;1–234;1–244;1–246;1–247;1–232;1–247;1–233;1–246;1–222;1–230;1–92;1–232;1–246;1–246;1–138;1–245;1–246;1–246;1–228;1–246;1–247;1–232;1–231;1–246;1–123;1–246;1–2261–246;1–222;1–246;1–248;1–246;1–246;1–246;1–246;1–239;1–230;1–233;1–246;1–246;1–245;1–246;1–238;1–245;1–246;1–219;1–246;1–121;1–246;1–246;1–246;1–122 |
| 17352 | 1–445;1–444;1–476;1–447 |
| 17353 | 1–414;4–319 |
| 17354 | 1–479;1–502;1–500;1–473;1–499;1–286 |
| 17355 | 1–402;1–345 |
| 17356 | 1–445;1–452;1–486;1–463;1–289;1–412;1–411;1–432;1–506 |
| 17357 | 1–291;1–290;1–291;1–127;1–250;1–291;1–291;1–291;1–290;1–291;1–290;1–126;1–290;1–291;1–291 |
| 17358 | 1–477;1–503 |
| 17359 | 1–482;1–357;1–389;1–424;1–384 |
| 17360 | 1–482;1–443;1–483 |
| 17361 | 1–423;1–468 |
| 17363 | 1–501;1–408;1–535 |
| 17364 | 1–298;2–393;2–408;2–416 |
| 17365 | 1–471;1–465;1–446 |
| 17367 | 1–408;1–174;1–437 |
| 17368 | 1–460;1–456;5–265 |
| 17369 | 1–492;158–591;319–573;319–591;319–578 |
| 17370 | 1–418;1–436;1–443;1–395;1–261 |
| 17373 | 1–483;1–502 |
| 17374 | 1–472;1–479 |
| 17375 | 1–358;1–500;1–500;1–500;1–501;1–480 |
| 17376 | 1–415;1–434;1–359 |
| 17377 | 1–412;1–441 |
| 17381 | 1–454;1–450;1–390;1–445;1–304;1–347;1–390;1–447;1–441;1–450;5–240 |
| 17383 | 1–384;1–411;1–475;1–472;1–346;1–472;1–472;1–472;1–201;1–412;1–472;1–472;1–472;1–470;1–472;1–421;1–460;1–472;1–411;1–472;1–434;1–463;1–271;1–245;1–472;1–472;1–418;1–409;1–458;1–422;1–472;1–472;1–472;1–472;1–481;1–472;1–410;1–391 |
| 17386 | 1–481;1–451 |
| 17388 | 1–278;1–318;1–312;1–312;1–312;1–312 |
| 17389 | 1–304;1–304;1–287;1–304;1–200;1–304 |
| 17390 | 1–232;1–219 |
| 17391 | 1–451;1–462;1–456;1–422;1–463;16–458;27–464;31–450;31–182;31–437;31–450;31–450;31–435;33–464;33–453;33–334;33–456;33–412;33–455;34–334;34–451;38–459;38–464;40–213;40–450;40–466;40–462;40–455;40–450;40–432;40–450;40–453;40–445;40–454;40–458;40–256;40–434;40–297;40–438;40–457;40–450;40–448;40–448;40–450;40–449;40–117;40–450;40–311;40–450;40–432;40–457;40–448;40–450;40–450;40–438;40– |

TABLE II-continued (Tiling path)

| Seq Id No. | Positions of biological 5'ESTs |
|---|---|
|  | 465;40–289;40–449;40–453;40–424;40–453;40–453;40–453;40–425;40–453;40–453;40–457;40–450;40–467;40–453;40–449;40–425;40–449;40–439;40–431;40–437;40–444;40–421;40–457;40–465;40–459;40–414;40–429;41–450;43–299;43–431;43–436;43–450;43–431;43–450;43–450;43–450 |
| 17392 | 1–78;1–297;1–300;1–293 |
| 17394 | 1–579;1–453 |
| 17396 | 1–464;1–375;1–371 |
| 17397 | 1–201;1–181 |
| 17398 | 1–453;1–383;1–457 |
| 17399 | 1–471;1–478;1–509;1–489;1–470;1–438;1–489;1–478;1–500;1–408;1–522;1–500;1–463;1–493;1–452;1–451;1–426;1–530;1–194;1–208;1–511 |
| 17400 | 1–456;1–273;1–493;1–459 |
| 17401 | 1–353;1–560;1–459;1–483;1–439 |
| 17402 | 1–462;1–491;28–439;28–480;28–270;30–381;446–741 |
| 17403 | 1–404;1–270;1–412 |
| 17404 | 1–272;1–285;1–285;1–240;1–281 |
| 17405 | 1–261;1–286;1–398 |
| 17407 | 1–117;1–174;1–173;1–173;1–173;1–173 |
| 17408 | 1–227;1–440;1–432;1–355 |
| 17409 | 1–160;1–547 |
| 17410 | 1–237;26–473 |
| 17411 | 1–452;32–430;32–388 |
| 17412 | 1–237;1–238;1–238;1–234;1–238;1–237;1–227;1–224;1–235;1–238;1–240;1–228;1–240;1–194;1–238;1–238;1–228;1–238;1–239;1–238;1–238;1–234;1–238;1–238;1–221;1–89;1–238;1–238;1–224;1–238;1–201;1–122;1–239;1–236;1–104;1–237;1–238;1–238;1–223;1–232;1–238;1–237;1–237;1–229;1–237;1–238;1–240;1–231;1–238;1–238;1–237;1–237;1–238;1–240;1–238;1–202;1–226;1–238;1–233 |
| 17424 | 1–504;1–481;1–381 |
| 17425 | 1–496;1–578 |
| 17426 | 1–432;1–343 |
| 17427 | 1–380;5–399 |
| 17428 | 1–481;1–340;1–496 |
| 17429 | 1–137;17–249;51–198;51–160 |
| 17430 | 1–220;1–337;1–145 |
| 17431 | 1–390;1–389;1–391 |
| 17432 | 1–255;1–427;1–307 |
| 17433 | 1–391;1–385;1–390 |
| 17434 | 1–53;1–51;1–82 |
| 17435 | 1–424;1–448 |
| 17437 | 1–497;20–151;20–431 |
| 17438 | 1–479;1–507 |
| 17440 | 1–292;1–214;1–383 |
| 17441 | 1–404;11–402 |
| 17442 | 29–128;29–130;29–129;30–113;30–125;30–131 |
| 17443 | 1–86;3–349 |
| 17445 | 1–465;1–398;1–448;1–471;1–454 |
| 17456 | 1–346;1–317 |
| 17458 | 1–432;1–509;1–596;1–470;1–499;1–516;1–514 |
| 17459 | 1–316;4–302;4–356;4–440;4–346;4–241;4–350;4–478;4–355;4–374 |
| 17460 | 1–466;47–362;50–287;50–396;50–401;50–392;50–420;50–402;50–348 |
| 17461 | 1–454;1–63 |
| 17462 | 1–364;1–359;1–358;1–359 |
| 17463 | 1–423;1–429;1–429;1–329;1–477 |
| 17464 | 1–197;1–468;1–470;1–474;1–437;1–447;1–144;1–489;1–473;1–495;373–848;373–844;373–824;373–835;373–874 |
| 17468 | 1–169;1–423;1–521 |
| 17469 | 1–356;20–346 |
| 17471 | 1–550;1–349 |
| 17472 | 1–97;1–113 |
| 17473 | 1–231;1–244;1–246;1–244 |
| 17474 | 1–440;1–233 |
| 17476 | 1–281;1–318;1–318 |
| 17477 | 1–67;1–67;1–64;1–64;1–65;1–67;1–64;1–65;1–67;1–67;1–65;1–67;1–65;1–64;1–65;1–67;1–67;1–67;1–65;1–65;1–64;1–64;1–65;1–65;1–65;1–65;1–64 |
| 17479 | 1–486;1–459;1–536;1–419 |
| 17481 | 1–503;1–416;1–496;1–504;24–523;34–367 |
| 17482 | 1–415;5–466;34–367 |
| 17484 | 1–401;1–452;1–441;1–299;1–420;1–491;1–415 |
| 17487 | 1–415;1–415 |
| 17488 | 1–482;2–385;2–480;2–482;2–416;2–252;2–389;2–402;2–392;2–428;2–154;2–417;3–486;3–513;3–521;3–518;3–384;3–401;3–485;19–474;19–481;23–303;23–460;23–536;23–394;23–612;23–382;23–512;29–482;29–413;29–475;29–550;29–499;29–538;33–549;33–521;33–511;33–463 |
| 17489 | 1–399;1–428;1–432 |
| 17492 | 1–375;226–379 |
| 17496 | 1–468;1–474;1–475;1–466;1–460;1–483;1–476 |
| 17498 | 1–521;115–496 |
| 17500 | 1–89;1–92 |
| 17504 | 1–492;1–442 |
| 17505 | 1–63;1–63 |
| 17506 | 1–90;1–91;1–91;1–91;1–92;1–92;1–90;1–91;1–91;1–91;1–91;1–92;4–92 |
| 17507 | 1–459;22–406;26–467;35–517;50–530;50–469;50–523;50–470 |
| 17508 | 1–245;1–224;14–232;25–446 |
| 17509 | 1–514;1–474 |
| 17511 | 1–522;1–347;1–445 |
| 17512 | 1–266;1–383;1–546;1–474;1–546;1–282 |
| 17513 | 1–478;1–483;2–251 |
| 17514 | 1–415;1–172 |
| 17515 | 1–440;1–113;1–474;1–490 |
| 17517 | 1–492;1–433;1–486 |
| 17518 | 1–421;1–578 |
| 17519 | 1–484;1–512 |
| 17521 | 1–326;1–355;1–325;1–401;1–372;1–333;1–384;1–333;1–326;1–354;1–379;1–326;1–371;1–278;1–149;1–315;1–326;1–354;5–364;5–384;336–566 |
| 17522 | 1–326;1–325;1–401;1–372;1–355;1–384;1–333;1–326;1–354;1–333;1–379;1–326;1–371;1–278;1–149;1–561;1–315;1–354;1–326;5–364;5–384 |
| 17523 | 1–415;1–156 |
| 17524 | 1–458;1–156 |
| 17525 | 1–541;127–580 |
| 17526 | 1–503;1–318;1–514 |
| 17528 | 1–209;1–133 |
| 17529 | 1–228;1–168;1–381 |
| 17530 | 1–423;1–365;1–404;1–412;1–414;1–423;1–417;251–423;251–423;251–423;251–407;251–423;251–423;251–423;251–412;251–423;251–423;251–425;251–423;251–423;251–423;251–411;251–421;251–407;251–346;251–373;251–372;251–372;251–401;251–423;251–423;251–407;251–374;251–424;251–381;251–401;251–412;251–423;251–393;251–408;251–423;251–423;251–373;251–423;251–381;251–407;251–423;251–401;251–381;251–422;251–423;251–388;251–372;251–423;251–423;251–372;251–406;251–423;251–407;251–412;251–423;251–422;251–406;251–410;251–423;251–396;251–423;251–423;251–418;251–423;251–411;251– |

TABLE II-continued (Tiling path)

| Seq Id No. | Positions of biological 5'ESTs |
|---|---|
| | 416;251–412;251–423;251–423;251–423;251–400;251–423;251–372;251–387;251–423;251–423;251–364;251–356;251–423;251–423;251–423;251–412;251–423;251–422;251–397;251–423;251–412;251–423;251–423;251–423;251–423;251–410;251–421 |
| 17531 | 1–387;1–449 |
| 17532 | 1–218;1–236;1–225 |
| 17533 | 1–319;1–364;1–387;1–464;1–458;1–319;1–464;1–387;1–458;1–464;1–452;1–290;1–376;1–416;1–517;1–387;1–382 |
| 17534 | 1–485;1–470 |
| 17535 | 1–178;1–243 |
| 17536 | 1–352;1–291 |
| 17537 | 1–476;1–460;1–311;87–589;87–536 |
| 17538 | 1–475;1–459;1–310;1–483 |
| 17539 | 1–468;1–500;1–544 |
| 17540 | 1–394;1–393 |
| 17541 | 1–410;1–342;1–419;1–413;1–420;1–390;1–419;1–416;1–341;1–402;1–137;1–252;1–420;1–360;1–145;1–424;1–342;1–402;1–421;1–390;1–421;1–419;1–414;1–354;1–326;1–384;1–421;1–380;1–421;1–385;1–419;1–410;1–417;1–360;1–388;1–416;1–381;1–410;1–390;1–418;1–145;1–419;1–419;1–421;1–406;1–413;1–413;1–409;1–420;1–416;1–420;1–422;1–421;1–421;1–70;1–326;1–418;1–410;1–423;1–352;1–386;1–183;1–404;1–418;1–413;1–406;1–411;1–424;1–388;1–408;1–413;1–413;1–421;1–91;1–413;1–421;1–360;1–419;1–298;1–405;4–224;4–224;4–224;4–225;4–225;4–225;4–225;4–225;4–225;4–224 |
| 17542 | 1–481;1–347 |
| 17543 | 1–299;1–368;1–400 |
| 17544 | 1–468;1–437;1–430 |
| 17545 | 1–177;1–257 |
| 17546 | 1–460;1–470;1–476;1–502;1–481;1–480;1–487;1–415;1–452;1–466;1–482 |
| 17549 | 1–405;1–120 |
| 17550 | 1–405;1–460;1–354 |
| 17551 | 1–393;1–279 |
| 17552 | 1–165;3–165 |
| 17553 | 1–432;1–344;1–387 |
| 17555 | 1–315;2–378 |
| 17560 | 1–494;282–705;282–781;282–777;282–694;282–822;282–769;282–820;282–785;282–670;282–467 |
| 17561 | 1–424;1–424;1–424;1–424;1–424 |
| 17562 | 1–344;1–433;1–354 |
| 17563 | 1–249;1–260;1–260 |
| 17564 | 1–427;1–435;86–409 |
| 17565 | 1–255;1–264;1–280;1–284;1–255;1–243;1–280;1–229;1–281;1–255;1–281;1–281;1–280;1–284;1–192;1–255;1–255;1–255;1–255;1–255;1–280;1–255;1–228;1–264;1–255;1–238;1–280;1–284;1–264;1–284;1–280;1–255;1–264;1–280;1–280;1–255;1–222;1–280;1–264;1–281;1–280;1–264;1–280;2–280 |
| 17567 | 1–304;1–325 |
| 17568 | 1–136;1–442 |
| 17569 | 1–535;283–627;289–628 |
| 17570 | 1–411;1–337;1–411 |
| 17571 | 1–383;1–426;1–474;1–389;4–410;4–466;8–454;8–503;40–547;40–396;40–264;40–501;40–455 |
| 17572 | 1–269;1–348;1–369;1–138;1–270;1–440;3–330;3–368;3–381;14–225;17–411;30–425;30–421;31–363;31–380;31–423;31–443;32–431;32–428;32–443;32–385;32–433;32–425;32–404;32–383;32–437;32–425;32–373;32–146;32–428;32–437;32–374;32–144;32–380;32–417;32–422;32–431;32–441;32–431;32–390;32–435;32–307;32–423;32–421;32–428;32–413;32–433;32–395;32–413;32–431;32–426;32–428;32–419;32–441;32–430;32–225;32–443;32–123;32–416;32–427;32–427;32–386;32–220;32–359;32–437;32–91;32–430;32–433;32–431;32–431;32–430;32–367;32–424;33–339;33–431;33–421;33–383;33–442;33–432;33–374;33–348;33–294;33–441;33–227;33–430;33–414;33–127;33–440;33–406;33–328;33–388;33–421;33–395;33–225;33–348;33–316;33–193;33–421;33–384;33–440;33–365;33–433;33–430;33–346;33–410;33–439;33–419;33–441;33–441;33–431;33–436;33–425;33–409;33–145;33–121;33–412;33–294;33–440;33–426;33–357;33–131;33–414;33–404;33–433;33–395;33–403;33–394;33–413;33–121;33–439;33–434;33–332;33–414;33–430;33–433;33–333;33–372;33–442;33–441;33–315;33–370;33–421;33–442;33–425;33–440;33–348;33–346;33–42 |
| 17574 | 1–425;1–482;1–566;485–939;485–913;485–1010;718–1157 |
| 17575 | 1–224;1–228;1–228;1–218 |
| 17576 | 1–421;1–372;1–396 |
| 17577 | 1–476;1–471;1–407;1–471;1–479;1–554;1–275;1–139 |
| 17578 | 1–73;1–183;1–174;1–112 |
| 17579 | 1–101;1–62;1–58;10–96;10–105;10–253;10–83 |
| 17580 | 1–306;1–176;2–184;13–294;31–184;31–184;31–166;31–184;31–132;31–162;31–267;31–367;31–261;31–184;31–184;31–184;31–300;31–184;31–319;31–184;31–184;31–246;31–184;31–184;31–182;31–184;31–184;31–184;31–184;31–184;31–184;31–184;31–184;31–184;31–246;31–158;31–184;31–183;31–88;31–184;31–308;31–184;31–246;36–182;39–184;39–349;39–305;39–184;39–184;39–213;39–363;39–368;39–179;39–357;39–159;39–358;39–184;39–246;39–185;39–184;39–246;39–170;39–358;39–184;39–184;39–307;39–332;39–127;39–184;39–320;39–258;39–307;39–184;39–305;39–184;39–112;39–184;39–175;46–246 |
| 17581 | 1–425;1–482;1–556 |
| 17582 | 1–224;1–311 |
| 17586 | 1–379;1–379 |
| 17587 | 1–472;1–454 |
| 17588 | 1–460;1–480;1–480 |
| 17591 | 1–366;1–104;1–478 |
| 17592 | 1475;1–422;1–444;1–410;1–447 |
| 17593 | 1–472;40–323 |
| 17595 | 1–356;1–441;1–454;1–503 |
| 17596 | 1–363;18–74;18–73;18–439;85–139;85–139 |
| 17597 | 1–412;19–70 |
| 17599 | 1–639;1–491 |
| 17600 | 1–468;1–449;1–487;1–460 |
| 17601 | 1–404;1–425 |
| 17602 | 1–329;1–326;1–327;1–326;1–329;1–329 |
| 17603 | 1–92;1–92;1–92;1–90;1–92;1–92;1–92;1–92 |
| 17604 | 1–352;1–120;1–339 |
| 17605 | 1–422;1–419;1–221;1–435 |
| 17606 | 1–504;1–454 |
| 17613 | 1–499;1–504 |
| 17614 | 1–442;1–382 |
| 17615 | 1–165;1–169 |
| 17616 | 1–69;1–416;1–458;1–92;1–131 |
| 17617 | 1–398;1–399;1–397;1–390;1–399;1–391;1–390;1–396;1–397;1–391 |

TABLE II-continued

(Tiling path)

| Seq Id No. | Positions of biological 5'ESTs |
|---|---|
| 17618 | 1–476;1–367 |
| 17619 | 1–277;1–277;1–277;1–277;1–259;1–277;1–277 |
| 17620 | 1–137;1–462 |
| 17621 | 1–546;1–410;1–536;10–493;10–277;10–597 |
| 17627 | 1–367;1–358 |
| 17628 | 1–416;190–557;190–700 |
| 17632 | 1–140;1–80;1–140;1–140;1–145;1–140 |
| 17633 | 1–479;1–485;1–475;1–484;1–495;1–457;1–488;1–457;1–509;1–466;1–484;1–487;1–492;1–481;1–457 |
| 17634 | 1–444;1–471 |
| 17636 | 1–368;31–461 |
| 17638 | 1–339;1–488;1–412;1–518;1–471;1–461;1–213;1–490;1–452;1–492;1–485;1–477;1–415;1–473;1–477;1–475;1–406;1–485;1–500;1–207;1–484;1–156;1–345;1–485;1–438;1–395;1–480;1–485;1–470 |
| 17639 | 1–358;1–275;1–405;1–464;1–502;1–441;1–534 |
| 17640 | 1;367;1–521;1–618;1–521;1–434;1–487;1–517;1–487;1–501;1–667;1–527;1–511;1–537;1–415;1–199;1–446;1–441;1–497;1–224;1–317;1–508;1–508;1–525;1–452 |
| 17641 | 1–93;1–351 |
| 17642 | 1–459;1–433 |
| 17643 | 1–440;1–78;1–448;1–474;1–515;1–508;1–487 |
| 17644 | 1–64;1–64;1–64;1–64;1–64;1–64;1–64;1–64;1–64;1–64;1–64;1–64;1–64;1–64;1–64;1–66;1–64;1–64;1–64;1–64;1–64;1–64;1–64;1–64;1–64;1–64;1–64;1–64;1–64;1–64;1–66;1–64;1–64;1–66;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–64;1–66;1–64;1–64;1–64;1–64;1–64;1–64;1–64;1–64;1–64;1–64;1–64;1–64;1–64;1–65;1–64;1–64;1–64;1–64;1–64;1–64;1–64;1–64;1–64;1–64;1–64;1–64;1–64;1–64;1–64;1–64;1–64;1–64;1–66;1–64;1–64;1–64;1–64;1–64;1–64;1–64;1–64;1–64;1–64;1–64;1–64;1–66;1–64;1–64;1–66;1–64;1–64;1–64;1–64;1–64;1–64;1–64;1–64;1–64;1–64;1–64;1–64;1–64;1–65;1–64;1–64;1–64;1–66;1–64;1–64;1–66;1–64;1–64;1–64;1–64;1–64;1–64;1–64;1–64;1–64;1–64;1–64;1–64;1–64;1–64;1–64;1–64;1–64;1–64;1–64;1–64;1–66;1–64;1–64;1–64;1–64;1–64;1–66;1–64;1–64;1–64;1–64;1–64 |
| 17646 | 1–537;1–506;1–337;1–484 |
| 17649 | 1–62;2–116;2–131;2–98;2–134;2–135;2–128;2–112;79–138;79–131;79–140;79–137;79–139;79–138 |
| 17650 | 1–478;1–482;1–491;1–354;92–593 |
| 17651 | 1–410;1–394;1–511;1–317;1–313;1–319;1–473;1–478;1–473;1–316;1–173;1–319;1–511;1–158;1–316;11–393;47–390;100–604;279–544 |
| 17652 | 1–323;2–323;2–323;2–333;2–329;2–71;2–323;2–323;2–314;2–322;2–321;2–333;2–323;2–323;2–304;2–313;2–304;2–323;2–304;2–323;2–323;2–323;2–320;2–323;2–280;2–252;2–322;2–321;2–323;2–323;2–323;2–322;2–324;2–310;2–322;2–324;2–323;2–333;2–323;2–324;2–321;2–322;2–310;2–323;2–323 |
| 17653 | 1–70;1–98 |
| 17656 | 1–412;1–447;1–487;1–446;1–354;1–438;1–414;1–447;1–472;1–459;1–446 |
| 17657 | 1–163;1–120;1–170;1–123;1–162;1–111;1–153;1–170;1–162 |
| 17658 | 1–453;1–493;1–511;1–336;1–477;1–429 |
| 17659 | 1–475;1–461 |
| 17660 | 1–314;1–305;1–246 |
| 17661 | 1–400;21–243 |
| 17662 | 1–443;1–71 |
| 17665 | 1–200;1–200;1–199 |
| 17666 | 1–461;1–509 |
| 17667 | 1–472;1–483 |
| 17668 | 1–416;5–248 |
| 17669 | 1–251;1–247;1–255 |
| 17671 | 1–472;1–493;1–478 |
| 17673 | 1–485;1–440;1–420;1–482;1–449;1–467;1–499;1–216;1–481;1–368;1–270;1–500;1–499;1–473 |
| 17674 | 1–485;1–216;1–440;1–481;1–420;1–368;1–482;1–495;1–270;1–449;1–473;1–467 |
| 17675 | 1–274;6–435 |
| 17676 | 1–475;1–286 |
| 17677 | 1–217;10–116 |
| 17678 | 1–306;1–306;1–268;1–293;1–306;1–307 |
| 17679 | 1–547;1–462;1–419;1–217;1–455;1–464;1–490;1–430;1–464 |
| 17680 | 1–329;1–327;1–433 |
| 17681 | 1–449;1–100;1–497;1–483;1–476 |
| 17682 | 1–449;1–100;1–483;1–510;1–476 |
| 17683 | 1–103;1–160;1–115;1–100;1–112;1–151;1–81 |
| 17685 | 1–339;1–339;69–410 |
| 17686 | 1–216;1–220 |
| 17688 | 1–378;1–392;1–491;1–400 |
| 17689 | 1–476;1–275;1–393 |
| 17692 | 1–429;1–447 |
| 17693 | 1–426;1–446 |
| 17694 | 1–384;46–386 |
| 17695 | 1–428;1–295 |
| 17697 | 1–213;1–249;1–241 |
| 17698 | 1–213;4–245 |
| 17700 | 1–531;1–504;1–484 |
| 17702 | 1–448;18–219;20–105;23–231 |
| 17703 | 1–265;7–387;8–217 |
| 17704 | 1–290;1–443 |
| 17705 | 1–474;1–474;1–371;1–402 |
| 17706 | 1–132;1–140;1–143;1–143;1–143;1–143;1–132;1–143;1–143;1–140;1–143;1–140;1–143;1–143;1–143;1–141;1–143;1–140;1–143;1–140;1–140;1–143;1–143;1–143;1–143;1–140;1–143;1–132;1–143;1–143 |
| 17707 | 1–460;1–465;1–536;1–454;2–305 |
| 17710 | 1–218;1–229;1–229;1–229;1–222;1–218;1–214;1–229;1–216;1–229;1–228;1–230;1–216;1–212;1–218;1–216;1–230;1–229;1–229;1–174;1–229;1–229;1–194;1–215;1–230;1–229;1–229;1–229;1–229;1–229;1–229;1–229;1–226;1–199;1–163;1–214;1–229;1–221;1–228;1–229;1–229;1–229;1–229;1–219;1–229;1–229;1–229;1–218;1–217 |
| 17711 | 1–489;1–398 |
| 17712 | 1–360;1–484;1–460;1–440;1–322;1–539;1–438;1–296;1–326;1–442;1–424;1–137;1–372;1–419;1–422;1–566;1–484;1–105;1–438;1–508;1–275;1–277;1–438;1–438;1–397 |
| 17714 | 1–477;1–483 |
| 17715 | 1–71;1–173;1–71;1–71;1–223;1–71;2–104 |
| 17716 | 1–71;1–173;1–71;1–71;1–71;1–72–104;5–536 |
| 17717 | 1–378;1–329;1–420;1–412;1–426;2–420;3–428;3–439;3–437;3–412;3–436;3–438;3–425;3–420;3–303;3–439;3–436;3–422;3–405;3–217;3–361;3–424;3–424;3–426;3–426;3–428;3–422;3–417;3–437;5–435;5– |

TABLE II-continued (Tiling path)

| Seq Id No. | Positions of biological 5'ESTs |
|---|---|
| | 426;5–434;5–330;5–435;5–431;13–428;13–417;14–418;14–307;14–326;14–424;14–421;14–420;14–421;14–412;14–436;14–426;15–438;15–435;15–88;15–328;15–425;15–435;15–88;15–436;15–421;15–88;15–88;16–437;16–426;16–438;16–418;16–437;16–420;16–438;16–417;16–121;16–440;16–421;16–424;16–432;16–396;16–437;16–420;16–423;16–434;16–440;16–335;16–422;16–428;16–438;17–403;20–393;20–412;20–420;20–423;20–437;20–424;20–427;20–437;20–414;20–436;20–420;20–439;20–424;20–423;20–438;20–436;20–437;20–424;20–424;20–440;20–437;20–420;20–422;20–426 |
| 17719 | 1–241;1–86;7–121;7–473 |
| 17720 | 1–265;1–265;1–265;1–252;1–255;1–265;1–248;1–265 |
| 17721 | 1–448;1–424 |
| 17722 | 1–213;1–69;1–265;1–350;1–213;1–306;1–220;1–266;1–207;1–327;1–398;1–208;1–319;1–288;1–176;1–332;1–213;1–196 |
| 17723 | 1–349;23–405 |
| 17724 | 1–436;1–470;1–499 |
| 17725 | 1–294;1–497;1–490 |
| 17726 | 1–60;1–60;1–60;1–60;1–60;1–58;1–60 |
| 17728 | 1–338;1–463;1–366;1–463;1–311;1–490;1–381;1–489;1–405;1–298;1–352;1–393 |
| 17731 | 1–432;1–438 |
| 17733 | 1–129;1–122;1–123 |
| 17734 | 1–486;1–470 |
| 17735 | 1–403;1–477;1–410;1–498 |
| 17736 | 1–64;1–68;1–64;1–64 |
| 17737 | 1–382;1–210 |
| 17738 | 1–512;1–322;1–483;1–455 |
| 17739 | 1–494;1–516 |
| 17740 | 1–453;1–491 |
| 17741 | 1–319;1–166;1–362 |
| 17742 | 1–430;1–402;1–502;1–462;1–490;1–392;1–452;1–213;1–262;28–408 |
| 17743 | 1–102;1–102;1–102;1–102;1–102;1–102;1–102;1–102 |
| 17744 | 1–116;1–149 |
| 17745 | 1–393;1–432 |
| 17746 | 1–459;1–440 |
| 17747 | 1–97;1–93;1–93;1–93;1–93;1–93;1–93;1–93;1–97;1–93;1–93;1–93;1–97;1–97;1–97;1–97;1–93;1–93;1–93;1–93;1–97 |
| 17748 | 1–264;1–388;1–378;1–395;1–386;1–400;1–400;1–399;1–401;1–394;1–401;1–399;1–400;1–395;1–400;1–376;1–400;1–400;1–401;1–374;1–355;1–393;1–400;1–401;1–386;1–240;1–395;1–343;1–400;1–377;1–187;1–399;1–387;1–391 |
| 17749 | 1–393;1–106;1–201;1–281;1–462;1–281;1–230;1–396;1–444;2–203 |
| 17750 | 1–190;1–410 |
| 17751 | 1–120;1–495;1–493;1–462;1–477 |
| 17752 | 1–131;1–129;1–131 |
| 17758 | 1–502;1–477;1–468;1–380;1–443;1–411;1–397;1–374;1–517;1–516;2–437 |
| 17759 | 1–236;1–236 |
| 17760 | 1–448;1–495 |
| 17761 | 1–196;35–522 |
| 17764 | 1–479;1–309;1–405;1–446;1–416;1–501 |
| 17768 | 1–431;1–103;1–111;1–115;1–331;2–115 |
| 17769 | 1–510;1–167 |
| 17770 | 1–472;1–459;1–491;1–451 |
| 17771 | 1–455;1–452 |
| 17772 | 1–418;1–285 |
| 17773 | 1–486;1–470;1–411 |
| 17774 | 1–399;1–355;1–390;1–412;1–362;1–387;1–390;1–390;1–389;1–291;1–400;1–413;1–390;1–399;1–393;1–398;1–306;1–399;1–399;1–387;1–399;1–390;1–347 |
| 17775 | 1–414;55–229;55–395;55–379;55–196 |
| 17776 | 1–282;1–285;1–266;1–282;1–282;1–175;1–282;1–271;1–281;1–279;1–269 |
| 17777 | 1–123;1–123;1–123 |
| 17778 | 1–421;1–449;1–458 |
| 17779 | 1–463;1–498 |
| 17780 | 1–419;5–69;5–446 |
| 17781 | 1–337;1–348 |
| 17782 | 1–392;1–390 |
| 17783 | 1–414;1–469;1–469 |
| 17784 | 1–196;1–212 |
| 17785 | 1–481;1–388 |
| 17786 | 1–441;2–251;2–51;4–187 |
| 17787 | 1–428;1–483 |
| 17789 | 1–553;1–455;1–490;1–491 |
| 17790 | 1–414;1–424 |
| 17791 | 1–451;4–358;11–501 |
| 17793 | 1–303;1–344;1–517;1–471 |
| 17794 | 1–253;1–85 |
| 17795 | 1–419;43–294;91–152 |
| 17796 | 1–349;1–347;1–360;1–336;1–347;1–357;1–343;1–347;1–347;1–360;1–339;1–360;1–346;1–347;1–360;1–281;1–360;1–354;1–353;1–360;1–344;1–360;1–360;1–360;1–180;1–347;1–360;1–360;1–347;1–360;1–345;1–360;1–360;1–340;1–359;1–360;1–360;1–349;1–360;1–347;1–360;1–364;1–362;1–345;1–326;1–346;1–360;1–347;1–351;1–360;1–364;1–360;1–358;1–347;1–347;1–364;1–360;1–359;1–360;1–360;1–359;1–360 |
| 17797 | 1–399;1–504 |
| 17799 | 1–434;1–437;1–192;1–449;1–490;1–525;1–402;1–490;1–446;1–509;1–490;1–466;1–468;1–419 |
| 17801 | 1–234;1–385;1–506;4–354 |
| 17802 | 1–459;1–395 |
| 17803 | 1–410;1–374;1–405;1–395;1–380;1–408;1–411;1–391;1–321;1–385;1–409;1–413;1–369;1–396;1–223;1–395;1–398;1–413 |
| 17804 | 1–477;1–425 |
| 17805 | 1–410;1–426 |
| 17806 | 1–292;1–365 |
| 17807 | 1–301;1–309;1–314;1–284 |
| 17808 | 1–386;4–432 |
| 17809 | 1–324;1–441 |
| 17810 | 1–285;1–374 |
| 17811 | 1–417;1–60;1–416;1–417;1–162;1–365;1–419;1–435;1–396;1–417;1–417 |
| 17813 | 1–429;1–434 |
| 17815 | 1–485;1–443;1–412;1–507;1–492;1–469;1–573 |
| 17817 | 1–392;1–269;1–485;1–416;1–475;1–495;1–109;1–482;5–287;5–82 |
| 17820 | 1–483;1–397;1–480;1–505;1–493;1–296;1–424;1–442;1–502;1–317;1–491;1–479;1–485;1–306;1–542;1–507;1–466;1–441;1–415;1–443;1–480;1–491;1–519;1–474;1–315;1–109;1–411;1–472 |
| 17821 | 1–138;1–269 |
| 17825 | 1–282;1–282;1–282 |
| 17827 | 1–407;1–444;1–235 |
| 17828 | 1–329;32–178;32–111;32–178;32–108 |
| 17829 | 1–464;1–415;50–449 |
| 17830 | 1–314;127–394 |
| 17831 | 1–333;1–309;1–388 |
| 17832 | 1–396;1–392 |
| 17833 | 1–428;2–427;34–445 |
| 17834 | 1–401;10–374;10–227;10–90;10–515 |
| 17835 | 1–453;1–452;1–449;1–452 |
| 17836 | 1–377;1–342;1–365;1–373 |

TABLE II-continued (Tiling path)

| Seq Id No. | Positions of biological 5'ESTs |
|---|---|
| 17837 | 1–290;1–306;1–308;1–308;1–307;1–295;1–305 |
| 17838 | 1–451;1–419;1–337;1–450 |
| 17839 | 1–381;1–349 |
| 17840 | 1–421;38–400 |
| 17841 | 1–416;1–53 |
| 17842 | 1–428;1–428 |
| 17843 | 1–468;1–472;1–490;1–460;1–543 |
| 17844 | 1–420;1–432 |
| 17845 | 1–257;1–257;1–257;1–179;1–257;1–257;1–257;1–185;1–254;1–257;1–257;1–257 |
| 17846 | 1–383;29–387 |
| 17847 | 1–343;1–343;1–339;1–343;1–313;1–343;1–343;1–343;1–343;1–343;1–343;1–314;2–299 |
| 17848 | 1–514;1–608 |
| 17849 | 1–269;1–245 |
| 17850 | 1–346;1–335;1–319;1–119;1–333;1–347;1–346;1–327;1–346;1–333;1–330;1–211;1–345;1–330;1–341;1–330;1–334;1–332;1–347;1–346;1–327;1–322;1–347;1–320;1–346;1–326;1–330;1–178;1–326;1–335;1–330;1–337;1–336;1–328;2–340;2–196;2–330;2–335;2–347;2–335;2–117;2–327;2–323;7–320;7–321 |
| 17852 | 1–407;153–585 |
| 17853 | 1–541;1–435;1–561 |
| 17855 | 1–180;1–181;1–181;1–182 |
| 17856 | 1–366;1–436 |
| 17857 | 1–377;1–382;1–405;105–368;157–378 |
| 17859 | 1–181;1–379;1–397;1–267 |
| 17862 | 1–414;1–283 |
| 17865 | 1–401;5–303 |
| 17869 | 1–349;1–344;1–345 |
| 17870 | 1–122;1–87;1–113;1–89 |
| 17873 | 1–433;1–350;1–355;1–470;1–425;1–463 |
| 17874 | 1–307;1–366;1–378;1–379;1–333;1–343;1–379 |
| 17876 | 1–422;1–430 |
| 17877 | 1–201;1–201;1–201 |
| 17878 | 1–512;1–496 |
| 17879 | 1–411;1–408;1–420;1–179;1–420;1–411;1–411;1–420;1–420;1–405;1–411;1–149;1–411;1–358;1–407;1–346;1–334 |
| 17881 | 1–378;1–294;24–493;36–423;39–492;39–408;39–481;39–482;59–448;59–479;59–477;60–481;60–467;60–448;60–435;60–482;60–478;60–494;60–492;60–504;60–200;60–501;60–469;60–483;60–410;60–490;60–478;60–501;60–388;60–358;60–477;60–481;60–487;61–486;61–493;61–480;61–203;61–501;61–451;61–493;61–501;61–472;61–494;61–495;61–422;61–445;61–482;61–444;61–500;61–493;61–472;61–496;61–468;61–492;61–480;61–485;61–469;61–438;61–487;61–485;61–477;61–483;61–432;61–476;61–435;61–504;61–501;61–495;61–406;61–503;61–482;61–503;61–356;61–278;61–475;61–478;61–493;61–430;61–501;61–493;61–492;61–489;61–497;61–496;61–482;61–484;61–473;61–473;61–459;61–503;61–478;61–314;61–306;61–481;61–481;61–450;61–493;61–434;61–504;61–488;61–425;61–499;61–493;61–456;61–358;61–501;61–499;61–448;61–478;61–445;61–480;61–499;61–483;61–493;61–478;61–367;61–493;61–476;61–484;61–373;61–480;61–355;61–496;61–424;63–470;65–351;65–482;65–469;65–416;65–486;65–482;70–485;75–491;75–480;82–263;82–442;82–494;82–479;82–482;96–487;198–469;361–493 |

TABLE II-continued (Tiling path)

| Seq Id No. | Positions of biological 5'ESTs |
|---|---|
| 17882 | 1–294;60–200;61–203;61–278;61–314;61–306;75–532;75–565;75–636;82–263 |
| 17883 | 1–438;1–427;2–354;2–144;2–425;2–370;2–413;2–431;2–421;2–434;3–425;3–422;3–422;3–302;3–426;4–432;4–411;4–458;4–445;4–449;4–332;4–445;4–392;4–423;4–463;4–436;4–421;5–389;5–374;5–437;5–388;5–424;5–147;5–416;5–426;5–395;5–437;5–300;5–445;5–416;5–440;5–439;5–421;5–444;5–366;5–430;5–431;5–437;5–440;5–412;5–424;5–459;5–429;5–413;5–382;5–436;5–429;5–451;5–445;5–376;5–379;5–420;5–350;5–439;5–449;5–447;5–426;5–447;5–394;5–427;5–419;5–422;5–437;5–445;5–447;5–437;5–436;5–438;5–441;5–417;5–426;5–472;5–428;5–433;5–417;5–403;5–444;5–422;5–258;5–250;5–425;5–425;5–222;5–378;5–437;5–449;5–424;5–422;5–443;5–437;5–400;5–432;5–420;5–443;5–302;5–392;5–389;5–428;5–437;5–427;5–422;5–311;5–437;5–443;5–369;5–368;5–440;5–299;5–444;5–424;5–317;7–414;9–430;9–360;9–295;9–413;9–426;9–426;14–429;19–424;19–435;26–386;26–207;26–438;26–423;26–426;40–431;142–413;305–437 |
| 17887 | 1–376;1–433;1–433;1–422;1–422;1–427;1–433;1–422;3–393 |
| 17888 | 1–482;1–486;1–485;1–494 |
| 17889 | 1–473;1–478 |
| 17890 | 1–462;1–460 |
| 17891 | 1–60;1–93;1–148;1–132;1–183 |
| 17892 | 1–426;23–143;42–270;44–245;45–284;60–204;60–193 |
| 17893 | 1–399;1–391 |
| 17894 | 1–510;1–80;1–447;1–519 |
| 17896 | 1–353;1–348;1–352;1–424;1–352;1–352;1–348;1–367;1–353;1–352;1–422;1–340;1–407;1–232;1–354 |
| 17897 | 1–354;1–261;1–448;1–289;15–435;29–413 |
| 17898 | 1–424;31–484;31–398 |
| 17899 | 1–353;1–501;1–361;1–362 |
| 17900 | 1–288;1–288;1–288 |
| 17901 | 1–402;56–198 |
| 17902 | 1–143;1–380 |
| 17903 | 1–360;1–483;1–417;1–342 |
| 17904 | 1–258;1–248 |
| 17905 | 1–237;10–268;25–259;25–296;25–348;25–453;25–131;25–117 |
| 17911 | 1–93;1–93;1–93;1–93 |
| 17912 | 1–461;1–487;1–500;1–369 |
| 17913 | 1–69;1–102;1–113;1–114;1–113;1–93;1–114;1–114;1–113;1–117;1–113;1–114;1–113;1–112;1–117;1–113;1–113;1–114;1–114;1–113;1–113;1–114;1–114;1–113;1–113;1–113;1–114;1–106;1–113;1–114;1–114;1–114;1–113;1–113;1–100;1–114;1–114;1–114;1–106;1–100;1–114;1–113;1–113;1–113;1–113;1–114;1–114;1–114;1–114;1–113;1–114;1–113;1–95;1–113;1–113;1–114;1–114;1–114;1–113;1–114;1–113;1–113;1–114;1–114;1–114;1–100;1–114;1–113;1–103;1–114;1–114;1–113;1–94;1–114;1–100;1–112;1–114;1–114;1–105;1–113;1–100;1–114;1–114;1–114;1–114;1–113;1–114;1–113;1–114;1–94;1–113;1–113;1–114;1–100;1–114;1–114;1–114;1–114;1–113;1–114;1–114;1–114;1–114;1–79;1–114;1–114;1–101;1–113;1–113;1–114;1–113;1–113;1–114;1–114;1–100;1–108;1–113;1–117;1–113;1–104;1–114;1–113;1–113;1–114;1–113;1–114;1–114;1–113;1–113;1– |

TABLE II-continued (Tiling path)

| Seq Id No. | Positions of biological 5'ESTs |
|---|---|
|  | 113;1–114;1–114;1–113;1–114;1–114;1–114;1–113;1–114;1–114;1–114;1–114;1–114;1–114;1–114;1–113;1–113;1–100;1–113;1–113;1–117;1–113;1–102;1–114;1–114;1–113;1–114;1–113;1–114;1–104;1–112;1–96;1–114 |
| 17915 | 1–353;4–481 |
| 17916 | 1–252;1–476;1–486;1–546 |
| 17917 | 1–252;57–512 |
| 17919 | 1–146;1–105;1–201;1–176;1–207;1–206;1–197 |
| 17950 | 1–441;1–460;1–465;1–520;1–385;1–371;1–461 |
| 17951 | 1–411;1–444 |
| 17952 | 1–446;1–445;1–415;1–459;1–479;1–473;1–447;1–489 |
| 17953 | 1–495;1–383 |
| 17954 | 1–437;1–258 |
| 17955 | 1–538;1–490 |
| 17956 | 1–215;1–214;1–214;1–219;1–213;1–214 |
| 17957 | 1–487;1–392;1–338 |
| 17958 | 1–395;1–298;1–400 |
| 17959 | 1–440;1–409 |
| 17960 | 1–478;1–401;1–459;1–445;1–360;1–457;1–410 |
| 17961 | 1–427;1–59 |
| 17962 | 1–385;1–376 |
| 17967 | 1–437;1–429;1–416;1–431;1–414;1–429;1–468;1–226 |
| 17968 | 1–483;1–519 |
| 17969 | 1–358;1–74;1–412 |
| 17970 | 1–226;1–232;1–226;1–225;1–226;1–226;1–232;1–226;1–226;1–226;1–226;1–226;1–226;1–226;1–232;1–227;1–226;1–181;1–205;1–226;1–226;1–226;1–220;1–226;1–226;1–226;1–226;1–204;1–226;1–227;1–226;1–214;1–226;1–226;1–226;1–226;1–226;1–226;1–226;1–226;1–226;1–226;1–226;1–232;1–226;1–226;1–228;1–226;1–226;1–226;1–226;1–226;1–226;1–226;1–205;1–226;1–226;1–226;1–226;1–226;1–226;1–223;1–226;1–218;1–226;1–226;1–226;1–226;1–214;1–226;1–226;1–226;1–213;1–226;1–226;1–226;1–226;1–226;1–226;1–226;1–226;1–226;1–155;1–232;1–226;1–232;1–215;1–226;1–232;1–226;1–226;1–226;1–226;1–226;1–232;1–225;1–226;1–226;1–225;1–226;1–226;1–204;1–213;1–226;1–226;1–226;1–192;1–226;1–167;1–226;1–232;1–226;1–226;1–227;1–227;1–226;1–226;1–226;1–226;1–226;1–226;1–186;1–226;1–226;1–226;1–226;1–226;1–226;1–213;1–226;1–207;1–226;1–213;1–184;1–196;1–226;1–226;1–226;1–232;1–226;1–223;1–226;1–226;1–226;1–226;1–213;1–221;1–226;1–226;1–226;1–226;1–226;1–226;1–195;1–223;1–226;1–226;1–156;1–227;1–226;1–226;1–226;1–226;1–225;1–215;1–226;1–22 |
| 17971 | 1–68;1–68;1–68;1–68 |
| 17972 | 1–336;1–326;3–138;3–137 |
| 17973 | 1–140;1–450;1–456;1–441;1–480;1–419;1–440;1–459;1–224;2–385;2–141;2–294;2–503;2–495;17–233;17–472;17–316;17–429 |
| 17974 | 1–221;1–137;2–382;2–138;2–291;2–472;17–230;17–313 |
| 17975 | 1–478;1–468 |
| 17976 | 1–445;1–437;1–420;1–446;1–480;1–381 |
| 17977 | 1–224;1–140;2–435;2–387;2–141;2–296;17–229;17–318 |
| 17978 | 1–361;1–355;1–383;1–427;1–381;1–371;1–348 |
| 17979 | 1–430;1–164;1–383;1–444;1–215;1–391;1–508 |
| 17980 | 1–382;1–315;6–181;21–483;21–370;21–266;21–510;21–504;21–384 |
| 17981 | 1–382;1–315;1–464;6–181;21–370;21–266;21–383 |
| 17982 | 1–442;1–426;1–404 |
| 17983 | 1–178;1–176;1–176;1–176;1–176;1–178;1–176;1–176;1–178;1–176;1–178;1–176;1–176;1–178;1–176;1–176;1–176;1–176;1–176;1–176;1–178 |
| 17984 | 1–388;66–517;66–532 |
| 17985 | 1–436;2–456;7–294 |
| 17986 | 1–62;1–50;1–63 |
| 17987 | 1–138;1–118 |
| 17988 | 1–273;1–281;1–289;1–304;1–304;1–304;1–292;1–304;1–292;1–291;1–186;1–173;1–292 |
| 17989 | 1–368;1–379;1–368;1–366;1–368;1–357;1–368;1–335;1–380;1–365;1–57;1–368;1–366;1–368;1–379;1–334;1–366;1–367;1–366;1–364;1–366;1–378;1–256;1–368;1–381;1–181 |
| 17990 | 1–116;5–133;5–212;100–208 |
| 17991 | 1–387;1–271;35–253 |
| 17992 | 1–343;1–346;1–419 |
| 17993 | 1–439;6–293 |
| 17994 | 1–443;1–421;1–469 |
| 17995 | 1–443;1–446;1–461 |
| 17996 | 1–352;1–232 |
| 17997 | 1–261;1–276;1–284;1–284;1–287;1–271 |
| 17999 | 1–317;1–295 |
| 18000 | 1–446;31–446;54–434;54–427;54–316 |
| 18006 | 1–322;1–181;1–307 |
| 18008 | 1–426;1–484 |
| 18009 | 1–426;1–472 |
| 18010 | 1–190;1–192;1–81;1–192;1–195;1–198;1–192;1–192;1–198;1–192;1–192;1–86;1–192;1–192;1–192;1–192 |
| 18011 | 1–456;1–497 |
| 18012 | 1–170;1–189 |
| 18013 | 1–375;1–365 |
| 18014 | 1–484;1–487;40–500;40–489 |
| 18015 | 1–136;1–484;1–469;1–455;1–132 |
| 18016 | 1–440;1–442;1–436;1–429 |
| 18017 | 1–54;1–71 |
| 18023 | 1–70;1–267 |
| 18024 | 1–71;15–505;15–434 |
| 18025 | 1–333;1–341;1–339;1–331 |
| 18026 | 1–451;1–298;1–415 |
| 18029 | 1–425;1–324;1–335 |
| 18031 | 1–345;1–476;1–521;1–393;1–422;1–515 |
| 18032 | 1–424;55–396;55–416 |
| 18033 | 1–474;1–456 |
| 18034 | 1–191;1–191 |
| 18035 | 1–206;1–205;1–205 |
| 18036 | 1–381;1–380;1–380;1–380;1–381 |
| 18037 | 1–208;1–111 |
| 18038 | 1–67;3–67 |
| 18039 | 1–145;1–145 |
| 18040 | 1–389;1–386 |
| 18041 | 1–241;1–245;1–241;1–241;1–242;1–242;1–221 |
| 18044 | 1–91;35–85 |
| 18045 | 1–86;1–85;1–86 |
| 18046 | 1–231;1–433 |
| 18048 | 1–106;1–105 |
| 18049 | 1–316;1–304;1–318;1–317 |
| 18050 | 1–219;1–363;1–219;1–324;1–78;9–219;9–218;9–219;9–102;12–284;79–263 |
| 18052 | 1–58;1–334;1–82;1–454;1–416;1–447 |
| 18053 | 1–468;1–477 |
| 18055 | 1–73;1–74 |
| 18056 | 1–93;1–125 |

TABLE II-continued (Tiling path)

| Seq Id No. | Positions of biological 5'ESTs |
|---|---|
| 18057 | 1–167;1–166 |
| 18059 | 1–381;1–444;1–472;2–477;3–450;3–436 |
| 18060 | 1–453;1–488;1–487;63–552;63–537;63–529;63–525;63–515;63–528 |
| 18064 | 1–438;1–443 |
| 18067 | 1–375;1–393;1–392;1–393 |
| 18070 | 1–427;1–415 |
| 18073 | 1–482;59–257;59–145;68–373;68–518;68–386;68–441 |
| 18074 | 13–162;13–133;19–193;19–180;19–180;19–153;19–183;19–124;19–193;19–192;19–174;19–193;19–183;19–193;19–172;19–198;19–193;19–180;19–193;19–164;19–193;19–192;19–198;19–198;19–185;19–174;19–184;19–193;19–193;19–193;19–180;19–192;19–148;19–192;19–188;19–180;19–193 |
| 18077 | 1–208;1–208;1–304 |
| 18078 | 1–482;1–66 |
| 18079 | 1–83;1–83;1–83;1–88;1–83;1–88;1–57;1–83;1–88;1–83;1–83;1–88;1–83;1–88;1–88;1–88;1–88;1–88 |
| 18080 | 1–449;1–458 |
| 18081 | 1–279;1–453;1–503;1–512;1–423;1–243;1–321;1–485;1–241;1–296;1–369;1–512 |
| 18082 | 1–114;1–122;1–217 |
| 18083 | 1–425;1–475 |
| 18085 | 1–211;1–211;1–210;1–210;1–123;1–211;1–211;1–210;1–208;1–211;1–211;1–210;1–211;1–210;1–211;1–211;1–143;1–210;1–210;1–210;1–211;1–210;1–211;1–211;1–210;1–211;1–197;1–211;1–210;1–179;1–210;1–210;1–211;1–211;1–210;1–211;1–210;1–220;1–211;1–210;1–210;1–210;1–211;1–210;1–211;1–210;1–211;1–210;1–210;1–211;1–211;1–210;1–211;1–211;1–210;1–210;1–210;1–210;1–210;1–211;1–211;1–210;1–211;1–211;1–210;1–210;1–210;1–211;1–211;1–210;1–210;1–210;1–211;1–210;1–211;1–212;1–211;1–210;1–211 |
| 18086 | 1–456;11–396;11–397 |
| 18089 | 1–256;1–257;1–259;1–255;1–257;1–257;1–257 |
| 18090 | 1–86;1–87;1–87 |
| 18092 | 1–480;1–333 |
| 18093 | 1–373;1–426;1–385 |
| 18094 | 1–375;1–312;1–375;1–415;1–473;1–415;1–415 |
| 18095 | 1–367;1–345;1–448;1–327 |
| 18096 | 1–188;1–188;1–188;1–188;1–187;5–193 |
| 18097 | 1–188;1–189;1–189;1–189;1–70;1–189;1–189 |
| 18098 | 1–378;1–411 |
| 18099 | 1–78;1–103 |
| 18100 | 1–298;1–312;1–298 |
| 18102 | 1–63;1–56 |
| 18107 | 1–620;1–54 |
| 18108 | 1–505;399–824 |
| 18111 | 1–448;1–467;1–414;1–482;3–360 |
| 18112 | 1–416;1–424 |
| 18113 | 1–449;1–507 |
| 18115 | 1–497;1–395;1–495 |
| 18116 | 1–103;1–467;131–408 |
| 18119 | 1–426;1–471;1–421;1–125;4–436;4–509;4–461;4–467;4–473;4–401;4–457;4–369;4–451;10–407;10–334;10–489;10–462 |
| 18120 | 1–403;1–395 |
| 18121 | 1–364;1–376;1–423;1–234;1–422;1–368;1–493;1–442 |
| 18122 | 1–56;1–62 |
| 18123 | 1–347;1–166;1–366 |
| 18124 | 1–69;1–69;1–69;1–69;1–69;1–69;1–69;1–69 |
| 18125 | 1–372;1–368 |
| 18126 | 1–362;1–139;1–361;1–390;1–352;1–361;3–350;3–398;3–334;3–365;3–398;3–55;3–368;3–164;3–164;3–409;3–340;5–388;5–362;5–362;5–389;5–164;5–361;5–412;5–403;5–350;5–412;5–325;5–350;5–359;5–387;5–397;5–293;5–388;5–338;5–398;6–399;12–399;12–412;12–412;12–389;12–412;12–412;12–354;12–280;12–146;12–379 |
| 18127 | 1–488;1–380;1–466;1–436;1–366 |
| 18129 | 1–452;1–458;1–486 |
| 18130 | 1–190;1–190;1–190;1–190;1–190;1–190;1–190;1–190;1–190;1–190;1–190;1–190;1–190;1–192;1–192;1–190;1–190;1–190;1–190;1–190;1–190;1–66;1–190;1–190;1–190;1–190;1–190;1–190;1–190;1–190;1–190;1–190;1–190;1–190;1–190;1–190;1–190;1–190;1–190;1–192;1–190;1–190;1–190;1–190;1–190;1–190;1–190;1–192;1–190;1–190;1–190;1–190;1–190;1–190;1–190;1–190;1–190;1–190;1–190;1–190;1–190;1–190;1–190;1–190;1–190;1–190;1–190;1–190;1–190;1–190;1–190;1–190;1–190;1–190;1–190;1–192;1–190;1–190 |
| 18131 | 1–314;1–309 |
| 18132 | 1–405;1–202;1–420;1–433;1–280;1–420;1–444;1–510;1–489;1–401;2–502;18–454;18–485;18–505;18–329;18–490;18–450;18–499;19–519;19–405;19–434;46–442;58–319;91–493;111–447 |
| 18133 | 1–56;1–394;1–386;1–324 |
| 18134 | 1–65;1–68;1–65;1–68;1–68;1–65 |
| 18136 | 1–432;1–446 |
| 18138 | 1–263;1–368;1–410 |
| 18139 | 1–163;1–249;1–348;1–162;1–349;1–347;1–352;1–355;1–356;1–349 |
| 18173 | 1–331;1–326;1–328;1–329;1–327;1–330 |
| 18174 | 1–449;67–501;67–501;67–599;93–495;95–624;95–583;95–497;95–348;95–608;95–560;95–470;95–470;95–484;95–599;95–336;95–691;95–563;95–599;95–44;96–385;96–631;96–563;96–599;96–524;96–501;96–599;96–549;96–470;96–496;96–655;96–476;96–563;96–604;96–495;96–599;96–563;96–582;96–470;96–682;96–549;96–558;96–487;96–414;96–624;96–365;96–547;96–599;96–609;96–496;96–582;96–599;96–377;96–629;96–563;96–183;96–560;96–563;96–653;96–563;96–607;96–631;96–599;96–563;96–404;96–496;96–472;96–626;96–705;96–609;96–630;96–630;96–524;96–583;96–631;96–608;96–501;96–599;96–624;96–599;96–492;96–644;96–562;96–549;96–501;96–599;96–563;96–540;96–626;96–676;96–563;96–599;96–401;96–497;96–500;96–599;96–583;96–547;96–472;96–518;96–631;96–563;96–599;96–484;97–679;97–682;97–211;98–549;98–477;98–520;98–583;98–469;98–628;98–351;99–160;99–609;101–549 |
| 18177 | 1–325;17–118;30–169 |
| 18178 | 1–498;1–393;1–474;1–475;1–458;1–458;1–379;1–496;1–458 |
| 18181 | 1–439;3–494 |
| 18182 | 1–347;1–348;1–350;1–329;1–360;1–350;1–206;1–337;1–349;1–352;1–348;1–339;1–349;1–363;1–350;1–340;1–339;1–349;1–348;1–362;1–355;1–349 |
| 18186 | 1–189;1–189 |
| 18189 | 1–141;1–249;6–141 |
| 18190 | 1–472;1–414;1–432;1–492;1–467 |
| 18193 | 1–495;1–354 |
| 18195 | 1–264;1–264;1–252;1–266 |
| 18196 | 1–483;1–537;1–486;1–484;1–357;2–449 |

TABLE II-continued (Tiling path)

| Seq Id No. | Positions of biological 5'ESTs |
|---|---|
| 18199 | 1–512;1–220;1–416;368–420;368–510;368–516;369–435;369–426;369–476;369–462;369–488 |
| 18210 | 1–395;1–487;1–407;1–485 |
| 18212 | 1–429;1–364;1–442 |
| 18218 | 1–466;1–555 |
| 18219 | 1–449;1–466 |
| 18222 | 1–430;1–341 |
| 18223 | 1–408;1–470;1–479;1–347;1–459;1–482;1–503;1–385;1–377;1–443;1–353;1–505;1–489;1–479;1–356;1–452;1–417;1–476;1–347;1–463;1–466 |
| 18224 | 1–343;1–343;1–343;1–339 |
| 18225 | 1–306;50–306 |
| 18226 | 1–443;1–492;1–448;2–71;11–538 |
| 18227 | 1–457;9–474;43–602;59–492;59–641;59–462;59–525;59–411;59–569;59–448;59–534;60–545;60–550;60–581;60–624;60–512;60–542;60–458;60–570;60–288;60–488;60–387;60–449;60–431;60–519;60–503;60–129;60–562;60–445;60–624;60–528;60–538;60–526;60–535;60–625;60–587;60–540;60–560;60–563;60–639;60–550;60–536;61–549;61–497;61–510;61–282;61–561;61–561;61–497;62–462;62–531;62–571;64–624;67–406;69–562;69–571;69–543;69–516;71–550;71–519;71–624;92–601;99–624 |
| 18230 | 1–413;1–437 |
| 18231 | 1–376;1–395 |
| 18232 | 1–63;1–71 |
| 18235 | 1–418;1–345 |
| 18237 | 1–507;227–660 |
| 18238 | 1–251;1–457 |
| 18239 | 1–453;1–330;1–453 |
| 18240 | 1–247;1–163;1–293 |
| 18241 | 1–126;1–402 |
| 18242 | 1–126;1–413 |
| 18245 | 1–418;21–418 |
| 18247 | 1–131;1–103;1–94;1–150 |
| 18248 | 1–60;1–50;1–148;53–133 |
| 18249 | 1–365;1–383 |
| 18251 | 1–581;2–480;2–474;2–501;2–123;2–470;2–513;2–417;2–514;2–327;2–447;2–360 |
| 18252 | 1–359;1–122;1–414;1–326 |
| 18253 | 1–429;1–118 |
| 18254 | 1–443;1–513 |
| 18257 | 1–295;26–438 |
| 18258 | 1–341;1–294;1–334;1–339;1–335;1–340 |
| 18259 | 1–496;1–386 |
| 18260 | 1–444;1–467 |
| 18261 | 1–279;1–348;1–433;1–437;1–577;1–497;1–349;1–321;1–235;1–413;1–324 |
| 18264 | 1–492;1–551 |
| 18265 | 1–507;1–501;1–422;1–319;1–513;1–460;1–478 |
| 18266 | 1–546;1–361;1–477;2–362;8–345;8–345;22–511 |
| 18270 | 1–270;1–249 |
| 18273 | 1–387;1–192 |
| 18274 | 1–169;1–121 |
| 18275 | 1–454;1–592;1–549 |
| 18277 | 1–204;1–204 |
| 18278 | 1–371;1–366;1–363 |
| 18280 | 1–386;1–392;1–359;1–397;1–382;1–397 |
| 18281 | 1–327;1–78;5–143 |
| 18282 | 1–438;1–435 |
| 18283 | 1–490;1–476;43–559;45–509;45–493;45–527;45–509;46–510;47–215 |
| 18284 | 1–339;1–354;1–363;1–354;1–345;1–349;1–361;1–346 |
| 18287 | 1–301;1–458 |
| 18288 | 1–408;80–433 |
| 18289 | 1–402;1–370;1–414;1–415;10–384;10–399;10–391;10–417;10–400;10–405;10–404;10–400;10–386;10–402;10–416;10–417;10–395;11–412;33–399;33–416;33–399;36–313;36–415;36–416;36–277;36–366;36–410;36–398;36–412;52–368;52–400;52–416;52–416;52–401;52–416;52–416;54–406;54–416;54–413;54–418;54–409;54–417;54–413;54–362;54–405;54–401;54–418;54–417;54–416;54–412;54–410;54–417 |
| 18294 | 1–75;1–383;1–400;1–389 |
| 18296 | 1–465;1–311 |
| 18297 | 1–341;1–426;1–376 |
| 18298 | 1–122;1–128 |
| 18300 | 1–474;1–494;1–481;1–474 |
| 18301 | 1–63;1–65;1–65;1–63;1–63;1–63;1–65;1–63;1–65;1–63;1–62;1–65;1–65;1–65;1–63;1–65;1–65;1–65;1–63;1–65;1–63;1–65;1–65;1–65;1–65;1–63;1–63;1–65 |
| 18303 | 1–417;1–519 |
| 18304 | 1–305;1–458;1–408;1–452;1–512;1–482;1–535 |
| 18305 | 1–401;1–335;1–512;1–412 |
| 18307 | 1–196;1–195 |
| 18308 | 1–402;1–502 |
| 18309 | 1–426;1–277 |
| 18310 | 1–487;12–462;12–474 |
| 18315 | 1–362;1–344;1–358 |
| 18316 | 1–472;1–345;1–357 |
| 18318 | 1–189;1–301 |
| 18319 | 1–510;1–184;84–590 |
| 18320 | 1–478;1–431 |
| 18321 | 1–146;1–154 |
| 18322 | 1–430;1–414;1–417;1–425;1–334;1–416;1–424;1–413;1–190;1–421;1–432;1–436;1–417;1–417;1–434;1–425;1–429;1–421;1–420;1–433;1–413;1–430;1–436;1–397;1–421 |
| 18323 | 1–517;1–476;1–471;1–497 |
| 18324 | 1–440;1–461 |
| 18325 | 1–398;1–399;1–382;1–92;1–393;1–146;1–399;1–399;1–399;1–311;1–399;1–400;1–388;1–400;1–399;1–400;1–400;1–390;1–382;1–375;1–399;1–402;1–399;1–384;1–401;1–383;1–396;1–388;1–400;1–400 |
| 18326 | 1–109;1–109 |
| 18327 | 1–118;1–136;1–136;1–139;1–125;1–122;1–136 |
| 18331 | 1–197;1–267;1–265;1–269;1–283;1–281;1–257;1–279;1–268;1–281;1–269;1–267;1–267;1–280;1–267;1–260;1–280;1–272;1–269;1–267;1–280;1–283;1–264;1–267;1–267;1–267;1–280;1–280;1–267;1–90;1–279;1–267;1–261;1–246;1–267 |
| 18335 | 1–82;1–473 |
| 18336 | 1–468;1–467 |
| 18337 | 1–552;1–386 |
| 18338 | 1–237;1–234;1–234 |
| 18339 | 1–490;40–129 |
| 18340 | 1–493;74–592;74–549 |
| 18342 | 1–52;1–53;1–70;1–66;1–72 |
| 18344 | 1–115;1–112;1–115;1–115;1–115 |
| 18345 | 1–247;1–478;1–437;1–445;1–438;1–452;1–465 |
| 18349 | 1–58;1–71;1–64 |
| 18350 | 1–544;1–455;1–372;1–375;1–454;1–473 |
| 18351 | 1–422;1–436;1–321;1–465;1–425 |
| 18352 | 1–464;3–420 |
| 18353 | 1–415;322–403;322–417 |
| 18354 | 1–446;1–494;1–446;1–442;1–456;1–426;1–495;1–445;1–457;1–442;1–442;1–442;1–446 |

TABLE II-continued

(Tiling path)

| Seq Id No. | Positions of biological 5'ESTs |
|---|---|
| 18357 | 1–165;1–133 |
| 18358 | 1–472;1–521 |
| 18360 | 1–404;1–398;1–377 |
| 18361 | 1–224;1–150;1–138 |
| 18362 | 1–307;25–135;27–150;27–154;27–265;28–272;31–143;31–184;31–184;31–291;31–184;31–92;31–101;31–256;31–167;31–184;31–167;31–143;32–92;32–156 |
| 18364 | 1–309;1–247;2–110;3–240;3–125;3–129;5–321;6–118;6–159;6–159;6–277;6–317;6–159;6–389;6–76;6–67;6–159;6–271;6–276;6–231;6–142;6–307;6–142;6–118;7–67;7–131;7–321;219–291 |
| 18365 | 1–309;1–247;2–110;3–240;3–125;3–129;6–118;6–382;6–159;6–159;6–277;6–315;6–276;6–159;6–76;6–67;6–159;6–307;6–271;6–231;6–142;6–380;6–377;6–142;6–118;7–67;7–131;219–291 |
| 18366 | 1–358;1–342;1–319;1–63;3–72;3–63;158–230 |
| 18372 | 1–239;1–285;1–284;1–261 |
| 18373 | 1–237;1–262;15–264;15–264;15–242;15–263;15–262;15–255;15–255;15–266;15–266;15–248;15–265;15–264;15–266;15–266;15–252;15–264;5–276;15–277;15–279;15–253;15–262;15–269;15–253 |
| 18377 | 1–112;2–116;2–112 |
| 18378 | 1–307;1–460 |
| 18379 | 1–203;1–410;1–436 |
| 18380 | 1–431;1–492;1–484 |
| 18381 | 1–498;1–454 |
| 18384 | 1–89;1–159 |
| 18385 | 1–94;1–97 |
| 18386 | 1–464;1–467;1–468;1–464;1–465;1–93;1–467;1–434;1–361;1–478;1–463 |
| 18387 | 1–244;1–74 |
| 18388 | 1–497;1–459;13–398 |
| 18389 | 1–470;1–485;1–439 |
| 18392 | 1–174;1–421;1–405;1–427;1–275;1–405;1–231;1–238;1–262;1–386;1–323;1–382;1–396;1–418;1–416;1–394;1–385;1–265;1–385;1–385;1–237;1–200 |
| 18394 | 1–487;1–538;1–308;1–478;1–498 |
| 18395 | 1–392;4–224 |
| 18396 | 1–347;1–346;1–348;1–346 |
| 18399 | 1–439;1–419;1–439 |
| 18400 | 1–182;1–183;1–183;1–183;1–183;1–180;1–183;1–183 |
| 18401 | 1–96;1–95;1–95 |
| 18402 | 1–344;1–249;1–355;1–342;1–356;1–355;1–344;1–356;1–354;1–344;1–356;1–355;1–338;1–342;1–339;1–340;1–337 |
| 18403 | 1–137;1–137;1–137;1–137;1–137;1–137;1–137 |
| 18405 | 1–533;1–464;1–120 |
| 18407 | 1–187;1–86 |
| 18408 | 1–503;1–349 |
| 18411 | 1–299;1–359;3–369 |
| 18415 | 1–366;1–361;1–175;1–367;1–366 |
| 18416 | 1–377;1–335 |
| 18417 | 1–512;1–522;1–491 |
| 18419 | 1–403;1–437;1–454;1–278;1–402;1–439;1–363;1–471;1–547;1–439;1–259;1–421;1–489 |
| 18420 | 1–97;1–88 |
| 18421 | 1–226;1–226;1–226;1–228;1–228 |
| 18422 | 1–102;1–100 |
| 18424 | 1–411;1–412 |
| 18426 | 1–143;1–143;1–143 |
| 18428 | 1–110;13–186 |
| 18429 | 1–509;1–377;2–376 |
| 18431 | 1–57;1–93 |
| 18435 | 1–55;1–54 |
| 18438 | 1–61;1–61 |
| 18439 | 1–478;6–149 |
| 18440 | 1–302;1–299 |
| 18441 | 1–464;1–408;1–453 |
| 18446 | 1–253;1–276;1–262;1–278;1–224;1–274;1–275;1–278;1–273;1–278;1–273;1–263;1–265;1–275;1–268;1–278;1–277;1–274;1–277;1–275;1–274;1–267;1–278;1–278;1–267;1–278;1–266;1–275;1–274;1–259;1–262;1–274;1–275;1–85 |
| 18447 | 1–214;1–202;1–213;1–213;1–193;1–213;1–213;1–213;1–206;1–213;1–213;1–213;1–213;1–213;1–213;1–213;1–213;1–213;1–213;1–204;1–214;1–216;1–200;1–213;1–213;1–214;1–214;1–208;1–212;1–213;1–213;1–214;1–214 |
| 18448 | 1–396;1–357 |
| 18449 | 1–387;1–423;1–343;1–410;1–409;1–409;1–138;1–231;1–421;1–425;1–377;1–424;1–394;1–407;1–418;1–424;1–418;1–400;1–407;1–405;1–405;1–407;1–411;1–258 |
| 18450 | 1–379;1–439;1–372;2–325;2–474;2–479;3–515 |
| 18451 | 1–493;1–473;1–379;1–439;1–372;2–325 |
| 18452 | 1–377;1–287;2–368;2–300;2–400;3–416;3–305 |
| 18458 | 1–104;1–148 |
| 18461 | 1–107;1–79;1–107 |
| 18462 | 1–51;1–56;1–56 |
| 18463 | 1–354;1–462;1–443;1–460;1–462;1–462 |
| 18464 | 1–76;1–76;1–76 |
| 18467 | 1–427;1–366 |
| 18471 | 1–410;1–350 |
| 18474 | 1–422;1–422;1–426 |
| 18476 | 1–324;1–316;1–319 |
| 18477 | 1–237;1–223 |
| 18478 | 3–453;3–455;3–448;3–455;3–454;3–454;3–454;3–413;3–375;12–440;12–452;12–413;12–452;12–412;12–451;12–442;24–452;25–434;25–109;25–449;25–449;25–446;25–455;25–448;25–454;25–453;25–455;25–453;25–433;25–436;25–448;25–375;25–415;25–450;25–434;25–454;25–453;25–453;25–453;25–451;25–455;25–434;25–452;25–423;25–451;25–444;25–452;26–452;26–453;26–452;26–453;26–454;26–349;26–447;26–358;26–442;26–452;26–407;26–94;26–454;26–455;26–451;26–415;27–442;27–455;27–478;27–453;27–108;27–450;27–455;27–450;27–443;27–446;27–415;27–454;27–400;27–136;27–445;27–455;27–442;27–436;27–442;27–443;27–474;27–451;27–452;27–432;27–449;27–452;27–446;27–453;27–441;27–448;27–454;27–453;27–454;27–454;27–444;27–404;27–453;27–443;27–452;27–475;27–452;27–403;27–455;27–426;27–375;27–453;27–452;28–448;29–452;29–100;29–453;29–448;29–445;30–449;30–452;30–445;30–282;30–452;30–440;30–441;30–438;30–452;30–452;30–452;30–438;30–449;30–452;30–436;30–136;30–441;30–451;30–411;30–452;30–452;30–451;30–440;30–452;30–438;30–358;30–438;30–446;30–452;30–452;30–40 |
| 18484 | 1–102;1–58 |
| 18485 | 1–398;1–472 |
| 18487 | 1–467;1–157;1–469;1–493;1–493 |
| 18490 | 1–395;1–390;1–393;1–393;1–386;1–405;1–391;1–391;1–385 |
| 18491 | 1–432;1–482;1–680;1–427 |
| 18492 | 1–472;1–482;1–454;1–368;4–416;4–553;4–471;4–132;4–210;4–479;4–271;14–498 |
| 18493 | 1–430;1–460;1–429 |

TABLE II-continued
(Tiling path)

| Seq Id No. | Positions of biological 5'ESTs |
|---|---|
| 18494 | 1–159;4–221;10–338;10–171;11–365;11–407 |
| 18495 | 1–195;1–447;28–441;31–272 |
| 18496 | 1–465;1–451 |
| 18497 | 1–427;1–469;1–402;1–461;1–457;9–106;9–408 |
| 18498 | 1–403;1–422;1–407;35–395 |
| 18500 | 1–370;1–508;1–483;1–314;1–393;1–372;1–438;1–505;1–490;1–478 |
| 18501 | 1–187;1–476 |
| 18505 | 1–498;1–289;1–289;1–433;1–254;1–472;1–396;1–554;1–420;1–499;1–440;1–293 |
| 18507 | 1–490;1–449;1–337;1–495;1–509;1–487;1–516;1–498;1–517;1–429;1–489;1–491;1–479;1–464;1–489;1–358;1–445;1–504;1–363;1–362;1–380;1–430;1–268;1–127;1–516;1–504;1–414;1–269;1–514;1–435;1–477;1–358;1–490;1–563;1–439;1–489;1–359;1–516;1–491;1–502;1–531;1–494;1–491;1–473;1–505;1–493;1–514;1–421;1–463;1–464;1–382;1–377 |
| 18508 | 1–449;1–414;1–269;1–337;1–485;1–435;1–477;1–358;1–439;1–359;1–429;1–479;1–464;1–358;1–445;1–473;1–421;1–463;1–464;1–363;1–382;1–362;1–380;1–377;1–127;1–430;1–268 |
| 18512 | 1–429;1–261;1–464;1–380;1–438;1–452;1–476;1–401;1–445;1–564;1–445;1–450;1–547 |
| 18513 | 1–442;1–450 |
| 18514 | 1–489;1–471;1–488;1–486;1–523;1–493 |
| 18515 | 1–74;1–83;4–160;6–127;8–162;8–96;8–190;8–157;8–111 |
| 18516 | 1–74;1–83;4–160;6–127;8–162;8–186;8–96;8–157;8–111;8–541 |
| 18517 | 1–74;1–83;4–160;6–127;8–357;8–380;8–162;8–188;8–96;8–157;8–111;8–357;8–387 |
| 18518 | 1–74;1–83;4–160;6–127;6–235;8–255;8–513;8–162;8–186;8–96;8–157;8–111;8–246;8–263;8–245;8–267;8–272 |
| 18519 | 1–83;1–74;4–160;6–127;6–403;6–413;7–393;7–391;8–399;8–400;8–384;8–397;8–188;8–357;8–414;8–400;8–96;8–402;8–401;8–401;8–157;8–111;8–393;8–397;8–401;8–391;8–357;8–162;8–412;8–403;8–398;8–390;8–398;8–416;8–402;8–398 |
| 18547 | 1–198;1–434;1–423 |
| 18548 | 1–464;22–432;32–460;32–450;32–369;36–366;54–487;65–489;65–501;65–451;65–509;65–489;65–277;65–488;65–501;65–424;65–502;90–490 |
| 18549 | 61–474;63–408;63–520;64–484;64–328;64–562;64–253;64–534;64–486;64–329;64–330;64–309;64–537;64–262;64–404;64–212;64–402;65–442;75–543;92–532;92–546;92–516;92–528;92–528;92–562;92–186;92–555;92–325;92–499;92–545;92–305;92–336;92–561;92–520;93–563;102–329;102–546;102–528;102–549;103–318;103–547;103–410;103–521;103–429;103–182;103–521;104–182;104–494;104–406;104–386;104–533;104–536;105–430;105–548 |
| 18552 | 1–472;1–464;1–454 |
| 18555 | 1–452;1–509 |
| 18556 | 1–566;1–474 |
| 18557 | 1–462;1–162;1–443;1–368;1–452;1–467 |
| 18558 | 1–488;1–513;1–415 |
| 18559 | 1–417;1–515 |
| 18560 | 1–110;1–468;1–511;1–463;1–356;1–397 |
| 18561 | 1–363;1–363;1–363;1–376;1–366;1–376;1–377;1–375;1–361;1–363;1–360;225–329 |
| 18562 | 1–541;1–384 |
| 18565 | 1–110;1–108;1–108;1–110;1–110;1–108;1–108;1–108;1–108;1–110;1–110;1–110;1–108;1–110 |
| 18566 | 1–429;1–449;1–435 |
| 18567 | 1–479;1–469;1–495;1–427 |
| 18568 | 1–413;1–414 |
| 18574 | 1–179;1–400 |
| 18575 | 1–409;1–484;1–443;1–432;1–334;1–472;1–487;1–433 |
| 18576 | 1–472;1–448;1–499;1–475;1–485;1–461 |
| 18577 | 1–334;28–497;28–419 |
| 18578 | 1–482;1–272;1–494 |
| 18579 | 1–427;38–283 |
| 18581 | 1–410;1–507;1–172;1–499;1–387;1–437 |
| 18584 | 1–394;1–395;1–407;1–262;1–386;1–409;1–395;1–409;1–393;1–390;1–403;1–407;1–397;1–408;1–400;1–409;1–409;1–409;1–394;1–408;1–407;1–394;1–395;1–389;1–404;1–395;1–407;1–408;1–410;1–402;1–407;1–394;1–409;1–409;1–410;1–394;1–410;1–394;1–394;1–407;1–400;1–197;1–408;1–397;1–381 |
| 18590 | 1–498;1–464;1–483;1–422;1–345;1–445 |
| 18591 | 1–140;1–452 |
| 18592 | 1–437;1–449;1–413;1–494;132–584 |
| 18593 | 1–285;1–288;1–288;1–288;1–285;1–288;1–288;1–288;1–288 |
| 18594 | 1–418;1–437;1–385;1–419;1–449 |
| 18596 | 1–217;67–546;218–534;218–553 |
| 18597 | 1–411;1–426;1–437 |
| 18598 | 1–398;1–402;1–319;1–397;1–381;1–386;1–358;1–402;1–387;1–255;1–390;1–405;1–394;1–404;1–404;1–392;1–404;1–404;1–392;1–401;1–386;1–403;1–386;1–354;1–390;1–405;1–386;1–401;1–383;1–387;1–384;1–386;1–405;1–402;1–401;1–403;1–384;1–389;1–383;1–406;1–403;1–402;1–402;1–403;1–396;1–402;1–404;1–378;1–405;1–400;1–389;1–405;1–387;1–77;1–382;1–386;1–369;1–385;1–386;1–383;1–386;1–368;1–391;1–388;1–386;1–387;1–393;1–394;1–403;1–386;1–386;1–386;1–403;1–386;1–404;1–397;1–122;1–398;1–369;1–395;1–388;1–382;1–351;1–404;1–144;1–386;1–90;1–386;1–108;1–402;1–404;1–404;1–385;1–405;1–405;1–386;1–386;1–402;1–384;1–402;1–402 |
| 18599 | 1–327;1–478;1–421;1–497;1–344;1–414;1–461;1–531;1–528;1–340;1–403;1–506;1–521;1–482;1–470;1–512;1–408;1–516;1–497;2–3;62 |
| 18600 | 1–289;27–476;27–426;27–289;27–446;27–516;27–426;27–437;27–515;27–454;28–389 |
| 18601 | 1–445;1–495;1–492;1–440;1–482;1–445;1–387;1–496;1–478;1–319 |
| 18602 | 1–314;1–311 |
| 18603 | 1–433;1–411 |
| 18604 | 1–263;2–419 |
| 18608 | 1–468;1–469;1–454 |
| 18610 | 1–52;2–417 |
| 18612 | 1–333;1–346 |
| 18613 | 1–398;1–480;2–53 |
| 18616 | 1–470;1–483;1–499;1–517;1–480;1–486;1–461;1–446;1–487;1–514;1–514;1–475;1–492;1–499;1–497;1–447;1–457;1–501;1–483 |
| 18619 | 1–483;1–452 |
| 18621 | 1–267;9–471;9–428;9–171;9–472;9–450;9–430;9–492;9–477;9–452;9–440;9–465;9–401;9–477;9–477;9–477;9–490;9–477;9–492;9–468;9–464;9–358;9–419 |
| 18624 | 1–225;1–336;1–296;1–332;1–316;1–335;1–250;1–328;28–336;29–325;29–295;29–479;29–147;29–270;29–298;29–336;29– |

TABLE II-continued (Tiling path)

| Seq Id No. | Positions of biological 5'ESTs |
|---|---|
| | 328;29–314;29–333;29–336;29–322;29–322;29–325;29–295;29–302;29–331;29–328;29–336;29–298;29–322;29–453;36–295 |
| 18625 | 1–224;1–249;29–269;29–405;29–146 |
| 18628 | 1–474;1–363 |
| 18630 | 1–388;1–412;1–423;1–481;2–493 |
| 18631 | 1–471;1–328 |
| 18636 | 1–410;1–433 |
| 18637 | 1–175;1–379;1–489;1–385;1–451 |
| 18638 | 1–192;13–383 |
| 18640 | 1–474;1–474;1–423 |
| 18641 | 1–540;16–489;16–523 |
| 18642 | 1–443;30–189;30–421;30–376;30–357;30–220;30–397;31–262;31–226;31–236;31–386;31–417;31–421;31–178 |
| 18643 | 1–332;1–375;11–459 |
| 18644 | 1–197;1–424 |
| 18645 | 1432;1–330;1–359;1–472;1–162;1–318;1–365;1–384;1–335;1–295;1–415;1–477;1–470 |
| 18649 | 1–462;1–516;1–437;1–444;1–478 |
| 18650 | 1–263;1–263;1–262 |
| 18651 | 1–518;3–327 |
| 18652 | 1–483;1–451;1–452;1–507 |
| 18653 | 1–391;1–66;1–397;1–397 |
| 18654 | 1–170;20–218 |
| 18655 | 1–333;1–361;1–361 |
| 18656 | 1–446;24–507 |
| 18657 | 1–463;202–584;202–581;206–727 |
| 18658 | 1–133;1–325;1–322;1–321;1–322 |
| 18661 | 1–209;1–209;1–209 |
| 18662 | 1–501;1–461;1–501;2–475 |
| 18663 | 1–485;1–458;1–471 |
| 18664 | 1–389;1–384;69–366 |
| 18666 | 1–483;1–425;1–410 |
| 18668 | 1–492;1–495;1–512 |
| 18669 | 1–450;1–552;12–442 |
| 18670 | 1–463;1–391 |
| 18672 | 1–408;2–415;2–426;2–414;2–416;2–225;2–290;2–411;2–225;2–401;2–436 |
| 18674 | 1–265;11–270 |
| 18675 | 1–493;1–424 |
| 18676 | 1–175;1–175;1–175;1–175;1–175;1–179;1–69;1–175;1–175;1–175 |
| 18677 | 1–152;1–405;1–405;1–405;1–405;1–120;1–405;1–405;1–405;1–405;1–405;1–394;1–405;1–405;1–405;1–405;1–405;1–405;1–405;1–405;1–405;1–405;1–405;1–405;1–405;1–405;1–405 |
| 18680 | 1–464;9–498 |
| 18681 | 1–458;1–501 |
| 18682 | 1–448;1–458;1–458 |
| 18683 | 1–358;1–360;1–309;1–350;1–357;1–361;373;1–361;1–340;1–375;1–326;1–361;1–358;1–336;1–344;1–375;1–344;1–361;1–363;1–360;1–350;1–363;1–375;1–240;1–343;1–361;1–376;1–363;1–374;1–358;1–361;1–335;1–374;1–312;1–347;1–377;1–358;1–330 |
| 18685 | 1–492;1–343;1–418;1–476;1–284;1–487;1–466;1–502;1–391;1–64;1–509 |
| 18687 | 1–50;1–446;1–422;1–475;1–480 |
| 18688 | 1–503;1–459 |
| 18691 | 1–56;1–62;1–68;2–63;2–63;2–61;2–63;2–63;2–61;2–63;2–65;2–63;2–65;2–63;2–65;2–63;3–63;3–57;3–63;3–63;3–61;3–63;3–65;3–58;4–63;4–63;5–64;5–60;5–65;5–62;5–63;5–59;5–61;5–63;5–70;5–65;5–63;5–66;5–57;5–61;5–66;5–59;5–63;5–65;5–60;5–63;5–61;5–64;5–63;5–62;5–60;5–61;5–63;5–59;5–63;5–61;5–61;5–59;5–63;5–65;5–65;5–63;5–62;5–63;5–57;5–55;5–66;5–67;5–69;5–63;5–61;5–63;5–60;5–59;5–61;5–63;5–59;5–60;5–63;5–63;5–63;5–61;5–64;5–66;5–68;5–63;5–63;5–61;5–61;5–68;5–62;5–70;5–65;5–63;5–61;5–67;5–59;5–61;5–63;5–63;5–62;5–63;5–68;5–58;6–64;6–66;6–64;6–65;6–63;6–65;6–65;6–65;6–60;6–63;6–68;6–63;6–62;6–62;6–61;6–56;6–63;6–61;6–63;6–62;6–60;7–63 |
| 18706 | 1–425;1–419;1–525 |
| 18721 | 1–341;17–332 |
| 18735 | 1–352;1–328;1–339;1–372;1–323;1–359;1–364;1–372;1–355;1–372;1–371;1–372;1–372;1–372;1–373;1–371;1–374;1–372;1–372;1–359;1–371;1–372;1–372;1–359;1–371;1–360;1–356;1–282;1–100;1–363;1–372;1–354;1–373;1–358;1–360;1–110;1–370;1–360;1–290;1–365;1–74;1–349;1–359;1–371;1–174;1–371;1–93;1–353;1–365 |
| 18740 | 1–405;1–283;1–100;1–110;1–291;1–74;1–174;1–93 |
| 18752 | 1–124;1–365 |
| 18756 | 1–351;1–385;1–379;1–386 |
| 18759 | 1–195;31–272;31–208;31–84;31–208;32–269;32–85;32–266;32–112;32–252;32–268;32–426;32–233;32–112;32–225;32–191;32–233;32–192;32–234;32–218;32–254;32–273;33–223;33–226;35–277 |
| 18779 | 1–390;11–306 |
| 18791 | 1–418;53–503;53–527;53–502;53–522;53–410;53–527 |
| 18792 | 1–439;1–466;1–441 |
| 18793 | 1–462;1–399;1–487;1–452;1–510;1–396;1–420;1–481 |
| 18794 | 1–434;1–453 |
| 18795 | 1–351;1–458;1–465;1–205;1–427 |
| 18796 | 1–475;1–462;1–495;1–503;1–351;1–479;1–205;1–427;1–479;1–497 |
| 18798 | 1–475;1–482 |
| 18799 | 1–403;1–381 |
| 18800 | 1–453;1–506 |
| 18801 | 1–438;1–600;1–433 |
| 18802 | 1–399;33–499 |
| 18803 | 1–492;1–433;7–485;7–495;7–528;7–91;16–423;17–127;17–167;55–150;55–167;55–167;55–167 |
| 18804 | 1–79;1–83 |
| 18805 | 1–481;1–490 |
| 18806 | 1–447;1–402 |
| 18807 | 1–438;1–165;1–388;1–275;1–447;1–447;1–398;1–447;1–439;1–447 |
| 18808 | 1–490;1–495;1–495 |
| 18810 | 1–231;1–297 |
| 18811 | 1–61;1–87 |
| 18812 | 1–506;1–464;1–447 |
| 18813 | 1–470;3–484 |
| 18814 | 1–446;321–824;321–795;321–788;321–821;321–687;321–786;321–787;321–587;321–895;321–754;440–875;440–903;503–991 |
| 18815 | 1–494;1–509 |
| 18816 | 1–238;39–561 |
| 18817 | 1–206;1–487 |
| 18818 | 1–474;12–249;12–504 |
| 18819 | 1–237;10–533 |
| 18820 | 1–406;1–440 |
| 18821 | 1–468;1–461;1–393;1–476;135–593 |
| 18825 | 1–486;1–490 |
| 18826 | 1–340;1–402;1–389 |
| 18828 | 1–445;17–333 |
| 18829 | 1–421;1–444 |
| 18830 | 1–282;1–256 |
| 18831 | 1–516;1–522 |
| 18832 | 1–522;1–452;1–506;1–465 |
| 18834 | 1–208;1–394 |
| 18835 | 1–512;1–532 |

TABLE II-continued (Tiling path)

| Seq Id No. | Positions of biological 5'ESTs |
|---|---|
| 18838 | 1–168;1–263;1–265;25–263;25–263;25–262;25–263;25–262;25–263;25–264 |
| 18839 | 1–374;1–259 |
| 18840 | 1–438;1–423;1–438;1–317;1–421;1–425;1–439;1–434;139–226 |
| 18841 | 1–434;1–423;1–317;1–421;1–452;1–425;1–434;139–226 |
| 18842 | 1–209;1–221;1–225 |
| 18843 | 1–360;1–438 |
| 18844 | 1–412;104–359 |
| 18845 | 1–470;11–291;25–494 |
| 18846 | 1–393;1–401 |
| 18847 | 1–352;20–177 |
| 18848 | 1–116;26–416 |
| 18849 | 1–489;1–299;1–479 |
| 18851 | 1–357;1–356 |
| 18852 | 1–357;1–324;1–334;1–357;1–360;1–349;1–341;1–352;1–349;1–351;1–349;1–344;1–347;1–360;1–353;1–342;1–350;1–300;1–357;11–351;11–344;11–359;11–83;11–282;11–342;11–339;11–342 |
| 18859 | 1–389;1–485;1–341 |
| 18861 | 1–338;1–453;1–451 |
| 18862 | 1–427;1–501 |
| 18863 | 1–353;1–353 |
| 18866 | 1–176;2–177;2–176;2–165;2–176;2–166;2–177;2–176;2–177;2–175;2–177;2–175;2–176;2–162;2–176;2–176;2–177;2–177;2–177 |
| 18867 | 1–446;1–423;1–446;1–270 |
| 18868 | 1–209;1–220;1–208 |
| 18869 | 1–488;306–716 |
| 18870 | 1–181;1–250;1–174 |
| 18871 | 1–234;1–182;1–226;1–238;1–175;1–222;1–238 |
| 18872 | 1–181;1–269;1–256;1–269;1–174 |
| 18873 | 1–181;1–300;1–288;1–174;1–296 |
| 18874 | 1–490;1–487;1–476;1–457;46–226;46–219 |
| 18875 | 1–475;1–274;1–482;1–278;1–386 |
| 18876 | 1–425;1–339 |
| 18877 | 1–462;1–501;1–427;1–356 |
| 18878 | 1–462;1–476;1–427;1–356 |
| 18880 | 1–553;1–467;104–563 |
| 18882 | 1–461;1–305 |
| 18883 | 1–427;1–485 |
| 18884 | 1–496;11–495;11–429;11–432 |
| 18885 | 1–414;1–370;1–417;323–936;323–384 |
| 18886 | 1–477;1–470;1–442;1–253 |
| 18889 | 1–449;1–443 |
| 18890 | 1–464;1–467;1–456 |
| 18891 | 1–491;1–471;1–502;1–465;1–401;1–429 |
| 18892 | 1–524;4–204;62–495 |
| 18895 | 1–57;1–426;39–302 |
| 18896 | 1–284;10–59 |
| 18897 | 1–82;1–344;1–253 |
| 18898 | 1–412;1–328 |
| 18899 | 1–378;1–298;1–356;30–111 |
| 18900 | 1–240;1–351 |
| 18901 | 1–452;1–507;1–466 |
| 18902 | 1–266;1–266;1–271;4–266 |
| 18903 | 1–479;1–449 |
| 18904 | 1–258;1–304 |
| 18908 | 1–395;1–400;6–424 |
| 18911 | 1–312;1–308;1–271;1–247;2–295;2–193;2–243;2–159;2–159;2–288;2–133;2–71;2–133;2–212;2–268;2–274;2–269;2–213;2–200;4–314;4–282;4–148;4–303;5–145;5–266;5–381;5–290;5–313;5–221;5–275;5–266;5–266;5–266 |
| 18916 | 1–447;21–110;21–93 |
| 18917 | 1–484;1–506;1–338;1–151;1–499 |
| 18919 | 1–466;1–485;1–479 |
| 18921 | 1–411;72–154;72–176 |
| 18930 | 1–485;1–458;1–462 |
| 18933 | 1–412;1–237;1–440;1–347;1–413 |
| 18934 | 1–380;1–439;1–582 |
| 18935 | 1–262;1–281 |
| 18936 | 1–341;1–341;1–336;1–341 |
| 18937 | 1–166;1–231;30–171;30–426 |
| 18940 | 1–154;1–424 |
| 18941 | 1–347;1–469 |
| 18943 | 1–98;1–97;1–99;1–146;1–149;1–147;1–99;1–146;1–134;1–99;1–134;1–100;1–146;1–95;1–145;1–115;1–99;1–99 |
| 18944 | 1–95;1–98;1–97;1–115;1–99;1–99;1–99;1–99;1–99;1–100;4–438 |
| 18945 | 1–488;1–404;1–524 |
| 18946 | 1–453;1–467;1–453;1–473;1–474;1–518;1–463;1–505 |
| 18950 | 1–397;1–88;2–425;19–468;19–283;20–433;21–427;2–404;21–200;21–454;23–452 |
| 18951 | 1–88;1–397;2–425;12–469;19–488;19–283;19–498;19–519;20–478;20484;20–433;21–480;21–504;21–492;21493;21–427;21–518;21–492;21–454;21–200;21–404;21–502;21–482;23–452 |
| 18953 | 1–306;1–304 |
| 18954 | 1469;3–297 |
| 18956 | 1–439;304–658;304–731;304–790;304–790;304–691;304–665;304–721;304–658 |
| 18957 | 1–517;1–489 |
| 18958 | 1–301;1–481;1–485;1–1030;1–466;1–294;1–404;1–432;1–481 |
| 18964 | 1–442;1–502;1–471;1–500;1–471;1–527;1–500;1–486;1–499;1–435 |
| 18966 | 1–261;1–516 |
| 18967 | 1–226;1–436;1–435;1–449;1–378;1–3951–95;1–425;1–261;1–388;1–414;1–435;1–54;1–433;1–325;1–348;1–419;1–436;1–393;1–393;1–432;1–440;1–415;1–384;1–361;1–424;1–433;1–66;1–435;1–424;1–397;1–431;1–436;1–353;1–448;1–432;1–433;1–419;1–434;1–411;1–152;1–158 |
| 18968 | 1–496;1–489;1–443;1–466 |
| 18969 | 1–489;1–443;1–466;35–569 |
| 18970 | 1–403;1–477;1–429 |
| 18971 | 1–69;24–466;24–438;24–228;70–602;70–563;70–578;70–562;99–401;99–607;102–517;102–596;113–466;113–601;113–594;113–465;113–441 |
| 18974 | 1–474;1–393;1–429 |
| 18975 | 1–388;1–449;1–431 |
| 18976 | 1–482;1–476 |
| 18977 | 1–467;30–194 |
| 18978 | 1–561;1–659 |
| 18979 | 1–451;1–318 |
| 18980 | 1–416;1–485;1–100;1–445;1–446 |
| 18981 | 1–463;2–399 |
| 18982 | 1–493;1–362;1–363;1–472 |
| 18984 | 1–441;1–507;1–423;1–462;1–449;1–475;1–357;4–187;10–434;11–470 |
| 18985 | 1–509;1–487;1–343;1–505;1–58;1–470 |
| 18986 | 1–63;1–433;1–64;1–74;1–318;27–165;31–180 |
| 18987 | 1–378;1–136;1–478;1–479;1–472 |
| 18988 | 1–310;1–473;1–107;1–361;1–394;1–471;1–489;1–434;45–431;127–424 |
| 18989 | 1–477;1–478;2–473 |
| 18991 | 1–528;1–511 |
| 18992 | 1–450;1–289;2–355;2–364;2–450;2400;2–464;2–364;2–448;2–375;2–506;2497;2–223;2–316;2–358;2–450;2–8;2–307;2–438;2–375;2–387;2–239;2–449;2–224;2–378;2–355;2–388;2–455;2–450;2–453;2–432;2–449;2–449;2–428;2–364;2–239;2–459;2–344;2–469;2–458;2–469;2–407;2–459;2–453;2–453;2–466;2–459;2–262;2–399;2–449;2–255;2–331;2–449;2–497;2– |

TABLE II-continued (Tiling path)

| Seq Id No. | Positions of biological 5'ESTs |
|---|---|
|  | 390;2–460;2–468;2–453;2–450;2–449;2–474;2–472;2–375;2–219;2–269;2–407;2–473;2–464;2–389;2–80;2–151;2–370;2–240;2–450;2–374;2–459;2–347;2–355;2–448;2–456;2–492;2–325;2–446;2–450;2–375;2–96;2–314;2–348;2–375;2–392;2–250;2–378;2–450;2–455;2–459;2–456;2–491;2–364;2–448;2–450;2–207;2–355;2–445;2–447;2–374;2–178;2–241;2–354;2–455;2–469;2–145;2–353;2–355;2–344;2–392;2–427;2–453;2–465;2–358;2–458;2–450;2–449;2–148;2–337;2–355;2–398;2–390;2–339;2–57;2–449;2–225;2–451;2–464;2–483;2–466;2–459;2–462;2–449;2–455;2–293;2–147;2–462;2–468;2–486;2–96;2–399;2–449;2–254;2–492;2–494;2–410;2–162;2–438;2–471;2–224;2–459;2–481;2–456;2–497;2–239;2–454;2–350;2–234;2–450;2–449;2–358;2–449;2–473;2–369;2–430;2–262;2–4 |
| 18998 | 1–299;1–443;1–429;13–458;13–476;13–484;13–455;13–465;13–365;13–444;13–511;13–446;13–472;13–496;13–239;13–441;13–445;13–469;13–409;13–517;13–293;13–332;13–514;13–379;13–446;13–356;13–379;13–518;13–485;14–465 |
| 18999 | 1–476;1–433;1–485;1–533 |
| 19002 | 1–458;14–459;14–404;14–397;14–479;14–448;14–441;14–434;14–458;14–458;14–457;4–822;14–382;14–384;14–402;96–457;96–457;97–675;98–481;98–488;98–458;99–502;100–177;100–456;100–466;100–457;100–230;100–481;100–457;100–408;100–471;100–304;100–457;100–458;100–383;100–507;100–485;100–481;100–502;117–481;117–495;117–457;117–456;120–460;120–457;120–458;120–480;120–459;120–445;120–457;120–407;120–384;120–457;120–457;120–448;120–572;120–456;120–501;120–456;120–447;120–481;120–564;120–429;120–406;128–195;128–445;144–458;144–448;158–456;158–442;158–448;158–549;158–379;158–505;158–458;158–457;158–457;158–573;158–637;158–456;158–471;158–457;158–615;158–457;158–457;158–429;159–456;160–458;167–458;195–456;197–383;197–459;198–435;207–456;209–458;210–347;226–503;226–458;226–556;226–457;371–793 |
| 19005 | 1–407;1–402;1–407 |
| 19006 | 1–488;1–510;3–303;283–701 |
| 19007 | 1–477;1–508;1–475 |
| 19008 | 1–478;1–453;1–443;1–477;1–374;1–411;1–399;1–399;1–402 |
| 19009 | 1–482;1–476;1–483;1–508 |
| 19010 | 1–436;1–412 |
| 19011 | 1–369;1–468;1–481;1–434 |
| 19017 | 1–424;1–483;1–412;1–454;1–420;1–484 |
| 19019 | 1–349;1–420;1–428 |
| 19020 | 1–411;1–455;1–497 |
| 19021 | 1–319;1–319;1–297;1–307;1–283;1–319;1–319;1–319;1–319;1–282;1–300;1–234;1–319;1–308;1–319;1–305;1–310;1–319;1–319;1–325;1–319;1–318;1–319;1–319;1–319;1–196;1–319;1–319;1–325;1–319;1–300;1–319;1–325;1–290;1–318;1–319;1–319;1–319;1–319;1–319;1–319;1–313;1–309;1–307;1–319;1–325;1–319;1–319;1–319;1–307;1–325;1–319;1–319;1–325;1–319;1–306;1–319;1–325;1–319;1–306;1–309;1–319;1–319;1–308;1–306;1–319;1–319;1–319;1–313;1–319;1–325;1–318;1–310;1–319;1–272;1–306;1–319;1–325;1–276;1–319;1–319;1–280;1–319;1–319;1–319;1–319;1–325;1–319;1–306;1–319;1–319;1–319;1–319;1–319;1–319;1–265;1–319;1–269;1–319;1–319;1–308;1–319;1–178;1–319;1–306;1–319;1–319;1–319;1–306;1–318;1–325;1–310;1–319;1–319;1–318;1–133;1–319;1–310;1–319;1–322;1–318;1–310;1–319;1–319;1–319;1–325;1–319;1–319;1–318;1–319;1–325;1–325;1–319;1–319;2–319 |
| 19022 | 1–67;1–438;1–360;1–465;1–490;1–441 |
| 19023 | 1–424;1–466;1–463;1–499;1–305;1–295;1–509;1–448;1–472;1–407;1–399;1–499;1–403;1–470;1–407;1–475;1–356;1–374;1–477;1–484 |
| 19024 | 1–424;1–466;1–499;1–463;1–295;1–305;1–514;1–448;1–499;1–399;1–407;1–472;1–403;1–407;1–470;1–475;1–356;1–374;1–477;1–484 |
| 19025 | 1–501;1–465 |
| 19026 | 1–293;1–282 |
| 19028 | 1–440;1–422 |
| 19029 | 1–442;1–550 |
| 19030 | 1–470;1–428 |
| 19031 | 1–81;48–509;48–531;48–528;48–527 |
| 19035 | 1–447;1–447;1–441;1–442 |
| 19037 | 1–391;5–491;5–516;5–487;5–470 |
| 19038 | 1–280;1–310;1–426 |
| 19039 | 1–482;1–580;1–404;1–284;1–472 |
| 19043 | 1–449;1–280;1–309 |
| 19044 | 1–62;1–62 |
| 19045 | 1–160;12–301;12–301;12–290;12–301;12–301;12–297;12–281;12–297;12–301;12–297;12–301;12–297;12–301;12–297;12–301;12–290;12–301;12–301;12–189;12–297;12–297;12–301;12–297 |
| 19046 | 1–363;1–462;1–342 |
| 19048 | 1–306;1–396;1–417 |
| 19049 | 1–383;1–536 |
| 19050 | 1–436;1–518 |
| 19051 | 1–480;1–508;1–487 |
| 19052 | 1–425;1–497;1–437;1–467 |
| 19053 | 1–450;2–408 |
| 19054 | 1–482;1–412;1–278 |
| 19055 | 1–465;1–465;1–463 |
| 19056 | 1–372;1–320 |
| 19057 | 1–465;61–175 |
| 19058 | 1–478;1–457 |
| 19059 | 1–468;1–401 |
| 19060 | 1–380;1–381;1–384 |
| 19062 | 1–500;1–109;1–463;1–299;1–478;1–285 |
| 19063 | 1–150;1–472;1–456 |
| 19064 | 1–515;1–513;1–472;4–419 |
| 19068 | 1–366;4–462;28–449;28–449;28–483;28–499;28–458;28–458;28–557;28–437;28–557;28–458;28–458;28–579;28–451;28–463;28–557;28–411;28–449;28–557;28–463;28–557;28–466;28–463;28–417;28–466;28–458;28–488;28–449;28–466;30–498;30–518;30–506;30–493;30–397;30–427;30–455;30–509;30–520;31–466;31–232;31–459;31–402;31–473;40–417;40–555 |
| 19073 | 1–426;3–313 |
| 19074 | 171–254;214–615 |
| 19078 | 1–423;1–131 |
| 19079 | 1–387;1–277 |
| 19080 | 1–586;1–445;1–228;1–449;1–513;1–483;1–552;1–577;1–427;1–242;1–547;1–579 |
| 19081 | 1–482;1–406;1–393;1–470;1–507 |
| 19082 | 1–468;1–406;1–393 |
| 19083 | 1–471;1–404;178–481 |
| 19085 | 1–375;1–474 |
| 19086 | 1–158;1–192 |

TABLE II-continued

(Tiling path)

| Seq Id No. | Positions of biological 5'ESTs |
|---|---|
| 19087 | 1–516;7–454;11–436 |
| 19088 | 1–427;2–471 |
| 19089 | 1–183;1–458;1–550;1–491 |
| 19090 | 1–469;1–436 |
| 19091 | 1–415;1–410 |
| 19092 | 1–426;2–467;2–470;2–372;385–839 |
| 19093 | 1–456;1–463;1–424 |
| 19094 | 1–516;1–366 |
| 19095 | 1–484;1–478;1–444;1–421 |
| 19096 | 1–354;1–354;1–354;1–356;1–354;1–356;1–356;1–356;1–356;1–261;1–354;1–354;1–264;1–356;1–354;1–356;1–281;1–356;1–355;1–354;1–354;1–356;1–354;1–350;1–342;1–356;1–356 |
| 19101 | 1–492;1–445;1–528 |
| 19102 | 1–444;1–252 |
| 19103 | 1–424;1–439;1–425;1–426 |
| 19104 | 1–480;1–414;1–477;1–556;1–532 |
| 19105 | 1–422;1–407 |
| 19106 | 1–396;1–417;1–426;1–503;1–242;1–473;1–256;1–321;1–453;1–322;1–394;1–394 |
| 19107 | 1–168;1–154;37–168 |
| 19108 | 1–548;1–536;1–538;1–77;1–445;1–465;1–410;1–440;1–448;1–452;1–465;1–385;1–448 |
| 19109 | 1–493;1–464;1–496;1–515;1–479 |
| 19110 | 1–473;1–449 |
| 19111 | 1–405;1–419;1–452;1–233 |
| 19112 | 1–480;1–480 |
| 19113 | 1–394;1–314 |
| 19114 | 1–315;6–354 |
| 19115 | 1–435;1–483;1–429;1–601;122–594;122–561;122–541;122–353;122–587;122–416;122–562;122–510;122–612;122–561;122–562;122–538;122–572;122–601;122–609;122–600;122–600;122–604;127–590 |
| 19117 | 1–449;1–472;1–487;1–464;1–493;1–409;1–472;1–490;1–443;1–450 |
| 19120 | 1–456;12–340 |
| 19121 | 1–202;2–200;2–200;2–188;2–201;2–185;2–201;2–201;2–188;2–201;2–201;2–201;2–201;2–188;2–201;2–201;2–190;2–164;2–201;2–191;2–201;2–191;2–187;2–201;2–201;2–201;2–201–2–201;2–201;2–201;2–201;2–191;2–121;2–135;2–178;2–201;2–201;2–188;2–202;2–188;2–201;2–200;2–155;2–90;2–175;2–201;2–192;2–197;2–201;2–201;2–201;2–188;2–190;2–188;2–188;2–201;2–196;2–201;2–188;2–201;2–201;2–201;2–187;2–187;2–201;2–184;2–201;2–201;2–201;2–187;2–190;2–161;2–201;2–203;2–201;2–98;2–201;2–88;2–201;2–201;2–202;2–201;2–188;2–121;2–190;2–188;2–188;2–188;2–117;3–201;3–202;3–201 |
| 19122 | 2–439;2–335;2–371;5–424;22–152;25–407;25–439;25–358;25–439;27–298 |
| 19125 | 1–448;14–438 |
| 19127 | 1–514;1–503;2–468 |
| 19128 | 1–452;1–466;1–453;1–351;1–394;1–469;1–444 |
| 19129 | 1–427;1–566;1–450 |
| 19130 | 1–454;1–517;1–454 |
| 19131 | 1–117;1–458 |
| 19132 | 1–136;1–134;1–136;1–124;1–124;1–136;1–134;1–136;1–134;1–134;1–136;1–134;1–134;1–136;1–134;1–136;1–136;1–136;1–134;1–134;1–136;1–136;1–136;1–134;1–136;1–134 |
| 19133 | 1–374;1–470;1–438;1–463;1–500;1–396;1–372;1–500;1–500;1–385 |
| 19135 | 1–469;272–682 |
| 19136 | 1–479;1–484 |
| 19137 | 1–126;1–142 |
| 19138 | 1–493;1–431;63–534;63–536;63–332;63–534;63–503;63–554 |
| 19141 | 1–340;1–339;1–339;1–328;1–337;1–353;1–339;1–331;1–340;1–351;1–340;1–354;1–352;1–355;1–330;1–340 |
| 19142 | 1–400;1–333 |
| 19147 | 1–480;1–438;1–444;1–440;1–457 |
| 19148 | 1–79;1–229;1–400;1–264;1–112;1–147;1–406;1–394;3–77;3–292;3–257;4–153;4–347;4–157;22–128;22–107 |
| 19149 | 1–332;1–337 |
| 19150 | 1–210;1–515 |
| 19151 | 1–258;1–77;1–71 |
| 19159 | 1–429;1–429;1–430;1–425;1–433;1–422;1–358;1–421;1–429;1–408;1–267;1–429;1–446;1–331;1–443;1–386;1–441;1–446;1–433;1–427;1–430;1–453;1–401;1–406;1–433;1–429;1–126;1–438;1–440;1–429;1–429 |
| 19161 | 1–533;1–319;1–495;1–550;1–366 |
| 19163 | 1–500;1–258;1–468;1–453;1–241;1–504 |
| 19164 | 1–416;1–418;1–435 |
| 19165 | 1–352;1–497 |
| 19166 | 1–497;1–485;1–127 |
| 19167 | 1–341;1–369 |
| 19168 | 1–371;1–382;1–400;1–396;1–161;1–364;1–381;1–382;1–384;1–380;1–385;1–159;1–383;1–377;1–387;1–384;1–397;1–188;1–391;1–397;1–368;1–102;1–382;1–382;1–400;1–386;1–385;1–387;1–378;1–382;1–286;1–400;1–386;1–400;1–388;1–387;1–211;1–398;1–382;1–369;1–382;1–384;1–376;1–397;1–385;1–384;1–373;1–373;1–368;1–397;1–382;1–345;1–382;1–397;1–352;1–397;2–77 |
| 19169 | 1–116;1–130;1–127;1–144;1–124;1–144;1–139;1–99;1–115;2–135 |
| 19170 | 1–434;7–62;7–298 |
| 19174 | 1–474;1–532;1–527 |
| 19175 | 1–519;1–423 |
| 19176 | 1–424;200–658 |
| 19177 | 1–287;1–276;1–286;1–285;1–291;1–291;1–266;1–303;1–133;1–262;1–297;1–292;1–244;1–301;1–287;1–300;1–300;1–290;1–288;1–277;1–202;1–138;1–288;1–269;1–153;1–301;1–302;1–277;1–143;1–277;1–288;1–300;1–277;1–283;1–243 |
| 19178 | 1–369;1–361 |
| 19179 | 1–500;1–391 |
| 19180 | 1–270;1–293;1–279;1–278 |
| 19181 | 1–558;1–436 |
| 19182 | 1–411;1–471;1–412 |
| 19185 | 1–88;1–88 |
| 19186 | 1–467;1–484;1–513 |
| 19187 | 1–464;1–370;1–460 |
| 19188 | 1–461;1–472 |
| 19189 | 1–473;1–460 |
| 19190 | 1–488;1–504;1–389;1–456;1–456;1–479;1–271;1–453;1–367;1–518;1–210 |
| 19191 | 1–380;36–131;36–134;36–132;36–131;36–131;36–131;36–134;36–132;36–132;36–134;36–132;36–132;36–132 |
| 19192 | 1–421;1–449 |
| 19193 | 1–196;1–214 |
| 19194 | 1–511;1–365;1–481;1–548;1–366;1–511;1–453;1–466;1–479;1–550;1–445;1–410;1–501;1–379;1–481 |
| 19205 | 1–468;1–364 |
| 19237 | 1–304;1–308;1–308;1–282;1–308 |
| 19282 | 1–377;1–355 |
| 19292 | 1–321;1–474;1–496 |
| 19303 | 1–199;3–489 |
| 19314 | 1–385;11–206 |

TABLE II-continued (Tiling path)

| Seq Id No. | Positions of biological 5'ESTs |
|---|---|
| 19325 | 1–355;1–249;1–359;1–320;1–366;1–359;1–354;1–335;1–359;1–334;1–367;1–390;1–351;1–388;1–76;1–389;1–375;1–274;1–375;1–389;1–367;1–334;1–367;1–390;1–272;1–361;1–376;1–354;1–389;1–358;1–375;1–355;1–366;1–367;1–375;1–370;1–374;1–367;1–367;10–377 |

TABLE III (Multivariant clusters)

| Internal designation | Variants |
|---|---|
| D1 | 15657,16303,16842 |
| D2 | 3523,17893,18827 |
| D3 | 422,2393,10295,11067,15100,15152 |
| D4 | 15266.15328 |
| D5 | 15420,15466,15520,15573,15614,15658,15711,15748,15855,15956,16025,16093,16156,16194,16252,16304,16362,16413,16472,16524,16584,16636,16680,16734,16789,16843 |
| D6 | 16947.17054 |
| D7 | 17118.17165 |
| D8 | 1666.196 |
| D9 | 1913.17346 |
| D10 | 236,238,247,251,18198,18341 |
| D11 | 18388.18448 |
| D12 | 18700.18743 |
| D13 | 175,3742,3749 |
| D14 | 3867.3879 |
| D15 | 997,1096,1130,7920,8104,8192 |
| D16 | 9217.9298 |
| D17 | 1186,10834,11557 |
| D18 | 2828.12719 |
| D19 | 314.1909 |
| D20 | 153.13674 |
| D21 | 471,13878,13957 |
| D22 | 112.203 |
| D23 | 14318.14392 |
| D24 | 2319,14701,14862 |
| D25 | 563,15032,15095,15101,15109,15113,15114,15117 |
| D26 | 2367,15153,15157,15165 |
| D27 | 2390.15207 |
| D28 | 578,15227,15231 |
| D29 | 2414,15291,15296 |
| D30 | 15303.15309 |
| D31 | 15329,15335,15342 |
| D32 | 1521.15457 |
| D33 | 614.248 |
| D34 | 15481,15490,15495,15497 |
| D35 | 2493.2497 |
| D36 | 15528.15535 |
| D37 | 2545,2549,2552,15620 |
| D38 | 358,366,2560 |
| D39 | 109.15645 |
| D40 | 15659,15666,15672 |
| D41 | 43,1362,1363,2587,15700 |
| D42 | 1817,1854 1945,2051 |
| D43 | 15731,15734,15737,15741,15749,15760 |
| D44 | 2623,2624,2625,2626,2627,2628,2629,2630,2631,2632,2633,2634,2636,2639,2643,2645,2646,3213,3274,15823,15844,15977,15996 |
| D45 | 16094.16098 |
| D46 | 686.16102 |
| D47 | 1672.1618 |

TABLE III-continued (Multivariant clusters)

| Internal designation | Variants |
|---|---|
| D48 | 2725.16224 |
| D49 | 1055,2731,16258 |
| D50 | 700.16273 |
| D51 | 1347.1348 |
| D52 | 3564.16314 |
| D53 | 715.716 |
| D54 | 16348.16356 |
| D55 | 16392,16398,16405,16414,16419,16424 |
| D56 | 277.1662 |
| D57 | 1403,2829,16474 |
| D58 | 16525,16529,16533,16544 |
| D59 | 16621.16626 |
| D60 | 16644,16649,16650 |
| D61 | 16656.1666 |
| D62 | 775.17 |
| D63 | 16709.16716 |
| D64 | 783,1852,16736,16741 |
| D65 | 1936.1675 |
| D66 | 790,794,799,2931,2938,2940,2948,16790,16819 |
| D67 | 16829.16836 |
| D68 | 805.16852 |
| D69 | 16873.16879 |
| D70 | 836,17099,17109 |
| D71 | 17130,17136,17140 |
| D72 | 275,275,1596,17200 |
| D73 | 880.3117 |
| D74 | 82,886,892,1453,1455,1461 |
| D75 | 3179.3184 |
| D76 | 17432.17439 |
| D77 | 3215,3218,17491 |
| D78 | 17541,17548,17554 |
| D79 | 17574.17581 |
| D80 | 3279.1763 |
| D81 | 958.3302 |
| D82 | 17719.17732 |
| D83 | 3319,3321,17753,17756 |
| D84 | 1893.1781 |
| D85 | 1033.1034 |
| D86 | 17985,17993,17998 |
| D87 | 18002.18007 |
| D88 | 18048,18054,18058,18062,18065,18066,18068,18071,18075 |
| D89 | 18083,18086,18091,18101,18106 |
| D90 | 3452,3453,18122,18126,18140,18148,18152,18158,18167,18170,18172,18175 |
| D91 | 3460,18181,18190 |
| D92 | 1102.3467 |
| D93 | 67,68,1704,18287 |
| D94 | 3500,18310,18317 |
| D95 | 18357,18363,18367,18368,18371 |
| D96 | 18396.18403 |
| D97 | 18478,18499,18506,18535 |
| D98 | 1172.18563 |
| D99 | 3591,3596,18581 |
| D100 | 18618.18622 |
| D101 | 1210,1212,1218,1219,1220,1222,3647,3651,3658,18659,18679,18686,18690,18692 |
| D102 | 18721.18726 |
| D103 | 18735.1874 |
| D104 | 368,3664,3666,3668,3677,18752,18756,18759,18763,18766,18773,18780,18789 |
| D105 | 1241.1885 |
| D106 | 1869.18859 |
| D107 | 18888.18893 |
| D108 | 3747,18905,18909,18912,18914,18920,18922,18923,18925,18926,18928,18929 |
| D109 | 1273.1558 |

TABLE III-continued (Multivariant clusters)

| Internal designation | Variants |
| --- | --- |
| D110 | 1285,1288,3779,3780,3796,3800,18984,19004 |
| D111 | 19038.19043 |
| D112 | 19064,19070,19077 |
| D113 | 19136.19139 |
| D114 | 1318,3862,19145 |
| D115 | 3869.3872 |
| D116 | 19303.19314 |
| D117 | 1320,3842,3843 |
| D118 | 7828,7837,7845,7851 |
| D119 | 1235,3728,3736,3752,3768,3804,3823,3827,7872 |
| D120 | 8005.8015 |
| D121 | 1176,8083,8125 |
| D122 | 3705.8143 |
| D123 | 1146.3681 |
| D124 | 1144.8233 |
| D125 | 1113.8307 |
| D126 | 1109.3621 |
| D127 | 926,941,8529,8538 |
| D128 | 3518,3519,8667,8678,8690,8699,8710,8721,8732,8742,8751,8758,8768,8777,8786 |
| D129 | 8805.8813 |
| D130 | 3478,8830,8841,8862,8873 |
| D131 | 1422.8885 |
| D132 | 8976.8986 |
| D133 | 292.1468 |
| D134 | 9177.9185 |
| D135 | 9208.9218 |
| D136 | 312.924 |
| D137 | 9372.938 |
| D138 | 3214,3216,3220,9396,9403,9411,9420,9428,9435,9444,9453,9463,9474,9484,9518,9525,9532,9539 |
| D139 | 9614.9622 |
| D140 | 9769.978 |
| D141 | 3078,9836,9853 |
| D142 | 3056,9861,9871 |
| D143 | 470.473 |
| D144 | 467,3020,3025 |
| D145 | 410,2984,9988 |
| D146 | 10010.10016 |
| D147 | 2944,2951,2952 |
| D148 | 2926.10106 |
| D149 | 2907.2914 |
| D150 | 10178,10185,10193,10203,10211,10220,10229,10237,10248,10258,10269,10278,10286,10297,10306 |
| D151 | 284.1097 |
| D152 | 10339.10348 |
| D153 | 10392.10401 |
| D154 | 2689.10504 |
| D155 | 2608,2617,10523,10531,10538,10554 |
| D156 | 929,3035,10591 |
| D157 | 876,10612,10627 |
| D158 | 2535.10679 |
| D159 | 10686.10694 |
| D160 | 1233.10763 |
| D161 | 2476,2483,10798,10817 |
| D162 | 10845.10852 |
| D163 | 577,2372,10990 |
| D164 | 530,11076,11090 |
| D165 | 2209,2363,2392 |
| D166 | 11247.11258 |
| D167 | 2194.2195 |
| D168 | 11378.11387 |
| D169 | 11457.11465 |
| D170 | 1206.11537 |
| D171 | 2094,2100,11606 |
| D172 | 11674.11685 |
| D173 | 11833.11843 |
| D174 | 11906.11916 |
| D175 | 11998.12008 |
| D176 | 12039,12050,12061 |
| D177 | 1420,12145,12166 |
| D178 | 12197.12208 |
| D179 | 953,956,12279 |
| D180 | 673,709,711,759,789,822,875,905,12356 |
| D181 | 3288,12532,12538,12546 |
| D182 | 561,2856,12571 |
| D183 | 1588.12605 |
| D184 | 370.1267 |
| D185 | 762,12687,12759,12795,12809 |
| D186 | 12854.12862 |
| D187 | 12879.1289 |
| D188 | 107.1516 |
| D189 | 2416.12945 |
| D190 | 650.12977 |
| D191 | 617.12995 |
| D192 | 229.13057 |
| D193 | 426.13078 |
| D194 | 387.2082 |
| D195 | 13359,13367,13375,13384,13392,13398,13407,13412,13420,13428,13435,13443 |
| D196 | 13449,13457,13464 |
| D197 | 235.1801 |
| D198 | 2144.13557 |
| D199 | 2099.2153 |
| D200 | 13627,13636,13642,13648 |
| D201 | 2121.13712 |
| D202 | 13722.13731 |
| D203 | 439,2132,13751,13760 |
| D204 | 13779,13788,13796,13801 |
| D205 | 1950.1965 |
| D206 | 480.14104 |
| D207 | 1773,1775,1776,1779,14134,14143 |
| D208 | 14224,14232,14240 |
| D209 | 1987.1425 |
| D210 | 2238.14266 |
| D211 | 14278.14286 |
| D212 | 2256.2258 |
| D213 | 14654,14673,14691 |
| D214 | 14781,14789,14798,14807 |
| D215 | 1617.1487 |
| D216 | 2334.14933 |
| D217 | 14986.14995 |
| D218 | 2348,15013,15023 |
| D219 | 15077.15088 |
| D220 | 165,356,1498,2354,15096 |
| D221 | 2355.15099 |
| D222 | 15104,15105,15106,15107 |
| D223 | 1436.15112 |
| D224 | 1387,1388,15115 |
| D225 | 2364,15120,15121,15122 |
| D226 | 564.565 |
| D227 | 15126,15127,15128 |
| D228 | 15131.15132 |
| D229 | 15133.15134 |
| D230 | 15137.15138 |
| D231 | 2369.15142 |
| D232 | 315,568,15150 |
| D233 | 570,1399,2373,2375,15156 |
| D234 | 15159.1516 |
| D235 | 1577.15161 |
| D236 | 15162.15163 |
| D237 | 2378.15169 |
| D238 | 2379,2380,15172 |
| D239 | 2382.15175 |
| D240 | 572,2384,15176 |
| D241 | 290,1850,1853 |
| D242 | 15190.15191 |
| D243 | 15196,15197,15198,15199,15200,15201,15202,15203,15204,15205,15206,15208,15209,15210 |

TABLE III-continued (Multivariant clusters)

| Internal designation | Variants |
|---|---|
| D244 | 15212,15214,15215 |
| D245 | 15220.15221 |
| D246 | 2396,15224,15225 |
| D247 | 15229.1523 |
| D248 | 15232,15233,15234 |
| D249 | 15237.15238 |
| D250 | 15244.15246 |
| D251 | 2401.2742 |
| D252 | 2403.15249 |
| D253 | 1570.2777 |
| D254 | 585.15252 |
| D255 | 2408.1526 |
| D256 | 15261,15262,15263 |
| D257 | 15268,15269,15270,15271 |
| D258 | 2411,15272,15274,15275,15276,15277,15278 |
| D259 | 586.587 |
| D260 | 15281.15282 |
| D261 | 1874.1887 |
| D262 | 15286.15287 |
| D263 | 1984.2417 |
| D264 | 15294.15295 |
| D265 | 2420,15297,15298 |
| D266 | 15301.15302 |
| D267 | 15306.15307 |
| D268 | 2423.1531 |
| D269 | 15312,15313,15314,15316,15317,15318,15319,15320,15321,15322,15323 |
| D270 | 731,2427,2428,2429 |
| D271 | 2431.15327 |
| D272 | 254.15332 |
| D273 | 2432.15333 |
| D274 | 15341.15343 |
| D275 | 360.15344 |
| D276 | 15348.1535 |
| D277 | 15351.15352 |
| D278 | 597,2434,15355 |
| D279 | 15356,15357,15358,15359,15360,15361,15362,15364,15365,15366,15367 |
| D280 | 858.15368 |
| D281 | 599.1537 |
| D282 | 260.261 |
| D283 | 15384.15385 |
| D284 | 2443,15386,15387,15388,15389 |
| D285 | 15395,15396 |
| D286 | 287.2446 |
| D287 | 604.2447 |
| D288 | 1415,1747,15404,15405,15406,15409 |
| D289 | 15411.15412 |
| D290 | 606,607,15414 |
| D291 | 1791.15418 |
| D292 | 2452,2453,2454,2457,2458,2459,2460,2855,2882 |
| D293 | 2461.15427 |
| D294 | 608,610,810,15433,15434 |
| D295 | 2470.15436 |
| D296 | 15437,15438,15439,15440,15441 |
| D297 | 15445.15446 |
| D298 | 1593,2474,15454 |
| D299 | 15456.15458 |
| D300 | 15460.15461 |
| D301 | 618,619,620,894,15465,15467,15468,15469,15470 |
| D302 | 2482.15472 |
| D303 | 623.15483 |
| D304 | 2485.15491 |
| D305 | 2487.15496 |
| D306 | 15500.15501 |
| D307 | 626.2489 |
| D308 | 15504.15505 |
| D309 | 307,308,1902,15506,15507,15508,15509,15510,15511 |
| D310 | 1471.15512 |
| D311 | 15513.15514 |
| D312 | 1876.2494 |
| D313 | 2498,15521,15522 |
| D314 | 15524.15525 |
| D315 | 15526.15527 |
| D316 | 15529.1553 |
| D317 | 15532.15533 |
| D318 | 2502.2503 |
| D319 | 15542.15543 |
| D320 | 632.633 |
| D321 | 15548.15549 |
| D322 | 328,2505,15551 |
| D323 | 2506.2507 |
| D324 | 2508.2509 |
| D325 | 15558.15559 |
| D326 | 1956.2511 |
| D327 | 1643.15562 |
| D328 | 2516.2517 |
| D329 | 74,75,1428 |
| D330 | 2523.2524 |
| D331 | 181,1416,15579 |
| D332 | 347.3016 |
| D333 | 2532,15586,15587 |
| D334 | 1651,1743,1762,1764,1766,1767,15589 |
| D335 | 15595.15596 |
| D336 | 2543.15599 |
| D337 | 2544,15601,15602 |
| D338 | 15604.15605 |
| D339 | 125,265,1569,1663,15607 |
| D340 | 1863.15611 |
| D341 | 2554.15623 |
| D342 | 123.1555 |
| D343 | 2013,2014,2015,2016,2017,15624,15625,15626 |
| D344 | 1760.15639 |
| D345 | 657.2571 |
| D346 | 659,2572,2573,15644 |
| D347 | 661,662,2576 |
| D348 | 2577,2578,15651,15652,15653,15654,15655,15656 |
| D349 | 15662,15663,15664 |
| D350 | 2579,2580,15667,15668,15669 |
| D351 | 15670.15671 |
| D352 | 2581,2582,2583 |
| D353 | 957,2584,2585,15675,15676 |
| D354 | 15677.15678 |
| D355 | 15685.15686 |
| D356 | 1657.2589 |
| D357 | 1793,15695,15696 |
| D358 | 15699.15701 |
| D359 | 15705.15706 |
| D360 | 15707.15708 |
| D361 | 73,1427,15713 |
| D362 | 15715.15716 |
| D363 | 111,671,15717 |
| D364 | 2612,2613,2614,3874,3880,15720 |
| D365 | 15722,15723,15724 |
| D366 | 1935.15725 |
| D367 | 1649,15730,15732 |
| D368 | 2619.15735 |
| D369 | 320,672,15738 |
| D370 | 15743.15744 |
| D371 | 15747,15750,15751,15752,15753,15754,15755,15756,15757,15758,15759,15761,15762,15763,15764,15765,15766,15767,15768,15769,15770,15771,15772,15773,15774,15775,15776,15777,15778,15779,15780,15781,15782,15783,15784,15785,15786,15787,15788,15789,15790,15792,1579 |

TABLE III-continued (Multivariant clusters)

| Internal designation | Variants |
|---|---|
| | 3,15794,15795,15796,15797,15798, 15799,15800,15801,15803,15804,15805,15806,15807,15808,15809,15810,15811,15812,15813,15814,15815, 15816,15817,15818,15819,15820,15821,15822,15824,15825,15826,15827,15828,15829,15830,15831,15832, 15833,15834,15835,15836,15837,15838,15839,15840,15841,15842,15843,15845,15846,15847,15848,15849, 15850,15851,15852,15853,15854,15856,15857,15858,15859,15860,15861,15862,15863,15864,15865,15866, 15867,15868,15869,15870,15871,15872,15873,15874,15875,15876,15877,15878,15879,15880,15881,15882, 15883,15884,15885,15886,15887,15888,15889,15890,15891,15892,15893,15894,15895,15896,15897,15898, 15899,15900,15901,15902,15903,15904,15905,15906,15907,15908,15909,15910,15911,15912,15913,15914, 15915,15916,15917,15918,15919,15920,15921,15922,15923,15924,15925 |
| D372 | 2637,15990,15991 |
| D373 | 15992,15993,15994,15995,15997,15998,15999,16000,16001 |
| D374 | 2638,2640,2641 |
| D375 | 16005.16006 |
| D376 | 16007,16008,16009,16010,16011,16012,16013,16014,16015,16016,16017,16018,16019,16020,16021,16022, 16023,16024,16026,16027,16028,16029,16030,16031,16032,16033,16034,16035,16037,16038,16039,16040, 16041,16042,16043,16044,16045,16046,16048,16049,16050,16051,16052,16053,16054,16055,16056,16057, 16058,16059,16060,16061 |
| D377 | 1544,16069,16070 |
| D378 | 179,16076,16077 |
| D379 | 2651.16078 |
| D380 | 16080,16081,16082 |
| D381 | 679,2652,2653 |
| D382 | 1536.2658 |
| D383 | 683,684,16090 |
| D384 | 16091.16092 |
| D385 | 2660,2661,16095,16096,16097,16099,16100 |
| D386 | 352,2662,16101 |
| D387 | 16108,16109,16110,16111 |
| D388 | 16113,16114,16115 |
| D389 | 16116,16117,16118,16120 |
| D390 | 2668.16122 |
| D391 | 16125.16126 |
| D392 | 16127,16128,16129,16130,16131,16132,16133,16134,16135,16136,16137,16138,16139,16140,16141,16142, 16143,16144,16145 |
| D393 | 2670.16147 |
| D394 | 2671,2672,2673,16148 |
| D395 | 1980.16149 |
| D396 | 16150,16151,16152 |
| D397 | 2675,16153,16154,16155 |
| D398 | 2679,2680,2681 |
| D399 | 2682,2683,2685,2686 |
| D400 | 16160,16161,16162,16163,16164,16165,16166,16167 |
| D401 | 140,149,2694,16171,16172 |
| D402 | 1644,1647,1841,16174,16175,16177 |
| D403 | 2701.16178 |
| D404 | 2706.16185 |
| D405 | 1620.2707 |
| D406 | 16188.16189 |
| D407 | 16191,16192,16193,16195 |
| D408 | 693.2712 |
| D409 | 2713,2714,2715,16197,16198,16199,16200,16201,16202,16203,16204,16205,16206 |
| D410 | 16207.16208 |
| D411 | 2718,3437,16209,16211,16212,16213,16214,16215,16216,16217,16218,16219 |
| D412 | 2723,2724,16225 |
| D413 | 16226.16227 |
| D414 | 16228.16229 |
| D415 | 16233.16234 |
| D416 | 16237,16238,16239,16240 |
| D417 | 697,2728,2729,2730 |
| D418 | 16248,16249,16250,16251,16253,16254,16255,16256,16257,16259,16260,16261,16262 |
| D419 | 16267.16268 |
| D420 | 154.2737 |
| D421 | 16270.16271 |
| D422 | 701.274 |
| D423 | 1344.3443 |
| D424 | 702.16279 |
| D425 | 16280.16281 |
| D426 | 2745.2746 |
| D427 | 704,16285,16286 |
| D428 | 16288,16289,16290,16291,16292,16293,16294,16295 |
| D429 | 707.16298 |
| D430 | 1959.2748 |
| D431 | 2750.16301 |
| D432 | 304,1600,16305,16306 |
| D433 | 39.1356 |
| D434 | 16312.16313 |
| D435 | 16315,16316,16317,16318,16319,16320,16321,16322,16323,16324 |
| D436 | 2762,2763,16325 |
| D437 | 16327.16328 |
| D438 | 712,1079,3570,16330 |
| D439 | 714,2765,16331 |
| D440 | 2766,2767,2768,2769,2770,2771,16332 |
| D441 | 16336.16337 |
| D442 | 16338,16339,16340,16341,16342,16343,16344,16345 |
| D443 | 16346,16347,16349,16350 |
| D444 | 2772,16351,16352,16353 |
| D445 | 16354.16355 |
| D446 | 178.16357 |
| D447 | 16358.16359 |
| D448 | 2778,3489,16373 |
| D449 | 2779.16375 |
| D450 | 16380.16381 |
| D451 | 2787.3583 |
| D452 | 1882.16391 |
| D453 | 2791,16393,16394 |
| D454 | 723,724,16396 |
| D455 | 16399.164 |
| D456 | 725,726,16406 |
| D457 | 16407,16408,16409 |
| D458 | 2795,2796,2797,2798,2799,2800,2801,2802,2803,2804,2805,16410,16411,16412,16415,16416,16417,16418,16420,16421 |
| D459 | 1454.1458 |
| D460 | 16425,16426,16428,16429,16430,16431,16432,16433,16434,16435 |
| D461 | 1602.1603 |
| D462 | 16437.16438 |
| D463 | 16440.16441 |
| D464 | 2812.16442 |
| D465 | 1088,2815,16449,16450 |
| D466 | 1962.1967 |

TABLE III-continued
(Multivariant clusters)

| Internal designation | Variants |
|---|---|
| D467 | 16452,16453,16454,16455,16456,16457,16458 |
| D468 | 16459,16460,16461 |
| D469 | 78.16462 |
| D470 | 16464.16465 |
| D471 | 16468.16469 |
| D472 | 736.1518 |
| D473 | 2825,2826,16475 |
| D474 | 1287.2827 |
| D475 | 16477,16478,16479,16480,16481,16482,16483,16485,16486,16487 |
| D476 | 1124,2832,16488,16489,16490,16491,16492,16493,16494,16495,16496 |
| D477 | 16497,16498,16499,16500,16501 |
| D478 | 739.2835 |
| D479 | 740.741 |
| D480 | 2836.16504 |
| D481 | 742.16505 |
| D482 | 16509.1651 |
| D483 | 16514,16515,16516 |
| D484 | 1693,1697,16520 |
| D485 | 744,1292,2844,2845,2846,2847,2848,16521,16522 |
| D486 | 746,747,748,749,750,751,1304,16526,16527,16528,16530,16531 |
| D487 | 752.16532 |
| D488 | 16534,16535,16536,16537,16538,16539,16540,16541,16542,16543,16545,16546,16547,16548 |
| D489 | 2851.16549 |
| D490 | 16550,16551,16552,16553,16555,16556,16557,16558,16559 |
| D491 | 754.2852 |
| D492 | 342,2853,16562 |
| D493 | 16563.16564 |
| D494 | 16569.1657 |
| D495 | 108,1519,1597 |
| D496 | 1952,1955,1958 |
| D497 | 16574.16575 |
| D498 | 16576,16577,16578 |
| D499 | 1971.16581 |
| D500 | 16587.16588 |
| D501 | 16593.16594 |
| D502 | 2868.16606 |
| D503 | 16607,16608,16609 |
| D504 | 1771,16610,16611 |
| D505 | 1308,2870,2871 |
| D506 | 16614.16615 |
| D507 | 36,16619,16620 |
| D508 | 2874.2875 |
| D509 | 40.16629 |
| D510 | 16630.16631 |
| D511 | 764.765 |
| D512 | 766,3767,3818 |
| D513 | 768,2888,16647 |
| D514 | 769,2892,2893 |
| D515 | 1867,16657,16658 |
| D516 | 1440.2896 |
| D517 | 772.2898 |
| D518 | 773,2900,16662,16663,16664 |
| D519 | 774,16665,16666 |
| D520 | 16668.16669 |
| D521 | 16670,16671,16672,16673 |
| D522 | 16677.16678 |
| D523 | 16679.16681 |
| D524 | 777.2902 |
| D525 | 16683,16684,16685,16686,16687,16688,16689,16690,16691,16692,16693,16694,16695,16696 |
| D526 | 2909,16705,16706,16707,16708,16710,16711,16712,16713,16714 |
| D527 | 16719,16720,16721 |
| D528 | 779.2911 |
| D529 | 16723,16724,16725 |
| D530 | 197,1712,16729,16730,16731,16732,16733,16735 |
| D531 | 198.1711 |
| D532 | 16738,16739,16740 |
| D533 | 16746.16747 |
| D534 | 16751.16752 |
| D535 | 2921,16753,16754,16755 |
| D536 | 2925,16758,16759,16760 |
| D537 | 16762.16763 |
| D538 | 16765,16766,16767,16768 |
| D539 | 16775,16776,16777,16778,16779,16780,16781,16782,16783,16784,16785,16786 |
| D540 | 2933,2934,2935,16787,16788,16791,16792,16793 |
| D541 | 2937.16795 |
| D542 | 788,16796,16797 |
| D543 | 791,1261,1500,16798,16799,16800,16801,16802,16803,16804,16805,16806,16807 |
| D544 | 16812,16813,16814 |
| D545 | 2945.2946 |
| D546 | 797,1819,2949 |
| D547 | 1741.1814 |
| D548 | 2003.2004 |
| D549 | 16825,16826,16827 |
| D550 | 16831.16832 |
| D551 | 801,16833,16834 |
| D552 | 16835.16837 |
| D553 | 1927.193 |
| D554 | 803.804 |
| D555 | 2967,16853,16854 |
| D556 | 91.2968 |
| D557 | 809.297 |
| D558 | 62.64 |
| D559 | 16868,16869,16870,16871,16872 |
| D560 | 2975.16878 |
| D561 | 817.1969 |
| D562 | 818,819,2981,2982,16893 |
| D563 | 1931.16897 |
| D564 | 2985,16899,16900 |
| D565 | 820.16901 |
| D566 | 1687.16903 |
| D567 | 119.16907 |
| D568 | 826,2990,2991,2992 |
| D569 | 1408.2001 |
| D570 | 16912.16913 |
| D571 | 351.16918 |
| D572 | 200,354,831 |
| D573 | 16919.16921 |
| D574 | 16922.16923 |
| D575 | 2043.2053 |
| D576 | 16925,16926,16927,16928,16929,16930,16931,16932,16933,16934,16935,16936,16937,16938,16939,16940,16941,16942,16943,16944,16945,16946,16949,16950,16951,16952,16953,16954,16955,16956,16957,16958,16960,16961,16962,16963,16964,16965,16966,16967,16968,16969,16970,16971,16972,16973,16974,16975,16976,16977,16978,16979,16980,16981,16982,16983,16984,16985,16986,16987,16988,16989,16990,16991,16992,16993,16994,16995,16996,16997,16998,16999,17001,17002,17003,17004,17005,17006,17007,17008,17009,17010,17012,17013,17014,17015,17016,17017,17018,17019,17020,17021,17022,17023,17024,17025,17026,17027,17028,17029,17030,17031,17033,17034,17035,17036,17037,17038,17039,17040,17041,17042,17044,17045,17046,17047,17048,17 |

TABLE III-continued

(Multivariant clusters)

| Internal designation | Variants |
|---|---|
| | 049,17050,17051,17052,17053,1705 |
| | 5,17056,17057,17058,17059,17060, |
| | 17061,17062,17063,17064,17066,17 |
| | 067,17068,17069,17070,17071,1707 |
| | 2,17073,17074,17075,17077,17078, |
| | 17079,17080,17081,17082,17083 |
| D577 | 3007,3008,3009 |
| D578 | 833.17088 |
| D579 | 17095,17096,17097 |
| D580 | 835,2027,2052 |
| D581 | 17103.17104 |
| D582 | 17114.17115 |
| D583 | 840.3024 |
| D584 | 29.1341 |
| D585 | 3027.1712 |
| D586 | 843.844 |
| D587 | 274.17124 |
| D588 | 1795,17125,17126 |
| D589 | 847.3031 |
| D590 | 17141.17142 |
| D591 | 17143,17144,17145,17146,17147,17 |
| | 148,17149,17151 |
| D592 | 851.17154 |
| D593 | 17159.1716 |
| D594 | 3039.304 |
| D595 | 17166.17167 |
| D596 | 17168.17169 |
| D597 | 3043,17170,17171,17172,17173 |
| D598 | 1683.3047 |
| D599 | 855,3050,3051 |
| D600 | 856.3052 |
| D601 | 17182,17183,17184,17185 |
| D602 | 17186,17187,17188 |
| D603 | 279.857 |
| D604 | 121.1469 |
| D605 | 3057.17193 |
| D606 | 861,3060,3061,3062,17197 |
| D607 | 862.17199 |
| D608 | 864,3064,17202 |
| D609 | 865.866 |
| D610 | 17205.17206 |
| D611 | 3066,3067,17207,17208,17209 |
| D612 | 867,868,17210 |
| D613 | 3070.17213 |
| D614 | 1682.3071 |
| D615 | 230.1783 |
| D616 | 17221,17222,17223 |
| D617 | 1894,1895,1898 |
| D618 | 1652.17228 |
| D619 | 3085.17229 |
| D620 | 17232.17233 |
| D621 | 3087,3088,3089,3090,3091,3092,17 |
| | 234,17235 |
| D622 | 872.1724 |
| D623 | 873,874,3099,3100,3101,17252 |
| D624 | 17257.17258 |
| D625 | 17262.17263 |
| D626 | 3105.3106 |
| D627 | 17268,17269,17270,17271 |
| D628 | 17272.17273 |
| D629 | 17276.17277 |
| D630 | 1914.1728 |
| D631 | 17285.17286 |
| D632 | 879,17291,17292 |
| D633 | 1998,17294,17295 |
| D634 | 17296.17297 |
| D635 | 881,3115,17300,17301 |
| D636 | 882.3116 |
| D637 | 17302.17303 |
| D638 | 3121,3122,17309 |
| D639 | 17310,17311,17312,17313 |
| D640 | 883,3124,3125 |
| D641 | 59.6 |
| D642 | 1918,17321,17322,17323 |
| D643 | 888.889 |
| D644 | 3133,3134,3135,3136 |
| D645 | 3137.17335 |
| D646 | 3138.17336 |
| D647 | 1737,1744,3142,17339 |
| D648 | 346,17343,17344 |
| D649 | 17350.17351 |
| D650 | 899,3156,17366 |
| D651 | 3157,3159,3160,3161 |
| D652 | 900.901 |
| D653 | 17368.1737 |
| D654 | 17371.17372 |
| D655 | 3166.17374 |
| D656 | 3169,3170,17378 |
| D657 | 1996,1997,2012,3175 |
| D658 | 3178,17379,17380 |
| D659 | 3181.17381 |
| D660 | 3182.17382 |
| D661 | 17383.17384 |
| D662 | 1973,17391,17392,17393 |
| D663 | 1587,1591,1592,3188 |
| D664 | 156.17402 |
| D665 | 17405.17406 |
| D666 | 17412,17413,17414,17415,17416,17 |
| | 417,17418,17419,17420,17421,1742 |
| | 2,17423 |
| D667 | 909.91 |
| D668 | 3206.3207 |
| D669 | 913,17442,17443,17444,17446,1744 |
| | 7,17448,17449,17450,17451,17452, |
| | 17453,17454,17455,17457 |
| D670 | 17459.1746 |
| D671 | 1485.17464 |
| D672 | 914,2026,2058,3211,17465,17466,1 |
| | 7467 |
| D673 | 17469.1747 |
| D674 | 17474.17475 |
| D675 | 17477.17478 |
| D676 | 17479.1748 |
| D677 | 17481,17482,17483 |
| D678 | 17485.17486 |
| D679 | 918,919,17493 |
| D680 | 17494.17495 |
| D681 | 17497.17499 |
| D682 | 17500,17501,17502,17503 |
| D683 | 3222.17508 |
| D684 | 17509.1751 |
| D685 | 921.922 |
| D686 | 3224.17516 |
| D687 | 3225.3226 |
| D688 | 3230.3231 |
| D689 | 17521.17522 |
| D690 | 17523.17524 |
| D691 | 17525,17526,17527 |
| D692 | 3236,3237,3238 |
| D693 | 3239,3240,3241 |
| D694 | 17537.17538 |
| D695 | 80,927,17547 |
| D696 | 1379,1828,3248 |
| D697 | 17553.17555 |
| D698 | 3250,3251,3252,3253,3254,3255,32 |
| | 56,3257,17556,17557,17558,17559 |
| D699 | 1345,1346,3262,3263,17571,17572, |
| | 17573 |
| D700 | 933.3264 |
| D701 | 934,17579,17580,17582,17583,1758 |
| | 4,17585 |
| D702 | 1528.1554 |
| D703 | 17589.1759 |
| D704 | 17593.17594 |
| D705 | 1393.17596 |
| D706 | 17597.17598 |
| D707 | 937.938 |
| D708 | 17608,17609,17610 |

TABLE III-continued (Multivariant clusters)

| Internal designation | Variants |
|---|---|
| D709 | 939,940,17611,17612 |
| D710 | 17624,17625,17626 |
| D711 | 3272.17629 |
| D712 | 1414,3273 |
| D713 | 3275,3276,17631 |
| D714 | 1843.3277 |
| D715 | 946.947 |
| D716 | 948.17637 |
| D717 | 17644.17645 |
| D718 | 3284.17647 |
| D719 | 17652.17653 |
| D720 | 17654.17655 |
| D721 | 17658.17659 |
| D722 | 17663.17664 |
| D723 | 954.3289 |
| D724 | 3290,3291,3292 |
| D725 | 17666.17667 |
| D726 | 17668,17669,17670,17672 |
| D727 | 955,17673,17674,17675 |
| D728 | 302,1878,1879,1886 |
| D729 | 1599,17681,17682 |
| D730 | 17683.17684 |
| D731 | 17685,17686,17687 |
| D732 | 17690.17691 |
| D733 | 243.181 |
| D734 | 17695.17696 |
| D735 | 185.273 |
| D736 | 17697.17698 |
| D737 | 17699.17701 |
| D738 | 3305.17702 |
| D739 | 966.3307 |
| D740 | 967.3309 |
| D741 | 971,972,17708,17709 |
| D742 | 974.17713 |
| D743 | 1822,17715,17716,17717,17718 |
| D744 | 3314.17721 |
| D745 | 977.17727 |
| D746 | 17728,17729,17730 |
| D747 | 978.979 |
| D748 | 1664,1667,1671 |
| D749 | 980.17749 |
| D750 | 17754,17755,17757 |
| D751 | 17760,17761,17762,17763 |
| D752 | 17765.17766 |
| D753 | 77.79 |
| D754 | 3323.17775 |
| D755 | 262.319 |
| D756 | 988.3325 |
| D757 | 350.991 |
| D758 | 17791.17792 |
| D759 | 17796.17798 |
| D760 | 3327.178 |
| D761 | 3329.333 |
| D762 | 3331.3332 |
| D763 | 1561.1562 |
| D764 | 996,17811,17812 |
| D765 | 71,17813,17814 |
| D766 | 17815.17816 |
| D767 | 3343,3344,3346,3347,3348,17817,17818 |
| D768 | 1953,1954,17819 |
| D769 | 998.17822 |
| D770 | 3352.17823 |
| D771 | 17824.17826 |
| D772 | 3354.3355 |
| D773 | 1001.1718 |
| D774 | 1002.17841 |
| D775 | 17850.17851 |
| D776 | 17853.17854 |
| D777 | 3362,3363,3364,3365,3366,3367 |
| D778 | 1005,1006,1007,1008,1009,1010,1011,1012,1013,1014,1015,1016,1017,1018,1019,1020,1021,1022,1023,1024,1025,1026,1027,1028,1029,3368,3369,3370,3371,3372,3373,3374,3375,3376,3377,3378,17858,17860,17861,17863,17864,17866,17867 |
| D779 | 17871.17872 |
| D780 | 1384.17875 |
| D781 | 1030.1031 |
| D782 | 1032.3382 |
| D783 | 17879.1788 |
| D784 | 17881,17882,17883,17884,17885,17886 |
| D785 | 17892.17895 |
| D786 | 3384,17896,17897 |
| D787 | 1630,17901,17902 |
| D788 | 17905,17906,17907,17908,17909,17910 |
| D789 | 17913.17914 |
| D790 | 3388,17916,17917,17918 |
| D791 | 17919,17920,17921,17922,17923,17924,17925,17926,17927,17928,17929,17930,17931,17932,17933,17934,17935,17936,17937,17938,17939,17940,17941,17942,17943,17944,17945,17946,17947,17948,17949 |
| D792 | 3391.1796 |
| D793 | 17962,17963,17964,17965,17966 |
| D794 | 264,17972,17973,17974,17975,17976,17977 |
| D795 | 17980.17981 |
| D796 | 17986.17987 |
| D797 | 1045.1046 |
| D798 | 263,1050,1837,18000,18001 |
| D799 | 1529.153 |
| D800 | 18003.18004 |
| D801 | 1858.18005 |
| D802 | 18008.18009 |
| D803 | 18018.18019 |
| D804 | 18020,18021,18022 |
| D805 | 18027.18028 |
| D806 | 18042.18043 |
| D807 | 3413.18045 |
| D808 | 1537,18046,18047 |
| D809 | 18050.18051 |
| D810 | 344.1951 |
| D811 | 18059.1806 |
| D812 | 1060.18063 |
| D813 | 240,1062,1063,1064,1066,1067,1068,1069,1070,1988,3421,3422,3423,3426,3427 |
| D814 | 3428.18069 |
| D815 | 3429.18072 |
| D816 | 1071,3430,18073 |
| D817 | 3431.3432 |
| D818 | 18074.18076 |
| D819 | 3433.18081 |
| D820 | 1072.18084 |
| D821 | 3434.18085 |
| D822 | 1073,2009,3435,3436,3438,18087 |
| D823 | 1989.18088 |
| D824 | 1517.18098 |
| D825 | 18104.18105 |
| D826 | 18109.1811 |
| D827 | 1076.18112 |
| D828 | 3445.18114 |
| D829 | 3446,18116,18117 |
| D830 | 340.108 |
| D831 | 18127.18128 |
| D832 | 1081.18132 |
| D833 | 1082.345 |
| D834 | 1083,1084,1085,1086,1087,18135 |
| D835 | 18139,18141,18142,18143,18144,18145,18146,18147,18149,18150,18151,18153,18154,18155,18156,18157,18159,18160,18161,18162,18163,18 |

TABLE III-continued (Multivariant clusters)

| Internal designation | Variants |
|---|---|
| | 164,18165,18166,18168,18169,18171 |
| D836 | 1089,3455,18176 |
| D837 | 1090,1091,1092,1093,1094,1095,3456,3457,3458,3459,3461,18177,18178,18179,18180 |
| D838 | 18182.18183 |
| D839 | 18184.18185 |
| D840 | 3462,18187,18188 |
| D841 | 18191.18192 |
| D842 | 278,282,283,1866,18194 |
| D843 | 18196.18197 |
| D844 | 202,1100,1101,1103,1105,1106,3463,3468,3469,18199,18200,18201,18202,18203,18204,18205,18206,18207,18208,18209,18211,18213,18214,18215,18216,18217 |
| D845 | 3470.18221 |
| D846 | 1107.1565 |
| D847 | 3472,18226,18227,18228,18229 |
| D848 | 18233.18234 |
| D849 | 3476,3477,18236 |
| D850 | 18241,18242,18243 |
| D851 | 3479.18244 |
| D852 | 1903,18245,18246 |
| D853 | 161.1825 |
| D854 | 18251.18252 |
| D855 | 18255.18256 |
| D856 | 18257.18258 |
| D857 | 3482,3483,3484,3485,3486,3487,3488,18262,18263 |
| D858 | 18267.18268 |
| D859 | 3490,3491,3492,18269 |
| D860 | 18271.18272 |
| D861 | 18275.18276 |
| D862 | 1116,3493,3494,18279 |
| D863 | 18285.18286 |
| D864 | 18289,18290,18291 |
| D865 | 1118,3496,18292,18293 |
| D866 | 3498.18295 |
| D867 | 1120.18299 |
| D868 | 18301.18302 |
| D869 | 18305.18306 |
| D870 | 1123,3501,3502,3503,18311,18312,18313,18314 |
| D871 | 18315.18316 |
| D872 | 1127.3506 |
| D873 | 18328,18329,18330 |
| D874 | 18332,18333,18334 |
| D875 | 3509,3510,3511,18340 |
| D876 | 18342.18343 |
| D877 | 3514,3515,18347 |
| D878 | 1131.18348 |
| D879 | 1665.1668 |
| D880 | 18354,18355,18356 |
| D881 | 168.18359 |
| D882 | 18362,18364,18365,18366,18369,18370 |
| D883 | 18372,18373,18374 |
| D884 | 18375.18376 |
| D885 | 1137.3522 |
| D886 | 18390.18391 |
| D887 | 18392.18393 |
| D888 | 18397.18398 |
| D889 | 3526.18404 |
| D890 | 18409.1841 |
| D891 | 1142,18412,18413,18414 |
| D892 | 3530.18418 |
| D893 | 18423.18425 |
| D894 | 1501.18427 |
| D895 | 1472.1478 |
| D896 | 1143.1843 |
| D897 | 173,1677,1680 |
| D898 | 18432,18433,18434 |
| D899 | 18436.18437 |
| D900 | 18442,18443,18444,18445 |
| D901 | 1541,1542,1545,1546,18450,18451,18452,18453,18454,18455,18456,18457 |
| D902 | 18459.1846 |
| D903 | 1149,3546,3547 |
| D904 | 18465.18466 |
| D905 | 3552,18467,18468 |
| D906 | 18469.1847 |
| D907 | 1350.18472 |
| D908 | 3555.3556 |
| D909 | 18479,18480,18481 |
| D910 | 222.1884 |
| D911 | 1154.2045 |
| D912 | 18482.18483 |
| D913 | 3560.18486 |
| D914 | 18488.18489 |
| D915 | 1156.18492 |
| D916 | 18494,18495,18496 |
| D917 | 18501.18502 |
| D918 | 18503.18504 |
| D919 | 1157.3562 |
| D920 | 1158,18507,18508,18509,18510,18511 |
| D921 | 3565.3566 |
| D922 | 1161,1162,1163,1164,1165,1166,1167,1963,3568,3569,3571,3572,18515,18516,18517,18518,18519,18520,18521,18522,18523,18524,18525,18526,18527,18528,18529,18530,18531,18532,18533,18534,18536,18537,18538,18539,18540,18541,18542,18543,18544,18545,18546 |
| D923 | 1168,18548,18549,18550 |
| D924 | 92.1658 |
| D925 | 1170,3578,18551 |
| D926 | 1552,1856,1871,1974,3581,3582,3584,3586,18553,18554 |
| D927 | 1171.3587 |
| D928 | 18562.18564 |
| D929 | 18569,18570,18571,18572,18573 |
| D930 | 1177.18575 |
| D931 | 1178.18577 |
| D932 | 1180,3593,18580 |
| D933 | 1181.18583 |
| D934 | 1659,18584,18585 |
| D935 | 18586,18587,18588 |
| D936 | 1182.3597 |
| D937 | 3598.18589 |
| D938 | 18594.18595 |
| D939 | 3600.3601 |
| D940 | 1184,3602,3603 |
| D941 | 1185,3604,3605,3606 |
| D942 | 1187.3607 |
| D943 | 1188.18598 |
| D944 | 1194.18604 |
| D945 | 3612,3613,18606,18607 |
| D946 | 3614.18609 |
| D947 | 18610.18611 |
| D948 | 1195.18614 |
| D949 | 1196.18615 |
| D950 | 18616.18617 |
| D951 | 1808,3618,3620,18620 |
| D952 | 1493.18621 |
| D953 | 1199.18623 |
| D954 | 18624,18625,18626,18627,18629 |
| D955 | 1606,1607,18631,18632,18633,18634,18635 |
| D956 | 3627,18638,18639 |
| D957 | 1203,1204,1205,1923,18642 |
| D958 | 293.3631 |
| D959 | 1487.18645 |
| D960 | 1377,18646,18647,18648 |

TABLE III-continued

(Multivariant clusters)

| Internal designation | Variants |
|---|---|
| D961 | 1355.18649 |
| D962 | 1208.1209 |
| D963 | 221,18654,18655,18656 |
| D964 | 3640,3641,3642,18660 |
| D965 | 3644.18662 |
| D966 | 3645.18663 |
| D967 | 18664.18665 |
| D968 | 18666.18667 |
| D969 | 35,1343,18671 |
| D970 | 18672.18673 |
| D971 | 18680.18681 |
| D972 | 18683.18684 |
| D973 | 1732,3653,3655 |
| D974 | 1216.18689 |
| D975 | 1217,3656,3657 |
| D976 | 1223,1224,1225,1227,3659,3660,3661,3665,3667,3669,18691,18693,18694,18695,18696,18697,18698,18699,18701,18702,18703,18704,18705,18707,18708,18709,18710,18711,18712,18713,18714,18715,18716,18717,18718,18719,18720,18722,18723,18724,18725,18727,18728,18729,18730,18731,18732,18733,18734,18736,18737,18738,18739,18741,18742,18744,18745,18746,18747,18748,18749,18750,18751,18753,18754,18755,18757,18758,18760,18761,18762,18764,18765,18767,18768,18769,18770,18771,18772,18774,18775,18776,18777,18778,18781,18782,18783,18784,18785,18786,18787,18788,18790 |
| D977 | 3670,3671,3672,3673,3674,3675 |
| D978 | 18795.18796 |
| D979 | 3676.18797 |
| D980 | 3678.18799 |
| D981 | 1375,18816,18818,18819,18820 |
| D982 | 1522.1526 |
| D983 | 18822,18823,18824 |
| D984 | 1231.369 |
| D985 | 1232,1604,1698,3693,3694,3696 |
| D986 | 18835.18836 |
| D987 | 1921.18837 |
| D988 | 18840.18841 |
| D989 | 3701.3702 |
| D990 | 3703.3704 |
| D991 | 1236.1237 |
| D992 | 1238,1891,18847 |
| D993 | 1239,1240,3708,3709,18848 |
| D994 | 3712,3713,3714,18852,18853,18854,18855,18856,18857,18858 |
| D995 | 3715,3716,3717,3718,18860 |
| D996 | 3719.372 |
| D997 | 18864.18865 |
| D998 | 18866.18867 |
| D999 | 18870,18871,18872,18873,18874 |
| D1000 | 18877,18878,18879 |
| D1001 | 18880.18881 |
| D1002 | 3730.18894 |
| D1003 | 3731,3732,18895 |
| D1004 | 3734,18897,18898,18899 |
| D1005 | 1563,1564,1566 |
| D1006 | 3738.3739 |
| D1007 | 1251,1252,1253,1254,1255,1256,1257,2044,3743,18906,18907 |
| D1008 | 1258.1259 |
| D1009 | 311,3744,3745,18911,18913,18915 |
| D1010 | 1262,1263,18916 |
| D1011 | 3748.18918 |
| D1012 | 18921,18924,18927 |
| D1013 | 3750.3751 |
| D1014 | 45,1366,18930 |
| D1015 | 18931.18932 |
| D1016 | 3754,3755,18934,18936,18937,18938,18939 |
| D1017 | 18941.18942 |
| D1018 | 3756,18943,18944 |
| D1019 | 1267.1268 |
| D1020 | 3758,18946,18947 |
| D1021 | 18948.18949 |
| D1022 | 1270,1271,1272,18950,18951,18952 |
| D1023 | 3762,18954,18955 |
| D1024 | 215,3763,3764,18957,18958,18959,18960 |
| D1025 | 18961,18962,18963 |
| D1026 | 18964.18965 |
| D1027 | 1275.377 |
| D1028 | 18968.18969 |
| D1029 | 3771,18971,18972,18973 |
| D1030 | 3775.18983 |
| D1031 | 1276,1277,1278 |
| D1032 | 1279.3776 |
| D1033 | 3778.18986 |
| D1034 | 18987.18988 |
| D1035 | 18989.1899 |
| D1036 | 18992,18993,18994,18995,18996,18997 |
| D1037 | 3782.3783 |
| D1038 | 19000.19001 |
| D1039 | 19002.19003 |
| D1040 | 196.272 |
| D1041 | 3792,3793,3794,3795,3797,3798,3799,19012,19013,19014,19015,19016,19018 |
| D1042 | 3801.3802 |
| D1043 | 19023.19024 |
| D1044 | 1290.19027 |
| D1045 | 167,365,1421,19031,19032,19033,19034 |
| D1046 | 19035.19036 |
| D1047 | 19037,19039,19040,19041 |
| D1048 | 1293.19042 |
| D1049 | 1296,1632,1635 |
| D1050 | 19045,19046,19047 |
| D1051 | 1300.381 |
| D1052 | 19059,19060,19061 |
| D1053 | 3813,3814,3815 |
| D1054 | 19065,19066,19067 |
| D1055 | 19068,19069,19071,19072 |
| D1056 | 3816.19073 |
| D1057 | 3817,19074,19075,19076 |
| D1058 | 3819.382 |
| D1059 | 3822.19079 |
| D1060 | 19081.19082 |
| D1061 | 19083.19084 |
| D1062 | 1305,1970,19093 |
| D1063 | 19095,19096,19097,19098,19099,19100 |
| D1064 | 1734.3828 |
| D1065 | 1309,1310,3832 |
| D1066 | 19115.19116 |
| D1067 | 19117.19118,19119 |
| D1068 | 19122,19123,19124 |
| D1069 | 1314,19125,19126 |
| D1070 | 1315,3837,19134 |
| D1071 | 3839.384 |
| D1072 | 1705.1748 |
| D1073 | 1317,1750,2006,3846,3847,19140 |
| D1074 | 3848,3849,3850,3851,3852,3853,3854,3855,3856,3857,3858,3859 |
| D1075 | 19143.19144 |
| D1076 | 19151,19152,19153,19154,19155,19156,19157,19158,19160 |
| D1077 | 19161.19162 |
| D1078 | 1322,1323,1324,1325,19169,19171,19172,19173 |
| D1079 | 1326,19175,19176 |

TABLE III-continued (Multivariant clusters)

| Internal designation | Variants |
|---|---|
| D1080 | 19182,19183 |
| D1081 | 3870,3871,19191 |

TABLE IVa (Novelty:95%)

| Seq Id No. | Positions of preferred fragments | Seq Id No. | Positions of preferred fragments |
|---|---|---|---|
| 24 | [1–342] | 91 | [1–97] |
| 25 | [1–47] | 92 | [1–586] |
| 30 | [1–54] | 93 | [1–311] |
| 31 | [1–506] | 94 | [1–26],[86–452] |
| 32 | [1–44] | 95 | [1–326] |
| 33 | [1–479] | 96 | [1–383] |
| 35 | [361–386] | 97 | [1–672] |
| 36 | [1–245] | 98 | [1–130],[384–451] |
| 38 | [1–491] | 100 | [1–498] |
| 39 | [1–678] | 102 | [1–248] |
| 41 | [279–353],[415–442] | 103 | [1–351] |
| 43 | [1–512] | 104 | [1–356] |
| 44 | [1–339] | 105 | [1–278] |
| 45 | [1–67],[516–544] | 106 | [1–104],[288–345] |
| 46 | [1–484] | 107 | [1–492] |
| 47 | [1–495] | 108 | [1–38],[235–301] |
| 48 | [1–308],[397–535] | 109 | [1–500] |
| 49 | [1–432] | 110 | [542–570] |
| 50 | [1–410] | 111 | [1–584] |
| 51 | [46–465] | 112 | [1–79] |
| 54 | [1–505] | 113 | [1–402] |
| 55 | [1–546] | 114 | [368–525] |
| 56 | [1–507] | 115 | [1–480] |
| 57 | [1–480] | 116 | [1–496] |
| 58 | [1–392] | 117 | [1–36] |
| 59 | [1–273] | 118 | [1–497] |
| 60 | [1–273] | 119 | [1–542] |
| 63 | [1–343] | 121 | [1–466] |
| 65 | [1–174] | 123 | [289–465] |
| 66 | [390–481] | 124 | [1–488] |
| 67 | [1–478] | 125 | [1–493] |
| 68 | [1–323] | 126 | [1–297] |
| 69 | [1–443] | 127 | [1–463] |
| 71 | [1–329] | 128 | [1–554] |
| 72 | [1–488] | 129 | [1–180],[421–467] |
| 73 | [169–268] | 130 | [1–457] |
| 74 | [1–417] | 131 | [1–392] |
| 75 | [1–420] | 132 | [1–477] |
| 76 | [1–486] | 134 | [1–422] |
| 78 | [1–793] | 135 | [85–286],[327–462],[498–570] |
| 80 | [1–308] | 136 | [1–44] |
| 82 | [1–570] | 137 | [1–502] |
| 86 | [1–516] | 138 | [1–495] |
| 87 | [1–674] | 139 | [1–646] |
| 88 | [1–402] | 140 | [1–36] |
| 89 | [1–473] | 141 | [1–456] |
| 90 | [1–474] | 142 | [1–488] |
| 143 | [1–219] | 198 | [1–178],[293–471] |
| 144 | [1–524] | 200 | [1–391],[523–829] |
| 145 | [1–39],[73–514] | 201 | [247–477] |
| 146 | [1–525] | 203 | [1–451] |
| 147 | [1–438] | 204 | [1–505] |
| 148 | [1–265] | 205 | [1–277] |
| 149 | [1–256] | 206 | [1–701] |
| 150 | [1–320] | 207 | [450–499] |
| 151 | [1–512] | 208 | [1–485] |
| 153 | [1–501] | 209 | [1–458] |
| 154 | [1–225] | 210 | [1–173] |
| 156 | [1–156] | 211 | [1–481] |
| 158 | [1–198] | 212 | [1–452] |

TABLE IVa-continued (Novelty:95%)

| Seq Id No. | Positions of preferred fragments | Seq Id No. | Positions of preferred fragments |
|---|---|---|---|
| 159 | [1–72],[406–533] | 213 | [1–472] |
| 161 | [1–307] | 214 | [1–191] |
| 162 | [1–721] | 215 | [1–321] |
| 163 | [1–495] | 216 | [1–472] |
| 165 | [1–594] | 217 | [1–461] |
| 166 | [1–501] | 220 | [93–480] |
| 168 | [141–195] | 222 | [1–46],[383–483] |
| 169 | [66–148] | 223 | [451–490] |
| 170 | [1–542] | 224 | [1–492] |
| 171 | [1–528] | 225 | [1–37] |
| 172 | [1–450] | 227 | [1–524] |
| 173 | [147–305] | 229 | [1–55] |
| 174 | [1–514] | 230 | [1–306] |
| 175 | [161–286] | 231 | [1–35],[238–308] |
| 176 | [1–501] | 233 | [80–253] |
| 177 | [1–31] | 234 | [1–405] |
| 178 | [1–542] | 235 | [1–594] |
| 179 | [1–194],[278–303] | 236 | [1–400] |
| 180 | [1–504] | 237 | [1–481] |
| 181 | [1–35] | 238 | [1–663] |
| 182 | [1–509] | 239 | [1–540] |
| 183 | [1–501] | 240 | [1–559] |
| 184 | [1–466] | 241 | [1–479] |
| 186 | [1–485] | 242 | [1–516] |
| 187 | [1–197],[486–521] | 243 | [1–558] |
| 188 | [1–332] | 244 | [1–478] |
| 189 | [1–262] | 245 | [1–438] |
| 190 | [1–79],[258–552] | 246 | [1–451] |
| 191 | [121–164] | 247 | [1–458] |
| 192 | [1–249] | 248 | [1–473] |
| 193 | [1–324] | 249 | [1–322] |
| 194 | [1–334] | 250 | [1–548] |
| 195 | [1–337] | 251 | [1–453] |
| 197 | [1–49] | 252 | [541–578] |
| 253 | [1–672] | 322 | [251–462] |
| 254 | [1–368] | 323 | [50–235] |
| 256 | [158–476] | 324 | [1–496] |
| 257 | [1–506] | 325 | [1–520] |
| 258 | [1–447] | 326 | [251–417] |
| 260 | [1–467] | 327 | [1–292] |
| 261 | [1–508] | 328 | [1–179],[435–515] |
| 262 | [1–477] | 330 | [1–26] |
| 263 | [1–238] | 333 | [1–496] |
| 264 | [1–571] | 334 | [1–461] |
| 265 | [1–155],[271–497] | 335 | [251–475] |
| 267 | [69–483] | 337 | [1–638] |
| 274 | [1–473] | 340 | [1–286],[346–511] |
| 275 | [1–27],[65–212] | 341 | [1–487] |
| 276 | [364–469] | 342 | [1–79],[138–460] |
| 278 | [1–472] | 343 | [1–452] |
| 282 | [1–490] | 344 | [1–478] |
| 283 | [1–479] | 345 | [40–142] |
| 284 | [1–489] | 346 | [1–537] |
| 285 | [1–466] | 347 | [1–488] |
| 286 | [1–451] | 348 | [1–470] |
| 287 | [1–609] | 349 | [1–564] |
| 288 | [1–296] | 350 | [1–494] |
| 289 | [1–503] | 351 | [1–520] |
| 290 | [1–386] | 352 | [1–490] |
| 291 | [1–499] | 353 | [1–491] |
| 293 | [1–112],[384–432] | 354 | [1–59],[286–363] |
| 295 | [1–322] | 356 | [1–522] |
| 296 | [1–40] | 357 | [1–485] |
| 297 | [1–496] | 358 | [1–470] |
| 298 | [1–451] | 359 | [1–332] |
| 300 | [1–53],[138–248] | 361 | [1–737] |
| 301 | [1–92],[319–378] | 362 | [410–470] |
| 302 | [1–483] | 363 | [1–451] |
| 303 | [1–496] | 364 | [1–488] |
| 305 | [1–522] | 366 | [1–455] |
| 306 | [1–140] | 367 | [1–494] |
| 307 | [1–25] | 369 | [1–482] |
| 309 | [1–483] | 370 | [1–513] |
| 310 | [1–467] | 371 | [1–437] |

TABLE IVa-continued (Novelty:95%)

| Seq Id No. | Positions of preferred fragments | Seq Id No. | Positions of preferred fragments |
|---|---|---|---|
| 312 | [1–88],[334–493] | 372 | [1–394] |
| 313 | [1–163],[442–570] | 373 | [1–474] |
| 314 | [1–386] | 374 | [1–319] |
| 315 | [32–128],[160–482] | 375 | [1–429] |
| 317 | [1–92],[371–460] | 376 | [1–524] |
| 318 | [1–557] | 377 | [1–459] |
| 319 | [1–587] | 378 | [1–284] |
| 379 | [1–496] | 436 | [1–64],[352–493] |
| 380 | [1–54],[422–495] | 437 | [1–457] |
| 382 | [1–300] | 438 | [1–343] |
| 383 | [1–569] | 439 | [1–428] |
| 384 | [1–480] | 440 | [1–537] |
| 385 | [1–421] | 441 | [1–28],[113–197] |
| 386 | [1–498] | 442 | [1–502] |
| 387 | [1–497] | 443 | [1–467] |
| 388 | [1–474] | 444 | [1–464] |
| 389 | [127–320] | 445 | [1–382] |
| 390 | [1–42] | 446 | [1–476] |
| 391 | [1–457] | 447 | [1–505] |
| 392 | [1–309] | 448 | [1–495] |
| 393 | [1–349] | 449 | [1–503] |
| 395 | [1–409] | 450 | [1–461] |
| 397 | [1–443] | 451 | [1–507] |
| 398 | [1–574] | 452 | [1–480] |
| 399 | [1–114] | 453 | [1–511] |
| 400 | [75–456] | 454 | [150–493] |
| 401 | [1–482] | 455 | [1–46] |
| 402 | [200–227] | 456 | [1–483] |
| 404 | [1–417] | 457 | [1–100] |
| 406 | [1–207],[330–450] | 458 | [1–378] |
| 407 | [1–510] | 459 | [1–517] |
| 408 | [1–435] | 461 | [1–528] |
| 409 | [1–485] | 463 | [1–323] |
| 410 | [1–37] | 465 | [227–303] |
| 411 | [1–482] | 466 | [1–497] |
| 412 | [1–482] | 467 | [439–480] |
| 413 | [1–419] | 469 | [1–388] |
| 414 | [1–463] | 470 | [1–478] |
| 415 | [1–219] | 471 | [1–467] |
| 416 | [1–460] | 472 | [1–33] |
| 417 | [1–474] | 473 | [1–550] |
| 419 | [1–172] | 474 | [1–303] |
| 420 | [1–505] | 475 | [1–169] |
| 421 | [1–504] | 476 | [1–471] |
| 425 | [1–407] | 477 | [1–252] |
| 426 | [282–324] | 478 | [1–472] |
| 427 | [1–322] | 479 | [1–510] |
| 428 | [1–498] | 480 | [1–505] |
| 430 | [1–83],[411–469] | 482 | [1–286] |
| 431 | [1–464] | 483 | [1–451] |
| 432 | [1–494] | 484 | [161–244] |
| 433 | [1–413] | 485 | [1–482] |
| 434 | [1–323] | 486 | [1–81],[156–383] |
| 435 | [1–548] | 487 | [1–370] |
| 489 | [1–234] | 542 | [1–455] |
| 490 | [1–458] | 543 | [1–469] |
| 491 | [1–457] | 544 | [77–490] |
| 492 | [1–486] | 545 | [1–467] |
| 493 | [1–452] | 546 | [1–454] |
| 494 | [1–295] | 547 | [1–485] |
| 495 | [1–63] | 548 | [1–526] |
| 496 | [1–83],[252–468] | 549 | [1–484] |
| 497 | [1–481] | 550 | [1–457] |
| 498 | [1–296] | 551 | [1–527] |
| 499 | [1–422] | 552 | [1–27] |
| 500 | [1–461] | 553 | [1–513] |
| 501 | [1–506] | 554 | [1–463] |
| 502 | [34–427] | 555 | [1–232] |
| 504 | [1–489] | 556 | [1–491] |
| 505 | [1–237],[287–374] | 557 | [1–474] |
| 506 | [207–458] | 558 | [1–471] |
| 508 | [1–473] | 559 | [1–384] |
| 509 | [1–469] | 560 | [1–470] |
| 510 | [1–486] | 561 | [137–504] |
| 512 | [1–270] | 563 | [1–373] |
| 513 | [1–470] | 564 | [1–481] |
| 514 | [1–383],[425–453] | 565 | [1–492] |
| 515 | [1–480] | 566 | [1–509] |
| 516 | [1–496] | 567 | [1–479] |
| 517 | [1–478] | 568 | [33–110],[139–361],[431–468] |
| 518 | [1–458] | 569 | [1–375] |
| 519 | [1–560] | 570 | [1–486] |
| 520 | [1–465] | 571 | [49–601] |
| 521 | [1–181] | 572 | [1–253] |
| 522 | [1–278] | 573 | [1–496] |
| 523 | [1–417] | 574 | [277–317] |
| 524 | [1–466] | 575 | [1–161] |
| 525 | [1–469] | 576 | [1–134] |
| 526 | [1–240] | 577 | [1–507] |
| 528 | [1–457] | 578 | [1–223] |
| 529 | [1–495] | 579 | [1–510] |
| 531 | [1–467] | 580 | [263–412] |
| 532 | [1–487] | 581 | [1–480] |
| 533 | [1–491] | 582 | [1–509] |
| 534 | [1–193] | 583 | [1–458] |
| 535 | [1–395] | 584 | [1–538] |
| 536 | [1–248] | 585 | [1–42],[145–513] |
| 537 | [1–501] | 586 | [1–531] |
| 538 | [1–225] | 587 | [1–329] |
| 539 | [1–401] | 588 | [1–491] |
| 540 | [285–472] | 589 | [1–525] |
| 590 | [1–452] | 645 | [1–322] |
| 591 | [1–523] | 646 | [1–336] |
| 592 | [1–470] | 647 | [1–368] |
| 593 | [1–95] | 648 | [1–483] |
| 594 | [169–238] | 649 | [1–511] |
| 595 | [1–374] | 650 | [1–138],[175–489] |
| 596 | [1–460] | 651 | [1–295] |
| 597 | [1–461] | 653 | [1–519] |
| 598 | [188–263] | 654 | [1–294] |
| 600 | [1–505] | 656 | [1–486] |
| 601 | [1–169] | 657 | [1–510] |
| 602 | [1–247] | 658 | [1–553] |
| 604 | [184–416] | 660 | [1–460] |
| 605 | [1–92] | 661 | [1–451] |
| 607 | [1–448] | 662 | [1–487] |
| 608 | [1–208] | 663 | [1–458] |
| 609 | [35–246] | 664 | [1–535] |
| 610 | [62–159] | 665 | [1–488] |
| 611 | [1–459] | 666 | [1–539] |
| 612 | [1–148] | 667 | [54–490] |
| 613 | [1–26] | 668 | [1–152],[289–498] |
| 614 | [1–506] | 669 | [1–540] |
| 615 | [1–488] | 670 | [1–497] |
| 616 | [1–481] | 671 | [1–506] |
| 617 | [1–494] | 673 | [1–35],[64–192] |
| 618 | [1–358] | 674 | [1–469] |
| 619 | [1–208] | 675 | [1–491] |
| 620 | [1–208] | 676 | [1–429] |
| 621 | [1–278] | 677 | [1–497] |
| 622 | [1–476] | 678 | [1–473] |
| 623 | [1–83] | 679 | [1–39] |
| 624 | [1–448] | 681 | [1–399] |
| 626 | [1–463] | 682 | [1–508] |
| 627 | [1–487] | 683 | [1–535] |
| 628 | [1–31] | 684 | [1–308] |
| 629 | [1–478] | 685 | [1–452] |
| 631 | [1–458] | 686 | [1–120] |
| 632 | [1–502] | 687 | [1–497] |
| 633 | [1–485] | 688 | [1–499] |
| 634 | [1–464] | 689 | [1–467] |
| 635 | [1–494] | 690 | [179–523] |
| 636 | [1–480] | 691 | [1–473] |
| 639 | [1–469] | 692 | [1–503] |
| 640 | [1–217] | 693 | [1–457] |
| 641 | [1–458] | 694 | [1–114],[276–541] |
| 642 | [321–497] | 695 | [1–339] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 643 | [1–272] | 696 | [1–172] | 843 | [1–536] | 894 | [1–257],[477–548] |
| 697 | [1–95] | 757 | [1–90],[462–494] | 844 | [1–526] | 895 | [1–499] |
| 698 | [1–435] | 758 | [1–392] | 845 | [1–58] | 896 | [1–323] |
| 699 | [1–518] | 759 | [1–169] | 846 | [1–170] | 898 | [1–453] |
| 700 | [1–387] | 760 | [1–467] | 847 | [1–471] | 900 | [1–422] |
| 701 | [94–332],[442–487] | 761 | [1–91] | 848 | [1–269] | 901 | [1–359] |
| 702 | [1–480] | 762 | [1–28] | 849 | [1–518] | 902 | [1–498] |
| 703 | [1–496] | 763 | [223–345] | 850 | [1–475] | 903 | [1–363] |
| 704 | [1–35],[462–492] | 764 | [1–472] | 851 | [1–492] | 904 | [1–539] |
| 705 | [1–479] | 765 | [1–457] | 852 | [1–474] | 905 | [1–170] |
| 706 | [1–369] | 766 | [460–492] | 853 | [1–290],[471–546] | 906 | [1–485] |
| 707 | [1–401] | 769 | [65–132],[286–327] | 854 | [1–241] | 907 | [1–464] |
| 708 | [1–501] | 770 | [1–477] | 855 | [1–484] | 908 | [1–469] |
| 709 | [1–170],[359–400] | 771 | [1–60],[92–506] | 858 | [1–514] | 909 | [1–707] |
| 710 | [1–318],[427–472] | 772 | [1–376] | 859 | [1–481] | 910 | [1–604] |
| 711 | [1–169] | 773 | [1–224],[392–440] | 860 | [1–508] | 911 | [260–286],[345–452] |
| 712 | [455–484] | 774 | [1–498] | 861 | [1–535] | 912 | [1–173] |
| 713 | [1–490] | 775 | [1–498] | 862 | [1–504] | 913 | [1–413] |
| 714 | [1–28] | 776 | [1–487] | 863 | [1–403] | 914 | [226–347] |
| 715 | [1–525] | 777 | [1–452],[629–748] | 864 | [1–56] | 916 | [1–492] |
| 716 | [1–454] | 778 | [1–250],[473–589] | 865 | [1–557] | 918 | [332–462] |
| 717 | [1–452] | 779 | [1–471] | 866 | [1–537] | 919 | [332–517] |
| 720 | [94–469] | 780 | [1–80],[223–264],[530–704] | 867 | [1–496] | 920 | [1–356] |
| 721 | [1–191] | 781 | [1–133] | 921 | [1–526] | 974 | [1–282] |
| 722 | [1–560] | 782 | [1–487] | 922 | [1–478] | 975 | [1–229] |
| 725 | [97–148] | 783 | [134–516] | 923 | [1–474] | 976 | [1–479] |
| 727 | [1–145] | 784 | [1–468] | 924 | [1–434] | 977 | [1–514] |
| 728 | [249–478] | 785 | [1–515] | 925 | [1–523] | 978 | [39–266] |
| 729 | [1–289] | 786 | [1–516] | 926 | [1–522] | 980 | [1–85] |
| 731 | [1–329] | 787 | [1–476] | 927 | [1–358] | 981 | [1–503] |
| 732 | [1–380] | 788 | [410–618] | 929 | [1–247] | 982 | [1–31] |
| 733 | [1–381] | 789 | [1–169] | 930 | [60–196] | 983 | [1–414] |
| 734 | [1–280] | 790 | [439–494] | 931 | [1–458] | 984 | [1–540] |
| 737 | [1–474] | 791 | [1–464] | 932 | [1–529] | 985 | [1–482] |
| 738 | [1–378] | 792 | [1–484] | 935 | [1–404] | 986 | [1–488] |
| 740 | [1–95],[363–454] | 793 | [1–130],[169–492] | 936 | [1–504] | 987 | [1–429] |
| 741 | [1–103],[371–463] | 794 | [410–453] | 937 | [1–602] | 988 | [1–492] |
| 742 | [1–503] | 796 | [1–489] | 938 | [1–495] | 989 | [1–509] |
| 743 | [1–327] | 798 | [1–478] | 939 | [1–521] | 990 | [283–383] |
| 745 | [1–473] | 800 | [1–198],[263–577] | 940 | [1–539] | 991 | [1–551] |
| 746 | [1–519] | 801 | [1–194] | 941 | [1–557] | 992 | [268–549] |
| 747 | [63–442] | 803 | [1–466] | 942 | [1–479] | 993 | [1–508] |
| 748 | [63–442] | 804 | [1–448] | 943 | [1–476] | 995 | [1–229] |
| 749 | [63–454] | 805 | [1–484] | 944 | [1–529] | 996 | [1–229] |
| 750 | [63–459] | 806 | [1–47],[132–510] | 945 | [1–605] | 1000 | [1–319] |
| 751 | [63–442] | 807 | [1–474] | 946 | [1–488] | 1001 | [1–490] |
| 754 | [1–487] | 809 | [1–96] | 947 | [1–285] | 1002 | [1–584] |
| 755 | [138–499] | 810 | [1–207] | 948 | [1–345] | 1003 | [1–520] |
| 811 | [1–38],[179–323],[410–451] | 868 | [1–491] | 949 | [1–557] | 1004 | [1–490] |
| 812 | [1–258] | 869 | [131–353] | 951 | [94–515] | 1005 | [1–452] |
| 814 | [1–484] | 870 | [1–209],[261–516] | 952 | [1–131] | 1006 | [1–348] |
| 815 | [1–543] | 871 | [1–183] | 953 | [1–260] | 1007 | [1–460] |
| 816 | [1–480] | 872 | [1–348] | 954 | [105–148] | 1008 | [1–443] |
| 817 | [1–507] | 873 | [331–365],[510–542] | 955 | [1–506] | 1009 | [1–425] |
| 818 | [1–69] | 874 | [304–339] | 956 | [1–267] | 1010 | [1–508] |
| 820 | [1–332] | 875 | [1–169] | 957 | [435–628] | 1011 | [1–468] |
| 821 | [1–409] | 877 | [1–246] | 958 | [1–525] | 1012 | [1–429] |
| 822 | [1–169] | 878 | [1–473] | 960 | [1–502] | 1013 | [1–494] |
| 826 | [1–331] | 879 | [1–486] | 961 | [1–525] | 1014 | [1–252] |
| 828 | [1–316] | 880 | [1–464] | 962 | [1–444] | 1015 | [1–429] |
| 829 | [1–482] | 882 | [1–489] | 964 | [1–384],[413–457] | 1016 | [63–413] |
| 831 | [1–58] | 883 | [1–504] | 965 | [1–498] | 1017 | [63–430] |
| 832 | [1–494] | 884 | [1–348] | 966 | [1–119],[162–311] | 1018 | [1–509] |
| 833 | [1–497] | 885 | [1–484] | 967 | [1–43] | 1019 | [1–516] |
| 834 | [1–650] | 886 | [1–499] | 968 | [1–549] | 1020 | [1–507] |
| 835 | [1–259] | 887 | [1–455] | 969 | [1–120] | 1021 | [1–411] |
| 836 | [1–486] | 888 | [1–452] | 970 | [1–459] | 1022 | [1–487] |
| 837 | [1–221] | 889 | [1–94],[124–489] | 971 | [1–492] | 1023 | [1–480] |
| 838 | [1–225] | 890 | [1–493] | 972 | [1–471] | 1024 | [1–443] |
| 840 | [1–510] | 891 | [1–408] | 973 | [35–181] | 1025 | [1–440] |
| 841 | [1–344] | 892 | [1–517] | 1026 | [1–464] | 1083 | [1–184] |
| 842 | [1–513] | 893 | [1–479] | 1027 | [63–524] | 1084 | [56–91],[166–418] |
|  |  |  |  | 1028 | [1—381] | 1086 | [165–415] |
|  |  |  |  | 1029 | [1–418] | 1088 | [1–33],[150–188] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 1030 | [1–474] | 1089 | [1–52] | 1184 | [1–486] | 1245 | [1–241] |
| 1031 | [1–556] | 1091 | [1–625] | 1186 | [75–189],[301–338], [483–548] | 1246 | [1–194] |
| 1032 | [1–537] | 1092 | [1–484] | | | | |
| 1033 | [1–425] | 1093 | [1–495] | 1187 | [1–510] | 1247 | [1–504] |
| 1034 | [1–462] | 1094 | [1–513] | 1188 | [1–472] | 1248 | [1–365] |
| 1035 | [1–455] | 1096 | [204–353],[386–439] | 1190 | [1–536] | 1249 | [1–468] |
| 1036 | [1–447] | 1097 | [1–550] | 1191 | [1–476] | 1250 | [1–537] |
| 1038 | [1–56] | 1098 | [1–517] | 1192 | [1–553] | 1251 | [1–568] |
| 1040 | [1–357] | 1099 | [1–485] | 1193 | [1–574] | 1252 | [1–492] |
| 1041 | [1–454] | 1102 | [1–88] | 1194 | [1–469] | 1253 | [1–528] |
| 1042 | [1–479] | 1104 | [1–487] | 1195 | [1–479] | 1254 | [1–515] |
| 1043 | [1–45] | 1107 | [1–361] | 1198 | [1–461] | 1255 | [1–512] |
| 1044 | [41–516] | 1108 | [1–526] | 1199 | [1–62] | 1256 | [1–481] |
| 1045 | [1–231] | 1109 | [1–194] | 1200 | [1–486] | 1257 | [1–484] |
| 1046 | [1–236] | 1110 | [1–523] | 1201 | [1–208] | 1258 | [1–170] |
| 1047 | [1–177] | 1113 | [179–484] | 1202 | [1–512] | 1259 | [342–386] |
| 1049 | [1–470] | 1114 | [1–220] | 1203 | [1–42],[123–148], [255–285] | 1260 | [67–371],[450–554] |
| 1050 | [1–238],[474—531] | 1115 | [222–261] | | | | |
| 1051 | [46–516] | 1116 | [1–367] | 1204 | [138–163],[270–300] | 1261 | [1–651] |
| 1056 | [1–486] | 1117 | [1–523] | 1262 | [1–97],[168–491] | 1323 | [1–204] |
| 1057 | [1–422] | 1118 | [1–135],[176–406] | 1264 | [1–490] | 1324 | [1–240] |
| 1058 | [1–450] | 1120 | [1–51] | 1265 | [1–540] | 1325 | [1–212] |
| 1059 | [1–567] | 1121 | [1–284] | 1266 | [1–308] | 1326 | [448–511] |
| 1060 | [1–452] | 1122 | [1–559] | 1267 | [1–516] | 1327 | [451–480] |
| 1061 | [1–92] | 1123 | [1–399] | 1268 | [1–612] | 1328 | [1–472] |
| 1062 | [1–402] | 1124 | [1–551] | 1270 | [1–210] | 1329 | [1–453] |
| 1063 | [1–468] | 1125 | [1–484] | 1271 | [1–311] | 1330 | [1–498] |
| 1064 | [1–557] | 1126 | [1–533] | 1272 | [1–249] | 1331 | [1–86] |
| 1066 | [1–315] | 1128 | [1–502] | 1273 | [1–435] | 1332 | [1–477] |
| 1067 | [1–483] | 1129 | [1–427] | 1274 | [1–227] | 1333 | [1–349] |
| 1068 | [1–379] | 1131 | [1–93],[439–471] | 1275 | [123–519] | 1334 | [1–394] |
| 1069 | [1–506] | 1132 | [1–528] | 1276 | [1–540] | 1335 | [1–341] |
| 1070 | [1–493] | 1133 | [1–349] | 1277 | [1–496] | 1336 | [1–318] |
| 1071 | [1–52],[413–529] | 1135 | [1–564] | 1278 | [1–487] | 1337 | [1–480] |
| 1072 | [1–396] | 1136 | [1–522] | 1279 | [1–315],[420–482] | 1338 | [30–212] |
| 1073 | [1–327] | 1137 | [1–524] | 1281 | [1–75] | 1342 | [1–464] |
| 1074 | [1–564] | 1138 | [1–356] | 1282 | [1–512] | 1345 | [121–225],[255–645] |
| 1075 | [1–492] | 1139 | [1–165] | 1283 | [1–519] | 1346 | [121–225],[255–422] |
| 1076 | [1–74] | 1140 | [1–479] | 1284 | [1–476] | 1347 | [1–169] |
| 1077 | [1–521] | 1141 | [1–494] | 1285 | [1–77] | 1348 | [1–86] |
| 1080 | [1–287],[347–509] | 1142 | [1–29],[149–219], [360–393] | 1287 | [1–490] | 1351 | [1–262] |
| | | | | 1288 | [1–74] | 1352 | [1–452] |
| 1081 | [1–190],[292–444] | 1143 | [1–510] | 1289 | [1–420] | 1354 | [1–511] |
| 1082 | [1–480] | 1144 | [1–468] | 1290 | [1–512] | 1355 | [1–619] |
| 1145 | [1–239] | 1205 | [1–42],[256–286] | 1291 | [1–527] | 1356 | [1–1108] |
| 1147 | [1–100] | 1206 | [1–153] | 1293 | [1–308],[390–484] | 1357 | [1–380] |
| 1149 | [1–505] | 1208 | [1–457] | 1294 | [1–366] | 1358 | [1–523] |
| 1151 | [1–529] | 1209 | [1–487] | 1295 | [1–467] | 1360 | [1–486] |
| 1152 | [1–371] | 1210 | [1–601] | 1296 | [1–263] | 1362 | [1–642] |
| 1153 | [1–452] | 1211 | [1–561] | 1297 | [1–27] | 1363 | [1–469] |
| 1154 | [1–223],[429–455] | 1212 | [1–454] | 1300 | [45–562] | 1364 | [1–489] |
| 1155 | [1–459] | 1213 | [1–243] | 1305 | [1–375] | 1365 | [1–567] |
| 1156 | [1–494] | 1214 | [48–268] | 1307 | [1–485] | 1366 | [1–67] |
| 1157 | [1–557] | 1215 | [1–357] | 1308 | [267–339] | 1368 | [1–498] |
| 1158 | [349–458] | 1216 | [1–505] | 1309 | [1–450] | 1369 | [1–232] |
| 1159 | [1–482] | 1218 | [1–455] | 1310 | [1–459] | 1372 | [1–514] |
| 1160 | [233–536] | 1219 | [1–453] | 1311 | [1–487] | 1374 | [1–514] |
| 1161 | [1–402],[464–507] | 1220 | [1–453] | 1312 | [1–516] | 1375 | [1–490] |
| 1162 | [1–401] | 1222 | [1–460] | 1313 | [1–471] | 1378 | [433–462] |
| 1163 | [1–401],[456–488] | 1226 | [1–202] | 1314 | [221–504] | 1379 | [1–34],[443–503] |
| 1164 | [1–405],[467–491] | 1228 | [1–594] | 1315 | [1–492] | 1380 | [1–475] |
| 1165 | [1–362] | 1229 | [1–579] | 1316 | [1–333] | 1381 | [271–470] |
| 1166 | [1–402],[464–488] | 1231 | [1–517] | 1317 | [446–471] | 1382 | [1–579] |
| 1167 | [1–400] | 1232 | [1–318] | 1318 | [44–144],[331–505] | 1383 | [1–362] |
| 1168 | [257–322] | 1233 | [1–42],[137–248] | 1319 | [1–562] | 1384 | [1–902] |
| 1169 | [1–388] | 1234 | [1–127],[183–489] | 1322 | [1–221] | 1385 | [1–471] |
| 1172 | [1–564] | 1235 | [1–317] | 1388 | [451–492] | 1448 | [1–461] |
| 1173 | [1–469] | 1236 | [1–485] | 1389 | [1–40] | 1449 | [1–240] |
| 1174 | [1–498] | 1237 | [1–455] | 1391 | [1–803] | 1450 | [1–239] |
| 1177 | [1–364] | 1238 | [376–536] | 1392 | [1–540] | 1451 | [1–240] |
| 1179 | [1–915] | 1239 | [1–468] | 1393 | [1–137] | 1452 | [1–239] |
| 1180 | [58–557] | 1240 | [1–567] | 1395 | [306–340] | 1453 | [1–686] |
| 1181 | [1–235] | 1242 | [1–409] | 1396 | [1–510] | 1455 | [1–506] |
| 1183 | [1–436] | 1244 | [1–563] | 1398 | [1–490] | 1456 | [1–491] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 1399 | [1–227],[311–477] | 1457 | [1–487] | 1549 | [1–425] | 1606 | [1–141] |
| 1400 | [1–428] | 1458 | [318–437] | 1550 | [1–544] | 1607 | [482–506] |
| 1401 | [293–426] | 1459 | [1–522] | 1551 | [1–508] | 1608 | [1–355] |
| 1402 | [1–496] | 1460 | [1–379] | 1552 | [1–44] | 1609 | [1–453] |
| 1403 | [474–524] | 1461 | [1–474] | 1553 | [1–679] | 1610 | [1–491] |
| 1404 | [1–484] | 1463 | [1–830] | 1554 | [1–225],[315–357] | 1611 | [252–354] |
| 1405 | [1–481] | 1465 | [573–623] | 1555 | [417–546] | 1612 | [1–311] |
| 1406 | [1–769] | 1466 | [211–411] | 1556 | [1–430] | 1615 | [1–513] |
| 1407 | [1–568] | 1469 | [1–481] | 1557 | [1–492] | 1616 | [1–954] |
| 1410 | [1–552] | 1470 | [1–505] | 1558 | [1–540] | 1617 | [1–441] |
| 1411 | [1–470] | 1472 | [1–72] | 1559 | [1–490] | 1618 | [1–461] |
| 1413 | [1–273] | 1473 | [1–76] | 1561 | [1–466] | 1619 | [1–468] |
| 1414 | [1–504] | 1475 | [1–472] | 1562 | [1–525] | 1620 | [82–113] |
| 1415 | [1–80],[114–583] | 1476 | [1–486] | 1563 | [1–515] | 1622 | [1–526] |
| 1417 | [1–420] | 1477 | [1–1111] | 1623 | [1–513] | 1679 | [1–459] |
| 1418 | [1–30],[417–498] | 1478 | [1–72],[450–516] | 1624 | [1–477] | 1680 | [147–305] |
| 1419 | [1–173],[479–525] | 1479 | [1–532] | 1625 | [1–396] | 1681 | [1–412] |
| 1420 | [1–490] | 1482 | [1–415] | 1626 | [1–463] | 1682 | [1–517] |
| 1422 | [1–520] | 1485 | [1–190],[440–512] | 1627 | [1–508] | 1683 | [1–36],[455–486] |
| 1423 | [1–476] | 1486 | [1–480] | 1628 | [1–321] | 1684 | [1–328],[405–523] |
| 1425 | [180–544] | 1489 | [1–436] | 1629 | [1–348] | 1685 | [1–691] |
| 1426 | [1–386],[469–554] | 1490 | [1–678] | 1630 | [1–486] | 1686 | [1–448] |
| 1428 | [1–325] | 1491 | [1–278],[308–453] | 1631 | [1–472] | 1687 | [1–517] |
| 1429 | [1–540] | 1492 | [1–483] | 1632 | [1–259] | 1688 | [1–456] |
| 1430 | [1–495] | 1493 | [1–496] | 1633 | [1–25],[198–453] | 1689 | [330–506] |
| 1431 | [144–494] | 1495 | [1–427] | 1634 | [1–485] | 1690 | [1–464] |
| 1434 | [1–500] | 1496 | [1–266],[306–510] | 1635 | [1–283],[413–457] | 1692 | [1–472] |
| 1435 | [1–216],[284–325],[379–510] | 1497 | [494–540] | 1636 | [1–476] | 1693 | [1–454] |
| 1436 | [123–255] | 1498 | [1–776] | 1637 | [1–183] | 1694 | [1–469] |
| 1437 | [107–497] | 1499 | [1–334] | 1638 | [1–437] | 1695 | [1–293] |
| 1438 | [1–336] | 1500 | [1–454] | 1639 | [1–478] | 1696 | [1–577] |
| 1440 | [293–339] | 1501 | [1–435] | 1640 | [1–182],[214–484] | 1697 | [1–465] |
| 1441 | [1–343] | 1502 | [1–270] | 1641 | [1–379] | 1698 | [1–433] |
| 1442 | [1–523] | 1503 | [1–372] | 1642 | [1–456] | 1700 | [1–782] |
| 1443 | [1–466] | 1504 | [1–374] | 1643 | [1–600] | 1701 | [1–85] |
| 1444 | [1–54],[240–401],[436–510] | 1505 | [1–517] | 1645 | [1–468] | 1702 | [1–172] |
| 1445 | [1–239] | 1506 | [1–524] | 1646 | [1–488] | 1703 | [1–42],[127–457] |
| 1446 | [1–484] | 1509 | [1–459] | 1647 | [1–248] | 1704 | [1–130],[583–621] |
| 1447 | [1–26],[318–364] | 1510 | [1–433] | 1648 | [1–414] | 1705 | [1–544] |
| 1511 | [1–537] | 1564 | [1–522] | 1650 | [1–413] | 1706 | [1–489] |
| 1514 | [1–509] | 1565 | [1–335] | 1651 | [1–437] | 1707 | [1–505] |
| 1516 | [1–543] | 1566 | [1–474] | 1652 | [1–107],[136–473] | 1708 | [1–457] |
| 1517 | [1–362],[623–752] | 1567 | [443–521] | 1653 | [1–517] | 1709 | [1–509] |
| 1519 | [1–63] | 1568 | [1–42],[303–386] | 1654 | [1–108],[325–505] | 1710 | [1–494] |
| 1520 | [1–426] | 1569 | [1–673] | 1655 | [1–474] | 1711 | [1–37],[192–511] |
| 1521 | [1–324] | 1571 | [1–482] | 1656 | [1–459] | 1712 | [1–50] |
| 1522 | [1–501] | 1572 | [1–322] | 1657 | [1–482] | 1713 | [1–356] |
| 1523 | [1–498] | 1573 | [1–502] | 1658 | [1–637] | 1714 | [1–481] |
| 1524 | [1–444] | 1574 | [1–566] | 1662 | [368–396] | 1715 | [1–475] |
| 1525 | [1–512] | 1576 | [1–529] | 1663 | [1–581] | 1716 | [73–497] |
| 1526 | [1–589] | 1577 | [1–62] | 1664 | [1–737] | 1717 | [1–496] |
| 1527 | [1–566] | 1579 | [1–494] | 1666 | [1–259] | 1718 | [1–476] |
| 1528 | [1–225] | 1580 | [1–510] | 1667 | [1–474] | 1719 | [1–506] |
| 1529 | [1–511] | 1582 | [1–487] | 1669 | [1–585] | 1720 | [1–511] |
| 1530 | [1–547] | 1583 | [1–455] | 1671 | [1–531] | 1721 | [1–1062] |
| 1532 | [331–372] | 1584 | [1–501] | 1673 | [190–416] | 1722 | [1–497] |
| 1533 | [279–327],[436–509] | 1585 | [1–492] | 1674 | [1–476] | 1723 | [301–498] |
| 1534 | [1–502] | 1587 | [159–237] | 1675 | [1–357] | 1724 | [1–444] |
| 1535 | [1–597] | 1588 | [1–484] | 1676 | [1–41],[112–406] | 1725 | [1–527] |
| 1536 | [156–492] | 1590 | [1–360] | 1677 | [148–306],[473–602] | 1726 | [1–494] |
| 1537 | [1–452] | 1591 | [1–36] | 1678 | [1–418] | 1727 | [98–202],[299–567] |
| 1538 | [1–496] | 1592 | [1–36],[471–518] | 1729 | [1–482] | 1783 | [1–714] |
| 1539 | [1–501] | 1593 | [1–611] | 1730 | [1–470] | 1785 | [1–477] |
| 1540 | [1–524] | 1595 | [95–467] | 1731 | [1–83],[115–483] | 1786 | [1–622] |
| 1541 | [1–268] | 1596 | [1–28],[70–112],[164–254],[305–391],[423–541] | 1732 | [1–491] | 1787 | [1–308] |
| 1542 | [1–215] | | | 1733 | [114–568] | 1789 | [1–172],[212–462] |
| 1543 | [1–923] | 1597 | [1–27] | 1734 | [1–357] | 1790 | [1–480] |
| 1544 | [1–463] | 1598 | [1–502] | 1735 | [59–440] | 1791 | [1–549] |
| 1545 | [1–218] | 1601 | [1–465] | 1736 | [1–505] | 1792 | [1–558] |
| 1546 | [1–213] | 1603 | [1–88] | 1737 | [1–712] | 1793 | [1–498] |
| 1547 | [1–465] | 1604 | [1–206],[289–678] | 1738 | [1–649] | 1794 | [125–192] |
| 1548 | [1–496] | 1605 | [164–200] | 1741 | [1–478] | 1795 | [115–513] |
| | | | | 1742 | [1–454] | 1796 | [1–41] |
| | | | | 1743 | [1–630] | 1797 | [1–497] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 1744 | [1–512] | 1798 | [1–513] | 1882 | [1–61],[92–501] | 1942 | [1–302] |
| 1745 | [1–767] | 1799 | [1–139] | 1883 | [1–515] | 1943 | [1–310] |
| 1746 | [1–363] | 1800 | [1–489] | 1884 | [1–46],[385–491] | 1944 | [1–281] |
| 1748 | [1–404] | 1801 | [1–428] | 1885 | [287–392] | 1945 | [1–168],[461–654] |
| 1749 | [1–394] | 1802 | [1–509] | 1886 | [1–646] | 1946 | [1–521] |
| 1750 | [368–587] | 1804 | [1–463] | 1887 | [1–515] | 1947 | [1–1013] |
| 1751 | [1–137],[262–380],[491–582] | 1805 | [1–477] | 1888 | [1–455] | 1948 | [1–510] |
| 1752 | [1–475] | 1807 | [1–485] | 1890 | [1–465] | 1949 | [1–472] |
| 1753 | [334–513] | 1808 | [1–230],[447–526] | 1892 | [136–443] | 1950 | [1–533] |
| 1754 | [1–475] | 1809 | [1–483] | 1893 | [1–66] | 1951 | [1–427] |
| 1755 | [1–487] | 1810 | [1–519] | 1894 | [1–613],[663–741] | 1952 | [1–204] |
| 1756 | [1–450] | 1811 | [1–544] | 1953 | [1–515] | 2009 | [1–34] |
| 1757 | [1–700] | 1813 | [172–412] | 1954 | [1–509] | 2011 | [1–514] |
| 1758 | [1–517] | 1814 | [1–712] | 1955 | [1–204] | 2012 | [1–461] |
| 1761 | [1–475] | 1816 | [1–475] | 1956 | [1–482] | 2018 | [1–502] |
| 1762 | [1–458] | 1817 | [1–94],[372–534] | 1957 | [44–486] | 2019 | [1–603] |
| 1763 | [1–420] | 1818 | [1–93],[171–196] | 1958 | [1–204] | 2020 | [1–473] |
| 1764 | [1–493] | 1820 | [1–580] | 1959 | [1–450] | 2021 | [161–246],[327–515] |
| 1765 | [1–544] | 1821 | [1–493] | 1960 | [1–239] | 2022 | [1–436] |
| 1766 | [1–468] | 1822 | [1–31],[533–579] | 1962 | [59–282],[407–508] | 2024 | [1–201],[458–594] |
| 1767 | [1–495] | 1823 | [1–170],[458–494] | 1963 | [1–482] | 2025 | [1–465] |
| 1768 | [1–492] | 1824 | [1–482] | 1964 | [1–534] | 2026 | [144–466] |
| 1769 | [1–216] | 1825 | [1–292] | 1965 | [1–491] | 2027 | [1–525] |
| 1770 | [1–460] | 1826 | [1–551] | 1966 | [1–497] | 2029 | [1–470] |
| 1771 | [1–664] | 1827 | [428–547] | 1967 | [101–325],[450–549] | 2031 | [1–291] |
| 1772 | [1–293],[324–581] | 1828 | [1–50],[373–433],[493–642] | 1968 | [1–145],[561–609] | 2032 | [1–450] |
| 1773 | [51–133] | 1829 | [1–352] | 1969 | [1–708] | 2033 | [1–558] |
| 1774 | [195–451] | 1830 | [1–462] | 1970 | [1–458] | 2034 | [1–506] |
| 1775 | [437–498] | 1831 | [1–476] | 1971 | [1–426] | 2035 | [1–492] |
| 1776 | [446–513] | 1832 | [1–465] | 1972 | [543–570] | 2036 | [1–27],[61–587] |
| 1778 | [1–460] | 1834 | [1–454] | 1974 | [1–116] | 2037 | [1–507] |
| 1780 | [372–424] | 1835 | [1–615] | 1977 | [1–478] | 2039 | [1–480] |
| 1781 | [1–525] | 1836 | [209–271] | 1978 | [1–491] | 2040 | [1–501] |
| 1782 | [444–512] | 1837 | [1–214],[374–486] | 1980 | [1–370] | 2041 | [1–395] |
| 1838 | [1–432] | 1895 | [1–542] | 1982 | [1–471] | 2042 | [1–365] |
| 1839 | [1–564] | 1896 | [1–482] | 1983 | [1–142] | 2044 | [1–481] |
| 1840 | [1–218],[420–473] | 1897 | [1–467] | 1984 | [1–834] | 2045 | [1–471] |
| 1843 | [1–29],[119–173] | 1898 | [1–480] | 1985 | [32–507] | 2046 | [1–462] |
| 1844 | [1–466] | 1899 | [1–484] | 1986 | [1–461] | 2047 | [1–457],[496–594] |
| 1847 | [1–462] | 1903 | [1–481] | 1988 | [1–350] | 2048 | [1–526] |
| 1848 | [1–462] | 1904 | [1–501] | 1989 | [1–458] | 2049 | [1–421] |
| 1849 | [1–459] | 1905 | [1–540] | 1990 | [1–487] | 2050 | [1–483] |
| 1850 | [1–526] | 1906 | [120–144],[452–486] | 1991 | [1–314],[374–538] | 2051 | [1–102],[337–539] |
| 1851 | [1–480] | 1907 | [1–474] | 1992 | [1–453] | 2052 | [1–399] |
| 1853 | [1–500] | 1908 | [1–485] | 1993 | [1–486] | 2053 | [414–532],[731–820] |
| 1854 | [1–181],[404–671] | 1909 | [1–499] | 1994 | [1–482] | 2054 | [1–402] |
| 1855 | [1–402] | 1910 | [1–460] | 1995 | [1–621] | 2055 | [1–662] |
| 1856 | [1–510] | 1911 | [1–462] | 1996 | [1–511] | 2057 | [1–262] |
| 1857 | [1–465] | 1912 | [1–503] | 1997 | [1–477] | 2058 | [144–226] |
| 1858 | [1–755] | 1914 | [1–456] | 1998 | [1–543] | 2059 | [1–483] |
| 1859 | [1–465] | 1915 | [1–506] | 2000 | [1–497] | 2060 | [1–483] |
| 1860 | [463–487] | 1916 | [1–127],[372–399],[440–469] | 2002 | [1–453] | 2061 | [1–43],[220–466] |
| | | | | 2003 | [162–567] | 2062 | [1–422] |
| 1861 | [1–270] | 1918 | [97–453] | 2004 | [172–490] | 2063 | [1–490] |
| 1862 | [1–613] | 1919 | [1–328] | 2005 | [473–626] | 2064 | [1–341] |
| 1863 | [175–216],[546–596] | 1920 | [1–663] | 2006 | [372–470] | 2065 | [1–448] |
| 1864 | [1–468] | 1921 | [1–181],[233–488] | 2007 | [1–432] | 2066 | [1–222] |
| 1865 | [1–492] | 1923 | [1–42],[123–148],[255–285] | 2008 | [1–495] | 2067 | [1–461] |
| | | | | 2068 | [1–49],[299–617] | 2124 | [1–448] |
| | | | | 2069 | [1–503] | 2125 | [1–437] |
| | | | | 2070 | [1–499] | 2126 | [1–455] |
| 1866 | [1–503] | 1924 | [1–79],[271–473] | 2071 | [1–343] | 2127 | [1–428] |
| 1867 | [1–405],[761–807] | 1926 | [1–464] | 2072 | [1–132],[341–461] | 2128 | [1–359] |
| 1869 | [1–476] | 1927 | [1–196] | 2073 | [1–92] | 2129 | [1–546] |
| 1870 | [1–440] | 1928 | [47–496] | 2074 | [1–460] | 2130 | [1–45],[96–354] |
| 1871 | [1–448] | 1929 | [1–471] | 2076 | [1–384] | 2131 | [1–513] |
| 1872 | [1–505] | 1930 | [1–202] | 2077 | [1–456] | 2132 | [1–388] |
| 1873 | [1–51],[218–935] | 1932 | [1–130],[272–469] | 2078 | [1–453] | 2133 | [1–432] |
| 1874 | [1–514] | 1934 | [1–530] | 2079 | [1–527] | 2134 | [1–277] |
| 1876 | [1–436] | 1936 | [1–650] | 2080 | [1–469] | 2135 | [1–503] |
| 1877 | [1–667] | 1937 | [1–302] | 2081 | [1–506] | 2137 | [1–508] |
| 1878 | [1–787] | 1938 | [1–471] | 2082 | [1–685] | 2138 | [1–158],[417–476] |
| 1879 | [1–493] | 1939 | [1–294] | 2083 | [1–504] | 2139 | [1–479] |
| 1880 | [1–466] | 1940 | [1–294] | 2084 | [1–463] | 2140 | [1–428] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 2085 | [1–54],[244–340] | 2141 | [1–463] | 2224 | [1–29],[185–383] | 2276 | [1–467] |
| 2087 | [1–496] | 2142 | [1–497] | 2225 | [1–422] | 2277 | [1–141],[188–451] |
| 2089 | [1–40],[70–483] | 2143 | [236–459] | 2226 | [1–93] | 2278 | [1–462] |
| 2090 | [1–480] | 2144 | [1–533] | 2227 | [437–464] | 2279 | [1–372] |
| 2091 | [1–488] | 2147 | [1–408] | 2280 | [1–457] | 2338 | [1–450] |
| 2092 | [1–483] | 2148 | [1–564] | 2281 | [1–484] | 2339 | [45–378] |
| 2093 | [1–311] | 2149 | [1–295] | 2282 | [1–172],[414–537] | 2340 | [1–445] |
| 2094 | [1–159],[284–408] | 2150 | [1–336] | 2283 | [1–199] | 2341 | [1–339] |
| 2095 | [1–446] | 2151 | [1–449] | 2284 | [1–559] | 2342 | [1–295] |
| 2096 | [1–495] | 2152 | [1–572] | 2285 | [1–464] | 2344 | [1–516] |
| 2098 | [1–460] | 2153 | [1–223] | 2286 | [1–460] | 2345 | [432–498] |
| 2099 | [1–223],[437–477] | 2154 | [1–523] | 2287 | [1–511] | 2346 | [1–466] |
| 2100 | [1–160],[285–408] | 2155 | [1–499] | 2289 | [34–75],[226–478] | 2347 | [1–480] |
| 2101 | [1–459] | 2156 | [1–600] | 2290 | [1–505] | 2348 | [1–32] |
| 2102 | [1–374] | 2157 | [451–510] | 2292 | [1–478] | 2349 | [1–317] |
| 2103 | [1–384] | 2158 | [1–486] | 2294 | [1–461] | 2350 | [1–278],[418–503] |
| 2104 | [1–554] | 2159 | [1–488] | 2295 | [1–267] | 2351 | [1–616] |
| 2105 | [32–476] | 2160 | [1–503] | 2296 | [1–346] | 2354 | [1–494] |
| 2106 | [1–71] | 2161 | [1–470] | 2297 | [1–476] | 2355 | [1–479] |
| 2107 | [1–461] | 2163 | [1–458] | 2298 | [1–43] | 2357 | [1–456] |
| 2108 | [1–544] | 2164 | [1–495] | 2300 | [1–433] | 2358 | [1–473] |
| 2109 | [1–515] | 2165 | [1–107] | 2301 | [1–369] | 2359 | [1–473] |
| 2110 | [1–352] | 2166 | [1–390],[419–520] | 2303 | [1–507] | 2360 | [1–540] |
| 2112 | [1–443] | 2167 | [274–512] | 2305 | [1–374] | 2361 | [1–470] |
| 2113 | [1–342] | 2168 | [1–398] | 2306 | [1–457] | 2362 | [1–485] |
| 2115 | [1–470] | 2169 | [1–493] | 2308 | [1–499] | 2363 | [1–495] |
| 2117 | [1–478] | 2170 | [1–532] | 2309 | [1–507] | 2364 | [1–358] |
| 2118 | [1–485] | 2171 | [1–419] | 2310 | [1–472] | 2365 | [377–482] |
| 2120 | [1–375] | 2172 | [1–506] | 2311 | [1–478] | 2366 | [1–143] |
| 2122 | [1–288] | 2173 | [1–491] | 2312 | [1–468] | 2367 | [1–32],[152–403] |
| 2123 | [1–533] | 2174 | [1–564] | 2313 | [45–329] | 2371 | [1–388] |
| 2175 | [1–474] | 2228 | [1–489] | 2315 | [1–46],[207–372] | 2372 | [1–556] |
| 2176 | [1–469] | 2229 | [1–55] | 2316 | [1–366] | 2373 | [1–175],[252–523] |
| 2177 | [1–56],[338–452] | 2230 | [1–440] | 2317 | [1–476] | 2374 | [1–446] |
| 2178 | [1–456] | 2233 | [1–475] | 2318 | [1–238] | 2375 | [1–175],[252–585] |
| 2179 | [164–482] | 2234 | [1–459] | 2319 | [1–499] | 2376 | [1–520] |
| 2181 | [1–467] | 2235 | [1–481] | 2320 | [1–473] | 2377 | [1–487] |
| 2182 | [1–474] | 2236 | [1–452] | 2323 | [1–489] | 2378 | [427–459] |
| 2183 | [1–469] | 2237 | [1–415] | 2324 | [1–182] | 2379 | [1–65],[471–535] |
| 2184 | [1–379] | 2238 | [1–456] | 2325 | [1–460] | 2380 | [1–65],[441–485] |
| 2185 | [1–413] | 2239 | [1–508] | 2327 | [1–493] | 2383 | [1–489] |
| 2186 | [1–483] | 2240 | [44–471] | 2328 | [1–496] | 2384 | [1–660] |
| 2187 | [173–451] | 2241 | [1–213],[409–467] | 2329 | [1–493] | 2385 | [1–491] |
| 2188 | [1–476] | 2242 | [1–220],[405–473] | 2330 | [1–413] | 2386 | [1–459] |
| 2189 | [1–43] | 2243 | [1–333] | 2331 | [1–492] | 2387 | [1–517] |
| 2190 | [1–379],[419–453] | 2244 | [1–511] | 2332 | [1–452] | 2388 | [1–516] |
| 2192 | [1–482] | 2245 | [1–472] | 2333 | [1–456] | 2389 | [1–499] |
| 2193 | [34–462] | 2246 | [1–463] | 2334 | [1–443] | 2390 | [220–277],[318–386],[423–523] |
| 2194 | [1–487] | 2247 | [1–342] | | | | |
| 2195 | [1–568] | 2248 | [1–467] | 2335 | [1–413] | 2391 | [1–45],[294–458] |
| 2196 | [1–306] | 2249 | [1–419] | 2336 | [1–479] | 2392 | [1–856] |
| 2197 | [1–462] | 2250 | [1–474] | 2337 | [1–311] | 2394 | [1–468] |
| 2198 | [1–439] | 2251 | [1–42] | 2396 | [1–58],[103–497] | 2451 | [1–349] |
| 2199 | [1–489] | 2252 | [1–529] | 2397 | [1–584] | 2452 | [1–467] |
| 2200 | [195–289] | 2253 | [1–381] | 2398 | [1–270],[311–479] | 2453 | [1–571] |
| 2201 | [1–485] | 2254 | [1–468] | 2399 | [1–559] | 2454 | [1–551] |
| 2203 | [1–474] | 2255 | [1–535] | 2400 | [1–459] | 2455 | [1–461] |
| 2204 | [1–361] | 2256 | [1–41],[470–553] | 2402 | [1–306] | 2456 | [1–481] |
| 2205 | [1–513] | 2257 | [1–469] | 2403 | [1–468] | 2457 | [1–468] |
| 2206 | [1–481] | 2258 | [1–41],[470–508] | 2404 | [1–341] | 2458 | [1–492] |
| 2209 | [1–892] | 2260 | [1–472] | 2405 | [1–467] | 2459 | [1–492] |
| 2210 | [1–54],[180–247] | 2261 | [1–460] | 2407 | [188–332] | 2460 | [1–511] |
| 2211 | [1–455] | 2262 | [1–599] | 2408 | [1–144] | 2461 | [1–675] |
| 2212 | [1–226],[442–474] | 2263 | [337–489] | 2409 | [1–516] | 2463 | [1–482] |
| 2213 | [1–499] | 2264 | [1–460] | 2410 | [1–468] | 2464 | [1–499] |
| 2214 | [1–457] | 2266 | [1–386] | 2412 | [1–506] | 2467 | [1–511] |
| 2215 | [1–479] | 2267 | [1–472] | 2414 | [469–548] | 2469 | [1–452] |
| 2216 | [1–481] | 2268 | [1–484] | 2415 | [1–268] | 2470 | [1–556] |
| 2217 | [1–239] | 2269 | [1–502] | 2416 | [1–490] | 2471 | [1–188] |
| 2218 | [1–131] | 2270 | [1–503] | 2417 | [1–930] | 2472 | [1–295] |
| 2219 | [1–471] | 2271 | [1–563] | 2418 | [1–489] | 2473 | [1–465] |
| 2220 | [1–473] | 2272 | [1–486] | 2420 | [156–531] | 2474 | [1–451] |
| 2221 | [1–55] | 2273 | [1–459] | 2421 | [1–476] | 2475 | [1–527] |
| 2223 | [302–459] | 2274 | [1–330] | 2422 | [254–312] | 2476 | [91–189] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 2423 | [1–501] | 2477 | [1–364] | 2614 | [1–189],[424–803] | 2669 | [1–485] |
| 2425 | [1–488] | 2478 | [1–467] | 2615 | [1–491] | 2670 | [1–455] |
| 2426 | [1–506] | 2479 | [1–360] | 2616 | [1–478] | 2674 | [1–330] |
| 2427 | [1–348] | 2480 | [1–502] | 2617 | [1–273] | 2675 | [1–748] |
| 2428 | [1–327] | 2481 | [1–537] | 2619 | [1–56] | 2676 | [1–502] |
| 2429 | [1–326] | 2482 | [1–479] | 2620 | [1–488] | 2677 | [1–497] |
| 2430 | [269–510] | 2483 | [91–189] | 2621 | [1–547] | 2678 | [1–468] |
| 2431 | [1–542] | 2484 | [1–514] | 2622 | [1–131],[401–429] | 2680 | [1–305] |
| 2432 | [204–255] | 2485 | [1–391] | 2623 | [1–437] | 2681 | [1–305] |
| 2433 | [1–223],[423–537] | 2486 | [1–210] | 2624 | [1–452] | 2682 | [1–217] |
| 2434 | [1–458] | 2487 | [1–198],[317–554] | 2625 | [1–445] | 2683 | [1–69] |
| 2435 | [1–557] | 2488 | [1–465] | 2626 | [1–442] | 2684 | [1–470] |
| 2436 | [67–166] | 2489 | [1–410] | 2627 | [1–446] | 2685 | [1–51] |
| 2437 | [1–363] | 2490 | [1–493] | 2628 | [1–448] | 2687 | [1–451] |
| 2438 | [1–433] | 2491 | [1–461] | 2629 | [1–441] | 2688 | [1–488] |
| 2439 | [1–480] | 2492 | [93–533] | 2630 | [1–475] | 2689 | [166–505] |
| 2441 | [1–319],[352–398] | 2493 | [168–714] | 2631 | [1–443] | 2690 | [1–491] |
| 2442 | [1–444] | 2494 | [1–561] | 2632 | [1–469] | 2691 | [1–507] |
| 2444 | [1–451] | 2495 | [1–451] | 2633 | [1–452] | 2692 | [1–526] |
| 2445 | [1–504] | 2497 | [1–612] | 2634 | [1–439] | 2693 | [1–523] |
| 2446 | [1–430] | 2498 | [1–491] | 2635 | [1–488] | 2694 | [1–50],[412–572] |
| 2447 | [1–86],[288–485] | 2499 | [1–780] | 2636 | [1–447] | 2695 | [1–544] |
| 2448 | [1–546] | 2500 | [1–242],[276–300] | 2638 | [265–388] | 2696 | [1–494] |
| 2449 | [349–517] | 2501 | [1–466] | 2639 | [1–444] | 2697 | [59–100] |
| 2450 | [1–463] | 2502 | [1–405] | 2641 | [251–394] | 2698 | [328–406] |
| 2503 | [1–476] | 2559 | [1–346] | 2642 | [1–444] | 2700 | [1–84],[395–452] |
| 2505 | [1–180],[509–543] | 2560 | [1–505] | 2643 | [1–439] | 2701 | [1–466] |
| 2506 | [1–507] | 2561 | [1–473] | 2644 | [1–493] | 2703 | [1–470] |
| 2507 | [124–311] | 2562 | [1–406] | 2645 | [1–444] | 2704 | [1–464] |
| 2508 | [1–488] | 2564 | [1–513] | 2646 | [1–448] | 2705 | [1–590] |
| 2509 | [1–482] | 2567 | [1–361] | 2647 | [1–522] | 2707 | [64–96],[298–483] |
| 2510 | [1–489] | 2568 | [1–70] | 2648 | [1–481] | 2708 | [1–517] |
| 2511 | [1–508] | 2570 | [1–624] | 2649 | [1–600] | 2709 | [1–474] |
| 2512 | [1–305],[416–471] | 2571 | [1–483] | 2650 | [1–492] | 2710 | [1–473] |
| 2513 | [331–478] | 2572 | [1–64] | 2651 | [1–357] | 2711 | [174–513] |
| 2514 | [1–498] | 2574 | [1–192],[361–589],[692–834] | 2652 | [1–59] | 2712 | [1–513] |
| 2515 | [276–321] | 2575 | [1–530] | 2653 | [1–34] | 2713 | [1–501] |
| 2516 | [1–553] | 2576 | [1–456] | 2655 | [1–512] | 2714 | [1–506] |
| 2517 | [1–468] | 2577 | [1–43],[98–215] | 2657 | [1–461] | 2715 | [1–471] |
| 2518 | [1–112],[321–484] | 2578 | [1–43],[98–215] | 2658 | [153–206],[334–414] | 2716 | [1–525] |
| 2519 | [1–459] | 2579 | [1–556] | 2659 | [1–336] | 2717 | [1–515] |
| 2522 | [1–49] | 2580 | [1–622] | 2662 | [1–402] | 2718 | [1–521] |
| 2523 | [1–538] | 2581 | [180–231] | 2663 | [1–489] | 2719 | [1–399] |
| 2524 | [1–600] | 2582 | [160–211] | 2664 | [1–490] | 2720 | [1–37],[251–481] |
| 2525 | [1–390] | 2583 | [180–231] | 2665 | [1–470] | 2721 | [1–497] |
| 2526 | [1–469] | 2584 | [479–647] | 2666 | [1–396] | 2723 | [1–156] |
| 2527 | [1–521] | 2585 | [290–476] | 2724 | [1–156] | 2776 | [1–504] |
| 2528 | [1–513] | 2586 | [1–482] | 2725 | [1–890] | 2778 | [1–490] |
| 2532 | [392–481] | 2587 | [1–560] | 2726 | [1–517] | 2779 | [1–471] |
| 2533 | [1–429],[461–487] | 2588 | [1–541] | 2727 | [1–583] | 2780 | [1–502] |
| 2534 | [1–465] | 2589 | [1–492] | 2728 | [1–79],[534–569] | 2781 | [1–630] |
| 2535 | [1–463] | 2591 | [1–541] | 2729 | [1–105] | 2784 | [457–555] |
| 2536 | [1–484] | 2592 | [1–575] | 2730 | [1–27] | 2785 | [1–527] |
| 2537 | [1–125],[292–533] | 2593 | [179–490] | 2732 | [1–477] | 2786 | [1–430] |
| 2538 | [1–516] | 2594 | [1–522] | 2733 | [1–606] | 2787 | [36–527] |
| 2539 | [317–362] | 2595 | [1–627] | 2734 | [303–554] | 2788 | [1–504] |
| 2540 | [1–985] | 2596 | [1–125],[207–506] | 2736 | [1–485] | 2789 | [1–485] |
| 2541 | [1–324],[418–508] | 2597 | [1–588] | 2737 | [1–552] | 2790 | [1–487] |
| 2542 | [1–484] | 2598 | [1–504] | 2738 | [1–451] | 2791 | [1–483] |
| 2543 | [1–544] | 2599 | [1–97],[169–465] | 2739 | [1–492] | 2792 | [1–903] |
| 2544 | [1–25] | 2600 | [1–627] | 2740 | [1–281],[391–549] | 2793 | [1–472] |
| 2545 | [1–233] | 2601 | [1–542] | 2741 | [1–493] | 2794 | [1–501] |
| 2547 | [1–50],[384–578] | 2602 | [1–451] | 2742 | [1–35] | 2795 | [1–455] |
| 2549 | [1–144] | 2603 | [1–453] | 2744 | [1–484] | 2796 | [1–460] |
| 2550 | [1–478] | 2605 | [1–538] | 2745 | [1–534] | 2797 | [1–459] |
| 2551 | [1–424] | 2606 | [1–270] | 2746 | [1–491] | 2798 | [1–457] |
| 2552 | [44–78],[126–170] | 2607 | [1–235] | 2747 | [145–330] | 2799 | [1–462] |
| 2554 | [1–165] | 2608 | [1–127] | 2748 | [1–472] | 2800 | [1–455] |
| 2555 | [1–28] | 2609 | [1–197] | 2749 | [1–407] | 2801 | [1–457] |
| 2556 | [1–502] | 2610 | [1–489] | 2750 | [1–41],[351–607] | 2802 | [1–457] |
| 2557 | [1–528] | 2611 | [1–468] | 2751 | [1–548] | 2803 | [1–456] |
| 2558 | [1–513] | 2612 | [1–173],[341–720] | 2752 | [1–496] | 2804 | [1–458] |
| 2613 | [1–251],[315–556] | 2668 | [1–42] | 2753 | [1–352] | 2805 | [1–472] |
| | | | | 2754 | [1–447] | 2806 | [1–388] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 2757 | [1–551] | 2807 | [1–474] | 2945 | [1–164] | 3000 | [1–482] |
| 2758 | [1–30] | 2808 | [1–464] | 2946 | [1–87],[303–402] | 3001 | [1–26] |
| 2759 | [135–563] | 2809 | [1–262] | 2948 | [406–498] | 3002 | [1–483] |
| 2760 | [1–670] | 2810 | [1–510] | 2950 | [1–540] | 3003 | [1–518] |
| 2761 | [159–183] | 2811 | [165–499] | 2951 | [1–506] | 3004 | [1–393] |
| 2762 | [1–48] | 2812 | [378–515] | 2952 | [1–525] | 3006 | [1–42] |
| 2763 | [1–48] | 2813 | [1–832] | 2953 | [1–272] | 3007 | [1–548] |
| 2764 | [1–481] | 2814 | [1–41],[98–552] | 2955 | [1–395] | 3008 | [1–513] |
| 2765 | [1–27],[368–509] | 2815 | [1–33] | 2956 | [1–251] | 3009 | [1–491] |
| 2766 | [1–436] | 2817 | [1–494] | 2957 | [1–257] | 3010 | [416–507] |
| 2767 | [1–86],[232–424] | 2818 | [1–253] | 2958 | [1–462] | 3011 | [1–674] |
| 2768 | [1–423] | 2819 | [1–428],[461–529] | 2959 | [1–590] | 3012 | [1–505] |
| 2769 | [1–416] | 2820 | [1–1035] | 2960 | [1–271] | 3013 | [1–557] |
| 2770 | [1–333] | 2821 | [1–492] | 2961 | [1–371] | 3014 | [1–467] |
| 2771 | [1–320] | 2822 | [1–509] | 2962 | [1–499] | 3015 | [1–338] |
| 2772 | [1–101],[158–203] | 2823 | [1–515] | 2963 | [1–539] | 3016 | [1–513] |
| 2773 | [1–517] | 2824 | [1–524] | 2964 | [1–499] | 3017 | [1–469] |
| 2774 | [1–572] | 2825 | [227–524] | 2966 | [1–452] | 3018 | [1–531] |
| 2775 | [1–647] | 2827 | [1–476] | 2968 | [1–97],[531–575] | 3019 | [1–390],[461–610] |
| 2828 | [1–516] | 2883 | [1–456] | 2969 | [1–520] | 3021 | [1–530] |
| 2829 | [1–69],[102–152] | 2884 | [1–560] | 2970 | [1–125] | 3022 | [1–128],[194–220], [261–436] |
| 2830 | [1–535] | 2885 | [1–478] | | | | |
| 2831 | [1–421] | 2886 | [1–31] | 2971 | [1–491] | 3023 | [1–494] |
| 2832 | [1–625] | 2887 | [1–503] | 2972 | [1–477] | 3024 | [1–488] |
| 2833 | [1–306],[347–461] | 2889 | [1–467] | 2975 | [1–611] | 3026 | [1–355] |
| 2834 | [1–63],[401–444] | 2890 | [289–331] | 2976 | [1–470] | 3027 | [1–807] |
| 2835 | [254–400] | 2891 | [444–489] | 2977 | [1–398] | 3028 | [1–254] |
| 2838 | [1–517] | 2892 | [65–132] | 2978 | [1–517] | 3029 | [1–533] |
| 2839 | [1–469] | 2893 | [1–459] | 2979 | [76–491] | 3030 | [1–505] |
| 2840 | [1–414] | 2894 | [1–547] | 2980 | [1–484] | 3031 | [1–520] |
| 2841 | [1–284] | 2895 | [272–459] | 2982 | [415–555] | 3032 | [1–585] |
| 2842 | [1–453] | 2896 | [349–395] | 2983 | [1–507] | 3033 | [76–420] |
| 2843 | [50–473] | 2897 | [1–463] | 2984 | [1–97] | 3034 | [1–407] |
| 2849 | [1–521] | 2898 | [1–527] | 2985 | [33–783] | 3035 | [1–156] |
| 2850 | [1–453] | 2899 | [1–511] | 2986 | [128–171] | 3036 | [1–136],[340–375] |
| 2851 | [1–470] | 2900 | [1–64],[451–486] | 2987 | [1–342] | 3037 | [1–462] |
| 2852 | [1–512] | 2901 | [1–284] | 2988 | [1–272] | 3038 | [269–356],[433–510] |
| 2853 | [1–81],[140–483] | 2902 | [1–479],[641–721] | 2989 | [1–478] | 3039 | [1–94],[361–483] |
| 2854 | [1–79],[370–522] | 2903 | [1–269] | 2990 | [1–482] | 3040 | [1–93] |
| 2855 | [1–527] | 2904 | [1–506] | 2991 | [1–417] | 3041 | [1–524] |
| 2856 | [134–528] | 2905 | [1–474] | 2992 | [1–431] | 3042 | [1–186] |
| 2857 | [1–444] | 2906 | [1–387] | 3043 | [1–486] | 3106 | [1–557] |
| 2858 | [1–496] | 2907 | [468–523] | 3044 | [1–491] | 3110 | [1–428] |
| 2859 | [1–488] | 2908 | [1–539] | 3045 | [1–328] | 3111 | [1–491] |
| 2860 | [1–510] | 2910 | [1–471] | 3046 | [1–477] | 3112 | [1–480] |
| 2861 | [1–486] | 2911 | [1–531] | 3047 | [1–240],[661–691] | 3113 | [1–236] |
| 2862 | [1–490] | 2912 | [1–475] | 3048 | [1–465] | 3114 | [1–525] |
| 2863 | [42–113] | 2913 | [1–483] | 3050 | [1–515] | 3115 | [1–30],[113–150] |
| 2864 | [1–29] | 2914 | [320–395] | 3051 | [1–642] | 3116 | [1–445] |
| 2866 | [1–494] | 2915 | [1–495] | 3052 | [712–751] | 3117 | [1–498] |
| 2867 | [1–539] | 2916 | [1–453] | 3055 | [136–561] | 3118 | [1–509] |
| 2868 | [1–713] | 2918 | [1–236] | 3057 | [1–468] | 3119 | [1–284] |
| 2869 | [1–476] | 2919 | [1–411],[476–519] | 3058 | [1–558] | 3120 | [1–494] |
| 2870 | [267–531] | 2920 | [1–454] | 3059 | [1–481] | 3121 | [604–632] |
| 2871 | [267–468] | 2921 | [1–243],[465–492] | 3060 | [1–494] | 3123 | [1–483] |
| 2872 | [278–496] | 2922 | [1–455] | 3061 | [1–523] | 3124 | [1–479] |
| 2873 | [1–524] | 2923 | [1–504] | 3062 | [1–537] | 3125 | [1–492] |
| 2874 | [1–486] | 2924 | [1–615] | 3063 | [1–470] | 3126 | [1–707] |
| 2875 | [1–494] | 2925 | [82–117],[169–237], [283–348] | 3064 | [1–112] | 3129 | [1–464] |
| | | | | 3065 | [1–494] | 3130 | [1–497] |
| 2876 | [1–486] | 2926 | [1–483] | 3066 | [1–456] | 3131 | [1–316] |
| 2877 | [1–706] | 2927 | [1–577] | 3067 | [1–561] | 3132 | [1–464] |
| 2878 | [1–531] | 2928 | [1–489] | 3068 | [184–233] | 3133 | [1–58],[463–487] |
| 2879 | [1–385] | 2929 | [1–474] | 3069 | [1–513] | 3134 | [1–52],[521–556] |
| 2880 | [1–482] | 2930 | [1–466] | 3070 | [1–484] | 3136 | [1–52] |
| 2881 | [1–575] | 2932 | [1–581] | 3071 | [1–473] | 3137 | [1–341] |
| 2882 | [1–543] | 2933 | [1–43] | 3073 | [466–506] | 3138 | [1–489] |
| 2934 | [1–146] | 2993 | [1–476] | 3074 | [1–484] | 3139 | [1–370] |
| 2936 | [1–206] | 2994 | [1–499] | 3075 | [125–459] | 3140 | [1–457] |
| 2937 | [1–515] | 2995 | [1–509] | 3076 | [1–500] | 3141 | [1–549] |
| 2941 | [1–61],[309–342] | 2996 | [49–466] | 3078 | [1–419] | 3142 | [1–438] |
| 2942 | [1–179],[215–518] | 2997 | [1–35],[94–284] | 3079 | [1–456] | 3143 | [1–513] |
| 2943 | [1–509] | 2998 | [1–546] | 3080 | [1–500] | 3144 | [1–167],[505–548] |
| 2944 | [1–465] | 2999 | [1–345] | 3081 | [1–566] | 3145 | [141–183],[286–410] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 3082 | [1–529] | 3146 | [1–476] | 3283 | [1–555] | 3342 | [1–464] |
| 3083 | [1–463] | 3147 | [1–500] | 3284 | [1–471] | 3343 | [1–165],[199–232], [262–404],[480–548] |
| 3084 | [1–32],[71–528] | 3148 | [1–462] | 3286 | [1–526] | 3344 | [1–45] |
| 3086 | [127–513] | 3149 | [1–46] | 3288 | [1–482] | 3345 | [1–184],[2261–550] |
| 3093 | [224–490] | 3150 | [1–864] | 3289 | [40–83] | 3346 | [93–123] |
| 3094 | [1–505] | 3151 | [1–655] | 3290 | [1–115],[355–489] | 3347 | [93–123] |
| 3095 | [1–552] | 3152 | [1–484] | 3291 | [1–270] | 3349 | [1–527] |
| 3096 | [136–185],[417–508] | 3153 | [1–459] | 3292 | [1–115],[355–435] | 3351 | [1–506] |
| 3100 | [306–340] | 3154 | [1–526] | 3293 | [1–460] | 3353 | [1–461] |
| 3101 | [152–187],[332–404] | 3155 | [1–505] | 3294 | [1–450] | 3354 | [1–263] |
| 3102 | [1–450] | 3157 | [172–238],[368–409] | 3296 | [1–461] | 3355 | [1–263] |
| 3103 | [1–490] | 3158 | [1–156],[251–482] | 3298 | [1–32],[293–360] | 3356 | [1–408] |
| 3104 | [1–501] | 3159 | [172–238],[368–471] | 3299 | [1–459] | 3357 | [1–532] |
| 3105 | [1–482] | 3160 | [1–109],[175–236] | 3300 | [1–450] | 3358 | [1–145],[387–475] |
| 3161 | [172–238],[368–451] | 3216 | [1–458] | 3301 | [1–542] | 3359 | [1–413] |
| 3162 | [1–494] | 3217 | [1–526] | 3302 | [1–418] | 3360 | [1–249],[302–593] |
| 3163 | [1–478] | 3218 | [1–517] | 3303 | [1–462] | 3361 | [1–509] |
| 3164 | [1–94],[275–508] | 3219 | [1–509] | 3306 | [1–478] | 3362 | [1–82],[296–699] |
| 3165 | [1–498] | 3220 | [1–461] | 3307 | [1–94],[134–471] | 3363 | [1–82],[296–579] |
| 3167 | [1–350] | 3221 | [1–381] | 3308 | [1–524] | 3364 | [1–82],[296–612] |
| 3168 | [68–471] | 3222 | [1–347] | 3309 | [1–43] | 3365 | [224–385] |
| 3169 | [1–490] | 3223 | [1–130],[482–517] | 3310 | [1–358] | 3366 | [1–51],[265–516] |
| 3170 | [1–563] | 3224 | [1–473] | 3311 | [207–444] | 3367 | [231–447] |
| 3171 | [1–31] | 3225 | [1–497] | 3312 | [1–932] | 3370 | [1–393] |
| 3173 | [1–92],[220–455] | 3226 | [1–601] | 3313 | [1–549] | 3371 | [1–508] |
| 3174 | [1–465] | 3227 | [1–516] | 3315 | [1–497] | 3372 | [1–384] |
| 3175 | [1–484] | 3228 | [1–513] | 3316 | [1–511] | 3373 | [1–366] |
| 3177 | [1–482] | 3229 | [1–525] | 3317 | [189–414] | 3375 | [1–482] |
| 3179 | [1–485] | 3230 | [500–548] | 3319 | [1–217],[334–476] | 3376 | [1–560] |
| 3180 | [1–240],[271–401] | 3232 | [1–210],[251–523] | 3321 | [1–212],[329–471] | 3377 | [1–364] |
| 3181 | [401–442],[488–517] | 3233 | [1–399] | 3322 | [1–125] | 3378 | [1–173] |
| 3182 | [1–144],[436–577] | 3234 | [284–532] | 3323 | [1–25] | 3380 | [1–490] |
| 3183 | [1–84],[149–207], [320–381] | 3237 | [350–499] | 3324 | [1–294] | 3381 | [1–487] |
| 3184 | [1–394] | 3238 | [342–587] | 3325 | [1–485] | 3382 | [1–738] |
| 3185 | [1–556] | 3239 | [1–748] | 3326 | [1–451] | 3383 | [43–486] |
| 3186 | [1–539] | 3240 | [1–468] | 3327 | [1–515] | 3384 | [520–560] |
| 3188 | [325–444] | 3241 | [1–690] | 3385 | [1–421] | 3436 | [1–475] |
| 3190 | [1–530] | 3243 | [1–104],[148–466] | 3386 | [1–456] | 3437 | [1–462] |
| 3191 | [1–452] | 3244 | [1–504] | 3387 | [1–480] | 3438 | [1–556] |
| 3192 | [1–527] | 3245 | [1–597] | 3388 | [1–579] | 3439 | [1–449] |
| 3193 | [1–757] | 3246 | [1–460] | 3389 | [1–162],[201–337], [534–566] | 3441 | [1–453] |
| 3194 | [240–503] | 3247 | [1–565] | 3390 | [1–452] | 3442 | [1–450] |
| 3195 | [1–486] | 3248 | [1–50],[372–432] | 3391 | [436–526] | 3443 | [285–515] |
| 3197 | [1–494] | 3249 | [1–314] | 3392 | [1–478] | 3444 | [1–439] |
| 3198 | [1–336] | 3250 | [268–409] | 3393 | [1–341] | 3445 | [1–168] |
| 3199 | [1–328] | 3251 | [273–456] | 3394 | [1–465] | 3446 | [1–298] |
| 3200 | [1–60],[155–484] | 3252 | [269–344] | 3395 | [1–469] | 3447 | [1–495] |
| 3201 | [1–463] | 3253 | [268–474] | 3396 | [2271–316] | 3448 | [1–518] |
| 3202 | [1–473] | 3257 | [1–151] | 3397 | [1–477] | 3449 | [1–508] |
| 3203 | [1–85] | 3258 | [1–533] | 3398 | [1–451] | 3450 | [1–503] |
| 3204 | [1–50],[90–443] | 3259 | [1–112] | 3399 | [1–468] | 3451 | [1–452] |
| 3205 | [1–533] | 3260 | [1–429] | 3400 | [1–431] | 3452 | [1–413] |
| 3206 | [1–191],[306–464] | 3261 | [1–462] | 3401 | [1–461] | 3453 | [1–325] |
| 3207 | [1–166],[281–521] | 3262 | [1–134],[180–235], [298–330] | 3402 | [1–109] | 3455 | [1–90] |
| 3209 | [1–505] | 3263 | [1–69],[139–321] | 3403 | [1–471] | 3456 | [1–450] |
| 3210 | [58–380] | 3264 | [401–469] | 3404 | [1–482] | 3457 | [1–571] |
| 3211 | [1–28] | 3265 | [1–239],[411–460] | 3406 | [1–726] | 3458 | [1–478] |
| 3212 | [1–157],[190–461] | 3266 | [1–511] | 3407 | [209–459] | 3459 | [1–565] |
| 3213 | [1–444] | 3267 | [287–425] | 3408 | [1–268] | 3460 | [1–375],[434–543] |
| 3214 | [1–457] | 3268 | [1–453] | 3409 | [1–31] | 3463 | [1–577] |
| 3215 | [1–474] | 3269 | [1–503] | 3410 | [1–451] | 3464 | [1–481] |
| 3270 | [1–415] | 3328 | [1–527] | 3412 | [1–484] | 3466 | [1–70],[168–586], [729–778] |
| 3272 | [1–353] | 3331 | [1–528] | 3413 | [1–390] | 3469 | [322–495] |
| 3273 | [1–401] | 3332 | [1–465] | 3414 | [1–473] | 3470 | [1–484] |
| 3274 | [1–447] | 3333 | [1–389] | 3415 | [1–278],[317–585] | 3471 | [1–512] |
| 3275 | [1–461] | 3334 | [1–65] | 3416 | [1–100],[133–519] | 3472 | [1–492] |
| 3276 | [1–628] | 3336 | [1–452] | 3417 | [1–547] | 3473 | [1–278] |
| 3277 | [1–29] | 3337 | [1–846] | 3418 | [482–509] | 3474 | [1–132],[250–512] |
| 3278 | [1–476] | 3338 | [1–386] | 3419 | [1–519] | 3475 | [1–497] |
| 3279 | [1–527] | 3339 | [1–474] | 3420 | [1–436] | 3476 | [1–270],[314–511] |
| 3281 | [1–513] | 3340 | [1–431] | 3421 | [1–472] | 3477 | [1–528] |
| 3282 | [1–486] | 3341 | [1–207] | | | | |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 3422 | [1–594] | 3478 | [1–498] | 3611 | [1–453] | 3673 | [84–110],[359–400] |
| 3423 | [1–429] | 3479 | [1–399] | 3613 | [1–84] | 3674 | [276–331] |
| 3424 | [1–386] | 3480 | [1–531] | 3614 | [271–493] | 3675 | [84–110],[359–400] |
| 3425 | [1–442] | 3481 | [1–539] | 3615 | [1–194],[312–491] | 3676 | [40–586] |
| 3426 | [1–431] | 3482 | [1–661] | 3616 | [1–311],[410–549] | 3677 | [433–465] |
| 3427 | [1–484] | 3483 | [1–556] | 3617 | [1–489] | 3678 | [1–471] |
| 3429 | [243–363] | 3484 | [1–518] | 3618 | [1–254],[445–753] | 3679 | [1–524] |
| 3430 | [1–52],[341–592],[669–804] | 3485 | [1–546] | 3619 | [1–393] | 3680 | [1–941] |
| 3432 | [1–25] | 3486 | [1–478] | 3620 | [1–179],[370–482] | 3684 | [1–303],[482–508] |
| 3433 | [1–473] | 3487 | [1–561] | 3621 | [1–42] | 3686 | [1–392] |
| 3434 | [1–107],[149–489] | 3488 | [1–478] | 3622 | [1–479] | 3687 | [1–532] |
| 3435 | [1–588] | 3489 | [1–527] | 3623 | [1–505] | 3688 | [1–471] |
| 3490 | [99–192],[414–482] | 3544 | [1–406] | 3624 | [1–479] | 3689 | [1–525] |
| 3491 | [112–205],[517–561] | 3545 | [1–281] | 3625 | [1–422] | 3690 | [1–513] |
| 3492 | [111–204] | 3546 | [1–466] | 3626 | [1–407] | 3691 | [1–564] |
| 3493 | [1–477] | 3547 | [1–470] | 3627 | [1–32],[289–553] | 3693 | [1–206],[289–473] |
| 3494 | [1–494] | 3548 | [1–496] | 3628 | [1–522] | 3694 | [1–96],[205–461] |
| 3495 | [183–533] | 3549 | [1–475] | 3629 | [1–466],[727–821] | 3695 | [1–422] |
| 3496 | [1–186],[229–419] | 3550 | [1–401] | 3631 | [476–500] | 3696 | [1–38],[153–365] |
| 3498 | [188–684] | 3551 | [1–494] | 3633 | [1–464] | 3697 | [1–469] |
| 3499 | [1–465] | 3552 | [1–43],[345–490] | 3634 | [1–408] | 3698 | [1–485] |
| 3501 | [1–511] | 3553 | [490–523] | 3635 | [1–483] | 3699 | [1–245] |
| 3502 | [1–490] | 3554 | [1–234] | 3637 | [1–488] | 3700 | [1–349] |
| 3503 | [1–513] | 3555 | [312–664] | 3638 | [1–474] | 3701 | [1–572] |
| 3504 | [1–394] | 3556 | [312–581] | 3639 | [1–486] | 3702 | [1–543] |
| 3506 | [268–394],[425–478] | 3557 | [1–244] | 3643 | [135–295] | 3703 | [1–503] |
| 3507 | [1–497] | 3558 | [1–462] | 3644 | [1–485] | 3704 | [1–485] |
| 3508 | [1–470] | 3559 | [1–548] | 3645 | [1–168],[449–474] | 3705 | [42–100] |
| 3509 | [1–27],[493–557] | 3560 | [1–461] | 3646 | [59–234],[416–473] | 3706 | [1–499] |
| 3510 | [1–25],[186–402],[460–495] | 3561 | [1–540] | 3647 | [1–527] | 3707 | [1–400] |
|  |  |  |  | 3648 | [1–490] | 3708 | [1–633] |
|  |  |  |  | 3649 | [1–32],[140–536] | 3709 | [1–504] |
| 3511 | [408–477] | 3562 | [1–453] | 3650 | [1–484] | 3710 | [1–560] |
| 3512 | [1–492] | 3563 | [1–465] | 3651 | [1–494] | 3711 | [1–261],[291–378] |
| 3513 | [1–461] | 3564 | [1–553] | 3652 | [1–31] | 3712 | [1–479] |
| 3514 | [421–469] | 3565 | [1–93],[350–491] | 3713 | [1–499] | 3773 | [1–505] |
| 3515 | [299–325] | 3566 | [1–93],[350–494] | 3714 | [1–480] | 3775 | [1–473] |
| 3516 | [1–255] | 3567 | [1–459] | 3715 | [1–507] | 3776 | [1–421],[537–1100] |
| 3517 | [1–297] | 3568 | [1–379],[491–538] | 3716 | [1–771] | 3777 | [1–516] |
| 3518 | [1–754] | 3569 | [1–441],[553–595] | 3717 | [1–599] | 3778 | [1–687] |
| 3519 | [1–657] | 3570 | [126–265] | 3718 | [1–475] | 3779 | [1–79] |
| 3520 | [1–490] | 3571 | [1–404] | 3719 | [162–511] | 3780 | [1–79],[524–555] |
| 3521 | [1–141] | 3572 | [1–401],[513–555] | 3720 | [162–816] | 3781 | [1–534] |
| 3522 | [1–530] | 3573 | [1–315],[345–504] | 3722 | [1–496] | 3782 | [1–467] |
| 3523 | [1–503] | 3575 | [1–494] | 3723 | [1–477] | 3784 | [1–484] |
| 3524 | [1–198] | 3576 | [1–282] | 3724 | [1–469] | 3785 | [1–153],[407–442] |
| 3525 | [1–572] | 3577 | [1–313] | 3725 | [208–373] | 3786 | [1–420] |
| 3526 | [1–343],[372–457] | 3579 | [1–308] | 3726 | [1–523] | 3787 | [1–505] |
| 3527 | [1–614] | 3580 | [1–407] | 3727 | [173–316],[270–462],[504–579] | 3788 | [384–453] |
| 3528 | [1–35],[473–502] | 3582 | [1–69] |  |  |  |  |
| 3530 | [1–454] | 3583 | [36–516] | 3728 | [1–455] | 3789 | [1–488] |
| 3531 | [1–385] | 3584 | [1–44] | 3729 | [1–450] | 3791 | [1–398] |
| 3532 | [1–511] | 3585 | [1–396] | 3730 | [1–394] | 3792 | [1–28] |
| 3535 | [1–482] | 3586 | [333–472] | 3731 | [1–494] | 3794 | [160–240],[292–321],[358–573] |
| 3536 | [1–428] | 3588 | [1–558] |  |  |  |  |
| 3537 | [1–424] | 3589 | [1–637] | 3732 | [1–524] | 3796 | [30–85] |
| 3538 | [1–96],[194–495] | 3590 | [1–79],[154–477] | 3733 | [1–479] | 3800 | [1–79] |
| 3539 | [1–498] | 3591 | [1–77],[121–162],[248–459] | 3735 | [1–377] | 3801 | [1–462] |
|  |  |  |  | 3736 | [1–496] | 3802 | [1–468] |
| 3540 | [1–500] | 3592 | [265–376] | 3738 | [1–73] | 3803 | [1–985] |
| 3542 | [1–526] | 3593 | [56–492] | 3739 | [1–26],[129–327] | 3804 | [1–509] |
| 3543 | [1–520] | 3594 | [1–512] | 3741 | [1–387] | 3805 | [1–400] |
| 3595 | [1–82],[117–571] | 3653 | [1–501] | 3742 | [1–36],[160–222],[264–316],[459–523] | 3806 | [1–450] |
| 3596 | [1–482] | 3654 | [1–595] |  |  |  |  |
| 3598 | [92–292] | 3655 | [1–490] | 3743 | [1–613] | 3809 | [1–590] |
| 3599 | [1–372] | 3658 | [1–456] | 3746 | [37–418] | 3810 | [43–503] |
| 3600 | [1–157],[210–236] | 3662 | [1–362] | 3747 | [1–27],[192–487] | 3811 | [1–528] |
| 3601 | [1–150],[203–394] | 3663 | [1–1043] | 3748 | [1–534] | 3812 | [1–519] |
| 3602 | [1–480] | 3665 | [324–385] | 3749 | [167–194],[337–378] | 3813 | [1–518] |
| 3603 | [1–460] | 3666 | [1–47] | 3752 | [1–468] | 3814 | [1–515] |
| 3606 | [443–469] | 3668 | [432–467] | 3753 | [1–238],[272–557] | 3815 | [1–480] |
| 3607 | [1–50],[114–488] | 3669 | [324–385] | 3754 | [383–429] | 3816 | [1–458] |
| 3608 | [1–501] | 3670 | [1–71],[322–363] | 3756 | [1–462] | 3821 | [384–449] |
| 3609 | [1–638] | 3671 | [84–110],[359–400] | 3757 | [1–473] | 3822 | [1–569] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 3758 | [171–483] | 3823 | [1–453] | 7821 | [1–361] | 7879 | [1–83] |
| 3759 | [1–518] | 3824 | [1–491] | 7822 | [1–317] | 7880 | [124–265] |
| 3763 | [1–82] | 3825 | [1–487] | 7823 | [1–343] | 7881 | [1–508] |
| 3764 | [1–96] | 3826 | [1–603] | 7824 | [1–343] | 7883 | [1–314] |
| 3765 | [1–504] | 3827 | [1–465] | 7825 | [1–208] | 7884 | [1–501] |
| 3766 | [1–620] | 3828 | [1–544] | 7826 | [76–293] | 7885 | [1–344] |
| 3767 | [414–478] | 3829 | [1–48],[90–294],[503–589] | 7827 | [1–242] | 7886 | [1–455] |
| 3768 | [1–480] | 3830 | [1–561] | 7828 | [1–384],[424–533] | 7887 | [1–401] |
| 3769 | [102–461] | 3831 | [1–542] | 7830 | [1–310] | 7888 | [1–171] |
| 3770 | [128–460] | 3832 | [41–456] | 7831 | [1–548] | 7889 | [1–77] |
| 3771 | [1–618] | 3833 | [1–463] | 7832 | [1–328] | 7890 | [1–328] |
| 3834 | [1–592] | 7749 | [1–108] | 7833 | [1–505] | 7891 | [1–395] |
| 3835 | [1–452] | 7750 | [1–96] | 7834 | [1–117] | 7892 | [1–501] |
| 3836 | [1–50],[248–298] | 7751 | [1–153] | 7836 | [1–307] | 7893 | [1–94],[125–329] |
| 3837 | [1–550] | 7752 | [1–108] | 7837 | [1–547] | 7895 | [1–170] |
| 3839 | [321–536] | 7753 | [1–101] | 7838 | [1–263] | 7896 | [1–170] |
| 3840 | [321–508] | 7754 | [1–108] | 7839 | [1–465] | 7898 | [1–475] |
| 3841 | [1–421] | 7755 | [1–113] | 7840 | [1–370] | 7899 | [1–314] |
| 3844 | [1–252] | 7756 | [1–108] | 7841 | [1–307] | 7900 | [1–476] |
| 3845 | [1–352] | 7757 | [1–108] | 7842 | [1–515] | 7901 | [1–440] |
| 3847 | [397–453] | 7758 | [1–108] | 7843 | [1–365] | 7902 | [1–357] |
| 3848 | [1–106],[140–674] | 7759 | [1–406] | 7844 | [1–308] | 7903 | [1–334] |
| 3849 | [1–515] | 7760 | [1–108] | 7845 | [1–532] | 7904 | [1–164] |
| 3850 | [1–514] | 7761 | [1–88] | 7846 | [1–488] | 7906 | [1–170] |
| 3851 | [1–514] | 7762 | [1–169] | 7847 | [1–467] | 7907 | [1–170] |
| 3852 | [1–104],[138–515] | 7763 | [1–108] | 7848 | [240–329] | 7909 | [1–445] |
| 3853 | [1–516] | 7764 | [1–108] | 7850 | [1–100] | 7910 | [1–51] |
| 3854 | [1–519] | 7765 | [1–108] | 7851 | [1–381] | 7911 | [1–350],[454–479] |
| 3855 | [1–104],[138–516] | 7766 | [1–169] | 7853 | [1–58] | 7912 | [1–84] |
| 3856 | [1–105],[139–428] | 7767 | [1–108] | 7855 | [1–90] | 7913 | [1–168] |
| 3857 | [1–105],[139–428] | 7768 | [1–134] | 7856 | [1–118] | 7914 | [1–52] |
| 3858 | [1–105],[139–516] | 7769 | [1–108] | 7858 | [1–73] | 7915 | [1–123] |
| 3859 | [1–515] | 7770 | [1–108] | 7916 | [1–31] | 7970 | [1–67] |
| 3860 | [1–468] | 7771 | [1–108] | 7917 | [1–321] | 7971 | [1–206] |
| 3861 | [1–31] | 7772 | [1–266] | 7919 | [1–271] | 7972 | [1–73] |
| 3863 | [1–201] | 7773 | [1–108] | 7920 | [40–171] | 7973 | [1–332] |
| 3864 | [1–513] | 7774 | [1–63] | 7921 | [1–356] | 7976 | [1–270] |
| 3865 | [264–495] | 7775 | [1–299] | 7922 | [1–299] | 7977 | [1–172] |
| 3866 | [1–470] | 7776 | [1–108] | 7923 | [1–354] | 7978 | [1–321] |
| 3868 | [1–500] | 7778 | [1–101] | 7924 | [1–455] | 7979 | [1–170] |
| 3869 | [1–489] | 7779 | [1–63] | 7925 | [1–425] | 7982 | [1–328] |
| 3870 | [1–503] | 7781 | [1–108] | 7926 | [1–83] | 7983 | [1–58] |
| 3871 | [252–298] | 7782 | [1–154] | 7927 | [1–313] | 7984 | [1–422] |
| 3872 | [1–480] | 7783 | [1–169] | 7928 | [1–314] | 7985 | [1–113] |
| 3873 | [1–523] | 7784 | [1–108] | 7929 | [1–313] | 7986 | [1–163] |
| 3874 | [1–173],[338–613] | 7785 | [1–108] | 7930 | [1–328] | 7987 | [76–100] |
| 3875 | [1–501] | 7786 | [1–366] | 7931 | [1–178],[211–409],[448–483] | 7988 | [1–171] |
| 3876 | [1–497] | 7787 | [1–101] | 7932 | [1–125] | 7989 | [1–104] |
| 3877 | [244–453] | 7788 | [1–444] | 7933 | [1–314] | 7990 | [1–171] |
| 3879 | [465–489] | 7789 | [1–108] | 7934 | [1–294] | 7991 | [1–519] |
| 3880 | [1–189],[457–707] | 7790 | [1–108] | 7935 | [1–408] | 7992 | [1–67] |
| 3881 | [1–459] | 7791 | [1–108] | 7936 | [1–279] | 7993 | [1–185] |
| 3883 | [1–231] | 7792 | [1–339] | 7937 | [1–65] | 7994 | [1–171] |
| 7744 | [1–108] | 7795 | [1–169] | 7940 | [1–263] | 7995 | [1–436] |
| 7745 | [1–89] | 7796 | [1–108] | 7942 | [1–315] | 7996 | [1–171] |
| 7746 | [1–108] | 7798 | [1–108] | 7943 | [1–458] | 7997 | [1–31] |
| 7747 | [1–108] | 7799 | [1–89] | 7944 | [1–309] | 7999 | [1–68] |
| 7748 | [1–154] | 7800 | [1–63] | 7945 | [1–238] | 8000 | [1–145],[343–385] |
| 7801 | [1–150] | 7860 | [1–112] | 7946 | [1–336] | 8001 | [1–324] |
| 7802 | [1–500] | 7861 | [1–100] | 7947 | [1–166] | 8002 | [1–481] |
| 7803 | [1–108] | 7862 | [1–27],[140–184] | 7948 | [1–140] | 8003 | [1–481] |
| 7804 | [1–108] | 7864 | [1–426] | 7949 | [1–316] | 8004 | [1–421] |
| 7805 | [1–108] | 7865 | [1–367] | 7950 | [33–412] | 8005 | [309–333] |
| 7806 | [1–297] | 7866 | [1–256] | 7951 | [1–431] | 8006 | [1–58] |
| 7807 | [1–357] | 7867 | [1–452] | 7952 | [1–83] | 8007 | [1–475] |
| 7809 | [1–25],[282–385] | 7870 | [1–349] | 7953 | [1–280] | 8008 | [373–435] |
| 7810 | [1–53] | 7871 | [1–177] | 7954 | [1–171] | 8009 | [1–314] |
| 7811 | [1–381] | 7872 | [1–494] | 7955 | [1–459] | 8010 | [1–337] |
| 7812 | [1–177] | 7874 | [1–216] | 7956 | [1–391] | 8011 | [1–310] |
| 7813 | [1–162] | 7875 | [1–106] | 7957 | [100–142] | 8013 | [1–376] |
| 7814 | [1–35] | 7876 | [1–172] | 7958 | [1–171] | 8014 | [1–463] |
| 7818 | [1–158] | 7877 | [1–233] | 7960 | [1–244] | 8016 | [1–60] |
| 7819 | [1–205] | 7878 | [1–155] | 7961 | [1–95] | 8017 | [1–408] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 7962 | [1–429] | 8018 | [1–103] | 8159 | [1–170],[217–291],[344–396] | 8217 | [1–368] |
| 7963 | [1–334] | 8019 | [1–73] | 8160 | [144–377] | 8218 | [1–180] |
| 7964 | [1–293] | 8020 | [1–96] | 8161 | [1–385] | 8219 | [1–377] |
| 7966 | [1–152] | 8021 | [1–121] | 8162 | [1–367] | 8222 | [1–359] |
| 7967 | [1–86] | 8022 | [1–67] | 8163 | [1–153] | 8223 | [1–468] |
| 7968 | [1–330] | 8023 | [1–58] | 8164 | [1–385] | 8224 | [1–407] |
| 8024 | [1–164] | 8073 | [1–177] | 8166 | [1–325] | 8226 | [1–473] |
| 8025 | [1–104] | 8074 | [1–165] | 8167 | [218–433] | 8227 | [1–535] |
| 8027 | [1–163] | 8075 | [1–104] | 8168 | [1–423] | 8228 | [1–378] |
| 8028 | [1–103] | 8076 | [1–58] | 8170 | [1–399] | 8229 | [1–432] |
| 8030 | [1–104] | 8077 | [1–454] | 8172 | [1–72] | 8230 | [1–404] |
| 8031 | [1–104] | 8078 | [1–103] | 8173 | [315–425] | 8231 | [1–72] |
| 8032 | [1–104] | 8080 | [1–103] | 8174 | [1–444] | 8233 | [1–356] |
| 8033 | [1–77] | 8081 | [1–127] | 8175 | [1–403] | 8235 | [1–452] |
| 8034 | [1–74] | 8082 | [1–102] | 8177 | [1–438] | 8236 | [1–155] |
| 8035 | [1–104] | 8084 | [1–103] | 8178 | [1–298] | 8237 | [1–432] |
| 8036 | [1–58] | 8085 | [1–146] | 8179 | [1–292] | 8238 | [1–444] |
| 8037 | [1–104] | 8086 | [1–164] | 8180 | [1–153] | 8240 | [1–116],[145–455] |
| 8038 | [1–90] | 8087 | [1–103] | 8181 | [1–352] | 8241 | [1–189] |
| 8039 | [1–65] | 8088 | [1–103] | 8182 | [1–70] | 8242 | [1–65],[180–221],[388–450] |
| 8040 | [1–166] | 8089 | [1–58] | | | | |
| 8041 | [1–103] | 8090 | [1–97] | | | | |
| 8042 | [1–79] | 8092 | [1–103] | 8183 | [1–347] | 8243 | [1–243] |
| 8043 | [1–103] | 8093 | [1–67] | 8184 | [1–382] | 8244 | [1–463] |
| 8044 | [1–150] | 8094 | [1–114] | 8185 | [1–318] | 8245 | [1–446] |
| 8045 | [1–360] | 8095 | [1–67] | 8186 | [1–383] | 8246 | [1–473] |
| 8046 | [1–104] | 8096 | [1–58] | 8187 | [1–430] | 8247 | [1–549] |
| 8047 | [1–71] | 8097 | [1–61] | 8188 | [1–370] | 8248 | [1–506] |
| 8048 | [1–92] | 8099 | [1–377] | 8249 | [1–525] | 8310 | [1–333] |
| 8049 | [1–103] | 8100 | [1–148] | 8250 | [1–435] | 8311 | [1–414] |
| 8050 | [1–103] | 8102 | [1–58] | 8251 | [1–413] | 8312 | [1–228] |
| 8051 | [1–132] | 8103 | [1–58] | 8252 | [1–299] | 8313 | [1–432] |
| 8052 | [1–92] | 8105 | [1–234] | 8253 | [1–350] | 8315 | [1–361] |
| 8053 | [1–103] | 8106 | [1–102] | 8254 | [1–430] | 8316 | [1–41] |
| 8054 | [1–103] | 8107 | [1–95] | 8257 | [1–63] | 8317 | [1–416] |
| 8055 | [1–88] | 8108 | [1–72] | 8259 | [1–420] | 8319 | [1–433] |
| 8056 | [1–103] | 8109 | [1–147] | 8261 | [1–419] | 8320 | [1–337] |
| 8057 | [1–57] | 8110 | [1–103] | 8262 | [1–39] | 8321 | [1–398] |
| 8058 | [1–191] | 8111 | [1–104] | 8263 | [1–33] | 8322 | [1–396] |
| 8059 | [1–75] | 8112 | [1–138] | 8264 | [1–139] | 8323 | [1–353] |
| 8060 | [1–365] | 8113 | [1–103] | 8265 | [1–188] | 8324 | [1–459] |
| 8061 | [1–65] | 8114 | [1–103] | 8267 | [1–447] | 8325 | [1–307] |
| 8062 | [1–58] | 8115 | [1–104] | 8269 | [1–256],[298–467] | 8327 | [1–277] |
| 8063 | [1–335] | 8116 | [1–103] | 8271 | [1–374] | 8328 | [1–141] |
| 8064 | [1–198] | 8117 | [1–58] | 8272 | [1–196] | 8329 | [1–360] |
| 8065 | [1–165] | 8118 | [1–164] | 8273 | [1–468] | 8330 | [1–349] |
| 8066 | [1–104] | 8119 | [1–58] | 8274 | [1–374] | 8331 | [1–457] |
| 8067 | [1–165] | 8120 | [1–75] | 8275 | [1–395] | 8333 | [1–167] |
| 8068 | [1–104] | 8121 | [1–76] | 8276 | [1–498] | 8334 | [1–386] |
| 8069 | [1–84] | 8123 | [1–104] | 8277 | [1–240] | 8335 | [1–242] |
| 8070 | [1–164] | 8124 | [1–58] | 8278 | [315–479] | 8336 | [1–356] |
| 8071 | [1–235] | 8125 | [1–205] | 8279 | [51–75],[124–160],[230–277],[348–413] | 8337 | [1–56] |
| 8072 | [1–104] | 8127 | [1–165] | | | | |
| 8128 | [1–104] | 8191 | [1–63] | 8281 | [1–180] | 8338 | [1–311] |
| 8130 | [1–317] | 8193 | [1–55] | 8282 | [1–62] | 8340 | [1–131] |
| 8133 | [1–352] | 8194 | [1–157] | 8283 | [1–442] | 8341 | [1–440] |
| 8134 | [1–390] | 8195 | [1–183] | 8284 | [1–480] | 8342 | [48–391] |
| 8135 | [1–441] | 8196 | [1–408] | 8286 | [1–202] | 8343 | [1–422] |
| 8136 | [291–316] | 8197 | [1–460] | 8289 | [1–316] | 8345 | [1–359] |
| 8137 | [1–243] | 8198 | [1–250],[355–459] | 8290 | [1–290] | 8346 | [1–387] |
| 8138 | [1–368] | 8199 | [1–447] | 8291 | [1–58] | 8348 | [1–365] |
| 8140 | [1–407] | 8200 | [1–62] | 8292 | [1–326],[394–457] | 8349 | [1–327] |
| 8141 | [1–390] | 8201 | [1–398] | 8294 | [1–287] | 8351 | [1–477] |
| 8143 | [474–499] | 8202 | [1–448] | 8295 | [1–218] | 8353 | [1–272] |
| 8144 | [1–537] | 8203 | [1–429] | 8296 | [50–222] | 8355 | [1–83] |
| 8145 | [1–266] | 8205 | [1–29],[59–85] | 8297 | [1–280] | 8356 | [1–534] |
| 8147 | [1–414] | 8206 | [1–321] | 8299 | [1–127],[203–244],[283–339] | 8358 | [1–472] |
| 8149 | [135–428] | 8207 | [1–452] | | | | |
| 8151 | [1–160] | 8208 | [1–183] | 8300 | [1–369] | 8359 | [1–416] |
| 8152 | [1–165] | 8210 | [1–297] | 8302 | [1–168] | 8360 | [1–424] |
| 8153 | [1–111] | 8211 | [1–167] | 8303 | [1–66] | 8361 | [1–349] |
| 8154 | [1–395] | 8212 | [1–403] | 8304 | [1–106] | 8363 | [1–361] |
| 8155 | [1–445] | 8213 | [1–172],[406–466] | 8305 | [1–358] | 8364 | [1–344] |
| 8156 | [1–407] | 8215 | [1–428] | 8306 | [1–425] | 8366 | [1–268] |

TABLE IVa-continued (Novelty:95%)

| Seq Id No. | Positions of preferred fragments | Seq Id No. | Positions of preferred fragments |
|---|---|---|---|
| 8307 | [1–38],[212–393] | 8367 | [1–370] |
| 8308 | [1–153],[296–338] | 8368 | [1–327] |
| 8309 | [1–216] | 8369 | [1–360] |
| 8370 | [1–498] | 8428 | [1–395] |
| 8371 | [1–77] | 8429 | [1–438] |
| 8372 | [1–389] | 8430 | [1–73] |
| 8374 | [1–398] | 8431 | [1–79] |
| 8375 | [1–405] | 8432 | [1–232] |
| 8376 | [1–143],[257–383] | 8434 | [1–427] |
| 8377 | [1–150] | 8435 | [1–309] |
| 8378 | [1–412] | 8436 | [1–586] |
| 8379 | [1–378] | 8437 | [1–423] |
| 8380 | [1–464] | 8438 | [1–465] |
| 8381 | [1–351] | 8439 | [1–304] |
| 8382 | [1–51] | 8440 | [1–68] |
| 8383 | [1–159] | 8441 | [1–125] |
| 8384 | [1–440] | 8443 | [1–330] |
| 8385 | [1–438] | 8444 | [1–403] |
| 8386 | [104–421] | 8445 | [1–419] |
| 8389 | [1–445] | 8446 | [158–265] |
| 8390 | [1–442] | 8447 | [1–67] |
| 8391 | [1–419] | 8448 | [1–238] |
| 8393 | [1–463] | 8449 | [1–449] |
| 8394 | [77–237] | 8451 | [1–349] |
| 8395 | [1–360] | 8452 | [1–547] |
| 8396 | [1–314] | 8453 | [1–75] |
| 8397 | [1–439] | 8455 | [1–349] |
| 8398 | [1–328] | 8456 | [1–350] |
| 8399 | [1–398] | 8458 | [1–378] |
| 8400 | [1–96] | 8460 | [1–77] |
| 8401 | [1–557] | 8461 | [1–494] |
| 8402 | [1–446] | 8462 | [1–421] |
| 8404 | [1–155] | 8464 | [1–369] |
| 8406 | [1–221] | 8465 | [1–480] |
| 8408 | [1–41] | 8466 | [1–508] |
| 8409 | [138–229] | 8467 | [1–460] |
| 8410 | [1–108] | 8468 | [1–466] |
| 8411 | [1–329] | 8470 | [1–430] |
| 8412 | [1–271] | 8471 | [1–332] |
| 8413 | [1–492] | 8472 | [1–445] |
| 8417 | [1–340] | 8473 | [1–375] |
| 8418 | [1–226] | 8474 | [1–256] |
| 8420 | [1–67] | 8475 | [1–355] |
| 8421 | [1–484] | 8476 | [1–342] |
| 8422 | [1–52] | 8477 | [1–38] |
| 8423 | [1–50] | 8478 | [1–445] |
| 8424 | [1–312] | 8479 | [1–206] |
| 8425 | [1–157] | 8480 | [1–138] |
| 8426 | [30–83] | 8481 | [1–67] |
| 8427 | [1–504] | 8482 | [1–29] |
| 8483 | [1–270] | 8539 | [1–351] |
| 8484 | [1–317] | 8540 | [1–423] |
| 8485 | [1–312] | 8541 | [1–394] |
| 8486 | [1–324] | 8543 | [1–480] |
| 8487 | [1–203] | 8544 | [1–408] |
| 8488 | [1–355] | 8545 | [1–302] |
| 8489 | [1–328] | 8546 | [1–348] |
| 8490 | [1–58] | 8547 | [1–84] |
| 8491 | [1–361] | 8548 | [1–88] |
| 8493 | [97–127] | 8549 | [1–183] |
| 8495 | [1–395] | 8550 | [1–146] |
| 8497 | [1–403] | 8551 | [1–147] |
| 8499 | [1–226],[391–416] | 8552 | [1–149] |
| 8500 | [1–432] | 8553 | [1–167] |
| 8501 | [1–462] | 8554 | [1–474] |
| 8502 | [1–451] | 8555 | [1–426] |
| 8503 | [1–365] | 8556 | [1–404] |
| 8504 | [1–359] | 8557 | [1–318] |
| 8505 | [1–375] | 8560 | [1–442] |
| 8506 | [1–364] | 8561 | [1–318] |
| 8507 | [1–401] | 8562 | [1–317] |
| 8508 | [395–421] | 8563 | [1–184] |
| 8509 | [1–429] | 8564 | [1–136] |
| 8510 | [1–406] | 8565 | [1–307] |
| 8511 | [1–394] | 8566 | [1–207] |
| 8512 | [1–427] | 8567 | [1–136] |
| 8514 | [1–396] | 8568 | [1–395] |
| 8515 | [1–494] | 8570 | [1–184] |
| 8516 | [1–350] | 8571 | [1–67] |
| 8517 | [1–388] | 8572 | [1–387] |
| 8518 | [1–322] | 8574 | [1–416] |
| 8519 | [1–286] | 8575 | [1–331] |
| 8520 | [1–150] | 8576 | [1–68] |
| 8521 | [1–303] | 8577 | [1–483] |
| 8522 | [1–157] | 8578 | [1–386] |
| 8523 | [1–354] | 8579 | [1–363] |
| 8524 | [1–398] | 8580 | [1–385] |
| 8525 | [1–83] | 8581 | [30–202] |
| 8526 | [1–326] | 8584 | [1–144] |
| 8527 | [1–315] | 8585 | [1–361] |
| 8528 | [41–374] | 8586 | [1–439] |
| 8529 | [1–460] | 8587 | [1–166] |
| 8534 | [1–369] | 8588 | [1–103] |
| 8535 | [1–154] | 8589 | [1–151] |
| 8536 | [1–433] | 8591 | [1–362] |
| 8537 | [1–391] | 8593 | [1–80] |
| 8538 | [1–459] | 8594 | [1–84] |
| 8597 | [1–144] | 8666 | [1–84] |
| 8598 | [1–348] | 8667 | [1–288],[405–468] |
| 8599 | [1–363] | 8668 | [1–58] |
| 8600 | [1–126] | 8671 | [1–116] |
| 8603 | [1–132] | 8672 | [1–97] |
| 8605 | [1–114] | 8673 | [1–82] |
| 8606 | [1–84] | 8675 | [1–222] |
| 8609 | [1–73] | 8677 | [1–164] |
| 8611 | [1–103] | 8678 | [1–291],[408–449] |
| 8613 | [1–89] | 8679 | [1–56] |
| 8614 | [1–361] | 8680 | [1–73] |
| 8616 | [1–361] | 8681 | [1–73] |
| 8617 | [1–164] | 8682 | [1–186] |
| 8620 | [1–345] | 8684 | [1–164] |
| 8621 | [1–361] | 8685 | [1–103] |
| 8622 | [1–58] | 8687 | [1–83] |
| 8623 | [1–159] | 8689 | [1–366] |
| 8625 | [1–97] | 8690 | [1–116] |
| 8626 | [1–103] | 8691 | [1–79] |
| 8628 | [1–58] | 8692 | [1–82] |
| 8630 | [1–164] | 8693 | [1–84] |
| 8632 | [1–139] | 8694 | [1–90] |
| 8633 | [1–103] | 8696 | [1–513] |
| 8635 | [1–103] | 8697 | [1–500] |
| 8636 | [1–164] | 8698 | [1–455] |
| 8637 | [1–103] | 8699 | [1–238] |
| 8638 | [1–361] | 8700 | [1–332] |
| 8639 | [1–75] | 8701 | [1–530] |
| 8641 | [1–58] | 8702 | [1–451] |
| 8643 | [1–361] | 8703 | [176–271] |
| 8644 | [1–148] | 8704 | [1–447] |
| 8645 | [1–58] | 8705 | [111–141] |
| 8646 | [1–58] | 8706 | [1–500] |
| 8647 | [1–361] | 8707 | [1–485] |
| 8649 | [1–103] | 8708 | [1–483] |
| 8651 | [1–166] | 8709 | [1–48],[153–433] |
| 8652 | [1–77] | 8710 | [1–260] |
| 8653 | [1–51] | 8711 | [1–251] |
| 8654 | [1–363] | 8712 | [1–115] |
| 8655 | [1–159] | 8713 | [1–447] |
| 8656 | [1–150] | 8714 | [1–431] |
| 8657 | [1–359] | 8715 | [1–454] |
| 8658 | [1–167] | 8716 | [1–62] |
| 8659 | [1–103] | 8717 | [1–309] |
| 8661 | [1–103] | 8718 | [1–384] |
| 8663 | [1–84] | 8719 | [1–375] |
| 8665 | [1–152] | 8721 | [1–236] |
| 8722 | [1–329] | 8775 | [30–336] |
| 8723 | [1–159] | 8776 | [1–273] |
| 8724 | [1–67] | 8777 | [1–226] |
| 8726 | [141–199] | 8778 | [1–226] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 8727 | [1–390] | 8779 | [1–276] | 8862 | [1–379] | 8915 | [1–58] |
| 8728 | [1–28] | 8780 | [1–215] | 8863 | [1–149] | 8916 | [1–103] |
| 8730 | [1–201] | 8781 | [1–410] | 8864 | [1–103] | 8917 | [1–103] |
| 8731 | [1–178] | 8782 | [1–136] | 8865 | [1–103] | 8918 | [1–103] |
| 8732 | [1–291],[408–465] | 8783 | [1–73] | 8866 | [1–58] | 8919 | [1–95] |
| 8733 | [1–172] | 8784 | [1–139] | 8867 | [1–71] | 8921 | [1–58] |
| 8734 | [1–384] | 8785 | [1–396] | 8868 | [1–103] | 8922 | [1–73] |
| 8735 | [1–78] | 8786 | [1–251] | 8869 | [1–164] | 8925 | [1–84] |
| 8736 | [1–52] | 8787 | [1–399] | 8870 | [1–103] | 8926 | [1–103] |
| 8738 | [1–294] | 8788 | [1–509] | 8871 | [1–89] | 8927 | [1–353] |
| 8739 | [1–398] | 8789 | [1–446] | 8872 | [1–381] | 8928 | [1–164] |
| 8740 | [1–337] | 8790 | [1–464] | 8873 | [1–482] | 8929 | [1–76] |
| 8741 | [1–81] | 8791 | [1–461] | 8874 | [1–103] | 8930 | [1–361] |
| 8742 | [1–283],[400–455] | 8792 | [1–235] | 8875 | [1–103] | 8931 | [1–103] |
| 8743 | [1–377] | 8793 | [1–408] | 8876 | [1–95] | 8932 | [1–104] |
| 8744 | [1–287] | 8794 | [1–421] | 8877 | [1–95] | 8935 | [1–132] |
| 8745 | [1–284] | 8796 | [1–159] | 8936 | [1–103] | 8994 | [1–522] |
| 8746 | [1–319] | 8797 | [1–71] | 8937 | [1–362] | 8995 | [1–206] |
| 8749 | [1–81] | 8798 | [1–354] | 8938 | [1–103] | 8996 | [1–62] |
| 8750 | [1–409] | 8799 | [1–408] | 8939 | [1–103] | 8998 | [1–603] |
| 8751 | [1–291],[408–476] | 8800 | [1–295] | 8942 | [1–149] | 9000 | [1–169] |
| 8752 | [1–354] | 8801 | [1–457] | 8944 | [1–103] | 9001 | [1–446] |
| 8753 | [1–327] | 8802 | [1–83] | 8946 | [1–392] | 9002 | [1–341] |
| 8754 | [1–422] | 8803 | [1–158] | 8947 | [1–138] | 9003 | [1–381] |
| 8755 | [1–150] | 8804 | [196–530] | 8948 | [1–65] | 9004 | [1–171] |
| 8756 | [1–94] | 8805 | [1–361] | 8950 | [1–95] | 9005 | [1–366] |
| 8757 | [1–148] | 8806 | [1–158] | 8951 | [1–88] | 9006 | [1–349] |
| 8758 | [1–290] | 8807 | [1–314] | 8952 | [1–152] | 9007 | [1–452] |
| 8759 | [1–289] | 8808 | [1–448] | 8955 | [1–445] | 9008 | [1–425] |
| 8760 | [1–314] | 8810 | [1–181] | 8957 | [1–95] | 9010 | [1–27] |
| 8761 | [1–154] | 8811 | [30–207] | 8958 | [1–103] | 9011 | [1–380] |
| 8762 | [1–203] | 8812 | [1–408] | 8959 | [1–95] | 9012 | [1–468] |
| 8763 | [1–374] | 8813 | [1–372] | 8960 | [1–104] | 9013 | [1–443] |
| 8764 | [58–360] | 8814 | [1–495] | 8961 | [1–89] | 9014 | [1–81] |
| 8765 | [1–384] | 8815 | [1–433] | 8962 | [1–90] | 9015 | [1–381] |
| 8766 | [1–73] | 8816 | [1–471] | 8963 | [1–103] | 9016 | [1–515] |
| 8767 | [1–375] | 8817 | [1–84] | 8964 | [1–103] | 9017 | [1–442] |
| 8768 | [1–281],[398–448] | 8818 | [1–444] | 8965 | [1–114] | 9018 | [1–460] |
| 8769 | [1–341] | 8819 | [1–472] | 8966 | [1–256] | 9019 | [1–261] |
| 8770 | [1–222],[278–342] | 8820 | [1–384] | 8967 | [1–103] | 9020 | [1–411] |
| 8771 | [1–236] | 8821 | [1–410] | 8968 | [1–103] | 9021 | [278–303] |
| 8772 | [1–386] | 8822 | [1–419] | 8969 | [1–89] | 9023 | [1–459] |
| 8773 | [152–211] | 8824 | [1–95] | 8970 | [1–103] | 9024 | [1–387] |
| 8825 | [1–54] | 8878 | [1–103] | 8971 | [1–152] | 9025 | [1–76] |
| 8826 | [1–485] | 8879 | [1–94] | 8972 | [1–164] | 9026 | [1–472] |
| 8827 | [1–434] | 8881 | [1–149] | 8973 | [1–94] | 9027 | [1–315] |
| 8828 | [1–487] | 8883 | [1–95] | 8974 | [1–103] | 9028 | [1–385] |
| 8829 | [1–281] | 8885 | [1–442] | 8975 | [1–103] | 9029 | [1–465] |
| 8830 | [1–544] | 8886 | [1–148] | 8976 | [1–399] | 9030 | [1–470] |
| 8831 | [1–74] | 8887 | [1–103] | 8977 | [1–96] | 9032 | [1–62] |
| 8833 | [1–103] | 8888 | [1–58] | 8978 | [1–103] | 9033 | [93–136] |
| 8834 | [1–103] | 8889 | [1–103] | 8980 | [1–103] | 9034 | [1–422] |
| 8836 | [1–103] | 8890 | [1–361] | 8981 | [1–92] | 9035 | [1–83] |
| 8837 | [1–58] | 8892 | [1–103] | 8982 | [1–372] | 9037 | [1–117] |
| 8838 | [1–361] | 8893 | [1–188] | 8983 | [1–430] | 9038 | [1–72] |
| 8839 | [1–76] | 8894 | [1–103] | 8984 | [1–418] | 9039 | [1–442] |
| 8840 | [1–71] | 8896 | [1–58] | 8986 | [1–323] | 9040 | [1–139] |
| 8841 | [1–475] | 8897 | [1–58] | 8987 | [1–542] | 9041 | [1–164],[286–523] |
| 8842 | [1–76] | 8898 | [1–103] | 8989 | [1–410] | 9042 | [45–432] |
| 8843 | [1–130] | 8899 | [1–150] | 8990 | [1–247] | 9043 | [1–455] |
| 8844 | [1–103] | 8900 | [1–128] | 8991 | [1–89] | 9045 | [1–372] |
| 8845 | [1–133] | 8901 | [1–103] | 8992 | [1–478] | 9046 | [1–508] |
| 8846 | [1–103] | 8902 | [1–84] | 8993 | [1–530] | 9047 | [1–467] |
| 8847 | [1–362] | 8903 | [1–89] | 9048 | [1–461] | 9105 | [1–72],[201–248] |
| 8848 | [1–103] | 8904 | [1–89] | 9049 | [1–232] | 9106 | [1–464] |
| 8849 | [1–73] | 8905 | [1–212] | 9050 | [1–132] | 9107 | [1–157] |
| 8850 | [1–103] | 8907 | [1–95] | 9051 | [109–434] | 9108 | [1–470] |
| 8852 | [1–103] | 8908 | [1–413] | 9052 | [1–63] | 9109 | [1–251] |
| 8855 | [1–103] | 8909 | [1–58] | 9054 | [1–392] | 9110 | [1–247] |
| 8856 | [1–103] | 8910 | [1–58] | 9055 | [1–404] | 9111 | [1–452] |
| 8857 | [1–103] | 8911 | [1–103] | 9056 | [1–149] | 9112 | [1–416] |
| 8858 | [1–84] | 8912 | [1–103] | 9057 | [1–386] | 9113 | [1–444] |
| 8859 | [1–95] | 8913 | [1–103] | 9058 | [1–381] | 9114 | [1–359] |
| 8860 | [1–58] | 8914 | [1–104] | 9059 | [1–79] | 9115 | [1–298] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 9060 | [1–459] | 9116 | [1–326] | 9209 | [1–448] | 9268 | [1–487] |
| 9063 | [1–181] | 9117 | [1–312] | 9210 | [1–283],[325–434] | 9269 | [1–63],[214–357] |
| 9064 | [1–439] | 9118 | [1–194] | 9213 | [1–457] | 9270 | [1–424] |
| 9067 | [1–319] | 9119 | [1–258] | 9214 | [1–388] | 9271 | [1–302],[341–578] |
| 9068 | [1–485] | 9121 | [116–434] | 9215 | [1–429] | 9272 | [1–471] |
| 9069 | [1–487] | 9122 | [1–212] | 9216 | [1–56] | 9273 | [1–449] |
| 9071 | [1–447] | 9123 | [1–410] | 9217 | [1–39],[169–465] | 9274 | [1–305] |
| 9072 | [1–403] | 9125 | [1–422] | 9219 | [1–448] | 9275 | [1–450] |
| 9073 | [1–327] | 9126 | [1–390] | 9220 | [1–225] | 9276 | [1–275],[305–419] |
| 9074 | [1–463] | 9127 | [1–453] | 9277 | [1–398] | 9333 | [1–234] |
| 9075 | [1–385] | 9128 | [107–496] | 9278 | [395–447] | 9334 | [1–472] |
| 9076 | [1–372] | 9130 | [1–275] | 9279 | [1–512] | 9335 | [1–166] |
| 9079 | [1–223] | 9132 | [1–27],[82–170] | 9280 | [1–178] | 9336 | [1–276],[308–381] |
| 9080 | [1–209] | 9133 | [1–93] | 9281 | [1–368] | 9337 | [1–425] |
| 9081 | [1–370] | 9134 | [1–94] | 9282 | [31–457] | 9338 | [1–447] |
| 9083 | [1–511] | 9135 | [1–303] | 9283 | [164–208] | 9339 | [1–483] |
| 9084 | [1–468] | 9136 | [1–235] | 9284 | [1–417] | 9341 | [1–447] |
| 9085 | [1–459] | 9138 | [59–89],[188–335] | 9285 | [1–347] | 9342 | [1–399] |
| 9086 | [1–97] | 9139 | [1–380] | 9286 | [1–438] | 9343 | [1–202] |
| 9087 | [1–498] | 9140 | [1–294] | 9287 | [1–126] | 9344 | [1–432] |
| 9088 | [1–183] | 9141 | [1–184],[262–304] | 9288 | [1–495] | 9345 | [1–138] |
| 9089 | [1–471] | 9142 | [1–359] | 9289 | [1–485] | 9346 | [1–420] |
| 9090 | [1–219] | 9143 | [1–366] | 9290 | [1–239] | 9347 | [1–168],[314–422] |
| 9091 | [1–448] | 9144 | [1–373] | 9291 | [1–431] | 9348 | [1–87] |
| 9093 | [1–175] | 9145 | [1–350] | 9292 | [1–463] | 9349 | [1–430] |
| 9094 | [1–267] | 9147 | [1–412] | 9294 | [1–193],[320–444] | 9350 | [1–513] |
| 9095 | [1–156] | 9148 | [1–422] | 9295 | [1–463] | 9351 | [1–470] |
| 9096 | [1–151],[237–305] | 9149 | [1–447] | 9298 | [1–271] | 9352 | [1–477] |
| 9097 | [1–556] | 9150 | [1–432] | 9299 | [1–299] | 9353 | [1–490] |
| 9098 | [1–429] | 9151 | [1–369] | 9300 | [37–85] | 9355 | [1–415] |
| 9099 | [1–475] | 9154 | [1–439] | 9302 | [1–293] | 9356 | [1–443] |
| 9100 | [1–442] | 9155 | [1–56] | 9303 | [1–385] | 9357 | [1–389] |
| 9101 | [1–475] | 9156 | [1–423] | 9304 | [1–451] | 9358 | [1–475] |
| 9102 | [1–460] | 9157 | [1–426] | 9305 | [1–444] | 9359 | [1–385] |
| 9103 | [1–413] | 9158 | [1–432] | 9306 | [1–510] | 9360 | [1–538] |
| 9104 | [1–26] | 9159 | [1–433] | 9307 | [1–420] | 9361 | [1–225] |
| 9161 | [1–436] | 9221 | [1–452] | 9309 | [1–535] | 9362 | [1–64] |
| 9163 | [1–277] | 9222 | [1–451] | 9310 | [1–534] | 9363 | [1–415] |
| 9164 | [1–395] | 9223 | [1–449] | 9311 | [1–370] | 9364 | [1–413] |
| 9167 | [1–168] | 9224 | [1–277] | 9312 | [1–484] | 9365 | [1–425] |
| 9168 | [1–401] | 9225 | [1–97] | 9313 | [1–538] | 9366 | [70–132],[308–456] |
| 9170 | [1–30] | 9226 | [1–355] | 9314 | [1–81] | 9367 | [1–498] |
| 9171 | [1–404] | 9228 | [218–371] | 9315 | [1–443] | 9368 | [1–373] |
| 9172 | [152–424] | 9229 | [82–384] | 9316 | [1–440] | 9369 | [1–390] |
| 9174 | [1–390] | 9230 | [1–379] | 9317 | [1–441] | 9370 | [1–544] |
| 9175 | [97–473] | 9231 | [1–409] | 9319 | [1–424] | 9371 | [1–451] |
| 9176 | [1–261],[349–428] | 9233 | [1–427] | 9320 | [1–446] | 9372 | [1–272] |
| 9177 | [1–384] | 9234 | [1–425] | 9322 | [1–390] | 9373 | [1–420] |
| 9178 | [1–470] | 9235 | [1–438] | 9323 | [1–217] | 9374 | [1–426] |
| 9179 | [1–435] | 9236 | [1–435] | 9324 | [1–258] | 9375 | [1–237] |
| 9180 | [1–185] | 9237 | [1–88] | 9326 | [1–369] | 9376 | [1–438] |
| 9181 | [1–278],[326–424] | 9238 | [1–455] | 9327 | [1–452] | 9377 | [1–480] |
| 9182 | [1–435] | 9240 | [1–73],[234–374] | 9328 | [1–336] | 9378 | [1–444] |
| 9183 | [1–427] | 9241 | [1–483] | 9329 | [1–272] | 9379 | [1–482] |
| 9184 | [1–422] | 9242 | [1–97],[135–496] | 9331 | [1–437] | 9380 | [1–250] |
| 9185 | [1–392] | 9243 | [1–214] | 9332 | [1–210],[286–425] | 9381 | [1–305] |
| 9186 | [1–191] | 9244 | [1–439] | 9382 | [1–325] | 9439 | [1–234] |
| 9187 | [1–411] | 9245 | [1–472] | 9383 | [1–381] | 9441 | [1–444] |
| 9188 | [1–460] | 9246 | [1–409] | 9385 | [1–436] | 9442 | [1–418] |
| 9189 | [1–426] | 9247 | [1–398] | 9386 | [1–127] | 9443 | [1–223] |
| 9190 | [1–308] | 9248 | [1–387] | 9387 | [1–336] | 9444 | [1–238] |
| 9191 | [1–224],[253–380] | 9250 | [1–203] | 9389 | [1–510] | 9445 | [1–467] |
| 9194 | [1–371] | 9251 | [1–440] | 9390 | [1–447] | 9447 | [1–405] |
| 9195 | [1–167] | 9252 | [1–163] | 9391 | [1–433] | 9448 | [1–191] |
| 9197 | [1–418] | 9255 | [1–402] | 9392 | [1–104] | 9449 | [1–416] |
| 9198 | [1–383] | 9256 | [1–531] | 9393 | [1–435] | 9450 | [1–415] |
| 9200 | [1–446] | 9257 | [1–402] | 9395 | [1–423] | 9452 | [1–279] |
| 9201 | [1–420] | 9258 | [1–461] | 9396 | [1–485] | 9453 | [1–328] |
| 9202 | [1–442] | 9259 | [1–504] | 9397 | [1–471] | 9454 | [1–392] |
| 9203 | [1–414] | 9260 | [1–291] | 9399 | [1–255],[286–420] | 9455 | [1–235] |
| 9204 | [1–423] | 9262 | [1–519] | 9400 | [1–411] | 9456 | [1–537] |
| 9205 | [81–149] | 9263 | [1–466] | 9401 | [1–407] | 9457 | [249–375] |
| 9206 | [1–89] | 9265 | [1–333] | 9402 | [1–263] | 9458 | [1–103] |
| 9207 | [1–378] | 9266 | [1–534] | 9403 | [1–176] | 9460 | [1–71] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 9404 | [1–317] | 9461 | [1–59] | 9548 | [1–73] | 9603 | [1–366] |
| 9405 | [1–455] | 9462 | [145–216] | 9549 | [1–527] | 9604 | [1–78] |
| 9406 | [1–255] | 9463 | [1–328] | 9550 | [1–487] | 9605 | [1–60] |
| 9407 | [1–276] | 9464 | [1–91] | 9606 | [1–435] | 9661 | [1–76] |
| 9408 | [1–454] | 9466 | [1–341] | 9608 | [86–163] | 9662 | [1–446] |
| 9411 | [1–553] | 9467 | [1–165] | 9609 | [1–397] | 9663 | [1–204] |
| 9412 | [1–451] | 9468 | [1–104] | 9610 | [55–502] | 9664 | [1–456] |
| 9413 | [1–407] | 9469 | [1–107] | 9611 | [1–431] | 9665 | [1–469] |
| 9414 | [1–308] | 9470 | [1–358] | 9612 | [1–420] | 9666 | [1–452] |
| 9415 | [204–408] | 9471 | [1–308] | 9613 | [1–248],[380–459] | 9667 | [1–216] |
| 9416 | [1–305] | 9472 | [1–104] | 9614 | [1–478] | 9668 | [1–195],[372–474] |
| 9417 | [1–439] | 9473 | [1–101] | 9615 | [1–336] | 9669 | [1–285] |
| 9419 | [1–430] | 9474 | [1–381] | 9616 | [1–386] | 9671 | [1–81] |
| 9420 | [1–368] | 9475 | [1–107] | 9617 | [1–86] | 9672 | [1–481] |
| 9421 | [1–413] | 9476 | [1–104] | 9618 | [79–117] | 9674 | [1–41] |
| 9422 | [1–422] | 9477 | [1–97] | 9619 | [1–357] | 9677 | [1–434] |
| 9424 | [356–435] | 9478 | [1–60] | 9620 | [1–422] | 9678 | [1–170] |
| 9425 | [1–426] | 9480 | [1–52] | 9621 | [1–80] | 9680 | [1–97] |
| 9426 | [1–490] | 9481 | [1–323] | 9622 | [1–511] | 9681 | [1–372] |
| 9427 | [1–302] | 9482 | [1–96] | 9624 | [1–44] | 9682 | [1–432] |
| 9428 | [1–234] | 9483 | [1–59] | 9625 | [1–327] | 9683 | [1–323] |
| 9429 | [1–440] | 9484 | [1–399] | 9626 | [1–86] | 9684 | [1–432] |
| 9430 | [1–560] | 9485 | [1–103] | 9627 | [1–101],[144–452] | 9685 | [1–90] |
| 9431 | [1–442] | 9486 | [1–61] | 9629 | [1–233] | 9686 | [1–461] |
| 9432 | [1–61] | 9487 | [1–107] | 9630 | [1–321] | 9687 | [1–361] |
| 9433 | [1–398] | 9489 | [1–96] | 9631 | [1–308] | 9688 | [1–416] |
| 9434 | [1–119] | 9491 | [1–88] | 9632 | [1–391] | 9689 | [1–67] |
| 9435 | [1–436] | 9492 | [1–107] | 9633 | [174–274],[414–455] | 9690 | [1–440] |
| 9437 | [114–160] | 9494 | [1–83] | 9634 | [1–433] | 9691 | [1–387] |
| 9495 | [1–88] | 9552 | [1–355] | 9635 | [1–292] | 9692 | [1–445] |
| 9496 | [1–102] | 9553 | [1–173] | 9636 | [1–37],[82–274] | 9693 | [1–51] |
| 9498 | [1–350] | 9556 | [264–405] | 9638 | [1–369] | 9694 | [1–254] |
| 9499 | [1–107] | 9559 | [1–488] | 9639 | [1–473] | 9695 | [1–421] |
| 9500 | [1–58] | 9561 | [1–53],[251–369] | 9640 | [1–292] | 9696 | [1–458] |
| 9501 | [1–96] | 9562 | [1–274] | 9643 | [1–266] | 9697 | [1–391] |
| 9502 | [1–112] | 9563 | [1–363] | 9645 | [1–501] | 9698 | [1–86] |
| 9503 | [1–54] | 9564 | [1–361] | 9646 | [1–134] | 9699 | [1–432] |
| 9504 | [1–105] | 9565 | [1–395] | 9647 | [1–364] | 9701 | [1–336] |
| 9505 | [1–107] | 9566 | [1–444] | 9648 | [1–347] | 9702 | [1–399] |
| 9507 | [1–104] | 9567 | [1–110],[153–191],[279–464] | 9649 | [1–157] | 9703 | [1–89] |
| 9508 | [1–101] | 9568 | [1–485] | 9650 | [1–171] | 9704 | [1–323] |
| 9510 | [1–316] | 9569 | [1–332] | 9651 | [1–430] | 9705 | [1–407] |
| 9511 | [1–421] | 9570 | [1–428] | 9652 | [1–389] | 9706 | [1–383] |
| 9513 | [1–351] | 9571 | [1–501] | 9654 | [1–206] | 9707 | [1–463] |
| 9514 | [1–352] | 9572 | [1–511] | 9655 | [1–137] | 9708 | [1–64],[288–405] |
| 9515 | [1–377] | 9573 | [1–76] | 9656 | [1–111] | 9710 | [1–367] |
| 9516 | [1–162],[237–297] | 9574 | [1–454] | 9657 | [1–244] | 9711 | [31–178] |
| 9518 | [1–240] | 9575 | [93–179] | 9658 | [1–332] | 9712 | [44–71] |
| 9519 | [1–521] | 9576 | [1–318] | 9659 | [1–80] | 9713 | [1–103] |
| 9520 | [99–295] | 9577 | [1–264] | 9660 | [1–389] | 9714 | [1–369] |
| 9521 | [1–579] | 9578 | [1–448] | 9715 | [1–316] | 9769 | [299–466] |
| 9522 | [1–83] | 9579 | [1–455] | 9717 | [1–359] | 9770 | [1–440] |
| 9523 | [1–383] | 9580 | [1–474] | 9718 | [1–57] | 9771 | [1–407] |
| 9525 | [1–328] | 9581 | [1–468] | 9719 | [1–434] | 9772 | [1–443] |
| 9526 | [1–160] | 9582 | [1–426] | 9721 | [1–378] | 9773 | [1–89] |
| 9527 | [1–245] | 9583 | [1–141] | 9722 | [1–55],[118–165],[195–368] | 9774 | [1–151] |
| 9528 | [1–505] | 9584 | [1–192] | 9723 | [1–300] | 9775 | [1–424] |
| 9530 | [33–81],[113–335] | 9585 | [1–359] | 9724 | [1–227] | 9776 | [186–248] |
| 9531 | [1–453] | 9586 | [1–115] | 9726 | [117–183] | 9777 | [1–322] |
| 9532 | [1–434] | 9587 | [1–138] | 9727 | [1–167] | 9779 | [1–106] |
| 9534 | [1–398] | 9588 | [1–63] | 9728 | [1–67] | 9782 | [1–431] |
| 9535 | [1–493] | 9589 | [1–72] | 9729 | [1–356] | 9783 | [1–353] |
| 9536 | [320–348] | 9590 | [1–73] | 9730 | [1–58] | 9784 | [1–346] |
| 9537 | [1–680] | 9591 | [1–135] | 9731 | [1–621] | 9785 | [1–435] |
| 9538 | [1–535] | 9592 | [1–78] | 9732 | [1–207] | 9786 | [1–380] |
| 9539 | [1–239] | 9594 | [1–331] | 9733 | [1–87] | 9787 | [1–362] |
| 9540 | [1–438] | 9595 | [73–138] | 9734 | [1–63] | 9788 | [1–500] |
| 9541 | [1–498] | 9596 | [1–194] | 9735 | [1–135] | 9789 | [1–250],[302–429] |
| 9542 | [1–44] | 9597 | [1–456] | 9736 | [1–93] | 9790 | [1–375] |
| 9543 | [1–72],[173–429] | 9598 | [1–403] | 9738 | [1–130],[218–273] | 9792 | [1–299] |
| 9544 | [1–410] | 9600 | [1–402] | 9739 | [1–146] | 9793 | [1–356] |
| 9545 | [1–371] | 9601 | [1–423] | 9740 | [1–61] | 9794 | [46–456] |
| 9546 | [1–511] | 9602 | [1–114] | 9741 | [1–57] | 9795 | [1–33],[68–385] |

TABLE IVa-continued (Novelty:95%)

| Seq Id No. | Positions of preferred fragments | Seq Id No. | Positions of preferred fragments |
|---|---|---|---|
| 9743 | [1–146] | 9796 | [1–374] |
| 9744 | [1–337] | 9797 | [1–393] |
| 9745 | [1–78] | 9799 | [1–425] |
| 9746 | [1–60] | 9801 | [1–462] |
| 9747 | [1–415] | 9802 | [1–91] |
| 9748 | [1–76],[269–410] | 9803 | [1–131],[191–236] |
| 9749 | [1–88],[196–406] | 9804 | [1–254] |
| 9750 | [1–109] | 9805 | [1–351] |
| 9751 | [1–371] | 9806 | [1–425] |
| 9752 | [1–103] | 9807 | [1–68] |
| 9753 | [1–83] | 9808 | [1–394] |
| 9754 | [1–224] | 9809 | [1–463] |
| 9755 | [1–462] | 9810 | [1–368] |
| 9756 | [1–86] | 9811 | [1–62] |
| 9757 | [1–398] | 9812 | [1–502] |
| 9759 | [1–487] | 9813 | [1–500] |
| 9760 | [1–130] | 9814 | [1–500] |
| 9761 | [1–432] | 9815 | [1–416] |
| 9762 | [1–483] | 9817 | [1–471] |
| 9763 | [1–323] | 9819 | [1–472] |
| 9764 | [1–337] | 9820 | [1–482] |
| 9766 | [1–284] | 9821 | [1–441] |
| 9767 | [1–76] | 9822 | [1–444] |
| 9768 | [1–135] | 9823 | [1–237] |
| 9824 | [1–79] | 9875 | [1–452] |
| 9825 | [1–452] | 9877 | [1–426] |
| 9826 | [1–155] | 9878 | [1–439] |
| 9827 | [1–438] | 9879 | [1–504] |
| 9828 | [1–463] | 9880 | [1–194] |
| 9829 | [1–487] | 9881 | [1–483] |
| 9830 | [1–479] | 9884 | [1–345] |
| 9831 | [1–79] | 9886 | [1–359] |
| 9832 | [1–426] | 9887 | [118–444] |
| 9833 | [1–369] | 9889 | [1–461] |
| 9834 | [1–500] | 9890 | [1–79] |
| 9835 | [1–343] | 9891 | [1–74],[306–439] |
| 9836 | [1–62] | 9893 | [1–482] |
| 9837 | [1–72] | 9895 | [1–379] |
| 9838 | [1–507] | 9896 | [1–449] |
| 9839 | [1–574] | 9897 | [1–478] |
| 9840 | [1–303] | 9898 | [1–414] |
| 9841 | [1–78] | 9899 | [1–177] |
| 9842 | [1–415] | 9900 | [1–245] |
| 9843 | [1–33],[152–214] | 9901 | [1–425] |
| 9844 | [1–529] | 9902 | [1–155] |
| 9845 | [1–71] | 9903 | [1–234],[270–308] |
| 9846 | [1–424] | 9904 | [1–79] |
| 9847 | [1–455] | 9905 | [1–77] |
| 9848 | [1–339] | 9906 | [1–429] |
| 9849 | [1–449] | 9907 | [1–143] |
| 9850 | [1–117] | 9908 | [1–180] |
| 9851 | [1–173] | 9909 | [1–265] |
| 9852 | [1–415] | 9910 | [1–424] |
| 9853 | [1–387] | 9911 | [1–73] |
| 9854 | [1–396] | 9912 | [1–309] |
| 9855 | [1–92] | 9913 | [1–414] |
| 9856 | [1–280] | 9914 | [1–442] |
| 9857 | [1–440] | 9915 | [112–167] |
| 9858 | [1–429] | 9916 | [1–138] |
| 9859 | [1–488] | 9917 | [1–412] |
| 9860 | [1–438] | 9918 | [1–891] |
| 9862 | [1–472] | 9919 | [1–200] |
| 9863 | [1–345] | 9921 | [1–164] |
| 9864 | [1–110] | 9923 | [1–414] |
| 9865 | [1–157] | 9924 | [1–169] |
| 9866 | [1–461] | 9925 | [1–69] |
| 9867 | [32–237] | 9926 | [1–441] |
| 9868 | [1–144] | 9928 | [1–457] |
| 9870 | [1–356] | 9929 | [1–54] |
| 9872 | [1–424] | 9930 | [218–251] |
| 9873 | [1–175] | 9931 | [1–419] |
| 9934 | [1–207] | 9992 | [1–448] |
| 9935 | [1–413] | 9993 | [1–355] |
| 9936 | [1–440] | 9994 | [1–77] |
| 9939 | [1–328] | 9995 | [1–481] |
| 9940 | [1–400] | 9996 | [1–367] |
| 9941 | [1–161] | 9997 | [1–86] |
| 9947 | [1–64] | 9998 | [1–327] |
| 9948 | [1–219] | 9999 | [217–348] |
| 9949 | [1–190] | 10000 | [1–479] |
| 9950 | [1–188] | 10001 | [1–391] |
| 9951 | [1–140] | 10002 | [1–325] |
| 9952 | [1–188] | 10004 | [1–437] |
| 9953 | [1–176] | 10005 | [1–364] |
| 9954 | [1–176] | 10006 | [1–476] |
| 9955 | [1–479] | 10008 | [1–415] |
| 9956 | [1–400] | 10009 | [1–289] |
| 9957 | [1–380] | 10010 | [1–440] |
| 9958 | [1–112] | 10011 | [1–326] |
| 9959 | [1–423] | 10012 | [276–361] |
| 9960 | [1–128] | 10013 | [1–514] |
| 9961 | [1–364] | 10014 | [1–476] |
| 9963 | [1–185] | 10015 | [1–289] |
| 9964 | [1–469] | 10016 | [1–411] |
| 9966 | [1–72] | 10017 | [1–246] |
| 9967 | [1–104] | 10018 | [1–432] |
| 9968 | [1–176] | 10019 | [1–502] |
| 9970 | [1–434] | 10020 | [1–326] |
| 9971 | [1–439] | 10021 | [1–106] |
| 9972 | [1–114] | 10022 | [1–445] |
| 9973 | [1–349] | 10023 | [1–212] |
| 9974 | [1–505] | 10024 | [1–119] |
| 9975 | [1–86] | 10025 | [1–337] |
| 9976 | [1–487] | 10026 | [1–146] |
| 9977 | [1–338] | 10027 | [1–468] |
| 9978 | [1–188] | 10028 | [1–396] |
| 9979 | [1–438] | 10029 | [1–436] |
| 9980 | [1–201] | 10030 | [1–452] |
| 9981 | [1–283] | 10031 | [1–471] |
| 9982 | [1–55] | 10032 | [1–376],[422–527] |
| 9983 | [1–388] | 10033 | [1–463] |
| 9984 | [1–71] | 10034 | [1–461] |
| 9985 | [1–485] | 10035 | [1–439] |
| 9986 | [1–162] | 10036 | [1–86] |
| 9987 | [1–455] | 10037 | [1–478] |
| 9988 | [116–488] | 10038 | [1–36] |
| 9990 | [1–491] | 10039 | [1–393] |
| 9991 | [1–500] | 10040 | [1–435] |
| 10041 | [1–177],[307–433] | 10092 | [1–476] |
| 10042 | [1–43] | 10093 | [1–445] |
| 10044 | [1–461] | 10094 | [1–227] |
| 10045 | [1–135] | 10095 | [1–398] |
| 10046 | [1–72] | 10096 | [1–67] |
| 10047 | [1–78] | 10097 | [1–46],[129–502] |
| 10048 | [1–230] | 10098 | [1–445] |
| 10049 | [1–162] | 10099 | [1–339] |
| 10051 | [1–120] | 10100 | [1–456] |
| 10052 | [1–329] | 10101 | [1–208] |
| 10053 | [225–438] | 10102 | [1–126] |
| 10054 | [1–120] | 10103 | [1–146] |
| 10055 | [1–227] | 10105 | [1–466] |
| 10056 | [1–94] | 10106 | [171–441] |
| 10057 | [1–430] | 10107 | [1–324] |
| 10058 | [1–473] | 10108 | [1–41] |
| 10059 | [1–161] | 10109 | [1–379] |
| 10060 | [1–344] | 10110 | [1–292] |
| 10061 | [1–496] | 10111 | [1–417] |
| 10062 | [1–382] | 10112 | [1–81] |
| 10063 | [160–272] | 10113 | [1–467] |
| 10064 | [1–530] | 10115 | [1–432] |
| 10066 | [1–398] | 10116 | [1–289] |
| 10067 | [1–170] | 10117 | [1–173],[230–335],[365–423] |
| 10068 | [1–404] | 10118 | [1–89] |
| 10069 | [1–103] | 10120 | [1–341] |
| 10070 | [1–120] | 10121 | [1–201] |
| 10071 | [1–261] | 10122 | [1–436] |
| 10072 | [1–322] | 10123 | [1–405] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 10073 | [1–509] | 10124 | [1–343] | 10260 | [1–381] | 10315 | [1–348] |
| 10074 | [1–399] | 10125 | [1–473] | 10261 | [1–433] | 10317 | [1–440] |
| 10075 | [1–484] | 10126 | [1–451] | 10262 | [1–336] | 10318 | [1–433] |
| 10076 | [1–292] | 10127 | [1–342] | 10264 | [1–170] | 10319 | [1–283] |
| 10077 | [1–316] | 10128 | [1–228] | 10265 | [279–373] | 10320 | [1–505] |
| 10078 | [1–390] | 10129 | [1–414] | 10266 | [1–498] | 10321 | [1–157] |
| 10079 | [1–498] | 10130 | [1–107] | 10267 | [1–532] | 10322 | [1–436] |
| 10080 | [1–223] | 10131 | [1–89] | 10268 | [1–563] | 10323 | [1–445] |
| 10082 | [1–284] | 10133 | [1–78] | 10269 | [1–266] | 10324 | [1–450] |
| 10083 | [1–410] | 10134 | [1–125] | 10272 | [1–452] | 10325 | [1–231] |
| 10084 | [1–407] | 10135 | [1–49] | 10273 | [1–352] | 10327 | [1–362] |
| 10085 | [47–345] | 10136 | [1–107] | 10274 | [1–429] | 10328 | [1–304] |
| 10086 | [1–136] | 10137 | [1–257] | 10276 | [1–441] | 10329 | [37–308] |
| 10087 | [1–461] | 10138 | [1–429] | 10277 | [1–237] | 10330 | [218–278] |
| 10088 | [1–519] | 10139 | [1–337] | 10278 | [1–252] | 10331 | [1–259] |
| 10089 | [1–187] | 10140 | [1–476] | 10279 | [1–437] | 10332 | [1–656] |
| 10090 | [1–465] | 10141 | [1–308] | 10280 | [1–52] | 10333 | [1–445] |
| 10091 | [1–67] | 10142 | [1–61] | 10281 | [1–343] | 10334 | [1–258],[387–589] |
| 10144 | [1–51] | 10200 | [1–476] | 10282 | [1–402] | 10335 | [86–160] |
| 10145 | [1–72] | 10201 | [1–78] | 10283 | [1–377] | 10336 | [464–498] |
| 10146 | [1–368] | 10202 | [289–365] | 10284 | [1–386] | 10337 | [1–517] |
| 10148 | [1–145] | 10203 | [1–257] | 10285 | [1–440] | 10338 | [1–493] |
| 10149 | [1–444] | 10204 | [1–215] | 10286 | [1–247] | 10339 | [1–525] |
| 10150 | [1–434] | 10205 | [1–379] | 10287 | [1–422] | 10340 | [1–293] |
| 10151 | [1–142] | 10206 | [1–92] | 10288 | [1–135] | 10342 | [1–399] |
| 10152 | [1–443] | 10207 | [1–487] | 10289 | [1–430] | 10343 | [1–523] |
| 10153 | [1–496] | 10208 | [1–51] | 10290 | [1–427] | 10344 | [1–332] |
| 10154 | [1–119] | 10209 | [1–367] | 10292 | [1–75] | 10345 | [1–370] |
| 10155 | [1–330] | 10210 | [1–88] | 10294 | [1–469] | 10346 | [1–330] |
| 10156 | [1–50] | 10211 | [1–299] | 10295 | [1–30],[68–457],[1103–1211] | 10347 | [1–75] |
| 10157 | [1–347] | 10212 | [1–435] | | | | |
| 10158 | [1–343] | 10213 | [1–77] | 10296 | [1–481] | 10348 | [1–557] |
| 10159 | [1–252] | 10214 | [1–322] | 10297 | [1–259] | 10349 | [1–428] |
| 10161 | [1–67] | 10215 | [1–288] | 10299 | [1–344],[444–519] | 10350 | [1–445] |
| 10162 | [1–323] | 10216 | [1–391] | 10300 | [1–310] | 10351 | [1–127],[164–397] |
| 10163 | [1–345] | 10217 | [1–490] | 10301 | [1–323] | 10352 | [1–451] |
| 10166 | [1–375] | 10218 | [1–448] | 10303 | [1–359] | 10353 | [1–237] |
| 10167 | [1–476] | 10219 | [1–39],[82–455] | 10304 | [1–303] | 10354 | [1–485] |
| 10169 | [1–355] | 10220 | [1–279] | 10305 | [1–462] | 10355 | [1–458] |
| 10170 | [1–472] | 10221 | [1–477] | 10356 | [1–293] | 10407 | [30–86],[250–478] |
| 10171 | [1–467] | 10222 | [1–386] | 10357 | [1–44] | 10408 | [1–536] |
| 10172 | [1–327] | 10223 | [1–395] | 10358 | [1–73] | 10409 | [1–213] |
| 10173 | [1–326] | 10224 | [1–359] | 10359 | [1–431] | 10410 | [1–481] |
| 10175 | [389–488] | 10226 | [55–102] | 10360 | [1–447] | 10411 | [1–468] |
| 10177 | [1–433] | 10227 | [1–271] | 10361 | [1–360] | 10412 | [1–445] |
| 10178 | [1–246] | 10228 | [1–570] | 10362 | [1–460] | 10413 | [1–505] |
| 10179 | [72–108] | 10229 | [1–252] | 10363 | [1–401] | 10414 | [1–510] |
| 10180 | [1–492] | 10230 | [1–488] | 10364 | [1–188] | 10416 | [1–185],[226–358] |
| 10181 | [1–77] | 10231 | [1–328] | 10365 | [1–496] | 10417 | [46–547] |
| 10182 | [1–188] | 10233 | [1–429] | 10367 | [1–449] | 10418 | [1–407] |
| 10183 | [1–40] | 10234 | [1–361] | 10368 | [1–337] | 10419 | [1–73] |
| 10184 | [1–191] | 10235 | [1–306] | 10369 | [1–448] | 10420 | [1–77] |
| 10185 | [1–255] | 10236 | [1–407] | 10370 | [1–116] | 10422 | [1–535] |
| 10186 | [1–326] | 10237 | [1–250] | 10371 | [1–453] | 10423 | [1–357] |
| 10187 | [1–503] | 10238 | [1–252] | 10372 | [1–450] | 10424 | [1–72] |
| 10188 | [1–161] | 10239 | [1–432] | 10373 | [1–427] | 10425 | [267–441] |
| 10190 | [1–314] | 10240 | [1–207] | 10374 | [1–323] | 10427 | [1–99] |
| 10191 | [1–136] | 10241 | [1–315] | 10375 | [1–426] | 10428 | [1–517] |
| 10192 | [1–337] | 10242 | [1–312] | 10376 | [1–489] | 10429 | [1–80] |
| 10193 | [1–271] | 10243 | [1–378] | 10377 | [1–257] | 10430 | [1–448] |
| 10194 | [89–418] | 10244 | [1–341] | 10378 | [1–444] | 10431 | [1–317] |
| 10196 | [1–77] | 10245 | [62–247] | 10379 | [1–574] | 10432 | [1–587] |
| 10197 | [1–76] | 10246 | [1–331] | 10380 | [1–271] | 10433 | [1–435] |
| 10198 | [1–398] | 10247 | [1–318] | 10381 | [1–539] | 10435 | [1–333] |
| 10199 | [1–452] | 10248 | [1–248] | 10382 | [1–232] | 10436 | [1–469] |
| 10249 | [1–460] | 10306 | [1–249] | 10383 | [1–147] | 10437 | [1–306] |
| 10250 | [1–136] | 10307 | [1–344] | 10384 | [1–417] | 10438 | [63–500] |
| 10252 | [1–400] | 10308 | [1–468] | 10385 | [1–478] | 10439 | [108–140],[270–486] |
| 10254 | [1–147] | 10309 | [1–486] | 10386 | [288–376] | 10440 | [1–360] |
| 10255 | [1–55] | 10310 | [187–391] | 10387 | [1–450] | 10441 | [1–452] |
| 10256 | [1–397] | 10311 | [1–72] | 10388 | [1–418] | 10442 | [1–75] |
| 10257 | [1–425] | 10312 | [1–70] | 10389 | [1–593] | 10443 | [1–466] |
| 10258 | [1–319] | 10313 | [1–426] | 10390 | [1–113] | 10444 | [1–463] |
| 10259 | [1–423] | 10314 | [1–444] | 10391 | [1–354] | 10445 | [1–474] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 10392 | [1–395] | 10446 | [1–431] | 10585 | [1–511] | 10641 | [1–169] |
| 10393 | [1–586] | 10448 | [1–505] | 10586 | [1–116] | 10642 | [1–155] |
| 10394 | [1–483] | 10449 | [1–559] | 10587 | [1–312] | 10643 | [1–440] |
| 10397 | [1–535] | 10450 | [189–226] | 10588 | [1–591] | 10644 | [1–129] |
| 10398 | [1–606] | 10451 | [1–515] | 10589 | [1–128], [160–503] | 10645 | [1–541] |
| 10399 | [1–486] | 10452 | [1–533] | 10590 | [1–572] | 10646 | [1–557] |
| 10400 | [1–416] | 10454 | [1–474] | 10592 | [1–127] | 10647 | [1–557] |
| 10401 | [162–503] | 10455 | [1–209],[317–500] | 10593 | [1–370] | 10648 | [1–484] |
| 10402 | [1–481] | 10456 | [1–418] | 10594 | [1–607] | 10649 | [1–553] |
| 10403 | [1–485] | 10457 | [1–362] | 10595 | [1–447] | 10650 | [1–538] |
| 10404 | [1–293] | 10458 | [1–477] | 10597 | [1–445] | 10651 | [1–497] |
| 10405 | [1–423] | 10461 | [1–69] | 10598 | [1–50] | 10652 | [1–445] |
| 10462 | [1–573] | 10514 | [1–142] | 10599 | [1–359] | 10653 | [1–309] |
| 10463 | [1–537] | 10515 | [1–164] | 10601 | [1–443] | 10654 | [1–426] |
| 10464 | [1–378] | 10516 | [1–524] | 10602 | [177–414] | 10655 | [1–234], [412–527] |
| 10465 | [1–105] | 10517 | [1–400] | 10603 | [1–494] | 10656 | [1–149] |
| 10466 | [1–63] | 10518 | [1–387] | 10604 | [1–480] | 10657 | [1–525] |
| 10467 | [1–28],[68–145] | 10519 | [1–408] | 10605 | [1–407] | 10658 | [1–470] |
| 10468 | [1–179],[258–282] | 10520 | [1–433] | 10606 | [50–235] | 10659 | [1–520] |
| 10469 | [1–349] | 10521 | [1–369] | 10607 | [89–303] | 10660 | [1–403] |
| 10470 | [1–89] | 10522 | [1–441] | 10608 | [219–250] | 10661 | [1–428] |
| 10471 | [1–64] | 10523 | [1–74],[284–534] | 10609 | [1–87] | 10662 | [1–367] |
| 10472 | [1–558] | 10525 | [1–473] | 10612 | [423–447] | 10663 | [1–213], [360–468], [529–562] |
| 10473 | [1–474] | 10526 | [114–140] | | | | |
| 10474 | [1–547] | 10527 | [1–51],[271–514] | 10613 | [1–338] | 10664 | [1–583] |
| 10475 | [1–529] | 10528 | [1–209] | 10614 | [1–437] | 10665 | [1–265] |
| 10476 | [1–515] | 10529 | [1–55] | 10615 | [1–480] | 10666 | [1–480] |
| 10477 | [1–454] | 10530 | [266–401] | 10616 | [1–503] | 10668 | [1–260] |
| 10478 | [1–145] | 10531 | [1–74],[274–300] | 10617 | [86–556] | 10669 | [1–493] |
| 10480 | [1–503] | 10532 | [1–416] | 10618 | [1–563] | 10670 | [1–345] |
| 10481 | [1–450] | 10533 | [1–481] | 10619 | [1–454] | 10671 | [1–196] |
| 10483 | [1–369] | 10537 | [1–428] | 10621 | [378–470] | 10672 | [1–447] |
| 10484 | [1–343] | 10538 | [1–405] | 10622 | [1–438] | 10673 | [1–429] |
| 10486 | [56–369] | 10539 | [1–442] | 10674 | [1–531] | 10724 | [1–383] |
| 10487 | [1–439] | 10540 | [1–75] | 10675 | [1–233] | 10725 | [1–414] |
| 10489 | [1–494] | 10542 | [1–493] | 10676 | [1–410] | 10726 | [1–485] |
| 10490 | [1–343] | 10543 | [1–193] | 10677 | [1–205], [238–271], [373–497] | 10727 | [1–270] |
| 10491 | [1–625] | 10545 | [1–506] | | | | |
| 10492 | [1–555] | 10546 | [1–504] | 10678 | [1–402] | 10728 | [1–492] |
| 10493 | [1–600] | 10547 | [1–154] | 10679 | [1–351] | 10729 | [1–496] |
| 10494 | [1–312] | 10548 | [1–501] | 10680 | [1–298] | 10730 | [1–483] |
| 10495 | [1–469] | 10549 | [1–127] | 10681 | [1–413] | 10731 | [1–269] |
| 10497 | [1–406] | 10550 | [1–439] | 10682 | [1–410] | 10732 | [1–168] |
| 10498 | [1–390] | 10551 | [1–409] | 10683 | [1–487] | 10733 | [1–266] |
| 10499 | [169–340] | 10552 | [1–72] | 10684 | [1–546] | 10734 | [1–472] |
| 10500 | [1–142] | 10554 | [1–74],[126–409] | 10685 | [1–501] | 10735 | [1–88] |
| 10501 | [1–467] | 10555 | [1–306] | 10686 | [261–293] | 10736 | [1–264] |
| 10502 | [1–487] | 10556 | [1–491] | 10687 | [1–477] | 10737 | [1–206] |
| 10503 | [1–454] | 10557 | [1–437] | 10688 | [1–447] | 10738 | [1–454] |
| 10504 | [1–399] | 10558 | [1–337] | 10690 | [1–67] | 10739 | [1–485] |
| 10505 | [1–433] | 10559 | [1–233] | 10691 | [1–429] | 10741 | [1–415] |
| 10506 | [1–402] | 10560 | [1–319] | 10692 | [1–356] | 10742 | [1–514] |
| 10507 | [1–395] | 10561 | [1–142] | 10693 | [1–361] | 10744 | [1–481] |
| 10508 | [1–155] | 10563 | [1–249] | 10695 | [1–270] | 10745 | [1–468] |
| 10509 | [1–338] | 10564 | [1–349] | 10696 | [1–521] | 10747 | [1–296] |
| 10510 | [1–99] | 10565 | [1–443] | 10697 | [1–344] | 10748 | [1–277] |
| 10511 | [1–577] | 10566 | [1–419] | 10698 | [1–379] | 10749 | [1–475] |
| 10512 | [181–386] | 10567 | [1–328] | 10699 | [1–419] | 10750 | [1–150] |
| 10513 | [1–151] | 10568 | [1–106] | 10700 | [1–208], [293–470] | 10751 | [1–375] |
| 10569 | [1–575] | 10623 | [368–451] | 10701 | [1–288] | 10752 | [1–239] |
| 10570 | [1–523] | 10624 | [1–529] | 10702 | [1–299] | 10753 | [1–360] |
| 10571 | [216–559] | 10625 | [1–512] | 10703 | [1–470] | 10754 | [1–455] |
| 10572 | [1–354] | 10626 | [1–562] | 10705 | [1–540] | 10755 | [1–258] |
| 10573 | [106–296] | 10627 | [287–337] | 10706 | [1–420] | 10757 | [1–271] |
| 10574 | [1–271] | 10628 | [1–501] | 10707 | [1–233], [265–304] | 10759 | [1–455] |
| 10576 | [1–353] | 10630 | [1–281] | 10708 | [1–499] | 10761 | [1–364] |
| 10577 | [1–314] | 10631 | [1–400] | 10709 | [1–418] | 10762 | [1–81], [211–476] |
| 10578 | [1–119] | 10632 | [1–511] | 10710 | [1–194] | 10763 | [1–70], [135–284] |
| 10579 | [1–351] | 10633 | [1–374] | 10711 | [1–474] | 10764 | [1–71] |
| 10580 | [1–80] | 10634 | [1–487] | 10712 | [1–486] | 10765 | [1–481] |
| 10581 | [1–361] | 10635 | [1–514] | 10713 | [1–58] | 10766 | [1–162] |
| 10582 | [1–39] | 10636 | [1–551] | 10714 | [1–468] | 10767 | [1–506] |
| 10583 | [1–535] | 10638 | [1–451] | 10715 | [1–59] | 10768 | [1–421] |
| 10584 | [1–57] | 10639 | [1–552] | 10716 | [1–433] | 10769 | [1–329] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 10717 | [1–396] | 10770 | [1–354] | 10914 | [197–229] | 10967 | [1–165], [367–591] |
| 10718 | [1–443] | 10771 | [1–127] | 10915 | [1–251] | 10968 | [1–485] |
| 10719 | [1–65] | 10772 | [46–263] | 10916 | [1–59] | 10969 | [1–221] |
| 10720 | [1–421] | 10773 | [1–320] | 10917 | [60–254] | 10970 | [1–397] |
| 10721 | [1–500] | 10774 | [1–203] | 10918 | [1–469] | 10971 | [1–72] |
| 10722 | [1–55], [99–149] | 10776 | [1–375] | 10919 | [1–353] | 10973 | [1–366] |
| 10723 | [1–54] | 10777 | [1–105], [246–372] | 10921 | [1–247] | 10975 | [1–430] |
| 10778 | [1–379] | 10836 | [47–348] | 10922 | [1–80] | 10976 | [1–520] |
| 10779 | [1–268] | 10837 | [1–51] | 10924 | [1–226] | 10977 | [1–374] |
| 10780 | [1–412] | 10838 | [1–55] | 10925 | [1–155], [184–243] | 10978 | [1–149], [230–272], [361–478] |
| 10781 | [1–462] | 10839 | [1–348] | | | | |
| 10782 | [1–431] | 10840 | [1–233] | 10926 | [1–345] | 10980 | [1–55] |
| 10783 | [1–232] | 10841 | [1–446] | 10927 | [1–512] | 10982 | [1–459] |
| 10785 | [1–154] | 10842 | [1–101] | 10928 | [1–463] | 10983 | [1–209] |
| 10786 | [1–434] | 10843 | [1–282] | 10929 | [1–131] | 10984 | [1–250] |
| 10787 | [1–152] | 10845 | [1–471] | 10930 | [1–241] | 10985 | [1–424] |
| 10788 | [1–343] | 10846 | [1–134] | 10931 | [1–242] | 10986 | [1–41], [81–188], [234–438] |
| 10789 | [1–247] | 10847 | [1–166] | | | | |
| 10790 | [1–441] | 10848 | [1–326] | 10933 | [1–386] | 10987 | [1–443] |
| 10791 | [1–93], [188–223] | 10850 | [1–390] | 10934 | [1–464] | 10988 | [1–341] |
| 10792 | [1–441] | 10851 | [1–243] | 10935 | [1–412] | 10989 | [1–274] |
| 10793 | [1–304] | 10852 | [1–483] | 10936 | [1–531] | 10990 | [1–328] |
| 10794 | [1–172] | 10853 | [1–435] | 10937 | [1–304] | 10991 | [1–442] |
| 10795 | [1–254] | 10854 | [1–93] | 10938 | [1–331] | 10993 | [1–178] |
| 10797 | [1–80] | 10856 | [1–487] | 10939 | [1–458] | 10994 | [1–309] |
| 10798 | [191–417] | 10857 | [1–349] | 10940 | [1–136] | 10995 | [1–412] |
| 10799 | [1–268] | 10858 | [1–470] | 10941 | [1–185] | 10997 | [1–246] |
| 10800 | [1–447] | 10859 | [1–433] | 10942 | [1–220] | 10998 | [1–487] |
| 10801 | [86–142] | 10860 | [1–450] | 10943 | [1–366] | 10999 | [1–167] |
| 10802 | [1–245] | 10861 | [1–333] | 11000 | [1–233], [265–292] | 11052 | [1–436] |
| 10803 | [1–124] | 10862 | [1–76], [110–350] | 11001 | [1–73] | 11053 | [1–466] |
| 10804 | [1–361] | 10863 | [1–184] | 11002 | [1–293] | 11054 | [1–483] |
| 10805 | [1–170] | 10864 | [1–450] | 11004 | [64–544] | 11055 | [1–442] |
| 10806 | [1–247] | 10865 | [1–438] | 11005 | [1–223] | 11056 | [1–347] |
| 10807 | [1–343] | 10866 | [1–256] | 11006 | [1–552] | 11057 | [1–355], [406–442] |
| 10811 | [1–188] | 10868 | [1–372] | 11007 | [1–53] | 11058 | [1–432] |
| 10812 | [1–447] | 10869 | [1–358] | 11008 | [1–491] | 11059 | [1–306] |
| 10813 | [1–52] | 10870 | [1–389] | 11009 | [1–155] | 11060 | [1–478] |
| 10814 | [1–237] | 10871 | [1–53] | 11010 | [1–452] | 11062 | [1–295], [390–500] |
| 10815 | [1–232] | 10872 | [1–296] | 11011 | [1–469] | 11063 | [1–85] |
| 10816 | [1–263] | 10873 | [1–378] | 11012 | [1–498] | 11065 | [1–468] |
| 10818 | [1–463] | 10874 | [1–294] | 11014 | [1–460] | 11066 | [1–484] |
| 10819 | [54–436] | 10875 | [1–157] | 11015 | [71–251], [353–468] | 11067 | [1–30], [68–457] |
| 10821 | [1–355] | 10876 | [1–484] | 11016 | [94–419] | 11068 | [1–483] |
| 10822 | [1–88] | 10877 | [1–77] | 11017 | [1–403] | 11069 | [1–283] |
| 10823 | [1–398] | 10878 | [1–438] | 11018 | [1–365] | 11070 | [1–488] |
| 10824 | [1–504] | 10879 | [1–288] | 11019 | [1–458] | 11071 | [1–95], [129–253] |
| 10825 | [1–45], [269–364] | 10880 | [1–58] | 11021 | [1–499] | 11072 | [53–235] |
| 10826 | [1–58] | 10881 | [1–300] | 11022 | [1–80] | 11073 | [1–499] |
| 10827 | [1–440] | 10882 | [1–238] | 11023 | [1–452] | 11074 | [1–401] |
| 10828 | [1–331] | 10883 | [1–340] | 11024 | [1–418] | 11075 | [1–444] |
| 10829 | [1–80] | 10884 | [1–358] | 11025 | [1–497] | 11076 | [114–448] |
| 10832 | [1–69] | 10885 | [1–171] | 11026 | [1–470] | 11077 | [1–209] |
| 10835 | [1–418] | 10886 | [1–429] | 11027 | [1–482] | 11078 | [247–273] |
| 10887 | [1–476] | 10944 | [1–359] | 11028 | [1–498] | 11079 | [1–331] |
| 10888 | [1–301] | 10947 | [1–344] | 11029 | [1–479] | 11080 | [50–235] |
| 10889 | [1–407] | 10948 | [1–391] | 11030 | [52–236] | 11081 | [1–488] |
| 10890 | [1–234], [274–497] | 10950 | [1–369] | 11031 | [1–470] | 11082 | [1–258] |
| 10891 | [1–53] | 10951 | [1–364] | 11032 | [1–416] | 11083 | [1–468] |
| 10892 | [1–360] | 10952 | [1–364] | 11033 | [1–414] | 11084 | [1–339] |
| 10893 | [1–436] | 10953 | [1–239] | 11034 | [1–484] | 11085 | [1–488] |
| 10896 | [1–67] | 10954 | [1–481] | 11035 | [1–489] | 11086 | [1–478] |
| 10898 | [1–156] | 10955 | [1–209] | 11036 | [1–470] | 11087 | [86–135] |
| 10900 | [1–159] | 10956 | [1–67] | 11037 | [1–76] | 11088 | [1–438] |
| 10902 | [1–479] | 10957 | [1–235], [372–428] | 11038 | [1–52], [81–127], [159–469] | 11091 | [1–62] |
| 10903 | [1–476] | 10958 | [1–114], [311–453] | | | | |
| 10904 | [1–373] | 10959 | [1–346] | 11039 | [1–487] | 11092 | [1–336] |
| 10905 | [1–369] | 10960 | [1–506] | 11040 | [1–475] | 11093 | [1–454] |
| 10906 | [1–103] | 10961 | [1–146] | 11041 | [1–482] | 11094 | [72–125] |
| 10907 | [1–68] | 10962 | [1–150] | 11042 | [1–391] | 11095 | [1–67] |
| 10908 | [1–349] | 10963 | [1–597] | 11043 | [1–424] | 11096 | [1–489] |
| 10909 | [1–138] | 10964 | [1–507] | 11045 | [1–306] | 11097 | [1–387] |
| 10911 | [1–184] | 10965 | [1–438] | 11046 | [1–443] | 11098 | [1–132] |
| 10912 | [1–197] | 10966 | [1–356] | 11047 | [1–491] | 11100 | [1–485] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 11048 | [1–252] | 11102 | [1–517] | 11244 | [1–103] | 11292 | [1–219] |
| 11049 | [1–414] | 11103 | [1–304] | 11245 | [1–186] | 11293 | [1–219] |
| 11051 | [1–89] | 11104 | [1–457] | 11246 | [1–161] | 11294 | [1–206] |
| 11105 | [1–476] | 11156 | [1–476] | 11247 | [1–374] | 11295 | [1–136] |
| 11106 | [72–108] | 11158 | [1–566] | 11248 | [1–265], [326–418] | 11296 | [1–219] |
| 11107 | [1–446] | 11159 | [1–293] | 11249 | [93–169] | 11297 | [1–219] |
| 11108 | [1–279], [318–397] | 11160 | [1–505] | 11250 | [1–467] | 11298 | [1–399] |
| 11109 | [1–379] | 11161 | [1–176] | 11251 | [1–288] | 11299 | [1–206] |
| 11110 | [1–488] | 11162 | [1–394] | 11252 | [1–250] | 11300 | [1–193] |
| 11111 | [1–414] | 11163 | [1–126] | 11253 | [1–219] | 11301 | [1–129] |
| 11113 | [1–432] | 11164 | [1–460] | 11254 | [1–74] | 11302 | [1–128] |
| 11114 | [1–471] | 11165 | [1–478] | 11255 | [1–219] | 11303 | [1–72] |
| 11115 | [1–452] | 11166 | [1–80] | 11257 | [1–72] | 11304 | [1–219] |
| 11117 | [1–376] | 11167 | [1–311] | 11258 | [1–447] | 11305 | [1–144] |
| 11118 | [1–434] | 11168 | [1–488] | 11259 | [1–219] | 11306 | [1–101] |
| 11119 | [1–457] | 11169 | [1–507] | 11260 | [1–219] | 11307 | [1–136] |
| 11120 | [1–421] | 11170 | [1–495] | 11261 | [1–219] | 11308 | [1–219] |
| 11122 | [1–168] | 11171 | [225–309] | 11262 | [1–282] | 11309 | [1–136] |
| 11123 | [1–469] | 11172 | [1–529] | 11263 | [1–219] | 11310 | [165–489] |
| 11124 | [1–338] | 11173 | [1–482] | 11264 | [1–219] | 11311 | [1–219] |
| 11125 | [1–446] | 11174 | [1–127] | 11265 | [1–73] | 11312 | [1–61] |
| 11126 | [1–398] | 11175 | [1–209] | 11266 | [1–224] | 11313 | [1–419] |
| 11127 | [1–478] | 11176 | [1–282] | 11267 | [1–399] | 11314 | [1–207] |
| 11128 | [1–409] | 11177 | [1–437] | 11315 | [1–207] | 11367 | [1–306] |
| 11129 | [1–397] | 11178 | [1–122] | 11316 | [1–111] | 11369 | [1–125], [332–498] |
| 11130 | [1–474] | 11179 | [1–522] | 11317 | [1–206] | 11370 | [1–439] |
| 11131 | [1–460] | 11180 | [1–137] | 11318 | [1–144] | 11371 | [1–341] |
| 11132 | [1–214] | 11181 | [1–386] | 11319 | [1–110] | 11372 | [151–278] |
| 11133 | [1–509] | 11182 | [1–473] | 11320 | [1–219] | 11373 | [1–157] |
| 11134 | [37–312] | 11183 | [1–278] | 11321 | [1–450] | 11374 | [1–644] |
| 11135 | [1–246] | 11184 | [1–478] | 11322 | [1–219] | 11375 | [1–610] |
| 11136 | [1–495] | 11185 | [1–518] | 11323 | [1–60] | 11376 | [1–489] |
| 11137 | [1–53] | 11187 | [1–502] | 11324 | [1–219] | 11377 | [1–482] |
| 11138 | [1–468] | 11188 | [1–408] | 11325 | [1–72] | 11378 | [216–295] |
| 11139 | [1–415] | 11189 | [1–488] | 11326 | [1–171] | 11381 | [1–361] |
| 11140 | [1–102] | 11190 | [1–60], [242–413] | 11327 | [1–225] | 11382 | [1–76] |
| 11141 | [86–121] | 11191 | [1–428] | 11328 | [1–221] | 11383 | [1–401] |
| 11142 | [1–437] | 11192 | [1–80] | 11329 | [1–219] | 11384 | [1–326] |
| 11143 | [1–439] | 11193 | [1–130] | 11330 | [1–237] | 11385 | [1–233] |
| 11144 | [1–540] | 11194 | [1–83] | 11331 | [1–153] | 11386 | [1–292] |
| 11146 | [1–481] | 11195 | [1–139] | 11332 | [1–219] | 11388 | [1–525] |
| 11147 | [1–273] | 11196 | [1–470] | 11333 | [1–219] | 11389 | [1–543] |
| 11148 | [1–240] | 11197 | [1–391] | 11334 | [1–207] | 11391 | [1–302] |
| 11149 | [1–362] | 11198 | [1–104] | 11335 | [1–121] | 11392 | [1–521] |
| 11150 | [1–491] | 11199 | [1–55] | 11336 | [1–187] | 11393 | [1–353] |
| 11151 | [1–438] | 11200 | [116–175], [451–499] | 11337 | [1–220] | 11394 | [50–94] |
| 11152 | [1–98] | 11202 | [1–492] | 11338 | [1–219] | 11395 | [1–212] |
| 11153 | [1–503] | 11203 | [1–494] | 11339 | [1–219] | 11396 | [1–285] |
| 11154 | [1–479] | 11204 | [40–68] | 11340 | [1–185] | 11398 | [1–147] |
| 11155 | [1–493] | 11205 | [1–515] | 11342 | [1–198] | 11399 | [1–375] |
| 11206 | [1–108] | 11268 | [1–168] | 11343 | [1–498] | 11400 | [1–234] |
| 11208 | [1–381] | 11269 | [1–219] | 11344 | [214–388] | 11401 | [1–77] |
| 11210 | [1–96] | 11270 | [1–219] | 11345 | [1–426] | 11402 | [1–394] |
| 11211 | [1–257] | 11271 | [1–228] | 11346 | [1–430] | 11403 | [1–406] |
| 11213 | [1–201] | 11272 | [1–219] | 11347 | [1–440] | 11404 | [1–350] |
| 11214 | [1–381] | 11273 | [1–219] | 11348 | [1–382] | 11406 | [1–193] |
| 11216 | [1–251] | 11274 | [1–219] | 11349 | [1–483] | 11407 | [1–294] |
| 11217 | [1–207] | 11275 | [1–189] | 11350 | [1–298], [329–378] | 11408 | [31–460] |
| 11219 | [1–34] | 11276 | [1–219] | 11351 | [1–34], [79–427] | 11409 | [1–401] |
| 11220 | [1–235] | 11277 | [1–219] | 11352 | [1–342] | 11410 | [1–428] |
| 11221 | [1–321] | 11278 | [1–118] | 11353 | [1–330] | 11411 | [1–203] |
| 11223 | [233–306] | 11279 | [1–469] | 11354 | [1–149], [188–409] | 11412 | [1–326] |
| 11224 | [1–169] | 11280 | [1–207] | 11355 | [1–471] | 11413 | [1–99] |
| 11228 | [1–134] | 11281 | [1–219] | 11356 | [1–307] | 11414 | [1–57] |
| 11229 | [79–425] | 11282 | [1–136] | 11357 | [1–107] | 11415 | [1–428] |
| 11231 | [74–248] | 11283 | [1–206] | 11358 | [1–330] | 11416 | [1–307] |
| 11234 | [1–201] | 11284 | [1–219] | 11362 | [418–523] | 11417 | [31–466] |
| 11236 | [1–405] | 11285 | [1–206] | 11363 | [1–415] | 11418 | [1–316] |
| 11238 | [1–362] | 11286 | [1–219] | 11365 | [1–281] | 11419 | [1–306] |
| 11239 | [1–39], [300–343] | 11287 | [1–111] | 11366 | [1–505] | 11420 | [1–136] |
| 11240 | [1–151] | 11288 | [1–219] | 11421 | [1–249] | 11478 | [1–149] |
| 11241 | [1–358] | 11289 | [1–219] | 11423 | [1–430] | 11479 | [1–418] |
| 11242 | [1–310] | 11290 | [1–74] | 11424 | [1–480] | 11480 | [1–415] |
| 11243 | [1–370] | 11291 | [1–136] | 11425 | [1–457] | 11482 | [1–442] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 11426 | [1–309] | 11483 | [1–385] | 11568 | [1–305] | 11617 | [1–225] |
| 11427 | [1–309] | 11484 | [1–476] | 11569 | [1–200] | 11619 | [1–200] |
| 11428 | [1–198] | 11485 | [1–426] | 11570 | [1–200] | 11620 | [1–322] |
| 11429 | [1–198] | 11486 | [1–118] | 11571 | [1–111] | 11621 | [1–369] |
| 11430 | [1–230] | 11487 | [1–351] | 11572 | [1–93] | 11622 | [1–166] |
| 11431 | [1–180] | 11488 | [1–443] | 11573 | [1–172] | 11623 | [1–170] |
| 11432 | [1–393] | 11490 | [1–370] | 11574 | [1–159] | 11624 | [1–152] |
| 11433 | [1–378] | 11491 | [1–349] | 11575 | [1–173] | 11625 | [1–144] |
| 11434 | [1–291] | 11492 | [1–422] | 11576 | [1–408] | 11626 | [1–225] |
| 11436 | [1–102] | 11493 | [1–132] | 11577 | [1–311] | 11627 | [1–226] |
| 11437 | [1–436] | 11494 | [1–106] | 11578 | [1–125] | 11628 | [1–341] |
| 11438 | [1–261] | 11495 | [1–392] | 11579 | [1–314] | 11629 | [1–173] |
| 11439 | [1–504] | 11496 | [270–366] | 11580 | [1–162] | 11630 | [1–316] |
| 11440 | [1–506] | 11497 | [1–79] | 11581 | [1–327] | 11631 | [1–78] |
| 11441 | [243–452] | 11498 | [1–553] | 11582 | [1–309] | 11632 | [1–195] |
| 11442 | [119–187] | 11499 | [1–504] | 11583 | [1–53] | 11633 | [1–78] |
| 11444 | [1–396] | 11500 | [1–55], [228–577] | 11634 | [1–221] | 11684 | [1–194] |
| 11445 | [1–261] | 11501 | [1–161] | 11635 | [1–242] | 11686 | [1–129] |
| 11446 | [1–137] | 11502 | [1–515] | 11636 | [1–134] | 11687 | [1–174] |
| 11447 | [256–367] | 11503 | [120–154] | 11638 | [1–173] | 11688 | [1–158] |
| 11448 | [11–346] | 11504 | [1–176] | 11639 | [1–127] | 11689 | [1–82] |
| 11449 | [1–486] | 11505 | [183–238] | 11640 | [1–216] | 11690 | [1–378] |
| 11451 | [1–352] | 11507 | [1–177] | 11641 | [1–303] | 11691 | [1–317] |
| 11452 | [1–241] | 11508 | [1–178] | 11642 | [1–336] | 11692 | [1–118] |
| 11453 | [1–400] | 11510 | [1–191] | 11643 | [1–112] | 11693 | [1–347] |
| 11454 | [1–495] | 11511 | [1–318] | 11644 | [1–170] | 11694 | [1–278] |
| 11456 | [1–286] | 11512 | [1–345] | 11645 | [1–109] | 11695 | [1–361] |
| 11457 | [1–374] | 11513 | [1–317] | 11646 | [1–122] | 11697 | [1–187] |
| 11458 | [1–366] | 11515 | [149–232] | 11647 | [1–294] | 11698 | [1–140] |
| 11459 | [1–365] | 11516 | [1–316] | 11648 | [1–189] | 11699 | [1–130] |
| 11460 | [1–388] | 11517 | [1–314] | 11649 | [1–301] | 11701 | [1–212] |
| 11463 | [1–384] | 11518 | [1–92] | 11650 | [1–152] | 11702 | [1–155] |
| 11464 | [1–339] | 11519 | [1–224] | 11651 | [1–55] | 11703 | [1–285] |
| 11465 | [1–349] | 11520 | [1–221] | 11652 | [1–109] | 11704 | [1–365] |
| 11468 | [1–398] | 11521 | [1–388] | 11653 | [1–201] | 11705 | [1–137] |
| 11469 | [1–453] | 11522 | [1–140] | 11654 | [1–110] | 11707 | [1–397] |
| 11470 | [1–169] | 11523 | [1–172] | 11655 | [1–333] | 11708 | [1–128] |
| 11471 | [1–446] | 11525 | [1–147] | 11656 | [1–127] | 11709 | [1–114] |
| 11472 | [1–396] | 11526 | [1–298] | 11657 | [1–62] | 11710 | [1–84] |
| 11473 | [1–311] | 11528 | [1–300] | 11658 | [1–63] | 11711 | [1–237] |
| 11474 | [1–441] | 11529 | [1–303] | 11659 | [1–361] | 11712 | [1–490] |
| 11475 | [1–367] | 11530 | [1–317] | 11660 | [1–149] | 11713 | [1–173] |
| 11476 | [1–348] | 11531 | [1–457] | 11661 | [1–162] | 11714 | [1–191] |
| 11532 | [1–402] | 11585 | [1–281] | 11662 | [1–225] | 11715 | [1–123] |
| 11533 | [1–387] | 11586 | [1–160] | 11663 | [1–99] | 11716 | [1–200] |
| 11534 | [1–175] | 11587 | [1–315] | 11665 | [1–347] | 11717 | [1–439] |
| 11535 | [1–312] | 11588 | [1–431] | 11666 | [1–173] | 11718 | [1–199] |
| 11537 | [1–37], [256–371] | 11589 | [1–320] | 11667 | [1–200] | 11719 | [1–163] |
| 11538 | [1–306] | 11590 | [1–200] | 11668 | [1–163] | 11720 | [1–195] |
| 11539 | [1–313] | 11591 | [1–200] | 11669 | [1–132] | 11721 | [1–231] |
| 11540 | [1–77] | 11592 | [1–171] | 11670 | [1–329] | 11722 | [1–172] |
| 11541 | [1–463] | 11593 | [1–162] | 11671 | [1–174] | 11723 | [1–339] |
| 11542 | [1–316] | 11594 | [1–118] | 11672 | [1–305] | 11724 | [1–171] |
| 11543 | [1–297] | 11595 | [217–245] | 11673 | [1–337] | 11725 | [1–343] |
| 11544 | [1–383] | 11596 | [1–86] | 11675 | [1–261] | 11726 | [1–394] |
| 11545 | [1–456] | 11597 | [1–347] | 11676 | [1–107] | 11727 | [1–358] |
| 11547 | [1–209] | 11598 | [1–200] | 11677 | [1–114] | 11728 | [1–200] |
| 11548 | [1–163] | 11599 | [1–299] | 11678 | [1–144] | 11729 | [1–278] |
| 11549 | [1–268] | 11600 | [1–347] | 11679 | [1–189] | 11730 | [1–303] |
| 11550 | [1–409] | 11601 | [1–114] | 11680 | [1–174] | 11731 | [1–126] |
| 11551 | [1–493] | 11602 | [1–168] | 11681 | [1–200] | 11732 | [1–142] |
| 11552 | [1–369] | 11603 | [1–200] | 11682 | [1–104] | 11733 | [1–181] |
| 11553 | [1–220] | 11604 | [1–371] | 11683 | [1–179] | 11734 | [1–311] |
| 11554 | [1–495] | 11605 | [1–280] | 11735 | [1–225] | 11784 | [1–222] |
| 11556 | [1–120] | 11606 | [1–157], [224–250] | 11736 | [1–213] | 11785 | [1–200] |
| 11557 | [295–320] | 11607 | [1–165] | 11737 | [1–179], [323–374] | 11786 | [1–162] |
| 11558 | [1–530] | 11608 | [1–353] | 11738 | [1–126] | 11787 | [1–254] |
| 11559 | [1–460] | 11609 | [1–385] | 11739 | [1–162] | 11788 | [1–172] |
| 11562 | [1–147] | 11610 | [1–383] | 11740 | [1–80] | 11789 | [1–186] |
| 11563 | [1–324] | 11611 | [1–174] | 11741 | [1–109] | 11790 | [1–479] |
| 11564 | [1–280] | 11612 | [1–295] | 11742 | [1–364] | 11791 | [1–316] |
| 11565 | [1–387] | 11613 | [1–68] | 11743 | [1–110] | 11792 | [1–133] |
| 11566 | [1–148] | 11614 | [1–160] | 11744 | [1–98] | 11793 | [1–358] |
| 11567 | [1–318] | 11615 | [1–281] | 11745 | [1–171] | 11794 | [1–226] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 11746 | [1–305] | 11795 | [1–192] | 11869 | [1–170] | 11923 | [1–155] |
| 11747 | [1–565] | 11796 | [1–186] | 11870 | [1–158] | 11924 | [1–172] |
| 11748 | [1–187] | 11797 | [1–90] | 11871 | [1–336] | 11925 | [1–172] |
| 11749 | [1–253] | 11798 | [1–298] | 11872 | [1–57] | 11926 | [1–171] |
| 11750 | [1–311] | 11799 | [1–106] | 11873 | [1–366] | 11927 | [146–509] |
| 11751 | [1–293] | 11800 | [1–118] | 11876 | [1–59] | 11928 | [1–100] |
| 11752 | [1–302] | 11801 | [1–224] | 11877 | [1–279] | 11929 | [1–307] |
| 11754 | [1–200] | 11802 | [1–197] | 11878 | [1–174] | 11930 | [1–298] |
| 11755 | [1–302] | 11803 | [1–213] | 11879 | [1–318] | 11931 | [1–201] |
| 11756 | [1–129] | 11804 | [1–226] | 11932 | [1–316] | 11979 | [1–201] |
| 11757 | [1–462] | 11805 | [1–340] | 11933 | [1–225] | 11980 | [1–132] |
| 11758 | [1–130] | 11806 | [1–345] | 11934 | [1–125] | 11981 | [124–350] |
| 11759 | [1–136] | 11807 | [1–243] | 11935 | [1–314] | 11982 | [1–311] |
| 11760 | [1–271] | 11808 | [1–171] | 11936 | [1–225] | 11983 | [1–371] |
| 11761 | [1–136] | 11809 | [1–207] | 11937 | [1–226] | 11984 | [1–331] |
| 11762 | [1–200] | 11810 | [1–126] | 11938 | [1–201] | 11985 | [1–200] |
| 11763 | [1–309] | 11811 | [1–235] | 11939 | [1–303] | 11986 | [1–173] |
| 11764 | [1–152] | 11812 | [1–121] | 11940 | [1–198] | 11987 | [1–110] |
| 11765 | [1–196] | 11813 | [1–172] | 11941 | [1–343] | 11988 | [1–112] |
| 11766 | [1–118] | 11814 | [1–331] | 11942 | [1–143] | 11989 | [1–92], [273–311] |
| 11767 | [1–111] | 11815 | [1–117] | 11943 | [1–292] | 11990 | [1–108] |
| 11768 | [1–448] | 11816 | [1–213] | 11944 | [1–82] | 11991 | [1–79] |
| 11769 | [1–283] | 11817 | [1–79] | 11945 | [1–173] | 11992 | [1–358] |
| 11770 | [1–340] | 11818 | [1–187] | 11946 | [1–200] | 11993 | [1–118] |
| 11771 | [1–173] | 11819 | [1–53] | 11947 | [1–343] | 11994 | [1–265] |
| 11772 | [1–200] | 11820 | [1–241] | 11948 | [1–113] | 11996 | [1–163] |
| 11773 | [1–200] | 11821 | [1–122] | 11949 | [1–82] | 11997 | [1–121] |
| 11774 | [1–257] | 11822 | [1–139] | 11950 | [1–137] | 11998 | [1–330] |
| 11775 | [1–174] | 11823 | [1–173] | 11951 | [1–301] | 11999 | [1–291] |
| 11776 | [1–296] | 11824 | [1–201] | 11952 | [1–136] | 12000 | [1–226] |
| 11777 | [1–170] | 11825 | [1–200] | 11953 | [1–108] | 12001 | [1–99] |
| 11778 | [1–200] | 11826 | [1–490] | 11954 | [1–165] | 12002 | [1–200] |
| 11779 | [1–207] | 11827 | [1–305] | 11955 | [1–119] | 12003 | [1–250] |
| 11781 | [1–110] | 11828 | [1–371] | 11956 | [1–479] | 12004 | [1–314] |
| 11782 | [1–226] | 11829 | [1–336] | 11957 | [1–152] | 12005 | [1–68] |
| 11783 | [1–126] | 11830 | [1–225] | 11958 | [1–78] | 12006 | [1–69] |
| 11831 | [1–306] | 11880 | [1–360] | 11959 | [1–273] | 12007 | [1–103] |
| 11832 | [1–142] | 11881 | [1–306] | 11960 | [1–200] | 12008 | [1–303] |
| 11833 | [1–492] | 11882 | [1–188] | 11961 | [1–235] | 12009 | [1–321] |
| 11834 | [1–225] | 11883 | [1–121] | 11962 | [1–118] | 12010 | [1–173] |
| 11835 | [1–200] | 11884 | [1–547] | 11963 | [1–173] | 12011 | [1–170] |
| 11836 | [1–377] | 11885 | [1–117] | 11964 | [1–108] | 12012 | [1–200] |
| 11837 | [1–303] | 11886 | [1–209] | 11965 | [1–200] | 12013 | [1–181] |
| 11838 | [1–156] | 11887 | [1–69] | 11966 | [1–174] | 12014 | [1–200] |
| 11839 | [1–181] | 11888 | [1–82] | 11967 | [1–61] | 12015 | [1–82] |
| 11840 | [1–213] | 11889 | [1–290] | 11968 | [1–312] | 12016 | [1–433] |
| 11841 | [1–82] | 11890 | [1–281] | 11969 | [1–314] | 12017 | [1–306] |
| 11842 | [1–120] | 11891 | [1–111] | 11970 | [1–57] | 12018 | [1–326] |
| 11843 | [1–507] | 11895 | [1–483] | 11971 | [1–312] | 12019 | [1–180] |
| 11844 | [1–200] | 11896 | [1–314] | 11972 | [1–110] | 12020 | [1–516] |
| 11845 | [1–158] | 11897 | [1–163] | 11973 | [1–316] | 12021 | [1–293] |
| 11846 | [1–200] | 11898 | [1–143] | 11974 | [1–78] | 12022 | [1–161] |
| 11847 | [1–190] | 11899 | [1–471] | 11975 | [1–89] | 12023 | [1–200] |
| 11848 | [1–166] | 11900 | [1–118] | 11976 | [1–314] | 12024 | [1–316] |
| 11849 | [1–364] | 11901 | [1–314] | 11977 | [1–437] | 12025 | [1–110] |
| 11850 | [1–213] | 11902 | [1–200] | 11978 | [1–106] | 12026 | [1–326] |
| 11851 | [1–246] | 11904 | [1–207] | 12027 | [1–142] | 12078 | [1–225] |
| 11852 | [1–314] | 11905 | [1–200] | 12028 | [1–126] | 12079 | [1–106] |
| 11853 | [1–200] | 11906 | [1–322] | 12029 | [1–219] | 12080 | [1–111] |
| 11854 | [1–373] | 11907 | [1–317] | 12030 | [1–294] | 12081 | [1–317] |
| 11855 | [1–345] | 11908 | [1–296] | 12031 | [1–355] | 12082 | [1–490] |
| 11856 | [1–187] | 11909 | [1–67] | 12032 | [1–335] | 12083 | [1–115] |
| 11857 | [1–148] | 11910 | [1–174] | 12033 | [1–315] | 12084 | [1–327] |
| 11858 | [1–200] | 11911 | [1–253] | 12035 | [1–187] | 12085 | [1–221] |
| 11859 | [1–128] | 11912 | [1–68] | 12036 | [1–189] | 12087 | [1–83] |
| 11860 | [1–174] | 11914 | [1–306] | 12037 | [1–77] | 12088 | [1–82] |
| 11861 | [1–99] | 11915 | [1–173] | 12038 | [1–144] | 12089 | [1–372] |
| 11862 | [1–344] | 11916 | [1–419] | 12040 | [1–220] | 12090 | [1–243] |
| 11863 | [1–164] | 11917 | [1–298] | 12041 | [1–294] | 12091 | [202–488] |
| 11864 | [1–82] | 11918 | [1–353] | 12042 | [1–125] | 12092 | [1–124] |
| 11865 | [1–200] | 11919 | [1–200] | 12043 | [1–129] | 12093 | [1–195] |
| 11866 | [1–141] | 11920 | [1–162] | 12044 | [1–200] | 12094 | [1–143] |
| 11867 | [1–304] | 11921 | [1–123] | 12045 | [1–120] | 12095 | [1–200] |
| 11868 | [1–96] | 11922 | [1–209] | 12046 | [1–344] | 12096 | [1–368] |

TABLE IVa-continued (Novelty:95%)

| Seq Id No. | Positions of preferred fragments | Seq Id No. | Positions of preferred fragments |
|---|---|---|---|
| 12047 | [1–173] | 12097 | [1–325] |
| 12048 | [1–78] | 12098 | [1–170] |
| 12049 | [1–154] | 12099 | [1–84] |
| 12051 | [1–163] | 12101 | [1–379] |
| 12052 | [1–166] | 12102 | [1–66] |
| 12053 | [1–145] | 12103 | [1–82] |
| 12054 | [1–263] | 12104 | [1–200] |
| 12055 | [1–313] | 12105 | [1–331] |
| 12056 | [1–221] | 12106 | [1–74] |
| 12057 | [1–194] | 12107 | [1–173] |
| 12058 | [1–175] | 12108 | [1–53] |
| 12059 | [1–333] | 12109 | [1–201] |
| 12060 | [1–199] | 12110 | [1–251] |
| 12062 | [1–419] | 12111 | [1–115] |
| 12063 | [1–447] | 12112 | [1–478] |
| 12064 | [1–306] | 12113 | [1–304] |
| 12065 | [1–200] | 12114 | [1–244] |
| 12066 | [1–117] | 12115 | [1–301] |
| 12067 | [1–383] | 12116 | [1–112] |
| 12068 | [1–173] | 12117 | [1–200] |
| 12069 | [1–114] | 12118 | [1–109] |
| 12070 | [1–161] | 12119 | [1–108] |
| 12071 | [1–452] | 12121 | [1–159] |
| 12072 | [1–301] | 12122 | [1–324] |
| 12073 | [1–174] | 12124 | [1–324] |
| 12074 | [1–164] | 12125 | [1–153] |
| 12075 | [1–163] | 12126 | [1–337] |
| 12076 | [1–170] | 12127 | [1–82] |
| 12077 | [1–240] | 12128 | [1–200] |
| 12129 | [1–164] | 12178 | [1–323] |
| 12130 | [1–77] | 12179 | [1–163] |
| 12131 | [1–82] | 12180 | [1–58] |
| 12132 | [1–200] | 12181 | [1–159] |
| 12133 | [1–113] | 12182 | [1–160] |
| 12135 | [1–52] | 12183 | [1–317] |
| 12136 | [1–200] | 12184 | [1–336] |
| 12137 | [1–82] | 12185 | [1–111] |
| 12138 | [1–321] | 12186 | [1–304] |
| 12139 | [1–56] | 12187 | [1–157] |
| 12140 | [1–104] | 12188 | [1–304] |
| 12141 | [1–200] | 12189 | [1–161] |
| 12142 | [1–420] | 12190 | [1–301] |
| 12143 | [1–136] | 12191 | [1–383] |
| 12144 | [1–108] | 12192 | [1–372] |
| 12145 | [1–458] | 12193 | [34–211] |
| 12146 | [1–459] | 12194 | [1–114] |
| 12147 | [1–373] | 12195 | [1–83] |
| 12148 | [1–171] | 12196 | [1–129] |
| 12149 | [1–289] | 12198 | [1–81] |
| 12150 | [1–57] | 12199 | [1–173] |
| 12151 | [1–173] | 12200 | [1–363] |
| 12152 | [1–207] | 12201 | [1–200] |
| 12153 | [1–284] | 12202 | [1–294] |
| 12154 | [1–225] | 12203 | [1–360] |
| 12155 | [1–162] | 12204 | [1–118] |
| 12156 | [1–200] | 12205 | [1–172] |
| 12157 | [1–156] | 12206 | [1–236] |
| 12158 | [1–200] | 12207 | [1–311] |
| 12159 | [1–307] | 12208 | [1–68] |
| 12160 | [1–98] | 12209 | [1–439] |
| 12161 | [1–91] | 12210 | [1–163] |
| 12162 | [1–120] | 12211 | [1–209] |
| 12163 | [1–257] | 12212 | [1–155] |
| 12165 | [1–50] | 12213 | [1–243] |
| 12166 | [1–477] | 12214 | [1–128] |
| 12167 | [1–118] | 12215 | [1–508] |
| 12168 | [1–383] | 12216 | [1–94] |
| 12169 | [1–312] | 12217 | [1–163] |
| 12170 | [1–371] | 12218 | [1–440] |
| 12171 | [1–172] | 12219 | [1–192] |
| 12172 | [1–175] | 12220 | [1–225] |
| 12173 | [1–125] | 12221 | [1–162] |
| 12174 | [1–127] | 12222 | [1–443] |
| 12175 | [1–83] | 12223 | [1–226] |
| 12176 | [1–371] | 12224 | [1–200] |
| 12177 | [1–520] | 12225 | [1–78] |
| 12226 | [1–127] | 12275 | [1–367] |
| 12227 | [1–361] | 12276 | [1–78] |
| 12228 | [1–134] | 12279 | [1–202] |
| 12229 | [1–176] | 12280 | [1–341] |
| 12231 | [1–63] | 12281 | [1–174] |
| 12232 | [1–457] | 12282 | [1–225] |
| 12233 | [1–172] | 12283 | [1–372] |
| 12234 | [1–343] | 12284 | [1–370] |
| 12235 | [1–174] | 12285 | [1–165] |
| 12236 | [1–313] | 12286 | [1–200] |
| 12237 | [1–383] | 12287 | [107–134], [250–488] |
| 12238 | [1–380] | 12288 | [1–310] |
| 12239 | [1–485] | 12289 | [1–209] |
| 12240 | [1–176] | 12290 | [1–351] |
| 12241 | [1–372] | 12291 | [1–124] |
| 12242 | [1–171] | 12292 | [1–215] |
| 12243 | [1–163] | 12293 | [1–485] |
| 12244 | [1–485] | 12294 | [1–174] |
| 12245 | [1–155] | 12295 | [1–300] |
| 12246 | [1–211] | 12296 | [1–339] |
| 12247 | [1–353] | 12297 | [1–243] |
| 12248 | [1–314] | 12298 | [1–67] |
| 12249 | [1–225] | 12299 | [1–78] |
| 12250 | [1–173] | 12300 | [1–170] |
| 12251 | [1–104] | 12301 | [1–200] |
| 12252 | [1–247] | 12302 | [1–174] |
| 12253 | [1–173] | 12303 | [1–309] |
| 12254 | [1–162] | 12304 | [1–74] |
| 12255 | [1–327] | 12305 | [1–246] |
| 12256 | [1–190] | 12306 | [248–304] |
| 12257 | [1–200] | 12308 | [1–162] |
| 12258 | [1–200] | 12309 | [1–92] |
| 12259 | [1–225] | 12310 | [1–296] |
| 12260 | [1–170] | 12311 | [1–149] |
| 12261 | [1–93] | 12312 | [1–401] |
| 12262 | [1–116] | 12313 | [1–235] |
| 12263 | [1–112] | 12314 | [1–40], [283–444] |
| 12264 | [1–159] | 12315 | [1–135] |
| 12266 | [1–77] | 12316 | [1–372] |
| 12267 | [1–438] | 12317 | [1–400] |
| 12268 | [1–365] | 12318 | [1–475] |
| 12269 | [1–302] | 12319 | [1–337] |
| 12270 | [1–175] | 12320 | [1–225] |
| 12271 | [1–124] | 12322 | [1–82] |
| 12272 | [1–175] | 12323 | [1–200] |
| 12273 | [1–99] | 12324 | [1–310] |
| 12274 | [1–187] | 12325 | [1–117] |
| 12326 | [1–289] | 12373 | [1–313] |
| 12327 | [1–128] | 12374 | [1–130] |
| 12328 | [1–141] | 12375 | [1–449] |
| 12329 | [1–314] | 12376 | [1–375] |
| 12330 | [1–123] | 12377 | [1–55] |
| 12331 | [1–174] | 12378 | [1–134] |
| 12332 | [1–53] | 12379 | [1–137] |
| 12333 | [1–302] | 12380 | [1–305] |
| 12334 | [1–163] | 12381 | [1–200] |
| 12335 | [1–162] | 12382 | [1–162] |
| 12336 | [1–173] | 12383 | [1–175] |
| 12337 | [1–142] | 12384 | [1–243] |
| 12338 | [1–155] | 12385 | [1–343] |
| 12339 | [1–366] | 12386 | [1–433] |
| 12340 | [1–314] | 12387 | [1–354] |
| 12341 | [1–80] | 12388 | [1–162] |
| 12342 | [1–360] | 12389 | [1–111] |
| 12343 | [1–225] | 12390 | [1–72] |
| 12344 | [1–187] | 12391 | [1–170] |
| 12345 | [1–173] | 12392 | [1–101] |
| 12346 | [1–147] | 12393 | [1–302] |
| 12347 | [1–354] | 12394 | [1–253] |
| 12348 | [1–108] | 12395 | [1–123] |
| 12349 | [1–225] | 12396 | [1–200] |
| 12350 | [1–224] | 12397 | [1–111] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 12351 | [1–307] | 12398 | [1–78] | 12530 | [1–53] | 12585 | [1–423] |
| 12352 | [1–144] | 12399 | [1–369] | 12531 | [1–302] | 12586 | [1–328] |
| 12353 | [1–200] | 12400 | [1–153] | 12532 | [1–465] | 12587 | [1–393] |
| 12354 | [1–132] | 12401 | [1–148] | 12533 | [1–445] | 12588 | [1–95] |
| 12355 | [1–318] | 12402 | [1–174] | 12534 | [1–106] | 12589 | [1–76] |
| 12356 | [1–169], [254–373] | 12403 | [1–108] | 12535 | [1–440] | 12590 | [1–440] |
| 12357 | [1–200] | 12404 | [1–66] | 12536 | [1–193] | 12591 | [1–222] |
| 12358 | [1–173] | 12405 | [1–311] | 12537 | [1–347] | 12592 | [1–156] |
| 12359 | [1–173] | 12406 | [1–156] | 12538 | [1–421] | 12593 | [1–473] |
| 12360 | [1–200] | 12407 | [1–158] | 12539 | [1–27] | 12594 | [1–412] |
| 12361 | [1–296] | 12408 | [1–293] | 12540 | [1–477] | 12595 | [1–33], [72–398] |
| 12362 | [1–213] | 12409 | [1–197] | 12541 | [1–473] | 12596 | [46–102] |
| 12363 | [1–96] | 12410 | [1–200] | 12542 | [1–133], [165–266] | 12597 | [1–370] |
| 12364 | [1–143] | 12411 | [1–200] | 12543 | [1–315] | 12598 | [1–461] |
| 12365 | [1–444] | 12412 | [1–486] | 12544 | [1–476] | 12599 | [1–54] |
| 12366 | [1–371] | 12413 | [1–277] | 12546 | [1–488] | 12600 | [1–169] |
| 12367 | [1–89] | 12414 | [1–163] | 12548 | [72–104] | 12601 | [1–243] |
| 12368 | [1–82] | 12415 | [1–173] | 12549 | [1–194] | 12602 | [1–397] |
| 12369 | [1–108] | 12416 | [1–162] | 12550 | [1–414] | 12603 | [1–478] |
| 12370 | [1–173] | 12417 | [1–109] | 12551 | [1–163] | 12604 | [1–321], [353–436] |
| 12371 | [1–105] | 12418 | [1–312] | 12552 | [1–450] | 12605 | [1–377] |
| 12372 | [1–202] | 12419 | [1–173] | 12554 | [1–307] | 12606 | [1–458] |
| 12420 | [1–355] | 12470 | [1–485] | 12555 | [1–468] | 12608 | [1–64] |
| 12421 | [1–163] | 12471 | [1–94] | 12556 | [1–425] | 12610 | [1–138], [181–521] |
| 12422 | [1–140] | 12472 | [1–485] | 12557 | [1–395] | 12612 | [1–200] |
| 12423 | [1–327] | 12473 | [1–450] | 12558 | [266–493] | 12613 | [1–409] |
| 12424 | [1–173] | 12474 | [1–217] | 12559 | [1–471] | 12614 | [1–376] |
| 12425 | [1–306] | 12476 | [1–478] | 12561 | [1–479] | 12615 | [1–397] |
| 12426 | [1–225] | 12477 | [1–473] | 12562 | [1–428] | 12616 | [1–506] |
| 12427 | [1–129] | 12478 | [1–460] | 12564 | [1–458] | 12617 | [1–458] |
| 12428 | [1–314] | 12479 | [1–437] | 12565 | [1–335] | 12618 | [1–427], [496–544] |
| 12429 | [1–83] | 12480 | [1–60] | 12566 | [1–77] | 12619 | [1–463] |
| 12430 | [1–97] | 12481 | [1–459] | 12567 | [1–422] | 12620 | [1–325] |
| 12431 | [1–158] | 12482 | [1–438] | 12568 | [1–373] | 12621 | [1–70] |
| 12432 | [1–125] | 12483 | [1–486] | 12569 | [1–392] | 12622 | [1–97] |
| 12433 | [1–367] | 12485 | [1–483] | 12571 | [121–314] | 12623 | [1–274] |
| 12434 | [1–82] | 12486 | [1–385] | 12572 | [1–477] | 12624 | [1–466] |
| 12435 | [1–346] | 12487 | [1–196] | 12573 | [1–134] | 12625 | [142–438] |
| 12436 | [1–70] | 12489 | [1–380] | 12574 | [1–428] | 12626 | [1–147] |
| 12437 | [1–507] | 12490 | [1–86] | 12575 | [1–70] | 12627 | [1–272] |
| 12438 | [1–158] | 12491 | [1–393] | 12577 | [1–318] | 12628 | [1–412] |
| 12439 | [1–294] | 12492 | [1–469] | 12578 | [1–59] | 12629 | [1–409] |
| 12440 | [1–70] | 12493 | [1–436] | 12630 | [1–456] | 12688 | [1–468] |
| 12441 | [1–94] | 12494 | [1–153], [252–458] | 12631 | [1–297] | 12689 | [1–281] |
| 12442 | [1–374] | 12495 | [1–230] | 12632 | [1–263] | 12690 | [1–453] |
| 12443 | [1–280] | 12496 | [1–494] | 12633 | [1–421] | 12691 | [1–460] |
| 12444 | [1–143] | 12497 | [1–468] | 12634 | [1–146] | 12692 | [1–61] |
| 12445 | [1–187] | 12498 | [1–454] | 12635 | [1–553] | 12693 | [1–193] |
| 12446 | [1–76] | 12499 | [1–146] | 12636 | [1–279], [310–426] | 12694 | [1–447] |
| 12447 | [1–331] | 12500 | [1–127] | 12638 | [1–449] | 12695 | [1–315] |
| 12448 | [1–107] | 12501 | [1–129] | 12642 | [1–291] | 12696 | [1–108] |
| 12449 | [1–173] | 12502 | [1–510] | 12643 | [1–488] | 12697 | [1–398] |
| 12450 | [1–83] | 12503 | [1–276] | 12644 | [1–344] | 12698 | [1–267] |
| 12451 | [1–200] | 12505 | [1–462] | 12645 | [1–316] | 12699 | [1–318] |
| 12453 | [1–154] | 12506 | [1–134] | 12646 | [1–139] | 12700 | [1–385] |
| 12454 | [1–69] | 12507 | [1–419] | 12647 | [1–122] | 12701 | [1–50] |
| 12455 | [1–99] | 12508 | [1–455] | 12648 | [1–331] | 12702 | [1–286] |
| 12456 | [1–408] | 12509 | [1–445] | 12649 | [1–424] | 12704 | [1–219] |
| 12457 | [1–455] | 12510 | [1–458] | 12650 | [1–395] | 12705 | [1–63] |
| 12459 | [1–369] | 12511 | [1–238] | 12651 | [1–344] | 12706 | [1–184] |
| 12460 | [1–432] | 12512 | [1–442] | 12652 | [1–60] | 12707 | [1–199] |
| 12461 | [1–422] | 12514 | [1–177] | 12653 | [1–347] | 12708 | [1–173], [211–258] |
| 12462 | [1–325] | 12515 | [1–406] | 12654 | [1–324] | 12710 | [1–81] |
| 12463 | [52–236] | 12516 | [1–75] | 12655 | [1–422] | 12711 | [1–293] |
| 12464 | [1–70] | 12518 | [86–118] | 12656 | [1–152] | 12712 | [1–372] |
| 12465 | [81–138], [226–287] | 12521 | [1–527] | 12657 | [1–54] | 12713 | [1–208] |
| 12466 | [1–418] | 12522 | [1–531] | 12659 | [1–321] | 12716 | [1–479] |
| 12468 | [1–325] | 12523 | [1–450] | 12660 | [1–240] | 12717 | [1–169] |
| 12469 | [1–414] | 12524 | [1–47] | 12661 | [1–292] | 12718 | [1–328] |
| 12525 | [1–448] | 12579 | [1–432] | 12662 | [1–177] | 12719 | [1–333] |
| 12526 | [1–415] | 12580 | [1–444] | 12663 | [1–87] | 12720 | [1–291] |
| 12527 | [1–312] | 12581 | [1–409] | 12664 | [1–424] | 12722 | [1–329] |
| 12528 | [1–472] | 12583 | [1–467] | 12665 | [1–275] | 12723 | [1–400] |
| 12529 | [1–483] | 12584 | [1–423] | 12667 | [1–380] | 12725 | [1–263] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 12669 | [1–490] | 12726 | [1–322] | 12866 | [1–356] | 12922 | [1–68] |
| 12670 | [1–526] | 12727 | [1–261] | 12867 | [1–208] | 12923 | [1–184] |
| 12671 | [1–120] | 12728 | [1–138] | 12868 | [1–319] | 12924 | [1–502] |
| 12672 | [1–459] | 12729 | [1–243] | 12869 | [1–443] | 12926 | [1–491] |
| 12673 | [1–505] | 12730 | [1–413] | 12871 | [1–320] | 12927 | [1–414] |
| 12674 | [1–292] | 12731 | [1–393] | 12873 | [1–359] | 12928 | [1–259] |
| 12675 | [1–444] | 12733 | [1–387] | 12874 | [1–400] | 12929 | [1–222] |
| 12676 | [1–298] | 12734 | [1–173] | 12876 | [1–81] | 12930 | [1–71] |
| 12677 | [1–429] | 12735 | [147–416] | 12878 | [1–357] | 12931 | [1–53] |
| 12679 | [1–297] | 12737 | [1–494] | 12879 | [1–235] | 12932 | [1–281] |
| 12680 | [1–318] | 12738 | [1–56] | 12880 | [1–425] | 12933 | [1–493] |
| 12681 | [1–88] | 12740 | [1–257] | 12881 | [1–106] | 12934 | [1–276] |
| 12682 | [1–83] | 12741 | [1–310] | 12882 | [1–473] | 12935 | [1–101] |
| 12683 | [1–460] | 12743 | [1–155] | 12885 | [1–101] | 12936 | [1–350] |
| 12685 | [243–361] | 12744 | [1–290] | 12886 | [1–439] | 12938 | [1–340] |
| 12746 | [1–443] | 12803 | [1–248] | 12887 | [1–307] | 12939 | [1–62] |
| 12749 | [231–434] | 12804 | [1–263] | 12888 | [1–297] | 12940 | [1–372] |
| 12750 | [1–184] | 12805 | [1–140] | 12889 | [1–68] | 12941 | [1–330] |
| 12753 | [1–187] | 12806 | [1–185] | 12891 | [1–454] | 12942 | [1–413] |
| 12754 | [1–224] | 12807 | [1–442] | 12892 | [1–130] | 12943 | [1–417] |
| 12755 | [1–412] | 12808 | [1–338] | 12893 | [1–184] | 12944 | [1–514] |
| 12756 | [1–343] | 12809 | [1–28] | 12894 | [1–289] | 12945 | [1–309], [400–482] |
| 12757 | [1–480] | 12810 | [1–455] | 12895 | [1–335] | 12946 | [1–324] |
| 12758 | [1–409] | 12811 | [1–97] | 12896 | [1–323] | 12947 | [1–399] |
| 12760 | [1–376] | 12813 | [1–308] | 12897 | [1–397] | 12948 | [136–281] |
| 12761 | [1–308] | 12814 | [1–226] | 12898 | [1–440] | 12950 | [1–513] |
| 12762 | [1–199] | 12815 | [1–345] | 12899 | [1–94] | 12951 | [1–308] |
| 12763 | [1–411] | 12816 | [1–500] | 12900 | [1–459] | 12952 | [1–82] |
| 12764 | [1–192] | 12818 | [1–122] | 12901 | [1–352] | 12953 | [37–315] |
| 12765 | [1–141] | 12819 | [1–67] | 12902 | [1–318] | 12954 | [1–509] |
| 12767 | [1–85] | 12820 | [1–435] | 12903 | [1–124] | 12955 | [1–175] |
| 12768 | [1–130] | 12821 | [1–472] | 12904 | [1–468] | 12956 | [1–473] |
| 12769 | [1–393] | 12822 | [1–169] | 12905 | [1–479] | 12957 | [1–452] |
| 12770 | [1–393] | 12823 | [1–530] | 12907 | [1–357] | 12958 | [1–324] |
| 12771 | [1–389] | 12824 | [1–101] | 12908 | [1–380] | 12959 | [1–311] |
| 12772 | [1–227] | 12825 | [1–154] | 12960 | [1–372] | 13011 | [1–91] |
| 12773 | [1–362] | 12826 | [64–373] | 12961 | [1–458] | 13012 | [1–364] |
| 12774 | [1–100] | 12827 | [1–58] | 12962 | [1–494] | 13013 | [1–184] |
| 12775 | [1–242] | 12828 | [1–505] | 12963 | [1–184], [228–287] | 13014 | [1–309] |
| 12776 | [1–424] | 12829 | [89–116] | 12964 | [1–366] | 13015 | [1–443] |
| 12777 | [1–458] | 12830 | [1–111] | 12965 | [1–288] | 13016 | [1–242], [282–508] |
| 12781 | [1–174] | 12831 | [1–398] | 12968 | [1–352] | 13017 | [1–420] |
| 12782 | [1–340] | 12832 | [1–475] | 12969 | [1–313] | 13018 | [1–487] |
| 12783 | [1–320] | 12834 | [1–429] | 12970 | [1–345] | 13019 | [1–347] |
| 12784 | [36–351] | 12835 | [1–552] | 12971 | [1–486] | 13020 | [1–435] |
| 12785 | [1–74] | 12836 | [1–358] | 12972 | [1–188] | 13022 | [1–311] |
| 12786 | [1–458] | 12837 | [1–363] | 12973 | [1–254] | 13023 | [94–143], [182–528] |
| 12787 | [1–274] | 12838 | [1–421] | 12974 | [1–526] | 13024 | [1–304] |
| 12788 | [1–405] | 12839 | [1–267] | 12975 | [1–477] | 13026 | [1–268] |
| 12789 | [1–118] | 12840 | [1–454] | 12976 | [1–471] | 13027 | [1–484] |
| 12790 | [1–473] | 12841 | [1–316] | 12977 | [1–161] | 13028 | [254–498] |
| 12791 | [1–185] | 12842 | [1–434] | 12978 | [1–397] | 13029 | [1–386] |
| 12792 | [53–369] | 12843 | [1–515] | 12979 | [1–361] | 13030 | [1–116] |
| 12793 | [1–152] | 12845 | [1–327] | 12980 | [1–195], [377–404] | 13031 | [1–433] |
| 12794 | [1–335] | 12846 | [1–442] | 12981 | [1–450] | 13032 | [1–64] |
| 12795 | [1–28] | 12847 | [1–222] | 12982 | [1–309] | 13033 | [1–336] |
| 12796 | [1–479] | 12848 | [1–451] | 12983 | [1–356] | 13034 | [1–524] |
| 12797 | [1–288] | 12849 | [1–441] | 12984 | [36–351] | 13035 | [1–170], [201–330] |
| 12798 | [1–392] | 12850 | [1–415] | 12985 | [1–465] | 13036 | [1–315] |
| 12799 | [191–253] | 12851 | [1–497] | 12986 | [1–188] | 13037 | [1–483] |
| 12800 | [1–343] | 12852 | [1–397] | 12987 | [1–439] | 13038 | [1–462] |
| 12802 | [1–438] | 12853 | [1–476] | 12988 | [46–103] | 13039 | [1–456] |
| 12854 | [1–513] | 12909 | [1–300] | 12989 | [1–294] | 13041 | [1–442] |
| 12855 | [1–115] | 12910 | [1–476] | 12990 | [1–299] | 13043 | [1–127] |
| 12856 | [1–97] | 12911 | [1–431] | 12992 | [1–307] | 13044 | [1–306] |
| 12857 | [1–267] | 12912 | [1–257] | 12993 | [1–348] | 13045 | [1–413] |
| 12858 | [1–144], [191–397] | 12913 | [1–271] | 12994 | [1–324] | 13046 | [1–309] |
| 12859 | [1–313] | 12914 | [1–283] | 12995 | [1–441] | 13047 | [1–109] |
| 12860 | [1–492] | 12915 | [1–259] | 12996 | [1–354] | 13048 | [1–152] |
| 12861 | [1–326] | 12916 | [1–307] | 12997 | [1–155] | 13049 | [1–59], [309–396] |
| 12862 | [1–303] | 12918 | [1–61] | 12999 | [1–419] | 13050 | [1–438] |
| 12863 | [1–536] | 12919 | [1–274] | 13000 | [1–137] | 13051 | [1–179] |
| 12864 | [1–238] | 12920 | [1–80], [120–209] | 13001 | [1–325] | 13052 | [1–425] |
| 12865 | [1–475] | 12921 | [1–338] | 13002 | [71–293] | 13053 | [1–204] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 13003 | [1–119] | 13054 | [1–381] | 13187 | [1–197] | 13242 | [1–432] |
| 13004 | [1–471] | 13055 | [1–178] | 13188 | [1–317] | 13243 | [1–89] |
| 13005 | [1–291] | 13056 | [1–542] | 13190 | [1–346] | 13245 | [385–467] |
| 13006 | [1–99] | 13057 | [1–109], [342–448] | 13191 | [1–455] | 13247 | [1–109] |
| 13007 | [1–94] | 13058 | [1–219] | 13193 | [42–66] | 13248 | [1–457] |
| 13008 | [1–346] | 13059 | [1–192] | 13194 | [1–160] | 13249 | [1–313], [347–485] |
| 13009 | [1–329] | 13060 | [1–294] | 13195 | [1–372] | 13250 | [1–445] |
| 13010 | [1–498] | 13061 | [1–430] | 13197 | [91–498] | 13251 | [1–174] |
| 13062 | [1–341] | 13116 | [1–317] | 13198 | [1–479] | 13252 | [219–469] |
| 13063 | [1–381] | 13117 | [1–113], [203–461] | 13199 | [1–227] | 13253 | [1–450] |
| 13064 | [1–442] | 13118 | [1–295] | 13200 | [1–420] | 13254 | [1–488] |
| 13065 | [1–295] | 13119 | [1–507] | 13201 | [1–73] | 13255 | [39–257] |
| 13066 | [1–127], [276–492] | 13120 | [1–258] | 13202 | [1–339] | 13256 | [104–479] |
| 13067 | [1–500] | 13121 | [1–357] | 13203 | [1–230] | 13257 | [1–464] |
| 13068 | [110–353] | 13122 | [1–125] | 13204 | [1–53] | 13258 | [1–338] |
| 13069 | [1–53] | 13123 | [1–82] | 13206 | [1–431] | 13260 | [1–475] |
| 13070 | [1–292] | 13124 | [1–298] | 13207 | [1–450] | 13261 | [1–289] |
| 13071 | [1–434] | 13125 | [1–85] | 13208 | [1–404] | 13264 | [1–94] |
| 13072 | [1–361] | 13126 | [1–185] | 13210 | [1–171] | 13265 | [1–467] |
| 13074 | [1–295] | 13127 | [1–327] | 13212 | [1–447] | 13266 | [1–79] |
| 13076 | [1–390] | 13128 | [1–322] | 13213 | [1–454] | 13268 | [1–30] |
| 13077 | [1–82] | 13129 | [1–319] | 13214 | [1–349] | 13269 | [1–404] |
| 13078 | [1–506] | 13130 | [1–473] | 13215 | [1–59] | 13271 | [1–367] |
| 13079 | [1–72] | 13132 | [1–204] | 13217 | [1–433] | 13272 | [1–465] |
| 13080 | [1–438] | 13133 | [1–389] | 13218 | [1–469] | 13273 | [1–199] |
| 13082 | [1–167] | 13134 | [1–256] | 13219 | [1–128] | 13274 | [1–322] |
| 13083 | [1–400] | 13135 | [1–444] | 13220 | [1–164], [230–271] | 13275 | [1–419] |
| 13084 | [1–59] | 13136 | [1–518] | 13221 | [1–459] | 13276 | [1–432] |
| 13085 | [1–458] | 13137 | [1–316] | 13277 | [1–466] | 13331 | [1–485] |
| 13086 | [1–207] | 13138 | [1–441] | 13278 | [1–351] | 13332 | [1–111] |
| 13087 | [1–461] | 13140 | [1–280] | 13279 | [1–465] | 13333 | [1–187] |
| 13088 | [1–416] | 13141 | [1–394] | 13280 | [1–434] | 13334 | [1–176] |
| 13089 | [1–319] | 13142 | [1–395] | 13283 | [1–341] | 13335 | [42–481] |
| 13090 | [1–266] | 13143 | [1–328] | 13284 | [1–442] | 13336 | [1–500] |
| 13091 | [1–311] | 13144 | [1–81] | 13285 | [1–32] | 13337 | [1–422] |
| 13092 | [1–426] | 13146 | [1–376] | 13287 | [1–305] | 13338 | [47–446] |
| 13093 | [1–219] | 13147 | [1–307] | 13288 | [1–455] | 13339 | [1–130] |
| 13094 | [1–320] | 13148 | [1–263] | 13289 | [1–360] | 13340 | [1–348] |
| 13095 | [1–97] | 13149 | [1–131] | 13290 | [1–414] | 13341 | [1–200] |
| 13096 | [1–179] | 13150 | [1–630] | 13291 | [1–269] | 13342 | [1–290] |
| 13097 | [1–289] | 13151 | [1–474] | 13292 | [1–313] | 13344 | [1–87] |
| 13101 | [1–503] | 13152 | [1–81] | 13293 | [1–200] | 13345 | [1–376] |
| 13102 | [1–272] | 13153 | [1–457] | 13294 | [94–257] | 13346 | [1–476] |
| 13103 | [1–282] | 13154 | [1–402] | 13295 | [1–171] | 13347 | [1–429] |
| 13104 | [1–302] | 13155 | [1–440] | 13296 | [1–269] | 13349 | [1–339] |
| 13105 | [1–370] | 13156 | [1–384] | 13297 | [1–192] | 13350 | [1–300] |
| 13106 | [1–69] | 13157 | [1–297] | 13298 | [1–474] | 13351 | [1–439] |
| 13107 | [1–272] | 13158 | [1–378] | 13299 | [1–87] | 13352 | [1–267] |
| 13108 | [1–319] | 13159 | [1–262] | 13300 | [1–75] | 13353 | [1–339] |
| 13109 | [1–235] | 13160 | [1–428] | 13302 | [1–300] | 13354 | [107–156] |
| 13111 | [1–325] | 13161 | [1–326] | 13303 | [1–338] | 13355 | [1–377] |
| 13112 | [1–259] | 13162 | [1–432] | 13304 | [1–347] | 13356 | [1–342] |
| 13113 | [1–179] | 13163 | [1–459] | 13305 | [1–250] | 13358 | [1–171] |
| 13114 | [1–219] | 13164 | [124–148], [355–438] | 13306 | [1–200] | 13360 | [464–513] |
| 13115 | [1–499] | 13165 | [1–445] | 13307 | [1–461] | 13362 | [1–291] |
| 13166 | [1–461] | 13222 | [1–477] | 13308 | [1–304] | 13363 | [1–130] |
| 13167 | [1–85] | 13223 | [1–56] | 13309 | [1–140] | 13364 | [1–225] |
| 13168 | [1–495] | 13224 | [1–318] | 13310 | [47–236] | 13370 | [1–25] |
| 13169 | [1–186], [306–340] | 13226 | [1–478] | 13311 | [1–325] | 13371 | [1–294] |
| 13170 | [1–50] | 13227 | [1–86] | 13312 | [1–415] | 13372 | [1–229] |
| 13171 | [1–113] | 13228 | [1–139], [170–419] | 13313 | [1–370] | 13373 | [1–267] |
| 13172 | [1–110] | 13229 | [1–446] | 13315 | [1–386] | 13374 | [1–279] |
| 13173 | [1–407] | 13230 | [1–517] | 13316 | [1–208] | 13378 | [1–303] |
| 13174 | [1–407] | 13231 | [1–444] | 13317 | [1–142] | 13379 | [1–208] |
| 13175 | [1–470] | 13232 | [1–443] | 13318 | [1–314] | 13381 | [1–66], [187–416] |
| 13176 | [1–438] | 13233 | [1–455] | 13319 | [1–355] | 13386 | [1–453] |
| 13177 | [1–421] | 13234 | [1–61] | 13320 | [1–319] | 13387 | [1–382] |
| 13178 | [1–431] | 13235 | [1–446] | 13321 | [1–382] | 13388 | [1–469] |
| 13179 | [1–493] | 13236 | [1–454] | 13322 | [1–375] | 13389 | [1–83] |
| 13180 | [270–667] | 13237 | [1–452] | 13323 | [1–33] | 13390 | [1–271] |
| 13181 | [1–197] | 13238 | [1–243] | 13324 | [1–467] | 13391 | [1–390] |
| 13182 | [1–457] | 13239 | [1–433] | 13325 | [1–380] | 13393 | [1–172] |
| 13184 | [1–325] | 13240 | [1–414] | 13327 | [1–298] | 13394 | [1–461] |
| 13186 | [1–454] | 13241 | [1–437] | 13329 | [1–129] | 13395 | [1–85] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 13330 | [1–160] | 13396 | [1–117] | 13545 | [1–200] | 13595 | [1–173] |
| 13397 | [1–60], [135–469] | 13462 | [1–267] | 13546 | [1–53] | 13596 | [1–111] |
| 13400 | [1–269] | 13463 | [1–370] | 13547 | [1–129] | 13597 | [1–270] |
| 13401 | [1–64] | 13464 | [1–91] | 13548 | [1–232] | 13598 | [1–306] |
| 13402 | [1–446] | 13465 | [1–263] | 13549 | [1–134] | 13599 | [1–225] |
| 13403 | [1–421] | 13466 | [1–482] | 13550 | [1–170] | 13600 | [1–157] |
| 13404 | [103–263] | 13467 | [1–459] | 13551 | [1–225] | 13601 | [1–81] |
| 13408 | [1–26] | 13468 | [1–132] | 13552 | [1–97] | 13602 | [1–375] |
| 13409 | [1–366] | 13469 | [1–69] | 13553 | [1–162] | 13603 | [1–125] |
| 13410 | [1–438] | 13470 | [238–428] | 13554 | [1–78] | 13604 | [1–312] |
| 13411 | [1–267] | 13471 | [1–426] | 13555 | [1–338] | 13605 | [1–342] |
| 13413 | [227–419] | 13472 | [76–461] | 13556 | [1–446] | 13606 | [116–183] |
| 13414 | [1–358] | 13473 | [1–464] | 13557 | [1–419] | 13607 | [1–112] |
| 13416 | [1–68] | 13475 | [1–342] | 13558 | [1–125] | 13608 | [1–120] |
| 13417 | [1–313] | 13476 | [1–126], [303–362] | 13559 | [1–129] | 13609 | [1–108] |
| 13418 | [155–187] | 13478 | [1–447] | 13560 | [1–380] | 13610 | [1–174] |
| 13419 | [1–311] | 13479 | [1–202] | 13561 | [1–285] | 13611 | [1–377] |
| 13421 | [1–457] | 13480 | [1–63] | 13563 | [1–383] | 13612 | [1–303] |
| 13422 | [1–466] | 13481 | [1–495] | 13564 | [1–92] | 13613 | [1–506] |
| 13423 | [1–440] | 13482 | [1–466] | 13566 | [1–93] | 13614 | [1–165] |
| 13424 | [1–447] | 13483 | [77–174] | 13567 | [1–119] | 13617 | [177–246] |
| 13426 | [1–99] | 13484 | [1–374] | 13618 | [1–494] | 13682 | [1–424] |
| 13427 | [1–480] | 13485 | [1–478] | 13619 | [1–436] | 13683 | [1–454] |
| 13429 | [1–169] | 13486 | [1–370] | 13620 | [1–92] | 13684 | [1–297], [344–505] |
| 13430 | [1–459] | 13487 | [1–170] | 13621 | [1–522] | 13685 | [143–173] |
| 13431 | [1–304] | 13488 | [1–200] | 13622 | [1–443] | 13686 | [1–376] |
| 13432 | [1–415] | 13490 | [1–200] | 13623 | [1–221], [302–460] | 13687 | [1–103], [211–469] |
| 13434 | [1–372] | 13491 | [55–214], [249–482] | 13624 | [1–386] | 13688 | [1–291] |
| 13436 | [1–313] | 13492 | [1–66] | 13625 | [1–476] | 13689 | [1–402] |
| 13438 | [1–464] | 13494 | [1–313] | 13628 | [1–115] | 13690 | [1–510] |
| 13439 | [1–464] | 13495 | [1–254] | 13630 | [1–232] | 13691 | [1–492] |
| 13440 | [1–147] | 13496 | [1–92] | 13631 | [1–471] | 13693 | [1–511] |
| 13442 | [1–511] | 13497 | [1–72] | 13633 | [1–60], [129–314], [374–466] | 13694 | [1–229] |
| 13444 | [1–120] | 13498 | [1–50] | | | | |
| 13445 | [1–441] | 13499 | [1–82] | 13634 | [1–513] | 13695 | [1–513] |
| 13446 | [1–300] | 13500 | [1–200] | 13637 | [1–504] | 13696 | [1–472] |
| 13447 | [1–388] | 13501 | [1–354] | 13638 | [1–465] | 13697 | [1–312] |
| 13448 | [1–54] | 13502 | [1–329] | 13640 | [1–443] | 13699 | [1–130] |
| 13449 | [1–269] | 13503 | [1–321] | 13641 | [1–385] | 13700 | [1–266] |
| 13450 | [1–403] | 13504 | [1–201] | 13643 | [1–328] | 13704 | [1–125], [167–479] |
| 13451 | [1–303] | 13505 | [1–481] | 13644 | [1–362] | 13705 | [1–462] |
| 13454 | [1–441] | 13508 | [1–330] | 13645 | [92–267] | 13706 | [85–474] |
| 13455 | [1–429] | 13509 | [1–336] | 13647 | [1–113] | 13707 | [1–203] |
| 13456 | [1–191] | 13510 | [1–383] | 13649 | [1–62] | 13708 | [1–486] |
| 13457 | [1–91] | 13511 | [1–112] | 13651 | [1–486] | 13709 | [1–431] |
| 13458 | [1–81] | 13512 | [1–293] | 13652 | [1–442] | 13710 | [1–425] |
| 13459 | [1–90] | 13513 | [1–495] | 13653 | [1–475] | 13711 | [1–468] |
| 13461 | [1–56] | 13515 | [1–337] | 13654 | [1–79] | 13712 | [158–358] |
| 13516 | [1–267] | 13568 | [1–297] | 13655 | [1–284] | 13713 | [45–421] |
| 13517 | [1–207] | 13569 | [1–156] | 13656 | [1–473] | 13714 | [1–237] |
| 13518 | [1–378] | 13570 | [1–324] | 13658 | [1–145] | 13715 | [1–467] |
| 13519 | [1–372] | 13571 | [1–115] | 13659 | [1–490] | 13716 | [1–499] |
| 13520 | [1–271] | 13572 | [1–109] | 13660 | [1–481] | 13717 | [1–504] |
| 13521 | [1–144] | 13573 | [1–224] | 13662 | [1–102] | 13718 | [1–489] |
| 13522 | [1–225] | 13574 | [1–342] | 13663 | [1–440] | 13719 | [1–420] |
| 13524 | [1–119] | 13575 | [1–200] | 13664 | [1–447] | 13720 | [1–507] |
| 13525 | [1–243] | 13576 | [1–161] | 13665 | [1–471] | 13721 | [1–487] |
| 13526 | [1–82] | 13577 | [1–149] | 13667 | [1–86], [175–253] | 13722 | [1–468] |
| 13527 | [1–92] | 13578 | [1–92] | 13668 | [387–475] | 13723 | [1–372] |
| 13528 | [1–200] | 13579 | [1–70] | 13671 | [1–371] | 13724 | [1–116] |
| 13529 | [1–170] | 13580 | [1–51] | 13673 | [1–460] | 13725 | [227–483] |
| 13530 | [1–337] | 13581 | [58–272] | 13674 | [1–447] | 13726 | [1–454] |
| 13532 | [1–133] | 13582 | [1–111] | 13675 | [1–479] | 13727 | [1–476] |
| 13534 | [1–115] | 13583 | [1–152] | 13676 | [1–70] | 13728 | [1–458] |
| 13535 | [1–374] | 13584 | [1–412] | 13677 | [193–468] | 13729 | [1–74], [117–417] |
| 13536 | [1–254] | 13585 | [87–118] | 13678 | [1–93], [189–467] | 13730 | [1–137] |
| 13537 | [1–296] | 13586 | [1–85], [153–504] | 13679 | [1–192] | 13731 | [1–370] |
| 13538 | [1–200] | 13587 | [1–374] | 13680 | [1–355] | 13732 | [1–113] |
| 13539 | [1–112] | 13588 | [1–313] | 13681 | [1–463] | 13733 | [45–408] |
| 13540 | [1–354] | 13589 | [1–107] | 13734 | [245–472] | 13791 | [1–500] |
| 13541 | [1–309] | 13590 | [1–366] | 13735 | [1–263] | 13793 | [255–433] |
| 13542 | [1–348] | 13591 | [1–175] | 13737 | [1–476] | 13794 | [1–215] |
| 13543 | [1–361] | 13592 | [1–91] | 13738 | [1–282] | 13795 | [1–507] |
| 13544 | [1–161] | 13594 | [1–144] | 13739 | [1–469] | 13796 | [1–363] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 13740 | [1–348] | 13797 | [1–146] | 13884 | [1–85] | 13938 | [1–340] |
| 13741 | [132–357] | 13798 | [1–209], [398–451] | 13885 | [1–403] | 13939 | [1–451] |
| 13742 | [1–136], [416–483] | 13799 | [1–294] | 13886 | [1–343] | 13940 | [1–413] |
| 13744 | [1–468] | 13800 | [1–343] | 13887 | [1–211] | 13941 | [1–426] |
| 13745 | [1–480] | 13801 | [1–420] | 13888 | [1–513] | 13942 | [1–218] |
| 13746 | [239–449] | 13802 | [1–134], [255–465] | 13889 | [1–214] | 13943 | [1–155], [199–395] |
| 13747 | [1–462] | 13803 | [1–369] | 13890 | [1–488] | 13944 | [1–507] |
| 13748 | [1–491] | 13805 | [1–139] | 13891 | [1–574] | 13945 | [1–487] |
| 13749 | [1–361] | 13806 | [59–100] | 13893 | [1–503] | 13946 | [1–223] |
| 13750 | [1–287] | 13807 | [1–348] | 13894 | [1–100] | 13947 | [80–456] |
| 13751 | [1–436] | 13808 | [1–72] | 13896 | [1–388] | 13948 | [1–123] |
| 13752 | [1–59] | 13809 | [1–125], [157–471] | 13897 | [75–543] | 13949 | [1–488] |
| 13755 | [1–461] | 13811 | [1–466] | 13898 | [1–521] | 13950 | [1–508] |
| 13756 | [1–93] | 13812 | [1–320] | 13899 | [1–133] | 13951 | [1–443] |
| 13758 | [1–433] | 13813 | [1–294] | 13900 | [73–127] | 13952 | [1–172], [283–449] |
| 13759 | [1–61] | 13814 | [1–475] | 13901 | [1–103] | 13953 | [1–89] |
| 13760 | [1–437] | 13815 | [1–481] | 13954 | [1–511] | 14008 | [1–478] |
| 13761 | [1–60] | 13816 | [1–41] | 13956 | [1–200] | 14009 | [1–336] |
| 13764 | [1–493] | 13818 | [1–443] | 13957 | [1–330] | 14011 | [1–281] |
| 13765 | [1–115] | 13820 | [1–105] | 13958 | [1–94] | 14012 | [1–524] |
| 13766 | [1–459] | 13821 | [1–428] | 13959 | [1–399] | 14013 | [1–529] |
| 13767 | [1–543] | 13822 | [1–485] | 13960 | [53–236] | 14014 | [1–343] |
| 13768 | [1–392] | 13823 | [1–257] | 13961 | [1–512] | 14015 | [1–231] |
| 13769 | [1–97] | 13824 | [1–139] | 13963 | [1–62] | 14016 | [1–518] |
| 13770 | [1–178] | 13825 | [1–477] | 13964 | [1–510] | 14017 | [1–57] |
| 13771 | [1–463] | 13826 | [37–460] | 13965 | [1–112] | 14018 | [1–440] |
| 13772 | [1–396] | 13827 | [1–481] | 13967 | [1–422] | 14019 | [1–496] |
| 13773 | [1–313] | 13828 | [1–52] | 13968 | [1–512] | 14020 | [1–499] |
| 13774 | [1–582] | 13829 | [1–471] | 13969 | [200–485] | 14021 | [1–428] |
| 13775 | [1–507] | 13830 | [1–428] | 13970 | [73–178] | 14022 | [1–387] |
| 13776 | [1–342] | 13831 | [1–32] | 13971 | [1–435] | 14023 | [1–382] |
| 13777 | [1–407] | 13832 | [224–496] | 13972 | [1–542] | 14024 | [1–87] |
| 13778 | [1–475] | 13833 | [1–402] | 13973 | [1–491] | 14025 | [1–255] |
| 13779 | [1–534] | 13834 | [1–479] | 13974 | [1–55] | 14026 | [211–502] |
| 13780 | [1–264] | 13835 | [1–487] | 13975 | [1–180] | 14027 | [1–317] |
| 13782 | [1–320], [363–485] | 13836 | [1–62] | 13976 | [1–77] | 14028 | [1–119] |
| 13783 | [1–81] | 13837 | [381–537] | 13977 | [1–266] | 14030 | [1–228] |
| 13784 | [1–266] | 13838 | [1–481] | 13978 | [1–327] | 14031 | [1–483] |
| 13786 | [1–499] | 13839 | [271–452] | 13979 | [1–387] | 14032 | [1–89] |
| 13787 | [1–478] | 13841 | [1–353] | 13980 | [1–339] | 14033 | [1–77] |
| 13788 | [1–605] | 13842 | [1–63] | 13982 | [1–417] | 14034 | [1–458] |
| 13789 | [48–472] | 13843 | [1–494] | 13984 | [1–241] | 14035 | [1–58], [214–440] |
| 13844 | [1–429] | 13903 | [89–176] | 13985 | [1–447] | 14036 | [1–312] |
| 13845 | [1–472] | 13904 | [1–74] | 13986 | [1–145] | 14037 | [1–460] |
| 13846 | [1–268] | 13905 | [1–40], [82–259] | 13987 | [1–100] | 14038 | [1–490] |
| 13847 | [1–316] | 13906 | [1–159] | 13988 | [1–499] | 14039 | [1–475] |
| 13848 | [214–390] | 13907 | [1–276] | 13989 | [79–150] | 14040 | [1–272], [385–478] |
| 13850 | [1–465] | 13908 | [1–181] | 13990 | [1–459] | 14041 | [1–510] |
| 13851 | [1–234] | 13909 | [1–69] | 13991 | [1–501] | 14043 | [1–535] |
| 13852 | [1–52] | 13911 | [1–600] | 13992 | [86–132] | 14044 | [1–319] |
| 13853 | [1–304] | 13912 | [1–183] | 13994 | [1–480] | 14045 | [1–479] |
| 13854 | [1–486] | 13913 | [216–327] | 13995 | [1–485] | 14046 | [1–485] |
| 13855 | [1–354] | 13914 | [1–254] | 13996 | [1–343] | 14048 | [1–371] |
| 13856 | [1–464] | 13915 | [1–75] | 13997 | [1–466] | 14049 | [1–290], [327–473] |
| 13859 | [1–667] | 13916 | [1–181] | 13999 | [1–479] | 14050 | [1–111] |
| 13860 | [147–353] | 13917 | [1–67] | 14000 | [1–467] | 14051 | [1–499] |
| 13862 | [1–506] | 13918 | [1–108] | 14001 | [1–368] | 14053 | [1–155] |
| 13863 | [1–480] | 13919 | [1–437] | 14002 | [1–325] | 14054 | [1–195], [247–486] |
| 13864 | [1–315] | 13920 | [1–64] | 14003 | [1–115] | 14055 | [1–513] |
| 13865 | [1–149], [237–516] | 13921 | [1–54], [345–463] | 14004 | [1–132], [395–447] | 14056 | [1–111], [260–383] |
| 13866 | [1–491] | 13922 | [1–304], [663–691] | 14005 | [1–418] | 14057 | [1–485] |
| 13868 | [1–468] | 13923 | [1–381] | 14006 | [1–492] | 14058 | [1–201] |
| 13869 | [1–382] | 13924 | [1–450] | 14007 | [1–447] | 14059 | [1–322] |
| 13872 | [1–278] | 13925 | [1–356] | 14061 | [1–129] | 14120 | [1–430] |
| 13873 | [1–386] | 13927 | [1–477] | 14062 | [81–421] | 14122 | [1–403] |
| 13875 | [1–502] | 13929 | [1–388] | 14066 | [238–282] | 14123 | [1–481] |
| 13876 | [1–239] | 13930 | [1–221] | 14067 | [1–170] | 14124 | [1–315] |
| 13878 | [1–248] | 13931 | [435–463] | 14068 | [1–242] | 14125 | [1–417] |
| 13879 | [1–480] | 13932 | [1–457] | 14069 | [1–484] | 14126 | [1–503] |
| 13880 | [1–313], [344–481] | 13933 | [1–127] | 14071 | [255–487] | 14127 | [1–493] |
| 13881 | [1–27], [90–131], [354–433] | 13934 | [1–154] | 14072 | [1–243] | 14128 | [1–182] |
| | | | | 14073 | [1–289] | 14129 | [1–385] |
| 13882 | [1–242] | 13935 | [1–173] | 14074 | [1–439] | 14130 | [1–62] |
| 13883 | [1–387] | 13937 | [1–57] | 14075 | [1–468] | 14131 | [1–295] |

TABLE IVa-continued (Novelty:95%)

| Seq Id No. | Positions of preferred fragments | Seq Id No. | Positions of preferred fragments |
|---|---|---|---|
| 14077 | [1–258] | 14132 | [1–496] |
| 14078 | [1–314] | 14133 | [1–452] |
| 14079 | [1–509] | 14134 | [60–372] |
| 14080 | [1–489] | 14135 | [1–449] |
| 14081 | [1–497] | 14136 | [1–438] |
| 14082 | [1–204] | 14137 | [1–181] |
| 14083 | [1–392] | 14138 | [1–472] |
| 14084 | [1–46] | 14139 | [1–444] |
| 14085 | [1–473] | 14141 | [59–87] |
| 14086 | [1–35], [351–414] | 14142 | [1–52] |
| 14087 | [1–445] | 14144 | [1–316] |
| 14089 | [1–441] | 14145 | [1–509] |
| 14090 | [1–394] | 14146 | [1–497] |
| 14092 | [1–501] | 14147 | [1–67] |
| 14093 | [180–326] | 14148 | [155–291] |
| 14094 | [1–514] | 14149 | [1–100] |
| 14095 | [1–504] | 14151 | [67–456] |
| 14096 | [1–186] | 14152 | [1–406] |
| 14098 | [1–225] | 14153 | [1–443] |
| 14100 | [287–432] | 14154 | [1–156] |
| 14102 | [1–354] | 14155 | [187–267] |
| 14103 | [1–454] | 14156 | [1–333] |
| 14104 | [1–607] | 14157 | [1–503] |
| 14105 | [1–69] | 14158 | [1–166], [286–328], [380–460] |
| 14106 | [36–429] | 14159 | [1–354] |
| 14107 | [1–379] | 14160 | [1–147] |
| 14108 | [1–488] | 14162 | [1–69] |
| 14109 | [1–240] | 14163 | [37–472] |
| 14110 | [1–171] | 14164 | [1–461] |
| 14112 | [1–74] | 14165 | [1–543] |
| 14113 | [1–481] | 14166 | [387–424] |
| 14114 | [63–191] | 14167 | [1–538] |
| 14115 | [1–259] | 14168 | [1–372] |
| 14116 | [1–125] | 14171 | [1–448] |
| 14117 | [1–483] | 14172 | [1–106] |
| 14118 | [1–]59], [200–473] | 14173 | [1–487] |
| 14174 | [1–491] | 14235 | [1–458] |
| 14175 | [1–600] | 14236 | [1–88], [364–407] |
| 14176 | [1–77] | 14238 | [1–477] |
| 14177 | [1–529] | 14239 | [1–213] |
| 14179 | [1–498] | 14240 | [1–216], [256–487] |
| 14180 | [1–301] | 14241 | [1–464] |
| 14181 | [1–439] | 14242 | [1–454] |
| 14182 | [1–203] | 14244 | [1–470] |
| 14183 | [1–436] | 14245 | [1–31], [137–367] |
| 14184 | [1–413] | 14246 | [1–81] |
| 14186 | [1–391] | 14247 | [1–262] |
| 14187 | [1–468] | 14248 | [1–227] |
| 14188 | [72–97] | 14249 | [1–410] |
| 14189 | [1–74] | 14250 | [1–27] |
| 14190 | [1–323] | 14251 | [1–272] |
| 14191 | [1–453] | 14252 | [1–462] |
| 14192 | [1–489] | 14253 | [1–431] |
| 14194 | [198–497] | 14254 | [1–100] |
| 14195 | [1–180] | 14255 | [1–391] |
| 14196 | [1–452] | 14257 | [1–171] |
| 14197 | [1–474] | 14258 | [1–364] |
| 14199 | [1–90], [122–156[, [247–444] | 14259 | [1–436] |
| 14200 | [311–390] | 14260 | [1–425] |
| 14203 | [1–275] | 14261 | [1–359] |
| 14204 | [1–200] | 14262 | [1–269] |
| 14205 | [1–52], [84–133], [174–484] | 14263 | [1–138] |
| 14206 | [388–434] | 14264 | [1–491] |
| 14207 | [1–300] | 14265 | [1–345] |
| 14209 | [1–465] | 14266 | [1–394] |
| 14210 | [110–232] | 14267 | [1–467] |
| 14211 | [1–341] | 14268 | [1–185] |
| 14212 | [1–106] | 14270 | [1–232] |
| 14213 | [1–466] | 14271 | [250–318], [434–467] |
| 14214 | [1–327] | 14273 | [1–62] |
| 14215 | [1–458] | 14274 | [1–278] |
| 14216 | [1–494] | 14275 | [1–396] |
| 14217 | [1–203], [278–466] | 14276 | [1–164] |
| 14218 | [1–462] | 14277 | [1–479] |
| 14220 | [1–248], [404–460] | 14278 | [1–523] |
| 14222 | [1–370] | 14280 | [1–316] |
| 14224 | [1–333], [373–475] | 14281 | [1–500] |
| 14225 | [1–312] | 14282 | [1–271] |
| 14226 | [1–457] | 14283 | [1–267] |
| 14227 | [1–457] | 14284 | [1–409] |
| 14229 | [1–455] | 14285 | [1–75] |
| 14232 | [1–334] | 14286 | [1–157] |
| 14234 | [1–118] | 14288 | [1–445] |
| 14289 | [1–434] | 14350 | [1–428] |
| 14291 | [1–339] | 14351 | [1–325] |
| 14292 | [1–418] | 14352 | [1–182] |
| 14293 | [1–85] | 14353 | [1–162] |
| 14294 | [1–491] | 14354 | [1–514] |
| 14295 | [1–433] | 14355 | [1–96] |
| 14297 | [1–445] | 14356 | [1–352] |
| 14299 | [1–379] | 14357 | [401–498] |
| 14300 | [1–454] | 14358 | [1–198] |
| 14301 | [1–363] | 14359 | [1–550] |
| 14303 | [1–431] | 14361 | [1–334] |
| 14304 | [1–453] | 14362 | [1–453] |
| 14305 | [1–425] | 14363 | [1–214], [316–347] |
| 14306 | [1–436] | 14364 | [1–495] |
| 14307 | [311–405] | 14368 | [1–310] |
| 14308 | [1–260] | 14369 | [1–454] |
| 14309 | [1–477] | 14370 | [1–297] |
| 14310 | [1–496] | 14371 | [1–121], [384–430] |
| 14311 | [1–378] | 14372 | [1–462] |
| 14313 | [1–442] | 14373 | [1–512] |
| 14314 | [1–282] | 14374 | [1–73] |
| 14315 | [1–66] | 14376 | [1–449] |
| 14316 | [1–371] | 14377 | [1–193] |
| 14318 | [1–429] | 14378 | [1–307] |
| 14319 | [1–299] | 14379 | [1–477] |
| 14320 | [1–111] | 14381 | [1–269] |
| 14322 | [1–156] | 14383 | [1–126], [338–483] |
| 14323 | [1–392] | 14384 | [1–412] |
| 14324 | [1–277] | 14385 | [1–239] |
| 14326 | [1–461] | 14387 | [49–451] |
| 14327 | [1–452] | 14389 | [1–443] |
| 14328 | [1–423] | 14390 | [1–145] |
| 14329 | [1–218] | 14391 | [1–115] |
| 14331 | [1–277] | 14392 | [1–451] |
| 14333 | [1–82] | 14393 | [1–470] |
| 14334 | [1–420] | 14394 | [1–474] |
| 14335 | [1–410] | 14395 | [1–442] |
| 14336 | [1–266] | 14396 | [1–372] |
| 14337 | [1–434] | 14397 | [1–122] |
| 14339 | [1–448] | 14398 | [1–457] |
| 14342 | [1–373], [412–481] | 14399 | [1–457] |
| 14343 | [1–416] | 14400 | [1–296] |
| 14344 | [1–464] | 14401 | [1–170] |
| 14346 | [1–289] | 14402 | [1–379] |
| 14347 | [1–383] | 14403 | [1–477] |
| 14348 | [1–313] | 14404 | [318–386] |
| 14349 | [1–418] | 14405 | [1–481] |
| 14406 | [1–477] | 14463 | [1–463] |
| 14407 | [1–474] | 14464 | [1–449] |
| 14410 | [1–357] | 14465 | [1–96] |
| 14412 | [1–320] | 14466 | [1–444] |
| 14414 | [1–476] | 14467 | [1–461] |
| 14415 | [1–301] | 14468 | [1–448] |
| 14416 | [1–169] | 14469 | [1–233] |
| 14417 | [1–439] | 14471 | [1–448] |
| 14418 | [1–343] | 14472 | [1–375] |
| 14419 | [1–71], [105–190], [248–302] | 14473 | [1–369] |
| 14420 | [1–171], [200–463] | 14474 | [1–229], [280–451] |
| 14421 | [1–45], [208–402] | 14475 | [1–458] |
| 14422 | [1–455] | 14476 | [1–197] |
| 14423 | [1–447] | 14477 | [1–441] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 14424 | [1–455] | 14479 | [1–151] | 14569 | [1–347] | 14625 | [1–484] |
| 14425 | [1–173] | 14480 | [1–422] | 14570 | [1–324] | 14626 | [1–359] |
| 14426 | [1–373] | 14481 | [1–329] | 14571 | [1–84] | 14627 | [1–52] |
| 14427 | [1–415] | 14482 | [1–93] | 14572 | [1–483] | 14628 | [1–511] |
| 14428 | [1–213] | 14484 | [1–401] | 14573 | [1–311] | 14629 | [1–233] |
| 14429 | [1–442] | 14485 | [1–344] | 14574 | [1–341] | 14630 | [1–129] |
| 14430 | [1–465] | 14488 | [1–441] | 14631 | [1–82] | 14683 | [1–419] |
| 14431 | [1–256] | 14489 | [1–334] | 14632 | [1–475] | 14685 | [1–320] |
| 14432 | [1–295] | 14490 | [1–443] | 14633 | [1–520] | 14687 | [1–314] |
| 14433 | [1–398] | 14491 | [1–386] | 14634 | [1–316] | 14688 | [1–97] |
| 14434 | [1–477] | 14492 | [1–82] | 14635 | [1–308] | 14689 | [1–92] |
| 14436 | [1–119] | 14493 | [141–324] | 14636 | [1–465] | 14690 | [1–340] |
| 14437 | [1–200] | 14494 | [1–408] | 14637 | [1–288] | 14693 | [1–77] |
| 14438 | [1–116] | 14495 | [1–417] | 14638 | [1–222] | 14694 | [1–75] |
| 14439 | [1–470] | 14496 | [1–446] | 14639 | [1–251] | 14697 | [1–368] |
| 14440 | [1–178] | 14497 | [183–217] | 14640 | [413–498] | 14699 | [1–365] |
| 14441 | [1–435] | 14498 | [1–433] | 14641 | [1–397] | 14700 | [1–288] |
| 14443 | [1–482] | 14499 | [1–453] | 14642 | [1–424] | 14701 | [1–124] |
| 14445 | [1–419] | 14500 | [1–171] | 14644 | [1–217] | 14702 | [1–357] |
| 14447 | [1–435] | 14501 | [1–453] | 14645 | [1–501] | 14703 | [1–60] |
| 14448 | [1–310] | 14503 | [1–298] | 14646 | [1–470] | 14704 | [1–195] |
| 14449 | [1–458] | 14504 | [1–475] | 14647 | [1–143], [223–293] | 14705 | [1–74] |
| 14450 | [1–432] | 14505 | [1–416] | 14648 | [1–58] | 14706 | [1–293] |
| 14451 | [72–443] | 14506 | [1–276], [307–432] | 14649 | [1–322] | 14708 | [1–345] |
| 14452 | [51–94], [139–415] | 14508 | [1–342] | 14650 | [1–486] | 14709 | [1–509] |
| 14453 | [1–433] | 14509 | [1–369] | 14651 | [1–478] | 14710 | [1–449] |
| 14454 | [1–215] | 14510 | [1–450] | 14652 | [1–447] | 14711 | [1–335] |
| 14455 | [1–461] | 14511 | [1–89] | 14653 | [1–438] | 14712 | [1–59] |
| 14456 | [59–322] | 14512 | [1–322] | 14654 | [341–388] | 14713 | [1–216] |
| 14457 | [1–473] | 14513 | [1–249] | 14655 | [43–79] | 14714 | [1–217] |
| 14458 | [1–374] | 14514 | [1–418] | 14656 | [1–482] | 14715 | [1–50] |
| 14459 | [1–457] | 14515 | [1–373] | 14657 | [1–508] | 14716 | [1–95] |
| 14460 | [1–70] | 14516 | [164–402] | 14658 | [1–329] | 14717 | [1–80] |
| 14519 | [1–320] | 14577 | [1–84] | 14659 | [1–398] | 14718 | [1–406] |
| 14520 | [1–448] | 14578 | [1–408] | 14661 | [1–194] | 14719 | [1–274] |
| 14522 | [1–333] | 14579 | [1–178] | 14662 | [183–497] | 14720 | [1–492] |
| 14523 | [1–384] | 14580 | [1–413] | 14663 | [1–484] | 14721 | [1–433] |
| 14524 | [1–26] | 14581 | [1–292], [400–488] | 14665 | [1–481] | 14722 | [1–135] |
| 14526 | [1–140] | 14582 | [1–322] | 14666 | [1–126] | 14723 | [1–420] |
| 14527 | [1–129] | 14583 | [1–399] | 14667 | [1–323] | 14724 | [1–94] |
| 14528 | [1–360] | 14584 | [1–482] | 14668 | [1–90] | 14725 | [1–483] |
| 14529 | [1–504] | 14585 | [1–325] | 14669 | [1–425] | 14726 | [1–465] |
| 14530 | [1–457] | 14586 | [1–399] | 14670 | [1–448] | 14728 | [1–217] |
| 14531 | [1–424] | 14587 | [1–332] | 14671 | [1–172] | 14729 | [1–73] |
| 14532 | [1–61] | 14588 | [1–280] | 14672 | [1–59] | 14731 | [45–184] |
| 14534 | [1–284] | 14589 | [1–284] | 14673 | [1–29] | 14732 | [1–433] |
| 14535 | [1–55] | 14590 | [1–357] | 14676 | [1–275] | 14733 | [1–304] |
| 14536 | [1–72] | 14591 | [1–364] | 14677 | [1–111] | 14734 | [1–437] |
| 14537 | [1–321] | 14592 | [1–109] | 14678 | [1–472] | 14735 | [1–461] |
| 14538 | [1–425] | 14593 | [1–478] | 14679 | [1–168] | 14737 | [1–148] |
| 14540 | [1–498] | 14594 | [1–507] | 14680 | [1–61] | 14738 | [1–411] |
| 14541 | [1–480] | 14595 | [1–238] | 14681 | [1–61] | 14739 | [1–517] |
| 14542 | [1–507] | 14596 | [1–433] | 14682 | [1–59] | 14740 | [1–308] |
| 14543 | [1–226] | 14597 | [1–492] | 14741 | [1–85] | 14798 | [61–259] |
| 14544 | [1–541] | 14599 | [1–167] | 14742 | [1–60] | 14799 | [1–61] |
| 14545 | [1–523] | 14600 | [240–483] | 14743 | [1–65] | 14800 | [1–55] |
| 14546 | [246–317], [363–583] | 14601 | [1–374] | 14744 | [1–404] | 14801 | [1–342] |
| 14547 | [1–487] | 14603 | [1–510] | 14745 | [1–498] | 14803 | [1–54] |
| 14548 | [1–367] | 14605 | [1–440] | 14746 | [1–463] | 14804 | [1–102] |
| 14550 | [1–166] | 14606 | [1–416] | 14747 | [1–413] | 14805 | [1–81] |
| 14551 | [1–487] | 14608 | [1–418] | 14748 | [109–195] | 14806 | [1–110] |
| 14552 | [1–451] | 14609 | [1–361] | 14749 | [1–89] | 14807 | [1–430] |
| 14553 | [1–359] | 14610 | [1–335] | 14750 | [1–70] | 14808 | [1–430] |
| 14554 | [1–447] | 14612 | [1–50] | 14751 | [1–83] | 14809 | [1–292] |
| 14555 | [1–498] | 14613 | [1–410] | 14752 | [1–284] | 14811 | [1–441] |
| 14556 | [1–56] | 14614 | [1–224] | 14753 | [1–67] | 14812 | [1–77] |
| 14558 | [1–464] | 14615 | [1–163] | 14754 | [1–61] | 14813 | [1–69] |
| 14559 | [1–471] | 14616 | [1–495] | 14755 | [1–195] | 14814 | [1–456] |
| 14560 | [1–87] | 14617 | [1–430] | 14756 | [1–63] | 14815 | [1–72] |
| 14562 | [222–382] | 14618 | [1–352] | 14757 | [1–90] | 14816 | [1–340] |
| 14563 | [1–424] | 14619 | [1–83] | 14758 | [54–209] | 14818 | [1–195] |
| 14565 | [1–464] | 14620 | [296–321] | 14759 | [1–527] | 14819 | [1–66] |
| 14566 | [1–301] | 14621 | [1–156], [190–491] | 14761 | [1–189] | 14820 | [1–54] |
| 14568 | [47–75] | 14623 | [1–483] | 14763 | [1–317] | 14821 | [1–436] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 14764 | [1–63] | 14822 | [1–343] | 14958 | [1–83] | 15013 | [1–61] |
| 14765 | [1–495] | 14823 | [1–317] | 14959 | [1–83] | 15014 | [37–481] |
| 14766 | [1–508] | 14824 | [1–78] | 14960 | [1–88] | 15016 | [1–434] |
| 14767 | [1–379] | 14825 | [1–62] | 14961 | [1–427] | 15017 | [1–162] |
| 14768 | [199–393] | 14826 | [1–386] | 14963 | [1–73] | 15018 | [1–83], [166–228] |
| 14769 | [1–474] | 14827 | [1–58] | 14964 | [1–30] | 15019 | [1–167] |
| 14770 | [1–263] | 14829 | [1–478] | 14965 | [1–458] | 15020 | [1–500] |
| 14771 | [1–528] | 14830 | [1–103] | 14966 | [1–63] | 15021 | [1–195] |
| 14772 | [450–510] | 14831 | [1–76] | 14967 | [1–118] | 15022 | [1–419] |
| 14773 | [1–514] | 14833 | [1–119], [154–405] | 14968 | [1–58] | 15023 | [1–32] |
| 14774 | [1–298] | 14834 | [1–61] | 14970 | [1–105] | 15024 | [1–81] |
| 14775 | [1–281] | 14835 | [1–86] | 14971 | [1–235] | 15026 | [1–243] |
| 14777 | [1–162] | 14836 | [1–494] | 14972 | [1–48], [259–469] | 15027 | [1–93] |
| 14778 | [1–445] | 14837 | [1–458] | 14973 | [1–180] | 15028 | [1–91] |
| 14781 | [61–269] | 14838 | [1–69] | 14974 | [1–89] | 15029 | [1–216] |
| 14782 | [1–162] | 14839 | [1–344] | 14976 | [1–178] | 15030 | [1–381] |
| 14783 | [1–83] | 14840 | [1–217] | 14979 | [177–214] | 15031 | [1–82] |
| 14784 | [1–417] | 14841 | [1–328] | 14980 | [1–413] | 15032 | [1–432] |
| 14786 | [1–83] | 14842 | [1–72] | 14981 | [1–448] | 15034 | [1–422] |
| 14787 | [1–75] | 14843 | [1–430] | 14982 | [1–380] | 15035 | [1–492] |
| 14788 | [1–442] | 14845 | [1–253] | 14983 | [1–217] | 15036 | [1–284] |
| 14790 | [1–264] | 14846 | [1–66] | 14984 | [1–305] | 15037 | [1–154] |
| 14791 | [1–301] | 14847 | [1–109] | 14985 | [1–507] | 15038 | [1–454] |
| 14795 | [1–356] | 14848 | [1–187], [268–387] | 14986 | [1–470] | 15039 | [1–338] |
| 14796 | [1–278] | 14849 | [1–87] | 14987 | [1–484] | 15040 | [1–119], [155–431] |
| 14797 | [1–328] | 14850 | [1–480] | 14988 | [1–363] | 15041 | [1–90] |
| 14851 | [1–196] | 14907 | [1–370] | 14989 | [1–53] | 15042 | [1–503] |
| 14852 | [1–423] | 14908 | [1–413] | 14991 | [1–433] | 15043 | [1–301] |
| 14853 | [1–65] | 14909 | [1–386] | 14992 | [1–125] | 15044 | [1–248] |
| 14854 | [1–480] | 14910 | [1–119] | 14993 | [1–113] | 15045 | [1–329] |
| 14855 | [1–138] | 14911 | [1–302] | 14994 | [1–54] | 15046 | [1–174] |
| 14856 | [1–309] | 14912 | [1–152] | 14995 | [1–487] | 15047 | [1–134] |
| 14857 | [1–323] | 14913 | [1–52] | 14996 | [1–92] | 15048 | [1–431] |
| 14858 | [1–64] | 14914 | [1–50] | 14997 | [1–447] | 15049 | [1–84] |
| 14859 | [1–85] | 14915 | [1–76] | 14998 | [1–387] | 15050 | [1–465] |
| 14860 | [1–71] | 14916 | [1–78] | 14999 | [1–166] | 15051 | [1–284] |
| 14861 | [1–470] | 14917 | [1–482] | 15000 | [1–156] | 15052 | [37–474] |
| 14862 | [1–103] | 14918 | [1–293] | 15001 | [1–155] | 15053 | [1–548] |
| 14863 | [1–166] | 14919 | [1–496] | 15002 | [1–114] | 15054 | [1–349] |
| 14865 | [1–495] | 14920 | [1–59] | 15003 | [1–169] | 15055 | [1–310] |
| 14866 | [1–217] | 14921 | [1–474] | 15004 | [1–67] | 15056 | [1–113] |
| 14868 | [1–473] | 14922 | [1–195] | 15005 | [115–245] | 15057 | [1–74] |
| 14869 | [1–69] | 14923 | [1–113] | 15006 | [1–217] | 15059 | [1–468] |
| 14870 | [1–276] | 14924 | [1–328] | 15008 | [1–419] | 15060 | [1–91] |
| 14871 | [1–93] | 14925 | [1–91] | 15009 | [1–192] | 15061 | [1–162] |
| 14873 | [1–417] | 14926 | [1–84] | 15010 | [1–446] | 15062 | [1–51] |
| 14874 | [1–197] | 14927 | [1–112] | 15064 | [1–72] | 15121 | [1–483] |
| 14876 | [1–154] | 14928 | [1–122] | 15066 | [1–70] | 15122 | [1–525] |
| 14877 | [1–435] | 14929 | [1–216] | 15067 | [1–445] | 15123 | [1–478] |
| 14879 | [1–323] | 14930 | [1–477] | 15068 | [1–281] | 15124 | [1–309], [350–375] |
| 14880 | [1–302] | 14931 | [1–91] | 15069 | [1–436] | 15127 | [126–165] |
| 14881 | [1–221] | 14932 | [1–234] | 15071 | [1–478] | 15131 | [1–617] |
| 14882 | [1–269] | 14933 | [1–339] | 15072 | [1–425] | 15132 | [1–540] |
| 14884 | [1–60] | 14934 | [1–313] | 15073 | [1–75] | 15133 | [1–232] |
| 14885 | [1–462] | 14935 | [1–449] | 15074 | [1–406] | 15134 | [1–351] |
| 14886 | [1–114] | 14936 | [1–62] | 15075 | [1–177] | 15135 | [1–440] |
| 14887 | [1–481] | 14937 | [1–144] | 15076 | [1–418] | 15136 | [1–189], [219–493] |
| 14888 | [1–389] | 14940 | [1–157] | 15077 | [1–349] | 15138 | [1–207] |
| 14889 | [1–194] | 14941 | [1–431] | 15078 | [1–75] | 15139 | [1–225] |
| 14890 | [1–240] | 14943 | [45–328] | 15079 | [1–177] | 15140 | [1–535] |
| 14891 | [1–301] | 14944 | [1–91] | 15081 | [1–409] | 15142 | [249–289] |
| 14892 | [1–75] | 14945 | [1–62] | 15082 | [1–189] | 15143 | [1–479] |
| 14893 | [1–357] | 14946 | [1–95] | 15086 | [1–255] | 15144 | [1–447] |
| 14894 | [1–386] | 14947 | [1–94] | 15087 | [1–132] | 15145 | [414–457] |
| 14895 | [1–481] | 14948 | [1–61] | 15088 | [1–373] | 15146 | [1–400] |
| 14896 | [1–181] | 14949 | [1–85] | 15089 | [1–162] | 15147 | [1–51] |
| 14897 | [1–485] | 14950 | [1–195] | 15090 | [1–79] | 15149 | [1–437] |
| 14898 | [1–330] | 14951 | [1–224] | 15091 | [1–98] | 15150 | [1–282], [334–570] |
| 14900 | [1–285] | 14952 | [1–486] | 15092 | [1–78] | 15151 | [1–464] |
| 14901 | [1–78] | 14953 | [1–94] | 15093 | [1–342] | 15154 | [1–43], [89–484] |
| 14903 | [1–435] | 14954 | [1–249] | 15094 | [33–64], [290–445] | 15155 | [1–239], [402–651] |
| 14905 | [1–71] | 14955 | [37–491] | 15096 | [1–371] | 15156 | [1–475] |
| 14906 | [1–297] | 14956 | [1–501] | 15098 | [1–520] | 15158 | [1–172] |
| 14957 | [1–124], [155–216] | 15011 | [1–365] | 15099 | [1–450] | 15162 | [1–420] |

TABLE IVa-continued (Novelty:95%)

| Seq Id No. | Positions of preferred fragments | Seq Id No. | Positions of preferred fragments |
|---|---|---|---|
| 15100 | [1–272] | 15163 | [227–436] |
| 15101 | [392–573] | 15164 | [1–533] |
| 15102 | [1–290] | 15166 | [1–484] |
| 15103 | [1–489] | 15167 | [266–291] |
| 15104 | [1–368] | 15168 | [1–294] |
| 15105 | [1–454] | 15169 | [1–85] |
| 15106 | [1–405] | 15170 | [1–478] |
| 15107 | [1–406] | 15171 | [1–50], [278–416] |
| 15108 | [1–337] | 15172 | [1–66] |
| 15109 | [1–163], [451–568] | 15173 | [1–475] |
| 15111 | [48–372] | 15174 | [1–201], [230–425] |
| 15112 | [129–255] | 15175 | [1–122] |
| 15113 | [1–406] | 15176 | [1–445] |
| 15114 | [425–539] | 15177 | [1–64] |
| 15116 | [1–558] | 15178 | [1–35] |
| 15117 | [412–529] | 15179 | [1–473] |
| 15118 | [1–407] | 15180 | [1–34] |
| 15119 | [1–306], [352–495] | 15181 | [1–591] |
| 15120 | [1–478] | 15182 | [1–250] |
| 15183 | [1–377] | 15233 | [1–398] |
| 15184 | [1–454] | 15234 | [1–389] |
| 15185 | [1–376] | 15237 | [1–152], [370–514] |
| 15186 | [1–436] | 15238 | [1–152], [369–442] |
| 15187 | [1–382] | 15239 | [72–112] |
| 15188 | [1–494] | 15240 | [1–475] |
| 15189 | [1–521] | 15241 | [1–435] |
| 15190 | [1–503] | 15242 | [1–394] |
| 15191 | [1–433] | 15244 | [1–601] |
| 15192 | [1–567] | 15245 | [1–506] |
| 15194 | [1–264] | 15246 | [1–521] |
| 15195 | [1–451] | 15247 | [1–468] |
| 15196 | [1–368] | 15248 | [1–345] |
| 15197 | [1–302] | 15249 | [1–293] |
| 15198 | [1–459] | 15251 | [1–577] |
| 15199 | [1–431] | 15252 | [1–425] |
| 15200 | [1–460] | 15253 | [1–185] |
| 15201 | [1–464] | 15254 | [1–434] |
| 15202 | [1–496] | 15256 | [1–501] |
| 15203 | [1–397] | 15257 | [1–493] |
| 15204 | [1–394] | 15258 | [1–454] |
| 15205 | [1–436] | 15259 | [1–466] |
| 15206 | [1–435] | 15261 | [1–402] |
| 15208 | [1–437] | 15262 | [1–448] |
| 15209 | [1–435] | 15263 | [1–492] |
| 15210 | [1–435] | 15264 | [1–381] |
| 15211 | [1–474] | 15268 | [145–201] |
| 15212 | [1–509] | 15269 | [145–201] |
| 15213 | [1–490] | 15270 | [145–180] |
| 15214 | [1–472] | 15273 | [487–512] |
| 15215 | [1–461] | 15274 | [47–187] |
| 15216 | [1–406] | 15279 | [1–533] |
| 15217 | [1–469] | 15280 | [1–459] |
| 15218 | [1–460] | 15281 | [1–460] |
| 15219 | [1–519] | 15282 | [1–506] |
| 15220 | [1–337] | 15283 | [1–641] |
| 15221 | [1–122] | 15284 | [1–295] |
| 15223 | [1–544] | 15286 | [1–292] |
| 15224 | [1–92], [137–494] | 15287 | [1–378] |
| 15225 | [1–59], [104–484] | 15289 | [1–377] |
| 15226 | [1–86] | 15290 | [1–533] |
| 15227 | [1–34] | 15291 | [59–348] |
| 15228 | [1–523] | 15292 | [1–230] |
| 15229 | [1–511] | 15294 | [1–142] |
| 15230 | [1–348] | 15295 | [1–73] |
| 15231 | [1–34] | 15296 | [59–203] |
| 15232 | [1–300] | 15297 | [1–31] |
| 15299 | [1–50], [80–491] | 15352 | [1–390] |
| 15300 | [1–416] | 15353 | [193–258] |
| 15301 | [1–412] | 15354 | [1–208], [322–350], [452–485] |
| 15302 | [1–53] | 15355 | [1–444] |
| 15303 | [1–784] | 15356 | [1–500] |
| 15304 | [1–488] | 15357 | [1–426] |
| 15305 | [1–130], [172–445] | 15358 | [1–415] |
| 15306 | [1–491] | 15359 | [1–413] |
| 15307 | [1–480] | 15360 | [1–416] |
| 15308 | [1–490] | 15361 | [1–412] |
| 15309 | [1–606] | 15362 | [1–416] |
| 15310 | [1–511] | 15363 | [1–433] |
| 15311 | [1–497] | 15364 | [1–414] |
| 15313 | [137–210] | 15365 | [1–454] |
| 15314 | [135–195] | 15366 | [1–425] |
| 15315 | [1–490] | 15367 | [1–413] |
| 15316 | [136–168] | 15368 | [1–442] |
| 15317 | [136–194] | 15369 | [1–549] |
| 15318 | [138–166] | 15371 | [1–501] |
| 15319 | [136–173] | 15372 | [1–495] |
| 15320 | [136–180] | 15374 | [1–420] |
| 15322 | [136–178] | 15375 | [1–526] |
| 15323 | [137–179] | 15376 | [1–496] |
| 15324 | [1–450] | 15377 | [1–569] |
| 15325 | [1–573] | 15379 | [1–125] |
| 15326 | [1–381] | 15380 | [1–506] |
| 15327 | [1–490] | 15383 | [1–39], [128–177], [270–491] |
| 15329 | [1–315] | 15390 | [1–417] |
| 15331 | [1–167] | 15391 | [1–442] |
| 15332 | [1–443] | 15392 | [1–128] |
| 15333 | [91–268], [417–454] | 15394 | [1–162], [420–444] |
| 15334 | [1–457] | 15395 | [1–482] |
| 15335 | [1–278] | 15396 | [1–472] |
| 15336 | [1–94], [140–361] | 15397 | [1–490] |
| 15337 | [70–186] | 15398 | [1–237], [266–431] |
| 15338 | [1–489] | 15399 | [1–486] |
| 15340 | [1–522] | 15400 | [1–575] |
| 15341 | [1–197] | 15401 | [1–490] |
| 15342 | [1–350] | 15402 | [1–483] |
| 15343 | [1–121] | 15403 | [1–486] |
| 15345 | [1–482] | 15404 | [1–49], [166–275] |
| 15346 | [1–499] | 15405 | [1–50] |
| 15347 | [1–447] | 15406 | [1–48] |
| 15348 | [1–395] | 15407 | [1–295] |
| 15349 | [93–263] | 15410 | [102–506] |
| 15350 | [1–392] | 15411 | [1–57] |
| 15351 | [1–517] | 15412 | [95–153] |
| 15414 | [1–445] | 15469 | [1–209] |
| 15415 | [1–362] | 15470 | [1–208] |
| 15416 | [173–221] | 15471 | [1–376] |
| 15417 | [102–201] | 15472 | [1–446] |
| 15418 | [1–472] | 15473 | [1–461] |
| 15419 | [54–83], [134–196], [248–414], [445–504] | 15474 | [1–466] |
| 15420 | [1–96] | 15475 | [1–283], [337–447] |
| 15421 | [1–515] | 15478 | [1–453] |
| 15422 | [1–416] | 15480 | [1–297] |
| 15423 | [1–60] | 15481 | [1–340] |
| 15425 | [1–490] | 15482 | [1–476] |
| 15426 | [1–801] | 15483 | [1–506] |
| 15427 | [1–216] | 15484 | [349–500] |
| 15428 | [1–495] | 15485 | [1–47], [172–257] |
| 15429 | [1–291] | 15486 | [1–185], [339–512] |
| 15431 | [1–69] | 15487 | [1–444] |
| 15432 | [43–314] | 15488 | [1–268] |
| 15433 | [1–488] | 15489 | [1–352] |
| 15434 | [1–212] | 15490 | [1–607] |
| 15435 | [1–410] | 15491 | [1–553] |
| 15436 | [1–179] | 15492 | [1–465] |
| 15439 | [78–164] | 15493 | [1–497] |
| 15442 | [1–297] | 15494 | [1–488] |
| 15443 | [1–200] | 15495 | [1–485] |
| 15445 | [1–568] | 15496 | [1–230] |
| 15446 | [1–477] | 15497 | [1–493] |
| 15447 | [1–148] | 15498 | [1–489] |
| 15448 | [1–205], [250–504] | 15499 | [1–477] |
| 15449 | [1–402] | 15502 | [1–367] |
| 15450 | [315–483] | 15503 | [1–516] |
| 15452 | [1–377] | 15504 | [161–208] |
| 15453 | [1–114] | 15506 | [217–321], [357–401] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 15454 | [1–411] | 15507 | [217–316] | 15657 | [1–467] | 15716 | [1–222] |
| 15455 | [1–153], [189–304], [370–540] | 15508 | [84–118], [163–229] | 15658 | [1–110] | 15717 | [1–409] |
| | | | | 15659 | [1–221] | 15719 | [1–277] |
| 15456 | [1–390] | 15509 | [1–26], [246–360] | 15661 | [1–308] | 15721 | [1–93], [126–420] |
| 15457 | [1–457] | 15510 | [1–25], [172–261] | 15664 | [178–210] | 15723 | [1–26], [181–287] |
| 15458 | [1–313] | 15514 | [1–44] | 15665 | [1–482] | 15724 | [1–36], [191–297] |
| 15459 | [1–492] | 15515 | [1–479] | 15666 | [1–26] | 15726 | [1–340] |
| 15460 | [1–410] | 15516 | [1–343] | 15667 | [1–324] | 15727 | [1–448] |
| 15461 | [1–378] | 15517 | [1–180] | 15668 | [1–374] | 15728 | [1–79] |
| 15462 | [1–468] | 15519 | [1–457] | 15669 | [1–234] | 15731 | [194–423] |
| 15463 | [1–517] | 15520 | [1–111] | 15670 | [1–464] | 15732 | [1–111], [152–246] |
| 15464 | [1–410] | 15521 | [1–442] | 15671 | [1–227] | 15734 | [191–476] |
| 15465 | [1–208] | 15522 | [1–415] | 15672 | [1–300] | 15735 | [1–26], [256–397] |
| 15466 | [1–114] | 15524 | [1–510] | 15673 | [94–560] | 15736 | [1–472] |
| 15467 | [1–209] | 15525 | [1–542] | 15674 | [1–493] | 15737 | [173–271] |
| 15468 | [1–208] | 15526 | [1–287] | 15675 | [1–244], [453–505] | 15739 | [1–423] |
| 15527 | [1–406] | 15578 | [1–821] | 15677 | [1–163] | 15741 | [173–259] |
| 15528 | [278–352] | 15580 | [1–488] | 15678 | [1–402] | 15742 | [1–323] |
| 15529 | [1–447] | 15531 | [1–389] | 15679 | [1–470] | 15743 | [1–370] |
| 15530 | [1–454] | 15583 | [1–519] | 15680 | [339–532] | 15744 | [1–380] |
| 15531 | [112–290] | 15584 | [1–331] | 15681 | [1–471] | 15745 | [1–58] |
| 15532 | [1–399] | 15586 | [1–561] | 15682 | [1–122] | 15746 | [1–64], [205–459] |
| 15533 | [1–272] | 15587 | [1–195] | 15683 | [1–239] | 15748 | [1–623] |
| 15535 | [278–352] | 15588 | [1–311] | 15684 | [1–475] | 15749 | [173–257] |
| 15536 | [1–585] | 15589 | [1–405] | 15685 | [1–428], [459–503] | 15760 | [173–273] |
| 15537 | [1–515] | 15590 | [1–513] | 15686 | [1–419] | 15768 | [1–98] |
| 15538 | [1–50] | 15591 | [1–569] | 15687 | [1–428] | 15791 | [1–483] |
| 15539 | [1–424] | 15592 | [1–368] | 15688 | [1–438] | 15801 | [1–101] |
| 15540 | [1–499] | 15593 | [82–393] | 15691 | [1–497] | 15802 | [1–541] |
| 15541 | [1–72] | 15595 | [1–436] | 15692 | [1–29], [294–386] | 15823 | [1–199] |
| 15542 | [1–188] | 15596 | [1–443] | 15693 | [1–587] | 15844 | [1–448] |
| 15543 | [1–184] | 15597 | [1–504] | 15694 | [1–201] | 15846 | [1–67] |
| 15544 | [1–499] | 15598 | [1–410] | 15695 | [1–296] | 15855 | [1–109] |
| 15545 | [1–476] | 15599 | [1–362] | 15696 | [1–525] | 15921 | [1–53] |
| 15546 | [1–353] | 15603 | [1–544] | 15697 | [1–466] | 15940 | [40–103] |
| 15547 | [1–501] | 15604 | [94–150] | 15698 | [1–250] | 15956 | [1–72] |
| 15548 | [1–490] | 15605 | [87–150] | 15699 | [1–464] | 15968 | [81–108] |
| 15549 | [1–469] | 15606 | [1–487] | 15977 | [1–443] | 16037 | [1–279] |
| 15550 | [1–508] | 15607 | [1–406] | 15990 | [50–439] | 16038 | [1–335] |
| 15551 | [1–231] | 15608 | [1–500] | 15991 | [46–220] | 16039 | [1–276] |
| 15552 | [1–456] | 15609 | [1–251] | 15992 | [1–151] | 16040 | [1–318] |
| 15553 | [1–162] | 15611 | [39–172], [276–317] | 15993 | [1–203] | 16041 | [1–338] |
| 15554 | [1–242] | 15612 | [1–481] | 15994 | [1–151] | 16042 | [1–365] |
| 15555 | [1–406] | 15613 | [1–220] | 15995 | [1–151] | 16043 | [1–280] |
| 15556 | [1–250], [348–418] | 15614 | [1–113], [235–485] | 15996 | [1–446] | 16044 | [1–334] |
| 15557 | [1–583] | 15615 | [1–450] | 15997 | [1–151] | 16045 | [1–333] |
| 15560 | [153–501] | 15617 | [74–372] | 15998 | [1–150] | 16046 | [1–280] |
| 15561 | [1–420] | 15618 | [1–456] | 15999 | [1–151] | 16047 | [1–175] |
| 15562 | [1–387] | 15619 | [1–597] | 16000 | [1–153] | 16048 | [1–371] |
| 15563 | [1–476] | 15620 | [1–162] | 16001 | [1–151] | 16049 | [1–296] |
| 15564 | [1–408] | 15622 | [313–348] | 16003 | [1–424] | 16050 | [1–332] |
| 15565 | [1–281] | 15623 | [1–41] | 16004 | [1–498] | 16051 | [1–336] |
| 15566 | [1–96] | 15625 | [1–47] | 16005 | [1–151] | 16052 | [1–329] |
| 15567 | [1–476] | 15627 | [1–576] | 16006 | [30–125] | 16053 | [1–332] |
| 15568 | [190–217] | 15628 | [54–476] | 16007 | [1–272] | 16054 | [1–281] |
| 15570 | [1–524] | 15629 | [1–381] | 16008 | [1–359] | 16055 | [1–319] |
| 15571 | [49–420] | 15630 | [49–324] | 16009 | [1–292] | 16056 | [1–320] |
| 15572 | [1–577] | 15631 | [1–503] | 16010 | [1–362] | 16057 | [1–306] |
| 15573 | [1–106], [441–580] | 15633 | [1–396] | 16011 | [1–281] | 16058 | [1–357] |
| 15574 | [1–484] | 15634 | [1–403] | 16012 | [1–329] | 16059 | [1–281] |
| 15575 | [1–433] | 15635 | [1–507] | 16013 | [1–336] | 16060 | [1–281] |
| 15576 | [1–43] | 15636 | [1–508] | 16014 | [1–306] | 16061 | [1–335] |
| 15577 | [1–504] | 15638 | [1–419] | 16015 | [1–339] | 16062 | [1–110] |
| 15639 | [1–505] | 15700 | [1–372] | 16016 | [1–282] | 16066 | [1–405] |
| 15641 | [1–510] | 15701 | [1–118] | 16017 | [1–302] | 16067 | [1–516] |
| 15643 | [1–418] | 15702 | [1–502] | 16018 | [1–327] | 16068 | [1–78] |
| 15645 | [1–322] | 15703 | [1–482] | 16019 | [1–359] | 16069 | [1–404] |
| 15646 | [1–316] | 15704 | [1–503] | 16020 | [1–305] | 16070 | [1–399] |
| 15647 | [1–525] | 15705 | [1–503] | 16021 | [1–296] | 16071 | [1–26], [194–482] |
| 15648 | [1–237] | 15706 | [1–401] | 16022 | [1–297] | 16073 | [1–75], [131–500] |
| 15649 | [1–72], [184–241], [283–353] | 15707 | [1–67], [109–211] | 16023 | [1–279] | 16075 | [1–470] |
| | | | | 16024 | [1–326] | 16076 | [1–219], [303–328] |
| 15650 | [1–526] | 15711 | [1–106] | 16025 | [1–102] | 16077 | [1–191] |
| 15651 | [1–43] | 15715 | [1–456] | 16026 | [1–347] | 16078 | [1–357] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 16027 | [1–324] | 16079 | [1–430] | 16224 | [1–585] | 16289 | [1–200] |
| 16028 | [1–315] | 16080 | [1–265] | 16225 | [1–112] | 16290 | [1–198] |
| 16029 | [1–282] | 16081 | [1–104], [375–415] | 16226 | [1–184], [220–299] | 16291 | [1–249] |
| 16030 | [1–307] | 16082 | [1–104], [375–415] | 16227 | [1–184], [220–300] | 16292 | [1–249] |
| 16031 | [1–332] | 16084 | [1–52] | 16228 | [1–409] | 16293 | [1–222] |
| 16032 | [1–333] | 16085 | [1–388] | 16229 | [1–416] | 16294 | [1–259] |
| 16033 | [1–297] | 16087 | [1–499] | 16230 | [1–516] | 16295 | [1–217] |
| 16034 | [1–281] | 16088 | [1–314] | 16231 | [1–483] | 16296 | [1–363] |
| 16035 | [1–306] | 16089 | [1–529] | 16232 | [1–385] | 16297 | [1–575] |
| 16036 | [1–526] | 16090 | [1–165] | 16233 | [1–56], [128–161] | 16298 | [1–319] |
| 16093 | [1–109] | 16147 | [1–410] | 16234 | [1–56], [108–182] | 16299 | [1–491] |
| 16094 | [1–572] | 16149 | [1–393] | 16236 | [1–598] | 16300 | [1–474] |
| 16096 | [258–288] | 16150 | [1–434] | 16237 | [1–249] | 16301 | [294–449] |
| 16098 | [1–556] | 16151 | [1–353] | 16238 | [1–124] | 16302 | [1–585] |
| 16099 | [257–304] | 16152 | [1–110] | 16239 | [1–87] | 16303 | [1–348] |
| 16100 | [257–331] | 16153 | [1–559] | 16240 | [1–122] | 16304 | [1–114] |
| 16102 | [1–104] | 16154 | [1–193] | 16241 | [1–317] | 16305 | [1–32], [211–300] |
| 16103 | [1–470] | 16155 | [1–498] | 16242 | [1–97] | 16306 | [1–34] |
| 16104 | [1–569] | 16156 | [1–72] | 16243 | [1–502] | 16307 | [1–275] |
| 16105 | [1–351] | 16157 | [1–512] | 16244 | [164–401] | 16308 | [193–457] |
| 16106 | [1–517] | 16158 | [1–476] | 16245 | [1–496] | 16309 | [1–55], [147–176] |
| 16108 | [1–272] | 16159 | [1–523] | 16246 | [1–337] | 16311 | [1–655] |
| 16109 | [1–255] | 16160 | [1–157] | 16248 | [1–57], [88–153] | 16314 | [1–415] |
| 16110 | [1–233] | 16161 | [1–201] | 16249 | [1–63] | 16317 | [161–231] |
| 16111 | [1–271] | 16162 | [1–202] | 16251 | [1–63] | 16320 | [162–242] |
| 16115 | [82–146] | 16163 | [1–201] | 16252 | [1–111] | 16324 | [161–242] |
| 16116 | [1–485] | 16164 | [1–201] | 16258 | [175–369] | 16327 | [1–141], [527–587] |
| 16117 | [1–528] | 16165 | [1–201] | 16260 | [1–56] | 16328 | [1–142], [528–559] |
| 16118 | [1–530] | 16166 | [1–200] | 16263 | [1–322] | 16329 | [1–489] |
| 16119 | [1–740] | 16167 | [1–202] | 16265 | [1–490] | 16331 | [1–29] |
| 16120 | [1–327] | 16168 | [1–527] | 16332 | [1–231], [290–504] | 16390 | [1–53], [325–440] |
| 16121 | [1–395] | 16170 | [1–409] | 16333 | [1–146] | 16391 | [1–456] |
| 16122 | [1–281] | 16171 | [1–36], [397–492] | 16334 | [1–487] | 16392 | [1–407] |
| 16123 | [1–45] | 16172 | [332–395] | 16335 | [1–204] | 16393 | [1–406] |
| 16124 | [1–120], [270–512] | 16173 | [1–479] | 16336 | [1–442] | 16394 | [1–376] |
| 16125 | [1–313] | 16178 | [1–531] | 16337 | [1–513] | 16395 | [1–449] |
| 16126 | [1–418] | 16180 | [1–404], [439–494] | 16338 | [1–205] | 16398 | [1–419] |
| 16127 | [1–151], [192–293] | 16181 | [1–196] | 16339 | [1–212] | 16399 | [116–508] |
| 16128 | [1–151], [192–326] | 16184 | [1–409] | 16340 | [1–241] | 16400 | [49–95], [132–433] |
| 16129 | [1–151], [192–319] | 16185 | [368–413] | 16341 | [1–216] | 16401 | [1–166], [365–848] |
| 16130 | [1–151], [188–301] | 16186 | [1–431] | 16342 | [1–210] | 16403 | [1–421] |
| 16131 | [1–151], [192–276] | 16188 | [308–405] | 16343 | [1–219] | 16404 | [60–496] |
| 16132 | [1–151], [192–306] | 16191 | [1–477] | 16344 | [1–229] | 16405 | [1–432] |
| 16133 | [1–151], [192–310] | 16192 | [1–488] | 16345 | [1–221] | 16407 | [1–180] |
| 16134 | [1–151], [192–310] | 16193 | [1–211] | 16346 | [1–239] | 16409 | [193–222] |
| 16135 | [1–151], [192–280] | 16194 | [1–112] | 16347 | [1–314] | 16410 | [1–569] |
| 16136 | [1–151], [192–347] | 16195 | [1–447] | 16348 | [1–499] | 16411 | [1–526] |
| 16137 | [1–151], [192–348] | 16196 | [1–493] | 16349 | [1–306] | 16412 | [1–372] |
| 16138 | [1–151], [192–351] | 16197 | [1–369] | 16350 | [1–447] | 16413 | [1–109] |
| 16139 | [1–151], [192–300] | 16198 | [1–441] | 16351 | [1–107], [230–304] | 16414 | [1–423] |
| 16140 | [1–151], [192–351] | 16199 | [1–478] | 16356 | [1–534] | 16415 | [1–402] |
| 16141 | [1–151], [192–273] | 16200 | [1–435] | 16358 | [1–473] | 16416 | [1–442] |
| 16142 | [1–274] | 16201 | [1–451] | 16359 | [1–494] | 16417 | [1–442] |
| 16143 | [1–151], [192–328] | 16202 | [1–492] | 16360 | [1–432] | 16418 | [1–395] |
| 16144 | [1–151], [192–328] | 16203 | [1–364] | 16361 | [1–281] | 16419 | [1–400] |
| 16145 | [1–151], [192–354] | 16204 | [1–146] | 16362 | [1–97] | 16420 | [1–403] |
| 16146 | [1–479] | 16205 | [1–467] | 16363 | [1–506] | 16421 | [1–371] |
| 16206 | [1–463] | 16266 | [1–353] | 16364 | [1–457] | 16422 | [1–392] |
| 16207 | [1–430] | 16267 | [1–461] | 16365 | [144–438] | 16423 | [1–464] |
| 16208 | [1–444] | 16268 | [196–451] | 16366 | [184–260] | 16424 | [1–413] |
| 16209 | [1–453] | 16269 | [1–430] | 16368 | [1–391] | 16425 | [1–193] |
| 16210 | [84–204] | 16273 | [1–450] | 16369 | [116–205] | 16426 | [1–317] |
| 16211 | [1–393] | 16274 | [1–337] | 16370 | [219–478] | 16427 | [183–504] |
| 16212 | [1–343] | 16277 | [1–263], [296–339] | 16371 | [1–406] | 16428 | [1–317] |
| 16213 | [1–404] | 16278 | [1–454] | 16373 | [1–515] | 16429 | [1–295] |
| 16214 | [1–478] | 16279 | [1–459] | 16374 | [1–495] | 16430 | [1–319] |
| 16215 | [1–478] | 16280 | [1–422] | 16375 | [1–436] | 16431 | [1–294] |
| 16216 | [1–363] | 16281 | [1–268] | 16376 | [1–441] | 16432 | [1–293] |
| 16217 | [1–322] | 16282 | [1–506] | 16380 | [1–400] | 16433 | [1–292] |
| 16218 | [1–359] | 16283 | [1–51] | 16381 | [1–167] | 16434 | [1–334] |
| 16219 | [1–348] | 16284 | [80–441] | 16382 | [1–82] | 16435 | [1–298] |
| 16220 | [1–536] | 16285 | [453–492] | 16383 | [1–497] | 16436 | [1–139] |
| 16221 | [1–291] | 16287 | [205–512] | 16385 | [1–41] | 16437 | [1–379] |
| 16222 | [1–493] | 16288 | [1–246] | 16386 | [466–490] | 16438 | [1–384] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 16387 | [1–391] | 16439 | [1–301], [330–505] | 16588 | [228–381] | 16639 | [1–367] |
| 16388 | [1–490] | 16440 | [1–374] | 16589 | [1–499] | 16640 | [1–180] |
| 16389 | [80–161] | 16441 | [1–474] | 16590 | [1–421] | 16642 | [1–464] |
| 16442 | [1–61] | 16502 | [1–429] | 16591 | [1–515] | 16643 | [1–67] |
| 16444 | [1–492] | 16503 | [1–61] | 16592 | [1–506] | 16644 | [1–348] |
| 16445 | [349–388] | 16504 | [1–305] | 16593 | [124–187] | 16645 | [1–414] |
| 16446 | [1–485] | 16505 | [1–439] | 16594 | [1–62] | 16646 | [1–293] |
| 16447 | [1–106], [203–240] | 16506 | [267–436] | 16595 | [1–510] | 16647 | [1–29] |
| 16448 | [1–489] | 16507 | [1–555] | 16596 | [1–422] | 16648 | [1–466] |
| 16449 | [1–122] | 16508 | [1–477] | 16597 | [1–574] | 16649 | [1–359] |
| 16450 | [47–71], [122–274] | 16509 | [1–362] | 16598 | [1–355] | 16650 | [1–381] |
| 16459 | [1–166], [251–374] | 16510 | [1–169] | 16599 | [1–404] | 16651 | [1–516] |
| 16460 | [1–198], [332–384] | 16511 | [58–509] | 16602 | [1–275] | 16652 | [1–436] |
| 16461 | [1–270], [390–467] | 16514 | [1–193] | 16603 | [1–343] | 16653 | [1–518] |
| 16462 | [1–495] | 16515 | [1–198] | 16604 | [1–468] | 16655 | [1–367] |
| 16464 | [1–473] | 16516 | [1–197] | 16605 | [1–72] | 16656 | [1–430] |
| 16465 | [1–441] | 16517 | [1–403] | 16606 | [1–399] | 16657 | [1–405], [805–837] |
| 16466 | [1–489] | 16519 | [1–382] | 16607 | [1–352] | 16659 | [1–457] |
| 16468 | [49–131] | 16520 | [1–465] | 16608 | [1–348] | 16660 | [1–188] |
| 16470 | [1–392] | 16521 | [197–287] | 16609 | [1–377] | 16661 | [1–475] |
| 16472 | [1–113] | 16522 | [47–76] | 16610 | [1–224] | 16662 | [1–250] |
| 16473 | [1–462] | 16524 | [1–110] | 16611 | [1–276] | 16663 | [1–187] |
| 16474 | [1–252] | 16525 | [1–413] | 16612 | [1–440] | 16664 | [1–130] |
| 16475 | [226–448] | 16526 | [1–358] | 16665 | [1–347] | 16725 | [1–373] |
| 16476 | [1–82] | 16528 | [1–59], [250–439] | 16666 | [1–488] | 16726 | [1–481] |
| 16477 | [1–98], [129–162] | 16529 | [1–430] | 16667 | [1–528] | 16727 | [1–339] |
| 16478 | [1–119] | 16530 | [1–59], [250–470] | 16668 | [1–472] | 16728 | [1–492] |
| 16479 | [1–95] | 16531 | [1–59], [250–466] | 16669 | [1–435] | 16729 | [1–37], [291–381] |
| 16480 | [1–104] | 16533 | [1–422] | 16672 | [455–479] | 16731 | [1–46] |
| 16481 | [1–134] | 16534 | [1–159] | 16674 | [1–527] | 16732 | [1–48] |
| 16482 | [1–93] | 16535 | [1–193] | 16675 | [1–395] | 16733 | [1–166], [202–316] |
| 16483 | [1–94], [125–154] | 16536 | [1–213] | 16676 | [1–398], [440–609] | 16734 | [1–110] |
| 16484 | [1–441] | 16537 | [1–194] | 16677 | [1–387] | 16736 | [1–298] |
| 16485 | [1–108] | 16538 | [1–185] | 16678 | [1–394] | 16737 | [1–527] |
| 16486 | [1–94], [125–154] | 16539 | [1–187] | 16679 | [1–216] | 16738 | [103–128] |
| 16487 | [1–92] | 16540 | [1–190] | 16680 | [1–113] | 16740 | [119–146] |
| 16488 | [1–568] | 16541 | [1–165] | 16681 | [1–531] | 16741 | [1–292] |
| 16489 | [1–297] | 16542 | [1–188] | 16682 | [1–571] | 16742 | [1–565] |
| 16490 | [1–419] | 16543 | [1–168] | 16685 | [85–112] | 16744 | [1–432] |
| 16491 | [1–297] | 16544 | [1–410] | 16686 | [85–146] | 16745 | [1–536] |
| 16492 | [1–298] | 16545 | [1–173] | 16688 | [85–145] | 16746 | [1–157] |
| 16493 | [1–189] | 16546 | [1–191] | 16689 | [85–120] | 16747 | [1–461] |
| 16494 | [1–296] | 16547 | [1–168] | 16690 | [86–118] | 16748 | [1–474] |
| 16495 | [1–297] | 16548 | [1–170] | 16691 | [85–145] | 16749 | [1–503] |
| 16496 | [1–298] | 16549 | [1–442] | 16692 | [85–164] | 16750 | [1–530] |
| 16497 | [1–513] | 16550 | [1–96], [179–235] | 16694 | [85–111] | 16751 | [446–625], [753–794] |
| 16498 | [1–513] | 16551 | [1–96] | 16695 | [85–146] | 16753 | [1–260] |
| 16499 | [1–503] | 16552 | [1–95] | 16696 | [86–127] | 16754 | [1–137], [359–488] |
| 16500 | [1–503] | 16553 | [1–95] | 16698 | [1–472] | 16755 | [49–431] |
| 16501 | [1–503] | 16554 | [1–44], [189–539] | 16699 | [357–498] | 16757 | [1–248] |
| 16555 | [1–96] | 16613 | [1–467] | 16700 | [1–513] | 16759 | [102–180] |
| 16556 | [1–95], [178–231] | 16614 | [466–523] | 16701 | [1–155] | 16760 | [1–112], [154–191] |
| 16557 | [1–96], [179–234] | 16615 | [1–55], [410–439] | 16702 | [1–498] | 16761 | [1–525] |
| 16558 | [1–95] | 16616 | [1–434] | 16703 | [1–39], [84–241] | 16762 | [1–514] |
| 16559 | [1–95], [178–233] | 16617 | [1–298] | 16704 | [1–481] | 16763 | [1–474] |
| 16560 | [1–472] | 16618 | [1–469] | 16706 | [379–408] | 16764 | [1–247], [325–498] |
| 16561 | [1–903] | 16619 | [1–111] | 16707 | [1–48] | 16770 | [1–358] |
| 16562 | [41–436] | 16620 | [1–116] | 16710 | [377–413] | 16771 | [1–412] |
| 16563 | [37–75] | 16621 | [1–96] | 16711 | [377–430] | 16772 | [1–542] |
| 16564 | [1–79] | 16622 | [248–431] | 16712 | [379–425] | 16774 | [1–256] |
| 16565 | [1–222] | 16623 | [1–60] | 16714 | [378–407] | 16775 | [1–115], [184–237] |
| 16567 | [1–112] | 16624 | [1–458] | 16715 | [1–443] | 16776 | [1–33] |
| 16569 | [1–161] | 16625 | [1–488] | 16716 | [155–260] | 16777 | [1–114], [183–253] |
| 16570 | [1–186] | 16626 | [1–90], [178–225] | 16717 | [146–176] | 16778 | [1–30], [109–135] |
| 16571 | [134–333], [393–445] | 16628 | [81–334] | 16718 | [1–527] | 16779 | [1–30], [110–185] |
| 16572 | [1–461] | 16629 | [209–325] | 16719 | [94–303] | 16780 | [1–30], [109–134] |
| 16573 | [178–222] | 16630 | [1–381] | 16720 | [1–488] | 16781 | [1–30], [109–157] |
| 16574 | [1–410] | 16631 | [1–340] | 16722 | [1–36], [98–214] | 16782 | [1–129] |
| 16575 | [1–471] | 16632 | [192–239] | 16723 | [1–485] | 16783 | [1–30], [109–140] |
| 16581 | [1–256], [295–356] | 16633 | [1–99], [164–194] | 16724 | [1–458] | 16784 | [1–30], [109–190] |
| 16582 | [1–382] | 16634 | [1–182] | 16785 | [1–30], [109–139] | 16840 | [1–515] |
| 16584 | [1–110] | 16635 | [1–399] | 16786 | [1–30], [109–140] | 16841 | [1–343] |
| 16585 | [1–447] | 16636 | [1–109] | 16787 | [1–26] | 16842 | [1–460] |
| 16586 | [57–157] | 16637 | [1–443] | 16788 | [1–26] | 16843 | [1–109] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 16789 | [1–111] | 16844 | [1–262] | 16954 | [215–253] | 17076 | [1–487] |
| 16790 | [106–480] | 16845 | [1–501] | 16958 | [216–242] | 17077 | [215–253] |
| 16792 | [1–52] | 16846 | [1–471] | 16965 | [208–293] | 17084 | [1–418] |
| 16794 | [1–482] | 16848 | [1–432] | 16972 | [216–243] | 17085 | [1–249] |
| 16795 | [1–429] | 16849 | [1–495] | 16973 | [215–241] | 17086 | [1–513] |
| 16796 | [1–44] | 16851 | [1–843] | 16974 | [215–244] | 17088 | [1–308] |
| 16797 | [1–51] | 16852 | [1–449] | 16975 | [216–243] | 17089 | [1–487] |
| 16798 | [1–108] | 16855 | [1–181], [234–517] | 16978 | [215–253] | 17090 | [1–370] |
| 16799 | [1–176] | 16856 | [1–275] | 16981 | [215–242] | 17091 | [1–30] |
| 16800 | [1–134] | 16857 | [1–66], [211–478] | 16983 | [213–277] | 17093 | [1–508] |
| 16801 | [1–175] | 16859 | [1–436] | 16986 | [216–242] | 17094 | [1–54] |
| 16802 | [1–175] | 16860 | [1–419] | 16987 | [215–253] | 17095 | [185–235] |
| 16803 | [1–174] | 16861 | [287–445] | 16988 | [213–256] | 17096 | [185–261] |
| 16804 | [1–175] | 16862 | [182–236] | 16989 | [215–283] | 17098 | [1–72] |
| 16805 | [1–214] | 16863 | [1–430] | 16990 | [216–241] | 17099 | [1–449] |
| 16806 | [1–241] | 16864 | [1–57], [329–436] | 16991 | [215–254] | 17100 | [1–710] |
| 16807 | [1–175] | 16865 | [1–400] | 17101 | [1–482] | 17158 | [1–478], [534–576] |
| 16808 | [1–207], [241–447] | 16866 | [1–302] | 17103 | [1–434] | 17159 | [72–441] |
| 16811 | [1–528] | 16868 | [1–122] | 17104 | [1–442] | 17160 | [75–502] |
| 16812 | [1–190] | 16869 | [1–156] | 17106 | [1–92] | 17162 | [1–416] |
| 16813 | [1–266] | 16870 | [1–168] | 17107 | [1–246], [326–477] | 17163 | [1–520] |
| 16814 | [1–214] | 16871 | [1–182] | 17108 | [1–411] | 17165 | [1–59] |
| 16815 | [1–55], [196–574] | 16872 | [1–179] | 17109 | [1–332] | 17168 | [1–473] |
| 16816 | [1–34], [351–506] | 16873 | [1–233] | 17110 | [1–139] | 17169 | [1–396] |
| 16817 | [1–455] | 16874 | [1–461] | 17112 | [1–184] | 17170 | [1–506] |
| 16820 | [1–524] | 16878 | [1–583] | 17113 | [1–510] | 17171 | [1–564] |
| 16821 | [1–559] | 16879 | [1–209] | 17116 | [1–136] | 17172 | [1–431] |
| 16822 | [1–504] | 16880 | [1–25] | 17117 | [1–91] | 17173 | [1–407] |
| 16823 | [310–498] | 16881 | [1–602] | 17118 | [1–59] | 17174 | [1–347] |
| 16824 | [1–35], [207–238] | 16882 | [1–424] | 17119 | [1–426] | 17175 | [223–477] |
| 16825 | [1–307] | 16883 | [1–313] | 17120 | [1–374] | 17176 | [1–853] |
| 16826 | [1–296], [351–448] | 16885 | [1–514] | 17121 | [1–255], [370–471] | 17177 | [41–68] |
| 16827 | [1–319] | 16886 | [1–268], [439–470] | 17122 | [1–452] | 17179 | [1–571] |
| 16828 | [325–499] | 16887 | [1–566] | 17124 | [1–426] | 17180 | [1–165] |
| 16829 | [1–476] | 16890 | [381–431] | 17125 | [1–562] | 17181 | [1–433] |
| 16831 | [1–310] | 16891 | [1–69] | 17126 | [120–173] | 17182 | [1–159] |
| 16832 | [1–349] | 16894 | [1–513] | 17127 | [1–505] | 17183 | [1–109] |
| 16833 | [1–140] | 16895 | [43–496] | 17128 | [1–379] | 17184 | [1–137] |
| 16834 | [1–141] | 16896 | [1–370] | 17129 | [1–415] | 17185 | [1–110] |
| 16835 | [1–291] | 16898 | [63–120], [203–540] | 17130 | [1–547] | 17186 | [1–354] |
| 16836 | [1–267] | 16899 | [33–337], [368–473] | 17133 | [1–371] | 17187 | [1–339] |
| 16837 | [1–459] | 16900 | [1–681] | 17134 | [1–510] | 17188 | [1–323] |
| 16839 | [1–526] | 16901 | [1–368] | 17135 | [1–476] | 17189 | [1–491] |
| 16902 | [1–50], [89–576] | 16993 | [216–242] | 17136 | [1–474] | 17190 | [278–375] |
| 16903 | [1–366] | 16997 | [216–242] | 17137 | [1–447] | 17191 | [1–450] |
| 16904 | [1–73] | 17000 | [70–372] | 17138 | [1–346] | 17192 | [1–460], [492–527] |
| 16905 | [1–527] | 17005 | [216–241] | 17139 | [1–503] | 17193 | [1–443] |
| 16906 | [1–431] | 17008 | [216–243] | 17140 | [1–374] | 17194 | [1–519] |
| 16907 | [1–451] | 17010 | [213–241] | 17142 | [1–30] | 17195 | [1–261] |
| 16908 | [1–449] | 17011 | [93–474] | 17143 | [1–169] | 17196 | [1–348] |
| 16909 | [1–349] | 17015 | [216–242] | 17144 | [1–101] | 17197 | [1–565] |
| 16910 | [1–40] | 17016 | [215–240] | 17145 | [1–144] | 17199 | [1–430] |
| 16911 | [1–435] | 17019 | [215–254] | 17146 | [1–149] | 17201 | [1–401] |
| 16912 | [1–98], [141–472] | 17022 | [215–253] | 17147 | [1–147] | 17202 | [1–364] |
| 16913 | [1–96], [139–439] | 17030 | [216–242] | 17148 | [1–144] | 17203 | [1–414] |
| 16914 | [1–449] | 17032 | [1–491} | 17149 | [1–146] | 17204 | [1–398] |
| 16915 | [1–510] | 17033 | [215–254] | 17150 | [1–505] | 17205 | [1–78], [235–369] |
| 16916 | [1–193] | 17039 | [216–247] | 17151 | [1–149] | 17206 | [1–225], [258–465] |
| 16917 | [106–503] | 17042 | [216–242] | 17152 | [1–26] | 17207 | [1–580] |
| 16918 | [1–445] | 17043 | [1–75], [158–487] | 17154 | [1–498] | 17208 | [1–450] |
| 16919 | [1–505] | 17046 | [216–242] | 17155 | [1–449] | 17209 | [1–510] |
| 16921 | [1–491] | 17047 | [215–241] | 17156 | [1–43] | 17210 | [1–478] |
| 16922 | [1–526] | 17048 | [214–253] | 17157 | [1–515] | 17211 | [1–54] |
| 16923 | [1–531] | 17049 | [215–270] | 17212 | [103–447] | 17278 | [1–486] |
| 16924 | [1–154] | 17053 | [216–245] | 17213 | [1–373] | 17279 | [1–421] |
| 16932 | [215–272] | 17054 | [1–500] | 17214 | [1–423] | 17280 | [1–524] |
| 16933 | [214–266] | 17056 | [215–253] | 17215 | [1–129], [251–404] | 17281 | [1–448] |
| 16936 | [213–269] | 17063 | [215–253] | 17216 | [1–246], [389–439] | 17283 | [68–111] |
| 16940 | [1–51] | 17064 | [217–256] | 17217 | [1–38], [264–432] | 17284 | [1–499] |
| 16942 | [216–243] | 17066 | [216–242] | 17219 | [1–400] | 17285 | [62–512] |
| 16946 | [215–253] | 17067 | [217–261] | 17220 | [1–136] | 17286 | [1–53] |
| 16947 | [1–528] | 17071 | [217–241] | 17221 | [1–112], [173–565] | 17287 | [1–246], [298–369] |
| 16950 | [215–250] | 17073 | [216–242] | 17222 | [1–112], [173–571] | 17288 | [1–510] |
| 16952 | [216–242] | 17074 | [215–253] | 17223 | [1–94], [154–362] | 17289 | [1–460] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 17225 | [1–285] | 17290 | [1–559] | 17366 | [1–87] | 17425 | [507–578] |
| 17226 | [1–462] | 17291 | [1–450] | 17367 | [1–76], [105–287], [331–437] | 17429 | [1–249] |
| 17227 | [1–126] | 17292 | [1–415] | 17368 | [1–460] | 17431 | [89–391] |
| 17228 | [1–377] | 17293 | [1–471] | 17370 | [1–443] | 17432 | [1–427] |
| 17229 | [318–382] | 17294 | [1–403] | 17371 | [162–250] | 17433 | [1–391] |
| 17232 | [1–391] | 17295 | [1–217] | 17372 | [1–50] | 17435 | [1–448] |
| 17233 | [1–387] | 17296 | [1–344] | 17373 | [1–502] | 17436 | [1–128], [239–353] |
| 17236 | [1–76] | 17297 | [1–330] | 17375 | [1–501] | 17437 | [1–81] |
| 17239 | [1–276] | 17298 | [1–488] | 17376 | [1–52], [407–434] | 17438 | [1–507] |
| 17240 | [1–324] | 17299 | [1–438] | 17377 | [1–441] | 17439 | [1–43], [212–447] |
| 17241 | [103–229], [272–455], [493–523] | 17301 | [61–93] | 17378 | [1–208], [420–504] | 17440 | [1–383] |
| 17242 | [1–329] | 17302 | [1–209] | 17379 | [1–111] | 17441 | [193–404] |
| 17243 | [1–510] | 17303 | [1–235] | 17382 | [1–148], [440–488] | 17442 | [1–131] |
| 17244 | [1–468] | 17304 | [1–348] | 17383 | [1–317] | 17443 | [1–349] |
| 17246 | [1–198], [236–318] | 17305 | [1–456] | 17384 | [1–316] | 17444 | [1–118] |
| 17247 | [261–311] | 17306 | [1–442] | 17445 | [1–471] | 17497 | [1–281] |
| 17248 | [1–199] | 17307 | [129–223] | 17446 | [1–141] | 17498 | [1–521] |
| 17249 | [254–457] | 17308 | [1–137] | 17447 | [1–148] | 17499 | [1–403] |
| 17251 | [1–37], [68–274] | 17309 | [51–149] | 17448 | [1–159] | 17502 | [67–137] |
| 17253 | [1–560] | 17313 | [101–181] | 17449 | [1–140] | 17503 | [67–126] |
| 17254 | [1–433] | 17314 | [1–471] | 17450 | [1–148] | 17504 | [1–492] |
| 17256 | [1–26], [143–722] | 17315 | [188–412] | 17451 | [1–153] | 17506 | [1–92] |
| 17257 | [379–447] | 17316 | [1–520] | 17452 | [1–144] | 17507 | [1–530] |
| 17260 | [1–480] | 17318 | [1–84] | 17453 | [1–131] | 17508 | [1–47], [402–446] |
| 17262 | [1–536] | 17319 | [1–173], [203–526] | 17454 | [1–129] | 17509 | [1–514] |
| 17263 | [1–466] | 17320 | [1–250] | 17455 | [1–130] | 17510 | [1–120] |
| 17265 | [1–489] | 17321 | [90–490] | 17456 | [1–346] | 17511 | [1–522] |
| 17266 | [1–472] | 17322 | [90–222] | 17457 | [1–140] | 17512 | [1–546] |
| 17267 | [1–334], [366–544] | 17323 | [1–425] | 17458 | [1–596] | 17513 | [181–483] |
| 17268 | [1–25], [84–199], [237–287], [415–443], [478–555] | 17324 | [1–498] | 17459 | [1–478] | 17515 | [144–490] |
| 17269 | [1–25], [84–394], [434–586] | 17325 | [1–517] | 17460 | [1–434] | 17516 | [1–444] |
| | | 17326 | [1–396] | 17461 | [1–454] | 17517 | [1–492] |
| 17272 | [173–264] | 17327 | [1–542] | 17462 | [1–364] | 17518 | [1–578] |
| 17274 | [1–321] | 17328 | [1–77], [111–207], [247–441] | 17463 | [1–477] | 17519 | [1–512] |
| | | | | 17464 | [1–874] | 17520 | [1–104] |
| 17275 | [1–473] | 17329 | [1–541] | 17465 | [80–147], [323–424] | 17521 | [1–567] |
| 17277 | [1–28] | 17330 | [1–334], [1375–1425] | 17467 | [144–176] | 17522 | [1–561] |
| | | | | 17468 | [1–521] | 17524 | [109–160] |
| | | | | 17469 | [1–29] | 17525 | [1–580] |
| | | | | 17470 | [1–73] | 17526 | [1–514] |
| 17331 | [1–346] | 17385 | [52–149] | 17472 | [1–113] | 17527 | [1–487] |
| 17332 | [1–492] | 17386 | [80–355], [400–481] | 17474 | [1–440] | 17528 | [1–209] |
| 17333 | [1–447] | 17388 | [1–318] | 17475 | [1–339], [368–460] | 17530 | [1–425] |
| 17334 | [1–499] | 17389 | [1–304] | 17476 | [1–318] | 17532 | [1–236] |
| 17335 | [1–437] | 17390 | [1–232] | 17477 | [1–67] | 17533 | [1–349] |
| 17336 | [1–275], [304–411] | 17391 | [1–28] | 17478 | [1–55] | 17534 | [1–485] |
| 17337 | [1–447] | 17392 | [1–27] | 17479 | [1–135], [333–536] | 17535 | [1–243] |
| 17338 | [1–169] | 17394 | [1–579] | 17480 | [1–132], [278–416] | 17536 | [1–352] |
| 17339 | [1–354], [384–481] | 17395 | [1–48] | 17481 | [461–523] | 17539 | [1–544] |
| 17340 | [1–536] | 17396 | [113–464] | 17483 | [1–33] | 17540 | [1–394] |
| 17343 | [1–301] | 17398 | [1–457] | 17484 | [1–491] | 17542 | [1–97], [172–481] |
| 17344 | [1–249] | 17399 | [157–532] | 17485 | [1–470] | 17543 | [1–400] |
| 17345 | [1–341] | 17400 | [1–493] | 17486 | [1–490] | 17544 | [1–468] |
| 17346 | [1–417] | 17401 | [1–35], [64–560] | 17487 | [1–415] | 17546 | [1–502] |
| 17347 | [1–347] | 17402 | [1–33], [213–620] | 17488 | [1–508], [538–612] | 17547 | [1–293] |
| 17348 | [1–116], [224–251], [427–672] | 17403 | [1–412] | 17489 | [1–432] | 17548 | [412–437] |
| | | | | 17491 | [1–362] | 17549 | [37–405] |
| | | | | 17492 | [1–250] | 17550 | [1–460] |
| 17349 | [1–333], [447–543] | 17407 | [1–26] | 17493 | [1–115], [144–382] | 17551 | [1–393] |
| 17350 | [233–257] | 17408 | [1–375] | 17494 | [1–467] | 17553 | [1–432] |
| 17352 | [1–476] | 17410 | [1–321] | 17495 | [1–407] | 17555 | [1–378] |
| 17353 | [313–414] | 17411 | [1–398] | 17496 | [1–483] | 17558 | [1–126], [316–369] |
| 17354 | [1–502] | 17412 | [1–240] | 17559 | [1–250] | 17619 | [1–192] |
| 17355 | [1–402] | 17413 | [1–223] | 17560 | [1–822] | 17620 | [1–462] |
| 17356 | [142–507] | 17414 | [1–225] | 17561 | [1–424] | 17621 | [1–597] |
| 17357 | [1–291] | 17415 | [1–228] | 17562 | [1–433] | 17622 | [1–33] |
| 17358 | [1–503] | 17416 | [1–225] | 17563 | [1–40], [82–260] | 17624 | [1–81], [219–243] |
| 17359 | [1–482] | 17417 | [1–225] | 17564 | [1–435] | 17625 | [1–81] |
| 17360 | [1–94], [126–483] | 17418 | [1–224] | 17565 | [1–284] | 17626 | [1–81], [219–279] |
| 17361 | [1–468] | 17419 | [1–225] | 17566 | [1–224], [321–390] | 17627 | [1–367] |
| 17362 | [1–136] | 17420 | [1–225] | 17567 | [1–325] | 17629 | [1–388] |
| 17363 | [1–535] | 17421 | [1–225] | 17568 | [1–442] | 17630 | [1–381] |
| 17364 | [1–416] | 17422 | [1–225] | 17569 | [1–111], [141–247] | 17631 | [1–443] |
| 17365 | [1–472] | 17423 | [1–224] | | | | |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 17571 | [1–283] | 17632 | [1–145] | 17723 | [1–35] | 17783 | [1–469] |
| 17572 | [1–213] | 17633 | [65–510] | 17725 | [1–497] | 17784 | [1–146] |
| 17573 | [1–70] | 17634 | [1–471] | 17726 | [1–60] | 17785 | [1–481] |
| 17574 | [1–1157] | 17635 | [1–226] | 17727 | [1–406] | 17787 | [1–483] |
| 17576 | [1–421] | 17636 | [162–461] | 17731 | [1–438] | 17788 | [1–433] |
| 17577 | [1–554] | 17637 | [1–340] | 17732 | [1–33] | 17789 | [282–343] |
| 17578 | [130–183] | 17638 | [215–518] | 17734 | [1–486] | 17791 | [73–501] |
| 17579 | [105–253] | 17639 | [1–534] | 17735 | [1–499] | 17792 | [177–383] |
| 17581 | [1–556] | 17640 | [1–667] | 17736 | [1–68] | 17793 | [86–517] |
| 17582 | [1–146], [176–224] | 17641 | [284–351] | 17794 | [1–253] | 17845 | [1–257] |
| 17586 | [1–379] | 17642 | [1–459] | 17795 | [1–419] | 17847 | [202–343] |
| 17587 | [1–472] | 17643 | [1–515] | 17796 | [1–364] | 17848 | [1–86] |
| 17588 | [1–480] | 17645 | [1–64] | 17797 | [32–504] | 17850 | [1–347] |
| 17589 | [1–194] | 17646 | [1–537] | 17798 | [1–50] | 17851 | [1–355] |
| 17590 | [1–364] | 17647 | [1–501] | 17799 | [1–525] | 17853 | [1–562] |
| 17592 | [1–475] | 17648 | [1–159] | 17800 | [1–448] | 17854 | [1–711] |
| 17593 | [341–472] | 17649 | [1–140] | 17801 | [1–506] | 17855 | [1–182] |
| 17594 | [80–116], [287–344] | 17650 | [1–593] | 17802 | [1–459] | 17856 | [399–436] |
| 17595 | [1–503] | 17651 | [1–604] | 17803 | [1–413] | 17857 | [1–405] |
| 17597 | [1–412] | 17652 | [1–333] | 17804 | [1–477] | 17859 | [1–397] |
| 17598 | [1–385] | 17653 | [1–98] | 17805 | [1–426] | 17860 | [1–307] |
| 17599 | [1–639] | 17654 | [1–322] | 17806 | [1–365] | 17861 | [1–344] |
| 17600 | [1–487] | 17655 | [1–396] | 17807 | [1–314] | 17862 | [1–209] |
| 17601 | [1–41], [278–425] | 17656 | [1–487] | 17809 | [1–441] | 17863 | [1–127] |
| 17602 | [1–329] | 17657 | [100–170] | 17810 | [1–66], [297–374] | 17864 | [1–395] |
| 17604 | [1–352] | 17659 | [1–475] | 17811 | [318–435] | 17866 | [1–361] |
| 17605 | [65–435] | 17660 | [1–314] | 17812 | [1–203] | 17867 | [1–408] |
| 17606 | [1–504] | 17663 | [1–399] | 17813 | [1–434] | 17868 | [1–33] |
| 17608 | [223–261] | 17664 | [1–214], [245–404] | 17814 | [1–481] | 17871 | [1–283] |
| 17610 | [223–269] | 17665 | [1–200] | 17815 | [1–573] | 17872 | [1–275] |
| 17611 | [1–345] | 17666 | [1–509] | 17816 | [1–384] | 17873 | [1–470] |
| 17612 | [1–204] | 17667 | [1–483] | 17817 | [93–123] | 17874 | [1–379] |
| 17614 | [1–442] | 17668 | [1–227] | 17819 | [1–355] | 17875 | [1–357] |
| 17615 | [50–99] | 17669 | [1–255] | 17821 | [1–269] | 17876 | [1–442] |
| 17616 | [232–458] | 17670 | [1–286] | 17822 | [160–204] | 17877 | [1–201] |
| 17618 | [1–476] | 17671 | [1–493] | 17823 | [30–81] | 17878 | [1–512] |
| 17672 | [195–382] | 17737 | [1–382] | 17824 | [169–211] | 17879 | [1–420] |
| 17673 | [1–500] | 17738 | [1–512] | 17825 | [1–246] | 17880 | [1–114] |
| 17674 | [1–495] | 17739 | [1–516] | 17826 | [168–193] | 17881 | [1–504] |
| 17675 | [1–435] | 17740 | [1–491] | 17827 | [1–444] | 17882 | [1–636] |
| 17676 | [1–475] | 17741 | [1–362] | 17828 | [1–140], [178–248] | 17883 | [1–472] |
| 17681 | [64–497] | 17742 | [1–502] | 17829 | [1–464] | 17884 | [1–386] |
| 17682 | [64–510] | 17744 | [1–149] | 17831 | [1–388] | 17885 | [1–432] |
| 17683 | [1–160] | 17745 | [1–432] | 17832 | [1–396] | 17886 | [1–508] |
| 17684 | [1–139] | 17746 | [1–459] | 17833 | [211–279], [353–445] | 17888 | [317–429] |
| 17685 | [1–48] | 17747 | [1–97] | 17834 | [1–515] | 17889 | [1–478] |
| 17686 | [1–56] | 17748 | [1–401] | 17835 | [1–364] | 17890 | [1–462] |
| 17688 | [1–491] | 17749 | [1–30] | 17836 | [1–377] | 17891 | [1–183] |
| 17689 | [1–476] | 17750 | [1–206] | 17837 | [1–308] | 17892 | [1–55] |
| 17690 | [1–140], [172–439] | 17751 | [1–495] | 17838 | [1–451] | 17893 | [1–399] |
| 17691 | [1–104], [143–348] | 17753 | [1–163], [280–477] | 17839 | [1–179] | 17897 | [332–448] |
| 17692 | [1–447] | 17756 | [1–211], [332–380] | 17840 | [383–421] | 17898 | [1–484] |
| 17693 | [1–446] | 17757 | [1–286] | 17841 | [1–416] | 17899 | [1–501] |
| 17694 | [1–32] | 17758 | [1–216], [402–517] | 17842 | [1–428] | 17900 | [1–288] |
| 17695 | [1–428] | 17759 | [1–236] | 17843 | [1–186] | 17901 | [1–402] |
| 17696 | [1–59] | 17760 | [1–495] | 17844 | [1–432] | 17902 | [1–380] |
| 17697 | [1–249] | 17761 | [1–522] | 17903 | [1–483] | 17951 | [1–444] |
| 17698 | [1–245] | 17762 | [1–384] | 17904 | [1–258] | 17952 | [44–127], [156–489] |
| 17699 | [1–153] | 17763 | [1–490] | 17905 | [1–453] | 17953 | [1–495] |
| 17700 | [1–531] | 17765 | [1–123], [311–353] | 17906 | [1–435] | 17954 | [1–437] |
| 17701 | [1–203] | 17766 | [1–44], [232–274] | 17907 | [1–299] | 17956 | [1–219] |
| 17703 | [235–387] | 17767 | [1–298] | 17908 | [1–464] | 17957 | [90–487] |
| 17705 | [1–354], [390–474] | 17768 | [1–210] | 17909 | [1–295] | 17958 | [1–400] |
| 17706 | [1–143] | 17769 | [1–510] | 17910 | [1–447] | 17959 | [1–440] |
| 17707 | [1–536] | 17770 | [1–491] | 17912 | [1–500] | 17960 | [437–478] |
| 17708 | [1–449] | 17771 | [1–455] | 17913 | [1–117] | 17961 | [1–427] |
| 17709 | [1–404] | 17772 | [1–418] | 17914 | [1–107] | 17962 | [1–43] |
| 17711 | [1–489] | 17773 | [1–486] | 17915 | [1–481] | 17963 | [1–43], [108–364] |
| 17712 | [1–566] | 17775 | [1–79] | 17916 | [1–546] | 17964 | [1–43], [108–360] |
| 17713 | [1–220] | 17776 | [1–285] | 17917 | [1–512] | 17965 | [1–43], [108–378] |
| 17714 | [1–483] | 17777 | [1–44] | 17918 | [1–293] | 17966 | [1–43], [108–233] |
| 17717 | [1–32] | 17778 | [1–458] | 17919 | [1–207] | 17967 | [1–468] |
| 17719 | [1–33] | 17781 | [1–348] | 17920 | [1–215] | 17969 | [1–412] |
| 17720 | [1–93] | 17782 | [1–392] | 17921 | [1–246] | 17970 | [1–232] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 17922 | [1–218] | 17971 | [1–68] | 18054 | [1–179] | 18109 | [1–96] |
| 17923 | [1–266] | 17972 | [1–336] | 18055 | [1–74] | 18110 | [1–553] |
| 17924 | [1–241] | 17973 | [1–503] | 18111 | [1–482] | 18185 | [1–203] |
| 17925 | [1–262] | 17974 | [1–472] | 18112 | [1–106], [300–424] | 18189 | [1–249] |
| 17926 | [1–259] | 17975 | [1–324] | 18113 | [1–507] | 18190 | [1–492] |
| 17927 | [1–270] | 17976 | [1–480] | 18115 | [1–497] | 18191 | [1–493] |
| 17928 | [1–217] | 17977 | [1–435] | 18116 | [1–106] | 18192 | [1–296] |
| 17929 | [1–235] | 17978 | [1–387] | 18117 | [1–149] | 18193 | [1–495] |
| 17930 | [1–225] | 17979 | [1–508] | 18119 | [1–346] | 18194 | [1–420] |
| 17931 | [1–248] | 17980 | [1–510] | 18120 | [1–403] | 18195 | [1–266] |
| 17932 | [1–225] | 17981 | [1–464] | 18121 | [1–493] | 18196 | [508–537] |
| 17933 | [1–226] | 17982 | [1–36], [94–442] | 18122 | [1–62] | 18198 | [1–436] |
| 17934 | [1–218] | 17983 | [1–178] | 18123 | [1–101], [182–366] | 18199 | [142–243] |
| 17935 | [1–228] | 17984 | [1–532] | 18124 | [1–69] | 18210 | [1–487] |
| 17936 | [1–241] | 17985 | [1–156], [185–456] | 18125 | [1–372] | 18212 | [1–442] |
| 17937 | [1–242] | 17986 | [1–63] | 18127 | [1–142], [327–488] | 18213 | [1–263] |
| 17938 | [1–247] | 17987 | [1–138] | 18128 | [1–169], [252–292] | 18214 | [33–419] |
| 17939 | [1–243] | 17989 | [1–381] | 18129 | [1–486] | 18218 | [1–555] |
| 17940 | [1–243] | 17991 | [1–387] | 18130 | [1–192] | 18219 | [1–466] |
| 17941 | [1–237] | 17993 | [1–155], [184–439] | 18131 | [1–314] | 18221 | [1–254] |
| 17942 | [1–236] | 17995 | [1–461] | 18132 | [1–191] | 18222 | [1–430] |
| 17943 | [1–248] | 17996 | [1–352] | 18133 | [1–394] | 18223 | [1–505] |
| 17944 | [1–214] | 17997 | [214–287] | 18134 | [42–68] | 18224 | [1–343] |
| 17945 | [1–245] | 17998 | [1–147] | 18135 | [1–174], [301–387] | 18226 | [1–538] |
| 17946 | [1–216] | 17999 | [1–317] | 18136 | [102–143] | 18227 | [1–546] |
| 17947 | [1–225] | 18000 | [1–268] | 18137 | [69–445] | 18228 | [1–409] |
| 17948 | [1–229] | 18001 | [1–372] | 18138 | [1–410] | 18229 | [1–461] |
| 17949 | [1–219] | 18002 | [1–514] | 18139 | [331–356] | 18231 | [211–395] |
| 17950 | [1–520] | 18003 | [1–293] | 18140 | [1–72] | 18232 | [1–71] |
| 18004 | [1–27], [187–510] | 18056 | [98–125] | 18143 | [332–375] | 18235 | [1–418] |
| 18005 | [1–302] | 18058 | [1–153] | 18149 | [330–362] | 18236 | [1–337] |
| 18006 | [107–322] | 18060 | [1–552] | 18151 | [330–365] | 18237 | [1–427] |
| 18007 | [1–431] | 18062 | [1–195] | 18153 | [330–357] | 18238 | [1–457] |
| 18008 | [1–484] | 18063 | [1–174] | 18155 | [330–360] | 18239 | [1–453] |
| 18009 | [1–472] | 18064 | [1–443] | 18160 | [333–361] | 18241 | [1–402] |
| 18010 | [1–198] | 18065 | [1–109] | 18168 | [330–356] | 18242 | [1–413] |
| 18011 | [1–497] | 18066 | [1–160] | 18170 | [397–423] | 18243 | [1–396] |
| 18012 | [1–189] | 18067 | [91–393] | 18171 | [1–46], [328–357] | 18244 | [1–509] |
| 18013 | [1–375] | 18068 | [1–162] | 18172 | [1–86] | 18246 | [1–380], [441–482] |
| 18015 | [1–484] | 18069 | [1–54] | 18173 | [1–331] | 18248 | [1–148] |
| 18016 | [1–442] | 18070 | [1–427] | 18175 | [1–178] | 18249 | [1–383] |
| 18017 | [1–71] | 18071 | [1–160] | 18177 | [1–325] | 18250 | [1–472] |
| 18018 | [1–167] | 18072 | [130–250] | 18178 | [337–498] | 18251 | [1–581] |
| 18019 | [1–174] | 18073 | [1–72], [361–518] | 18179 | [1–353] | 18252 | [1–414] |
| 18020 | [1–278] | 18074 | [1–49] | 18180 | [1–364] | 18253 | [1–429] |
| 18021 | [1–502] | 18075 | [1–120] | 18181 | [1–494] | 18254 | [1–513] |
| 18022 | [1–59] | 18076 | [1–209] | 18182 | [1–363] | 18255 | [1–407] |
| 18025 | [1–341] | 18077 | [144–304] | 18183 | [1–333] | 18256 | [1–153] |
| 18026 | [1–451] | 18078 | [1–422] | 18184 | [1–196] | 18257 | [1–438] |
| 18027 | [1–59], [89–181] | 18079 | [1–33] | 18258 | [1–341] | 18309 | [1–426] |
| 18028 | [1–59], [89–155] | 18080 | [1–458] | 18259 | [1–496] | 18310 | [261–380] |
| 18029 | [1–425] | 18081 | [1–512] | 18260 | [1–467] | 18311 | [1–168] |
| 18031 | [1–521] | 18083 | [63–379], [408–475] | 18261 | [1–577] | 18312 | [1–444] |
| 18032 | [1–424] | 18084 | [1–114] | 18262 | [1–430] | 18313 | [1–452] |
| 18033 | [1–474] | 18085 | [1–41], [87–135] | 18263 | [1–445] | 18314 | [1–422] |
| 18034 | [1–191] | 18086 | [63–273], [307–456] | 18264 | [1–551] | 18315 | [1–362] |
| 18035 | [1–206] | 18088 | [1–407] | 18265 | [1–513] | 18316 | [1–472] |
| 18036 | [1–381] | 18089 | [1–259] | 18266 | [1–546] | 18318 | [1–301] |
| 18037 | [1–208] | 18090 | [1–87] | 18267 | [105–476] | 18319 | [1–590] |
| 18038 | [1–67] | 18091 | [63–270] | 18268 | [76–106] | 18320 | [1–58], [115–478] |
| 18039 | [1–145] | 18092 | [1–480] | 18269 | [1–93] | 18321 | [1–154] |
| 18040 | [1–389] | 18094 | [1–473] | 18270 | [1–270] | 18322 | [1–436] |
| 18041 | [1–245] | 18095 | [1–98] | 18271 | [1–385] | 18323 | [1–517] |
| 18042 | [1–406] | 18096 | [148–193] | 18272 | [1–318] | 18325 | [1–402] |
| 18043 | [1–462] | 18097 | [1–189] | 18273 | [1–387] | 18327 | [1–139] |
| 18045 | [1–86] | 18098 | [1–160], [283–411] | 18274 | [1–108] | 18328 | [1–242] |
| 18046 | [1–433] | 18100 | [1–312] | 18275 | [1–496], [528–557] | 18329 | [1–276] |
| 18047 | [206–400] | 18101 | [41–412] | 18276 | [1–453] | 18330 | [1–261] |
| 18048 | [1–106] | 18102 | [1–63] | 18277 | [1–204] | 18332 | [1–191] |
| 18049 | [1–318] | 18103 | [64–98] | 18278 | [65–371] | 18333 | [1–173] |
| 18050 | [1–363] | 18104 | [1–64] | 18279 | [1–365] | 18334 | [1–98] |
| 18051 | [1–235] | 18105 | [1–104] | 18280 | [1–397] | 18335 | [196–473] |
| 18052 | [1–454] | 18107 | [1–620] | 18282 | [1–438] | 18337 | [1–552] |
| 18053 | [1–477] | 18108 | [1–825] | 18283 | [1–250], [534–559] | 18338 | [1–237] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 18285 | [1–64] | 18340 | [1–161], [562–592] | 18492 | [1–553] | 18542 | [1–400] |
| 18286 | [1–53] | 18341 | [1–413] | 18493 | [164–216] | 18543 | [1–409] |
| 18287 | [78–151] | 18342 | [1–72] | 18494 | [55–101], [290–407] | 18544 | [1–416] |
| 18288 | [1–433] | 18343 | [1–60] | 18495 | [346–384] | 18545 | [1–401] |
| 18289 | [1–219] | 18344 | [1–115] | 18496 | [46–92] | 18546 | [1–402] |
| 18290 | [1–166], [326–368] | 18345 | [1–33], [453–478] | 18497 | [1–469] | 18547 | [1–434] |
| 18291 | [1–184] | 18347 | [1–53] | 18498 | [1–250] | 18548 | [1–509] |
| 18292 | [1–354] | 18348 | [1–51], [370–440] | 18500 | [1–508] | 18549 | [36–61], [255–563] |
| 18293 | [39–159] | 18349 | [1–71] | 18501 | [1–476] | 18550 | [164–457] |
| 18294 | [1–400] | 18350 | [1–544] | 18502 | [1–473] | 18552 | [1–472] |
| 18295 | [162–340] | 18351 | [1–465] | 18503 | [1–445] | 18553 | [1–274] |
| 18296 | [1–465] | 18352 | [1–464] | 18504 | [1–289] | 18554 | [1–121] |
| 18297 | [1–426] | 18353 | [1–238] | 18505 | [1–554] | 18555 | [1–509] |
| 18298 | [1–128] | 18354 | [1–495] | 18506 | [165–446] | 18556 | [1–329], [484–567] |
| 18299 | [1–73], [399–425] | 18355 | [1–503] | 18507 | [448–563] | 18557 | [1–467] |
| 18300 | [1–494] | 18356 | [1–518] | 18509 | [449–505] | 18558 | [1–513] |
| 18302 | [1–108], [161–200] | 18359 | [1–424] | 18510 | [447–510] | 18559 | [1–515] |
| 18303 | [1–519] | 18360 | [1–404] | 18512 | [1–564] | 18560 | [1–511] |
| 18304 | [1–535] | 18364 | [325–389] | 18513 | [1–450] | 18561 | [1–377] |
| 18305 | [1–512] | 18367 | [168–203] | 18514 | [1–523] | 18562 | [1–541] |
| 18306 | [1–438] | 18372 | [1–285] | 18515 | [1–190] | 18563 | [1–378] |
| 18308 | [1–100], [457–503] | 18373 | [1–279] | 18516 | [1–541] | 18564 | [1–427] |
| 18374 | [1–58] | 18430 | [1–427] | 18517 | [1–259] | 18567 | [1–495] |
| 18375 | [103–172] | 18431 | [1–93] | 18518 | [1–513] | 18568 | [1–414] |
| 18376 | [105–202] | 18432 | [78–115] | 18519 | [1–259], [371–416] | 18569 | [1–352] |
| 18378 | [1–460] | 18433 | [78–134] | 18520 | [1–401], [463–487] | 18570 | [1–359] |
| 18379 | [1–55], [173–437] | 18434 | [78–137] | 18521 | [1–401] | 18571 | [1–397] |
| 18380 | [1–492] | 18438 | [1–61] | 18522 | [1–400] | 18572 | [1–359] |
| 18381 | [1–498] | 18440 | [1–230] | 18523 | [1–403] | 18573 | [1–388] |
| 18382 | [149–250] | 18441 | [54–464] | 18524 | [1–406] | 18575 | [1–242] |
| 18384 | [1–103], [134–159] | 18442 | [1–61], [92–142], [181–518] | 18525 | [1–399] | 18576 | [39–160] |
| | | | | 18526 | [1–402] | 18577 | [1–464] |
| 18385 | [1–97] | 18443 | [43–377] | 18527 | [1–404] | 18578 | [1–494] |
| 18388 | [1–450] | 18444 | [38–169], [210–387] | 18528 | [1–400] | 18580 | [53–266] |
| 18389 | [1–485] | 18445 | [1–275] | 18529 | [1–432] | 18581 | [38–507] |
| 18390 | [1–166] | 18446 | [1–278] | 18530 | [1–393] | 18582 | [118–364] |
| 18391 | [1–95] | 18447 | [101–216] | 18531 | [1–400] | 18583 | [1–231], [274–434] |
| 18392 | [1–427] | 18448 | [1–396] | 18532 | [1–407], [469–493] | 18585 | [80–209] |
| 18393 | [1–388] | 18449 | [1–425] | 18533 | [1–404], [466–492] | 18586 | [1–67] |
| 18395 | [1–392] | 18450 | [159–353] | 18534 | [1–401] | 18587 | [1–180] |
| 18396 | [1–348] | 18451 | [159–353] | 18535 | [1–59] | 18588 | [1–193] |
| 18397 | [137–258] | 18452 | [159–260] | 18536 | [1–401] | 18590 | [1–498] |
| 18398 | [199–448] | 18453 | [1–215] | 18537 | [1–403] | 18593 | [1–288] |
| 18399 | [1–439] | 18455 | [1–215] | 18594 | [1–450] | 18657 | [1–727] |
| 18401 | [1–96] | 18456 | [1–215] | 18595 | [52–510] | 18658 | [1–180] |
| 18402 | [1–356] | 18458 | [1–148] | 18596 | [1–422] | 18659 | [1–431] |
| 18403 | [1–137] | 18460 | [1–338] | 18597 | [1–437] | 18661 | [1–209] |
| 18404 | [1–391] | 18461 | [1–107] | 18598 | [1–406] | 18662 | [1–501] |
| 18405 | [1–533] | 18462 | [1–56] | 18599 | [1–64], [125–531] | 18663 | [1–225] |
| 18406 | [1–113] | 18463 | [1–462] | 18600 | [1–516] | 18664 | [37–389] |
| 18407 | [1–187] | 18465 | [1–62], [220–287] | 18601 | [1–249], [279–496] | 18665 | [1–348] |
| 18408 | [1–503] | 18466 | [1–97], [166–398] | 18602 | [1–314] | 18666 | [1–83] |
| 18409 | [1–315] | 18467 | [1–392] | 18603 | [1–433] | 18667 | [1–83] |
| 18410 | [1–44] | 18469 | [1–439] | 18604 | [1–419] | 18668 | [1–512] |
| 18411 | [1–369] | 18470 | [1–412] | 18605 | [1–176] | 18670 | [1–463] |
| 18412 | [1–50] | 18472 | [1–440] | 18606 | [1–79] | 18671 | [394–421] |
| 18413 | [159–232] | 18473 | [1–163] | 18608 | [1–469] | 18674 | [168–270] |
| 18415 | [1–227], [273–367] | 18474 | [1–426] | 18612 | [1–346] | 18675 | [1–493] |
| 18416 | [1–377] | 18476 | [1–324] | 18613 | [354–480] | 18676 | [1–179] |
| 18417 | [1–522] | 18477 | [1–237] | 18614 | [1–410] | 18677 | [1–405] |
| 18418 | [1–36], [69–483] | 18478 | [85–478] | 18615 | [1–269] | 18678 | [104–357] |
| 18419 | [1–547] | 18479 | [1–46] | 18616 | [1–517] | 18679 | [1–474] |
| 18421 | [1–228] | 18480 | [1–46] | 18617 | [1–500] | 18680 | [1–498] |
| 18422 | [1–102] | 18481 | [1–49] | 18618 | [1–508] | 18681 | [1–501] |
| 18423 | [1–80] | 18482 | [1–437] | 18619 | [1–483] | 18682 | [1–458] |
| 18424 | [1–412] | 18483 | [1–353] | 18620 | [1–63] | 18683 | [1–377] |
| 18425 | [387–478] | 18484 | [1–102] | 18621 | [1–492] | 18684 | [1–354] |
| 18427 | [1–64] | 18485 | [1–472] | 18622 | [1–470] | 18685 | [309–475] |
| 18428 | [1–186] | 18486 | [1–577] | 18623 | [1–354] | 18686 | [1–360] |
| 18429 | [1–509] | 18487 | [1–54], [143–493] | 18624 | [1–28] | 18687 | [1–510] |
| 18488 | [1–199] | 18538 | [1–360] | 18625 | [1–28] | 18688 | [1–503] |
| 18489 | [1–200], [230–435] | 18539 | [1–400] | 18628 | [1–474] | 18689 | [1–399] |
| 18490 | [1–405] | 18540 | [1–401] | 18630 | [1–144] | 18690 | [1–368] |
| 18491 | [1–680] | 18541 | [1–425] | 18631 | [118–222] | 18691 | [1–70] |

TABLE IVa-continued (Novelty:95%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 18633 | [369–442] | 18692 | [1–373] | 18919 | [1–485] | 18974 | [1–474] |
| 18635 | [37–104] | 18701 | [56–99] | 18920 | [1–52] | 18975 | [1–449] |
| 18636 | [1–433] | 18706 | [1–525] | 18921 | [1–411] | 18977 | [1–146], [228–280] |
| 18637 | [1–489] | 18718 | [1–62] | 18922 | [1–52] | 18978 | [1–659] |
| 18638 | [279–332] | 18720 | [146–235] | 18923 | [1–52] | 18979 | [1–451] |
| 18639 | [274–405] | 18721 | [1–341] | 18925 | [1–51] | 18980 | [1–485] |
| 18641 | [1–540] | 18726 | [1–486] | 18926 | [1–52] | 18982 | [1–493] |
| 18642 | [151–176], [283–313] | 18733 | [1–28] | 18928 | [1–51] | 18983 | [1–378] |
| 18643 | [1–459] | 18735 | [31–374] | 18929 | [1–53] | 18984 | [1–77] |
| 18645 | [105–145], [188–241] | 18740 | [31–406] | 18930 | [1–128] | 18985 | [168–327] |
| 18647 | [72–335] | 18747 | [1–51] | 18931 | [1–355] | 18986 | [1–433] |
| 18648 | [171–282] | 18749 | [1–89] | 18932 | [1–330] | 18987 | [57–308] |
| 18649 | [1–516] | 18750 | [63–93] | 18934 | [1–395] | 18988 | [1–129] |
| 18650 | [1–263] | 18752 | [124–365] | 18935 | [226–281] | 18989 | [1–478] |
| 18651 | [1–229], [452–479] | 18753 | [1–50] | 18936 | [60–133] | 18990 | [1–460] |
| 18652 | [57–507] | 18759 | [278–312], [389–426] | 18938 | [1–197] | 18991 | [1–79] |
| 18765 | [255–376] | 18849 | [1–489] | 18939 | [179–351] | 18992 | [1–506] |
| 18773 | [432–457] | 18851 | [1–357] | 18940 | [1–424] | 18993 | [1–377] |
| 18779 | [1–390] | 18852 | [1–360] | 18941 | [75–469] | 18994 | [1–367] |
| 18791 | [1–527] | 18853 | [1–360] | 18942 | [67–325] | 18995 | [1–188] |
| 18792 | [1–466] | 18854 | [1–377] | 18943 | [1–149] | 18996 | [1–543] |
| 18793 | [1–510] | 18855 | [1–382] | 18944 | [1–438] | 18997 | [1–347] |
| 18794 | [1–453] | 18856 | [1–383] | 18945 | [133–444], [488–524] | 18998 | [1–272] |
| 18795 | [1–348] | 18857 | [1–427] | 18948 | [1–519] | 19000 | [1–190] |
| 18796 | [1–348] | 18858 | [1–391] | 18949 | [1–469] | 19001 | [1–199] |
| 18797 | [120–444] | 18859 | [1–485] | 18950 | [1–468] | 19002 | [1–463], [502–687] |
| 18798 | [1–482] | 18860 | [1–335] | 18951 | [1–519] | 19003 | [1–314] |
| 18799 | [1–403] | 18861 | [1–453] | 18952 | [1–150] | 19004 | [1–74] |
| 18800 | [1–506] | 18862 | [1–501] | 18953 | [1–73] | 19005 | [1–407] |
| 18801 | [1–600] | 18863 | [1–353] | 18954 | [445–470] | 19006 | [1–701] |
| 18805 | [1–490] | 18866 | [1–177] | 18956 | [1–790] | 19007 | [1–508] |
| 18806 | [1–447] | 18867 | [1–446] | 18957 | [1–88], [415–517] | 19008 | [1–478] |
| 18807 | [1–447] | 18869 | [1–716] | 18958 | [1–124], [452–1030] | 19009 | [1–508] |
| 18810 | [1–74] | 18870 | [1–250] | 18959 | [1–38] | 19010 | [1–436] |
| 18811 | [1–87] | 18871 | [1–238] | 18960 | [1–324] | 19011 | [1–481] |
| 18812 | [1–506] | 18872 | [1–269] | 18961 | [1–311], [340–379] | 19017 | [1–484] |
| 18813 | [1–484] | 18873 | [1–300] | 18962 | [1–311], [340–403] | 19019 | [1–428] |
| 18814 | [208–250] | 18874 | [1–490] | 19021 | [1–325] | 19086 | [1–192] |
| 18815 | [1–509] | 18875 | [1–482] | 19022 | [1–490] | 19087 | [1–94] |
| 18816 | [1–561] | 18876 | [119–425] | 19025 | [1–501] | 19088 | [1–471] |
| 18817 | [1–46], [78–487] | 18877 | [1–501] | 19026 | [1–293] | 19089 | [1–550] |
| 18818 | [1–504] | 18878 | [1–476] | 19027 | [82–470] | 19090 | [1–469] |
| 18819 | [1–533] | 18879 | [1–319] | 19028 | [1–66], [111–440] | 19091 | [1–415] |
| 18820 | [1–440] | 18880 | [1–463], [498–563] | 19029 | [1–550] | 19092 | [1–839] |
| 18821 | [1–593] | 18881 | [1–460] | 19030 | [57–98], [214–470] | 19093 | [1–463] |
| 18825 | [1–490] | 18882 | [1–461] | 19033 | [1–30] | 19094 | [1–516] |
| 18827 | [1–433] | 18883 | [1–485] | 19040 | [1–106] | 19095 | [1–484] |
| 18830 | [1–282] | 18884 | [1–170], [209–239], [301–395] | 19041 | [1–70] | 19096 | [1–356] |
| 18831 | [1–275], [486–522] | 18885 | [253–308], [909–936] | 19042 | [1–325], [357–392] | 19097 | [1–203] |
| 18832 | [1–54], [453–522] | 18887 | [1–49], [110–138] | 19045 | [1–301] | 19098 | [1–348] |
| 18835 | [1–532] | 18889 | [1–449] | 19046 | [1–462] | 19099 | [1–351] |
| 18836 | [1–464] | 18890 | [1–467] | 19047 | [1–326] | 19100 | [1–184] |
| 18837 | [1–188] | 18891 | [1–170] | 19048 | [1–417] | 19102 | [1–444] |
| 18838 | [1–75] | 18892 | [1–524] | 19049 | [1–537] | 19103 | [1–439] |
| 18839 | [1–374] | 18893 | [183–250] | 19050 | [1–518] | 19104 | [1–556] |
| 18840 | [1–439] | 18894 | [1–409] | 19051 | [1–508] | 19105 | [1–422] |
| 18841 | [1–452] | 18895 | [1–426] | 19052 | [1–497] | 19106 | [1–503] |
| 18842 | [1–225] | 18898 | [1–147] | 19053 | [1–378], [417–450] | 19107 | [1–168] |
| 18843 | [1–438] | 18899 | [1–35] | 19054 | [76–482] | 19108 | [1–548] |
| 18844 | [97–141] | 18900 | [1–47] | 19056 | [1–337] | 19109 | [427–515] |
| 18845 | [1–374] | 18901 | [1–507] | 19057 | [203–465] | 19110 | [1–473] |
| 18846 | [1–401] | 18903 | [1–479] | 19058 | [1–478] | 19111 | [1–452] |
| 18848 | [1–416] | 18904 | [256–304] | 19059 | [1–468] | 19112 | [1–480] |
| 18905 | [1–51] | 18963 | [1–311], [340–384] | 19060 | [170–384] | 19113 | [1–394] |
| 18906 | [1–155] | 18964 | [1–527] | 19061 | [195–403] | 19114 | [1–354] |
| 18907 | [1–155] | 18965 | [1–458] | 19062 | [1–500] | 19117 | [1–493] |
| 18909 | [1–51] | 18966 | [1–516] | 19063 | [1–472] | 19118 | [1–387] |
| 18910 | [1–91] | 18968 | [1–496] | 19064 | [1–515] | 19119 | [1–449] |
| 18912 | [1–52] | 18969 | [1–569] | 19065 | [1–396] | 19120 | [268–456] |
| 18914 | [1–51] | 18970 | [1–477] | 19066 | [1–362] | 19121 | [1–203] |
| 18916 | [1–117] | 18971 | [1–566] | 19067 | [1–381] | 19122 | [1–439] |
| 18917 | [1–506] | 18972 | [1–457] | 19068 | [1–37] | 19123 | [1–369] |
| 18918 | [1–215] | 18973 | [1–415] | 19070 | [1–501] | 19124 | [1–427] |
|  |  |  |  | 19071 | [1–436] | 19125 | [279–448] |

TABLE IVa-continued (Novelty:95%)

| Seq Id No. | Positions of preferred fragments | Seq Id No. | Positions of preferred fragments |
|---|---|---|---|
| 19072 | [1–412] | 19126 | [1–84], [270–406] |
| 19073 | [1–426] | 19127 | [1–514] |
| 19074 | [1–78], [207–454] | 19128 | [1–469] |
| 19077 | [1–518] | 19130 | [1–517] |
| 19078 | [112–423] | 19132 | [1–136] |
| 19079 | [1–387] | 19133 | [1–500] |
| 19080 | [1–586] | 19134 | [1–429] |
| 19083 | [1–481] | 19135 | [1–682] |
| 19084 | [1–429] | 19136 | [32–484] |
| 19085 | [1–474] | 19137 | [1–142] |
| 19138 | [1–554] | 19199 | [1–315] |
| 19139 | [32–466] | 19201 | [1–424] |
| 19141 | [1–355] | 19203 | [1–467] |
| 19142 | [1–400] | 19204 | [1–420] |
| 19143 | [1–196] | 19205 | [1–468] |
| 19144 | [1–249] | 19206 | [1–236] |
| 19146 | [372–465] | 19208 | [1–72] |
| 19147 | [1–480] | 19209 | [1–299] |
| 19150 | [1–515] | 19211 | [1–208] |
| 19153 | [1–419] | 19212 | [1–260] |
| 19159 | [1–453] | 19214 | [1–164] |
| 19160 | [314–373] | 19215 | [1–146] |
| 19161 | [1–495] | 19216 | [1–58] |
| 19162 | [1–432], [533–623] | 19217 | [1–103] |
| 19163 | [1–505] | 19218 | [1–352] |
| 19164 | [1–435] | 19220 | [52–541] |
| 19165 | [1–497] | 19221 | [1–467] |
| 19166 | [1–150] | 19222 | [1–464] |
| 19167 | [1–369] | 19223 | [328–371] |
| 19168 | [1–207] | 19224 | [1–84] |
| 19169 | [1–144] | 19225 | [1–321] |
| 19170 | [1–361], [391–434] | 19226 | [1–221] |
| 19171 | [1–151] | 19228 | [1–469] |
| 19172 | [1–170] | 19230 | [1–444] |
| 19173 | [1–162] | 19231 | [339–419] |
| 19174 | [1–532] | 19232 | [1–338] |
| 19175 | [1–519] | 19233 | [1–334] |
| 19176 | [1–658] | 19234 | [113–196] |
| 19177 | [1–303] | 19235 | [1–505] |
| 19178 | [1–369] | 19236 | [1–401], [442–513] |
| 19179 | [1–500] | 19238 | [1–467] |
| 19180 | [1–293] | 19239 | [38–401] |
| 19181 | [118–558] | 19240 | [1–317] |
| 19182 | [1–471] | 19241 | [1–369] |
| 19183 | [1–563] | 19244 | [1–453] |
| 19186 | [1–513] | 19245 | [1–136] |
| 19187 | [1–464] | 19247 | [1–522] |
| 19188 | [1–68], [108–472] | 19248 | [1–492] |
| 19189 | [1–473] | 19249 | [1–490] |
| 19190 | [1–518] | 19250 | [1–44], [294–477] |
| 19191 | [1–255] | 19252 | [241–347] |
| 19192 | [1–449] | 19253 | [1–480] |
| 19193 | [1–214] | 19255 | [1–419] |
| 19194 | [1–550] | 19256 | [1–375] |
| 19195 | [1–165] | 19257 | [1–177] |
| 19196 | [1–444] | 19258 | [1–287] |
| 19197 | [1–130] | 19259 | [1–266] |
| 19260 | [1–58] | 19315 | [1–101] |
| 19261 | [1–113] | 19316 | [1–108] |
| 19262 | [1–329] | 19317 | [1–169] |
| 19263 | [1–72] | 19318 | [1–63] |
| 19264 | [1–348] | 19319 | [1–133] |
| 19266 | [1–330] | 19321 | [1–108] |
| 19267 | [1–319] | 19322 | [1–119] |
| 19268 | [1–313] | 19325 | [1–390] |
| 19269 | [1–160] | 19326 | [1–168] |
| 19270 | [1–90] | 19327 | [1–387] |
| 19271 | [1–110] | 19328 | [1–169] |
| 19272 | [1–132] | 19329 | [1–169] |
| 19273 | [1–101] | 19330 | [1–108] |
| 19274 | [1–265] | 19331 | [1–101] |
| 19275 | [1–325] | 19332 | [1–404] |
| 19276 | [1–171] | 19334 | [1–499] |
| 19277 | [1–90] | 19335 | [1–63] |
| 19278 | [1–182] | | |
| 19279 | [1–59] | | |
| 19280 | [1–353] | | |
| 19281 | [1–107] | | |
| 19282 | [1–200], [261–377] | | |
| 19283 | [1–270] | | |
| 19284 | [1–348] | | |
| 19285 | [1–338] | | |
| 19286 | [1–63] | | |
| 19288 | [1–101] | | |
| 19289 | [1–108] | | |
| 19290 | [1–101] | | |
| 19291 | [1–108] | | |
| 19292 | [96–496] | | |
| 19293 | [1–108] | | |
| 19294 | [1–63] | | |
| 19295 | [1–108] | | |
| 19296 | [1–108] | | |
| 19298 | [1–108] | | |
| 19299 | [1–108] | | |
| 19300 | [1–108] | | |
| 19303 | [1–489] | | |
| 19304 | [1–108] | | |
| 19306 | [1–29] | | |
| 19308 | [1–205] | | |
| 19309 | [1–102] | | |
| 19311 | [1–108] | | |
| 19312 | [1–108] | | |
| 19313 | [1–109] | | |
| 19314 | [1–385] | | |

TABLE IVb (Novelty: 100%)

| Seq Id No. | Positions of preferred fragments | Seq Id No. | Positions of preferred fragments |
|---|---|---|---|
| 24 | [1–342] | 75 | [1–420] |
| 25 | [1–365] | 76 | [1–486] |
| 26 | [1–557] | 77 | [1–436] |
| 27 | [1–514] | 78 | [1–793] |
| 29 | [1–167] | 79 | [1–443] |
| 30 | [1–368] | 80 | [1–308] |
| 31 | [1–506] | 81 | [210–323] |
| 32 | [1–44] | 82 | [1–570] |
| 33 | [1–479] | 83 | [156–393] |
| 34 | [65–397] | 84 | [1–461] |
| 35 | [1–126],[298–386] | 85 | [1–244],[358–468] |
| 36 | [1–454] | 86 | [1–516] |
| 37 | [1–172],[319–482] | 87 | [1–674] |
| 38 | [1–491] | 88 | [1–402] |
| 39 | [1–678] | 89 | [1–473] |
| 41 | [1–442] | 90 | [1–474] |
| 42 | [1–425] | 91 | [1–97],[411–490] |
| 43 | [1–512] | 92 | [1–586] |
| 44 | [1–339] | 93 | [1–311] |
| 45 | [1–544] | 94 | [1–452] |
| 46 | [1–484] | 95 | [1–326] |
| 47 | [1–495] | 96 | [1–383] |
| 48 | [1–535] | 97 | [1–672] |
| 49 | [1–432] | 98 | [1–451] |
| 50 | [1–410] | 99 | [1–30] |
| 51 | [1–465] | 100 | [1–498] |
| 52 | [1–547] | 101 | [1–504] |
| 54 | [1–505] | 102 | [1–248] |
| 55 | [1–546] | 103 | [1–351] |
| 56 | [1–507] | 104 | [1–356] |
| 57 | [1–480] | 105 | [1–278] |
| 58 | [1–392] | 106 | [1–487] |
| 59 | [1–273] | 107 | [1–492] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 60 | [1–273] | 108 | [1–376] | 226 | [85–430] | 275 | [1–27],[65–213],[251–542] |
| 61 | [33–273] | 109 | [1–500] | 227 | [1–524] | 276 | [59–469] |
| 62 | [1–256] | 110 | [1–570] | 228 | [1–190] | 277 | [394–484] |
| 63 | [1–343] | 111 | [1–584] | 229 | [1–199],[233–450] | 278 | [1–472] |
| 65 | [1–174] | 112 | [1–417] | 230 | [1–306] | 279 | [1–511] |
| 66 | [1–481] | 113 | [1–402] | 231 | [1–351] | 280 | [1–499] |
| 67 | [1–478] | 114 | [1–525] | 232 | [1–260] | 281 | [1–221],[442–472] |
| 68 | [1–323] | 115 | [1–480] | 233 | [1–253] | 282 | [1–490] |
| 69 | [1–443] | 116 | [1–496] | 234 | [1–405] | 283 | [1–479] |
| 70 | [1–473] | 117 | [1–623] | 235 | [1–594] | 284 | [1–489] |
| 71 | [1–329] | 118 | [1–497] | 236 | [1–400] | 285 | [1–466] |
| 72 | [1–488] | 119 | [1–542] | 237 | [1–481] | 286 | [1–451] |
| 73 | [169–268] | 120 | [1–453] | 238 | [1–663] | 287 | [1–609] |
| 74 | [1–417] | 121 | [1–466] | 239 | [1–540] | 288 | [1–296] |
| 122 | [1–213] | 169 | [1–148],[229–490] | 240 | [1–559] | 289 | [1–503] |
| 123 | [1–465] | 170 | [1–542] | 241 | [1–479] | 290 | [1–386] |
| 124 | [1–488] | 171 | [1–528] | 242 | [1–516] | 291 | [1–499] |
| 125 | [1–493] | 172 | [1–450] | 243 | [1–558] | 292 | [1–671] |
| 126 | [1–489] | 173 | [1–599] | 244 | [1–478] | 293 | [1–112],[384–512] |
| 127 | [1–463] | 174 | [1–514] | 245 | [1–470] | 294 | [1–288],[326–490] |
| 128 | [1–554] | 175 | [1–286] | 246 | [1–451] | 295 | [1–322] |
| 129 | [1–180],[421–467] | 176 | [1–501] | 247 | [1–458] | 296 | [1–40] |
| 130 | [1–457] | 177 | [1–31] | 248 | [1–473] | 297 | [1–496] |
| 131 | [1–392] | 178 | [1–542] | 249 | [1–322] | 298 | [1–492] |
| 132 | [1–477] | 179 | [1–303] | 250 | [1–548] | 299 | [1–478] |
| 133 | [1–252] | 180 | [1–504] | 251 | [1–453] | 300 | [1–248] |
| 134 | [1–422] | 181 | [1–35],[146–320],[444–542] | 252 | [1–578] | 301 | [1–455] |
| 135 | [1–462],[498–570] | 182 | [1–509] | 253 | [1–672] | 302 | [1–483] |
| 136 | [1–282] | 183 | [1–501] | 254 | [1–368],[437–479] | 303 | [1–496] |
| 137 | [1–502] | 184 | [1–466] | 255 | [1–115],[158–327] | 304 | [1–477],[509–622] |
| 138 | [1–495] | 185 | [51–267] | 256 | [158–476] | 305 | [1–522] |
| 139 | [1–646] | 186 | [1–485] | 257 | [1–506] | 306 | [1–500] |
| 140 | [1–36],[411–497] | 187 | [1–521] | 258 | [1–447] | 307 | [1–25] |
| 141 | [1–456] | 188 | [1–332] | 259 | [1–433] | 308 | [1–495] |
| 142 | [1–488] | 189 | [1–262] | 260 | [1–467] | 309 | [1–483] |
| 143 | [1–219] | 190 | [1–552] | 261 | [1–508] | 310 | [1–467] |
| 144 | [1–524] | 191 | [30–164] | 262 | [1–477] | 311 | [1–156],[219–272],[332–435] |
| 145 | [1–514] | 192 | [1–249] | 312 | [1–90],[332–493] | 360 | [158–413] |
| 146 | [1–525] | 193 | [1–324] | 313 | [1–570] | 361 | [1–737] |
| 147 | [1–438] | 194 | [1–334] | 314 | [1–386] | 362 | [1–470] |
| 148 | [1–265] | 195 | [1–337] | 315 | [1–482] | 363 | [1–451] |
| 149 | [1–256] | 196 | [1–296],[462–491] | 316 | [55–478] | 364 | [1–488] |
| 150 | [1–320] | 197 | [1–56] | 317 | [1–460] | 365 | [1–299],[476–597] |
| 151 | [1–512] | 198 | [1–471] | 318 | [1–557] | 366 | [1–455] |
| 152 | [1–497] | 199 | [1–523] | 319 | [1–587] | 367 | [1–494] |
| 153 | [1–501] | 200 | [1–465],[523–829] | 320 | [1–32],[177–260],[422–489] | 368 | [1–412] |
| 154 | [1–225] | 201 | [143–477] | 321 | [50–475] | 369 | [1–482] |
| 155 | [1–542] | 202 | [33–523] | 322 | [53–462] | 370 | [1–513] |
| 156 | [1–211] | 203 | [1–451] | 323 | [50–474] | 371 | [1–437] |
| 157 | [50–475] | 204 | [1–505] | 324 | [1–496] | 372 | [1–394] |
| 158 | [1–587] | 205 | [1–277] | 325 | [1–520] | 373 | [1–474] |
| 159 | [1–533] | 206 | [1–701] | 326 | [50–480] | 374 | [1–319] |
| 160 | [1–479] | 207 | [125–162],[191–499] | 327 | [1–292] | 375 | [1–429] |
| 161 | [1–307] | 208 | [1–485] | 328 | [1–515] | 376 | [1–524] |
| 162 | [1–721] | 209 | [1–458] | 329 | [32–513] | 377 | [1–459] |
| 163 | [1–495] | 210 | [1–559] | 330 | [1–543] | 378 | [1–284] |
| 164 | [143–213],[338–493] | 211 | [1–481] | 331 | [50–475] | 379 | [1–496] |
| 165 | [1–594] | 212 | [1–452] | 332 | [32–495] | 380 | [1–54],[83–495] |
| 166 | [1–501] | 213 | [1–472] | 333 | [1–496] | 381 | [36–530] |
| 167 | [1–481] | 214 | [1–444] | 334 | [1–461] | 382 | [1–300] |
| 168 | [141–351],[469–562] | 215 | [1–321] | 335 | [50–475] | 383 | [1–569] |
| 216 | [1–472] | 263 | [1–503] | 337 | [1–638] | 384 | [1–480] |
| 217 | [1–461] | 264 | [1–571] | 338 | [1–519] | 385 | [1–421] |
| 218 | [36–469] | 265 | [1–497] | 339 | [68–252] | 386 | [1–498] |
| 219 | [36–468] | 267 | [1–483] | 340 | [1–286],[346–511] | 387 | [1–497] |
| 220 | [91–480] | 268 | [1–114],[153–350],[442–599] | 341 | [1–487] | 388 | [1–474] |
| 221 | [54–364] | 269 | [1–467] | 342 | [1–460] | 389 | [127–320] |
| 222 | [1–46],[107–483] | 270 | [1–173] | 343 | [1–452] | 390 | [1–490] |
| 223 | [1–76],[174–490] | 271 | [37–251],[317–376],[518–630] | 344 | [1–478] | 391 | [1–457] |
| | | | | 345 | [1–472] | 392 | [1–309] |
| 224 | [1–492] | 272 | [207–291],[344–479] | 346 | [1–537] | 393 | [1–349] |
| | | | | 347 | [1–488] | 394 | [1–146] |
| 225 | [1–564] | 274 | [1–473] | 348 | [1–470] | 395 | [1–409] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 349 | [1–564] | 396 | [1–146],[175–223] | 517 | [1–478] | 564 | [1–481] |
| 350 | [1–494] | 397 | [1–443] | 518 | [1–458] | 565 | [1–492] |
| 351 | [1–520] | 398 | [1–574] | 519 | [1–560] | 566 | [1–509] |
| 352 | [1–490] | 399 | [1–370] | 520 | [1–465] | 567 | [1–479] |
| 353 | [1–491] | 400 | [1–456] | 521 | [1–361] | 568 | [31–468] |
| 354 | [1–363] | 401 | [1–482] | 522 | [1–278] | 569 | [1–375] |
| 355 | [1–234] | 402 | [1–287] | 523 | [1–417] | 570 | [1–486] |
| 356 | [1–522] | 403 | [121–216] | 524 | [1–466] | 571 | [1–601] |
| 357 | [1–485] | 404 | [1–417] | 525 | [1–469] | 572 | [1–253] |
| 358 | [1–470] | 405 | [1–436] | 526 | [1–352],[394–460] | 573 | [1–496] |
| 359 | [1–332] | 406 | [1–450] | 527 | [1–483] | 574 | [1–115],[277–432] |
| 407 | [1–510] | 454 | [1–493] | 528 | [1–457] | 575 | [1–449] |
| 408 | [1–435] | 455 | [1–256],[314–593] | 529 | [1–495] | 576 | [1–300],[413–451] |
| 409 | [1–485] | 456 | [1–483] | 530 | [1–63],[135–219],[295–474] | 577 | [1–507] |
| 410 | [1–237] | 457 | [1–368] | 531 | [1–467] | 578 | [1–409] |
| 411 | [1–482] | 458 | [1–378] | 532 | [1–487] | 579 | [1–510] |
| 412 | [1–482] | 459 | [1–517] | 533 | [1–491] | 580 | [1–112],[263–412] |
| 413 | [1–419] | 460 | [1–475] | 534 | [1–193] | 581 | [1–480] |
| 414 | [1–463] | 461 | [1–528] | 535 | [1–395] | 582 | [1–509] |
| 415 | [1–219] | 462 | [1–285] | 536 | [1–504] | 583 | [1–458] |
| 416 | [1–460] | 463 | [1–457] | 537 | [1–501] | 584 | [1–538] |
| 417 | [1–474] | 464 | [1–188] | 538 | [1–225] | 585 | [1–513] |
| 418 | [158–300],[389–507] | 465 | [227–382] | 539 | [1–401] | 586 | [1–531] |
| 419 | [1–172] | 466 | [1–497] | 540 | [39–472] | 587 | [1–329] |
| 420 | [1–505] | 467 | [48–183],[439–480] | 541 | [1–180],[355–452] | 588 | [1–491] |
| 421 | [1–504] | 468 | [1–492] | 542 | [1–506] | 589 | [1–736] |
| 422 | [1–271] | 469 | [1–388] | 543 | [1–469] | 590 | [1–452] |
| 423 | [1–239] | 470 | [1–478] | 544 | [77–490] | 591 | [1–523] |
| 424 | [1–213] | 471 | [1–467] | 545 | [1–467] | 592 | [1–470] |
| 425 | [1–407] | 472 | [1–527] | 546 | [1–454] | 593 | [1–95[,[129–233] |
| 426 | [1–324] | 473 | [1–550] | 547 | [1–485] | 594 | [1–238] |
| 427 | [1–377] | 474 | [1–303] | 595 | [1–374] | 642 | [1–497] |
| 428 | [1–498] | 475 | [1–169] | 596 | [1–460] | 643 | [1–272] |
| 429 | [1–274] | 476 | [1–471] | 597 | [1–461] | 644 | [255–353] |
| 430 | [1–83],[411–469] | 477 | [1–252] | 598 | [88–263],[372–434] | 645 | [1–546] |
| 431 | [1–464] | 478 | [1–472] | 599 | [1–521] | 646 | [1–336] |
| 432 | [1–494] | 479 | [1–510] | 600 | [1–505] | 647 | [1–368] |
| 433 | [1–413] | 480 | [1–505] | 601 | [1–169] | 648 | [1–483] |
| 434 | [1–323] | 481 | [1–352] | 602 | [1–247] | 649 | [1–511] |
| 435 | [1–548] | 482 | [1–286] | 603 | [33–101],[417–530] | 650 | [1–489] |
| 436 | [1–493] | 483 | [1–451] | 604 | [1–61],[184–416] | 651 | [1–511] |
| 437 | [1–457] | 484 | [1–244] | 605 | [1–454] | 652 | [1–489] |
| 438 | [1–343] | 485 | [1–482] | 606 | [33–328] | 653 | [1–519] |
| 439 | [1–428] | 486 | [1–81],[156–383] | 607 | [1–448] | 654 | [1–343] |
| 440 | [1–537] | 487 | [1–370] | 608 | [1–383] | 655 | [40–81],[154–198], [275–309],[414–508] |
| 441 | [1–28],[113–360] | 488 | [1–160] | | | | |
| 442 | [1–502] | 489 | [1–234] | 609 | [1–246],[383–419] | 656 | [1–486] |
| 443 | [1–467] | 490 | [1–458] | 610 | [1–416] | 657 | [1–510] |
| 444 | [1–464] | 491 | [1–457] | 611 | [1–459] | 658 | [1–553] |
| 445 | [1–504] | 492 | [1–486] | 612 | [1–340] | 659 | [37–78],[177–265] |
| 446 | [1–476] | 493 | [1–452] | 613 | [1–473] | 660 | [1–460] |
| 447 | [1–505] | 494 | [1–295] | 614 | [1–506] | 661 | [1–451] |
| 448 | [1–495] | 495 | [1–286],[353–487] | 615 | [1–488] | 662 | [1–487] |
| 449 | [1–503] | 496 | [1–468] | 616 | [1–481] | 663 | [1–458] |
| 450 | [1–461] | 497 | [1–481] | 617 | [1–494] | 664 | [1–535] |
| 451 | [1–507] | 498 | [1–296] | 618 | [1–358] | 665 | [1–488] |
| 452 | [1–480] | 499 | [1–422] | 619 | [1–208] | 666 | [1–539] |
| 453 | [1–511] | 500 | [1–461] | 620 | [1–309] | 667 | [54–490] |
| 501 | [1–506] | 548 | [1–526] | 621 | [1–278] | 668 | [1–498] |
| 502 | [1–427] | 549 | [1–484] | 622 | [1–476] | 669 | [1–540] |
| 503 | [154–481] | 550 | [1–457] | 623 | [1–412] | 670 | [1–497] |
| 504 | [1–489] | 551 | [1–527] | 624 | [1–448] | 671 | [1–506] |
| 505 | [1–237],[287–502] | 552 | [1–459] | 625 | [179–552] | 672 | [1–32],[225–259], [421–492] |
| 506 | [1–458] | 553 | [1–513] | | | | |
| 507 | [1–288],[368–502] | 554 | [1–463] | 626 | [1–463] | 673 | [1–218],[278–465] |
| 508 | [1–473] | 555 | [1–232] | 627 | [1–487] | 674 | [1–469] |
| 509 | [1–469] | 556 | [1–149] | 628 | [1–479] | 675 | [1–491] |
| 510 | [1–486] | 557 | [1–474] | 629 | [1–478] | 676 | [1–429] |
| 511 | [1–51],[159–205] | 558 | [1–471] | 630 | [1–607] | 677 | [1–497] |
| 512 | [1–318] | 559 | [1–384] | 631 | [1–458] | 678 | [1–473] |
| 513 | [1–470] | 560 | [1–470] | 632 | [1–502] | 679 | [1–366] |
| 514 | [1–453] | 561 | [137–504] | 633 | [1–485] | 680 | [1–401] |
| 515 | [1–480] | 562 | [1–488] | 634 | [1–464] | 681 | [1–399] |
| 516 | [1–496] | 563 | [1–469] | 635 | [1–494] | 682 | [1–508] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 636 | [1–480] | 683 | [1–535] | 804 | [1–448] | 852 | [1–474] |
| 637 | [175–246] | 684 | [1–308] | 805 | [1–484] | 853 | [1–546] |
| 638 | [1–177],[210–344] | 685 | [1–452] | 806 | [1–510] | 854 | [1–499] |
| 639 | [1–469] | 686 | [1–495] | 807 | [1–474] | 855 | [1–484] |
| 640 | [1–426] | 687 | [1–497] | 808 | [1–221] | 856 | [195–473] |
| 641 | [1–458] | 688 | [1–499] | 809 | [1–96] | 857 | [1–502] |
| 689 | [1–467] | 737 | [1–474] | 810 | [1–389] | 858 | [1–514] |
| 690 | [179–523] | 738 | [1–498] | 811 | [1–451] | 859 | [1–481] |
| 691 | [1–473] | 739 | [30–195],[448–516] | 812 | [1–258] | 860 | [1–508] |
| 692 | [1–503] | 740 | [1–454] | 813 | [1–191] | 861 | [1–535] |
| 693 | [1–457] | 741 | [1–463] | 814 | [1–484] | 862 | [1–504] |
| 694 | [1–541] | 742 | [1–503] | 815 | [1–543] | 863 | [1–403] |
| 695 | [1–339] | 743 | [1–327] | 816 | [1–480] | 864 | [1–56] |
| 696 | [1–172] | 744 | [1–65] | 817 | [1–507] | 865 | [1–557] |
| 697 | [1–558] | 745 | [1–473] | 818 | [1–69],[156–307],[415–477] | 866 | [1–537] |
| 698 | [1–435] | 746 | [1–519] | 819 | [156–307],[415–477] | 867 | [1–496] |
| 699 | [1–518] | 747 | [1–442] | 820 | [1–332] | 868 | [1–491] |
| 700 | [1–387] | 748 | [1–442] | 821 | [1–409] | 869 | [1–353] |
| 701 | [1–487] | 749 | [1–454] | 822 | [1–212],[254–376] | 870 | [1–516] |
| 702 | [1–480] | 750 | [1–459] | 824 | [1–351] | 871 | [1–374] |
| 703 | [1–496] | 751 | [1–442] | 825 | [1–326] | 872 | [1–348] |
| 704 | [1–262],[462–492] | 752 | [1–120],[156–377] | 826 | [1–466] | 873 | [1–365],[510–542] |
| 705 | [1–479] | 753 | [97–146] | 827 | [1–420] | 874 | [1–339] |
| 706 | [1–369],[407–672] | 754 | [1–487] | 828 | [1–316] | 875 | [1–211],[253–369] |
| 707 | [1–401] | 755 | [138–499] | 829 | [1–482] | 876 | [199–426] |
| 708 | [1–501] | 756 | [1–131],[199–307] | 830 | [1–501] | 877 | [1–246] |
| 709 | [1–213],[255–400] | 757 | [1–494] | 831 | [1–175] | 878 | [1–473] |
| 710 | [1–318],[359–472] | 758 | [1–392] | 879 | [1–486] | 926 | [1–522] |
| 711 | [1–211],[253–370] | 759 | [1–211],[253–368] | 880 | [1–464] | 927 | [1–358] |
| 712 | [1–484] | 760 | [1–467] | 881 | [1–711] | 928 | [32–512] |
| 713 | [1–490] | 761 | [1–311] | 882 | [1–489] | 929 | [1–247] |
| 714 | [1–534] | 762 | [1–326] | 883 | [1–504] | 930 | [1–486] |
| 715 | [1–525] | 763 | [1–386] | 884 | [1–348] | 931 | [1–458] |
| 716 | [1–454] | 764 | [1–472] | 885 | [1–484] | 932 | [1–529] |
| 717 | [1–452] | 765 | [1–457] | 886 | [1–499] | 934 | [34–233] |
| 718 | [1–495] | 766 | [1–492] | 887 | [1–455] | 935 | [1–404] |
| 719 | [1–223] | 767 | [1–39],[225–520] | 888 | [1–452] | 936 | [1–504] |
| 720 | [1–469] | 768 | [1–42],[181–262] | 889 | [1–489] | 937 | [1–602] |
| 721 | [1–485] | 769 | [65–538] | 890 | [1–525] | 938 | [1–495] |
| 722 | [1–560] | 770 | [1–477] | 891 | [1–408] | 939 | [1–521] |
| 723 | [1–32],[237–280],[451–499] | 771 | [1–506] | 892 | [1–517] | 940 | [1–539] |
| 724 | [36–242],[374–427] | 772 | [1–376] | 893 | [1–479] | 941 | [1–557] |
| 725 | [97–148],[448–531] | 773 | [1–321],[392–499] | 894 | [1–257],[477–548] | 942 | [1–479] |
| 726 | [34–270] | 774 | [1–498] | 895 | [1–499] | 943 | [1–476] |
| 727 | [1–396] | 775 | [1–498] | 896 | [1–323] | 944 | [1–529] |
| 728 | [1–167],[249–478] | 776 | [1–487] | 897 | [1–467] | 945 | [1–605] |
| 729 | [1–470] | 777 | [1–479],[629–748] | 898 | [1–453] | 946 | [1–488] |
| 730 | [1–406] | 778 | [1–589] | 899 | [1–497] | 947 | [1–285] |
| 732 | [1–380] | 779 | [1–471] | 900 | [1–422] | 948 | [1–345] |
| 733 | [1–381] | 780 | [1–169],[223–704] | 901 | [1–359] | 949 | [1–557] |
| 734 | [1–280] | 781 | [1–133] | 902 | [1–498] | 950 | [269–353] |
| 735 | [1–490] | 782 | [1–487] | 903 | [1–363] | 951 | [1–515] |
| 736 | [70–134],[187–270],[448–497] | 783 | [1–42],[134–516] | 904 | [1–539] | 952 | [1–131] |
| 784 | [1–468] | 832 | [1–494] | 905 | [1–213],[255–369] | 953 | [1–466] |
| 785 | [1–515] | 833 | [1–497] | 906 | [1–485] | 954 | [1–283],[432–476] |
| 786 | [1–516] | 834 | [1–650] | 907 | [1–464] | 955 | [1–506] |
| 787 | [1–476] | 835 | [1–259] | 908 | [1–469] | 956 | [1–440] |
| 788 | [1–618] | 836 | [1–486] | 909 | [1–707] | 957 | [155–628] |
| 789 | [1–212],[294–378] | 837 | [1–301] | 910 | [1–604] | 958 | [1–525] |
| 790 | [57–264],[439–494] | 838 | [1–225] | 911 | [1–452] | 959 | [116–497] |
| 791 | [1–464] | 839 | [142–537] | 912 | [1–173] | 960 | [1–502] |
| 792 | [1–484] | 840 | [1–510] | 913 | [1–413] | 961 | [1–525] |
| 793 | [1–130],[169–492] | 841 | [1–344] | 914 | [1–402] | 962 | [1–444] |
| 794 | [1–235],[410–453] | 842 | [1–513] | 915 | [85–245] | 963 | [70–109] |
| 795 | [177–547] | 843 | [1–536] | 916 | [1–492] | 964 | [1–457] |
| 796 | [1–489] | 844 | [1–526] | 917 | [54–274] | 965 | [1–498] |
| 797 | [1–280] | 845 | [1–345] | 918 | [1–462] | 966 | [1–311] |
| 798 | [1–478] | 846 | [1–170],[273–503] | 919 | [1–517] | 967 | [1–182] |
| 799 | [1–235],[410–453] | 847 | [1–471] | 920 | [1–356] | 968 | [1–549] |
| 800 | [1–577] | 848 | [1–274] | 921 | [1–526] | 969 | [1–120],[277–495] |
| 801 | [1–194] | 849 | [1–518] | 922 | [1–478] | 970 | [1–459] |
| 802 | [1–444] | 850 | [1–475] | 923 | [1–474] | 971 | [1–492] |
| 803 | [1–466] | 851 | [1–492] | 924 | [1–434] | 972 | [1–471] |
|  |  |  |  | 925 | [1–900] | 973 | [35–224] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 974 | [1–282] | 1022 | [1–487] | 1098 | [1–517] | 1147 | [1–528] |
| 975 | [1–322] | 1023 | [1–480] | 1099 | [1–485] | 1148 | [1–56] |
| 976 | [1–479] | 1024 | [1–443] | 1100 | [33–465] | 1149 | [1–505] |
| 977 | [1–514] | 1025 | [1–440] | 1101 | [33–482] | 1150 | [1–518] |
| 978 | [39–266] | 1026 | [1–464] | 1102 | [1–235] | 1151 | [1–529] |
| 979 | [1–260] | 1027 | [1–524] | 1104 | [1–487] | 1152 | [1–371] |
| 980 | [1–481] | 1028 | [1–381] | 1105 | [33–514] | 1153 | [1–452] |
| 981 | [1–503] | 1029 | [1–479] | 1106 | [33–493] | 1154 | [1–455] |
| 982 | [1–388] | 1030 | [1–474] | 1107 | [1–361] | 1155 | [1–459] |
| 983 | [1–414] | 1031 | [1–556] | 1108 | [1–526] | 1156 | [1–494] |
| 984 | [1–540] | 1032 | [1–537] | 1109 | [1–438] | 1157 | [1–557] |
| 985 | [1–482] | 1033 | [1–425] | 1110 | [1–523] | 1158 | [1–458] |
| 986 | [1–488] | 1034 | [1–462] | 1111 | [1–351] | 1159 | [1–482] |
| 987 | [1–429] | 1035 | [1–455] | 1112 | [1–257] | 1160 | [1–536] |
| 988 | [1–492] | 1036 | [1–447] | 1113 | [1–484] | 1161 | [1–402],[464–507] |
| 989 | [1–509] | 1037 | [144–450] | 1114 | [1–331] | 1162 | [1–401] |
| 990 | [1–132],[283–383] | 1038 | [1–65],[141–418] | 1115 | [1–261] | 1163 | [1–488] |
| 991 | [1–551] | 1039 | [1–291] | 1116 | [1–367] | 1164 | [1–405],[467–491] |
| 992 | [1–72],[105–549] | 1040 | [1–483] | 1117 | [1–523] | 1165 | [1–362],[424–476] |
| 993 | [1–565] | 1041 | [1–454] | 1118 | [1–406] | 1166 | [1–402],[464–488] |
| 994 | [45–189],[425–502] | 1042 | [1–479] | 1167 | [1–400] | 1215 | [1–524] |
| 995 | [1–229] | 1043 | [1–532] | 1168 | [1–94],[137–196],[257–322] | 1216 | [1–505] |
| 996 | [1–327] | 1044 | [1–516] | 1169 | [1–388] | 1217 | [1–254] |
| 997 | [1–220] | 1045 | [1–236] | 1171 | [1–139] | 1218 | [1–455] |
| 999 | [1–357] | 1046 | [1–236] | 1172 | [1–564] | 1219 | [1–453] |
| 1000 | [1–319] | 1047 | [1–177] | 1173 | [1–469] | 1220 | [1–453] |
| 1001 | [1–490] | 1048 | [1–496] | 1174 | [1–498] | 1221 | [1–486] |
| 1002 | [1–584] | 1049 | [1–470] | 1175 | [1–261] | 1222 | [1–460] |
| 1003 | [1–520] | 1050 | [1–531] | 1176 | [1–216],[258–442] | 1223 | [1–94],[222–387] |
| 1004 | [1–490] | 1051 | [1–516] | 1177 | [1–531] | 1224 | [1–218],[292–386] |
| 1005 | [1–452] | 1052 | [1–274] | 1178 | [1–394] | 1225 | [1–348] |
| 1006 | [1–348] | 1053 | [1–515] | 1179 | [1–915] | 1226 | [1–202] |
| 1007 | [1–460] | 1054 | [1–175],[229–457] | 1180 | [58–557] | 1227 | [293–387] |
| 1008 | [1–443] | 1056 | [1–486] | 1181 | [1–235] | 1228 | [1–594] |
| 1009 | [1–425] | 1057 | [1–422] | 1182 | [1–70],[254–567] | 1229 | [1–579] |
| 1010 | [1–508] | 1058 | [1–450] | 1183 | [1–436] | 1230 | [1–163],[302–504] |
| 1011 | [1–468] | 1059 | [1–567] | 1184 | [1–486] | 1231 | [1–517] |
| 1012 | [1–429] | 1060 | [1–452] | 1185 | [1–599] | 1232 | [1–318] |
| 1013 | [1–494] | 1061 | [1–228] | 1186 | [75–189],[269–338],[426–548] | 1233 | [1–43],[137–252] |
| 1014 | [1–533] | 1062 | [1–402] | 1187 | [1–510] | 1234 | [1–489] |
| 1015 | [1–429] | 1063 | [1–468] | 1188 | [1–472] | 1235 | [1–317] |
| 1016 | [1–413] | 1064 | [1–557] | 1189 | [1–116],[192–472] | 1236 | [1–485] |
| 1017 | [1–430] | 1065 | [1–486] | 1190 | [1–536] | 1237 | [1–455] |
| 1018 | [1–509] | 1066 | [1–315] | 1191 | [1–476] | 1238 | [1–93],[280–536] |
| 1019 | [1–516] | 1067 | [1–483] | 1192 | [1–553] | 1239 | [1–468] |
| 1020 | [1–507] | 1068 | [1–379] | 1193 | [1–574] | 1240 | [1–567] |
| 1021 | [1–411] | 1069 | [1–506] | 1194 | [1–469] | 1241 | [78–248] |
| 1070 | [1–493] | 1119 | [1–248] | 1195 | [1–479] | 1242 | [1–409] |
| 1071 | [1–529] | 1120 | [1–616] | 1196 | [1–554] | 1243 | [1–232] |
| 1072 | [1–396] | 1121 | [1–284] | 1197 | [1–482] | 1244 | [1–563] |
| 1073 | [1–327] | 1122 | [1–559] | 1198 | [1–461] | 1245 | [1–241] |
| 1074 | [1–564] | 1123 | [1–399] | 1199 | [1–467] | 1246 | [1–478] |
| 1075 | [1–492] | 1124 | [1–ss1] | 1200 | [1–486] | 1247 | [1–504] |
| 1076 | [1–480] | 1125 | [1–484] | 1201 | [1–208] | 1248 | [1–527] |
| 1077 | [1–521] | 1126 | [1–533] | 1202 | [1–512] | 1249 | [1–468] |
| 1078 | [1–480] | 1127 | [1–223] | 1203 | [1–42],[123–750] | 1250 | [1–537] |
| 1079 | [1–538] | 1128 | [1–502] | 1204 | [1–57],[138–534] | 1251 | [1–568] |
| 1080 | [1–287],[347–509] | 1129 | [1–427] | 1205 | [1–42],[123–452] | 1252 | [1–492] |
| 1081 | [1–190],[220–444] | 1130 | [57–258] | 1206 | [1–186],[411–465] | 1253 | [1–528] |
| 1082 | [1–480] | 1131 | [1–471] | 1207 | [127–469] | 1254 | [1–515] |
| 1083 | [1–490] | 1132 | [1–528] | 1208 | [1–457] | 1255 | [1–512] |
| 1084 | [56–418] | 1133 | [1–349] | 1209 | [1–487] | 1256 | [1–481] |
| 1085 | [165–491] | 1134 | [112–506] | 1210 | [1–601] | 1257 | [1–484] |
| 1086 | [93–415] | 1135 | [1–564] | 1211 | [1–561] | 1258 | [1–360] |
| 1087 | [1–482] | 1136 | [1–522] | 1212 | [1–454] | 1259 | [1–525] |
| 1088 | [1–33],[150–254] | 1137 | [1–524] | 1213 | [1–402] | 1260 | [1–371],[450–554] |
| 1089 | [1–133] | 1138 | [1–356] | 1214 | [48–268],[480–519] | 1261 | [1–651] |
| 1091 | [1–625] | 1139 | [1–609] | 1262 | [1–491] | 1312 | [1–516] |
| 1092 | [1–484] | 1140 | [1–479] | 1263 | [1–508] | 1313 | [1–471] |
| 1093 | [1–495] | 1141 | [1–494] | 1264 | [1–490] | 1314 | [1–504] |
| 1094 | [1–513] | 1142 | [1–94],[49–393] | 1265 | [1–540] | 1315 | [1–492] |
| 1095 | [1–101],[195–294],[385–519] | 1143 | [1–510] | 1266 | [1–308] | 1316 | [1–333] |
| 1096 | [1–353],[386–439] | 1144 | [1–468] | 1267 | [1–516] | 1317 | [159–471] |
| 1097 | [1–550] | 1145 | [1–239] | | | | |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 1268 | [1–612] | 1318 | [1–505] | 1392 | [1–540] | 1440 | [1–203],[293–587] |
| 1269 | [499–544] | 1319 | [1–562] | 1393 | [1–137],[194–498] | 1441 | [1–343] |
| 1270 | [1–497] | 1320 | [1–369] | 1394 | [1–174] | 1442 | [1–523] |
| 1271 | [1–530] | 1321 | [1–375],[414–470] | 1395 | [1–340] | 1443 | [1–466] |
| 1272 | [1–474] | 1322 | [1–249] | 1396 | [1–510] | 1444 | [1–510] |
| 1273 | [1–435] | 1323 | [1–204] | 1398 | [1–490] | 1445 | [1–239] |
| 1274 | [1–227] | 1324 | [1–240] | 1399 | [1–227],[311–477] | 1446 | [1–484] |
| 1275 | [113–519] | 1325 | [1–212] | 1400 | [1–428] | 1447 | [1–26],[318–364] |
| 1276 | [1–540] | 1326 | [1–511] | 1401 | [1–426] | 1448 | [1–461] |
| 1277 | [1–496] | 1327 | [1–480] | 1402 | [1–496] | 1449 | [1–240] |
| 1278 | [1–487] | 1328 | [1–472] | 1403 | [1–524] | 1450 | [1–239] |
| 1279 | [1–482] | 1329 | [1–453] | 1404 | [1–484] | 1451 | [1–240] |
| 1280 | [1–603] | 1330 | [1–498] | 1405 | [1–481] | 1452 | [1–239] |
| 1281 | [1–75] | 1331 | [1–86],[177–527] | 1406 | [1–769] | 1453 | [1–686] |
| 1282 | [1–512] | 1332 | [1–477] | 1407 | [1–568] | 1454 | [1–98],[344–421] |
| 1283 | [1–519] | 1333 | [1–349] | 1408 | [1–241] | 1455 | [1–506] |
| 1284 | [1–476] | 1334 | [1–394] | 1456 | [1–491] | 1503 | [1–372] |
| 1285 | [1–304],[361–478] | 1335 | [1–341] | 1457 | [1–487] | 1504 | [1–374] |
| 1286 | [226–518] | 1336 | [1–318] | 1458 | [318–437] | 1505 | [1–559] |
| 1287 | [1–490] | 1337 | [1–480] | 1459 | [1–522] | 1506 | [1–524] |
| 1288 | [1–301],[358–490] | 1338 | [1–212] | 1460 | [1–379] | 1508 | [1–692] |
| 1289 | [1–420] | 1339 | [1–409] | 1461 | [1–474] | 1509 | [1–459] |
| 1290 | [1–512] | 1340 | [255–358],[465–509] | 1462 | [425–469] | 1510 | [1–433] |
| 1291 | [1–527] | 1341 | [168–279] | 1463 | [1–830] | 1511 | [1–537] |
| 1292 | [1–160] | 1342 | [1–464] | 1464 | [354–496] | 1512 | [100–456] |
| 1293 | [1–484] | 1343 | [328–602] | 1465 | [573–623] | 1513 | [1–484] |
| 1294 | [1–366] | 1345 | [1–83],[121–225],[255–645] | 1466 | [1–82],[211–411] | 1514 | [1–509] |
| 1295 | [1–467] | 1346 | [1–83],[121–225],[255–422],[455–648] | 1467 | [1–360],[402–510] | 1515 | [1–124] |
| 1296 | [1–493] | 1347 | [1–169],[522–582] | 1468 | [1–487] | 1516 | [1–543] |
| 1297 | [1–27] | 1348 | [1–442] | 1469 | [1–481] | 1517 | [1–752] |
| 1298 | [150–472] | 1349 | [204–489] | 1470 | [1–505] | 1518 | [37–101],[154–453] |
| 1300 | [1–562] | 1350 | [177–201],[240–509] | 1471 | [1–603] | 1519 | [1–358] |
| 1301 | [170–502] | 1351 | [1–262] | 1472 | [1–113],[361–486] | 1520 | [1–426] |
| 1302 | [1–639] | 1352 | [1–452] | 1473 | [1–387] | 1521 | [1–461] |
| 1305 | [1–375] | 1353 | [1–477] | 1474 | [101–219],[254–520] | 1522 | [1–501] |
| 1306 | [1–265],[370–484] | 1354 | [1–511] | 1475 | [1–472] | 1523 | [1–498] |
| 1307 | [1–485] | 1355 | [1–619] | 1476 | [1–486] | 1524 | [1–444] |
| 1308 | [1–339] | 1356 | [1–1108] | 1477 | [1–1111] | 1525 | [1–512] |
| 1309 | [1–450] | 1357 | [1–380] | 1478 | [1–113],[361–414],[450–516] | 1526 | [1–589] |
| 1310 | [1–459] | 1358 | [1–523] | 1479 | [1–532] | 1527 | [1–566] |
| 1311 | [1–487] | 1359 | [58–389],[447–518] | 1480 | [1–468] | 1528 | [1–349] |
| 1360 | [1–486] | 1409 | [1–475] | 1481 | [244–444] | 1529 | [1–511] |
| 1361 | [212–822] | 1410 | [1–552] | 1482 | [1–415] | 1530 | [1–547] |
| 1362 | [1–642] | 1411 | [1–470] | 1483 | [1–573] | 1532 | [1–459] |
| 1363 | [1–469] | 1412 | [1–475] | 1484 | [1–450] | 1533 | [1–327],[436–509] |
| 1364 | [1–489] | 1413 | [1–273] | 1485 | [1–512] | 1534 | [1–502] |
| 1365 | [1–567] | 1414 | [1–504] | 1486 | [1–480] | 1535 | [1–597] |
| 1366 | [1–106],[526–639] | 1415 | [1–80],[114–583] | 1487 | [104–485] | 1536 | [1–492] |
| 1367 | [39–148] | 1416 | [1–65],[132–404] | 1488 | [1–520] | 1537 | [1–452] |
| 1368 | [1–498] | 1417 | [1–420] | 1489 | [1–436] | 1538 | [1–496] |
| 1369 | [1–617] | 1418 | [1–498] | 1490 | [1–678] | 1539 | [1–501] |
| 1370 | [1–452] | 1419 | [1–525] | 1491 | [1–453] | 1540 | [1–524] |
| 1371 | [1–511] | 1420 | [1–490] | 1492 | [1–483] | 1541 | [1–536] |
| 1372 | [1–514] | 1421 | [1–539] | 1493 | [1–496] | 1542 | [1–451] |
| 1373 | [1–453] | 1422 | [1–520] | 1494 | [172–229],[262–370] | 1543 | [1–923] |
| 1374 | [1–514] | 1423 | [1–476] | 1495 | [1–427] | 1544 | [1–463] |
| 1375 | [1–490] | 1424 | [90–430] | 1496 | [1–510] | 1545 | [1–480] |
| 1376 | [1–25],[266–476] | 1425 | [1–544] | 1497 | [1–86],[494–540] | 1546 | [1–213] |
| 1377 | [1–41],[159–434] | 1426 | [1–386],[469–596] | 1498 | [1–776] | 1547 | [1–465] |
| 1378 | [112–476] | 1427 | [1–356] | 1499 | [1–334] | 1548 | [1–496] |
| 1379 | [1–503] | 1428 | [1–325] | 1500 | [1–454] | 1549 | [1–468] |
| 1380 | [1–475] | 1429 | [1–540] | 1501 | [1–435] | 1550 | [1–544] |
| 1381 | [271–470] | 1430 | [1–495] | 1502 | [1–270] | 1551 | [1–508] |
| 1382 | [1–579] | 1431 | [1–494] | 1552 | [1–124],[244–375],[415–440] | 1599 | [176–207],[317–682] |
| 1383 | [1–362] | 1432 | [39–553] | 1553 | [1–679] | 1600 | [1–292] |
| 1384 | [1–902] | 1433 | [59–389] | 1554 | [1–357] | 1601 | [1–465] |
| 1385 | [1–504] | 1434 | [1–500] | 1555 | [1–546] | 1602 | [79–561] |
| 1387 | [1–337] | 1435 | [1–510] | 1556 | [1–430] | 1603 | [1–555] |
| 1388 | [1–337],[451–492] | 1436 | [1–255],[322–433] | 1557 | [1–492] | 1604 | [1–678] |
| 1389 | [1–40] | 1437 | [1–497] | 1558 | [1–540] | 1605 | [1–200] |
| 1390 | [1–412] | 1438 | [1–336] | 1559 | [1–490] | 1606 | [1–583] |
| 1391 | [1–803] | 1439 | [198–352] | 1560 | [152–584] | 1607 | [1–67],[153–433],[482–506] |
| | | | | 1561 | [1–466] | 1608 | [1–355] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 1562 | [1–525] | 1609 | [1–453] | 1680 | [1–686] | 1727 | [1–567] |
| 1563 | [1–515] | 1610 | [1–491] | 1681 | [1–412] | 1728 | ]104–507] |
| 1564 | [1–522] | 1611 | [193–354] | 1682 | [1–517] | 1729 | [1–482] |
| 1565 | [1–478] | 1612 | [1–427] | 1683 | [1–166],[455–486] | 1730 | [1–470] |
| 1566 | [1–474] | 1613 | [1–425] | 1684 | [1–523] | 1731 | [1–483] |
| 1567 | [1–521] | 1614 | [245–464] | 1685 | [1–691] | 1732 | [1–491] |
| 1568 | [1–499] | 1615 | [1–513] | 1686 | [1–448] | 1733 | [1–568] |
| 1569 | [1–673] | 1616 | [1–954] | 1687 | [1–517] | 1734 | [1–540] |
| 1570 | [69–509] | 1617 | [1–483] | 1688 | [1–456] | 1735 | [41–440] |
| 1571 | [1–482] | 1618 | [1–461] | 1689 | [1–506] | 1736 | [1–505] |
| 1572 | [1–322] | 1619 | [1–468] | 1690 | [1–464] | 1737 | [1–712] |
| 1573 | [1–502] | 1620 | [82–113],[336–397] | 1691 | [1–415] | 1738 | [1–649] |
| 1574 | [1–566] | 1621 | [284–499] | 1692 | [1–472] | 1739 | [122–231],[421–451] |
| 1575 | [213–503] | 1622 | [1–526] | 1740 | [1–296] | 1787 | [1–308] |
| 1576 | [1–529] | 1623 | [1–513] | 1741 | [1–478] | 1788 | [60–327] |
| 1577 | [1–187],[241–468] | 1624 | [1–477] | 1742 | [1–454] | 1789 | [1–462] |
| 1578 | [1–267],[303–404] | 1625 | [1–521] | 1743 | [1–630] | 1790 | [1–480] |
| 1579 | [1–494] | 1626 | [1–463] | 1744 | [1–512] | 1791 | [1–549] |
| 1580 | [1–510] | 1627 | [1–508] | 1745 | [1–767] | 1792 | [1–558] |
| 1581 | [125–435] | 1628 | [1–321] | 1746 | [1–363] | 1793 | [1–498] |
| 1582 | [1–487] | 1629 | [1–348] | 1747 | [1–380],[409–478] | 1794 | [1–477] |
| 1583 | [1–455] | 1630 | [1–486] | 1748 | [1–404] | 1795 | [1–513] |
| 1584 | [1–501] | 1631 | [1–472] | 1749 | [1–394] | 1796 | [1–41],[281–341], [383–554] |
| 1585 | [1–492] | 1632 | [1–545] | | | | |
| 1586 | [64–499] | 1633 | [1–453] | 1750 | [1–237],[311–587] | 1797 | [1–497] |
| 1587 | [90–258] | 1634 | [1–485] | 1751 | [1–380],[491–582] | 1798 | [1–513] |
| 1588 | [1–484] | 1635 | [1–342],[413–457], [493–570] | 1752 | [1–475] | 1799 | [1–503] |
| | | | | 1753 | [1–513] | 1800 | [1–489] |
| 1589 | [1–428] | 1636 | [1–476] | 1754 | [1–475] | 1801 | [1–428] |
| 1590 | [1–360] | 1637 | [1–183] | 1755 | [1–487] | 1802 | [1–509] |
| 1591 | [1–486] | 1638 | [1–437] | 1756 | [1–450] | 1803 | [1–55],[85–285], [314–361],[441–565] |
| 1592 | [1–36],[471–518] | 1639 | [1–478] | | | | |
| 1593 | [1–611] | 1640 | [1–183],[213–484] | 1757 | [1–700] | 1804 | [1–463] |
| 1594 | [1–362] | 1641 | [1–379] | 1758 | [1–517] | 1805 | [1–477] |
| 1595 | [1–467] | 1642 | [1–456] | 1759 | [1–253] | 1806 | [1–405] |
| 1596 | [1–28],[70–112], [164–254],[305–541] | 1643 | [1–600] | 1760 | [1–288] | 1807 | [1–485] |
| | | | | 1761 | [1–475] | 1808 | [1–526] |
| 1597 | [1–232],[398–435] | 1644 | [1–352] | 1762 | [1–458] | 1809 | [1–483] |
| 1598 | [1–502] | 1645 | [1–468] | 1763 | [1–420] | 1810 | [1–519] |
| 1646 | [1–488] | 1693 | [1–454] | 1764 | [1–493] | 1811 | [1–544] |
| 1647 | [1–370] | 1694 | [1–469] | 1765 | [1–544] | 1812 | [1–490] |
| 1648 | [1–414] | 1695 | [1–293] | 1766 | [1–468] | 1813 | [172–464] |
| 1649 | [1–167],[241–316], [348–398],[428–548] | 1696 | [1–577] | 1767 | [1–495] | 1814 | [1–712] |
| | | | | 1768 | [1–492] | 1815 | [128–165],[268–364], [435–516] |
| 1650 | [1–413] | 1697 | [1–465] | | | | |
| 1651 | [1–437] | 1698 | [1–433] | 1769 | [1–265] | 1816 | [1–475] |
| 1652 | [1–473] | 1699 | [1–354] | 1770 | [1–460] | 1817 | [1–534] |
| 1653 | [1–517] | 1700 | [1–782] | 1771 | [1–664] | 1818 | [1–214],[289–519] |
| 1654 | [1–505] | 1701 | [1–85] | 1772 | [1–581] | 1819 | [84–197],[353–495] |
| 1655 | [1–474] | 1702 | [1–320],[378–456] | 1773 | [51–472] | 1820 | [1–580] |
| 1656 | [1–459] | 1703 | [1–42],[127–457] | 1774 | [195–451] | 1821 | [1–493] |
| 1657 | [1–482] | 1704 | [1–130],[583–621] | 1775 | [1–394],[437–556] | 1822 | [1–579] |
| 1658 | [1–637] | 1705 | [1–544] | 1776 | [446–513] | 1823 | [1–494] |
| 1659 | [1–205],[271–381],[456–552] | 1706 | [1–489] | 1777 | [1–426] | 1824 | [1–482] |
| 1660 | [1–451] | 1707 | [1–542] | 1778 | [1–460] | 1825 | [1–292] |
| 1661 | [1–489] | 1708 | [1–457] | 1779 | [1–434] | 1826 | [1–551] |
| 1662 | [1–396] | 1709 | [1–509] | 1780 | [1–424] | 1827 | [1–547] |
| 1663 | [1–581] | 1710 | [1–494] | 1781 | [1–525] | 1828 | [1–433],[493–642] |
| 1664 | [1–737] | 1711 | [1–511] | 1782 | [295–512] | 1829 | [1–352] |
| 1665 | [37–377] | 1712 | [1–57],[177–529] | 1783 | [1–714] | 1830 | [1–462] |
| 1666 | [1–641] | 1713 | [1–356] | 1784 | [1–175],[280–456] | 1831 | [1–476] |
| 1667 | [1–474] | 1714 | [1–481] | 1785 | [1–477] | 1832 | [1–465] |
| 1668 | [36–377],[429–491] | 1715 | [1–475] | 1786 | [1–622] | 1833 | [249–429],[466–517] |
| 1669 | [1–585] | 1716 | [73–497] | 1834 | [1–454] | 1883 | [1–515] |
| 1670 | [79–267] | 1717 | [1–496] | 1835 | [1–615] | 1884 | [146],[385–491] |
| 1671 | [1–531] | 1718 | [1–476] | 1836 | [1–271],[305–458] | 1885 | [1–392] |
| 1672 | [221–471] | 1719 | [1–506] | 1837 | [1–486] | 1886 | [1–646] |
| 1673 | [1–416] | 1720 | [1–511] | 1838 | [1–470] | 1887 | [1–515] |
| 1674 | [1–476] | 1721 | [1–1062] | 1839 | [1–564] | 1888 | [1–455] |
| 1675 | [1–357] | 1722 | [1–552] | 1840 | [1–473] | 1889 | [1–457] |
| 1676 | [1–406] | 1723 | [301–498] | 1841 | [1–438] | 1890 | [1–465] |
| 1677 | [1–602] | 1724 | [1–444] | 1842 | [1–127],[43 1–476] | 1891 | [1–364],[572–640] |
| 1678 | [1–418] | 1725 | [1–527] | 1843 | [1–29],[119–363] | 1892 | [1–443] |
| 1679 | [1–459] | 1726 | [1–494] | 1844 | [1–466] | 1893 | [1–66] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 1845 | [1–570] | 1894 | [1–741] | 1968 | [1–609] | 2015 | [1–41],[205–354] |
| 1847 | [1–462] | 1895 | [1–542] | 1969 | [1–708] | 2016 | [205–479] |
| 1848 | [1–462] | 1896 | [1–482] | 1970 | [1–496] | 2017 | [1–635] |
| 1849 | [1–459] | 1897 | [1–467] | 1971 | [1–488] | 2018 | [1–502] |
| 1850 | [1–526] | 1898 | [1–480] | 1972 | [1–380],[425–570] | 2019 | [1–603] |
| 1851 | [1–480] | 1899 | [1–484] | 1973 | [328–368],[442–467] | 2020 | [1–473] |
| 1852 | [1–98],[204–517] | 1900 | [1–422] | 1974 | [1–116],[232–426] | 2021 | [1–33],[161–246],[327–515] |
| 1853 | [1–500] | 1902 | [1–25],[365–494] | | | | |
| 1854 | [1–671] | 1903 | [1–481] | 1975 | [98–470] | 2022 | [1–436] |
| 1855 | [1–402] | 1904 | [1–501] | 1976 | [105–398] | 2023 | [1–229] |
| 1856 | [1–510] | 1905 | [1–540] | 1977 | [1–478] | 2024 | [1–594] |
| 1857 | [1–465] | 1906 | [1–144],[452–486] | 2025 | [1–465] | 2072 | [1–461] |
| 1858 | [1–755] | 1907 | [1–474] | 2026 | [144–466] | 2073 | [1–351] |
| 1859 | [1–465] | 1908 | [1–485] | 2027 | [1–525] | 2074 | [1–460] |
| 1860 | [1–420],[462–487] | 1909 | [1–499] | 2028 | [1–345] | 2075 | [1–558] |
| 1861 | [1–270] | 1910 | [1–460] | 2029 | [1–470] | 2076 | [1–384] |
| 1862 | [1–613] | 1911 | [1–462] | 2030 | [140–534] | 2077 | [1–456] |
| 1863 | [175–377],[466–596] | 1912 | [1–503] | 2031 | [1–291] | 2078 | [1–453] |
| 1864 | [1–468] | 1913 | [393–509] | 2032 | [1–450] | 2079 | [1–527] |
| 1865 | [1–492] | 1914 | [1–456] | 2033 | [1–558] | 2080 | [1–469] |
| 1866 | [1–503] | 1915 | [1–506] | 2034 | [1–506] | 2081 | [1–506] |
| 1867 | [1–545],[576–934] | 1916 | [1–234],[284–399],[440–469] | 2035 | [1–492] | 2082 | [1–685] |
| | | | | 2036 | [1–587] | 2083 | [1–504] |
| 1868 | [1–475] | 1917 | [63–484] | 2037 | [1–507] | 2084 | [1–463] |
| 1869 | [1–476] | 1918 | [97–453] | 2038 | [1–99],[128–466] | 2085 | [1–54],[244–419] |
| 1870 | [1–440],[482–509] | 1919 | [1–471] | 2039 | [1–480] | 2086 | [1–504] |
| 1871 | [1–448] | 1920 | [1–663] | 2040 | [1–501] | 2087 | [1–496] |
| 1872 | [1–505] | 1921 | [1–488] | 2041 | [1–395] | 2088 | [1–40],[73–432] |
| 1873 | [1–935] | 1922 | [32–492] | 2042 | [1–494] | 2089 | [1–483] |
| 1874 | [1–514] | 1923 | [1–42],[123–388] | 2043 | [1–483] | 2090 | [1–480] |
| 1876 | [1–436] | 1924 | [1–473] | 2044 | [1–481] | 2091 | [1–488] |
| 1877 | [1–667] | 1925 | [1–487] | 2045 | [1–471] | 2092 | [1–483] |
| 1878 | [1–787] | 1926 | [1–464] | 2046 | [1–462] | 2093 | [1–311] |
| 1879 | [1–493] | 1927 | [1–475] | 2047 | [1–594] | 2094 | [1–159],[284–452] |
| 1880 | [1–466] | 1928 | [47–496] | 2048 | [1–526] | 2095 | [1–446] |
| 1881 | [1–319] | 1929 | [1–471] | 2049 | [1–421] | 2096 | [1–495] |
| 1882 | [1–501] | 1930 | [1–488] | 2050 | [1–483] | 2097 | [1–478] |
| 1931 | [1–36],[248–475] | 1978 | [1–491] | 2051 | [1–539] | 2098 | [1–460] |
| 1932 | [1–232],[272–509] | 1979 | [30–212] | 2052 | [1–399] | 2099 | [1–223],[278–346],[437–477] |
| 1933 | [1–451] | 1980 | [1–370] | | | | |
| 1934 | [1–530] | 1981 | [1–334] | 2053 | [414–532],[731–820) | 2100 | [1–160],[285–505] |
| 1935 | [1–63],[239–320],[421–542] | 1982 | [1–471] | 2054 | [1–402] | 2101 | [1–459] |
| 1936 | [1–650] | 1983 | [1–142] | 2055 | [1–662] | 2102 | [1–374] |
| 1937 | [1–302] | 1984 | [1–834] | 2056 | [1–154] | 2103 | [1–384] |
| 1938 | [1–471] | 1985 | [1–507] | 2057 | [1–262] | 2104 | [1–554] |
| 1939 | [1–294] | 1986 | [1–491] | 2058 | [144–475] | 2105 | [1–476] |
| 1940 | [1–294] | 1987 | [1–413] | 2059 | [1–483] | 2106 | [1–71],[113–491] |
| 1941 | [262–315] | 1988 | [1–350] | 2060 | [1–483] | 2107 | [1–461] |
| 1942 | [1–302] | 1989 | [1–458] | 2061 | [1–466] | 2108 | [1–544] |
| 1943 | [1–310] | 1990 | [1–487] | 2062 | [1–422] | 2109 | [1–515] |
| 1944 | [1–281] | 1991 | [1–538] | 2063 | [1–490] | 2110 | [1–352] |
| 1945 | [1–654] | 1992 | [1–453] | 2064 | [1–341] | 2111 | [92–178] |
| 1946 | [1–521] | 1993 | [1–486] | 2065 | [1–448] | 2112 | [1–443] |
| 1947 | [1–1013] | 1994 | [1–482] | 2066 | [1–222] | 2113 | [1–342] |
| 1948 | [1–510] | 1995 | [1–621] | 2067 | [1–461] | 2114 | [62–479] |
| 1949 | [1–472] | 1996 | [1–511] | 2068 | [1–174),[207–617] | 2115 | [[1–470] |
| 1950 | [1–533] | 1997 | [1–477] | 2069 | [1–503] | 2116 | [1–403] |
| 1951 | [1–427] | 1998 | [1–543] | 2070 | [1–499] | 2117 | [1–478] |
| 1952 | [1–449] | 1999 | [1–355] | 2071 | [1–343] | 2118 | [1–485] |
| 1953 | [1–515] | 2000 | [1–497] | 2119 | [1–302],[337–434] | 2166 | [1–520] |
| 1954 | [1–509] | 2001 | [1–486] | 2120 | [1–375] | 2167 | [1–512] |
| 1955 | [1–449] | 2002 | [1–453] | 2121 | [1–407] | 2168 | [1–398] |
| 1956 | [1–482] | 2003 | [85–567] | 2122 | [1–395] | 2169 | [1–493] |
| 1957 | [1–486] | 2004 | [95–490] | 2123 | [1–533] | 2170 | [1–532] |
| 1958 | [1–449] | 2005 | [1–626] | 2124 | [1–448] | 2171 | [1–419] |
| 1959 | [1–450] | 2006 | [319–800] | 2125 | [1–437] | 2172 | [1–506] |
| 1960 | [1–552] | 2007 | [1–432] | 2126 | [1–455] | 2173 | [1–491] |
| 1961 | [1–191],[252–333] | 2008 | [1–495] | 2127 | [1–428] | 2174 | [1–564] |
| 1962 | [1–508] | 2009 | [1–34],[20–216],[245–522] | 2128 | [1–359] | 2175 | [1–474] |
| 1963 | [1–482] | 2010 | [51–421] | 2129 | [1–546] | 2176 | [1–520] |
| 1964 | [1–534] | 2011 | [1–514] | 2130 | [1–501] | 2177 | [1–452] |
| 1965 | [1–491] | 2012 | [1–461] | 2131 | [1–513] | 2178 | [1–456] |
| 1966 | [1–497] | 2013 | [1–42],[206–355] | 2132 | [1–388] | 2179 | [1–482] |
| 1967 | [1–549] | 2014 | [1–518] | 2133 | [1–432] | 2180 | [87–323] |

TABLE IVb-continued (Novelty: 100%)

| Seq Id No | Positions of preferred fragments | Seq Id No | Positions of preferred fragments | Seq Id No | Positions of preferred fragments | Seq Id No | Positions of preferred fragments |
|---|---|---|---|---|---|---|---|
| 2134 | [1–277] | 2181 | [1–467] | 2254 | [1–468] | 2301 | [1–369] |
| 2135 | [1–503] | 2182 | [1–474] | 2255 | [1–535] | 2302 | [1–428] |
| 2136 | [209–458] | 2183 | [1–469] | 2256 | [1–553] | 2303 | [1–507] |
| 2137 | [1–508] | 2184 | [1–379] | 2257 | [1–469] | 2304 | [164–471] |
| 2138 | [1–476] | 2185 | [1–413] | 2258 | [1–508] | 2305 | [1–374] |
| 2139 | [1–479] | 2186 | [1–483] | 2259 | [139–420] | 2306 | [1–457] |
| 2140 | [1–428] | 2187 | [1–451] | 2307 | [67–469] | 2354 | [1–494] |
| 2141 | [1–463] | 2188 | [1–476] | 2308 | [1–499] | 2355 | [1–479] |
| 2142 | [1–497] | 2189 | [1–43] | 2309 | [1–507] | 2356 | [1–79] |
| 2143 | [236–459] | 2190 | [1–379],[419–453] | 2310 | [1–472] | 2357 | [1–456] |
| 2144 | [1–533] | 2191 | [256–569] | 2311 | [1–478] | 2358 | [1–473] |
| 2145 | [149–217] | 2192 | [1–482] | 2312 | [1–468] | 2359 | [1–473] |
| 2146 | [1–431] | 2193 | [34–462] | 2313 | [45–329] | 2360 | [1–540] |
| 2147 | [1–408] | 2194 | [1–487] | 2314 | [1–302] | 2361 | [1–470] |
| 2148 | [1–564] | 2195 | [1–568] | 2315 | [1–372] | 2362 | [1–485] |
| 2149 | [1–295] | 2196 | [1–306] | 2316 | [1–423] | 2363 | [1–495] |
| 2150 | [1–336] | 2197 | [1–462] | 2317 | [1–476] | 2364 | [1–358] |
| 2151 | [1–449] | 2198 | [1–439] | 2318 | [1–238] | 2365 | [154–482] |
| 2152 | [1–572] | 2199 | [1–489] | 2319 | [1–499] | 2366 | [1–355] |
| 2153 | [1–223] | 2200 | [1–544] | 2320 | [1–473] | 2367 | [1–88],[150–469] |
| 2154 | [1–523] | 2201 | [1–485] | 2321 | [1–67],[215–466] | 2368 | [88–218],[269–333],[379–472] |
| 2155 | [1–499] | 2202 | [1–492] | | | | |
| 2156 | [1–600] | 2203 | [1–474] | 2322 | [234–424] | 2369 | [93–262],[326–489] |
| 2157 | [400–510] | 2204 | [1–361] | 2323 | [1–489] | 2370 | [1–248],[307–454] |
| 2158 | [1–486] | 2205 | [1–513] | 2324 | [1–182] | 2371 | [1–388] |
| 2159 | [1–488] | 2206 | [1–481] | 2325 | [1–460] | 2372 | [1–556] |
| 2160 | [1–503] | 2207 | [1–31] | 2326 | [1–269] | 2373 | [1–523] |
| 2161 | [1–470] | 2208 | [1–73],[399–463] | 2327 | [1–493] | 2374 | [1–446] |
| 2162 | [1–169],[332–391] | 2209 | [1–892] | 2328 | [1–496] | 2375 | [1–585] |
| 2163 | [1–458] | 2210 | [1–54],[180–499] | 2329 | [1–493] | 2376 | [1–520] |
| 2164 | [1–495] | 2211 | [1–455] | 2330 | [1–413] | 2377 | [1–487] |
| 2165 | [1–145] | 2212 | [1–474] | 2331 | [1–492] | 2378 | [1–459] |
| 2213 | [1–499] | 2260 | [1–472] | 2332 | [1–452] | 2379 | [1–65],[471–535] |
| 2214 | [1–457] | 2261 | [1–460] | 2333 | [1–456] | 2380 | [1–65],[200–485] |
| 2215 | [1–479] | 2262 | [1–599] | 2334 | [1–443] | 2381 | [37–269] |
| 2216 | [1–481] | 2263 | [59–489] | 2335 | [1–413] | 2382 | [1–155],[184–437] |
| 2217 | [1–239] | 2264 | [1–460] | 2336 | [1–479] | 2383 | [1–489] |
| 2218 | [1–162],[358–510] | 2265 | [105–460] | 2337 | [1–311] | 2384 | [1–660] |
| 2219 | [1–471] | 2266 | [1–386] | 2338 | [1–450] | 2385 | [1–491] |
| 2220 | [1–473] | 2267 | [1–472] | 2339 | [45–378] | 2386 | [1–459] |
| 2221 | [1–286] | 2268 | [1–484] | 2340 | [1–445] | 2387 | [1–517] |
| 2222 | [127–197] | 2269 | [1–502] | 2341 | [1–339] | 2388 | [1–516] |
| 2223 | [77–459] | 2270 | [1–503] | 2342 | [1–295] | 2389 | [1–499] |
| 2224 | [1–102],[185–383] | 2271 | [1–563] | 2343 | [67–478] | 2390 | [199–277],[318–386],[423–523] |
| 2225 | [1–422] | 2272 | [1–486] | | | | |
| 2226 | [1–93],[225–333],[390–526] | 2273 | [1–459] | 2344 | [1–516] | 2391 | [1–45],[282–458] |
| | | | | 2345 | [1–498] | 2392 | [1–856] |
| 2227 | [130–464] | 2274 | [1–330] | 2346 | [1–466] | 2393 | [58–457] |
| 2228 | [1–489] | 2275 | [111–153],[487–514] | 2347 | [1–480] | 2394 | [1–468] |
| 2229 | [1–296] | 2276 | [1–467] | 2348 | [1–202],[236–415] | 2395 | [1–475] |
| 2230 | [1–440] | 2277 | [1–451] | 2349 | [1–317] | 2396 | [1–497] |
| 2231 | [48–457] | 2278 | [1–462] | 2350 | [1–503] | 2397 | [1–584] |
| 2232 | [1–423] | 2279 | [1–372] | 2351 | [1–616] | 2398 | [1–479] |
| 2233 | [1–475] | 2280 | [1–457] | 2352 | [1–115] | 2399 | [1–559] |
| 2234 | [1–459] | 2281 | [1–484] | 2353 | [1–469] | 2400 | [1–459] |
| 2235 | [1–481] | 2282 | [1–537] | 2401 | [189–487] | 2448 | [1–546] |
| 2236 | [1–452] | 2283 | [1–370] | 2402 | [1–306] | 2449 | [1–517] |
| 2237 | [1–415] | 2284 | [1–559] | 2403 | [1–468] | 2450 | [1–463] |
| 2238 | [1–456] | 2285 | [1–464] | 2404 | [1–341] | 2451 | [1–349] |
| 2239 | [1–508] | 2286 | [1–460] | 2405 | [1–467] | 2452 | [1–467] |
| 2240 | [44–471] | 2287 | [1–511] | 2406 | [1–358] | 2453 | [1–571] |
| 2241 | [1–213],[409–467] | 2288 | [1–274],[330–439] | 2407 | [1–438] | 2454 | [1–551] |
| 2242 | [1–473] | 2289 | [34–478] | 2408 | [1–181],[279–374] | 2455 | [1–461] |
| 2243 | [1–333] | 2290 | [1–505] | 2409 | [1–516] | 2456 | [1–481] |
| 2244 | [1–511] | 2291 | [85–502] | 2410 | [1–468] | 2457 | [1–468] |
| 2245 | [1–472] | 2292 | [1–478] | 2411 | [1–325],[394–857] | 2458 | [1–492] |
| 2246 | [1–463] | 2293 | [295–477] | 2412 | [1–506] | 2459 | [1–492] |
| 2247 | [1–494] | 2294 | [1–461] | 2413 | [43–512] | 2460 | [1–511] |
| 2248 | [1–467] | 2295 | [1–311] | 2414 | [1–62],[98–129],[220–548] | 2461 | [1–675] |
| 2249 | [1–419] | 2296 | [1–346] | 2415 | [1–268] | 2462 | [249–498] |
| 2250 | [1–474] | 2297 | [1–476] | 2416 | [1–490] | 2463 | [1–482] |
| 2251 | [1–42],[113–305],[368–499] | 2298 | [1–386] | 2417 | [1–930] | 2464 | [1–499] |
| 2252 | [1–529] | 2299 | [1–181],[216–274] | 2418 | [1–489] | 2465 | [59–498] |
| 2253 | [1–381] | 2300 | [1–433] | 2419 | [1–32],[188–302] | 2466 | [322–489] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 2420 | [1–531] | 2467 | [1–511] | 2542 | [1–484] | 2590 | [1–314],[407–497] |
| 2421 | [1–476] | 2468 | [378–493] | 2591 | [1–541] | 2638 | [80–388] |
| 2422 | [37–360] | 2469 | [1–452] | 2592 | [1–575] | 2639 | [1–444] |
| 2423 | [1–501] | 2470 | [1–556] | 2593 | [179–490] | 2640 | [69–404] |
| 2424 | [1–347] | 2471 | [1–287] | 2594 | [1–522] | 2641 | [66–394] |
| 2425 | [1–488] | 2472 | [1–295] | 2595 | [1–627] | 2642 | [1–444] |
| 2426 | [1–506] | 2473 | [1–465] | 2596 | [1–176],[207–506] | 2643 | [1–439] |
| 2427 | [1–413] | 2474 | [1–451] | 2597 | [1–588] | 2644 | [1–493] |
| 2428 | [1–392] | 2475 | [1–527] | 2598 | [1–504] | 2645 | [1–444] |
| 2429 | [1–391] | 2476 | [91–397] | 2599 | [1–97],[169–465] | 2646 | [1–448] |
| 2430 | [1–510] | 2477 | [1–364] | 2600 | [1–627] | 2647 | [1–522] |
| 2431 | [1–542] | 2478 | [1–467] | 2601 | [1–542] | 2648 | [1–481] |
| 2432 | [1–490] | 2479 | [1–360] | 2602 | [1–451] | 2649 | [1–600] |
| 2433 | [1–537] | 2480 | [1–502] | 2603 | [1–453] | 2650 | [1–492] |
| 2434 | [1–458] | 2481 | [1–537] | 2604 | [148–455] | 2651 | [1–357] |
| 2435 | [1–557] | 2482 | [1–479] | 2605 | [1–538] | 2652 | [1–386] |
| 2436 | [67–493] | 2483 | [91–397] | 2606 | [1–270] | 2653 | [1–361],[509–540] |
| 2437 | [1–363] | 2484 | [1–514] | 2607 | [1–235] | 2654 | [1–440] |
| 2438 | [1–433] | 2485 | [1–582] | 2608 | [1–471] | 2655 | [1–512] |
| 2439 | [1–500],[557–581] | 2486 | [1–420] | 2609 | [1–530] | 2657 | [1–461] |
| 2440 | [1–522] | 2487 | [1–554] | 2610 | [1–489] | 2658 | [1–414] |
| 2441 | [1–319],[352–473] | 2488 | [1–465] | 2611 | [1–468] | 2659 | [1–336] |
| 2442 | [1–444] | 2489 | [1–410] | 2612 | [1–720] | 2660 | [1–341],[379–444] |
| 2443 | [49–451] | 2490 | [1–493] | 2613 | [1–251],[315–556] | 2661 | [1–337] |
| 2444 | [1–451] | 2491 | [1–461] | 2614 | [1–803] | 2662 | [1–465] |
| 2445 | [1–504] | 2492 | [69–533] | 2615 | [1–491] | 2663 | [1–489] |
| 2446 | [1–430] | 2493 | [1–895] | 2616 | [1–478] | 2664 | [1–490] |
| 2447 | [1–485] | 2494 | [1–561] | 2617 | [1–578] | 2665 | [1–470] |
| 2495 | [1–451] | 2543 | [1–544] | 2618 | [1–154],[291–407] | 2666 | [1–396] |
| 2496 | [1–354] | 2544 | [1–25],[56–165],[279–450] | 2619 | [1–276],[313–356],[401–460] | 2667 | [1–368] |
| 2497 | [1–793] | 2545 | [1–584] | 2620 | [1–488] | 2668 | [1–42],[82–553] |
| 2498 | [1–491] | 2546 | [1–438] | 2621 | [1–547] | 2669 | [1–485] |
| 2499 | [1–780] | 2547 | [1–578] | 2622 | [1–429] | 2670 | [1–455] |
| 2500 | [1–300] | 2548 | [159–497] | 2623 | [1–437] | 2671 | [11–117],[508–607] |
| 2501 | [1–466] | 2549 | [1–459] | 2624 | [1–452] | 2672 | [213–479] |
| 2502 | [1–405] | 2550 | [1–478] | 2625 | [1–445] | 2673 | [367–452] |
| 2503 | [1–476] | 2551 | [1–424] | 2626 | [1–442] | 2674 | [1–330] |
| 2504 | [1–219],[327–456] | 2552 | [44–484] | 2627 | [1–446] | 2675 | [1–748] |
| 2505 | [1–180],[509–543] | 2553 | [1–51],[249–390] | 2628 | [1–448] | 2676 | [1–502] |
| 2506 | [1–507] | 2554 | [1–488] | 2629 | [1–441] | 2677 | [1–497] |
| 2507 | [1–311],[388–513] | 2555 | [1–263],[316–477] | 2630 | [1–475] | 2678 | [1–468] |
| 2508 | [1–488] | 2556 | [1–502] | 2631 | [1–443] | 2679 | [1–322],[397–482] |
| 2509 | [1–482] | 2557 | [1–528] | 2632 | [1–469] | 2680 | [1–520] |
| 2510 | [1–489] | 2558 | [1–513] | 2633 | [1–452] | 2681 | [1–484] |
| 2511 | [1–508] | 2559 | [1–346] | 2634 | [1–439] | 2682 | [1–481] |
| 2512 | [1–471] | 2560 | [1–505] | 2635 | [1–488] | 2683 | [1–69],[250–496] |
| 2513 | [1–47],[95–478] | 2561 | [1–473] | 2636 | [1–447] | 2684 | [1–470] |
| 2514 | [1–498] | 2562 | [1–589] | 2637 | [1–484] | 2685 | [1–478] |
| 2515 | [48–152],[198–446] | 2563 | [1–502] | 2686 | [48–350] | 2733 | [1–606] |
| 2516 | [1–553] | 2564 | [1–513] | 2687 | [1–451] | 2734 | [121–554] |
| 2517 | [1–468] | 2566 | [64–510] | 2688 | [1–488] | 2735 | [54–142] |
| 2518 | [1–484] | 2567 | [1–361] | 2689 | [1–505] | 2736 | [1–485] |
| 2519 | [1–488] | 2568 | [1–70],[342–483] | 2690 | [1–491] | 2737 | [1–552] |
| 2520 | [443–525] | 2569 | [1–500] | 2691 | [1–507] | 2738 | [1–451] |
| 2521 | [1–457] | 2570 | [1–624] | 2692 | [1–526] | 2739 | [1–492] |
| 2522 | [1–49],[125–452] | 2571 | [1–483] | 2693 | [1–523] | 2740 | [1–549] |
| 2523 | [1–538] | 2572 | [1–70],[184–345] | 2694 | [1–572] | 2741 | [1–493] |
| 2524 | [1–600] | 2573 | [37–78],[177–363] | 2695 | [1–544] | 2742 | [1–35],[64–182],[251–453] |
| 2525 | [1–390] | 2574 | [1–834] | | | | |
| 2526 | [1–469] | 2575 | [1–530] | 2696 | [1–494] | 2743 | [1–546] |
| 2527 | [1–521] | 2576 | [1–456] | 2697 | [1–100] | 2744 | [1–484] |
| 2528 | [1–513] | 2577 | [1–43],[98–534] | 2698 | [1–292],[328–461] | 2745 | [1–534] |
| 2530 | [274–500] | 2578 | [1–43],[98–534] | 2699 | [1–499] | 2746 | [1–491] |
| 2531 | [190–484] | 2579 | [1–556] | 2700 | [1–552] | 2747 | [132–330] |
| 2532 | [1–481] | 2580 | [1–622] | 2701 | [1–466] | 2748 | [1–472] |
| 2533 | [1–429],[459–487] | 2581 | [1–231] | 2702 | [1–224],[253–308],[385–409] | 2749 | [1–407] |
| 2534 | [1–465] | 2582 | [1–211] | 2703 | [1–511] | 2750 | [1–607] |
| 2535 | [1–463] | 2583 | [1–231] | 2704 | [1–464] | 2751 | [1–548] |
| 2536 | [1–484] | 2584 | [155–647] | 2705 | [1–590] | 2752 | [1–496] |
| 2537 | [1–125],[292–533] | 2585 | [1–476] | 2706 | [97–484] | 2753 | [1–352] |
| 2538 | [1–516] | 2586 | [1–482] | 2707 | [64–196],[298–483] | 2754 | [1–447] |
| 2539 | [1–183],[317–484] | 2587 | [1–560] | 2708 | [1–517] | 2755 | [79–302],[465–526] |
| 2540 | [1–985] | 2588 | [1–541] | 2709 | [1–474] | 2757 | [1–551] |
| 2541 | [1–508] | 2589 | [1–492] | 2710 | [1–473] | 2758 | [1–476] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 2711 | [1–513] | 2759 | [131–563] | 2880 | [1–482] | 2927 | [1–577] |
| 2712 | [1–513] | 2760 | [1–670] | 2881 | [1–575] | 2928 | [1–489] |
| 2713 | [1–501] | 2761 | [1–183] | 2882 | [1–543] | 2929 | [1–474] |
| 2714 | [1–506] | 2762 | [1–241],[355–472] | 2883 | [1–456] | 2930 | [1–466] |
| 2715 | [1–471] | 2763 | [1–48] | 2884 | [1–560] | 2931 | [1–199],[376–709] |
| 2716 | [1–525] | 2764 | [1–481] | 2885 | [1–478] | 2932 | [1–581] |
| 2717 | [1–515] | 2765 | [1–509] | 2886 | [1–36] | 2933 | [1–300],[342–407], [455–530] |
| 2718 | [1–521] | 2766 | [1–436] | | | | |
| 2719 | [1–399] | 2767 | [1–424] | 2887 | [1–503] | 2934 | [1–218],[410–486] |
| 2720 | [1–107],[138–481] | 2768 | [1–423] | 2888 | [102–166] | 2935 | [221–471] |
| 2721 | [1–497] | 2769 | [1–556] | 2889 | [1–467] | 2936 | [1–464] |
| 2722 | [1–126],[382–414] | 2770 | [1–333] | 2890 | [174–331],[399–482] | 2937 | [1–515] |
| 2723 | [1–498] | 2771 | [1–320] | 2891 | [1–489] | 2938 | [57–264],[439–772] |
| 2724 | [1–506] | 2772 | [1–247],[403–506] | 2892 | [65–284],[329–499] | 2939 | [35–103],[240–278] |
| 2725 | [1–890] | 2773 | [1–517] | 2893 | [1–459] | 2940 | [1–199],[376–687] |
| 2726 | [1–517] | 2774 | [1–572] | 2894 | [1–547] | 2941 | [1–440] |
| 2727 | [1–583] | 2775 | [1–647] | 2895 | [1–76],[223–459] | 2942 | [1–179],[215–518] |
| 2728 | [1–201],[324–569] | 2776 | [1–504] | 2896 | [1–296],[349–644] | 2943 | [1–509] |
| 2729 | [1–549] | 2777 | [69–506] | 2897 | [1–463] | 2944 | [1–465] |
| 2730 | [1–153],[276–470] | 2778 | [1–490] | 2898 | [1–527] | 2945 | [1–543] |
| 2731 | [129–279] | 2779 | [1–471] | 2899 | [1–511] | 2946 | [1–402] |
| 2732 | [1–477] | 2780 | [1–502] | 2900 | [1–390],[451–486] | 2947 | [226–296] |
| 2781 | [1–630] | 2828 | [1–516] | 2901 | [1–284] | 2948 | [1–233],[340–498] |
| 2782 | [133–482] | 2829 | [1–152] | 2902 | [1–721] | 2949 | [46–505] |
| 2783 | [1–195],[428–488] | 2830 | [1–535] | 2903 | [1–269] | 2950 | [1–540] |
| 2784 | [1–555] | 2831 | [1–421] | 2904 | [1–506] | 2951 | [1–506] |
| 2785 | [1–527] | 2832 | [1–625] | 2905 | [1–474] | 2952 | [1–525] |
| 2786 | [1–430] | 2833 | [1–461] | 2906 | [1–387] | 2953 | [1–272] |
| 2787 | [1–527] | 2834 | [1–444] | 2907 | [1–523] | 2954 | [1–519] |
| 2788 | [1–504] | 2835 | [1–400] | 2908 | [1–539] | 2955 | [1–395] |
| 2789 | [1–485] | 2836 | [1–542] | 2909 | [1–255] | 2956 | [1–251] |
| 2790 | [1–487] | 2837 | [1–467] | 2910 | [1–471] | 2957 | [1–257] |
| 2791 | [1–483] | 2838 | [1–517] | 2911 | [1–531] | 2958 | [1–462] |
| 2792 | [1–903] | 2839 | [1–469] | 2912 | [1–475] | 2959 | [1–590] |
| 2793 | [1–472] | 2840 | [1–414] | 2913 | [1–483] | 2960 | [1–271] |
| 2794 | [1–501] | 2841 | [1–284] | 2914 | [1–122],[320–571] | 2961 | [1–371] |
| 2795 | [1–455] | 2842 | [1–453] | 2915 | [1–495] | 2962 | [1–499] |
| 2796 | [1–460] | 2843 | [50–473] | 2916 | [1–453] | 2963 | [1–539] |
| 2797 | [1–459] | 2844 | [1–88],[201–305] | 2917 | [77–368] | 2964 | [1–499] |
| 2798 | [1–457] | 2845 | [1–192],[493–567] | 2918 | [1–236] | 2965 | [80–452] |
| 2799 | [1–462] | 2846 | [1–158] | 2919 | [1–519] | 2966 | [1–452] |
| 2800 | [1–455] | 2847 | [1–72] | 2920 | [1–454] | 2968 | [1–97],[411–575] |
| 2801 | [1–457] | 2848 | [1–158] | 2921 | [1–392],[452–492] | 2969 | [1–520] |
| 2802 | [1–457] | 2849 | [1–521] | 2970 | [1–447],[508–534] | 3017 | [1–469] |
| 2803 | [1–456] | 2850 | [1–453] | 2971 | [1–491] | 3018 | [1–531] |
| 2804 | [1–458] | 2851 | [1–470] | 2972 | [1–477] | 3019 | [1–390],[452–610] |
| 2805 | [1–472] | 2852 | [1–512] | 2973 | [1–119] | 3020 | [119–466] |
| 2806 | [1–483] | 2853 | [1–483] | 2974 | [36–517] | 3021 | [1–530] |
| 2807 | [1–474] | 2854 | [1–522] | 2975 | [1–611] | 3022 | [1–436] |
| 2808 | [1–464] | 2855 | [1–527] | 2976 | [1–470] | 3023 | [1–494] |
| 2809 | [1–262],[316–605] | 2856 | [1–528] | 2977 | [1–398] | 3024 | [1–488] |
| 2810 | [1–510] | 2857 | [1–444] | 2978 | [1–517] | 3025 | [471–582] |
| 2811 | [1–499] | 2858 | [1–496] | 2979 | [1–491] | 3026 | [1–355] |
| 2812 | [1–515] | 2859 | [1–488] | 2980 | [1–484] | 3027 | [1–807] |
| 2813 | [1–832] | 2860 | [1–510] | 2981 | [140–291],[399–577] | 3028 | [1–254] |
| 2814 | [1–41],[98–552] | 2861 | [1–486] | 2982 | [51–555] | 3029 | [1–533] |
| 2815 | [1–33],[200–407] | 2862 | [1–490] | 2983 | [1–507] | 3030 | [1–505] |
| 2816 | [1–31] | 2863 | [1–330],[437–536] | 2984 | [1–349] | 3031 | [1–520] |
| 2817 | [1–494] | 2864 | [1–495] | 2985 | [1–783] | 3032 | [1–585] |
| 2818 | [1–253] | 2865 | [1–497] | 2986 | [128–502] | 3033 | [76–420] |
| 2819 | [1–529] | 2866 | [1–494] | 2987 | [1–342] | 3034 | [1–407] |
| 2820 | [1–1035] | 2867 | [1–539] | 2988 | [1–272] | 3035 | [1–156] |
| 2821 | [1–492] | 2868 | [1–713] | 2989 | [1–478] | 3036 | [1–375] |
| 2822 | [1–509] | 2869 | [1–476] | 2990 | [1–482] | 3037 | [1–462] |
| 2823 | [1–515] | 2870 | [69–145],[267–531] | 2991 | [1–515] | 3038 | [1–510] |
| 2824 | [1–524] | 2871 | [69–145],[267–468] | 2992 | [1–480] | 3039 | [1–139],[260–483] |
| 2825 | [138–524] | 2872 | [49–496] | 2993 | [1–476] | 3040 | [1–93],[149–409] |
| 2826 | [218–469] | 2873 | [1–524] | 2994 | [1–499] | 3041 | [1–524] |
| 2827 | [1–476] | 2874 | [1–486] | 2995 | [1–509] | 3042 | [1–504] |
| 2875 | [1–494] | 2922 | [1–518] | 2996 | [49–466] | 3043 | [1–486] |
| 2876 | [1–486] | 2923 | [1–504] | 2997 | [1–486] | 3044 | [1–491] |
| 2877 | [1–706] | 2924 | [1–615] | 2998 | [1–546] | 3045 | [1–519] |
| 2878 | [1–531] | 2925 | [1–514] | 2999 | [1–345] | 3046 | [1–477] |
| 2879 | [1–502] | 2926 | [1–483] | 3000 | [1–482] | 3047 | [1–523],[661–691] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 3001 | [1–26] | 3048 | [1–465] | 3170 | [1–563] | 3218 | [1–517] |
| 3002 | [1–483] | 3049 | [177–300],[367–563] | 3171 | [1–409] | 3219 | [1–509] |
| 3003 | [1–518] | 3050 | [1–515] | 3172 | [1–172],[218–470],[596–826] | 3220 | [1–461] |
| 3004 | [1–393] | 3051 | [1–642] | 3173 | [1–455] | 3221 | [1–492] |
| 3005 | [1–61],[354–557] | 3052 | [160–751] | 3174 | [1–465] | 3222 | [1–347] |
| 3006 | [1–388] | 3053 | [1–418],[760–787] | 3175 | [1–484] | 3223 | [1–517] |
| 3007 | [1–548] | 3054 | [1–386] | 3176 | [1–45],[106–273],[307–482] | 3224 | [1–473] |
| 3008 | [1–513] | 3055 | [1–561] | 3177 | [1–482] | 3225 | [1–497] |
| 3009 | [1–491] | 3056 | [1–233] | 3178 | [1–497] | 3226 | [1–601] |
| 3010 | [138–507] | 3057 | [1–468] | 3179 | [1–485] | 3227 | [1–516] |
| 3011 | [1–674] | 3058 | [1–558] | 3180 | [1–401] | 3228 | [1–513] |
| 3012 | [1–505] | 3059 | [1–481] | 3181 | [1–246],[372–442],[488–517] | 3229 | [1–525] |
| 3013 | [1–557] | 3060 | [1–494] | 3182 | [1–577] | 3230 | [1–103],[448–548] |
| 3014 | [1–467] | 3061 | [1–523] | 3183 | [1–84],[149–207],[320–451] | 3231 | [1–103],[381–440] |
| 3015 | [1–338] | 3062 | [1–537] | 3184 | [1–394] | 3232 | [1–523] |
| 3016 | [1–513] | 3063 | [1–470] | 3185 | [1–556] | 3233 | [1–399] |
| 3064 | [1–519] | 3113 | [1–451] | 3186 | [1–539] | 3234 | [197–532] |
| 3065 | [1–494] | 3114 | [1–525] | 3188 | [1–444] | 3235 | [1–436] |
| 3066 | [1–456] | 3115 | [1–475] | 3189 | [1–225] | 3236 | [540–580] |
| 3067 | [1–561] | 3116 | [1–445] | 3190 | [1–530] | 3237 | [1–499] |
| 3068 | [1–116],[184–340],[408–463] | 3117 | [1–498] | 3191 | [1–452] | 3238 | [342–587] |
| 3069 | [1–513] | 3118 | [1–509] | 3192 | [1–527] | 3239 | [1–748] |
| 3070 | [1–484] | 3119 | [1–284] | 3193 | [1–757] | 3240 | [1–468] |
| 3071 | [1–473] | 3120 | [1–494] | 3194 | [1–503] | 3241 | [1–690] |
| 3072 | [1–297] | 3121 | [232–436],[604–632] | 3195 | [1–486] | 3242 | [1–92],[172–266],[359–525] |
| 3073 | [1–56],[156–200],[243–506] | 3122 | [232–616] | 3196 | [161–390],[420–489] | 3243 | [1–466] |
| 3074 | [1–484] | 3123 | [1–483] | 3197 | [1–494] | 3244 | [1–504] |
| 3075 | [125–459] | 3124 | [1–479] | 3198 | [1–336] | 3245 | [1–597] |
| 3076 | [1–500] | 3125 | [1–492] | 3199 | [1–328] | 3246 | [1–460] |
| 3077 | [1–44] | 3126 | [1–707] | 3200 | [1–484] | 3247 | [1–565] |
| 3078 | [1–419] | 3127 | [372–503] | 3201 | [1–463] | 3248 | [1–80],[128–432] |
| 3079 | [1–456] | 3128 | [146–479] | 3202 | [1–473] | 3249 | [1–314] |
| 3080 | [1–500] | 3129 | [1–464] | 3203 | [1–85],[379–419] | 3250 | [1–503] |
| 3081 | [1–566] | 3130 | [1–497] | 3204 | [1–443] | 3251 | [1–456] |
| 3082 | [1–529] | 3131 | [1–316] | 3205 | [1–533] | 3252 | [1–344] |
| 3083 | [1–463] | 3132 | [1–464] | 3206 | [1–464] | 3253 | [1–474] |
| 3084 | [1–528] | 3133 | [1–58],[93–546] | 3207 | [1–521] | 3254 | [1–552] |
| 3085 | [1–279] | 3134 | [1–52],[87–556] | 3255 | [1–315],[368–482] | 3302 | [1–418] |
| 3086 | [1–513] | 3135 | [56–452] | 3256 | [1–463] | 3303 | [1–462] |
| 3087 | [290–392] | 3136 | [1–52],[87–460] | 3257 | [1–496] | 3304 | [1–406] |
| 3088 | [290–398] | 3137 | [1–341] | 3258 | [1–533] | 3305 | [101–460] |
| 3099 | [290–400] | 3138 | [1–489] | 3259 | [1–464] | 3306 | [1–478] |
| 3092 | [290–396] | 3139 | [1–408] | 3260 | [1–429] | 3307 | [1–471] |
| 3093 | [1–49],[165–490] | 340 | [1–457] | 3261 | [1–462] | 3308 | [1–524] |
| 3094 | [1–505] | 3141 | [1–549] | 3262 | [1–134],[180–330] | 3309 | [1–309] |
| 3095 | [1–552] | 3142 | [1–438] | 3263 | [1–321] | 3310 | [1–358] |
| 3096 | [1–185],[270–508] | 3143 | [1–513] | 3264 | [401–469] | 3311 | [1–444] |
| 3097 | [1–263],[378–476] | 3144 | [1–336],[505–548] | 3265 | [1–460] | 3312 | [1–932] |
| 3098 | [1–155] | 3145 | [69–238],[286–725] | 3266 | [1–511] | 3313 | [1–549] |
| 3099 | [1–533] | 3146 | [1–476] | 3267 | [1–425] | 3314 | [105–472] |
| 3100 | [1–340] | 3147 | [1–500] | 3268 | [1–453] | 3315 | [1–497] |
| 3101 | [80–187],[332–404] | 3148 | [1–462] | 3269 | [1–503] | 3316 | [1–511] |
| 3102 | [1–450] | 3149 | [1–523] | 3270 | [1–415] | 3317 | [1–414] |
| 3103 | [1–490] | 3150 | [1–864] | 3271 | [167–292],[367–412],[465–529] | 3318 | [1–117],[159–289] |
| 3104 | [1–501] | 3151 | [1–655] | 3272 | [1–353] | 3319 | [1–217],[334–476] |
| 3105 | [1–482] | 3152 | [1–484] | 3273 | [1–401] | 3320 | [1–416] |
| 3106 | [1–557] | 3153 | [1–459] | 3274 | [1–447] | 3321 | [1–212],[329–471] |
| 3107 | [166–542] | 3154 | [1–526] | 3275 | [1–461] | 3322 | [1–133],[218–473] |
| 3108 | [1–451] | 3155 | [1–505] | 3276 | [1–628] | 3323 | [1–254],[406–479] |
| 3109 | [1–484] | 3156 | [308–605] | 3277 | [1–29],[117–475] | 3324 | [1–294] |
| 3110 | [1–428] | 3157 | [1–238],[368–409] | 3278 | [1–476] | 3325 | [1–485] |
| 3111 | [1–491] | 3158 | [1–156],[251–482] | 3279 | [1–527] | 3326 | [1–451] |
| 3112 | [1–480] | 3159 | [172–238],[368–471] | 3280 | [1–185],[392–505] | 3327 | [1–515] |
| 3160 | [1–326],[373–494] | 3208 | [71–222],[344–465] | 3281 | [1–513] | 3328 | [1–527] |
| 3161 | [1–238],[368–451] | 3209 | [1–505] | 3282 | [1–486] | 3329 | [1–74],[148–199],[318–481] |
| 3162 | [1–494] | 3210 | [58–380] | 3283 | [1–555] | 3330 | [1–74],[148–199],[318–370] |
| 3163 | [1–478] | 3211 | [1–578] | | | | |
| 3164 | [1–508] | 3212 | [1–461] | 3284 | [1–471] | 3331 | [1–528] |
| 3165 | [1–498] | 3213 | [1–444] | 3285 | [1–48] | 3332 | [1–465] |
| 3166 | [84–111] | 3214 | [1–457] | 3286 | [1–526] | 3333 | [1–389] |
| 3167 | [1–350] | 3215 | [1–474] | 3287 | [1–479] | 3334 | [1–151],[206–348] |
| 3168 | [1–471] | 3216 | [1–458] | | | | |
| 3169 | [1–490] | 3217 | [1–526] | | | | |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 3288 | [1–482] | 3335 | [1–479] | 3456 | [1–450] | 3503 | [1–513] |
| 3289 | [40–218],[440–489] | 3336 | [1–452] | 3457 | [1–571] | 3504 | [1–394] |
| 3290 | [1–176],[221–318],[355–489] | 3337 | [1–846] | 3458 | [1–478] | 3505 | [220–502] |
| 3291 | [1–270] | 3338 | [1–386] | 3459 | [1–565] | 3506 | [268–394],[425–478] |
| 3292 | [1–176],[221–318],[355–435] | 3339 | [1–474] | 3460 | [1–543] | 3507 | [1–497] |
| 3293 | [1–460] | 3340 | [1–431] | 3461 | [130–183],[218–365],[413–461] | 3508 | [1–470] |
| 3294 | [1–450] | 3341 | [1–505] | 3462 | [51–546] | 3509 | [1–98],[149–557] |
| 3295 | [273–513] | 3342 | [1–464] | 3463 | [1–577] | 3510 | [1–25],[64–96],[147–495] |
| 3296 | [1–461] | 3343 | [1–441],[480–596] | 3464 | [1–481] | 3511 | [1–57],[408–477] |
| 3297 | [1–432] | 3344 | [1–496] | 3465 | [1–526] | 3512 | [1–492] |
| 3298 | [1–32],[70–360] | 3345 | [1–550] | 3466 | [1–75],[168–586],[667–778],[815–875] | 3513 | [1–461] |
| 3299 | [1–459] | 3346 | [78–123],[326–466] | 3467 | [1–99],[272–314],[386–412] | 3514 | [259–469] |
| 3300 | [1–450] | 3347 | [78–351] | 3468 | [33–546] | 3515 | [267–325] |
| 3301 | [1–542] | 3348 | [1–286] | 3469 | [33–495] | 3516 | [1–255] |
| 3349 | [1–527] | 3397 | [1–477] | 3470 | [1–484] | 3517 | [1–297] |
| 3350 | [1–320] | 3398 | [1–451] | 3471 | [1–512] | 3518 | [1–754] |
| 3351 | [1–506] | 3399 | [1–468] | 3472 | [1–492] | 3519 | [1–657] |
| 3353 | [1–461] | 3400 | [1–431] | 3473 | [1–438] | 3520 | [1–490] |
| 3354 | [1–263] | 3401 | [1–461] | 3474 | [1–133],[250–512] | 3521 | [1–517] |
| 3355 | [1–415] | 3402 | [1–319] | 3475 | [1–497] | 3522 | [1–530] |
| 3356 | [1–408] | 3403 | [1–471] | 3476 | [1–511] | 3523 | [1–503] |
| 3357 | [1–532] | 3404 | [1–482] | 3477 | [1–528] | 3524 | [1–545] |
| 3358 | [1–147],[379–475] | 3405 | [1–508] | 3478 | [1–498] | 3525 | [1–572] |
| 3359 | [1–413] | 3406 | [1–726] | 3479 | [1–478] | 3526 | [1–457] |
| 3360 | [1–249],[296–593] | 3407 | [1–170],[209–459] | 3480 | [1–531] | 3527 | [1–614] |
| 3361 | [1–509] | 3408 | [1–455] | 3481 | [1–539] | 3528 | [1–36],[119–502] |
| 3362 | [1–82],[296–699] | 3409 | [1–450] | 3482 | [1–661] | 3529 | [1–182],[261–288],[384–476] |
| 3363 | [1–82],[296–579] | 3410 | [1–451] | | | | |
| 3364 | [1–82],[296–612] | 3411 | [1–417],[451–495] | 3483 | [1–556] | 3530 | [1–454] |
| 3365 | [224–385] | 3412 | [1–484] | 3484 | [1–518] | 3531 | [1–385] |
| 3366 | [1–516] | 3413 | [1–390] | 3485 | [1–546] | 3532 | [1–511] |
| 3367 | [231–447] | 3414 | [1–473] | 3486 | [1–478] | 3533 | [1–421] |
| 3368 | [1–118],[197–568] | 3415 | [1–585] | 3487 | [1–561] | 3534 | [184–218] |
| 3369 | [1–152],[232–397] | 3416 | [1–100],[130–519] | 3488 | [1–478] | 3535 | [1–482] |
| 3370 | [1–501] | 3417 | [1–547] | 3489 | [1–527] | 3536 | [1–428] |
| 3371 | [1–508] | 3418 | [1–509] | 3490 | [1–70],[99–284],[337–482] | 3537 | [1–424] |
| 3372 | [1–384] | 3419 | [1–519] | 3538 | [1–495] | 3587 | [153–489] |
| 3373 | [1–414] | 3420 | [1–436] | 3539 | [1–498] | 3588 | [1–558] |
| 3374 | [1–467] | 3421 | [1–472] | 3540 | [1–500] | 3589 | [1–637] |
| 3375 | [1–544] | 3422 | [1–594] | 3541 | [1–293] | 3590 | [1–477] |
| 3376 | [1–560] | 3423 | [1–429] | 3542 | [1–526] | 3591 | [1–459] |
| 3377 | [1–424] | 3424 | [1–386] | 3543 | [1–520] | 3592 | [101–135],[211–502] |
| 3378 | [1–528] | 3425 | [1–442] | 3544 | [1–406] | 3593 | [56–492] |
| 3379 | [1–461] | 3426 | [1–431] | 3545 | [1–281] | 3594 | [1–512] |
| 3380 | [1–490] | 3427 | [1–484] | 3546 | [1–466] | 3595 | [1–571] |
| 3381 | [1–487] | 3428 | [1–455] | 3547 | [1–470] | 3596 | [1–482] |
| 3382 | [1–738] | 3429 | [243–363] | 3548 | [1–496] | 3597 | [1–70] |
| 3383 | [43–486] | 3430 | [1–804] | 3549 | [1–475] | 3598 | [49–415],[60–756],[786–826] |
| 3384 | [1–162],[332–560] | 3431 | [1–524] | | | | |
| 3385 | [1–421] | 3432 | [1–479] | 3550 | [1–401] | 3599 | [1–656] |
| 3386 | [1–456] | 3433 | [1–473] | 3551 | [1–494] | 3600 | [1–157],[210–236],[284–477] |
| 3387 | [1–480] | 3434 | [1–489] | | | | |
| 3388 | [1–579] | 3435 | [1–588] | 3552 | [1–43],[99–490] | 3601 | [1–150],[203–394] |
| 3389 | [1–566] | 3436 | [1–475] | 3553 | [1–210],[339–523] | 3602 | [1–480] |
| 3390 | [1–452] | 3437 | [1–462] | 3554 | [1–234] | 3603 | [1–460] |
| 3391 | [144–302],[436–526] | 3438 | [1–556] | 3555 | [1–118],[312–664] | 3604 | [1–441] |
| 3392 | [1–478] | 3439 | [1–449] | 3556 | [1–118],[312–581] | 3605 | [1–486] |
| 3393 | [1–341] | 3440 | [1–608] | 3557 | [1–244] | 3606 | [1–469] |
| 3394 | [1–465] | 3441 | [1–453] | 3558 | [1–462] | 3607 | [1–488] |
| 3395 | [1–469] | 3442 | [1–450] | 3559 | [1–548] | 3608 | [1–501] |
| 3396 | [1–316] | 3443 | [1–443],[285–515] | 3560 | [1–461] | 3609 | [1–638] |
| 3444 | [1–439] | 3491 | [30–83],[112–561] | 3561 | [1–540] | 3610 | [1–490] |
| 3445 | [1–168] | 3492 | [30–82],[111–522] | 3562 | [1–453] | 3611 | [1–453] |
| 3446 | [1–741] | 3493 | [1–477] | 3563 | [1–465] | 3612 | [1–204],[383–550],[610–642] |
| 3447 | [1–495] | 3494 | [1–494] | | | | |
| 3448 | [1–518] | 3495 | [183–533] | 3564 | [1–553] | 3613 | [1–377] |
| 3449 | [1–508] | 3496 | [1–470] | 3565 | [1–138],[301–491] | 3614 | [217–493] |
| 3450 | [1–503] | 3497 | [118–520] | 3566 | [1–138],[301–494] | 3615 | [1–194),[239–491] |
| 3451 | [1–452] | 3498 | [1–684] | 3567 | [1–459] | 3616 | [1–549] |
| 3452 | [1–413] | 3499 | [1–465] | 3568 | [1–379],[491–538] | 3617 | [1–489] |
| 3453 | [1–325] | 3500 | [1–609] | 3569 | [1–441],[553–595] | 3618 | [1–753] |
| 3454 | [51–283] | 3501 | [1–511] | 3570 | [1–265] | 3619 | [1–393] |
| 3455 | [1–540] | 3502 | [1–490] | | | | |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 3571 | [1–404] | 3620 | [1–482] | 3743 | [1–613] | 3790 | [1–495] |
| 3572 | [1–401],[513–555] | 3621 | [1–299] | 3744 | [1–42],[129–376] | 3791 | [1–398] |
| 3573 | [1–504] | 3622 | [1–479] | 3745 | [1–39],[126–268],[391–427] | 3792 | [1–28],[94–272] |
| 3574 | [1–557] | 3623 | [1–505] | 3746 | [1–418] | 3794 | [1–124],[160–240], [292–321],[358–652] |
| 3575 | [1–494] | 3624 | [1–479] |  |  |  |  |
| 3576 | [1–282] | 3625 | [1–422] | 3747 | [1–27],[192–487] | 3795 | [1–217],[432–471] |
| 3577 | [1–313] | 3626 | [1–407] | 3748 | [1–534] | 3796 | [1–380] |
| 3579 | [1–308] | 3627 | [1–32],[289–553] | 3749 | [1–194],[337–506] | 3797 | [1–186],[259–473] |
| 3580 | [1–407] | 3628 | [1–522] | 3750 | [1–71],[193–424] | 3799 | [1–51],[487–511] |
| 3582 | [1–296] | 3629 | [1–821] | 3751 | [1–444] | 3800 | [1–135] |
| 3583 | [1–516] | 3630 | [1–319] | 3752 | [1–468] | 3801 | [1–462] |
| 3584 | [1–162] | 3631 | [476–500] | 3753 | [1–557] | 3802 | [1–468] |
| 3585 | [1–396] | 3632 | [253–476] | 3754 | [380–495] | 3803 | [1–985] |
| 3586 | [1–472] | 3633 | [1–464] | 3755 | [62–499] | 3804 | [1–509] |
| 3634 | [1–408] | 3683 | [1–243],[411–479] | 3756 | [1–525] | 3805 | [1–400] |
| 3635 | [1–483] | 3684 | [1–370],[482–508] | 3757 | [1–473] | 3806 | [1–450] |
| 3636 | [165–419] | 3685 | [1–427] | 3758 | [1–483] | 3807 | [1–498] |
| 3637 | [1–488] | 3686 | [1–392] | 3759 | [1–518] | 3808 | [1–499] |
| 3638 | [1–474] | 3687 | [1–532] | 3760 | [1–258] | 3809 | [1–590] |
| 3639 | [1–486] | 3688 | [1–471] | 3761 | [1–63],[187–324] | 3810 | [1–503] |
| 3640 | [1–404] | 3689 | [1–525] | 3762 | [1–345] | 3811 | [1–528] |
| 3641 | [1–452] | 3690 | [1–513] | 3763 | [1–477] | 3812 | [1–519] |
| 3642 | [1–484] | 3691 | [1–564] | 3764 | [1–96],[280–480] | 3813 | [1–518] |
| 3643 | [1–295] | 3692 | [116–323],[363–452] | 3765 | [1–504] | 3814 | [1–515] |
| 3644 | [1–485] | 3693 | [1–473] | 3766 | [1–728] | 3815 | [1–480] |
| 3645 | [1–474] | 3694 | [1–461] | 3767 | [42–149],[348–478] | 3816 | [1–458] |
| 3646 | [59–258],[416–473] | 3695 | [1–422] | 3768 | [1–480] | 3817 | [1–329] |
| 3647 | [1–527] | 3696 | [1–365] | 3769 | [1–461] | 3818 | [1–484] |
| 3648 | [1–490] | 3697 | [1–469] | 3770 | [1–460] | 3819 | [1–383],[479–527] |
| 3649 | [1–536] | 3698 | [1–485] | 3771 | [1–618] | 3820 | [1–94],[445–480] |
| 3650 | [1–484] | 3699 | [1–245],[357–716] | 3772 | [220–492] | 3821 | [1–316],[378–449] |
| 3651 | [1–494] | 3700 | [1–526] | 3773 | [1–505] | 3822 | [1–569] |
| 3652 | [1–381] | 3701 | [1–572] | 3774 | [1–60],[102–1041], [1074–1108] | 3823 | [1–453] |
| 3653 | [1–501] | 3702 | [1–543] |  |  |  |  |
| 3654 | [1–595] | 3703 | [1–503] | 3775 | [1–473] | 3824 | [1–491] |
| 3655 | [1–490] | 3704 | [1–485] | 3776 | [1–1100] | 3825 | [1–487] |
| 3656 | [1–30],[271–459] | 3705 | [42–215] | 3826 | [1–603] | 3873 | [1–523] |
| 3657 | [51–457] | 3706 | [1–499] | 3827 | [1–465] | 3874 | [1–613] |
| 3658 | [1–456] | 3707 | [1–400] | 3828 | [1–544] | 3875 | [1–501] |
| 3659 | [1–112],[333–495] | 3708 | [1–633] | 3829 | [1–294],[392–589] | 3876 | [1–497] |
| 3660 | [1–296],[355–423] | 3709 | [1–504] | 3830 | [1–561] | 3877 | [1–453] |
| 3661 | [1–97],[225–297] | 3710 | [1–560] | 3831 | [1–542] | 3878 | [1–275],[352–505] |
| 3662 | [1–362] | 3711 | [1–261],[291–461] | 3832 | [41–456] | 3879 | [1–489] |
| 3663 | [1–1043] | 3712 | [1–479] | 3833 | [1–463] | 3880 | [1–315],[426–707] |
| 3664 | [1–82],[177–445],[497–536] | 3713 | [1–499] | 3834 | [1–592] | 3881 | [1–459] |
| 3665 | [1–94],[222–294],[324–385] | 3714 | [1–480] | 3835 | [1–452] | 3882 | [1–168],[221–485] |
| 3666 | [1–81],[176–444],[496–567] | 3715 | [1–507] | 3836 | [1–298] | 3883 | [1–231] |
| 3667 | [323–397] | 3716 | [1–771] | 3837 | [1–550] | 7744 | [1–108] |
| 3668 | [1–367],[413–467] | 3717 | [1–599] | 3838 | [68–470] | 7745 | [1–89] |
| 3669 | [1–94],[222–294],[324–385] | 3718 | [1–475] | 3839 | [320–536] | 7746 | [1–108] |
| 3670 | [1–71],[322–550] | 3719 | [1–511] | 3840 | [320–508] | 7747 | [1–108] |
| 3671 | [1–110],[288–400] | 3720 | [1–816] | 3841 | [1–421] | 7748 | [1–154] |
| 3673 | [1–110],[359–400] | 3721 | [1–469] | 3842 | [1–377] | 7749 | [1–108] |
| 3674 | [1–426] | 3722 | [1–496] | 3843 | [1–296] | 7750 | [1–96] |
| 3675 | [1–110],[359–400] | 3723 | [1–477] | 3844 | [1–252] | 7751 | [1–153] |
| 3676 | [1–586] | 3724 | [1–469] | 3845 | [1–352] | 7752 | [1–108] |
| 3677 | [70–368],[414–465] | 3725 | [1–60],[208–373] | 3846 | [149–768] | 7753 | [1–101] |
| 3678 | [1–471] | 3726 | [1–523] | 3847 | [172–453] | 7754 | [1–108] |
| 3679 | [1–524] | 3727 | [1–221],[270–579] | 3848 | [1–106],[140–674] | 7755 | [1–113] |
| 3680 | [1–941] | 3728 | [1–455] | 3849 | [1–515] | 7756 | [1–108] |
| 3682 | [1–336] | 3729 | [1–450] | 3850 | [1–514] | 7757 | [1–108] |
| 3730 | [1–394] | 3777 | [1–516] | 3851 | [1–514] | 7758 | [1–108] |
| 3731 | [1–494] | 3778 | [1–687] | 3852 | [1–104],[138–515] | 7759 | [1–406] |
| 3732 | [1–524] | 3779 | [1–203] | 3853 | [1–516] | 7760 | [1–108] |
| 3733 | [1–479] | 3780 | [1–203],[524–555] | 3854 | [1–519] | 7761 | [1–88] |
| 3734 | [193–451] | 3781 | [1–534] | 3855 | [1–516] | 7762 | [1–169] |
| 3735 | [1–377] | 3782 | [1–467] | 3856 | [1–105],[139–428] | 7763 | [1–108] |
| 3736 | [1–496] | 3783 | [1–467] | 3857 | [1–105],[139–428] | 7764 | [1–108] |
| 3737 | [1–458] | 3784 | [1–484] | 3858 | [1–105],[139–516] | 7765 | [1–108] |
| 3738 | [1–145],[376–564] | 3785 | [1–153],[388–442] | 3859 | [1–515] | 7766 | [1–169] |
| 3739 | [1–100],[129–327] | 3786 | [1–420] | 3860 | [1–468] | 7767 | [1–108] |
| 3740 | [1–246] | 3787 | [1–505] | 3861 | [1–99],[355–425] | 7768 | [1–134] |
| 3741 | [1–387] | 3788 | [54–300],[384–491] | 3862 | [1–508] | 7769 | [1–108] |
| 3742 | [1–127],[160–316],[459–603] | 3789 | [[1–488] | 3863 | [1–251] | 7770 | [1–108] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 3864 | [1–513] | 7771 | [1–108] | 7900 | [1–476] | 7948 | [1–140] |
| 3865 | [263–495] | 7772 | [1–266] | 7901 | [1–440] | 7949 | [1–316] |
| 3866 | [1–470] | 7773 | [1–108] | 7902 | [1–357] | 7950 | [1–412] |
| 3867 | [1–482] | 7774 | [1–63] | 7903 | [1–334] | 7951 | [1–431] |
| 3868 | [1–500] | 7775 | [1–299] | 7904 | [1–164] | 7952 | [1–83] |
| 3869 | [1–489] | 7776 | [1–108] | 7906 | [1–170] | 7953 | [1–280] |
| 3870 | [1–503] | 7778 | [1–101] | 7907 | [1–170] | 7954 | [1–171] |
| 3871 | [1–298] | 7779 | [1–63] | 7908 | [143–431] | 7955 | [1–459] |
| 3872 | [1–480] | 7781 | [1–108] | 7909 | [1–445] | 7956 | [1–391] |
| 7782 | [1–154] | 7833 | [1–505] | 7910 | [1–51] | 7957 | [1–384] |
| 7783 | [1–169] | 7834 | [1–187] | 7911 | [1–479] | 7958 | [1–171] |
| 7784 | [1–108] | 7836 | [1–307] | 7912 | [1–84] | 7959 | [1–397] |
| 7785 | [1–108] | 7837 | [1–547] | 7913 | [1–314] | 7960 | [1–244] |
| 7786 | [1–366] | 7838 | [1–263] | 7914 | [1–52] | 7961 | [1–95] |
| 7787 | [1–101] | 7839 | [1–465] | 7915 | [1–123] | 7962 | [1–429] |
| 7788 | [1–144] | 7840 | [1–409] | 7916 | [1–61] | 7963 | [1–334] |
| 7789 | [1–108] | 7841 | [1–307] | 7917 | [1–321] | 7964 | [1–293] |
| 7790 | [1–108] | 7842 | [1–515] | 7918 | [1–65] | 7965 | [212–442] |
| 7791 | [1–108] | 7843 | [1–365] | 7919 | [1–271] | 7966 | [1–152] |
| 7792 | [1–339] | 7844 | [1–308] | 7920 | [1–171] | 7967 | [1–86] |
| 7793 | [1–79] | 7845 | [1–562] | 7921 | [1–356] | 7968 | [1–330] |
| 7794 | [1–63] | 7846 | [1–488] | 7922 | [1–299] | 7969 | [165–442] |
| 7795 | [1–169] | 7847 | [1–467] | 7923 | [1–354] | 7970 | [1–67] |
| 7796 | [1–108] | 7848 | [1–329] | 7924 | [1–455] | 7971 | [1–206] |
| 7798 | [1–108] | 7849 | [1–100] | 7925 | [1–425] | 7972 | [1–73] |
| 7799 | [1–89] | 7850 | [1–100] | 7926 | [1–83] | 7973 | [1–332] |
| 7800 | [1–63] | 7851 | [1–449] | 7927 | [1–313] | 7974 | [1–449] |
| 7801 | [1–150] | 7852 | [1–116] | 7928 | [1–314] | 7976 | [1–270] |
| 7802 | [1–500] | 7853 | [1–58] | 7929 | [1–313] | 7977 | [1–172] |
| 7803 | [1–108] | 7854 | [1–81] | 7978 | [1–321] | 8028 | [1–103] |
| 7804 | [1–108] | 7855 | [1–90] | 7979 | [1–170] | 8030 | [1–104] |
| 7805 | [1–108] | 7856 | [1–118] | 7982 | [1–328] | 8031 | [1–104] |
| 7806 | [1–297] | 7857 | [1–115] | 7983 | [1–58] | 8032 | [1–104] |
| 7807 | [1–357] | 7858 | [1–73] | 7984 | [1–422] | 8033 | [1–77] |
| 7809 | [1–385] | 7859 | [1–56] | 7985 | [1–113] | 8034 | [1–74] |
| 7810 | [1–53] | 7860 | [1–112] | 7986 | [1–163] | 8035 | [1–104] |
| 7811 | [1–381] | 7861 | [1–100] | 7987 | [76–312] | 8036 | [1–58] |
| 7812 | [1–177] | 7862 | [1–184] | 7988 | [1–171] | 8037 | [1–104] |
| 7813 | [1–162] | 7863 | [1–237] | 7989 | [1–192] | 8038 | [1–90] |
| 7814 | [1–319] | 7864 | [1–426] | 7990 | [1–171] | 8039 | [1–65] |
| 7815 | [1–36] | 7865 | [1–367] | 7991 | [1–519] | 8040 | [1–166] |
| 7817 | [1–157] | 7866 | [1–256] | 7992 | [1–67] | 8041 | [1–103] |
| 7818 | [1–158] | 7867 | [1–452] | 7993 | [1–185] | 8042 | [1–79] |
| 7819 | [1–205] | 7869 | [70–214] | 7994 | [1–171] | 8043 | [1–103] |
| 7820 | [84–366] | 7870 | [1–349] | 7995 | [1–436] | 8044 | [1–150] |
| 7821 | [1–361] | 7871 | [1–177] | 7996 | [1–171] | 8045 | [1–360] |
| 7822 | [1–317] | 7872 | [1–494] | 7997 | [1–176] | 8046 | [1–104] |
| 7823 | [1–343] | 7873 | [1–276] | 7998 | [1–429] | 8047 | [1–71] |
| 7824 | [1–343] | 7874 | [1–216] | 7999 | [1–68] | 8048 | [1–92] |
| 7825 | [1–208] | 7875 | [1–106] | 8000 | [1–385] | 8049 | [1–103] |
| 7826 | [76–293] | 7876 | [1–172] | 8001 | [1–324] | 8050 | [1–103] |
| 7827 | [1–242] | 7877 | [1–233] | 8002 | [1–481] | 8051 | [1–132] |
| 7828 | [1–584] | 7878 | [1–155] | 8003 | [1–481] | 8052 | [1–92] |
| 7830 | [1–310] | 7879 | [1–83] | 8004 | [1–421] | 8053 | [1–103] |
| 7831 | [1–548] | 7880 | [1–265] | 8005 | [1–333] | 8054 | [1–103] |
| 7832 | [1–328] | 7881 | [1–508] | 8006 | [1–58] | 8055 | [1–88] |
| 7882 | [1–363] | 7930 | [1–328] | 8007 | [1–475] | 8056 | [1–103] |
| 7883 | [1–314] | 7931 | [1–483] | 8008 | [1–283],[367–435] | 8057 | [1–57] |
| 7884 | [1–501] | 7932 | [1–125] | 8009 | [1–314] | 8058 | [1–191] |
| 7885 | [1–344] | 7933 | [1–314] | 8010 | [1–337] | 8059 | [1–75] |
| 7886 | [1–455] | 7934 | [1–294] | 8011 | [1–310] | 8060 | [1–365] |
| 7887 | [1–401] | 7935 | [1–408] | 8012 | [1–60] | 8061 | [1–65] |
| 7888 | [1–171] | 7936 | [1–279] | 8013 | [1–376] | 8062 | [1–58] |
| 7889 | [1–77] | 7937 | [1–65] | 8014 | [1–463] | 8063 | [1–335] |
| 7890 | [1–328] | 7938 | [1–270] | 8015 | [1–329] | 8064 | [1–198] |
| 7891 | [1–395] | 7939 | [1–369] | 8016 | [1–60] | 8065 | [1–165] |
| 7892 | [1–501] | 7940 | [1–263] | 8017 | [1–408] | 8066 | [1–104] |
| 7893 | [1–329] | 7941 | [141–320] | 8018 | [1–103] | 8067 | [1–165] |
| 7894 | [238–419] | 7942 | [1–315] | 8019 | [1–73] | 8068 | [1–104] |
| 7895 | [1–170] | 7943 | [1–458] | 8020 | [1–96] | 8069 | [1–84] |
| 7896 | [1–170] | 7944 | [1–309] | 8021 | [1–121] | 8070 | [1–164] |
| 7897 | [54–437] | 7945 | [1–238] | 8022 | [1–67] | 8071 | [1–235] |
| 7898 | [1–475] | 7946 | [1–336] | 8023 | [1–58] | 8072 | [1–104] |
| 7899 | [1–314] | 7947 | [1–166] | 8024 | [1–164] | 8073 | [1–177] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 8025 | [1–104] | 8074 | [1–165] | 8204 | [1–344] | 8251 | [1–413] |
| 8027 | [1–163] | 8075 | [1–104] | 8205 | [1–29],[59–85] | 8252 | [1–299] |
| 8076 | [1–58] | 8127 | [1–165] | 8206 | [1–321] | 8253 | [1–350] |
| 8077 | [1–454] | 8128 | [1–104] | 8207 | [1–452] | 8254 | [1–430] |
| 8078 | [1–103] | 8129 | [1–236] | 8208 | [1–185] | 8255 | [1–230] |
| 8080 | [1–103] | 8130 | [1–317] | 8209 | [239–490] | 8257 | [1–63] |
| 8081 | [1–127] | 8131 | [42–463] | 8210 | [1–297] | 8258 | [1–275],[352–393] |
| 8082 | [1–102] | 8132 | [1–54] | 8211 | [1–167] | 8259 | [1–420] |
| 8083 | [139–170] | 8133 | [1–352] | 8212 | [1–403] | 8260 | [1–438] |
| 8084 | [1–103] | 8134 | [1–390] | 8213 | [1–466] | 8261 | [1–419] |
| 8085 | [1–146] | 8135 | [1–441] | 8214 | [1–389] | 8262 | [1–319] |
| 8086 | [1–164] | 8136 | [1–528] | 8215 | [1–428] | 8263 | [1–89] |
| 8087 | [1–103] | 8137 | [1–243] | 8216 | [185–403] | 8264 | [1–139] |
| 8088 | [1–103] | 8138 | [1–368] | 8217 | [1–368] | 8265 | [1–188] |
| 8089 | [1–58] | 8140 | [1–407] | 8218 | [1–197] | 8266 | [1–371] |
| 8090 | [1–97] | 8141 | [1–390] | 8219 | [1–377] | 8267 | [1–447] |
| 8092 | [1–103] | 8143 | [36–151],[474–499] | 8220 | [66–386] | 8268 | [1–402] |
| 8093 | [1–67] | 8144 | [1–537] | 8221 | [1–50] | 8269 | [1–467] |
| 8094 | [1–114] | 8145 | [1–266] | 8222 | [1–359] | 8270 | [1–97],[231–342] |
| 8095 | [1–67] | 8147 | [1–414] | 8223 | [1–468] | 8271 | [1–374] |
| 8096 | [1–58] | 8148 | [71–460] | 8224 | [1–407] | 8272 | [1–196] |
| 8097 | [1–61] | 8149 | [80–428] | 8225 | [1–83] | 8273 | [1–468] |
| 8098 | [1–74] | 8150 | [1–412] | 8226 | [1–473] | 8274 | [1–374] |
| 8099 | [1–377] | 8151 | [1–160] | 8275 | [1–395] | 8323 | [1–353] |
| 8100 | [1–148] | 8152 | [1–165] | 8276 | [1–498] | 8324 | [1–459] |
| 8102 | [1–58] | 8153 | [1–111] | 8277 | [1–240] | 8325 | [1–307] |
| 8103 | [1–58] | 8154 | [1–395] | 8278 | [34–479] | 8326 | [40–412] |
| 8104 | [1–55] | 8155 | [1–445] | 8279 | [1–160],[230–413] | 8327 | [1–277] |
| 8105 | [1–234] | 8156 | [1–407] | 8281 | [1–180] | 8328 | [1–378] |
| 8106 | [1–102] | 8159 | [1–170],[200–396] | 8282 | [1–62] | 8329 | [1–360] |
| 8107 | [1–95] | 8160 | [66–377] | 8283 | [1–442] | 8330 | [1–349] |
| 8108 | [1–72] | 8161 | [1–385] | 8284 | [1–480] | 8331 | [1–457] |
| 8109 | [1–147] | 8162 | [1–367] | 8285 | [1–234],[269–404] | 8332 | [1–90] |
| 8110 | [1–103] | 8163 | [1–153] | 8286 | [1–202] | 8333 | [1–167] |
| 8111 | [1–104] | 8164 | [1–385] | 8287 | [1–353] | 8334 | [1–386] |
| 8112 | [1–138] | 8165 | [1–89] | 8288 | [1–296] | 8335 | [1–389] |
| 8113 | [1–103] | 8166 | [1–325] | 8289 | [1–316] | 8336 | [1–356] |
| 8114 | [1–103] | 8167 | [1–433] | 8290 | [1–290] | 8337 | [1–56] |
| 8115 | [1–104] | 8168 | [1–423] | 8291 | [1–327] | 8338 | [1–311] |
| 8116 | [1–103] | 8170 | [1–399] | 8292 | [1–326],[394–457] | 8339 | [143–289] |
| 8117 | [1–58] | 8171 | [1–56] | 8293 | [1–241] | 8340 | [1–289] |
| 8118 | [1–164] | 8172 | [1–72] | 8294 | [1–287] | 8341 | [1–440] |
| 8119 | [1–58] | 8173 | [34–425] | 8295 | [1–218] | 8342 | [48–391] |
| 8120 | [1–75] | 8174 | [1–444] | 8296 | [1–292] | 8343 | [1–422] |
| 8121 | [1–76] | 8175 | [1–403] | 8297 | [1–280] | 8344 | [1–189],[218–363] |
| 8123 | [1–104] | 8176 | [296–338] | 8298 | [1–100] | 8345 | [1–359] |
| 8124 | [1–58] | 8177 | [1–438] | 8299 | [1–244],[283–339] | 8346 | [1–387] |
| 8125 | [1–210],[371–399] | 8178 | [1–298] | 8300 | [1–369] | 8347 | [1–304] |
| 8126 | [1–29] | 8179 | [1–292] | 8301 | [1–121],[198–346] | 8348 | [1–365] |
| 8180 | [1–153] | 8227 | [1–535] | 8302 | [1–168] | 8349 | [1–327] |
| 8181 | [1–352] | 8228 | [1–378] | 8303 | [1–66] | 8350 | [277–393] |
| 8182 | [1–70] | 8229 | [1–432] | 8304 | [1–106] | 8351 | [1–477] |
| 8183 | [1–347] | 8230 | [1–404] | 8305 | [1–358] | 8352 | [1–425] |
| 8184 | [1–382] | 8231 | [1–72] | 8306 | [1–425] | 8353 | [1–272] |
| 8185 | [1–318] | 8232 | [35–410] | 8307 | [1–393] | 8354 | [1–203] |
| 8186 | [1–383] | 8233 | [1–356] | 8308 | [1–338] | 8355 | [1–83] |
| 8187 | [1–430] | 8234 | [1–122] | 8309 | [1–216] | 8356 | [1–534] |
| 8188 | [1–370] | 8235 | [1–452] | 8310 | [1–333] | 8357 | [1–211] |
| 8189 | [1–157],[192–283] | 8236 | [1–155] | 8311 | [1–414] | 8358 | [1–472] |
| 8190 | [1–379] | 8237 | [1–432] | 8312 | [1–228] | 8359 | [1–416] |
| 8191 | [1–63] | 8238 | [1–444] | 8313 | [1–432] | 8360 | [1–424] |
| 8192 | [1–50] | 8239 | [297–445] | 8314 | [1–107] | 8361 | [1–349] |
| 8193 | [1–310] | 8240 | [1–455] | 8315 | [1–361] | 8363 | [1–361] |
| 8194 | [1–157] | 8241 | [1–189] | 8316 | [1–41],[81–341] | 8364 | [1–344] |
| 8195 | [1–183] | 8242 | [1–65],[180–221],[388–450] | 8317 | [1–416] | 8365 | [1–180] |
| 8196 | [1–408] | 8243 | [1–243] | 8318 | [1–353] | 8366 | [1–268] |
| 8197 | [1–460] | 8244 | [1–463] | 8319 | [1–433] | 8367 | [1–370] |
| 8198 | [1–459] | 8245 | [1–446] | 8320 | [1–337] | 8368 | [1–327] |
| 8199 | [1–447] | 8246 | [1–473] | 8321 | [1–398] | 8369 | [1–360] |
| 8200 | [1–62] | 8247 | [1–549] | 8322 | [1–396] | 8370 | [1–498] |
| 8201 | [1–398] | 8248 | [1–506] | 8371 | [1–77] | 8423 | [1–50] |
| 8202 | [1–448] | 8249 | [1–525] | 8372 | [1–389] | 8424 | [1–312] |
| 8203 | [1–429] | 8250 | [1–435] | 8373 | [1–358] | 8425 | [1–157] |
|  |  |  |  | 8374 | [1–398] | 8426 | [1–83] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 8375 | [1–405] | 8427 | [1–504] | 8505 | [1–375] | 8555 | [1–426] |
| 8376 | [1–143],[257–383] | 8428 | [1–395] | 8506 | [1–364] | 8556 | [1–404] |
| 8377 | [1–150] | 8429 | [1–438] | 8507 | [1–401] | 8557 | [1–318] |
| 8378 | [1–412] | 8430 | [1–73] | 8508 | [1–268],[302–421] | 8558 | [1–171] |
| 8379 | [1–378] | 8431 | [1–79] | 8509 | [1–429] | 8559 | [1–312] |
| 8380 | [1–464] | 8432 | [1–232] | 8510 | [1–406] | 8560 | [1–442] |
| 8381 | [1–351] | 8434 | [1–427] | 8511 | [1–394] | 8561 | [1–318] |
| 8382 | [1–51] | 8435 | [1–309] | 8512 | [1–427] | 8562 | [1–317] |
| 8383 | [1–159] | 8436 | [1–586] | 8514 | [1–396] | 8563 | [1–184] |
| 8384 | [1–440] | 8437 | [1–423] | 8515 | [1–494] | 8564 | [1–136] |
| 8385 | [1–438] | 8438 | [1–465] | 8516 | [1–350] | 8565 | [1–307] |
| 8386 | [90–421] | 8439 | [1–304] | 8517 | [1–388] | 8566 | [1–207] |
| 8387 | [1–401] | 8440 | [1–68] | 8518 | [1–322] | 8567 | [1–136] |
| 8389 | [1–445] | 8441 | [1–125] | 8519 | [1–286] | 8568 | [1–395] |
| 8390 | [1–442] | 8442 | [108–355] | 8520 | [1–411] | 8569 | [1–152] |
| 8391 | [1–419] | 8443 | [1–330] | 8521 | [1–303] | 8570 | [1–184] |
| 8393 | [1–463] | 8444 | [1–403] | 8571 | [1–67] | 8635 | [1–103] |
| 8394 | [77–237],[300–393] | 8445 | [1–419] | 8572 | [1–387] | 8636 | [1–164] |
| 8395 | [1–360] | 8446 | [158–265] | 8573 | [1–191] | 8637 | [1–103] |
| 8396 | [1–314] | 8447 | [1–67] | 8574 | [1–416] | 8638 | [1–361] |
| 8397 | [1–439] | 8448 | [1–238] | 8575 | [1–331] | 8639 | [1–75] |
| 8398 | [1–328] | 8449 | [1–449] | 8576 | [1–68] | 8640 | [1–91] |
| 8399 | [1–398] | 8451 | [1–349] | 8577 | [1–483] | 8641 | [1–58] |
| 8400 | [1–96] | 8452 | [1–547] | 8578 | [1–386] | 8643 | [1–361] |
| 8401 | [1–557] | 8453 | [1–75] | 8579 | [1–363] | 8644 | [1–148] |
| 8402 | [1–446] | 8454 | [1–268] | 8580 | [1–385] | 8645 | [1–58] |
| 8403 | [1–379] | 8455 | [1–349] | 8581 | [1–202] | 8646 | [1–58] |
| 8404 | [1–155] | 8456 | [1–350] | 8583 | [1–130] | 8647 | [1–361] |
| 8406 | [1–221] | 8457 | [31–73] | 8584 | [1–144] | 8649 | [1–103] |
| 8407 | [1–27] | 8458 | [1–378] | 8585 | [1–361] | 8651 | [1–166] |
| 8408 | [1–398] | 8460 | [1–77] | 8586 | [1–439] | 8652 | [1–77] |
| 8409 | [1–229] | 8461 | [1–494] | 8587 | [1–166] | 8653 | [1–51] |
| 8410 | [1–108] | 8462 | [1–421] | 8588 | [1–103] | 8654 | [1–363] |
| 8411 | [1–329] | 8464 | [1–369] | 8589 | [1–151] | 8655 | [1–159] |
| 8412 | [1–271] | 8465 | [1–480] | 8591 | [1–362] | 8656 | [1–150] |
| 8413 | [1–492] | 8466 | [1–508] | 8592 | [1–85] | 8657 | [1–359] |
| 8414 | [236–391] | 8467 | [1–460] | 8593 | [1–80] | 8658 | [1–167] |
| 8416 | [1–283] | 8468 | [1–466] | 8594 | [1–84] | 8659 | [1–103] |
| 8417 | [1–340] | 8469 | [1–121] | 8597 | [1–144] | 8660 | [1–96] |
| 8418 | [1–226] | 8470 | [1–430] | 8598 | [1–348] | 8661 | [1–103] |
| 8420 | [1–67] | 8471 | [1–332] | 8599 | [1–363] | 8663 | [1–84] |
| 8421 | [1–484] | 8472 | [1–445] | 8600 | [1–126] | 8664 | [1–96] |
| 8422 | [1–52] | 8473 | [1–375] | 8603 | [1–132] | 8665 | [1–152] |
| 8474 | [1–256] | 8522 | [1–157] | 8605 | [1–114] | 8666 | [1–84] |
| 8475 | [1–355] | 8523 | [1–354] | 8606 | [1–84] | 8667 | [1–288],[405–468] |
| 8476 | [1–342] | 8524 | [1–398] | 8607 | [1–96] | 8668 | [1–58] |
| 8477 | [1–369] | 8525 | [1–83] | 8609 | [1–73] | 8671 | [1–116] |
| 8478 | [1–445] | 8526 | [1–326] | 8611 | [1–103] | 8672 | [1–97] |
| 8479 | [1–206] | 8527 | [1–315] | 8613 | [1–89] | 8673 | [1–82] |
| 8480 | [1–138] | 8528 | [1–374] | 8614 | [1–361] | 8674 | [1–96] |
| 8481 | [1–67] | 8529 | [1–460] | 8616 | [1–361] | 8675 | [1–222] |
| 8482 | [1–96] | 8530 | [365–434] | 8617 | [1–164] | 8677 | [1–164] |
| 8483 | [1–270] | 8531 | [1–114] | 8620 | [1–345] | 8678 | [1–449] |
| 8484 | [1–317] | 8532 | [1–508] | 8621 | [1–361] | 8679 | [1–56] |
| 8485 | [1–312] | 8534 | [1–369] | 8622 | [1–58] | 8680 | [1–73] |
| 8486 | [1–324] | 8535 | [1–154] | 8623 | [1–159] | 8681 | [1–73] |
| 8487 | [1–203] | 8536 | [1–433] | 8625 | [1–97] | 8682 | [1–186] |
| 8488 | [1–355] | 8537 | [1–391] | 8626 | [1–103] | 8684 | [1–164] |
| 8489 | [1–328] | 8538 | [1–459] | 8627 | [1–506] | 8685 | [1–103] |
| 8490 | [1–58] | 8539 | [1–351] | 8628 | [1–58] | 8687 | [1–83] |
| 8491 | [1–361] | 8540 | [1–423] | 8630 | [1–164] | 8689 | [1–366] |
| 8492 | [1–109],[175–295] | 8541 | [1–394] | 8632 | [1–139] | 8690 | [1–116] |
| 8493 | [1–333] | 8543 | [1–480] | 8633 | [1–103] | 8691 | [1–79] |
| 8494 | [1–81] | 8544 | [1–408] | 8692 | [1–82] | 8742 | [1–283],[400–455] |
| 8495 | [1–395] | 8545 | [1–302] | 8693 | [1–84] | 8743 | [1–377] |
| 8496 | [1–104] | 8546 | [1–348] | 8694 | [1–90] | 8744 | [1–287] |
| 8497 | [1–403] | 8547 | [1–84] | 8696 | [1–513] | 8745 | [1–284] |
| 8498 | [1–91] | 8548 | [1–88] | 8697 | [1–500] | 8746 | [1–319] |
| 8499 | [1–226],[391–416] | 8549 | [1–183] | 8698 | [1–455] | 8747 | [1–327] |
| 8500 | [1–432] | 8550 | [1–146] | 8699 | [1–238] | 8748 | [1–322] |
| 8501 | [1–462] | 8551 | [1–147] | 8700 | [1–565] | 8749 | [1–81] |
| 8502 | [1–451] | 8552 | [1–149] | 8701 | [1–530] | 8750 | [1–409] |
| 8503 | [1–365] | 8553 | [1–167] | 8702 | [1–451] | 8751 | [1–476] |
| 8504 | [1–359] | 8554 | [1–474] | 8703 | [1–271] | 8752 | [1–354] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 8704 | [1–447] | 8753 | [1–327] | 8827 | [1–434] | 8875 | [1–103] |
| 8705 | [1–141] | 8754 | [1–422] | 8828 | [1–487] | 8876 | [1–95] |
| 8706 | [1–500] | 8755 | [1–150] | 8829 | [1–342] | 8877 | [1–95] |
| 8707 | [1–485] | 8756 | [1–94] | 8830 | [1–544] | 8878 | [1–103] |
| 8708 | [1–483] | 8757 | [1–148] | 8831 | [1–74] | 8879 | [1–94] |
| 8709 | [1–48],[153–433] | 8758 | [1–402] | 8832 | [1–96] | 8880 | [1–96] |
| 8710 | [1–260] | 8759 | [1–289] | 8833 | [1–103] | 8881 | [1–149] |
| 8711 | [1–251] | 8760 | [1–314] | 8834 | [1–103] | 8882 | [1–96] |
| 8712 | [1–115] | 8761 | [1–154] | 8836 | [1–103] | 8883 | [1–95] |
| 8713 | [1–447] | 8762 | [1–203] | 8885 | [1–442] | 8933 | [1–83] |
| 8714 | [1–431] | 8763 | [1–374] | 8886 | [1–148] | 8934 | [1–93],[195–239] |
| 8715 | [1–454] | 8764 | [58–360] | 8887 | [1–103] | 8935 | [1–132] |
| 8716 | [1–73],[161–222] | 8765 | [1–384] | 8888 | [1–58] | 8936 | [1–103] |
| 8717 | [1–309] | 8766 | [1–73] | 8889 | [1–103] | 8937 | [1–362] |
| 8718 | [1–384] | 8767 | [1–375] | 8890 | [1–361] | 8938 | [1–103] |
| 8719 | [1–375] | 8768 | [1–281],[398–448] | 8892 | [1–103] | 8939 | [1–103] |
| 8720 | [77–251] | 8769 | [1–341] | 8893 | [1–188] | 8940 | [1–96] |
| 8721 | [1–236] | 8770 | [1–414] | 8894 | [1–103] | 8941 | [1–76] |
| 8722 | [1–329] | 8771 | [1–236] | 8895 | [1–96] | 8942 | [1–149] |
| 8723 | [1–159] | 8772 | [1–386] | 8896 | [1–58] | 8943 | [1–29] |
| 8724 | [1–342] | 8773 | [152–211] | 8897 | [1–58] | 8944 | [1–103] |
| 8725 | [1–74] | 8774 | [1–191] | 8898 | [1–103] | 8945 | [1–76] |
| 8726 | [1–199] | 8775 | [30–336] | 8899 | [1–150] | 8946 | [1–392] |
| 8727 | [1–390] | 8776 | [1–273] | 8900 | [1–128] | 8947 | [1–138] |
| 8728 | [1–28],[78–322] | 8777 | [1–226] | 8901 | [1–103] | 8948 | [1–65] |
| 8730 | [1–201] | 8778 | [1–226] | 8902 | [1–84] | 8949 | [1–96] |
| 8731 | [1–178] | 8779 | [1–380] | 8903 | [1–89] | 8950 | [1–95] |
| 8732 | [1–291],[408–465] | 8780 | [1–215] | 8904 | [1–89] | 8951 | [1–88] |
| 8733 | [1–172] | 8781 | [1–410] | 8905 | [1–212] | 8952 | [1–152] |
| 8734 | [1–384] | 8782 | [1–136] | 8906 | [1–96] | 8953 | [1–85] |
| 8735 | [1–78] | 8783 | [1–73] | 8907 | [1–95] | 8954 | [1–96] |
| 8736 | [1–52] | 8784 | [1–139] | 8908 | [1–413] | 8955 | [1–445] |
| 8738 | [1–294] | 8785 | [1–396] | 8909 | [1–58] | 8956 | [1–96] |
| 8739 | [1–398] | 8786 | [1–251] | 8910 | [1–58] | 8957 | [1–95] |
| 8740 | [1–337] | 8787 | [1–399] | 8911 | [1–103] | 8958 | [1–103] |
| 8741 | [1–239] | 8788 | [1–509] | 8912 | [1–103] | 8959 | [1–95] |
| 8789 | [1–446] | 8837 | [1–58] | 8913 | [1–103] | 8960 | [1–104] |
| 8790 | [1–464] | 8838 | [1–361] | 8914 | [1–104] | 8961 | [1–89] |
| 8791 | [1–461] | 8839 | [1–76] | 8915 | [1–58] | 8962 | [1–90] |
| 8792 | [1–235] | 8840 | [1–71] | 8916 | [1–103] | 8963 | [1–103] |
| 8793 | [1–408] | 8841 | [1–475] | 8917 | [1–103] | 8964 | [1–103] |
| 8794 | [1–421] | 8842 | [1–76] | 8918 | [1–103] | 8965 | [1–114] |
| 8795 | [212–390] | 8843 | [1–130] | 8919 | [1–95] | 8966 | [1–256] |
| 8796 | [1–159] | 8844 | [1–103] | 8920 | [1–96] | 8967 | [1–103] |
| 8797 | [1–71] | 8845 | [1–133] | 8921 | [1–58] | 8968 | [1–103] |
| 8798 | [1–354] | 8846 | [1–103] | 8922 | [1–73] | 8969 | [1–89] |
| 8799 | [1–408] | 8847 | [1–362] | 8923 | [1–96] | 8970 | [1–103] |
| 8800 | [1–295] | 8848 | [1–103] | 8924 | [1–96] | 8971 | [1–152] |
| 8801 | [1–457] | 8849 | [1–73] | 8925 | [1–84] | 8972 | [1–164] |
| 8802 | [1–83] | 8850 | [1–103] | 8926 | [1–103) | 8973 | [1–94] |
| 8803 | [1–158] | 8851 | [1–83] | 8927 | [1–353] | 8974 | [1–103] |
| 8804 | [196–530] | 8852 | [1–103] | 8928 | [1–164] | 8975 | [1–103] |
| 8805 | [1–361] | 8853 | [1–96] | 8929 | [1–76] | 8976 | [1–399] |
| 8806 | [1–158] | 8854 | [1–85] | 8930 | [1–361] | 8977 | [1–96] |
| 8807 | [1–314] | 8855 | [1–103] | 8931 | [1–103] | 8978 | [1–103] |
| 8808 | [1–448] | 8856 | [1–103] | 8932 | [1–104] | 8979 | [1–96] |
| 8809 | [208–251] | 8857 | [1–103] | 8980 | [1–103] | 9030 | [1–470] |
| 8810 | [1–181] | 8858 | [1–84] | 8981 | [1–92] | 9031 | [1–484] |
| 8811 | [1–207] | 8859 | [1–95] | 8982 | [1–372] | 9032 | [1–62] |
| 8812 | [1–408] | 8860 | [1–58] | 8983 | [1–430] | 9033 | [93–136] |
| 8813 | [1–372] | 8861 | [1–96] | 8984 | [1–418] | 9034 | [1–422] |
| 8814 | [1–495] | 8862 | [1–379] | 8985 | [1–482] | 9035 | [1–83] |
| 8815 | [1–433] | 8863 | [1–149] | 8986 | [1–323] | 9036 | [1–280] |
| 8816 | [1–471] | 8864 | [1–103] | 8987 | [1–542] | 9037 | [1–117] |
| 8817 | [1–84] | 8865 | [1–103] | 8989 | [1–410] | 9038 | [1–72] |
| 8818 | [1–444] | 8866 | [1–58] | 8990 | [1–247] | 9039 | [1–442] |
| 8819 | [1–472] | 8867 | [1–71] | 8991 | [1–89] | 9040 | [1–139] |
| 8820 | [1–384] | 8868 | [1–103] | 8992 | [1–478] | 9041 | [1–229],[279–523] |
| 8821 | [1–410] | 8869 | [1–164] | 8993 | [1–530] | 9042 | [1–432] |
| 8822 | [1–419] | 8870 | [1–103] | 8994 | [1–522] | 9043 | [1–455] |
| 8823 | [1–154],[352–477] | 8871 | [1–89] | 8995 | [1–206] | 9044 | [35–206] |
| 8824 | [1–95] | 8872 | [1–381] | 8996 | [1–62] | 9045 | [1–372] |
| 8825 | [1–54] | 8873 | [1–482] | 8998 | [1–603] | 9046 | [1–508] |
| 8826 | [1–485] | 8874 | [1–103] | 9000 | [1–169] | 9047 | [1–467] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 9001 | [1–446] | 9048 | [1–461] | 9124 | [1–286] | 9171 | [1–404] |
| 9002 | [1–341] | 9049 | [1–232] | 9125 | [1–422] | 9172 | [1–424] |
| 9003 | [1–381] | 9050 | [1–132] | 9173 | [1–350] | 9223 | [1–449] |
| 9004 | [1–171] | 9051 | [1–434] | 9174 | [1–390] | 9224 | [1–277] |
| 9005 | [1–366] | 9052 | [1–63] | 9175 | [1–473] | 9225 | [1–97] |
| 9006 | [1–349] | 9053 | [1–366] | 9176 | [1–428] | 9226 | [1–355] |
| 9007 | [1–452] | 9054 | [1–392] | 9177 | [1–384] | 9228 | [1–83],[218–371] |
| 9008 | [1–425] | 9055 | [1–404] | 9178 | [1–470] | 9229 | [82–384] |
| 9009 | [1–422] | 9056 | [1–149] | 9179 | [1–435] | 9230 | [1–379] |
| 9010 | [1–234] | 9057 | [1–386] | 9180 | [1–185] | 9231 | [1–409] |
| 9011 | [1–380] | 9058 | [1–381] | 9181 | [1–424] | 9232 | [1–408] |
| 9012 | [1–468] | 9059 | [1–79] | 9182 | [1–435] | 9233 | [1–427] |
| 9013 | [1–443] | 9060 | [1–459] | 9183 | [1–427] | 9234 | [1–425] |
| 9014 | [1–81] | 9061 | [53–358] | 9184 | [1–422] | 9235 | [1–438] |
| 9015 | [1–381] | 9062 | [281–423] | 9185 | [1–392] | 9236 | [1–435] |
| 9016 | [1–515] | 9063 | [1–181] | 9186 | [1–191] | 9237 | [1–88] |
| 9017 | [1–442] | 9064 | [1–439] | 9187 | [1–411] | 9238 | [1–455] |
| 9018 | [1–460] | 9066 | [287–455] | 9188 | [1–460] | 9240 | [1–76],[232–377] |
| 9019 | [1–261] | 9067 | [1–439] | 9189 | [1–426] | 9241 | [1–483] |
| 9020 | [1–411] | 9068 | [1–485] | 9190 | [1–308] | 9242 | [1–496] |
| 9021 | [1–48],[113–303] | 9069 | [1–487] | 9191 | [1–380] | 9243 | [1–214] |
| 9022 | [1–111],[227–281] | 9070 | [1–361] | 9192 | [67–313] | 9244 | [1–439] |
| 9023 | [1–509] | 9071 | [1–447] | 9194 | [1–371] | 9245 | [1–472] |
| 9024 | [1–387] | 9072 | [1–403] | 9195 | [1–167] | 9246 | [1–409] |
| 9025 | [1–76] | 9073 | [1–383] | 9196 | [1–283] | 9247 | [1–398] |
| 9026 | [1–472] | 9074 | [1–463] | 9197 | [1–418] | 9248 | [1–387] |
| 9027 | [1–315] | 9075 | [1–385] | 9198 | [1–383] | 9250 | [1–203] |
| 9028 | [1–385] | 9076 | [1–372] | 9199 | [1–40] | 9251 | [1–440] |
| 9029 | [1–465] | 9077 | [1–147] | 9200 | [1–446] | 9252 | [1–163] |
| 9079 | [1–223] | 9126 | [1–390] | 9201 | [1–420] | 9253 | [1–142] |
| 9080 | [1–209] | 9127 | [1–453] | 9202 | [1–442] | 9254 | [161–441] |
| 9081 | [1–370] | 9128 | [1–496] | 9203 | [1–414] | 9255 | [1–402] |
| 9082 | [1–303] | 9129 | [1–271] | 9204 | [1–423] | 9256 | [1–531] |
| 9083 | [1–511] | 9130 | [1–275] | 9205 | [1–149] | 9257 | [1–402] |
| 9084 | [1–468] | 9131 | [65–108] | 9206 | [1–89] | 9258 | [1–461] |
| 9085 | [1–459] | 9132 | [1–170] | 9207 | [1–378] | 9259 | [1–504] |
| 9086 | [1–97] | 9133 | [1–93] | 9209 | [1–448] | 9260 | [1–291] |
| 9087 | [1–498] | 9134 | [1–94] | 9210 | [1–283],[325–434] | 9261 | [1–590] |
| 9088 | [1–183] | 9135 | [1–303] | 9212 | [1–361] | 9262 | [1–519] |
| 9089 | [1–471] | 9136 | [1–235] | 9213 | [1–457] | 9263 | [1–466] |
| 9090 | [1–219] | 9137 | [34–465] | 9214 | [1–388] | 9264 | [1–455] |
| 9091 | [1–448] | 9138 | [1–335] | 9215 | [1–429] | 9265 | [1–491] |
| 9092 | [1–420] | 9139 | [1–380] | 9216 | [1–56] | 9266 | [1–534] |
| 9093 | [1–175] | 9140 | [1–294] | 9217 | [1–465] | 9267 | [1–252] |
| 9094 | [1–267] | 9141 | [1–184],[262–477] | 9218 | [1–261],[326–684] | 9268 | [1–487] |
| 9095 | [1–156] | 9142 | [1–359] | 9219 | [1–448] | 9269 | [1–357] |
| 9096 | [1–151],[237–305] | 9143 | [1–366] | 9220 | [1–225] | 9270 | [1–424] |
| 9097 | [1–556] | 9144 | [1–373] | 9221 | [1–452] | 9271 | [1–578] |
| 9098 | [1–429] | 9145 | [1–350] | 9222 | [1–451] | 9272 | [1–471] |
| 9099 | [1–475] | 9146 | [36–102] | 9273 | [1–449] | 9321 | [58–265] |
| 9100 | [1–442] | 9147 | [1–412] | 9274 | [1–305] | 9322 | [1–390] |
| 9101 | [1–475] | 9148 | [1–422] | 9275 | [1–450] | 9323 | [1–217] |
| 9102 | [1–460] | 9149 | [1–447] | 9276 | [1–419] | 9324 | [1–258] |
| 9103 | [1–413] | 9150 | [1–432] | 9277 | [1–398] | 9326 | [1–369] |
| 9104 | [1–414] | 9151 | [1–369] | 9278 | [1–447] | 9327 | [1–452] |
| 9105 | [1–83],[113–248] | 9152 | [52–432] | 9279 | [1–512] | 9328 | [1–336] |
| 9106 | [1–464] | 9153 | [1–398] | 9280 | [1–178] | 9329 | [1–428] |
| 9107 | [1–157] | 9154 | [1–439] | 9281 | [1–368] | 9330 | [1–90] |
| 9108 | [1–470] | 9155 | [1–56] | 9282 | [1–457] | 9331 | [1–437] |
| 9109 | [1–251] | 9156 | [1–423] | 9283 | [164–208] | 9332 | [1–425] |
| 9110 | [1–247] | 9157 | [1–426] | 9284 | [1–417] | 9333 | [1–234] |
| 9111 | [1–452] | 9158 | [1–432] | 9285 | [1–347] | 9334 | [1–472] |
| 9112 | [1–416] | 9159 | [1–433] | 9286 | [1–438] | 9335 | [1–166] |
| 9113 | [1–444] | 9160 | [1–392] | 9287 | [1–126] | 9336 | [1–381] |
| 9114 | [1–359] | 9161 | [1–436] | 9288 | [1–495] | 9337 | [1–425] |
| 9115 | [1–298] | 9162 | [1–52] | 9289 | [1–485] | 9338 | [1–447] |
| 9116 | [1–326] | 9163 | [1–367] | 9290 | [1–239] | 9339 | [1–483] |
| 9117 | [1–312] | 9164 | [1–395] | 9291 | [1–431] | 9340 | [1–446] |
| 9118 | [1–277] | 9165 | [1–464] | 9292 | [1–463] | 9341 | [1–447] |
| 9119 | [1–258] | 9166 | [1–190] | 9293 | [1–426] | 9342 | [1–399] |
| 9120 | [37–219],[355–494] | 9167 | [1–168] | 9294 | [1–444] | 9343 | [1–202] |
| 9121 | [1–434] | 9168 | [1–401] | 9295 | [1–463] | 9344 | [1–432] |
| 9122 | [1–212] | 9169 | [1–385] | 9296 | [1–342] | 9345 | [1–138] |
| 9123 | [1–410] | 9170 | [1–469] | 9297 | [125–448] | 9346 | [1–420] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 9298 | [1–271] | 9347 | [1–422] | 9472 | [1–104] | 9525 | [1–328] |
| 9299 | [1–299] | 9348 | [1–107] | 9473 | [1–101] | 9526 | [1–160] |
| 9300 | [1–85] | 9349 | [1–430] | 9474 | [1–381] | 9527 | [1–245] |
| 9301 | [1–433] | 9350 | [1–513] | 9475 | [1–107] | 9528 | [1–505] |
| 9302 | [1–293] | 9351 | [1–470] | 9476 | [1–104] | 9529 | [1–55] |
| 9303 | [1–385] | 9352 | [1–477] | 9477 | [1–97] | 9530 | [33–81],[113–335] |
| 9304 | [1–451] | 9353 | [1–490] | 9478 | [1–60] | 9531 | [1–453] |
| 9305 | [1–444] | 9354 | [1–443] | 9480 | [1–52] | 9532 | [1–434] |
| 9306 | [1–510] | 9355 | [1–415] | 9481 | [1–323] | 9533 | [1–429] |
| 9307 | [1–420] | 9356 | [1–443] | 9482 | [1–96] | 9534 | [1–427] |
| 9308 | [1–96],[145–281],[312–414] | 9357 | [1–389] | 9483 | [1–59] | 9535 | [1–493] |
| 9309 | [1–535] | 9358 | [1–475] | 9484 | [1–399] | 9536 | [1–348] |
| 9310 | [1–534] | 9359 | [1–385] | 9485 | [1–103] | 9537 | [1–680] |
| 9311 | [1–370] | 9360 | [1–538] | 9486 | [1–61] | 9538 | [1–535] |
| 9312 | [1–484] | 9361 | [1–447] | 9487 | [1–107] | 9539 | [1–239] |
| 9313 | [1–538] | 9362 | [1–64] | 9489 | [1–96] | 9540 | [1–438] |
| 9314 | [1–81] | 9363 | [1–415] | 9491 | [1–88] | 9541 | [1–498] |
| 9315 | [1–443] | 9364 | [1–413] | 9492 | [1–107] | 9542 | [1–274] |
| 9316 | [1–440] | 9365 | [1–425] | 9493 | [1–240] | 9543 | [1–429] |
| 9317 | [1–441] | 9366 | [39–456] | 9494 | [1–83] | 9544 | [1–410] |
| 9319 | [1–424] | 9367 | [1–498] | 9495 | [1–88] | 9545 | [1–371] |
| 9320 | [1–446] | 9368 | [1–373] | 9496 | [1–102] | 9546 | [1–511] |
| 9369 | [1–390] | 9417 | [1–439] | 9498 | [1–350] | 9547 | [1–42],[102–297] |
| 9370 | [1–544] | 9418 | [162–464] | 9499 | [1–107] | 9548 | [1–73] |
| 9371 | [1–451] | 9419 | [1–430] | 9500 | [1–58] | 9549 | [1–527] |
| 9372 | [1–272] | 9420 | [1–368] | 9501 | [1–96] | 9550 | [1–487] |
| 9373 | [1–420] | 9421 | [1–413] | 9502 | [1–112] | 9551 | [1–40I] |
| 9374 | [1–426] | 9422 | [1–422] | 9503 | [1–54] | 9552 | [1–355] |
| 9375 | [1–237] | 9423 | [1–396] | 9504 | [1–105] | 9553 | [1–173] |
| 9376 | [1–438] | 9424 | [1–315],[356–435] | 9505 | [1–107] | 9556 | [264–405] |
| 9377 | [1–480] | 9425 | [1–426] | 9507 | [1–104] | 9558 | [189–281] |
| 9378 | [1–444] | 9426 | [1–490] | 9508 | [1–101] | 9559 | [1–488] |
| 9379 | [1–482] | 9427 | [1–302] | 9510 | [1–316] | 9560 | [1–306] |
| 9380 | [1–250] | 9428 | [1–234] | 9511 | [1–421] | 9561 | [1–168],[228–369] |
| 9381 | [1–305] | 9429 | [1–440] | 9512 | [1–167] | 9562 | [1–274] |
| 9382 | [1–325] | 9430 | [1–560] | 9513 | [1–351] | 9563 | [1–363] |
| 9383 | [1–381] | 9431 | [1–442] | 9514 | [1–352] | 9564 | [1–361] |
| 9384 | [1–362] | 9432 | [1–61] | 9515 | [1–377] | 9565 | [1–395] |
| 9385 | [1–436] | 9433 | [1–398] | 9516 | [1–297] | 9566 | [1–444] |
| 9386 | [1–127] | 9434 | [1–119] | 9517 | [1–210],[245–361] | 9567 | [1–191],[279–464] |
| 9387 | [1–336] | 9435 | [1–436] | 9518 | [1–240] | 9568 | [1–485] |
| 9388 | [63–88] | 9436 | [87–147] | 9519 | [1–521] | 9569 | [1–332] |
| 9389 | [1–510] | 9437 | [1–212] | 9570 | [1–428] | 9617 | [1–86] |
| 9390 | [1–447] | 9439 | [1–263] | 9571 | [1–501] | 9618 | [79–117] |
| 9391 | [1–433] | 9440 | [1–299] | 9572 | [1–511] | 9619 | [1–357] |
| 9392 | [1–104] | 9441 | [1–444] | 9573 | [1–76] | 9620 | [1–422] |
| 9393 | [1–435] | 9442 | [1–418] | 9574 | [1–454] | 9621 | [1–80] |
| 9394 | [207–414] | 9443 | [1–448) | 9575 | [1–179] | 9622 | [1–511] |
| 9395 | [1–423] | 9444 | [1–238] | 9576 | [1–318] | 9623 | [1–389] |
| 9396 | [1–485] | 9445 | [1–467] | 9577 | [1–264] | 9624 | [1–268] |
| 9397 | [1–471] | 9446 | [156–295] | 9578 | [1–448] | 9625 | [1–327] |
| 9398 | [1–445] | 9447 | [1–405] | 9579 | [1–455] | 9626 | [1–86] |
| 9399 | [1–420] | 9448 | [1–191] | 9580 | [1–474] | 9627 | [1–101],[144–452] |
| 9400 | [1–411] | 9449 | [1–416] | 9581 | [1–468] | 9628 | [1–102] |
| 9401 | [1–407] | 9450 | [1–415] | 9582 | [1–426] | 9629 | [1–233] |
| 9402 | [1–263] | 9451 | [1–427] | 9583 | [1–141] | 9630 | [1–321] |
| 9403 | [1–176] | 9452 | [1–279] | 9584 | [1–192] | 9631 | [1–308] |
| 9404 | [1–317] | 9453 | [1–328] | 9585 | [1–359] | 9632 | [1–391] |
| 9405 | [1–455] | 9454 | [1–392] | 9586 | [1–115] | 9633 | [139–274],[414–455] |
| 9406 | [1–255] | 9455 | [1–235] | 9587 | [1–138] | 9634 | [1–433] |
| 9407 | [1–276] | 9456 | [1–537] | 9588 | [1–63] | 9635 | [1–292] |
| 9408 | [1–454] | 9457 | [58–375] | 9589 | [1–72] | 9636 | [1–274] |
| 9409 | [1–137],[285–444] | 9458 | [1–103] | 9590 | [1–73] | 9637 | [31–297] |
| 9410 | [1–553] | 9460 | [1–71] | 9591 | [1–135] | 9638 | [1–369] |
| 9412 | [1–451] | 9461 | [1–59] | 9592 | [1–78] | 9639 | [1–473] |
| 9413 | [1–407] | 9462 | [1–61],[145–441] | 9593 | [245–420] | 9640 | [1–292] |
| 9414 | [1–308] | 9463 | [1–328] | 9594 | [1–331] | 9642 | [1–211] |
| 9415 | [32–144],[191–408] | 9464 | [1–91] | 9595 | [73–138] | 9643 | [1–468] |
| 9416 | [1–305] | 9466 | [1–341] | 9596 | [1–194] | 9644 | [1–93] |
| 9467 | [1–165] | 9520 | [99–295] | 9597 | [1–456] | 9645 | [1–501] |
| 9468 | [1–104] | 9521 | [1–579] | 9598 | [1–403] | 9646 | [1–134] |
| 9469 | [1–107] | 9522 | [1–83] | 9599 | [35–480] | 9647 | [1–364] |
| 9470 | [1–358] | 9523 | [1–383] | 9600 | [1–402] | 9648 | [1–347] |
| 9471 | [1–308] | 9524 | [83–312] | 9601 | [1–423] | 9649 | [1–157] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 9602 | [1–114] | 9650 | [1–171] | 9678 | [1–170] | 9727 | [1–167] |
| 9603 | [1–366] | 9651 | [1–430] | 9679 | [1–261] | 9728 | [1–67] |
| 9604 | [1–78] | 9652 | [1–569] | 9680 | [1–97] | 9729 | [1–356] |
| 9605 | [1–423] | 9653 | [1–306] | 9681 | [1–372] | 9730 | [1–58] |
| 9606 | [1–435] | 9654 | [1–206] | 9682 | [1–432] | 9731 | [1–621] |
| 9607 | [1–378] | 9655 | [1–137] | 9683 | [1–323] | 9732 | [1–207] |
| 9608 | [61–163] | 9656 | [1–111] | 9684 | [1–432] | 9733 | [1–87] |
| 9609 | [1–397] | 9657 | [1–244] | 9685 | [1–90] | 9734 | [1–63] |
| 9610 | [1–502] | 9658 | [1–332] | 9686 | [1–461] | 9735 | [1–135] |
| 9611 | [1–431] | 9659 | [1–80] | 9687 | [1–361] | 9736 | [1–93] |
| 9612 | [1–420] | 9660 | [1–389] | 9688 | [1–416] | 9738 | [1–429] |
| 9613 | [1–459] | 9661 | [1–76] | 9689 | [1–67] | 9739 | [1–146] |
| 9614 | [1–478] | 9662 | [1–446] | 9690 | [1–440] | 9740 | [1–61] |
| 9615 | [1–336] | 9663 | [1–204] | 9691 | [1–387] | 9741 | [1–57] |
| 9616 | [1–386] | 9664 | [1–456] | 9692 | [1–445] | 9742 | [76–108] |
| 9570 | [1–428] | 9617 | [1–86] | 9693 | [1–51] | 9743 | [1–146] |
| 9571 | [1–501] | 9618 | [79–117] | 9694 | [1–254] | 9744 | [1–337] |
| 9572 | [1–511] | 9619 | [1–357] | 9695 | [1–421] | 9745 | [1–78] |
| 9573 | [1–76] | 9620 | [1–422] | 9696 | [1–458] | 9746 | [1–60] |
| 9574 | [1–454] | 9621 | [1–80] | 9697 | [1–391] | 9747 | [1–415] |
| 9575 | [1–179] | 9622 | [1–511] | 9698 | [1–86] | 9748 | [1–76],[269–410] |
| 9576 | [1–318] | 9623 | [1–389] | 9699 | [1–432] | 9749 | [1–406] |
| 9577 | [1–264] | 9624 | [1–268] | 9700 | [1–93],[271–440] | 9750 | [1–109] |
| 9578 | [1–448] | 9625 | [1–327] | 9701 | [1–336] | 9751 | [1–371] |
| 9579 | [1–455] | 9626 | [1–86] | 9702 | [1–399] | 9752 | [1–103] |
| 9580 | [1–474] | 9627 | [1–101],[144–452] | 9703 | [1–89] | 9753 | [1–83] |
| 9581 | [1–468] | 9628 | [1–102] | 9704 | [1–323] | 9754 | [1–224] |
| 9582 | [1–426] | 9629 | [1–233] | 9705 | [1–407] | 9755 | [1–462] |
| 9583 | [1–141] | 9630 | [1–321] | 9706 | [1–383] | 9756 | [1–86] |
| 9584 | [1–192] | 9631 | [1–308] | 9707 | [1–463] | 9757 | [1–398] |
| 9585 | [1–359] | 9632 | [1–391] | 9708 | [1–405] | 9758 | [96–272],[370–477] |
| 9586 | [1–115] | 9633 | [139–274],[414–455] | 9710 | [1–367] | 9759 | [1–487] |
| 9587 | [1–138] | 9634 | [1–433] | 9711 | [31–305],[364–411] | 9760 | [1–130] |
| 9588 | [1–63] | 9635 | [1–292] | 9712 | [1–71] | 9761 | [1–432] |
| 9589 | [1–72] | 9636 | [1–274] | 9713 | [1–103] | 9762 | [1–483] |
| 9590 | [1–73] | 9637 | [31–297] | 9763 | [1–323] | 9812 | [1–502] |
| 9591 | [1–135] | 9638 | [1–369] | 9764 | [1–337] | 9813 | [1–500] |
| 9592 | [1–78] | 9639 | [1–473] | 9765 | [1–126] | 9814 | [1–500] |
| 9593 | [245–420] | 9640 | [1–292] | 9766 | [1–284] | 9815 | [1–416] |
| 9594 | [1–331] | 9642 | [1–211] | 9767 | [1–76] | 9816 | [52–370] |
| 9595 | [73–138] | 9643 | [1–468] | 9768 | [1–135] | 9817 | [1–471] |
| 9596 | [1–194] | 9644 | [1–93] | 9769 | [233–466] | 9818 | [53–400] |
| 9597 | [1–456] | 9645 | [1–501] | 9770 | [1–440] | 9819 | [1–472] |
| 9598 | [1–403] | 9646 | [1–134] | 9771 | [1–407] | 9820 | [1–482] |
| 9599 | [35–480] | 9647 | [1–364] | 9772 | [1–443] | 9821 | [1–441] |
| 9600 | [1–402] | 9648 | [1–347] | 9773 | [1–89] | 9822 | [1–444] |
| 9601 | [1–423] | 9649 | [1–157] | 9774 | [1–151] | 9823 | [1–237] |
| 9602 | [1–114] | 9650 | [1–171] | 9775 | [1–424] | 9824 | [1–79] |
| 9603 | [1–366] | 9651 | [1–430] | 9776 | [1–248] | 9825 | [1–452] |
| 9604 | [1–78] | 9652 | [1–569] | 9777 | [1–322] | 9826 | [1–155] |
| 9605 | [1–423] | 9653 | [1–306] | 9778 | [1–68] | 9827 | [1–438] |
| 9606 | [1–435] | 9654 | [1–206] | 9779 | [1–399] | 9828 | [1–463] |
| 9607 | [1–378] | 9655 | [1–137] | 9780 | [233–481] | 9829 | [1–487] |
| 9608 | [61–163] | 9656 | [1–111] | 9782 | [1–431] | 9830 | [1–479] |
| 9609 | [1–397] | 9657 | [1–244] | 9783 | [1–353] | 9831 | [1–79] |
| 9610 | [1–502] | 9658 | [1–332] | 9784 | [1–346] | 9832 | [1–426] |
| 9611 | [1–431] | 9659 | [1–80] | 9785 | [1–435] | 9833 | [1–369] |
| 9612 | [1–420] | 9660 | [1–389] | 9786 | [1–380] | 9834 | [1–500] |
| 9613 | [1–459] | 9661 | [1–76] | 9787 | [1–362] | 9835 | [1–343] |
| 9614 | [1–478] | 9662 | [1–446] | 9788 | [1–500] | 9836 | [1–62],[162–497] |
| 9615 | [1–336] | 9663 | [1–204] | 9789 | [1–250],[302–429] | 9837 | [1–72] |
| 9616 | [1–386] | 9664 | [1–456] | 9790 | [1–375] | 9838 | [1–507] |
| 9665 | [1–469] | 9714 | [1–369] | 9791 | [1–257],[354–425] | 9839 | [1–574] |
| 9666 | [1–452] | 9715 | [1–316] | 9792 | [1–299] | 9840 | [1–303] |
| 9667 | [1–216] | 9717 | [1–359] | 9793 | [1–356] | 9841 | [1–78] |
| 9668 | [1–242],[372–474] | 9718 | [1–57] | 9794 | [1–456] | 9842 | [1–415] |
| 9669 | [1–285] | 9719 | [1–434] | 9795 | [1–385] | 9843 | [1–52],[100–214] |
| 9671 | [1–81] | 9720 | [1–434] | 9796 | [1–374] | 9844 | [1–529] |
| 9672 | [1–481] | 9721 | [1–378] | 9797 | [1–393] | 9845 | [1–71] |
| 9673 | [281–488] | 9722 | [1–368] | 9798 | [1–375] | 9846 | [1–424] |
| 9674 | [1–53] | 9723 | [1–300] | 9799 | [1–425] | 9847 | [1–455] |
| 9675 | [52–378] | 9724 | [1–227] | 9801 | [1–462] | 9848 | [1–339] |
| 9676 | [1–429] | 9725 | [1–297] | 9802 | [1–91] | 9849 | [1–449] |
| 9677 | [1–434] | 9726 | [117–183] | 9803 | [1–236] | 9850 | [1–117] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 9804 | [1–254] | 9851 | [1–173] | 9980 | [1–423] | 10027 | [1–468] |
| 9805 | [1–351] | 9852 | [1–444] | 9981 | [1–283] | 10028 | [1–396] |
| 9806 | [1–425] | 9853 | [1–387] | 9982 | [1–55] | 10029 | [1–436] |
| 9807 | [1–68] | 9854 | [1–396] | 9983 | [1–388] | 10030 | [1–452] |
| 9808 | [1–394] | 9855 | [1–92] | 9984 | [1–71] | 10031 | [1–471] |
| 9809 | [1–463] | 9856 | [1–439] | 9985 | [1–485] | 10032 | [1–527] |
| 9810 | [1–368] | 9857 | [1–440] | 9986 | [1–162] | 10033 | [1–463] |
| 9811 | [1–62] | 9858 | [1–429] | 9987 | [1–455] | 10034 | [1–461] |
| 9859 | [1–488] | 9909 | [1–265] | 9988 | [116–488] | 10035 | [1–439] |
| 9860 | [1–438] | 9910 | [1–424] | 9989 | [1–383] | 10036 | [1–86] |
| 9862 | [1–472] | 9911 | [1–73] | 9990 | [1–491] | 10037 | [1–478] |
| 9863 | [1–345] | 9912 | [1–441] | 9991 | [1–500] | 10038 | [1–36] |
| 9864 | [1–110] | 9913 | [1–414] | 9992 | [1–448] | 10039 | [1–393] |
| 9865 | [1–157] | 9914 | [1–442] | 9993 | [1–355] | 10040 | [1–435] |
| 9866 | [1–461] | 9915 | [112–167] | 9994 | [1–77] | 10041 | [1–433] |
| 9867 | [32–475] | 9916 | [1–138] | 9995 | [1–481] | 10042 | [1–43],[305–366], [446–483] |
| 9868 | [1–144] | 9917 | [1–412] | | | | |
| 9869 | [242–502] | 9918 | [1–891] | 9996 | [1–367] | 10043 | [1–437] |
| 9870 | [1–356] | 9919 | [1–200] | 9997 | [1–86] | 10044 | [1–461] |
| 9871 | [1–165] | 9920 | [1–134] | 9998 | [1–327] | 10045 | [1–135] |
| 9872 | [1–424] | 9921 | [1–164] | 9999 | [164–348] | 10046 | [1–72] |
| 9873 | [1–175] | 9922 | [1–468] | 10000 | [1–479] | 10047 | [1–78] |
| 9875 | [1–452] | 9923 | [1–414] | 10001 | [1–391] | 10048 | [1–230] |
| 9876 | [1–137] | 9924 | [1–169] | 10002 | [1–325] | 10049 | [1–162] |
| 9877 | [1–426] | 9925 | [1–69] | 10003 | [1–367] | 10050 | [214–391] |
| 9878 | [1–439] | 9926 | [1–441] | 10004 | [1–437] | 10051 | [1–120] |
| 9879 | [1–504] | 9927 | [1–96] | 10005 | [1–364] | 10052 | [1–329] |
| 9880 | [1–194] | 9928 | [1–457] | 10006 | [1–476] | 10053 | [1–438] |
| 9881 | [1–483] | 9929 | [1–54] | 10007 | [1–486] | 10054 | [1–120] |
| 9882 | [1–335],[411–438] | 9930 | [1–379] | 10055 | [1–227] | 10102 | [1–126] |
| 9883 | [323–581] | 9931 | [1–419] | 10056 | [1–94] | 10103 | [1–146] |
| 9884 | [1–345] | 9932 | [1–422] | 10057 | [1–430] | 10105 | [1–466] |
| 9885 | [1–280] | 9933 | [1–198] | 10058 | [1–473] | 10106 | [1–441] |
| 9886 | [1–359] | 9934 | [1–207] | 10059 | [1–161] | 10107 | [1–324] |
| 9887 | [1–444] | 9935 | [1–413] | 10060 | [1–344] | 10108 | [1–41] |
| 9889 | [1–461] | 9936 | [1–440] | 10061 | [1–496] | 10109 | [1–379] |
| 9890 | [1–79] | 9937 | [168–391] | 10062 | [1–382] | 10110 | [1–375] |
| 9891 | [1–137],[306–439] | 9938 | [127–308] | 10063 | [1–272] | 10111 | [1–417] |
| 9892 | [1–68] | 9939 | [1–328] | 10064 | [1–530] | 10112 | [1–81] |
| 9893 | [1–482] | 9940 | [1–400] | 10065 | [1–44],[129–473] | 10113 | [1–467] |
| 9894 | [1–145] | 9941 | [1–161] | 10066 | [1–398] | 10115 | [1–432] |
| 9895 | [1–379] | 9942 | [1–169] | 10067 | [1–170] | 10116 | [1–289] |
| 9896 | [1–449] | 9944 | [148–172] | 10068 | [1–404] | 10117 | [1–423] |
| 9897 | [1–478] | 9945 | [1–138] | 10069 | [1–103] | 10118 | [1–89] |
| 9898 | [1–414] | 9947 | [1–64] | 10070 | [1–120] | 10120 | [1–341] |
| 9899 | [1–177] | 9948 | [1–219] | 10071 | [1–261] | 10121 | [1–201] |
| 9900 | [1–245] | 9949 | [1–190] | 10072 | [1–322] | 10122 | [1–436] |
| 9901 | [1–425] | 9950 | [1–188] | 10073 | [1–509] | 10123 | [1–405] |
| 9902 | [1–155] | 9951 | [1–140] | 10074 | [1–399] | 10124 | [1–343] |
| 9903 | [1–308] | 9952 | [1–188] | 10075 | [1–484] | 10125 | [1–473] |
| 9904 | [1–79] | 9953 | [1–176] | 10076 | [1–292] | 10126 | [1–451] |
| 9905 | [1–296] | 9954 | [1–176] | 10077 | [1–316] | 10127 | [1–342] |
| 9906 | [1–429] | 9955 | [1–479] | 10078 | [1–390] | 10128 | [1–228] |
| 9907 | [1–174] | 9956 | [1–400] | 10079 | [1–498] | 10129 | [1–414] |
| 9908 | [1–180] | 9957 | [1–380] | 10080 | [1–223] | 10130 | [1–107] |
| 9958 | [1–112] | 10008 | [1–415] | 10081 | [50–472] | 10131 | [1–89] |
| 9959 | [1–423] | 10009 | [1–289] | 10082 | [1–284] | 10132 | [1–223] |
| 9960 | [1–128] | 10010 | [1–440] | 10083 | [1–410] | 10133 | [1–78] |
| 9961 | [1–364] | 10011 | [1–326] | 10084 | [1–407] | 10134 | [1–125] |
| 9963 | [1–185] | 10012 | [1–361] | 10085 | [47–345] | 10135 | [1–128],[215–440] |
| 9964 | [1–469] | 10013 | [1–514] | 10086 | [1–136] | 10136 | [1–107],[189–348] |
| 9966 | [1–72] | 10014 | [1–476] | 10087 | [1–461] | 10137 | [1–257] |
| 9967 | [1–104] | 10015 | [1–289] | 10088 | [1–519] | 10138 | [1–429] |
| 9968 | [1–176] | 10016 | [1–411] | 10089 | [1–187] | 10139 | [1–337] |
| 9970 | [1–434] | 10017 | [1–246] | 10090 | [1–465] | 10140 | [1–476] |
| 9971 | [1–439] | 10018 | [1–432] | 10091 | [1–67] | 10141 | [1–308] |
| 9972 | [1–114] | 10019 | [1–502] | 10092 | [1–476] | 10142 | [1–61] |
| 9973 | [1–349] | 10020 | [1–326] | 10093 | [1–445] | 10143 | [1–173] |
| 9974 | [1–505] | 10021 | [1–106] | 10094 | [1–227] | 10144 | [1–176] |
| 9975 | [1–86] | 10022 | [1–445] | 10095 | [1–398] | 10145 | [1–72] |
| 9976 | [1–487] | 10023 | [1–212] | 10096 | [1–67],[164–367] | 10146 | [1–368] |
| 9977 | [1–338] | 10024 | [1–119] | 10097 | [1–46],[129–502] | 10147 | [52–357] |
| 9978 | [1–387] | 10025 | [1–337] | 10098 | [1–445] | 10148 | [1–145] |
| 9979 | [1–438] | 10026 | [1–146] | 10099 | [1–339] | 10149 | [1–444] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 10100 | [1–456] | 10150 | [1–434] | 10276 | [1–441] | 10325 | [1–445] |
| 10101 | [1–208] | 10151 | [1–142] | 10277 | [1–237] | 10326 | [165–342] |
| 10152 | [1–443] | 10203 | [1–257] | 10278 | [1–252] | 10327 | [1–362] |
| 10153 | [1–496] | 10204 | [1–215] | 10279 | [1–437] | 10328 | [1–304] |
| 10154 | [1–119] | 10205 | [1–379] | 10280 | [1–340] | 10329 | [37–308] |
| 10155 | [1–330] | 10206 | [1–92],[308–419] | 10281 | [1–343] | 10330 | [218–278] |
| 10156 | [1–50] | 10207 | [1–487] | 10282 | [1–402] | 10331 | [1–259] |
| 10157 | [1–347] | 10208 | [1–51] | 10283 | [1–377] | 10332 | [1–656] |
| 10158 | [1–343] | 10209 | [1–367] | 10284 | [1–386] | 10333 | [1–445] |
| 10159 | [1–252] | 10210 | [1–88] | 10285 | [1–440] | 10334 | [1–589] |
| 10161 | [1–67] | 10211 | [1–299] | 10286 | [1–247] | 10335 | [61–160] |
| 10162 | [1–323] | 10212 | [1–435] | 10287 | [1–422] | 10336 | [331–498] |
| 10163 | [1–345] | 10213 | [1–77] | 10288 | [1–135] | 10337 | [1–517] |
| 10164 | [79–244] | 10214 | [1–322] | 10289 | [1–430] | 10338 | [1–493] |
| 10165 | [1–484] | 10215 | [1–288] | 10290 | [1–427] | 10339 | [1–525] |
| 10166 | [1–375] | 10216 | [1–391] | 10291 | [1–422] | 10340 | [1–293] |
| 10167 | [1–476] | 10217 | [1–490] | 10292 | [1–75] | 10341 | [276–447] |
| 10169 | [1–355] | 10218 | [1–448] | 10293 | [1–477] | 10342 | [1–399] |
| 10170 | [1–472] | 10219 | [1–455] | 10294 | [1–469] | 10343 | [1–523] |
| 10171 | [1–467] | 10220 | [1–279] | 10295 | [1–488],[540–1211] | 10344 | [1–332] |
| 10172 | [1–327] | 10221 | [1–477] | 10296 | [1–481] | 10345 | [1–370] |
| 10173 | [1–326] | 10222 | [1–386] | 10297 | [1–259] | 10346 | [1–330] |
| 10174 | [52–369] | 10223 | [1–395] | 10347 | [1–75] | 10394 | [1–483] |
| 10175 | [88–488] | 10224 | [1–359] | 10348 | [1–557] | 10395 | [60–541] |
| 10177 | [1–433] | 10225 | [37–107] | 10349 | [1–428] | 10396 | [32–510] |
| 10178 | [1–246] | 10226 | [55–209] | 10350 | [1–445] | 10397 | [1–535] |
| 10179 | [49–108] | 10227 | [1–271] | 10351 | [1–397] | 10398 | [1–606] |
| 10180 | [1–492] | 10228 | [1–570] | 10352 | [1–451] | 10399 | [1–486] |
| 10181 | [1–77] | 10229 | [1–252] | 10353 | [1–417] | 10400 | [1–416] |
| 10182 | [1–188] | 10230 | [1–488] | 10354 | [1–485] | 10401 | [162–503] |
| 10183 | [1–40] | 10231 | [1–328] | 10355 | [1–458] | 10402 | [1–481] |
| 10184 | [1–191] | 10232 | [32–485] | 10356 | [1–293] | 10403 | [1–485] |
| 10185 | [1–255] | 10233 | [1–429] | 10357 | [1–220] | 10404 | [1–293] |
| 10186 | [1–326] | 10234 | [1–361] | 10358 | [1–73] | 10405 | [1–423] |
| 10187 | [1–503] | 10235 | [1–306] | 10359 | [1–431] | 10406 | [1–46],[109–427] |
| 10188 | [1–161] | 10236 | [1–407] | 10360 | [1–447] | 10407 | [30–86],[250–478] |
| 10190 | [1–314] | 10237 | [1–250] | 10361 | [1–360] | 10408 | [1–536] |
| 10191 | [1–486] | 10238 | [1–252] | 10362 | [1–460] | 10409 | [1–473] |
| 10192 | [1–337] | 10239 | [1–432] | 10363 | [1–401] | 10410 | [1–481] |
| 10193 | [1–271] | 10240 | [1–207] | 10364 | [1–188] | 10411 | [1–468] |
| 10194 | [89–418] | 10241 | [1–315] | 10365 | [1–496] | 10412 | [1–445] |
| 10195 | [1–130] | 10242 | [1–312] | 10366 | [32–496] | 10413 | [1–505] |
| 10196 | [1–77] | 10243 | [1–378] | 10367 | [1–449] | 10414 | [1–510] |
| 10197 | [1–76] | 10244 | [1–341] | 10368 | [1–337] | 10415 | [50–461] |
| 10198 | [1–398] | 10245 | [1–247] | 10369 | [1–448] | 10416 | [1–358] |
| 10199 | [1–452] | 10246 | [1–331] | 10370 | [1–116] | 10417 | [46–547] |
| 10200 | [1–476] | 10247 | [1–318] | 10371 | [1–453] | 10418 | [1–487] |
| 10201 | [1–78] | 10248 | [1–248] | 10372 | [1–450] | 10419 | [1–73] |
| 10202 | [289–365] | 10249 | [1–460] | 10373 | [1–427] | 10420 | [1–77] |
| 10250 | [1–136] | 10299 | [1–344],[444–519] | 10374 | [1–323] | 10421 | [228–425] |
| 10251 | [151–206] | 10300 | [1–310] | 10375 | [1–426] | 10422 | [1–535] |
| 10252 | [1–400] | 10301 | [1–323] | 10376 | [1–489] | 10423 | [1–357] |
| 10253 | [170–414] | 10302 | [90–290] | 10377 | [1–257] | 10424 | [1–72] |
| 10254 | [1–147] | 10303 | [1–359] | 10378 | [1–444] | 10425 | [1–441] |
| 10255 | [1–55] | 10304 | [1–303] | 10379 | [1–574] | 10426 | [1–184],[301–388] |
| 10256 | [1–397] | 10305 | [1–462] | 10380 | [1–271] | 10427 | [1–198] |
| 10257 | [1–425] | 10306 | [1–249] | 10381 | [1–539] | 10428 | [1–517] |
| 10258 | [1–319] | 10307 | [1–344] | 10382 | [1–232] | 10429 | [1–80] |
| 10259 | [1–423] | 10308 | [1–468] | 10383 | [1–147] | 10430 | [1–483] |
| 10260 | [1–381] | 10309 | [1–486] | 10384 | [1–417] | 10431 | [1–317] |
| 10261 | [1–433] | 10310 | [1–391] | 10385 | [1–478] | 10432 | [1–587] |
| 10262 | [1–336] | 10311 | [1–72] | 10386 | [1–376],[433–583] | 10433 | [1–435] |
| 10263 | [1–110] | 10312 | [1–70] | 10387 | [1–450] | 10435 | [1–333] |
| 10264 | [1–170] | 10313 | [1–426] | 10388 | [1–418] | 10436 | [1–469] |
| 10265 | [1–493] | 10314 | [1–444] | 10389 | [1–593] | 10437 | [1–306] |
| 10266 | [1–498] | 10315 | [1–348] | 10390 | [1–113] | 10438 | [1–500] |
| 10267 | [1–532] | 10317 | [1–440] | 10391 | [1–354] | 10439 | [1–140],[200–486] |
| 10268 | [1–563] | 10318 | [1–433] | 10392 | [1–395] | 10440 | [1–360] |
| 10269 | [1–266] | 10319 | [1–283] | 10393 | [1–586] | 10441 | [1–452] |
| 10270 | [95–466] | 10320 | [1–505] | 10442 | [1–75] | 10491 | [1–625] |
| 10271 | [1–28],[101–157] | 10321 | [1–157] | 10443 | [1–466] | 10492 | [1–555] |
| 10272 | [1–452] | 10322 | [1–436] | 10444 | [1–463] | 10493 | [1–600] |
| 10273 | [1–352] | 10323 | [1–445] | 10445 | [1–474] | 10494 | [1–312] |
| 10274 | [1–429] | 10324 | [1–450] | 10446 | [1–431] | 10495 | [1–469] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 10448 | [1–505] | 10496 | [52–373] | 10570 | [1–523] | 10618 | [1–563] |
| 10449 | [1–559] | 10497 | [1–406] | 10571 | [1–559] | 10619 | [1–454] |
| 10450 | [187–226] | 10498 | [1–390] | 10572 | [1–354] | 10621 | [1–470] |
| 10451 | [1–515] | 10499 | [1–63],[169–340] | 10573 | [106–296] | 10622 | [1–438] |
| 10452 | [1–533] | 10500 | [1–142] | 10574 | [1–271] | 10623 | [46–451] |
| 10454 | [1–474] | 10501 | [1–467] | 10575 | [1–90] | 10624 | [1–529] |
| 10455 | [1–500] | 10502 | [1–487] | 10576 | [1–353] | 10625 | [1–512] |
| 10456 | [1–418] | 10503 | [1–454] | 10577 | [1–314] | 10626 | [1–562] |
| 10457 | [1–362] | 10504 | [1–399] | 10578 | [1–119] | 10627 | [1–106],[137–337] |
| 10458 | [1–477] | 10505 | [1–433] | 10579 | [1–351] | 10628 | [1–501] |
| 10459 | [1–465] | 10506 | [1–402] | 10580 | [1–80] | 10629 | [1–365],[454–489] |
| 10460 | [1–519] | 10507 | [1–395] | 10581 | [1–361] | 10630 | [1–281] |
| 10461 | [1–69] | 10508 | [1–155] | 10582 | [1–47],[83–120] | 10631 | [1–400] |
| 10462 | [1–573] | 10509 | [1–338] | 10583 | [1–535] | 10632 | [1–511] |
| 10463 | [1–537] | 10510 | [1–346] | 10584 | [1–57] | 10633 | [1–374] |
| 10464 | [1–378] | 10511 | [1–577] | 10585 | [1–511] | 10634 | [1–487] |
| 10465 | [1–105] | 10512 | [1–386] | 10635 | [1–514] | 10682 | [1–410] |
| 10466 | [1–63] | 10513 | [1–151] | 10636 | [1–551] | 10683 | [1–487] |
| 10467 | [1–145] | 10514 | [1–142] | 10637 | [50–466] | 10684 | [1–546] |
| 10468 | [1–282] | 10515 | [1–164] | 10638 | [1–451] | 10685 | [1–501] |
| 10469 | [1–349] | 10516 | [1–524] | 10639 | [1–552] | 10686 | [1–293] |
| 10470 | [1–89] | 10517 | [1–400] | 10640 | [1–456] | 10687 | [1–477] |
| 10471 | [1–64] | 10518 | [1–387] | 10641 | [1–169] | 10688 | [1–447] |
| 10472 | [1–558] | 10519 | [1–408] | 10642 | [1–155] | 10689 | [1–84] |
| 10473 | [1–474] | 10520 | [1–433] | 10643 | [1–440] | 10690 | [1–67] |
| 10474 | [1–547] | 10521 | [1–369] | 10644 | [1–129] | 10691 | [1–429] |
| 10475 | [1–529] | 10522 | [1–441] | 10645 | [1–541] | 10692 | [1–356] |
| 10476 | [1–515] | 10523 | [1–534] | 10646 | [1–557] | 10693 | [1–361] |
| 10477 | [1–454] | 10524 | [1–274] | 10647 | [1–557] | 10694 | [1–162],[216–271] |
| 10478 | [1–145] | 10525 | [1–473] | 10648 | [1–484] | 10695 | [1–270] |
| 10479 | [1–419] | 10526 | [112–140] | 10649 | [1–553] | 10696 | [1–521] |
| 10480 | [1–503] | 10527 | [1–514] | 10650 | [1–538] | 10697 | [1–344] |
| 10481 | [1–450] | 10528 | [1–209] | 10651 | [1–497] | 10698 | [1–379] |
| 10482 | [1–398] | 10529 | [1–55] | 10652 | [1–445] | 10699 | [1–419] |
| 10483 | [1–369] | 10530 | [1–26],[70–232],[265–401] | 10653 | [1–309] | 10700 | [1–208],[293–470] |
| 10484 | [1–343] | 10531 | [1–300] | 10654 | [1–426] | 10701 | [1–288] |
| 10485 | [395–474] | 10532 | [1–416] | 10655 | [1–527] | 10702 | [1–299] |
| 10486 | [56–369] | 10533 | [1–481] | 10656 | [1–149] | 10703 | [1–470] |
| 10487 | [1–439] | 10534 | [50–474] | 10657 | [1–525] | 10704 | [1–85] |
| 10488 | [63–435] | 10535 | [1–188] | 10658 | [1–470] | 10705 | [1–540] |
| 10489 | [1–494] | 10536 | [50–474] | 10659 | [1–520] | 10706 | [1–420] |
| 10490 | [1–343] | 10537 | [1–428] | 10660 | [1–403] | 10707 | [1–233],[264–304] |
| 10538 | [1–581] | 10586 | [1–116] | 10661 | [1–428] | 10708 | [1–499] |
| 10539 | [1–442] | 10587 | [1–312] | 10662 | [1–503] | 10709 | [1–418] |
| 10540 | [1–294] | 10588 | [1–591] | 10663 | [1–468],[529–562] | 10710 | [1–194] |
| 10542 | [1–493] | 10589 | [1–129],[160–503] | 10664 | [1–583] | 10711 | [1–474] |
| 10543 | [1–193] | 10590 | [1–572] | 10665 | [1–265] | 10712 | [1–486] |
| 10544 | [1–396] | 10591 | [65–491] | 10666 | [1–480] | 10713 | [1–58] |
| 10545 | [1–506] | 10592 | [1–127] | 10667 | [89–433] | 10714 | [1–468] |
| 10546 | [1–504] | 10593 | [1–370] | 10668 | [1–260] | 10715 | [1–59] |
| 10547 | [1–154] | 10594 | [1–607] | 10669 | [1–493] | 10716 | [1–433] |
| 10548 | [1–501] | 10595 | [1–447] | 10670 | [1–345] | 10717 | [1–396] |
| 10549 | [1–127] | 10596 | [1–532] | 10671 | [1–196] | 10718 | [1–443] |
| 10550 | [1–439] | 10597 | [1–445] | 10672 | [1–447] | 10719 | [1–65] |
| 10551 | [1–409] | 10598 | [1–50] | 10673 | [1–429] | 10720 | [1–421] |
| 10552 | [1–72] | 10599 | [1–453] | 10674 | [1–531] | 10721 | [1–500] |
| 10553 | [32–494] | 10600 | [1–425] | 10675 | [1–233] | 10722 | [1–149] |
| 10554 | [1–409] | 10601 | [1–443] | 10676 | [1–410] | 10723 | [1–109] |
| 10555 | [1–306] | 10602 | [1–482] | 10677 | [1–497] | 10724 | [1–383] |
| 10556 | [1–491] | 10603 | [1–494] | 10678 | [1–402] | 10725 | [1–414] |
| 10557 | [1–437] | 10604 | [1–480] | 10679 | [1–351] | 10726 | [1–485] |
| 10558 | [1–337] | 10605 | [1–407] | 10680 | [1–298] | 10727 | [1–270] |
| 10559 | [1–233],[267–403] | 10606 | [50–472] | 10681 | [1–413] | 10728 | [1–492] |
| 10560 | [1–319] | 10607 | [89–303] | 10729 | [1–496] | 10779 | [1–268] |
| 10561 | [1–142] | 10608 | [1–250] | 10730 | [1–483] | 10780 | [1–479] |
| 10562 | [229–385] | 10609 | [1–87] | 10731 | [1–269] | 10781 | [1–462] |
| 10563 | [1–249] | 10611 | [1–391] | 10732 | [1–168] | 10782 | [1–431] |
| 10564 | [1–349] | 10612 | [1–187],[337–447] | 10733 | [1–266] | 10783 | [1–232] |
| 10565 | [1–443] | 10613 | [1–338] | 10734 | [1–472] | 10784 | [1–63] |
| 10566 | [1–419] | 10614 | [1–437] | 10735 | [1–88] | 10785 | [1–154] |
| 10567 | [1–328] | 10615 | [1–480] | 10736 | [1–264] | 10786 | [1–434] |
| 10568 | [1–106] | 10616 | [1–503] | 10737 | [1–206] | 10787 | [1–152] |
| 10569 | [1–575] | 10617 | [1–556] | 10738 | [1–454] | 10788 | [1–343] |
|  |  |  |  | 10739 | [1–485] | 10789 | [1–247] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 10740 | [1–291] | 10790 | [1–441] | 10865 | [1–438] | 10914 | [1–229] |
| 10741 | [1–415] | 10791 | [1–223] | 10866 | [1–256] | 10915 | [1–251] |
| 10742 | [1–514] | 10792 | [1–441] | 10867 | [1–197] | 10916 | [1–59] |
| 10744 | [1–481] | 10793 | [1–304] | 10868 | [1–372] | 10917 | [1–477] |
| 10745 | [1–468] | 10794 | [1–172] | 10869 | [1–358] | 10918 | [1–469] |
| 10746 | [1–478] | 10795 | [1–254] | 10870 | [1–389] | 10919 | [1–353] |
| 10747 | [1–468] | 10796 | [1–374] | 10871 | [1–53] | 10920 | [1–112] |
| 10748 | [1–277] | 10797 | [1–80] | 10872 | [1–296] | 10921 | [1–247] |
| 10749 | [1–475] | 10798 | [91–417] | 10873 | [1–378] | 10922 | [1–80] |
| 10750 | [1–150] | 10799 | [1–268] | 10923 | [72–218] | 10971 | [1–72] |
| 10751 | [1–375] | 10800 | [1–447] | 10924 | [1–226] | 10973 | [1–366] |
| 10752 | [1–305] | 10801 | [61–142] | 10925 | [1–243] | 10974 | [1–497] |
| 10753 | [1–360] | 10802 | [1–245] | 10926 | [1–463] | 10975 | [1–430] |
| 10754 | [1–455] | 10803 | [1–168] | 10927 | [1–512] | 10976 | [1–520] |
| 10755 | [1–258] | 10804 | [1–361] | 10928 | [1–463] | 10977 | [1–374] |
| 10756 | [52–376] | 10805 | [1–170] | 10929 | [1–131] | 10978 | [1–149],[230–292], [361–478] |
| 10757 | [1–271] | 10806 | [1–376] | | | | |
| 10759 | [1–455] | 10807 | [1–343] | 10930 | [1–312] | 10979 | [31–461] |
| 10761 | [1–364] | 10808 | [1–221] | 10931 | [1–242] | 10980 | [1–55] |
| 10762 | [1–81],[211–476] | 10809 | [86–264] | 10932 | [1–79] | 10981 | [1–456] |
| 10763 | [1–70],[135–440] | 10811 | [1–188] | 10933 | [1–386] | 10982 | [1–459] |
| 10764 | [1–71] | 10812 | [1–447] | 10934 | [1–464] | 10983 | [1–209] |
| 10765 | [1–481] | 10813 | [1–52] | 10935 | [1–412] | 10984 | [1–250] |
| 10766 | [1–162] | 10814 | [1–237] | 10936 | [1–531] | 10985 | [1–424] |
| 10767 | [1–506] | 10815 | [1–232] | 10937 | [1–304] | 10986 | [1–438] |
| 10768 | [1–421] | 10816 | [1–263] | 10938 | [1–372] | 10987 | [1–443] |
| 10769 | [1–329] | 10817 | [1–401] | 10939 | [1–458] | 10988 | [1–341] |
| 10770 | [1–354] | 10818 | [1–463] | 10940 | [1–136] | 10989 | [1–274] |
| 10771 | [1–127] | 10819 | [1–436] | 10941 | [1–185] | 10990 | [1–328] |
| 10772 | [46–263] | 10820 | [1–222] | 10942 | [1–220] | 10991 | [1–442] |
| 10773 | [1–320] | 10821 | [1–355] | 10943 | [1–366] | 10992 | [1–410] |
| 10774 | [1–203] | 10822 | [1–88] | 10944 | [1–359] | 10993 | [1–322] |
| 10775 | [1–347] | 10823 | [1–398] | 10946 | [80–200] | 10994 | [1–309] |
| 10776 | [1–375] | 10824 | [1–504] | 10947 | [1–344] | 10995 | [1–412] |
| 10777 | [1–372] | 10825 | [1–45],[269–364] | 10948 | [1–391] | 10996 | [50–471] |
| 10778 | [1–379] | 10826 | [1–58] | 10949 | [1–87] | 10997 | [1–246] |
| 10827 | [1–440] | 10874 | [1–294] | 10950 | [1–369] | 10998 | [1–487] |
| 10828 | [1–331] | 10875 | [1–157] | 10951 | [1–364] | 10999 | [1–167] |
| 10829 | [1–80] | 10876 | [1–484] | 10952 | [1–364] | 11000 | [1–233],[264–292] |
| 10830 | [1–234] | 10877 | [1–475] | 10953 | [1–239] | 11001 | [1–73] |
| 10831 | [1–429] | 10878 | [1–438] | 10954 | [1–481] | 11002 | [1–293] |
| 10832 | [1–69] | 10879 | [1–288] | 10955 | [1–209] | 11003 | [137–212],[270–395] |
| 10833 | [54–189] | 10880 | [1–58] | 10956 | [1–67] | 11004 | [1–544] |
| 10834 | [130–440] | 10881 | [1–300] | 10957 | [1–428] | 11005 | [1–223] |
| 10835 | [1–418] | 10882 | [1–238] | 10958 | [1–453] | 11006 | [1–552] |
| 10836 | [1–348] | 10883 | [1–340] | 10959 | [1–346] | 11007 | [1–53] |
| 10837 | [1–51] | 10884 | [1–358] | 10960 | [1–506] | 11008 | [1–491] |
| 10838 | [1–130] | 10885 | [1–171] | 10961 | [1–146] | 11009 | [1–155] |
| 10839 | [1–348] | 10886 | [1–429] | 10962 | [1–150] | 11010 | [1–452] |
| 10840 | [1–233] | 10887 | [1–476] | 10963 | [1–597] | 11011 | [1–469] |
| 10841 | [1–446] | 10888 | [1–301] | 10964 | [1–507] | 11012 | [1–498] |
| 10842 | [1–101] | 10889 | [1–407] | 10965 | [1–438] | 11013 | [1–376] |
| 10843 | [1–282] | 10890 | [1–497] | 10966 | [1–356] | 11014 | [1–460] |
| 10844 | [1–199] | 10891 | [1–53] | 10967 | [1–591] | 11015 | [71–318],[353–468] |
| 10845 | [1–471] | 10892 | [1–360] | 10968 | [1–485] | 11016 | [1–419] |
| 10846 | [1–134] | 10893 | [1–436] | 10969 | [1–418] | 11017 | [1–403] |
| 10847 | [1–166] | 10895 | [1–358] | 10970 | [1–397] | 11018 | [1–365] |
| 10848 | [1–326] | 10896 | [1–67] | 11019 | [1–458] | 11067 | [1–531] |
| 10849 | [1–246] | 10897 | [218–278] | 11021 | [1–499] | 11068 | [1–483] |
| 10850 | [1–390] | 10898 | [1–156] | 11022 | [1–80] | 11069 | [1–312] |
| 10851 | [1–243] | 10899 | [1–85],[131–215] | 11023 | [1–452] | 11070 | [1–488] |
| 10852 | [1–483] | 10900 | [1–159] | 11024 | [1–418] | 11071 | [1–253] |
| 10853 | [1–435] | 10901 | [1–375] | 11025 | [1–497] | 11072 | [53–398] |
| 10854 | [1–93] | 10902 | [1–479] | 11026 | [1–470] | 11073 | [1–499] |
| 10855 | [1–217] | 10903 | [1–476] | 11027 | [1–482] | 11074 | [1–401] |
| 10856 | [1–487] | 10904 | [1–373] | 11028 | [1–498] | 11075 | [1–444] |
| 10857 | [1–349] | 10905 | [1–369] | 11029 | [1–479] | 11076 | [1–448] |
| 10858 | [1–470] | 10906 | [1–103] | 11030 | [52–357] | 11077 | [1–332],[446–482] |
| 10859 | [1–433] | 10907 | [1–68] | 11031 | [1–470] | 11078 | [228–273] |
| 10860 | [1–450] | 10908 | [1–349] | 11032 | [1–416] | 11079 | [1–331] |
| 10861 | [1–333] | 10909 | [1–138] | 11033 | [1–414] | 11080 | [50–391] |
| 10862 | [1–76],[110–350] | 10911 | [1–184] | 11034 | [1–484] | 11081 | [1–488] |
| 10863 | [1–184] | 10912 | [1–197] | 11035 | [1–489] | 11082 | [1–258] |
| 10864 | [1–450] | 10913 | [1–227] | 11036 | [1–501] | 11083 | [1–468] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 11037 | [1–76] | 11084 | [1–339] | 11159 | [1–293] | 11209 | [1–58],[89–205] |
| 11038 | [1–128],[159–469] | 11085 | [1–488] | 11160 | [1–505] | 11210 | [1–96] |
| 11039 | [1–487] | 11086 | [1–478] | 11161 | [1–176] | 11211 | [1–257] |
| 11040 | [1–475] | 11087 | [61–135] | 11213 | [1–201] | 11265 | [1–73] |
| 11041 | [1–482] | 11088 | [1–438] | 11214 | [1–381] | 11266 | [1–224] |
| 11042 | [1–391] | 11090 | [1–61] | 11216 | [1–251] | 11267 | [1–399] |
| 11043 | [1–424] | 11091 | [1–62] | 11217 | [1–207] | 11268 | [1–168] |
| 11044 | [1–481] | 11092 | [1–336] | 11218 | [1–132] | 11269 | [1–219] |
| 11045 | [1–306] | 11093 | [1–454] | 11219 | [1–245] | 11270 | [1–219] |
| 11046 | [1–443] | 11094 | [49–125] | 11220 | [1–235] | 11271 | [1–228] |
| 11047 | [1–491] | 11095 | [1–67] | 11221 | [1–321] | 11272 | [1–219] |
| 11048 | [1–252] | 11096 | [1–489] | 11222 | [1–281] | 11273 | [1–219] |
| 11049 | [1–414] | 11097 | [1–387] | 11223 | [109–306] | 11274 | [1–219] |
| 11050 | [53–416] | 11098 | [1–132] | 11224 | [1–169] | 11275 | [1–189] |
| 11051 | [1–89] | 11099 | [53–395] | 11225 | [1–260] | 11276 | [1–219] |
| 11052 | [1–436] | 11100 | [1–485] | 11226 | [1–270] | 11277 | [1–219] |
| 11053 | [1–466] | 11101 | [1–422] | 11227 | [208–481] | 11278 | [1–118] |
| 11054 | [1–483] | 11102 | [1–517] | 11228 | [1–318] | 11279 | [1–469] |
| 11055 | [1–442] | 11103 | [1–304] | 11229 | [1–425] | 11280 | [1–207] |
| 11056 | [1–347] | 11104 | [1–457] | 11230 | [1–356] | 11281 | [1–219] |
| 11057 | [1–492] | 11105 | [1–476] | 11231 | [74–248] | 11282 | [1–136] |
| 11058 | [1–432] | 11106 | [49–108] | 11232 | [1–51],[96–407] | 11283 | [1–206] |
| 11059 | [1–306] | 11107 | [1–446] | 11234 | [1–201] | 11284 | [1–219] |
| 11060 | [1–478] | 11108 | [1–397] | 11236 | [1–405] | 11285 | [1–206] |
| 11061 | [53–436] | 11109 | [1–379] | 11238 | [1–362] | 11286 | [1–219] |
| 11062 | [1–500] | 11110 | [1–488] | 11239 | [1–343] | 11287 | [1–111] |
| 11063 | [1–85] | 11111 | [1–414] | 11240 | [1–151] | 11288 | [1–219] |
| 11064 | [64–337] | 11112 | [1–399] | 11241 | [1–358] | 11289 | [1–219] |
| 11065 | [1–468] | 11113 | [1–432] | 11242 | [1–310] | 11290 | [1–74] |
| 11066 | [1–484] | 11114 | [1–471] | 11243 | [1–370] | 11291 | [1–136] |
| 11115 | [1–452] | 11162 | [1–394] | 11244 | [1–103] | 11292 | [1–219] |
| 11116 | [50–474] | 11163 | [1–126] | 11245 | [1–186] | 11293 | [1–219] |
| 11117 | [1–376] | 11164 | [1–460] | 11246 | [1–444] | 11294 | [1–206] |
| 11118 | [1–434] | 11165 | [1–478] | 11247 | [1–374] | 11295 | [1–136] |
| 11119 | [1–457] | 11166 | [1–80] | 11248 | [1–418] | 11296 | [1–219] |
| 11120 | [1–421] | 11167 | [1–311] | 11249 | [1–169] | 11297 | [1–219] |
| 11121 | [53–399] | 11168 | [1–488] | 11250 | [1–467] | 11298 | [1–399] |
| 11122 | [1–168] | 11169 | [1–507] | 11251 | [1–288] | 11299 | [1–206] |
| 11123 | [1–469] | 11170 | [1–495] | 11252 | [1–250] | 11300 | [1–193] |
| 11124 | [1–338] | 11171 | [1–309] | 11253 | [1–219] | 11301 | [1–129] |
| 11125 | [1–446] | 11172 | [1–529] | 11254 | [1–74] | 11302 | [1–128] |
| 11126 | [1–398] | 11173 | [1–482] | 11255 | [1–219] | 11303 | [1–72] |
| 11127 | [1–478] | 11174 | [1–127] | 11257 | [1–72] | 11304 | [1–219] |
| 11128 | [1–481] | 11175 | [1–209],[292–391] | 11258 | [1–447] | 11305 | [1–144] |
| 11129 | [1–397] | 11176 | [1–282] | 11259 | [1–219] | 11306 | [1–101] |
| 11130 | [1–474] | 11177 | [1–437] | 11260 | [1–219] | 11307 | [1–136] |
| 11131 | [1–460] | 11178 | [1–122] | 11261 | [1–219] | 11308 | [1–219] |
| 11132 | [1–214] | 11179 | [1–522] | 11262 | [1–282] | 11309 | [1–136] |
| 11133 | [1–509] | 11180 | [1–137] | 11263 | [1–219] | 11310 | [1–489] |
| 11134 | [37–312] | 11181 | [1–386] | 11264 | [1–219] | 11311 | [1–219] |
| 11135 | [1–469] | 11182 | [1–473] | 11312 | [1–61] | 11360 | [365–464] |
| 11136 | [1–495] | 11183 | [1–278] | 11313 | [1–419] | 11362 | [1–370],[418–523] |
| 11137 | [1–53] | 11184 | [1–478] | 11314 | [1–207] | 11363 | [1–415] |
| 11138 | [1–468] | 11185 | [1–518] | 11315 | [1–207] | 11364 | [328–447] |
| 11139 | [1–415] | 11187 | [1–502] | 11316 | [1–111] | 11365 | [1–281] |
| 11140 | [1–102] | 11188 | [1–408] | 11317 | [1–206] | 11366 | [1–505] |
| 11141 | [53–121] | 11189 | [1–488] | 11318 | [1–144] | 11367 | [1–306] |
| 11142 | [1–437] | 11190 | [1–413] | 11319 | [1–110] | 11368 | [1–440] |
| 11143 | [1–439] | 11191 | [1–428] | 11320 | [1–219] | 11369 | [1–498] |
| 11144 | [1–540] | 11192 | [1–80] | 11321 | [1–450] | 11370 | [1–439] |
| 11145 | [403–449] | 11193 | [1–130] | 11322 | [1–219] | 11371 | [1–341] |
| 11146 | [1–481] | 11194 | [1–83] | 11323 | [1–60] | 11372 | [124–278] |
| 11147 | [1–273] | 11195 | [1–139] | 11324 | [1–219] | 11373 | [1–325] |
| 11148 | [1–240] | 11196 | [1–470] | 11325 | [1–72] | 11374 | [1–644] |
| 11149 | [1–362] | 11197 | [1–391] | 11326 | [1–171] | 11375 | [1–610] |
| 11150 | [1–491] | 11198 | [1–104] | 11327 | [1–225] | 11376 | [1–489] |
| 11151 | [1–438] | 11199 | [1–55] | 11328 | [1–221] | 11377 | [1–482] |
| 11152 | [1–98] | 11200 | [1–175],[451–499] | 11329 | [1–219] | 11378 | [1–295] |
| 11153 | [1–503] | 11202 | [1–492] | 11330 | [1–237] | 11380 | [34–334] |
| 11154 | [1–479] | 11203 | [1–494] | 11331 | [1–153] | 11381 | [1–437] |
| 11155 | [1–493] | 11204 | [1–68] | 11332 | [1–219] | 11382 | [1–105] |
| 11156 | [1–476] | 11205 | [1–515] | 11333 | [1–219] | 11383 | [1–401] |
| 11157 | [52–370] | 11206 | [1–108] | 11334 | [1–207] | 11384 | [1–326] |
| 11158 | [1–566] | 11208 | [1–381] | 11335 | [1–121] | 11385 | [1–233] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 11336 | [1–187] | 11386 | [1–292] | 11507 | [1–177] | 11554 | [1–495] |
| 11337 | [1–220] | 11387 | [1–493] | 11508 | [1–178] | 11555 | [1–328] |
| 11338 | [1–219] | 11388 | [1–525] | 11509 | [1–212] | 11556 | [1–120] |
| 11339 | [1–219] | 11389 | [1–543] | 11510 | [1–191] | 11557 | [1–70],[117–320] |
| 11340 | [1–185] | 11390 | [1–146] | 11511 | [1–318] | 11558 | [1–530] |
| 11342 | [1–198] | 11391 | [1–302] | 11512 | [1–345] | 11559 | [1–460] |
| 11343 | [1–498] | 11392 | [1–521] | 11513 | [1–317] | 11560 | [1–114] |
| 11344 | [214–388] | 11393 | [1–353] | 11514 | [56–355] | 11561 | [1–396] |
| 11345 | [1–426] | 11394 | [50–126],[194–236] | 11515 | [149–479] | 11562 | [1–147] |
| 11346 | [1–430] | 11395 | [1–212] | 11516 | [1–316] | 11563 | [1–324] |
| 11347 | [1–440] | 11396 | [1–285] | 11517 | [1–314] | 11564 | [1–280] |
| 11348 | [1–382] | 11397 | [1–148] | 11518 | [1–299] | 11565 | [1–387] |
| 11349 | [1–483] | 11398 | [1–147] | 11519 | [1–224] | 11566 | [1–148] |
| 11350 | [1–410] | 11399 | [1–375] | 11520 | [1–221] | 11567 | [1–318] |
| 11351 | [1–427] | 11400 | [1–234] | 11521 | [1–388] | 11568 | [1–305] |
| 11352 | [1–342] | 11401 | [1–77] | 11522 | [1–140] | 11569 | [1–200] |
| 11353 | [1–330] | 11402 | [1–394] | 11523 | [1–172] | 11570 | [1–200] |
| 11354 | [1–149],[188–409] | 11403 | [1–406] | 11524 | [1–413] | 11571 | [1–111] |
| 11355 | [1–471] | 11404 | [1–350] | 11525 | [1–147] | 11572 | [1–93] |
| 11356 | [1–307] | 11405 | [1–64] | 11526 | [1–298] | 11573 | [1–172] |
| 11357 | [1–107] | 11406 | [1–193] | 11527 | [1–597] | 11574 | [1–159] |
| 11358 | [1–330] | 11407 | [1–294] | 11528 | [1–300] | 11575 | [1–173] |
| 11359 | [54–192] | 11408 | [1–460] | 11529 | [1–303] | 11576 | [1–408] |
| 11409 | [1–401] | 11456 | [1–286] | 11530 | [1–317] | 11577 | [1–311] |
| 11410 | [1–428] | 11457 | [1–374] | 11531 | [1–457] | 11578 | [1–125] |
| 11411 | [1–203] | 11458 | [1–366] | 11532 | [1–402] | 11579 | [1–314] |
| 11412 | [1–326] | 11459 | [1–365] | 11533 | [1–387] | 11580 | [1–162] |
| 11413 | [1–99] | 11460 | [1–388] | 11534 | [1–175] | 11581 | [1–327] |
| 11414 | [1–57] | 11461 | [1–120] | 11535 | [1–312] | 11582 | [1–309] |
| 11415 | [1–428] | 11462 | [1–373] | 11536 | [1–61] | 11583 | [1–53] |
| 11416 | [1–307] | 11463 | [1–384] | 11537 | [1–371] | 11584 | [1–333] |
| 11417 | [1–466] | 11464 | [1–339] | 11538 | [1–306] | 11585 | [1–281] |
| 11418 | [1–316] | 11465 | [1–349] | 11539 | [1–313] | 11586 | [1–160] |
| 11419 | [1–306] | 11466 | [1–95] | 11540 | [1–77] | 11587 | [1–315] |
| 11420 | [1–136] | 11467 | [1–386] | 11541 | [1–463] | 11588 | [1–431] |
| 11421 | [1–249] | 11468 | [1–398] | 11542 | [1–316] | 11589 | [1–320] |
| 11422 | [1–224],[308–608] | 11469 | [1–453] | 11543 | [1–297] | 11590 | [1–200] |
| 11423 | [1–430] | 11470 | [1–172] | 11544 | [1–383] | 11591 | [1–200] |
| 11424 | [1–480] | 11471 | [1–446] | 11545 | [1–456] | 11592 | [1–171] |
| 11425 | [1–457] | 11472 | [1–425] | 11546 | [139–180] | 11593 | [1–162] |
| 11426 | [1–309] | 11473 | [1–311] | 11547 | [1–209] | 11594 | [1–118] |
| 11427 | [1–309] | 11474 | [1–441] | 11548 | [1–163] | 11595 | [32–245] |
| 11428 | [1–198] | 11475 | [1–367] | 11549 | [1–268] | 11596 | [1–86] |
| 11429 | [1–198] | 11476 | [1–348] | 11597 | [1–347] | 11646 | [1–122] |
| 11430 | [1–230] | 11477 | [1–178] | 11598 | [1–200] | 11647 | [1–294] |
| 11431 | [1–180] | 11478 | [1–149] | 11599 | [1–299] | 11648 | [1–189] |
| 11432 | [1–393] | 11479 | [1–418] | 11600 | [1–347] | 11649 | [1–301] |
| 11433 | [1–378] | 11480 | [1–415] | 11601 | [1–114] | 11650 | [1–152] |
| 11434 | [1–291] | 11481 | [116–323] | 11602 | [1–168] | 11651 | [1–55] |
| 11435 | [1–472] | 11482 | [1–442] | 11603 | [1–200] | 11652 | [1–109] |
| 11436 | [1–102] | 11483 | [1–385] | 11604 | [1–371] | 11653 | [1–201] |
| 11437 | [1–436] | 11484 | [1–476] | 11605 | [1–280] | 11654 | [1–110] |
| 11438 | [1–261] | 11485 | [1–426] | 11606 | [1–157],[224–250] | 11655 | [1–333] |
| 11439 | [1–504] | 11486 | [1–118] | 11607 | [1–165] | 11656 | [1–127] |
| 11440 | [1–506] | 11487 | [1–351] | 11608 | [1–353] | 11657 | [1–62] |
| 11441 | [1–452] | 11488 | [1–443] | 11609 | [1–385] | 11658 | [1–63] |
| 11442 | [40–255] | 11489 | [1–140] | 11610 | [1–383] | 11659 | [1–361] |
| 11443 | [1–244] | 11490 | [1–370] | 11611 | [1–174] | 11660 | [1–149] |
| 11444 | [1–396] | 11491 | [1–406] | 11612 | [1–295] | 11661 | [1–162] |
| 11445 | [1–261] | 11492 | [1–422] | 11613 | [1–68] | 11662 | [1–225] |
| 11446 | [1–137] | 11493 | [1–132] | 11614 | [1–160] | 11663 | [1–99] |
| 11447 | [1–367] | 11494 | [1–106] | 11615 | [1–281] | 11664 | [1–81] |
| 11448 | [1–346] | 11495 | [1–392] | 11616 | [39–87] | 11665 | [1–347] |
| 11449 | [1–486] | 11496 | [152–366] | 11617 | [1–225] | 11666 | [1–173] |
| 11450 | [1–318] | 11497 | [1–79] | 11619 | [1–200] | 11667 | [1–200] |
| 11451 | [1–352] | 11498 | [1–553] | 11620 | [1–322] | 11668 | [1–163] |
| 11452 | [1–241] | 11499 | [1–504] | 11621 | [1–369] | 11669 | [1–132] |
| 11453 | [1–400] | 11500 | [1–577] | 11622 | [1–166] | 11670 | [1–329] |
| 11454 | [1–495] | 11501 | [1–161] | 11623 | [1–170] | 11671 | [1–174] |
| 11455 | [1–117] | 11502 | [1–515] | 11624 | [1–152] | 11672 | [1–305] |
| 11503 | [1–154] | 11550 | [1–409] | 11625 | [1–144] | 11673 | [1–337] |
| 11504 | [1–176] | 11551 | [1–493] | 11626 | [1–225] | 11674 | [1–75],[183–224],[275–473] |
| 11505 | [1–238] | 11552 | [1–369] | 11627 | [1–226] | 11675 | [1–261] |
| 11506 | [1–174] | 11553 | [1–220] | | | | |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 11628 | [1–341] | 11676 | [1–107] | 11798 | [1–298] | 11845 | [1–158] |
| 11629 | [1–173] | 11677 | [1–114] | 11799 | [1–106] | 11846 | [1–200] |
| 11630 | [1–316] | 11678 | [1–144] | 11800 | [1–118] | 11847 | [1–190] |
| 11631 | [1–78] | 11679 | [1–189] | 11801 | [1–224] | 11848 | [1–166] |
| 11632 | [1–195] | 11680 | [1–174] | 11802 | [1–197] | 11849 | [1–364] |
| 11633 | [1–78] | 11681 | [1–200] | 11803 | [1–213] | 11850 | [1–213] |
| 11634 | [1–221] | 11682 | [1–104] | 11804 | [1–226] | 11851 | [1–246] |
| 11635 | [1–242] | 11683 | [1–179] | 11805 | [1–340] | 11852 | [1–314] |
| 11636 | [1–134] | 11684 | [1–194] | 11806 | [1–345] | 11853 | [1–200] |
| 11638 | [1–173] | 11685 | [125–167] | 11807 | [1–243] | 11854 | [1–373] |
| 11639 | [1–127] | 11686 | [1–129] | 11808 | [1–171] | 11855 | [1–345] |
| 11640 | [1–216] | 11687 | [1–174] | 11809 | [1–207] | 11856 | [1–187] |
| 11641 | [1–303] | 11688 | [1–158] | 11810 | [1–126] | 11857 | [1–148] |
| 11642 | [1–336] | 11689 | [1–82] | 11811 | [1–235] | 11858 | [1–200] |
| 11643 | [1–112] | 11690 | [1–378] | 11812 | [1–121] | 11859 | [1–128] |
| 11644 | [1–170] | 11691 | [1–317] | 11813 | [1–172] | 11860 | [1–174] |
| 11645 | [1–109] | 11692 | [1–118] | 11814 | [1–331] | 11861 | [1–99] |
| 11693 | [1–347] | 11740 | [1–80] | 11815 | [1–117] | 11862 | [1–344] |
| 11694 | [1–278] | 11741 | [1–109] | 11816 | [1–213] | 11863 | [1–164] |
| 11695 | [1–361] | 11742 | [1–364] | 11817 | [1–79] | 11864 | [1–82] |
| 11696 | [1–430] | 11743 | [1–110] | 11818 | [1–187] | 11865 | [1–200] |
| 11697 | [1–187] | 11744 | [1–98] | 11819 | [1–53] | 11866 | [1–141] |
| 11698 | [1–140] | 11745 | [1–171] | 11820 | [1–241] | 11867 | [1–304] |
| 11699 | [1–130] | 11746 | [1–305] | 11821 | [1–122] | 11868 | [1–96] |
| 11700 | [1–373] | 11747 | [1–565] | 11822 | [1–139] | 11869 | [1–170] |
| 11701 | [1–212] | 11748 | [1–187] | 11823 | [1–173] | 11870 | [1–158] |
| 11702 | [1–155] | 11749 | [1–253] | 11824 | [1–201] | 11871 | [1–336] |
| 11703 | [1–285] | 11750 | [1–311] | 11825 | [1–200] | 11872 | [1–57] |
| 11704 | [1–365] | 11751 | [1–293] | 11826 | [1–490] | 11873 | [1–366] |
| 11705 | [1–137] | 11752 | [1–302] | 11827 | [1–305] | 11874 | [35–79] |
| 11706 | [1–377] | 11754 | [1–200] | 11828 | [1–371] | 11875 | [1–37],[75–381] |
| 11707 | [1–397] | 11755 | [1–302] | 11829 | [1–336] | 11876 | [1–59] |
| 11708 | [1–128] | 11756 | [1–129] | 11830 | [1–225] | 11877 | [1–279] |
| 11709 | [1–114] | 11757 | [1–462] | 11831 | [1–306] | 11878 | [1–174] |
| 11710 | [1–84] | 11758 | [1–130] | 11832 | [1–142] | 11879 | [1–318] |
| 11711 | [1–237] | 11759 | [1–136] | 11833 | [1–492] | 11880 | [1–360] |
| 11712 | [1–490] | 11760 | [1–271] | 11834 | [1–225] | 11881 | [1–306] |
| 11713 | [1–173] | 11761 | [1–136] | 11882 | [1–188] | 11930 | [1–298] |
| 11714 | [1–191] | 11762 | [1–200] | 11883 | [1–121] | 11931 | [1–201] |
| 11715 | [1–123] | 11763 | [1–309] | 11884 | [1–547] | 11932 | [1–316] |
| 11716 | [1–200] | 11764 | [1–152] | 11885 | [1–117] | 11933 | [1–225] |
| 11717 | [1–439] | 11765 | [1–196] | 11886 | [1–209] | 11934 | [1–125] |
| 11718 | [1–199] | 11766 | [1–118] | 11887 | [1–69] | 11935 | [1–314] |
| 11719 | [1–163] | 11767 | [1–111] | 11888 | [1–82] | 11936 | [1–225] |
| 11720 | [1–195] | 11768 | [1–448] | 11889 | [1–290] | 11937 | [1–226] |
| 11721 | [1–231] | 11769 | [1–283] | 11890 | [1–281] | 11938 | [1–201] |
| 11722 | [1–172] | 11770 | [1–340] | 11891 | [1–111] | 11939 | [1–303] |
| 11723 | [1–339] | 11771 | [1–173] | 11892 | [1–98] | 11940 | [1–198] |
| 11724 | [1–171] | 11772 | [1–200] | 11893 | [1–97] | 11941 | [1–343] |
| 11725 | [1–343] | 11773 | [1–200] | 11894 | [1–99] | 11942 | [1–143] |
| 11726 | [1–394] | 11774 | [1–257] | 11895 | [1–483] | 11943 | [1–292] |
| 11727 | [1–358] | 11775 | [1–174] | 11896 | [1–314] | 11944 | [1–82] |
| 11728 | [1–200] | 11776 | [1–296] | 11897 | [1–163] | 11945 | [1–173] |
| 11729 | [1–278] | 11777 | [1–170] | 11898 | [1–143] | 11946 | [1–200] |
| 11730 | [1–303] | 11778 | [1–200] | 11899 | [1–471] | 11947 | [1–343] |
| 11731 | [1–126] | 11779 | [1–207] | 11900 | [1–118] | 11948 | [1–113] |
| 11732 | [1–142] | 11780 | [1–214] | 11901 | [1–314] | 11949 | [1–82] |
| 11733 | [1–181] | 11781 | [1–110] | 11902 | [1–200] | 11950 | [1–137] |
| 11734 | [1–311] | 11782 | [1–226] | 11903 | [1–101] | 11951 | [1–301] |
| 11735 | [1–225] | 11783 | [1–126] | 11904 | [1–207] | 11952 | [1–136] |
| 11736 | [1–213] | 11784 | [1–222] | 11905 | [1–200] | 11953 | [1–108] |
| 11737 | [1–525] | 11785 | [1–200] | 11906 | [1–322] | 11954 | [1–165] |
| 11738 | [1–126] | 11786 | [1–162] | 11907 | [1–317] | 11955 | [1–119] |
| 11739 | [1–162] | 11787 | [1–254] | 11908 | [1–296] | 11956 | [1–479] |
| 11788 | [1–172] | 11835 | [1–200] | 11909 | [1–67] | 11957 | [1–152] |
| 11789 | [1–186] | 11836 | [1–377] | 11910 | [1–174] | 11958 | [1–78] |
| 11790 | [1–479] | 11837 | [1–303] | 11911 | [1–253] | 11959 | [1–273] |
| 11791 | [1–316] | 11838 | [1–156] | 11912 | [1–68] | 11960 | [1–200] |
| 11792 | [1–133] | 11839 | [1–181] | 11914 | [1–306] | 11961 | [1–235] |
| 11793 | [1–358] | 11840 | [1–213] | 11915 | [1–173] | 11962 | [1–118] |
| 11794 | [1–226] | 11841 | [1–82] | 11916 | [1–419] | 11963 | [1–173] |
| 11795 | [1–192] | 11842 | [1–120] | 11917 | [1–298] | 11964 | [1–108] |
| 11796 | [1–186] | 11843 | [1–507] | 11918 | [1–353] | 11965 | [1–200] |
| 11797 | [1–90] | 11844 | [1–200] | 11919 | [1–200] | 11966 | [1–174] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 11920 | [1–162] | 11967 | [1–61] | 12088 | [1–82] | 12135 | [1–52] |
| 11921 | [1–123] | 11968 | [1–312] | 12089 | [1–372] | 12136 | [1–200] |
| 11922 | [1–209] | 11969 | [1–314] | 12090 | [1–243] | 12137 | [1–82] |
| 11923 | [1–155] | 11970 | [1–57] | 12091 | [174–488] | 12138 | [1–321] |
| 11924 | [1–172] | 11971 | [1–312] | 12092 | [1–124] | 12139 | [1–56] |
| 11925 | [1–172] | 11972 | [1–110] | 12093 | [1–195] | 12140 | [1–104] |
| 11926 | [1–171] | 11973 | [1–316] | 12094 | [1–143] | 12141 | [1–200] |
| 11927 | [1–509] | 11974 | [1–78] | 12095 | [1–200] | 12142 | [1–420] |
| 11928 | [1–100] | 11975 | [1–89] | 12096 | [1–368] | 12143 | [1–136] |
| 11929 | [1–307] | 11976 | [1–314] | 12097 | [1–325] | 12144 | [1–108] |
| 11977 | [1–437] | 12024 | [1–316] | 12098 | [1–170] | 12145 | [1–458] |
| 11978 | [1–106] | 12025 | [1–110] | 12099 | [1–84] | 12146 | [1–459] |
| 11979 | [1–201] | 12026 | [1–326] | 12100 | [1–472] | 12147 | [1–373] |
| 11980 | [1–132] | 12027 | [1–142] | 12101 | [1–379] | 12148 | [1–171] |
| 11981 | [1–350] | 12028 | [1–126] | 12102 | [1–66] | 12149 | [1–289] |
| 11982 | [1–311] | 12029 | [1–219] | 12103 | [1–82] | 12150 | [1–57] |
| 11983 | [1–371] | 12030 | [1–294] | 12104 | [1–200] | 12151 | [1–173] |
| 11984 | [1–331] | 12031 | [1–355] | 12105 | [1–331] | 12152 | [1–207] |
| 11985 | [1–200] | 12032 | [1–335] | 12106 | [1–74] | 12153 | [1–284] |
| 11986 | [1–173] | 12033 | [1–315] | 12107 | [1–173] | 12154 | [1–225] |
| 11987 | [1–110] | 12034 | [209–484] | 12108 | [1–53] | 12155 | [1–162] |
| 11988 | [1–112] | 12035 | [1–187] | 12109 | [1–201] | 12156 | [1–200] |
| 11989 | [1–150],[273–311] | 12036 | [1–189] | 12110 | [1–251] | 12157 | [1–156] |
| 11990 | [1–108] | 12037 | [1–77] | 12111 | [1–115] | 12158 | [1–200] |
| 11991 | [1–79] | 12038 | [1–144] | 12112 | [1–478] | 12159 | [1–307] |
| 11992 | [1–358] | 12039 | [99–154] | 12113 | [1–304] | 12160 | [1–98] |
| 11993 | [1–118] | 12040 | [1–220] | 12114 | [1–244] | 12161 | [1–91] |
| 11994 | [1–265] | 12041 | [1–294] | 12115 | [1–301] | 12162 | [1–120] |
| 11995 | [1–102] | 12042 | [1–125] | 12116 | [1–112] | 12163 | [1–257] |
| 11996 | [1–163] | 12043 | [1–129] | 12117 | [1–200] | 12165 | [1–50] |
| 11997 | [1–121] | 12044 | [1–200] | 12166 | [1–477] | 12213 | [1–243] |
| 11998 | [1–330] | 12045 | [1–120] | 12167 | [1–118] | 12214 | [1–128] |
| 11999 | [1–291] | 12046 | [1–344] | 12168 | [1–383] | 12215 | [1–508] |
| 12000 | [1–226] | 12047 | [1–173] | 12169 | [1–312] | 12216 | [1–94] |
| 12001 | [1–99] | 12048 | [1–78] | 12170 | [1–371] | 12217 | [1–163] |
| 12002 | [1–200] | 12049 | [1–154] | 12171 | [1–172] | 12218 | [1–440] |
| 12003 | [1–250] | 12050 | [99–154] | 12172 | [1–175] | 12219 | [1–192] |
| 12004 | [1–314] | 12051 | [1–163] | 12173 | [1–125] | 12220 | [1–225] |
| 12005 | [1–68] | 12052 | [1–166] | 12174 | [1–127] | 12221 | [1–162] |
| 12006 | [1–69] | 12053 | [1–145] | 12175 | [1–83] | 12222 | [1–443] |
| 12007 | [1–103] | 12054 | [1–263] | 12176 | [1–371] | 12223 | [1–226] |
| 12008 | [1–303] | 12055 | [1–313] | 12177 | [1–520] | 12224 | [1–200] |
| 12009 | [1–321] | 12056 | [1–221] | 12178 | [1–323] | 12225 | [1–78] |
| 12010 | [1–173] | 12057 | [1–194] | 12179 | [1–163] | 12226 | [1–127] |
| 12011 | [1–170] | 12058 | [1–175] | 12180 | [1–58] | 12227 | [1–361] |
| 12012 | [1–200] | 12059 | [1–333] | 12181 | [1–159] | 12228 | [1–134] |
| 12013 | [1–181] | 12060 | [1–199] | 12182 | [1–160] | 12229 | [1–176] |
| 12014 | [1–200] | 12061 | [1–155] | 12183 | [1–317] | 12231 | [1–63] |
| 12015 | [1–82] | 12062 | [1–419] | 12184 | [1–336] | 12232 | [1–457] |
| 12016 | [1–433] | 12063 | [1–447] | 12185 | [1–111] | 12233 | [1–172] |
| 12017 | [1–306] | 12064 | [1–306] | 12186 | [1–304] | 12234 | [1–343] |
| 12018 | [1–326] | 12065 | [1–200] | 12187 | [1–157] | 12235 | [1–174] |
| 12019 | [1–180] | 12066 | [1–117] | 12188 | [1–304] | 12236 | [1–313] |
| 12020 | [1–516] | 12067 | [1–383] | 12189 | [1–161] | 12237 | [1–383] |
| 12021 | [1–293] | 12068 | [1–173] | 12190 | [1–301] | 12238 | [1–380] |
| 12022 | [1–161] | 12069 | [1–114] | 12191 | [1–383] | 12239 | [1–485] |
| 12023 | [1–200] | 12070 | [1–161] | 12192 | [1–372] | 12240 | [1–176] |
| 12071 | [1–452] | 12118 | [1–109] | 12193 | [33–211] | 12241 | [1–372] |
| 12072 | [1–301] | 12119 | [1–108] | 12194 | [1–114] | 12242 | [1–171] |
| 12073 | [1–174] | 12120 | [1–424] | 12195 | [1–83] | 12243 | [1–163] |
| 12074 | [1–164] | 12121 | [1–159] | 12196 | [1–129] | 12244 | [1–485] |
| 12075 | [1–163] | 12122 | [1–324] | 12197 | [171–387] | 12245 | [1–155] |
| 12076 | [1–170] | 12123 | [186–254] | 12198 | [1–81] | 12246 | [1–211] |
| 12077 | [1–240] | 12124 | [1–324] | 12199 | [1–173] | 12247 | [1–353] |
| 12078 | [1–225] | 12125 | [1–153] | 12200 | [1–363] | 12248 | [1–314] |
| 12079 | [1–106] | 12126 | [1–337] | 12201 | [1–200] | 12249 | [1–225] |
| 12080 | [1–111] | 12127 | [1–82] | 12202 | [1–294] | 12250 | [1–173] |
| 12081 | [1–317] | 12128 | [1–200] | 12203 | [1–360] | 12251 | [1–104] |
| 12082 | [1–490] | 12129 | [1–164] | 12204 | [1–118] | 12252 | [1–247] |
| 12083 | [1–115] | 12130 | [1–77] | 12205 | [1–172] | 12253 | [1–173] |
| 12084 | [1–327] | 12131 | [1–82] | 12206 | [1–236] | 12254 | [1–162] |
| 12085 | [1–221] | 12132 | [1–200] | 12207 | [1–311] | 12255 | [1–327] |
| 12086 | [1–37],[70–242] | 12133 | [1–113] | 12208 | [1–312] | 12256 | [1–190] |
| 12087 | [1–83] | 12134 | [1–51] | 12209 | [1–439] | 12257 | [1–200] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 12210 | [1–163] | 12258 | [1–200] | 12381 | [1–200] | 12428 | [1–314] |
| 12211 | [1–209] | 12259 | [1–225] | 12382 | [1–162] | 12429 | [1–83] |
| 12212 | [1–155] | 12260 | [1–170] | 12383 | [1–175] | 12430 | [1–97] |
| 12261 | [1–93] | 12309 | [1–92] | 12384 | [1–243] | 12431 | [1–158] |
| 12262 | [1–116] | 12310 | [1–296] | 12385 | [1–343] | 12432 | [1–125] |
| 12263 | [1–112] | 12311 | [1–149] | 12386 | [1–433] | 12433 | [1–367] |
| 12264 | [1–159] | 12312 | [1–401] | 12387 | [1–354] | 12434 | [1–82] |
| 12266 | [1–77] | 12313 | [1–235] | 12388 | [1–162] | 12435 | [1–346] |
| 12267 | [1–438] | 12314 | [1–444] | 12389 | [1–111] | 12436 | [1–70] |
| 12268 | [1–365] | 12315 | [1–135] | 12390 | [1–72] | 12437 | [1–507] |
| 12269 | [1–302] | 12316 | [1–372] | 12391 | [1–170] | 12438 | [1–158] |
| 12270 | [1–175] | 12317 | [1–400] | 12392 | [1–101] | 12439 | [1–294] |
| 12271 | [1–124] | 12318 | [1–475] | 12393 | [1–302] | 12440 | [1–70] |
| 12272 | [1–175] | 12319 | [1–337] | 12394 | [1–253] | 12441 | [1–94] |
| 12273 | [1–99] | 12320 | [1–225] | 12395 | [1–123] | 12442 | [1–374] |
| 12274 | [1–187] | 12322 | [1–82] | 12396 | [1–200] | 12443 | [1–280] |
| 12275 | [1–367] | 12323 | [1–200] | 12397 | [1–111] | 12444 | [1–143] |
| 12276 | [1–78] | 12324 | [1–310] | 12398 | [1–78] | 12445 | [1–187] |
| 12277 | [1–98] | 12325 | [1–117] | 12399 | [1–369] | 12446 | [1–76] |
| 12278 | [1–219] | 12326 | [1–289] | 12400 | [1–153] | 12447 | [1–331] |
| 12279 | [1–360] | 12327 | [1–128] | 12401 | [1–148] | 12448 | [1–107] |
| 12280 | [1–341] | 12328 | [1–141] | 12402 | [1–174] | 12449 | [1–173] |
| 12281 | [1–174] | 12329 | [1–314] | 12403 | [1–108] | 12450 | [1–83] |
| 12282 | [1–225] | 12330 | [1–123] | 12451 | [1–200] | 12500 | [1–127] |
| 12283 | [1–372] | 12331 | [1–174] | 12453 | [1–154] | 12501 | [1–129] |
| 12284 | [1–370] | 12332 | [1–53] | 12454 | [1–69] | 12502 | [1–510] |
| 12285 | [1–165] | 12333 | [1–302] | 12455 | [1–99] | 12503 | [1–276] |
| 12286 | [1–200] | 12334 | [1–163] | 12456 | [1–408] | 12504 | [50–470] |
| 12287 | [1–488] | 12335 | [1–162] | 12457 | [1–455] | 12505 | [1–462] |
| 12288 | [1–310] | 12336 | [1–173] | 12459 | [1–369] | 12506 | [1–134] |
| 12289 | [1–209] | 12337 | [1–142] | 12460 | [1–432] | 12507 | [1–419] |
| 12290 | [1–351] | 12338 | [1–155] | 12461 | [1–422] | 12508 | [1–455] |
| 12291 | [1–124] | 12339 | [1–366] | 12462 | [1–325] | 12509 | [1–445] |
| 12292 | [1–255] | 12340 | [1–314] | 12463 | [52–372] | 12510 | [1–458] |
| 12293 | [1–485] | 12341 | [1–80] | 12464 | [1–70] | 12511 | [1–238] |
| 12294 | [1–174] | 12342 | [1–360] | 12465 | [81–138],[190–287] | 12512 | [1–442] |
| 12295 | [1–300] | 12343 | [1–225] | 12466 | [1–418] | 12514 | [1–233] |
| 12296 | [1–339] | 12344 | [1–187] | 12467 | [1–34],[121–440] | 12515 | [1–406] |
| 12297 | [1–243] | 12345 | [1–173] | 12468 | [1–325] | 12516 | [1–75] |
| 12298 | [1–67] | 12346 | [1–147] | 12469 | [1–414] | 12517 | [53–399] |
| 12299 | [1–78] | 12347 | [1–354] | 12470 | [1–485] | 12518 | [53–118] |
| 12300 | [1–170] | 12348 | [1–108] | 12471 | [1–94] | 12519 | [32–495] |
| 12301 | [1–200] | 12349 | [1–225] | 12472 | [1–485] | 12520 | [1–240] |
| 12302 | [1–174] | 12350 | [1–224] | 12473 | [1–450] | 12521 | [1–527] |
| 12303 | [1–309] | 12351 | [1–307] | 12474 | [1–217] | 12522 | [1–531] |
| 12304 | [1–74] | 12352 | [1–144] | 12475 | [1–335] | 12523 | [1–450] |
| 12305 | [1–246] | 12353 | [1–200] | 12476 | [1–478] | 12524 | [1–104] |
| 12306 | [1–489] | 12354 | [1–132] | 12477 | [1–473] | 12525 | [1–448] |
| 12307 | [1–215] | 12355 | [1–318] | 12478 | [1–460] | 12526 | [1–415] |
| 12308 | [1–162] | 12356 | [1–212],[254–373] | 12479 | [1–437] | 12527 | [1–312] |
| 12357 | [1–200] | 12404 | [1–66] | 12480 | [1–60] | 12528 | [1–472] |
| 12358 | [1–173] | 12405 | [1–311] | 12481 | [1–459] | 12529 | [1–483] |
| 12359 | [1–173] | 12406 | [1–156] | 12482 | [1–438] | 12530 | [1–53] |
| 12360 | [1–200] | 12407 | [1–158] | 12483 | [1–486] | 12531 | [1–302] |
| 12361 | [1–344] | 12408 | [1–293] | 12484 | [1–489] | 12532 | [1–465] |
| 12362 | [1–213] | 12409 | [1–197] | 12485 | [1–483] | 12533 | [1–445] |
| 12363 | [1–96] | 12410 | [1–200] | 12486 | [1–385] | 12534 | [1–106] |
| 12364 | [1–143] | 12411 | [1–200] | 12487 | [1–196] | 12535 | [1–440] |
| 12365 | [1–444] | 12412 | [1–486] | 12488 | [32–509] | 12536 | [1–193] |
| 12366 | [1–371] | 12413 | [1–277] | 12489 | [1–380] | 12537 | [1–347] |
| 12367 | [1–89] | 12414 | [1–163] | 12490 | [1–299] | 12538 | [1–421] |
| 12368 | [1–82] | 12415 | [1–173] | 12491 | [1–393] | 12539 | [1–103] |
| 12369 | [1–108] | 12416 | [1–162] | 12492 | [1–469] | 12540 | [1–477] |
| 12370 | [1–173] | 12417 | [1–109] | 12493 | [1–436] | 12541 | [1–473] |
| 12371 | [1–105] | 12418 | [1–312] | 12494 | [1–458] | 12542 | [1–266] |
| 12372 | [1–202] | 12419 | [1–173] | 12495 | [1–230] | 12543 | [1–315] |
| 12373 | [1–313] | 12420 | [1–355] | 12496 | [1–494] | 12544 | [1–476] |
| 12374 | [1–130] | 12421 | [1–163] | 12497 | [1–468] | 12545 | [1–443] |
| 12375 | [1–449] | 12422 | [1–140] | 12498 | [1–454] | 12546 | [1–488] |
| 12376 | [1–375] | 12423 | [1–327] | 12499 | [1–146] | 12547 | [1–146] |
| 12377 | [1–55] | 12424 | [1–173] | 12548 | [49–104] | 12596 | [46–102] |
| 12378 | [1–134] | 12425 | [1–306] | 12549 | [1–194] | 12597 | [1–370] |
| 12379 | [1–137] | 12426 | [1–225] | 12550 | [1–414] | 12598 | [1–461] |
| 12380 | [1–305] | 12427 | [1–129] | 12551 | [1–163] | 12599 | [1–54] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 12552 | [1–450] | 12600 | [1–169] | 12676 | [1–298] | 12726 | [1–322] |
| 12553 | [1–419] | 12601 | [1–243] | 12677 | [1–429] | 12727 | [1–261] |
| 12554 | [1–307] | 12602 | [1–397] | 12678 | [251–326],[367–397] | 12728 | [1–138] |
| 12555 | [1–468] | 12603 | [1–478] | 12679 | [1–328] | 12729 | [1–243] |
| 12556 | [1–425] | 12604 | [1–436] | 12680 | [1–318] | 12730 | [1–413] |
| 12557 | [1–395] | 12605 | [1–377] | 12681 | [1–88] | 12731 | [1–393] |
| 12558 | [1–146],[266–493] | 12606 | [1–458] | 12682 | [1–83] | 12733 | [1–387] |
| 12559 | [1–471] | 12607 | [1–90] | 12683 | [1–460] | 12734 | [1–173] |
| 12560 | [1–234] | 12608 | [1–64] | 12684 | [1–177] | 12735 | [71–416] |
| 12561 | [1–479] | 12609 | [55–106],[203–255] | 12685 | [1–361] | 12736 | [1–45],[219–348] |
| 12562 | [1–428] | 12610 | [1–521] | 12687 | [1–145] | 12737 | [1–494] |
| 12564 | [1–458] | 12611 | [34–347] | 12688 | [1–468] | 12738 | [1–56] |
| 12565 | [1–335] | 12612 | [1–200] | 12689 | [1–281] | 12740 | [1–257] |
| 12566 | [1–77] | 12613 | [1–409] | 12690 | [1–453] | 12741 | [1–310] |
| 12567 | [1–422] | 12614 | [1–376] | 12691 | [1–460] | 12743 | [1–155] |
| 12568 | [1–373] | 12615 | [1–397] | 12692 | [1–61] | 12744 | [1–290] |
| 12569 | [1–392] | 12616 | [1–506] | 12746 | [1–443] | 12796 | [1–479] |
| 12570 | [53–393] | 12617 | [1–458] | 12749 | [1–434] | 12797 | [1–288] |
| 12571 | [1–90],[121–314] | 12618 | [1–544] | 12750 | [1–274] | 12798 | [1–392] |
| 12572 | [1–477] | 12619 | [1–463] | 12751 | [73–397] | 12799 | [1–253] |
| 12573 | [1–134] | 12620 | [1–325] | 12752 | [1–432] | 12800 | [1–445] |
| 12574 | [1–428] | 12621 | [1–70] | 12753 | [1–187] | 12801 | [32–339] |
| 12575 | [1–70] | 12622 | [1–97] | 12754 | [1–224] | 12802 | [1–438] |
| 12576 | [1–304] | 12623 | [1–274] | 12755 | [1–412] | 12803 | [1–249],[281–396] |
| 12577 | [1–318] | 12624 | [1–466] | 12756 | [1–343] | 12804 | [1–263] |
| 12578 | [1–59] | 12625 | [1–109],[142–438] | 12757 | [1–480] | 12805 | [1–140] |
| 12579 | [1–432] | 12626 | [1–147] | 12758 | [1–409] | 12806 | [1–185] |
| 12580 | [1–444] | 12627 | [1–272] | 12759 | [1–329] | 12807 | [1–442] |
| 12581 | [1–409] | 12628 | [1–412] | 12760 | [1–376] | 12808 | [1–338] |
| 12582 | [1–224],[311–444] | 12629 | [1–409] | 12761 | [1–308] | 12809 | [1–236] |
| 12583 | [1–467] | 12630 | [1–456] | 12762 | [1–199] | 12810 | [1–455] |
| 12584 | [1–423] | 12631 | [1–297] | 12763 | [1–411] | 12811 | [1–97] |
| 12585 | [1–423] | 12632 | [1–263] | 12764 | [1–192] | 12812 | [1–180] |
| 12586 | [1–328] | 12633 | [1–421] | 12765 | [1–141] | 12813 | [1–308] |
| 12587 | [1–393] | 12634 | [1–146] | 12766 | [236–480] | 12814 | [1–226] |
| 12588 | [1–95] | 12635 | [1–553] | 12767 | [1–85] | 12815 | [1–345] |
| 12589 | [1–76] | 12636 | [1–426] | 12768 | [1–130] | 12816 | [1–500] |
| 12590 | [1–440] | 12638 | [1–449] | 12769 | [1–393] | 12817 | [1–115] |
| 12591 | [1–222] | 12639 | [1–432] | 12770 | [1–393] | 12818 | [1–122] |
| 12592 | [1–156] | 12640 | [1–67] | 12771 | [1–389] | 12819 | [1–67] |
| 12593 | [1–473] | 12641 | [105–402] | 12772 | [1–227] | 12820 | [1–435] |
| 12594 | [1–412] | 12642 | [1–291] | 12773 | [1–362] | 12821 | [1–472] |
| 12595 | [1–398] | 12643 | [1–488] | 12774 | [1–100] | 12822 | [1–169] |
| 12644 | [1–344] | 12693 | [1–193] | 12775 | [1–242] | 12823 | [1–530] |
| 12645 | [1–316] | 12694 | [1–447] | 12776 | [1–424] | 12824 | [1–101] |
| 12646 | [1–139] | 12695 | [1–315] | 12777 | [1–458] | 12825 | [1–154] |
| 12647 | [1–122] | 12696 | [1–108] | 12778 | [1–64] | 12826 | [64–373] |
| 12648 | [1–331] | 12697 | [1–398] | 12779 | [1–43],[76–271] | 12827 | [1–58] |
| 12649 | [1–424] | 12698 | [1–267] | 12781 | [1–174] | 12828 | [1–505] |
| 12650 | [1–395] | 12699 | [1–318] | 12782 | [1–340] | 12829 | [1–116] |
| 12651 | [1–344] | 12700 | [1–385] | 12783 | [1–320] | 12830 | [1–111] |
| 12652 | [1–60] | 12701 | [1–50] | 12784 | [1–351] | 12831 | [1–398] |
| 12653 | [1–347] | 12702 | [1–286] | 12785 | [1–74] | 12832 | [1–475] |
| 12654 | [1–324] | 12703 | [124–315] | 12786 | [1–458] | 12833 | [1–67] |
| 12655 | [1–422] | 12704 | [1–219] | 12787 | [1–274] | 12834 | [1–429] |
| 12656 | [1–152] | 12705 | [1–63] | 12788 | [1–405] | 12835 | [1–552] |
| 12657 | [1–54] | 12706 | [1–184] | 12789 | [1–118] | 12836 | [1–358] |
| 12658 | [1–145] | 12707 | [1–199] | 12790 | [1–473] | 12837 | [1–363] |
| 12659 | [1–321] | 12708 | [1–299] | 12791 | [1–185] | 12838 | [1–421] |
| 12660 | [1–240] | 12710 | [1–81] | 12792 | [1–369] | 12839 | [1–267] |
| 12661 | [1–292] | 12711 | [1–293] | 12793 | [1–152] | 12840 | [1–454] |
| 12662 | [1–177] | 12712 | [1–372] | 12794 | [1–335] | 12841 | [1–316] |
| 12663 | [1–87] | 12713 | [1–208] | 12795 | [1–236] | 12842 | [1–434] |
| 12664 | [1–424] | 12714 | [97–264] | 12843 | [1–515] | 12891 | [1–454] |
| 12665 | [1–396] | 12715 | [1–120] | 12845 | [1–327] | 12892 | [1–130] |
| 12667 | [1–380] | 12716 | [1–479] | 12846 | [1–442] | 12893 | [1–184] |
| 12668 | [1–182] | 12717 | [1–169] | 12847 | [1–285] | 12894 | [1–289] |
| 12669 | [1–490] | 12718 | [1–328] | 12848 | [1–451] | 12895 | [1–335] |
| 12670 | [1–526] | 12719 | [1–333] | 12849 | [1–441] | 12896 | [1–323] |
| 12671 | [1–120] | 12720 | [1–291] | 12850 | [1–415] | 12897 | [1–397] |
| 12672 | [1–459] | 12722 | [1–329] | 12851 | [1–497] | 12898 | [1–440] |
| 12673 | [1–505] | 12723 | [1–400] | 12852 | [1–397] | 12899 | [1–345] |
| 12674 | [1–292] | 12724 | [1–224],[311–499] | 12853 | [1–476] | 12900 | [1–459] |
| 12675 | [1–444] | 12725 | [1–263] | 12854 | [1–513] | 12901 | [1–352] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 12855 | [1–115] | 12902 | [1–318] | 12976 | [1–471] | 13024 | [1–304] |
| 12856 | [1–97] | 12903 | [1–124] | 12977 | [1–161] | 13025 | [311–435] |
| 12857 | [1–267] | 12904 | [1–468] | 12978 | [1–397] | 13026 | [1–268] |
| 12858 | [1–144],[191–397] | 12905 | [1–479] | 12979 | [1–361] | 13027 | [1–484] |
| 12859 | [1–313] | 12906 | [99–288] | 12980 | [1–404] | 13028 | [91–498] |
| 12860 | [1–492] | 12907 | [1–357] | 12981 | [1–450] | 13029 | [1–386] |
| 12861 | [1–326] | 12908 | [1–380] | 12982 | [1–309] | 13030 | [1–445] |
| 12862 | [1–303] | 12909 | [1–300] | 12983 | [1–356] | 13031 | [1–433] |
| 12863 | [1–536] | 12910 | [1–476] | 12984 | [1–351] | 13032 | [1–64] |
| 12864 | [1–238] | 12911 | [1–431] | 13033 | [1–336] | 13082 | [1–320] |
| 12865 | [1–475] | 12912 | [1–257] | 13034 | [1–524] | 13083 | [1–400] |
| 12866 | [1–356] | 12913 | [1–271] | 13035 | [1–330] | 13084 | [1–59] |
| 12867 | [1–208] | 12914 | [1–283] | 13036 | [1–315] | 13085 | [1–458] |
| 12868 | [1–319] | 12915 | [1–297] | 13037 | [1–483] | 13086 | [1–207] |
| 12869 | [1–443] | 12916 | [1–307] | 13038 | [1–462] | 13087 | [1–461] |
| 12870 | [1–118] | 12917 | [44–203] | 13039 | [1–456] | 13088 | [1–416] |
| 12871 | [1–320] | 12918 | [1–61] | 13040 | [1–468] | 13089 | [1–319] |
| 12872 | [31–440] | 12919 | [1–274] | 13041 | [1–442] | 13090 | [1–266] |
| 12873 | [1–359] | 12920 | [1–80],[120–209] | 13042 | [327–486] | 13091 | [1–311] |
| 12874 | [1–400] | 12921 | [1–338] | 13043 | [1–127] | 13092 | [1–426] |
| 12875 | [1–443] | 12922 | [1–68] | 13044 | [1–306] | 13093 | [1–219] |
| 12876 | [1–129] | 12923 | [1–184] | 13045 | [1–413] | 13094 | [1–320] |
| 12877 | [1–484] | 12924 | [1–502] | 13046 | [1–309] | 13095 | [1–97] |
| 12878 | [1–357] | 12925 | [148–421] | 13047 | [1–109] | 13096 | [1–179] |
| 12879 | [1–611] | 12926 | [1–491] | 13048 | [1–152] | 13097 | [1–289] |
| 12880 | [1–425] | 12927 | [1–414] | 13049 | [1–59],[141–396] | 13098 | [1–360],[459–496] |
| 12881 | [1–106] | 12928 | [1–259] | 13050 | [1–438] | 13100 | [1–346] |
| 12882 | [1–473] | 12929 | [1–222] | 13051 | [1–179] | 13101 | [1–503] |
| 12883 | [1–397] | 12930 | [1–71] | 13052 | [1–425] | 13102 | [1–272] |
| 12884 | [1–496] | 12931 | [1–53] | 13053 | [1–204] | 13103 | [1–282] |
| 12885 | [1–101] | 12932 | [1–339] | 13054 | [1–381] | 13104 | [1–302] |
| 12886 | [1–439] | 12933 | [1–493] | 13055 | [1–178] | 13105 | [1–370] |
| 12887 | [1–307] | 12934 | [1–276] | 13056 | [1–542] | 13106 | [1–69] |
| 12888 | [1–297] | 12935 | [1–135] | 13057 | [1–198],[295–448] | 13107 | [1–272] |
| 12889 | [1–68] | 12936 | [1–350] | 13058 | [1–219] | 13108 | [1–319] |
| 12890 | [1–211] | 12937 | [1–109],[188–256] | 13059 | [1–192] | 13109 | [1–235] |
| 12938 | [1–340] | 12985 | [1–465] | 13060 | [1–294] | 13110 | [1–375] |
| 12939 | [1–62] | 12986 | [1–188] | 13061 | [1–430] | 13111 | [1–325] |
| 12940 | [1–372] | 12987 | [1–439] | 13062 | [1–341] | 13112 | [1–298] |
| 12941 | [1–330] | 12988 | [46–103] | 13063 | [1–381] | 13113 | [1–179] |
| 12942 | [1–413] | 12989 | [1–294] | 13064 | [1–442] | 13114 | [1–219] |
| 12943 | [1–417] | 12990 | [1–299] | 13065 | [1–295] | 13115 | [1–499] |
| 12944 | [1–514] | 12991 | [1–440] | 13066 | [1–492] | 13116 | [1–317] |
| 12945 | [1–482] | 12992 | [1–307] | 13067 | [1–500] | 13117 | [1–461] |
| 12946 | [1–324] | 12993 | [1–348] | 13068 | [1–353] | 13118 | [1–295] |
| 12947 | [1–399] | 12994 | [1–324] | 13069 | [1–53] | 13119 | [1–507] |
| 12948 | [36–281] | 12995 | [1–441] | 13070 | [1–292] | 13120 | [1–258] |
| 12949 | [217–365] | 12996 | [1–354] | 13071 | [1–434] | 13121 | [1–357] |
| 12950 | [1–513] | 12997 | [1–155] | 13072 | [1–361] | 13122 | [1–125] |
| 12951 | [1–308] | 12998 | [99–156] | 13073 | [1–469] | 13123 | [1–82] |
| 12952 | [1–82] | 12999 | [1–419] | 13074 | [1–295] | 13124 | [1–298] |
| 12953 | [1–315] | 13000 | [1–359] | 13076 | [1–390] | 13125 | [1–85] |
| 12954 | [1–509] | 13001 | [1–325] | 13077 | [1–82] | 13126 | [1–185] |
| 12955 | [1–175] | 13002 | [1–293] | 13078 | [1–506] | 13127 | [1–327] |
| 12956 | [1–473] | 13003 | [1–119] | 13079 | [1–72] | 13128 | [1–322] |
| 12957 | [1–452] | 13004 | [1–471] | 13080 | [1–438] | 13129 | [1–319] |
| 12958 | [1–324] | 13005 | [1–291] | 13130 | [1–473] | 13179 | [1–493] |
| 12959 | [1–311] | 13006 | [1–99] | 13132 | [1–204] | 13180 | [1–230],[270–667] |
| 12960 | [1–372] | 13007 | [1–94] | 13133 | [1–389] | 13181 | [1–197] |
| 12961 | [1–458] | 13008 | [1–346] | 13134 | [1–256] | 13182 | [1–457] |
| 12962 | [1–494] | 13009 | [1–329] | 13135 | [1–444] | 13184 | [1–325] |
| 12963 | [1–184],[228–287] | 13010 | [1–498] | 13136 | [1–518] | 13185 | [196–385] |
| 12964 | [1–366] | 13011 | [1–91] | 13137 | [1–316] | 13186 | [1–454] |
| 12965 | [1–288] | 13012 | [1–364] | 13138 | [1–441] | 13187 | [1–197] |
| 12966 | [1–376],[460–509] | 13013 | [1–284] | 13140 | [1–280] | 13188 | [1–317] |
| 12967 | [1–497] | 13014 | [1–309] | 13141 | [1–394] | 13190 | [1–346] |
| 12968 | [1–540] | 13015 | [1–443] | 13142 | [1–395] | 13191 | [1–455] |
| 12969 | [1–313] | 13016 | [1–508] | 13143 | [1–328] | 13192 | [1–486] |
| 12970 | [1–345] | 13017 | [1–420] | 13144 | [1–81] | 13193 | [1–66] |
| 12971 | [1–486] | 13018 | [1–487] | 13145 | [1–280] | 13194 | [1–160] |
| 12972 | [1–188] | 13019 | [1–347] | 13146 | [1–376] | 13195 | [1–372] |
| 12973 | [1–254] | 13020 | [1–435] | 13147 | [1–307] | 13196 | [1–185] |
| 12974 | [1–526] | 13022 | [1–311] | 13148 | [1–263] | 13197 | [91–498] |
| 12975 | [1–477] | 13023 | [94–528] | 13149 | [1–131] | 13198 | [1–479] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 13150 | [1–630] | 13199 | [1–227] | 13275 | [1–419] | 13323 | [1–85] |
| 13151 | [1–474] | 13200 | [1–420] | 13276 | [1–432] | 13324 | [1–467] |
| 13152 | [1–81] | 13201 | [1–73] | 13325 | [1–380] | 13374 | [1–279] |
| 13153 | [1–457] | 13202 | [1–339] | 13326 | [1–432] | 13375 | [1–159],[208–349] |
| 13154 | [1–402] | 13203 | [1–230] | 13327 | [1–298] | 13377 | [284–434] |
| 13155 | [1–440] | 13204 | [1–92],[233–297] | 13328 | [1–159] | 13378 | [1–303] |
| 13156 | [1–384] | 13205 | [1–374] | 13329 | [1–129] | 13379 | [1–208],[264–437] |
| 13157 | [1–297] | 13206 | [1–431] | 13330 | [1–160] | 13380 | [82–287] |
| 13158 | [1–378] | 13207 | [1–450] | 13331 | [1–485] | 13381 | [1–137],[171–416] |
| 13159 | [1–262] | 13208 | [1–404] | 13332 | [1–111] | 13382 | [1–228],[328–460] |
| 13160 | [1–428] | 13209 | [59–105],[237–490] | 13333 | [1–187] | 13383 | [1–409] |
| 13161 | [1–326] | 13210 | [1–171] | 13334 | [1–176] | 13384 | [66–134],[183–337] |
| 13162 | [1–432] | 13211 | [32–76] | 13335 | [42–481] | 13385 | [1–335] |
| 13163 | [1–459] | 13212 | [1–447] | 13336 | [1–500] | 13386 | [1–453] |
| 13164 | [1–148],[301–438] | 13213 | [1–454] | 13337 | [1–422] | 13387 | [1–473] |
| 13165 | [1–445] | 13214 | [1–349] | 13338 | [1–446] | 13388 | [1–469] |
| 13166 | [1–461] | 13215 | [1–59] | 13339 | [1–130] | 13389 | [1–83] |
| 13167 | [1–85] | 13217 | [1–433] | 13340 | [1–348] | 13390 | [1–378] |
| 13168 | [1–495] | 13218 | [1–469] | 13341 | [1–200] | 13391 | [1–390] |
| 13169 | [1–340] | 13219 | [1–128] | 13342 | [1–290] | 13392 | [93–160] |
| 13170 | [1–198] | 13220 | [1–351] | 13343 | [1–195] | 13393 | [1–172] |
| 13171 | [1–113] | 13221 | [1–459] | 13344 | [1–87] | 13394 | [1–461] |
| 13172 | [1–382] | 13222 | [1–477] | 13345 | [1–376] | 13395 | [1–85] |
| 13173 | [1–407] | 13223 | [1–56] | 13346 | [1–476] | 13396 | [1–117] |
| 13174 | [1–407] | 13224 | [1–318] | 13347 | [1–429] | 13397 | [1–469] |
| 13175 | [1–470] | 13225 | [1–499] | 13348 | [1–179] | 13398 | [1–134],[183–326] |
| 13176 | [1–438] | 13226 | [1–478] | 13349 | [1–339] | 13399 | [1–280] |
| 13177 | [1–421] | 13227 | [1–86] | 13350 | [1–300] | 13400 | [1–269] |
| 13178 | [1–431] | 13228 | [1–419] | 13351 | [1–439] | 13401 | [1–225] |
| 13229 | [1–446] | 13277 | [1–466] | 13352 | [1–267] | 13402 | [1–446] |
| 13230 | [1–517] | 13278 | [1–351] | 13353 | [1–339] | 13403 | [1–421] |
| 13231 | [1–444] | 13279 | [1–465] | 13354 | [1–156] | 13404 | [1–263] |
| 13232 | [1–443] | 13280 | [1–434] | 13355 | [1–377] | 13406 | [1–202],[287–481] |
| 13233 | [1–455] | 13281 | [66–202] | 13356 | [1–342] | 13407 | [93–160],[209–357] |
| 13234 | [1–444] | 13283 | [1–341] | 13357 | [1–352] | 13408 | [1–26] |
| 13235 | [1–446] | 13284 | [1–442] | 13358 | [1–171] | 13409 | [1–366] |
| 13236 | [1–454] | 13285 | [1–441] | 13359 | [66–134],[183–293] | 13410 | [1–438] |
| 13237 | [1–452] | 13286 | [264–303] | 13360 | [464–513] | 13411 | [1–267] |
| 13238 | [1–473] | 13287 | [1–305] | 13361 | [155–345] | 13412 | [93–161],[209–366] |
| 13239 | [1–433] | 13288 | [1–455] | 13362 | [1–291] | 13413 | [1–419] |
| 13240 | [1–414] | 13289 | [1–455] | 13363 | [1–130],[174–212],[278–342] | 13414 | [1–358] |
| 13241 | [1–437] | 13290 | [1–487] | 13364 | [1–225] | 13415 | [1–268] |
| 13242 | [1–432] | 13291 | [1–269] | 13367 | [66–134],[183–342] | 13416 | [1–68] |
| 13243 | [1–89] | 13292 | [1–313] | 13368 | [1–438] | 13417 | [1–313] |
| 13244 | [47–387] | 13293 | [1–200] | 13369 | [1–79] | 13418 | [147–187] |
| 13245 | [1–467] | 13294 | [94–257] | 13370 | [1–335] | 13419 | [1–311] |
| 13246 | [376–459] | 13295 | [1–171] | 13371 | [1–294] | 13420 | [93–160],[209–351] |
| 13247 | [1–109] | 13296 | [1–269] | 13372 | [1–229] | 13421 | [1–457] |
| 13248 | [1–457] | 13297 | [1–192] | 13373 | [1–267] | 13422 | [1–466] |
| 13249 | [1–316],[347–485] | 13298 | [1–474] | 13423 | [1–440] | 13471 | [1–426] |
| 13250 | [1–445] | 13299 | [1–87] | 13424 | [1–447] | 13472 | [1–461] |
| 13251 | [1–174] | 13300 | [1–75] | 13425 | [248–369] | 13473 | [1–464] |
| 13252 | [1–167],[213–469] | 13301 | [1–449] | 13426 | [1–99] | 13474 | [111–350] |
| 13253 | [1–450] | 13302 | [1–300] | 13427 | [1–480] | 13475 | [1–342] |
| 13254 | [1–488] | 13303 | [1–338] | 13428 | [1–159] | 13476 | [1–126],[162–362] |
| 13255 | [39–257] | 13304 | [1–423] | 13429 | [1–169] | 13478 | [1–447] |
| 13256 | [91–479] | 13305 | [1–250] | 13430 | [1–459] | 13479 | [1–202] |
| 13257 | [1–464] | 13306 | [1–200] | 13431 | [1–304] | 13480 | [1–63] |
| 13258 | [1–469] | 13307 | [1–461] | 13432 | [1–415] | 13481 | [1–495] |
| 13259 | [1–28],[90–184] | 13308 | [1–304] | 13433 | [155–219],[256–426] | 13482 | [1–466] |
| 13260 | [1–475] | 13309 | [1–140] | 13434 | [1–372] | 13483 | [1–295] |
| 13261 | [1–289] | 13310 | [1–236] | 13435 | [57–141] | 13484 | [1–374] |
| 13262 | [132–175] | 13311 | [1–325] | 13436 | [1–313] | 13485 | [1–478] |
| 13264 | [1–94] | 13312 | [1–415] | 13438 | [1–464] | 13486 | [1–370] |
| 13265 | [1–467] | 13313 | [1–370] | 13439 | [1–464] | 13487 | [1–170] |
| 13266 | [1–197] | 13314 | [1–50] | 13440 | [1–147] | 13488 | [1–200] |
| 13267 | [1–36],[124–173] | 13315 | [1–386] | 13441 | [53–293] | 13490 | [1–200] |
| 13268 | [1–30],[79–171] | 13316 | [1–208] | 13442 | [1–511] | 13491 | [36–214],[245–482] |
| 13269 | [1–404] | 13317 | [1–142] | 13443 | [93–160] | 13492 | [1–66] |
| 13270 | [1–215] | 13318 | [1–314] | 13444 | [1–120] | 13494 | [1–313] |
| 13271 | [1–367] | 13319 | [1–355] | 13445 | [1–441] | 13495 | [1–254] |
| 13272 | [1–465] | 13320 | [1–319] | 13446 | [1–300] | 13496 | [1–150],[247–312] |
| 13273 | [1–199] | 13321 | [1–382] | 13447 | [1–388] | 13497 | [1–72] |
| 13274 | [1–322] | 13322 | [1–375] | | | | |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 13448 | [1–54] | 13498 | [1–50] | 13623 | [1–221],[302–460] | 13675 | [1–479] |
| 13449 | [1–269] | 13499 | [1–82] | 13624 | [1–386] | 13676 | [1–70] |
| 13450 | [1–403] | 13500 | [1–200] | 13625 | [1–476] | 13677 | [147–468] |
| 13451 | [1–303] | 13501 | [1–354] | 13628 | [1–115] | 13678 | [1–467] |
| 13452 | [1–181],[285–328] | 13502 | [1–329] | 13629 | [1–514] | 13679 | [1–192] |
| 13453 | [1–99],[218–465] | 13503 | [1–321] | 13630 | [1–232] | 13680 | [1–355] |
| 13454 | [1–441] | 13504 | [1–201] | 13631 | [1–471] | 13681 | [1–463] |
| 13455 | [1–429] | 13505 | [1–481] | 13632 | [1–105],[166–507] | 13682 | [1–424] |
| 13456 | [1–191] | 13508 | [1–330] | 13633 | [1–466] | 13683 | [1–454] |
| 13457 | [1–91] | 13509 | [1–336] | 13634 | [1–513] | 13684 | [1–297],[344–505] |
| 13458 | [1–81] | 13510 | [1–383] | 13635 | [1–169],[230–321] | 13685 | [143–173] |
| 13459 | [1–90],[158–205],[252–341] | 13511 | [1–112] | 13636 | [151–257] | 13686 | [1–376] |
| 13460 | [271–312] | 13512 | [1–293] | 13637 | [1–504] | 13687 | [1–103],[211–469] |
| 13461 | [1–56] | 13513 | [1–495] | 13638 | [1–465] | 13688 | [1–291] |
| 13462 | [1–267] | 13514 | [1–483] | 13640 | [1–443] | 13689 | [1–402] |
| 13463 | [1–370] | 13515 | [1–337] | 13641 | [1–385] | 13690 | [1–510] |
| 13464 | [1–91] | 13516 | [1–267] | 13643 | [1–328] | 13691 | [1–492] |
| 13465 | [1–263] | 13517 | [1–207] | 13644 | [1–362] | 13693 | [1–511] |
| 13466 | [1–482] | 13518 | [1–378] | 13645 | [1–480] | 13694 | [1–229] |
| 13467 | [1–459] | 13519 | [1–372] | 13646 | [1–116] | 13695 | [1–513] |
| 13468 | [1–132] | 13520 | [1–271] | 13647 | [1–113] | 13696 | [1–472] |
| 13469 | [1–69] | 13521 | [1–144] | 13648 | [1–269] | 13697 | [1–312] |
| 13470 | [217–428] | 13522 | [1–225] | 13649 | [1–62] | 13698 | [1–424] |
| 13523 | [1–215] | 13572 | [1–109] | 13650 | [57–182] | 13699 | [1–130] |
| 13524 | [1–119] | 13573 | [1–224] | 13651 | [1–486] | 13700 | [1–266] |
| 13525 | [1–243] | 13574 | [1–342] | 13652 | [1–442] | 13701 | [1–466] |
| 13526 | [1–82] | 13575 | [1–200] | 13653 | [1–475] | 13702 | [1–366] |
| 13527 | [1–150],[247–310] | 13576 | [1–161] | 13654 | [1–79] | 13703 | [1–446] |
| 13528 | [1–200] | 13577 | [1–149] | 13655 | [1–284] | 13704 | [1–479] |
| 13529 | [1–170] | 13578 | [1–150],[247–312] | 13656 | [1–473] | 13705 | [1–462] |
| 13530 | [1–337] | 13579 | [1–70] | 13658 | [1–145] | 13706 | [1–474] |
| 13531 | [1–63] | 13580 | [1–51] | 13659 | [1–490] | 13707 | [1–203] |
| 13532 | [1–133] | 13581 | [1–272] | 13660 | [1–481] | 13708 | [1–486] |
| 13533 | [1–97] | 13582 | [1–111] | 13661 | [1–202] | 13709 | [1–431] |
| 13534 | [1–115] | 13583 | [1–152] | 13662 | [1–102] | 13710 | [1–425] |
| 13535 | [1–374] | 13584 | [1–412] | 13663 | [1–440] | 13711 | [1–468] |
| 13536 | [1–254] | 13585 | [1–118] | 13664 | [1–447] | 13712 | [158–358] |
| 13537 | [1–344] | 13586 | [1–504] | 13665 | [1–471] | 13713 | [1–498] |
| 13538 | [1–200] | 13587 | [1–374] | 13666 | [1–55] | 13714 | [1–237],[383–465] |
| 13539 | [1–112] | 13588 | [1–313] | 13667 | [1–253] | 13715 | [1–467] |
| 13540 | [1–354] | 13589 | [1–175] | 13668 | [1–475] | 13716 | [1–499] |
| 13541 | [1–309] | 13590 | [1–366] | 13669 | [1–456] | 13717 | [1–504] |
| 13542 | [1–348] | 13591 | [1–175] | 13670 | [1–230] | 13718 | [1–489] |
| 13543 | [1–361] | 13592 | [1–91] | 13671 | [1–371] | 13719 | [1–420] |
| 13544 | [1–161] | 13593 | [1–235] | 13720 | [1–507] | 13768 | [1–392] |
| 13545 | [1–200] | 13594 | [1–144] | 13721 | [1–487] | 13769 | [1–97] |
| 13546 | [1–186] | 13595 | [1–173] | 13722 | [1–468] | 13770 | [1–178] |
| 13547 | [1–129] | 13596 | [1–111] | 13723 | [1–372] | 13771 | [1–463] |
| 13548 | [1–232] | 13597 | [1–270] | 13724 | [1–116] | 13772 | [1–396] |
| 13549 | [1–134] | 13598 | [1–306] | 13725 | [1–483] | 13773 | [1–313] |
| 13550 | [1–170] | 13599 | [1–225] | 13726 | [1–454] | 13774 | [1–582] |
| 13551 | [1–225] | 13600 | [1–157] | 13727 | [1–510] | 13775 | [1–507] |
| 13552 | [1–97] | 13601 | [1–81] | 13728 | [1–458] | 13776 | [1–342] |
| 13553 | [1–162] | 13602 | [1–375] | 13729 | [1–417] | 13777 | [1–407] |
| 13554 | [1–78] | 13603 | [1–125] | 13730 | [1–137] | 13778 | [1–475] |
| 13555 | [1–338] | 13604 | [1–312] | 13731 | [1–370] | 13779 | [1–534] |
| 13556 | [1–446] | 13605 | [1–342] | 13732 | [1–113] | 13780 | [1–348] |
| 13557 | [1–419] | 13606 | [1–183] | 13733 | [45–408] | 13781 | [1–196] |
| 13558 | [1–125] | 13607 | [1–112] | 13734 | [168–472] | 13782 | [1–485] |
| 13559 | [1–129] | 13608 | [1–120] | 13735 | [1–263] | 13783 | [1–134] |
| 13560 | [1–380] | 13609 | [1–108] | 13736 | [1–70],[418–483] | 13784 | [1–266] |
| 13561 | [1–285] | 13610 | [1–399] | 13737 | [1–476] | 13785 | [137–417] |
| 13563 | [1–383] | 13611 | [1–377] | 13738 | [1–282] | 13786 | [1–499] |
| 13564 | [1–310] | 13612 | [1–303] | 13739 | [1–469] | 13787 | [1–478] |
| 13566 | [1–93] | 13613 | [1–506] | 13740 | [1–348] | 13788 | [1–605] |
| 13567 | [1–119] | 13614 | [1–165] | 13741 | [132–357] | 13789 | [1–472] |
| 13568 | [1–297] | 13615 | [1–504] | 13742 | [1–483] | 13790 | [1–83] |
| 13569 | [1–156] | 13617 | [1–108],[159–246] | 13743 | [132–396] | 13791 | [1–500] |
| 13570 | [1–324] | 13618 | [1–494] | 13744 | [1–468] | 13792 | [395–449] |
| 13571 | [1–115] | 13619 | [1–436] | 13745 | [1–480] | 13793 | [1–433] |
| 13620 | [1–92] | 13672 | [1–173] | 13746 | [1–191],[239–449] | 13794 | [1–394] |
| 13621 | [1–522] | 13673 | [1–460] | 13747 | [1–462] | 13795 | [1–507] |
| 13622 | [1–443] | 13674 | [1–447] | 13748 | [1–491] | 13796 | [1–363] |
|  |  |  |  | 13749 | [1–361] | 13797 | [1–146] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 13750 | [1–287] | 13798 | [1–518] | 13920 | [1–64] | 13969 | [1–485] |
| 13751 | [1–436] | 13799 | [1–294] | 13921 | [1–463] | 13970 | [1–178] |
| 13752 | [1–59] | 13800 | [1–343] | 13922 | [1–691] | 13971 | [1–435] |
| 13753 | [1–63] | 13801 | [1–420] | 13923 | [1–381] | 13972 | [1–542] |
| 13755 | [1–461] | 13802 | [1–465] | 13924 | [1–450] | 13973 | [1–491] |
| 13756 | [1–93] | 13803 | [1–369] | 13925 | [1–356] | 13974 | [1–55] |
| 13757 | [110–493] | 13804 | [124–477] | 13927 | [1–477] | 13975 | [1–180] |
| 13758 | [1–433] | 13805 | [1–139] | 13929 | [1–388] | 13976 | [1–77] |
| 13759 | [1–61] | 13806 | [59–316] | 13930 | [1–221] | 13977 | [1–266] |
| 13760 | [1–437] | 13807 | [1–348] | 13931 | [1–111],[151–189], [272–463] | 13978 | [1–327] |
| 13761 | [1–60] | 13808 | [1–72] | | | | |
| 13762 | [1–136] | 13809 | [1–125],[157–471] | 13932 | [1–457] | 13979 | [1–387] |
| 13763 | [250–335] | 13810 | [53–193],[294–333] | 13933 | [1–127] | 13980 | [1–339] |
| 13764 | [1–493] | 13811 | [1–466] | 13934 | [1–154] | 13982 | [1–417] |
| 13765 | [1–115] | 13812 | [1–320] | 13935 | [1–173] | 13983 | [50–481] |
| 13766 | [1–459] | 13813 | [1–294] | 13936 | [31–187] | 13984 | [1–241] |
| 13767 | [1–543] | 13814 | [1–475] | 13937 | [1–57] | 13985 | [1–447] |
| 13815 | [1–481] | 13863 | [1–480] | 13938 | [1–340] | 13986 | [1–145] |
| 13816 | [1–41] | 13864 | [1–315] | 13939 | [1–451] | 13987 | [1–100] |
| 13817 | [1–369],[431–472] | 13865 | [1–516] | 13940 | [1–413] | 13988 | [1–499] |
| 13818 | [1–443] | 13866 | [1–491] | 13941 | [1–426] | 13989 | [1–150] |
| 13819 | [1–372] | 13867 | [81–479] | 13942 | [1–218] | 13990 | [1–459] |
| 13820 | [1–105] | 13868 | [1–468] | 13943 | [1–395] | 13991 | [1–501] |
| 13821 | [1–428] | 13869 | [1–382] | 13944 | [1–507] | 13992 | [61–132] |
| 13822 | [1–485] | 13870 | [183–268] | 13945 | [1–487] | 13993 | [1–376] |
| 13823 | [1–257] | 13871 | [81–534] | 13946 | [1–223] | 13994 | [1–480] |
| 13824 | [1–139] | 13872 | [1–278] | 13947 | [1–456] | 13995 | [1–485] |
| 13825 | [1–477] | 13873 | [1–386] | 13948 | [1–395] | 13996 | [1–343] |
| 13826 | [1–460] | 13874 | [70–379] | 13949 | [1–488] | 13997 | [1–466] |
| 13827 | [1–481] | 13875 | [1–502] | 13950 | [1–508] | 13998 | [1–415] |
| 13828 | [1–52] | 13876 | [1–239] | 13951 | [1–443] | 13999 | [1–479] |
| 13829 | [1–471] | 13878 | [1–248] | 13952 | [1–449] | 14000 | [1–467] |
| 13830 | [1–428] | 13879 | [1–480] | 13953 | [1–89] | 14001 | [1–368] |
| 13831 | [1–84] | 13880 | [1–481] | 13954 | [1–511] | 14002 | [1–325] |
| 13832 | [1–84],[224–496] | 13881 | [1–433] | 13955 | [1–36],[134–347] | 14003 | [1–115] |
| 13833 | [1–402] | 13882 | [1–242] | 13956 | [1–200] | 14004 | [1–132],[395–447] |
| 13834 | [1–479] | 13883 | [1–387] | 13957 | [1–330] | 14005 | [1–418] |
| 13835 | [1–487] | 13884 | [1–85] | 13958 | [1–94] | 14006 | [1–492] |
| 13836 | [1–71] | 13885 | [1–403] | 13959 | [1–399] | 14007 | [1–447] |
| 13837 | [99–537] | 13886 | [1–343] | 14008 | [1–478] | 14058 | [1–201] |
| 13838 | [1–481] | 13887 | [1–211] | 14009 | [1–336] | 14059 | [1–322] |
| 13839 | [66–227],[259–452] | 13888 | [1–513] | 14011 | [1–281] | 14060 | [85–176] |
| 13840 | [1–177] | 13889 | [1–447] | 14012 | [1–524] | 14061 | [1–129] |
| 13841 | [1–353] | 13890 | [1–488] | 14013 | [1–529] | 14062 | [1–421] |
| 13842 | [1–63] | 13891 | [1–574] | 14014 | [1–343] | 14063 | [50–119] |
| 13843 | [1–494] | 13892 | [1–289] | 14015 | [1–231] | 14064 | [1–444] |
| 13844 | [1–429] | 13893 | [1–503] | 14016 | [1–518] | 14065 | [1–477] |
| 13845 | [1–472] | 13894 | [1–100] | 14017 | [1–57] | 14066 | [238–282] |
| 13846 | [1–268] | 13895 | [37–138] | 14018 | [1–440] | 14067 | [1–170] |
| 13847 | [1–316] | 13896 | [1–388] | 14019 | [1–496] | 14068 | [1–242] |
| 13848 | [69–108],[214–390] | 13897 | [75–543] | 14020 | [1–499] | 14069 | [1–484] |
| 13849 | [1–147] | 13898 | [1–521] | 14021 | [1–428] | 14071 | [1–207],[255–487] |
| 13850 | [1–544] | 13899 | [1–133] | 14022 | [1–387] | 14072 | [1–243] |
| 13851 | [1–234] | 13900 | [73–127] | 14023 | [1–382] | 14073 | [1–289] |
| 13852 | [1–52] | 13901 | [1–103] | 14024 | [1–87] | 14074 | [1–439] |
| 13853 | [1–304] | 13902 | [73–131] | 14025 | [1–255] | 14075 | [1–468] |
| 13854 | [1–486] | 13903 | [89–176] | 14026 | [1–502] | 14076 | [184–298] |
| 13855 | [1–354] | 13904 | [1–74] | 14027 | [1–317] | 14077 | [1–258] |
| 13856 | [1–464] | 13905 | [1–259] | 14028 | [1–119] | 14078 | [1–314] |
| 13858 | [1–127],[156–187], [226–451] | 13906 | [1–159] | 14029 | [53–399] | 14079 | [1–509] |
| | | | | 14030 | [1–228] | 14080 | [1–489] |
| 13859 | [1–667] | 13907 | [1–276] | 14031 | [1–483] | 14081 | [1–497] |
| 13860 | [1–353] | 13908 | [1–181] | 14032 | [1–89] | 14082 | [1–204] |
| 13861 | [1–419] | 13909 | [1–69] | 14033 | [1–77] | 14083 | [1–392] |
| 13862 | [1–506] | 13910 | [33–186] | 14034 | [1–458] | 14084 | [1–267] |
| 13911 | [1–600] | 13960 | [53–441] | 14035 | [1–440] | 14085 | [1–473] |
| 13912 | [1–183] | 13961 | [1–512] | 14036 | [1–312] | 14086 | [1–113],[232–414] |
| 13913 | [1–327] | 13962 | [1–526] | 14037 | [1–460] | 14087 | [1–445] |
| 13914 | [1–254] | 13963 | [1–62] | 14038 | [1–490] | 14088 | [239–503] |
| 13915 | [1–75] | 13964 | [1–510] | 14039 | [1–475] | 14089 | [1–441] |
| 13916 | [1–181] | 13965 | [1–112] | 14040 | [1–478] | 14090 | [1–394] |
| 13917 | [1–67] | 13966 | [1–162],[199–288] | 14041 | [1–510] | 14091 | [1–508] |
| 13918 | [1–108] | 13967 | [1–422] | 14042 | [232–472] | 14092 | [1–501] |
| 13919 | [1–437] | 13968 | [1–512] | 14043 | [1–535] | 14093 | [180–326] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 14044 | [1–319] | 14094 | [1–514] | 14217 | [1–466] | 14265 | [1–345] |
| 14045 | [1–479] | 14095 | [1–504] | 14218 | [1–462] | 14266 | [1–394] |
| 14046 | [1–485] | 14096 | [1–186] | 14219 | [1–503] | 14267 | [1–467] |
| 14048 | [1–371] | 14097 | [1–174] | 14220 | [1–460] | 14268 | [1–295] |
| 14049 | [1–473] | 14098 | [1–225] | 14221 | [1–446] | 14269 | [1–476] |
| 14050 | [1–111] | 14099 | [81–382] | 14222 | [1–370] | 14270 | [1–440] |
| 14051 | [1–499] | 14100 | [287–432] | 14223 | [1–67],[164–456] | 14271 | [1–467] |
| 14053 | [1–333] | 14102 | [1–354] | 14224 | [1–333],[373–475] | 14272 | [84–263] |
| 14054 | [1–195],[247–486] | 14103 | [1–454] | 14225 | [1–312] | 14273 | [1–62] |
| 14055 | [1–513] | 14104 | [1–607] | 14226 | [1–457] | 14274 | [1–278] |
| 14056 | [1–383] | 14105 | [1–69] | 14227 | [1–457] | 14275 | [1–396] |
| 14057 | [1–485] | 14106 | [36–429] | 14228 | [1–191],[327–354] | 14276 | [1–164] |
| 14107 | [1–379] | 14156 | [1–333] | 14229 | [1–455] | 14277 | [1–479] |
| 14108 | [1–488] | 14157 | [1–503] | 14231 | [1–113] | 14278 | [1–523] |
| 14109 | [1–240] | 14158 | [1–166],[286–328],[380–460] | 14232 | [1–334] | 14279 | [218–458] |
| 14110 | [1–171] | 14159 | [1–354] | 14233 | [1–413] | 14280 | [1–316] |
| 14112 | [1–74] | 14160 | [1–147] | 14234 | [1–338] | 14281 | [1–500] |
| 14113 | [1–481] | 14161 | [1–337] | 14235 | [1–458] | 14282 | [1–398] |
| 14114 | [1–194] | 14162 | [1–69] | 14236 | [1–407] | 14283 | [1–267] |
| 14115 | [1–259] | 14163 | [37–472] | 14237 | [160–367] | 14284 | [1–409] |
| 14116 | [1–309] | 14164 | [1–461] | 14238 | [1–477] | 14285 | [1–75] |
| 14117 | [1–483] | 14165 | [1–543] | 14239 | [1–213] | 14286 | [1–157] |
| 14118 | [1–473] | 14166 | [1–424] | 14240 | [1–216],[256–487] | 14287 | [72–165] |
| 14119 | [1–487] | 14167 | [1–538] | 14241 | [1–464] | 14288 | [1–445] |
| 14120 | [1–430] | 14168 | [1–372] | 14242 | [1–454] | 14289 | [1–434] |
| 14121 | [1–56] | 14169 | [1–392] | 14243 | [1–474] | 14290 | [1–391] |
| 14122 | [1–403] | 14170 | [75–347] | 14244 | [1–470] | 14291 | [1–339] |
| 14123 | [1–481] | 14171 | [1–448] | 14245 | [1–367] | 14292 | [1–418] |
| 14124 | [1–315] | 14172 | [1–106] | 14246 | [1–81] | 14293 | [1–305] |
| 14125 | [1–417] | 14173 | [1–487] | 14247 | [1–262] | 14294 | [1–491] |
| 14126 | [1–503] | 14174 | [1–491] | 14248 | [1–227] | 14295 | [1–433] |
| 14127 | [1–493] | 14175 | [1–600] | 14249 | [1–410] | 14296 | [1–356] |
| 14128 | [1–182] | 14176 | [1–77] | 14250 | [1–27],[221–502] | 14297 | [1–445] |
| 14129 | [1–385] | 14177 | [1–529] | 14298 | [69–113] | 14347 | [1–383] |
| 14130 | [1–62] | 14178 | [48–564] | 14299 | [1–379] | 14348 | [1–313] |
| 14131 | [1–295] | 14179 | [1–498] | 14300 | [1–454] | 14349 | [1–418] |
| 14132 | [1–496] | 14180 | [1–301] | 14301 | [1–363] | 14350 | [1–428] |
| 14133 | [1–452] | 14181 | [1–439] | 14302 | [1–456] | 14351 | [1–325] |
| 14134 | [60–372] | 14182 | [1–203] | 14303 | [1–431] | 14352 | [1–182] |
| 14135 | [1–449] | 14183 | [1–436] | 14304 | [1–453] | 14353 | [1–162] |
| 14136 | [1–438] | 14184 | [1–413] | 14305 | [1–425] | 14354 | [1–514] |
| 14137 | [1–181] | 14185 | [102–483] | 14306 | [1–436] | 14355 | [1–96] |
| 14138 | [1–472] | 14186 | [1–391] | 14307 | [1–405] | 14356 | [1–352] |
| 14139 | [1–444] | 14187 | [1–468] | 14308 | [1–260] | 14357 | [1–498] |
| 14140 | [1–236] | 14188 | [1–97] | 14309 | [1–477] | 14358 | [1–198] |
| 14141 | [59–235] | 14189 | [1–74] | 14310 | [1–496] | 14359 | [1–550] |
| 14142 | [1–52] | 14190 | [1–323] | 14311 | [1–378] | 14360 | [1–56] |
| 14143 | [1–439] | 14191 | [1–453] | 14312 | [116–409] | 14361 | [1–334] |
| 14144 | [1–316] | 14192 | [1–489] | 14313 | [1–442] | 14362 | [1–453] |
| 14145 | [1–509] | 14193 | [237–392] | 14314 | [1–459] | 14363 | [1–230],[260–347] |
| 14146 | [1–497] | 14194 | [1–497] | 14315 | [1–66] | 14364 | [1–495] |
| 14147 | [1–67] | 14195 | [1–180] | 14316 | [1–371] | 14365 | [68–161] |
| 14148 | [155–291] | 14196 | [1–452] | 14317 | [1–458] | 14366 | [62–478] |
| 14149 | [1–100] | 14197 | [1–474] | 14318 | [1–429] | 14367 | [1–437] |
| 14151 | [1–456] | 14198 | [116–184],[252–353] | 14319 | [1–299] | 14368 | [1–310] |
| 14152 | [1–406] | 14199 | [1–444] | 14320 | [1–452] | 14369 | [1–454],[491–566] |
| 14153 | [1–443] | 14200 | [77–390] | 14322 | [1–156] | 14370 | [1–297] |
| 14154 | [1–156],[194–328] | 14201 | [1–317] | 14323 | [1–392] | 14371 | [1–430] |
| 14155 | [187–267] | 14202 | [1–101] | 14324 | [1–277] | 14372 | [1–462] |
| 14203 | [1–275] | 14251 | [1–272] | 14325 | [1–420] | 14373 | [1–512] |
| 14204 | [1–200] | 14252 | [1–462] | 14326 | [1–461] | 14374 | [1–73] |
| 14205 | [1–484] | 14253 | [1–431] | 14327 | [1–452] | 14375 | [1–81] |
| 14206 | [1–434] | 14254 | [1–100] | 14328 | [1–423] | 14376 | [1–449] |
| 14207 | [1–300] | 14255 | [1–391] | 14329 | [1–218] | 14377 | [1–193] |
| 14208 | [1–367] | 14256 | [1–288] | 14331 | [1–277] | 14378 | [1–307] |
| 14209 | [1–465] | 14257 | [1–171] | 14332 | [1–402] | 14379 | [1–477] |
| 14210 | [110–357] | 14258 | [1–364] | 14333 | [1–82] | 14380 | [1–126],[173–231] |
| 14211 | [1–341] | 14259 | [1–436] | 14334 | [1–420] | 14381 | [1–269] |
| 14212 | [1–106] | 14260 | [1–425] | 14335 | [1–410] | 14383 | [1–483] |
| 14213 | [1–466] | 14261 | [1–359] | 14336 | [1–426] | 14384 | [1–412] |
| 14214 | [1–327] | 14262 | [1–269] | 14337 | [1–434] | 14385 | [1–239] |
| 14215 | [1–458] | 14263 | [1–138] | 14338 | [310–406] | 14386 | [1–46],[99–372] |
| 14216 | [1–494] | 14264 | [1–491] | 14339 | [1–448] | 14387 | [1–451] |
|  |  |  |  | 14340 | [74–466] | 14388 | [1–467] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 14341 | [166–314] | 14389 | [1–443] | 14512 | [1–322] | 14561 | [1–229] |
| 14342 | [1–481] | 14390 | [1–145] | 14513 | [1–249] | 14562 | [1–382] |
| 14343 | [1–416] | 14391 | [1–115] | 14514 | [1–418] | 14563 | [1–424] |
| 14344 | [1–464] | 14392 | [1–451] | 14515 | [1–373] | 14565 | [1–464] |
| 14345 | [1–274] | 14393 | [1–470] | 14516 | [164–402] | 14566 | [1–301] |
| 14346 | [1–289] | 14394 | [1–474] | 14517 | [1–440] | 14567 | [1–187] |
| 14395 | [1–442] | 14442 | [1–231],[295–336] | 14519 | [1–461] | 14568 | [1–75] |
| 14396 | [1–372] | 14443 | [1–482] | 14520 | [1–448] | 14569 | [1–347] |
| 14397 | [1–122] | 14444 | [1–469] | 14521 | [1–437] | 14570 | [1–324] |
| 14398 | [1–457] | 14445 | [1–419] | 14522 | [1–333] | 14571 | [1–84] |
| 14399 | [1–457] | 14446 | [1–326] | 14523 | [1–384] | 14572 | [1–483] |
| 14400 | [1–296] | 14447 | [1–435] | 14524 | [1–240] | 14573 | [1–477] |
| 14401 | [1–170] | 14448 | [1–310] | 14525 | [1–386],[427–466] | 14574 | [1–341] |
| 14402 | [1–379] | 14449 | [1–458] | 14526 | [1–140] | 14575 | [1–287],[322–424] |
| 14403 | [1–477] | 14450 | [1–432] | 14527 | [1–129] | 14576 | [1–56],[122–308] |
| 14404 | [239–419] | 14451 | [72–443] | 14528 | [1–360] | 14577 | [1–84] |
| 14405 | [1–481] | 14452 | [51–94],[139–415] | 14529 | [1–504] | 14578 | [1–408] |
| 14406 | [1–477] | 14453 | [1–433] | 14530 | [1–457] | 14579 | [1–469] |
| 14407 | [1–474] | 14454 | [1–447] | 14531 | [1–424] | 14580 | [1–413] |
| 14408 | [104–356] | 14455 | [1–461] | 14532 | [1–61] | 14581 | [1–488] |
| 14409 | [1–478] | 14456 | [59–322] | 14533 | [1–62] | 14582 | [1–322] |
| 14410 | [1–460] | 14457 | [1–473] | 14534 | [1–392] | 14583 | [1–399] |
| 14411 | [1–220] | 14458 | [1–374] | 14535 | [1–55] | 14584 | [1–482] |
| 14412 | [1–320] | 14459 | [1–457] | 14536 | [1–72] | 14585 | [1–325] |
| 14413 | [1–441] | 14460 | [1–128],[225–292] | 14537 | [1–321] | 14586 | [1–399] |
| 14414 | [1–476] | 14462 | [1–337] | 14538 | [1–425] | 14587 | [1–332] |
| 14415 | [1–301] | 14463 | [1–463] | 14588 | [1–280] | 14637 | [1–288] |
| 14416 | [1–169] | 14464 | [1–449] | 14589 | [1–284] | 14638 | [1–222] |
| 14417 | [1–439] | 14465 | [1–96] | 14590 | [1–357] | 14639 | [1–251] |
| 14418 | [1–343] | 14466 | [1–444] | 14591 | [1–364] | 14640 | [1–498] |
| 14419 | [1–404] | 14467 | [1–461] | 14592 | [1–109] | 14641 | [1–397] |
| 14420 | [1–171],[200–463] | 14468 | [1–448] | 14593 | [1–478] | 14642 | [1–424] |
| 14421 | [1–129],[180–402] | 14469 | [1–233] | 14594 | [1–507] | 14644 | [1–217] |
| 14422 | [1–497] | 14470 | [1–28],[324–466] | 14595 | [1–238] | 14645 | [1–501] |
| 14423 | [1–447] | 14471 | [1–448] | 14596 | [1–433] | 14646 | [1–470] |
| 14424 | [1–455] | 14472 | [1–375] | 14597 | [1–492] | 14647 | [1–293] |
| 14425 | [1–173] | 14473 | [1–369] | 14598 | [1–371] | 14648 | [1–298] |
| 14426 | [1–373] | 14474 | [1–451] | 14599 | [1–167] | 14649 | [1–322] |
| 14427 | [1–415] | 14475 | [1–458] | 14600 | [50–483] | 14650 | [1–486] |
| 14428 | [1–213] | 14476 | [1–197] | 14601 | [1–407] | 14651 | [1–478] |
| 14429 | [1–442] | 14477 | [1–441] | 14603 | [1–510] | 14652 | [1–447] |
| 14430 | [1–465] | 14478 | [1–61] | 14604 | [67–109],[153–598] | 14653 | [1–438] |
| 14431 | [1–256] | 14479 | [1–151] | 14605 | [1–440] | 14654 | [1–388] |
| 14432 | [1–295] | 14480 | [1–422] | 14606 | [1–416] | 14655 | [1–79] |
| 14433 | [1–398] | 14481 | [1–329] | 14608 | [1–502] | 14656 | [1–482] |
| 14434 | [1–477] | 14482 | [1–93] | 14609 | [1–361] | 14657 | [1–508] |
| 14435 | [1–343] | 14483 | [1–118] | 14610 | [1–335] | 14658 | [1–329] |
| 14436 | [1–119] | 14484 | [1–401] | 14611 | [1–206] | 14659 | [1–398] |
| 14437 | [1–200] | 14485 | [1–344] | 14612 | [1–50] | 14660 | [1–116] |
| 14438 | [1–116] | 14486 | [1–143] | 14613 | [1–410] | 14661 | [1–274] |
| 14439 | [1–470] | 14488 | [1–441] | 14614 | [1–423] | 14662 | [183–497] |
| 14440 | [1–280] | 14489 | [1–334] | 14615 | [1–163] | 14663 | [1–484] |
| 14441 | [1–435] | 14490 | [1–443] | 14616 | [1–495] | 14664 | [1–461] |
| 14491 | [1–420] | 14539 | [424–453] | 14617 | [1–430] | 14665 | [1–481] |
| 14492 | [1–103] | 14540 | [1–498] | 14618 | [1–352] | 14666 | [1–126] |
| 14493 | [141–324] | 14541 | [1–480] | 14619 | [1–83] | 14667 | [1–323] |
| 14494 | [1–408] | 14542 | [1–507] | 14620 | [1–321] | 14668 | [1–90] |
| 14495 | [1–417] | 14543 | [1–226] | 14621 | [1–491] | 14669 | [1–425] |
| 14496 | [1–446] | 14544 | [1–541] | 14622 | [40–492] | 14670 | [1–448] |
| 14497 | [1–306] | 14545 | [1–523] | 14623 | [1–483] | 14671 | [1–172] |
| 14498 | [1–433] | 14546 | [178–317],[363–583] | 14624 | [61–347],[405–472] | 14672 | [1–308] |
| 14499 | [1–453] | 14547 | [1–487] | 14625 | [1–484] | 14673 | [1–236] |
| 14500 | [1–171] | 14548 | [1–367] | 14626 | [1–359] | 14674 | [100–158],[189–464] |
| 14501 | [1–453] | 14549 | [1–505] | 14627 | [1–52] | 14676 | [1–275] |
| 14502 | [1–374] | 14550 | [1–166] | 14628 | [1–511] | 14677 | [1–111] |
| 14503 | [1–298] | 14551 | [1–487] | 14629 | [1–233] | 14678 | [1–472] |
| 14504 | [1–475] | 14552 | [1–451] | 14630 | [1–129] | 14679 | [1–168] |
| 14505 | [1–416] | 14553 | [1–359] | 14631 | [1–82] | 14680 | [1–61] |
| 14506 | [1–276],[307–432] | 14554 | [1–447] | 14632 | [1–475] | 14681 | [1–61] |
| 14507 | [1–350] | 14555 | [1–498] | 14633 | [1–520] | 14682 | [1–59] |
| 14508 | [1–342] | 14556 | [1–56] | 14634 | [1–316] | 14683 | [1–419] |
| 14509 | [1–369] | 14558 | [1–464] | 14635 | [1–308] | 14684 | [48–448] |
| 14510 | [1–450] | 14559 | [1–471] | 14636 | [1–465] | 14685 | [1–320] |
| 14511 | [1–89] | 14560 | [1–87] | 14687 | [1–314] | 14736 | [1–474] |

TABLE IVb-continued (Novelty: 100%)

| Seq Id No | Positions of preferred fragments | Seq Id No | Positions of preferred fragments | Seq Id No | Positions of preferred fragments | Seq Id No | Positions of preferred fragments |
|---|---|---|---|---|---|---|---|
| 14688 | [1–97] | 14737 | [1–148] | 14815 | [1–72] | 14863 | [1–166] |
| 14689 | [1–92] | 14738 | [1–411] | 14816 | [1–340] | 14864 | [39–470] |
| 14690 | [1–340] | 14739 | [1–517] | 14817 | [1–508] | 14865 | [1–495] |
| 14691 | [1–157] | 14740 | [1–308] | 14818 | [1–195] | 14866 | [1–217] |
| 14692 | [109–444] | 14741 | [1–85] | 14819 | [1–66] | 14867 | [38–377] |
| 14693 | [1–77] | 14742 | [1–60] | 14820 | [1–54] | 14868 | [1–473] |
| 14694 | [1–75] | 14743 | [1–65] | 14821 | [1–436] | 14869 | [1–69] |
| 14695 | [1–406] | 14744 | [1–404] | 14822 | [1–343] | 14870 | [1–276] |
| 14697 | [1–368] | 14745 | [1–498] | 14823 | [1–317] | 14871 | [1–93] |
| 14698 | [37–73] | 14746 | [1–463] | 14824 | [1–78] | 14872 | [1–330] |
| 14699 | [1–365] | 14747 | [1–413] | 14825 | [1–62] | 14873 | [1–417] |
| 14700 | [1–288] | 14748 | [109–195] | 14826 | [1–386] | 14874 | [1–197] |
| 14701 | [1–124] | 14749 | [1–89] | 14827 | [1–58] | 14875 | [1–112] |
| 14702 | [1–357] | 14750 | [1–70] | 14829 | [1–478] | 14876 | [1–154] |
| 14703 | [1–60] | 14751 | [1–83] | 14830 | [1–103] | 14877 | [1–435] |
| 14704 | [1–195] | 14752 | [1–284] | 14831 | [1–76] | 14879 | [1–323] |
| 14705 | [1–74] | 14753 | [1–67] | 14832 | [39–464] | 14880 | [1–302] |
| 14706 | [1–293] | 14754 | [1–61] | 14833 | [1–405] | 14881 | [1–221] |
| 14707 | [252–470] | 14755 | [1–195] | 14834 | [1–61] | 14882 | [1–269] |
| 14708 | [1–345] | 14756 | [1–63] | 14883 | [1–432] | 14931 | [1–91] |
| 14709 | [1–509] | 14757 | [1–90] | 14884 | [1–60] | 14932 | [1–234] |
| 14710 | [1–449] | 14758 | [1–209] | 14885 | [1–462] | 14933 | [1–434] |
| 14711 | [1–339] | 14759 | [1–527] | 14886 | [1–114] | 14934 | [1–313] |
| 14712 | [1–59] | 14760 | [1–62] | 14887 | [1–481] | 14935 | [1–449] |
| 14713 | [1–216] | 14761 | [1–189] | 14888 | [1–389] | 14936 | [1–62] |
| 14714 | [1–217] | 14762 | [1–365] | 14889 | [1–194] | 14937 | [1–144] |
| 14715 | [1–50] | 14763 | [1–317] | 14890 | [1–240] | 14938 | [1–216] |
| 14716 | [1–95] | 14764 | [1–63] | 14891 | [1–301] | 14940 | [1–157] |
| 14717 | [1–80] | 14765 | [1–495] | 14892 | [1–75] | 14941 | [1–431] |
| 14718 | [1–406] | 14766 | [1–508] | 14893 | [1–357] | 14942 | [1–77],[174–255] |
| 14719 | [1–274] | 14767 | [1–379] | 14894 | [1–386] | 14943 | [45–328] |
| 14720 | [1–492] | 14768 | [1–393] | 14895 | [1–481] | 14944 | [1–91] |
| 14721 | [1–433] | 14769 | [1–474] | 14896 | [1–181] | 14945 | [1–62] |
| 14722 | [1–135] | 14770 | [1–263] | 14897 | [1–485] | 14946 | [1–95] |
| 14723 | [1–420] | 14771 | [1–528] | 14898 | [1–330] | 14947 | [1–94] |
| 14724 | [1–94] | 14772 | [126–510] | 14899 | [99–330] | 14948 | [1–61] |
| 14725 | [1–483] | 14773 | [1–514] | 14900 | [1–285] | 14949 | [1–85] |
| 14726 | [1–465] | 14774 | [1–298] | 14901 | [1–78] | 14950 | [1–195] |
| 14728 | [1–217] | 14775 | [1–281] | 14903 | [1–435] | 14951 | [1–224] |
| 14729 | [1–73] | 14776 | [1–457] | 14904 | [101–279] | 14952 | [1–486] |
| 14730 | [130–407] | 14777 | [1–162] | 14905 | [1–71] | 14953 | [1–94] |
| 14731 | [43–184] | 14778 | [1–445] | 14906 | [1–297] | 14954 | [1–249] |
| 14732 | [1–433] | 14779 | [1–268] | 14907 | [1–370] | 14955 | [37–491] |
| 14733 | [1–304] | 14781 | [61–269] | 14908 | [1–413] | 14956 | [1–501] |
| 14734 | [1–437] | 14782 | [1–162] | 14909 | [1–386] | 14957 | [1–216] |
| 14735 | [1–461] | 14783 | [1–83] | 14910 | [1–119] | 14958 | [1–83] |
| 14784 | [1–417] | 14835 | [1–86] | 14911 | [1–302] | 14959 | [1–83] |
| 14785 | [50–240] | 14836 | [1–494] | 14912 | [1–152] | 14960 | [1–88] |
| 14786 | [1–83] | 14837 | [1–458] | 14913 | [1–52] | 14961 | [1–427] |
| 14787 | [1–75] | 14838 | [1–69] | 14914 | [1–50] | 14962 | [1–89] |
| 14788 | [1–442] | 14839 | [1–344] | 14915 | [1–76] | 14963 | [1–73] |
| 14790 | [1–264] | 14840 | [1–217] | 14916 | [1–78] | 14964 | [1–30] |
| 14791 | [1–301] | 14841 | [1–328] | 14917 | [1–482] | 14965 | [1–458] |
| 14792 | [1–72] | 14842 | [1–72] | 14918 | [1–293] | 14966 | [1–63] |
| 14793 | [62–348],[380–432] | 14843 | [1–430] | 14919 | [1–496] | 14967 | [1–118] |
| 14795 | [1–356] | 14844 | [1–65],[199–270] | 14920 | [1–59] | 14968 | [1–58] |
| 14796 | [1–278] | 14845 | [1–253] | 14921 | [1–474] | 14969 | [167–223] |
| 14797 | [1–328] | 14846 | [1–66] | 14922 | [1–195] | 14970 | [1–105] |
| 14798 | [61–259] | 14847 | [1–109] | 14923 | [1–113] | 14971 | [1–235] |
| 14799 | [1–61] | 14848 | [1–187],[268–387] | 14924 | [1–328] | 14972 | [1–469] |
| 14800 | [1–55] | 14849 | [1–87] | 14925 | [1–91] | 14973 | [1–180] |
| 14801 | [1–474] | 14850 | [1–480] | 14926 | [1–84] | 14974 | [1–89] |
| 14802 | [39–427] | 14851 | [1–196] | 14927 | [1–112] | 14975 | [50–146] |
| 14803 | [1–54] | 14852 | [1–423] | 14928 | [1–122] | 14976 | [1–178] |
| 14804 | [1–102] | 14853 | [1–65] | 14929 | [1–216] | 14977 | [91–403] |
| 14805 | [1–81] | 14854 | [1–480] | 14930 | [1–477] | 14978 | [32–185] |
| 14806 | [1–110] | 14855 | [1–138] | 14979 | [1–71],[132–214] | 15028 | [1–91] |
| 14807 | [1–430] | 14856 | [1–309] | 14980 | [1–413] | 15029 | [1–216] |
| 14808 | [1–430] | 14857 | [1–323] | 14981 | [1–448] | 15030 | [1–381] |
| 14809 | [1–292] | 14858 | [1–64] | 14982 | [1–380] | 15031 | [1–82] |
| 14811 | [1–441] | 14859 | [1–85] | 14983 | [1–217] | 15032 | [1–432] |
| 14812 | [1–77] | 14860 | [1–71] | 14984 | [1–305] | 15033 | [1–302] |
| 14813 | [1–69] | 14861 | [1–470] | 14985 | [1–507] | 15034 | [1–422] |
| 14814 | [1–456] | 14862 | [1–103] | 14986 | [1–470] | 15035 | [1–492] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 14987 | [1–484] | 15036 | [1–284] | 15112 | [1–255],[322–391] | 15164 | [1–533] |
| 14988 | [1–363] | 15037 | [1–154] | 15113 | [1–406] | 15166 | [1–484] |
| 14989 | [1–53] | 15038 | [1–454] | 15114 | [1–539] | 15167 | [79–120],[266–291] |
| 14990 | [1–120] | 15039 | [1–338] | 15115 | [1–339] | 15168 | [1–294] |
| 14991 | [1–433] | 15040 | [1–431] | 15116 | [1–558] | 15169 | [1–107] |
| 14992 | [1–125] | 15041 | [1–90] | 15117 | [1–529] | 15170 | [1–478] |
| 14993 | [1–113] | 15042 | [1–503] | 15118 | [1–407] | 15171 | [1–50],[278–416] |
| 14994 | [1–54] | 15043 | [1–301] | 15119 | [1–495] | 15172 | [1–437] |
| 14995 | [1–487] | 15044 | [1–248] | 15120 | [1–478] | 15173 | [1–475] |
| 14996 | [1–92] | 15045 | [1–329] | 15121 | [1–483] | 15174 | [1–508] |
| 14997 | [1–447] | 15046 | [1–174] | 15122 | [1–525] | 15175 | [1–127] |
| 14998 | [1–387] | 15047 | [1–134] | 15123 | [1–478] | 15176 | [1–445] |
| 14999 | [1–166] | 15048 | [1–431] | 15177 | [1–64],[129–478] | 15225 | [1–484] |
| 15000 | [1–156] | 15049 | [1–84] | 15178 | [1–312] | 15226 | [1–86] |
| 15001 | [1–155] | 15050 | [1–465] | 15179 | [1–473] | 15227 | [1–417] |
| 15002 | [1–114] | 15051 | [1–284] | 15180 | [1–101] | 15228 | [1–523] |
| 15003 | [1–169] | 15052 | [37–474] | 15181 | [1–591] | 15229 | [1–511] |
| 15004 | [1–67] | 15053 | [1–548] | 15182 | [1–250] | 15230 | [1–348] |
| 15005 | [115–245] | 15054 | [1–349] | 15183 | [1–377] | 15231 | [1–517] |
| 15006 | [1–217] | 15055 | [1–310] | 15184 | [1–454] | 15232 | [1–300] |
| 15008 | [1–419] | 15056 | [1–113] | 15185 | [1–376] | 15233 | [1–398] |
| 15009 | [1–192] | 15057 | [1–74] | 15186 | [1–436] | 15234 | [1–389] |
| 15010 | [1–446] | 15058 | [1–464] | 15187 | [1–382] | 15235 | [1–285] |
| 15011 | [1–365] | 15059 | [1–468] | 15188 | [1–494] | 15236 | [1–74],[202–311] |
| 15012 | [39–442] | 15060 | [1–91] | 15189 | [1–521] | 15237 | [1–514] |
| 15013 | [1–580] | 15061 | [1–162] | 15190 | [1–503] | 15238 | [1–442] |
| 15014 | [37–481] | 15062 | [1–399] | 15191 | [1–433] | 15239 | [72–394] |
| 15015 | [1–408] | 15063 | [1–126] | 15192 | [1–567] | 15240 | [1–475] |
| 15016 | [1–434] | 15064 | [1–72] | 15193 | [35–92] | 15241 | [1–435] |
| 15017 | [1–162] | 15065 | [130–477] | 15194 | [1–264] | 15242 | [1–394] |
| 15018 | [1–83],[113–228] | 15066 | [1–70] | 15195 | [1–451] | 15243 | [191–276] |
| 15019 | [1–167] | 15067 | [1–445] | 15196 | [1–368] | 15244 | [1–601] |
| 15020 | [1–500] | 15068 | [1–281] | 15197 | [1–302] | 15245 | [1–506] |
| 15021 | [1–195] | 15069 | [1–436] | 15198 | [1–459] | 15246 | [1–521] |
| 15022 | [1–419] | 15071 | [1–478] | 15199 | [1–431] | 15247 | [1–468] |
| 15023 | [1–444] | 15072 | [1–425] | 15200 | [1–460] | 15248 | [1–345] |
| 15024 | [1–81] | 15073 | [1–75] | 15201 | [1–464] | 15249 | [1–293] |
| 15026 | [1–422] | 15074 | [1–406] | 15202 | [1–496] | 15251 | [1–577] |
| 15027 | [1–93] | 15075 | [1–177] | 15203 | [1–397] | 15252 | [1–425] |
| 15076 | [1–418] | 15124 | [1–309],[350–375] | 15204 | [1–394] | 15253 | [1–185] |
| 15077 | [1–349] | 15127 | [124–165] | 15205 | [1–436] | 15254 | [1–434] |
| 15078 | [1–75] | 15129 | [1–235] | 15206 | [1–435] | 15255 | [1–159] |
| 15079 | [1–177] | 15130 | [1–421] | 15207 | [138–278],[315–386] | 15256 | [1–501] |
| 15081 | [1–409] | 15131 | [1–617] | 15208 | [1–437] | 15257 | [1–493] |
| 15082 | [1–189] | 15132 | [1–540] | 15209 | [1–435] | 15258 | [1–454] |
| 15083 | [1–50],[81–321] | 15133 | [1–232] | 15210 | [1–435] | 15259 | [1–466] |
| 15084 | [1–77] | 15134 | [1–351] | 15211 | [1–474] | 15260 | [1–199] |
| 15085 | [1–436] | 15135 | [1–440] | 15212 | [1–509] | 15261 | [1–402] |
| 15086 | [1–255] | 15136 | [1–493] | 15213 | [1–490] | 15262 | [1–448] |
| 15087 | [1–132] | 15137 | [1–89],[122–348] | 15214 | [1–472] | 15263 | [1–492] |
| 15088 | [1–373] | 15138 | [1–399] | 15215 | [1–461] | 15264 | [1–381] |
| 15089 | [1–162] | 15139 | [1–225] | 15216 | [1–406] | 15266 | [187–332],[373–437] |
| 15090 | [1–79] | 15140 | [1–535] | 15217 | [1–469] | 15267 | [1–277] |
| 15091 | [1–98] | 15141 | [1–375] | 15218 | [1–460] | 15268 | [141–201] |
| 15092 | [1–78] | 15142 | [226–289] | 15219 | [1–519] | 15269 | [141–201] |
| 15093 | [1–342] | 15143 | [1–479] | 15220 | [1–337],[487–544] | 15270 | [1–180] |
| 15094 | [1–64],[290–445] | 15144 | [1–447] | 15221 | [1–311] | 15271 | [1–163] |
| 15095 | [1–351] | 15145 | [1–457] | 15223 | [1–544] | 15272 | [52–226] |
| 15096 | [1–371] | 15146 | [1–462] | 15224 | [1–494] | 15273 | [1–512] |
| 15097 | [1–278],[338–506] | 15147 | [1–311] | 15274 | [1–187] | 15323 | [137–179] |
| 15098 | [1–520] | 15148 | [1–486] | 15275 | [47–155] | 15324 | [1–450] |
| 15099 | [1–450] | 15149 | [1–437] | 15276 | [1–106] | 15325 | [1–573] |
| 15100 | [1–440] | 15150 | [1–570] | 15278 | [1–157] | 15326 | [1–381] |
| 15101 | [1–573] | 15151 | [1–464] | 15279 | [1–533] | 15327 | [1–490] |
| 15102 | [1–290] | 15152 | [1–107],[166–201] | 15280 | [1–459] | 15328 | [1–267],[414–504] |
| 15103 | [1–489] | 15154 | [1–484] | 15281 | [1–460] | 15329 | [1–315] |
| 15104 | [1–368] | 15155 | [1–896] | 15282 | [1–506] | 15330 | [1–407] |
| 15105 | [1–454] | 15156 | [1–475] | 15283 | [1–641] | 15331 | [1–167] |
| 15106 | [1–405] | 15158 | [1–172],[204–315] | 15284 | [1–295] | 15332 | [1–443] |
| 15107 | [1–406] | 15159 | [85–357] | 15285 | [1–445] | 15333 | [91–454] |
| 15108 | [1–337] | 15160 | [83–495] | 15286 | [1–292] | 15334 | [1–457] |
| 15109 | [1–568] | 15161 | [1–203] | 15287 | [1–378] | 15335 | [1–278] |
| 15110 | [122–314] | 15162 | [1–420] | 15288 | [1–503] | 15336 | [1–94],[140–361] |
| 15111 | [48–372] | 15163 | [227–436] | 15289 | [1–377] | 15337 | [1–186] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 15290 | [1–533] | 15338 | [1–489] | 15412 | [1–153],[232–348] | 15462 | [1–468] |
| 15291 | [40–404] | 15339 | [1–200] | 15413 | [1–144] | 15463 | [1–569] |
| 15292 | [1–230] | 15340 | [1–522] | 15414 | [1–445] | 15464 | [1–410] |
| 15293 | [1–534] | 15341 | [1–197] | 15415 | [1–362] | 15465 | [1–208] |
| 15294 | [1–142] | 15342 | [1–350] | 15416 | [1–221] | 15466 | [1–114],[231–291] |
| 15295 | [1–73] | 15343 | [1–121] | 15417 | [1–201],[333–471] | 15467 | [1–392] |
| 15296 | [40–412] | 15344 | [1–428] | 15468 | [1–393] | 15519 | [1–457] |
| 15297 | [1–254],[390–564] | 15345 | [1–482] | 15469 | [1–406] | 15520 | [1–202],[320–463] |
| 15298 | [1–172] | 15346 | [1–499] | 15470 | [1–208] | 15521 | [1–442] |
| 15299 | [1–491] | 15347 | [1–447] | 15471 | [1–376] | 15522 | [1–415] |
| 15300 | [1–416] | 15348 | [1–395] | 15472 | [1–446] | 15523 | [30–497] |
| 15301 | [1–412] | 15349 | [93–263] | 15473 | [1–461] | 15524 | [1–510] |
| 15302 | [1–53] | 15350 | [1–392] | 15474 | [1–466] | 15525 | [1–542] |
| 15303 | [1–784] | 15351 | [1–517] | 15475 | [1–447] | 15526 | [1–287] |
| 15304 | [1–488] | 15352 | [1–390] | 15476 | [1–478] | 15527 | [1–406] |
| 15305 | [1–445] | 15353 | [1–95],[135–258] | 15477 | [378–403] | 15528 | [48–352] |
| 15306 | [1–491] | 15354 | [1–485] | 15478 | [1–453] | 15529 | [1–447] |
| 15307 | [1–480] | 15355 | [1–444] | 15480 | [1–297] | 15530 | [1–454] |
| 15308 | [1–490] | 15356 | [1–500] | 15481 | [1–340] | 15531 | [112–290] |
| 15309 | [1–606] | 15357 | [1–426] | 15482 | [1–476] | 15532 | [1–507] |
| 15310 | [1–511] | 15358 | [1–415] | 15483 | [1–506] | 15533 | [1–272] |
| 15311 | [1–497] | 15359 | [1–413] | 15484 | [1–272],[331–500] | 15534 | [86–463] |
| 15313 | [137–210] | 15360 | [1–416] | 15485 | [1–470] | 15535 | [48–352] |
| 15314 | [113–195] | 15361 | [1–412] | 15486 | [1–512] | 15536 | [1–585] |
| 15315 | [1–490] | 15362 | [1–416] | 15487 | [1–444] | 15537 | [1–515] |
| 15316 | [1–168] | 15363 | [1–433] | 15488 | [1–355] | 15538 | [1–50] |
| 15317 | [113–194] | 15364 | [1–414] | 15489 | [1–352] | 15539 | [1–424] |
| 15318 | [114–166] | 15365 | [1–454] | 15490 | [1–607] | 15540 | [1–499] |
| 15319 | [113–173] | 15366 | [1–425] | 15491 | [1–553] | 15541 | [1–72] |
| 15320 | [113–180] | 15367 | [1–413] | 15492 | [1–465] | 15542 | [1–188] |
| 15321 | [114–215] | 15368 | [1–442] | 15493 | [1–497] | 15543 | [1–184] |
| 15322 | [1–178] | 15369 | [1–549] | 15494 | [1–488] | 15544 | [1–499] |
| 15370 | [1–487] | 15418 | [1–472] | 15495 | [1–485] | 15545 | [1–476] |
| 15371 | [1–501] | 15419 | [1–83],[134–414],[445–504],[544–593] | 15496 | [1–352] | 15546 | [1–358] |
| | | | | 15497 | [1–493] | 15547 | [1–501] |
| 15372 | [1–495] | 15420 | [1–116],[162–280] | 15498 | [1–489] | 15548 | [1–490] |
| 15373 | [1–136] | 15421 | [1–515] | 15499 | [1–477] | 15549 | [1–469] |
| 15374 | [1–420] | 15422 | [1–416] | 15500 | [1–436] | 15550 | [1–508] |
| 15375 | [1–526] | 15423 | [1–479] | 15501 | [1–432] | 15551 | [1–231] |
| 15376 | [1–496] | 15424 | [1–250],[295–462] | 15502 | [1–367] | 15552 | [1–456] |
| 15377 | [1–569] | 15425 | [1–490] | 15503 | [1–516] | 15553 | [1–162] |
| 15378 | [52–189] | 15426 | [1–801] | 15504 | [161–208] | 15554 | [1–242] |
| 15379 | [1–125] | 15427 | [1–216] | 15506 | [1–321],[357–401] | 15555 | [1–406] |
| 15380 | [1–506] | 15428 | [1–495] | 15507 | [1–417] | 15556 | [1–418] |
| 15381 | [1–487] | 15429 | [1–291] | 15508 | [1–383] | 15557 | [1–583] |
| 15382 | [1–413] | 15430 | [1–508] | 15509 | [1–360] | 15558 | [149–276] |
| 15383 | [1–39],[128–491] | 15431 | [1–88],[130–361] | 15510 | [1–261] | 15559 | [1–109] |
| 15385 | [1–71],[117–465] | 15432 | [1–314] | 15511 | [1–400] | 15560 | [1–501] |
| 15386 | [144–172] | 15433 | [1–488] | 15513 | [1–168],[377–444] | 15561 | [1–420] |
| 15387 | [1–274] | 15434 | [1–241] | 15514 | [1–44] | 15562 | [1–387] |
| 15388 | [32–543] | 15435 | [1–410] | 15515 | [1–479] | 15563 | [1–476] |
| 15389 | [33–313] | 15436 | [1–179] | 15516 | [1–343] | 15564 | [1–408] |
| 15390 | [1–417] | 15439 | [78–164] | 15517 | [1–180] | 15565 | [1–307] |
| 15391 | [1–442] | 15440 | [129–163] | 15566 | [1–96] | 15613 | [1–220] |
| 15392 | [1–128] | 15442 | [1–384] | 15567 | [1–476] | 15614 | [1–133],[235–485] |
| 15393 | [1–76],[122–224] | 15443 | [1–200] | 15568 | [121–217] | 15615 | [1–450] |
| 15394 | [1–444] | 15444 | [1–498] | 15569 | [1–407] | 15616 | [1–124] |
| 15395 | [1–482] | 15445 | [1–568] | 15570 | [1–524] | 15617 | [74–372] |
| 15396 | [1–472] | 15446 | [1–477] | 15571 | [49–420] | 15618 | [1–456] |
| 15397 | [1–490] | 15447 | [1–148] | 15572 | [1–577] | 15619 | [1–597] |
| 15398 | [1–431] | 15448 | [1–504] | 15573 | [1–171],[439–580] | 15620 | [1–162] |
| 15399 | [1–486] | 15449 | [1–402] | 15574 | [1–484] | 15621 | [391–462] |
| 15400 | [1–575] | 15450 | [1–483] | 15575 | [1–433] | 15622 | [1–348],[437–566] |
| 15401 | [1–490] | 15451 | [367–511] | 15576 | [1–98],[183–424] | 15623 | [1–504] |
| 15402 | [1–483] | 15452 | [1–377] | 15577 | [1–504] | 15624 | [1–336] |
| 15403 | [1–486] | 15453 | [1–114] | 15578 | [1–821] | 15625 | [1–47] |
| 15404 | [1–275] | 15454 | [1–411] | 15579 | [1–65],[132–446] | 15626 | [205–348] |
| 15405 | [1–216],[245–313] | 15455 | [1–153],[189–540] | 15580 | [1–488] | 15627 | [1–576] |
| 15406 | [1–48] | 15456 | [1–390] | 15581 | [1–389] | 15628 | [1–476] |
| 15407 | [1–295] | 15457 | [1–457] | 15582 | [1–126],[219–243],[347–389] | 15629 | [1–381] |
| 15408 | [1–221] | 15458 | [1–313] | 15583 | [1–519] | 15630 | [37–324] |
| 15409 | [1–166] | 15459 | [1–492] | 15584 | [1–331] | 15631 | [1–503] |
| 15410 | [1–506] | 15460 | [1–410] | 15585 | [57–252],[315–399] | 15632 | [1–63] |
| 15411 | [1–57] | 15461 | [1–378] | 15586 | [1–561] | 15633 | [1–396] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 15587 | [1–195] | 15634 | [1–403] | 15707 | [1–211] | 15792 | [1–99] |
| 15588 | [1–311] | 15635 | [1–507] | 15708 | [1–62] | 15793 | [1–82] |
| 15589 | [1–405] | 15636 | [1–508] | 15794 | [1–97] | 15993 | [1–203] |
| 15590 | [1–513] | 15637 | [1–372] | 15797 | [1–97] | 15994 | [1–197] |
| 15591 | [1–569] | 15638 | [1–419] | 15801 | [1–101] | 15995 | [1–151] |
| 15592 | [1–368] | 15639 | [1–505] | 15802 | [1–541] | 15996 | [1–446] |
| 15593 | [82–393] | 15640 | [1–224] | 15804 | [1–97] | 15997 | [1–151] |
| 15594 | [148–493] | 15641 | [1–510] | 15806 | [1–102] | 15998 | [1–150] |
| 15595 | [1–436] | 15642 | [298–324] | 15816 | [1–100] | 15999 | [1–151] |
| 15596 | [1–443] | 15643 | [1–418] | 15823 | [1–199] | 16000 | [1–153] |
| 15597 | [1–504] | 15644 | [37–78],[177–422] | 15834 | [1–80] | 16001 | [1–151] |
| 15598 | [1–410] | 15645 | [1–322] | 15837 | [1–97] | 16002 | [1–310] |
| 15599 | [1–362] | 15646 | [1–316] | 15843 | [1–98] | 16003 | [1–424] |
| 15600 | [180–446] | 15647 | [1–525] | 15844 | [1–448] | 16004 | [1–498] |
| 15601 | [1–31],[175–246] | 15648 | [1–240] | 15846 | [1–67] | 16005 | [1–369] |
| 15602 | [1–31],[175–246],[343–405] | 15649 | [1–241],[283–466] | 15853 | [1–100] | 16006 | [1–125] |
| 15603 | [1–544] | 15650 | [1–526] | 15855 | [1–151],[319–451] | 16007 | [1–272] |
| 15604 | [1–489] | 15651 | [1–425] | 15856 | [1–97] | 16008 | [1–359] |
| 15605 | [1–214] | 15652 | [60–373] | 15880 | [1–97] | 16009 | [1–292] |
| 15606 | [1–487] | 15654 | [60–371] | 15881 | [1–97] | 16010 | [1–362] |
| 15607 | [1–406] | 15655 | [60–370] | 15885 | [71–127] | 16011 | [1–281] |
| 15608 | [1–500] | 15656 | [60–370] | 15886 | [1–98] | 16012 | [1–329] |
| 15609 | [1–251] | 15657 | [1–467] | 15889 | [1–104] | 16013 | [1–336] |
| 15610 | [1–601] | 15658 | [1–130],[176–202],[320–397] | 15896 | [1–98] | 16014 | [1–306] |
| 15611 | [39–172],[276–317] | 15659 | [1–221] | 15902 | [1–102] | 16015 | [1–339] |
| 15612 | [1–481] | 15660 | [1–215] | 15904 | [1–86] | 16016 | [1–282] |
| 15661 | [1–308] | 15710 | [1–328] | 15908 | [1–101] | 16017 | [1–302] |
| 15663 | [1–207] | 15711 | [1–197],[315–458] | 15909 | [1–98] | 16018 | [1–327] |
| 15664 | [178–210] | 15713 | [1–150] | 15915 | [1–83] | 16019 | [1–359] |
| 15665 | [1–482] | 15714 | [1–489] | 15917 | [1–83] | 16020 | [1–305] |
| 15666 | [1–26] | 15715 | [1–456] | 15919 | [1–75] | 16021 | [1–296] |
| 15667 | [1–324] | 15716 | [1–222] | 15921 | [1–53] | 16022 | [1–297] |
| 15668 | [1–374] | 15717 | [1–409] | 15930 | [1–69] | 16023 | [1–279] |
| 15669 | [1–234] | 15718 | [439–551] | 15931 | [1–97] | 16024 | [1–326] |
| 15670 | [1–464] | 15719 | [1–393] | 15932 | [1–84] | 16025 | [1–458] |
| 15671 | [1–227] | 15720 | [100–178] | 15933 | [1–97] | 16026 | [1–347] |
| 15672 | [1–300] | 15721 | [1–420] | 15936 | [1–97] | 16027 | [1–324] |
| 15673 | [1–560] | 15722 | [103–410] | 15940 | [40–103] | 16028 | [1–315] |
| 15674 | [1–493] | 15723 | [1–26],[181–331] | 15945 | [1–101] | 16029 | [1–282] |
| 15675 | [1–505] | 15724 | [1–36],[191–341] | 15956 | [1–386] | 16030 | [1–307] |
| 15676 | [155–434] | 15725 | [1–178] | 15967 | [1–100] | 16031 | [1–332] |
| 15677 | [1–163] | 15726 | [1–340] | 15968 | [81–108] | 16032 | [1–333] |
| 15678 | [1–402] | 15727 | [1–448] | 15975 | [1–60] | 16033 | [1–297] |
| 15679 | [1–470] | 15728 | [1–184] | 15977 | [1–443] | 16034 | [1–281] |
| 15680 | [1–532] | 15729 | [154–184],[225–471] | 15982 | [1–97] | 16035 | [1–306] |
| 15681 | [1–471] | 15730 | [1–408] | 15986 | [1–98] | 16036 | [1–526] |
| 15682 | [1–122] | 15731 | [1–42],[106–423] | 15990 | [1–439] | 16037 | [1–279] |
| 15683 | [1–239] | 15732 | [1–246] | 15991 | [1–390] | 16038 | [1–335] |
| 15684 | [1–475] | 15733 | [1–179] | 15992 | [1–151] | 16039 | [1–276] |
| 15685 | [1–428],[459–532] | 15734 | [1–476] | 16040 | [1–318] | 16089 | [1–529] |
| 15686 | [1–419] | 15735 | [1–397] | 16041 | [1–338] | 16090 | [1–165] |
| 15687 | [1–428] | 15736 | [1–505] | 16042 | [1–365] | 16091 | [1–302] |
| 15688 | [1–438] | 15737 | [1–271] | 16043 | [1–280] | 16092 | [1–270] |
| 15689 | [204–349] | 15738 | [1–92],[149–263],[433–494] | 16044 | [1–334] | 16093 | [1–200],[318–378] |
| | | | | 16045 | [1–333] | 16094 | [1–572] |
| | | | | 16046 | [1–280] | 16095 | [148–188],[229–280] |
| | | | | 16047 | [1–175] | 16096 | [115–164],[247–288] |
| 15690 | [114–438] | 15739 | [1–423] | 16048 | [1–371] | 16097 | [1–51] |
| 15691 | [1–497] | 15741 | [1–259] | 16049 | [1–296] | 16098 | [1–556] |
| 15692 | [1–386] | 15742 | [1–323] | 16050 | [1–332] | 16099 | [1–65],[246–304] |
| 15693 | [1–587] | 15743 | [1–370] | 16051 | [1–336] | 16100 | [246–331] |
| 15694 | [1–201] | 15744 | [1–380] | 16052 | [1–329] | 16101 | [1–93] |
| 15695 | [1–296] | 15745 | [1–142],[434–503] | 16053 | [1–332] | 16102 | [1–321] |
| 15696 | [1–525] | 15746 | [1–459] | 16054 | [1–281] | 16103 | [1–470] |
| 15697 | [1–466] | 15747 | [70–134] | 16055 | [1–319] | 16104 | [1–569] |
| 15698 | [1–284] | 15748 | [1–623] | 16056 | [1–320] | 16105 | [1–351] |
| 15699 | [1–464] | 15749 | [107–257] | 16057 | [1–306] | 16106 | [1–517] |
| 15700 | [1–372] | 15754 | [1–101] | 16058 | [1–357] | 16107 | [41–83],[295–466] |
| 15701 | [1–118] | 15755 | [1–86] | 16059 | [1–281] | 16108 | [1–272] |
| 15702 | [1–502] | 15760 | [107–273] | 16060 | [1–281] | 16109 | [1–255] |
| 15703 | [1–482] | 15768 | [1–98] | 16061 | [1–335] | 16110 | [1–233] |
| 15704 | [1–503] | 15770 | [1–99] | 16062 | [1–110] | 16111 | [1–271] |
| 15705 | [1–503] | 15773 | [1–101] | 16063 | [96–167] | 16112 | [122–440] |
| 15706 | [1–401] | 15791 | [1–483] | 16064 | [99–450] | 16115 | [82–146] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 16065 | [1–227] | 16116 | [1–485] | 16239 | [1–87] | 16288 | [1–246] |
| 16066 | [1–405] | 16117 | [1–528] | 16240 | [1–122] | 16289 | [1–200] |
| 16067 | [1–516] | 16118 | [1–530] | 16241 | [1–317] | 16290 | [1–198] |
| 16068 | [1–234] | 16119 | [1–740] | 16242 | [1–97] | 16291 | [1–249] |
| 16069 | [1–404] | 16120 | [1–327] | 16243 | [1–502] | 16292 | [1–249] |
| 16070 | [1–399] | 16121 | [1–395] | 16244 | [1–401] | 16293 | [1–222] |
| 16071 | [1–26],[194–482] | 16122 | [1–281] | 16245 | [1–496] | 16294 | [1–259] |
| 16073 | [1–75],[131–500] | 16123 | [1–45],[111–272] | 16246 | [1–337] | 16295 | [1–217] |
| 16074 | [125–276] | 16124 | [1–512] | 16248 | [1–57],[88–192],[253–300], [355–514],[561–631] | 16296 | [1–363] |
| 16075 | [1–470] | 16125 | [1–313] | | | 16297 | [1–575] |
| 16076 | [1–219],[303–328] | 16126 | [1–418] | 16249 | [1–63] | 16298 | [1–319] |
| 16077 | [1–191] | 16127 | [1–153],[187–293] | 16250 | [1–56] | 16299 | [1–491] |
| 16078 | [1–357] | 16128 | [1–153],[187–326] | 16251 | [1–63] | 16300 | [1–474] |
| 16079 | [1–430] | 16129 | [1–153],[187–319] | 16252 | [1–203],[321–445] | 16301 | [1–449] |
| 16080 | [1–265] | 16130 | [1–153],[187–301] | 16253 | [1–63] | 16302 | [1–585] |
| 16081 | [1–415] | 16131 | [1–153],[187–323] | 16255 | [1–56] | 16303 | [1–348] |
| 16082 | [1–415] | 16132 | [1–153],[187–306] | 16256 | [1–56] | 16304 | [1–114] |
| 16084 | [1–52] | 16133 | [1–153],[187–310] | 16257 | [1–56] | 16305 | [1–300] |
| 16085 | [1–388] | 16134 | [1–153],[187–310] | 16258 | [1–369] | 16306 | [1–297] |
| 16086 | [1–376] | 16135 | [1–153],[187–341] | 16259 | [1–57] | 16307 | [1–495] |
| 16087 | [1–499] | 16136 | [1–153],[187–347] | 16260 | [1–56] | 16308 | [1–457] |
| 16088 | [1–422] | 16137 | [1–153],[187–348] | 16261 | [1–64] | 16309 | [1–176] |
| 16138 | [1–153],[187–351] | 16186 | [1–431] | 16263 | [1–322] | 16311 | [1–655] |
| 16139 | [1–153],[187–300] | 16187 | [1–144] | 16264 | [61–226] | 16312 | [254–542] |
| 16140 | [1–153],[187–351] | 16188 | [1–407] | 16265 | [1–490] | 16313 | [254–420] |
| 16141 | [1–153],[187–327] | 16190 | [1–96],[263–458] | 16266 | [1–353] | 16314 | [1–415] |
| 16142 | [1–322] | 16191 | [1–477] | 16267 | [1–461] | 16317 | [161–231] |
| 16143 | [1–153],[187–328] | 16192 | [1–488] | 16268 | [1–451] | 16320 | [1–83],[162–242] |
| 16144 | [1–153],[187–328] | 16193 | [1–211] | 16269 | [1–430] | 16324 | [161–242] |
| 16145 | [1–153],[187–354] | 16194 | [1–132] | 16270 | [155–408] | 16325 | [1–155],[288–413] |
| 16146 | [1–479] | 16195 | [1–447] | 16271 | [155–508] | 16326 | [1–389] |
| 16147 | [1–410] | 16196 | [1–493] | 16272 | [169–281] | 16327 | [1–587] |
| 16148 | [1–183] | 16197 | [1–369] | 16273 | [1–450] | 16328 | [1–559] |
| 16149 | [1–393] | 16198 | [1–441] | 16274 | [1–337] | 16329 | [1–489] |
| 16150 | [1–434] | 16199 | [1–478] | 16275 | [1–127] | 16330 | [1–482] |
| 16151 | [1–353] | 16200 | [1–435] | 16276 | [112–459] | 16331 | [1–396] |
| 16152 | [1–110] | 16201 | [1–451] | 16277 | [1–412] | 16332 | [1–504] |
| 16153 | [1–559] | 16202 | [1–492] | 16278 | [1–454] | 16333 | [1–146] |
| 16154 | [1–193] | 16203 | [1–364] | 16279 | [1–459] | 16334 | [1–487] |
| 16155 | [1–498] | 16204 | [1–146] | 16280 | [1–422] | 16335 | [1–493] |
| 16156 | [1–390] | 16205 | [1–467] | 16281 | [1–268] | 16336 | [1–442] |
| 16157 | [1–512] | 16206 | [1–463] | 16282 | [1–506] | 16337 | [1–513] |
| 16158 | [1–476] | 16207 | [1–430] | 16338 | [1–205] | 16387 | [1–391] |
| 16159 | [1–523] | 16208 | [1–444] | 16339 | [1–212] | 16388 | [1–490] |
| 16160 | [1–157] | 16209 | [1–453] | 16340 | [1–241] | 16389 | [80–161] |
| 16161 | [1–201] | 16210 | [1–204] | 16341 | [1–216] | 16390 | [1–440] |
| 16162 | [1–202] | 16211 | [1–393] | 16342 | [1–210] | 16391 | [1–456] |
| 16163 | [1–201] | 16212 | [1–343] | 16343 | [1–219] | 16392 | [1–407] |
| 16164 | [1–201] | 16213 | [1–440] | 16344 | [1–229] | 16393 | [1–406] |
| 16165 | [1–201] | 16214 | [1–478] | 16345 | [1–221] | 16394 | [1–376] |
| 16166 | [1–200] | 16215 | [1–478] | 16346 | [1–239] | 16395 | [1–449] |
| 16167 | [1–202] | 16216 | [1–363] | 16347 | [1–314] | 16396 | [1–141],[217–331], [560–611] |
| 16168 | [1–527] | 16217 | [1–322] | | | | |
| 16170 | [1–409] | 16218 | [1–359] | 16348 | [1–499] | 16397 | [262–472] |
| 16171 | [1–492] | 16219 | [1–348] | 16349 | [1–306] | 16398 | [1–419] |
| 16172 | [1–395] | 16220 | [1–536] | 16350 | [1–447] | 16399 | [1–60],[116–508] |
| 16173 | [1–479] | 16221 | [1–291] | 16351 | [1–304] | 16400 | [1–433] |
| 16174 | [1–333] | 16222 | [1–493] | 16352 | [1–64],[97–416] | 16401 | [1–848] |
| 16175 | [236–342] | 16223 | [230–313] | 16353 | [1–53],[146–289] | 16402 | [1–257] |
| 16176 | [1–81],[229–316] | 16224 | [1–585] | 16354 | [104–139],[253–312], [418–447] | 16403 | [1–421] |
| 16177 | [1–363] | 16225 | [1–112],[427–498] | | | | |
| 16178 | [1–531] | 16226 | [1–184],[220–299] | 16355 | [104–139],[253–436] | 16404 | [1–496] |
| 16179 | [1–403] | 16227 | [1–184],[220–300] | 16356 | [1–534] | 16405 | [1–432] |
| 16180 | [1–494] | 16228 | [1–409] | 16357 | [1–304] | 16407 | [1–180] |
| 16181 | [1–396] | 16229 | [1–416] | 16358 | [1–473] | 16408 | [1–204] |
| 16182 | [1–547] | 16230 | [1–516] | 16359 | [1–494] | 16409 | [1–222] |
| 16183 | [1–99],[288–481] | 16231 | [1–483] | 16360 | [1–432] | 16410 | [1–569] |
| 16184 | [1–409] | 16232 | [1–385] | 16361 | [1–281] | 16411 | [1–526] |
| 16185 | [75–413] | 16233 | [1–161] | 16362 | [1–97] | 16412 | [1–372] |
| 16234 | [1–182] | 16283 | [1–210] | 16363 | [1–506] | 16413 | [1–457] |
| 16235 | [78–312] | 16284 | [1–47],[80–441] | 16364 | [1–457] | 16414 | [1–423] |
| 16236 | [1–598] | 16285 | [1–492] | 16365 | [1–438] | 16415 | [1–402] |
| 16237 | [1–249] | 16286 | [1–202] | 16366 | [1–290] | 16416 | [1–442] |
| 16238 | [1–124] | 16287 | [1–512] | 16367 | [1–315] | 16417 | [1–442] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 16368 | [1–391] | 16418 | [1–395] | 16544 | [1–410] | 16592 | [1–506] |
| 16369 | [116–267],[365–452] | 16419 | [1–400] | 16545 | [1–173] | 16593 | [1–187] |
| 16370 | [1–478] | 16420 | [1–403] | 16546 | [1–191] | 16594 | [1–62] |
| 16371 | [1–406] | 16421 | [1–371] | 16547 | [1–168] | 16595 | [1–510] |
| 16372 | [1–449],[486–542] | 16422 | [1–392] | 16548 | [1–170] | 16596 | [1–422] |
| 16373 | [1–515] | 16423 | [1–464] | 16549 | [1–442] | 16597 | [1–574] |
| 16374 | [1–495] | 16424 | [1–413] | 16550 | [1–235] | 16598 | [1–355] |
| 16375 | [1–436] | 16425 | [1–193] | 16551 | [1–201] | 16599 | [1–404] |
| 16376 | [1–491] | 16426 | [1–317] | 16552 | [1–192] | 16600 | [1–110] |
| 16377 | [1–83],[132–364] | 16427 | [1–504] | 16553 | [1–184] | 16601 | [1–487] |
| 16380 | [1–400] | 16428 | [1–317] | 16554 | [1–44],[89–539] | 16602 | [1–275] |
| 16381 | [1–167] | 16429 | [1–295] | 16555 | [1–179] | 16603 | [1–343] |
| 16382 | [1–82] | 16430 | [1–319] | 16556 | [1–231] | 16604 | [1–468] |
| 16383 | [1–497] | 16431 | [1–294] | 16557 | [1–234] | 16605 | [1–72] |
| 16384 | [1–472] | 16432 | [1–293] | 16558 | [1–182] | 16606 | [1–399] |
| 16385 | [1–72] | 16433 | [1–292] | 16559 | [1–233] | 16607 | [1–352] |
| 16386 | [1–490] | 16434 | [1–334] | 16560 | [1–472] | 16608 | [1–348] |
| 16435 | [1–298] | 16484 | [1–441] | 16561 | [1–903] | 16609 | [1–377] |
| 16436 | [1–139] | 16485 | [1–108] | 16562 | [1–436] | 16610 | [1–224] |
| 16437 | [1–379] | 16486 | [1–94],[125–154] | 16563 | [1–438] | 16611 | [1–276] |
| 16438 | [1–384] | 16487 | [1–92] | 16564 | [1–165] | 16612 | [1–440] |
| 16439 | [1–505] | 16488 | [1–568] | 16565 | [1–222] | 16613 | [1–467] |
| 16440 | [1–424] | 16489 | [1–297] | 16566 | [1–381] | 16614 | [1–83],[145–201],[232–285],[346–523] |
| 16441 | [1–474] | 16490 | [1–419] | | | | |
| 16442 | [1–278] | 16491 | [1–297] | 16567 | [1–112] | 16615 | [1–110],[172–228],[259–439] |
| 16444 | [1–492] | 16492 | [1–298] | | | | |
| 16445 | [88–388] | 16493 | [1–189] | 16568 | [1–324],[375–606] | 16616 | [1–434] |
| 16446 | [1–485] | 16494 | [1–296] | 16569 | [1–161] | 16617 | [1–298] |
| 16447 | [1–155],[203–363] | 16495 | [1–297] | 16570 | [1–186],[219–469] | 16618 | [1–469] |
| 16448 | [1–489] | 16496 | [1–298] | 16571 | [134–333],[393–445] | 16619 | [1–111],[141–452] |
| 16449 | [1–413],[446–486] | 16497 | [1–513] | 16572 | [1–461] | 16620 | [1–116],[146–326] |
| 16450 | [1–71],[122–274] | 16498 | [1–513] | 16573 | [178–222] | 16621 | [1–96] |
| 16451 | [56–93] | 16499 | [1–503] | 16574 | [1–495] | 16622 | [248–431] |
| 16452 | [192–355] | 16500 | [1–503] | 16575 | [1–471] | 16623 | [1–60] |
| 16453 | [122–175] | 16501 | [1–503] | 16576 | [34–300] | 16624 | [1–458] |
| 16454 | [122–203] | 16502 | [1–429] | 16577 | [34–403] | 16625 | [1–488] |
| 16455 | [48–115] | 16503 | [1–61] | 16578 | [1–458] | 16626 | [1–473] |
| 16456 | [164–192] | 16504 | [1–305] | 16580 | [1–127],[219–342] | 16627 | [1–490] |
| 16457 | [48–115] | 16505 | [1–439] | 16581 | [1–256],[295–356] | 16628 | [1–334] |
| 16458 | [48–115],[148–204] | 16506 | [43–484] | 16629 | [71–325] | 16676 | [1–398],[428–609] |
| 16459 | [1–166],[251–374] | 16507 | [1–555] | 16630 | [1–381] | 16677 | [1–387] |
| 16460 | [1–198],[332–486] | 16508 | [1–477] | 16631 | [1–340] | 16678 | [1–394] |
| 16461 | [1–521] | 16509 | [1–362] | 16632 | [192–239] | 16679 | [1–216] |
| 16462 | [1–495] | 16510 | [1–169] | 16633 | [1–259] | 16680 | [1–113],[230–290] |
| 16463 | [372–454] | 16511 | [58–509] | 16634 | [1–182] | 16681 | [1–531] |
| 16464 | [1–473] | 16512 | [1–421] | 16635 | [1–399] | 16682 | [1–571] |
| 16465 | [1–441] | 16514 | [1–193] | 16636 | [1–129],[320–460] | 16684 | [229–361] |
| 16466 | [1–489] | 16515 | [1–198] | 16637 | [1–443] | 16685 | [85–112] |
| 16468 | [49–131],[180–271] | 16516 | [1–197] | 16638 | [330–402] | 16686 | [85–146] |
| 16469 | [69–160] | 16517 | [1–403] | 16639 | [1–367] | 16688 | [85–145] |
| 16470 | [1–392] | 16518 | [52–446] | 16640 | [1–361] | 16689 | [85–120] |
| 16471 | [1–486] | 16519 | [1–382] | 16641 | [1–482] | 16690 | [84–118] |
| 16472 | [1–113],[230–290] | 16520 | [1–465] | 16642 | [1–464] | 16691 | [85–145] |
| 16473 | [1–462] | 16521 | [1–304] | 16643 | [1–67] | 16692 | [83–164] |
| 16474 | [1–415] | 16522 | [1–126] | 16644 | [1–348] | 16694 | [85–111] |
| 16475 | [1–448] | 16524 | [1–374] | 16645 | [1–414] | 16695 | [85–146] |
| 16476 | [1–124] | 16525 | [1–413] | 16646 | [1–293],[446–488] | 16696 | [81–127] |
| 16477 | [1–98],[129–162] | 16526 | [1–496] | 16647 | [1–373] | 16697 | [1–394] |
| 16478 | [1–119] | 16528 | [1–59],[120–439] | 16648 | [1–466] | 16698 | [1–472] |
| 16479 | [1–95] | 16529 | [1–430] | 16649 | [1–359] | 16699 | [81–498] |
| 16480 | [1–104] | 16530 | [1–59],[120–470] | 16650 | [1–381] | 16700 | [1–513] |
| 16481 | [1–134] | 16531 | [1–59],[120–503] | 16651 | [1–516] | 16701 | [1–155] |
| 16482 | [1–137] | 16532 | [1–350] | 16652 | [1–436] | 16702 | [1–498] |
| 16483 | [1–154] | 16533 | [1–422] | 16653 | [1–518] | 16703 | [1–241] |
| 16534 | [1–159] | 16582 | [1–382] | 16654 | [342–375] | 16704 | [1–481] |
| 16535 | [1–193] | 16583 | [315–488] | 16655 | [1–367] | 16705 | [1–366] |
| 16536 | [1–213] | 16584 | [1–130] | 16656 | [1–430] | 16706 | [1–189],[257–330],[379–408] |
| 16537 | [1–194] | 16585 | [1–447] | | | | |
| 16538 | [1–185] | 16586 | [57–157] | 16657 | [1–545],[576–877] | 16707 | [1–369] |
| 16539 | [1–187] | 16587 | [1–365] | 16658 | [1–121] | 16708 | [93–326] |
| 16540 | [1–190] | 16588 | [1–381] | 16659 | [1–457] | 16709 | [1–162],[238–484] |
| 16541 | [1–165] | 16589 | [1–499] | 16660 | [1–188],[314–463] | 16710 | [1–189],[257–413] |
| 16542 | [1–188] | 16590 | [1–421] | 16661 | [1–475] | 16711 | [1–189],[257–430] |
| 16543 | [1–168] | 16591 | [1–515] | 16662 | [1–348],[419–452] | 16712 | [379–425] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 16663 | [1–475] | 16713 | [1–160] | 16835 | [1–291] | 16885 | [1–514] |
| 16664 | [1–285] | 16714 | [1–329],[378–407] | 16836 | [1–267] | 16886 | [1–470] |
| 16665 | [1–375] | 16715 | [1–443] | 16837 | [1–459] | 16887 | [1–602] |
| 16666 | [1–488] | 16716 | [1–496] | 16839 | [1–526] | 16888 | [1–85] |
| 16667 | [1–528] | 16717 | [141–176] | 16840 | [1–515] | 16889 | [108–342] |
| 16668 | [1–472] | 16718 | [1–527] | 16841 | [1–343] | 16890 | [1–431] |
| 16669 | [1–435] | 16719 | [1–303] | 16842 | [1–460] | 16891 | [1–69] |
| 16670 | [1–234],[330–550] | 16720 | [1–488] | 16843 | [1–200],[318–458] | 16892 | [171–298] |
| 16671 | [1–519] | 16721 | [52–152] | 16844 | [1–417] | 16893 | [45–379] |
| 16672 | [1–479] | 16722 | [1–39],[70–214] | 16845 | [1–501] | 16894 | [1–513] |
| 16673 | [1–529] | 16723 | [1–485] | 16846 | [1–471] | 16895 | [1–496] |
| 16674 | [1–527] | 16724 | [1–458] | 16847 | [1–197] | 16896 | [1–561] |
| 16675 | [1–395] | 16725 | [1–373] | 16848 | [1–432] | 16897 | [1–347] |
| 16726 | [1–581] | 16774 | [1–256] | 16849 | [1–495] | 16898 | [36–540] |
| 16727 | [1–339] | 16775 | [1–359] | 16850 | [1–429] | 16899 | [1–473] |
| 16728 | [1–492] | 16776 | [1–132] | 16851 | [1–843] | 16900 | [1–681] |
| 16729 | [1–44],[291–381] | 16777 | [1–253] | 16852 | [1–449] | 16901 | [1–368] |
| 16730 | [1–76],[231–344] | 16778 | [1–135] | 16854 | [202–323],[384–409] | 16902 | [1–50],[89–576] |
| 16731 | [1–176] | 16779 | [1–185] | 16855 | [1–517] | 16903 | [1–366] |
| 16732 | [1–55],[176–433] | 16780 | [1–134] | 16856 | [1–275] | 16904 | [1–286],[316–397],[431–456] |
| 16733 | [1–316] | 16781 | [1–157] | | | | |
| 16734 | [1–130] | 16782 | [1–129] | 16857 | [1–478] | 16905 | [1–527] |
| 16735 | [1–331] | 16783 | [1–140] | 16858 | [196–418] | 16906 | [1–431] |
| 16736 | [1–298] | 16784 | [1–190] | 16859 | [1–436] | 16907 | [1–451] |
| 16737 | [1–527] | 16785 | [1–139] | 16860 | [1–419] | 16908 | [1–449] |
| 16738 | [1–128] | 16786 | [1–140] | 16861 | [43–167],[287–445] | 16909 | [1–349] |
| 16739 | [1–82] | 16787 | [1–36],[129–213] | 16862 | [1–284] | 16910 | [1–40] |
| 16740 | [1–85],[118–146] | 16788 | [1–26],[128–157] | 16863 | [1–430] | 16911 | [1–435] |
| 16741 | [1–292] | 16789 | [1–131],[322–455] | 16864 | [1–57],[255–436] | 16912 | [1–472] |
| 16742 | [1–565] | 16790 | [1–577],[608–639] | 16865 | [1–400] | 16913 | [1–439] |
| 16743 | [1–342] | 16791 | [1–77],[112–280] | 16866 | [1–302] | 16914 | [1–449] |
| 16744 | [1–432] | 16792 | [1–71],[324–382] | 16868 | [1–122] | 16915 | [1–510] |
| 16745 | [1–536] | 16793 | [1–78],[113–281] | 16869 | [1–156] | 16916 | [1–193] |
| 16746 | [1–402] | 16794 | [1–482] | 16870 | [1–168] | 16917 | [1–503] |
| 16747 | [1–461] | 16795 | [1–429] | 16918 | [1–445] | 16981 | [215–242] |
| 16748 | [1–474] | 16796 | [1–423] | 16919 | [1–505] | 16982 | [1–236] |
| 16749 | [1–503] | 16797 | [1–426] | 16920 | [292–478] | 16983 | [1–277] |
| 16750 | [1–530] | 16798 | [1–108] | 16921 | [1–491] | 16985 | [1–162] |
| 16751 | [77–625],[753–794] | 16799 | [1–176] | 16922 | [1–526] | 16986 | [216–242] |
| 16752 | [78–350] | 16800 | [1–134] | 16923 | [1–531] | 16987 | [215–253] |
| 16753 | [1–490] | 16801 | [1–175] | 16924 | [1–154] | 16988 | [1–74],[213–256] |
| 16754 | [1–488] | 16802 | [1–175] | 16925 | [1–219] | 16989 | [215–283] |
| 16755 | [49–431] | 16803 | [1–174] | 16926 | [1–235] | 16990 | [216–241] |
| 16757 | [1–248] | 16804 | [1–175] | 16927 | [1–224] | 16991 | [215–254] |
| 16758 | [38–222] | 16805 | [1–214] | 16929 | [1–97] | 16992 | [1–161] |
| 16759 | [1–180] | 16806 | [1–241] | 16930 | [1–75] | 16993 | [216–242] |
| 16760 | [1–191] | 16807 | [1–175] | 16931 | [1–75] | 16996 | [1–237] |
| 16761 | [1–525] | 16808 | [1–447] | 16932 | [1–74],[215–272] | 16997 | [216–242] |
| 16762 | [1–514] | 16809 | [100–457] | 16933 | [1–266] | 16998 | [1–237] |
| 16763 | [1–474] | 16810 | [1–69],[307–400] | 16934 | [1–23]] | 17000 | [1–372] |
| 16764 | [1–247],[325–498] | 16811 | [1–528] | 16935 | [1–236] | 17003 | [1–235] |
| 16765 | [1–330] | 16812 | [1–190] | 16936 | [1–74],[213–269] | 17004 | [1–97] |
| 16766 | [185–233] | 16813 | [1–266] | 16937 | [1–75] | 17005 | [216–241] |
| 16767 | [427–470] | 16814 | [1–214] | 16939 | [1–162] | 17008 | [216–243] |
| 16768 | [1–304] | 16815 | [1–55],[91–574] | 16940 | [1–79] | 17010 | [213–241] |
| 16769 | [50–464] | 16816 | [1–34],[171–506] | 16941 | [1–236] | 17011 | [93–474] |
| 16770 | [1–358] | 16817 | [1–455] | 16942 | [1–75],[216–243] | 17012 | [1–97] |
| 16771 | [1–412] | 16818 | [242–290] | 16943 | [1–236] | 17013 | [1–162] |
| 16772 | [1–542] | 16819 | [151–270] | 16945 | [1–162] | 17014 | [1–236] |
| 16773 | [1–389] | 16820 | [1–524] | 16946 | [215–253] | 17015 | [216–242] |
| 16821 | [1–559] | 16871 | [1–182] | 16947 | [1–528] | 17016 | [215–240] |
| 16822 | [1–504] | 16872 | [1–179] | 16948 | [1–153],[221–425] | 17018 | [1–75] |
| 16823 | [1–73],[145–531] | 16873 | [1–233] | 16950 | [215–250] | 17019 | [215–254] |
| 16824 | [1–371] | 16874 | [1–461] | 16952 | [216–242] | 17020 | [1–75] |
| 16825 | [1–405] | 16875 | [1–122] | 16953 | [1–161] | 17022 | [215–253] |
| 16826 | [1–448] | 16876 | [35–183] | 16954 | [215–253] | 17023 | [1–237] |
| 16827 | [1–417] | 16877 | [1–454] | 16955 | [1–162] | 17025 | [1–75] |
| 16828 | [316–499] | 16878 | [1–583] | 16958 | [216–242] | 17027 | [1–161] |
| 16829 | [1–476] | 16879 | [1–209] | 16959 | [1–93],[209–387] | 17029 | [1–162] |
| 16830 | [158–450] | 16880 | [1–25],[86–548] | 16960 | [1–74] | 17030 | [216–242] |
| 16831 | [1–310] | 16881 | [1–602] | 16962 | [1–232] | 17032 | [1–491] |
| 16832 | [1–349] | 16882 | [1–424] | 16965 | [208–293] | 17033 | [215–254] |
| 16833 | [1–140] | 16883 | [1–313] | 16969 | [1–160] | 17034 | [1–236] |
| 16834 | [1–141] | 16884 | [1–293],[438–482] | 16970 | [1–162] | 17035 | [1–162] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 16972 | [216–243] | 17036 | [1–161] | 17173 | [1–407] | 17220 | [1–158],[198–535] |
| 16973 | [1–161],[215–241] | 17039 | [216–247] | 17174 | [1–347] | 17221 | [1–565] |
| 16974 | [215–244] | 17040 | [1–74] | 17175 | [223–477] | 17222 | [1–571] |
| 16975 | [216–243] | 17042 | [216–242] | 17176 | [1–853] | 17223 | [1–362] |
| 16976 | [1–75] | 17043 | [1–75],[158–487] | 17177 | [41–498] | 17225 | [1–285] |
| 16978 | [215–253] | 17044 | [1–220] | 17178 | [117–142] | 17226 | [1–462] |
| 16980 | [1–234] | 17046 | [216–242] | 17179 | [1–571] | 17227 | [1–126] |
| 17047 | [1–161],[215–241] | 17106 | [1–92] | 17180 | [1–165] | 17228 | [1–377] |
| 17048 | [30–161],[214–253] | 17107 | [1–246],[326–477] | 17181 | [1–433] | 17229 | [1–65],[204–382] |
| 17049 | [215–270] | 17108 | [1–411] | 17182 | [1–159] | 17232 | [1–391] |
| 17051 | [1–161] | 17109 | [1–332] | 17183 | [1–109] | 17233 | [1–387] |
| 17052 | [1–161] | 17110 | [1–139] | 17184 | [1–137] | 17235 | [1–422] |
| 17053 | [216–245] | 17111 | [229–402] | 17185 | [1–110] | 17236 | [1–286] |
| 17054 | [1–500] | 17112 | [1–449] | 17186 | [1–354] | 17237 | [1–463] |
| 17055 | [1–75] | 17113 | [1–510] | 17187 | [1–339] | 17238 | [1–134],[308–415] |
| 17056 | [215–253] | 17114 | [71–143],[340–389] | 17188 | [1–323] | 17239 | [1–276] |
| 17057 | [1–76] | 17115 | [1–458] | 17189 | [1–491] | 17240 | [1–324] |
| 17062 | [1–174] | 17116 | [1–136] | 17190 | [1–98],[278–375] | 17241 | [35–455],[493–523] |
| 17063 | [215–253] | 17117 | [1–91] | 17191 | [1–450] | 17242 | [1–329] |
| 17064 | [1–256] | 17118 | [1–147],[226–507] | 17192 | [1–527] | 17243 | [1–510] |
| 17066 | [216–242] | 17119 | [1–426] | 17193 | [1–443] | 17244 | [1–468] |
| 17067 | [217–261] | 17120 | [1–421] | 17194 | [1–519] | 17245 | [94–194],[250–424] |
| 17069 | [1–236] | 17121 | [1–255],[370–471] | 17195 | [1–261] | 17246 | [1–318] |
| 17070 | [1–236] | 17122 | [1–452] | 17196 | [1–348] | 17247 | [261–311] |
| 17071 | [1–174],[217–241] | 17123 | [149–312] | 17197 | [1–565] | 17248 | [1–384] |
| 17072 | [1–235] | 17124 | [1–426] | 17198 | [1–54] | 17249 | [1–457] |
| 17073 | [216–242] | 17125 | [1–562] | 17199 | [1–430] | 17250 | [32–291] |
| 17074 | [215–253] | 17126 | [120–410] | 17251 | [1–274] | 17299 | [1–438] |
| 17076 | [1–487] | 17127 | [1–505] | 17252 | [1–164],[206–443] | 17300 | [1–325] |
| 17077 | [215–253] | 17128 | [1–379] | 17253 | [1–560] | 17301 | [1–130] |
| 17078 | [1–235] | 17129 | [1–415] | 17254 | [1–433] | 17302 | [1–209] |
| 17081 | [1–236] | 17130 | [1–547] | 17255 | [73–194] | 17303 | [1–235] |
| 17084 | [1–418] | 17131 | [1–470] | 17256 | [1–722] | 17304 | [1–348] |
| 17085 | [1–249] | 17132 | [1–520] | 17257 | [1–447] | 17305 | [1–456] |
| 17086 | [1–513] | 17133 | [1–371] | 17258 | [1–479] | 17306 | [1–442] |
| 17087 | [1–43],[94–223] | 17134 | [1–510] | 17259 | [1–34] | 17307 | [1–235],[468–499] |
| 17088 | [1–308] | 17135 | [1–476] | 17260 | [1–480] | 17308 | [1–137] |
| 17089 | [1–487] | 17136 | [1–474] | 17262 | [1–536] | 17309 | [51–149],[301–478] |
| 17090 | [1–506] | 17137 | [1–447] | 17263 | [1–466] | 17310 | [1–124] |
| 17091 | [1–214] | 17138 | [1–346] | 17264 | [1–212],[299–454] | 17313 | [1–181] |
| 17092 | [1–256] | 17139 | [1–503] | 17265 | [1–489] | 17314 | [1–471] |
| 17093 | [1–508] | 17140 | [1–374] | 17266 | [1–472] | 17315 | [1–412] |
| 17094 | [1–414] | 17141 | [1–123] | 17267 | [1–544] | 17316 | [1–520] |
| 17095 | [1–235] | 17142 | [1–75],[183–258] | 17268 | [1–384],[415–443],[478–555] | 17318 | [1–84] |
| 17096 | [1–261] | 17143 | [1–169] | | | | |
| 17097 | [1–83] | 17144 | [1–133] | 17269 | [1–586] | 17319 | [1–526] |
| 17098 | [1–72] | 17145 | [1–144] | 17270 | [116–464] | 17320 | [1–250] |
| 17099 | [1–449] | 17146 | [1–149] | 17271 | [222–294] | 17321 | [87–490] |
| 17100 | [1–710] | 17147 | [1–147] | 17272 | [1–366] | 17322 | [90–253] |
| 17101 | [1–482] | 17148 | [1–144] | 17273 | [1–199] | 17323 | [1–425] |
| 17102 | [175–534] | 17149 | [1–146] | 17274 | [1–321] | 17324 | [1–498] |
| 17103 | [1–434] | 17150 | [1–505] | 17275 | [1–473] | 17325 | [1–517] |
| 17104 | [1–442] | 17151 | [1–149] | 17276 | [1–222] | 17326 | [1–396] |
| 17105 | [1–542] | 17152 | [1–114] | 17277 | [1–191] | 17327 | [1–542] |
| 17153 | [65–269] | 17200 | [1–248] | 17278 | [1–486] | 17328 | [1–77],[111–207],[247–441],[549–595] |
| 17154 | [1–498] | 17201 | [1–401] | | | | |
| 17155 | [1–449] | 17202 | [1–364] | 17279 | [1–421] | 17329 | [1–541] |
| 17156 | [1–43],[129–356] | 17203 | [1–414] | 17280 | [1–524] | 17330 | [1–334],[473–683],[917–1137],[1267–1549] |
| 17157 | [1–515] | 17204 | [1–398] | | | | |
| 17158 | [1–576] | 17205 | [1–369] | 17281 | [1–448] | | |
| 17159 | [1–441] | 17206 | [1–465] | 17282 | [1–223] | 17331 | [1–346] |
| 17160 | [75–502] | 17207 | [1–580] | 17283 | [1–468] | 17332 | [1–492] |
| 17161 | [293–417] | 17208 | [1–450] | 17284 | [1–499] | 17333 | [1–447] |
| 17162 | [1–416] | 17209 | [1–510] | 17285 | [1–512] | 17334 | [1–499] |
| 17163 | [1–520] | 17210 | [1–478] | 17286 | [1–53] | 17335 | [1–437] |
| 17164 | [192–501] | 17211 | [1–462] | 17287 | [1–369] | 17336 | [1–411] |
| 17165 | [1–147],[226–474] | 17212 | [103–447] | 17288 | [1–510] | 17337 | [1–447] |
| 17166 | [1–477] | 17213 | [1–373] | 17289 | [1–460] | 17338 | [1–169] |
| 17167 | [1–591] | 17214 | [1–423] | 17290 | [1–559] | 17339 | [1–354],[384–481] |
| 17168 | [1–473] | 17215 | [1–404] | 17291 | [1–450] | 17340 | [1–536] |
| 17169 | [1–396] | 17216 | [1–343],[389–439] | 17292 | [1–415] | 17341 | [1–204],[239–443] |
| 17170 | [1–506] | 17217 | [1–432] | 17293 | [1–471] | 17342 | [1–171],[205–392] |
| 17171 | [1–564] | 17218 | [1–157] | 17294 | [1–403] | 17343 | [1–301] |
| 17172 | [1–431] | 17219 | [1–400] | 17295 | [1–217] | 17344 | [1–249] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 17296 | [1–344] | 17345 | [1–391] | 17469 | [1–65],[242–356] | 17517 | [1–492] |
| 17297 | [1–330] | 17346 | [1–417] | 17470 | [1–365] | 17518 | [1–578] |
| 17298 | [1–488] | 17347 | [1–470] | 17471 | [282–550] | 17519 | L1–512] |
| 17348 | [1–116],[224–672] | 17396 | [1–464] | 17472 | [1–113] | 17520 | [1–104],[225–394] |
| 17349 | [1–543] | 17398 | [1–457] | 17473 | [154–246] | 17521 | [1–567] |
| 17350 | [1–257] | 17399 | [1–532] | 17474 | [1–440] | 17522 | [1–561] |
| 17352 | [1–476] | 17400 | [1–493] | 17475 | [1–460] | 17523 | [1–415] |
| 17353 | [51–414] | 17401 | [1–560] | 17476 | [1–318] | 17524 | [1–305],[434–458] |
| 17354 | [1–502] | 17402 | [1–620] | 17477 | [1–67] | 17525 | [1–580] |
| 17355 | [1–402] | 17403 | [1–412] | 17478 | [1–55] | 17526 | [1–514] |
| 17356 | [1–507] | 17404 | [1–285] | 17479 | [1–536] | 17527 | [1–487] |
| 17357 | [1–291] | 17405 | [1–398] | 17480 | [1–416] | 17528 | [1–209] |
| 17358 | [1–503] | 17406 | [86–386] | 17481 | [1–523] | 17529 | [68–381] |
| 17359 | [1–482] | 17407 | [1–174] | 17482 | [1–466] | 17530 | [1–425] |
| 17360 | [1–483] | 17408 | [1–375] | 17483 | [1–300] | 17531 | [139–449] |
| 17361 | [1–468] | 17409 | [1–547] | 17484 | [1–491] | 17532 | [1–236] |
| 17362 | [1–328] | 17410 | [1–321],[426–473] | 17485 | [1–470] | 17533 | [1–517] |
| 17363 | [1–535] | 17411 | [1–452] | 17486 | [1–490] | 17534 | [1–485] |
| 17364 | [1–416] | 17412 | [1–240] | 17487 | [1–415] | 17535 | [1–243] |
| 17365 | [1–472] | 17413 | [1–223] | 17488 | [1–612] | 17536 | [1–352] |
| 17366 | [1–87] | 17414 | [1–225] | 17489 | [1–432] | 17537 | [179–278],[340–589] |
| 17367 | [1–437] | 17415 | [1–228] | 17490 | [244–317] | 17538 | [333–483] |
| 17368 | [1–460] | 17416 | [1–225] | 17491 | [1–362] | 17539 | [1–544] |
| 17369 | [1–267],[544–591] | 17417 | [1–225] | 17540 | [1–394] | 17588 | [1–480] |
| 17370 | [1–443] | 17418 | [1–224] | 17541 | [102–251],[383–424] | 17589 | [1–194] |
| 17371 | [1–66],[162–250] | 17419 | [1–225] | 17542 | [1–481] | 17590 | [1–364] |
| 17372 | [1–50] | 17420 | [1–225] | 17543 | [1–400] | 17591 | [1–478] |
| 17373 | [1–502] | 17421 | [1–225] | 17544 | [1–468] | 17592 | [1–475] |
| 17374 | [1–34],[87–479] | 17422 | [1–225] | 17545 | [1–257] | 17593 | [1–68],[294–472] |
| 17375 | [1–501] | 17423 | [1–224] | 17546 | [1–502] | 17594 | [1–344] |
| 17376 | [1–434] | 17424 | [184–504] | 17547 | [1–293] | 17595 | [1–503] |
| 17377 | [1–441] | 17425 | [507–578] | 17548 | [102–147],[383–437] | 17596 | [40–106],[162–439] |
| 17378 | [1–222],[408–504] | 17426 | [1–432] | 17549 | [37–405] | 17597 | [1–412] |
| 17379 | [1–111] | 17427 | [56–399] | 17550 | [1–460] | 17598 | [1–385] |
| 17380 | [1–446] | 17429 | [1–249] | 17551 | [1–393] | 17599 | [1–639] |
| 17381 | [1–116] | 17430 | [33–337] | 17552 | [1–165] | 17600 | [1–487] |
| 17382 | [1–488] | 17431 | [1–391] | 17553 | [1–432] | 17601 | [1–41],[100–425] |
| 17383 | [1–481] | 17432 | [1–427] | 17554 | [1–251] | 17602 | [1–329] |
| 17384 | [1–474] | 17433 | [1–391] | 17555 | [1–378] | 17604 | [1–352] |
| 17385 | [52–149] | 17434 | [1–82] | 17556 | [1–186] | 17605 | [65–435] |
| 17386 | [80–481] | 17435 | [1–448] | 17557 | [1–416] | 17606 | [1–504] |
| 17387 | [1–480] | 17436 | [1–353] | 17558 | [1–369] | 17607 | [104–228] |
| 17388 | [1–318] | 17437 | [1–81],[141–497] | 17559 | [1–250] | 17608 | [223–261] |
| 17389 | [1–304] | 17438 | [1–507] | 17560 | [1–822] | 17610 | [223–269] |
| 17390 | [1–232] | 17439 | [1–447] | 17561 | [1–424] | 17611 | [1–345] |
| 17391 | [1–28],[144–376] | 17440 | [1–383] | 17562 | [1–433] | 17612 | [1–204] |
| 17392 | [1–221] | 17441 | [1–404] | 17563 | [1–40],[82–260] | 17613 | [71–441] |
| 17393 | [101–333] | 17442 | [1–131] | 17564 | [1–435] | 17614 | [1–442] |
| 17394 | [1–579] | 17443 | [1–349] | 17565 | [1–284] | 17615 | [50–169] |
| 17395 | [1–97] | 17444 | [1–118] | 17566 | [1–224],[321–390] | 17616 | [1–458] |
| 17445 | [1–471] | 17492 | [1–379] | 17567 | [1–325] | 17618 | [1–476] |
| 17446 | [1–141] | 17493 | [1–382] | 17568 | [1–442] | 17619 | [1–199] |
| 17447 | [1–148] | 17494 | [1–467] | 17569 | [1–628] | 17620 | [1–462] |
| 17448 | [1–159] | 17495 | [1–407] | 17570 | [59–281] | 17621 | [1–597] |
| 17449 | [1–140] | 17496 | [1–483] | 17571 | [1–283],[329–547] | 17622 | [1–249] |
| 17450 | [1–148] | 17497 | [1–281] | 17572 | [1–390] | 17623 | [61]–221] |
| 17451 | [1–153] | 17498 | [1–521] | 17573 | [1–70] | 17624 | [1–243] |
| 17452 | [1–144] | 17499 | [1–403] | 17574 | [1–1157] | 17625 | [1–81],[115–215] |
| 17453 | [1–131] | 17500 | [1–92] | 17576 | [1–421] | 17626 | [1–279] |
| 17454 | [1–129] | 17501 | [1–103] | 17577 | [1–554] | 17627 | [1–367] |
| 17455 | [1–130] | 17502 | [1–137] | 17578 | [1–80],[112–183] | 17628 | [1–33],[65–107], [227–397],[436–700] |
| 17456 | [1–346] | 17503 | [1–126] | | | | |
| 17457 | [1–140] | 17504 | [1–492] | 17579 | [105–253] | 17629 | [1–388] |
| 17458 | [1–596] | 17506 | [1–92] | 17580 | [1–336] | 17630 | [1–381] |
| 17459 | [1–478] | 17507 | [1–530] | 17581 | [1–556] | 17631 | [1–443] |
| 17460 | [1–466] | 17508 | [1–367],[402–446] | 17582 | [1–224] | 17632 | [1–145] |
| 17461 | [1–454] | 17509 | [1–514] | 17583 | [1–341] | 17633 | [1–510] |
| 17462 | [1–364] | 17510 | [1–120] | 17584 | [61–247] | 17634 | [1–471] |
| 17463 | [1–477] | 17511 | [1–522] | 17585 | [1–239] | 17635 | [1–440] |
| 17464 | [1–874] | 17512 | [1–546] | 17586 | [1–379] | 17636 | [162–461] |
| 17465 | [80–147],[181–424] | 17513 | [181–483] | 17587 | [1–472] | 17637 | [1–340] |
| 17466 | [1–167] | 17514 | [1–415] | 17638 | [1–518] | 17687 | [1–382] |
| 17467 | [144–176] | 17515 | [144–490] | 17639 | [1–534] | 17688 | [1–491] |
| 17468 | [1–521] | 17516 | [1–444] | 17640 | [1–667] | 17689 | [1–476] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 17641 | [1–351] | 17690 | [1–140],[172–439] | 17766 | [1–364] | 17813 | [1–434] |
| 17642 | [1–459] | 17691 | [1–348] | 17767 | [1–298] | 17814 | [1–481] |
| 17643 | [1–515] | 17692 | [1–447] | 17768 | [1–210],[247–336],[367–431] | 17815 | [1–573] |
| 17644 | [1–66] | 17693 | [1–446] | 17769 | [1–510] | 17816 | [1–384] |
| 17645 | [1–64] | 17694 | [1–32],[94–216] | 17770 | [1–491] | 17817 | [78–123],[326–495] |
| 17646 | [1–537] | 17695 | [1–428] | 17771 | [1–455] | 17818 | [1–296] |
| 17647 | [1–501] | 17696 | [1–59] | 17772 | [1–418] | 17819 | [1–355] |
| 17648 | [1–159] | 17697 | [1–249] | 17773 | [1–486] | 17820 | [1–65],[242–542] |
| 17649 | [1–140] | 17698 | [1–245] | 17774 | [1–257],[373–413] | 17821 | [1–269] |
| 17650 | [1–593] | 17699 | [1–153] | 17775 | [1–195] | 17822 | [1–204] |
| 17651 | [1–604] | 17700 | [1–531] | 17776 | [1–285] | 17823 | [30–204],[265–449] |
| 17652 | [1–333] | 17701 | [1–232] | 17777 | [1–123] | 17824 | [119–211] |
| 17653 | [1–98] | 17702 | [158–448] | 17778 | [1–458] | 17825 | [1–246] |
| 17654 | [1–322] | 17703 | [1–387] | 17779 | [1–498] | 17826 | [168–193] |
| 17655 | [1–396] | 17704 | [1–274] | 17780 | [120–335] | 17827 | [1–444] |
| 17656 | [1–487] | 17705 | [1–474] | 17781 | [1–348] | 17828 | [1–329] |
| 17657 | [31–170] | 17706 | [1–143] | 17782 | [1–392] | 17829 | [1–464] |
| 17658 | [86–127],[214–511] | 17707 | [1–536] | 17830 | [1–229] | 17877 | [1–201] |
| 17659 | [1–475] | 17708 | [1–449] | 17831 | [1–388] | 17878 | [1–512] |
| 17660 | [1–314] | 17709 | [1–404] | 17832 | [1–396] | 17879 | [1–420] |
| 17661 | [1–400] | 17710 | [1–230] | 17833 | [1–445] | 17880 | [1–114] |
| 17662 | [1–443] | 17711 | [1–489] | 17834 | [1–515] | 17881 | [1–504] |
| 17663 | [1–399] | 17712 | [1–566] | 17835 | [1–414] | 17882 | [1–636] |
| 17664 | [1–404] | 17713 | [1–220] | 17836 | [1–377] | 17883 | [1–472] |
| 17665 | [1–200] | 17714 | [1–483] | 17837 | [1–308] | 17884 | [1–386] |
| 17666 | [1–509] | 17715 | [1–223] | 17838 | [1–451] | 17885 | [1–432] |
| 17667 | [1–483] | 17716 | [1–500] | 17839 | [1–381] | 17886 | [1–508] |
| 17668 | [1–416] | 17717 | [1–173],[310–383] | 17840 | [1–421] | 17887 | [1–433] |
| 17669 | [1–255] | 17718 | [74–324] | 17841 | [1–416] | 17888 | [1–196],[240–494] |
| 17670 | [1–286] | 17719 | [1–375] | 17842 | [1–428] | 17889 | [1–478] |
| 17671 | [1–493] | 17720 | [1–265] | 17843 | [1–377] | 17890 | [1–462] |
| 17672 | [56–382] | 17721 | [118–448] | 17844 | [1–432] | 17891 | [1–183] |
| 17673 | [1–500] | 17722 | [1–398] | 17845 | [1–257] | 17892 | [1–86],[301–426] |
| 17674 | [1–495] | 17723 | [1–35],[161–405] | 17846 | [1–387] | 17893 | [1–399] |
| 17675 | [1–435] | 17724 | [1–499] | 17847 | [1–343] | 17894 | [32–519] |
| 17676 | [1–475] | 17725 | [1–497] | 17848 | [1–577] | 17895 | [1–43],[127–315] |
| 17678 | [1–154] | 17726 | [1–60] | 17849 | [1–173] | 17896 | [1–255],[294–424] |
| 17680 | [1–273],[350–433] | 17727 | [1–406] | 17850 | [1–347] | 17897 | [1–162],[332–448] |
| 17681 | [64–497] | 17728 | [1–490] | 17851 | [1–355] | 17898 | [1–484] |
| 17682 | [64–510] | 17729 | [1–267] | 17852 | [1–585] | 17899 | [1–501] |
| 17683 | [1–160] | 17730 | [1–322] | 17853 | [1–562] | 17900 | [1–288] |
| 17684 | [1–139] | 17731 | [1–438] | 17854 | [1–711] | 17901 | [1–402] |
| 17685 | [1–410] | 17732 | [1–137],[241–500] | 17855 | [1–182] | 17902 | [1–380] |
| 17686 | [1–220] | 17734 | [1–486] | 17856 | [1–436] | 17903 | [1–483] |
| 17735 | [1–499] | 17783 | [1–469] | 17857 | [1–405] | 17904 | [1–258] |
| 17736 | [1–68] | 17784 | [1–212] | 17858 | [247–334] | 17905 | [1–453] |
| 17737 | [1–382] | 17785 | [1–481] | 17859 | [1–397] | 17906 | [1–435] |
| 17738 | [1–512] | 17786 | [1–441] | 17860 | [1–307] | 17907 | [1–299] |
| 17739 | [1–516] | 17787 | [1–483] | 17861 | [1–435] | 17908 | [1–464] |
| 17740 | [1–491] | 17788 | [1–433] | 17862 | [1–414] | 17909 | [1–295] |
| 17741 | [1–362] | 17789 | [282–343] | 17863 | [1–127] | 17910 | [1–447] |
| 17742 | [1–502] | 17790 | [59–424] | 17864 | [1–395] | 17912 | [1–500] |
| 17743 | [1–102] | 17791 | [1–501] | 17865 | [1–65] | 17913 | [1–117] |
| 17744 | [1–149] | 17792 | [50–383] | 17866 | [1–361] | 17914 | [1–107] |
| 17745 | [1–432] | 17793 | [57–517] | 17867 | [1–408] | 17915 | [1–481] |
| 17746 | [1–459] | 17794 | [1–253] | 17868 | [1–223] | 17916 | [1–546] |
| 17747 | [1–97] | 17795 | [1–419] | 17869 | [45–349] | 17917 | [1–512] |
| 17748 | [1–401] | 17796 | [1–364] | 17870 | [1–122] | 17918 | [1–293] |
| 17749 | [1–300] | 17797 | [1–504] | 17871 | [1–283] | 17919 | [1–207] |
| 17750 | [1–410] | 17798 | [1–50] | 17872 | [1–275] | 17920 | [1–215] |
| 17751 | [1–495] | 17799 | [1–525] | 17873 | [1–470] | 17921 | [1–246] |
| 17753 | [1–163],[280–477] | 17800 | [1–448] | 17874 | [1–379] | 17922 | [1–218] |
| 17754 | [74–342],[459–488] | 17801 | [1–506] | 17875 | [1–357] | 17923 | [1–266] |
| 17755 | [64–475] | 17802 | [1–459] | 17876 | [1–442] | 17924 | [1–241] |
| 17756 | [1–380] | 17803 | [1–413] | 17925 | [1–262] | 17972 | [1–336] |
| 17757 | [1–399] | 17804 | [1–477] | 17926 | [1–259] | 17973 | [1–503] |
| 17758 | [1–217],[402–517] | 17805 | [1–426] | 17927 | [1–270] | 17974 | [1–472] |
| 17759 | [1–236] | 17806 | [1–365] | 17928 | [1–217] | 17975 | [1–447] |
| 17760 | [1–495] | 17807 | [1–314] | 17929 | [1–235] | 17976 | [1–480] |
| 17761 | [1–522] | 17808 | [1–432] | 17930 | [1–225] | 17977 | [1–435] |
| 17762 | [1–384] | 17809 | [1–441] | 17931 | [1–248] | 17978 | [1–427] |
| 17763 | [1–490] | 17810 | [1–66],[297–374] | 17932 | [1–225] | 17979 | [1–508] |
| 17764 | [34–448] | 17811 | [75–217],[259–435] | 17933 | [1–226] | 17980 | [1–510] |
| 17765 | [1–505] | 17812 | [1–404] | | | | |

TABLE IVb-continued (Novelty: 100%)

| Seq Id No. | Positions of preferred fragments | Seq Id No. | Positions of preferred fragments |
|---|---|---|---|
| 17934 | [1–218] | 17981 | [1–464] |
| 17935 | [1–228] | 17982 | [1–55],[91–442] |
| 17936 | [1–241] | 17983 | [1–178] |
| 17937 | [1–242] | 17984 | [1–532] |
| 17938 | [1–247] | 17985 | [1–456] |
| 17939 | [1–243] | 17986 | [1–63] |
| 17940 | [1–243] | 17987 | [1–138] |
| 17941 | [1–237] | 17988 | [1–304] |
| 17942 | [1–236] | 17989 | [1–381] |
| 17943 | [1–248] | 17990 | [1–212] |
| 17944 | [1–214] | 17991 | [1–387] |
| 17945 | [1–245] | 17993 | [1–439] |
| 17946 | [1–216] | 17994 | [1–469] |
| 17947 | [1–225] | 17995 | [1–461] |
| 17948 | [1–229] | 17996 | [1–352] |
| 17949 | [1–219] | 17997 | [181–287] |
| 17950 | [1–520] | 17998 | [1–147] |
| 17951 | [1–444] | 17999 | [1–317] |
| 17952 | [44–489] | 18000 | [1–446] |
| 17953 | [1–495] | 18001 | [1–417] |
| 17954 | [1–437] | 18002 | [1–514] |
| 17955 | [1–538] | 18003 | [1–293] |
| 17956 | [1–219] | 18004 | [1–510] |
| 17957 | [1–487] | 18005 | [1–302] |
| 17958 | [1–400] | 18006 | [1–322] |
| 17959 | [1–440] | 18007 | [1–431] |
| 17960 | [144–302],[437–478] | 18008 | [1–484] |
| 17961 | [1–427] | 18009 | [1–472] |
| 17962 | [1–202] | 18010 | [1–198] |
| 17963 | [1–43],[108–364] | 18011 | [1–497] |
| 17964 | [1–43],[108–360] | 18012 | [1–189] |
| 17965 | [1–43],[108–378] | 18013 | [1–375] |
| 17966 | [1–43],[108–516] | 18014 | [1–124],[208–337] |
| 17967 | [1–468] | 18015 | [1–484] |
| 17968 | [1–63] | 18016 | [1–442] |
| 17969 | [1–412] | 18017 | [1–71] |
| 17970 | [1–232] | 18018 | [1–167] |
| 17971 | [1–68] | 18019 | [1–174] |
| 18020 | [1–278] | 18069 | [1–54] |
| 18021 | [1–502] | 18070 | [1–427] |
| 18022 | [1–59] | 18071 | [1–160] |
| 18023 | [1–64] | 18072 | [130–250],[422–450] |
| 18024 | [1–505] | 18073 | [1–518] |
| 18025 | [1–341] | 18074 | [1–198] |
| 18026 | [1–451] | 18075 | [1–120] |
| 18027 | [1–181] | 18076 | [1–209] |
| 18028 | [1–187] | 18077 | [144–304] |
| 18029 | [1–425] | 18078 | [1–483] |
| 18031 | [1–521] | 18079 | [1–33] |
| 18032 | [1–424] | 18080 | [1–458] |
| 18033 | [1–474] | 18081 | [1–512] |
| 18034 | [1–191] | 18082 | [1–217] |
| 18035 | [1–206] | 18083 | [63–475] |
| 18036 | [1–381] | 18084 | [1–114] |
| 18037 | [1–208] | 18085 | [1–42],[87–220] |
| 18038 | [1–67] | 18086 | [63–456] |
| 18039 | [1–145] | 18087 | [1–335] |
| 18040 | [1–389] | 18088 | [1–407] |
| 18041 | [1–245] | 18089 | [1–259] |
| 18042 | [1–406] | 18090 | [1–87] |
| 18043 | [1–462] | 18091 | [63–270] |
| 18044 | [1–91] | 18092 | [1–480] |
| 18045 | [1–86] | 18093 | [128–426] |
| 18046 | [1–433] | 18094 | [1–473] |
| 18047 | [1–400] | 18095 | [1–448] |
| 18048 | [1–106] | 18096 | [1–193] |
| 18049 | [1–318] | 18097 | [1–189] |
| 18050 | [1–363] | 18098 | [1–160],[238–411] |
| 18051 | [1–235] | 18099 | [58–103] |
| 18052 | [1–454] | 18100 | [1–312] |
| 18053 | [1–477] | 18101 | [41–441] |
| 18054 | [1–179] | 18102 | [1–63] |
| 18055 | [1–74] | 18103 | [64–311] |
| 18056 | [1–125] | 18104 | [1–64] |
| 18058 | [1–153] | 18105 | [1–458] |
| 18059 | [75–218],[282–477] | 18106 | [175–233],[319–428] |
| 18060 | [1–552] | 18107 | [1–620] |
| 18061 | [1–392] | 18108 | [1–825] |
| 18062 | [1–195] | 18109 | [1–96] |
| 18063 | [1–364] | 18110 | [1–553] |
| 18064 | [1–443] | 18111 | [1–482] |
| 18065 | [1–109] | 18112 | [1–424] |
| 18066 | [1–160] | 18113 | [1–507] |
| 18067 | [91–393] | 18114 | [173–338] |
| 18068 | [1–162] | 18115 | [1–497] |
| 18116 | [1–467] | 18163 | [1–44],[149–348] |
| 18117 | [1–175] | 18164 | [1–44],[148–344] |
| 18118 | [1–270] | 18165 | [1–44],[148–320] |
| 18119 | [1–509] | 18166 | [1–45],[149–321] |
| 18120 | [1–403] | 18167 | [167–266] |
| 18121 | [1–493] | 18168 | [1–44],[148–356] |
| 18122 | [1–62] | 18169 | [1–44],[148–320] |
| 18123 | [1–366] | 18170 | [1–88],[160–196],[397–423] |
| 18124 | [1–69] | 18171 | [1–46],[150–357] |
| 18125 | [1–372] | 18172 | [1–86] |
| 18126 | [164–201],[368–4]2] | 18173 | [1–331] |
| 18127 | [1–268],[327–488] | 18174 | [1–46],[95–240],[276–469],[501–631] |
| 18128 | [1–169],[252–292] | 18175 | [1–178] |
| 18129 | [1–486] | 18176 | [1–406] |
| 18130 | [1–192] | 18177 | [1–325] |
| 18131 | [1–314] | 18178 | [192–498] |
| 18132 | [1–191],[221–519] | 18179 | [1–353] |
| 18133 | [1–394] | 18180 | [1–364] |
| 18134 | [1–68] | 18181 | [1–494] |
| 18135 | [1–387] | 18182 | [1–363] |
| 18136 | [1–63],[102–259],[345–446] | 18183 | [1–333] |
| 18137 | [1–445] | 18184 | [1–196] |
| 18138 | [1–410] | 18185 | [1–203] |
| 18139 | [1–45],[149–356] | 18186 | [1–189] |
| 18140 | [1–72] | 18187 | [51–202] |
| 18141 | [1–336] | 18188 | [83–367] |
| 18142 | [1–44],[171–319] | 18189 | [1–249] |
| 18143 | [1–44],[149–375] | 18190 | [1–492] |
| 18144 | [1–45],[150–321] | 18191 | [1–493] |
| 18145 | [1–44],[148–350] | 18192 | [1–296] |
| 18146 | [1–44],[148–344] | 18193 | [1–495] |
| 18147 | [1–322] | 18194 | [1–420] |
| 18148 | [163–200],[268–403] | 18195 | [1–266] |
| 18149 | [1–113],[148–362] | 18196 | [1–537] |
| 18150 | [1–44],[148–343] | 18197 | [1–437] |
| 18151 | [1–44],[149–365] | 18198 | [1–436] |
| 18152 | [1–72],[142–199] | 18199 | [50–476] |
| 18153 | [1–44],[172–357] | 18200 | [33–256] |
| 18154 | [1–44],[148–340] | 18201 | [1–250] |
| 18155 | [1–44],[149–360] | 18202 | [1–247] |
| 18156 | [1–45],[150–350] | 18203 | [1–207] |
| 18157 | [1–44],[148–348] | 18204 | [1–345] |
| 18158 | [156–221],[271–406] | 18205 | [33–336] |
| 18159 | [1–44],[148–348] | 18206 | [33–512] |
| 18160 | [1–44],[149–361] | 18207 | [33–339] |
| 18161 | [1–44],[149–362] | 18208 | [33–428] |
| 18162 | [1–44],[149–320] | 18209 | [33–418] |
| 18210 | [1–487] | 18260 | [1–467] |
| 18211 | [1–244] | 18261 | [1–577] |
| 18212 | [1–442] | 18262 | [1–430] |
| 18213 | [1–263] | 18263 | [1–445] |
| 18214 | [1–419] | 18264 | [1–551] |
| 18215 | [33–448] | 18265 | [1–513] |
| 18216 | [33–219] | 18266 | [1–546] |
| 18217 | [33–365] | 18267 | [1–476] |
| 18218 | [1–555] | 18268 | [1–106] |
| 18219 | [1–466] | 18269 | [1–403] |
| 18220 | [85–172] | 18270 | [1–270] |
| 18221 | [1–254] | 18271 | [1–385] |
| 18222 | [1–430] | 18272 | [1–318] |
| 18223 | [1–505] | 18273 | [1–387] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 18224 | [1–343] | 18274 | [1–169] | 18348 | [1–440] | 18396 | [1–348] |
| 18225 | [1–306] | 18275 | [1–592] | 18349 | [1–71] | 18397 | [1–258],[298–361] |
| 18226 | [1–538] | 18276 | [1–453] | 18350 | [1–544] | 18398 | [66–448] |
| 18227 | [1–546] | 18277 | [1–204] | 18351 | [1–465] | 18399 | [1–439] |
| 18228 | [1–409] | 18278 | [63–371] | 18352 | [1–464] | 18400 | [90–183] |
| 18229 | [1–461] | 18279 | [1–365] | 18353 | [1–244] | 18401 | [1–96] |
| 18231 | [70–395] | 18280 | [1–397] | 18354 | [1–495] | 18402 | [1–356] |
| 18232 | [1–71] | 18281 | [1–204] | 18355 | [1–503] | 18403 | [1–137] |
| 18233 | [1–436] | 18282 | [1–438] | 18404 | [1–391] | 18451 | [54–353] |
| 18235 | [1–418] | 18283 | [1–559] | 18405 | [1–533] | 18452 | [54–282] |
| 18236 | [1–337] | 18284 | [84–363] | 18406 | [1–145] | 18453 | [1–215] |
| 18237 | [1–661] | 18285 | [1–446] | 18407 | [1–187] | 18454 | [159–235],[339–373] |
| 18238 | [1–457] | 18286 | [1–86],[187–355] | 18408 | [1–503] | 18455 | [1–406] |
| 18239 | [1–453] | 18287 | [1–151] | 18409 | [1–315] | 18456 | [1–421] |
| 18240 | [162–293] | 18288 | [1–433] | 18410 | [1–499] | 18457 | [1–55] |
| 18241 | [1–402] | 18289 | [1–418] | 18411 | [1–369] | 18458 | [1–148] |
| 18242 | [1–413] | 18290 | [1–368] | 18412 | [1–50],[377–408] | 18460 | [1–338] |
| 18243 | [1–396] | 18291 | [1–387] | 18413 | [159–389] | 18461 | [1–107] |
| 18244 | [1–509] | 18292 | [1–354] | 18414 | [1–340] | 18462 | [1–56] |
| 18245 | [1–200],[230–418] | 18293 | [39–439] | 18415 | [1–367] | 18463 | [1–462] |
| 18246 | [1–380],[441–540] | 18294 | [1–400] | 18416 | [1–377] | 18465 | [1–414] |
| 18248 | [1–148] | 18295 | [1–340] | 18417 | [1–522] | 18466 | [1–398] |
| 18249 | [1–383] | 18296 | [1–465] | 18418 | [1–483] | 18467 | [1–394] |
| 18250 | [1–472] | 18297 | [1–426] | 18419 | [1–547] | 18468 | [1–289] |
| 18251 | [1–581] | 18298 | [1–128] | 18420 | [1–97] | 18469 | [1–439] |
| 18252 | [1–414] | 18299 | [1–73],[157–425] | 18421 | [1–228] | 18470 | [1–412] |
| 18253 | [1–429] | 18300 | [1–494] | 18422 | [1–102] | 18471 | [1–410] |
| 18254 | [1–513] | 18302 | [1–239] | 18423 | [1–476] | 18472 | [1–440] |
| 18255 | [1–407] | 18303 | [1–519] | 18424 | [1–412] | 18473 | [1–417] |
| 18256 | [1–153] | 18304 | [1–535] | 18425 | [1–478] | 18474 | [1–426] |
| 18257 | [1–438] | 18305 | [1–512] | 18426 | [1–143] | 18475 | [1–271] |
| 18258 | [1–341] | 18306 | [1–438] | 18427 | [1–64] | 18476 | [1–324] |
| 18259 | [1–496] | 18307 | [1–115] | 18428 | [1–186] | 18477 | [1–237] |
| 18308 | [1–100],[192–349],[419–503] | 18356 | [1–518] | 18429 | [1–509] | 18478 | [39–478] |
| 18309 | [1–426] | 18357 | [1–165] | 18430 | [1–427] | 18479 | [1–46] |
| 18310 | [1–380] | 18358 | [131–240],[400–521] | 18431 | [1–93] | 18480 | [1–46] |
| 18311 | [1–168] | 18359 | [1–424] | 18432 | [78–115] | 18481 | [1–326] |
| 18312 | [1–444] | 18360 | [1–404] | 18433 | [78–134] | 18482 | [1–437] |
| 18313 | [1–452] | 18361 | [137–224] | 18434 | [78–137] | 18483 | [1–353] |
| 18314 | [1–422] | 18362 | [64–141] | 18435 | [1–55] | 18484 | [1–102] |
| 18315 | [1–362] | 18363 | [1–250] | 18436 | [60–358] | 18485 | [1–472] |
| 18316 | [1–472] | 18364 | [39–389] | 18437 | [1–96],[253–414] | 18486 | [1–577] |
| 18318 | [1–301] | 18365 | [39–315] | 18438 | [1–61] | 18487 | [1–493] |
| 18319 | [1–590] | 18366 | [36–358] | 18439 | [1–129],[259–443] | 18488 | [1–286] |
| 18320 | [1–478] | 18367 | [1–203] | 18440 | [1–269] | 18489 | [1–435] |
| 18321 | [1–154] | 18368 | [1–183] | 18441 | [1–464] | 18490 | [1–405] |
| 18322 | [1–436] | 18369 | [1–111] | 18442 | [1–518] | 18491 | [1–680] |
| 18323 | [1–517] | 18370 | [35–401] | 18443 | [1–377] | 18492 | [1–553] |
| 18324 | [1–461] | 18371 | [1–183] | 18444 | [1–387] | 18493 | [1–216] |
| 18325 | [1–402] | 18372 | [1–285] | 18445 | [1–275] | 18494 | [55–101],[162–407] |
| 18326 | [39–109] | 18373 | [1–279] | 18446 | [1–278] | 18495 | [124–447] |
| 18327 | [1–139] | 18374 | [1–58] | 18447 | [1–216] | 18496 | [46–465] |
| 18328 | [1–242] | 18375 | [1–172] | 18448 | [1–396] | 18497 | [1–469] |
| 18329 | [1–276] | 18376 | [1–202] | 18449 | [1–425] | 18498 | [1–422] |
| 18330 | [1–261] | 18377 | [1–116] | 18450 | [54–353] | 18500 | [1–508] |
| 18331 | [1–283] | 18378 | [1–460] | 18501 | [1–476] | 18548 | [1–509] |
| 18332 | [1–191] | 18379 | [1–437] | 18502 | [1–473] | 18549 | [1–93],[136–194],[255–563] |
| 18333 | [1–173] | 18380 | [1–492] | 18503 | [1–445] | 18550 | [45–105],[164–457] |
| 18334 | [1–98] | 18381 | [1–498] | 18504 | [1–289] | 18551 | [1–462] |
| 18335 | [1–473] | 18382 | [1–250] | 18505 | [1–554] | 18552 | [1–472] |
| 18336 | [329–468] | 18384 | [1–103],[134–159] | 18506 | [146–446] | 18553 | [1–350] |
| 18337 | [1–552] | 18385 | [1–97] | 18507 | [1–563] | 18554 | [1–247],[356–459] |
| 18338 | [1–237] | 18386 | [1–478] | 18508 | [1–485] | 18555 | [1–509] |
| 18339 | [1–206],[435–490] | 18387 | [175–244] | 18509 | [1–505] | 18556 | [1–567] |
| 18340 | [1–172],[218–592] | 18388 | [1–497] | 18510 | [1–510] | 18557 | [1–467] |
| 18341 | [1–413] | 18389 | [1–485] | 18511 | [1–488] | 18558 | [1–513] |
| 18342 | [1–72] | 18390 | [1–166] | 18512 | [1–564] | 18559 | [1–515] |
| 18343 | [1–60] | 18391 | [1–95] | 18513 | [1–450] | 18560 | [1–511] |
| 18344 | [1–115] | 18392 | [1–427] | 18514 | [1–523] | 18561 | [1–377] |
| 18345 | [1–478] | 18393 | [1–388] | 18515 | [1–190] | 18562 | [1–541] |
| 18346 | [1–391] | 18394 | [1–65],[101–432] | 18516 | [1–541] | 18563 | [1–378] |
| 18347 | [1–55],[146–190],[267–351] | 18395 | [1–392] | 18517 | [1–259],[321–387] | 18564 | [1–427] |
|  |  |  |  | 18518 | [1–513] | 18566 | [167–449] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 18519 | [1–259],[371–416] | 18567 | [1–495] | 18641 | [1–540] | 18689 | [1–399] |
| 18520 | [1–487] | 18568 | [1–414] | 18642 | [1–313] | 18690 | [1–368] |
| 18521 | [1–471] | 18569 | [1–352] | 18643 | [1–459] | 18691 | [1–70] |
| 18522 | [1–400] | 18570 | [1–359] | 18692 | [1–373] | 18758 | [1–109] |
| 18523 | [1–403] | 18571 | [1–397] | 18693 | [1–137] | 18759 | [1–3 1],[125–343],[389–426] |
| 18524 | [1–406],[468–508] | 18572 | [1–359] | | | | |
| 18525 | [1–461] | 18573 | [1–388] | 18694 | [1–94],[222–337] | 18760 | [1–461] |
| 18526 | [1–402],[464–507] | 18574 | [51–400] | 18695 | [1–81] | 18761 | [1–70] |
| 18527 | [1–404] | 18575 | [1–341] | 18696 | [1–161] | 18762 | [140–249],[325–487] |
| 18528 | [1–450] | 18576 | [1–499] | 18697 | [1–66],[194–255] | 18763 | [1–44],[110–405] |
| 18529 | [1–432] | 18577 | [1–497] | 18701 | [1–177],[228–393] | 18764 | [1–94],[174–220],[294–359] |
| 18530 | [1–393] | 18578 | [1–494] | | | | |
| 18531 | [1–400] | 18579 | [295–427] | 18704 | [1–178],[225–385] | 18765 | [1–182],[255–376] |
| 18532 | [1–407],[469–493] | 18580 | [53–266] | 18706 | [1–525] | 18766 | [94–367] |
| 18533 | [1–404],[466–492] | 18581 | [37–507] | 18707 | [1–94] | 18768 | [1–68] |
| 18534 | [1–401] | 18582 | [1–364] | 18709 | [1–93],[139–218],[292–388] | 18769 | [1–216],[327–404] |
| 18535 | [1–59] | 18583 | [1–231],[274–434] | | | | |
| 18536 | [1–401] | 18584 | [1–205] | 18710 | [1–236] | 18770 | [1–59] |
| 18537 | [1–403] | 18585 | [1–386] | 18711 | [1–94],[140–232],[322–387] | 18771 | [1–266] |
| 18538 | [1–360],[422–478] | 18586 | [1–67] | | | | |
| 18539 | [1–400] | 18587 | [1–180] | 18715 | [1–94],[140–204] | 18772 | [1–97],[225–271],[326–391] |
| 18540 | [1–401] | 18588 | [1–193] | | | | |
| 18541 | [1–425] | 18589 | [1–147] | 18716 | [1–314] | 18773 | [95–361],[413–457] |
| 18542 | [1–400] | 18590 | [1–498] | 18717 | [1–94] | 18774 | [1–228],[302–339] |
| 18543 | [1–475] | 18591 | [1–452] | 18718 | [1–62] | 18775 | [1–71] |
| 18544 | [1–416] | 18592 | [1–584] | 18719 | [1–69] | 18777 | [1–109] |
| 18545 | [1–472] | 18593 | [1–288] | 18720 | [1–235] | 18778 | [1–94] |
| 18546 | [1–402] | 18594 | [1–450] | 18721 | [1–341] | 18779 | [1–390] |
| 18547 | [1–434] | 18595 | [52–510] | 18722 | [1–94] | 18780 | [94–346] |
| 18596 | [1–422] | 18644 | [1–30],[73–179] | 18725 | [1–94] | 18781 | [1–93] |
| 18597 | [1–437] | 18645 | [105–477] | 18726 | [1–486] | 18783 | [1–94] |
| 18598 | [1–406] | 18647 | [1–335] | 18727 | [1–50] | 18784 | [1–66] |
| 18599 | [1–531] | 18648 | [171–282] | 18728 | [84–110],[173–221] | 18786 | [1–67] |
| 18600 | [1–516] | 18649 | [1–516] | 18730 | [1–63] | 18787 | [1–67] |
| 18601 | [1–496] | 18650 | [1–263] | 18731 | [1–44],[84–110],[225–403] | 18788 | [140–229] |
| 18602 | [1–314] | 18651 | [1–518] | 18732 | [1–70] | 18789 | [94–435] |
| 18603 | [1–433] | 18652 | [1–507] | 18733 | [1–63] | 18791 | [1–527] |
| 18604 | [1–419] | 18653 | [250–397] | 18734 | [1–70] | 18792 | [1–466] |
| 18605 | [1–176] | 18654 | [117–218] | 18735 | [31–374] | 18793 | [1–510] |
| 18606 | [1–208] | 18655 | [1–284] | 18736 | [1–89],[170–384] | 18794 | [1–453] |
| 18607 | [1–85],[121–396] | 18656 | [1–159] | 18737 | [1–109] | 18795 | [1–465] |
| 18608 | [1–469] | 18657 | [1–727] | 18740 | [31–406] | 18796 | [1–503] |
| 18609 | [46–168] | 18658 | [1–180] | 18742 | [1–63] | 18797 | [1–444] |
| 18610 | [136–190],[246–417] | 18659 | [1–431] | 18743 | [231–255] | 18798 | [1–482] |
| 18612 | [1–346] | 18660 | [67–411] | 18745 | [227–289] | 18799 | [1–403] |
| 18613 | [228–293],[354–480] | 18661 | [1–209] | 18746 | [1–93] | 18800 | [1–506] |
| 18614 | [1–410] | 18662 | [1–501] | 18747 | [1–51] | 18801 | [1–600] |
| 18615 | [1–269] | 18663 | [1–485] | 18748 | [1–64] | 18802 | [73–245],[423–499] |
| 18616 | [1–517] | 18664 | [37–389] | 18749 | [1–181],[296–431] | 18803 | [97–204],[445–487] |
| 18617 | [1–500] | 18665 | [1–348] | 18750 | [1–93],[220–247] | 18804 | [1–83] |
| 18618 | [1–508] | 18666 | [1–83],[212–483] | 18752 | [1–365] | 18805 | [1–490] |
| 18619 | [1–483] | 18667 | [1–83],[212–403] | 18753 | [1–50] | 18806 | [1–447] |
| 18620 | [1–63] | 18668 | [1–512] | 18754 | [111–221],[295–319] | 18807 | [1–447] |
| 18621 | [1–492] | 18669 | [1–174],[216–297] | 18756 | [1–304],[350–386] | 18808 | [1–495] |
| 18622 | [1–470] | 18670 | [1–463] | 18757 | [1–44],[84–389] | 18810 | [1–297] |
| 18623 | [1–437] | 18671 | [1–332],[394–421] | 18811 | [1–87] | 18862 | [1–501] |
| 18624 | [1–28],[138–331],[362–479] | 18672 | [38–315] | 18812 | [1–506] | 18863 | [1–353] |
| | | | | 18813 | [1–484] | 18864 | [1–132] |
| 18625 | [1–28],[137–405] | 18673 | [37–314] | 18814 | [1–176],[208–896] | 18865 | [186–228] |
| 18626 | [108–325] | 18674 | [1–270] | 18815 | [1–509] | 18866 | [1–177] |
| 18627 | [109–331] | 18675 | [1–493] | 18816 | [1–561] | 18867 | [1–446] |
| 18628 | [1–474] | 18676 | [1–179] | 18817 | [1–487] | 18869 | [1–716] |
| 18629 | [108–307] | 18677 | [1–405] | 18818 | [1–504] | 18870 | [1–250] |
| 18630 | [1–493] | 18678 | [104–357] | 18819 | [1–533] | 18871 | [1–238] |
| 18631 | [118–222],[424–471] | 18679 | [1–474] | 18820 | [1–440] | 18872 | [1–269] |
| 18632 | [1–160],[300–441] | 18680 | [1–498] | 18821 | [1–593] | 18873 | [1–300] |
| 18633 | [62–442] | 18681 | [1–501] | 18825 | [1–490] | 18874 | [1–490] |
| 18634 | [62–160],[300–441] | 18682 | [1–458] | 18826 | [1–402] | 18875 | [1–482] |
| 18635 | [1–104] | 18683 | [1–377] | 18827 | [1–433] | 18876 | [105–425] |
| 18636 | [1–433] | 18684 | [1–354] | 18828 | [43–445] | 18877 | [1–501] |
| 18637 | [1–489] | 18685 | [1–509] | 18830 | [1–282] | 18878 | [1–476] |
| 18638 | [1–332] | 18686 | [1–360] | 18831 | [1–399],[486–522] | 18879 | [1–319] |
| 18639 | [1–405] | 18687 | [1–510] | 18832 | [1–522] | 18880 | [1–463],[498–563] |
| 18640 | [157–474] | 18688 | [1–503] | 18833 | [40–445] | 18881 | [1–460] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 18834 | [101–394] | 18882 | [1–461] | 18956 | [1–790] | 19003 | [1–354] |
| 18835 | [1–532] | 18883 | [1–485] | 18957 | [1–517] | 19004 | [1–415] |
| 18836 | [1–464] | 18884 | [1–496] | 18958 | [1–1030] | 19005 | [1–407] |
| 18837 | [1–188] | 18885 | [253–936] | 19006 | [1–701] | 19053 | [1–450] |
| 18838 | [1–265] | 18886 | [1–138],[207–410] | 19007 | [1–508] | 19054 | [1–482] |
| 18839 | [1–374] | 18887 | [1–49],[110–138] | 19008 | [1–478] | 19055 | [176–465] |
| 18840 | [1–439] | 18889 | [1–449] | 19009 | [1–508] | 19056 | [1–337] |
| 18841 | [1–452] | 18890 | [1–467] | 19010 | [1–436] | 19057 | [1–465] |
| 18842 | [1–225] | 18891 | [1–170] | 19011 | [1–481] | 19058 | [1–478] |
| 18843 | [1–438] | 18892 | [1–524] | 19012 | [1–142],[288–483] | 19059 | [1–468] |
| 18844 | [1–141],[173–208],[305–412] | 18893 | [1–250] | 19013 | [1–216],[289–448] | 19060 | [1–132],[170–384] |
| 18845 | [1–494] | 18894 | [1–409] | 19014 | [1–51],[289–428] | 19061 | [1–403] |
| 18846 | [1–401] | 18895 | [1–426] | 19015 | [1–51] | 19062 | [1–500] |
| 18847 | [1–352] | 18896 | [1–284] | 19016 | [1–67] | 19063 | [1–472] |
| 18848 | [1–416] | 18897 | [60–89],[136–344] | 19017 | [1–484] | 19064 | [1–515] |
| 18849 | [1–489] | 18898 | [1–154],[189–218],[265–301] | 19018 | [1–142] | 19065 | [1–396] |
|  |  |  |  | 19019 | [1–428] | 19066 | [1–413] |
|  |  |  |  | 19020 | [1–451] | 19067 | [1–381] |
| 18850 | [1–80] | 18899 | [1–35],[89–378] | 19021 | [1–325] | 19068 | [1–580] |
| 18851 | [1–357] | 18900 | [1–351] | 19022 | [1–490] | 19069 | [1–526] |
| 18852 | [1–360] | 18901 | [1–507] | 19023 | [97–350],[388–509] | 19070 | [1–501] |
| 18853 | [1–360] | 18903 | [1–479] | 19024 | [97–350],[388–514] | 19071 | [1–436] |
| 18854 | [1–377] | 18904 | [256–304] | 19025 | [1–501] | 19072 | [1–412] |
| 18855 | [1–382] | 18905 | [1–51] | 19026 | [1–293] | 19073 | [1–426] |
| 18856 | [1–383] | 18906 | [1–155] | 19027 | [1–470] | 19074 | [1–489] |
| 18857 | [1–427] | 18907 | [1–155] | 19028 | [1–69],[110–440] | 19075 | [1–433] |
| 18858 | [1–391] | 18908 | [179–424] | 19029 | [1–550] | 19076 | [1–87],[239–465] |
| 18859 | [1–485] | 18909 | [1–51] | 19030 | [1–470] | 19077 | [1–518] |
| 18860 | [1–335] | 18910 | [1–150],[214–361] | 19031 | [1–531] | 19078 | [1–423] |
| 18861 | [1–453] | 18911 | [1–42],[129–381] | 19032 | [1–505] | 19079 | [1–387] |
| 18912 | [1–52] | 18959 | [1–38],[237–419] | 19033 | [1–252] | 19080 | [1–586] |
| 18913 | [1–44],[131–273] | 18960 | [1–324] | 19034 | [1–253] | 19081 | [1–507] |
| 18914 | [1–51] | 18961 | [1–379] | 19035 | [1–447] | 19082 | [1–468] |
| 18915 | [1–41],[128–333] | 18962 | [1–403] | 19036 | [131–368] | 19083 | [1–481] |
| 18916 | [1–447] | 18963 | [1–384] | 19037 | [72–516] | 19084 | [1–429] |
| 18917 | [1–506] | 18964 | [1–527] | 19038 | [238–426] | 19085 | [1–474] |
| 18918 | [1–215] | 18965 | [1–458] | 19039 | [57–580] | 19086 | [1–192] |
| 18919 | [1–485] | 18966 | [1–516] | 19040 | [1–309] | 19087 | [1–516] |
| 18920 | [1–52] | 18967 | [128–281] | 19041 | [1–70] | 19088 | [1–471] |
| 18921 | [1–411] | 18968 | [1–496] | 19042 | [1–424] | 19089 | [1–550] |
| 18922 | [1–52] | 18969 | [1–569] | 19043 | [238–295],[419–449] | 19090 | [1–469] |
| 18923 | [1–52] | 18970 | [1–477] | 19044 | [1–62] | 19091 | [1–415] |
| 18924 | [1–421] | 18971 | [1–566] | 19045 | [1–301] | 19092 | [1–839] |
| 18925 | [1–51] | 18972 | [1–457] | 19046 | [1–462] | 19093 | [1–463] |
| 18926 | [1–52] | 18973 | [1–415] | 19047 | [1–326] | 19094 | [1–516] |
| 18927 | [182–307] | 18974 | [1–474] | 19048 | [1–417] | 19095 | [1–484] |
| 18928 | [1–51] | 18975 | [1–449] | 19049 | [1–537] | 19096 | [1–356] |
| 18929 | [1–53] | 18976 | [1–437] | 19050 | [1–518] | 19097 | [1–203] |
| 18930 | [1–485] | 18977 | [1–411] | 19051 | [1–508] | 19098 | [1–348] |
| 18931 | [1–355] | 18978 | [1–659] | 19052 | [1–497] | 19099 | [1–351] |
| 18932 | [1–330] | 18979 | [1–451] | 19100 | [1–184] | 19148 | [1–124],[253–406] |
| 18933 | [120–378] | 18980 | [1–485] | 19101 | [1–528] | 19149 | [1–337] |
| 18934 | [1–582] | 18981 | [379–463] | 19102 | [1–444] | 19150 | [1–515] |
| 18935 | [1–281] | 18982 | [1–493] | 19103 | [1–439] | 19151 | [1–174] |
| 18936 | [60–341] | 18983 | [1–378] | 19104 | [1–556] | 19152 | [1–167],[207–391] |
| 18937 | [194–426] | 18984 | [1–77],[449–507] | 19105 | [1–422] | 19153 | [1–419] |
| 18938 | [1–451] | 18985 | [1–114],[168–509] | 19106 | [1–503] | 19154 | [1–166] |
| 18939 | [1–351] | 18986 | [1–433] | 19107 | [1–168] | 19155 | [1–351] |
| 18940 | [1–424] | 18987 | [1–308] | 19108 | [1–548] | 19156 | [1–167],[207–389] |
| 18941 | [1–469] | 18988 | [1–489] | 19109 | [141–515] | 19157 | [1–167],[207–390] |
| 18942 | [1–325] | 18989 | [1–478] | 19110 | [1–473] | 19158 | [208–427] |
| 18943 | [1–149] | 18990 | [1–460] | 19111 | [1–452] | 19159 | [1–453] |
| 18944 | [1–438] | 18991 | [1–528] | 19112 | [1–480] | 19160 | [1–163],[314–494] |
| 18945 | [39–524] | 18992 | [1–506] | 19113 | [1–394] | 19161 | [1–495] |
| 18946 | [73–518] | 18993 | [1–377] | 19114 | [1–354] | 19162 | [1–495],[533–623] |
| 18947 | [85–409] | 18994 | [1–367] | 19115 | [1–612] | 19163 | [1–505] |
| 18948 | [1–519] | 18995 | [1–188] | 19116 | [1–484] | 19164 | [1–435] |
| 18949 | [1–469] | 18996 | [1–543] | 19117 | [1–493] | 19165 | [1–497] |
| 18950 | [1–468] | 18997 | [1–347] | 19118 | [1–387] | 19166 | [1–150] |
| 18951 | [1–519] | 18998 | [1–518] | 19119 | [1–449] | 19167 | [1–369] |
| 18952 | [1–256] | 18999 | [204–533] | 19120 | [41–456] | 19168 | [1–207] |
| 18953 | [1–73],[221–306] | 19000 | [1–190] | 19121 | [1–203] | 19169 | [1–144] |
| 18954 | [114–470] | 19001 | [1–199] | 19122 | [1–439] | 19170 | [1–362],[391–434] |
| 18955 | [336–458] | 19002 | [1–822] | 19123 | [1–445] | 19171 | [1–151] |

TABLE IVb-continued (Novelty: 100%)

| Seq Id No. | Positions of preferred fragments | Seq Id No. | Positions of preferred fragments | Seq Id No. | Positions of preferred fragments | Seq Id No. | Positions of preferred fragments |
|---|---|---|---|---|---|---|---|
| 19124 | [1–427] | 19172 | [1–170] | 19289 | [1–108] | | |
| 19125 | [1–448] | 19173 | [1–162] | 19290 | [1–101] | | |
| 19126 | [1–406] | 19174 | [1–532] | 19291 | [1–108] | | |
| 19127 | [1–514] | 19175 | [1–519] | 19292 | [1–496] | | |
| 19128 | [1–469] | 19176 | [1–658] | 19293 | [1–108] | | |
| 19130 | [1–517] | 19177 | [1–303] | 19294 | [1–63] | | |
| 19131 | [1–458] | 19178 | [1–369] | 19295 | [1–108] | | |
| 19132 | [1–136] | 19179 | [1–500] | 19296 | [1–108] | | |
| 19133 | [1–500] | 19180 | [1–293] | 19298 | [1–108] | | |
| 19134 | [1–429] | 19181 | [78–558] | 19299 | [1–108] | | |
| 19135 | [1–682] | 19182 | [1–471] | 19300 | [1–108] | | |
| 19136 | [1–484] | 19183 | [1–563] | 19301 | [1–80] | | |
| 19137 | [1–142] | 19184 | [326–385] | 19302 | [1–101] | | |
| 19138 | [1–554] | 19186 | [1–513] | 19303 | [1–489] | | |
| 19139 | [1–466] | 19187 | [1–464] | 19304 | [1–108] | | |
| 19140 | [316–440] | 19188 | [1–472] | 19305 | [1–81] | | |
| 19141 | [1–355] | 19189 | [1–473] | 19306 | [1–29] | | |
| 19142 | [1–400] | 19190 | [1–518] | 19307 | [35–81] | | |
| 19143 | [1–196] | 19191 | [1–380] | 19308 | [1–205] | | |
| 19144 | [1–249] | 19192 | [1–449] | 19309 | [1–102] | | |
| 19145 | [149–327] | 19193 | [1–214] | 19311 | [1–108] | | |
| 19146 | [200–465] | 19194 | [1–550] | 19312 | [1–108] | | |
| 19147 | [1–480] | 19195 | [1–165] | 19313 | [1–109] | | |
| 19196 | [1–444] | 19246 | [1–459] | 19314 | [1–385] | | |
| 19197 | [1–130] | 19247 | [1–522] | 19315 | [1–101] | | |
| 19198 | [1–298],[353–406] | 19248 | [1–492] | 19316 | [1–108] | | |
| 19199 | [1–315] | 19249 | [1–490] | 19317 | [1–169] | | |
| 19200 | [1–552] | 19250 | [1–44],[294–477] | 19318 | [1–63] | | |
| 19201 | [1–424] | 19251 | [1–307] | 19319 | [1–133] | | |
| 19202 | [1–161] | 19252 | [241–519] | 19320 | [35–80] | | |
| 19203 | [1–467] | 19253 | [1–480] | 19321 | [1–108] | | |
| 19204 | [1–420] | 19255 | [1–419] | 19322 | [1–119] | | |
| 19205 | [1–468] | 19256 | [1–375] | 19323 | [1–101] | | |
| 19206 | [1–236] | 19257 | [1–177] | 19325 | [1–390] | | |
| 19208 | [1–184] | 19258 | [1–287] | 19326 | [1–168] | | |
| 19209 | [1–299] | 19259 | [1–266] | 19327 | [1–387] | | |
| 19210 | [1–61] | 19260 | [1–58] | 19328 | [1–169] | | |
| 19211 | [1–423] | 19261 | [1–204] | 19329 | [1–169] | | |
| 19212 | [1–260] | 19262 | [1–329] | 19330 | [1–108] | | |
| 19213 | [86–164] | 19263 | [1–72] | 19331 | [1–101] | | |
| 19214 | [1–164] | 19264 | [1–348] | 19332 | [1–404] | | |
| 19215 | [1–146] | 19265 | [1–439] | 19334 | [1–499] | | |
| 19216 | [1–58] | 19266 | [1–330] | 19335 | [1–63] | | |
| 19217 | [1–103] | 19267 | [1–319] | | | | |
| 19218 | [1–352] | 19268 | [1–313] | | | | |
| 19220 | [1–541] | 19269 | [1–160] | | | | |
| 19221 | [1–467] | 19270 | [1–90] | | | | |
| 19222 | [1–464] | 19271 | [1–110] | | | | |
| 19223 | [1–144],[178–371] | 19272 | [1–132] | | | | |
| 19224 | [1–247] | 19273 | [1–101] | | | | |
| 19225 | [1–321] | 19274 | [1–265] | | | | |
| 19226 | [1–221] | 19275 | [1–325] | | | | |
| 19227 | [99–177] | 19276 | [1–171] | | | | |
| 19228 | [1–469] | 19277 | [1–90] | | | | |
| 19229 | [73–477] | 19278 | [1–182] | | | | |
| 19230 | [1–444] | 19279 | [1–59] | | | | |
| 19231 | [339–419] | 19280 | [1–353] | | | | |
| 19232 | [1–338] | 19281 | [1–107] | | | | |
| 19233 | [1–334] | 19282 | [1–377] | | | | |
| 19234 | [1–196] | 19283 | [1–270] | | | | |
| 19235 | [1–505] | 19284 | [1–348] | | | | |
| 19236 | [1–513] | 19285 | [1–338] | | | | |
| 19237 | [134–246] | 19286 | [1–63] | | | | |
| 19238 | [1–467] | 19288 | [1–101] | | | | |
| 19239 | [1–401] | 19289 | [1–108] | | | | |
| 19240 | [1–476] | 19290 | [1–101] | | | | |
| 19241 | [1–369] | 19291 | [1–108] | | | | |
| 19242 | [1–85] | 19292 | [1–496] | | | | |
| 19244 | [1–453] | 19293 | [1–108] | | | | |
| 19245 | [1–136] | 19294 | [1–63] | | | | |
| 19284 | [1–348] | | | | | | |
| 19285 | [1–338] | | | | | | |
| 19286 | [1–63] | | | | | | |
| 19288 | [1–101] | | | | | | |

TABLE V (Spatial distribution)

| Seq Id No. | Tissue distribution | Seq Id No. | Tissue distribution |
|---|---|---|---|
| 24 | H:1 | 71 | I:3 |
| 25 | C:1 | 72 | D:9 |
| 26 | B:6 | 73 | H:1 |
| 27 | K:1 | 74 | B:3 |
| 28 | B:3 C:1 | 75 | B:1 |
| 29 | F:1 | 76 | K:2 |
| 30 | F:1 K:1 | 77 | I:1 |
| 31 | C:1 | 78 | A:3 C:8 D:1 |
| 32 | C:1 F:1 | 79 | I:1 |
| 33 | I:4 | 80 | K:1 |
| 34 | A:1 | 81 | H:1 |
| 35 | C:1 | 82 | F:1 K:4 |
| 36 | A:1 B:1 | 83 | A:4 |
| 37 | F:1 | 84 | K:1 |
| 38 | F:39 K:20 | 85 | K:1 |
| 39 | K:3 | 86 | I:1 |
| 40 | D:1 K:4 | 87 | D:1 F:2 |
| 41 | A:1 | 88 | A:2 |
| 42 | C:4 H:2 | 89 | B:1 |

TABLE V-continued (Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 43 | F:21 K:7 | 90 | C:5 | 161 | B:1 | 208 | A:1 |
| 44 | H:6 | 91 | A:9 B:8 D:1 H:4 I:8 K:1 | 162 | C:1 F:1 | 209 | A:2 H:1 K:2 |
| 45 | I:13 | 92 | A:1 B:5 C:5 D:3 F:3 K:1 | 163 | A:1 | 210 | I:1 |
| 46 | A:1 | 93 | H:1 | 211 | K:1 | 258 | A:1 |
| 47 | E:1 | 94 | A:2 | 212 | K:2 | 259 | H:2 |
| 48 | A:2 B:1 | 95 | H:2 | 213 | K:1 | 260 | F:3 K:3 |
| 49 | A:1 F:1 | 96 | H:1 | 214 | K:1 | 261 | F:2 K:6 |
| 50 | H:1 | 97 | A:14 | 215 | D:1 | 262 | C:1 |
| 51 | B:4 | 98 | B:1 | 216 | A:1 | 263 | A:6 F:1 |
| 52 | I:1 | 99 | B:4 | 217 | C:2 H:10 | 264 | A:5 C:6 I:1 |
| 53 | F:1 | 100 | B:2 | 218 | I:1 | 265 | C:8 |
| 54 | D:2 | 101 | C:3 | 219 | I:1 | 266 | C:3 |
| 55 | C:1 H:4 | 102 | C:1 | 220 | A:2 | 267 | B:1 |
| 56 | F:6 | 103 | B:2 | 221 | H:1 | 268 | F:15 K:3 |
| 57 | F:1 | 104 | C:1 | 222 | B:1 | 269 | D:1 |
| 58 | H:1 | 105 | C:1 | 223 | B:1 | 270 | D:1 |
| 59 | B:1 | 106 | I:1 | 224 | B:3 | 271 | A:1 B:3 |
| 60 | B:1 | 107 | C:1 | 225 | K:2 | 272 | C:1 H:3 |
| 61 | F:1 | 108 | K:2 | 226 | H:1 | 273 | I:2 |
| 62 | F:1 | 109 | F:1 K:1 | 227 | F:1 K:14 | 274 | D:1 |
| 63 | H:3 | 110 | K:2 | 228 | B:3 | 275 | C:2 H:4 K:1 |
| 64 | F:3 | 111 | A:1 C:10 K:1 | 229 | A:4 | 276 | A:1 |
| 65 | F:11 K:5 | 112 | H:3 | 230 | C:1 | 277 | H:6 |
| 66 | H:1 | 113 | I:1 | 231 | H:2 | 278 | A:1 |
| 67 | K:2 | 114 | A:9 | 232 | A:1 I:10 | 279 | F:3 |
| 68 | F:2 | 115 | C:3 | 233 | F:1 | 280 | A:4 C:1 F:1 J:1 |
| 69 | J:1 | 116 | A:1 | 234 | A:1 | 281 | K:1 |
| 70 | B:2 | 117 | C:1 I:1 | 235 | I:5 | 282 | A:1 |
| 118 | A:6 | 164 | A:1 | 236 | F:1 K:1 | 283 | C:2 I:1 |
| 119 | C:5 | 165 | K:7 | 237 | F:1 K:1 | 284 | F:10 |
| 120 | H:4 | 166 | A:1 | 238 | F:6 K:1 | 285 | F:2 |
| 121 | F:1 | 167 | F:2 K:2 | 239 | H:3 I:1 | 286 | F:1 |
| 122 | H:1 | 168 | K:1 | 240 | K:1 | 287 | F:3 K:2 |
| 123 | K:2 | 169 | B:1 | 241 | A:2 | 288 | K:1 |
| 124 | F:1 | 170 | B:2 D:1 | 242 | I:2 | 289 | F:1 |
| 125 | K:3 | 171 | D:1 | 243 | J:18 | 290 | F:1 |
| 126 | A:1 | 172 | H:3 | 244 | A:1 | 291 | H:1 |
| 127 | H:2 | 173 | F:11 K:9 | 245 | A:1 | 292 | K:3 |
| 128 | A:2 B:13 | 174 | A:5 H:1 | 246 | B:1 | 293 | A:2 F:1 |
| 129 | A:1 | 175 | A:2 D:2 | 247 | F:1 | 294 | F:1 |
| 130 | A:1 | 176 | A:8 | 248 | B:3 | 295 | A:1 |
| 131 | H:1 | 177 | A:1 | 249 | C:3 | 296 | K:1 |
| 132 | A:1 H:1 | 178 | H:3 | 250 | K:1 | 297 | A:2 |
| 133 | F:1 | 179 | F:6 K:1 | 251 | F:1 | 298 | C:8 |
| 134 | A:5 | 180 | A:5 | 252 | F:2 | 299 | F:1 |
| 135 | A:50 B:35 C:24 D:12 F:4 H:29 J:1 K:1 | 181 | A:5 B:3 C:128 H:15 | 253 | F:2 K:4 | 300 | A:2 |
| 136 | C:2 | 182 | C:9 | 254 | A:2 | 301 | I:3 |
| 137 | F:6 K:2 | 183 | E:1 | 255 | D:1 | 302 | F:1 K:2 |
| 138 | F:2 | 184 | F:1 | 256 | B:1 | 303 | B:1 F:1 I:1 |
| 139 | A:1 F:7 K:3 | 185 | I:1 K:1 | 257 | A:1 | 304 | A:31 B:6 F:3 K:2 |
| 140 | A:4 B:5 | 186 | B:2 | 305 | H:1 I:6 | 352 | A:1 |
| 141 | K:1 | 187 | A:1 C:1 F:1 | 306 | A:2 B:3 | 353 | D:1 |
| 142 | K:1 | 188 | A:1 | 307 | K:1 | 354 | A:1 |
| 143 | K:1 | 189 | B:1 | 308 | D:1 | 355 | B:1 |
| 144 | F:4 | 190 | A:6 | 309 | A:1 | 356 | F:1 K:6 |
| 145 | F:1 | 191 | I:1 | 310 | K:1 | 357 | B:1 |
| 146 | D:1 F:1 | 192 | K:1 | 311 | C:1 | 358 | A:1 |
| 147 | A:1 | 193 | A:1 | 312 | K:1 | 359 | H:1 |
| 148 | C:1 | 194 | A:1 | 313 | A:1 C:6 | 360 | D:1 |
| 149 | A:1 K:1 | 195 | A:1 | 314 | K:1 | 361 | K:5 |
| 150 | H:2 | 196 | C:1 | 315 | A:1 | 362 | A:1 |
| 151 | F:1 K:3 | 197 | A:1 | 316 | A:1 | 363 | A:1 |
| 152 | A:4 | 198 | A:1 | 317 | D:1 | 364 | F:8 K:1 |
| 153 | B:5 H:1 | 199 | H:3 | 318 | A:11 | 365 | F:6 K:25 |
| | | 200 | A:6 B:10 C:7 D:3 F:8 H:3 K:14 | 319 | F:2 | 366 | A:1 |
| | | | | 320 | H:3 | 367 | D:1 |
| 154 | K:1 | 201 | C:1 | 321 | K:1 | 368 | H:3 |
| 155 | F:5 K:2 | 202 | K:1 | 322 | K:1 | 369 | C:1 |
| 156 | B:1 | 203 | H:2 | 323 | K:1 | 370 | B:1 C:2 D:1 H:6 |
| 157 | K:1 | 204 | I:2 | 324 | A:4 | 371 | B:1 |
| 158 | A:5 | 205 | K:1 | 325 | H:1 | 372 | B:1 |
| 159 | C:34 | 206 | I:4 | 326 | K:1 | 373 | K:1 |
| 160 | C:1 K:1 | 207 | A:1 F:1 H:1 | 327 | A:1 | 374 | H:1 |

TABLE V-continued (Spatial distribution)

| Seq Id No. | Tissue distribution | Seq Id No. | Tissue distribution |
|---|---|---|---|
| 328 | A:7 C:1 | 375 | K:1 |
| 329 | K:1 | 376 | F:2 K:2 |
| 330 | F:2 I:1 | 377 | I:1 |
| 331 | K:1 | 378 | F:1 |
| 332 | K:1 | 379 | A:1 |
| 333 | I:1 | 380 | K:2 |
| 334 | H:1 | 381 | H:1 K:1 |
| 335 | F:1 | 382 | H:1 |
| 336 | B:1 | 383 | B:4 |
| 337 | H:2 | 384 | F:1 |
| 338 | B:3 H:1 | 385 | C:1 |
| 339 | A:1 | 386 | C:1 |
| 340 | K:1 | 387 | F:1 K:7 |
| 341 | B:5 | 388 | C:1 |
| 342 | A:1 K:1 | 389 | C:1 |
| 343 | A:1 | 390 | B:1 |
| 344 | H:2 I:1 | 391 | F:1 |
| 345 | K:1 | 392 | I:1 |
| 346 | F:8 | 393 | C:1 |
| 347 | D:1 K:2 | 394 | C:1 |
| 348 | A:1 B:1 | 395 | I:1 |
| 349 | B:3 H:2 | 396 | H:7 |
| 350 | F:1 | 397 | I:1 |
| 351 | B:1 | 398 | I:1 |
| 399 | I:1 | 446 | C:1 |
| 400 | F:1 | 447 | D:1 |
| 401 | B:1 | 448 | K:1 |
| 402 | B:1 | 449 | H:1 I:3 |
| 403 | C:1 | 450 | C:1 |
| 404 | C:1 | 451 | F:2 |
| 405 | B:1 | 452 | D:1 |
| 406 | I:1 | 453 | B:1 |
| 407 | B:2 | 454 | B:1 |
| 408 | B:1 | 455 | D:1 |
| 409 | I:1 | 456 | D:1 |
| 410 | B:1 | 457 | D:1 |
| 411 | F:1 | 458 | D:1 |
| 412 | F:1 | 459 | A:6 |
| 413 | B:1 | 460 | C:2 |
| 414 | F:1 | 461 | F:1 |
| 415 | I:1 | 462 | F:1 |
| 416 | F:1 | 463 | D:1 |
| 417 | C:1 | 464 | F:1 |
| 418 | F:2 K:2 | 465 | F:1 |
| 419 | I:1 | 466 | F:1 |
| 420 | D:1 | 467 | D:2 |
| 421 | D:1 | 468 | F:1 |
| 422 | H:1 | 469 | A:1 |
| 423 | D:1 | 470 | F:1 K:1 |
| 424 | K:1 | 471 | F:1 |
| 425 | D:1 | 472 | F:1 K:3 |
| 426 | F:17 K:3 | 473 | I:4 |
| 427 | I:3 | 474 | A:1 |
| 428 | D:1 | 475 | K:1 |
| 429 | I:1 | 476 | A:1 |
| 430 | D:1 | 477 | C:1 |
| 431 | D:1 | 478 | A:1 |
| 432 | D:1 | 479 | A:1 |
| 433 | F:1 | 480 | B:3 |
| 434 | D:1 | 481 | A:1 |
| 435 | B:1 | 482 | F:1 |
| 436 | D:1 | 483 | D:1 |
| 437 | D:1 | 484 | K:1 |
| 438 | F:1 | 485 | K:1 |
| 439 | K:4 | 486 | A:1 |
| 440 | K:4 | 487 | A:1 |
| 441 | F:1 | 488 | A:1 |
| 442 | B:1 | 489 | A:1 |
| 443 | D:1 | 490 | A:1 |
| 444 | D:1 | 491 | D:1 |
| 445 | D:1 | 492 | A:1 |
| 493 | A:1 | 540 | A:1 |
| 494 | K:1 | 541 | A:1 |

TABLE V-continued (Spatial distribution)

| Seq Id No. | Tissue distribution | Seq Id No. | Tissue distribution |
|---|---|---|---|
| 495 | D:1 | 542 | K:1 |
| 496 | B:1 | 543 | A:1 |
| 497 | A:1 | 544 | K:1 |
| 498 | A:1 | 545 | A:1 |
| 499 | A:1 | 546 | A:1 |
| 500 | B:1 | 547 | A:1 |
| 501 | K:1 | 548 | K:1 |
| 502 | A:1 | 549 | A:1 |
| 503 | A:1 | 550 | A:1 |
| 504 | A:2 | 551 | A:1 |
| 505 | B:1 | 552 | A:1 |
| 506 | A:1 | 553 | K:1 |
| 507 | A:1 | 554 | A:1 |
| 508 | A:1 | 555 | A:1 |
| 509 | B:1 | 556 | K:1 |
| 510 | D:1 | 557 | A:1 |
| 511 | A:1 | 558 | A:1 |
| 512 | K:1 | 559 | K:1 |
| 513 | F:1 K:1 | 560 | B:1 |
| 514 | A:1 | 561 | A:1 F:2 H:1 |
| 515 | K:1 | 562 | K:4 |
| 516 | K:1 | 563 | K:1 |
| 517 | A:1 | 564 | B:3 |
| 518 | B:1 | 565 | B:1 |
| 519 | D:1 | 566 | F:30 K:14 |
| 520 | A:1 | 567 | K:1 |
| 521 | B:3 | 568 | A:1 |
| 522 | K:1 | 569 | K:1 |
| 523 | F:1 | 570 | F:1 K:1 |
| 524 | K:1 | 571 | A:4 K:1 |
| 525 | A:1 | 572 | F:1 |
| 526 | K:1 | 573 | H:3 |
| 527 | K:1 | 574 | A:2 H:1 |
| 528 | F:1 | 575 | H:2 |
| 529 | A:1 | 576 | K:1 |
| 530 | F:1 | 577 | B:1 |
| 531 | A:1 | 578 | C:1 F:9 |
| 532 | K:1 | 579 | F:5 K:22 |
| 533 | A:1 | 580 | B:1 |
| 534 | A:1 | 581 | C:5 |
| 535 | K:1 | 582 | A:5 C:20 H:1 K:1 |
| 536 | F:1 | 583 | K:1 |
| 537 | A:1 | 584 | D:2 |
| 538 | A:1 | 585 | H:2 |
| 539 | K:1 | 586 | F:4 K:4 |
| 587 | K:1 | 634 | A:3 |
| 588 | A:2 | 635 | K:1 |
| 589 | A:1 D:1 | 636 | A:2 |
| 590 | H:1 | 637 | H:3 |
| 591 | F:3 K:2 | 638 | F:1 |
| 592 | K:1 | 639 | F:1 |
| 593 | A:3 | 640 | F:1 |
| 594 | K:1 | 641 | K:1 |
| 595 | B:1 | 642 | A:6 F:9 K:1 |
| 596 | H:1 | 643 | B:1 |
| 597 | F:2 K:3 | 644 | B:1 C:1 |
| 598 | B:1 | 645 | F:8 K:1 |
| 599 | K:2 | 646 | F:8 K:3 |
| 600 | K:1 | 647 | A:1 |
| 601 | K:1 | 648 | F:1 |
| 602 | C:1 | 649 | A:7 |
| 603 | K:1 | 650 | F:5 K:1 |
| 604 | K:1 | 651 | C:10 |
| 605 | H:1 | 652 | I:4 |
| 606 | A:1 F:1 | 653 | F:1 |
| 607 | K:1 | 654 | C:1 |
| 608 | A:1 | 655 | A:13 B:1 |
| 609 | A:1 | 656 | C:1 |
| 610 | A:1 | 657 | K:4 |
| 611 | I:4 | 658 | F:1 |
| 612 | K:1 | 659 | K:1 |
| 613 | C:1 F:1 H:14 | 660 | K:1 |
| 614 | A:1 | 661 | I:1 K:1 |

TABLE V-continued

(Spatial distribution)

| Seq Id No. | Tissue distribution | Seq Id No. | Tissue distribution |
|---|---|---|---|
| 615 | K:1 | 662 | B:4 H:2 K:1 |
| 616 | A:1 | 663 | H:2 |
| 617 | K:2 | 664 | K:1 |
| 618 | H:1 | 665 | F:1 |
| 619 | H:1 | 666 | K:2 |
| 620 | H:1 | 667 | A:3 |
| 621 | A:1 | 668 | F:1 |
| 622 | A:2 | 669 | A:6 |
| 623 | H:1 | 670 | F:1 |
| 624 | H:2 | 671 | C:3 K:1 |
| 625 | A:2 | 672 | H:3 |
| 626 | B:1 C:1 | 673 | A:1 |
| 627 | A:5 B:2 | 674 | F:7 K:1 |
| 628 | K:1 | 675 | F:1 |
| 629 | K:1 | 676 | K:1 |
| 630 | K:2 | 677 | A:3 |
| 631 | K:1 | 678 | H:1 |
| 632 | C:4 | 679 | A:1 |
| 633 | A:11 | 680 | H:1 |
| 681 | H:1 | 728 | A:1 C:1 |
| 682 | F:4 | 729 | K:1 |
| 683 | F:2 K:19 | 730 | A:2 I:1 |
| 684 | K:1 | 731 | A:2 B:2 C:9 D:2 F:1 H:2 K:2 |
| 685 | B:1 | 732 | H:3 |
| 686 | C:35 I:2 | 733 | H:1 |
| 687 | A:3 | 734 | K:1 |
| 688 | B:2 | 735 | K:1 |
| 689 | A:1 C:1 H:2 | 736 | C:1 |
| 690 | K:2 | 737 | K:1 |
| 691 | H:1 | 738 | B:1 |
| 692 | A:3 | 739 | A:2 B:1 C:2 D:4 |
| 693 | B:1 | 740 | B:1 J:1 |
| 694 | C:7 | 741 | J:1 |
| 695 | C:1 | 742 | B:7 C:2 H:2 |
| 696 | B:1 | 743 | C:1 |
| 697 | A:2 B:11 C:9 D:2 E:1 F:2 H:4 I:1 | 744 | A:1 |
| 698 | K:1 | 745 | K:1 |
| 699 | H:1 | 746 | F:1 |
| 700 | K:1 | 747 | F:1 |
| 701 | A:1 | 748 | K:1 |
| 702 | B:1 F:1 | 749 | F:1 |
| 703 | F:1 K:1 | 750 | F:1 |
| 704 | B:1 F:3 | 751 | F:1 |
| 705 | F:10 K:8 | 752 | B:1 |
| 706 | B:2 C:8 H:4 K:3 | 753 | B:2 |
| 707 | F:1 | 754 | F:1 H:1 I:2 |
| 708 | B:1 | 755 | B:1 |
| 709 | K:1 | 756 | H:1 |
| 710 | D:2 | 757 | A:1 C:1 |
| 711 | K:1 | 758 | H:3 |
| 712 | A:4 | 759 | K:1 |
| 713 | B:1 | 760 | F:1 K:1 |
| 714 | B:3 C:1 F:4 K:1 | 761 | K:1 |
| 715 | F:24 K:7 | 762 | H:1 |
| 716 | I:1 | 763 | H:1 |
| 717 | H:1 | 764 | C:3 |
| 718 | A:4 | 765 | H:1 |
| 719 | A:1 B:4 C:1 | 766 | B:1 |
| 720 | F:2 H:1 I:1 K:1 | 767 | C:1 |
| 721 | A:2 | 768 | A:2 B:3 C:4 E:1 I:1 K:3 |
| 722 | K:5 | 769 | A:29 |
| 723 | B:1 | 770 | H:1 |
| 724 | D:1 | 771 | C:2 H:1 |
| 725 | B:3 | 772 | H:1 |
| 726 | F:2 | 773 | I:3 |
| 727 | H:3 | 774 | A:8 |
| 775 | F:1 K4 | 821 | H:1 |
| 776 | B:1 | 822 | K:1 |
| 777 | B:6 C:1 H:2 | 823 | H:1 |
| 778 | B:2 C:1 D:1 F:9 H:2 K:15 | 824 | K:2 |
| 779 | A:1 | 825 | H:1 |
| 780 | B:4 C:11 D:1 H:2 | 826 | A:1 B:1 |
| 781 | F:1 K:7 | 827 | H:4 |
| 782 | B:1 | 828 | B:1 |
| 783 | A:1 D:1 | 829 | K:1 |
| 784 | K:1 | 830 | B:1 |
| 785 | K:1 | 831 | A:1 |
| 786 | B:2 D:1 K:1 | 832 | C:8 J:1 |
| 787 | I:2 | 833 | D:1 |
| 788 | F:10 K:8 | 834 | B:2 F:1 |
| 789 | K:1 | 835 | K:1 |
| 790 | A:13 B:17 C:30 D:10 F:9 H:75 I:1 J:1 K:13 | 836 | C:2 |
| 791 | F:1 | 837 | K:1 |
| 792 | F:1 K:1 | 838 | K:1 |
| 793 | C:3 | 839 | C:1 F:3 K:3 |
| 794 | H:1 | 840 | I:1 |
| 795 | C:1 H:11 | 841 | H:1 |
| 796 | A:2 | 842 | D:1 H:1 |
| 797 | A:1 B:8 C:9 D:1 H:4 J:2 | 843 | D:1 F:1 |
| 798 | K:5 | 844 | B:1 F:1 |
| 799 | H:1 | 845 | B:1 |
| 800 | A:1 F:5 H:1 K:2 | 846 | F:8 K:7 |
| 801 | K:1 | 847 | A:1 |
| 802 | K:2 | 848 | A:1 H:2 K:1 |
| 803 | F:3 K:2 | 849 | F:9 K:1 |
| 804 | F:3 K:1 | 850 | H:2 |
| 805 | K:3 | 851 | F:3 |
| 806 | C:1 H:1 | 852 | H:2 |
| 807 | K:1 | 853 | K:1 |
| 808 | H:1 | 854 | B:2 H:2 I:1 |
| 809 | C:1 D:2 | 855 | F:1 K:4 |
| 810 | B:1 | 856 | F:1 K:4 |
| 811 | K:3 | 857 | F:2 K:1 |
| 812 | K:1 | 858 | F:1 |
| 813 | H:2 | 859 | F:2 |
| 814 | K:1 | 860 | F:1 K:1 |
| 815 | A:5 B:3 | 861 | F:11 K:6 |
| 816 | H:1 | 862 | C:6 F:1 |
| 817 | B:9 | 863 | H:1 |
| 818 | A:3 B:6 C:21 D:1 F:1 H:2 J:1 K:1 | 864 | A:1 B:5 |
| 819 | A:4 B:6 C:26 D:2 F:2 H:4 J:1 K:1 | 865 | K:7 |
| 820 | H:4 | 866 | K:1 |
| 868 | A:13 | 867 | A:13 |
| 869 | K:1 | 915 | H:3 |
| 870 | K:1 | 916 | C:1 |
| 871 | B:3 | 917 | H:2 |
| 872 | K:1 | 918 | C:8 |
| 873 | A:8 B:34 C:14 D:2 H:5 | 919 | C:12 |
| 874 | C:1 | 920 | H:1 |
| 875 | K:1 | 921 | B:2 C:1 |
| 876 | K:1 | 922 | K:1 |
| 877 | H:1 | 923 | B:2 |
| 878 | H:4 | 924 | F:1 K:1 |
| 879 | F:1 | 925 | F:6 K:4 |
| 880 | A:5 | 926 | K:3 |
| 881 | A:26 B:5 C:4 D:1 F:1 H:13 I:1 | 927 | K:1 |
| 882 | A:2 | 928 | K:1 |
| 883 | A:3 H:3 | 929 | A:1 B:3 D:1 K:3 |
| 884 | H:1 | 930 | I:2 |
| 885 | A:5 | 931 | H:2 I:1 |
| 886 | K:4 | 932 | B:3 |
| 887 | F:1 K:1 | 933 | A:1 B:2 K:2 |
| 888 | A:1 H:3 | 934 | C:1 |
| 889 | D:1 | 935 | H:1 |
| 890 | F:3 | 936 | F:1 K:1 |
| 891 | H:1 | 937 | A:12 B:6 C:10 F:1 H:2 |
| 892 | F:5 K:2 | 938 | H:4 |
| 893 | I:2 | 939 | C:21 |
| 894 | D:2 F:3 H:2 K:3 | 940 | C:21 |
| 895 | K:1 | 941 | K:2 |
|  |  | 942 | K:2 |

TABLE V-continued

(Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 896 | K:1 | 943 | F:2 K:1 | 1063 | K:1 | 1109 | K:2 |
| 897 | K:2 | 944 | H:1 I:1 | 1064 | K:1 | 1110 | K:1 |
| 898 | H:4 | 945 | F:7 K:2 | 1065 | F:1 K:2 | 1111 | H:1 |
| 899 | J:1 | 946 | B:3 | 1066 | K:1 | 1112 | H:1 |
| 900 | H:1 | 947 | C:1 | 1067 | K:1 | 1113 | A:6 |
| 901 | H:1 | 948 | B:1 | 1068 | K:1 | 1114 | K:1 |
| 902 | B:3 | 949 | F:11 K:6 | 1069 | F:1 | 1115 | H:1 |
| 903 | K:1 | 950 | H:3 | 1070 | K:1 | 1116 | K:1 |
| 904 | F:4 | 951 | F:2 K:1 | 1071 | F:2 K:15 | 1117 | K:1 |
| 905 | F:2 K:7 | 952 | F:3 | 1072 | K:1 | 1118 | A:1 |
| 906 | K:2 | 953 | B:1 F:1 K:3 | 1073 | K:1 | 1119 | H:2 |
| 907 | A:5 | 954 | I:2 | 1074 | A:3 H:7 | 1120 | D:1 F:4 |
| 908 | F:1 K:1 | 955 | D:1 F:1 | 1075 | B:3 | 1121 | H:1 |
| 909 | A:15 B:11 C:7 H:4 K:1 | 956 | F:1 H:1 K:1 | 1076 | B:2 | 1122 | D:1 H:1 |
| 910 | A:2 B:5 C:2 H:2 K:1 | 957 | A:1 B:2 F:3 H:1 | 1077 | K:1 | 1123 | F:1 K:2 |
| 911 | A:3 K:2 | 958 | A:2 | 1078 | K:2 | 1124 | A:4 B:1 C:6 F:7 H:2 K:9 |
| 912 | H:1 | 959 | F:5 K:5 | 1079 | A:14 B:1 | 1125 | F:5 K:1 |
| 913 | B:2 H:2 | 960 | K:3 | 1080 | K:1 | 1126 | K:1 |
| 914 | A:1 | 961 | F:8 K:3 | 1081 | F:2 K:1 | 1127 | A:1 |
| 962 | I:3 | 1009 | A:1 | 1082 | H:5 | 1128 | F:1 K:1 |
| 963 | B:1 H:1 | 1010 | A:1 | 1083 | A:2 B:3 H:1 | 1129 | H:1 |
| 964 | K:1 | 1011 | A:1 | 1084 | H:1 K:1 | 1130 | F:1 |
| 965 | C:1 | 1012 | A:1 | 1085 | A:3 B:1 H:1 K:1 | 1131 | D:1 |
| 966 | C:15 | 1013 | A:1 | 1086 | A:1 | 1132 | K:2 |
| 967 | B:1 | 1014 | B:1 | 1087 | B:1 | 1133 | F:1 |
| 968 | A:9 D:1 | 1015 | B:1 | 1088 | A:10 B:21 C:18 D:11 E:2 F:3 H:12 I:5 J:2 | 1134 | F:1 K:2 |
| 969 | F:4 | 1016 | B:1 | 1089 | A:2 B:28 C:5 F:1 I:2 K:3 | 1135 | A:3 I:5 |
| 970 | K:1 | 1017 | B:1 | 1090 | C:15 J:2 | 1136 | K:1 |
| 971 | D:1 H:1 | 1018 | B:1 | 1091 | F:1 K:24 | 1137 | B:2 C:1 H:1 |
| 972 | A:5 F:1 | 1019 | B:1 | 1092 | C:2 | 1138 | B:1 |
| 973 | A:4 K:3 | 1020 | A:1 | 1093 | K:4 | 1139 | H:1 |
| 974 | C:2 | 1021 | A:1 | 1094 | A:1 F:6 K:11 | 1140 | H:1 K:1 |
| 975 | H:2 | 1022 | A:1 | 1095 | H:1 | 1141 | A:5 |
| 976 | F:1 I:3 K:1 | 1023 | A:1 | 1096 | J:1 | 1142 | A:1 |
| 977 | F:2 K:4 | 1024 | B:1 | 1097 | K:6 | 1143 | D:1 |
| 978 | A:8 | 1025 | A:1 | 1098 | K:1 | 1144 | F:4 K:25 |
| 979 | B:1 F:1 K:4 | 1026 | A:1 | 1099 | K:1 | 1145 | B:2 |
| 980 | A:1 C:1 | 1027 | B:1 | 1100 | K:1 | 1146 | F:1 K:1 |
| 981 | H:5 | 1028 | A:1 | 1101 | K:1 | 1147 | D:2 |
| 982 | H:1 | 1029 | A:1 | 1149 | B:4 | 1148 | B:1 I:1 |
| 983 | H:1 | 1030 | B:2 H:7 I:1 | 1150 | K:1 | 1194 | B:1 |
| 984 | F:4 | 1031 | B:1 C:1 H:8 I:8 | 1151 | A:2 H:3 | 1195 | F:2 K:2 |
| 985 | K:2 | 1032 | K:3 | 1152 | H:1 | 1196 | F:6 H:2 K:1 |
| 986 | K:1 | 1033 | B:3 | 1153 | K:1 | 1197 | A:1 B:2 H:2 |
| 987 | H:2 | 1034 | A:1 | 1154 | A:1 | 1198 | H:2 |
| 988 | K:4 | 1035 | K:2 | 1155 | H:1 | 1199 | H:1 |
| 989 | B:6 K:1 | 1036 | K:3 | 1156 | A:4 | 1200 | F:1 K:2 |
| 990 | K:1 | 1037 | K:3 | 1157 | K:6 | 1201 | H:1 |
| 991 | K:1 | 1038 | F:2 | 1158 | C:4 H:1 | 1202 | K:2 |
| 992 | A:1 D:1 | 1039 | H:1 | 1159 | K:1 | 1203 | F:4 K:19 |
| 993 | F:7 K:5 | 1040 | C:9 | 1160 | B:1 C:1 D:1 K:1 | 1204 | F:4 K:16 |
| 994 | F:6 K:21 | 1041 | K:1 | 1161 | B:1 | 1205 | K:1 |
| 995 | H:1 | 1042 | I:2 | 1162 | D:1 | 1206 | C:1 |
| 996 | H:1 | 1043 | A:1 C:1 H:1 I:2 | 1163 | C:1 | 1207 | A:10 B:3 |
| 997 | H:1 | 1044 | B:2 | 1164 | A:1 | 1208 | B:6 C:1 |
| 998 | C:2 | 1045 | A:2 | 1165 | B:1 | 1209 | B:8 C:1 |
| 999 | H:1 | 1046 | A:1 | 1166 | B:1 | 1210 | B:1 C:2 F:33 H:1 K:19 |
| 1000 | H:1 | 1047 | K:1 | 1167 | J:1 | 1211 | K:1 |
| 1001 | B:1 | 1048 | C:1 H:1 I:1 | 1168 | H:1 | 1212 | F:1 |
| 1002 | C:6 D:1 H:1 J:6 | 1049 | F:1 | 1169 | H:1 | 1213 | H:1 |
| 1003 | F:13 K:1 | 1050 | H:1 | 1170 | C:17 | 1214 | K:2 |
| 1004 | F:1 K:1 | 1051 | F:13 K:4 | 1171 | A:1 | 1215 | C:12 I:3 |
| 1005 | A:1 B:1 | 1052 | H:1 | 1172 | J:53 | 1216 | K:2 |
| 1006 | B:4 | 1053 | D:1 | 1173 | F:2 K:2 | 1217 | B:2 C:1 |
| 1007 | A:1 | 1054 | F:7 K:1 | 1174 | F:8 K:1 | 1218 | F:1 |
| 1008 | A:1 | 1055 | H:7 | 1175 | H:2 | 1219 | F:1 |
| 1056 | F:3 K2 | 1102 | H:1 | 1176 | B:1 | 1220 | A:1 |
| 1057 | H:1 | 1103 | F:1 | 1177 | F:2 K:1 | 1221 | C:3 |
| 1058 | K:3 | 1104 | F:1 | 1178 | F:4 | 1222 | K:1 |
| 1059 | B:3 | 1105 | K:1 | 1179 | F:7 K:2 | 1223 | C:1 |
| 1060 | B:1 | 1106 | K:1 | 1180 | F:5 K:39 | 1224 | I:1 |
| 1061 | C:1 H:1 | 1107 | A:5 F:2 | 1181 | A:2 F:2 H:1 K:13 | 1225 | H:1 |
| 1062 | F:4 K:11 | 1108 | K:1 | | | 1226 | J:1 |

TABLE V-continued
(Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 1182 | K:6 | 1227 | B:1 | 1345 | B:59 C:47 D:2 H:20 I:2 J:3 | 1392 | H:3 |
| 1183 | H:1 | 1228 | F:5 K:1 | 1346 | B:17 C:22 D:2 H:14 J:4 K:1 | 1393 | B:2 |
| 1184 | F:1 | 1229 | K:3 | 1347 | D:3 F:3 H:1 K:1 | 1394 | B:1 |
| 1185 | A:1 B:3 C:12 D:1 F:3 H:3 I:1 K:12 | 1230 | B:2 | 1348 | D:3 F:2 | 1395 | H:2 |
| 1186 | A:17 B:42 C:27 D:11 F:5 H:29 I:2 J:11 K:2 | 1231 | F:7 | 1349 | C:1 | 1396 | K:1 |
|  |  | 1232 | H:1 | 1350 | I:1 | 1397 | F:7 K:1 |
| 1187 | A:1 B:3 C:1 H:1 | 1233 | F:1 K:1 | 1351 | K:1 | 1398 | C:5 H:1 |
| 1188 | C:4 F:1 | 1234 | A:1 K:1 | 1352 | B:1 | 1399 | F:1 |
| 1189 | C:4 K:1 | 1235 | F:1 | 1353 | D:1 | 1400 | H:1 |
| 1190 | B:9 K:1 | 1236 | A:6 B:1 C:1 D:2 | 1354 | H:1 | 1401 | H:1 |
| 1191 | F:5 K:2 | 1237 | A:2 C:17 D:1 | 1355 | F:1 K:6 | 1402 | F:2 |
| 1192 | K:2 | 1238 | F:2 K:4 | 1356 | K:3 | 1403 | B:2 H:3 |
| 1193 | F:1 K:1 | 1239 | A:5 | 1357 | H:4 | 1404 | D:2 |
| 1241 | K:1 | 1240 | F:1 K:3 | 1358 | C:13 | 1405 | H:5 |
| 1242 | H:1 | 1287 | C:5 | 1359 | D:2 | 1406 | K:4 |
| 1243 | A:2 B:3 | 1288 | C:1 | 1360 | F:4 | 1407 | F:5 K:1 |
| 1244 | K:1 | 1289 | C:3 H:1 | 1361 | K:2 | 1408 | A:3 B:8 C:15 |
| 1245 | B:4 C:27 | 1290 | K:5 | 1362 | F:24 K:8 | 1409 | C:32 H:1 |
| 1246 | C:4 | 1291 | K:1 | 1363 | F:2 K:2 | 1410 | C:2 |
| 1247 | B:3 | 1292 | B:1 | 1364 | F:1 K:1 | 1411 | K:1 |
| 1248 | A:3 B:1 D:1 K:3 | 1293 | K:2 | 1365 | F:1 K:3 | 1412 | B:1 H:3 |
| 1249 | H:1 | 1294 | H:1 | 1366 | I:18 | 1413 | H:1 |
| 1250 | F:31 K:11 | 1295 | C:1 H:3 I:4 | 1367 | C:2 D:1 I:1 | 1414 | D:1 |
| 1251 | A:18 B:24 C:32 F:43 H:49 I:32 J:1 K:17 | 1296 | A:6 H:3 I:3 | 1368 | C:2 | 1415 | A:75 B:75 C:94 D:36 E:1 F:13 H:33 I:1 J:1 K:22 |
|  |  | 1297 | H:1 | 1369 | D:1 H:2 |  |  |
| 1252 | A:4 B:4 C:7 F:21 H:24 I:9 K:7 | 1298 | A:1 B:2 F:1 | 1370 | H:1 | 1416 | A:2 C:128 H:5 |
|  |  | 1299 | B:1 C:1 | 1371 | A:2 | 1417 | J:2 |
| 1253 | A:2 B:2 C:3 F:8 H:7 I:2 K:4 | 1300 | D:1 F:3 H:1 | 1372 | K:1 | 1418 | A:2 B:3 C:1 |
| 1254 | A:1 | 1301 | A:1 F:7 H:6 I:2 K:2 | 1373 | C:1 | 1419 | C:30 J:2 K:2 |
| 1255 | C:1 | 1302 | H:4 I:10 | 1374 | K:1 | 1420 | I:4 |
| 1256 | C:1 | 1303 | B:5 D:1 H:1 | 1375 | F:1 K:2 | 1421 | B:1 F:3 K:5 |
| 1257 | A:1 | 1304 | F:1 K:3 | 1376 | A:2 | 1422 | K:2 |
| 1258 | F:3 K:2 | 1305 | I:2 | 1377 | D:6 F:21 | 1423 | D:1 |
| 1259 | F:4 K:3 | 1306 | A:1 B:1 H:2 | 1378 | K:2 | 1424 | H:1 |
| 1260 | A:2 B:1 C:1 D:3 H:1 K:5 | 1307 | F:3 | 1379 | F:3 | 1425 | A:2 |
| 1261 | F:36 K:15 | 1308 | A:2 H:1 I:2 | 1380 | H:1 | 1426 | A:1 B:1 |
| 1262 | K:3 | 1309 | B:1 | 1427 | H:1 | 1474 | D:1 |
| 1263 | D:1 | 1310 | C:1 | 1428 | A:1 | 1475 | A:1 |
| 1264 | H:6 | 1311 | B:2 | 1429 | K:1 | 1476 | D:1 |
| 1265 | A:1 F:1 | 1312 | F:12 H:2 K:12 | 1430 | I:4 | 1477 | C:2 |
| 1266 | H:1 | 1313 | F:1 K:1 | 1431 | K:2 | 1478 | A:3 D:4 |
| 1267 | F:2 K:6 | 1314 | A:1 D:1 K:1 | 1432 | B:1 K:4 | 1479 | K:1 |
| 1268 | F:8 K:8 | 1315 | K:1 | 1433 | C:1 | 1480 | A:10 H:1 |
| 1269 | K:2 | 1316 | H:1 | 1434 | F:3 | 1481 | A:1 |
| 1270 | F:1 K:2 | 1317 | A:1 | 1435 | C:9 | 1482 | A:1 |
| 1271 | F:1 | 1318 | C:2 | 1436 | K:1 | 1483 | K:12 |
| 1272 | F:1 | 1319 | H:4 | 1437 | F:1 K:2 | 1484 | C:3 |
| 1273 | K:2 | 1320 | K:1 | 1438 | K:1 | 1485 | A:2 B:9 |
| 1274 | K:1 | 1321 | C:1 D:1 H:1 | 1439 | H:1 | 1486 | B:1 |
| 1275 | A:7 | 1322 | F:1 | 1440 | A:1 H:1 | 1487 | A:2 B:1 C:5 |
| 1276 | F:3 | 1323 | F:1 | 1441 | F:1 | 1488 | B:5 |
| 1277 | K:2 | 1324 | K:1 | 1442 | B:1 | 1489 | H:2 |
| 1278 | H:1 | 1325 | K:1 | 1443 | K:1 | 1490 | F:2 K:2 |
| 1279 | B:7 | 1326 | A:9 K:1 | 1444 | F:1 | 1491 | F:2 |
| 1280 | B:1 C:6 H:1 | 1327 | B:3 C:1 H:1 | 1445 | B:1 | 1492 | D:1 |
| 1281 | B:3 | 1328 | F:1 K:1 | 1446 | F:3 K:1 | 1493 | F:1 K:1 |
| 1282 | F:4 K:5 | 1329 | F:4 K:2 | 1447 | K:2 | 1494 | A:1 |
| 1283 | F:9 K:5 | 1330 | K:2 | 1448 | K:2 | 1495 | F:9 H:1 K:1 |
| 1284 | F:2 K:1 | 1331 | H:1 | 1449 | B:1 | 1496 | B:3 |
| 1285 | J:1 | 1332 | H:1 | 1450 | B:1 | 1497 | A:10 |
| 1286 | F:6 | 1333 | H:1 | 1451 | B:1 | 1498 | K:2 |
| 1334 | H:1 | 1381 | D:1 | 1452 | B:1 | 1499 | K:1 |
| 1335 | H:1 | 1382 | K:2 | 1453 | F:3 | 1500 | F:1 |
| 1336 | H:1 | 1383 | K:1 | 1454 | C:1 D:1 H:1 | 1501 | F:1 |
| 1337 | F:2 | 1384 | F:2 K:6 | 1455 | F:3 K:4 | 1502 | B:2 |
| 1338 | H:1 | 1385 | H:1 | 1456 | B:1 | 1503 | C:1 |
| 1339 | H:6 I:1 | 1386 | C:1 D:3 F:2 | 1457 | B:1 | 1504 | C:1 |
| 1340 | D:1 | 1387 | A:1 C:1 D:1 K:2 | 1458 | A:1 H:1 | 1505 | A:1 |
| 1341 | D:1 | 1388 | C:4 | 1459 | B:1 | 1506 | K:1 |
| 1342 | D:1 | 1389 | K:4 | 1460 | F:1 | 1507 | D:1 |
| 1343 | C:48 J:1 | 1390 | A:1 | 1461 | F:2 K:3 | 1508 | B:1 |
| 1344 | D:2 | 1391 | K:4 | 1462 | H:2 | 1509 | D:1 |
|  |  |  |  | 1463 | C:2 K:1 | 1510 | C:1 |

TABLE V-continued

(Spatial distribution)

| Seq Id No. | Tissue distribution | Seq Id No. | Tissue distribution |
|---|---|---|---|
| 1464 | B:1 | 1511 | K:1 |
| 1465 | A:1 B:5 C:1 F:3 H:2 | 1512 | K:1 |
| 1466 | A:2 | 1513 | I:4 |
| 1467 | D:1 | 1514 | H:1 |
| 1468 | K:2 | 1515 | H:3 |
| 1469 | K:1 | 1516 | C:36 |
| 1470 | A:3 | 1517 | H:3 I:1 K:1 |
| 1471 | F:4 K:1 | 1518 | B:1 |
| 1472 | A:5 D:4 | 1519 | A:1 C:18 D:1 |
| 1473 | H:2 | 1520 | A:1 |
| 1521 | H:5 | 1568 | A:1 |
| 1522 | F:1 H:15 | 1569 | K:7 |
| 1523 | A:1 | 1570 | F:1 K:2 |
| 1524 | A:3 | 1571 | A:2 |
| 1525 | D:3 | 1572 | C:1 |
| 1526 | A:12 F:1 H:12 | 1573 | A:1 |
| 1527 | B:3 | 1574 | C:2 |
| 1528 | D:1 | 1575 | C:2 |
| 1529 | J:1 | 1576 | H:1 |
| 1530 | F:1 J:25 K:1 | 1577 | D:1 |
| 1531 | B:1 | 1578 | H:3 |
| 1532 | D:1 H:1 | 1579 | D:1 |
| 1533 | I:2 | 1580 | K:8 |
| 1534 | A:2 | 1581 | K:1 |
| 1535 | A:1 B:1 | 1582 | F:1 K:1 |
| 1536 | B:1 H:1 | 1583 | H:1 |
| 1537 | F:1 | 1584 | F:1 |
| 1538 | K:2 | 1585 | B:2 |
| 1539 | C:3 | 1586 | B:2 |
| 1540 | A:4 | 1587 | C:3 H:1 |
| 1541 | K:1 | 1588 | F:2 H:1 |
| 1542 | B:1 | 1589 | H:1 |
| 1543 | F:3 K:4 | 1590 | C:1 |
| 1544 | K:1 | 1591 | A:1 B:1 C:12 H:1 |
| 1545 | H:1 | 1592 | A:1 C:23 H:1 |
| 1546 | C:1 D:2 H:4 K:6 | 1593 | F:2 |
| 1547 | H:1 | 1594 | F:1 K:3 |
| 1548 | A:2 | 1595 | K:1 |
| 1549 | I:1 | 1596 | A:12 B:29 C:22 F:38 H:20 I:9 K:12 |
| 1550 | H:1 | 1597 | K:1 |
| 1551 | B:3 | 1598 | F:1 |
| 1552 | A:26 B:8 D:7 F:3 H:3 K:1 | 1599 | D:1 F:1 |
| 1553 | H:14 | 1600 | H:3 I:3 |
| 1554 | H:1 | 1601 | B:2 |
| 1555 | K:3 | 1602 | B:7 |
| 1556 | H:1 | 1603 | B:9 C:1 |
| 1557 | A:3 | 1604 | D:1 K:2 |
| 1558 | C:2 | 1605 | A:1 |
| 1559 | C:1 | 1606 | B:3 C:52 D:2 H:1 |
| 1560 | H:1 | 1607 | A:3 |
| 1561 | F:1 | 1608 | A:1 |
| 1562 | F:18 K:3 | 1609 | H:1 |
| 1563 | A:15 B:5 C:56 D:3 F:1 H:6 K:2 | 1610 | F:1 K:2 |
| 1564 | A:15 B:5 C:50 D:3 F:1 H:6 K:2 | | |
| 1565 | A:1 | 1611 | H:2 |
| 1566 | C:1 | 1612 | H:1 |
| 1567 | D:4 | 1613 | B:2 |
| 1614 | D:1 | 1661 | K:1 |
| 1615 | C:15 | 1662 | H:1 |
| 1616 | C:4 | 1663 | K:2 |
| 1617 | K:3 | 1664 | F:2 K:12 |
| 1618 | H:1 | 1665 | A:2 |
| 1619 | K:1 | 1666 | F:1 K:6 |
| 1620 | A:2 | 1667 | K:4 |
| 1621 | A:1 C:1 | 1668 | A:1 |
| 1622 | A:2 C:6 | 1669 | F:10 K:36 |
| 1623 | K:1 | 1670 | K:2 |
| 1624 | A:4 | 1671 | K:6 |
| 1625 | F:7 K:1 | 1672 | K:4 |
| 1626 | B:2 | 1673 | H:1 |
| 1627 | B:4 | 1674 | A:1 |
| 1628 | B:1 | 1675 | F:1 |
| 1629 | B:2 | 1676 | K:1 |
| 1630 | K:2 | 1677 | F:18 K:22 |
| 1631 | A:2 | 1678 | C:8 |
| 1632 | A:22 H:2 I:3 | 1679 | K:1 |
| 1633 | K:1 | 1680 | F:4 K:4 |
| 1634 | A:2 | 1681 | K:1 |
| 1635 | A:19 H:3 I:3 | 1682 | B:1 K:1 |
| 1636 | H:1 | 1683 | C:21 J:1 |
| 1637 | B:1 | 1684 | K:1 |
| 1638 | A:1 D:1 | 1685 | K:2 |
| 1639 | K:1 | 1686 | K:1 |
| 1640 | F:2 | 1687 | F:2 |
| 1641 | F:1 | 1688 | H:1 |
| 1642 | C:2 | 1689 | D:1 |
| 1643 | F:4 K:20 | 1690 | D:1 |
| 1644 | H:1 | 1691 | H:1 |
| 1645 | H:1 | 1692 | K:1 |
| 1646 | C:9 J:1 | 1693 | K:1 |
| 1647 | H:9 | 1694 | H:1 |
| 1648 | I:1 | 1695 | K:1 |
| 1649 | C:2 D:1 F:11 H:5 K:31 | 1696 | F:2 |
| 1650 | H:3 | 1697 | K:1 |
| 1651 | D:1 | 1698 | K:1 |
| 1652 | C:7 | 1699 | H:1 |
| 1653 | B:4 | 1700 | K:1 |
| 1654 | F:4 K:1 | 1701 | A:1 |
| 1655 | F:3 K:1 | 1702 | B:1 |
| 1656 | A:1 | 1703 | K:1 |
| 1657 | F:1 | 1704 | K:2 |
| 1658 | A:3 B:2 F:1 I:3 | 1705 | F:14 K:3 |
| 1659 | A:1 B:4 C:3 D:1 K:1 | 1706 | K:2 |
| 1660 | K:3 | 1707 | A:1 C:1 D:2 H:1 |
| 1708 | K:1 | 1755 | A:2 |
| 1709 | H:2 | 1756 | A:1 |
| 1710 | B:1 | 1757 | K:2 |
| 1711 | A:3 C:4 D:2 F:1 H:1 | 1758 | K:2 |
| 1712 | A:1 | 1759 | B:2 I:1 |
| 1713 | A:1 | 1760 | A:2 B:1 K:2 |
| 1714 | J:3 | 1761 | B:2 |
| 1715 | B:1 | 1762 | I:1 |
| 1716 | F:1 | 1763 | F:1 |
| 1717 | F:3 K:1 | 1764 | I:1 |
| 1718 | B:1 F:1 | 1765 | H:3 |
| 1719 | B:2 C:8 | 1766 | I:1 |
| 1720 | H:2 | 1767 | I:1 |
| 1721 | F:4 | 1768 | A:1 |
| 1722 | K:1 | 1769 | D:1 |
| 1723 | K:9 | 1770 | H:3 |
| 1724 | K:1 | 1771 | K:2 |
| 1725 | K:1 | 1772 | H:5 |
| 1726 | A:2 | 1773 | A:1 J:2 |
| 1727 | F:2 | 1774 | H:1 |
| 1728 | H:1 | 1775 | D:1 H:6 J:133 |
| 1729 | F:1 | 1776 | J:1 |
| 1730 | A:1 | 1777 | B:2 |
| 1731 | C:1 | 1778 | K:1 |
| 1732 | I:1 | 1779 | J:1 |
| 1733 | C:8 J:7 | 1780 | A:1 |
| 1734 | K:3 | 1781 | K:1 |
| 1735 | F:1 | 1782 | I:2 |
| 1736 | F:3 K:3 | 1783 | A:1 F:1 K:6 |
| 1737 | K:5 | 1784 | A:1 |
| 1738 | F:2 K:1 | 1785 | K:1 |
| 1739 | D:1 | 1786 | K:2 |
| 1740 | F:3 K:10 | 1787 | F:18 K:8 |
| 1741 | K:3 | 1788 | C:3 |
| 1742 | A:1 | 1789 | B:1 |
| 1743 | A:4 | 1790 | B:1 |
| 1744 | K:2 | 1791 | C:15 J:1 |
| 1745 | K:2 | 1792 | F:18 K:1 |
| 1746 | A:1 | 1793 | K:1 |
| 1747 | C:1 | 1794 | F:3 |

TABLE V-continued (Spatial distribution)

| Seq Id No. | Tissue distribution | Seq Id No. | Tissue distribution |
|---|---|---|---|
| 1748 | H:1 | 1795 | K:5 |
| 1749 | F:1 | 1796 | D:1 H:8 |
| 1750 | A:68 | 1797 | K:3 |
| 1751 | H:1 | 1798 | D:1 |
| 1752 | A:1 | 1799 | B:3 |
| 1753 | H:1 | 1800 | K:1 |
| 1754 | A:3 | 1801 | I:3 |
| 1802 | C:3 | 1849 | K:1 |
| 1803 | A:30 B:5 F:1 I:6 | 1850 | F:1 K:1 |
| 1804 | H:1 | 1851 | A:1 |
| 1805 | K:1 | 1852 | C:3 |
| 1806 | A:8 B:7 C:1 D:1 F:3 H:8 I:1 K:12 | 1853 | K:1 |
| 1807 | B:1 | 1854 | B:1 C:1 D:2 H:4 J:12 |
| 1808 | A:4 B:3 C:3 F:1 H:31 | 1855 | F:1 |
| 1809 | K:J | 1856 | A:4 B:6 H:1 K:1 |
| 1810 | J:1 | 1857 | D:1 |
| 1811 | K:1 | 1858 | K:1 |
| 1812 | H:3 | 1859 | A:3 |
| 1813 | K:1 | 1860 | F:3 K:37 |
| 1814 | K:2 | 1861 | D:1 |
| 1815 | B:2 | 1862 | F:1 K:1 |
| 1816 | B:1 | 1863 | A:5 B:5 D:4 F:2 H:1 K:9 |
| 1817 | H:1 | 1864 | H:3 |
| 1818 | F:1 K:1 | 1865 | H:1 |
| 1819 | B:8 C:10 D:1 H:4 J:2 | 1866 | C:6 I:1 |
| 1820 | F:2 | 1867 | A:8 B:36 C:13 D:7 F:1 H:1 J:1 |
| 1821 | D:1 | 1868 | D:1 |
| 1822 | A:1 F:1 I:4 K:4 | 1869 | K:2 |
| 1823 | A:1 | 1870 | B:3 |
| 1824 | K:2 | 1871 | A:1 |
| 1825 | H:1 | 1872 | K:1 |
| 1826 | H:1 | 1873 | A:3 K:3 |
| 1827 | A:1 B:2 C:3 I:2 | 1874 | F:5 K:1 |
| 1828 | F:1 K:2 | 1875 | K:4 |
| 1829 | K:1 | 1876 | K:1 |
| 1830 | I:2 | 1877 | K:3 |
| 1831 | A:1 | 1878 | F:1 |
| 1832 | A:1 | 1879 | F:1 K:1 |
| 1833 | H:2 | 1880 | B:1 |
| 1834 | D:1 | 1881 | B:1 C:5 F:1 |
| 1835 | C:5 H:2 I:3 | 1882 | F:1 |
| 1836 | A:2 | 1883 | F:1 |
| 1837 | A:1 F:4 K:1 | 1884 | A:1 B:6 |
| 1838 | C:1 | 1885 | K:1 |
| 1839 | A:9 K:1 | 1886 | K:1 |
| 1840 | H:1 | 1887 | F:5 K:1 |
| 1841 | H:1 | 1888 | I:1 |
| 1842 | C:2 | 1889 | B:1 |
| 1843 | A:1 | 1890 | D:1 |
| 1844 | D:1 | 1891 | F:1 K:4 |
| 1845 | A:1 D:4 H:9 | 1892 | B:2 |
| 1846 | A:1 | 1893 | A:2 C:2 K:1 |
| 1847 | B:2 | 1894 | K:1 |
| 1848 | A:2 | 1895 | K:1 |
| 1896 | I:1 | 1943 | C:1 |
| 1897 | A:1 | 1944 | C:1 |
| 1898 | K:1 | 1945 | B:1 C:1 D:1 H:4 J:12 |
| 1899 | A:1 | 1946 | B:1 |
| 1900 | B:2 | 1947 | C:11 |
| 1901 | K:2 | 1948 | B:1 |
| 1902 | D:1 | 1949 | B:1 |
| 1903 | D:1 | 1950 | F:3 K:2 |
| 1904 | I:2 | 1951 | H:3 |
| 1905 | F:5 | 1952 | C:1 |
| 1906 | A:1 H:1 | 1953 | K:1 |
| 1907 | A:4 | 1954 | K:1 |
| 1908 | K:1 | 1955 | C:5 |
| 1909 | K:2 | 1956 | B:1 |
| 1910 | B:1 | 1957 | B:2 |
| 1911 | K:1 | 1958 | C:1 |
| 1912 | B:1 | 1959 | F:1 |
| 1913 | A:13 | 1960 | E:1 K:2 |
| 1914 | B:2 | 1961 | A:4 H:1 |
| 1915 | C:1 | 1962 | F:3 K:1 |
| 1916 | I:1 | 1963 | B:2 D:1 K:3 |
| 1917 | H:1 | 1964 | H:3 |
| 1918 | H:3 | 1965 | F:4 K:1 |
| 1919 | B:2 | 1966 | D:1 |
| 1920 | F:1 K:2 | 1967 | H:4 |
| 1921 | A:1 | 1968 | B:3 |
| 1922 | K:1 | 1969 | B:3 |
| 1923 | K:7 | 1970 | D:2 |
| 1924 | A:1 | 1971 | A:1 F:3 K:1 |
| 1925 | B:2 | 1972 | F:18 K:6 |
| 1926 | A:1 | 1973 | A:2 B:6 C:72 D:1 F:2 H:5 J:5 K:3 |
| 1927 | A:1 | 1974 | A:15 B:3 F:2 |
| 1928 | A:1 | 1975 | I:2 |
| 1929 | B:1 | 1976 | B:3 |
| 1930 | A:10 H:1 I:1 | 1977 | B:2 |
| 1931 | E:1 | 1978 | A:4 |
| 1932 | K:1 | 1979 | A:4 |
| 1933 | A:1 | 1980 | A:2 B:1 D:1 |
| 1934 | B:2 | 1981 | H:1 |
| 1935 | A:1 | 1982 | A:2 |
| 1936 | F:1 K:7 | 1983 | C:9 |
| 1937 | C:1 | 1984 | A:1 C:15 H:1 |
| 1938 | K:1 | 1985 | F:2 |
| 1939 | C:1 | 1986 | A:1 |
| 1940 | C:1 | 1987 | C:1 |
| 1941 | K:1 | 1988 | K:1 |
| 1942 | C:1 | 1989 | H:1 |
| 1990 | C:1 | 2036 | K:3 |
| 1991 | K:1 | 2037 | F:3 |
| 1992 | C:1 | 2038 | C:2 |
| 1993 | A:3 | 2039 | I:1 |
| 1994 | F:2 K:1 | 2040 | K:3 |
| 1995 | K:4 | 2041 | K:1 |
| 1996 | K:1 | 2042 | C:1 F:1 |
| 1997 | F:1 K:5 | 2043 | I:2 |
| 1998 | C:3 | 2044 | B:1 C:3 F:6 H:3 I:2 K:4 |
| 1999 | A:1 | 2045 | A:1 |
| 2000 | A:2 | 2046 | H:3 |
| 2001 | C:1 | 2047 | K:1 |
| 2002 | F:1 | 2048 | B:3 |
| 2003 | A:5 B:1 D:1 F:1 | 2049 | K:1 |
| 2004 | A:6 D:1 F:1 | 2050 | H:3 |
| 2005 | A:1 B:3 C:29 D:4 H:2 J:1 | 2051 | A:2 B:2 C:8 D:2 H:1 |
| 2006 | A:26 | 2052 | K:1 |
| 2007 | H:2 | 2053 | A:2 C:2 I:1 |
| 2008 | K:2 | 2054 | K:1 |
| 2009 | A:7 B:20 C:41 D:5 F:6 H:36 I:4 K:12 | 2055 | F:1 K:2 |
| 2010 | A:9 | 2056 | H:1 |
| 2011 | C:9 | 2057 | H:1 |
| 2012 | K:1 | 2058 | K:1 |
| 2013 | K:1 | 2059 | F:1 |
| 2014 | K:1 | 2060 | B:1 |
| 2015 | K:1 | 2061 | C:1 |
| 2016 | F:1 | 2062 | C:1 |
| 2017 | A:2 B:13 C:1 F:10 H:1 K:38 | 2063 | C:1 |
| 2018 | C:1 D:1 F:2 K:1 | 2064 | C:1 |
| 2019 | K:3 | 2065 | C:1 |
| 2020 | B:2 | 2066 | C:1 |
| 2021 | C:18 J:1 | 2067 | I:2 |
| 2022 | B:1 | 2068 | A:1 H:1 |
| 2023 | D:1 | 2069 | K:3 |
| 2024 | K:4 | 2070 | C:1 |
| 2025 | C:1 | 2071 | C:1 |
| 2026 | K:1 | 2072 | I:1 |
| 2027 | K:1 | 2073 | I:1 |
| 2028 | B:2 | 2074 | C:1 |
| 2029 | F:2 K:2 | 2075 | K:2 |
| 2030 | H:2 | 2076 | C:1 |
|  |  | 2077 | C:1 |

TABLE V-continued (Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 2031 | K:1 | 2078 | C:1 | 2198 | H:2 | 2245 | A:1 |
| 2032 | A:1 | 2079 | C:1 | 2199 | A:1 | 2246 | A:1 |
| 2033 | K:1 | 2080 | C:1 | 2200 | C:8 | 2247 | K:1 |
| 2034 | K:4 | 2081 | I:1 | 2201 | A:1 | 2248 | A:1 |
| 2035 | F:1 K:1 | 2082 | C:55 H:5 K:2 | 2202 | A:1 | 2249 | A:1 |
| 2083 | C:1 | 2130 | D:1 | 2203 | A:1 | 2250 | K:1 |
| 2084 | I:1 | 2131 | I:1 | 2204 | A:1 | 2251 | A:1 |
| 2085 | C:1 | 2132 | B:3 H:1 | 2205 | A:1 | 2252 | A:1 |
| 2086 | C:1 | 2133 | I:1 | 2206 | A:1 | 2253 | D:1 |
| 2087 | C:1 | 2134 | D:1 | 2207 | A:1 | 2254 | A:1 |
| 2088 | I:1 | 2135 | I:1 | 2208 | D:1 | 2255 | A:1 |
| 2089 | C:1 | 2136 | C:1 | 2209 | K:3 | 2256 | B:1 F:9 I:1 K:3 |
| 2090 | F:5 K:2 | 2137 | D:1 | 2210 | K:2 | 2257 | A:1 |
| 2091 | I:1 | 2138 | D:1 | 2211 | C:1 | 2258 | B:1 D:1 F:1 I:1 K:1 |
| 2092 | C:1 | 2139 | D:1 | 2212 | F:1 | 2259 | K:1 |
| 2093 | C:1 | 2140 | B:1 | 2213 | A:1 | 2260 | C:8 |
| 2094 | K:1 | 2141 | B:1 | 2214 | A:1 | 2261 | B:3 |
| 2095 | C:1 | 2142 | D:1 | 2215 | A:1 | 2262 | K:3 |
| 2096 | I:1 | 2143 | D:1 | 2216 | C:1 | 2263 | A:1 |
| 2097 | C:1 | 2144 | H:2 | 2217 | D:1 | 2264 | A:1 |
| 2098 | I:1 | 2145 | D:1 | 2218 | A:2 | 2265 | A:1 |
| 2099 | K:1 | 2146 | B:1 | 2219 | D:1 | 2266 | A:1 |
| 2100 | F:7 K:44 | 2147 | B:1 | 2220 | B:2 | 2267 | A:1 |
| 2101 | C:1 | 2148 | B:1 | 2221 | F:1 | 2268 | A:1 |
| 2102 | D:1 | 2149 | D:1 | 2222 | A:1 | 2269 | A:1 |
| 2103 | C:1 | 2150 | D:1 | 2223 | A:1 | 2270 | A:1 |
| 2104 | E:1 | 2151 | D:1 | 2271 | B:1 | 2318 | F:1 |
| 2105 | I:1 | 2152 | B:1 | 2272 | K:1 | 2319 | A:1 |
| 2106 | D:1 | 2153 | F:1 | 2273 | K:1 | 2320 | A:1 |
| 2107 | C:1 | 2154 | D:1 | 2274 | A:1 | 2321 | A:1 |
| 2108 | I:1 | 2155 | C:1 | 2275 | D:1 | 2322 | F:1 |
| 2109 | J:1 | 2156 | F:2 K:2 | 2276 | A:1 | 2323 | K:1 |
| 2110 | C:1 | 2157 | D:1 | 2277 | K:1 | 2324 | A:1 |
| 2111 | I:1 | 2158 | D:1 | 2278 | A:1 | 2325 | A:1 |
| 2112 | I:1 | 2159 | D:1 | 2279 | A:1 | 2326 | B:1 |
| 2113 | J:1 | 2160 | D:1 | 2280 | F:1 | 2327 | K:1 |
| 2114 | D:1 | 2161 | B:1 | 2281 | A:1 | 2328 | K:1 |
| 2115 | I:1 | 2162 | B:1 | 2282 | A:11 | 2329 | A:1 |
| 2116 | D:1 | 2163 | B:1 | 2283 | A:1 | 2330 | K:1 |
| 2117 | C:1 | 2164 | D:1 | 2284 | A:1 | 2331 | F:1 |
| 2118 | C:1 | 2165 | D:1 | 2285 | A:1 | 2332 | A:1 |
| 2119 | D:1 | 2166 | D:1 | 2286 | K:1 | 2333 | A:1 |
| 2120 | C:1 | 2167 | A:6 | 2287 | K:1 | 2334 | F:2 K:1 |
| 2121 | B:1 D:1 H:7 | 2168 | D:1 | 2288 | A:1 | 2335 | A:1 |
| 2122 | D:1 | 2169 | D:1 | 2289 | A:1 | 2336 | K:1 |
| 2123 | K:2 | 2170 | B:5 | 2290 | K:1 | 2337 | K:1 |
| 2124 | C:1 | 2171 | D:1 | 2291 | A:1 | 2338 | A:1 |
| 2125 | C:1 | 2172 | E:1 | 2292 | A:1 | 2339 | A:1 |
| 2126 | C:1 | 2173 | F:1 | 2293 | A:1 | 2340 | A:1 |
| 2127 | I:1 | 2174 | F:5 K:2 | 2294 | A:1 | 2341 | A:1 |
| 2128 | C:1 | 2175 | J:1 | 2295 | K:1 | 2342 | K:1 |
| 2129 | C:1 | 2176 | F:1 | 2296 | K:1 | 2343 | A:1 |
| 2177 | D:1 | 2224 | A:1 | 2297 | A:1 | 2344 | A:1 |
| 2178 | F:1 | 2225 | A:1 | 2298 | A:1 | 2345 | A:1 |
| 2179 | F:1 | 2226 | C:1 | 2299 | A:1 | 2346 | A:1 |
| 2180 | B:1 | 2227 | A:1 | 2300 | A:1 | 2347 | A:1 |
| 2181 | F:1 | 2228 | A:1 | 2301 | A:1 | 2348 | B:1 |
| 2182 | D:1 | 2229 | F:1 | 2302 | A:1 | 2349 | A:1 |
| 2183 | F:1 | 2230 | C:1 | 2303 | A:1 | 2350 | A:1 |
| 2184 | D:1 | 2231 | A:1 | 2304 | K:1 | 2351 | H:2 |
| 2185 | J:1 | 2232 | A:1 | 2305 | K:1 | 2352 | A:1 |
| 2186 | B:1 | 2233 | K:1 | 2306 | A:1 | 2353 | K:1 |
| 2187 | A:1 D:1 | 2234 | K:1 | 2307 | A:1 | 2354 | K:1 |
| 2188 | F:1 | 2235 | K:1 | 2308 | A:1 | 2355 | K:3 |
| 2189 | A:2 | 2236 | A:1 | 2309 | F:1 | 2356 | F:2 K:6 |
| 2190 | A:1 | 2237 | A:1 | 2310 | K:1 | 2357 | K:1 |
| 2191 | A:1 | 2238 | H:1 | 2311 | A:1 | 2358 | K:1 |
| 2192 | D:1 | 2239 | A:5 | 2312 | F:1 K:1 | 2359 | K:1 |
| 2193 | A:1 | 2240 | A:1 | 2313 | A:1 | 2360 | F:1 H:1 K:1 |
| 2194 | C:2 H:4 | 2241 | A:1 | 2314 | A:1 | 2361 | K:1 |
| 2195 | C:2 H:4 | 2242 | C:1 | 2315 | C:1 | 2362 | K:1 |
| 2196 | D:1 | 2243 | B:1 | 2316 | C:1 | 2363 | K:1 |
| 2197 | C:1 | 2244 | K:1 | 2317 | C:1 | 2364 | K:1 |

TABLE V-continued

(Spatial distribution)

| Seq Id No. | Tissue distribution | Seq Id No. | Tissue distribution |
|---|---|---|---|
| 2365 | K:1 | | K:2 |
| 2366 | B:4 | 2412 | K:1 |
| 2367 | F:34 K:160 | 2413 | K:1 |
| 2368 | K:4 | 2414 | A:2 J:2 |
| 2369 | B:3 | 2415 | K:1 |
| 2370 | F:1 K:4 | 2416 | A:1 B:5 C:1 D:1 K:2 |
| 2371 | H:6 | 2417 | A:2 C:14 H:1 |
| 2372 | A:3 B:2 C:2 D:1 I:1 K:1 | 2418 | F:2 |
| 2373 | F:8 K:2 | 2419 | A:1 I:1 |
| 2374 | K:1 | 2420 | K:1 |
| 2375 | F:1 | 2421 | K:2 |
| 2376 | K:3 | 2422 | A:1 |
| 2377 | K:1 | 2423 | F:1 K:2 |
| 2378 | D:1 | 2424 | A:2 |
| 2379 | A:113 | 2425 | K:2 |
| 2380 | A:1 | 2426 | A:4 |
| 2381 | B:1 | 2427 | A:2 B:3 C:8 D:2 F:2 H:2 K:3 |
| 2382 | A:1 | 2428 | C:1 |
| 2383 | K:1 | 2429 | H:1 |
| 2384 | A:2 B:2 F:68 H:1 K:16 | 2430 | B:1 |
| 2385 | A:1 | 2431 | F:7 K:3 |
| 2386 | K:1 | 2432 | F:1 K:2 |
| 2387 | C:6 | 2433 | F:4 |
| 2388 | K:1 | 2434 | K:1 |
| 2389 | K:1 | 2435 | F:2 K:3 |
| 2390 | C:7 | 2436 | A:2 D:1 H:1 |
| 2391 | K:1 | 2437 | K:1 |
| 2392 | F:1 K:1 | 2438 | I:2 |
| 2393 | C:1 | 2439 | K:3 |
| 2394 | K:1 | 2440 | F:1 K:4 |
| 2395 | B:1 | 2441 | A:1 |
| 2396 | A:1 D:1 H:1 | 2442 | H:2 |
| 2397 | F:1 K:15 | 2443 | D:1 |
| 2398 | K:1 | 2444 | B:1 |
| 2399 | K:1 | 2445 | C:2 |
| 2400 | F:2 | 2446 | F:2 |
| 2401 | A:1 B:6 H:1 | 2447 | H:1 K:1 |
| 2402 | A:1 | 2448 | K:1 |
| 2403 | H:1 | 2449 | K:1 |
| 2404 | A:1 | 2450 | K:1 |
| 2405 | K:1 | 2451 | K:1 |
| 2406 | K:1 | 2452 | F:7 K:4 |
| 2407 | K:2 | 2453 | D:3 F:15 I:1 K:61 |
| 2408 | H:2 | 2454 | D:1 H:2 K:7 |
| 2409 | A:1 | 2455 | C:1 |
| 2410 | F:1 K:3 | 2456 | A:1 |
| 2411 | A:18 B:11 C:11 F:1 H:6 I:3 J:3 | 2457 | K:1 |
| 2458 | K:1 | 2504 | K:1 |
| 2459 | F:1 | 2505 | A:6 B:2 C:2 D:1 F:1 |
| 2460 | K:1 | 2506 | F:1 K:1 |
| 2461 | K:1 | 2507 | A:1 |
| 2462 | B:3 | 2508 | F:2 K:48 |
| 2463 | K:1 | 2509 | K:1 |
| 2464 | F:1 K:1 | 2510 | K:2 |
| 2465 | I:4 | 2511 | A:1 C:5 |
| 2466 | H:5 | 2512 | B:1 |
| 2467 | K:6 | 2513 | A:1 |
| 2468 | A:2 D:3 H:1 K:1 | 2514 | A:1 |
| 2469 | F:1 K:1 | 2515 | K:1 |
| 2470 | F:3 K:8 | 2516 | H:2 |
| 2471 | F:3 | 2517 | B:1 |
| 2472 | K:1 | 2518 | K:1 |
| 2473 | K:1 | 2519 | K:1 |
| 2474 | K:1 | 2520 | A:9 B:1 I:1 |
| 2475 | B:2 | 2521 | A:1 |
| 2476 | C:1 | 2522 | K:3 |
| 2477 | A:1 | 2523 | F:11 H:2 |
| 2478 | F:10 | 2524 | F:11 H:3 |
| 2479 | C:3 | 2525 | K:1 |
| 2480 | A:1 | 2526 | K:1 |
| 2481 | K:2 | 2527 | K:1 |
| 2482 | D:1 H:1 | 2528 | A:6 |
| 2483 | C:1 | 2529 | C:18 |
| 2484 | B:3 | 2530 | C:6 |
| 2485 | A:17 B:7 C:2 D:7 H:4 | 2531 | K:1 |
| 2486 | B:2 | 2532 | K:1 |
| 2487 | A:24 B:81 C:60 D:28 F:6 H:69 I:2 J:9 K:30 | 2533 | K:1 |
| 2488 | K:1 | 2534 | K:1 |
| 2489 | B:3 | 2535 | K:2 |
| 2490 | F:1 K:2 | 2536 | K:1 |
| 2491 | K:1 | 2537 | K:1 |
| 2492 | F:1 K:1 | 2538 | K:1 |
| 2493 | A:1 K:3 | 2539 | C:2 |
| 2494 | F:2 K:10 | 2540 | A:6 B:5 C:1 H:7 |
| 2495 | K:1 | 2541 | K:2 |
| 2496 | B:2 | 2542 | K:2 |
| 2497 | A:2 | 2543 | K:3 |
| 2498 | K:1 | 2544 | B:3 |
| 2499 | A:2 | 2545 | D:49 |
| 2500 | F:5 K:3 | 2546 | C:11 |
| 2501 | K:1 | 2547 | K:1 |
| 2502 | A:3 | 2548 | F:1 K:1 |
| 2503 | A:5 D:1 | 2549 | D:1 |
| 2551 | K:1 | 2550 | A:5 |
| 2552 | D:1 | 2598 | A:2 |
| 2553 | F:1 K:1 | 2599 | F:1 K:3 |
| 2554 | H:1 | 2600 | K:1 |
| 2555 | K:1 | 2601 | K:1 |
| 2556 | K:1 | 2602 | A:1 |
| 2557 | K:1 | 2603 | A:1 |
| 2558 | B:1 | 2604 | B:1 |
| 2559 | C:1 | 2605 | K:3 |
| 2560 | A:8 | 2606 | C:1 |
| 2561 | B:1 | 2607 | A:1 |
| | | 2608 | A:3 B:21 C:43 D:2 H:18 I:1 K:4 |
| 2562 | C:9 H:1 | 2609 | K:1 |
| 2563 | B:1 | 2610 | K:1 |
| 2564 | K:3 | 2611 | K:1 |
| 2565 | K:1 | 2612 | A:20 B:2 |
| 2566 | F:5 | 2613 | A:1 B:2 C:4 |
| 2567 | B:1 | 2614 | A:20 B:2 |
| 2568 | B:1 K:3 | 2615 | K:1 |
| 2569 | K:1 | 2616 | A:1 |
| 2570 | K:1 | 2617 | K:3 |
| 2571 | K:2 | 2618 | F:2 K:4 |
| 2572 | F:2 | 2619 | C:1 F:2 H:8 I:3 |
| 2573 | B:1 | 2620 | B:2 |
| 2574 | B:2 F:1 K:3 | 2621 | K:1 |
| 2575 | K:2 | 2622 | A:1 B:1 |
| 2576 | C:1 K:1 | 2623 | F:13 K:32 |
| 2577 | B:3 C:2 D:2 H:1 | 2624 | K:1 |
| 2578 | B:4 C:2 D:1 H:1 | 2625 | K:1 |
| 2579 | B:2 C:1 D:1 F:2 | 2626 | K:1 |
| 2580 | C:1 F:15 | 2627 | K:1 |
| 2581 | K:1 | 2628 | F:1 |
| 2582 | K:2 | 2629 | K:1 |
| 2583 | K:1 | 2630 | K:1 |
| 2584 | A:3 B:3 C:2 D:1 F:5 H:1 | 2631 | K:1 |
| 2585 | D:1 | 2632 | K:1 |
| 2586 | B:1 | 2633 | K:1 |
| 2587 | F:25 K:7 | 2634 | K:1 |
| 2588 | K:1 | 2635 | F:1 K:2 |
| 2589 | K:4 | 2636 | K:1 |
| 2590 | K:1 | 2637 | K:1 |
| 2591 | F:1 K:8 | 2638 | A:1 B:1 C:15 D:1 J:2 |
| 2592 | K:7 | 2639 | K:1 |
| 2593 | B:2 | 2640 | B:1 |
| 2594 | F:10 K:1 | 2641 | B:1 |
| 2595 | K:1 | 2642 | F:1 K:1 |
| 2596 | C:5 J:2 | 2643 | K:1 |
| 2597 | K:1 | 2644 | A:3 |
| 2645 | K:1 | 2692 | K:1 |
| 2646 | K:1 | 2693 | K:2 |

TABLE V-continued
(Spatial distribution)

| Seq Id No. | Tissue distribution | Seq Id No. | Tissue distribution |
|---|---|---|---|
| 2647 | A:9 | 2694 | A:1 B:2 H:1 |
| 2648 | K:1 | 2695 | K:1 |
| 2649 | K:1 | 2696 | K:1 |
| 2650 | K:1 | 2697 | A:2 |
| 2651 | K:5 | 2698 | F:1 K:1 |
| 2652 | A:13 B:1 C:11 D:1 F:4 H:1 K:17 | 2699 | K:3 |
| 2653 | C:1 | 2700 | K:1 |
| 2654 | K:2 | 2701 | F:1 |
| 2655 | K:2 | 2702 | A:2 |
| 2656 | A:7 | 2703 | F:2 K:2 |
| 2657 | A:2 | 2704 | F:1 K:1 |
| 2658 | D:1 H:1 | 2705 | K:1 |
| 2659 | K:1 | 2706 | B:1 |
| 2660 | A:3 B:1 C:1 F:1 H:13 I:3 J:2 K:1 | 2707 | A:5 |
| 2661 | H:1 | 2708 | K:1 |
| 2662 | H:1 | 2709 | B:2 |
| 2663 | K:4 | 2710 | A:2 |
| 2664 | K:3 | 2711 | F:9 K:3 |
| 2665 | B:3 | 2712 | C:1 |
| 2666 | K:1 | 2713 | A:12 C:1 |
| 2667 | H:4 | 2714 | C:1 |
| 2668 | A:4 B:1 H:1 | 2715 | C:1 |
| 2669 | K:2 | 2716 | B:1 |
| 2670 | K:1 | 2717 | K:3 |
| 2671 | A:4 B:8 C:74 D:1 F:3 H:16 I:2 | 2718 | B:1 C:1 |
| 2672 | B:1 C:6 H:17 | 2719 | C:1 |
| 2673 | B:1 C:16 H:7 | 2720 | F:1 K:1 |
| 2674 | B:1 | 2721 | F:2 K:1 |
| 2675 | F:13 K:101 | 2722 | A:4 |
| 2676 | B:1 | 2723 | A:1 F:2 H:1 |
| 2677 | C:4 | 2724 | H:1 |
| 2678 | K:1 | 2725 | K:1 |
| 2679 | A:3 | 2726 | K:1 |
| 2680 | A:16 | 2727 | C:2 |
| 2681 | A:12 | 2728 | A:15 B:56 C:25 D:20 F:2 H:16 I:1 J:5 K:1 |
| 2682 | A:1 F:2 | 2729 | C:3 D:1 H:1 |
| 2683 | F:1 K:9 | 2730 | C:1 |
| 2684 | K:1 | 2731 | H:2 |
| 2685 | K:1 | 2732 | H:3 |
| 2686 | D:1 | 2733 | K:1 |
| 2687 | K:1 | 2734 | D:2 K:1 |
| 2688 | B:1 | 2735 | A:2 |
| 2689 | D:1 | 2736 | K:1 |
| 2690 | H:1 I:2 | 2737 | K:1 |
| 2691 | A:1 B:2 | 2785 | A:2 D:2 F:1 H:10 |
| 2738 | K:1 | 2786 | H:2 |
| 2739 | F:3 | 2787 | F:4 K:3 |
| 2740 | A:6 B:1 C:1 D:3 H:6 | 2788 | B:1 |
| 2741 | K:1 | 2789 | K:1 |
| 2742 | C:1 | 2790 | A:9 |
| 2743 | C:25 | 2791 | A:16 C:2 D:1 I:1 |
| 2744 | K:3 | 2792 | K:2 |
| 2745 | A:1 D:3 | 2793 | K:1 |
| 2746 | D:1 | 2794 | C:7 |
| 2747 | K:1 | 2795 | J:1 |
| 2748 | F:1 K:1 | 2796 | J:1 |
| 2749 | B:1 | 2797 | J:1 |
| 2750 | B:1 C:1 D:1 F:1 H:2 K:2 | 2798 | J:1 |
| 2751 | K:1 | 2799 | J:1 |
| 2752 | K:1 | 2800 | J:1 |
| 2753 | B:1 | 2801 | J:1 |
| 2754 | A:4 C:1 J:2 | 2802 | J:1 |
| 2755 | B:1 | 2803 | J:1 |
| 2756 | B:2 | 2804 | J:1 |
| 2757 | K:1 | 2805 | J:1 |
| 2758 | B:1 | 2806 | K:1 |
| 2759 | C:4 H:1 J:1 | 2807 | F:4 K:4 |
| 2760 | C:2 D:1 K:1 | 2808 | K:1 |
| 2761 | C:26 D:1 | 2809 | K:1 |
| 2762 | B:2 | | |
| 2763 | B:3 | 2810 | K:1 |
| 2764 | K:1 | 2811 | K:1 |
| 2765 | F:3 | 2812 | H:1 |
| 2766 | B:5 C:25 D:1 H:1 J:3 K:2 | 2813 | B:3 C:8 |
| 2767 | B:4 | 2814 | K:1 |
| 2768 | B:3 C:26 D:1 H:1 J:3 K:2 | 2815 | A:11 B:24 C:19 D:11 E:2 F:3 H:12 I:5 J:2 |
| 2769 | A:9 B:5 C:36 D:2 H:1 J:3 K:3 | 2816 | H:19 K:2 |
| 2770 | C:1 | 2817 | B:1 |
| 2771 | C:1 | 2818 | K:1 |
| 2772 | B:7 C:12 D:1 H:1 K:1 | 2819 | K:1 |
| 2773 | A:2 B:6 K:2 | 2820 | A:3 |
| 2774 | K:1 | 2821 | K:1 |
| 2775 | K:1 | 2822 | D:2 |
| 2776 | K:1 | 2823 | C:3 |
| 2777 | K:3 | 2824 | K:1 |
| 2778 | B:1 | 2825 | A:1 D:1 |
| 2779 | F:1 K:1 | 2826 | B:1 |
| 2780 | A:7 | 2827 | B:1 C:1 D:1 |
| 2781 | K:1 | 2828 | A:1 C:34 J:1 |
| 2782 | B:2 C:1 F:1 H:2 | 2829 | K:1 |
| 2783 | B:2 | 2830 | K:1 |
| 2784 | K:1 | 2878 | A:1 H:1 |
| 2831 | K:1 | 2879 | C:4 |
| 2832 | B:1 F:4 I:1 K:3 | 2880 | K:2 |
| 2833 | K:1 | 2881 | F:2 K:23 |
| 2834 | B:3 C:11 I:1 | 2882 | K:1 |
| 2835 | A:1 | 2883 | B:1 |
| 2836 | D:2 H:1 | 2884 | B:5 C:1 |
| 2837 | K:1 | 2885 | K:1 |
| 2838 | F:3 | 2886 | D:1 |
| 2839 | A:1 B:2 H:2 | 2887 | F:4 |
| 2840 | K:1 | 2888 | A:2 C:1 F:1 H:1 K:3 |
| 2841 | K:1 | 2889 | F:1 |
| 2842 | K:1 | 2890 | F:1 |
| 2843 | K:1 | 2891 | A:1 B:1 C:1 F:1 H:1 |
| 2844 | A:1 B:1 C:2 | 2892 | A:7 |
| 2845 | A:4 B:26 C:39 D:6 H:3 J:1 K:2 | 2893 | F:1 K:7 |
| 2846 | D:1 | 2894 | F:4 K:10 |
| 2847 | B:1 | 2895 | B:1 |
| 2848 | C:1 | 2896 | H:3 |
| 2849 | A:2 | 2897 | F:1 |
| 2850 | K:1 | 2898 | H:1 |
| 2851 | C:1 | 2899 | K:5 |
| 2852 | F:5 K:6 | 2900 | B:1 I:1 |
| 2853 | A:1 F:1 H:8 | 2901 | F:1 |
| 2854 | B:1 C:5 | 2902 | B:6 C:1 |
| 2855 | D:1 K:10 | 2903 | F:1 |
| 2856 | A:1 H:1 K:1 | 2904 | C:7 |
| 2857 | B:1 | 2905 | A:3 |
| 2858 | K:1 | 2906 | B:1 |
| 2859 | B:1 | 2907 | F:1 H:2 |
| 2860 | A:2 B:3 C:1 | 2908 | C:15 |
| 2861 | B:1 | 2909 | C:1 |
| 2862 | F:1 | 2910 | F:1 |
| 2863 | A:7 F:15 K:21 | 2911 | A:2 B:2 C:8 D:1 |
| 2864 | D:1 H:1 | 2912 | K:2 |
| 2865 | A:2 | 2913 | K:2 |
| 2866 | K:2 | 2914 | A:3 F:1 H:1 |
| 2867 | F:1 K:3 | 2915 | F:1 |
| 2868 | K:3 | 2916 | C:15 |
| 2869 | B:4 | 2917 | B:1 |
| 2870 | A:12 B:2 D:3 H:1 I:11 | 2918 | F:1 |
| 2871 | I:1 | 2919 | B:1 D:1 K:2 |
| 2872 | F:1 | 2920 | B:2 |
| 2873 | K:3 | 2921 | F:2 K:9 |
| 2874 | F:3 K:35 | 2922 | B:3 |
| 2875 | K:1 | 2923 | F:1 |
| 2876 | H:3 | 2924 | A:1 B:4 |
| 2877 | B:2 C:1 | 2971 | B:2 |
| 2925 | B:1 C:2 H:20 I:1 K2 | 2972 | F:1 |
| 2926 | F:3 | 2973 | K:1 |
| 2927 | H:2 | | |

TABLE V-continued

(Spatial distribution)

| Seq Id No. | Tissue distribution | Seq Id No. | Tissue distribution |
|---|---|---|---|
| 2928 | H:2 | 2974 | C:4 I:1 |
| 2929 | F:1 | 2975 | K:1 |
| 2930 | F:1 | 2976 | K:2 |
| 2931 | A:1 B:3 C:18 D:1 F:1 H:46 | 2977 | B:1 |
| 2932 | K:3 | 2978 | B:6 |
| 2933 | A:8 B:3 C:30 F:1 I:2 | 2979 | A:2 |
| 2934 | F:1 K:1 | 2980 | B:4 |
| 2935 | D:1 | 2981 | A:5 B:9 C:42 D:3 F:2 H:7 J:1 K:3 |
| 2936 | B:3 | 2982 | E:1 |
| 2937 | H:6 | 2983 | B:1 |
| 2938 | A:18 B:38 C:77 D:28 E:2 F:13 H:129 I:1 J:4 K:19 | 2984 | I:5 |
| | | 2985 | A:7 |
| 2939 | F:1 | 2986 | I:3 |
| 2940 | A:1 B:5 C:2 D:1 F:1 H:46 | 2987 | C:1 |
| 2941 | I:3 | 2988 | F:1 |
| 2942 | F:1 | 2989 | B:2 |
| 2943 | B:3 | 2990 | H:2 |
| 2944 | C:5 | 2991 | D:3 H:2 |
| 2945 | A:27 H:8 I:1 | 2992 | H:1 |
| 2946 | A:1 | 2993 | F:1 |
| 2947 | K:2 | 2994 | B:1 |
| 2948 | H:1 | 2995 | F:1 K:13 |
| 2949 | B:4 C:6 | 2996 | A:1 B:1 |
| 2950 | F:1 | 2997 | C:15 |
| 2951 | D:3 | 2998 | K:2 |
| 2952 | A:2 H:2 | 2999 | B:1 |
| 2953 | F:1 | 3000 | K:1 |
| 2954 | B:1 | 3001 | A:10 B:9 |
| 2955 | C:1 | 3002 | C:1 D:1 |
| 2956 | F:1 | 3003 | B:1 C:1 D:1 H:2 |
| 2957 | F:1 | 3004 | F:1 |
| 2958 | F:1 | 3005 | C:7 D:1 F:4 K:31 |
| 2959 | C:2 | 3006 | A:1 F:2 H:1 K:3 |
| 2960 | F:1 | 3007 | A:3 B:2 C:11 D:1 H:1 K:1 |
| 2961 | F:1 | 3008 | C:2 H:1 K:1 |
| 2962 | K:2 | 3009 | B:1 |
| 2963 | K:2 | 3010 | C:5 |
| 2964 | B:6 | 3011 | C:1 K:2 |
| 2965 | F:1 | 3012 | A:2 |
| 2966 | F:1 K:1 | 3013 | F:5 K:9 |
| 2967 | H:1 | 3014 | K:2 |
| 2968 | A:8 B:7 D:1 H:4 I:6 K:1 | 3015 | C:1 |
| 2969 | H:2 | 3016 | A:1 D:2 |
| 2970 | A:3 B:7 C:8 D:2 H:2 K:2 | 3017 | A:2 |
| 3018 | F:1 K:2 | 3065 | B:1 |
| 3019 | H:2 | 3066 | K:3 |
| 3020 | H:1 | 3067 | K:10 |
| 3021 | K:2 | 3068 | A:8 |
| 3022 | I:2 | 3069 | F:8 K:2 |
| 3023 | A:4 | 3070 | K:2 |
| 3024 | I:4 | 3071 | F:1 K:1 |
| 3025 | C:11 H:1 | 3072 | A:9 C:1 |
| 3026 | K:1 | 3073 | K:1 |
| 3027 | K:2 | 3074 | K:1 |
| 3028 | K:1 | 3075 | K:1 |
| 3029 | J:15 | 3076 | C:3 |
| 3030 | A:13 | 3077 | K:1 |
| 3031 | B:2 | 3078 | H:1 |
| 3032 | F:1 K:1 | 3079 | K:1 |
| 3033 | K:1 | 3080 | K:1 |
| 3034 | A:8 F:14 I:2 K:5 | 3081 | K:1 |
| 3035 | D:1 | 3082 | K:1 |
| 3036 | F:2 K:1 | 3083 | K:1 |
| 3037 | H:2 | 3084 | F:21 K:2 |
| 3038 | H:3 | 3085 | H:2 |
| 3039 | B:1 I:3 | 3086 | B:2 |
| 3040 | H:1 | 3087 | C:15 |
| 3041 | A:3 B:1 F:7 | 3088 | C:1 |
| 3042 | K:1 | 3089 | C:1 |
| 3043 | K:1 | 3090 | C:1 |
| 3044 | B:3 | 3091 | C:1 |
| 3045 | K:1 | 3092 | C:1 |
| 3046 | F:1 K:3 | 3093 | K:4 |
| 3047 | C:20 J:1 K:1 | 3094 | K:3 |
| 3048 | K:1 | 3095 | K:1 |
| 3049 | A:2 B:12 C:3 D:1 H:1 | 3096 | F:4 K:16 |
| 3050 | K:1 | 3097 | C:1 |
| 3051 | K:1 | 3098 | D:1 |
| 3052 | K:1 | 3099 | A:5 B:6 C:14 H:2 |
| 3053 | F:2 K:1 | 3100 | B:1 |
| 3054 | K:1 | 3101 | B:1 |
| 3055 | K:1 | 3102 | H:1 |
| 3056 | A:1 B:1 K:1 | 3103 | K:2 |
| 3057 | F:3 K:1 | 3104 | K:3 |
| 3058 | K:3 | 3105 | K:1 |
| 3059 | F:2 | 3106 | K:1 |
| 3060 | F:3 K:5 | 3107 | C:7 |
| 3061 | F:2 K:7 | 3108 | H:1 |
| 3062 | K:1 | 3109 | F:8 K:1 |
| 3063 | K:1 | 3110 | H:1 |
| 3064 | B:2 | 3111 | A:1 C:4 D:1 |
| 3112 | B:3 | 3158 | A:4 |
| 3113 | K:1 | 3159 | A:5 B:1 C:2 D:3 F:1 H:3 K:2 |
| 3114 | F:1 K:3 | 3160 | A:4 C:2 D:3 F:1 H:2 K:1 |
| 3115 | C:2 | 3161 | A:1 |
| 3116 | F:1 K:3 | 3162 | F:11 K:4 |
| 3117 | A:6 | 3163 | K:3 |
| 3118 | K:2 | 3164 | C:4 J:1 |
| 3119 | F:1 | 3165 | A:6 |
| 3120 | F:1 | 3166 | K:2 |
| 3121 | A:7 D:7 F:21 H:9 K:21 | 3167 | F:1 |
| 3122 | A:7 B:1 D:7 F:21 H:9 K:20 | 3168 | A:2 D:1 |
| 3123 | F:1 | 3169 | F:1 K:1 |
| 3124 | A:2 | 3170 | K:8 |
| 3125 | A:2 | 3171 | F:2 |
| 3126 | I:1 K:1 | 3172 | A:15 C:13 H:1 |
| 3127 | C:5 H:1 | 3173 | K:2 |
| 3128 | B:1 F:4 K:1 | 3174 | K:1 |
| 3129 | F:1 | 3175 | K:3 |
| 3130 | A:4 | 3176 | D:1 F:1 |
| 3131 | B:1 | 3177 | F:2 |
| 3132 | F:1 | 3178 | A:1 B:5 C:13 D:2 H:4 I:1 |
| 3133 | A:2 B:8 C:55 D:5 H:9 J:4 K:3 | 3179 | A:1 H:3 |
| 3134 | E:1 | 3180 | F:1 |
| 3135 | D:1 | 3181 | A:2 B:1 D:2 |
| 3136 | H:1 | 3182 | A:1 B:4 C:16 J:1 |
| 3137 | K:1 | 3183 | C:20 H:1 |
| 3138 | F:1 K:1 | 3184 | B:1 |
| 3139 | D:1 H:1 | 3185 | F:1 |
| 3140 | F:1 | 3186 | K:7 |
| 3141 | F:1 | 3187 | A:4 |
| 3142 | F:1 K:1 | 3188 | A:2 C:5 H:1 |
| 3143 | B:2 | 3189 | F:1 |
| 3144 | A:10 B:25 C:47 D:4 F:1 H:8 I:1 J:2 K:2 | 3190 | F:1 |
| | | 3191 | F:1 |
| 3145 | A:4 B:4 C:14 D:2 F:3 H:2 K:24 | 3192 | A:1 B:3 H:2 K:1 |
| 3146 | F:2 K:3 | 3193 | F:2 K:1 |
| 3147 | A:5 B:1 | 3194 | A:8 |
| 3148 | A:3 | 3195 | C:3 |
| 3149 | A:1 F:5 H:4 K:12 | 3196 | A:3 |
| 3150 | K:3 | 3197 | B:2 |
| 3151 | D:1 F:1 H:3 K:3 | 3198 | B:1 |
| 3152 | F:1 K:4 | 3199 | K:2 |
| 3153 | H:4 | 3200 | F:1 |
| 3154 | K:1 | 3201 | F:1 |
| 3155 | F:5 | 3202 | B:1 |
| 3156 | A:3 B:1 C:14 F:1 J:67 | 3203 | B:1 |
| 3157 | A:2 B:2 C:2 F:1 | 3204 | A:6 B:1 C:4 H:24 I:3 K:1 |
| 3205 | C:7 | 3252 | A:2 B:2 C:2 H:25 K:9 |
| 3206 | F:1 | 3253 | A:2 B:2 C:2 H:26 K:9 |
| 3207 | F:1 | 3254 | A:48 B:29 C:8 D:18 E:2 F:25 H:235 K:85 |
| 3208 | F:1 K:2 | | |

TABLE V-continued
(Spatial distribution)

| Seq Id No. | Tissue distribution | Seq Id No. | Tissue distribution |
|---|---|---|---|
| 3209 | F:1 K:1 | 3255 | F:1 |
| 3210 | F:1 | 3256 | A:1 |
| 3211 | B:1 C:4 H:2 | 3257 | H:1 |
| 3212 | B:1 | 3258 | D:2 |
| 3213 | K:1 | 3259 | A:2 |
| 3214 | K:1 | 3260 | H:1 |
| 3215 | C:2 | 3261 | H:1 |
| 3216 | K:1 | 3262 | C:1 |
| 3217 | A:10 | 3263 | B:1 |
| 3218 | I:1 | 3264 | A:3 |
| 3219 | F:5 K:1 | 3265 | A:2 |
| 3220 | K:1 | 3266 | C:17 |
| 3221 | K:2 | 3267 | H:1 |
| 3222 | A:1 | 3268 | H:1 |
| 3223 | F:5 K:1 | 3269 | B:4 |
| 3224 | A:1 | 3270 | H:1 |
| 3225 | B:1 F:3 K:1 | 3271 | B:4 C:1 D:3 E:1 K:3 |
| 3226 | A:1 B:1 C:1 I:3 K:2 | 3272 | H:1 |
| 3227 | C:5 | 3273 | I:2 |
| 3228 | K:3 | 3274 | K:1 |
| 3229 | H:1 | 3275 | F:2 K:7 |
| 3230 | A:4 B:2 C:2 F:2 K:1 | 3276 | F:2 K:15 |
| 3231 | A:1 B:4 K:1 | 3277 | A:1 H:1 |
| 3232 | K:2 | 3278 | H:1 |
| 3233 | H:1 | 3279 | K:1 |
| 3234 | H:1 | 3280 | F:4 K:1 |
| 3235 | H:1 | 3281 | K:2 |
| 3236 | B:2 D:3 H:2 I:2 | 3282 | F:1 K:5 |
| 3237 | B:1 C:1 | 3283 | H:4 |
| 3238 | B:4 | 3284 | D:1 |
| 3239 | A:1 B:1 C:8 D:1 H:4 J:3 K:1 | 3285 | A:1 B:1 |
| 3240 | C:3 | 3286 | H:1 |
| 3241 | A:2 C:6 D:1 H:2 J:3 | 3287 | A:1 D:1 |
| 3242 | B:8 C:1 H:1 | 3288 | B:1 C:1 |
| 3243 | D:2 | 3289 | B:1 |
| 3244 | B:1 | 3290 | C:23 |
| 3245 | K:2 | 3291 | C:1 |
| 3246 | H:1 | 3292 | C:1 |
| 3247 | H:1 | 3293 | K:2 |
| 3248 | F:2 K:1 | 3294 | H:1 |
| 3249 | B:2 | 3295 | C:19 D:1 |
| 3250 | A:2 B:2 C:7 H:20 K:9 | 3296 | H:1 |
| 3251 | A:2 B:2 C:2 H:20 K:12 | 3297 | A:3 B:3 C:1 D:3 H:1 K:2 |
| 3298 | H:1 | 3344 | A:2 B:1 C:26 D:4 H:2 J:3 |
| 3299 | H:1 | 3345 | H:6 |
| 3300 | H:1 | 3346 | B:1 C:11 |
| 3301 | F:5 K:1 | 3347 | B:1 C:4 |
| 3302 | I:1 | 3348 | D:1 |
| 3303 | H:1 | 3349 | B:2 |
| 3304 | C:1 | 3350 | B:1 |
| 3305 | A:2 B:4 C:9 D:1 H:4 K:1 | 3351 | B:1 |
| 3306 | F:1 K:1 | 3352 | B:1 |
| 3307 | I:1 | 3353 | K:2 |
| 3308 | K:4 | 3354 | C:15 |
| 3309 | B:3 | 3355 | C:1 |
| 3310 | H:1 | 3356 | H:1 |
| 3311 | A:3 B:1 | 3357 | F:5 K:1 |
| 3312 | K:2 | 3358 | D:2 |
| 3313 | H:1 | 3359 | H:1 |
| 3314 | A:1 | 3360 | K:2 |
| 3315 | H:1 | 3361 | F:1 K:1 |
| 3316 | H:1 | 3362 | A:2 B:5 C:58 D:2 F:22 H:3 I:3 J:9 K:122 |
| 3317 | H:1 | | |
| 3318 | H:1 | 3363 | A:1 B:4 C:39 D:2 F:22 H:3 I:3 J:9 K:106 |
| 3319 | K:4 | | |
| 3320 | F:1 | 3364 | A:1 B:5 C:54 D:2 F:22 H:3 I:3 J:9 K:130 |
| 3321 | K:2 | 3365 | C:1 |
| 3322 | F:11 K:2 | 3366 | F:1 |
| 3323 | H:8 | 3367 | H:1 |
| 3324 | K:1 | 3368 | A:5 D:1 |
| 3325 | K:17 | 3369 | A:26 B:12 C:2 K:1 |
| 3326 | H:1 | 3370 | D:1 |
| 3327 | D:1 F:1 | 3371 | B:1 |
| 3328 | A:4 | 3372 | A:1 |
| 3329 | B:2 | 3373 | A:1 |
| 3330 | B:1 C:1 | 3374 | A:1 |
| 3331 | A:5 B:5 C:1 H:1 K:4 | 3375 | A:1 |
| 3332 | A:1 | 3376 | A:1 |
| 3333 | H:1 | 3377 | A:1 |
| 3334 | H:1 | 3378 | A:1 |
| 3335 | A:2 | 3379 | A:2 |
| 3336 | H:1 | 3380 | K:2 |
| 3337 | B:2 C:1 K:1 | 3381 | B:1 |
| 3338 | C:2 D:1 F:2 K:4 | 3382 | F:3 H:1 K:11 |
| 3339 | H:1 | 3383 | H:2 |
| 3340 | K:2 | 3384 | A:1 C:17 D:2 H:3 |
| 3341 | K:2 | 3385 | H:4 |
| 3342 | A:3 | 3386 | H:1 |
| 3343 | A:19 B:70 C:89 D:29 F:1 H:36 I:1 J:1 K:14 | 3387 | I:3 |
| | | 3388 | K:3 |
| 3389 | K:2 | 3436 | K:4 |
| 3390 | H:1 | 3437 | B:1 |
| 3391 | F:9 K:1 | 3438 | F:1 K:5 |
| 3392 | F:2 | 3439 | B:1 |
| 3393 | H:1 | 3440 | A:1 B:1 C:3 |
| 3394 | I:2 | 3441 | H:9 |
| 3395 | H:2 | 3442 | B:5 |
| 3396 | F:1 K:1 | 3443 | D:3 |
| 3397 | H:3 | 3444 | F:1 K:1 |
| 3398 | H:1 | 3445 | F:1 |
| 3399 | H:1 | 3446 | H:4 |
| 3400 | H:1 | 3447 | K:2 |
| 3401 | H:1 | 3448 | C:9 H:2 |
| 3402 | K:2 | 3449 | H:1 |
| 3403 | H:1 | 3450 | H:6 |
| 3404 | H:1 | 3451 | B:3 |
| 3405 | H:1 | 3452 | K:1 |
| 3406 | A:11 | 3453 | K:1 |
| 3407 | H:1 | 3454 | B:1 F:6 |
| 3408 | H:1 | 3455 | F:1 K:3 |
| 3409 | K:1 | 3456 | F:1 K:6 |
| 3410 | C:2 | 3457 | F:1 K:21 |
| 3411 | F:5 K:2 | 3458 | F:5 |
| 3412 | A:1 B:1 | 3459 | C:6 H:1 J:1 |
| 3413 | K:1 | 3460 | B:1 H:4 K:4 |
| 3414 | H:1 | 3461 | D:1 |
| 3415 | A:1 C:1 | 3462 | K:2 |
| 3416 | H:1 | 3463 | H:1 |
| 3417 | F:1 K:2 | 3464 | H:1 |
| 3418 | A:2 K:1 | 3465 | A:1 D:1 |
| 3419 | H:12 | 3466 | A:51 B:69 C:43 D:16 E:2 F:6 H:2 I:23 J:9 K:20 |
| 3420 | F:2 | | |
| 3421 | A:1 F:1 K:5 | 3467 | B:3 |
| 3422 | F:26 K:172 | 3468 | K:1 |
| 3423 | F:5 K:14 | 3469 | K:1 |
| 3424 | B:1 | 3470 | K:1 |
| 3425 | H:1 | 3471 | H:1 |
| 3426 | K:1 | 3472 | K:2 |
| 3427 | F:1 | 3473 | I:2 |
| 3428 | I:1 | 3474 | H:2 |
| 3429 | B:1 | 3475 | H:1 |
| 3430 | F:4 K:35 | 3476 | A:1 B:1 C:1 |
| 3431 | A:1 B:4 C:9 D:1 | 3477 | K:1 |
| 3432 | B:1 | 3478 | B:2 |
| 3433 | F:5 K:2 | 3479 | F:1 |
| 3434 | D:2 | 3480 | H:1 |
| 3435 | F:1 K:8 | 3481 | H:1 |
| 3482 | F:4 K:19 | 3529 | B:1 |
| 3483 | F:5 K:7 | 3530 | K:1 |
| 3484 | F:2 K:15 | 3531 | H:1 |
| 3485 | F:1 | 3532 | H:1 |
| 3486 | K:1 | 3533 | H:1 |
| 3487 | K:1 | 3534 | H:1 K:3 |
| 3488 | F:1 | 3535 | I:2 |

TABLE V-continued

(Spatial distribution)

| Seq Id No. | Tissue distribution |
|---|---|
| 3489 | B:2 |
| 3490 | A:1 B:10 H:1 |
| 3491 | A:7 B:1 D:3 H:1 K:1 |
| 3492 | A:5 B:1 D:1 H:1 K:1 |
| 3493 | K:2 |
| 3494 | K:2 |
| 3495 | H:1 |
| 3496 | K:1 |
| 3497 | A:1 K:1 |
| 3498 | C:1 D:3 H:1 |
| 3499 | B:2 |
| 3500 | B:1 E:1 H:1 |
| 3501 | F:1 K:6 |
| 3502 | K:1 |
| 3503 | F:1 |
| 3504 | H:1 |
| 3505 | F:2 |
| 3506 | A:1 |
| 3507 | K:2 |
| 3508 | F:1 K:1 |
| 3509 | A:1 B:14 C:42 D:16 F:6 H:10 K:9 |
| 3510 | B:3 C:4 D:2 F:4 H:4 K:3 |
| 3511 | D:1 |
| 3512 | F:3 |
| 3513 | H:1 |
| 3514 | A:1 C:15 D:1 H:1 |
| 3515 | B:1 |
| 3516 | H:1 |
| 3517 | H:1 |
| 3518 | A:3 D:1 H:2 |
| 3519 | A:1 H:2 |
| 3520 | A:2 |
| 3521 | B:2 |
| 3522 | B:1 F:7 |
| 3523 | K:3 |
| 3524 | A:3 B:1 D:1 K:2 |
| 3525 | A:3 B:4 D:1 F:1 |
| 3526 | H:1 |
| 3527 | K:1 |
| 3528 | A:16 |
| 3576 | H:1 |
| 3577 | H:1 |
| 3578 | C:6 |
| 3579 | H:1 |
| 3580 | H:1 |
| 3581 | H:2 I:4 |
| 3582 | A:7 B:6 C:1 D:19 K:1 |
| 3583 | F:5 K:2 |
| 3584 | A:27 B:8 D:7 F:3 H:3 K:1 |
| 3585 | H:1 |
| 3586 | D:1 |
| 3587 | D:1 |
| 3588 | F:10 K:5 |
| 3589 | K:2 |
| 3590 | K:15 |
| 3591 | K:2 |
| 3592 | H:1 |
| 3593 | F:6 K:36 |
| 3594 | H:6 |
| 3595 | F:1 K:5 |
| 3596 | K:1 |
| 3597 | K:6 |
| 3598 | A:1 D:1 |
| 3599 | F:2 H:1 K:4 |
| 3600 | A:2 C:3 |
| 3601 | C:27 |
| 3602 | F:1 |
| 3603 | F:1 |
| 3604 | B:2 |
| 3605 | D:1 |
| 3536 | H:1 |
| 3537 | H:1 |
| 3538 | A:8 |
| 3539 | K:1 |
| 3540 | B:3 |
| 3541 | H:1 |
| 3542 | H:1 |
| 3543 | H:1 |
| 3544 | H:1 |
| 3545 | H:1 |
| 3546 | B:4 |
| 3547 | B:1 C:1 |
| 3548 | H:2 |
| 3549 | H:1 |
| 3550 | H:1 |
| 3551 | I:3 |
| 3552 | A:2 |
| 3553 | A:13 |
| 3554 | H:1 |
| 3555 | C:28 D:3 K:3 |
| 3556 | C:31 D:3 K:2 |
| 3557 | F:3 K:1 |
| 3558 | H:1 |
| 3559 | F:1 K:2 |
| 3560 | D:1 |
| 3561 | A:10 B:1 C:3 H:5 |
| 3562 | K:1 |
| 3563 | H:1 |
| 3564 | A:37 |
| 3565 | A:5 |
| 3566 | A:1 |
| 3567 | K:2 |
| 3568 | A:3 B:35 C:23 D:6 F:2 H:3 K:3 |
| 3569 | A:9 B:42 C:42 D:2 H:9 K:6 |
| 3570 | F:1 |
| 3571 | C:1 |
| 3572 | C:1 |
| 3573 | F:11 K:1 |
| 3574 | A:1 B:2 |
| 3575 | H:1 |
| 3623 | C:4 |
| 3624 | B:3 |
| 3625 | H:1 |
| 3626 | H:1 |
| 3627 | C:2 D:2 H:4 K:1 |
| 3628 | F:6 K:2 |
| 3629 | F:1 K:3 |
| 3630 | K:1 |
| 3631 | A:4 |
| 3632 | C:1 |
| 3633 | H:1 |
| 3634 | H:1 |
| 3635 | B:1 |
| 3636 | H:1 |
| 3637 | H:6 |
| 3638 | F:1 K:1 |
| 3639 | C:3 |
| 3640 | C:1 |
| 3641 | C:1 |
| 3642 | B:1 |
| 3643 | H:1 |
| 3644 | F:1 K:3 |
| 3645 | B:1 |
| 3646 | H:1 |
| 3647 | K:1 |
| 3648 | H:1 |
| 3649 | H:1 |
| 3650 | A:2 |
| 3651 | F:1 |
| 3652 | A:1 B:4 C:2 D:1 F:1 |
| 3606 | K:1 |
| 3607 | A:1 D:1 |
| 3608 | F:14 K:3 |
| 3609 | A:1 B:3 |
| 3610 | A:3 |
| 3611 | H:1 |
| 3612 | A:11 B:7 C:10 H:5 K:1 |
| 3613 | A:1 |
| 3614 | C:3 F:1 H:1 |
| 3615 | C:2 |
| 3616 | C:14 D:1 F:1 J:1 |
| 3617 | K:2 |
| 3618 | A:6 B:5 C:3 F:1 H:31 |
| 3619 | H:1 |
| 3620 | A:1 |
| 3621 | K:1 |
| 3622 | K:2 |
| 3669 | B:1 |
| 3670 | K:7 |
| 3671 | C:3 |
| 3672 | C:14 H:3 |
| 3673 | C:1 |
| 3674 | K:1 |
| 3675 | C:1 |
| 3676 | K:2 |
| 3677 | K:1 |
| 3678 | K:2 |
| 3679 | F:8 K:1 |
| 3680 | K:4 |
| 3681 | F:6 K:4 |
| 3682 | H:1 |
| 3683 | D:1 |
| 3684 | A:10 |
| 3685 | A:2 |
| 3686 | H:1 |
| 3687 | K:1 |
| 3688 | H:2 |
| 3689 | K:3 |
| 3690 | F:6 |
| 3691 | K:12 |
| 3692 | H:1 |
| 3693 | D:1 H:1 |
| 3694 | H:2 |
| 3695 | H:1 |
| 3696 | F:1 |
| 3697 | K:2 |
| 3698 | H:5 |
| 3699 | K:2 |
| 3700 | H:1 |
| 3701 | F:3 K:25 |
| 3702 | F:2 K:5 |
| 3703 | C:14 |
| 3704 | C:1 |
| 3705 | A:1 |
| 3706 | F:2 K:3 |
| 3707 | H:1 |
| 3708 | A:2 C:7 H:3 K:2 |
| 3709 | A:1 B:2 C:1 H:2 K:1 |
| 3710 | K:2 |
| 3711 | F:3 |
| 3712 | F:1 K:8 |
| 3713 | F:2 H:1 K:14 |
| 3714 | K:1 |
| 3715 | B:2 |
| 3763 | C:4 |
| 3764 | B:2 |
| 3765 | K:1 |
| 3766 | A:2 B:2 |
| | H:3 K:1 |
| 3653 | A:5 |
| 3654 | H:1 |
| 3655 | I:1 |
| 3656 | C:1 |
| 3657 | H:1 |
| 3658 | F:1 |
| 3659 | C:1 |
| 3660 | H:1 |
| 3661 | C:1 |
| 3662 | B:2 |
| 3663 | K:2 |
| 3664 | A:9 B:6 C:73 D:5 F:122 H:112 K:44 |
| 3665 | B:1 |
| 3666 | A:7 B:2 C:24 D:3 F:67 H:58 K:25 |
| 3667 | B:1 |
| 3668 | K:1 |
| 3716 | A:2 F:1 K:3 |
| 3717 | A:1 C:7 K:7 |
| 3718 | H:1 |
| 3719 | F:2 K:11 |
| 3720 | F:2 K:15 |
| 3721 | K:2 |
| 3722 | C:9 |
| 3723 | F:6 |
| 3724 | F:2 |
| 3725 | H:1 |
| 3726 | C:4 |
| 3727 | F:1 K:3 |
| 3728 | K:1 |
| 3729 | H:1 |
| 3730 | A:1 |
| 3731 | F:2 |
| 3732 | F:1 K:3 |
| 3733 | F:3 K:1 |
| 3734 | H:1 |
| 3735 | H:1 |
| 3736 | F:1 |
| 3737 | H:1 |
| 3738 | C:1 C:55 D:6 J:18 |
| 3739 | C:4 |
| 3740 | B:3 |
| 3741 | K:1 |
| 3742 | A:8 B:8 C:16 D:3 F:9 H:6 I:3 K:5 |
| 3743 | A:2 |
| 3744 | A:9 B:12 C:18 D:1 H:4 K:1 |
| 3745 | D:1 |
| 3746 | H:3 |
| 3747 | B:1 |
| 3748 | C:1 D:2 H:2 |
| 3749 | A:1 B:3 C:11 D:1 H:2 |
| 3750 | A:1 B:4 C:1 |
| 3751 | A:1 B:1 H:1 |
| 3752 | F:1 |
| 3753 | A:3 B:5 C:9 D:4 H:7 I:1 K:1 |
| 3754 | A:5 F:1 |
| 3755 | K:1 |
| 3756 | A:3 C:21 D:1 |
| 3757 | C:1 H:2 |
| 3758 | B:1 |
| 3759 | A:3 B:5 D:2 H:3 I:1 |
| 3760 | F:3 |
| 3761 | B:3 |
| 3762 | K:1 |
| 3808 | F:1 K:1 |
| 3809 | A:4 B:1 C:1 H:1 I:2 |
| 3810 | F:2 |
| 3811 | F:1 K:6 |

TABLE V-continued

(Spatial distribution)

| Seq Id No. | Tissue distribution | Seq Id No. | Tissue distribution |
|---|---|---|---|
| 3767 | H:1 K:1 | 3812 | K:2 |
| 3768 | K:1 | 3813 | C:5 |
| 3769 | F:2 | 3814 | A:2 B:1 |
| 3770 | E:1 | 3815 | A:2 |
| 3771 | C:4 F:6 H:2 I:1 K:4 | 3816 | A:2 |
| 3772 | B:3 | 3817 | A:1 H:1 |
| 3773 | F:2 | 3818 | B:1 K:1 |
| 3774 | A:1 B:6 C:1 D:1 H:1 | 3819 | B:2 |
| 3775 | C:27 J:2 | 3820 | B:2 |
| 3776 | A:4 B:5 C:9 D:2 I:1 | 3821 | B:2 |
| 3777 | K:2 | 3822 | C:21 |
| 3778 | A:4 F:11 H:6 K:1 | 3823 | K:1 |
| 3779 | A:11 B:26 C:69 D:8 F:2 H:4 I:1 J:4 K:3 | 3824 | F:1 |
|  |  | 3825 | A:2 |
| 3780 | A:11 B:27 C:77 D:9 F:2 H:4 I:1 J:5 K:3 | 3826 | A:15 B:30 C:26 F:1 H:3 K:1 |
|  |  | 3827 | F:13 K:76 |
| 3781 | H:1 K:1 | 3828 | K:1 |
| 3782 | F:1 K:1 | 3829 | A:3 D:1 F:5 K:9 |
| 3783 | H:1 | 3830 | F:1 K:10 |
| 3784 | K:3 | 3831 | H:2 |
| 3785 | F:4 | 3832 | A:1 |
| 3786 | F:10 K:8 | 3833 | H:1 |
| 3787 | F:2 | 3834 | K:2 |
| 3788 | K:2 | 3835 | K:2 |
| 3789 | A:2 | 3836 | H:1 |
| 3790 | A:4 | 3837 | K:2 |
| 3791 | B:6 | 3838 | H:1 |
| 3792 | A:9 | 3839 | A:1 F:7 K:16 |
| 3793 | A:130 B:1 C:1 H:2 I:1 | 3840 | A:1 F:5 K:16 |
| 3794 | A:155 B:3 C:1 H:2 I:3 | 3841 | H:1 |
| 3795 | A:1 | 3842 | K:1 |
| 3796 | H:1 | 3843 | K:1 |
| 3797 | A:1 | 3844 | F:1 |
| 3798 | A:1 | 3845 | H:2 |
| 3799 | A:1 | 3846 | A:2 |
| 3800 | F:1 | 3847 | A:1 |
| 3801 | A:7 | 3848 | A:55 |
| 3802 | A:7 | 3849 | A:1 |
| 3803 | A:11 C:1 F:1 H:1 K:3 | 3850 | A:1 |
| 3804 | K:1 | 3851 | A:1 |
| 3805 | H:1 | 3852 | A:1 |
| 3806 | H:1 | 3853 | A:1 |
| 3807 | A:1 C:5 | 3854 | A:1 |
| 3855 | A:1 | 7762 | H:1 |
| 3856 | A:1 | 7763 | H:1 |
| 3857 | A:1 | 7764 | H:1 |
| 3858 | A:1 | 7765 | H:1 |
| 3859 | A:1 | 7766 | H:1 |
| 3860 | A:2 | 7767 | H:1 |
| 3861 | B:3 | 7768 | H:1 |
| 3862 | C:1 | 7769 | H:1 |
| 3863 | H:1 | 7770 | H:1 |
| 3864 | B:2 | 7771 | H:1 |
| 3865 | A:1 H:9 | 7772 | H:1 |
| 3866 | B:4 | 7773 | H:1 |
| 3867 | F:1 | 7774 | H:1 |
| 3868 | F:4 K:13 | 7775 | H:1 |
| 3869 | I:1 | 7776 | H:1 |
| 3870 | F:1 K:1 | 7777 | H:1 |
| 3871 | F:1 | 7778 | H:1 |
| 3872 | I:1 | 7779 | H:1 |
| 3873 | H:1 | 7780 | H:1 |
| 3874 | A:8 | 7781 | H:1 |
| 3875 | H:1 | 7782 | H:1 |
| 3876 | H:1 | 7783 | H:1 |
| 3877 | H:1 | 7784 | H:1 |
| 3878 | H:1 | 7785 | H:1 |
| 3879 | K:1 | 7786 | H:1 |
| 3880 | A:8 | 7787 | H:1 |
| 3881 | H:1 | 7788 | H:1 |
| 3882 | A:3 B:4 C:2 | 7789 | H:1 |
| 3883 | H:1 | 7790 | H:1 |
| 7744 | H:1 | 7791 | H:1 |
| 7745 | H:1 | 7792 | H:1 |
| 7746 | H:1 | 7793 | H:1 |
| 7747 | H:1 | 7794 | H:1 |
| 7748 | H:1 | 7795 | H:1 |
| 7749 | H:1 | 7796 | H:1 |
| 7750 | H:1 | 7797 | H:1 |
| 7751 | H:1 | 7798 | H:1 |
| 7752 | H:1 | 7799 | H:1 |
| 7753 | H:1 | 7800 | H:1 |
| 7754 | H:1 | 7801 | H:1 |
| 7755 | H:1 | 7802 | H:1 |
| 7756 | H:1 | 7803 | H:1 |
| 7757 | H:1 | 7804 | H:1 |
| 7758 | H:1 | 7805 | H:1 |
| 7759 | H:1 | 7806 | H:1 |
| 7760 | H:1 | 7807 | H:1 |
| 7761 | H:1 | 7808 | H:1 |
| 7809 | H:1 | 7856 | H:1 |
| 7810 | H:1 | 7857 | H:1 |
| 7811 | H:1 | 7858 | H:1 |
| 7812 | H:1 | 7859 | H:1 |
| 7813 | H:1 | 7860 | H:1 |
| 7814 | H:1 | 7861 | H:1 |
| 7815 | H:1 | 7862 | H:1 |
| 7816 | H:1 | 7863 | H:1 |
| 7817 | H:1 | 7864 | H:1 |
| 7818 | H:1 | 7865 | H:1 |
| 7819 | H:11 | 7866 | H:1 |
| 7820 | H:1 | 7867 | H:1 |
| 7821 | H:1 | 7868 | H:1 |
| 7822 | H:1 | 7869 | H:1 |
| 7823 | H:1 | 7870 | H:1 |
| 7824 | H:1 | 7871 | H:1 |
| 7825 | H:1 | 7872 | F:25 K:136 |
| 7826 | H:1 | 7873 | H:1 |
| 7827 | H:1 | 7874 | H:1 |
| 7828 | F:1 K:3 | 7875 | H:1 |
| 7829 | H:1 | 7876 | H:1 |
| 7830 | H:1 | 7877 | H:1 |
| 7831 | H:1 | 7878 | H:1 |
| 7832 | H:1 | 7879 | H:1 |
| 7833 | H:1 | 7880 | H:1 |
| 7834 | H:1 | 7881 | H:1 |
| 7835 | H:1 | 7882 | H:1 |
| 7836 | H:1 | 7883 | H:1 |
| 7837 | F:1 K:3 | 7884 | H:1 |
| 7838 | H:1 | 7885 | H:1 |
| 7839 | H:1 | 7886 | H:1 |
| 7840 | H:1 | 7887 | H:1 |
| 7841 | H:1 | 7888 | H:1 |
| 7842 | H:1 | 7889 | H:1 |
| 7843 | H:1 | 7890 | H:1 |
| 7844 | H:1 | 7891 | H:1 |
| 7845 | F:1 K:3 | 7892 | H:1 |
| 7846 | H:1 | 7893 | H:1 |
| 7847 | H:1 | 7894 | H:1 |
| 7848 | H:1 | 7895 | H:1 |
| 7849 | H:1 | 7896 | H:1 |
| 7850 | H:1 | 7897 | H:1 |
| 7851 | F:1 K:1 | 7898 | H:1 |
| 7852 | H:1 | 7899 | H:1 |
| 7853 | H:1 | 7900 | H:1 |
| 7854 | H:1 | 7901 | H:1 |
| 7855 | H:1 | 7902 | H:1 |
| 7903 | H:1 | 7950 | H:1 |
| 7904 | H:1 | 7951 | H:1 |
| 7905 | H:1 | 7952 | H:1 |
| 7906 | H:1 | 7953 | H:1 |
| 7907 | H:1 | 7954 | H:1 |
| 7908 | H:1 | 7955 | H:1 |
| 7909 | H:1 | 7956 | H:1 |
| 7910 | H:1 | 7957 | H:1 |

TABLE V-continued

(Spatial distribution)

| Seq Id No. | Tissue distribution | Seq Id No. | Tissue distribution |
|---|---|---|---|
| 7911 | H:1 | 7958 | H:1 |
| 7912 | H:1 | 7959 | H:1 |
| 7913 | H:1 | 7960 | H:1 |
| 7914 | H:1 | 7961 | H:1 |
| 7915 | H:1 | 7962 | H:1 |
| 7916 | H:1 | 7963 | B:7 |
| 7917 | H:1 | 7964 | H:1 |
| 7918 | H:1 | 7965 | H:1 |
| 7919 | H:1 | 7966 | H:1 |
| 7920 | A:1 B:1 D:1 E:1 F:1 | 7967 | H:1 |
| 7921 | H:1 | 7968 | H:1 |
| 7922 | H:1 | 7969 | H:1 |
| 7923 | H:1 | 7970 | H:1 |
| 7924 | H:1 | 7971 | H:1 |
| 7925 | H:1 | 7972 | H:1 |
| 7926 | H:1 | 7973 | H:1 |
| 7927 | H:1 | 7974 | H:1 |
| 7928 | H:1 | 7975 | H:1 |
| 7929 | H:1 | 7976 | H:1 |
| 7930 | H:1 | 7977 | H:1 |
| 7931 | H:1 | 7978 | H:1 |
| 7932 | H:1 | 7979 | H:1 |
| 7933 | H:1 | 7980 | H:1 |
| 7934 | H:1 | 7981 | H:1 |
| 7935 | H:1 | 7982 | H:1 |
| 7936 | H:1 | 7983 | H:1 |
| 7937 | H:1 | 7984 | H:1 |
| 7938 | H:1 | 7935 | H:1 |
| 7939 | H:1 | 7986 | H:1 |
| 7940 | H:1 | 7987 | H:1 |
| 7941 | H:1 | 7988 | H:1 |
| 7942 | H:1 | 7989 | H:1 |
| 7943 | H:1 | 7990 | H:1 |
| 7944 | H:1 | 7991 | F:1 K:3 |
| 7945 | H:2 | 7992 | H:1 |
| 7946 | H:1 | 7993 | H:1 |
| 7947 | H:1 | 7994 | H:1 |
| 7948 | H:1 | 7995 | H:1 |
| 7949 | H:1 | 7996 | H:1 |
| 7997 | H:1 | 8044 | H:1 |
| 7998 | H:1 | 8045 | H:1 |
| 7999 | H:1 | 8046 | H:1 |
| 8000 | H:1 | 8047 | H:1 |
| 8001 | H:1 | 8048 | H:1 |
| 8002 | H:1 | 8049 | H:1 |
| 8003 | H:1 | 8050 | H:1 |
| 8004 | H:1 | 8051 | H:1 |
| 8005 | B:1 | 8052 | H:1 |
| 8006 | H:1 | 8053 | H:1 |
| 8007 | H:1 | 8054 | H:1 |
| 8008 | H:1 | 8055 | H:1 |
| 8009 | H:1 | 8056 | H:1 |
| 8010 | H:1 | 8057 | H:1 |
| 8011 | H:1 | 8058 | H:1 |
| 8012 | H:1 | 8059 | H:1 |
| 8013 | H:1 | 8060 | H:1 |
| 8014 | H:1 | 8061 | H:1 |
| 8015 | B:1 | 8062 | H:1 |
| 8016 | H:1 | 8063 | H:1 |
| 8017 | H:1 | 8064 | H:1 |
| 8018 | H:1 | 8065 | H:1 |
| 8019 | H:1 | 8066 | H:1 |
| 8020 | H:1 | 8067 | H:1 |
| 8021 | H:1 | 8068 | H:1 |
| 8022 | H:1 | 8069 | H:1 |
| 8023 | H:1 | 8070 | H:1 |
| 8024 | H:1 | 8071 | H:1 |
| 8025 | H:1 | 8072 | H:1 |
| 8026 | H:1 | 8073 | H:1 |
| 8027 | H:1 | 8074 | H:1 |
| 8028 | H:1 | 8075 | H:1 |
| 8029 | H:1 | 8076 | H:1 |
| 8030 | H:1 | 8077 | H:1 |
| 8031 | H:1 | 8078 | H:1 |
| 8032 | H:1 | 8079 | H:1 |
| 8033 | H:1 | 8080 | H:1 |
| 8034 | H:1 | 8081 | H:1 |
| 8035 | H:1 | 8082 | H:1 |
| 8036 | H:1 | 8083 | A:1 |
| 8037 | H:1 | 8084 | H:1 |
| 8038 | H:1 | 8085 | H:1 |
| 8039 | H:1 | 8086 | H:1 |
| 8040 | H:1 | 8087 | H:1 |
| 8041 | H:1 | 8088 | H:1 |
| 8042 | H:1 | 8089 | H:1 |
| 8043 | H:1 | 8090 | H:1 |
| 8091 | H:1 | 8138 | H:1 |
| 8092 | H:1 | 8139 | H:1 |
| 8093 | H:1 | 8140 | H:1 |
| 8094 | H:1 | 8141 | H:1 |
| 8095 | H:1 | 8142 | H:1 |
| 8096 | H:1 | 8143 | K:1 |
| 8097 | H:1 | 8144 | H:1 |
| 8098 | H:1 | 8145 | H:1 |
| 8099 | H:1 | 8146 | H:1 |
| 8100 | H:1 | 8147 | H:1 |
| 8101 | H:1 | 8148 | H:1 |
| 8102 | H:1 | 8149 | H:1 |
| 8103 | H:1 | 8150 | H:1 |
| 8104 | C:1 | 8151 | H:1 |
| 8105 | H:1 | 8152 | H:1 |
| 8106 | H:1 | 8153 | H:1 |
| 8107 | H:1 | 8154 | H:1 |
| 8108 | H:1 | 8155 | H:1 |
| 8109 | H:1 | 8156 | H:1 |
| 8110 | H:1 | 8157 | H:1 |
| 8111 | H:1 | 8158 | H:1 |
| 8112 | H:1 | 8159 | H:1 |
| 8113 | H:1 | 8160 | H:1 |
| 8114 | H:1 | 8161 | H:1 |
| 8115 | H:1 | 8162 | H:1 |
| 8116 | H:1 | 8163 | H:1 |
| 8117 | H:1 | 8164 | H:1 |
| 8118 | H:1 | 8165 | H:1 |
| 8119 | H:1 | 8166 | H:1 |
| 8120 | H:1 | 8167 | H:1 |
| 8121 | H:1 | 8168 | H:1 |
| 8122 | H:1 | 8169 | H:1 |
| 8123 | H:1 | 8170 | H:1 |
| 8124 | H:1 | 8171 | H:1 |
| 8125 | F:1 | 8172 | H:1 |
| 8126 | H:1 | 8173 | H:1 |
| 8127 | H:1 | 8174 | H:1 |
| 8128 | H:1 | 8175 | H:1 |
| 8129 | H:1 | 8176 | H:1 |
| 8130 | H:1 | 8177 | H:1 |
| 8131 | H:1 | 8178 | H:1 |
| 8132 | H:1 | 8179 | H:1 |
| 8133 | H:1 | 8180 | H:1 |
| 8134 | H:1 | 8181 | H:1 |
| 8135 | H:1 | 8182 | H:1 |
| 8136 | H:1 | 8183 | H:1 |
| 8137 | H:1 | 8184 | H:1 |
| 8185 | H:1 | 8232 | H:1 |
| 8186 | H:1 | 8233 | K:1 |
| 8187 | H:1 | 8234 | H:1 |
| 8188 | H:1 | 8235 | H:1 |
| 8189 | H:1 | 8236 | H:1 |
| 8190 | H:1 | 8237 | H:1 |
| 8191 | H:1 | 8238 | H:1 |
| 8192 | C:1 | 8239 | H:1 |
| 8193 | H:1 | 8240 | H:1 |
| 8194 | H:1 | 8241 | H:1 |
| 8195 | H:1 | 8242 | K:2 |
| 8196 | H:1 | 8243 | H:1 |
| 8197 | H:1 | 8244 | H:1 |

TABLE V-continued
(Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 8198 | H:1 | 8245 | H:1 | 8318 | H:1 | 8365 | H:1 |
| 8199 | H:1 | 8246 | H:1 | 8319 | H:1 | 8366 | H:1 |
| 8200 | H:1 | 8247 | H:1 | 8320 | H:1 | 8367 | H:1 |
| 8201 | H:1 | 8248 | H:1 | 8321 | H:1 | 8368 | H:1 |
| 8202 | H:1 | 8249 | H:1 | 8322 | H:1 | 8369 | H:1 |
| 8203 | H:1 | 8250 | H:1 | 8323 | H:1 | 8370 | H:1 |
| 8204 | H:1 | 8251 | H:1 | 8324 | K:2 | 8371 | H:1 |
| 8205 | H:1 | 8252 | H:1 | 8325 | H:1 | 8372 | H:1 |
| 8206 | H:1 | 8253 | H:1 | 8373 | H:1 | 8420 | H:1 |
| 8207 | H:1 | 8254 | H:1 | 8374 | H:1 | 8421 | A:5 |
| 8208 | H:1 | 8255 | H:1 | 8375 | H:1 | 8422 | H:1 |
| 8209 | H:1 | 8256 | H:1 | 8376 | H:1 | 8423 | H:1 |
| 8210 | H:1 | 8257 | H:1 | 8377 | F:1 K:2 | 8424 | H:1 |
| 8211 | H:1 | 8258 | H:1 | 8378 | H:1 | 8425 | H:1 |
| 8212 | H:1 | 8259 | H:1 | 8379 | H:1 | 8426 | H:1 |
| 8213 | H:1 | 8260 | H:1 | 8380 | H:1 | 8427 | H:1 |
| 8214 | H:1 | 8261 | H:1 | 8381 | H:1 | 8428 | H:1 |
| 8215 | H:1 | 8262 | H:1 | 8382 | H:1 | 8429 | H:1 |
| 8216 | H:1 | 8263 | H:1 | 8383 | H:1 | 8430 | H:1 |
| 8217 | H:1 | 8264 | H:1 | 8384 | H:1 | 8431 | H:1 |
| 8218 | H:1 | 8265 | H:1 | 8385 | B:2 | 8432 | H:1 |
| 8219 | H:1 | 8266 | H:1 | 8386 | H:1 | 8433 | H:1 |
| 8220 | H:1 | 8267 | H:1 | 8387 | H:1 | 8434 | H:1 |
| 8221 | H:1 | 8268 | H:1 | 8388 | H:1 | 8435 | H:1 |
| 8222 | H:1 | 8269 | H:1 | 8389 | H:1 | 8436 | K:3 |
| 8223 | H:1 | 8270 | H:1 | 8390 | H:1 | 8437 | H:1 |
| 8224 | H:1 | 8271 | H:1 | 8391 | H:1 | 8438 | H:1 |
| 8225 | H:1 | 8272 | H:1 | 8392 | H:1 | 8439 | H:1 |
| 8226 | H:1 | 8273 | H:1 | 8393 | H:2 | 8440 | H:1 |
| 8227 | H:1 | 8274 | H:1 | 8394 | H:1 | 8441 | H:1 |
| 8228 | H:1 | 8275 | H:1 | 8395 | H:1 | 8442 | H:1 |
| 8229 | H:1 | 8276 | H:1 | 8396 | H:1 | 8443 | H:1 |
| 8230 | H:1 | 8277 | H:1 | 8397 | H:1 | 8444 | H:1 |
| 8231 | H:1 | 8278 | H:1 | 8398 | H:1 | 8445 | H:1 |
| 8279 | H:1 | 8326 | H:1 | 8399 | H:1 | 8446 | H:1 |
| 8280 | H:1 | 8327 | H:1 | 8400 | H:1 | 8447 | H:1 |
| 8281 | H:1 | 8328 | H:1 | 8401 | F:5 K:2 | 8448 | H:1 |
| 8282 | H:1 | 8329 | H:1 | 8402 | H:1 | 8449 | H:1 |
| 8283 | H:1 | 8330 | H:1 | 8403 | H:1 | 8450 | H:1 |
| 8284 | H:1 | 8331 | H:1 | 8404 | H:1 | 8451 | H:1 |
| 8285 | H:1 | 8332 | H:1 | 8405 | H:1 | 8452 | F:1 K:1 |
| 8286 | H:1 | 8333 | H:1 | 8406 | H:1 | 8453 | H:1 |
| 8287 | H:1 | 8334 | H:1 | 8407 | H:1 | 8454 | H:1 |
| 8288 | H:1 | 8335 | H:1 | 8408 | H:1 | 8455 | H:1 |
| 8289 | H:1 | 8336 | H:1 | 8409 | H:1 | 8456 | H:1 |
| 8290 | H:1 | 8337 | H:1 | 8410 | H:1 | 8457 | H:1 |
| 8291 | H:1 | 8338 | H:1 | 8411 | H:1 | 8458 | H:1 |
| 8292 | C:6 | 8339 | H:1 | 8412 | H:1 | 8459 | H:1 |
| 8293 | H:1 | 8340 | H:1 | 8413 | K:2 | 8460 | H:1 |
| 8294 | H:1 | 8341 | H:1 | 8414 | H:1 | 8461 | H:1 |
| 8295 | H:1 | 8342 | H:1 | 8415 | H:1 | 8462 | H:1 |
| 8296 | H:1 | 8343 | H:1 | 8416 | H:1 | 8463 | H:1 |
| 8297 | H:1 | 8344 | H:1 | 8417 | H:1 | 8464 | H:1 |
| 8298 | H:1 | 8345 | H:1 | 8418 | H:1 | 8465 | H:1 |
| 8299 | H:1 | 8346 | H:1 | 8419 | H:1 | 8466 | H:1 |
| 8300 | H:1 | 8347 | H:1 | 8467 | H:1 | 8514 | H:1 |
| 8301 | H:1 | 8348 | H:1 | 8468 | H:1 | 8515 | H:1 |
| 8302 | H:1 | 8349 | H:1 | 8469 | H:1 | 8516 | H:1 |
| 8303 | H:1 | 8350 | H:1 | 8470 | H:1 | 8517 | H:1 |
| 8304 | H:1 | 8351 | C:2 J:2 | 8471 | H:1 | 8518 | H:1 |
| 8305 | H:1 | 8352 | H:1 | 8472 | H:1 | 8519 | H:1 |
| 8306 | H:1 | 8353 | H:1 | 8473 | H:1 | 8520 | H:1 |
| 8307 | I:1 | 8354 | H:1 | 8474 | H:1 | 8521 | H:1 |
| 8308 | H:1 | 8355 | H:1 | 8475 | H:1 | 8522 | H:1 |
| 8309 | H:1 | 8356 | H:1 | 8476 | H:1 | 8523 | H:1 |
| 8310 | H:1 | 8357 | H:1 | 8477 | D:1 F:1 | 8524 | H:1 |
| 8311 | H:1 | 8358 | H:1 | 8478 | H:1 | 8525 | H:1 |
| 8312 | H:1 | 8359 | H:1 | 8479 | H:1 | 8526 | H:1 |
| 8313 | H:1 | 8360 | H:1 | 8480 | H:1 | 8527 | H:1 |
| 8314 | H:1 | 8361 | H:1 | 8481 | H:1 | 8528 | H:1 |
| 8315 | H:1 | 8362 | H:1 | 8482 | H:1 | 8529 | F:1 K:2 |
| 8316 | H:1 | 8363 | H:1 | 8483 | H:1 | 8530 | H:1 |
| 8317 | H:1 | 8364 | H:1 | 8484 | H:1 | 8531 | H:1 |

TABLE V-continued
(Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 8485 | H:1 | 8532 | H:1 | 8605 | H:1 | 8652 | H:1 |
| 8486 | H:1 | 8533 | H:1 | 8606 | H:1 | 8653 | H:1 |
| 8487 | H:1 | 8534 | H:1 | 8607 | H:1 | 8654 | H:1 |
| 8488 | H:1 | 8535 | H:1 | 8655 | H:1 | 8702 | H:1 |
| 8489 | H:1 | 8536 | H:1 | 8656 | H:1 | 8703 | H:1 |
| 8490 | H:1 | 8537 | H:1 | 8657 | H:1 | 8704 | H:1 |
| 8491 | H:1 | 8538 | F:1 K:3 | 8658 | H:1 | 8705 | H:1 |
| 8492 | H:1 | 8539 | H:1 | 8659 | H:1 | 8706 | H:1 |
| 8493 | H:1 | 8540 | H:1 | 8660 | H:1 | 8707 | H:1 |
| 8494 | H:1 | 8541 | H:1 | 8661 | H:1 | 8708 | H:1 |
| 8495 | H:1 | 8542 | H:1 | 8662 | H:1 | 8709 | H:1 |
| 8496 | H:1 | 8543 | H:1 | 8663 | H:1 | 8710 | A:1 |
| 8497 | H:1 | 8544 | H:1 | 8664 | H:1 | 8711 | H:1 |
| 8498 | H:1 | 8545 | H:1 | 8665 | H:1 | 8712 | H:1 |
| 8499 | H:1 | 8546 | H:1 | 8666 | H:1 | 8713 | H:1 |
| 8500 | H:1 | 8547 | H:1 | 8667 | A:1 | 8714 | H:1 |
| 8501 | H:1 | 8548 | H:1 | 8668 | H:1 | 8715 | H:1 |
| 8502 | H:1 | 8549 | H:1 | 8669 | H:1 | 8716 | H:1 |
| 8503 | H:1 | 8550 | H:1 | 8670 | H:1 | 8717 | H:1 |
| 8504 | H:1 | 8551 | H:1 | 8671 | H:1 | 8718 | H:1 |
| 8505 | H:1 | 8552 | H:1 | 8672 | H:1 | 8719 | H:1 |
| 8506 | H:1 | 8553 | H:1 | 8673 | H:1 | 8720 | H:1 |
| 8507 | H:1 | 8554 | H:1 | 8674 | H:1 | 8721 | A:1 |
| 8508 | A:7 | 8555 | H:1 | 8675 | H:1 | 8722 | H:1 |
| 8509 | H:1 | 8556 | H:1 | 8676 | H:1 | 8723 | H:1 |
| 8510 | H:1 | 8557 | H:1 | 8677 | H:1 | 8724 | H:1 |
| 8511 | H:1 | 8558 | H:1 | 8678 | A:1 | 8725 | H:1 |
| 8512 | H:1 | 8559 | H:1 | 8679 | H:1 | 8726 | H:1 |
| 8513 | H:1 | 8560 | H:4 | 8680 | H:1 | 8727 | H:1 |
| 8561 | H:1 | 8608 | H:1 | 8681 | H:1 | 8728 | H:1 |
| 8562 | H:1 | 8609 | H:1 | 8682 | H:1 | 8729 | H:1 |
| 8563 | H:1 | 8610 | H:1 | 8683 | H:1 | 8730 | H:1 |
| 8564 | H:1 | 8611 | H:1 | 8684 | H:1 | 8731 | H:1 |
| 8565 | H:1 | 8612 | H:1 | 8685 | H:1 | 8732 | A:1 |
| 8566 | H:1 | 8613 | H:1 | 8686 | H:1 | 8733 | H:1 |
| 8567 | H:1 | 8614 | H:1 | 8687 | H:1 | 8734 | H:1 |
| 8568 | H:1 | 8615 | H:1 | 8688 | H:1 | 8735 | H:1 |
| 8569 | H:1 | 8616 | H:1 | 8689 | B:2 | 8736 | H:1 |
| 8570 | H:1 | 8617 | H:1 | 8690 | A:1 | 8737 | H:1 |
| 8571 | H:1 | 8618 | H:1 | 8691 | H:1 | 8738 | H:1 |
| 8572 | H:1 | 8619 | H:1 | 8692 | H:1 | 8739 | H:1 |
| 8573 | H:1 | 8620 | H:1 | 8693 | H:1 | 8740 | H:1 |
| 8574 | H:1 | 8621 | H:1 | 8694 | H:1 | 8741 | H:1 |
| 8575 | H:1 | 8622 | H:1 | 8695 | H:1 | 8742 | B:1 |
| 8576 | H:1 | 8623 | H:1 | 8696 | H:1 | 8743 | H:1 |
| 8577 | H:1 | 8624 | H:1 | 8697 | H:1 | 8744 | H:1 |
| 8578 | H:1 | 8625 | H:1 | 8698 | H:1 | 8745 | H:1 |
| 8579 | H:1 | 8626 | H:1 | 8699 | A:1 | 8746 | H:1 |
| 8580 | H:1 | 8627 | A:2 | 8700 | H:1 | 8747 | H:1 |
| 8581 | H:1 | 8628 | H:1 | 8701 | H:1 | 8748 | H:1 |
| 8582 | H:1 | 8629 | H:1 | 8749 | H:1 | 8796 | H:1 |
| 8583 | H:1 | 8630 | H:1 | 8750 | H:1 | 8797 | H:1 |
| 8584 | H:1 | 8631 | H:1 | 8751 | A:1 | 8798 | H:1 |
| 8585 | H:1 | 8632 | H:1 | 8752 | H:1 | 8799 | H:1 |
| 8586 | I:2 | 8633 | H:1 | 8753 | H:1 | 8800 | H:1 |
| 8587 | H:1 | 8634 | H:1 | 8754 | H:1 | 8801 | H:1 |
| 8588 | H:1 | 8635 | H:1 | 8755 | H:1 | 8802 | H:1 |
| 8589 | H:1 | 8636 | H:1 | 8756 | H:1 | 8803 | H:1 |
| 8590 | H:1 | 8637 | H:1 | 8757 | H:1 | 8804 | H:1 |
| 8591 | H:1 | 8638 | H:1 | 8758 | A:1 | 8805 | K:1 |
| 8592 | H:1 | 8639 | H:1 | 8759 | H:1 | 8806 | H:1 |
| 8593 | H:1 | 8640 | H:1 | 8760 | H:1 | 8807 | H:1 |
| 8594 | H:1 | 8641 | H:1 | 8761 | H:1 | 8808 | H:1 |
| 8595 | H:1 | 8642 | H:1 | 8762 | H:1 | 8809 | H:1 |
| 8596 | H:1 | 8643 | H:1 | 8763 | H:1 | 8810 | H:1 |
| 8597 | H:1 | 8644 | H:1 | 8764 | H:1 | 8811 | H:1 |
| 8598 | H:1 | 8645 | H:1 | 8765 | H:1 | 8812 | H:1 |
| 8599 | H:1 | 8646 | H:1 | 8766 | H:1 | 8813 | K:1 |
| 8600 | H:1 | 8647 | H:1 | 8767 | H:1 | 8814 | H:1 |
| 8601 | H:1 | 8648 | H:1 | 8768 | B:1 | 8815 | H:1 |
| 8602 | H:1 | 8649 | H:1 | 8769 | H:1 | 8816 | H:1 |
| 8603 | H:1 | 8650 | H:1 | 8770 | H:1 | 8817 | H:1 |
| 8604 | H:1 | 8651 | H:1 | 8771 | H:1 | 8818 | H:1 |

TABLE V-continued

(Spatial distribution)

| Seq Id No. | Tissue distribution | Seq Id No. | Tissue distribution |
|---|---|---|---|
| 8772 | H:1 | 8819 | H:1 |
| 8773 | H:1 | 8820 | H:1 |
| 8774 | H:1 | 8821 | H:2 |
| 8775 | H:1 | 8822 | H:1 |
| 8776 | H:1 | 8823 | H:1 |
| 8777 | A:1 | 8824 | H:1 |
| 8778 | H:1 | 8825 | H:1 |
| 8779 | H:1 | 8826 | H:1 |
| 8780 | H:1 | 8827 | H:1 |
| 8781 | H:1 | 8828 | H:1 |
| 8782 | H:1 | 8829 | H:1 |
| 8783 | H:1 | 8830 | C:20 |
| 8784 | H:1 | 8831 | H:1 |
| 8785 | H:1 | 8832 | H:1 |
| 8786 | B:1 | 8833 | H:1 |
| 8787 | H:1 | 8834 | H:1 |
| 8788 | H:1 | 8835 | H:1 |
| 8789 | H:1 | 8836 | H:1 |
| 8790 | H:1 | 8837 | H:1 |
| 8791 | H:1 | 8838 | H:1 |
| 8792 | H:1 | 8839 | H:1 |
| 8793 | H:1 | 8840 | H:1 |
| 8794 | H:1 | 8841 | C:2 |
| 8795 | H:1 | 8842 | H:1 |
| 8843 | H:1 | 8890 | H:1 |
| 8844 | H:1 | 8891 | H:1 |
| 8845 | H:1 | 8892 | H:1 |
| 8846 | H:1 | 8893 | H:1 |
| 8847 | H:1 | 8894 | H:1 |
| 8848 | H:1 | 8895 | H:1 |
| 8849 | H:1 | 8896 | H:1 |
| 8850 | H:1 | 8897 | H:1 |
| 8851 | H:1 | 8898 | H:1 |
| 8852 | H:1 | 8899 | H:1 |
| 8853 | H:1 | 8900 | H:1 |
| 8854 | H:1 | 8901 | H:1 |
| 8855 | H:1 | 8902 | H:1 |
| 8856 | H:1 | 8903 | H:1 |
| 8857 | H:1 | 8904 | H:1 |
| 8858 | H:1 | 8905 | B:4 |
| 8859 | H:1 | 8906 | H:1 |
| 8860 | H:1 | 8907 | H:1 |
| 8861 | H:1 | 8908 | H:1 |
| 8862 | C:7 | 8909 | H:1 |
| 8863 | H:1 | 8910 | H:1 |
| 8864 | H:1 | 8911 | H:1 |
| 8865 | H:1 | 8912 | H:1 |
| 8866 | H:1 | 8913 | H:1 |
| 8867 | H:1 | 8914 | H:1 |
| 8868 | H:1 | 8915 | H:1 |
| 8869 | H:1 | 8916 | H:1 |
| 8870 | H:1 | 8917 | H:1 |
| 8871 | H:1 | 8918 | H:1 |
| 8872 | H:1 | 8919 | H:1 |
| 8873 | D:1 | 8920 | H:1 |
| 8874 | H:1 | 8921 | H:1 |
| 8875 | H:1 | 8922 | H:1 |
| 8876 | H:1 | 8923 | H:1 |
| 8877 | H:1 | 8924 | H:1 |
| 8878 | H:1 | 8925 | H:1 |
| 8879 | H:1 | 8926 | H:1 |
| 8880 | H:1 | 8927 | H:1 |
| 8881 | H:1 | 8928 | H:1 |
| 8882 | H:1 | 8929 | H:1 |
| 8883 | H:1 | 8930 | H:1 |
| 8884 | C:58 | 8931 | H:1 |
| 8885 | F:1 K:1 | 8932 | H:1 |
| 8886 | H:1 | 8933 | H:1 |
| 8887 | H:1 | 8934 | H:1 |
| 8888 | H:1 | 8935 | H:1 |
| 8889 | H:1 | 8936 | H:1 |
| 8937 | H:1 | 8984 | H:1 |
| 8938 | H:1 | 8985 | H:1 |
| 8939 | H:1 | 8986 | K:1 |
| 8940 | H:1 | 8987 | H:1 |
| 8941 | H:1 | 8988 | H:1 |
| 8942 | H:1 | 8989 | H:1 |
| 8943 | H:1 | 8990 | H:1 |
| 8944 | H:1 | 8991 | H:1 |
| 8945 | H:1 | 8992 | F:2 K:1 |
| 8946 | H:1 | 8993 | H:1 |
| 8947 | H:1 | 8994 | H:1 |
| 8948 | H:1 | 8995 | H:1 |
| 8949 | H:1 | 8996 | H:1 |
| 8950 | H:1 | 8997 | H:1 |
| 8951 | H:1 | 8998 | H:1 |
| 8952 | H:1 | 8999 | H:1 |
| 8953 | H:1 | 9000 | H:1 |
| 8954 | H:1 | 9001 | H:1 |
| 8955 | F:2 K:1 | 9002 | H:1 |
| 8956 | H:1 | 9003 | H:1 |
| 8957 | H:1 | 9004 | H:1 |
| 8958 | H:1 | 9005 | H:1 |
| 8959 | H:1 | 9006 | H:1 |
| 8960 | H:1 | 9007 | H:1 |
| 8961 | H:1 | 9008 | H:1 |
| 8962 | H:1 | 9009 | H:1 |
| 8963 | H:1 | 9010 | H:1 |
| 8964 | H:1 | 9011 | H:1 |
| 8965 | H:1 | 9012 | H:1 |
| 8966 | H:1 | 9013 | H:1 |
| 8967 | H:1 | 9014 | H:1 |
| 8968 | H:1 | 9015 | H:1 |
| 8969 | H:1 | 9016 | I:2 |
| 8970 | H:1 | 9017 | H:1 |
| 8971 | H:1 | 9018 | H:1 |
| 8972 | H:1 | 9019 | H:1 |
| 8973 | H:1 | 9020 | H:1 |
| 8974 | H:1 | 9021 | H:1 |
| 8975 | H:1 | 9022 | H:1 |
| 8976 | K:2 | 9023 | H:1 |
| 8977 | H:1 | 9024 | B:2 |
| 8978 | H:1 | 9025 | H:1 |
| 8979 | H:1 | 9026 | H:1 |
| 8980 | H:1 | 9027 | H:1 |
| 8981 | H:1 | 9028 | H:1 |
| 8982 | H:1 | 9029 | H:1 |
| 8983 | H:1 | 9030 | H:1 |
| 9031 | H:1 | 9078 | H:1 |
| 9032 | H:1 | 9079 | H:1 |
| 9033 | H:1 | 9080 | H:1 |
| 9034 | H:1 | 9081 | H:1 |
| 9035 | H:1 | 9082 | H:1 |
| 9036 | H:1 | 9083 | H:1 |
| 9037 | H:1 | 9084 | H:1 |
| 9038 | H:1 | 9085 | H:1 |
| 9039 | H:1 | 9086 | H:1 |
| 9040 | H:1 | 9087 | H:1 |
| 9041 | H:1 | 9088 | H:1 |
| 9042 | H:1 | 9089 | H:1 |
| 9043 | H:1 | 9090 | H:1 |
| 9044 | H:1 | 9091 | H:1 |
| 9045 | H:1 | 9092 | H:1 |
| 9046 | H:1 | 9093 | F:19 K:3 |
| 9047 | H:1 | 9094 | H:1 |
| 9048 | H:1 | 9095 | H:1 |
| 9049 | H:1 | 9096 | H:1 |
| 9050 | H:1 | 9097 | F:5 K:2 |
| 9051 | H:1 | 9098 | H:1 |
| 9052 | H:1 | 9099 | H:1 |
| 9053 | H:1 | 9100 | H:1 |
| 9054 | H:1 | 9101 | H:1 |
| 9055 | H:1 | 9102 | H:1 |
| 9056 | H:1 | 9103 | H:1 |
| 9057 | H:1 | 9104 | H:1 |
| 9058 | H:1 | 9105 | H:1 |

TABLE V-continued

(Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 9059 | H:1 | 9106 | H:1 | 9226 | H:1 | 9273 | H:1 |
| 9060 | H:1 | 9107 | H:1 | 9227 | H:1 | 9274 | H:1 |
| 9061 | H:1 | 9108 | H:1 | 9228 | H:1 | 9275 | H:1 |
| 9062 | H:1 | 9109 | H:1 | 9229 | H:1 | 9276 | H:1 |
| 9063 | H:1 | 9110 | H:1 | 9230 | H:1 | 9277 | H:1 |
| 9064 | F:1 K:2 | 9111 | H:1 | 9231 | H:1 | 9278 | H:1 |
| 9065 | H:1 | 9112 | H:1 | 9232 | H:1 | 9279 | F:5 K:3 |
| 9066 | H:1 | 9113 | H:1 | 9233 | H:1 | 9280 | H:1 |
| 9067 | H:1 | 9114 | H:1 | 9234 | H:1 | 9281 | H:1 |
| 9068 | H:1 | 9115 | H:1 | 9235 | H:1 | 9282 | H:1 |
| 9069 | H:1 | 9116 | H:1 | 9236 | H:1 | 9283 | H:1 |
| 9070 | H:1 | 9117 | H:1 | 9237 | H:1 | 9284 | H:1 |
| 9071 | H:1 | 9118 | H:1 | 9238 | H:1 | 9285 | H:1 |
| 9072 | H:1 | 9119 | H:1 | 9239 | H:1 | 9286 | H:1 |
| 9073 | H:1 | 9120 | H:1 | 9240 | K:1 | 9287 | H:1 |
| 9074 | H:1 | 9121 | B:3 | 9241 | H:1 | 9288 | H:1 |
| 9075 | H:1 | 9122 | H:1 | 9242 | H:1 | 9289 | H:1 |
| 9076 | H:1 | 9223 | H:1 | 9243 | H:1 | 9290 | H:1 |
| 9077 | H:1 | 9124 | H:1 | 9244 | H:1 | 9291 | H:1 |
| 9125 | H:1 | 9172 | H:1 | 9245 | H:1 | 9292 | H:1 |
| 9126 | H:1 | 9173 | H:1 | 9246 | H:1 | 9293 | H:1 |
| 9127 | H:1 | 9174 | H:1 | 9247 | H:1 | 9294 | H:1 |
| 9128 | H:1 | 9175 | H:1 | 9248 | H:1 | 9295 | H:1 |
| 9129 | H:1 | 9176 | H:1 | 9249 | H:1 | 9296 | H:1 |
| 9130 | H:1 | 9177 | A:182 K:2 | 9250 | H:1 | 9297 | H:1 |
| 9131 | H:1 | 9178 | H:1 | 9251 | H:1 | 9298 | C:1 |
| 9132 | H:1 | 9179 | H:1 | 9252 | H:1 | 9299 | K:2 |
| 9133 | H:1 | 9180 | H:1 | 9253 | H:1 | 9300 | H:1 |
| 9134 | H:1 | 9181 | H:1 | 9254 | H:1 | 9301 | H:1 |
| 9135 | H:1 | 9182 | H:1 | 9255 | H:1 | 9302 | H:1 |
| 9136 | H:1 | 9183 | H:1 | 9256 | F:14 K:7 | 9303 | H:1 |
| 9137 | H:1 | 9184 | H:1 | 9257 | H:1 | 9304 | H:1 |
| 9138 | H:1 | 9185 | A:186 K:2 | 9258 | H:1 | 9305 | H:1 |
| 9139 | H:1 | 9186 | H:1 | 9259 | H:1 | 9306 | H:1 |
| 9140 | H:1 | 9187 | H:1 | 9260 | H:1 | 9307 | C:6 |
| 9141 | H:1 | 9188 | H:1 | 9261 | H:1 | 9308 | H:1 |
| 9142 | H:1 | 9189 | H:1 | 9262 | H:1 | 9309 | H:1 |
| 9143 | H:1 | 9190 | H:1 | 9263 | H:1 | 9310 | H;1 |
| 9144 | H:1 | 9191 | H:1 | 9264 | H:1 | 9311 | H:1 |
| 9145 | H:1 | 9192 | C:5 | 9265 | H:1 | 9312 | H:1 |
| 9146 | H:1 | 9193 | H:1 | 9313 | H:1 | 9360 | H:1 |
| 9147 | H:1 | 9194 | H:1 | 9314 | H:1 | 9361 | H:1 |
| 9148 | H:1 | 9195 | H:1 | 9315 | H:1 | 9362 | A:4 |
| 9149 | H:1 | 9196 | H:1 | 9316 | H:1 | 9363 | H:1 |
| 9150 | H:1 | 9197 | H:1 | 9317 | H:1 | 9364 | H:1 |
| 9151 | H:1 | 9198 | H:1 | 9318 | H:1 | 9365 | H:1 |
| 9152 | H:1 | 9199 | H:1 | 9319 | H:1 | 9366 | H:1 |
| 9153 | H:1 | 9200 | H:1 | 9320 | H:1 | 9367 | H:1 |
| 9154 | H:1 | 9201 | H:1 | 9321 | H:1 | 9368 | H:1 |
| 9155 | H:1 | 9202 | H:1 | 9322 | H:1 | 9369 | H:1 |
| 9156 | H:1 | 9203 | H:1 | 9323 | H:1 | 9370 | H:1 |
| 9157 | H:1 | 9204 | H:1 | 9324 | H:1 | 9371 | H:1 |
| 9158 | H:1 | 9205 | H:1 | 9325 | H:1 | 9372 | C:1 |
| 9159 | H:1 | 9206 | H:1 | 9326 | H:1 | 9373 | H:1 |
| 9160 | H:1 | 9207 | H:1 | 9327 | H:1 | 9374 | H:1 |
| 9161 | H:1 | 9208 | A:2 | 9328 | H:1 | 9375 | H:1 |
| 9162 | H:1 | 9209 | H:1 | 9329 | H:1 | 9376 | H:1 |
| 9163 | H:1 | 9210 | H:1 | 9330 | H:1 | 9377 | H:1 |
| 9164 | H:1 | 9211 | H:1 | 9331 | H:1 | 9378 | H:1 |
| 9165 | H:1 | 9212 | H:1 | 9332 | H:1 | 9379 | H:1 |
| 9166 | H:1 | 9213 | H:1 | 9333 | H:1 | 9380 | C:1 |
| 9167 | H:1 | 9214 | H:1 | 9334 | H:1 | 9381 | H:1 |
| 9168 | H:1 | 9215 | H:1 | 9335 | H:1 | 9382 | H:1 |
| 9169 | H:1 | 9216 | H:1 | 9336 | H:1 | 9383 | H:1 |
| 9170 | H:1 | 9217 | C:32 | 9337 | H:1 | 9384 | H:1 |
| 9171 | H:1 | 9218 | A:3 | 9338 | H:1 | 9385 | H:1 |
| 9219 | H:1 | 9266 | H:1 | 9339 | A:2 | 9386 | H:1 |
| 9220 | H:1 | 9267 | H:1 | 9340 | H:1 | 9387 | H:1 |
| 9221 | H:1 | 9268 | H:1 | 9341 | H:1 | 9388 | H:1 |
| 9222 | H:1 | 9269 | H:1 | 9342 | H:1 | 9389 | H:1 |
| 9223 | H:1 | 9270 | H:1 | 9343 | H:1 | 9390 | H:1 |
| 9224 | H:1 | 9271 | H:1 | 9344 | H:1 | 9391 | H:1 |
| 9225 | H:1 | 9272 | H:1 | 9345 | H:1 | 9392 | H:1 |

TABLE V-continued
(Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 9346 | H:1 | 9393 | H:1 | 9513 | F:1 | 9560 | F:1 |
| 9347 | H:1 | 9394 | H:1 | 9514 | F:1 | 9561 | F:1 |
| 9348 | H:1 | 9395 | H:1 | 9515 | F:1 | 9562 | F:1 |
| 9349 | H:1 | 9396 | F:14 K:89 | 9516 | F:1 | 9563 | F:1 |
| 9350 | H:1 | 9397 | H:1 | 9517 | F:1 | 9564 | F:1 |
| 9351 | H:1 | 9398 | H:1 | 9518 | K:1 | 9565 | F:1 |
| 9352 | H:1 | 9399 | H:1 | 9519 | F:1 | 9566 | F:1 |
| 9353 | H:1 | 9400 | H:1 | 9520 | F:1 | 9567 | F:1 |
| 9354 | H:1 | 9401 | H:1 | 9521 | F:1 | 9568 | F:1 |
| 9355 | H:1 | 9402 | H:1 | 9522 | F:1 | 9569 | F:1 |
| 9356 | H:1 | 9403 | F:1 K:3 | 9523 | F:1 | 9570 | F:1 |
| 9357 | F:1 K:1 | 9404 | H:1 | 9524 | F:1 | 9571 | F:1 |
| 9358 | H:1 | 9405 | H:1 | 9525 | K:1 | 9572 | F:1 |
| 9359 | H:1 | 9406 | H:1 | 9526 | F:1 | 9573 | F:1 |
| 9407 | H:1 | 9454 | H:1 | 9527 | F:1 | 9574 | F:1 |
| 9408 | H:1 | 9455 | H:1 | 9528 | F:1 | 9575 | F:1 |
| 9409 | H:1 | 9456 | H:1 | 9529 | F:1 | 9576 | F:1 |
| 9410 | H:1 | 9457 | H:1 | 9530 | F:1 | 9577 | F:1 |
| 9411 | F:55 K:295 | 9458 | H:1 | 9531 | F:1 | 9578 | F:1 |
| 9412 | H:1 | 9459 | H:1 | 9532 | K:1 | 9579 | F:1 |
| 9413 | H:1 | 9460 | H:1 | 9533 | F:1 | 9580 | F:1 |
| 9414 | H:1 | 9461 | H:1 | 9534 | F:1 | 9581 | F:1 |
| 9415 | H:1 | 9462 | A:1 D:1 | 9535 | F:1 | 9582 | F:1 |
| 9416 | H:1 | 9463 | K:1 | 9536 | F:1 | 9583 | F:1 |
| 9417 | H:1 | 9464 | H:1 | 9537 | F:1 | 9584 | F:1 |
| 9418 | H:1 | 9465 | H:1 | 9538 | F:1 | 9585 | F:1 |
| 9419 | H:1 | 9466 | H:1 | 9539 | K:1 | 9586 | F:1 |
| 9420 | F:11 K:4 | 9467 | H:1 | 9540 | F:1 | 9587 | F:1 |
| 9421 | H:1 | 9468 | H:1 | 9541 | F:1 | 9588 | F:1 |
| 9422 | H:1 | 9469 | H:1 | 9542 | F:1 | 9589 | F:1 |
| 9423 | H:1 | 9470 | H:1 | 9543 | F:1 | 9590 | F:1 |
| 9424 | H:1 | 9471 | H:1 | 9544 | F:1 | 9591 | F:1 |
| 9425 | H:1 | 9472 | H:1 | 9545 | F:1 | 9592 | F:1 |
| 9426 | H:1 | 9473 | H:1 | 9546 | A:2 F:1 K:3 | 9593 | F:1 |
| 9427 | H:1 | 9474 | F:1 | 9547 | F:1 | 9594 | F:1 |
| 9428 | K:1 | 9475 | H:1 | 9595 | F:1 | 9642 | F:1 |
| 9429 | H:1 | 9476 | H:1 | 9596 | F:1 | 9643 | C:4 |
| 9430 | H:1 | 9477 | H:1 | 9597 | K:2 | 9644 | F:1 |
| 9431 | H:1 | 9478 | H:1 | 9598 | K:1 | 9645 | F:1 |
| 9432 | H:1 | 9479 | H:1 | 9599 | F:1 | 9646 | F:1 |
| 9433 | H:1 | 9480 | H:1 | 9600 | F:1 | 9647 | F:1 |
| 9434 | H:1 | 9481 | H:1 | 9601 | F:1 | 9648 | F:1 |
| 9435 | K:1 | 9482 | H:1 | 9602 | F:1 | 9649 | F:1 |
| 9436 | H:1 | 9483 | H:1 | 9603 | F:1 | 9650 | F:1 |
| 9437 | H:1 | 9484 | K:1 | 9604 | F:1 | 9651 | F:1 |
| 9438 | H:1 | 9485 | H:1 | 9605 | F:1 | 9652 | B:1 D:1 |
| 9439 | H:1 | 9486 | H:1 | 9606 | F:1 | 9653 | F:1 |
| 9440 | H:1 | 9487 | H:1 | 9607 | F:1 | 9654 | F:1 |
| 9441 | H:1 | 9488 | H:1 | 9608 | F:1 | 9655 | F:1 |
| 9442 | H:1 | 9489 | H:1 | 9609 | F:1 | 9656 | F:1 |
| 9443 | H:1 | 9490 | H:1 | 9610 | F:1 | 9657 | F:1 |
| 9444 | K:1 | 9491 | H:1 | 9611 | F:1 | 9658 | F:1 |
| 9445 | H:1 | 9492 | H:1 | 9612 | F:1 | 9659 | F:1 |
| 9446 | H:1 | 9493 | H:1 | 9613 | F:1 | 9660 | F:1 |
| 9447 | H:1 | 9494 | H:1 | 9614 | K:2 | 9661 | F:1 |
| 9448 | H:1 | 9495 | H:1 | 9615 | F:1 | 9662 | F:1 |
| 9449 | H:1 | 9496 | H:1 | 9616 | F:1 | 9663 | F:1 |
| 9450 | H:1 | 9497 | H:1 | 9617 | F:1 | 9664 | F:1 |
| 9451 | H:1 | 9498 | H:1 | 9618 | F:1 | 9665 | F:1 |
| 9452 | H:1 | 9499 | H:1 | 9619 | F:1 | 9666 | F:1 |
| 9453 | F:1 | 9500 | H:1 | 9620 | F:1 | 9667 | F:1 |
| 9501 | H:1 | 9548 | F:1 | 9621 | F:1 | 9668 | F:1 |
| 9502 | H:1 | 9549 | F:1 | 9622 | F:4 K:3 | 9669 | H:2 |
| 9503 | H:1 | 9550 | F:1 | 9623 | F:1 | 9670 | F:1 |
| 9504 | H:1 | 9551 | F:1 | 9624 | F:1 | 9671 | F:1 |
| 9505 | H:1 | 9552 | F:1 | 9625 | F:1 | 9672 | F:1 |
| 9506 | H:1 | 9553 | H:2 | 9626 | F:1 | 9673 | F:1 |
| 9507 | H:1 | 9554 | F:1 | 9627 | F:1 | 9674 | F:1 |
| 9508 | H:1 | 9555 | F:1 | 9628 | F:1 | 9675 | F:1 |
| 9509 | H:1 | 9556 | F:1 | 9629 | F:1 | 9676 | H:1 |
| 9510 | F:1 | 9557 | F:1 | 9630 | F:1 | 9677 | A:2 |
| 9511 | F:1 | 9558 | F:1 | 9631 | F:1 | 9678 | H:1 |
| 9512 | F:1 | 9559 | F:1 | 9632 | F:1 | 9679 | H:1 |

TABLE V-continued

(Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 9633 | F:4 | 9680 | H:1 | 9800 | C:41 | 9847 | K:1 |
| 9634 | F:1 | 9681 | H:1 | 9801 | K:1 | 9848 | K:1 |
| 9635 | F:1 | 9682 | H:1 | 9802 | K:1 | 9849 | K:1 |
| 9636 | F:1 | 9683 | H:1 | 9803 | K:1 | 9850 | K:1 |
| 9637 | F:1 | 9684 | H:1 | 9804 | K:1 | 9851 | K:1 |
| 9638 | F:1 | 9685 | H:1 | 9805 | K:1 | 9852 | K:1 |
| 9639 | F:1 | 9686 | H:1 | 9806 | K:1 | 9853 | H:1 |
| 9640 | F:1 | 9687 | H:1 | 9807 | K:1 | 9854 | K:1 |
| 9641 | F:1 | 9688 | H:1 | 9808 | K:1 | 9855 | K:1 |
| 9689 | H:1 | 9736 | K:1 | 9809 | K:1 | 9856 | K:1 |
| 9690 | H:1 | 9737 | K:1 | 9810 | K:1 | 9857 | K:1 |
| 9691 | H:1 | 9738 | K:1 | 9811 | K:1 | 9858 | K:1 |
| 9692 | H:1 | 9739 | K:1 | 9812 | K:1 | 9859 | K:1 |
| 9693 | H:1 | 9740 | K:1 | 9813 | K:1 | 9860 | K:1 |
| 9694 | H:1 | 9741 | K:1 | 9814 | K:1 | 9861 | B:3 C:2 D:2 F:1 K:2 |
| 9695 | H:1 | 9742 | K:1 | 9815 | K:1 | 9862 | K:1 |
| 9696 | H:1 | 9743 | K:1 | 9816 | K:1 | 9863 | K:1 |
| 9697 | H:1 | 9744 | K:1 | 9817 | K:1 | 9864 | K:1 |
| 9698 | H:1 | 9745 | K:1 | 9818 | K:1 | 9865 | K:1 |
| 9699 | H:1 | 9746 | K:1 | 9819 | K:1 | 9866 | K:1 |
| 9700 | H:1 | 9747 | K:1 | 9820 | K:1 | 9867 | K:1 |
| 9701 | H:1 | 9748 | F:1 K:1 | 9821 | K:1 | 9868 | K:1 |
| 9702 | H:1 | 9749 | K:1 | 9822 | K:1 | 9869 | K:1 |
| 9703 | H:1 | 9750 | K:1 | 9823 | K:1 | 9870 | K:1 |
| 9704 | H:1 | 9751 | K:1 | 9824 | K:1 | 9871 | A:1 |
| 9705 | H:1 | 9752 | K:1 | 9825 | K:1 | 9872 | K:1 |
| 9706 | H:1 | 9753 | K:1 | 9826 | K:1 | 9873 | K:1 |
| 9707 | H:1 | 9754 | K:1 | 9827 | K:1 | 9874 | K:1 |
| 9708 | H:1 | 9755 | K:1 | 9828 | K:1 | 9875 | K:1 |
| 9709 | H:1 | 9756 | K:1 | 9829 | K:1 | 9876 | K:1 |
| 9710 | H:1 | 9757 | K:1 | 9877 | K:1 | 9924 | A:1 |
| 9711 | H:1 | 9758 | K:1 | 9878 | K:1 | 9925 | A:1 |
| 9712 | H:1 | 9759 | K:2 | 9879 | K:5 | 9926 | A:1 |
| 9713 | H:1 | 9760 | K:1 | 9880 | F:6 K:33 | 9927 | A:1 |
| 9714 | H:1 | 9761 | K:1 | 9881 | K:1 | 9928 | A:1 |
| 9715 | H:1 | 9762 | K:1 | 9882 | K:1 | 9929 | A:1 |
| 9716 | H:1 | 9763 | K:1 | 9883 | K:1 | 9930 | A:1 |
| 9717 | H:1 | 9764 | K:1 | 9884 | K:1 | 9931 | A:1 |
| 9718 | H:1 | 9765 | K:1 | 9885 | B:2 H:6 | 9932 | A:1 |
| 9719 | H:1 | 9766 | K:1 | 9886 | K:1 | 9933 | A:1 |
| 9720 | H:1 | 9767 | K:1 | 9887 | K:1 | 9934 | A:1 |
| 9721 | B:4 C:3 | 9768 | K:1 | 9888 | K:1 | 9935 | A:1 |
| 9722 | H:1 | 9769 | B:2 | 9889 | K:1 | 9936 | A:1 |
| 9723 | H:1 | 9770 | K:1 | 9890 | K:1 | 9937 | A:1 |
| 9724 | H:1 | 9771 | K:1 | 9891 | K:1 | 9938 | A:1 |
| 9725 | H:1 | 9772 | K:1 | 9892 | K:1 | 9939 | A:1 |
| 9726 | H:1 | 9773 | K:1 | 9893 | I:2 | 9940 | A:1 |
| 9727 | H:1 | 9774 | K:1 | 9894 | K:1 | 9941 | A:1 |
| 9728 | K:1 | 9775 | K:1 | 9895 | K:1 | 9942 | A:1 |
| 9729 | K:1 | 9776 | K:1 | 9896 | K:1 | 9943 | A:1 |
| 9730 | K:1 | 9777 | K:1 | 9897 | K:1 | 9944 | A:1 |
| 9731 | A:28 | 9778 | K:1 | 9898 | K:1 | 9945 | A:1 |
| 9732 | K:1 | 9779 | K:1 | 9899 | K:1 | 9946 | A:1 |
| 9733 | K:1 | 9780 | B:1 C:8 F:1 H:1 | 9900 | K:1 | 9947 | A:1 |
| 9734 | K:1 | 9781 | K:1 | 9901 | K:1 | 9948 | A:1 |
| 9735 | K:1 | 9782 | K:1 | 9902 | K:1 | 9949 | A:1 |
| 9783 | K:1 | 9830 | K:1 | 9903 | K:1 | 9950 | A:1 |
| 9784 | K:1 | 9831 | K:1 | 9904 | K:1 | 9951 | A:1 |
| 9785 | K:1 | 9832 | K:1 | 9905 | K:1 | 9952 | A:1 |
| 9786 | K:1 | 9833 | K:1 | 9906 | K:1 | 9953 | A:1 |
| 9787 | K:1 | 9834 | K:1 | 9907 | K:1 | 9954 | A:1 |
| 9788 | K:1 | 9835 | K:1 | 9908 | K:1 | 9955 | A:1 |
| 9789 | K:1 | 9836 | H:1 I:4 | 9909 | K:1 | 9956 | A:1 |
| 9790 | K:1 | 9837 | K:1 | 9910 | K:1 | 9957 | A:1 |
| 9791 | K:1 | 9838 | K:1 | 9911 | K:1 | 9958 | A:1 |
| 9792 | K:1 | 9839 | K:1 | 9912 | A:1 | 9959 | A:1 |
| 9793 | K:1 | 9840 | K:1 | 9913 | A:1 | 9960 | A:1 |
| 9794 | K:1 | 984 | K:1 | 9914 | A:1 | 9961 | A:1 |
| 9795 | K:1 | 9842 | K:1 | 9915 | A:1 | 9962 | A:1 |
| 9796 | K:1 | 9843 | K:1 | 9916 | A:1 | 9963 | A:1 |
| 9797 | K:1 | 9844 | K:1 | 9917 | A:1 | 9964 | F:1 K:1 |
| 9798 | K:1 | 9845 | K:1 | 9918 | A:1 B:1 C:20 | 9965 | A:1 |
| 9799 | K:1 | 9846 | K:1 | 9919 | A:1 | 9966 | A:1 |

TABLE V-continued

(Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 9920 | A:1 | 9967 | A:1 | 10087 | F:1 | 10134 | F:1 |
| 9921 | A:1 | 9968 | A:1 | 10088 | K:2 | 10135 | F:1 |
| 9922 | A:1 | 9969 | A:1 | 10089 | F:1 | 10136 | F:1 |
| 9923 | A:1 | 9970 | A:1 | 10090 | F:1 | 10137 | F:1 |
| 9971 | F:1 | 10018 | F:1 | 10091 | F:1 | 10138 | F:1 |
| 9972 | F:1 | 10019 | F:1 | 10092 | F:1 | 10139 | F:1 |
| 9973 | F:1 | 10020 | F:1 | 10093 | F:1 | 10140 | F:1 |
| 9974 | F:1 | 10021 | F:1 | 10094 | F:1 | 10141 | F:1 |
| 9975 | F:1 | 10022 | F:1 | 10095 | F:1 | 10142 | F:1 |
| 9976 | F:1 | 10023 | F:1 | 10096 | F:1 | 10143 | F:1 |
| 9977 | F:1 | 10024 | F:1 | 10097 | F:1 | 10144 | F:1 |
| 9978 | F:1 | 10025 | F:1 | 10098 | F:1 | 10145 | F:1 |
| 9979 | F:1 | 10026 | F:1 | 10099 | F:1 | 10146 | F:1 |
| 9980 | F:1 | 10027 | F:1 | 10100 | F:1 | 10147 | F:1 |
| 9981 | F:1 | 10028 | F:1 | 10101 | F:1 | 10148 | F:1 |
| 9982 | F:1 | 10029 | F:1 | 10102 | F:1 | 10149 | F:1 |
| 9983 | F:1 | 10030 | F:1 | 10103 | F:1 | 10150 | F:1 |
| 9984 | F:1 | 10031 | F:1 | 10104 | F:1 | 10151 | F:1 |
| 9985 | F:1 | 10032 | A:1 C:4 H:1 | 10105 | F:1 | 10152 | F:1 |
| 9986 | F:1 | 10033 | F:1 | 10106 | F:1 K:1 | 10153 | F:9 K:1 |
| 9987 | F:1 | 0034 | F:1 | 10107 | F:1 | 10154 | F:1 |
| 9988 | A:7 | 10035 | F:1 | 10108 | F:1 | 10155 | F:1 |
| 9989 | F:1 | 10036 | F:1 | 10109 | F:1 | 10156 | F:1 |
| 9990 | F:1 | 10037 | F:1 | 10110 | F:1 | 10157 | F:1 |
| 9991 | F:1 | 10038 | F:1 | 10111 | F:1 | 10158 | F:1 |
| 9992 | F:1 | 10039 | F:1 | 10159 | F:1 | 10206 | F:1 |
| 9993 | F:1 | 10040 | F:1 | 10160 | F:1 | 10207 | F:1 |
| 9994 | F:1 | 10041 | F:1 | 10161 | F:1 | 10208 | F:1 |
| 9995 | F:1 | 10042 | A:2 | 10162 | F:1 | 10209 | F:1 |
| 9996 | F:1 | 10043 | F:1 | 10163 | F:1 | 10210 | F:1 |
| 9997 | F:1 | 10044 | F:1 | 10164 | F:1 | 10211 | F:1 |
| 9998 | F:1 | 10045 | F:1 | 10165 | F:1 | 10212 | F:1 |
| 9999 | F:1 | 10046 | F:1 | 10166 | F:1 | 10213 | F:1 |
| 10000 | F:1 | 10047 | F:1 | 10167 | F:1 | 10214 | F:1 |
| 10001 | F:1 | 10048 | F:1 | 10168 | F:2 | 10215 | F:1 |
| 10002 | F:1 | 10049 | F:1 | 10169 | F:1 | 10216 | F:1 |
| 10003 | F:1 | 10050 | F:1 | 10170 | F:1 | 10217 | F:1 |
| 10004 | F:1 | 10051 | F:1 | 10171 | F:1 | 10218 | F:1 |
| 10005 | F:1 | 10052 | F:1 | 10172 | F:1 | 10219 | F:1 |
| 10006 | F:1 | 10053 | F:1 | 10173 | F:1 | 10220 | F:1 |
| 10007 | F:1 | 10054 | F:1 | 10174 | F:1 | 10221 | F:1 |
| 10008 | F:1 | 10055 | F:1 | 10175 | F:1 | 10222 | F:1 |
| 10009 | F:1 | 10056 | F:1 | 10176 | F:1 | 10223 | F:1 |
| 10010 | F:1 | 10057 | F:1 | 10177 | F:1 | 10224 | F:1 |
| 10011 | F:1 | 10058 | F:1 | 10178 | F:10 K:4 | 10225 | F:1 |
| 10012 | F:1 | 10059 | F:1 | 10179 | F:1 | 10226 | K:1 |
| 10013 | F:1 | 10060 | F:1 | 10180 | F:1 | 10227 | K:1 |
| 10014 | F:1 | 10061 | F:1 | 10181 | F:1 | 10228 | K:1 |
| 10015 | F:1 | 10062 | F:1 | 10182 | F:1 | 10229 | F:1 |
| 10016 | F:1 | 10063 | F:1 | 10183 | F:1 | 10230 | K:1 |
| 10017 | F:1 | 10064 | F:1 | 10184 | F:1 | 10231 | K;1 |
| 10065 | F:1 | 10112 | F:1 | 10185 | K:1 | 10232 | K:1 |
| 10066 | F:1 | 10113 | F:1 | 10186 | F:1 | 10233 | K:1 |
| 10067 | F:1 | 10114 | F:1 | 10187 | F:1 | 10234 | K:1 |
| 10068 | F:1 | 10115 | F:1 | 10188 | F:1 | 10235 | K:1 |
| 10069 | F:1 | 10116 | F:1 | 10189 | F:2 | 10236 | K:1 |
| 10070 | F:1 | 10117 | F:1 | 10190 | F:1 | 10237 | F:1 |
| 10071 | F:1 | 10118 | F:1 | 10191 | F:1 | 10238 | K:1 |
| 10072 | F:1 | 10119 | F:1 | 10192 | F:1 | 10239 | K:1 |
| 10073 | F:1 K:1 | 10120 | F:1 | 10193 | K:1 | 10240 | K:1 |
| 10074 | F:1 | 10121 | F:1 | 10194 | F:1 | 10241 | K:1 |
| 10075 | F:1 | 10122 | F:1 | 10195 | F:1 | 10242 | K:1 |
| 10076 | F:1 | 10123 | F:1 | 10196 | F:1 | 10243 | K:1 |
| 10077 | F:1 | 10124 | F:1 | 10197 | F:1 | 10244 | K:1 |
| 10078 | F:1 | 10125 | F:1 | 10198 | F:1 | 10245 | K:1 |
| 10079 | C:4 | 10126 | F:1 | 10199 | F:1 | 10246 | K:1 |
| 10080 | F:1 | 10127 | F:1 | 10200 | F:1 | 10247 | K:1 |
| 10081 | F:1 | 10128 | F:1 | 10201 | F:1 | 10248 | F:1 |
| 10082 | F:1 | 10129 | F:1 | 10202 | F:1 | 10249 | K:1 |
| 10083 | F:1 | 10130 | F:1 | 10203 | F:1 | 10250 | K:1 |
| 10084 | F:1 | 10131 | F:1 | 10204 | F:1 | 10251 | K:1 |
| 10085 | F:1 | 10132 | F:1 | 10205 | F:1 | 10252 | K:1 |
| 10086 | F:1 | 10133 | F:1 | 10253 | K:1 | 10299 | K:1 |

TABLE V-continued (Spatial distribution)

| Seq Id No. | Tissue distribution | Seq Id No. | Tissue distribution |
|---|---|---|---|
| 10254 | K:1 | 10300 | K:1 |
| 10255 | K:1 | 10301 | K:1 |
| 10256 | K:1 | 10302 | K:1 |
| 10257 | K:1 | 10303 | K:1 |
| 10258 | F:1 | 10304 | K:1 |
| 10259 | K:1 | 10305 | K:1 |
| 10260 | K:1 | 10306 | F:1 |
| 10261 | K:1 | 10307 | K:1 |
| 10262 | K:1 | 10308 | K:1 |
| 10263 | K:1 | 10309 | K:1 |
| 10264 | K:1 | 10310 | K:1 |
| 10265 | K:1 | 10311 | K:1 |
| 10266 | K:1 | 10312 | K:1 |
| 10267 | K:1 | 10313 | K:1 |
| 10268 | K:1 | 10314 | K:1 |
| 10269 | F:1 | 10315 | K:1 |
| 10270 | K:1 | 10316 | K:1 |
| 10271 | K:1 | 10317 | K:1 |
| 10272 | K:1 | 10318 | K:1 |
| 10273 | K:1 | 10319 | K:1 |
| 10274 | K:1 | 10320 | K:1 |
| 10275 | K:1 | 10321 | K:1 |
| 10276 | K:1 | 10322 | K:1 |
| 10277 | K:1 | 10323 | K:1 |
| 10278 | F:1 | 10324 | K:1 |
| 10279 | K:1 | 10325 | K:1 |
| 10280 | K:1 | 10326 | K:1 |
| 10281 | K:1 | 10327 | K:1 |
| 10282 | K:1 | 10328 | K:1 |
| 10283 | K:1 | 10329 | K:1 |
| 10284 | K:1 | 10330 | K:1 |
| 10285 | K:1 | 10331 | F:1 K:1 |
| 10286 | F:1 | 10332 | K:1 |
| 10287 | K:1 | 10333 | K:1 |
| 10288 | K:1 | 10334 | K:1 |
| 10289 | K:1 | 10335 | K:1 |
| 10290 | K:1 | 10336 | K:1 |
| 10291 | K:1 | 10337 | K:1 |
| 10292 | K:1 | 10338 | K:1 |
| 10293 | K:1 | 10339 | F:9 K:3 |
| 10294 | K:1 | 10340 | K:1 |
| 10295 | A:13 B:18 C:60 D:6 F:3 H:53 I:1 K:7 | 10341 | K:1 |
| 10296 | A:6 | 10342 | K:1 |
| 10297 | F:1 | 10343 | K:1 |
| 10298 | K:1 | 10344 | K:1 |
| 10346 | K:1 | 10393 | K:1 |
| 10347 | K:1 | 10394 | K:1 |
| 10348 | F:9 K:4 | 10395 | K:1 |
| 10349 | K:1 | 10396 | K:1 |
| 10350 | K:1 | 10397 | K:1 |
| 10351 | K:1 | 10398 | K:1 |
| 10352 | K:1 | 10399 | K:1 |
| 10353 | K:1 | 10400 | K:1 |
| 10354 | K:1 | 10401 | A:1 |
| 10355 | K:1 | 10402 | K:1 |
| 10356 | K:1 | 10403 | K:1 |
| 10357 | K:1 | 10404 | K:1 |
| 10358 | K:1 | 10405 | K:1 |
| 10359 | K:1 | 10406 | K:1 |
| 10360 | K:1 | 10407 | K:1 |
| 10361 | K:1 | 10408 | K:3 |
| 10362 | K:1 | 10409 | K:1 |
| 10363 | K:2 | 10410 | K:1 |
| 10364 | K:1 | 10411 | K:1 |
| 10365 | K:1 | 10412 | K:1 |
| 10366 | K:1 | 10413 | A:3 |
| 10367 | K:1 | 10414 | K:1 |
| 10368 | K:1 | 10415 | K:1 |
| 10369 | K:1 | 10416 | K:1 |
| 10370 | K:1 | 10417 | K:1 |
| 10371 | K:1 | 10418 | K:1 |
| 10372 | K:1 | 10419 | K:1 |
| 10373 | K:1 | 10420 | K:1 |
| 10374 | K:1 | 10421 | I:2 |
| 10375 | K:1 | 10422 | K:1 |
| 10376 | K:1 | 10423 | K:1 |
| 10377 | A:4 | 10424 | K:1 |
| 10378 | H:2 | 10425 | K:1 |
| 10379 | K:1 | 10426 | K:1 |
| 10380 | K:1 | 10427 | B:2 |
| 10381 | K:1 | 10428 | K:1 |
| 10382 | K:1 | 10429 | K:1 |
| 10383 | K:1 | 10430 | K:1 |
| 10384 | K:1 | 10431 | K:1 |
| 10385 | K:1 | 10432 | K:1 |
| 10386 | K:1 | 10433 | K:1 |
| 10387 | K:1 | 10434 | K:1 |
| 10388 | K:1 | 10435 | K:1 |
| 10389 | K:1 | 10436 | K:1 |
| 10390 | K:1 | 10437 | K:1 |
| 10391 | K:1 | 10438 | F:4 K:2 |
| 10392 | F:1 | 10439 | K:1 |
| 10440 | K:1 | 10487 | K:1 |
| 10441 | K:1 | 10488 | K:1 |
| 10442 | K:1 | 10489 | K:1 |
| 10443 | K:1 | 10490 | K:1 |
| 10444 | F:1 K:1 | 10491 | K:1 |
| 10445 | A:5 | 10492 | K:1 |
| 10446 | K:1 | 10493 | K:1 |
| 10447 | K:1 | 10494 | K:1 |
| 10448 | K:1 | 10495 | K:1 |
| 10449 | K:1 | 10496 | K:1 |
| 10450 | K:1 | 10497 | K:1 |
| 10451 | K:1 | 10498 | K:1 |
| 10452 | K:1 | 10499 | K:1 |
| 10453 | A:5 | 10500 | K:1 |
| 10454 | K:1 | 10501 | K:1 |
| 10455 | K:1 | 10502 | K:1 |
| 10456 | K:1 | 10503 | K:1 |
| 10457 | K:1 | 10504 | A:1 |
| 10458 | K:1 | 10505 | K:1 |
| 10459 | K:1 | 10506 | K:1 |
| 10460 | K:1 | 10507 | K:1 |
| 10461 | K:1 | 10508 | K:1 |
| 10462 | K:1 | 10509 | K:1 |
| 10463 | K:1 | 10510 | K:1 |
| 10464 | K:1 | 10511 | K:1 |
| 10465 | K:1 | 10512 | K:1 |
| 10466 | K:1 | 10513 | K:1 |
| 10467 | K:1 | 10514 | K:1 |
| 10468 | K:1 | 10515 | K:1 |
| 10469 | K:1 | 10516 | K:1 |
| 10470 | K:1 | 10517 | K:1 |
| 10471 | K:1 | 10518 | K:1 |
| 10472 | K:1 | 10519 | K:1 |
| 10473 | K:1 | 10520 | K:1 |
| 10474 | K:1 | 10521 | K:1 |
| 10475 | K:1 | 10522 | K:1 |
| 10476 | K:1 | 10523 | B:1 C:2 |
| 10477 | K:1 | 10524 | K:1 |
| 10478 | A:1 | 10525 | K:1 |
| 10479 | K:1 | 10526 | K:1 |
| 10480 | K:1 | 10527 | K:1 |
| 10481 | K:1 | 10528 | K:1 |
| 10482 | K:1 | 10529 | K:1 |
| 10483 | K:1 | 10530 | K:1 |
| 10484 | K:1 | 10531 | C:1 H:1 |
| 10485 | K:1 | 10532 | K:1 |
| 10486 | K:1 | 10533 | K:1 |
| 10534 | K:1 | 10581 | K:1 |
| 10535 | K:1 | 10582 | K:1 |
| 10536 | K:1 | 10583 | K:1 |
| 10537 | K:1 | 10584 | K:1 |
| 10538 | A:1 B:2 H:1 K:1 | 10585 | K:1 |
| 10539 | K:1 | 10586 | K:1 |

TABLE V-continued

(Spatial distribution)

| Seq Id No. | Tissue distribution | Seq Id No. | Tissue distribution |
|---|---|---|---|
| 10540 | K:1 | 10587 | K:1 |
| 10541 | K:1 | 10588 | K:1 |
| 10542 | K:1 | 10589 | K:1 |
| 10543 | K:1 | 10590 | K:1 |
| 10544 | K:1 | 10591 | D:1 |
| 10545 | K:1 | 10592 | K:1 |
| 10546 | K:1 | 10593 | K:1 |
| 10547 | K:1 | 10594 | K:1 |
| 10548 | K:1 | 10595 | K:1 |
| 10549 | K:1 | 10596 | K:1 |
| 10550 | K:1 | 10597 | K:2 |
| 10551 | K:1 | 10598 | K:1 |
| 10552 | K:1 | 10599 | K:1 |
| 10553 | K:1 | 10600 | K:1 |
| 10554 | C:1 | 10601 | K:1 |
| 10555 | K:1 | 10602 | K:1 |
| 10556 | K:1 | 10603 | K:1 |
| 10557 | K:1 | 10604 | K:1 |
| 10558 | K:1 | 10605 | K:1 |
| 10559 | K:1 | 10606 | K:1 |
| 10560 | K:1 | 10607 | K:1 |
| 10561 | K:1 | 10608 | K:1 |
| 10562 | K:1 | 10609 | K:1 |
| 10563 | K:1 | 10610 | K:1 |
| 10564 | K:1 | 10611 | K:1 |
| 10565 | K:1 | 10612 | K:1 |
| 10566 | K:1 | 10613 | K:1 |
| 10567 | K:1 | 10614 | K:1 |
| 10568 | K:1 | 10615 | K:1 |
| 10569 | K:1 | 10616 | K:1 |
| 10570 | K:1 | 10617 | K:1 |
| 10571 | K:1 | 10618 | K:1 |
| 10572 | K:1 | 10619 | K:1 |
| 10573 | K:1 | 10620 | K:1 |
| 10574 | K:1 | 10621 | K:1 |
| 10575 | K:1 | 10622 | K:1 |
| 10576 | K:1 | 10623 | K:1 |
| 10577 | K:1 | 10624 | K:1 |
| 10578 | K:1 | 10625 | K:1 |
| 10579 | K:1 | 10626 | K:1 |
| 10580 | K:1 | 10627 | K:1 |
| 10628 | K:1 | 10675 | K:1 |
| 10629 | K:1 | 10676 | K:1 |
| 10630 | K:1 | 10677 | K:1 |
| 10631 | K:1 | 10678 | K:1 |
| 10632 | K:1 | 10679 | F:1 K:1 |
| 10633 | K:1 | 10680 | K:1 |
| 10634 | K:1 | 10681 | K:1 |
| 10635 | K:1 | 10682 | K:1 |
| 10636 | K:1 | 10683 | K:1 |
| 10637 | K:1 | 10684 | K:1 |
| 10638 | K:1 | 10685 | K:1 |
| 10639 | K:1 | 10686 | K:1 |
| 10640 | K:1 | 10687 | K:1 |
| 10641 | K:1 | 10688 | K:1 |
| 10642 | K:1 | 10689 | K:1 |
| 10643 | K:1 | 10690 | K:1 |
| 10644 | K:1 | 10691 | K:1 |
| 10645 | K:1 | 10692 | K:1 |
| 10646 | K:1 | 10693 | K:1 |
| 10647 | K:1 | 10694 | K:1 |
| 10648 | K:1 | 10695 | K:1 |
| 10649 | K:1 | 10696 | K:1 |
| 10650 | K:1 | 10697 | K:1 |
| 10651 | K:1 | 10698 | K:1 |
| 10652 | F:1 K:3 | 10699 | K:1 |
| 10653 | K:1 | 10700 | F:2 K:1 |
| 10654 | K:1 | 10701 | K:1 |
| 10655 | K:1 | 10702 | K:1 |
| 10656 | K:1 | 10703 | K:1 |
| 10657 | K:1 | 10704 | K:1 |
| 10658 | K:1 | 10705 | K:1 |
| 10659 | K:1 | 10706 | K:1 |
| 10660 | K:1 | 10707 | K:1 |
| 10661 | C:13 | 10708 | K:1 |
| 10662 | K:1 | 10709 | C:3 |
| 10663 | K:1 | 10710 | K:1 |
| 10664 | K:1 | 10711 | K:1 |
| 10665 | K:1 | 10712 | K:1 |
| 10666 | K:1 | 10713 | K:1 |
| 10667 | K:1 | 10714 | K:1 |
| 10668 | K:1 | 10715 | K:1 |
| 10669 | K:1 | 10716 | K:1 |
| 10670 | K:1 | 10717 | K:1 |
| 10671 | K:1 | 10718 | K:1 |
| 10672 | K:1 | 10719 | K:1 |
| 10673 | K:1 | 10720 | K:1 |
| 10674 | K:1 | 10721 | K:1 |
| 10722 | K:1 | 10769 | K:1 |
| 10723 | K:1 | 10770 | K:1 |
| 10724 | K:1 | 10771 | K:1 |
| 10725 | K:1 | 10772 | K:1 |
| 10726 | K:1 | 10773 | K:1 |
| 10727 | K:1 | 10774 | K:1 |
| 10728 | K:1 | 10775 | K:1 |
| 10729 | K:1 | 10776 | K:1 |
| 10730 | K:1 | 10777 | K:1 |
| 10731 | K:1 | 10778 | K:1 |
| 10732 | K:1 | 10779 | K:1 |
| 10733 | K:1 | 10780 | K:1 |
| 10734 | H:3 | 10781 | K:1 |
| 10735 | K:1 | 10782 | K:1 |
| 10736 | K:1 | 10783 | K:1 |
| 10737 | K:1 | 10784 | K:1 |
| 10738 | K:1 | 10785 | K:1 |
| 10739 | K:1 | 10786 | K:1 |
| 10740 | K:1 | 10787 | K:1 |
| 10741 | K:1 | 10788 | K:1 |
| 10742 | K:1 | 10789 | K:1 |
| 10743 | K:1 | 10790 | K:1 |
| 10744 | K:1 | 10791 | K:1 |
| 10745 | K:1 | 10792 | K:1 |
| 10746 | K:1 | 10793 | K:1 |
| 10747 | K:1 | 10794 | K:1 |
| 10748 | K:1 | 10795 | K:1 |
| 10749 | K:1 | 10796 | K:1 |
| 10750 | K:1 | 10797 | K:1 |
| 10751 | K:1 | 10798 | C:15 |
| 10752 | K:1 | 10799 | K:1 |
| 10753 | K:1 | 10800 | K:1 |
| 10754 | K:1 | 10801 | K:1 |
| 10755 | K:1 | 10802 | K:1 |
| 10756 | K:1 | 10803 | K:1 |
| 10757 | K:1 | 10804 | K:1 |
| 10758 | K:1 | 10805 | K:1 |
| 10759 | K:1 | 10806 | K:1 |
| 10760 | K:1 | 10807 | K:1 |
| 10761 | K:1 | 10808 | K:1 |
| 10762 | K:1 | 10809 | K:1 |
| 10763 | F:1 | 10810 | K:1 |
| 10764 | K:1 | 10811 | K:1 |
| 10765 | K:1 | 10812 | K:1 |
| 10766 | K:1 | 10813 | K:1 |
| 10767 | K:1 | 10814 | K:1 |
| 10768 | K:1 | 10815 | K:1 |
| 10816 | K:1 | 10863 | K:1 |
| 10817 | C:1 | 10864 | K:1 |
| 10818 | K:1 | 10865 | K:1 |
| 10819 | K:1 | 10866 | K:1 |
| 10820 | K:1 | 10867 | K:1 |
| 10821 | K:1 | 10868 | K:1 |
| 10822 | K:1 | 10869 | K:1 |
| 10823 | K:1 | 10870 | K:1 |
| 10824 | K:1 | 10871 | K:1 |
| 10825 | K:1 | 10872 | K:1 |
| 10826 | K:1 | 10873 | K:1 |

TABLE V-continued (Spatial distribution)

| Seq Id No. | Tissue distribution | Seq Id No. | Tissue distribution |
|---|---|---|---|
| 10827 | K:1 | 10874 | K:1 |
| 10828 | K:1 | 10875 | K:1 |
| 10829 | K:1 | 10876 | K:1 |
| 10830 | K:1 | 10877 | K:1 |
| 10831 | K:1 | 10878 | K:1 |
| 10832 | K:1 | 10879 | K:1 |
| 10833 | K:1 | 10880 | K:1 |
| 10834 | B:1 C:1 H:3 | 10881 | K:1 |
| 10835 | K:2 | 10882 | K:1 |
| 10836 | K:1 | 10883 | K:1 |
| 10837 | K:1 | 10884 | K:1 |
| 10838 | K:1 | 10885 | K:1 |
| 10839 | K:1 | 10886 | K:1 |
| 10840 | K:1 | 10887 | K:1 |
| 10841 | K:1 | 10888 | K:1 |
| 10842 | K:1 | 10889 | K:1 |
| 10843 | K:1 | 10890 | K:1 |
| 10844 | K:1 | 10891 | K:1 |
| 10845 | F:3 | 10892 | K:1 |
| 10846 | K:1 | 10893 | K:1 |
| 10847 | K:1 | 10894 | K:1 |
| 10848 | K:1 | 10895 | K:1 |
| 10849 | K:1 | 10896 | K:1 |
| 10850 | K:1 | 10897 | K:1 |
| 10851 | K:1 | 10898 | K:1 |
| 10852 | F:1 | 10899 | K:1 |
| 10853 | K:1 | 10900 | K:1 |
| 10854 | K:1 | 10901 | K:1 |
| 10855 | K:1 | 10902 | K:1 |
| 10856 | K:1 | 10903 | A:3 |
| 10857 | K:1 | 10904 | K:1 |
| 10858 | K:1 | 10905 | K:1 |
| 10859 | K:1 | 10906 | K:1 |
| 10860 | K:1 | 10907 | K:1 |
| 10861 | K:1 | 10908 | K:1 |
| 10862 | K:1 | 10909 | K:1 |
| 10910 | K:1 | 10957 | K:1 |
| 10911 | K:1 | 10958 | K:1 |
| 10912 | K:1 | 10959 | K:1 |
| 10913 | K:1 | 10960 | K:1 |
| 10914 | K:1 | 10961 | K:1 |
| 10915 | K:1 | 10962 | K:1 |
| 10916 | K:1 | 10963 | H:2 |
| 10917 | K:1 | 10964 | K:1 |
| 10918 | K:1 | 10965 | K:1 |
| 10919 | K:1 | 10966 | K:1 |
| 10920 | K:1 | 10967 | K:1 |
| 10921 | K:1 | 10968 | K:1 |
| 10922 | K:1 | 10969 | K:1 |
| 10923 | K:1 | 10970 | K:1 |
| 10924 | K:1 | 10971 | K:1 |
| 10925 | K:1 | 10972 | K:1 |
| 10926 | K:1 | 10973 | K:1 |
| 10927 | K:1 | 10974 | K:1 |
| 10928 | K:1 | 10975 | K:1 |
| 10929 | K:1 | 10976 | F:4 H:4 K:1 |
| 10930 | K:1 | 10977 | K:1 |
| 10931 | K:1 | 10978 | K:1 |
| 10932 | K:1 | 10979 | K:1 |
| 10933 | K:1 | 10980 | K:1 |
| 10934 | K:1 | 10981 | K:1 |
| 10935 | K:1 | 10982 | K:1 |
| 10936 | K:1 | 10983 | K:1 |
| 10937 | K:1 | 10984 | K:1 |
| 10938 | K:1 | 10985 | K:1 |
| 10939 | K:1 | 10986 | K:1 |
| 10940 | K:1 | 10987 | K:1 |
| 10941 | K:1 | 10988 | K:1 |
| 10942 | K:1 | 10989 | K:1 |
| 10943 | K:1 | 10990 | B:1 |
| 10944 | K:1 | 10991 | K:1 |
| 10945 | K:1 | 10992 | K:1 |
| 10946 | K:1 | 10993 | K:1 |
| 10947 | K:1 | 10994 | K:1 |
| 10948 | K:1 | 10995 | K:1 |
| 10949 | K:1 | 10996 | K:1 |
| 10950 | K:1 | 10997 | K:1 |
| 10951 | K:1 | 10998 | K:1 |
| 10952 | K:1 | 10999 | K:1 |
| 10953 | K:1 | 11000 | K:1 |
| 10954 | K.1 | 11001 | K:1 |
| 10955 | K:1 | 11002 | K:1 |
| 10956 | K:1 | 11003 | K:1 |
| 11004 | A:13 | 11051 | K:1 |
| 11005 | K:1 | 11052 | K:1 |
| 11006 | K:1 | 11053 | K:1 |
| 11007 | K:1 | 11054 | K:1 |
| 11008 | K:1 | 11055 | K:1 |
| 11009 | K:1 | 11056 | A:4 |
| 11010 | K:1 | 11057 | K:1 |
| 11011 | I:2 | 11058 | K:1 |
| 11012 | K:1 | 11059 | K:1 |
| 11013 | K:1 | 11060 | K:1 |
| 11014 | K:1 | 11061 | K:1 |
| 11015 | K:1 | 11062 | K:1 |
| 11016 | K:1 | 11063 | K:1 |
| 11017 | K:1 | 11064 | K:1 |
| 11018 | K:1 | 11065 | K:1 |
| 11019 | F:6 K:1 | 11066 | K:1 |
| 11020 | K:1 | 11067 | A:12 B:15 C:58 D:6 F:3 H:57 I:1 K:7 |
| 11021 | K:1 | | |
| 11022 | K:1 | 11068 | K:1 |
| 11023 | K:1 | 11069 | K:1 |
| 11024 | K:1 | 11070 | K:1 |
| 11025 | K:1 | 11071 | K:1 |
| 11026 | K:1 | 11072 | K:1 |
| 11027 | K:1 | 11073 | K:1 |
| 11028 | K:1 | 11074 | K:1 |
| 11029 | K:1 | 11075 | K:1 |
| 11030 | K:1 | 11076 | B:1 D:1 |
| 11031 | K:1 | 11077 | K:1 |
| 11032 | K:1 | 11078 | K:1 |
| 11033 | K:1 | 11079 | K:1 |
| 11034 | K:1 | 11080 | K:1 |
| 11035 | K:1 | 11081 | K:1 |
| 11036 | C:4 | 11082 | K:1 |
| 11037 | K:1 | 11083 | K:1 |
| 11038 | K:1 | 11084 | K:1 |
| 11039 | K:1 | 11085 | K:1 |
| 11040 | K:1 | 11086 | K:1 |
| 11041 | K:1 | 11087 | K:1 |
| 11042 | K:1 | 11088 | K:1 |
| 11043 | K:1 | 11089 | K:1 |
| 11044 | K:1 | 11090 | A:1 K:1 |
| 11045 | K:1 | 11091 | K:1 |
| 11046 | K:1 | 11092 | K:1 |
| 11047 | K:1 | 11093 | K:1 |
| 11048 | K:1 | 11094 | K:1 |
| 11049 | K:1 | 11095 | K:1 |
| 11050 | K:1 | 11096 | K:1 |
| 11097 | K:1 | 11144 | B:2 |
| 11098 | K:1 | 11145 | K:1 |
| 11099 | K:1 | 11146 | K:1 |
| 11100 | K:1 | 11147 | K:1 |
| 11101 | K:1 | 11148 | K:1 |
| 11102 | K:1 | 11149 | K:1 |
| 11103 | K:1 | 11150 | K:1 |
| 11104 | K:1 | 11151 | K:1 |
| 11105 | K:1 | 11152 | K:1 |
| 11106 | K:1 | 11153 | K:1 |
| 11107 | K:1 | 11154 | K:1 |
| 11108 | K:1 | 11155 | K:1 |
| 11109 | K:1 | 11156 | K:1 |
| 11110 | K:1 | 11157 | K:1 |
| 11111 | K:1 | 11158 | H:10 |
| 11112 | K:1 | 11159 | K:1 |

TABLE V-continued (Spatial distribution)

| Seq Id No. | Tissue distribution | Seq Id No. | Tissue distribution |
|---|---|---|---|
| 11113 | K:1 | 11160 | K:1 |
| 11114 | K:1 | 11161 | K:1 |
| 11115 | K:1 | 11162 | K:1 |
| 11116 | K:1 | 11163 | K:1 |
| 11117 | K:1 | 11164 | K:1 |
| 11118 | K:1 | 11165 | K:1 |
| 11119 | K:1 | 11166 | K:1 |
| 11120 | K:1 | 11167 | K:1 |
| 11121 | K:1 | 11168 | K:1 |
| 11122 | K:1 | 11169 | K:1 |
| 11123 | K:1 | 11170 | K:1 |
| 11124 | K:1 | 11171 | K:1 |
| 11125 | K:1 | 11172 | K:3 |
| 11126 | K:1 | 11173 | K:1 |
| 11127 | K:1 | 11174 | K:1 |
| 11128 | K:1 | 11175 | K:1 |
| 11129 | K:1 | 11176 | K:1 |
| 11130 | K:1 | 11177 | K:1 |
| 11131 | K:1 | 11178 | K:1 |
| 11132 | K:1 | 11179 | F:5 |
| 11133 | K:1 | 11180 | K:1 |
| 11134 | K:1 | 11181 | K:1 |
| 11135 | K:2 | 11182 | K:1 |
| 11136 | K:1 | 11183 | K:1 |
| 11137 | K:1 | 11184 | K:1 |
| 11138 | K:1 | 11185 | K:1 |
| 11139 | K:1 | 11186 | K:1 |
| 11140 | K:1 | 11187 | K:1 |
| 11141 | K:1 | 11188 | K:1 |
| 11142 | K:1 | 11189 | F:1 K:1 |
| 11143 | K:1 | 11190 | K:1 |
| 11191 | K:1 | 11238 | K:1 |
| 11192 | K:1 | 11239 | K:1 |
| 11193 | K:1 | 11240 | K:1 |
| 11194 | K:1 | 11241 | K:1 |
| 11195 | K:1 | 11242 | K:1 |
| 11196 | K:1 | 11243 | K:1 |
| 11197 | K:1 | 11244 | K:1 |
| 11198 | K:1 | 12445 | K:1 |
| 11199 | K:1 | 11246 | K:1 |
| 11200 | K:1 | 11247 | H:1 |
| 11201 | K:1 | 11248 | K:1 |
| 11202 | K:1 | 11249 | K:1 |
| 11203 | K:1 | 11250 | A:1 |
| 11204 | K:1 | 11251 | A:1 |
| 11205 | K:1 | 11252 | A:1 |
| 11206 | K:3 | 11253 | A:1 |
| 11207 | F:1 K:4 | 11254 | A:1 |
| 11208 | K:1 | 11255 | A:1 |
| 11209 | F:1 | 11256 | A:1 |
| 11210 | F:1 | 11257 | A:1 |
| 11211 | F:1 | 11258 | A:1 |
| 11212 | F:1 | 11259 | A:1 |
| 11213 | F:1 | 11260 | A:1 |
| 11214 | C:2 | 11261 | A:1 |
| 11215 | F:1 | 11262 | A:1 |
| 11216 | F:1 | 11263 | A:1 |
| 11217 | F:1 | 11264 | A:1 |
| 11218 | F:1 | 11265 | A:1 |
| 11219 | F:1 | 11266 | A:1 |
| 11220 | F:1 | 11267 | A:1 |
| 11221 | F:1 | 11268 | A:1 |
| 11222 | F:1 | 11269 | A:1 |
| 11223 | F:1 | 11270 | A:1 |
| 11224 | F:1 | 11271 | A:1 |
| 11225 | F:1 | 11272 | A:1 |
| 11226 | F:1 | 11273 | A:1 |
| 11227 | F:1 | 11274 | A:1 |
| 11228 | F:1 | 11275 | A:1 |
| 11229 | F:1 | 11276 | A:1 |
| 11230 | F:1 | 11277 | A:1 |
| 11231 | F:1 | 11278 | A:1 |
| 11232 | F:1 | 11279 | A:1 H:2 |
| 11233 | F:1 | 11280 | A:1 |
| 11234 | F:1 | 11281 | A:1 |
| 11235 | F:1 | 11282 | A:1 |
| 11236 | F:1 | 11283 | A:1 |
| 11237 | F:1 | 11284 | A:1 |
| 11285 | A:1 | 11332 | A:1 |
| 11286 | A:1 | 11333 | A:1 |
| 11287 | A:1 | 11334 | A:1 |
| 11288 | A:1 | 11335 | A:1 |
| 11289 | A:1 | 11336 | A:1 |
| 11290 | A:1 | 11337 | A:1 |
| 11291 | A:1 | 11338 | A:1 |
| 11292 | A:1 | 11339 | A:1 |
| 11293 | A:1 | 11340 | B:1 |
| 11294 | A:1 | 11341 | A:8 |
| 11295 | A:1 | 11342 | B:1 |
| 11296 | A:1 | 11343 | B:1 |
| 11297 | A:1 | 11344 | B:1 |
| 11298 | A:1 | 11345 | B:1 |
| 11299 | A:1 | 11346 | B:1 |
| 11300 | A:1 | 11347 | B:1 |
| 11301 | A:1 | 11348 | B:1 |
| 11302 | A:1 | 11349 | B:1 |
| 11303 | A:1 | 11350 | K:2 |
| 11304 | A:1 | 11351 | B:1 |
| 11305 | A:1 | 11352 | B:1 |
| 11306 | A:1 | 11353 | B:1 |
| 11307 | A:1 | 11354 | B:1 |
| 11308 | A:1 | 11355 | B:1 |
| 11309 | A:1 | 11356 | B:1 |
| 11310 | A:5 | 11357 | B:1 |
| 11311 | A:1 | 11358 | B:1 |
| 11312 | A:1 | 11359 | B:1 |
| 11313 | A:1 | 11360 | C:2 |
| 11314 | A:1 | 11361 | B:1 |
| 11315 | A:1 | 11362 | B:1 |
| 11316 | A:1 | 11363 | B:1 |
| 11317 | A:1 | 11364 | B:1 |
| 11318 | A:1 | 11365 | B:1 |
| 11319 | A:1 | 11366 | K:2 |
| 11320 | A:1 | 11367 | B:1 |
| 11321 | H:2 | 11368 | B:1 |
| 11322 | A:1 | 11369 | B:1 |
| 11323 | A:1 | 11370 | B:1 |
| 11324 | A:1 | 11371 | B:1 |
| 11325 | A:1 | 11372 | B:1 |
| 11326 | A:1 | 11373 | B:1 |
| 11327 | A:1 | 11374 | B:1 |
| 11328 | A:1 | 11375 | B:1 |
| 11329 | A:1 | 11376 | B:1 |
| 11330 | A:1 | 11377 | B:1 |
| 11331 | A:1 | 11378 | B:3 F:1 |
| 11379 | B:1 | 11426 | B:1 |
| 11380 | B:1 | 11427 | B:1 |
| 11381 | B:1 | 11428 | B:1 |
| 11382 | B:1 | 11429 | B:1 |
| 11383 | B:1 | 11430 | B:1 |
| 11384 | B:1 | 11431 | B:1 |
| 11385 | B:1 | 11432 | B:1 |
| 11386 | B:1 | 11433 | B:1 |
| 11387 | B:3 F:11 H:2 | 11434 | B:1 |
| 11388 | B:1 | 11435 | B:1 |
| 11389 | B:1 | 11436 | B:1 |
| 11390 | B:1 | 11437 | B:1 |
| 11391 | B:1 | 11438 | B:1 |
| 11392 | B:1 | 11439 | C:1 |
| 11393 | B:1 | 11440 | C:1 |
| 11394 | B:1 | 11441 | C:1 |
| 11395 | B:1 | 11442 | C:1 |
| 11396 | B:1 | 11443 | C:1 |
| 11397 | B:1 | 11444 | C:1 |
| 11398 | B:1 | 11445 | C:1 |
| 11399 | B:1 | 11446 | C:1 |

TABLE V-continued
(Spatial distribution)

| Seq Id No. | Tissue distribution | Seq Id No. | Tissue distribution |
|---|---|---|---|
| 11400 | B:1 | 11447 | C:1 |
| 11401 | B:1 | 11448 | C:1 |
| 11402 | B:1 | 11449 | K:2 |
| 11403 | B:1 | 11450 | C:1 |
| 11404 | B:1 | 11451 | C:1 |
| 11405 | B:1 | 11452 | C:1 |
| 11406 | B:1 | 11453 | C:1 |
| 11407 | B:1 | 11454 | C:1 |
| 11408 | B:1 | 11455 | C:1 |
| 11409 | B:1 | 11456 | C:1 |
| 11410 | B:1 | 11457 | F:1 K:2 |
| 11411 | B:1 | 11458 | C:1 |
| 11412 | B:1 | 11459 | C:1 |
| 11413 | B:1 | 11460 | C:1 |
| 11414 | B:1 | 11461 | C:1 |
| 11415 | B:1 | 11462 | C:1 |
| 11416 | B:1 | 11463 | C:1 |
| 11417 | B:1 | 11464 | C:1 |
| 11418 | B:1 | 11465 | F:1 K:2 |
| 11419 | B:1 | 11466 | C:1 |
| 11420 | B:1 | 11467 | C:1 |
| 11421 | B:1 | 11468 | C:1 |
| 11422 | B:1 | 11469 | C:1 |
| 11423 | B:1 | 11470 | C:1 |
| 11424 | B:1 | 11471 | C:1 |
| 11425 | B:1 | 11472 | C:1 |
| 11473 | H:2 | 11520 | C:1 |
| 11474 | C:1 | 11521 | C:1 |
| 11475 | C:1 | 11522 | C:1 |
| 11476 | C:1 | 11523 | C:1 |
| 11477 | C:1 | 11524 | C:1 |
| 11478 | C:1 | 11525 | C:1 |
| 11479 | C:1 | 11526 | C:1 |
| 11480 | C:1 | 11527 | A:2 D:1 K:1 |
| 11481 | C:1 | 11528 | C:1 |
| 11482 | C:1 | 11529 | C:1 |
| 11483 | C:1 | 11530 | C:1 |
| 11484 | F:2 K:2 | 11531 | C:1 |
| 11485 | C:1 | 11532 | C:1 |
| 11486 | C:1 | 11533 | C:1 |
| 11487 | C:1 | 11534 | C:1 |
| 11488 | C:1 | 11535 | C:1 |
| 11489 | C:1 | 11536 | C:1 |
| 11490 | C:1 | 11537 | H:2 |
| 11491 | C:1 | 11538 | C:1 |
| 11492 | C:1 | 11539 | J:1 |
| 11493 | C:1 | 11540 | J:1 |
| 11494 | C:1 | 11541 | J:1 |
| 11495 | C:1 | 11542 | J:1 |
| 11496 | C:1 | 11543 | J:1 |
| 11497 | C:1 | 11544 | J:1 |
| 11498 | C:1 | 11545 | J:1 |
| 11499 | F:2 K:2 | 11546 | J:1 |
| 11500 | C:1 | 11547 | J:1 |
| 11501 | C:1 | 11548 | J:1 |
| 11502 | C:1 | 11549 | J:1 |
| 11503 | C:1 | 11550 | J:1 |
| 11504 | C:1 | 11551 | J:1 |
| 11505 | C:1 | 11552 | J:1 |
| 11506 | C:1 | 11553 | E:1 |
| 11507 | C:1 | 11554 | E:1 |
| 11508 | C:1 | 11555 | E:1 |
| 11509 | A:3 | 11556 | E:1 |
| 11510 | C:1 | 11557 | C:1 |
| 11511 | C:1 | 11558 | E:1 |
| 11512 | C:1 | 11559 | E:1 |
| 11513 | C:1 | 11560 | E:1 |
| 11514 | C:1 | 11561 | E:1 |
| 11515 | C:1 | 11562 | C:1 |
| 11516 | C:1 | 11563 | C:1 |
| 11517 | C:1 | 11564 | C:1 |
| 11518 | C:1 | 11565 | K:3 |
| 11519 | C:1 | 11566 | C:1 |
| 11567 | C:1 | 11614 | C:1 |
| 11568 | C:1 | 11615 | C:1 |
| 11569 | C:1 | 11616 | C:1 |
| 11570 | C:1 | 11617 | C:1 |
| 11571 | C:1 | 11618 | C:1 |
| 11572 | C:1 | 11619 | C:1 |
| 11573 | C:1 | 11620 | C:1 |
| 11574 | C:1 | 11621 | C:1 |
| 11575 | C:1 | 11622 | C:1 |
| 11576 | C:1 | 11623 | C:1 |
| 11577 | C:1 | 11624 | C:1 |
| 11578 | C:1 | 11625 | C:1 |
| 11579 | C:1 | 11626 | C:1 |
| 11580 | C:1 | 11627 | C:1 |
| 11581 | C:1 | 11628 | C:1 |
| 11582 | C:1 | 11629 | C:1 |
| 11583 | C:1 | 11630 | C:1 |
| 11584 | B:1 C:2 | 11631 | C:1 |
| 11585 | C:1 | 11632 | C:1 |
| 11586 | C:1 | 11633 | C:1 |
| 11587 | C:1 | 11634 | C:1 |
| 11588 | C:1 | 11635 | C:1 |
| 11589 | C:1 | 11636 | C:1 |
| 11590 | C:1 | 11637 | C:1 |
| 11591 | C:1 | 11638 | C:1 |
| 11592 | C:1 | 11639 | C:1 |
| 11593 | C:1 | 11640 | C:1 |
| 11594 | C:1 | 11641 | C:1 |
| 11595 | B:3 | 11642 | C:1 |
| 11596 | C:1 | 11643 | C:1 |
| 11597 | C:1 | 11644 | C:1 |
| 11598 | C:1 | 11645 | C:1 |
| 11599 | C:1 | 11646 | C:1 |
| 11600 | C:1 | 11647 | C:1 |
| 11601 | C:1 | 11648 | C:1 |
| 11602 | C:1 | 11649 | C:1 |
| 11603 | C:1 | 11650 | C:1 |
| 11604 | C:1 | 11651 | C:1 |
| 11605 | C:1 | 11652 | C:1 |
| 11606 | K:2 | 11653 | C:1 |
| 11607 | C:1 | 11654 | C:1 |
| 11608 | C:1 | 11655 | C:1 |
| 11609 | C:1 | 11656 | C:1 |
| 11610 | C:1 | 11657 | C:1 |
| 11611 | C:1 | 11658 | C:1 |
| 11612 | C:1 | 11659 | C:1 |
| 11613 | C:1 | 11660 | C:1 |
| 11661 | C:1 | 11708 | C:1 |
| 11662 | C:1 | 11709 | C:1 |
| 11663 | C:1 | 11710 | C:1 |
| 11664 | C:1 | 11711 | C:1 |
| 11665 | C:1 | 11712 | C:1 |
| 11666 | C:1 | 11713 | C:1 |
| 11667 | C:1 | 11714 | C:1 |
| 11668 | C:1 | 11715 | C:1 |
| 11669 | C:1 | 11716 | C:1 |
| 11670 | C:1 | 11717 | F:2 |
| 11671 | C:1 | 11718 | C:1 |
| 11672 | C:1 | 11719 | C:1 |
| 11673 | C:1 | 11720 | C:1 |
| 11674 | F:1 | 11721 | C:1 |
| 11675 | C:1 | 11722 | C:1 |
| 11676 | C:1 | 11723 | C:1 |
| 11677 | C:1 | 11724 | C:1 |
| 11678 | C:1 | 11725 | C:1 |
| 11679 | C:1 | 11726 | C:1 |
| 11680 | C:1 | 11727 | C:1 |
| 11681 | C:1 | 11728 | C:1 |
| 11682 | C:1 | 11729 | C:1 |
| 11683 | C:1 | 11730 | C:1 |
| 11684 | C:1 | 11731 | C:1 |
| 11685 | F:1 | 11732 | C:1 |
| 11686 | C:1 | 11733 | C:1 |

TABLE V-continued (Spatial distribution)

| Seq Id No. | Tissue distribution | Seq Id No. | Tissue distribution |
|---|---|---|---|
| 11687 | C:1 | 11734 | C:1 |
| 11688 | C:1 | 11735 | C:1 |
| 11689 | C:1 | 11736 | C:1 |
| 11690 | C:1 | 11737 | K:5 |
| 11691 | C:1 | 11738 | C:1 |
| 11692 | C:1 | 11739 | C:1 |
| 11693 | C:1 | 11740 | C:1 |
| 11694 | C:1 | 11741 | C:1 |
| 11695 | C:1 | 11742 | C:1 |
| 11696 | C:6 | 11743 | C:1 |
| 11697 | C:1 | 11744 | C:1 |
| 11698 | C:1 | 11745 | C:1 |
| 11699 | C:1 | 11746 | C:1 |
| 11700 | C:1 | 11747 | F:2 K:22 |
| 11701 | C:1 | 11748 | C:1 |
| 11702 | C:1 | 11749 | C:1 |
| 11703 | C:1 | 11750 | C:1 |
| 11704 | C:1 | 11751 | C:1 |
| 11705 | C:1 | 11752 | C:1 |
| 11706 | C:1 | 11753 | C:1 |
| 11707 | H:3 | 11754 | C:1 |
| 11755 | C:1 | 11802 | C:1 |
| 11756 | C:1 | 11803 | C:1 |
| 11757 | K:2 | 11804 | C:1 |
| 11758 | C:1 | 11805 | C:1 |
| 11759 | C:1 | 11806 | C:1 |
| 11760 | C:1 | 11807 | C:1 |
| 11761 | C:1 | 11808 | C:1 |
| 11762 | C:1 | 11809 | C:1 |
| 11763 | C:1 | 11810 | C:1 |
| 11764 | C:1 | 11811 | B:2 |
| 11765 | C:1 | 11812 | C:1 |
| 11766 | C:1 | 11813 | C:1 |
| 11767 | C:1 | 11814 | C:1 |
| 11768 | B:3 | 11815 | C:1 |
| 11769 | C:1 | 11816 | C:1 |
| 11770 | C:1 | 11817 | C:1 |
| 11771 | C:1 | 11818 | C:1 |
| 11772 | C:1 | 11819 | C:1 |
| 11773 | C:1 | 11820 | C:1 |
| 11774 | C:1 | 11821 | C:1 |
| 11775 | C:1 | 11822 | F:13 K:2 |
| 11776 | C:1 | 11823 | C:1 |
| 11777 | C:1 | 11824 | C:1 |
| 11778 | C:1 | 11825 | C:1 |
| 11779 | F:1 K:4 | 11826 | C:1 |
| 11780 | C:1 | 11827 | C:1 |
| 11781 | C:1 | 11828 | C:1 |
| 11782 | C:1 | 11829 | C:1 |
| 11783 | C:1 | 11830 | C:1 |
| 11784 | C:1 | 11831 | C:1 |
| 11785 | C:1 | 11832 | C:1 |
| 11786 | C:1 | 11833 | F:5 |
| 11787 | C:1 | 11834 | C:1 |
| 11788 | C:1 | 11835 | C:1 |
| 11789 | C:1 | 11836 | C:1 |
| 11790 | H:5 | 11837 | C:1 |
| 11791 | C:1 | 11838 | C:1 |
| 11792 | C:1 | 11839 | C:1 |
| 11793 | C:1 | 11840 | C:1 |
| 11794 | C:1 | 11841 | C:1 |
| 11795 | C:1 | 11842 | C:1 |
| 11796 | C:1 | 11843 | F:1 |
| 11797 | C:1 | 11844 | C:1 |
| 11798 | C:1 | 11845 | C:1 |
| 11799 | C:1 | 11846 | C:1 |
| 11800 | C:1 | 11847 | C:1 |
| 11801 | C:4 | 11848 | C:1 |
| 11849 | C:1 | 11896 | C:1 |
| 11850 | C:1 | 11897 | C:1 |
| 11851 | C:1 | 11898 | C:1 |
| 11852 | C:1 | 11899 | C:1 |
| 11853 | C:1 | 11900 | C:1 |
| 11854 | K:3 | 11901 | C:1 |
| 11855 | C:1 | 11902 | C:1 |
| 11856 | C:1 | 11903 | C:1 |
| 11857 | C:1 | 11904 | C:1 |
| 11858 | C:1 | 11905 | C:1 |
| 11859 | C:1 | 11906 | A:1 |
| 11860 | C:1 | 11907 | C:1 |
| 11861 | C:1 | 11908 | C:1 |
| 11862 | C:1 | 11909 | C:1 |
| 11863 | C:1 | 11910 | C:1 |
| 11864 | C:1 | 11911 | C:1 |
| 11865 | C:1 | 11912 | C:1 |
| 11866 | C:1 | 11913 | C:1 |
| 11867 | C:1 | 11914 | C:1 |
| 11868 | C:1 | 11915 | C:1 |
| 11869 | C:1 | 11916 | K:1 |
| 11870 | C:1 | 11917 | C:1 |
| 11871 | C:1 | 11918 | C:1 |
| 11872 | C:1 | 11919 | C:1 |
| 11873 | C:1 | 11920 | C:1 |
| 11874 | C:1 | 11921 | C:1 |
| 11875 | C:1 | 11922 | C:1 |
| 11876 | C:1 | 11923 | C:1 |
| 11877 | C:1 | 11924 | C:1 |
| 11878 | C:1 | 11925 | C:1 |
| 11879 | C:1 | 11926 | C:1 |
| 11880 | C:1 | 11927 | B:2 |
| 11881 | C:1 | 11928 | C:1 |
| 11882 | C:1 | 11929 | C:1 |
| 11883 | C:1 | 11930 | C:1 |
| 11884 | H:2 | 11931 | C:1 |
| 11885 | C:1 | 11932 | C:1 |
| 11886 | C:1 | 11933 | C:1 |
| 11887 | C:1 | 11934 | C:1 |
| 11888 | C:1 | 11935 | C:1 |
| 11889 | C:1 | 11936 | C:1 |
| 11890 | C:1 | 11937 | C:1 |
| 11891 | C:1 | 11938 | C:1 |
| 11892 | C:1 | 11939 | C:1 |
| 11893 | C:1 | 11940 | C:1 |
| 11894 | C:1 | 11941 | C:1 |
| 11895 | F:13 | 11942 | C:1 |
| 11943 | C:1 | 11990 | C:1 |
| 11944 | C:1 | 11991 | C:1 |
| 11945 | C:1 | 11992 | C:1 |
| 11946 | C:1 | 11993 | C:1 |
| 11947 | C:1 | 11994 | C:1 |
| 11948 | C:1 | 11995 | C:1 |
| 11949 | C:1 | 11996 | C:1 |
| 11950 | C:1 | 11997 | C:1 |
| 11951 | C:1 | 11998 | K:1 |
| 11952 | C:1 | 11999 | C:1 |
| 11953 | C:1 | 12000 | C:1 |
| 11954 | C:1 | 12001 | C:1 |
| 11955 | C:1 | 12002 | C:1 |
| 11956 | C:1 | 12003 | C:1 |
| 11957 | C:1 | 12004 | C:1 |
| 11958 | C:1 | 12005 | C:1 |
| 11959 | C:1 | 12006 | C:1 |
| 11960 | C:1 | 12007 | C:1 |
| 11961 | C:1 | 12008 | F:1 |
| 11962 | C:1 | 12009 | C:1 |
| 11963 | C:1 | 12010 | C:1 |
| 11964 | C:1 | 12011 | C:1 |
| 11965 | C:1 | 12012 | C:1 |
| 11966 | C:1 | 12013 | C:1 |
| 11967 | C:1 | 12014 | C:1 |
| 11968 | C:1 | 12015 | C:1 |
| 11969 | C:1 | 12016 | C:1 |
| 11970 | C:1 | 12017 | C:1 |
| 11971 | C:1 | 12018 | C:1 |
| 11972 | C:1 | 12019 | C:1 |
| 11973 | C:1 | 12020 | C:1 |

TABLE V-continued (Spatial distribution)

| Seq Id No. | Tissue distribution | Seq Id No. | Tissue distribution |
|---|---|---|---|
| 11974 | C:1 | 12021 | C:1 |
| 11975 | C:1 | 12022 | C:1 |
| 11976 | C:1 | 12023 | C:1 |
| 11977 | H:2 | 12024 | C:1 |
| 11978 | C:1 | 12025 | C:1 |
| 11979 | C:1 | 12026 | C:1 |
| 11980 | C:1 | 12027 | C:1 |
| 11981 | C:1 | 12028 | C:1 |
| 11982 | C:1 | 12029 | C:1 |
| 11983 | C:1 | 12030 | C:1 |
| 11984 | C:1 | 12031 | C:1 |
| 11985 | C:1 | 12032 | C:1 |
| 11986 | C:1 | 12033 | C:1 |
| 11987 | C:1 | 12034 | C:1 |
| 11988 | C:1 | 12035 | C:1 |
| 11989 | C:1 | 12036 | C:1 |
| 12037 | C:1 | 12084 | C:1 |
| 12038 | C:1 | 12085 | C:1 |
| 12039 | B:1 | 12086 | C:1 |
| 12040 | C:1 | 12087 | C:1 |
| 12041 | C:1 | 12088 | C:1 |
| 12042 | C:1 | 12089 | C:1 |
| 12043 | C:1 | 12090 | C:1 |
| 12044 | C:1 | 12091 | B:2 |
| 12045 | C:1 | 12092 | C:1 |
| 12046 | C:1 | 12093 | C:1 |
| 12047 | C:1 | 12094 | C:1 |
| 12048 | C:1 | 12095 | C:1 |
| 12049 | C:1 | 12096 | C:1 |
| 12050 | B:1 | 12097 | C:1 |
| 12051 | C:1 | 12098 | C:1 |
| 12052 | C:1 | 12099 | C:1 |
| 12053 | C:1 | 12100 | C:1 |
| 12054 | C:1 | 12101 | C:1 |
| 12055 | C:1 | 1202 | C:1 |
| 12056 | C:1 | 12103 | C:1 |
| 12057 | C:1 | 12104 | C:1 |
| 12058 | C:1 | 12105 | C:1 |
| 12059 | C:1 | 12106 | C:1 |
| 12060 | C:1 | 12107 | C:1 |
| 12061 | B:1 | 12108 | C:1 |
| 12062 | C:1 | 12109 | C:1 |
| 12063 | C:1 | 12110 | C:1 |
| 12064 | C:1 | 12111 | C:1 |
| 12065 | C:1 | 12112 | F:2 |
| 12066 | C:1 | 12113 | C:1 |
| 12067 | C:1 | 12114 | C:1 |
| 12068 | C:1 | 12115 | C:1 |
| 12069 | C:1 | 12116 | C:1 |
| 12070 | C:1 | 12117 | C:1 |
| 12071 | H:2 | 12118 | C:1 |
| 12072 | H:2 | 12119 | C:1 |
| 12073 | C:1 | 12120 | C:1 |
| 12074 | C:1 | 12121 | C:1 |
| 12075 | C:1 | 12122 | C:1 |
| 12076 | C:1 | 12123 | B:2 |
| 12077 | C:1 | 12124 | C:1 |
| 12078 | C:1 | 12125 | C:1 |
| 12079 | C:1 | 12126 | C:1 |
| 12080 | C:1 | 12127 | C:1 |
| 12081 | C:1 | 12128 | C:1 |
| 12082 | K:2 | 12129 | C:1 |
| 12083 | C:1 | 12130 | C:1 |
| 12131 | C:1 | 12178 | C:1 |
| 12132 | C:1 | 12179 | C:1 |
| 12133 | C:1 | 12180 | C:1 |
| 12134 | H:2 | 12181 | C:1 |
| 12135 | C:1 | 12182 | C:1 |
| 12136 | C:1 | 12183 | C:1 |
| 12137 | C:1 | 12184 | C:1 |
| 12138 | C:1 | 12185 | C:1 |
| 12139 | C:1 | 12186 | C:1 |
| 12140 | C:1 | 12187 | C:1 |
| 12141 | C:1 | 12188 | C:1 |
| 12142 | C:1 | 12189 | C:1 |
| 12143 | C:1 | 12190 | C:1 |
| 12144 | C:1 | 12191 | C:1 |
| 12145 | F:2 | 12192 | C:1 |
| 12146 | C:1 | 12193 | C:1 |
| 12147 | C:1 | 12194 | C:1 |
| 12148 | C:1 | 12195 | C:1 |
| 12149 | C:1 | 12196 | C:1 |
| 12150 | C:1 | 12197 | C:4 |
| 12151 | C:1 | 12198 | C:1 |
| 12152 | C:1 | 12199 | C:1 |
| 12153 | C:1 | 12200 | C:1 |
| 12154 | C:1 | 12201 | C:1 |
| 12155 | C:1 | 12202 | C:1 |
| 12156 | C:1 | 12203 | C:1 |
| 12157 | C:1 | 12204 | C:1 |
| 12158 | C:1 | 12205 | C:1 |
| 12159 | C:1 | 12206 | C:1 |
| 12160 | C:1 | 12207 | C:1 |
| 12161 | C:1 | 12208 | B:4 C:1 |
| 12162 | C:1 | 12209 | C:1 |
| 12163 | C:1 | 12210 | C:1 |
| 12164 | C:1 | 12211 | C:1 |
| 12165 | C:1 | 12212 | C:1 |
| 12166 | K:1 | 12213 | C:1 |
| 12167 | C:1 | 12214 | C:1 |
| 12168 | C:1 | 12215 | C:1 |
| 12169 | C:1 | 12216 | C:1 |
| 12170 | C:1 | 12217 | C:1 |
| 12171 | C:1 | 12218 | B:2 |
| 12172 | C:1 | 12219 | C:1 |
| 12173 | C:1 | 12220 | C:1 |
| 12174 | C:1 | 12221 | C:1 |
| 12175 | C:1 | 12222 | C:1 |
| 12176 | C:1 | 12223 | C:1 |
| 12177 | A:5 | 12224 | C:1 |
| 12225 | C:1 | 12272 | C:1 |
| 12226 | C:1 | 12273 | C:1 |
| 12227 | C:1 | 12274 | C:1 |
| 12228 | C:1 | 12275 | C:1 |
| 12229 | C:1 | 12276 | C:1 |
| 12230 | C:1 | 12277 | C:1 |
| 12231 | C:1 | 12278 | A:1 B:1 |
| 12232 | C:1 | 12279 | H:1 |
| 12233 | C:1 | 12280 | C:1 |
| 12234 | C:1 | 12281 | C:1 |
| 12235 | C:1 | 12282 | C:1 |
| 12236 | C:1 | 12283 | C:1 |
| 12237 | C:1 | 12284 | C:1 |
| 12238 | C:1 | 12285 | C:1 |
| 12239 | A:4 | 12286 | C:1 |
| 12240 | C:1 | 12287 | C:1 |
| 12241 | C:1 | 12288 | C:1 |
| 12242 | C:1 | 12289 | C:1 |
| 12243 | C:1 | 12290 | C:1 |
| 12244 | C:1 | 12291 | C:1 |
| 12245 | C:1 | 12292 | C:1 |
| 12246 | C:1 | 12293 | C:1 |
| 12247 | C:1 | 12294 | C:1 |
| 12248 | C:1 | 12295 | C:1 |
| 12249 | C:1 | 12296 | C:1 |
| 12250 | C:1 | 12297 | C:1 |
| 12251 | C:1 | 12298 | C:1 |
| 12252 | C:1 | 12299 | C:1 |
| 12253 | C:1 | 12300 | C:1 |
| 12254 | C:1 | 12301 | C:1 |
| 12255 | C:1 | 12302 | C:1 |
| 12256 | C:1 | 12303 | C:1 |
| 12257 | C:1 | 12304 | C:1 |
| 12258 | C:1 | 12305 | C:1 |
| 12259 | C:1 | 12306 | D:1 |
| 12260 | C:1 | 12307 | C:1 |

TABLE V-continued

(Spatial distribution)

| Seq Id No. | Tissue distribution | Seq Id No. | Tissue distribution |
|---|---|---|---|
| 12261 | C:1 | 12308 | C:1 |
| 12262 | C:1 | 12309 | C:1 |
| 12263 | C:1 | 12310 | C:1 |
| 12264 | C:1 | 12311 | C:1 |
| 12265 | C:1 | 12312 | C:1 |
| 12266 | C:1 | 12313 | C:1 |
| 12267 | C:1 | 12314 | C:1 |
| 12268 | C:1 | 12315 | C:1 |
| 12269 | C:1 | 12316 | C:1 |
| 12270 | C:1 | 12317 | I:2 |
| 12271 | C:1 | 12318 | C:1 |
| 12319 | C:1 | 12366 | C:1 |
| 12320 | C:1 | 12367 | C:1 |
| 12321 | C:1 | 12368 | C:1 |
| 12322 | C:1 | 12369 | C:1 |
| 12323 | C:1 | 12370 | C:1 |
| 12324 | C:1 | 12371 | C:1 |
| 12325 | C:1 | 12372 | C:1 |
| 12326 | C:1 | 12373 | C:1 |
| 12327 | C:98 | 12374 | C:1 |
| 12328 | C:1 | 12375 | C:1 |
| 12329 | C:1 | 12376 | C:1 |
| 12330 | C:1 | 12377 | C:1 |
| 12331 | C:1 | 12378 | C:1 |
| 12332 | C:1 | 12379 | C:1 |
| 12333 | C:1 | 12380 | C:1 |
| 12334 | C:1 | 12381 | C:1 |
| 12335 | C:1 | 12382 | C:1 |
| 12336 | C:1 | 12383 | C:1 |
| 12337 | C:1 | 12384 | C:1 |
| 12338 | C:1 | 12385 | C:1 |
| 12339 | C:1 | 12386 | C:1 |
| 12340 | C:1 | 12387 | C:1 |
| 12341 | C:1 | 12388 | C:1 |
| 12342 | C:1 | 12389 | C:1 |
| 12343 | C:1 | 12390 | C:1 |
| 12344 | C:1 | 12391 | C:1 |
| 12345 | C:1 | 12392 | C:1 |
| 12346 | C:1 | 12393 | C:1 |
| 12347 | C:1 | 12394 | C:1 |
| 12348 | C:1 | 12395 | C:1 |
| 12349 | C:1 | 12396 | C:1 |
| 12350 | C:1 | 12397 | C:1 |
| 12351 | C:1 | 12398 | C:1 |
| 12352 | C:1 | 12399 | C:1 |
| 12353 | C:1 | 12400 | C:1 |
| 12354 | C:1 | 12401 | C:1 |
| 12355 | C:1 | 12402 | C:1 |
| 12356 | K:1 | 12403 | C:1 |
| 12357 | C:1 | 12404 | C:1 |
| 12358 | C:1 | 12405 | C:1 |
| 12359 | C:1 | 12406 | C:1 |
| 12360 | C:1 | 12407 | C:1 |
| 12361 | C:1 | 12408 | C:1 |
| 12362 | C:1 | 12409 | C:1 |
| 12363 | C:1 | 12410 | C:1 |
| 12364 | C:1 | 12411 | C:1 |
| 12365 | C:1 | 12412 | C:1 |
| 12413 | C:1 | 12460 | K:1 |
| 12414 | C:1 | 12461 | K:1 |
| 12415 | C:1 | 12462 | K:1 |
| 12416 | C:1 | 12463 | K:1 |
| 12417 | C:1 | 12464 | K:1 |
| 12418 | C:1 | 12465 | H:1 |
| 12419 | C:1 | 12466 | K:1 |
| 12420 | C:1 | 12467 | K:1 |
| 12421 | C:1 | 12468 | K:1 |
| 12422 | C:1 | 12469 | K:1 |
| 12423 | C:1 | 12470 | K:1 |
| 12424 | C:1 | 12471 | K:1 |
| 12425 | C:1 | 12472 | K:1 |
| 12426 | C:1 | 12473 | K:1 |
| 12427 | C:1 | 12474 | K:1 |
| 12428 | C:1 | 12475 | K:1 |
| 12429 | C:1 | 12476 | K:4 |
| 12430 | C:1 | 12477 | K:1 |
| 12431 | C:1 | 12478 | K:1 |
| 12432 | C:1 | 12479 | K:1 |
| 12433 | C:1 | 12480 | K:1 |
| 12434 | C:1 | 12481 | K:1 |
| 12435 | C:1 | 12482 | K:1 |
| 12436 | C:1 | 12483 | K:1 |
| 12437 | A:8 | 12484 | K:1 |
| 12438 | C:1 | 12485 | B:7 C:1 |
| 12439 | C:1 | 12486 | K:1 |
| 12440 | C:1 | 12487 | K:1 |
| 12441 | C:1 | 12488 | K:1 |
| 12442 | C:1 | 12489 | K:1 |
| 12443 | C:1 | 12490 | K:1 |
| 12444 | C:1 | 12491 | K:1 |
| 12445 | C:1 | 12492 | K:1 |
| 12446 | C:1 | 12493 | K:1 |
| 12447 | C:1 | 12494 | K:1 |
| 12448 | C:1 | 12495 | K:1 |
| 12449 | C:1 | 12496 | K:1 |
| 12450 | C:1 | 12497 | K:1 |
| 12451 | C:1 | 12498 | K:1 |
| 12452 | C:1 | 12499 | K:1 |
| 12453 | C:1 | 12500 | K:1 |
| 12454 | C:1 | 12501 | K:1 |
| 12455 | C:1 | 12502 | K:1 |
| 12456 | K:1 | 12503 | K:1 |
| 12457 | K:1 | 12504 | K:J |
| 12458 | K:1 | 12505 | K:1 |
| 12459 | K:1 | 12506 | K:1 |
| 12507 | K:1 | 12554 | K:1 |
| 12508 | K:1 | 12555 | K:1 |
| 12509 | F:1 K:4 | 12556 | K:1 |
| 12510 | K:1 | 12557 | K:1 |
| 12511 | K:1 | 12558 | K:1 |
| 12512 | K:1 | 12559 | K:1 |
| 12513 | K:1 | 12560 | K:1 |
| 12514 | K:1 | 12561 | K:1 |
| 12515 | K:1 | 12562 | K:1 |
| 12516 | K:1 | 12563 | K:1 |
| 12517 | K:1 | 12564 | K:1 |
| 12518 | K:1 | 12565 | K:1 |
| 12519 | K:1 | 12566 | K:1 |
| 12520 | K:1 | 12567 | K:1 |
| 12521 | K:1 | 12568 | K:1 |
| 12522 | K:1 | 12569 | K:1 |
| 12523 | K:1 | 12570 | K:1 |
| 12524 | K:1 | 12571 | H:1 |
| 12525 | K:1 | 12572 | K:1 |
| 12526 | K:1 | 12573 | K:1 |
| 12527 | K:1 | 12574 | K:1 |
| 12528 | K:1 | 12575 | K:1 |
| 12529 | K:1 | 12576 | K:1 |
| 12530 | K:1 | 12577 | K:1 |
| 12531 | K:1 | 12578 | K:1 |
| 12532 | F:1 | 12579 | B:1 |
| 12533 | K:1 | 12580 | H:2 |
| 12534 | K:1 | 12581 | B:1 |
| 12535 | K:1 | 12582 | B:1 |
| 12536 | K:1 | 12583 | B:1 |
| 12537 | K:1 | 12584 | B:1 |
| 12538 | K:1 | 12585 | B:1 |
| 12539 | K:1 | 12586 | B:1 |
| 12540 | K:1 | 12587 | B:1 |
| 12541 | K:1 | 12588 | B:1 |
| 12542 | K:1 | 12589 | B:1 |
| 12543 | K:1 | 12590 | B:2 |
| 12544 | K:1 | 12591 | B:1 |
| 12545 | K:1 | 12592 | B:1 |
| 12546 | K:1 | 12593 | B:1 |
| 12547 | K:1 | 12594 | B:1 |

TABLE V-continued

(Spatial distribution)

| Seq Id No. | Tissue distribution | Seq Id No. | Tissue distribution |
|---|---|---|---|
| 12548 | K:1 | 12595 | B:1 |
| 12549 | K:1 | 12596 | B:1 |
| 12550 | K:1 | 12597 | B:1 |
| 12551 | K:1 | 12598 | B:1 |
| 12552 | K:1 | 12599 | B:1 |
| 12553 | K:1 | 12600 | B:1 |
| 12601 | B:1 | 12648 | B:1 |
| 12602 | B:1 | 12649 | B:1 |
| 12603 | B:1 | 12650 | B:1 |
| 12604 | B:1 | 12651 | B:1 |
| 12605 | H:2 | 12652 | B:1 |
| 12606 | B:1 | 12653 | B:1 |
| 12607 | B:1 | 12654 | B:1 |
| 12608 | B:1 | 12655 | B:1 |
| 12609 | B:1 | 12656 | B:1 |
| 12610 | B:1 | 12657 | B:1 |
| 12611 | B:1 | 12658 | B:1 |
| 12612 | B:1 | 12659 | B:1 |
| 12613 | B:1 | 12660 | B:1 |
| 12614 | B:1 | 12661 | B:1 |
| 12615 | B:1 | 12662 | B:1 |
| 12616 | B:1 | 12663 | B:1 |
| 12617 | B:1 | 12664 | B:1 |
| 12618 | F:2 K:5 | 12665 | B:1 |
| 12619 | B:1 | 12666 | B:1 |
| 12620 | B:1 | 12667 | B:1 |
| 12621 | B:1 | 12668 | B:1 |
| 12622 | B:1 | 12669 | B:1 |
| 12623 | B:1 | 12670 | B:1 H:2 |
| 12624 | B:1 | 12671 | B:1 |
| 12625 | D:1 I:1 | 12672 | B:1 |
| 12626 | B:1 | 12673 | B:1 |
| 12627 | B:1 | 12674 | B:1 |
| 12628 | B:1 | 12675 | B:1 |
| 12629 | B:1 | 12676 | B:1 |
| 12630 | B:1 | 12677 | B:1 |
| 12631 | B:1 | 12678 | I:2 |
| 12632 | B:1 | 12679 | B:1 |
| 12633 | B:1 | 12680 | B:1 |
| 12634 | B:1 | 12681 | B:1 |
| 12635 | K:2 | 12682 | B:1 |
| 12636 | K:2 | 12683 | B:1 |
| 12637 | B:1 | 12684 | B:1 |
| 12638 | B:1 | 12685 | B:1 |
| 12639 | B:1 | 12686 | B:1 |
| 12640 | B:1 | 12687 | A:1 B:5 F:1 H:1 |
| 12641 | B:1 | 12688 | B:1 |
| 12642 | B:1 | 12689 | B:1 |
| 12643 | B:1 | 12690 | B:1 |
| 12644 | B:1 | 12691 | B:1 |
| 12645 | B:1 | 12692 | B:1 |
| 12646 | B:1 | 12693 | B:1 |
| 12647 | B:1 | 12694 | B:1 |
| 12695 | B:1 | 12742 | B:1 |
| 12696 | B:1 | 12743 | B:1 |
| 12697 | B:1 | 12744 | B:1 |
| 12698 | B:1 | 12745 | B:1 |
| 12699 | B:1 | 12746 | B:1 |
| 12700 | B:1 | 12747 | B:1 |
| 12701 | B:1 | 12748 | B:1 |
| 12702 | B:1 | 12749 | B:1 |
| 12703 | B:1 | 12750 | B:1 |
| 12704 | B:1 | 12751 | B:1 |
| 12705 | B:1 | 12752 | B:1 |
| 12706 | B:1 | 12753 | B:1 |
| 12707 | B:1 | 12754 | B:1 |
| 12708 | B:1 | 12755 | B:1 |
| 12709 | B:1 | 12756 | B:1 |
| 12710 | B:1 | 12757 | B:1 |
| 12711 | B:1 | 12758 | B:1 |
| 12712 | B:1 | 12759 | D:1 |
| 12713 | B:1 | 12760 | B:1 |
| 12714 | B:1 | 12761 | B:1 |
| 12715 | B:1 | 12762 | B:1 |
| 12716 | B:1 | 12763 | B:1 |
| 12717 | B:1 | 12764 | B:1 |
| 12718 | B:1 | 12765 | B:1 |
| 12719 | C:2 | 12766 | B:1 |
| 12720 | B:1 | 12767 | B:1 |
| 12721 | B:1 | 12768 | B:1 |
| 12722 | B:1 | 12769 | B:1 |
| 12723 | B:1 | 12770 | B:1 |
| 12724 | B:1 | 12771 | B:1 |
| 12725 | B:1 | 12772 | B:1 |
| 12726 | B:1 | 12773 | B:1 |
| 12727 | B:1 | 12774 | B:1 |
| 12728 | B:1 | 12775 | B:1 |
| 12729 | B:1 | 12776 | B:1 |
| 12730 | B:1 | 12777 | B:1 |
| 12731 | B:1 | 12778 | B:1 |
| 12732 | B:1 | 12779 | B:1 |
| 12733 | B:1 | 12780 | B:1 |
| 12734 | B:1 | 12781 | B:1 |
| 12735 | B:1 | 12782 | B:1 |
| 12736 | B:1 | 12783 | B:1 |
| 12737 | B:1 | 12784 | B:1 |
| 12738 | B:1 | 12785 | B:1 |
| 12739 | B:1 | 12786 | B:1 |
| 12740 | B:1 | 12787 | B:1 |
| 12741 | B:1 | 12788 | B:1 |
| 12789 | B:1 | 12836 | B:1 |
| 12790 | B:1 | 12837 | B:1 |
| 12791 | B:1 | 12838 | B:1 |
| 12792 | B:1 | 12839 | B:1 |
| 12793 | B:1 | 12840 | B:1 |
| 12794 | B:1 | 12841 | B:1 |
| 12795 | H:1 | 12842 | B:1 |
| 12796 | B:1 | 12843 | B:1 |
| 12797 | B:1 | 12844 | A:3 |
| 12798 | B:1 | 12845 | B:1 |
| 12799 | B:1 | 12846 | B:1 |
| 12800 | B:1 | 12847 | B:1 |
| 12801 | B:1 | 12848 | B:1 |
| 12802 | B:1 | 12849 | B:1 |
| 12803 | B:1 | 12850 | B:1 |
| 12804 | B:1 | 12851 | B:1 |
| 12805 | B:1 | 12852 | B:1 |
| 12806 | B:1 | 12853 | B:1 |
| 12807 | B:1 | 12854 | F:1 K:3 |
| 12808 | B:1 | 12855 | B:1 |
| 12809 | H:1 | 12856 | B:1 |
| 12810 | B:1 | 12857 | B:1 |
| 12811 | B:1 | 12858 | B:1 |
| 12812 | B:1 | 12859 | B:1 |
| 12813 | B:1 | 12860 | B:1 |
| 12814 | B:1 | 12861 | B:1 |
| 12815 | B:1 | 12862 | K:1 |
| 12816 | B:1 | 12863 | B:1 |
| 12817 | B:1 | 12864 | B:1 |
| 12818 | B:1 | 12865 | B:1 |
| 12819 | B:1 | 12866 | B:1 |
| 12820 | B:1 | 12867 | B:1 |
| 12821 | B:1 | 12868 | B:1 |
| 12822 | B:1 | 12869 | B:1 |
| 12823 | B:1 | 12870 | B:1 |
| 12824 | B:1 | 12871 | B:1 |
| 12825 | B:1 | 12872 | B:1 |
| 12826 | B:1 | 12873 | B:1 |
| 12827 | B:1 | 12874 | B:1 |
| 12828 | B:1 | 12875 | B:1 |
| 12829 | B:1 | 12876 | B:1 |
| 12830 | B:1 | 12877 | B:1 |
| 12831 | B:1 | 12878 | B:1 |
| 12832 | B:1 | 12879 | A:8 B:3 C:2 |
| 12833 | B:1 | 12880 | B:1 |
| 12834 | B:1 | 12881 | B:1 |

TABLE V-continued (Spatial distribution)

| Seq Id No. | Tissue distribution | Seq Id No. | Tissue distribution |
|---|---|---|---|
| 12835 | K:2 | 12882 | B:1 |
| 12883 | B:1 | 12930 | B:1 |
| 12884 | B:1 | 12931 | B:1 |
| 12885 | B:1 | 12932 | B:1 |
| 12886 | B:1 | 12933 | B:1 |
| 12887 | B:1 | 12934 | B:1 |
| 12888 | B:1 | 12935 | B:1 |
| 12889 | B:1 | 12936 | B:1 |
| 12890 | B:1 | 12937 | B:1 |
| 12891 | B:1 | 12938 | B:1 |
| 12892 | B:1 | 12939 | B:1 |
| 12893 | B:1 | 12940 | B:1 |
| 12894 | B:1 | 12941 | B:1 |
| 12895 | B:1 | 12942 | B:1 |
| 12896 | B:1 | 12943 | B:1 |
| 12897 | B:1 | 12944 | B:1 |
| 12898 | B:1 | 12945 | A:1 B:3 I:1 K:1 |
| 12899 | B:1 | 12946 | B:1 |
| 12900 | H:3 | 12947 | B:1 |
| 12901 | B:1 | 12948 | B:1 |
| 12902 | B:1 | 12949 | B:1 |
| 12903 | B:1 | 12950 | B:1 |
| 12904 | B:1 | 12951 | B:1 |
| 12905 | B:1 | 12952 | B:1 |
| 12906 | B:1 | 12953 | B:1 |
| 12907 | B:1 | 12954 | B:1 |
| 12908 | B:1 | 12955 | B:1 |
| 12909 | B:1 | 12956 | B:1 |
| 12910 | B:1 | 12957 | B:1 |
| 12911 | B:1 | 12958 | B:1 |
| 12912 | B:1 | 12959 | B:1 |
| 12913 | B:1 | 12960 | B:1 |
| 12914 | B:1 | 12961 | B:1 |
| 12915 | B:1 | 12962 | B:1 |
| 12916 | B:1 | 12963 | B:1 |
| 12917 | B:1 | 12964 | B:1 |
| 12918 | B:1 | 12965 | B:1 |
| 12919 | B:1 | 12966 | B:1 |
| 12920 | B:1 | 12967 | B:1 |
| 12921 | B:1 | 12968 | B:1 |
| 12922 | B:1 | 12969 | B:1 |
| 12923 | B:1 | 12970 | B:1 |
| 12924 | B:1 | 12971 | B:1 |
| 12925 | B:1 | 12972 | B:1 |
| 12926 | B:1 | 12973 | B:1 |
| 12927 | B:1 | 12974 | B:1 |
| 12928 | B:1 | 12975 | B:1 |
| 12929 | B:1 | 12976 | B:1 |
| 12977 | F:1 | 13024 | B:1 |
| 12978 | B:1 | 13025 | B:1 |
| 12979 | B:1 | 13026 | B:1 |
| 12980 | B:1 | 13027 | B:1 |
| 12981 | B:1 | 13028 | B:1 |
| 12982 | B:1 | 13029 | B:1 |
| 12983 | B:1 | 13030 | B:1 |
| 12984 | B:1 | 13031 | B:1 |
| 12985 | B:1 | 13032 | B:1 |
| 12986 | B:1 | 13033 | B:1 |
| 12987 | B:1 | 13034 | B:1 |
| 12988 | B:1 | 13035 | B:1 |
| 12989 | B:1 | 13036 | B:1 |
| 12990 | B:1 | 13037 | B:1 |
| 12991 | B:1 | 13038 | B:1 |
| 12992 | B:1 | 13039 | B:1 |
| 12993 | B:1 | 13040 | B:1 |
| 12994 | B:1 | 13041 | B:1 |
| 12995 | K:1 | 13042 | B:1 |
| 12996 | B:1 | 13043 | B:1 |
| 12997 | B:1 | 13044 | B:1 |
| 12998 | B:1 | 13045 | B:1 |
| 12999 | B:1 | 13046 | B:1 |
| 13000 | B:1 | 13047 | B:1 |
| 13001 | B:1 | 13048 | B:1 |
| 13002 | B:1 | 13049 | B:1 |
| 13003 | B:1 | 13050 | B:1 |
| 13004 | B:1 | 13051 | B:1 |
| 13005 | B:1 | 13052 | B:1 |
| 13006 | B:1 | 13053 | B:1 |
| 13007 | B:1 | 13054 | B:1 |
| 13008 | K:2 | 13055 | B:1 |
| 13009 | B:1 | 13056 | F:1 K:1 |
| 13010 | B:1 | 13057 | B:1 |
| 13011 | B:1 | 13058 | B:1 |
| 13012 | B:1 | 13059 | B:1 |
| 13013 | B:1 | 13060 | B:1 |
| 13014 | B:1 | 13061 | B:1 |
| 13015 | B:1 | 13062 | B:1 |
| 13016 | B:1 | 13063 | B:1 |
| 13017 | B:1 | 13064 | B:1 |
| 13018 | B:1 | 13065 | B:1 |
| 13019 | B:1 | 13066 | B:1 |
| 13020 | B:1 | 13067 | B:1 |
| 13021 | B:1 | 13068 | B:1 |
| 13022 | B:1 | 13069 | B:1 |
| 13023 | B:1 | 13070 | B:1 |
| 13071 | B:1 | 13118 | B:1 |
| 13072 | B:1 | 13119 | B:1 |
| 13073 | B:1 | 13120 | B:1 |
| 13074 | B:1 | 13121 | B:1 |
| 13075 | B:1 | 13122 | B:1 |
| 13076 | B:1 | 13123 | B:1 |
| 13077 | B:1 | 13124 | B:1 |
| 13078 | K:3 | 13125 | B:1 |
| 13079 | B:1 | 13126 | B:1 |
| 13080 | B:1 | 13127 | B:1 |
| 13081 | B:1 | 13128 | B:1 |
| 13082 | B:1 | 13129 | B:1 |
| 13083 | B:1 | 13130 | B:1 |
| 13084 | B:1 | 13131 | B:1 |
| 13085 | B:2 | 13132 | B:1 |
| 13086 | B:1 | 13133 | A:6 |
| 13087 | B:1 | 13134 | B:1 |
| 13088 | B:1 | 13135 | B:1 |
| 13089 | B:1 | 13136 | B:1 |
| 13090 | B:2 | 13137 | B:1 |
| 13091 | B:1 | 13138 | B:1 |
| 13092 | B:1 | 13139 | B:1 |
| 13093 | B:1 | 13140 | B:1 |
| 13094 | B:1 | 13141 | B:1 |
| 13095 | B:1 | 13142 | H:2 |
| 13096 | B:1 | 13143 | B:1 |
| 13097 | B:1 | 13144 | B:1 |
| 13098 | B:1 | 13145 | B:1 |
| 13099 | B:1 | 13146 | B:1 |
| 13100 | B:1 | 13147 | B:1 |
| 13101 | B:1 | 13148 | B:1 |
| 13102 | B:1 | 13149 | B:1 |
| 13103 | B:1 | 13150 | K:3 |
| 13104 | B:1 | 13151 | B:1 |
| 13105 | B:1 | 13152 | B:1 |
| 13106 | B:1 | 13153 | B:1 |
| 13107 | B:1 | 13154 | B;1 |
| 13108 | B:1 | 13155 | B:1 |
| 13109 | B:1 | 13156 | B:1 |
| 13110 | K:2 | 13157 | B:1 |
| 13111 | B:1 | 13158 | B:1 |
| 13112 | B:1 | 13159 | B:1 |
| 13113 | B:1 | 13160 | B:1 |
| 13114 | B:1 | 13161 | B:1 |
| 13115 | B:1 | 13162 | B:1 |
| 13116 | B:1 | 13163 | B:1 |
| 13317 | A:2 | 13164 | B:1 |
| 13165 | B:1 | 13212 | C:1 |
| 13166 | B:1 | 13213 | C:1 |
| 13167 | B:1 | 13214 | C:1 |
| 13168 | C:1 | 13215 | C:1 |

TABLE V-continued (Spatial distribution)

| Seq Id No. | Tissue distribution | Seq Id No. | Tissue distribution |
|---|---|---|---|
| 13169 | C:1 | 13216 | C:1 |
| 13170 | C:1 | 13217 | C:1 |
| 13171 | C:1 | 13218 | C:1 |
| 13172 | K:2 | 13219 | C:1 |
| 13173 | C:1 | 13220 | C:1 |
| 13174 | C:1 | 13221 | C:1 |
| 13175 | C:1 | 13222 | C:1 |
| 13176 | C:1 | 13223 | K:1 |
| 13177 | C:1 | 13224 | C:1 |
| 13178 | C:1 | 13225 | C:1 |
| 13179 | C:1 | 13226 | C:1 |
| 13180 | A:1 F:1 | 13227 | C:1 |
| 13181 | C:1 | 13228 | C:1 |
| 13182 | C:1 | 13229 | C:1 |
| 13183 | C:1 | 13230 | C:1 |
| 13184 | C:1 | 13231 | C:1 |
| 13185 | C:1 | 13232 | C:1 |
| 13186 | C:1 | 13233 | A:2 |
| 13187 | C:1 | 13234 | C:1 |
| 13188 | H:2 | 13235 | C:1 |
| 13189 | C:1 | 13236 | C:1 |
| 13190 | C:1 | 13237 | C:1 |
| 13191 | C:1 | 13238 | C:1 |
| 13192 | C:1 | 13239 | C:1 |
| 13193 | H:2 | 13240 | C:2 |
| 13194 | C:1 | 13241 | C:1 |
| 13195 | C:1 | 13242 | C:1 |
| 13196 | C:1 | 13243 | C:1 |
| 13197 | C:1 | 13244 | C:1 |
| 13198 | B:3 | 13245 | C:1 |
| 13199 | C:1 | 13246 | C:1 |
| 13200 | C:1 | 13247 | C:1 |
| 13201 | C:1 | 13248 | C:1 |
| 13202 | C:1 | 13249 | C:1 |
| 13203 | C:1 | 13250 | C:1 |
| 13204 | C:1 | 13251 | C:1 |
| 13205 | C:1 | 13252 | C:1 |
| 13206 | C:1 | 13253 | C:1 |
| 13207 | F:1 K:1 | 13254 | C:1 |
| 13208 | C:1 | 13255 | C:1 |
| 13209 | C:1 | 13256 | C:1 |
| 13210 | C:1 | 13257 | C:1 |
| 13211 | C:1 | 13258 | C:1 |
| 13259 | C:1 | 13306 | C:1 |
| 13260 | C:1 | 13307 | C:1 |
| 13261 | C:1 | 13308 | C:1 |
| 13262 | C:1 | 13309 | C:1 |
| 13263 | C:1 | 13310 | C:1 |
| 13264 | C:1 | 13311 | C:1 |
| 13265 | C:1 | 13312 | C:1 |
| 13266 | C:1 | 13313 | C:1 |
| 13267 | A:9 H:1 | 13314 | C:1 |
| 13268 | C:1 | 13315 | C:1 |
| 13269 | C:1 | 13316 | C:1 |
| 13270 | C:1 | 13317 | C:1 |
| 13271 | C:1 | 13318 | C:1 |
| 13272 | C:1 | 13319 | C:1 |
| 13273 | C:1 | 13320 | C:1 |
| 13274 | C:1 | 13321 | C:1 |
| 13275 | C:1 | 13322 | C:1 |
| 13276 | C:1 | 13323 | C:1 |
| 13277 | K:2 | 13324 | C:1 |
| 13278 | C:1 | 13325 | C:1 |
| 13279 | C:1 | 13326 | C:1 |
| 13280 | C:1 | 13327 | C:1 |
| 13281 | C:1 | 13328 | C:1 |
| 13282 | C:1 | 13329 | C:1 |
| 13283 | C:1 | 13330 | K:2 |
| 13284 | C:1 | 13331 | C:1 |
| 13285 | C:1 | 13332 | C:1 |
| 13286 | B:2 | 13333 | C:1 |
| 13287 | C:1 | 13334 | C:1 |
| 13288 | C:1 | 13335 | C:1 |
| 13289 | C:1 | 13336 | K:2 |
| 13290 | C:1 | 13337 | C:1 |
| 13291 | C:1 | 13338 | C:1 |
| 13292 | C:1 | 13339 | C:1 |
| 13293 | C:1 | 13340 | C:1 |
| 13294 | K:2 | 13341 | C:1 |
| 13295 | C:1 | 13342 | C:1 |
| 13296 | C:1 | 13343 | C:1 |
| 13297 | C:1 | 13344 | C:1 |
| 13298 | C:1 | 13345 | C:1 |
| 13299 | C:1 | 13346 | B:1 |
| 13300 | C:1 | 13347 | C:1 |
| 13301 | C:1 | 13348 | C:1 |
| 13302 | C:1 | 13349 | C:1 |
| 13303 | C:1 | 13350 | C:1 |
| 13304 | C:1 | 13351 | C:1 |
| 13305 | C:1 | 13352 | C:1 |
| 13353 | C:1 | 13400 | I:1 |
| 13354 | I:1 | 13401 | I:1 |
| 13355 | I:1 | 13402 | I:1 |
| 13356 | I:1 | 13403 | I:1 |
| 13357 | I:1 | 13404 | I:1 |
| 13358 | I:1 | 13405 | I:1 |
| 13359 | C:1 | 13406 | I:1 |
| 13360 | I:1 | 13407 | C:1 |
| 13361 | I:1 | 13408 | I:1 |
| 13362 | I:1 | 13409 | I:1 |
| 13363 | I:1 | 13410 | I:1 |
| 13364 | I:1 | 13411 | I:1 |
| 13365 | I:1 | 13412 | C:1 |
| 13366 | B:8 | 13413 | I:1 |
| 13367 | C:1 | 13414 | I:1 |
| 13368 | I:1 | 13415 | I:1 |
| 13369 | I:1 | 13416 | I:1 |
| 13370 | I:1 | 13417 | I:1 |
| 13371 | I:1 | 13418 | I:1 |
| 13372 | I:1 | 13419 | I:1 |
| 13373 | I:1 | 13420 | C:1 |
| 13374 | I:1 | 13421 | I:1 |
| 13375 | C:1 | 13422 | I:1 |
| 13376 | I:1 | 13423 | I:1 |
| 13377 | I:1 | 13424 | I:1 |
| 13378 | I:1 | 13425 | I:1 |
| 13379 | I:1 | 13426 | I:1 |
| 13380 | I:1 | 13427 | I:1 |
| 13381 | I:1 | 13428 | C:1 |
| 13382 | I:1 | 13429 | I:1 |
| 13383 | I:1 | 13430 | I:1 |
| 13384 | C:1 | 13431 | I:1 |
| 13385 | I:1 | 13432 | I:1 |
| 13386 | I:1 | 13433 | I:1 |
| 13387 | I:1 | 13434 | I:1 |
| 13388 | I:1 | 13435 | C:1 |
| 13389 | I:1 | 13436 | I:1 |
| 13390 | I:1 | 13437 | I:1 |
| 13391 | I:1 | 13438 | I:1 |
| 13392 | C:1 | 13439 | I:1 |
| 13393 | I:1 | 13440 | I:1 |
| 13394 | I:1 | 13441 | I:1 |
| 13395 | I:1 | 13442 | I:1 |
| 13396 | I:1 | 13443 | C:1 |
| 13397 | I:1 | 13444 | I:1 |
| 13398 | C:1 | 13445 | I:1 |
| 13399 | I:1 | 13446 | I:1 |
| 13447 | I:1 | 13494 | C:1 |
| 13448 | I:1 | 13495 | C:1 |
| 13449 | C:122 | 13496 | C:1 |
| 13450 | I:1 | 13497 | C:1 |
| 13451 | I:1 | 13498 | C:1 |
| 13452 | I:1 | 13499 | C:1 |
| 13453 | I:1 | 13500 | C:1 |
| 13454 | I:1 | 13501 | C:1 |
| 13455 | I:1 | 13502 | C:1 |

TABLE V-continued (Spatial distribution)

| Seq Id No. | Tissue distribution | Seq Id No. | Tissue distribution |
|---|---|---|---|
| 13456 | I:1 | 13503 | C:1 |
| 13457 | C:1 | 13504 | C:1 |
| 13458 | I:1 | 13505 | C:1 |
| 13459 | I:1 | 13506 | C:1 |
| 13460 | I:1 | 13507 | C:1 |
| 13461 | I:1 | 13508 | C:1 |
| 13462 | I:1 | 13509 | C:1 |
| 13463 | I:1 | 13510 | C:1 |
| 13464 | C:1 | 13511 | C:1 |
| 13465 | I:1 | 13512 | C:1 |
| 13466 | I:1 | 13513 | C:1 |
| 13467 | I:1 | 13514 | C:1 |
| 13468 | I:1 | 13515 | C:1 |
| 13469 | I:1 | 13516 | C:1 |
| 13470 | I:1 | 13517 | C:1 |
| 13471 | I:1 | 13518 | C:1 |
| 13472 | I:1 | 13519 | C:1 |
| 13473 | I:1 | 13520 | A:10 |
| 13474 | I:1 | 13521 | C:1 |
| 13475 | I:1 | 13522 | C:1 |
| 13476 | I:1 | 13523 | C:1 |
| 13477 | I:1 | 13524 | C:1 |
| 13478 | I:1 | 13525 | C:1 |
| 13479 | I:1 | 13526 | C:1 |
| 13480 | I:1 | 13527 | C:1 |
| 13481 | I:1 | 13528 | C:1 |
| 13482 | I:1 | 13529 | C:1 |
| 13483 | I:1 | 13530 | C:1 |
| 13484 | I:1 | 13531 | C:1 |
| 13485 | I:1 | 13532 | C:1 |
| 13486 | C:1 | 13533 | C:1 |
| 13487 | C:1 | 13534 | C:1 |
| 13488 | C:1 | 13535 | C:1 |
| 13489 | C:1 | 13536 | C:1 |
| 13490 | C:1 | 13537 | C:1 |
| 13491 | F:4 | 13538 | C:1 |
| 13492 | C:1 | 13539 | C:1 |
| 13493 | C:1 | 13540 | C:1 |
| 13541 | C:1 | 13588 | C:1 |
| 13542 | C:1 | 13589 | C:1 |
| 13543 | C:1 | 13590 | C:1 |
| 13544 | C:1 | 13591 | C:1 |
| 13545 | C:1 | 13592 | H:2 |
| 13546 | C:1 | 13593 | C:1 |
| 13547 | C:1 | 13594 | C:1 |
| 13548 | C:1 | 13595 | C:1 |
| 13549 | C:1 | 13596 | C:1 |
| 13550 | C:1 | 13597 | C:1 |
| 13551 | C:1 | 13598 | C:1 |
| 13552 | C:1 | 13599 | C:1 |
| 13553 | C:1 | 13600 | C:1 |
| 13554 | C:1 | 13601 | C:1 |
| 13555 | C:1 | 13602 | C:1 |
| 13556 | C:1 | 13603 | C:1 |
| 13557 | H:1 | 13604 | C:1 |
| 13558 | C:1 | 13605 | C:1 |
| 13559 | C:1 | 13606 | C:1 |
| 13560 | C:1 | 13607 | C:1 |
| 13561 | C:1 | 13608 | C:1 |
| 13562 | C:1 | 13609 | C:1 |
| 13563 | C:1 | 13610 | D:1 |
| 13564 | C:1 | 13611 | D:1 |
| 13565 | C:1 | 13612 | D:1 |
| 13566 | C:1 | 13613 | D:1 |
| 13567 | C:1 | 13614 | H:4 |
| 13568 | C:1 | 13615 | D:1 |
| 13569 | C:1 | 13616 | D:1 |
| 13570 | C:1 | 13617 | D:1 |
| 13571 | C:1 | 13618 | D:1 |
| 13572 | C:1 | 13619 | D:1 |
| 13573 | C:1 | 13620 | D:1 |
| 13574 | C:1 | 13621 | K:6 |
| 13575 | C:1 | 13622 | D:1 |
| 13576 | C:1 | 13623 | D:1 |
| 13577 | C:1 | 13624 | D:1 |
| 13578 | C:1 | 13625 | D:1 |
| 13579 | C:1 | 13626 | D:1 |
| 13580 | C:1 | 13627 | H:48 |
| 13581 | C:1 | 13628 | D:1 |
| 13582 | C:1 | 13629 | D:1 |
| 13583 | C:1 | 13630 | D:1 |
| 13584 | C:1 | 13631 | D:1 |
| 13585 | C:1 | 13632 | D:1 |
| 13586 | C:1 | 13633 | D:1 |
| 13587 | C:1 | 13634 | D:1 |
| 13635 | D:1 | 13682 | D:1 |
| 13636 | H:1 | 13683 | D:1 |
| 13637 | D:1 | 13684 | D:1 |
| 13638 | D:1 | 13685 | D:1 |
| 13639 | D:1 | 13686 | D:1 |
| 13640 | D:1 | 13687 | D:1 |
| 13641 | D:1 | 13688 | D:1 |
| 13642 | H:1 | 13689 | D:1 |
| 13643 | D:1 | 13690 | F:2 K:7 |
| 13644 | D:1 | 13691 | D:1 |
| 13645 | D:1 | 13692 | D:1 |
| 13646 | D:1 | 13693 | D:1 |
| 13647 | D:1 | 13694 | D:1 |
| 13648 | H:1 | 13695 | D:1 |
| 13649 | D:1 | 13696 | D:1 |
| 13650 | D:1 | 13697 | D:1 |
| 13651 | D:1 | 13698 | D:1 |
| 13652 | D:1 | 13699 | D:1 |
| 13653 | A:4 | 13700 | D:1 |
| 13654 | D:1 | 13701 | D:1 |
| 13655 | D:1 | 13702 | D:1 |
| 13656 | D:1 | 13703 | D:1 |
| 13657 | D:1 | 13704 | D:1 |
| 13658 | D:1 | 13705 | D:1 |
| 13659 | D:1 | 13706 | D:1 |
| 13660 | D:1 | 13707 | D:1 |
| 13661 | D:1 | 13708 | D:1 |
| 13662 | D:1 | 13709 | D:1 |
| 13663 | D:1 | 13710 | D:1 |
| 13664 | D:1 | 13711 | D:1 |
| 13665 | D:1 | 13712 | F:1 H:7 |
| 13666 | D:1 | 13713 | D:1 |
| 13667 | D:1 | 13714 | D:1 |
| 13668 | D:1 | 13715 | D:1 |
| 13669 | D:1 | 13716 | D:1 |
| 13670 | D:1 | 13717 | D:1 |
| 13671 | D:1 | 13718 | D:1 |
| 13672 | D:1 | 13719 | D:1 |
| 13673 | D:1 | 13720 | D:1 |
| 13674 | H:1 | 13721 | D:1 |
| 13675 | H:1 I:5 | 13722 | K:4 |
| 13676 | D:1 | 13723 | D:1 |
| 13677 | D:1 | 13724 | D:1 |
| 13678 | D:1 | 13725 | D:1 |
| 13679 | D:1 | 13726 | D:1 |
| 13680 | D:1 | 13727 | D:1 |
| 13681 | D:1 | 13728 | D:1 |
| 13729 | D:1 | 13776 | D:1 |
| 13730 | D:1 | 13777 | D:1 |
| 13731 | K:3 | 13778 | D:1 |
| 13732 | D:1 | 13779 | K:2 |
| 13733 | D:1 | 13780 | D:1 |
| 13734 | D:1 | 13781 | D:1 |
| 13735 | B:2 | 13782 | D:1 |
| 13736 | D:1 | 13783 | D:1 |
| 13737 | D:1 | 13784 | D:1 |
| 13738 | D:1 | 13785 | D:1 |
| 13739 | D:1 | 13786 | D:1 |
| 13740 | D:1 | 13787 | D:1 |
| 13741 | D:1 | 13788 | B:4 D:3 F:1 H:1 K:5 |
| 13742 | D:1 | 13789 | D:1 |

TABLE V-continued (Spatial distribution)

| Seq Id No. | Tissue distribution | Seq Id No. | Tissue distribution |
|---|---|---|---|
| 13743 | D:1 | 13790 | D:1 |
| 13744 | D:1 | 13791 | D:1 |
| 13745 | D:1 | 13792 | D:1 |
| 13746 | D:1 | 13793 | D:1 |
| 13747 | D:1 | 13794 | D:1 |
| 13748 | D:1 | 13795 | D:1 |
| 13749 | D:1 | 13796 | A:1 |
| 13750 | D:1 | 13797 | D:1 |
| 13751 | K:1 | 13798 | D:1 |
| 13752 | D:1 | 13799 | D:1 |
| 13753 | D:1 | 13800 | D:1 |
| 13754 | D:1 | 13801 | C:1 |
| 13755 | D:1 | 13802 | D:1 |
| 13756 | D:1 | 13803 | D:1 |
| 13757 | D:1 | 13804 | D:1 |
| 13758 | D:1 | 13805 | D:1 |
| 13759 | D:1 | 13806 | D:1 |
| 13760 | F:1 | 13807 | D:1 |
| 13761 | D:1 | 13808 | D:1 |
| 13762 | D:1 | 13809 | F:2 K:1 |
| 13763 | D:1 | 13810 | D:1 |
| 13764 | D:1 | 13811 | D:1 |
| 13765 | D:1 | 13812 | D:1 |
| 13766 | D:1 | 13813 | D:1 |
| 13767 | H:23 | 13814 | D:1 |
| 13768 | D:1 | 13815 | D:1 |
| 13769 | D:1 | 13816 | D:1 |
| 13770 | D:1 | 13817 | D:1 |
| 13771 | D:1 | 13818 | D:1 |
| 13772 | D:1 | 13819 | D:1 |
| 13773 | D:1 | 13820 | D:1 |
| 13774 | F:3 K:17 | 13821 | D:1 |
| 13775 | D:1 | 13822 | D:1 |
| 13823 | D:1 | 13870 | F:1 K:1 |
| 13824 | D:1 | 13871 | D:1 |
| 13825 | D:1 | 13872 | D:1 |
| 13826 | D:1 | 13873 | D:1 |
| 13827 | D:1 | 13874 | D:1 |
| 13828 | D:1 | 13875 | D:1 |
| 13829 | D:1 | 13876 | D:1 |
| 13830 | D:1 | 13877 | D:1 |
| 13831 | D:1 | 13878 | C:1 |
| 13832 | D:1 | 13879 | K:2 |
| 13833 | D:1 | 13880 | D:1 |
| 13834 | D:1 | 13881 | D:1 |
| 13835 | C:8 | 13882 | D:1 |
| 13836 | D:1 | 13883 | D:1 |
| 13837 | D:1 | 13884 | D:1 |
| 13838 | D:1 | 13885 | D:1 |
| 13839 | D:1 | 13886 | D:1 |
| 13840 | D:1 | 13887 | D:1 |
| 13841 | D:1 | 13888 | D:1 |
| 13842 | D:1 | 13889 | D:1 |
| 13843 | D:1 | 13890 | D:1 |
| 13844 | D:1 | 13891 | K:2 |
| 13845 | D:1 | 13892 | D:1 |
| 13846 | D:1 | 13893 | D:1 |
| 13847 | D:1 | 13894 | D:1 |
| 13848 | D:1 | 13895 | D:1 |
| 13849 | D:1 | 13896 | D:1 |
| 13850 | F:1 K:3 | 13897 | D:1 |
| 13851 | D:1 | 13898 | D:1 |
| 13852 | D:1 | 13899 | D:1 |
| 13853 | D:1 | 13900 | D:1 |
| 13854 | D:1 | 13901 | D:1 |
| 13855 | D:1 | 13902 | D:1 |
| 13856 | D:1 | 13903 | D:1 |
| 13857 | D:1 | 13904 | D:1 |
| 13858 | D:1 | 13905 | D:1 |
| 13859 | F:16 K:3 | 13906 | D:1 |
| 13860 | D:1 | 13907 | D:1 |
| 13861 | D:1 | 13908 | D:1 |
| 13862 | D:1 | 13909 | D:1 |
| 13863 | D:1 | 13910 | D:1 |
| 13864 | D:1 | 13911 | K:2 |
| 13865 | D:1 | 13912 | D:1 |
| 13866 | D:1 | 13913 | D:1 |
| 13867 | D:1 | 13914 | D:1 |
| 13868 | D:1 | 13915 | D:1 |
| 13869 | D:1 | 13916 | D:1 |
| 13917 | D:1 | 13964 | F:1 |
| 13918 | D:1 | 13965 | F:1 |
| 13919 | D:1 | 13966 | F:1 |
| 13920 | D:1 | 13967 | F:1 |
| 13921 | D:1 | 13968 | F:1 |
| 13922 | A:1 F:1 | 13969 | F:1 K:1 |
| 13923 | D:1 | 13970 | F:1 |
| 13924 | D:1 | 13971 | F:1 |
| 13925 | D:1 | 13972 | F:1 |
| 13926 | D:1 | 13973 | F:1 |
| 13927 | D:1 | 13974 | F:1 |
| 13928 | D:1 | 13975 | F:1 |
| 13929 | D:1 | 13976 | F:1 |
| 13930 | D:1 | 13977 | F:1 |
| 13931 | K:2 | 13978 | F:1 |
| 13932 | D:1 | 13979 | F:1 |
| 13933 | D:1 | 13980 | F:1 |
| 13934 | D:1 | 13981 | F:1 |
| 13935 | D:1 | 13982 | F:1 |
| 13936 | D:1 | 13983 | F:1 |
| 13937 | D:1 | 13984 | F:1 |
| 13938 | D:1 | 13985 | F:1 |
| 13939 | D:1 | 13986 | F:1 |
| 13940 | D:1 | 13987 | F:1 |
| 13941 | D:1 | 13988 | F:1 |
| 13942 | D:1 | 13989 | F:1 |
| 13943 | F:1 | 13990 | F:1 |
| 13944 | F:1 | 13991 | F:1 |
| 13945 | F:1 | 13992 | F:1 |
| 13946 | F:1 | 13993 | F:1 |
| 13947 | F:6 | 13994 | F:1 |
| 13948 | F:1 | 13995 | F:1 |
| 13949 | F:1 | 13996 | F:1 |
| 13950 | F:1 | 13997 | F:1 |
| 13951 | F:1 | 13998 | F:1 |
| 13952 | F:1 | 13999 | F:1 |
| 13953 | F:1 | 14000 | F:1 |
| 13954 | F:1 | 14001 | F:1 |
| 13955 | F:1 | 14002 | F:1 |
| 13956 | F:1 | 14003 | F:1 |
| 13957 | A:1 | 14004 | F:1 |
| 13958 | F:1 | 14005 | F:1 |
| 13959 | F:1 | 14006 | F:1 |
| 13960 | F:1 | 14007 | F:1 |
| 13961 | F:1 | 14008 | F:1 |
| 13962 | F:1 | 14009 | F:1 |
| 13963 | F:1 | 14010 | F:1 |
| 14011 | F:1 | 14058 | A:1 |
| 14012 | F:1 | 14059 | A:1 |
| 14013 | F:1 | 14060 | A:1 |
| 14014 | F:1 | 14061 | A:1 |
| 14015 | F:1 | 14062 | A:1 |
| 14016 | F:1 | 14063 | A:1 |
| 14017 | F:1 | 14064 | A:1 |
| 14018 | F:1 | 14065 | 1:2 |
| 14019 | F:1 | 14066 | A:1 |
| 14020 | F:1 | 14067 | A:1 |
| 14021 | F:1 | 14068 | A:1 |
| 14022 | F:10 K:2 | 14069 | A:1 |
| 14023 | F:1 | 14070 | A:1 |
| 14024 | F:1 | 14071 | A:1 |
| 14025 | F:1 | 14072 | A:1 |
| 14026 | F:1 | 14073 | A:1 |
| 14027 | F:1 | 14074 | A:1 |
| 14028 | F:1 | 14075 | K:2 |
| 14029 | F:1 | 14076 | A:1 |

TABLE V-continued (Spatial distribution)

| Seq Id No. | Tissue distribution | Seq Id No. | Tissue distribution |
|---|---|---|---|
| 14030 | F:1 | 14077 | A:1 |
| 14031 | F:1 | 14078 | A:1 |
| 14032 | F:1 | 14079 | A:1 |
| 14033 | F:1 | 14080 | A:1 |
| 14034 | F:1 | 14081 | A:1 |
| 14035 | A:1 | 14082 | A:1 |
| 14036 | A:1 | 14083 | A:1 |
| 14037 | A:1 | 14084 | A:1 |
| 14038 | A:1 | 14085 | A:1 |
| 14039 | A:1 | 14086 | A:1 |
| 14040 | A:1 | 14087 | A:1 |
| 14041 | A:1 | 14088 | K:3 |
| 14042 | A:1 | 14089 | A:1 |
| 14043 | A:1 | 14090 | A:1 |
| 14044 | A:1 | 14091 | A:1 |
| 14045 | A:1 | 14092 | A:1 |
| 14046 | A:1 | 14093 | F:1 K:2 |
| 14047 | A:1 | 14094 | K:2 |
| 14048 | A:1 | 14095 | A:1 |
| 14049 | A:1 | 14096 | A:1 |
| 14050 | A:1 | 14097 | A:1 |
| 14051 | A:1 | 14098 | A:1 |
| 14052 | A:1 | 14099 | A:1 |
| 14053 | A:1 | 14100 | A:1 |
| 14054 | A:1 | 14101 | A:1 |
| 14055 | A:1 | 14102 | A:1 |
| 14056 | A:1 | 14103 | A:1 |
| 14057 | A:1 | 14104 | B:3 |
| 14105 | A:1 | 14152 | A:1 |
| 14106 | A:1 | 14153 | A:1 |
| 14107 | A:1 | 14154 | A:1 |
| 14108 | A:1 | 14155 | A:1 |
| 14109 | A:1 | 14156 | A:1 |
| 14110 | A:1 | 14157 | A:1 |
| 14111 | A:1 | 14158 | A:1 |
| 14112 | A:1 | 14159 | A:1 |
| 14113 | A:1 | 14160 | A:1 |
| 14114 | A:1 | 14161 | A:1 |
| 14115 | A:1 | 14162 | A:1 |
| 14116 | A:1 | 14163 | A:1 |
| 14117 | A:1 | 14164 | A:1 |
| 14118 | A:1 | 14165 | A:1 |
| 14119 | A:1 | 14166 | A:1 |
| 14120 | A:1 | 14167 | A:1 |
| 14121 | A:1 | 14168 | A:1 |
| 14122 | A:1 | 14169 | A:1 |
| 14123 | A:1 | 14170 | A:1 |
| 14124 | A:1 | 14171 | A:1 |
| 14125 | A:1 | 14172 | A:1 |
| 14126 | A:1 | 14173 | A:1 |
| 14127 | A:1 | 14174 | A:1 |
| 14128 | A:1 | 14175 | A:1 |
| 14129 | A:1 | 14176 | A:1 |
| 14130 | A:1 | 14177 | A:1 |
| 14131 | A:1 | 14178 | A:1 |
| 14132 | A:1 | 14179 | A:1 |
| 14133 | A:1 | 14180 | B:3 |
| 14134 | D:1 J:2 | 14181 | A:1 |
| 14135 | A:1 | 14182 | A:1 |
| 14136 | A:1 | 14183 | A:1 |
| 14137 | A:1 | 14184 | A:1 |
| 14138 | A:1 | 14185 | A:1 |
| 14139 | A:1 | 14186 | A:1 |
| 14140 | A:1 | 14187 | A:1 |
| 14141 | A:1 | 14188 | A:1 |
| 14142 | A:1 | 14189 | A:1 |
| 14143 | A:1 J:2 | 14190 | A:1 |
| 14144 | A:1 | 14191 | A:1 |
| 14145 | A:1 | 14192 | A:1 |
| 14146 | A:1 | 14193 | A:1 |
| 14147 | A:1 | 14194 | A:1 |
| 14148 | A:1 | 14195 | A:1 |
| 14149 | A:1 | 14196 | A:1 |
| 14150 | A:1 | 14197 | A:1 |
| 14151 | A:1 | 14198 | A:1 |
| 14199 | A 1 | 14246 | A:1 |
| 14200 | A:1 | 14247 | A:1 |
| 14201 | A:1 | 14248 | A:1 |
| 14202 | A:1 | 14249 | A:1 |
| 14203 | A:1 | 14250 | C:8 |
| 14204 | A:1 | 14251 | A:1 |
| 14205 | A:1 | 14252 | A:1 |
| 14206 | A:1 | 14253 | A:1 |
| 14207 | A:1 | 14254 | A:1 |
| 14208 | A:1 | 14255 | A:1 |
| 14209 | A:1 | 14256 | A:1 |
| 14210 | B:1 | 14257 | A:1 |
| 14211 | A:1 | 14258 | A:1 |
| 14212 | A:1 | 14259 | A:1 |
| 14213 | A:1 | 14260 | A:1 |
| 14214 | A:1 | 14261 | A:1 |
| 14215 | A:1 | 14262 | A:1 |
| 14216 | A:1 | 14263 | A:1 |
| 14217 | A:1 | 14264 | A:1 |
| 14218 | A:1 | 14265 | A:1 |
| 14219 | A:1 | 14266 | H:1 |
| 14220 | A:1 | 14267 | A:1 |
| 14221 | A:1 | 14268 | A:1 |
| 14222 | A:1 | 14269 | A:1 |
| 14223 | A:1 | 14270 | A:1 |
| 14224 | C:1 F:1 K:1 | 14271 | A:1 |
| 14225 | A:1 | 14272 | A:1 |
| 14226 | A:1 | 14273 | A:1 |
| 14227 | A:1 | 14274 | A:1 |
| 14228 | A:1 | 14275 | A:1 |
| 14229 | A:1 | 14276 | A:1 |
| 14230 | A:1 | 14277 | A:1 |
| 14231 | A:1 | 14278 | B:3 C:6 H:1 |
| 14232 | B:1 C:1 | 14279 | A:1 |
| 14233 | A:1 | 14280 | A:1 |
| 14234 | A:1 | 14281 | A:1 |
| 14235 | A:1 | 14282 | A:1 |
| 14236 | A:1 | 14283 | A:1 |
| 14237 | A:1 | 14284 | A:1 |
| 14238 | A:1 | 14285 | A:1 |
| 14239 | A:1 | 14286 | F:13 K:6 |
| 14240 | D:1 | 14287 | A:1 |
| 14241 | A:1 | 14288 | A:1 |
| 14242 | A:1 | 14289 | A:1 |
| 14243 | A:1 | 14290 | A:1 |
| 14244 | A:1 | 14291 | A:1 |
| 14245 | A:1 | 14292 | A:1 |
| 14293 | A 1 | 14340 | A:1 |
| 14294 | A:1 | 14341 | C:2 |
| 14295 | A:1 C:5 | 14342 | A:1 |
| 14296 | A:1 | 14343 | A:1 |
| 14297 | A:1 | 14344 | A:1 |
| 14298 | A:1 | 14345 | A:1 |
| 14299 | A:1 | 14346 | A:1 |
| 14300 | A:1 | 14347 | A:1 |
| 14301 | A:1 | 14348 | A:1 |
| 14302 | A:1 | 14349 | A:1 |
| 14303 | A:1 | 14350 | A:1 |
| 14304 | F:5 K:1 | 14351 | A:1 |
| 14305 | A:1 | 14352 | A:1 |
| 14306 | A:1 | 14353 | A:1 |
| 14307 | A:1 | 14354 | A:1 |
| 14308 | A:1 | 14355 | A:1 |
| 14309 | A:1 | 14356 | A:1 |
| 14310 | A:1 | 14357 | A:1 |
| 14311 | A:1 | 14358 | A:1 |
| 14312 | K:2 | 14359 | A:1 |
| 14313 | A:1 | 14360 | A:1 |
| 14314 | A:1 | 14361 | A:1 |
| 14315 | A:1 | 14362 | A:1 |
| 14316 | A:1 | 14363 | A:1 |

TABLE V-continued

(Spatial distribution)

| Seq Id No. | Tissue distribution | Seq Id No. | Tissue distribution |
|---|---|---|---|
| 14317 | A:1 | 14364 | A:1 |
| 14318 | K:1 | 14365 | A:1 |
| 14319 | A:1 | 14366 | A:1 |
| 14320 | A:1 | 14367 | H:3 |
| 14321 | A:1 | 14368 | A:1 |
| 14322 | A:1 | 14369 | A:1 |
| 14323 | A:1 | 14370 | A:1 |
| 14324 | A:1 | 14371 | A:1 |
| 14325 | A:1 | 14372 | A:1 |
| 14326 | A:1 | 14373 | A:1 |
| 14327 | A:1 | 14374 | A:1 |
| 14328 | A:1 | 14375 | A:1 |
| 14329 | A:1 | 14376 | A:1 |
| 14330 | A:1 | 14377 | A:1 |
| 14331 | A:1 | 14378 | A:1 |
| 14332 | A:1 | 14379 | A:1 |
| 14333 | A:1 | 14380 | A:1 |
| 14334 | A:1 | 14381 | A:1 |
| 14335 | A:1 | 14382 | A:1 |
| 14336 | A:1 | 14383 | A:1 |
| 14337 | A:1 | 14384 | A:1 |
| 14338 | A:1 | 14385 | A:1 |
| 14339 | A:1 | 14386 | K:2 |
| 14387 | A:1 | 14434 | A:1 |
| 14388 | A:1 | 14435 | A:1 |
| 14389 | A:1 | 14436 | A:1 |
| 14390 | A:1 | 14437 | A:1 |
| 14391 | A:1 | 14438 | A:1 |
| 14392 | K:1 | 14439 | A:1 |
| 14393 | A:1 | 14440 | A:1 |
| 14394 | A:1 | 14441 | A:1 |
| 14395 | A:1 | 14442 | A:1 |
| 14396 | A:1 | 14443 | A:1 |
| 14397 | A:1 | 14444 | A:1 |
| 14398 | A:1 | 14445 | A:1 |
| 14399 | A:1 | 14446 | A:1 |
| 14400 | A:1 | 14447 | A:1 |
| 14401 | A:1 | 14448 | A:1 |
| 14402 | A:1 | 14449 | A:1 |
| 14403 | A:1 | 14450 | A:1 |
| 14404 | A:1 | 14451 | A:1 |
| 14405 | A:1 | 14452 | A:1 |
| 14406 | A:1 | 14453 | A:1 |
| 14407 | A:1 | 14454 | A:1 |
| 14408 | A:1 | 14455 | H:2 |
| 14409 | A:1 | 14456 | A:1 |
| 14410 | A:1 | 14457 | A:1 |
| 14411 | A:1 | 14458 | A:1 |
| 14412 | A:1 | 14459 | A:1 |
| 14413 | A:1 | 14460 | A:1 |
| 14414 | A:1 | 14461 | A:1 |
| 14415 | A:1 | 14462 | A:1 |
| 14416 | A:1 | 14463 | A:1 |
| 14417 | A:1 | 14464 | A:1 |
| 14418 | A:1 | 14465 | F:1 K:1 |
| 14419 | A:1 | 14466 | A:1 |
| 14420 | A:1 | 14467 | A:1 |
| 14421 | A:1 | 14468 | A:1 |
| 14422 | A:1 | 14469 | A:1 |
| 14423 | A:1 | 14470 | A:1 |
| 14424 | A:1 | 14471 | A:1 |
| 14425 | A:1 | 14472 | A:1 |
| 14426 | A:1 | 14473 | A:1 |
| 14427 | F:1 K:1 | 14474 | A:1 |
| 14428 | A:1 | 14475 | H:3 |
| 14429 | A:1 | 14476 | A:1 |
| 14430 | A:1 | 14477 | A:1 |
| 14431 | A:1 | 14478 | A:1 |
| 14432 | A:1 | 14479 | A:1 |
| 14433 | A:1 | 14480 | A:1 |
| 14481 | A:1 | 14528 | A:1 |
| 14482 | A:1 | 14529 | F:1 K:1 |
| 14483 | A:1 | 14530 | A:1 |
| 14484 | A:1 | 14531 | A:1 |
| 14485 | A:1 | 14532 | A:1 |
| 14486 | A:1 | 14533 | A:1 |
| 14487 | A:1 | 14534 | A:1 |
| 14488 | A:1 | 14535 | A:1 |
| 14489 | A:1 | 14536 | A:1 |
| 14490 | A:1 | 14537 | A:1 |
| 14491 | A:1 | 14538 | H:3 |
| 14492 | A:1 | 14539 | A:1 |
| 14493 | A:1 | 14540 | A:1 |
| 14494 | A:1 | 14541 | A:1 |
| 14495 | A:1 | 14542 | A:1 |
| 14496 | A:1 | 14543 | A:1 |
| 14497 | A:1 | 14544 | A:1 |
| 14498 | A:1 | 14545 | A:1 |
| 14499 | A:1 | 14546 | A:19 B:16 C:31 D:14 F:2 H:17 K:3 |
| 14500 | A:1 | 14547 | A:1 |
| 14501 | A:1 | 14548 | A:1 |
| 14502 | A:1 | 14549 | A:1 |
| 14503 | A:1 | 14550 | A:1 |
| 14504 | A:1 | 14551 | A:1 |
| 14505 | A:1 | 14552 | A:1 |
| 14506 | A:1 | 14553 | A:1 |
| 14507 | A:1 | 14554 | A:1 |
| 14508 | B:4 | 14555 | A:1 |
| 14509 | A:1 | 14556 | A:1 |
| 14510 | A:1 | 14557 | A:1 |
| 14511 | A:1 | 14558 | A:1 |
| 14512 | A:1 | 14559 | H:3 |
| 14513 | A:1 | 14560 | A:1 |
| 14514 | A:1 | 14561 | A:1 |
| 14515 | A:1 | 14562 | A:1 |
| 14516 | A:1 | 14563 | A:1 |
| 14517 | A:1 | 14564 | A:1 |
| 14518 | A:1 | 14565 | A:1 |
| 14519 | K:2 | 14566 | A:1 |
| 14520 | A:1 | 14567 | A:1 |
| 14521 | A:1 | 14568 | A:1 |
| 14522 | A:1 | 14569 | A:1 |
| 14523 | A:1 | 14570 | A:1 |
| 14524 | A:1 | 14571 | A:1 |
| 14525 | A:1 | 14572 | A:1 |
| 14526 | A:1 | 14573 | A:1 |
| 14527 | A:1 | 14574 | A:1 |
| 14575 | A:1 | 14621 | A:1 |
| 14576 | A:1 | 14622 | A:1 |
| 14577 | A:1 | 14623 | A:1 |
| 14578 | A:1 | 14624 | B:2 |
| 14579 | A:1 | 14625 | A:1 |
| 14580 | A:1 | 14626 | A:1 |
| 14581 | A:1 | 14627 | A:1 |
| 14582 | A:1 | 14628 | A:1 |
| 14583 | A:1 | 14629 | A:1 |
| 14584 | A:1 | 14630 | F:10 K:5 |
| 14585 | A:1 | 14631 | A:1 |
| 14586 | A:1 | 14632 | A:1 |
| 14587 | A:1 | 14633 | A:1 |
| 14588 | A:1 | 14634 | A:1 |
| 14589 | A:1 | 14635 | A:1 |
| 14590 | A:1 | 14636 | A:1 |
| 14591 | A:1 | 14637 | A:1 |
| 14592 | A:1 | 14638 | A:1 |
| 14593 | A:1 | 14639 | A:1 |
| 14594 | A:1 | 14640 | A:1 |
| 14595 | K:2 | 14641 | A:1 |
| 14596 | A:1 | 14642 | A:1 |
| 14597 | A:1 | 14643 | A:1 |
| 14598 | A:1 | 14644 | A:1 |
| 14599 | A:1 | 14645 | A:1 |
| 14600 | A:1 | 14646 | A:1 |
| 14601 | A:1 | 14647 | A:1 |
| 14602 | A:1 | 14648 | A:1 |
| | | 14649 | A:1 |

TABLE V-continued

(Spatial distribution)

| Seq Id No. | Tissue distribution | Seq Id No. | Tissue distribution |
|---|---|---|---|
| 14603 | A:1 | 14650 | A:1 |
| 14604 | B:4 | 14651 | A:1 |
| 14605 | A:1 | 14652 | A:1 |
| 14606 | A:1 | 14653 | A:1 |
| 14607 | A:1 | 14654 | B:1 C:106 H:1 |
| 14608 | A:1 | 14655 | A:1 |
| 14609 | A:1 | 14656 | A:1 |
| 14610 | H:2 | 14657 | A:1 |
| 14611 | A:1 | 14658 | A:1 |
| 14612 | A:1 | 14659 | A:1 |
| 14613 | A:1 | 14660 | A:1 |
| 14614 | A:1 | 14661 | A:1 |
| 14615 | A:1 | 14662 | A:1 |
| 14616 | A:1 | 14663 | A:1 |
| 14617 | A:1 | 14664 | A:1 |
| 14618 | A:1 | 14665 | A:1 |
| 14619 | A:1 | 14666 | A:1 |
| 14620 | A:1 | 14667 | A:1 |
| 14668 | A:1 | 14715 | A:1 |
| 14669 | A:1 | 14716 | A:1 |
| 14670 | A:1 | 14717 | A:1 |
| 14671 | A:1 | 14718 | A:1 |
| 14672 | A:1 | 14719 | K:2 |
| 14673 | B:1 | 14720 | A:1 |
| 14674 | A:1 | 14721 | A:1 |
| 14675 | A:1 | 14722 | A:1 |
| 14676 | A:1 | 14723 | A:1 |
| 14677 | A:1 | 14724 | A:1 |
| 14678 | A:1 | 14725 | A:1 |
| 14679 | A:1 | 14726 | A:1 |
| 14680 | A:1 | 14727 | A:1 |
| 14681 | A:1 | 14728 | A:1 |
| 14682 | A:1 | 14729 | A:1 |
| 14683 | A:1 | 14730 | B:3 |
| 14684 | A:1 | 14731 | A:1 |
| 14685 | A:1 | 14732 | A:1 |
| 14686 | A:1 | 14733 | A:1 |
| 14687 | A:1 | 14734 | A:1 |
| 14688 | A:1 | 14735 | A:1 |
| 14689 | A:1 | 14736 | A:1 |
| 14690 | A:1 | 14737 | A:1 |
| 14691 | C:1 | 14738 | A:1 |
| 14692 | A:1 | 14739 | A:1 |
| 14693 | A:1 | 14740 | A:1 |
| 14694 | A:1 | 14741 | A:1 |
| 14695 | A:1 | 14742 | A:1 |
| 14696 | A:1 | 14743 | A:1 |
| 14697 | A:1 | 14744 | A:1 |
| 14698 | A:1 | 14745 | A:1 |
| 14699 | A:1 | 14746 | F:1 K:2 |
| 14700 | A:1 | 14747 | A:1 |
| 14701 | B:1 | 14748 | A:1 |
| 14702 | A:1 | 14749 | A:1 |
| 14703 | A:1 | 14750 | A:1 |
| 14704 | A:1 | 14751 | A:1 |
| 14705 | A:1 | 14752 | A:1 |
| 14706 | A:1 | 14753 | A:1 |
| 14707 | A:1 | 14754 | A:1 |
| 14708 | A:1 | 14755 | A:1 |
| 14709 | F:3 K:2 | 14756 | A:1 |
| 14710 | A:1 | 14757 | A:1 |
| 14711 | A:1 | 14758 | A:1 |
| 14712 | A:1 | 14759 | A:1 |
| 14713 | A:1 | 14760 | A:1 |
| 14714 | A:1 | 14761 | A:1 |
| 14762 | A:1 | 14809 | A:1 |
| 14763 | A:1 | 14810 | A:1 |
| 14764 | A:1 | 14811 | A:1 |
| 14765 | A:1 | 14812 | A:1 |
| 14766 | A:1 | 14813 | A:1 |
| 14767 | A:1 | 14814 | A:1 |
| 14768 | A:1 | 14815 | A:1 |
| 14769 | A:1 | 14816 | A:1 |
| 14770 | A:1 | 14817 | B:4 C:1 D:1 |
| 14771 | A:1 | 14818 | A:1 |
| 14772 | A:1 | 14819 | A:1 |
| 14773 | A:1 | 14820 | A:1 |
| 14774 | A:1 | 14821 | A:1 |
| 14775 | A:1 | 14822 | A:1 |
| 14776 | A:1 | 14823 | A:1 |
| 14777 | A:1 | 14824 | A:1 |
| 14778 | A:1 | 14825 | A:1 |
| 14779 | A:1 | 14826 | A:1 |
| 14780 | A:1 | 14827 | A:1 |
| 14781 | B:1 | 14828 | A:1 |
| 14782 | A:1 | 14829 | A:1 |
| 14783 | A:1 | 14830 | A:1 |
| 14784 | A:1 | 14831 | A:1 |
| 14785 | A:1 | 14832 | A:1 |
| 14786 | A:1 | 14833 | A:1 |
| 14787 | A:1 | 14834 | A:1 |
| 14788 | A:1 | 14835 | A:1 |
| 14789 | K:1 | 14836 | A:1 |
| 14790 | A:1 | 14837 | A:1 |
| 14791 | A:1 | 14838 | A:1 |
| 14792 | A:1 | 14839 | A:1 |
| 14793 | A:1 | 14840 | A:1 |
| 14794 | A:1 | 14841 | A:1 |
| 14795 | A:1 | 14842 | A:1 |
| 14796 | A:1 | 14843 | A:1 |
| 14797 | A:1 | 14844 | A:1 |
| 14798 | B:1 | 14845 | A:1 |
| 14799 | A:1 | 14846 | A:1 |
| 14800 | A:1 | 14847 | A:1 |
| 14801 | A:1 | 14848 | A:1 |
| 14802 | A:1 | 14849 | A:1 |
| 14803 | A:1 | 14850 | A:1 |
| 14804 | A:1 | 14851 | A:1 |
| 14805 | A:1 | 14852 | C:9 |
| 14806 | A:1 | 14853 | A:1 |
| 14807 | F:1 | 14854 | A:1 |
| 14808 | A:1 | 14855 | A:1 |
| 14856 | A:1 | 14903 | A:1 |
| 14857 | A:1 | 14904 | A:1 |
| 14858 | A:1 | 14905 | A:1 |
| 14859 | A:1 | 14906 | A:1 |
| 14860 | A:1 | 14907 | A:1 |
| 14861 | A:1 | 14908 | A:1 |
| 14862 | B:1 | 14909 | A:1 |
| 14863 | A:1 | 14910 | A:1 |
| 14864 | A:1 | 14911 | A:1 |
| 14865 | A:1 | 14912 | A:1 |
| 14866 | A:1 | 14913 | A:1 |
| 14867 | A:1 | 14914 | A:1 |
| 14868 | A:1 | 14915 | A:1 |
| 14869 | A:1 | 14916 | A:1 |
| 14870 | F:1 | 14917 | A:1 |
| 14871 | A:1 | 14918 | A:1 |
| 14872 | A:1 | 14919 | A:1 |
| 14873 | A:1 | 14920 | A:1 |
| 14874 | A:1 | 14921 | A:1 |
| 14875 | A:1 | 14922 | A:1 |
| 14876 | A:1 | 14923 | A:1 |
| 14877 | A:1 | 14924 | A:1 |
| 14878 | A:1 | 14925 | A:1 |
| 14879 | A:1 | 14926 | A:1 |
| 14880 | A:1 | 14927 | A:1 |
| 14881 | A:1 | 14928 | A:1 |
| 14882 | A:1 | 14929 | A:1 |
| 14883 | A:1 | 14930 | A:1 |
| 14884 | A:1 | 14931 | A:1 |
| 14885 | A:1 | 14932 | A:1 |
| 14886 | A:1 | 14933 | F:1 K:1 |
| 14887 | A:1 | 14934 | A:1 |
| 14888 | A:1 | 14935 | A:1 |
| 14889 | A:1 | 14936 | A:1 |

TABLE V-continued

(Spatial distribution)

| Seq Id No. | Tissue distribution |
|---|---|
| 14890 | A:1 |
| 14891 | A:1 |
| 14892 | A:1 |
| 14893 | A:1 |
| 14894 | A:1 |
| 14895 | A:1 |
| 14896 | A:1 |
| 14897 | A:1 |
| 14898 | A:1 |
| 14899 | A:1 |
| 14900 | A:1 |
| 14901 | A:1 |
| 14902 | A:1 |
| 14950 | A:1 |
| 14951 | A:1 |
| 14952 | A:1 |
| 14953 | A:1 |
| 14954 | A:1 |
| 14955 | A:1 |
| 14956 | F:1 K:1 |
| 14957 | A:1 |
| 14958 | A:1 |
| 14959 | A:1 |
| 14960 | A:1 |
| 14961 | A:1 |
| 14962 | A:1 |
| 14963 | A:1 |
| 14964 | H:5 |
| 14965 | A:1 |
| 14966 | A:1 |
| 14967 | A:1 |
| 14968 | A:1 |
| 14969 | A:1 |
| 14970 | A:1 |
| 14971 | A:1 |
| 14972 | A:1 |
| 14973 | A:1 |
| 14974 | A:1 |
| 14975 | A:1 |
| 14976 | A:1 |
| 14977 | A:1 |
| 14978 | A:1 |
| 14979 | A:1 |
| 14980 | A:1 |
| 14981 | A:1 |
| 14982 | A:1 |
| 14983 | A:1 |
| 14984 | A:1 |
| 14985 | A:1 |
| 14986 | F:1 |
| 14987 | A:1 |
| 14988 | A:1 |
| 14989 | A:1 |
| 14990 | A:1 |
| 14991 | A:1 |
| 14992 | A:1 |
| 14993 | A:1 |
| 14994 | A:1 |
| 14995 | K:1 |
| 14996 | A:1 |
| 15044 | A:1 |
| 15045 | A:1 |
| 15046 | A:1 |
| 15047 | A:1 |
| 15048 | A:1 |
| 15049 | A:1 |
| 15050 | A:1 |
| 15051 | A:1 |
| 15052 | A:1 |
| 15053 | A:5 |
| 15054 | A:1 |
| 15055 | A:1 |
| 14937 | A:1 |
| 14938 | A:1 |
| 14939 | A:1 |
| 14940 | A:1 |
| 14941 | A:1 |
| 14942 | A:1 |
| 14943 | A:1 |
| 14944 | A:1 |
| 14945 | A:1 |
| 14946 | A:1 |
| 14947 | A:1 |
| 14948 | A:1 |
| 14949 | A:1 |
| 14997 | A:1 |
| 14998 | A:1 |
| 14999 | A:1 |
| 15000 | A:1 |
| 15001 | A:1 |
| 15002 | A:1 |
| 15003 | A:1 |
| 15004 | A:1 |
| 15005 | B:4 |
| 15006 | A:1 |
| 15007 | A:1 |
| 15008 | A:1 |
| 15009 | A:1 |
| 15010 | A:1 |
| 15011 | A:1 |
| 15012 | A:1 |
| 15013 | A:8 B:23 C:7 D:1 H:1 I:1 K:3 |
| 15014 | A:1 |
| 15015 | A:1 |
| 15016 | A:1 |
| 15017 | A:1 |
| 15018 | A:1 |
| 15019 | A:1 |
| 15020 | A:1 |
| 15021 | A:1 |
| 15022 | A:1 |
| 15023 | B:1 |
| 15024 | A:1 |
| 15025 | A:1 |
| 15026 | A:1 |
| 15027 | A:1 |
| 15028 | A:1 |
| 15029 | A:1 |
| 15030 | A:1 |
| 15031 | A:1 |
| 15032 | H:1 K:1 |
| 15033 | A:1 |
| 15034 | A:1 |
| 15035 | A:1 |
| 15036 | A:1 |
| 15037 | A:1 |
| 15038 | A:1 |
| 15039 | A:1 |
| 15040 | A:1 |
| 15041 | A:1 |
| 15042 | F:1 K:4 |
| 15043 | A:1 |
| 15091 | A:1 |
| 15092 | A:1 |
| 15093 | A:1 |
| 15094 | A:1 |
| 15095 | F:1 K:1 |
| 15096 | K:1 |
| 15097 | A:1 H:1 |
| 15098 | A:3 |
| 15099 | F:1 |
| 15100 | H:1 |
| 15101 | C:3 F:1 J:2 |
| 15102 | H:2 |
| 15056 | A:1 |
| 15057 | A:1 |
| 15058 | A:1 |
| 15059 | A:1 |
| 15060 | A:1 |
| 15061 | A:1 |
| 15062 | A:1 |
| 15063 | A:1 |
| 15064 | A:1 |
| 15065 | A:1 |
| 15066 | A:1 |
| 15067 | A:1 |
| 15068 | A:1 |
| 15069 | A:1 |
| 15070 | A:1 |
| 15071 | A:1 |
| 15072 | A:1 |
| 15073 | A:1 |
| 15074 | A:1 |
| 15075 | A:1 |
| 15076 | A:1 |
| 15077 | C:3 |
| 15078 | A:1 |
| 15079 | A:1 |
| 15080 | A:1 |
| 15081 | A:1 |
| 15082 | A:1 |
| 15083 | A:1 |
| 15084 | A:1 |
| 15085 | A:1 |
| 15086 | A:1 |
| 15087 | A:1 |
| 15088 | B:4 C:1 |
| 15089 | A:1 |
| 15090 | A:1 |
| 15138 | A:4 |
| 15139 | F:9 K:2 |
| 15140 | A:3 |
| 15141 | A:8 B:2 C:23 J:1 |
| 15142 | K:1 |
| 15143 | B:2 |
| 15144 | K:1 |
| 15145 | F:2 |
| 15146 | C:3 |
| 15147 | H:2 |
| 15148 | K:3 |
| 15149 | B:4 |
| 15150 | F:1 K:3 |
| 15151 | A:2 |
| 15152 | H:1 |
| 15153 | F:1 K:1 |
| 15154 | I:3 |
| 15155 | C:1 H:3 |
| 15156 | K:1 |
| 15157 | K:3 |
| 15158 | B:2 |
| 15159 | A:2 |
| 15160 | B:1 C:1 |
| 15161 | H:1 |
| 15162 | H:3 |
| 15163 | A:1 |
| 15164 | F:2 K:6 |
| 15165 | F:1 K:4 |
| 15166 | C:6 |
| 15167 | K:1 |
| 15168 | B:2 |
| 15169 | C:1 |
| 15170 | C:10 |
| 15171 | K:2 |
| 15172 | A:1 |
| 15173 | A:1 B:1 |
| 15174 | A:6 |
| 15175 | A:5 |
| 15103 | A:2 H:5 |
| 15104 | F:4 K:8 |
| 15105 | F:3 K:4 |
| 15106 | K:1 |
| 15107 | K:1 |
| 15108 | A:4 |
| 15109 | K:1 |
| 15110 | H:2 |
| 15111 | B:5 |
| 15112 | K:1 |
| 15113 | H:2 |
| 15114 | F:2 H:4 K:2 |
| 15115 | C:1 H:2 |
| 15116 | F:11 |
| 15117 | H:1 |
| 15118 | F:1 K:1 |
| 15119 | F:1 K:1 |
| 15120 | K:3 |
| 15121 | K:2 |
| 15122 | K:3 |
| 15123 | H:3 |
| 15124 | B:2 |
| 15125 | F:11 K:3 |
| 15126 | A:2 |
| 15127 | A:1 |
| 15128 | A:1 |
| 15129 | C:55 H:1 K:2 |
| 15130 | A:2 |
| 15131 | F:1 K:2 |
| 15132 | K:2 |
| 15133 | K:1 |
| 15134 | K:1 |
| 15135 | B:2 |
| 15136 | F:5 K:2 |
| 15137 | H:5 |
| 15185 | A:4 |
| 15186 | A:3 |
| 15187 | H:2 |
| 15188 | K:3 |
| 15189 | F:1 K:1 |
| 15190 | F:1 K:1 |
| 15191 | F:1 K:1 |
| 15192 | B:3 |
| 15193 | C:2 |
| 15194 | F:2 K:1 |
| 15195 | F:1 K:1 |
| 15196 | A:1 B:11 C:20 D:1 H:2 K:1 |
| 15197 | B: C:1 D:1 K:1 |
| 15198 | A:1 B:1 C:7 D:1 H:1 K:1 |
| 15199 | B:1 C:1 D:2 K:1 |
| 15200 | A:4 B:31 C:72 D:20 F:3 H:29 I:3 J:3 K:19 |
| 15201 | A:6 B:2 F:2 H:3 K:1 |
| 15202 | A:4 B:27 C:60 D:18 F:1 H:16 I:3 J:2 K:12 |
| 15203 | H:1 |
| 15204 | C:1 |
| 15205 | D:1 |
| 15206 | C:1 |
| 15207 | C:1 |
| 15208 | B:1 |
| 15209 | C:1 |
| 15210 | H:1 |
| 15211 | K:3 |
| 15212 | F:1 K:1 |
| 15213 | K:3 |
| 15214 | F:1 K:1 |
| 15215 | F:1 K:1 |
| 15216 | H:2 |
| 15217 | K:2 |
| 15218 | K:2 |
| 15219 | F:7 K:1 |
| 15220 | A:1 C:10 D:1 |

TABLE V-continued

(Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 15176 | K:1 | 15221 | F:1 | 15340 | B:2 | 15387 | B:1 |
| 15177 | B:2 | 15222 | F:1 K:4 | 15341 | C:45 | 15388 | K:1 |
| 15178 | H:2 | 15223 | F:5 | 15342 | K:1 | 15389 | K:1 |
| 15179 | B:2 | 15224 | K:2 | 15343 | C:1 | 15390 | C:3 J:2 |
| 15180 | A:1 H:1 | 15225 | D:1 H:1 | 15344 | H:8 | 15391 | B:3 |
| 15181 | K:3 | 15226 | A:6 | 15345 | A:12 | 15392 | H:5 |
| 15182 | H:14 | 15227 | B:3 C:1 | 15346 | F:2 | 15393 | K:1 |
| 15183 | K:2 | 15228 | K:2 | 15347 | F:4 | 15394 | B:6 |
| 15184 | F:1 K:3 | 15229 | C:10 | 15348 | F:9 K:2 | 15395 | F:1 |
| 15230 | C:1 | 15277 | A:1 | 15349 | H:2 | 15396 | K:1 |
| 15231 | A:1 B:5 C:2 F:1 K:2 | 15278 | A:1 | 15350 | F:1 | 15397 | F:2 |
| 15232 | A:2 | 15279 | B:2 | 15351 | K:1 | 15398 | F:2 |
| 15233 | F:1 | 15280 | B:2 | 15352 | K:1 | 15399 | B:3 |
| 15234 | F:1 | 15281 | F:8 K:1 | 15353 | A:1 | 15400 | D:1 I:1 |
| 15235 | H:2 | 15282 | F:10 K:2 | 15354 | K:2 | 15401 | K:2 |
| 15236 | H:6 | 15283 | F:1 K:1 | 15355 | K:1 | 15402 | H:2 |
| 15237 | A:1 C:1 H:3 K:1 | 15284 | B:2 | 15356 | F:11 K:6 | 15403 | K:5 |
| 15238 | A:1 C:1 H:4 | 15285 | B:3 | 15357 | F:1 | 15404 | A:2 B:3 C:2 D:1 F:1 H:21 I:1 K:1 |
| 15239 | K:2 | 15286 | F:1 | | | | |
| 15240 | F:1 K:2 | 15287 | K:1 | 15358 | F:1 | 15405 | A:9 B:9 C:12 D:5 E:1 F:1 H:1 I:1 K:4 |
| 15241 | B:5 | 15288 | A:2 B:1 | 15359 | F:1 | | |
| 15242 | H:2 | 15289 | B:2 | 15360 | F:1 | 15406 | A:2 B:3 C:3 D:1 E:1 H:2 I:1 K:1 |
| 15243 | C:6 | 15290 | B:4 | | | | |
| 15244 | H:42 | 15291 | B:2 | | | 15407 | A:2 |
| 15245 | F:1 K:2 | 15292 | B:2 | 15361 | K:1 | 15408 | K:2 |
| 15246 | H:1 | 15293 | B:2 | 15362 | F:1 | 15409 | C:1 |
| 15247 | K:2 | 15294 | F:277 K:66 | 15363 | H:6 | 15410 | C:1 |
| 15248 | K:3 | 15295 | K:1 | 15364 | F:1 | 15411 | K:1 |
| 15249 | H:1 | 15296 | B:2 | 15365 | F:1 | 15412 | F:1 |
| 15250 | B:2 | 15297 | D:3 F:6 K:25 | 15366 | K:1 | 15413 | A:4 |
| 15251 | C:1 H:1 | 15298 | K:1 | 15367 | F:1 | 15414 | K:1 |
| 15252 | A:1 | 15299 | F:1 K:2 | 15368 | F:1 K:2 | 15415 | C:4 |
| 15253 | I:3 | 15300 | H:2 | 15369 | F:2 K:6 | 15416 | A:6 |
| 15254 | K:2 | 15301 | C:26 | 15370 | F:1 | | |
| 15255 | D:1 | 15302 | C:1 | 15417 | F:2 | 15464 | F:1 K:1 |
| 15256 | B:3 | 15303 | F:1 K:6 | 15418 | C:5 J:1 | 15465 | H:1 |
| 15257 | K:4 | 15304 | A:2 | 15419 | D:1 F:8 H:3 K:64 | 15466 | A:1 B:3 C:1 |
| 15258 | F:1 K:1 | 15305 | A:2 | 15420 | B:3 | 15467 | H:1 |
| 15259 | C:1 J:1 | 15306 | A:1 | 15421 | F:2 | 15468 | H:1 |
| 15260 | H:2 | 15307 | A:1 | 15422 | K:2 | 15469 | H:1 |
| 15261 | K:7 | 15308 | B:3 | 15423 | A:3 | 15470 | H:1 |
| 15262 | K:2 | 15309 | F:1 K:6 | 15424 | F:5 | 15471 | K:2 |
| 15263 | K:1 | 15310 | K:3 | 15425 | C:7 | 15472 | D:1 |
| 15264 | C:2 | 15311 | C:6 | 15426 | A:1 B:2 | 15473 | B:3 |
| 15265 | K:2 | 15312 | F:12 K:6 | 15427 | K:1 | 15474 | B:3 |
| 15266 | B:2 | 15313 | K:1 | 15428 | F:3 | 15475 | A:2 |
| 15267 | F:4 | 15314 | F:1 | 15429 | B:3 | 15476 | B:1 F:6 H:4 |
| 15268 | K:1 | 15315 | F:1 K:1 | 15430 | H:3 | 15477 | K:3 |
| 15269 | K:1 | 15316 | K:1 | 15431 | H:2 | 15478 | D:1 H:1 |
| 15270 | K:1 | 15317 | K:1 | 15432 | K:3 | 15479 | B:2 |
| 15271 | F:1 | 15318 | K:1 | 15433 | A:1 C:1 I:2 | 15480 | H:2 |
| 15272 | C:1 | 15319 | F:1 | 15434 | C:1 | 15481 | F:1 K:1 |
| 15273 | I:2 | 15320 | F:1 | 15435 | F:2 | 15482 | C:3 J:1 |
| 15274 | H:1 | 15321 | F:1 | 15436 | K:1 | 15483 | H:3 |
| 15275 | J:1 | 15322 | F:1 | 15437 | F:1 | 15484 | A:2 |
| 15276 | C:1 | 15323 | K:1 | 15438 | F:1 | 15485 | A:4 |
| 15324 | C:3 | 15371 | A:2 | 15439 | F:1 | 15486 | K:3 |
| 15325 | F:1 K:3 | 15372 | F:5 | 15440 | F:1 | 15487 | A:2 |
| 15326 | B:2 | 15373 | C:2 | 15441 | F:1 | 15488 | B:5 |
| 15327 | F:6 K:2 | 15374 | C:4 | 15442 | F:3 K:1 | 15489 | K:2 |
| 15328 | B:2 | 15375 | B:2 | 15443 | C:10 | 15490 | A:3 B:5 C:253 D:5 F:5 H:6 J:7 K:6 |
| 15329 | K:1 | 15376 | K:2 | 15444 | A:4 | | |
| 15330 | F:7 K:3 | 15377 | A:3 | 15445 | F:1 K:5 | 15491 | A:8 B:3 D:2 |
| 15331 | I:2 | 15378 | A:2 B:1 C:1 D:1 H:1 I:1 K:1 | 15446 | K:1 | 15492 | F:3 K:2 |
| | | | | 15447 | F:9 K:7 | 15493 | C:2 |
| 15332 | A:1 | 15379 | A:7 | 15448 | K:2 | 15494 | C:8 |
| 15333 | K:1 | 15380 | B:2 | 15449 | B:2 | 15495 | A:1 |
| 15334 | A:2 | 15381 | F:3 | 15450 | C:10 | 15496 | A:1 |
| 15335 | K:1 | 15382 | H:1 | 15451 | F:2 | 15497 | K:1 |
| 15336 | F:3 | 15383 | H:2 | 15452 | C:3 | 15498 | F:2 |
| 15337 | K:1 | 15384 | F:2 | 15453 | F:15 K:84 | 15499 | A:2 |
| 15338 | K:2 | 15385 | F:2 | 15454 | K:2 | 15500 | B:2 |
| 15339 | F:14 K:2 | 15386 | F:1 K:4 | 15455 | A:1 B:1 | 15501 | K:2 |
| | | | | 15456 | K:1 | 15502 | K:2 |

TABLE V-continued (Spatial distribution)

| Seq Id No. | Tissue distribution |
|---|---|
| 15457 | C:2 |
| 15458 | H:1 |
| 15459 | F:3 K:1 |
| 15460 | F:2 K:1 |
| 15461 | K:1 |
| 15462 | A:2 |
| 15463 | H:5 |
| 15510 | K:1 |
| 15511 | C:1 |
| 15512 | F:24 K:4 |
| 15513 | A:2 B:1 C:1 I:1 |
| 15514 | C:1 |
| 15515 | F:5 |
| 15516 | H:2 |
| 15517 | F:3 K:1 |
| 15518 | B:5 |
| 15519 | F:3 K:1 |
| 15520 | A:13 B:69 C:71 D:3 F:2 H:33 I:3 K:1 |
| 15521 | K:1 |
| 15522 | K:1 |
| 15523 | A:11 |
| 15524 | K:3 |
| 15525 | K:3 |
| 15526 | K:1 |
| 15527 | K:1 |
| 15528 | K:1 |
| 15529 | K:2 |
| 15530 | K:1 |
| 15531 | B:3 |
| 15532 | F:5 K:2 |
| 15533 | K:1 |
| 15534 | B:2 |
| 15535 | K:1 |
| 15536 | H:2 |
| 15537 | H:3 |
| 15538 | K:1 |
| 15539 | K:2 |
| 15540 | F:1 K:1 |
| 15541 | A:1 C:1 |
| 15542 | A:339 |
| 15543 | A:1 |
| 15544 | F:1 K:5 |
| 15545 | F:1 K:1 |
| 15546 | H:2 |
| 15547 | H:2 |
| 15548 | C:7 |
| 15549 | C:1 |
| 15550 | A:5 |
| 15551 | A:1 |
| 15552 | C:4 |
| 15553 | H:44 |
| 15554 | C:3 |
| 15555 | K:5 |
| 15602 | I:1 |
| 15603 | C:14 |
| 15604 | B:3 |
| 15605 | C:14 |
| 15606 | F:1 K:2 |
| 15607 | K:2 |
| 15608 | K:2 |
| 15609 | B:2 |
| 15610 | F:1 K:4 |
| 15611 | B:1 |
| 15612 | F:1 K:1 |
| 15613 | F:33 K:7 |
| 15614 | A:11 B:2 C:1 D:2 H:3 K:1 |
| 15615 | F:3 |
| 15616 | A:1 |
| 15617 | B:2 |
| 15618 | F:1 K:1 |
| 15503 | K:3 |
| 15504 | H:1 |
| 15505 | H:1 |
| 15506 | K:1 |
| 15507 | F:1 |
| 15508 | K:1 |
| 15509 | K:1 |
| 15556 | H:4 |
| 15557 | C:26 |
| 15558 | A:1 C:24 |
| 15559 | C:1 |
| 15560 | J:4 |
| 15561 | I:2 |
| 15562 | F:3 K:9 |
| 15563 | A:2 |
| 15564 | F:13 |
| 15565 | F:1 K:1 |
| 15566 | F:5 K:2 |
| 15567 | A:7 |
| 15568 | A:34 B:8 |
| 15569 | I:2 |
| 15570 | F:3 |
| 15571 | F:1 K:1 |
| 15572 | K:2 |
| 15573 | A:17 B:53 C:55 D:4 F:3 H:25 J:3 K:1 |
| 15574 | K:3 |
| 15575 | H:2 |
| 15576 | A:2 |
| 15577 | F:1 K:3 |
| 15578 | K:4 |
| 15579 | A:1 |
| 15580 | I:2 |
| 15581 | H:2 |
| 15582 | I:2 |
| 15583 | A:2 |
| 15584 | H:2 |
| 15585 | D:1 |
| 15586 | F:1 K:12 |
| 15587 | K:1 |
| 15588 | C:21 |
| 15589 | A:1 |
| 15590 | K:2 |
| 15591 | K:3 |
| 15592 | B:3 |
| 15593 | F:2 K:1 |
| 15594 | H:29 |
| 15595 | C:1 H:1 |
| 15596 | C:5 |
| 15597 | B:2 |
| 15598 | F:1 H:1 |
| 15599 | H:1 |
| 15600 | A:5 |
| 15601 | I:1 |
| 15649 | F:1 K:1 |
| 15650 | A:1 H:1 |
| 15651 | B:1 C:32 H:1 |
| 15652 | B:1 |
| 15653 | D:1 |
| 15654 | B:1 |
| 15655 | B:1 |
| 15656 | B:1 |
| 15657 | F:4 K:11 |
| 15658 | A:5 B:4 C:8 D:3 F:1 H:8 K:1 |
| 15659 | D:1 F:6 K:25 |
| 15660 | C:1 |
| 15661 | K:2 |
| 15662 | A:4 |
| 15663 | A:4 |
| 15664 | A:1 |
| 15665 | F:1 K:1 |
| 15619 | F:1 K:2 |
| 15620 | D:1 |
| 15621 | A:2 |
| 15622 | K:2 |
| 15623 | C:1 H:5 |
| 15624 | K:1 |
| 15625 | K:1 |
| 15626 | K:1 |
| 15627 | K:3 |
| 15628 | A:2 |
| 15629 | F:1 K:2 |
| 15630 | H:1 K:1 |
| 15631 | B:6 |
| 15632 | A:2 |
| 15633 | H:3 |
| 15634 | F:1 K:1 |
| 15635 | K:2 |
| 15636 | K:3 |
| 15637 | F:1 K:1 |
| 15638 | I:2 |
| 15639 | C:4 H:1 K:1 |
| 15640 | C:75 |
| 15641 | F:2 |
| 15642 | F:1 K:1 |
| 15643 | C:16 |
| 15644 | F:1 |
| 15645 | K:1 |
| 15646 | B:2 |
| 15647 | K:2 |
| 15648 | F:1 |
| 15696 | F:1 |
| 15697 | K:2 |
| 15698 | H:4 |
| 15699 | F:1 |
| 15700 | K:1 |
| 15701 | F:1 |
| 15702 | K:2 |
| 15703 | I:2 |
| 15704 | F:5 K:2 |
| 15705 | A:2 C:7 J:1 |
| 15706 | C:1 |
| 15707 | K:1 |
| 15708 | C:1 |
| 15709 | H:2 |
| 15710 | H:4 |
| 15711 | A:19 B:70 C:72 D:4 F:3 H:37 I:3 K:1 |
| 15712 | H:4 |
| 15713 | I:1 |
| 15714 | F:3 |
| 15715 | A:5 |
| 15716 | A:1 |
| 15717 | A:1 C:2 |
| 15718 | C:3 |
| 15719 | A:2 |
| 15720 | H:1 |
| 15721 | F:4 K:5 |
| 15722 | A:1 C:1 H:2 |
| 15723 | H:1 |
| 15724 | K:1 |
| 15725 | A:1 |
| 15726 | K:3 |
| 15727 | B:2 |
| 15728 | I:2 |
| 15729 | D:1 |
| 15730 | A:4 B:1 |
| 15731 | A:3 H:1 |
| 15732 | C:1 |
| 15733 | H:2 |
| 15734 | B:1 C:1 |
| 15735 | H:2 |
| 15736 | F:3 |
| 15737 | B:1 |
| 15666 | K:2 |
| 15667 | H:1 |
| 15668 | B:1 |
| 15669 | H:1 |
| 15670 | F:3 |
| 15671 | F:1 |
| 15672 | K:1 |
| 15673 | F:2 |
| 15674 | F:3 |
| 15675 | B:3 |
| 15676 | A:2 I:3 H:1 |
| 15677 | K:6 |
| 15678 | F:7 K:17 |
| 15679 | A:4 |
| 15680 | H:2 |
| 15681 | H:2 |
| 15682 | B:4 |
| 15683 | A:2 |
| 15684 | F:2 |
| 15685 | H:23 |
| 15686 | H:1 |
| 15687 | H:2 I:1 |
| 15688 | H:3 |
| 15689 | A:1 |
| 15690 | F:2 K:1 |
| 15691 | F:3 K:1 |
| 15692 | B:1 |
| 15693 | K:3 |
| 15694 | F:1 H:2 |
| 15695 | K:1 |
| 15742 | H:2 |
| 15743 | F:3 K:1 |
| 15744 | |
| 15745 | C:1 H:2 |
| 15746 | C:11 |
| 15747 | C:38 H:154 I:1 |
| 15748 | A:15 B:46 C:53 D:8 F:4 H:28 J:3 K:2 |
| 15749 | B:1 |
| 15750 | C:1 |
| 15751 | C:1 |
| 15752 | C:1 |
| 15753 | C:1 |
| 15754 | C:1 |
| 15755 | C:1 |
| 15756 | C:1 |
| 15757 | C:1 |
| 15758 | C:1 |
| 15759 | C:1 |
| 15760 | B:1 |
| 15761 | H:1 |
| 15762 | C:1 |
| 15763 | H:1 |
| 15764 | C:1 |
| 15765 | C:1 |
| 15766 | C:1 |
| 15767 | C:1 |
| 15768 | C:1 |
| 15769 | C:1 |
| 15770 | C:1 |
| 15771 | C:1 |
| 15772 | C:1 |
| 15773 | C:1 |
| 15774 | C:1 |
| 15775 | C:1 |
| 15776 | C:1 |
| 15777 | H:1 |
| 15778 | C:1 |
| 15779 | C:1 |
| 15780 | C:1 |
| 15781 | C:1 |
| 15782 | C:1 |
| 15783 | C:1 |

TABLE V-continued

(Spatial distribution)

| Seq Id No. | Tissue distribution |
|---|---|
| 15738 | H:2 K:1 |
| 15739 | K:2 |
| 15740 | A:1 B:1 |
| 15741 | B:1 |
| 15788 | C:1 |
| 15789 | H:1 |
| 15790 | C:1 |
| 15791 | C:4 |
| 15792 | C:1 |
| 15793 | C:1 |
| 15794 | H:1 |
| 15795 | C:1 |
| 15796 | C:1 |
| 15797 | C:1 |
| 15798 | H:1 |
| 15799 | C:1 |
| 15800 | C:1 |
| 15801 | H:1 |
| 15802 | K:3 |
| 15803 | C:1 |
| 15804 | C:1 |
| 15805 | C:1 |
| 15806 | C:1 |
| 15807 | C:1 |
| 15808 | C:1 |
| 15809 | C:1 |
| 15810 | C:1 |
| 15811 | C:1 |
| 15812 | C:1 |
| 15813 | C:1 |
| 15814 | C:1 |
| 15815 | C:1 |
| 15816 | C:1 |
| 15817 | C:1 |
| 15818 | C:1 |
| 15819 | C:1 |
| 15820 | C:1 |
| 15821 | C:1 |
| 15822 | C:1 |
| 15823 | K:2 |
| 15824 | C:1 |
| 15825 | C:1 |
| 15826 | C:1 |
| 15827 | C:1 |
| 15828 | C:1 |
| 15829 | C:1 |
| 15830 | C:1 |
| 15831 | H:1 |
| 15832 | H:1 |
| 15833 | C:1 |
| 15834 | C:1 |
| 15835 | C:1 |
| 15836 | C:1 |
| 15837 | C:1 |
| 15838 | C:1 |
| 15839 | C:1 |
| 15840 | C:1 |
| 15841 | C:1 |
| 15842 | C:1 |
| 15843 | C:1 |
| 15844 | F:1 |
| 15845 | C:1 |
| 15846 | C:1 |
| 15847 | C:1 |
| 15848 | C:1 |
| 15849 | C:1 |
| 15850 | C:1 |
| 15851 | C:1 |
| 15852 | C:1 |
| 15853 | C:1 |
| 15854 | C:1 |
| 15855 | H:1 |
| 15856 | C:1 |
| 15857 | C:1 |
| 15858 | C:1 |
| 15859 | C:1 |
| 15860 | C:1 |
| 15861 | H:1 |
| 15862 | C:1 |
| 15863 | H:1 |
| 15864 | C:1 |
| 15865 | C:1 |
| 15866 | C:1 |
| 15867 | C:1 |
| 15868 | C:1 |
| 15869 | C:1 |
| 15870 | C:1 |
| 15871 | C:1 |
| 15872 | C:1 |
| 15873 | C:1 |
| 15874 | H:1 |
| 15875 | C:1 |
| 15876 | C:1 |
| 15877 | H:1 |
| 15878 | C:1 |
| 15879 | C:1 |
| 15880 | C:1 |
| 15881 | H:1 |
| 15882 | C:1 |
| 15883 | C:1 |
| 15884 | C:1 |
| 15885 | H:1 |
| 15886 | C:1 |
| 15887 | C:1 |
| 15888 | H:1 |
| 15889 | H:1 |
| 15890 | H:1 |
| 15891 | C:1 |
| 15892 | C:1 |
| 15893 | C:1 |
| 15894 | H:1 |
| 15895 | C:1 |
| 15896 | C:1 |
| 15897 | C:1 |
| 15898 | C:1 |
| 15899 | C:1 |
| 15900 | C:1 |
| 15901 | C:1 |
| 15902 | H:1 |
| 15903 | C:1 |
| 15784 | C:1 |
| 15785 | C:1 |
| 15786 | C:1 |
| 15787 | C:1 |
| 15929 | C:1 |
| 15930 | H:1 |
| 15931 | H:1 |
| 15932 | C:1 |
| 15933 | C:1 |
| 15934 | C:1 |
| 15935 | C:1 |
| 15936 | C:1 |
| 15937 | C:1 |
| 15938 | C:1 |
| 15939 | C:1 |
| 15940 | C:1 |
| 15941 | C:1 |
| 15942 | C:1 |
| 15943 | C:1 |
| 15944 | C:1 |
| 15945 | C:1 |
| 15946 | H:1 |
| 15947 | C:1 |
| 15948 | C:1 |
| 15949 | C:1 |
| 15950 | C:1 |
| 15904 | H:1 |
| 15905 | C:1 |
| 15906 | C:1 |
| 15907 | C:1 |
| 15908 | C:1 |
| 15909 | C:1 |
| 15910 | C:1 |
| 15911 | C:1 |
| 15912 | C:1 |
| 15913 | C:1 |
| 15914 | C:1 |
| 15915 | H:1 |
| 15916 | C:1 |
| 15917 | H:1 |
| 15918 | C:1 |
| 15919 | H:1 |
| 15920 | C:1 |
| 15921 | H:1 |
| 15922 | C:1 |
| 15923 | C:1 |
| 15924 | C:1 |
| 15925 | C:1 |
| 15926 | C:1 |
| 15927 | C:1 |
| 15928 | C:1 |
| 15976 | C:1 |
| 15977 | K:1 |
| 15978 | H:1 |
| 15979 | H:1 |
| 15980 | C:1 |
| 15981 | H:1 |
| 15982 | C:1 |
| 15983 | C:1 |
| 15984 | C:1 |
| 15985 | C:1 |
| 15986 | C:1 |
| 15987 | H:1 |
| 15988 | C:1 |
| 15989 | H:1 |
| 15990 | B:1 |
| 15991 | A:1 |
| 15992 | H:4 |
| 15993 | H:1 |
| 15994 | H:1 |
| 15995 | H:1 |
| 15996 | F:1 |
| 15997 | H:1 |
| 15998 | H:1 |
| 15999 | H:1 |
| 16000 | H:1 |
| 16001 | H:1 |
| 16002 | A:2 |
| 16003 | H:3 |
| 16004 | K:5 |
| 16005 | A:1 |
| 16006 | H:1 |
| 16007 | A:12 |
| 16008 | A:1 |
| 16009 | A:1 |
| 16010 | A:1 |
| 16011 | A:1 |
| 16012 | A:1 |
| 16013 | A:1 |
| 16014 | A:1 |
| 16015 | A:1 |
| 16016 | A:1 |
| 16017 | A:1 |
| 16018 | A:1 |
| 16019 | A:1 |
| 16020 | A:1 |
| 16021 | A:1 |
| 16022 | A:1 |
| 16070 | K:2 |
| 15951 | C:1 |
| 15952 | C:1 |
| 15953 | C:1 |
| 15954 | C:1 |
| 15955 | C:1 |
| 15956 | B:1 |
| 15957 | C:1 |
| 15958 | C:1 |
| 15959 | H:1 |
| 15960 | H:1 |
| 15961 | C:1 |
| 15962 | C:1 |
| 15963 | C:1 |
| 15964 | C:1 |
| 15965 | C:1 |
| 15966 | C:1 |
| 15967 | C:1 |
| 15968 | C:1 |
| 15969 | C:1 |
| 15970 | C:1 |
| 15971 | C:1 |
| 15972 | C:1 |
| 15973 | C:1 |
| 15974 | C:1 |
| 15975 | C:1 |
| 16023 | A:1 |
| 16024 | A:1 |
| 16025 | H:1 |
| 16026 | A:1 |
| 16027 | A:1 |
| 16028 | A:1 |
| 16029 | A:1 |
| 16030 | A:1 |
| 16031 | A:1 |
| 16032 | A:1 |
| 16033 | A:1 |
| 16034 | A:1 |
| 16035 | A:1 |
| 16036 | F:2 |
| 16037 | A:1 |
| 16038 | A:1 |
| 16039 | A:1 |
| 16040 | A:1 |
| 16041 | A:1 |
| 16042 | A:1 |
| 16043 | A:1 |
| 16044 | A:1 |
| 16045 | A:1 |
| 16046 | A:1 |
| 16047 | A:2 |
| 16048 | A:1 |
| 16049 | A:1 |
| 16050 | A:1 |
| 16051 | A:1 |
| 16052 | A:1 |
| 16053 | A:1 |
| 16054 | A:1 |
| 16055 | A:1 |
| 16056 | A:1 |
| 16057 | A:1 |
| 16058 | A:1 |
| 16059 | A:1 |
| 16060 | A:1 |
| 16061 | A:1 |
| 16062 | K:2 |
| 16063 | H:2 |
| 16064 | F:1 K:6 |
| 16065 | C:27 |
| 16066 | K:3 |
| 16067 | A:1 I:1 |
| 16068 | B:2 |
| 16069 | K:2 |
| 16117 | F:1 K:6 |

TABLE V-continued

(Spatial distribution)

| Seq Id No. | Tissue distribution | Seq Id No. | Tissue distribution |
|---|---|---|---|
| 16071 | A:5 | 16118 | K:1 |
| 16072 | A:1 F:3 H:10 I:10 K:1 | 16119 | H:2 |
| 16073 | A:4 B:1 | 16120 | H:1 |
| 16074 | B:3 | 16121 | K:2 |
| 16075 | K:2 | 16122 | H:1 |
| 16076 | F:7 | 16123 | B:2 |
| 16077 | F:1 | 16124 | B:2 |
| 16078 | F:1 K:1 | 16125 | H:1 |
| 16079 | B:2 | 16126 | C:1 |
| 16080 | K:1 | 16127 | H:58 |
| 16081 | K:1 | 16128 | H:1 |
| 16082 | K:1 | 16129 | H:1 |
| 16083 | F:8 K:2 | 16130 | H:1 |
| 16084 | H:2 | 16131 | H:1 |
| 16085 | H:3 | 16132 | H:1 |
| 16086 | H:2 | 16133 | H:1 |
| 16087 | F:1 K:2 | 16134 | H:1 |
| 16088 | A:3 | 16135 | H:1 |
| 16089 | D:2 | 16136 | H:1 |
| 16090 | K:1 | 16137 | H:1 |
| 16091 | B:3 C:40 | 16138 | H:1 |
| 16092 | C:1 | 16139 | H:1 |
| 16093 | C:1 | 16140 | H:1 |
| 16094 | K:5 | 16141 | H:1 |
| 16095 | B:2 C:1 D:1 | 16142 | H:1 |
| 16096 | F:1 | 16143 | H:1 |
| 16097 | H:1 | 16144 | H:1 |
| 16098 | F:1 K:1 | 16145 | H:1 |
| 16099 | K:1 | 16146 | C:2 |
| 16100 | K:1 | 16147 | K:1 |
| 16101 | E:1 | 16148 | H:1 |
| 16102 | C:3 | 16149 | I:1 |
| 16103 | F:3 | 16150 | A:1 C:1 |
| 16104 | K:2 | 16151 | B:6 C:100 |
| 16105 | C:4 | 16152 | C:1 |
| 16106 | A:4 | 16153 | F:20 K:102 |
| 16107 | F:1 K:2 | 16154 | F:1 K:2 |
| 16108 | B:1 | 16155 | K:1 |
| 16109 | B:1 | 16156 | B:1 |
| 16110 | B:1 | 16157 | K:2 |
| 16111 | B:1 | 16158 | D:2 |
| 16112 | H:4 | 16159 | F:3 H:1 |
| 16113 | K:2 | 16160 | A:2 |
| 16114 | K:1 | 16161 | A:1 |
| 16115 | K:1 | 16162 | A:1 |
| 16116 | K:4 | 16163 | A:1 |
| 16164 | A:1 | 16211 | B:2 |
| 16165 | A:1 | 16212 | D:1 K:1 |
| 16166 | A:1 | 16213 | F:3 |
| 16167 | A:1 | 16214 | B:2 |
| 16168 | A:8 | 16215 | K:1 |
| 16169 | B:2 | 16216 | C:1 |
| 16170 | F:3 K:1 | 16217 | K:1 |
| 16171 | A:1 B:2 | 16218 | D:1 |
| 16172 | B:6 | 16219 | B:1 |
| 16173 | F:2 | 16220 | K:2 |
| 16174 | H:2 | 16221 | B:4 |
| 16175 | H:1 | 16222 | H:3 |
| 16176 | F:1 K:1 | 16223 | I:3 |
| 16177 | H:1 | 16224 | K:4 |
| 16178 | F:2 | 16225 | D:1 |
| 16179 | A:2 I:1 | 16226 | K:1 |
| 16180 | A:1 | 16227 | K:1 |
| 16181 | K:2 | 16228 | K:3 |
| 16182 | F:3 K:23 | 16229 | K:4 |
| 16183 | K:2 | 16230 | F:8 K:3 |
| 16184 | K:2 | 16231 | H:19 |
| 16185 | A:1 C:43 | 16232 | H:3 |
| 16186 | C:2 | 16233 | K:1 |
| 16187 | B:4 | 16234 | F:1 |
| 16188 | D:1 | 16235 | A:3 |
| 16189 | B:1 | 16236 | C:4 H:2 |
| 16190 | D:1 | 16237 | A:98 F:2 K:2 |
| 16191 | F:18 K:4 | 16238 | A:488 |
| 16192 | F:18 K:4 | 16239 | A:1 |
| 16193 | F:2 | 16240 | A:1 |
| 16194 | B:1 | 16241 | F:13 K:5 |
| 16195 | K:1 | 16242 | H:14 |
| 16196 | A:3 | 16243 | F:9 K:16 |
| 16197 | C:1 | 16244 | A:2 |
| 16198 | C:1 | 16245 | K:2 |
| 16199 | C:1 | 16246 | F:2 K:2 |
| 16200 | C:1 | 16247 | D:2 |
| 16201 | C:1 | 16248 | A:11 B:10 C:16 D:2 E:1 F:241 H:6 I:13 K:62 |
| 16202 | C:1 | | |
| 16203 | C:1 | 16249 | F:1 |
| 16204 | C:1 | 16250 | K:1 |
| 16205 | C:1 | 16251 | K:1 |
| 16206 | C:1 | 16252 | A:1 |
| 16207 | A:1 B:2 | 16253 | F:1 |
| 16208 | H:1 | 16254 | K:1 |
| 16209 | B:1 | 16255 | K:1 |
| 16210 | B:3 | 16256 | K:1 |
| 16257 | K:1 | 16304 | B:1 |
| 16258 | H:1 | 16305 | I:1 |
| 16259 | F:1 | 16306 | A:1 |
| 16260 | K:1 | 16307 | D:1 H:1 |
| 16261 | F:1 | 16308 | H:3 |
| 16262 | K:1 | 16309 | F:2 K:1 |
| 16263 | B:2 | 16310 | B:2 |
| 16264 | B:6 | 16311 | B:5 |
| 16265 | B:2 | 16312 | C:28 |
| 16266 | H:2 | 16313 | C:1 |
| 16267 | F:1 | 16314 | A:1 |
| 16268 | A:1 | 16315 | H:5 |
| 16269 | A:2 | 16316 | H:1 |
| 16270 | C:2 | 16317 | H:1 |
| 16271 | C:3 | 16318 | H:1 |
| 16272 | A:2 | 16319 | H:1 |
| 16273 | K:1 | 16320 | H:1 |
| 16274 | F:1 K:1 | 16321 | H:1 |
| 16275 | A:2 | 16322 | H:1 |
| 16276 | C:5 | 16323 | H:1 |
| 16277 | H:23 | 16324 | H:1 |
| 16278 | F:2 | 16325 | K:2 |
| 16279 | B:1 | 16326 | A:1 |
| 16280 | D:1 | 16327 | C:7 K:2 |
| 16281 | D:1 | 16328 | C:2 K:3 |
| 16282 | F:2 | 16329 | K:2 |
| 16283 | D:1 | 16330 | H:1 |
| 16284 | D:1 | 16331 | F:1 |
| 16285 | B:2 | 16332 | A:2 B:3 C:35 D:1 H:1 I:3 K:3 |
| 16286 | B:1 | 16333 | K:2 |
| 16287 | B:2 | 16334 | B:2 |
| 16288 | K:1 | 16335 | B:2 |
| 16289 | K:1 | 16336 | F:5 |
| 16290 | K:1 | 16337 | F:4 K:1 |
| 16291 | F:1 | 16338 | F:5 |
| 16292 | F:1 | 16339 | F:1 |
| 16293 | F:1 | 16340 | F:1 |
| 16294 | K:1 | 16341 | F:1 |
| 16295 | F:1 | 16342 | F:1 |
| 16296 | H:2 | 16343 | F:1 |
| 16297 | F:1 K:1 | 16344 | F:1 |
| 16298 | F:1 | 16345 | F:1 |
| 16299 | F:4 | 16346 | K:3 |
| 16300 | K:2 | 16347 | K:1 |
| 16301 | F:1 H:2 | 16348 | F:2 |
| 16302 | F:3 K:41 | 16349 | K:1 |
| 16303 | K:2 | 16350 | K:1 |
| 16351 | B:7 C:28 D:1 H:1 K:1 | 16397 | A:1 D:1 |
| 16352 | B:11 C:58 D:1 H:1 K:1 | 16398 | C:1 |
| 16353 | B:1 | 16399 | A:2 C:1 |

TABLE V-continued (Spatial distribution)

| Seq Id No. | Tissue distribution | Seq Id No. | Tissue distribution |
|---|---|---|---|
| 16354 | A:1 B:4 C:4 H:2 | 16400 | A:1 |
| 16355 | B:10 C:6 H:2 | 16401 | A:1 C:1 |
| 16356 | K:1 | 16402 | A:8 |
| 16357 | A:1 | 16403 | K:2 |
| 16358 | H:2 | 16404 | A:2 |
| 16359 | H:5 | 16405 | C:1 |
| 16360 | K:3 | 16406 | C:1 |
| 16361 | B:1 C:1 | 16407 | B:1 |
| 16362 | C:1 | 16408 | B:1 |
| 16363 | A:2 | 16409 | B:1 |
| 16364 | B:2 | 16410 | D:1 H:2 I:6 |
| 16365 | A:2 | 16411 | B:2 D:1 H:1 J:346 |
| 16366 | F:1 | 16412 | J:17 |
| 16367 | K:2 | 16413 | H:1 |
| 16368 | B:10 C:7 | 16414 | C:1 |
| 16369 | D:1 H:1 | 16415 | J:1 |
| 16370 | F:2 K:1 | 16416 | J:1 |
| 16371 | H:2 | 16417 | J:1 |
| 16372 | C:10 D:2 F:1 H:1 K:1 | 16418 | J:1 |
| 16373 | C:1 | 16419 | C:1 |
| 16374 | C:5 | 16420 | J:1 |
| 16375 | H:1 | 16421 | J:1 |
| 16376 | F:7 | 16422 | A:2 |
| 16377 | K:1 | 16423 | H:3 |
| 16378 | H:4 | 16424 | C:1 |
| 16379 | H:2 | 16425 | F:1 K:1 |
| 16380 | K:2 | 16426 | F:1 |
| 16381 | C:1 | 16427 | F:1 K:1 |
| 16382 | F:10 K:5 | 16428 | F:1 |
| 16383 | A:3 | 16429 | F:1 |
| 16384 | F:2 | 16430 | F:1 |
| 16385 | K:4 | 16431 | F:1 |
| 16386 | A:4 | 16432 | F:1 |
| 16387 | H:2 | 16433 | K:1 |
| 16388 | K:2 | 16434 | F:1 |
| 16389 | C:8 | 16435 | F:1 |
| 16390 | A:2 | 16436 | K:6 |
| 16391 | K:1 | 16437 | K:1 |
| 16392 | C:1 | 16438 | K:1 |
| 16393 | A:16 B:13 C:44 | 16439 | C:3 D:2 F:1 |
| 16394 | B:1 | 16440 | H:1 |
| 16395 | A:5 | 16441 | A:1 |
| 16396 | A:15 B:14 C:17 D:9 H:6 I:1 J:4 K:2 | 16442 | H:1 |
| 16444 | K:2 | 16443 | F:1 K:3 |
| 16445 | B:4 | 16491 | F:1 |
| 16446 | A:3 | 16492 | F:1 |
| 16447 | H:2 | 16493 | B:1 |
| 16448 | A:1 C:3 I:1 | 16494 | F:1 |
| 16449 | B:6 D:1 H:1 | 16495 | F:1 |
| 16450 | A:1 | 16496 | F:1 |
| 16451 | J:2 | 16497 | F:3 K:29 |
| 16452 | B:2 C:6 J:1 | 16498 | K:4 |
| 16453 | C:8 J:1 | 16499 | K:1 |
| 16454 | D:1 | 16500 | K:1 |
| 16455 | C:1 | 16501 | K:1 |
| 16456 | A:1 | 16502 | F:2 |
| 16457 | C:1 | 16503 | B:6 C:1 |
| 16458 | K:1 | 16504 | B:1 |
| 16459 | F:1 K:1 | 16505 | H:1 |
| 16460 | F:2 K:3 | 16506 | B:1 H:1 |
| 16461 | A:6 K:1 | 16507 | K:3 |
| 16462 | B:2 C:2 | 16508 | A:4 |
| 16463 | A:1 B:1 | 16509 | H:1 |
| 16464 | K:1 | 16510 | D:1 |
| 16465 | F:1 | 16511 | A:8 |
| 16466 | A:2 | 16512 | C:1 |
| 16467 | A:2 | 16513 | A:2 |
| 16468 | I:1 | 16514 | K:1 |
| 16469 | I:1 | 16515 | K:1 |
| 16470 | B:1 H:1 | 16516 | K:1 |
| 16471 | A:11 B:3 C:7 D:1 I:2 | 16517 | A:3 |
| 16472 | B:1 | 16518 | I:3 |
|  |  | 16519 | F:1 K:2 |
| 16473 | C:3 | 16520 | K:1 |
| 16474 | B:1 F:1 | 16521 | C:3 |
| 16475 | A:1 | 16522 | C:1 |
| 16476 | B:1 | 16523 | F:1 K:1 |
| 16477 | B:5 C:96 | 16524 | H:1 |
| 16478 | C:1 | 16525 | K:4 |
| 16479 | C:1 | 16526 | F:1 K:4 |
| 16480 | C:1 | 16527 | K:1 |
| 16481 | C:1 | 16528 | A:1 |
| 16482 | C:1 | 16529 | K:7 |
| 16483 | C:1 | 16530 | A:1 |
| 16484 | K:2 | 16531 | A:1 |
| 16485 | C:1 | 16532 | K:1 |
| 16486 | C:1 | 16533 | K:1 |
| 16487 | C:1 | 16534 | F:2 K:1 |
| 16488 | A:3 B:1 C:7 F:6 H:2 K:8 | 16535 | F:1 |
| 16489 | F:1 | 16536 | F:1 |
| 16490 | A:1 | 16537 | F:1 |
| 16538 | F:1 | 16585 | C:3 |
| 16539 | F:1 | 16586 | H:2 K:1 |
| 16540 | F:1 | 16587 | K:1 |
| 16541 | F:1 | 16588 | K:1 |
| 16542 | F:1 | 16589 | F:4 K:1 |
| 16543 | F:1 | 16590 | H:2 |
| 16544 | F:1 | 16591 | F:3 K:1 |
| 16545 | F:1 | 16592 | A:1 B:1 |
| 16546 | F:1 | 16593 | B:2 |
| 16547 | F:1 | 16594 | H:1 |
| 16548 | K:1 | 16595 | B:3 |
| 16549 | C:1 | 16596 | H:2 |
| 16550 | K:1 | 16597 | F:4 K:23 |
| 16551 | K:1 | 16598 | F:1 K:5 |
| 16552 | K:1 | 16599 | A:5 B:2 |
| 16553 | K:1 | 16600 | H:2 |
| 16554 | A:3 | 16601 | H:2 |
| 16555 | K:1 | 16602 | H:3 |
| 16556 | K:1 | 16603 | F:11 K:2 |
| 16557 | K:1 | 16604 | F:1 K:1 |
| 16558 | K:1 | 16605 | B:4 H:1 |
| 16559 | K:1 | 16606 | K:1 |
| 16560 | H:2 | 16607 | C:1 |
| 16561 | A:1 B:2 | 16608 | D:1 |
| 16562 | K:1 | 16609 | I:1 |
| 16563 | B:1 K:1 | 16610 | K:1 |
| 16564 | B:2 | 16611 | K:1 |
| 16565 | A:2 B:2 | 16612 | H:2 |
| 16566 | H:2 | 16613 | F:2 |
| 16567 | A:3 | 16614 | B:1 K:1 |
| 16568 | D:2 | 16615 | B:1 F:3 K:1 |
| 16569 | H:1 | 16616 | H:2 |
| 16570 | C:1 | 16617 | H:2 |
| 16571 | C:4 | 16618 | F:9 K:3 |
| 16572 | K:2 | 16619 | A:1 |
| 16573 | C:2 | 16620 | D:1 |
| 16574 | A:4 B:3 I:1 | 16621 | K:2 |
| 16575 | A:1 | 16622 | C:5 |
| 16576 | B:4 | 16623 | C:2 |
| 16577 | B:4 | 16624 | A:2 |
| 16578 | B:1 | 16625 | F:1 K:3 |
| 16579 | B:2 | 16626 | F:1 K:1 |
| 16580 | K:2 | 16627 | A:10 |
| 16581 | F:1 | 16628 | H:5 |
| 16582 | C:5 | 16629 | H:1 |
| 16583 | A:4 | 16630 | K:1 |
| 16584 | H:1 | 16631 | K:1 |
| 16632 | B:1 | 16679 | C:7 |
| 16633 | F:2 K:1 | 16680 | B:1 |
| 16634 | A:7 | 16681 | K:7 |
| 16635 | H:2 | 16682 | F:1 K:3 |
| 16636 | B:1 | 16683 | F:11 K:2 |
| 16637 | F:3 | 16684 | F:27 K:2 |
| 16638 | A:2 | 16685 | F:1 |
| 16639 | B:2 | 16686 | F:1 |

TABLE V-continued (Spatial distribution)

| Seq Id No. | Tissue distribution | Seq Id No. | Tissue distribution |
|---|---|---|---|
| 16640 | A:2 | 16687 | F:1 |
| 16641 | F:1 K:1 | 16688 | F:1 |
| 16642 | F:2 | 16689 | F:1 |
| 16643 | B:1 C:9 | 16690 | F:1 |
| 16644 | F:4 K:1 | 16691 | F:1 |
| 16645 | F:2 | 16692 | K:1 |
| 16646 | K:1 | 16693 | K:1 |
| 16647 | H:1 | 16694 | K:1 |
| 16648 | C:2 | 16695 | F:1 |
| 16649 | F:1 | 16696 | F:1 |
| 16650 | F:1 | 16697 | I:2 |
| 16651 | F:3 | 16698 | F:1 K:3 |
| 16652 | K:3 | 16699 | K:2 |
| 16653 | F:3 K:7 | 16700 | F:1 K:6 |
| 16654 | A:5 | 16701 | A:2 |
| 16655 | B:2 | 16702 | F:11 |
| 16656 | K:2 | 16703 | K:2 |
| 16657 | A:5 B:19 C:13 D:6 F:1 H:1 J:2 | 16704 | A:4 |
| 16658 | C:1 | 16705 | H:1 |
| 16659 | F:1 K:2 | 16706 | H:1 |
| 16660 | F:4 | 16707 | K:1 |
| 16661 | C:4 | 16708 | C:1 |
| 16662 | I:2 | 16709 | A:2 F:8 K:5 |
| 16663 | H:1 I:2 | 16710 | H:1 |
| 16664 | I:1 | 16711 | H:1 |
| 16665 | A:1 I:2 | 16712 | K:1 |
| 16666 | A:1 | 16713 | C:1 |
| 16667 | C:6 | 16714 | H:1 |
| 16668 | B:2 | 16715 | A:4 |
| 16669 | B:1 | 16716 | F:2 K:1 |
| 16670 | F:1 K:5 | 16717 | B:2 |
| 16671 | F:1 K:6 | 16718 | A:8 |
| 16672 | K:1 | 16719 | H:1 |
| 16673 | K:1 | 16720 | D:1 |
| 16674 | H:11 | 16721 | F:1 |
| 16675 | B:1 K:1 | 16722 | F:3 K:11 |
| 16676 | F:1 K:1 | 16723 | K:2 |
| 16677 | B:1 | 16724 | K:1 |
| 16678 | B:1 | 16725 | K:1 |
| 16819 | H:1 | 16866 | I:3 |
| 16820 | C:4 | 16867 | F:31 K:9 |
| 16821 | B:2 | 16868 | F:2 |
| 16822 | B:5 | 16869 | F:1 |
| 16823 | H:2 | 16870 | F:1 |
| 16824 | A:2 B:1 F:1 H:2 K:2 | 16871 | K:1 |
| 16825 | F:1 | 16872 | F:1 |
| 16826 | F:1 H:1 | 16873 | K:1 |
| 16827 | H:1 | 16874 | K:2 |
| 16828 | K:2 | 16875 | K:2 |
| 16829 | A:1 | 16876 | K:2 |
| 16830 | B:2 | 16877 | F:2 |
| 16831 | K:1 | 16878 | F:11 K:51 |
| 16832 | K:1 | 16879 | K:1 |
| 16833 | K:1 | 16880 | A:1 C:5 H:2 K:1 |
| 16834 | K:1 | 16881 | H:1 K:1 |
| 16835 | K:1 | 16882 | H:4 |
| 16836 | H:1 | 16883 | K:2 |
| 16837 | F:1 | 16884 | C:4 J:2 |
| 16838 | B:3 | 16885 | F:1 K:2 |
| 16839 | F:1 K:8 | 16886 | A:3 |
| 16840 | K:3 | 16887 | A:21 |
| 16841 | B:3 | 16888 | D:1 H:1 |
| 16842 | K:1 | 16889 | K:2 |
| 16843 | C:1 | 16890 | A:1 B:1 D:1 H:2 |
| 16844 | A:2 | 16891 | F:2 K:2 |
| 16845 | F:2 K:3 | 16892 | H:2 |
| 16846 | H:3 | 16893 | A:1 |
| 16847 | A:4 | 16894 | A:2 |
| 16848 | K:2 | 16895 | H:2 |
| 16849 | H:5 | 16896 | K:4 |
| 16850 | F:1 K:1 | 16897 | C:1 |
| 16851 | A:1 I:1 | 16898 | K:5 |
| 16852 | K:1 | 16899 | A:6 |
| 16853 | B:4 C:3 H:2 | 16900 | A:2 |
| 16854 | A:1 | 16901 | C:1 H:4 |
| 16855 | B:2 | 16902 | K:3 |
| 16856 | A:2 | 16903 | F:1 |
| 16857 | B:2 | 16904 | C:4 |
| 16858 | K:1 | 16905 | J:49 |
| 16859 | C:6 | 16906 | I:2 |
| 16860 | A:3 | 16907 | C:1 |
| 16861 | A:2 | 16908 | B:3 |
| 16862 | H:1 | 16909 | B:3 |
| 16863 | K:2 | 16910 | F:4 |
| 16864 | F:1 I:1 | 16911 | H:2 |
| 16865 | C:38 | 16912 | K:2 |
| 16913 | K:2 | 16960 | C:1 |
| 16914 | H:2 | 16961 | C:1 |
| 16915 | F:4 | 16962 | C:1 |
| 16916 | A:6 | 16963 | C:1 |
| 16917 | F:9 K:2 | 16964 | C:1 |
| 16918 | B:1 | 16965 | D:1 |
| 16919 | H:2 | 16966 | C:1 |
| 16920 | A:2 | 16967 | C:1 |
| 16921 | K:1 | 16968 | C:1 |
| 16922 | A:1 | 16969 | C:1 |
| 16923 | C:1 | 16970 | C:1 |
| 16924 | F:3 | 16971 | C:1 |
| 16925 | B:1 C:10 | 16972 | C:1 |
| 16926 | C:1 | 16973 | C:1 |
| 16927 | C:1 | 16974 | C:1 |
| 16928 | C:1 | 16975 | C:1 |
| 16929 | B:1 | 16976 | C:1 |
| 16930 | A:1 | 16977 | C:1 |
| 16931 | B:1 | 16978 | C:1 |
| 16932 | C:1 | 16979 | C:1 |
| 16933 | F:1 | 16980 | C:1 |
| 16934 | C:1 | 16981 | C:1 |
| 16935 | C:1 | 16982 | C:1 |
| 16936 | C:1 | 16983 | D:1 |
| 16937 | B:1 | 16984 | C:1 |
| 16938 | C:1 | 16985 | B:1 |
| 16939 | C:1 | 16986 | C:1 |
| 16940 | C:1 | 16987 | C:1 |
| 16941 | C:1 | 16988 | C:1 |
| 16942 | C:1 | 16989 | H:1 |
| 16943 | C:1 | 16990 | C:1 |
| 16944 | C:1 | 16991 | C:1 |
| 16945 | C:1 | 16992 | J:1 |
| 16946 | C:1 | 16993 | C:1 |
| 16947 | K:3 | 16994 | C:1 |
| 16948 | A:1 C:1 | 16995 | C:1 |
| 16949 | C:1 | 16996 | C:1 |
| 16950 | C:1 | 16997 | C:1 |
| 16951 | C:1 | 16998 | C:1 |
| 16952 | C:1 | 16999 | C:1 |
| 16953 | J:1 | 17000 | H:4 |
| 16954 | C:1 | 17001 | C:1 |
| 16955 | C:1 | 17002 | C:1 |
| 16956 | C:1 | 17003 | C:1 |
| 16957 | B:1 | 17004 | B:1 |
| 16958 | C:1 | 17005 | C:1 |
| 16959 | B:1 C:1 H:19 J:3 | 17006 | C:1 |
| 17007 | C:1 | 17054 | K:1 |
| 17008 | C:1 | 17055 | B:1 |
| 17009 | C:1 | 17056 | J:1 |
| 17010 | C:1 | 17057 | B:1 |
| 17011 | H:4 | 17058 | C:1 |
| 17012 | B:1 | 17059 | C:1 |
| 17013 | H:1 | 17060 | C:1 |
| 17014 | C:1 | 17061 | C:1 |
| 17015 | C:1 | 17062 | C:1 |
| 17016 | C:1 | 17063 | C:1 |
| 17017 | C:1 | 17064 | C:1 |
| 17018 | B:1 | 17065 | B:4 C:1 |

TABLE V-continued

(Spatial distribution)

| Seq Id No. | Tissue distribution | Seq Id No. | Tissue distribution |
|---|---|---|---|
| 17019 | C:1 | 17066 | C:1 |
| 17020 | B:1 | 17067 | D:1 |
| 17021 | C:1 | 17068 | C:1 |
| 17022 | C:1 | 17069 | C:1 |
| 17023 | C:1 | 17070 | C:1 |
| 17024 | C:1 | 17071 | D:1 |
| 17025 | B:1 | 17072 | C:1 |
| 17026 | C:1 | 17073 | C:1 |
| 17027 | C:1 | 17074 | C:1 |
| 17028 | C:1 | 17075 | C:1 |
| 17029 | C:1 | 17076 | C:3 |
| 17030 | C:1 | 17077 | C:1 |
| 17031 | C:1 | 17078 | C:1 |
| 17032 | K:2 | 17079 | C:1 |
| 17033 | C:1 | 17080 | C:1 |
| 17034 | C:1 | 17081 | C:1 |
| 17035 | C:1 | 17082 | C:1 |
| 17036 | C:1 | 17083 | C:1 |
| 17037 | C:1 | 17084 | K:2 |
| 17038 | C:1 | 17085 | B:4 |
| 17039 | B:1 | 17086 | F:4 |
| 17040 | C:1 | 17087 | A:2 |
| 17041 | C:1 | 17088 | A:1 |
| 17042 | C:1 | 17089 | A:2 |
| 17043 | A:2 | 17090 | K:1 |
| 17044 | C:1 | 17091 | A:3 C:1 F:1 I:1 |
| 17045 | C:1 | 17092 | K:2 |
| 17046 | C:1 | 17093 | K:2 |
| 17047 | C:1 | 17094 | B:3 |
| 17048 | C:1 | 17095 | F:1 |
| 17049 | H:1 | 17096 | F:1 |
| 17050 | B:1 | 17097 | F:1 |
| 17051 | J:1 | 17098 | F:5 K:1 |
| 17052 | C:1 | 17099 | C:2 |
| 17053 | C:1 | 17100 | B:1 D:1 H:1 |
| 17101 | H:11 | 17148 | C:1 |
| 17102 | A:7 | 17149 | C:1 |
| 17103 | H:1 | 17150 | K:4 |
| 17104 | K:1 | 17151 | C:1 |
| 17105 | K:2 | 17152 | A:15 |
| 17106 | H:2 | 17153 | B:2 |
| 17107 | K:2 | 17154 | C:4 F:1 |
| 17108 | F:2 | 17155 | K:2 |
| 17109 | C:1 | 17156 | C:3 |
| 17110 | F:3 K:1 | 17157 | F:2 K:1 |
| 17111 | H:1 | 17158 | B:2 |
| 17112 | A:2 | 17159 | K:1 |
| 17113 | K:2 | 17160 | K:1 |
| 17114 | A:1 | 17161 | H:2 |
| 17115 | A:1 | 17162 | F:2 K:3 |
| 17116 | K:1 | 17163 | K:3 |
| 17117 | H:9 | 17164 | I:4 |
| 17118 | C:9 | 17165 | C:1 |
| 17119 | B:1 H:1 | 17166 | F:6 K:17 |
| 17120 | C:1 | 17167 | F:7 K:30 |
| 17121 | C:2 | 17168 | K:1 |
| 17122 | F:1 K:1 | 17169 | K:1 |
| 17123 | C:13 | 17170 | F:6 K:13 |
| 17124 | A:1 | 17171 | F:1 K:8 |
| 17125 | F:1 K:4 | 17172 | K:1 |
| 17126 | K:1 | 17173 | K:1 |
| 17127 | K:3 | 17171 | F:2 |
| 17128 | K:2 | 17175 | F:2 |
| 17129 | A:7 | 17176 | C:8 H:1 |
| 17130 | F:3 K:1 | 17177 | K:2 |
| 17131 | I:2 K:1 | 17178 | F:42 K:13 |
| 17132 | A:2 | 17179 | F:1 K:1 |
| 17133 | C:11 | 17180 | K:2 |
| 17134 | F:2 K:1 | 17181 | B:2 |
| 17135 | A:2 | 17182 | K:1 |
| 17136 | F:1 | 17183 | K:1 |
| 17137 | K:3 | 17184 | K:1 |
| 17138 | K:2 | 17185 | K:1 |
| 17139 | C:6 J:1 | 17186 | K:1 |
| 17140 | K:1 | 17187 | K:1 |
| 17141 | K:3 | 17188 | K:1 |
| 17142 | K:1 | 17189 | K:2 |
| 17143 | C:67 | 17190 | H:2 |
| 17144 | C:1 | 17191 | K:2 |
| 17145 | C:1 | 17192 | K:3 |
| 17146 | C:1 | 17193 | F:2 K:7 |
| 17147 | C:1 | 17194 | F:1 K:8 |
| 17195 | C:8 | 17242 | I:2 |
| 17196 | B:2 | 17243 | K:2 |
| 17197 | F:7 K:17 | 17244 | B:2 |
| 17198 | F:32 K:6 | 17245 | A:1 D:1 F:1 H:1 I:1 |
| 17199 | C:1 | 17246 | K:1 |
| 17200 | B:1 | 17247 | B:2 |
| 17201 | F:16 K:3 | 17248 | B:1 H:1 |
| 17202 | H:1 | 17249 | K:3 |
| 17203 | A:2 | 17250 | H:2 |
| 17204 | A:3 | 17251 | F:3 K:1 |
| 17205 | C:5 | 17252 | C:1 |
| 17206 | C:15 | 17253 | C:4 |
| 17207 | K:2 | 17254 | H:1 K:1 |
| 17208 | F:1 K:1 | 17255 | B:3 |
| 17209 | F:1 | 17256 | A:1 H:1 |
| 17210 | I:1 | 17257 | F:1 H:2 K:1 |
| 17211 | B:3 | 17258 | C:1 F:1 H:2 |
| 17212 | F:1 K:1 | 17259 | B:2 |
| 17213 | F:1 | 17260 | F:2 |
| 17214 | I:1 | 17261 | A:1 |
| 17215 | H:2 | 17262 | F:1 K:1 |
| 17216 | K:2 | 17263 | F:1 K:3 |
| 17217 | A:1 D:1 | 17264 | H:5 |
| 17218 | C:3 | 17265 | A:2 |
| 17219 | C:8 | 17266 | C:2 J:29 |
| 17220 | C:8 J:1 | 17267 | K:9 |
| 17221 | A:1 B:4 C:1 | 17268 | C:3 F:6 K:49 |
| 17222 | A:1 B:3 C:1 D:1 | 17269 | C:3 F:12 K:112 |
| 17223 | H:1 | 17270 | H:3 K:3 |
| 17224 | F:19 K:9 | 17271 | K:1 |
| 17225 | F:1 K:1 | 17272 | H:1 |
| 17226 | F:1 K:2 | 17273 | B:1 |
| 17227 | F:19 | 17274 | K:2 |
| 17228 | C:2 | 17275 | B:2 |
| 17229 | B:1 | 17276 | I:1 |
| 17230 | K:2 | 17277 | H:1 |
| 17231 | C:18 | 17278 | F:1 K:2 |
| 17232 | D:1 | 17279 | F:2 |
| 17233 | D:1 | 17280 | A:2 C:5 |
| 17234 | C:1 | 17281 | B:3 |
| 17235 | C:1 | 17282 | K:2 |
| 17236 | H:2 | 17283 | H:1 K:1 |
| 17237 | F:3 K:2 | 17284 | K:4 |
| 17238 | A:1 H:1 I:2 K:1 | 17285 | H:1 |
| 17239 | H:2 | 17286 | C:1 |
| 17240 | F:2 | 17287 | B:1 C:1 |
| 17241 | K:2 | 17288 | B:2 |
| 17289 | B:3 | 17336 | K:1 |
| 17290 | F:1 K:1 | 17337 | H:3 |
| 17291 | K:1 | 17338 | D:2 |
| 17292 | K:1 | 17339 | K:2 |
| 17293 | A:3 | 17340 | F:10 K:4 |
| 17294 | C:1 | 17341 | K:2 |
| 17295 | B:1 | 17342 | A:1 B:1 |
| 17296 | B:1 | 17343 | F:12 K:5 |
| 17297 | B:1 | 17344 | F:1 |
| 17298 | A:3 | 17345 | B:2 |
| 17299 | H:1 | 17346 | H:1 |
| 17300 | A:11 B:5 C:1 D:1 H:2 I:1 | 17347 | C:2 D:1 |
| 17301 | A:4 B:3 | 17348 | A:3 C:1 |
| 17302 | K:2 | 17349 | A:5 B:1 K:1 |
| 17303 | K:1 | 17350 | C:36 |
| 17304 | B:2 | 17351 | C:99 |
| 17305 | B:2 | 17352 | B:4 |

TABLE V-continued (Spatial distribution)

| Seq Id No. | Tissue distribution | Seq Id No. | Tissue distribution |
|---|---|---|---|
| 17306 | K:2 | 17353 | K:2 |
| 17307 | K:2 | 17354 | F:6 |
| 17308 | A:13 | 17355 | H:2 |
| 17309 | K:2 | 17356 | C:1 F:8 |
| 17310 | H:1 | 17357 | F:12 K:3 |
| 17311 | H:1 | 17358 | B:2 |
| 17312 | H:1 | 17359 | F:1 K:4 |
| 17313 | H:1 | 17360 | H:3 |
| 17314 | F:3 | 17361 | K:2 |
| 17315 | F:1 H:1 | 17362 | K:1 |
| 17316 | F:1 K:11 | 17363 | A:3 |
| 17317 | F:4 K:2 | 17364 | F:2 K:2 |
| 17318 | H:21 | 17365 | F:1 K:2 |
| 17319 | B:4 | 17366 | C:1 |
| 17320 | F:2 | 17367 | A:3 |
| 17321 | H:2 | 17368 | A:1 B:2 |
| 17322 | H:2 | 17369 | A:1 B:3 D:1 |
| 17323 | H:1 | 17370 | A:5 |
| 17324 | B:2 | 17371 | H:1 |
| 17325 | B:4 | 17372 | A:1 |
| 17326 | K:2 | 17373 | F:2 |
| 17327 | B:2 | 17374 | K:2 |
| 17328 | K:3 | 17375 | B:6 |
| 17329 | B:3 | 17376 | F:1 K:2 |
| 17330 | A:1 H:38 K:1 | 17377 | K:2 |
| 17331 | A:2 | 17378 | F:1 |
| 17332 | F:2 K:1 | 17379 | K:1 |
| 17333 | B:3 C:1 | 17380 | B:1 |
| 17334 | K:2 | 17381 | B:1 C:10 |
| 17335 | K:1 | 17382 | D:1 |
| 17383 | C:38 | 17430 | B:3 |
| 17384 | C:1 | 17431 | B:3 |
| 17385 | H:1 | 17432 | H:3 |
| 17386 | K:2 | 17433 | A:3 |
| 17387 | F:1 | 17434 | H:3 |
| 17388 | H:6 | 17435 | I:2 |
| 17389 | C:6 | 17436 | A:1 |
| 17390 | B:2 | 17437 | A:2 B:1 |
| 17391 | A:3 B:7 C:59 D:1 F:3 H:5 J:6 K:7 | 17438 | F:1 K:1 |
| 17392 | B:3 C:1 | 17439 | C:1 |
| 17393 | A:1 | 17440 | B:3 |
| 17394 | H:2 | 17441 | A:1 C:1 |
| 17395 | H:1 | 17442 | B:1 C:1 H:4 |
| 17396 | H:3 | 17443 | H:2 |
| 17397 | B:2 | 17444 | I:1 |
| 17398 | B:3 | 17445 | B:5 |
| 17399 | C:21 | 17446 | H:1 |
| 17400 | F:4 | 17447 | H:1 |
| 17401 | F:4 K:1 | 17448 | H:1 |
| 17402 | A:3 H:4 | 17449 | H:1 |
| 17403 | F:1 K:2 | 17450 | H:1 |
| 17404 | B:5 | 17451 | H:1 |
| 17405 | H:3 | 17452 | H:1 |
| 17406 | H:1 | 17453 | H:1 |
| 17407 | A:6 | 17454 | H:1 |
| 17408 | F:3 K:1 | 17455 | H:1 |
| 17409 | B:2 | 17456 | K:2 |
| 17410 | B:1 I:1 | 17457 | F:1 |
| 17411 | H:2 I:1 | 17458 | F:5 K:2 |
| 17412 | C:59 | 17459 | A:1 C:1 F:7 K:1 |
| 17413 | C:1 | 17460 | A:1 C:1 F:5 K:2 |
| 17414 | C:1 | 17461 | K:2 |
| 17415 | C:1 | 17462 | H:4 |
| 17416 | C:1 | 17463 | K:5 |
| 17417 | C:1 | 17464 | A:15 |
| 17418 | C:1 | 17465 | A:1 |
| 17419 | C:1 | 17466 | A:1 |
| 17420 | C:1 | 17467 | F:1 |
| 17421 | C:1 | 17468 | C:3 |
| 17422 | C:1 | 17469 | A:1 C:1 |
| 17423 | C:1 | 17470 | D:1 |
| 17424 | B:3 | 17471 | K:2 |
| 17425 | K:2 | 17472 | K:2 |
| 17426 | B:2 | 17473 | B:4 |
| 17427 | A:2 | 17474 | F:1 K:1 |
| 17428 | C:3 | 17475 | K:1 |
| 17429 | A:4 | 17476 | B:3 |
| 17477 | F:23 K:4 | 17524 | A:1 D:1 |
| 17478 | K:1 | 17525 | K:2 |
| 17479 | K:4 | 17526 | F:1 K:2 |
| 17480 | F:1 | 17527 | F:1 |
| 17481 | B:4 D:1 H:1 | 17528 | F:2 |
| 17482 | B:1 H:1 K:1 | 17529 | K:3 |
| 17483 | B:1 | 17530 | B:7 C:91 |
| 17484 | H:7 | 17531 | A:2 |
| 17485 | K:1 | 17532 | B:3 |
| 17486 | F:1 | 17533 | H:17 |
| 17487 | B:2 | 17534 | K:2 |
| 17488 | F:7 K:31 | 17535 | I:2 |
| 17489 | C:3 | 17536 | A:2 |
| 17490 | D:1 | 17537 | A:3 B:1 C:1 |
| 17491 | F:1 | 17538 | A:4 |
| 17492 | H:1 K:1 | 17539 | A:3 |
| 17493 | H:1 | 17540 | B:2 |
| 17494 | K:1 | 17541 | F:13 K:77 |
| 17495 | K:1 | 17542 | F:2 |
| 17496 | A:7 | 17543 | F:2 K:1 |
| 17497 | K:1 | 17544 | H:3 |
| 17498 | H:2 | 17545 | A:1 H:1 |
| 17499 | A:1 | 17546 | F:10 K:1 |
| 17500 | F:1 K:1 | 17547 | K:1 |
| 17501 | K:1 | 17548 | K:1 |
| 17502 | F:1 | 17549 | C:2 |
| 17503 | F:1 | 17550 | F:2 K:1 |
| 17504 | A:2 | 17551 | H:2 |
| 17505 | D:2 | 17552 | A:1 B:1 |
| 17506 | F:11 K:2 | 17553 | H:3 |
| 17507 | F:1 K:7 | 17554 | K:1 |
| 17508 | H:4 | 17555 | H:2 |
| 17509 | K:2 | 17556 | D:1 |
| 17510 | K:1 | 17557 | A:1 |
| 17511 | F:2 K:1 | 17558 | H:1 |
| 17512 | F:5 K:1 | 17559 | H:1 |
| 17513 | K:3 | 17560 | K:11 |
| 17514 | F:2 | 17561 | A:5 |
| 17515 | B:3 C:1 | 17562 | F:1 K:2 |
| 17516 | C:1 | 17563 | D:3 |
| 17517 | H:3 | 17564 | F:2 K:1 |
| 17518 | H:2 | 17565 | A:44 |
| 17519 | K:2 | 17566 | H:1 |
| 17520 | H:1 | 17567 | F:1 K:1 |
| 17521 | F:10 K:11 | 17568 | K:2 |
| 17522 | F:11 K:10 | 17569 | A:2 B:1 |
| 17523 | A:2 | 17570 | F:2 K:1 |
| 17571 | A:3 B:6 C:2 D:2 | 17618 | H:2 |
| 17572 | B:79 C:62 D:2 H:25 I:2 J:4 K:2 | 17619 | H:7 |
| 17573 | H:1 | 17620 | B:2 |
| 17574 | H:1 K:6 | 17621 | K:6 |
| 17575 | B:4 | 17622 | E:1 |
| 17576 | K:3 | 17623 | F:1 |
| 17577 | F:2 K:6 | 17624 | K:1 |
| 17578 | C:4 | 17625 | K:1 |
| 17579 | A:1 B:1 C:5 | 17626 | K:1 |
| 17580 | A:7 B:22 C:34 D:3 H:10 J:1 K:1 | 17627 | K:2 |
| 17581 | K:3 | 17628 | B:1 H:2 |
| 17582 | H:2 | 17629 | H:1 |
| 17583 | C:1 | 17630 | K:1 |
| 17584 | D:1 | 17631 | K:1 |
| 17585 | B:1 | 17632 | H:6 |
| 17586 | B:2 | 17633 | C:15 |
| 17587 | B:2 | 17634 | K:2 |
| 17588 | F:3 | 17635 | A:1 |
| 17589 | K:1 | 17636 | F:1 K:1 |

TABLE V-continued
(Spatial distribution)

| Seq Id No. | Tissue distribution | Seq Id No. | Tissue distribution |
|---|---|---|---|
| 17590 | H:1 | 17637 | B:1 |
| 17591 | H:3 | 17638 | F:4 K:25 |
| 17592 | A:5 | 17639 | F:1 K:6 |
| 17593 | C:1 D:1 | 17640 | F:2 K:22 |
| 17594 | H:1 | 17641 | B:1 C:1 |
| 17595 | A:4 | 17642 | F:1 K:1 |
| 17596 | A:3 B:1 K:2 | 17643 | A:7 |
| 17597 | F:1 K:1 | 17644 | C:263 |
| 17598 | H:1 | 17645 | C:1 |
| 17599 | B:2 | 17646 | I:4 |
| 17600 | B:4 | 17647 | D:1 |
| 17601 | H:2 | 17648 | A:1 |
| 17602 | F:5 K:1 | 17649 | A:14 |
| 17603 | A:8 | 17650 | A:4 B:1 |
| 17604 | K:3 | 17651 | C:10 D:1 H:1 I:2 J:5 |
| 17605 | C:4 | 17652 | F:3 K:42 |
| 17606 | F:1 K:1 | 17653 | K:2 |
| 17607 | F:1 | 17654 | F:1 |
| 17608 | A:1 | 17655 | K:1 |
| 17609 | A:1 | 17656 | A:11 |
| 17610 | A:1 | 17657 | C:8 J:1 |
| 17611 | C:1 | 17658 | C:6 |
| 17612 | C:1 | 17659 | H:2 |
| 17613 | B:1 C:1 | 17660 | F:3 |
| 17614 | K:2 | 17661 | A:1 K:1 |
| 17615 | H:2 | 17662 | A:2 |
| 17616 | B:5 | 17663 | K:1 |
| 17617 | C:10 | 17664 | K:1 |
| 17665 | F:3 | 17712 | F:20 K:5 |
| 17666 | F:1 K:1 | 17713 | B:1 |
| 17667 | K:2 | 17714 | B:2 |
| 17668 | C:2 | 17715 | A:1 I:4 K:2 |
| 17669 | C:3 | 17716 | A:1 F:1 I:4 K:1 |
| 17670 | C:1 | 17717 | A:1 B:21 C:45 D:3 E:1 F:4 H:4 I:4 J:7 K:16 |
| 17671 | A:3 | | |
| 17672 | H:1 | 17718 | H:1 |
| 17673 | F:2 K:12 | 17719 | A:1 B:1 C:1 K:1 |
| 17674 | F:2 K:10 | 17720 | C:8 |
| 17675 | F:1 K:1 | 17721 | K:2 |
| 17676 | F:2 | 17722 | H:18 |
| 17677 | B:2 | 17723 | B:1 H:1 |
| 17678 | B:6 | 17724 | B:3 |
| 17679 | F:7 K:2 | 17725 | K:3 |
| 17680 | F:1 K:2 | 17726 | F:7 |
| 17681 | K:5 | 17727 | K:1 |
| 17682 | K:5 | 17728 | F:1 K:11 |
| 17683 | F:3 K:4 | 17729 | D:1 |
| 17684 | K:1 | 17730 | K:1 |
| 17685 | A:1 B:2 | 17731 | H:2 |
| 17686 | B:2 | 17732 | D:1 |
| 17687 | A:1 | 17733 | C:1 F:1 K:1 |
| 17688 | I:4 | 17734 | K:2 |
| 17689 | F:2 K:1 | 17735 | F:1 K:3 |
| 17690 | H:1 | 17736 | F:3 K:1 |
| 17691 | A:1 | 17737 | J:2 |
| 17692 | H:2 | 17738 | I:4 |
| 17693 | B:2 | 17739 | K:2 |
| 17694 | H:2 | 17740 | K:2 |
| 17695 | B:2 | 17741 | F:2 K:1 |
| 17696 | B:1 | 17742 | F:8 K:2 |
| 17697 | H:3 | 17743 | A:8 |
| 17698 | H:2 | 17744 | K:2 |
| 17699 | K:1 | 17745 | A:2 |
| 17700 | B:3 | 17746 | B:2 |
| 17701 | K:1 | 17747 | F:17 K:4 |
| 17702 | C:2 D:2 | 17748 | C:34 |
| 17703 | H:3 | 17749 | C:9 J:1 |
| 17704 | B:2 | 17750 | H:2 |
| 17705 | F:1 K:3 | 17751 | K:5 |
| 17706 | F:27 K:4 | 17752 | D:3 |
| 17707 | A:5 | 17753 | K:1 |
| 17708 | H:1 | 17754 | A:1 |
| 17709 | H:1 | 17755 | A:1 |
| 17710 | C:49 | 17756 | F:1 |
| 17711 | C:1 D:1 | 17757 | H:1 |
| 17758 | F:3 K:8 | 17805 | A:2 |
| 17759 | A:2 | 17806 | K:2 |
| 17760 | F:1 K:1 | 17807 | C:4 |
| 17761 | K:2 | 17808 | H:2 |
| 17762 | K:1 | 17809 | K:2 |
| 17763 | K:1 | 17810 | C:1 H:1 |
| 17764 | A:6 | 17811 | A:11 |
| 17765 | A:1 | 17812 | H:1 |
| 17766 | F:1 | 17813 | I:2 |
| 17767 | D:1 | 17814 | C:1 |
| 17768 | C:5 D:1 | 17815 | F:6 K:1 |
| 17769 | K:2 | 17816 | F:1 |
| 17770 | F:2 K:2 | 17817 | B:1 C:9 |
| 17771 | B:2 | 17818 | H:1 |
| 17772 | I:2 | 17819 | K:1 |
| 17773 | B:3 | 17820 | A:11 C:17 |
| 17774 | C:23 | 17821 | F:1 K:1 |
| 17775 | H:5 | 17822 | B:1 |
| 17776 | C:11 | 17823 | B:1 |
| 17777 | I:3 | 17824 | K:1 |
| 17778 | B:3 | 17825 | A:3 |
| 17779 | A:2 | 17826 | K:1 |
| 17780 | A:2 H:1 | 17827 | I:3 |
| 17781 | K:2 | 17828 | A:2 B:1 H:2 |
| 17782 | H:2 | 17829 | B:1 H:2 |
| 17783 | F:3 | 17830 | H:2 |
| 17784 | F:2 | 17831 | A:3 |
| 17785 | K:2 | 17832 | A:2 |
| 17786 | H:4 | 17833 | A:1 D:2 |
| 17787 | B:2 | 17834 | F:3 K:2 |
| 17788 | A:1 | 17835 | B:4 |
| 17789 | F:4 | 17836 | F:1 K:3 |
| 17790 | H:2 | 17837 | B:7 |
| 17791 | B:1 C:1 H:1 | 17838 | F:3 K:1 |
| 17792 | I:1 | 17839 | C:2 |
| 17793 | C:4 | 17840 | F:1 K:1 |
| 17794 | A:2 | 17841 | C:2 |
| 17795 | A:1 B:1 D:1 | 17842 | B:2 |
| 17796 | C:62 | 17843 | F:4 K:1 |
| 17797 | F:2 | 17844 | F:2 |
| 17798 | C:1 | 17845 | A:12 |
| 17799 | F:9 K:5 | 17846 | C:1 H:1 |
| 17800 | K:1 | 17847 | C:13 |
| 17801 | H:4 | 17848 | K:2 |
| 17802 | F:2 | 17849 | H:2 |
| 17803 | F:18 | 17850 | C:45 |
| 17804 | K:2 | 17851 | B:1 |
| 17852 | A:1 H:1 | 17899 | C:4 |
| 17853 | F:1 K:2 | 17900 | H:3 |
| 17854 | K:1 | 17901 | F:1 K:1 |
| 17855 | K:4 | 17902 | K:2 |
| 17856 | K:2 | 17903 | F:3 K:1 |
| 17857 | F:2 K:3 | 17904 | K:2 |
| 17858 | A:1 | 17905 | C:7 H:1 |
| 17859 | K:4 | 17906 | C:1 |
| 17860 | A:1 | 17907 | F:1 |
| 17861 | A:1 | 17908 | C:1 |
| 17862 | K:2 | 17909 | K:1 |
| 17863 | B:1 | 17910 | C:1 |
| 17864 | A:1 | 17911 | A:4 |
| 17865 | H:2 | 17912 | K:4 |
| 17866 | A:1 | 17913 | C:171 |
| 17867 | A:1 | 17914 | C:1 |
| 17868 | D:1 | 17915 | D:1 H:1 |
| 17869 | B:3 | 17916 | K:4 |
| 17870 | C:4 | 17917 | K:2 |
| 17871 | I:1 | 17918 | K:1 |
| 17872 | I:1 | 17919 | K:7 |
| 17873 | F:2 K:4 | 17920 | F:1 |
| 17874 | F:7 | 17921 | F:1 |
| 17875 | K:1 | 17922 | F:1 |

TABLE V-continued (Spatial distribution)

| Seq Id No. | Tissue distribution | Seq Id No. | Tissue distribution |
|---|---|---|---|
| 17876 | F:1 K:1 | 17923 | F:1 |
| 17877 | B:3 | 17924 | F:1 |
| 17878 | K:2 | 17925 | F:1 |
| 17879 | C:17 | 17926 | K:1 |
| 17880 | C:1 | 17927 | F:1 |
| 17881 | F:32 K:110 | 17928 | F:1 |
| 17882 | F:2 K:8 | 17929 | F:1 |
| 17883 | F:29 K:110 | 17930 | F:1 |
| 17884 | K:1 | 17931 | F:1 |
| 17885 | K:1 | 17932 | F:1 |
| 17886 | K:1 | 17933 | F:1 |
| 17887 | H:9 | 17934 | F:1 |
| 17888 | F:3 K:1 | 17935 | F:1 |
| 17889 | F:2 | 17936 | F:1 |
| 17890 | A:2 | 17937 | F:1 |
| 17891 | H:5 | 17938 | F:1 |
| 17892 | A:3 B:2 H:1 K:1 | 17939 | F:1 |
| 17893 | F:1 K:1 | 17940 | F:1 |
| 17894 | K:4 | 17941 | F:1 |
| 17895 | H:1 | 17942 | F:1 |
| 17896 | A:15 | 17943 | F:1 |
| 17897 | C:5 H:1 | 17944 | F:1 |
| 17898 | B:1 H:1 K:1 | 17945 | K:1 |
| 17946 | F:1 | 17993 | K:2 |
| 17947 | K:1 | 17994 | C:3 |
| 17948 | F:1 | 17995 | K:3 |
| 17949 | F:1 | 17996 | B:2 |
| 17950 | F:4 K:3 | 17997 | B:6 |
| 17951 | F:1 K:1 | 17998 | K:1 |
| 17952 | A:8 | 17999 | H:2 |
| 17953 | K:2 | 18000 | A:4 F:1 |
| 17954 | K:2 | 18001 | A:1 |
| 17955 | K:2 | 18002 | B:1 |
| 17956 | H:6 | 18003 | H:1 |
| 17957 | H:3 | 18004 | F:1 |
| 17958 | A:3 | 18005 | K:1 |
| 17959 | K:2 | 18006 | H:3 |
| 17960 | F:6 K:1 | 18007 | B:1 |
| 17961 | A:2 | 18008 | K:2 |
| 17962 | K:2 | 18009 | F:1 K:1 |
| 17963 | K:1 | 18010 | A:16 |
| 17964 | K:1 | 18011 | C:2 |
| 17965 | K:1 | 18012 | B:2 |
| 17966 | K:1 | 18013 | B:2 |
| 17967 | F:6 K:2 | 18014 | C:2 I:2 |
| 17968 | F:2 | 18015 | F:5 |
| 17969 | F:3 | 18016 | K:4 |
| 17970 | A:213 | 18017 | A:2 |
| 17971 | A:4 | 18018 | B:1 |
| 17972 | A:2 B:2 | 18019 | B:1 |
| 17973 | A:15 C:2 F:1 | 18020 | H:1 |
| 17974 | A:5 C:3 | 18021 | H:1 |
| 17975 | B:2 | 18022 | H:1 |
| 17976 | A:6 | 18023 | F:2 |
| 17977 | A:5 C:3 | 18024 | A:1 I:2 |
| 17978 | H:7 | 18025 | B:3 C:1 |
| 17979 | F:5 K:2 | 18026 | F:1 K:2 |
| 17980 | F:4 K:5 | 18027 | F:1 |
| 17981 | F:1 K:6 | 18028 | K:1 |
| 17982 | K:3 | 18029 | H:3 |
| 17983 | F:16 K:5 | 18030 | H:1 |
| 17984 | B:2 C:1 | 18031 | F:1 H:5 |
| 17985 | K:3 | 18032 | C:2 H:1 |
| 17986 | C:3 | 18033 | F:1 K:1 |
| 17987 | K:2 | 18034 | K:2 |
| 17988 | A:13 | 18035 | B:3 |
| 17989 | C:26 | 18036 | F:4 K:1 |
| 17990 | A:2 B:1 I:1 | 18037 | F:1 K:1 |
| 17991 | A:1 B:2 | 18038 | B:1 C:1 |
| 17992 | C:3 | 18039 | H:2 |
| 18040 | A:2 | 18087 | B:1 |
| 18041 | A:7 | 18088 | H:1 |
| 18042 | K:1 | 18089 | A:7 |
| 18043 | K:1 | 18090 | B:3 |
| 18044 | A:2 | 18091 | A:1 |
| 18045 | K:3 | 18092 | K:2 |
| 18046 | B:2 | 18093 | H:3 |
| 18047 | H:1 | 18094 | H:7 |
| 18048 | H:2 | 18095 | F:4 |
| 18049 | B:4 | 18096 | H:6 |
| 18050 | A:4 B:2 C:4 H:1 | 18097 | K:7 |
| 18051 | B:1 | 18098 | K:2 |
| 18052 | C:6 | 18099 | B:2 |
| 18053 | A:2 | 18100 | B:3 |
| 18054 | H:1 | 18101 | A:1 |
| 18055 | B:1 D:1 | 18102 | D:2 |
| 18056 | F:1 K:1 | 18103 | F:1 |
| 18057 | B:2 | 18104 | F:1 |
| 18058 | H:1 | 18105 | K:1 |
| 18059 | H:3 I:3 | 18106 | C:1 |
| 18060 | A:9 | 18107 | K:2 |
| 18061 | A:1 | 18108 | A:1 H:1 |
| 18062 | H:1 | 18109 | K:1 |
| 18063 | H:1 | 18110 | K:1 |
| 18064 | D:2 | 18111 | F:4 K:1 |
| 18065 | H:1 | 18112 | B:2 |
| 18066 | H:1 | 18113 | K:2 |
| 18067 | A:4 | 18114 | F:1 |
| 18068 | H:1 | 18115 | A:3 |
| 18069 | D:1 | 18116 | H:3 |
| 18070 | B:2 | 18117 | H:1 |
| 18071 | H:1 | 18118 | A:1 |
| 18072 | B:1 | 18119 | F:9 K:8 |
| 18073 | K:7 | 18120 | K:2 |
| 18074 | H:37 | 18121 | K:8 |
| 18075 | H:1 | 18122 | A:2 |
| 18076 | B:1 | 18123 | K:3 |
| 18077 | H:3 | 18124 | A:8 |
| 18078 | K:2 | 18125 | B:2 |
| 18079 | F:14 K:4 | 18126 | F:14 H:1 K:32 |
| 18080 | H:2 | 18127 | K:5 |
| 18081 | F:2 K:10 | 18128 | K:1 |
| 18082 | A:1 B:1 F:1 | 18129 | F:3 |
| 18083 | A:2 | 18130 | J:73 |
| 18084 | K:1 | 18131 | F:1 K:1 |
| 18085 | F:22 K:62 | 18132 | A:2 B:5 C:3 F:9 H:1 K:5 |
| 18086 | I:1 K:2 | 18133 | C:4 |
| 18134 | F:5 K:1 | 18181 | F:2 |
| 18135 | B:1 | 18182 | C:22 |
| 18136 | F:1 K:1 | 18183 | C:1 |
| 18137 | B:1 | 18184 | K:1 |
| 18138 | K:3 | 18185 | K:1 |
| 18139 | J:10 | 18186 | K:2 |
| 18140 | K:1 | 18187 | F:1 |
| 18141 | J:1 | 18188 | F:1 |
| 18142 | J:1 | 18189 | B:3 |
| 18143 | J:1 | 18190 | F:4 K:1 |
| 18144 | J:1 | 18191 | A:1 |
| 18145 | J:1 | 18192 | H:1 |
| 18146 | J:1 | 18193 | B:2 |
| 18147 | J:1 | 18194 | A:1 |
| 18148 | F:1 | 18195 | B:4 |
| 18149 | J:1 | 18196 | F:5 K:1 |
| 18150 | J:1 | 18197 | F:1 |
| 18151 | J:1 | 18198 | K:1 |
| 18152 | K:1 | 18199 | A:1 B:2 C:3 D:1 F:1 K:3 |
| 18153 | J:1 | 18200 | K:1 |
| 18154 | J:1 | 18201 | K:1 |
| 18155 | J:1 | 18202 | K:1 |
| 18156 | J:1 | 18203 | K:1 |
| 18157 | J:1 | 18204 | K:1 |
| 18158 | K:1 | 18205 | K:1 |
| 18159 | J:1 | 18206 | K:1 |
| 18160 | J:1 | 18207 | K:1 |
| 18161 | J:1 | 18208 | F:1 |

TABLE V-continued
(Spatial distribution)

| Seq Id No. | Tissue distribution | Seq Id No. | Tissue distribution |
|---|---|---|---|
| 18162 | J:1 | 18209 | K:1 |
| 18163 | J:1 | 18210 | A:4 |
| 18164 | J:1 | 18211 | K:1 |
| 18165 | J:1 | 18212 | A:3 |
| 18166 | J:1 | 18213 | K:1 |
| 18167 | F:1 | 18214 | K:1 |
| 18168 | J:1 | 18215 | K:1 |
| 18169 | J:1 | 18216 | K:1 |
| 18170 | K:1 | 18217 | K:1 |
| 18171 | J:1 | 18218 | K:2 |
| 18172 | K:1 | 18219 | B:2 |
| 18173 | C:6 | 18220 | H:1 |
| 18174 | A:19 B:20 C:11 D:46 F:22 | 18221 | K:1 |
| 18175 | K:1 | 18222 | H:2 |
| 18176 | H:1 | 18223 | F:1 K:20 |
| 18177 | A:1 K:2 | 18224 | K:4 |
| 18178 | C:9 | 18225 | B:2 |
| 18179 | H:1 | 18226 | B:3 H:1 K:1 |
| 18180 | C:1 K:6 | 18227 | A:8 B:5 C:20 D:9 F:3 H:10 J:2 |
| | | 18274 | A:2 |
| 18228 | C:1 | 18275 | F:1 K:2 |
| 18229 | K:1 | 18276 | K:1 |
| 18230 | H:2 | 18277 | B:2 |
| 18231 | D:2 | 18278 | B:3 |
| 18232 | A:2 | 18279 | K:1 |
| 18233 | I:1 | 18280 | C:6 |
| 18234 | I:1 | 18281 | H:3 |
| 18235 | F:2 | 18282 | K:2 |
| 18236 | H:1 | 18283 | B:8 C:1 |
| 18237 | A:1 D:1 | 18284 | C:8 |
| 18238 | F:2 | 18285 | A:1 |
| 18239 | F:1 K:2 | 18286 | B:1 |
| 18240 | B:3 | 18287 | B:2 |
| 18241 | F:1 K:1 | 18288 | D:2 |
| 18242 | K:2 | 18289 | A:1 B:20 C:21 F:3 H:6 K:1 |
| 18243 | K:1 | 18290 | B:1 |
| 18244 | K:1 | 18291 | C:1 |
| 18245 | K:2 | 18292 | F:1 |
| 18246 | K:1 | 18293 | F:1 |
| 18247 | H:4 | 18294 | B:4 |
| 18248 | A:3 H:1 | 18295 | H:1 |
| 18249 | A:2 | 18296 | K:2 |
| 18250 | A:1 | 18297 | F:1 K:2 |
| 18251 | F:3 K:9 | 18298 | F:1 K:1 |
| 18252 | F:2 K:2 | 18299 | F:1 |
| 18253 | C:2 | 18300 | F:2 K:2 |
| 18254 | K:2 | 18301 | F:23 K:6 |
| 18255 | K:1 | 18302 | H:1 |
| 18256 | D:1 | 18303 | K:2 |
| 18257 | C:1 H:1 | 18304 | F:1 K:6 |
| 18258 | C:6 | 18305 | C:1 H:2 K:1 |
| 18259 | D:1 F:1 | 18306 | A:1 |
| 18260 | I:2 | 18307 | K:2 |
| 18261 | H:11 | 18308 | B:2 |
| 18262 | F:1 | 18309 | K:2 |
| 18263 | K:1 | 18310 | B:2 C:1 |
| 18264 | K:2 | 18311 | K:1 |
| 18265 | A:7 | 18312 | F:1 |
| 18266 | K:7 | 18313 | F:1 |
| 18267 | I:1 | 18314 | F:1 |
| 18268 | H:1 | 18315 | K:3 |
| 18269 | A:1 | 18316 | K:3 |
| 18270 | C:2 | 18317 | H:1 |
| 18271 | H:1 | 18318 | C:2 |
| 18272 | B:1 | 18319 | F:1 I:2 |
| 18273 | A:2 | 18320 | K:2 |
| 18321 | H:2 | 18368 | K:1 |
| 18322 | C:25 | 18369 | C:1 |
| 18323 | A:4 | 18370 | H:1 |
| 18324 | K:2 | 18371 | K:1 |
| 18325 | C:31 | 18372 | B:4 |

TABLE V-continued
(Spatial distribution)

| Seq Id No. | Tissue distribution | Seq Id No. | Tissue distribution |
|---|---|---|---|
| 18326 | K:2 | 18373 | B:2 C:24 |
| 18327 | C:7 | 18374 | C:1 |
| 18328 | K:1 | 18375 | B:1 |
| 18329 | K:1 | 18376 | B:1 |
| 18330 | F:1 | 18377 | B:1 H:2 |
| 18331 | C:35 | 18378 | A:2 |
| 18332 | F:1 | 18379 | H:3 |
| 18333 | K:1 | 18380 | A:3 |
| 18334 | K:1 | 18381 | A:2 |
| 18335 | F:1 H:1 | 18382 | A:1 |
| 18336 | A:2 | 18383 | F:1 |
| 18337 | K:2 | 18384 | C:1 K:1 |
| 18338 | F:3 K:1 | 18385 | C:2 |
| 18339 | K:2 | 18386 | A:11 |
| 18340 | B:2 K:1 | 18387 | K:2 |
| 18341 | K:1 | 18388 | H:1 I:2 |
| 18342 | F:5 | 18389 | I:3 |
| 18343 | F:1 | 18390 | K:1 |
| 18344 | F:4 K:1 | 18391 | K:1 |
| 18345 | F:6 K:1 | 18392 | C:22 |
| 18346 | B:1 | 18393 | C:1 |
| 18347 | C:1 | 18394 | F:4 K:1 |
| 18348 | D:1 | 18395 | F:1 K:1 |
| 18349 | F:1 K:2 | 18396 | B:4 |
| 18350 | H:6 | 18397 | A:1 |
| 18351 | C:5 | 18398 | D:1 |
| 18352 | K:2 | 18399 | B:3 |
| 18353 | D:1 H:2 | 18400 | F:8 |
| 18354 | F:11 K:2 | 18401 | K:3 |
| 18355 | F:1 | 18402 | C:17 |
| 18356 | F:1 | 18403 | A:7 |
| 18357 | K:2 | 18404 | H:1 |
| 18358 | K:2 | 18405 | F:1 K:2 |
| 18359 | C:1 | 18406 | K:1 |
| 18360 | B:3 | 18407 | A:2 |
| 18361 | B:3 | 18408 | B:2 |
| 18362 | A:5 B:3 C:6 D:6 | 18409 | K:1 |
| 18363 | K:1 | 18410 | A:1 |
| 18364 | A:4 B:3 C:12 D:6 H:2 K:1 | 18411 | H:3 |
| 18365 | A:4 B:3 C:10 D:6 H:4 K:1 | 18412 | H:1 |
| 18366 | B:1 C:5 D:1 | 18413 | A:1 |
| 18367 | K:1 | 18414 | B:1 |
| 18415 | C:5 | 18462 | H:3 |
| 18416 | K:2 | 18463 | A:6 |
| 18417 | B:2 C:1 | 18464 | H:3 |
| 18418 | K:1 | 18465 | D:1 |
| 18419 | H:13 | 18466 | F:1 |
| 18420 | C:2 | 18467 | H:2 |
| 18421 | F:1 K:4 | 18468 | B:1 |
| 18422 | K:2 | 18469 | H:1 |
| 18423 | A:1 | 18470 | C:1 |
| 18424 | B:2 | 18471 | H:2 |
| 18425 | A:1 | 18472 | H:1 |
| 18426 | I:3 | 18473 | A:1 |
| 18427 | A:1 | 18474 | K:3 |
| 18428 | K:2 | 18475 | A:1 |
| 18429 | K:3 | 18476 | F:1 K:2 |
| 18430 | D:1 | 18477 | F:2 |
| 18431 | B:2 | 18478 | A:2 B:66 C:96 D:3 F:3 H:114 I:3 J:1 K:5 |
| 18432 | H:1 | 18479 | K:1 |
| 18433 | H:1 | 18480 | K:1 |
| 18434 | H:1 | 18481 | H:1 |
| 18435 | F:1 K:1 | 18482 | A:1 |
| 18436 | F:1 | 18483 | A:1 |
| 18437 | F:1 | 18484 | A:2 |
| 18438 | A:2 | 18485 | F:1 K:1 |
| 18439 | A:2 | 18486 | B:1 |
| 18440 | K:2 | 18487 | A:5 |
| 18441 | F:2 K:1 | 18488 | K:1 |
| 18442 | K:1 | 18489 | F;1 |
| 18443 | K:1 | | |

TABLE V-continued

(Spatial distribution)

| Seq Id No. | Tissue distribution | Seq Id No. | Tissue distribution |
|---|---|---|---|
| 18444 | K:1 | 18490 | C:9 |
| 18445 | K:1 | 18491 | H:4 |
| 18446 | C:34 | 18492 | A:12 |
| 18447 | B:8 C:26 | 18493 | A:3 |
| 18448 | H:2 | 18494 | A:5 C:1 |
| 18449 | C:24 | 18495 | A:2 B:2 |
| 18450 | A:3 B:3 D:1 | 18496 | C:2 |
| 18451 | A:5 B:1 | 18497 | F:6 K:1 |
| 18452 | A:2 B:2 C:1 H:2 | 18498 | B:4 |
| 18453 | B:1 | 18499 | K:1 |
| 18454 | K:1 | 18500 | F:9 K:1 |
| 18455 | B:1 | 18501 | K:2 |
| 18456 | B:1 | 18502 | K:1 |
| 18457 | C:1 | 18503 | H:1 |
| 18458 | A:2 | 18504 | H:1 |
| 18459 | K:1 | 18505 | F:1 K:11 |
| 18460 | A:1 | 18506 | H:1 |
| 18461 | A:3 | 18507 | C:52 |
| 18508 | C:27 | 18555 | B:2 |
| 18509 | C:1 | 18556 | K:2 |
| 18510 | C:1 | 18557 | F:3 K:3 |
| 18511 | C:1 | 18558 | K:3 |
| 18512 | F:10 K:3 | 18559 | F:1 K:1 |
| 18513 | K:2 | 18560 | F:6 |
| 18514 | C:6 | 18561 | C:12 |
| 18515 | B:4 C:4 H:1 | 18562 | H:2 |
| 18516 | A:1 B:4 C:5 | 18563 | J:1 |
| 18517 | B:7 C:6 | 18564 | H:1 |
| 18518 | B:7 C:8 D:2 | 18565 | F:13 K:1 |
| ;8519 | B:18 C:17 K:1 | 18566 | B:3 |
| 18520 | C:1 | 18567 | B:3 C:1 |
| 18521 | B:1 | 18568 | H:2 |
| 18522 | J:1 | 18569 | K:1 |
| 18523 | B:1 | 18570 | K:1 |
| 18524 | B:1 | 18571 | F:1 |
| 18525 | C:1 | 18572 | K:1 |
| 18526 | B:1 | 18573 | K:1 |
| 18527 | C:1 | 18574 | H:2 |
| 18528 | A:1 | 18575 | F:5 K:3 |
| 18529 | H:1 | 18576 | C:6 |
| 18530 | B:1 | 18577 | A:2 C:1 |
| 18531 | B:1 | 18578 | B:3 |
| 18532 | A:1 | 18579 | A:1 K:1 |
| 18533 | K:1 | 18580 | K:1 |
| 18534 | B:1 | 18581 | F:4 K:2 |
| 18535 | H:1 | 18582 | H:1 |
| 18536 | B:1 | 18583 | A:1 |
| 18537 | K:1 | 18584 | C:45 |
| 18538 | B:1 | 18585 | H:1 |
| 18539 | C:1 | 18586 | K:1 |
| 18540 | C:1 | 18587 | K:1 |
| 18541 | C:1 | 18588 | K:1 |
| 18542 | C:1 | 18589 | D:1 |
| 18543 | B:1 | 18590 | A:6 |
| 18544 | C:1 | 18591 | F:2 |
| 18545 | C:1 | 18592 | A:4 B:1 |
| 18546 | C:1 | 18593 | F:8 K:1 |
| 18547 | B:3 | 18594 | B:5 |
| 18548 | B:7 F:4 K:7 | 18595 | B:1 |
| 18549 | A:2 B:6 C:34 D:4 H:8 | 18596 | A:1 B:1 H:2 |
| 18550 | C:1 | 18597 | K:3 |
| 18551 | C:1 | 18598 | C:102 |
| 18552 | K:3 | 18599 | F:4 K:16 |
| 18553 | K:1 | 18600 | F:10 K:1 |
| 18554 | D:1 | 18601 | F:10 |
| 18602 | F:1 K:1 | 18649 | F:5 |
| 18603 | B:2 | 18650 | B:3 |
| 18604 | A:1 K:1 | 18651 | F:2 |
| 18605 | F:1 | 18652 | A:4 |
| 18606 | A:1 | 18653 | K:4 |
| 18607 | A:1 | 18654 | A:1 C:1 |
| 18608 | F:1 K:2 | 18655 | H:3 |
| 18609 | A:1 | 18656 | B:2 |
| 18610 | I:1 K:1 | 18657 | A:1 F:1 K:2 |
| 18611 | A:1 | 18658 | C:5 |
| 18612 | B:2 | 18659 | K:1 |
| 18613 | F:2 K:1 | 18660 | C:1 |
| 18614 | K:1 | 18661 | H:3 |
| 18615 | K:1 | 18662 | K:4 |
| 18616 | F:14 K:5 | 18663 | B:3 |
| 18617 | F:1 | 18664 | K:3 |
| 18618 | A:1 | 18665 | K:1 |
| 18619 | K:2 | 18666 | A:3 |
| 18620 | H:1 | 18667 | A:1 |
| 18621 | F:2 K:21 | 18668 | C:3 |
| 18622 | A:1 | 18669 | B:2 C:1 |
| 18623 | F:1 | 18670 | A:2 |
| 18624 | A:1 B:1 C:1 D:2 F:1 K:26 | 18671 | C:1 |
| 18625 | D:2 K:3 | 18672 | F:6 K:5 |
| 18626 | K:1 | 18673 | F:1 |
| 18627 | F:1 | 18674 | D:1 K:1 |
| 18628 | K:2 | 18675 | H:2 |
| 18629 | K:1 | 18676 | H:11 |
| 18630 | H:5 | 18671 | C:27 |
| 18631 | H:2 | 18678 | I:1 |
| 18632 | C:1 | 18679 | K:1 |
| 18633 | C:1 | 18680 | K:2 |
| 18634 | C:1 | 18681 | F:2 |
| 18635 | B:1 | 18682 | I:3 |
| 18636 | B:2 | 18683 | C:38 |
| 18637 | F:1 K:4 | 18684 | C:1 |
| 18638 | H:1 K:1 | 18685 | F:1 H:2 K:8 |
| 18639 | H:1 | 18686 | C:1 |
| 18640 | A:3 | 18687 | B:4 C:1 |
| 18641 | F:1 K:2 | 18688 | B:2 |
| 18642 | F:3 K:11 | 18689 | K:1 |
| 18643 | F:1 K:2 | 18690 | F:1 |
| 18644 | C:2 | 18691 | A:29 B:47 C:41 D:1 F:1 J:3 K:5 |
| 18645 | A:13 | 18692 | K:1 |
| 18646 | C:1 | 18693 | C:1 |
| 18647 | A:1 | 18694 | K:1 |
| 18648 | D:1 | 18695 | H:1 |
| 18696 | F:1 | 18743 | A:1 |
| 18697 | K:1 | 18744 | H:1 |
| 18698 | D:1 | 18745 | H:1 |
| 18699 | B:1 | 18746 | C:1 |
| 18700 | A:1 | 18747 | D:1 |
| 18701 | H:1 | 18748 | C:1 |
| 18702 | A:1 | 18749 | K:1 |
| 18703 | B:1 | 18750 | C:1 |
| 18704 | C:1 | 18751 | C:1 |
| 18705 | B:1 | 18752 | A:2 |
| 18706 | K:3 | 18753 | B:1 |
| 18707 | C:1 | 18754 | H:1 |
| 18708 | C:1 | 18755 | C:1 |
| 18709 | C:1 | 18756 | C:4 |
| 18710 | A:1 | 18757 | H:1 |
| 18711 | K:1 | 18758 | F:1 |
| 18712 | C:1 | 18759 | B:1 C:5 F:6 H:9 K:4 |
| 18713 | A:1 | 18760 | A:1 |
| 18714 | B:1 | 18761 | A:1 |
| 18715 | B:1 | 18762 | B:1 |
| 18716 | H:1 | 18763 | H:1 |
| 18717 | C:1 | 18764 | C:1 |
| 18718 | A:1 | 18765 | H:1 |
| 18719 | C:1 | 18766 | H:1 |
| 18720 | H:1 | 18767 | A:1 |
| 18721 | D:1 H:1 | 18768 | A:1 |
| 18722 | J:1 | 18769 | C:1 |
| 18723 | C:1 | 18770 | B:1 |
| 18724 | C:1 | 18771 | H:1 |
| 18725 | B:1 | 18772 | H:1 |
| 18726 | B:1 | 18773 | H:1 |

TABLE V-continued (Spatial distribution)

| Seq Id No. | Tissue distribution | Seq Id No. | Tissue distribution |
|---|---|---|---|
| 18727 | B:1 | 18774 | H:1 |
| 18728 | C:1 | 18775 | C:1 |
| 18729 | B:1 | 18776 | D:1 |
| 18730 | C:1 | 18777 | H:1 |
| 18731 | C:1 | 18778 | I:1 |
| 18732 | C:1 | 18779 | A:1 H:1 |
| 18733 | B:1 | 18780 | C:1 |
| 18734 | C:1 | 18781 | C:1 |
| 18735 | C:50 | 18782 | E:1 |
| 18736 | H:1 | 18783 | B:1 |
| 18737 | B:1 | 18784 | A:1 |
| 18738 | I:1 | 18785 | H:1 |
| 18739 | C:1 | 18786 | C:1 |
| 18740 | C:8 | 18787 | C:1 |
| 18741 | I:1 | 18788 | C:1 |
| 18742 | C:1 | 18789 | F:1 |
| 18790 | C:1 | 18837 | C:1 |
| 18791 | A:7 | 18838 | B:8 C:1 |
| 18792 | B:3 | 18839 | K:2 |
| 18793 | F:8 | 18840 | A:8 K:1 |
| 18794 | I:2 | 18841 | A:7 K:1 |
| 18795 | C:5 | 18842 | H:3 |
| 18796 | C:10 | 18843 | F:1 K:1 |
| 18797 | A:1 | 18844 | A:1 C:1 |
| 18798 | A:2 | 18845 | F:1 K:2 |
| 18799 | K:2 | 18846 | B:2 |
| 18800 | B:2 | 18847 | F:1 K:1 |
| 18801 | K:3 | 18848 | A:2 |
| 18802 | A:1 C:1 | 18849 | K:3 |
| 18803 | B:9 C:3 K:1 | 18850 | C:1 |
| 18804 | H:2 | 18851 | C:2 |
| 18805 | B:2 | 18852 | F:19 K:8 |
| 18806 | B:2 | 18853 | K:1 |
| 18807 | F:8 K:2 | 18854 | K:1 |
| 18808 | B:3 | 18855 | K:1 |
| 18809 | B:1 | 18856 | F:1 |
| 18810 | A:2 | 18857 | K:1 |
| 18811 | B:2 | 18858 | K:1 |
| 18812 | B:3 | 18859 | K:3 |
| 18813 | A:2 | 18860 | H:1 |
| 18814 | D:1 F:1 K:12 | 18861 | F:3 |
| 18815 | B:2 | 18862 | K:2 |
| 18816 | K:2 | 18863 | K:2 |
| 18817 | K:2 | 18864 | F:1 |
| 18818 | K:3 | 18865 | K:1 |
| 18819 | K:2 | 18866 | F:17 K:2 |
| 18820 | F:2 | 18867 | F:3 K:1 |
| 18821 | F:4 K:1 | 18868 | H:3 |
| 18822 | K:1 | 18869 | A:1 B:1 |
| 18823 | K:1 | 18870 | C:2 J:1 |
| 18824 | K:1 | 18871 | C:6 J:1 |
| 18825 | A:2 | 18872 | C:1 J:4 |
| 18826 | K:3 | 18873 | C:4 J:1 |
| 18827 | K:1 | 18874 | A:4 C:1 J:1 |
| 18828 | A:1 H:1 | 18875 | F:1 K:4 |
| 18829 | I:2 | 18876 | H:2 |
| 18830 | K:2 | 18877 | K:4 |
| 18831 | K:2 | 18878 | K:4 |
| 18832 | K:4 | 18879 | K:1 |
| 18833 | B:1 | 18880 | F:1 K:2 |
| 18834 | K:2 | 18881 | K:1 |
| 18835 | F:1 K:1 | 18882 | F:1 K:1 |
| 18836 | K:1 | 18883 | F:2 |
| 18884 | F:2 K:2 | 18931 | F:1 |
| 18885 | H:3 K:2 | 18932 | K:1 |
| 18886 | A:4 | 18933 | K:5 |
| 18887 | C:1 | 18934 | F:1 K:2 |
| 18888 | K:1 | 18935 | B:2 |
| 18889 | H:2 | 18936 | F:3 K:1 |
| 18890 | A:3 | 18937 | A:3 C:1 |
| 18891 | F:5 K:1 | 18938 | K:1 |
| 18892 | K:3 | 18939 | K:1 |
| 18893 | K:1 | 18940 | K:2 |
| 18894 | D:1 | 18941 | F:1 K:1 |
| 18895 | F:1 K:2 | 18942 | K:1 |
| 18896 | A:2 | 18943 | C:18 |
| 18897 | C:2 H:1 | 18944 | A:1 C:10 |
| 18898 | K:2 | 18945 | F:2 K:1 |
| 18899 | C:1 H:3 | 18946 | A:8 |
| 18900 | F:1 K:1 | 18947 | H:1 |
| 18901 | A:3 | 18948 | A:1 |
| 18902 | K:4 | 18949 | A:1 |
| 18903 | F:1 K:1 | 18950 | F:3 K:8 |
| 18904 | B:2 | 18951 | F:11 K:13 |
| 18905 | F:1 | 18952 | F:1 |
| 18906 | F:1 | 18953 | B:2 |
| 18907 | F:1 | 18954 | K:2 |
| 18908 | K:3 | 18955 | K:1 |
| 18909 | F:1 | 18956 | C:1 H:8 |
| 18910 | K:1 | 18957 | D:2 |
| 18911 | A:9 B:7 C:11 D:1 H:4 K:1 | 18958 | F:7 K:2 |
| 18912 | F:1 | 18959 | D:1 |
| 18913 | H:1 | 18960 | I:1 |
| 18914 | F:1 | 18961 | K:1 |
| 18915 | C:1 | 18962 | K:1 |
| 18916 | K:3 | 18963 | K:1 |
| 18917 | B:5 | 18964 | C:10 |
| 18918 | B:1 | 18965 | C:1 |
| 18919 | B:3 | 18966 | H:2 |
| 18920 | F:1 | 18967 | C:42 |
| 18921 | A:1 C:1 H:1 | 18968 | F:2 K:2 |
| 18922 | F:1 | 18969 | F:2 K:2 |
| 18923 | F:1 | 18970 | B:3 |
| 18924 | H:1 | 18971 | C:1 F:5 H:4 K:7 |
| 18925 | F:1 | 18972 | K:1 |
| 18926 | F:1 | 18973 | F:1 |
| 18927 | B:1 | 18974 | F:2 K:1 |
| 18928 | F:1 | 18975 | K:3 |
| 18929 | F:1 | 18976 | D:2 |
| 18930 | I:3 | 18977 | C:1 D:1 |
| 18978 | K:2 | 19025 | B:2 |
| 18979 | K:2 | 19026 | A:2 |
| 18980 | H:5 | 19027 | K:1 |
| 18981 | D:2 | 19028 | I:2 |
| 18982 | F:1 K:3 | 19029 | F:1 K:1 |
| 18983 | B:1 | 19030 | K:2 |
| 18984 | A:2 C:5 J:2 K:1 | 19031 | F:2 K:3 |
| 18985 | B:5 C:1 | 19032 | F:1 |
| 18986 | A:6 F:1 | 19033 | K:1 |
| 18987 | F:4 K:1 | 19034 | K:1 |
| 18988 | F:1 K:9 | 19035 | B:4 |
| 18989 | K:3 | 19036 | H:1 |
| 18990 | F:1 | 19037 | H:1 K:4 |
| 18991 | F:1 K:1 | 19038 | A:3 |
| 18992 | F:67 K:329 | 19039 | K:5 |
| 18993 | K:1 | 19040 | K:1 |
| 18994 | K:1 | 19041 | K:1 |
| 18995 | K:1 | 19042 | K:1 |
| 18996 | F:1 | 19043 | A:3 |
| 18997 | K:1 | 19044 | E:2 |
| 18998 | F:21 K:9 | 19045 | F:21 K:3 |
| 18999 | F:3 K:1 | 19046 | K:3 |
| 19000 | K:1 | 19047 | K:1 |
| 19001 | K:1 | 19048 | H:3 |
| 19002 | A:28 B:11 C:32 D:5 F:11 H:6 K:8 | 19049 | K:2 |
| 19003 | A:1 | 19050 | K:2 |
| 19004 | B:1 | 19051 | C:2 J:1 |
| 19005 | A:3 | 19052 | I:4 |
| 19006 | H:1 K:3 | 19053 | K:2 |
| 19007 | F:1 K:2 | 19054 | F:1 K:2 |
| 19008 | F:8 K:1 | 19055 | A:3 |
| 19009 | A:4 | 19056 | B:2 |
| 19010 | H:2 | 19057 | C:1 D:1 |
| 19011 | F:3 K:1 | 19058 | A:1 D:1 |

TABLE V-continued (Spatial distribution)

| Seq Id No. | Tissue distribution | Seq Id No. | Tissue distribution | Seq Id No. | Tissue distribution | Seq Id No. | Tissue distribution |
|---|---|---|---|---|---|---|---|
| 19012 | A:1 | 19059 | A:2 | 19179 | H:2 | 19226 | H:1 |
| 19013 | A:1 | 19060 | B:3 | 19180 | A:4 | 19227 | H:1 |
| 19014 | A:1 | 19061 | A:1 | 19181 | F:1 K:1 | 19228 | H:1 |
| 19015 | A:1 | 19062 | C:6 | 19182 | F:2 K:1 | 19229 | H:1 |
| 19016 | F:1 | 19063 | K:3 | 19183 | K:1 | 19230 | H:1 |
| 19017 | F:3 K:3 | 19064 | K:4 | 19184 | H:1 | 19231 | H:1 |
| 19018 | A:1 | 19065 | B:1 | 19185 | I:2 | 19232 | H:1 |
| 19019 | K:3 | 19066 | H:1 | 19186 | B:3 | 19233 | H:1 |
| 19020 | A:3 | 19067 | B:1 | 19187 | A:3 | 19234 | H:1 |
| 19021 | A:135 | 19068 | A:27 B:5 C:4 D:2 H:3 I:5 | 19188 | K:2 | 19235 | H:1 |
| 19022 | H:6 | 19069 | A:1 | 19189 | K:2 | 19236 | H:1 |
| 19023 | F:5 K:15 | 19070 | K:1 | 19190 | F:9 K:2 | 19237 | F:1 K:4 |
| 19024 | F:5 K:15 | 19071 | A:1 | 19191 | F:11 K:3 | 19238 | H:1 |
| 19072 | H 1 | 19119 | K:1 | 19192 | F:1 K:1 | 19239 | H:1 |
| 19073 | F:2 | 19120 | D:1 H:1 | 19193 | C:1 J:1 | 19240 | H:1 |
| 19074 | A:1 H:1 | 19121 | C:92 | 19194 | F:14 K:1 | 19241 | H:1 |
| 19075 | A:1 | 19122 | B:1 D:1 H:7 J:1 | 19195 | H:1 | 19242 | H:1 |
| 19076 | A:1 | 19123 | H:1 | 19196 | H:1 | 19243 | H:1 |
| 19077 | F:1 | 19124 | H:1 | 19197 | H:1 | 19244 | H:1 |
| 19078 | K:2 | 19125 | H:2 | 19198 | H:1 | 19245 | H:1 |
| 19079 | C:2 | 19126 | H:1 | 19199 | H:1 | 19246 | H:1 |
| 19080 | F:2 K:10 | 19127 | K:3 | 19200 | H:1 | 19247 | H:1 |
| 19081 | F:5 | 19128 | F:6 K:1 | 19201 | H:1 | 19248 | H:1 |
| 19082 | F:2 K:1 | 19129 | K:3 | 19202 | H:1 | 19249 | H:1 |
| 19083 | F:2 I:1 | 19130 | C:3 | 19203 | H:1 | 19250 | H:1 |
| 19084 | H:1 | 19131 | K:2 | 19204 | H:1 | 19251 | H:1 |
| 19085 | H:2 | 19132 | F:17 K:9 | 19205 | K:2 | 19252 | H:1 |
| 19086 | H:2 | 19133 | F:8 K:2 | 19206 | H:1 | 19253 | H:1 |
| 19087 | A:1 B:1 I:1 | 19134 | C:1 | 19207 | H:1 | 19254 | H:1 |
| 19088 | C:2 | 19135 | H:1 I:1 | 19208 | H:1 | 19255 | H:1 |
| 19089 | K:4 | 19136 | B:2 | 19209 | H:1 | 19256 | H:1 |
| 19090 | B:2 | 19137 | K:2 | 19210 | H:1 | 19257 | H:1 |
| 19091 | B:2 | 19138 | C:6 H:2 | 19211 | H:1 | 19258 | H:1 |
| 19092 | F:3 H:1 K:1 | 19139 | B:1 | 19212 | H:1 | 19259 | H:1 |
| 19093 | C:1 H:2 | 19140 | A:1 | 19260 | H:1 | 19307 | H:1 |
| 19094 | F:1 K:1 | 19141 | C:16 | 19261 | H:1 | 19308 | H:1 |
| 19095 | A:4 | 19142 | H:2 | 19262 | H:1 | 19309 | H:1 |
| 19096 | F:23 K:4 | 19143 | K:1 | 19263 | H:1 | 19310 | H:1 |
| 19097 | F:1 | 19144 | K:1 | 19264 | H:1 | 19311 | H:1 |
| 19098 | F:1 | 19145 | A:1 | 19265 | H:1 | 19312 | H:1 |
| 19099 | F:1 | 19146 | C:1 | 19266 | H:1 | 19313 | H:1 |
| 19100 | F:1 | 19147 | A:5 | 19267 | H:1 | 19314 | K:2 |
| 19101 | F:1 K:2 | 19148 | A:9 F:1 H:2 I:4 | 19268 | H:1 | 19315 | H:1 |
| 19102 | K:2 | 19149 | A:2 | 19269 | H:1 | 19316 | H:1 |
| 19103 | B:4 | 19150 | B:2 | 19270 | H:1 | 19317 | H:1 |
| 19104 | A:5 | 19151 | A:2 K:1 | 19271 | H:1 | 19318 | H:1 |
| 19105 | B:2 | 19152 | A:1 | 19272 | H:1 | 19319 | H:1 |
| 19106 | H:12 | 19153 | K:1 | 19273 | H:1 | 19320 | H:1 |
| 19107 | F:1 K:2 | 19154 | A:1 | 19274 | H:1 | 19321 | H:1 |
| 19108 | H:14 | 19155 | K:1 | 19275 | H:1 | 19322 | H:1 |
| 19109 | C:5 | 19156 | A:1 | 19276 | H:1 | 19323 | H:1 |
| 19110 | K:2 | 19157 | A:1 | 19277 | H:1 | 19324 | H:1 |
| 19111 | K:4 | 19158 | A:1 | 19278 | H:1 | 19325 | C:39 D:1 |
| 19112 | C:2 | 19159 | C:31 | 19279 | H:1 | 19326 | H:1 |
| 19113 | K:2 | 19160 | K:1 | 19280 | H:1 | 19327 | H:1 |
| 19114 | A:1 H:1 | 19161 | K:5 | 19281 | H:1 | 19328 | H:1 |
| 19115 | A:1 C:18 F:1 K:3 | 19162 | K:1 | 19282 | K:2 | 19329 | H:1 |
| 19116 | C:1 | 19163 | F:5 K:1 | 19283 | H:1 | 19330 | H:1 |
| 19117 | C:10 | 19164 | B:3 | 19284 | H:1 | 19331 | H:1 |
| 19118 | F:1 | 19165 | H:2 | 19285 | H:1 | 19332 | H:1 |
| 19166 | F:3 | 19213 | H:1 | 19286 | H:1 | 19333 | H:1 |
| 19167 | B:2 | 19214 | H:1 | 19287 | H:1 | 19334 | H:1 |
| 19168 | C:57 | 19215 | H:1 | 19288 | H:1 | 19335 | H:1 |
| 19169 | F:8 K:2 | 19216 | H:1 | 19289 | H:1 | | |
| 19170 | K:3 | 19217 | H:1 | 19290 | H:1 | | |
| 19171 | F:1 | 19218 | H:1 | 19291 | H:1 | | |
| 19172 | F:1 | 19219 | H:1 | 19292 | C:3 | | |
| 19173 | F:1 | 19220 | H:1 | 19293 | H:1 | | |
| 19174 | K:3 | 19221 | H:1 | 19294 | H:1 | | |
| 19175 | F:2 | 19222 | H:1 | 19295 | H:1 | | |
| 19176 | F:2 | 19223 | H:1 | 19296 | H:1 | | |
| 19177 | C:35 | 19224 | H:1 | 19297 | H:1 | | |
| 19178 | C:2 | 19225 | H:1 | 19298 | H:1 | | |

TABLE V-continued (Spatial distribution)

| Seq Id No. | Tissue distribution | Seq Id No. | Tissue distribution |
|---|---|---|---|
| 19299 | H:1 | | |
| 19300 | H:1 | | |
| 19301 | H:1 | | |
| 19302 | H:1 | | |
| 19303 | K:2 | | |
| 19304 | H:1 | | |
| 19305 | H:1 | | |
| 19306 | H:1 | | |

TABLE VI (Tissue type)

| Letter Code | Tissue type |
|---|---|
| A | Brain |
| B | FoetalBrain |
| C | FoetalKidney |
| D | FoetalLiver |
| E | Hypophysis |
| F | Liver |
| G | Placenta |
| H | Prostate |
| I | Salivary Gland |
| J | Stomach/Intestine |
| K | Testis |

(Biais in spatial distribution)

| Seq Id No. | Low frequency | High frequency |
|---|---|---|
| 38 | Brain, Prostate, fetalBrain, fetalKidney | Liver, Testis |
| 43 | fetalKidney | |
| 91 | Testis, fetalKidney | |
| 135 | Liver, Testis, fetalKidney | Brain, Prostate, fetalBrain, fetalLiver |
| 159 | Testis | fetalKidney |
| 181 | Brain, Liver, Testis, fetalBrain, fetalLiver | fetalKidney |
| 304 | Testis, fetalKidney | Brain |
| 365 | fetalKidney | Testis |
| 566 | Brain, Prostate, fetalKidney | Liver, Testis |
| 579 | fetalKidney | |
| 582 | | fetalKidney |
| 686 | Brain, Testis | fetalKidney |
| 697 | Testis | |
| 715 | fetalKidney | |
| 769 | Testis, fetalKidney | |
| 778 | fetalKidney | Testis |
| 790 | Brain, Liver, Testis | Prostate |
| 818 | Testis | fetalKidney |
| 819 | Testis | fetalKidney |
| 873 | Liver, Testis | fetalBrain |
| 881 | Liver, Testis, fetalKidney | Brain, Prostate |
| 909 | Testis | Brain |
| 937 | Testis | |
| 994 | fetalKidney | |
| 1088 | Liver, Testis | fetalBrain |
| 1089 | Liver | |
| 1091 | fetalKidney | |
| 1144 | fetalKidney | Testis |
| 1172 | Brain, Liver, Prostate, Testis, fetalBrain, fetalKidney | |
| 1180 | Brain, Prostate, fetalKidney | Testis |
| 1185 | Brain | Testis |
| 1186 | Liver, Testis | Prostate, fetalBrain, fetalLiver |
| 1203 | fetalKidney | |
| 1210 | Brain, Prostate, fetalBrain, fetalKidney | Liver, Testis |
| 1245 | Testis | fetalKidney |
| 1250 | Brain, fetalKidney | Liver |
| 1251 | Brain, Stomach_Intestine Testis, fetalKidney, fetalLiver | Liver, Prostate |
| 1252 | Brain, fetalKidney | Liver, Prostate |
| 1261 | Brain, Prostate, fetalBrain, fetalKidney | Liver, Testis |
| 1312 | fetalKidney | |
| 1343 | Brain, Liver, Prostate, Testis, fetalBrain | fetalKidney |
| 1345 | Brain, Liver, Testis | fetalBrain, fetalKidney |
| 1346 | Brain, Liver, Testis | Prostate, fetalBrain, fetalKidney |
| 1362 | fetalKidney | |

-continued (Biais in spatial distribution)

| Seq Id No. | Low frequency | High frequency |
|---|---|---|
| 1377 | fetalKidney | |
| 1408 | | fetalKidney |
| 1409 | Testis | fetalKidney |
| 1415 | Liver, Stomach_Intestine, Testis, salivaryGland | Brain, fetalBrain, fetalLiver |
| 1416 | Brain, Liver, Prostate, Testis, fetalBrain | fetalKidney |
| 1419 | | fetalKidney |
| 1516 | Brain, Testis | fetalKidney |
| 1526 | fetalKidney | |
| 1530 | fetalKidney | |
| 1552 | Testis, fetalKidney | Brain |
| 1563 | Liver, Testis | fetalKidney |
| 1564 | Liver, Testis | fetalKidney |
| 1592 | | fetalKidney |
| 1596 | Brain, Testis, fetalKidney, fetalLiver | Liver, fetalBrain |
| 1606 | Brain, Liver, Prostate, Testis | fetalKidney |
| 1632 | fetalKidney | |
| 1635 | fetalKidney | |
| 1643 | fetalKidney | |
| 1649 | Brain, fetalBrain, fetalKidney | Testis |
| 1669 | Brain, Prostate, fetalBrain, fetalKidney | Testis |
| 1677 | Brain, fetalKidney | Liver, Testis |
| 1683 | | fetalKidney |
| 1750 | Liver, Prostate, Testis, fetalBrain, fetalKidney | Brain |
| 1775 | Brain, Liver, Prostate, Testis, fetalBrain, fetalKidney | |
| 1787 | fetalKidney | |
| 1803 | Liver, Testis, fetalKidney | Brain |
| 1806 | fetalKidney | |
| 1808 | Liver, Testis, fetalKidney | |
| 1819 | | fetalKidney |
| 1860 | Brain, fetalKidney | Testis |
| 1863 | fetalKidney | |
| 1867 | Liver, Prostate, Testis | fetalBrain |
| 1972 | fetalKidney | |
| 1973 | Brain, Liver, Prostate, Testis | fetalKidney |
| 2005 | Brain, Liver, Testis | fetalKidney |
| 2006 | fetalKidney | |
| 2009 | Brain, Liver, Testis | Prostate, fetalKidney |
| 2017 | Brain, Prostate, fetalKidney | Testis, fetalBrain |
| 2082 | Brain, Liver, Testis, fetalBrain | fetalKidney |
| 2100 | Brain, Prostate, fetalBrain, fetalKidney | Testis |
| 2367 | Brain, Prostate, Stomach_Intestine, fetalBrain, fetalKidney, fetalLiver | Testis |
| 2379 | Liver, Prostate, Testis, fetalBrain, fetalKidney | Brain |
| 2384 | Brain, Prostate, fetalBrain, fetalKidney | Liver |
| 2411 | Liver, Testis | Brain, fetalBrain |
| 2453 | Brain, Prostate, fetalBrain, fetalKidney | Testis |
| 2485 | Testis, fetalKidney | Brain |
| 2487 | Brain, Liver, Testis | Prostate, fetalBrain, fetalLiver |
| 2508 | Brain, Prostate, fetalBrain, fetalKidney | Testis |
| 2545 | Brain, Liver, Prostate, Testis, fetalBrain, fetalKidney | |
| 2587 | fetalKidney | |
| 2608 | Brain, Liver, Testis | Prostate, fetalBrain, fetalKidney |
| 2612 | fetalKidney | |
| 2614 | fetalKidney | |
| 2623 | Brain, Prostate, fetalKidney | Liver, Testis |
| 2652 | Prostate, fetalBrain | Brain, Testis |
| 2660 | fetalKidney | |
| 2671 | Brain, Liver, Testis | fetalKidney |
| 2673 | | fetalKidney |
| 2675 | Brain, Prostate, fetalBrain, fetalKidney | Testis |
| 2728 | Liver, Testis | fetalBrain, fetalLiver |
| 2743 | | fetalKidney |
| 2761 | | fetalKidney |
| 2766 | Brain | fetalKidney |
| 2768 | Brain | fetalKidney |
| 2769 | Liver, Prostate, Testis | fetalKidney |
| 2772 | | fetalKidney |
| 2815 | Liver, Testis | fetalBrain |
| 2828 | Brain, Testis | fetalKidney |
| 2845 | Brain, Liver, Prostate, Testis | fetalBrain, fetalKidney |
| 2863 | Prostate, fetalKidney | Liver, Testis |
| 2870 | Testis, fetalKidney | |
| 2874 | Brain, fetalKidney | Testis |

-continued (Biais in spatial distribution)

| Seq Id No. | Low frequency | High frequency |
|---|---|---|
| 2881 | fetalKidney | |
| 2931 | Brain, Liver, Testis | Prostate |
| 2933 | Liver, Prostate, Testis | fetalKidney |
| 2938 | Brain, Liver, Testis, salivaryGland | Prostate, fetalLiver |
| 2940 | Brain, Liver, Testis, fetalKidney | Prostate |
| 2945 | Testis, fetalKidney | Brain |
| 2968 | fetalKidney | |
| 2981 | Liver, Testis | fetalKidney |
| 3005 | Brain, Prostate | Testis |
| 3034 | fetalKidney | |
| 3047 | | fetalKidney |
| 3084 | fetalKidney | |
| 3099 | | fetalKidney |
| 3121 | fetalBrain, fetalKidney | Liver, Testis |
| 3122 | fetalBrain, fetalKidney | Liver, Testis |
| 3133 | Brain, Liver, Testis | fetalKidney |
| 3144 | Liver, Testis | fetalBrain, fetalKidney |
| 3145 | | Testis |
| 3149 | fetalKidney | |
| 3156 | Brain, Liver, Prostate, Testis, fetalBrain | |
| 3172 | Testis | fetalKidney |
| 3178 | | fetalKidney |
| 3182 | | fetalKidney |
| 3204 | Liver, Testis | |
| 3250 | Liver | |
| 3251 | fetalKidney | Testis |
| 3252 | Liver, fetalKidney | |
| 3253 | Liver, fetalKidney | |
| 3254 | Brain, Liver, Stomach_Intestine, fetalBrain, fetalKidney, salivaryGland | Prostate |
| 3290 | | fetalKidney |
| 3343 | Brain, Liver, Stomach_Intestine, Testis, salivaryGland | fetalBrain, fetalKidney, fetalLiver |
| 3344 | Testis | fetalKidney |
| 3362 | Brain, Prostate, fetalBrain, fetalLiver | Testis |
| 3363 | Brain, Prostate, fetalBrain | Testis |
| 3364 | Brain, Prostate, fetalBrain, fetalLiver | Testis |
| 3369 | Liver, Testis, fetalKidney | Brain |
| 3384 | | fetalKidney |
| 3422 | Brain, Prostate, Stomach_Intestine, fetalBrain, fetalKidney, fetalLiver | Testis |
| 3430 | Brain, fetalKidney | Testis |
| 3457 | fetalKidney | |
| 3466 | Liver, Prostate, Testis, fetalKidney | Brain, fetalBrain, fetalLiver, salivaryGland |
| 3482 | fetalKidney | |
| 3509 | Brain, Liver, Testis | fetalKidney |
| 3555 | | fetalKidney |
| 3556 | Brain | fetalKidney |
| 3564 | Testis, fetalKidney | Brain |
| 3568 | Brain, Liver, Prostate, Testis | fetalBrain |
| 3569 | Liver, Testis | fetalBrain, fetalKidney |
| 3582 | Testis, fetalKidney | |
| 3584 | Testis, fetalKidney | Brain |
| 3593 | Brain, fetalKidney | Testis |
| 3601 | | fetalKidney |
| 3612 | Testis | |
| 3618 | Liver, Testis, fetalKidney | Prostate |
| 3664 | Brain Stomach_Intestine, Testis, fetalBrain, fetalLiver, salivaryGland | Liver, Prostate |
| 3666 | Brain, fetalBrain, fetalKidney | Liver, Prostate |
| 3701 | fetalKidney | |
| 3738 | Brain, Liver, Prostate, Testis, fetalBrain | fetalKidney |
| 3744 | Liver, Testis | fetalKidney |
| 3753 | Testis | |
| 3756 | | fetalKidney |
| 3775 | Testis | fetalKidney |
| 3778 | fetalKidney | |
| 3779 | Liver, Prostate, Testis | fetalBrain, fetalKidney |
| 3780 | Brain, Liver, Prostate, Testis | fetalBrain, fetalKidney |
| 3793 | Liver, Prostate, Testis, fetalBrain, fetalKidney | Brain |
| 3794 | Liver, Prostate, Testis, fetalBrain, fetalKidney, fetalLiver | Brain |
| 3826 | Liver, Prostate, Testis | fetalBrain, fetalKidney |
| 3827 | Brain, Prostate, fetalBrain, fetalKidney | Testis |
| 3839 | fetalKidney | |

-continued (Biais in spatial distribution)

| Seq Id No. | Low frequency | High frequency |
|---|---|---|
| 3840 | fetalKidney | |
| 3848 | Liver, Prostate, Testis, fetalBrain, fetalKidney | Brain |
| 7872 | Brain, Prostate, fetalBrain, fetalKidney, fetalLiver | Testis |
| 8884 | Brain, Liver, Prostate, Testis, fetalBrain | fetalKidney |
| 9093 | fetalKidney | |
| 9177 | Liver, Prostate, Testis, fetalBrain, fetalKidney, fetalLiver | Brain |
| 9185 | Liver, Prostate, Stomach_Intestine, Testis, fetalBrain, fetalKidney, fetalLiver | Brain |
| 9217 | Testis | fetalKidney |
| 9396 | Brain, Prostate, fetalBrain, fetalKidney | Testis |
| 9411 | Brain, Prostate, Stomach_Intestine, fetalBrain, fetalKidney, fetalLiver, salivaryGland | Testis |
| 9731 | fetalKidney | |
| 9800 | Brain, Liver, Testis | fetalKidney |
| 9880 | Brain, fetalKidney | Testis |
| 9918 | | fetalKidney |
| 10295 | Brain, Liver, Testis | Prostate, fetalKidney |
| 11067 | Brain, Liver, Testis | Prostate, fetalKidney |
| 11747 | fetalKidney | |
| 12327 | Brain, Liver, Prostate, Testis, fetalBrain | fetalKidney |
| 13449 | Brain, Liver, Prostate, Testis, fetalBrain | fetalKidney |
| 13627 | Brain, Liver, Testis, fetalBrain, fetalKidney | Prostate |
| 13767 | fetalKidney | |
| 14546 | Liver, Testis | |
| 14654 | Brain, Liver, Prostate, Testis, fetalBrain | fetalKidney |
| 15013 | Liver, Prostate | |
| 15129 | Brain, Liver, Prostate, Testis, fetalBrain | fetalKidney |
| 15141 | Testis | fetalKidney |
| 15196 | Brain, Testis | fetalKidney |
| 15200 | Brain, Liver, Testis | fetalBrain, fetalKidney, fetalLiver |
| 15202 | Brain, Liver, Testis | fetalBrain, fetalKidney, fetalLiver |
| 15244 | Brain, Liver, Testis, fetalKidney | |
| 15294 | Brain, Prostate, Stomach_Intestine, fetalBrain, fetalKidney, fetalLiver, salivaryGland | Liver |
| 15297 | fetalKidney | Testis |
| 15301 | | fetalKidney |
| 15341 | Brain, Liver, Prostate, Testis | fetalKidney |
| 15405 | Liver | |
| 15419 | Brain, Prostate, fetalBrain, fetalKidney | Testis |
| 15453 | Brain, Prostate, fetalBrain, fetalKidney | Testis |
| 15490 | Brain, Liver, Prostate, Testis, fetalBrain, salivaryGland | fetalKidney |
| 15512 | fetalKidney | |
| 15520 | Brain, Liver, Testis | Prostate, fetalBrain, fetalKidney |
| 15542 | Liver, Prostate, Stomach_Intestine, Testis, fetalBrain, fetalKidney, fetalLiver, salivaryGland | Brain |
| 15553 | Brain, Liver, Testis, fetalKidney | Prostate |
| 15557 | | fetalKidney |
| 15558 | | fetalKidney |
| 15568 | Liver, Testis, fetalKidney | Brain |
| 15573 | Liver, Testis | fetalBrain, fetalKidney |
| 15594 | Testis, fetalKidney | |
| 15613 | Brain, fetalKidney | Liver |
| 15640 | Brain, Liver, Prostate, Testis, fetalBrain | fetalKidney |
| 15651 | Testis | fetalKidney |
| 15658 | Testis | |
| 15659 | fetalKidney | Testis |
| 15678 | fetalKidney | |
| 15685 | fetalKidney | |
| 15711 | Brain, Liver, Testis | Prostate, fetalBrain, fetalKidney |
| 15747 | Brain, Liver, Stomach_Intestine, Testis, fetalBrain, fetalLiver | Prostate |
| 15748 | Liver, Testis | Prostate, fetalBrain, fetalKidney |
| 16065 | | fetalKidney |
| 16072 | fetalKidney | |
| 16091 | Brain, Liver, Prostate, Testis | fetalKidney |
| 16127 | Brain, Liver, Testis, fetalBrain, fetalKidney | Prostate |
| 16151 | Brain, Liver, Prostate, Testis | fetalKidney |
| 16153 | Brain, Prostate, fetalBrain, fetalKidney | Testis |
| 16182 | fetalKidney | |
| 16185 | Brain, Liver, Prostate, Testis | fetalKidney |
| 16191 | fetalKidney | |
| 16192 | fetalKidney | |

-continued (Biais in spatial distribution)

| Seq Id No. | Low frequency | High frequency |
|---|---|---|
| 16237 | Liver, Prostate, Testis, fetalBrain, fetalKidney | Brain |
| 16238 | Liver, Prostate, Stomach_Intestine, Testis, fetalBrain, fetalKidney, fetalLiver, salivaryGland | Brain |
| 16243 | fetalKidney | |
| 16248 | Brain, Prostate, Stomach_Intestine, fetalBrain, fetalKidney, fetalLiver | Liver |
| 16277 | fetalKidney | |
| 16302 | Brain, Prostate, fetalKidney | Testis |
| 16312 | | fetal Kidney |
| 16332 | Brain, Liver, Prostate, Testis | fetalKidney |
| 16351 | Brain, Testis | fetalKidney |
| 16352 | Brain, Liver, Prostate, Testis | fetalKidney |
| 16393 | Liver, Prostate, Testis | fetalKidney |
| 16396 | Liver, Testis | fetalBrain |
| 16411 | Brain, Liver, Prostate, Testis, fetalBrain, fetalKidney, fetalLiver, salivaryGland | Stomach_Intestine |
| 16477 | Brain, Liver, Prostate, Testis, fetalBrain | fetalKidney |
| 16497 | fetalKidney | Testis |
| 16597 | fetalKidney | |
| 16657 | Liver, Prostate, Testis | fetalBrain |
| 16684 | fetalKidney | |
| 16738 | Brain, fetalKidney | |
| 16776 | Brain, Liver, Testis | fetalKidney |
| 16790 | Brain, Liver, Testis, salivaryGland | Prostate, fetalLiver |
| 16865 | Brain, Testis | fetalKidney |
| 16867 | Brain, fetalKidney | Liver |
| 16878 | Brain, Prostate, fetalBrain, fetalKidney | Testis |
| 16905 | Brain, Liver, Prostate, Testis, fetalBrain, fetalKidney | |
| 16959 | fetalKidney | |
| 17143 | Brain, Liver, Prostate, Testis, fetalBrain | fetalKidney |
| 17166 | fetalKidney | |
| 17167 | Brain, fetalKidney | Testis |
| 17178 | Brain, Prostate, fetalBrain, fetalKidney | Liver |
| 17197 | fetalKidney | |
| 17198 | Brain, fetalKidney | |
| 17224 | fetalKidney | |
| 17266 | Testis, fetalKidney | |
| 17268 | Brain, Prostate, fetalBrain, fetal Kidney | Testis |
| 17269 | Brain, Prostate, fetalBrain, fetalKidney | Testis |
| 17330 | Brain, Liver, Testis, fetalKidney | |
| 17350 | Brain, Testis | fetalKidney |
| 17351 | Brain, Liver, Prostate, Testis, fetalBrain | fetalKidney |
| 17383 | Brain, Testis | fetalKidney |
| 17391 | Brain, Liver, Testis | fetalKidney |
| 17412 | Brain, Liver, Prostate, Testis, fetalBrain | fetalKidney |
| 17477 | fetalKidney | |
| 17488 | Brain, fetalKidney | Testis |
| 17530 | Brain, Liver, Prostate, Testis | fetalKidney |
| 17541 | Brain, Prostate, fetalBrain, fetalKidney | Testis |
| 17565 | Liver, Prostate, Testis, fetalKidney | Brain |
| 17572 | Brain, Liver, Testis | fetalBrain, fetalKidney |
| 17580 | Liver, Testis | fetalBrain, fetalKidney |
| 17638 | fetalKidney | Testis |
| 17640 | fetalKidney | |
| 17644 | Brain, Liver, Prostate, Stomach_Intestine, Testis, fetalBrain, fetalLiver, salivaryGland | fetalKidney |
| 17652 | Brain, Prostate, fetalKidney | Testis |
| 17706 | fetalKidney | |
| 17710 | Brain, Liver, Prostate, Testis, fetalBrain | fetalKidney |
| 17712 | fetalKidney | |
| 17717 | Brain, Liver, Prostate | fetalBrain, fetalKidney |
| 17748 | Testis | fetalKidney |
| 17774 | | fetalKidney |
| 17796 | Brain, Liver, Prostate, Testis, fetalBrain | fetalKidney |
| 17820 | | fetalKidney |
| 17850 | Brain, Liver, Prostate, Testis | fetalKidney |
| 17881 | Brain, Prostate, fetalBrain, fetalKidney, fetalLiver | Liver, Testis |
| 17883 | Brain, Prostate, fetalBrain, fetalKidney | Liver, Testis |
| 17913 | Brain, Liver, Prostate, Testis, fetalBrain, fetalLiver | fetalKidney |

-continued

(Biais in spatial distribution)

| Seq Id No. | Low frequency | High frequency |
|---|---|---|
| 17970 | Liver, Prostate, Stomach_Intestine, Testis, fetalBrain, fetalKidney, fetalLiver | Brain |
| 17989 | | fetalKidney |
| 18074 | Brain, Testis, fetalKidney | |
| 18085 | Brain, Prostate, fetalBrain, fetalKidney | Liver, Testis |
| 18126 | Brain, Prostate, fetalBrain, fetalKidney | Liver, Testis |
| 18130 | Brain, Liver, Prostate, Testis, fetalBrain, fetalKidney | |
| 18174 | Prostate, Testis, fetalKidney | fetalBrain |
| 18182 | | fetalKidney |
| 18289 | Brain, Testis | fetalBrain, fetalKidney |
| 18301 | fetalKidney | |
| 18322 | | fetalKidney |
| 18325 | Testis | fetalKidney |
| 18331 | Brain, Testis | fetalKidney |
| 18364 | | fetalKidney |
| 18373 | | fetalKidney |
| 18392 | | fetalKidney |
| 18446 | Testis | fetalKidney |
| 18447 | Testis | fetalKidney |
| 18449 | | fetalKidney |
| 18478 | Brain, Liver, Stomach_Intestine, Testis, fetalLiver | Prostate, fetalBrain, fetalKidney |
| 18507 | Brain, Liver, Prostate, Testis, fetalBrain | fetalKidney |
| 18508 | | fetalKidney |
| 18519 | Brain, Testis | fetalKidney |
| 18549 | Brain, Liver, Testis | fetalKidney |
| 18584 | Brain, Liver, Prostate, Testis | fetalKidney |
| 18598 | Brain, Liver, Prostate, Testis, fetalBrain | fetalKidney |
| 18621 | fetalKidney | |
| 18624 | fetalKidney | Testis |
| 18677 | | fetalKidney |
| 18683 | Brain, Testis | fetalKidney |
| 18691 | Liver, Prostate, Testis | Brain, fetalBrain, fetalKidney |
| 18735 | Brain, Liver, Prostate, Testis, fetalBrain | fetalKidney |
| 18852 | fetalKidney | |
| 18911 | Testis | |
| 18951 | fetalKidney | |
| 18967 | Brain, Liver, Testis | fetalKidney |
| 18992 | Brain, Prostate, Stomach_Intestine, fetalBrain, fetalKidney, fetalLiver, salivaryGland | Liver, Testis |
| 18998 | fetalKidney | |
| 19002 | Testis | Brain, fetalKidney |
| 19021 | Liver, Prostate, Testis, fetalBrain, fetalKidney | Brain |
| 19045 | fetalKidney | |
| 19068 | Liver, Testis, fetalKidney | Brain |
| 19096 | fetalKidney | |
| 19115 | | fetalKidney |
| 19121 | Brain, Liver, Prostate, Testis, fetalBrain | fetalKidney |
| 19132 | fetalKidney | |
| 19159 | Testis | fetalKidney |
| 19168 | Brain, Liver, Prostate, Testis, fetalBrain | fetalKidney |
| 19177 | Brain, Testis | fetalKidney |
| 19325 | Brain, Liver, Testis | fetalKidney |

SEQUENCE LISTING

The patent contains a lengthy "Sequence Listing" section. A copy of the "Sequence Listing" is available in electronic form from the USPTO web site (http://seqdata.uspto.gov/sequence.html?DocID=6639063B1). An electronic copy of the "Sequence Listing" will also be available from the USPTO upon request and payment of the fee set forth in 37 CFR 1.19(b)(3).

What is claimed is:

1. An isolated, purified, or recombinant polynucleotide encoding a signal peptide, wherein:
    a) the polynucleotide encodes a signal peptide consisting of residues −102 to −1 of SEQ ID NO: 3986; and
    b) wherein said signal peptide directs the secretion of a polypeptide when located at the amino terminus of a polypeptide.

2. The isolated, purified, or recombinant polynucleotide of claim 1, wherein:
    said polynucleotide consists of nucleotides 144 to 449 of SEQ ID NO: 126.

3. An isolated, purified, or recombinant polynucleotide encoding a signal peptide, wherein:
    a) said polynucleotide, consists of a nucleic acid sequence having at least 90% homology to the polynucleotide of claim 2; and
    b) said polynucleotide, encodes a signal peptide that directs the secretion of a polypeptide when located at the amino terminus of a polypeptide.

4. The isolated, purified or recombinant polynucleotide according to claim 1, further comprising a nucleic acid sequence fused in frame to the polynucleotide of claim 1 and wherein the nucleic acid sequence encodes a heterologous polypeptide.

5. The isolated, purified or recombinant polynucleotide according to 2, further comprising a nucleic acid sequence fused in frame to the polynucleotide of claim 2 and wherein the nucleic acid sequence encodes a heterologous polypeptide.

6. The isolated, purified, or recombinant polynucleotide according to 3, further comprising a nucleic acid sequence fused in frame to the polynucleotide of claim 3 and wherein the nucleic acid sequence encodes a heterologous polypeptide.

7. A vector comprising a polynucleotide selected from the group consisting of the polynucleotides set forth in claim 1, 2, 3, 4, 5, or 6.

8. The vector according to claim 7, wherein the vector comprises a polynucleotide according to claim 1.

9. The vector according to claim 7, wherein the vector comprises a polynucleotide according to claim 2.

10. The vector according to claim 7, wherein the vector comprises a polynucleotide according to claim 3.

11. The vector according to claim 7, wherein the vector comprises a polynucleotide according to claim 4.

12. The vector according to claim 7, wherein the vector comprises a polynucleotide according to claim 5.

13. The vector according to claim 7, wherein the vector comprises a polynucleotide according to claim 6.

14. A host cell comprising a vector selected from the group consisting of vectors set forth in claim 8, 9, 10, 11, 12, or 13.

15. The host cell according to claim 14, wherein the vector comprises a polynucleotide according to claim 8.

16. The host cell according to claim 14, wherein the vector comprises a polynucleotide according to claim 9.

17. The host cell according to claim 14, wherein the vector comprises a polynucleotide according to claim 10.

18. The host cell according to claim 14, wherein the vector comprises a polynucleotide according to claim 11.

19. The host cell according to claim 14, wherein the vector comprises a polynucleotide according to claim 12.

20. The host cell according to claim 14, wherein the vector comprises a polynucleotide according to claim 13.

* * * * *

UNITED STATES PATENT AND TRADEMARK OFFICE
CERTIFICATE OF CORRECTION

PATENT NO. : 6,639,063 B1
DATED : October 28, 2003
INVENTOR(S) : Jean-Baptiste Dumas Milne Edwards, Severin Jobert, Jean-Yves Giordano It is certified that error appears in the above-identified patent and that said Letters Patent is hereby corrected as shown below:

Title page,
Item [57], ABSTRACT,
Line 10, "ESTs." should read -- 5' ESTs. --.

Column 2,
Line 5, "CDNA" should read -- cDNA --.

Column 6,
Line 36, "RNA/NA" should read -- RNA/DNA --.

Column 8,
Line 21, "CDNA" should read -- cDNA --.

Column 18,
Line 46, "12, 15, 18, 90, 23" should read -- 12, 15, 18, 20, 23 --.

Column 26,
Line 54, "1000V" should read -- 10000V --.

Column 27,
Line 34, "5ESTs" should read -- 5' ESTs --.

Column 51,
Line 8, "*FEBS Left.*," should read -- *FEBS* Lett., --.

Column 56,
Line 43, "Cytokine Cell" should read -- Cytokine, Cell --.

Column 65,
Line 25, "inhibin a" should read -- inhibin α --.
Line 53, "chemoatactic/chemokinetic" should read -- chemotactic/chemokinetic --.
Lines 57-58, "mast cells eosinophils" should read -- mast cells, eosinophils --.
Line 61, "proteins of" should read -- proteins or --.

Column 77,
Line 25, "60(7):3170-3179;" should read -- 160(7):3170-3179; --.

Column 79,
Line 37, "position EST-related" should read -- positional segments of EST-related --.

UNITED STATES PATENT AND TRADEMARK OFFICE
CERTIFICATE OF CORRECTION

PATENT NO. : 6,639,063 B1
DATED : October 28, 2003
INVENTOR(S) : Jean-Baptiste Dumas Milne Edwards, Severin Jobert, Jean-Yves Giordano It is certified that error appears in the above-identified patent and that said Letters Patent is hereby corrected as shown below:

Column 80,
Line 49, "Nucleic Acids Positional" should read -- nucleic acids, positional --.

Column 84,
Line 16, "Nucleic Acids Positional" should read -- nucleic acids, positional --.

Column 87,
Line 2, "Nucleic Acids Positional" should read -- nucleic acids, positional --.
Line 49, "Nucleic Acids Positional" should read -- nucleic acids, positional --.

Column 94,
Line 61, "Triton X1100" should read -- Triton X-100 --.

Column 95,
Line 24, "Nucleic Acids Positional" should read -- nucleic acids, positional --.

Column 97,
Line 58, "p13H2" should read -- P13H2 --.

Column 101,
Line 65, "$1 \times 10^4 M$" should read -- $1 \times 10^{-4} M$ --.

Column 102,
Lines 41-42, "ligonucleotides" should read -- oligonucleotides --.

Column 107,
Line 1, "components 105" should read -- components 110 --.
Line 13, "device 18" should read -- device 118 --.
Line 14, "devices 101" should read -- devices 110 --.

UNITED STATES PATENT AND TRADEMARK OFFICE
CERTIFICATE OF CORRECTION

PATENT NO. : 6,639,063 B1
DATED : October 28, 2003
INVENTOR(S) : Jean-Baptiste Dumas Milne Edwards, Severin Jobert, Jean-Yves Giordano It is certified that error appears in the above-identified patent and that said Letters Patent is hereby corrected as shown below:

<u>Column 110,</u>
Line 64, "feature+s" should read -- feature's --.

Signed and Sealed this

First Day of June, 2004

JON W. DUDAS
*Acting Director of the United States Patent and Trademark Office*